US012685735B2

(12) United States Patent
Anthony et al.

(10) Patent No.: US 12,685,735 B2
(45) Date of Patent: Jul. 21, 2026

(54) BAF COMPLEX MODULATING COMPOUNDS

(71) Applicant: Foghorn Therapeutics Inc., Indianapolis, IN (US)

(72) Inventors: Neville John Anthony, Northborough, MA (US); Rishi G. Vaswani, Lexington, MA (US); David Simon Millan, Stow, MA (US); Shawn E.R. Schiller, Haverhill, MA (US); Kevin J. Wilson, Roslindale, MA (US)

(73) Assignee: Foghorn Therapeutics Inc., Watertown, MA (US)

( * ) Notice: Subject to any disclaimer, the term of this patent is extended or adjusted under 35 U.S.C. 154(b) by 898 days.

(21) Appl. No.: 17/795,747

(22) PCT Filed: Jan. 29, 2021

(86) PCT No.: PCT/US2021/015938

§ 371 (c)(1),
(2) Date: Jul. 27, 2022

(87) PCT Pub. No.: WO2021/155316

PCT Pub. Date: Aug. 5, 2021

(65) Prior Publication Data

US 2023/0149414 A1 May 18, 2023

Related U.S. Application Data

(60) Provisional application No. 62/967,186, filed on Jan. 29, 2020.

(51) Int. Cl.

| | |
|---|---|
| ***A61K 31/5377*** | (2006.01) |
| ***A61K 31/427*** | (2006.01) |
| ***A61K 31/4439*** | (2006.01) |
| ***A61K 31/444*** | (2006.01) |
| ***A61K 31/506*** | (2006.01) |
| ***A61K 45/06*** | (2006.01) |
| ***A61P 35/00*** | (2006.01) |
| ***C07D 277/46*** | (2006.01) |
| ***C07D 417/10*** | (2006.01) |
| ***C07D 417/14*** | (2006.01) |

(52) U.S. Cl.

CPC ........ *A61K 31/5377* (2013.01); *A61K 31/427* (2013.01); *A61K 31/4439* (2013.01); *A61K 31/444* (2013.01); *A61K 31/506* (2013.01); *A61K 45/06* (2013.01); *A61P 35/00* (2018.01); *C07D 277/46* (2013.01); *C07D 417/10* (2013.01); *C07D 417/14* (2013.01)

(58) Field of Classification Search

CPC .. A61K 31/5377; A61K 31/427; A61K 45/06; A61P 35/00; C07D 277/46; C07D 417/12

See application file for complete search history.

(56) References Cited

U.S. PATENT DOCUMENTS

2016/0032402 A1* 2/2016 Jagani .................. C12Q 1/6886 435/6.12

FOREIGN PATENT DOCUMENTS

| | | |
|---|---|---|
| WO | 2019152437 A1 | 8/2019 |
| WO | 2020160100 A1 | 8/2020 |

OTHER PUBLICATIONS

Papillon JPN, Nakajima K, Adair CD, et al. Discovery of Orally Active Inhibitors of Brahma Homolog (BRM)/SMARCA2 ATPase Activity for the Treatment of Brahma Related Gene 1 (BRG1)/SMARCA4-Mutant Cancers. J Med Chem. 2018;61(22):10155-10172. doi:10.1021/acs.jmedchem.8b01318 (Year: 2018).*

Wu Q., Sharma S., Cui H., LeBlanc S. E., Zhang H., Muthuswami R., Nickerson J. A., Imbalzano A. N. Targeting the chromatin remodeling enzyme BRG1 increases the efficacy of chemotherapy drugs in breast cancer cells. Oncotarget. 2016; 7: 27158-27175 (Year: 2017).*

PCT International Search Report and the Written Opinion of the International Searching Authority pertaining to international Application No. PCT/2021/015938; Date of Mailing: Jun. 3, 2021; 9 pages.

National Center for Biotechnology Information. "PubChem Substance Record for SID 386738040, SCHEMBL21241898, Source: SureChEMBL" PubChem, https://pubchem.ncbi.nlm.nih.gov/substance/386738040. Accessed Jun. 24, 2022.

* cited by examiner

*Primary Examiner* — Kortney L. Klinkel
(74) *Attorney, Agent, or Firm* — Bradley W. Crawford

(57) ABSTRACT

The present disclosure features compounds useful for the treatment of BAF complex-related disorders.

40 Claims, 3 Drawing Sheets

BAF COMPLEX MODULATING COMPOUNDS

BACKGROUND

The invention relates to compounds useful for modulating BRG1- or BRM-associated factors (BAF) complexes. In particular, the invention relates to compounds useful for treatment of disorders associated with BAF complex function.

Chromatin regulation is essential for gene expression, and ATP-dependent chromatin remodeling is a mechanism by which such gene expression occurs. The human Switch/Sucrose Non-Fermentable (SWI/SNF) chromatin remodeling complex, also known as BAF complex, has two SWN2-like ATPases known as BRG1 (Brahma-related gene-1) and BRM (Brahma). The transcription activator BRG1, also known as ATP-dependent chromatin remodeler SMARCA4, is encoded by the SMARCA4 gene on chromosome 19. BRG1 is overexpressed in some cancer tumors and is needed for cancer cell proliferation. BRM, also known as probable global transcription activator SNF2L2 and/or ATP-dependent chromatin remodeler SMARCA2, is encoded by the SMARCA2 gene on chromosome 9 and has been shown to be essential for tumor cell growth in cells characterized by loss of BRG1 function mutations. Deactivation of BRG and/or BRM results in downstream effects in cells, including cell cycle arrest and tumor suppression.

SUMMARY

The present invention features compounds useful for modulating a BAF complex. In some embodiments, the compounds are useful for the treatment of disorders associated with an alteration in a BAF complex, e.g., a disorder associated with an alteration in one or both of the BRG1 and BRM proteins. The compounds of the invention, alone or in combination with other pharmaceutically active agents, can be used for treating such disorders.

In an aspect, the invention features, a compound having the structure:

Formula I

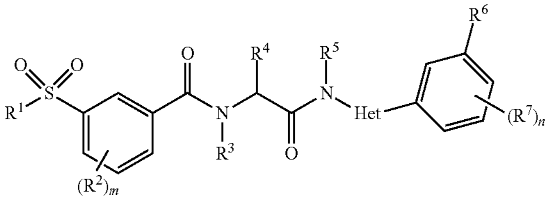

wherein m is 0, 1, 2, 3, or 4;

n is 0, 1, 2, 3, or 4;

$R^1$ is optionally substituted $C_3$-$C_8$ branched alkyl, or $R^1$ combines with $R^2$ and the atoms to which they are attached to form a 5- to 7-membered ring;

each $R^2$ is, independently, halo, hydroxy, thiol, optionally substituted $C_1$-$C_6$alkyl, optionally substituted $C_1$-$C_6$ heteroalkyl, or optionally substituted amino, or one $R^2$ combines with another $R^2$ and the atoms to which they are attached to form a 5- to 7-membered ring;

$R^3$ and $R^5$ are, independently, hydrogen or optionally substituted $C_1$-$C_6$ alkyl;

$R^4$ is hydrogen, optionally substituted $C_1$-$C_6$ alkyl, optionally substituted $C_1$-$C_6$ heteroalkyl, optionally substituted $C_1$-$C_6$ alkyl $C_6$-$C_{10}$ aryl, or optionally substituted $C_1$-$C_6$ alkyl $C_2$-$C_9$ heteroaryl;

Het is 5- or 6-membered heterocycle;

$R^6$ is hydrogen, halo, cyano, optionally substituted $C_1$-$C_6$ alkoxy, optionally substituted $C_1$-$C_6$ heteroalkyl, carboxyl, optionally substituted amide, optionally substituted $C_2$-$C_9$ heteroaryl, optionally substituted $C_2$-$C_9$ heterocyclyl, or optionally substituted $C_6$-$C_{10}$ aryl; and $R^7$ is cyano, halo, optionally substituted $C_1$-$C_6$ alkyl or optionally substituted $C_1$-$C_6$ heteroalkyl, or a pharmaceutically acceptable salt thereof.

In some embodiments, $R^3$ is hydrogen. In some embodiments, $R^5$ is hydrogen. In some embodiments, $R^4$ is hydrogen. In some embodiments, $R^4$ is optionally substituted $C_1$-$C_6$ heteroalkyl (e.g.,

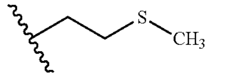

or

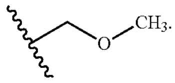

In some embodiments, $R^4$ is optionally substituted $C_1$-$C_6$ alkyl (e.g., methyl).

In some embodiments, Het is

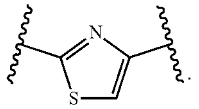 [SMILES: *c1csc(*)n1]

In some embodiments, Het is

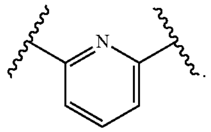 [SMILES: *c1cccc(*)n1]

In some embodiments, $R^1$ is iso-propyl. In some embodiments, $R^1$ is

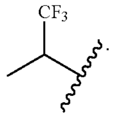 [SMILES: *C(C)C(F)(F)F]

In some embodiments, $R^1$ is

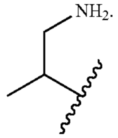

In some embodiments, $R^1$ is

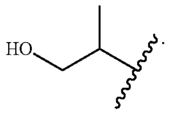 [SMILES: *C(C)CO]

In some embodiments, $R^1$ is

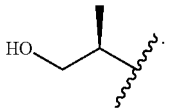 [SMILES: *[C@H](C)CO]

In some embodiments, $R^1$ is

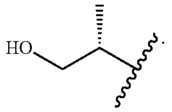 [SMILES: *[C@@H](C)CO]

In some embodiments, m is 0. In some embodiments, m is 1. In some embodiments, m is 2.

In some embodiments, at least one $R^2$ is optionally substituted $C_1$-$C_6$ alkyl or halo. In some embodiments, $R^2$ is methyl. In some embodiments, $R^2$ is optionally substituted $C_1$-$C_6$ heteroalkyl (e.g., (e.g., 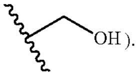 ).

In some embodiments, $R^2$ is optionally substituted amino (e.g., —$NH_2$).

In some embodiments, $R^1$ combines with $R^2$ and the atoms to which they are attached to form a 5- to 7-membered ring. In some embodiments, the compound has the structure of Formula Ia:

Formula Ia

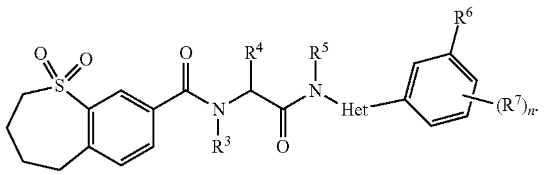

In some embodiments, n is 0. In some embodiments, n is 1. In some embodiments, at least one $R^7$ is cyano. In some embodiments, $R^6$ is hydrogen. In some embodiments, $R^6$ is cyano. In some embodiments, $R^6$ is optionally substituted $C_1$-$C_6$ heteroalkyl (e.g.,

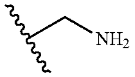 or 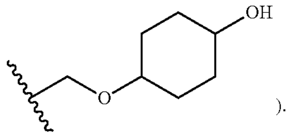 ).

In some embodiments, $R^6$ is carboxyl. In some embodiments, $R^6$ is optionally substituted $C_2$-$C_9$ heteroaryl (e.g.,

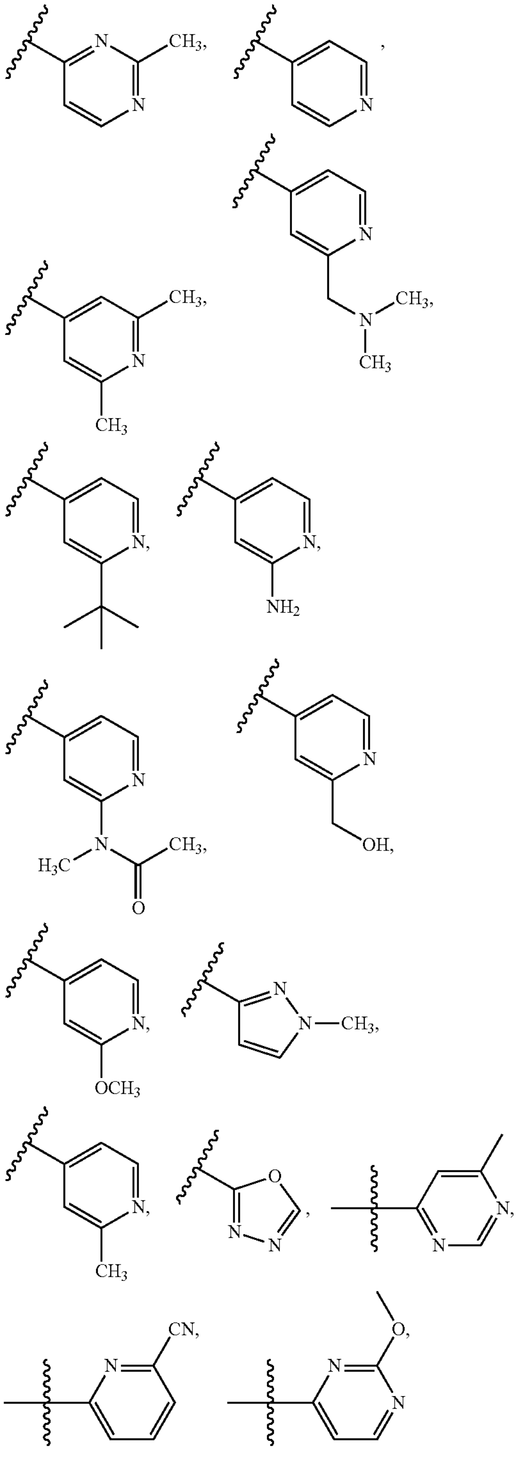

-continued

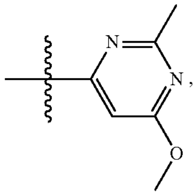, 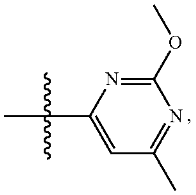,

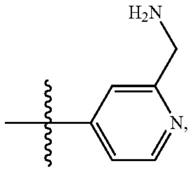 or 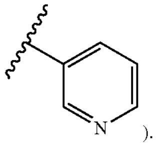).

In some embodiments, $R^6$ is optionally substituted $C_2$-$C_9$ heteroaryl (e.g.,

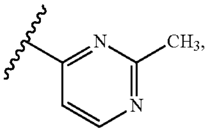, 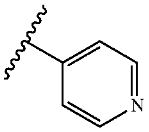,

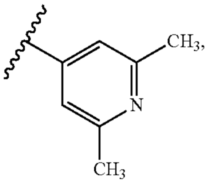, 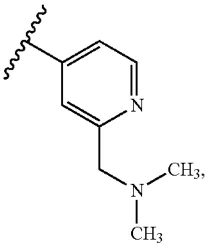,

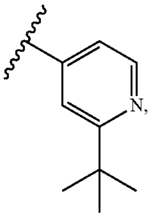, 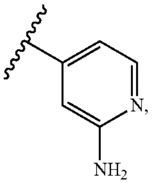,

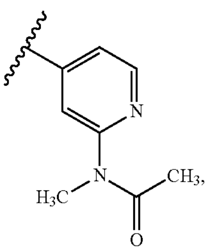, 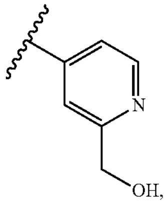,

-continued

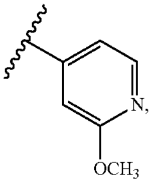, 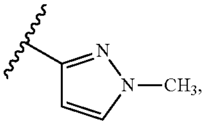,

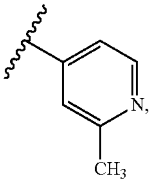, 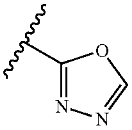, or

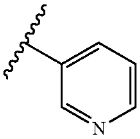).

In some embodiments, $R^6$ is optionally substituted $C_2$-$C_9$ heterocyclyl (e.g.,

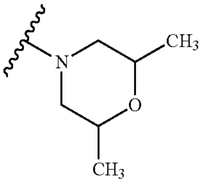 or 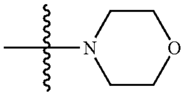).

In some embodiments. $R^6$ is optionally substituted $C_6$-$C_{10}$ aryl (e.g., 3,5-dicyano-phenyl, 3-hydroxymethyl-5-cyano-phenyl, 3-cyano-phenyl, 3-hydroxymethyl-5-trifluoromethyl-phenyl, 3-chloro-phenyl, 3,5-dichloro-phenyl, 3-aminomethyl-phenyl,

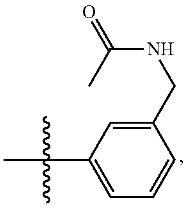 [SMILES: *c1cccc(CNC(C)=O)c1], or 4-aminomethyl-phenyl).

In some embodiments, the compound is any one of compounds 12-47 in Table 1a. In some embodiments, the compound is any one of compounds 110-129 in Table 1b.

TABLE 1a
| Compounds of the invention | |
|---|---|
| # | Compound |
| 12 | 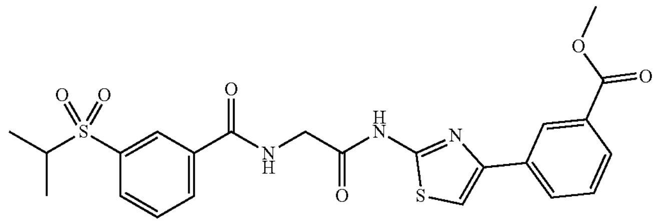 [SMILES: COC(=O)c1cccc(-c2csc(NC(=O)CNC(=O)c3cccc(S(=O)(=O)C(C)C)c3)n2)c1] |
| 13 | 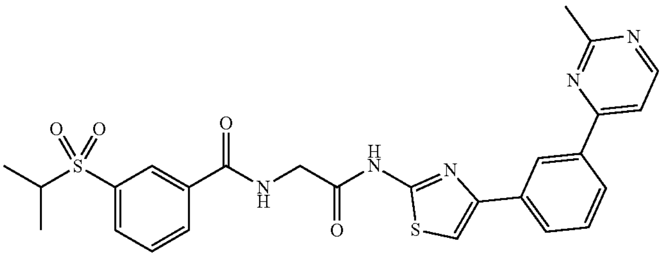 [SMILES: Cc1nccc(-c2cccc(-c3csc(NC(=O)CNC(=O)c4cccc(S(=O)(=O)C(C)C)c4)n3)c2)n1] |
| 14 | 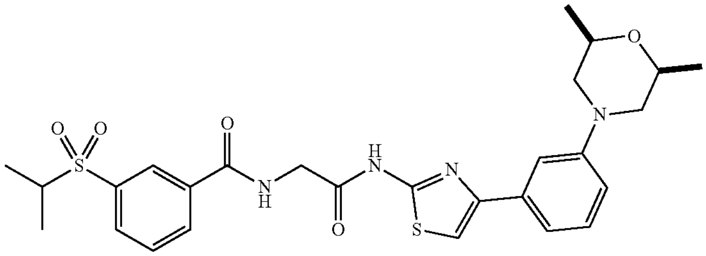 [SMILES: CC(C)S(=O)(=O)c1cccc(C(=O)NCC(=O)Nc2nc(-c3cccc(N4C[C@@H](C)O[C@@H](C)C4)c3)cs2)c1] |
| 15 | 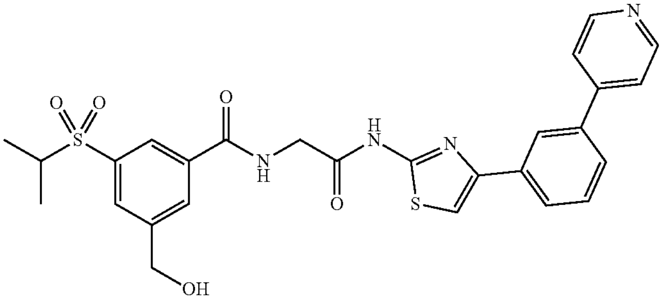 [SMILES: CC(C)S(=O)(=O)c1cc(CO)cc(C(=O)NCC(=O)Nc2nc(-c3cccc(-c4ccncc4)c3)cs2)c1] |
| 16 | 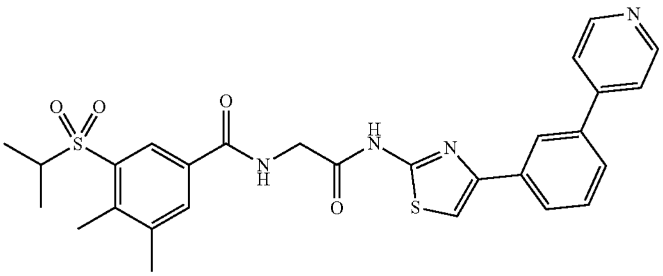 [SMILES: Cc1cc(C(=O)NCC(=O)Nc2nc(-c3cccc(-c4ccncc4)c3)cs2)cc(S(=O)(=O)C(C)C)c1C] |

TABLE 1a-continued
| Compounds of the invention | |
|---|---|
| # | Compound |
| 17 | 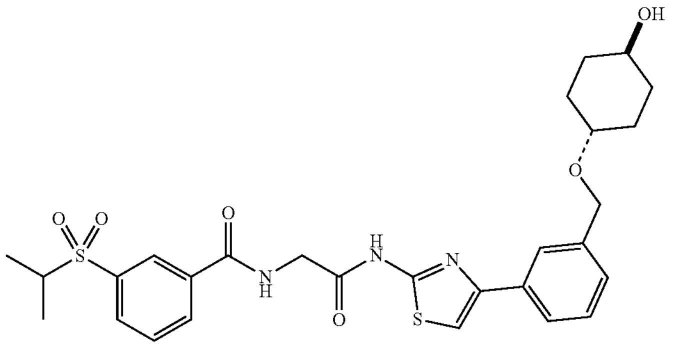 |
| 18 | 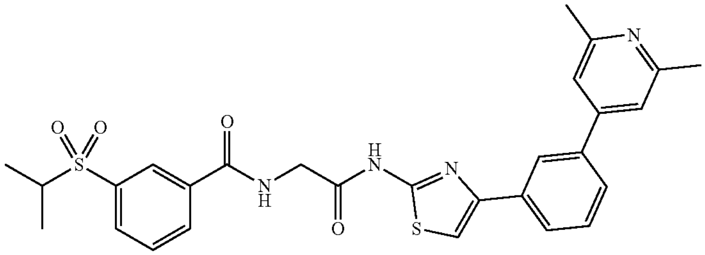 [SMILES: Cc1cc(-c2cccc(-c3csc(NC(=O)CNC(=O)c4cccc(S(=O)(=O)C(C)C)c4)n3)c2)cc(C)n1] |
| 19 | 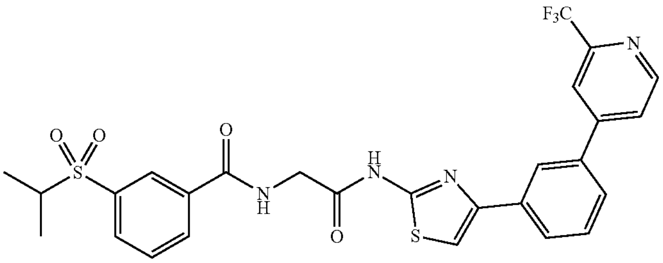 [SMILES: CC(C)S(=O)(=O)c1cccc(C(=O)NCC(=O)Nc2nc(-c3cccc(-c4ccnc(C(F)(F)F)c4)c3)cs2)c1] |
| 20 | 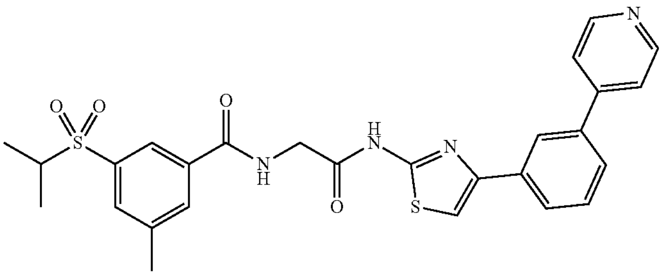 [SMILES: Cc1cc(C(=O)NCC(=O)Nc2nc(-c3cccc(-c4ccncc4)c3)cs2)cc(S(=O)(=O)C(C)C)c1] |
| 21 | 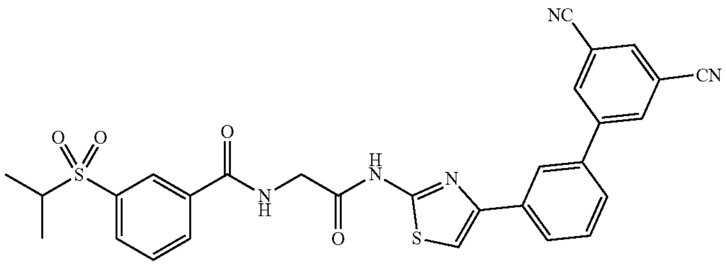 [SMILES: CC(C)S(=O)(=O)c1cccc(C(=O)NCC(=O)Nc2nc(-c3cccc(-c4cc(C#N)cc(C#N)c4)c3)cs2)c1] |

TABLE 1a-continued
| Compounds of the invention | |
|---|---|
| # | Compound |
| 22 | 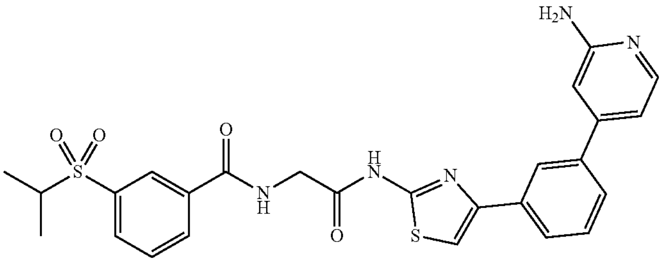 [SMILES: CC(C)S(=O)(=O)c1cccc(C(=O)NCC(=O)Nc2nc(-c3cccc(-c4ccnc(N)c4)c3)cs2)c1] |
| 23 | 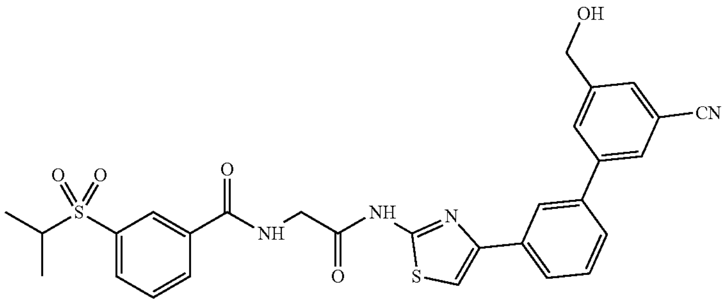 [SMILES: CC(C)S(=O)(=O)c1cccc(C(=O)NCC(=O)Nc2nc(-c3cccc(-c4cc(C#N)cc(CO)c4)c3)cs2)c1] |
| 24 | 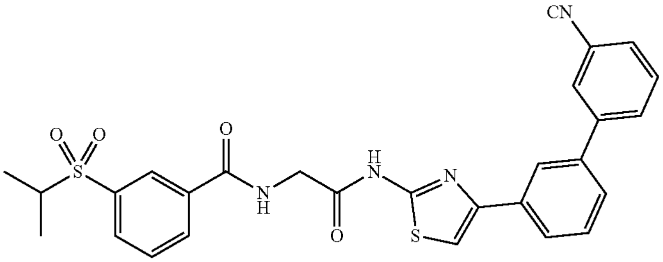 |
| 25 | 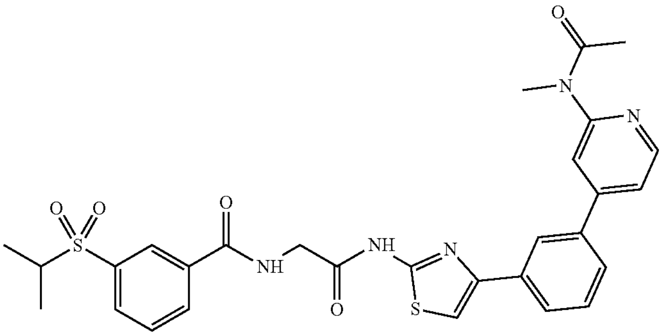 [SMILES: CC(=O)N(C)c1cc(-c2cccc(-c3csc(NC(=O)CNC(=O)c4cccc(S(=O)(=O)C(C)C)c4)n3)c2)ccn1] |
| 26 | 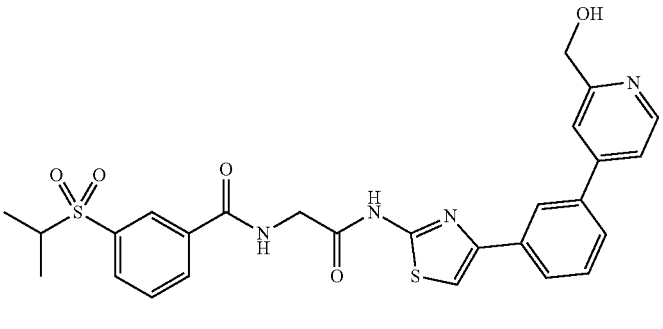 [SMILES: CC(C)S(=O)(=O)c1cccc(C(=O)NCC(=O)Nc2nc(-c3cccc(-c4ccnc(CO)c4)c3)cs2)c1]

TABLE 1a-continued
| Compounds of the invention | |
|---|---|
| # | Compound |
| 27 | 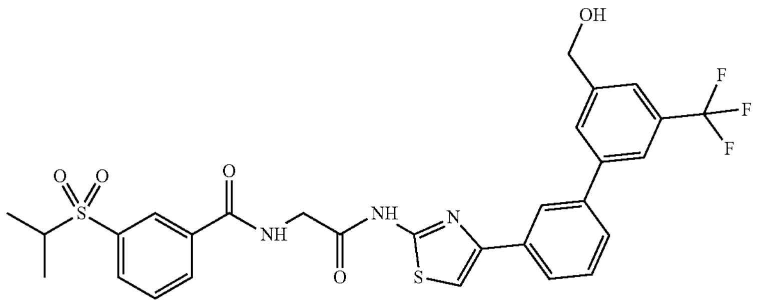 [SMILES: CC(C)S(=O)(=O)c1cccc(C(=O)NCC(=O)Nc2nc(-c3cccc(-c4cc(CO)cc(C(F)(F)F)c4)c3)cs2)c1] |
| 28 | 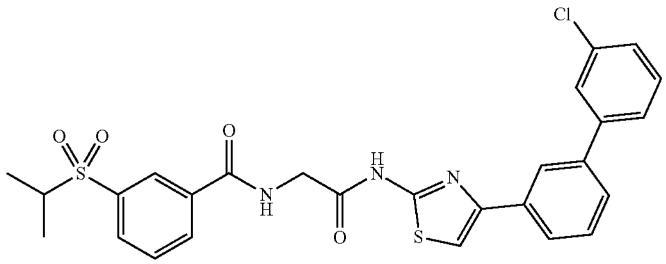 [SMILES: CC(C)S(=O)(=O)c1cccc(C(=O)NCC(=O)Nc2nc(-c3cccc(-c4cccc(Cl)c4)c3)cs2)c1] |
| 29 | 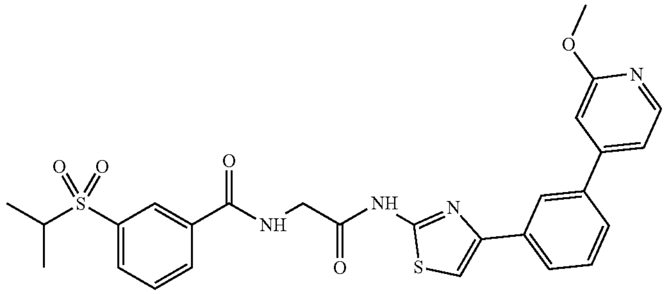 [SMILES: COc1cc(-c2cccc(-c3csc(NC(=O)CNC(=O)c4cccc(S(=O)(=O)C(C)C)c4)n3)c2)ccn1] |
| 30 | 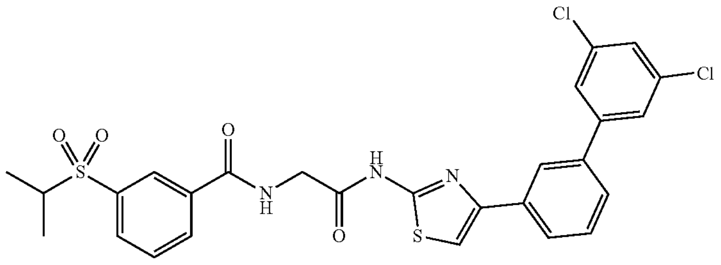 [SMILES: CC(C)S(=O)(=O)c1cccc(C(=O)NCC(=O)Nc2nc(-c3cccc(-c4cc(Cl)cc(Cl)c4)c3)cs2)c1] |
| 31 | 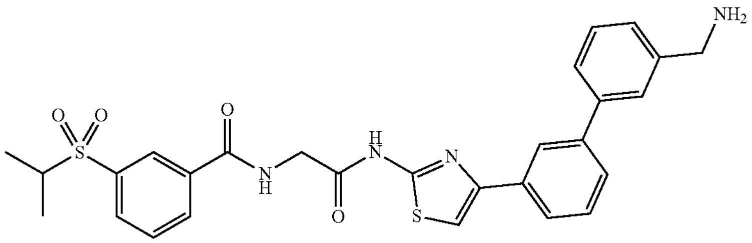 [SMILES: CC(C)S(=O)(=O)c1cccc(C(=O)NCC(=O)Nc2nc(-c3cccc(-c4cccc(CN)c4)c3)cs2)c1] |

TABLE 1a-continued
| Compounds of the invention | |
|---|---|
| # | Compound |
| 32 | 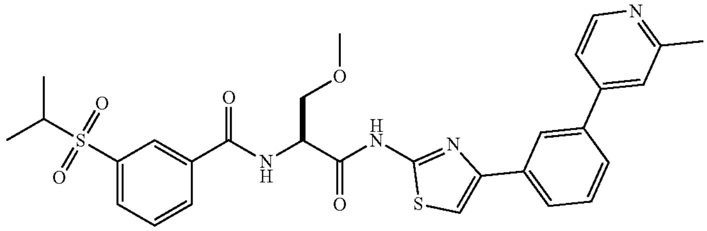 [SMILES: COC[C@H](NC(=O)c1cccc(S(=O)(=O)C(C)C)c1)C(=O)Nc1nc(-c2cccc(-c3ccnc(C)c3)c2)cs1] |
| 33 | 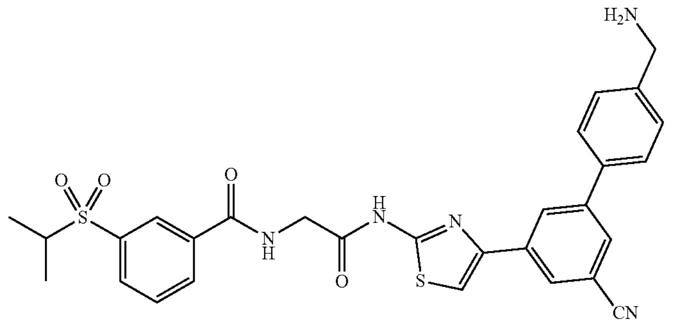 [SMILES: CC(C)S(=O)(=O)c1cccc(C(=O)NCC(=O)Nc2nc(-c3cc(C#N)cc(-c4ccc(CN)cc4)c3)cs2)c1] |
| 34 | 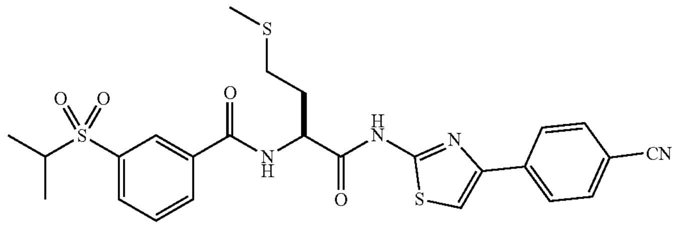 [SMILES: CSCC[C@H](NC(=O)c1cccc(S(=O)(=O)C(C)C)c1)C(=O)Nc1nc(-c2ccc(C#N)cc2)cs1] |
| 35 | 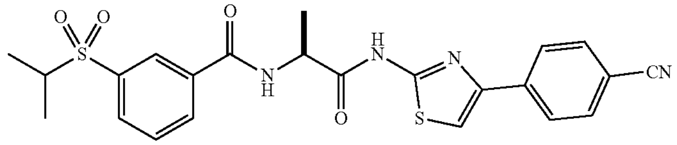 [SMILES: CC(C)S(=O)(=O)c1cccc(C(=O)N[C@@H](C)C(=O)Nc2nc(-c3ccc(C#N)cc3)cs2)c1] |
| 36 | 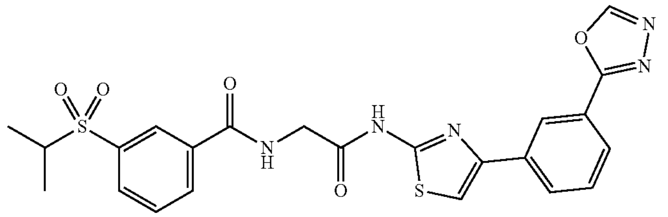 [SMILES: CC(C)S(=O)(=O)c1cccc(C(=O)NCC(=O)Nc2nc(-c3cccc(-c4nnco4)c3)cs2)c1] |
| 37 | 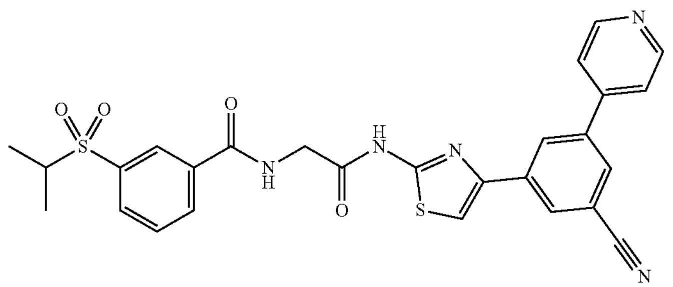 [SMILES: CC(C)S(=O)(=O)c1cccc(C(=O)NCC(=O)Nc2nc(-c3cc(C#N)cc(-c4ccncc4)c3)cs2)c1] |

TABLE 1a-continued
| Compounds of the invention | |
|---|---|
| # | Compound |
| 38 | 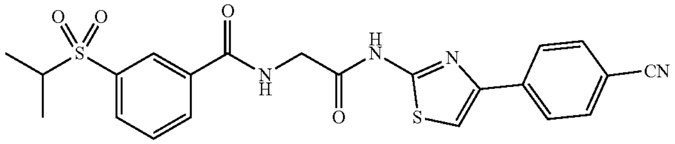 [SMILES: CC(C)S(=O)(=O)c1cccc(C(=O)NCC(=O)Nc2nc(-c3ccc(C#N)cc3)cs2)c1] |
| 39 | 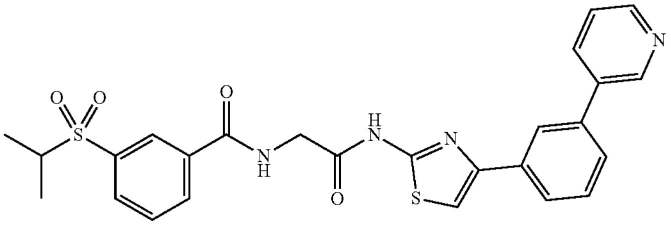 [SMILES: CC(C)S(=O)(=O)c1cccc(C(=O)NCC(=O)Nc2nc(-c3cccc(-c4cccnc4)c3)cs2)c1] |
| 40 | 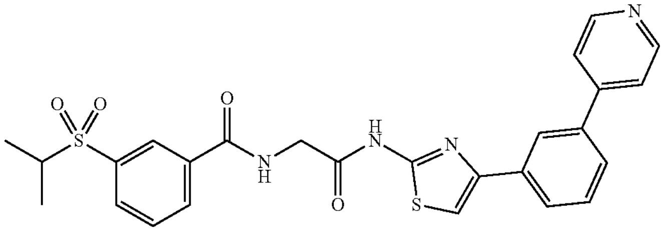 [SMILES: CC(C)S(=O)(=O)c1cccc(C(=O)NCC(=O)Nc2nc(-c3cccc(-c4ccncc4)c3)cs2)c1] |
| 41 | 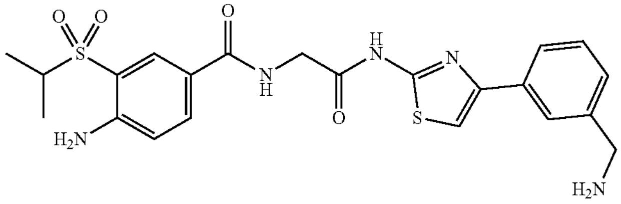 [SMILES: CC(C)S(=O)(=O)c1cc(C(=O)NCC(=O)Nc2nc(-c3cccc(CN)c3)cs2)ccc1N] |
| 42 | 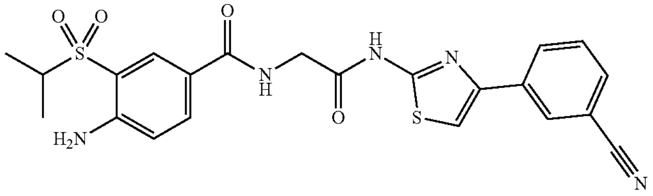 [SMILES: CC(C)S(=O)(=O)c1cc(C(=O)NCC(=O)Nc2nc(-c3cccc(C#N)c3)cs2)ccc1N] |
| 43 | 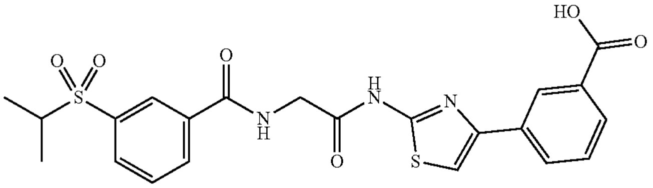 [SMILES: CC(C)S(=O)(=O)c1cccc(C(=O)NCC(=O)Nc2nc(-c3cccc(C(=O)O)c3)cs2)c1] |
| 44 | 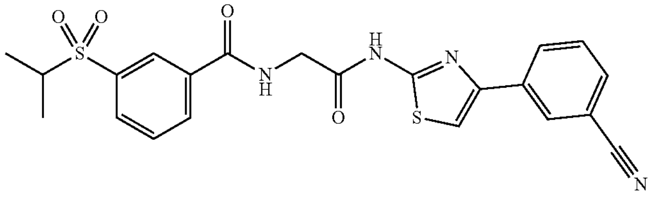 [SMILES: CC(C)S(=O)(=O)c1cccc(C(=O)NCC(=O)Nc2nc(-c3cccc(C#N)c3)cs2)c1] |

TABLE 1a-continued
| Compounds of the invention | |
|---|---|
| # | Compound |
| 45 | 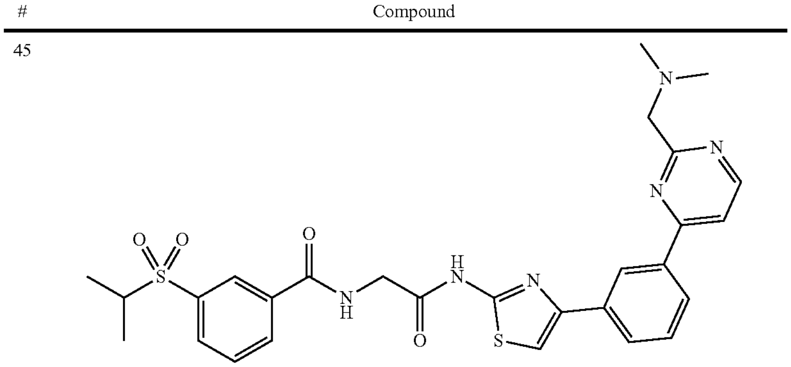 |
| 46 | 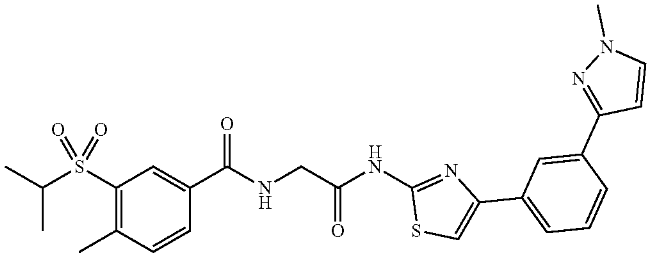 [SMILES: Cc1ccc(C(=O)NCC(=O)Nc2nc(-c3cccc(-c4ccn(C)n4)c3)cs2)cc1S(=O)(=O)C(C)C] |
| 47 | 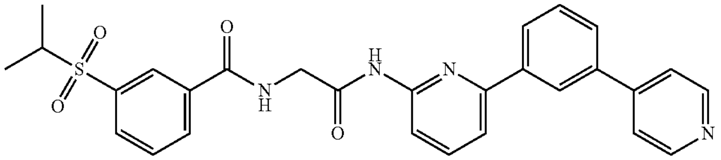 [SMILES: CC(C)S(=O)(=O)c1cccc(C(=O)NCC(=O)Nc2cccc(-c3cccc(-c4ccncc4)c3)n2)c1] |
TABLE 1b
| Compounds of the Invention | |
|---|---|
| # | Compound |
| 110 | 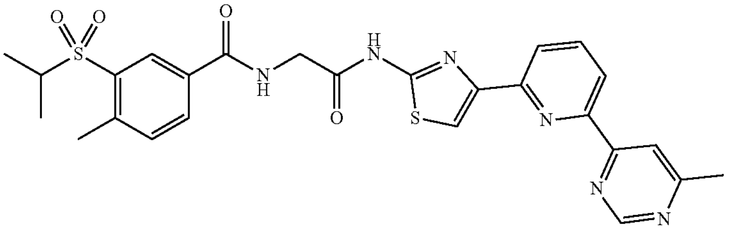 [SMILES: Cc1cc(-c2cccc(-c3csc(NC(=O)CNC(=O)c4ccc(C)c(S(=O)(=O)C(C)C)c4)n3)n2)ncn1] |
| 111 | 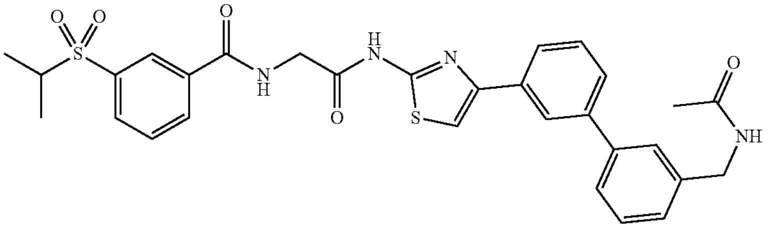 [SMILES: CC(=O)NCc1cccc(-c2cccc(-c3csc(NC(=O)CNC(=O)c4cccc(S(=O)(=O)C(C)C)c4)n3)c2)c1] |

TABLE 1b-continued
| Compounds of the Invention | |
|---|---|
| # | Compound |
| 112 | 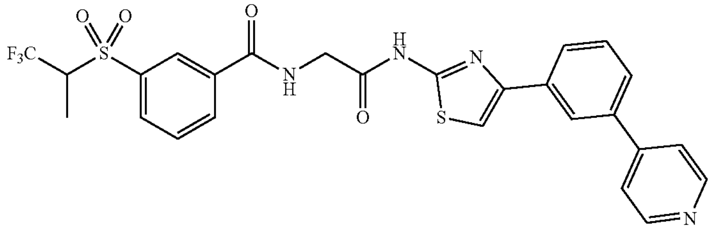 [SMILES: CC(C(F)(F)F)S(=O)(=O)c1cccc(C(=O)NCC(=O)Nc2nc(-c3cccc(-c4ccncc4)c3)cs2)c1] |
| 113 | 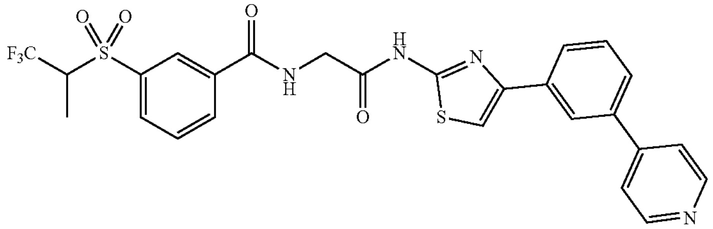 [SMILES: CC(C(F)(F)F)S(=O)(=O)c1cccc(C(=O)NCC(=O)Nc2nc(-c3cccc(-c4ccncc4)c3)cs2)c1] |
| 114 | 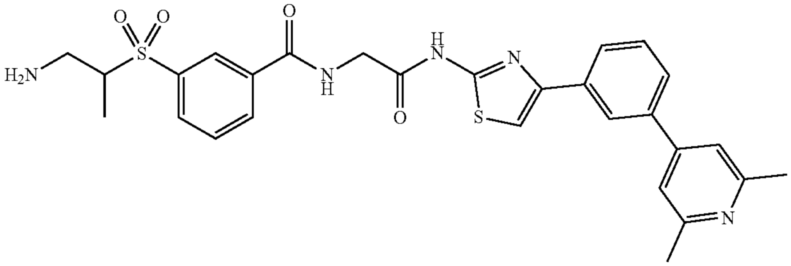 [SMILES: Cc1cc(-c2cccc(-c3csc(NC(=O)CNC(=O)c4cccc(S(=O)(=O)C(C)CN)c4)n3)c2)cc(C)n1] |
| 115 | 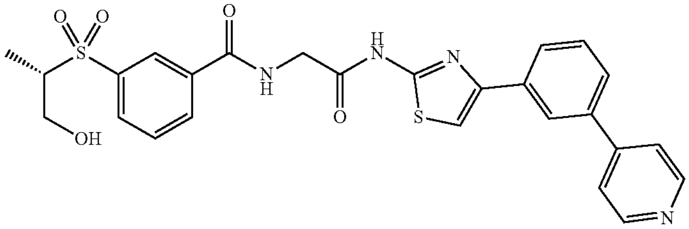 [SMILES: C[C@@H](CO)S(=O)(=O)c1cccc(C(=O)NCC(=O)Nc2nc(-c3cccc(-c4ccncc4)c3)cs2)c1] |
| 116 | 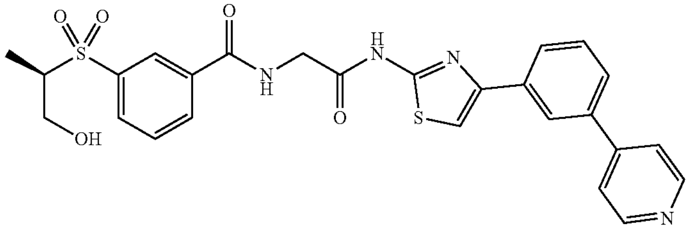 [SMILES: C[C@H](CO)S(=O)(=O)c1cccc(C(=O)NCC(=O)Nc2nc(-c3cccc(-c4ccncc4)c3)cs2)c1] |
| 117 | 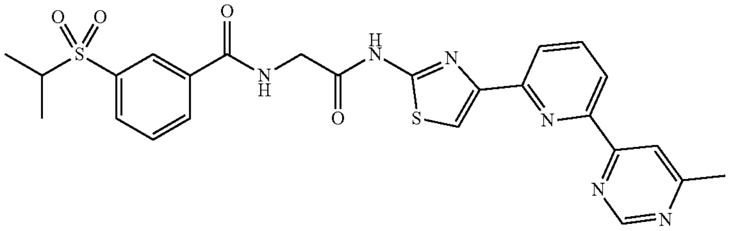 [SMILES: Cc1cc(-c2cccc(-c3csc(NC(=O)CNC(=O)c4cccc(S(=O)(=O)C(C)C)c4)n3)n2)ncn1] |

TABLE 1b-continued
| Compounds of the Invention | |
|---|---|
| # | Compound |
| 118 | 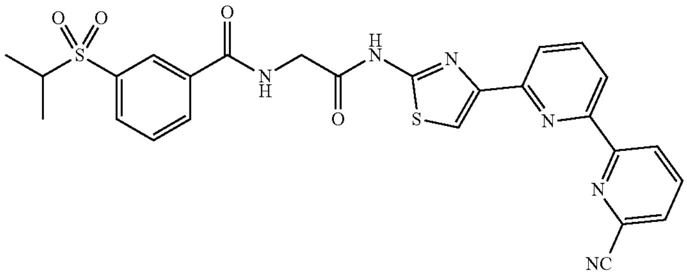 [SMILES: CC(C)S(=O)(=O)c1cccc(C(=O)NCC(=O)Nc2nc(-c3cccc(-c4cccc(C#N)n4)n3)cs2)c1] |
| 119 | 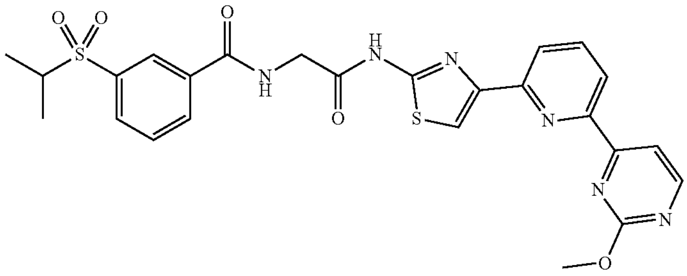 [SMILES: COc1nccc(-c2cccc(-c3csc(NC(=O)CNC(=O)c4cccc(S(=O)(=O)C(C)C)c4)n3)n2)n1] |
| 120 | 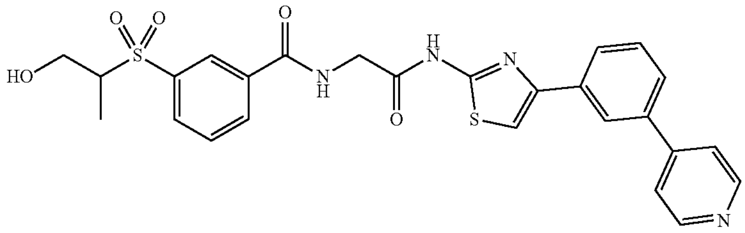 [SMILES: CC(CO)S(=O)(=O)c1cccc(C(=O)NCC(=O)Nc2nc(-c3cccc(-c4ccncc4)c3)cs2)c1] |
| 121 | 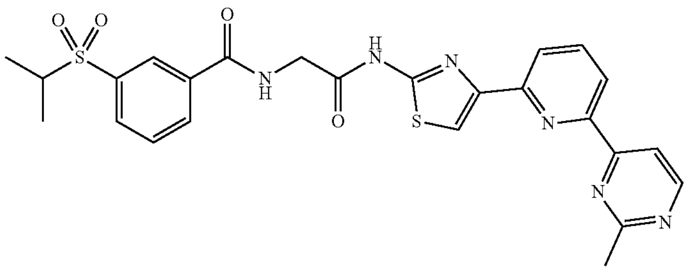 [SMILES: Cc1nccc(-c2cccc(-c3csc(NC(=O)CNC(=O)c4cccc(S(=O)(=O)C(C)C)c4)n3)n2)n1] |
| 122 | 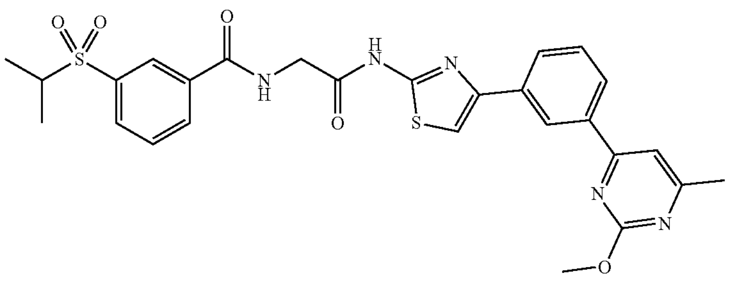 [SMILES: COc1nc(C)cc(-c2cccc(-c3csc(NC(=O)CNC(=O)c4cccc(S(=O)(=O)C(C)C)c4)n3)c2)n1] |

TABLE 1b-continued
| Compounds of the Invention | |
|---|---|
| # | Compound |
| 123 | 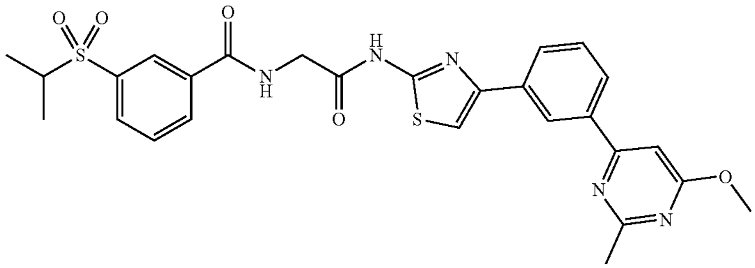 [SMILES: COc1cc(-c2cccc(-c3csc(NC(=O)CNC(=O)c4cccc(S(=O)(=O)C(C)C)c4)n3)c2)nc(C)n1] |
| 124 | 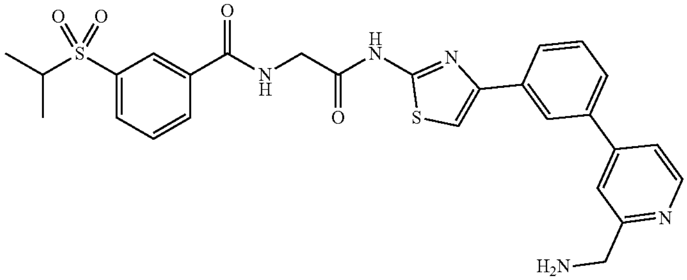 [SMILES: CC(C)S(=O)(=O)c1cccc(C(=O)NCC(=O)Nc2nc(-c3cccc(-c4ccnc(CN)c4)c3)cs2)c1] |
| 125 | 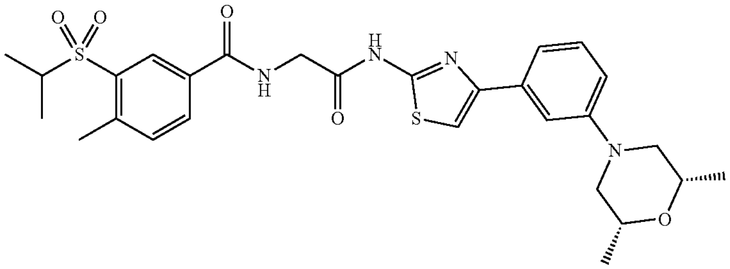 [SMILES: Cc1ccc(C(=O)NCC(=O)Nc2nc(-c3cccc(N4C[C@@H](C)O[C@@H](C)C4)c3)cs2)cc1S(=O)(=O)C(C)C] |
| 126 | 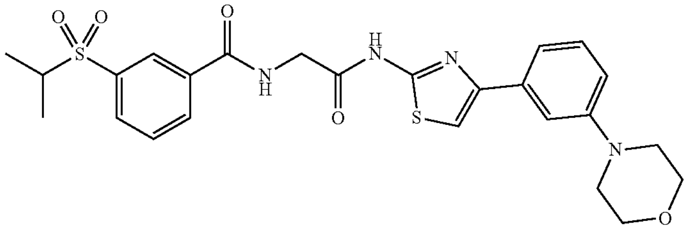 [SMILES: CC(C)S(=O)(=O)c1cccc(C(=O)NCC(=O)Nc2nc(-c3cccc(N4CCOCC4)c3)cs2)c1] |
| 127 | 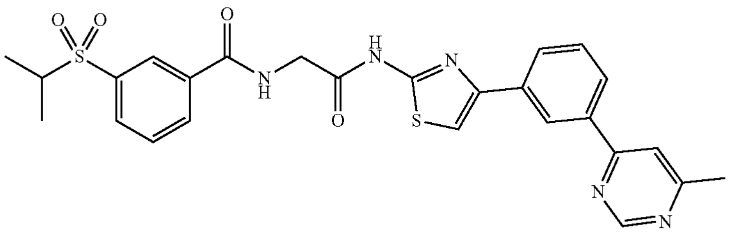 [SMILES: Cc1cc(-c2cccc(-c3csc(NC(=O)CNC(=O)c4cccc(S(=O)(=O)C(C)C)c4)n3)c2)ncn1] |

TABLE 1b-continued

| Compounds of the Invention | |
|---|---|
| # | Compound |
| 128 | 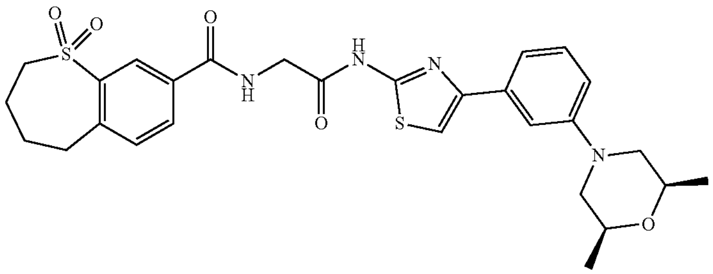 [SMILES: C[C@@H]1CN(c2cccc(-c3csc(NC(=O)CNC(=O)c4ccc5c(c4)S(=O)(=O)CCCC5)n3)c2)C[C@H](C)O1] |
| 129 | 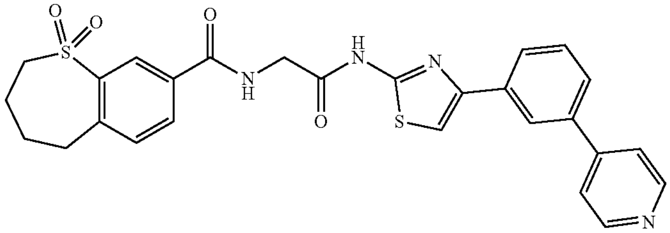 [SMILES: O=C(CNC(=O)c1ccc2c(c1)S(=O)(=O)CCCC2)Nc1nc(-c2cccc(-c3ccncc3)c2)cs1] |

In an aspect, the invention features a compound having the structure:

Formula II

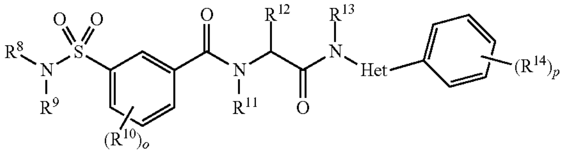

wherein o is 0, 1, 2, 3, or 4;

p is 0, 1, 2, 3, 4, or 5;

$R^8$ and $R^9$ are, independently, hydrogen or optionally substituted $C_1$-$C_6$ alkyl, or $R^9$ combines with an $R^{10}$ and the atoms to which they are attached to form a 5- to 8-membered ring;

each $R^{10}$ is, independently, halo, optionally substituted $C_1$-$C_6$ alkyl, or optionally substituted $C_1$-$C_6$ heteroalkyl or an $R^{10}$ combines with $R^9$ and the atoms to which they are attached to form a 5- to 8-membered ring;

$R^{11}$ and $R^{13}$ are, independently, hydrogen or optionally substituted $C_1$-$C_6$ alkyl;

$R^{12}$ is hydrogen, optionally substituted $C_1$-$C_6$ alkyl, or optionally substituted $C_1$-$C_6$ heteroalkyl;

Het is optionally substituted $C_2$-$C_9$ heteroaryl; and each $R^{14}$ is, independently, optionally substituted amide, cyano, optionally substituted $C_1$-$C_6$ heteroalkyl, carboxyl, optionally substituted $C_2$-$C_9$ heteroaryl, optionally substituted $C_2$-$C_9$ heterocyclyl, or optionally substituted $C_6$-$C_{10}$ aryl;

or a pharmaceutically acceptable salt thereof.

In some embodiments, $R^{11}$ is hydrogen. In some embodiments, $R^{13}$ is hydrogen. In some embodiments, $R^{12}$ is hydrogen. In some embodiments, $R^8$ is optionally substituted $C_1$-$C_6$ alkyl (e.g., methyl). In some embodiments, $R^9$ is optionally substituted $C_1$-$C_6$ alkyl (e.g. methyl). In some embodiments, o is 0.

In some embodiments, $R^9$ combines with an $R^{10}$ and the atoms to which they are attached to form a 5- to 8-membered ring. In some embodiments, the compound has the structure of Formula IIa:

Formula IIa

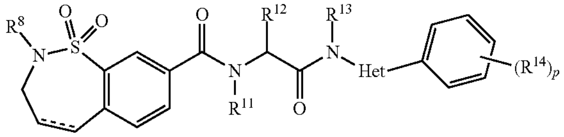

wherein the dotted line is an optional double bond.

In some embodiments, Het is

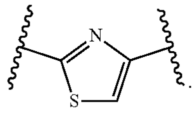 [SMILES: *c1csc(*)n1].

In some embodiments, p is 1. In some embodiments, $R^{14}$ is optionally substituted amide (e.g., $R^{14}$ is

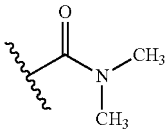).

In some embodiments, $R^{14}$ is carboxyl. In some embodiments, $R^{14}$ is optionally substituted $C_2$-$C_9$ heteroaryl (e.g.,

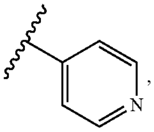,
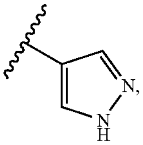
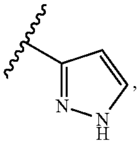,
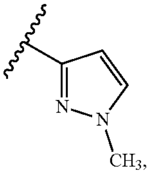
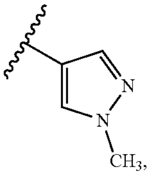
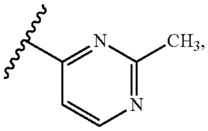
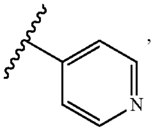,
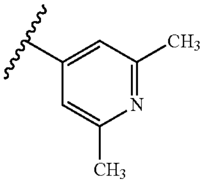,
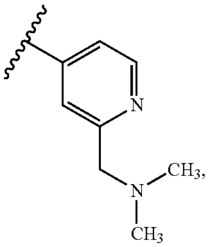
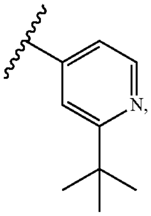
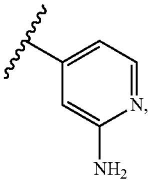
-continued
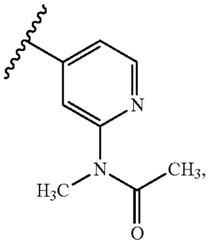
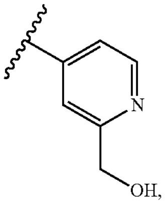
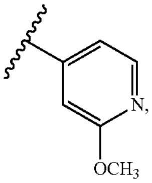
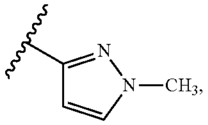
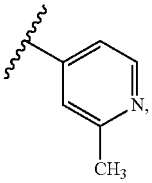
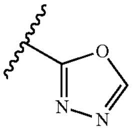, or
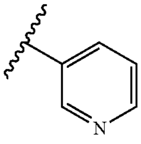).
In some embodiments, the compound is any one of compounds 1-11 in Table 2a. In some embodiments, the compound is any one of compounds 130 or 131 in Table 2b.
TABLE 2a
| Compounds of the invetion | |
|---|---|
| # | Compound |
| 1 | 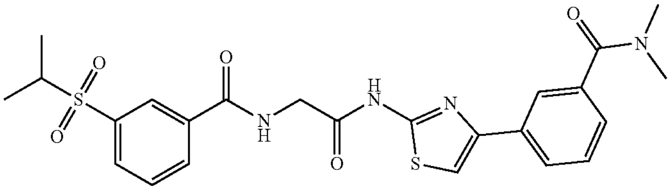 [SMILES: CC(C)S(=O)(=O)c1cccc(C(=O)NCC(=O)Nc2nc(-c3cccc(C(=O)N(C)C)c3)cs2)c1] |
| 2 | 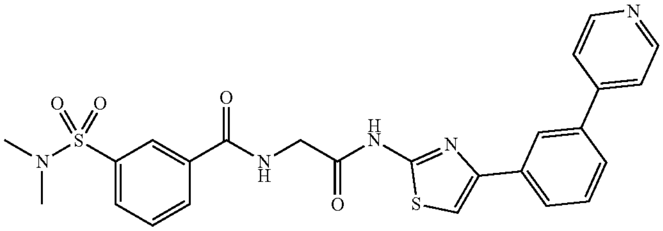 [SMILES: CN(C)S(=O)(=O)c1cccc(C(=O)NCC(=O)Nc2nc(-c3cccc(-c4ccncc4)c3)cs2)c1] |

TABLE 2a-continued
| Compounds of the invetion | |
|---|---|
| # | Compound |
| 3 | 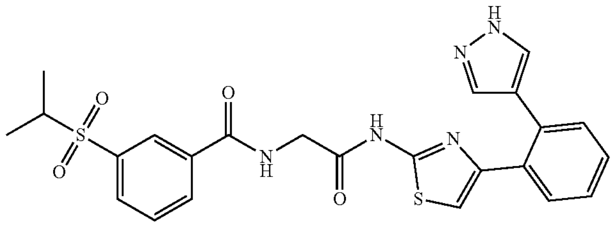 [SMILES: CC(C)S(=O)(=O)c1cccc(C(=O)NCC(=O)Nc2nc(-c3ccccc3-c3cn[nH]c3)cs2)c1] |
| 4 | 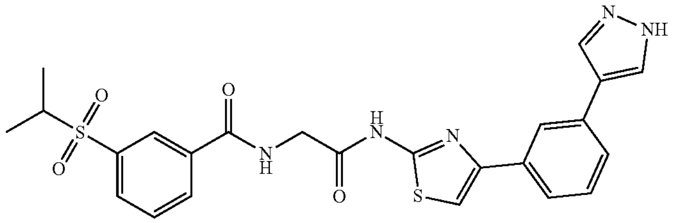 [SMILES: CC(C)S(=O)(=O)c1cccc(C(=O)NCC(=O)Nc2nc(-c3cccc(-c4cn[nH]c4)c3)cs2)c1] |
| 5 | 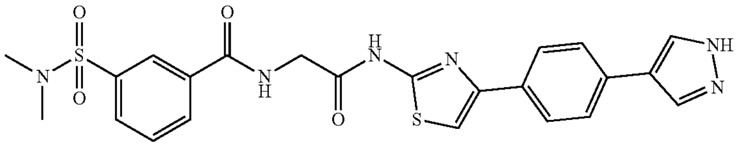 [SMILES: CN(C)S(=O)(=O)c1cccc(C(=O)NCC(=O)Nc2nc(-c3ccc(-c4cn[nH]c4)cc3)cs2)c1] |
| 6 | 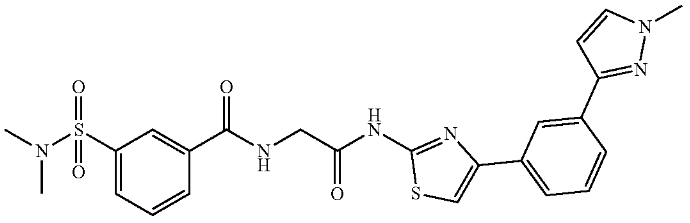 |
| 7 | 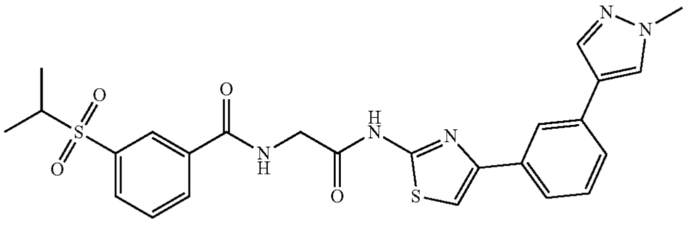 [SMILES: CC(C)S(=O)(=O)c1cccc(C(=O)NCC(=O)Nc2nc(-c3cccc(-c4cnn(C)c4)c3)cs2)c1] |
| 8 | 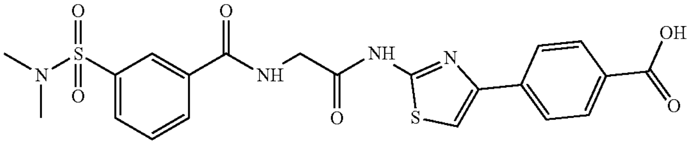 [SMILES: CN(C)S(=O)(=O)c1cccc(C(=O)NCC(=O)Nc2nc(-c3ccc(C(=O)O)cc3)cs2)c1] |
| 9 | 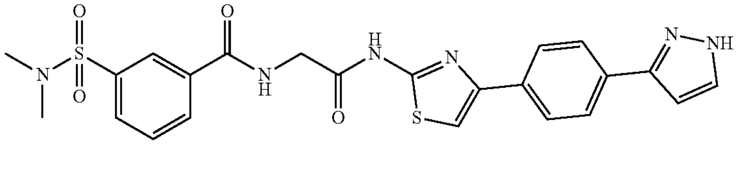 [SMILES: CN(C)S(=O)(=O)c1cccc(C(=O)NCC(=O)Nc2nc(-c3ccc(-c4cc[nH]n4)cc3)cs2)c1] |

TABLE 2a-continued

| Compounds of the invetion | |
|---|---|
| # | Compound |
| 10 | 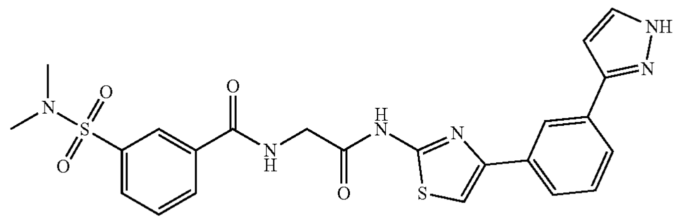 [SMILES: CN(C)S(=O)(=O)c1cccc(C(=O)NCC(=O)Nc2nc(-c3cccc(-c4cc[nH]n4)c3)cs2)c1] |
| 11 | 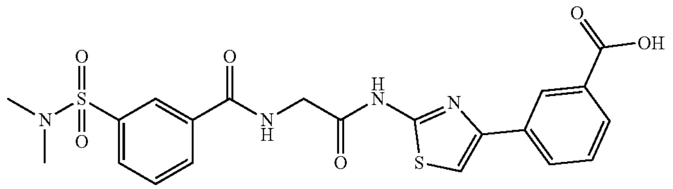 [SMILES: CN(C)S(=O)(=O)c1cccc(C(=O)NCC(=O)Nc2nc(-c3cccc(C(=O)O)c3)cs2)c1] |

TABLE 2b

| Compounds of the Invention | |
|---|---|
| # | Compound |
| 130 | 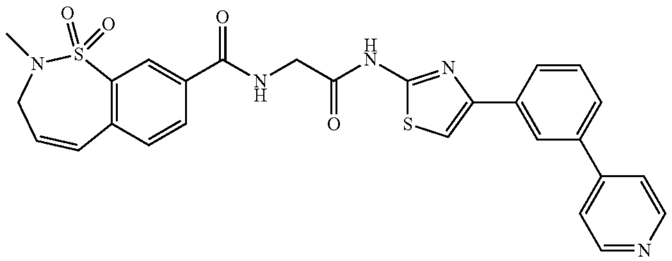 [SMILES: CN1CC=Cc2ccc(C(=O)NCC(=O)Nc3nc(-c4cccc(-c5ccncc5)c4)cs3)cc2S1(=O)=O] |
| 131 | 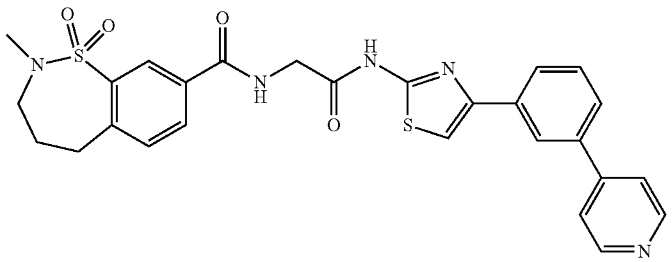 [SMILES: CN1CCCc2ccc(C(=O)NCC(=O)Nc3nc(-c4cccc(-c5ccncc5)c4)cs3)cc2S1(=O)=O] |

In an aspect, the invention features a compound having the structure:

Formula IIIa

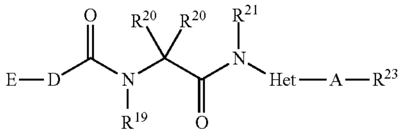

wherein E is hydrogen, hydroxy, amino, cyano, optionally substituted $C_1$-$C_6$ alkyl, optionally substituted $C_1$-$C_6$ hydroxyalkyl, optionally substituted $C_1$-$C_6$ aminoalkyl, optionally substituted silyl, optionally substituted $C_2$-$C_9$ heterocyclyl, or optionally substituted $C_3$-$C_8$ cycloalkyl;

D is optionally substituted $C_6$-$C_{10}$ aryl or optionally substituted $C_2$-$C_9$ heretoaryl;

$R^{19}$ and $R^{21}$ are, independently, hydrogen or optionally substituted $C_1$-$C_6$alkyl;

each $R^{20}$ is, independently, hydrogen, optionally substituted $C_1$-$C_6$ alkyl, or optionally substituted $C_1$-$C_6$ heteroalkyl, or two $R^{20}$ groups combine with the carbon to which they are attached to form an optionally substituted $C_3$-$C_8$ cycloalkyl;

Het is optionally substituted $C_2$-$C_9$ heteroaryl;

A is optionally substituted $C_6$-$C_{10}$ aryl or optionally substituted $C_2$-$C_9$ heteroaryl; and $R^{23}$ is, independently, hydrogen, cyano, optionally substituted $C_1$-$C_6$ alkyl, optionally substituted $C_1$-$C_6$ alkoxy, optionally substituted amide, optionally substituted $C_1$-$C_6$ heteroalkyl, optionally substituted $C_3$-$C_8$ cycloalkyl, optionally substituted $C_2$-$C_9$ heteroaryl, optionally substituted $C_2$-$C_9$ heterocyclyl, or optionally substituted $C_6$-$C_{10}$ aryl, or $R^{23}$ combines with an $R^{22}$ and the carbons to which they are attached to form an optionally substituted $C_2$-$C_9$ heterocyclyl;

or a pharmaceutically acceptable salt thereof.

In some embodiments, E is hydrogen. In some embodiments, E is hydroxy. In some embodiments, E is amino. i.e., —$NH_2$. In some embodiments, E is cyano. In some embodiments, E is optionally substituted $C_1$-$C_6$ alkyl, e.g., t-butyl. In some embodiments, E is optionally substituted $C_1$-$C_6$ hydroxyalkyl, e.g.,

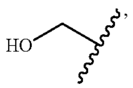,
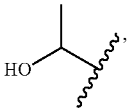,
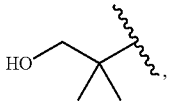, or
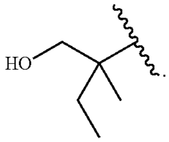.

In some embodiments, E is optionally substituted $C_1$-$C_6$ aminoalkyl, e.g.,

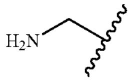 or
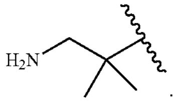.

In some embodiments, E is optionally substituted silyl, e.g., trimethylsilyl. In some embodiments, E is optionally substituted $C_2$-$C_9$ heterocyclyl, e.g.,

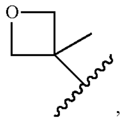,
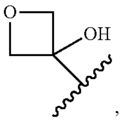,
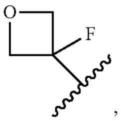,
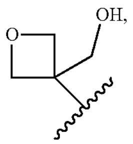
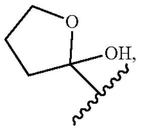 or
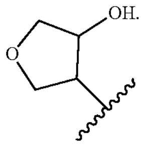

In some embodiments, E is optionally substituted $C_3$-$C_8$cycloalkyl, e.g.,

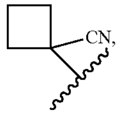
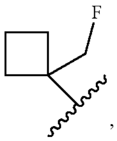,
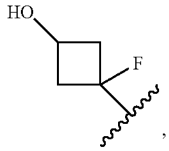, or
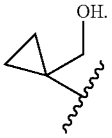

In some embodiments, D is optionally substituted $C_6$-$C_{10}$ aryl. In some embodiments, D is optionally substituted $C_6$-$C_{10}$ monocyclic aryl, e.g.,

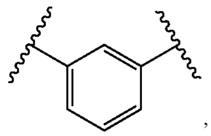,
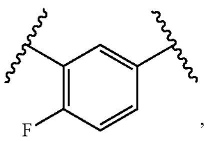,
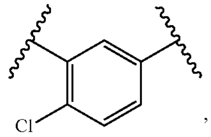,
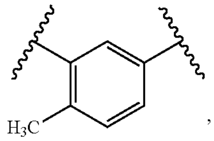, or
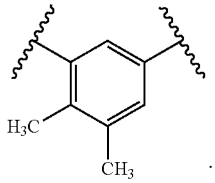.

In some embodiments, D is optionally substituted $C_6$-$C_{10}$ polycyclic aryl, e.g.,

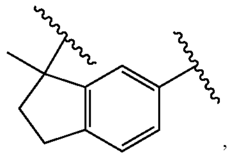,
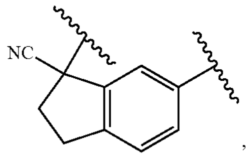,
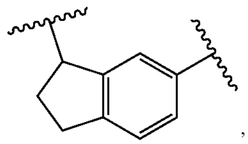,
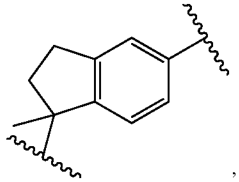,

-continued
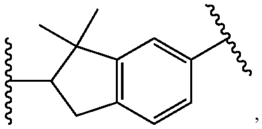
,
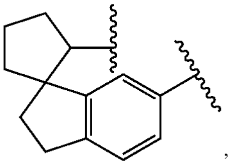
,
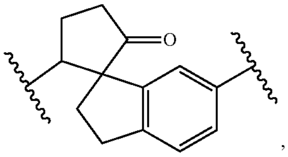
, or
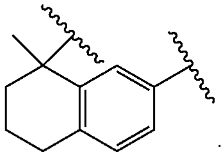
.
In some embodiments, D is optionally substituted $C_2$-$C_9$ heteroaryl. In some embodiments, D is optionally substituted $C_2$-$C_9$ monocyclic heteroaryl, e.g.,
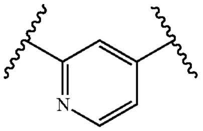
or
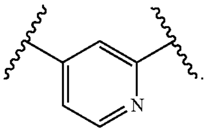
In some embodiments, D is optionally substituted $C_2$-$C_9$ polycyclic heteroaryl, e.g.,
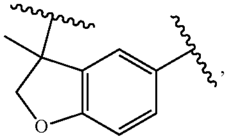
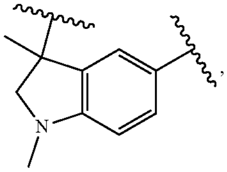
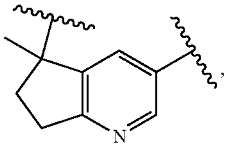
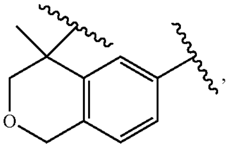
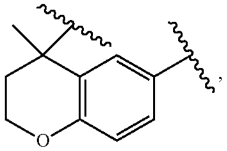
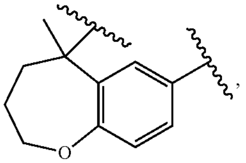
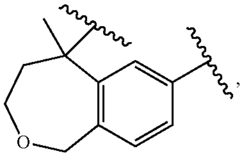
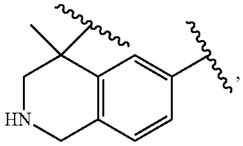
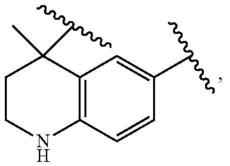
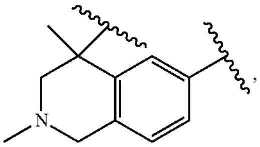
-continued
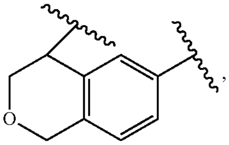
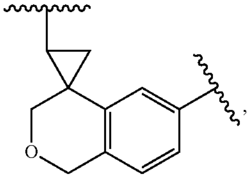
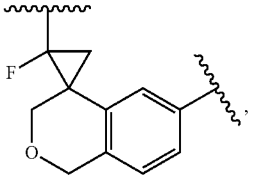
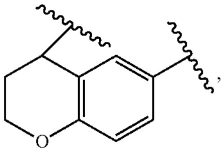
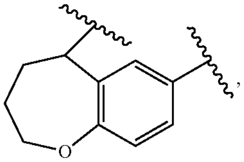
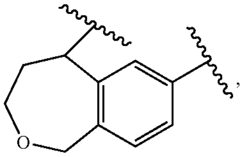
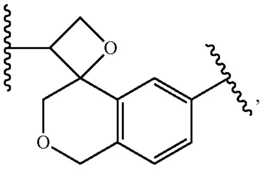
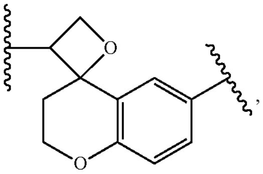
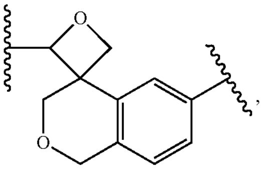
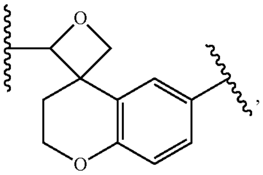
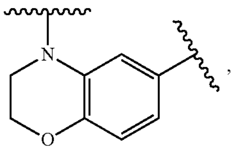
, or
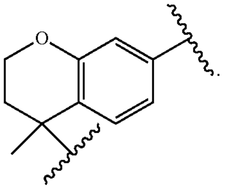

In some embodiments, Het is

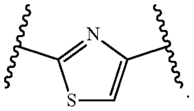 [SMILES: *c1csc(*)n1]

In some embodiments, at least one $R^{20}$ is hydrogen (preferably, both $R^{20}$ are hydrogen).

In some embodiments, the compound of formula IIIa is a compound of the following structure:

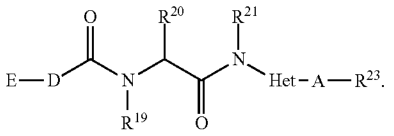

In some embodiments, $R^{20}$ is optionally substituted $C_1$-$C_6$ heteroalkyl (e.g.,

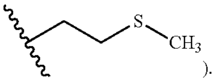

).

In some embodiments. $R^{20}$ is optionally substituted $C_1$-$C_6$ alkyl (e.g., methyl). In some embodiments, r is 0.

In some embodiments, A is optionally substituted $C_6$-$C_{10}$ aryl, e.g., or

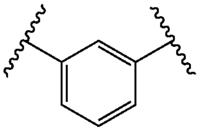

or

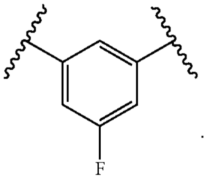

.

In some embodiments, A is optionally substituted $C_6$-$C_{10}$ heteroaryl, e.g.,

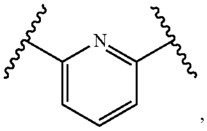

,

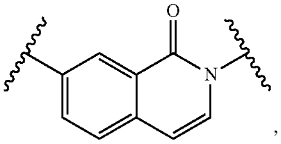

,

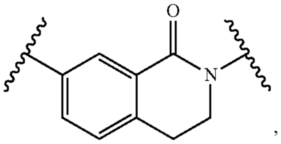

,

-continued

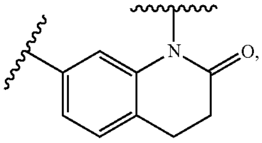

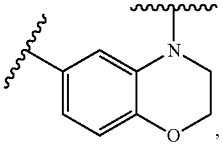

,

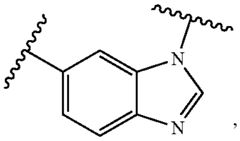

, or

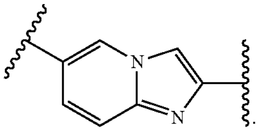

In some embodiments, $R^{23}$ is hydrogen. In some embodiments, $R^{23}$ is cyano. In some embodiments, $R^{23}$ is optionally substituted $C_1$-$C_6$ alkyl, e.g., methyl. In some embodiments, $R^{23}$ is optionally substituted $C_3$-$C_8$ cycloalkyl, e.g.,

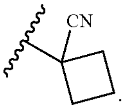 [SMILES: *C1(C#N)CCC1]

In some embodiments, $R^{23}$ is optionally substituted $C_1$-$C_6$ heteroalkyl (e.g.,

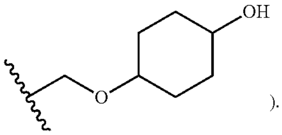 [SMILES: *COC1CCC(O)CC1]

).

In some embodiments, $R^{23}$ is optionally substituted $C_2$-$C_9$ heteroaryl (e.g.,

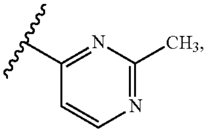

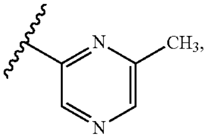

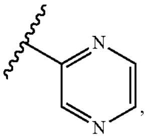

,

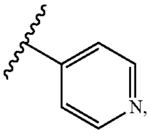

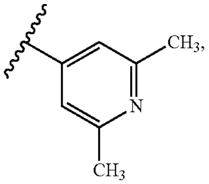

-continued

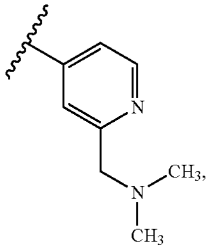 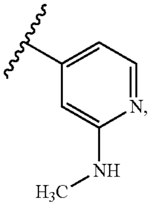
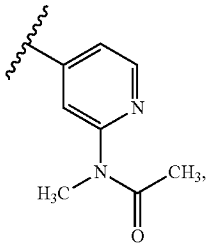 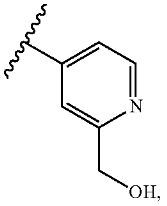
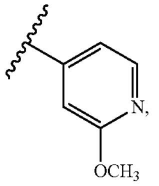 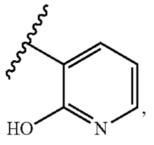
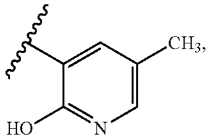 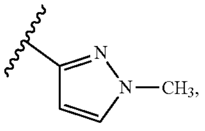
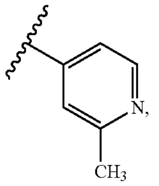 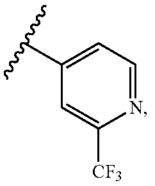 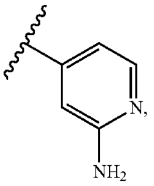
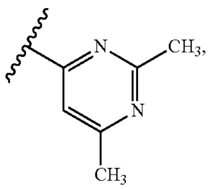 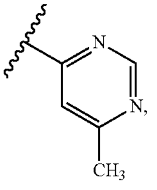
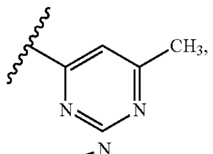 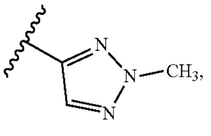 or
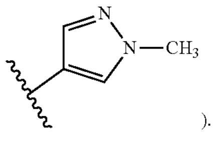
).

In some embodiments, $R^{23}$ is optionally substituted $C_2$-$C_9$ heterocyclyl (e.g.,

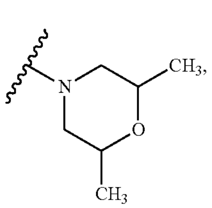 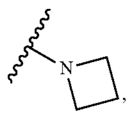 or

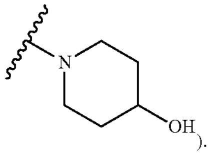).

In some embodiments, $R^{23}$ is optionally substituted $C_6$-$C_{10}$ aryl (e.g., 3,5-di-cyano-phenyl, 3-hydroxymethyl-5-trifluoromethyl-phenyl, 3-chloro-phenyl, 3-cyano-phenyl, 3,5-di-chloro-phenyl, 3-aminomethyl-phenyl or 3-hydroxymethyl-5-cyano-phenyl).

In some embodiments, r is 0. In some embodiments, $R^{23}$ combines with an $R^{22}$ and the carbons to which they are attached to form an optionally substituted $C_2$-$C_9$ heterocyclyl.

In an aspect, the invention features a compound having the structure:

Formula III

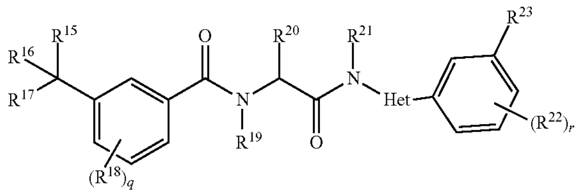

wherein q and r are, independently, 0, 1, 2, 3, or 4;

$R^{15}$ is optionally substituted $C_1$-$C_6$ alkyl or halo, or $R^{15}$ combines with $R^{17}$ and the carbon to which they are attached to form an optionally substituted $C_3$-$C_8$ cycloalkyl or optionally substituted $C_2$-$C_9$ heterocyclyl;

$R^{16}$ is optionally substituted $C_1$-$C_6$ alkyl, optionally substituted $C_1$-$C_6$ perfluoroalkyl, or $R^{16}$ combines with an $R^{18}$ and the carbons to which they are attached to form an optionally substituted $C_3$-$C_8$ cycloalkyl or optionally substituted $C_2$-$C_9$ heterocyclyl, or $R^{18}$ combines with $R^{15}$ and the carbons to which they are attached to form an optionally substituted $C_3$-$C_8$ cycloalkyl or optionally substituted $C_2$-$C_9$ heterocyclyl;

$R^{17}$ is cyano, optionally substituted amino, hydroxy, optionally substituted $C_1$-$C_6$ alkyl, optionally substituted $C_1$-$C_6$ hydroxyalkyl, optionally substituted $C_1$-$C_6$ aminoalkyl, or

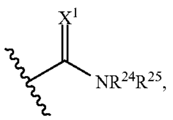

or $R^{17}$ combines with an $R^{18}$ and the carbons to which they are attached to form an optionally substituted $C_3$-$C_8$ cycloalkyl or optionally substituted $C_2$-$C_9$ heterocyclyl;

$X^1$ is O or —N—OH;

each $R^{18}$ is, independently, halo, optionally substituted $C_1$-$C_6$ alkyl, or optionally substituted $C_1$-$C_6$ heteroalkyl, or an $R^{18}$ combines with $R^{16}$ and the carbons to which they are attached to form an optionally substituted $C_3$-$C_8$ cycloalkyl or optionally substituted $C_2$-$C_9$ heterocyclyl or an $R^{18}$ combines with an $R^{17}$ and the carbons to which they are attached to form an optionally substituted $C_3$-$C_8$ cycloalkyl or optionally substituted $C_2$-$C_9$ heterocyclyl;

$R^{19}$, $R^{21}$, $R^{24}$, and $R^{25}$ are, independently, hydrogen or optionally substituted $C_1$-$C_6$ alkyl;

$R^{20}$ is hydrogen, optionally substituted $C_1$-$C_6$ alkyl, or optionally substituted $C_1$-$C_6$ heteroalkyl;

Het is optionally substituted $C_2$-$C_9$ heteroaryl; and each $R^{22}$ is, independently, hydroxy, halo, optionally substituted $C_1$-$C_6$ alkyl, or optionally substituted $C_1$-$C_6$ heteroalkyl, or an $R^{22}$ combines with $R^{22}$ and the carbons to which they are attached to form an optionally substituted $C_2$-$C_9$ heterocyclyl;

$R^{23}$ is, independently, hydrogen, cyano, optionally substituted $C_1$-$C_6$ alkoxy, optionally substituted amide, optionally substituted $C_1$-$C_6$ heteroalkyl, optionally substituted $C_2$-$C_9$ heteroaryl, optionally substituted $C_2$-$C_9$ heterocyclyl, or optionally substituted $C_6$-$C_{10}$ aryl, or $R^{23}$ combines with an $R^{22}$ and the carbons to which they are attached to form an optionally substituted $C_2$-$C_9$ heterocyclyl;

or a pharmaceutically acceptable salt thereof.

In some embodiments, r is 0 or 1. In some embodiments, $R^{19}$ is hydrogen. In some embodiments, $R^{21}$ is hydrogen.

In some embodiments, Het is

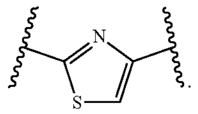 [SMILES: *c1csc(*)n1]

In some embodiments, $R^{20}$ is hydrogen. In some embodiments, $R^{20}$ is optionally substituted $C_1$-$C_6$ heteroalkyl (e.g.,

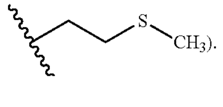

In some embodiments, $R^{20}$ is optionally substituted $C_1$-$C_6$ alkyl (e.g., methyl). In some embodiments, q is 0. In some embodiments, q is 1. In some embodiments, q is 2. In some embodiments, each $R^{18}$ is optionally substituted $C_1$-$C_6$ alkyl (e.g., methyl or ethyl). In some embodiments, an $R^{18}$ combines with $R^{18}$ and the carbons to which they are attached to form an optionally substituted $C_3$-$C_8$ cycloalkyl or optionally substituted $C_2$-$C_9$ heterocyclyl. In some embodiments, an $R^{18}$ combines with $R^{16}$ and the carbons to which they are attached to form an optionally substituted $C_3$-$C_8$ cycloalkyl.

In some embodiments, the compound has the structure:

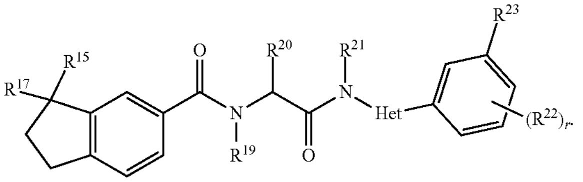

In some embodiments, an $R^{18}$ combines with $R^{16}$ and the carbons to which they are attached to form an optionally substituted $C_2$-$C_9$ heterocyclyl.

In some embodiments, the compound has the structure:

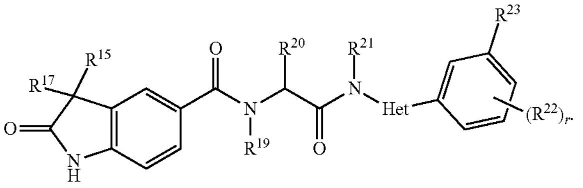

In some embodiments, the compound has the structure:

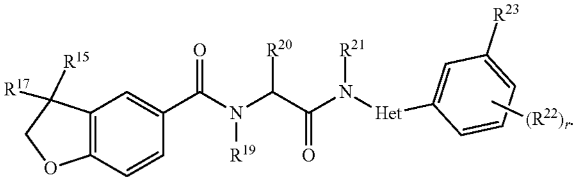

In some embodiments, the compound has the structure:

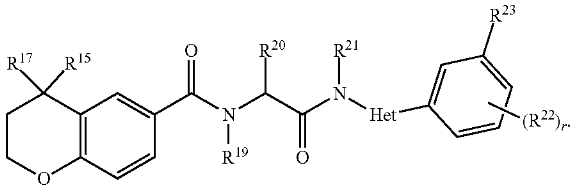

In some embodiments, an $R^{18}$ combines with $R^{17}$ and the carbons to which they are attached to form an optionally substituted $C_3$-$C_8$ cycloalkyl.

In some embodiments, the compound has the structure:

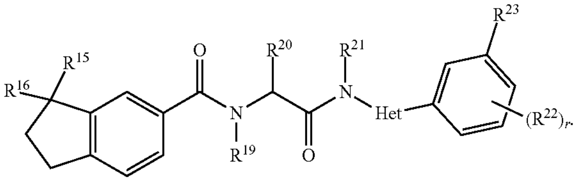

In some embodiments, $R^{10}$ is optionally substituted $C_1$-$C_6$ alkyl (e.g., methyl or ethyl). In some embodiments, $R^{16}$ is optionally substituted $C_1$-$C_6$ perfluoroalkyl (e.g., trifluoromethyl). In some embodiments, $R^{16}$ combines with $R^{15}$ and the carbons to which they are attached to form an optionally substituted $C_3$-$C_8$ cycloalkyl or optionally substituted $C_2$-$C_9$ heterocyclyl. In some embodiments, $R^{16}$ combines with $R^{15}$ and the carbons to which they are attached to form an optionally substituted $C_3$-$C_8$ cycloalkyl.

In some embodiments, the compound has the structure:

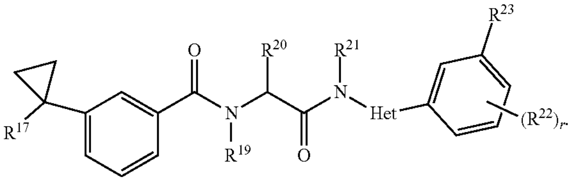

In some embodiments, $R^{16}$ combines with $R^{15}$ and the carbons to which they are attached to form an optionally substituted $C_2$-$C_9$ heterocyclyl.

In some embodiments, the compound has the structure:

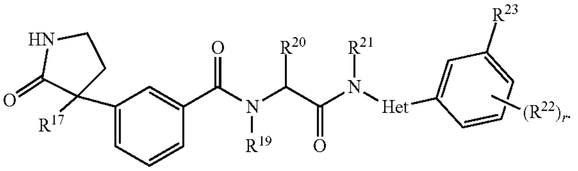

In some embodiments, the compound has the structure:

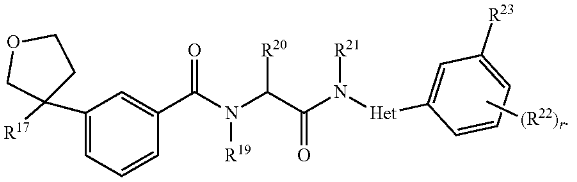

In some embodiments. $R^{15}$ is optionally substituted $C_1$-$C_6$ alkyl (e.g., methyl). In some embodiments, $R^{17}$ is cyano. In some embodiments, $R^{17}$ is optionally substituted amino (e.g., —$NH_2$). In some embodiments, $R^{17}$ is hydroxy. In some embodiments, $R^{17}$ is optionally substituted $C_1$-$C_6$ alkyl (e.g., methyl, ethyl, or iso-propyl). In some embodiments. $R^{17}$ is optionally substituted $C_1$-$C_6$ hydroxyalkyl (e.g., —$CH_2OH$). In some embodiments, $R^{17}$ is optionally substituted $C_1$-$C_6$ aminoalkyl (e.g., —$CH_2NH_2$). In some embodiments, $R^{17}$ is

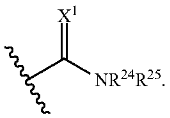

In some embodiments, $X^1$ is O. In some embodiments, $X^1$ is —N—OH.

In some embodiments, $R^{24}$ is hydrogen. In some embodiments $R^{25}$ is hydrogen. In some embodiments, $R^{23}$ is hydrogen. In some embodiments. $R^{23}$ is cyano. In some embodiments, $R^{23}$ is optionally substituted $C_1$-$C_6$ heteroalkyl (e.g.,

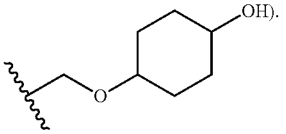

In some embodiments, $R^{23}$ is optionally substituted $C_2$-$C_9$ heteroaryl (e.g.,

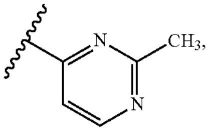

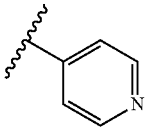
,

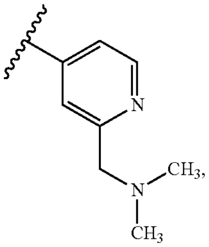

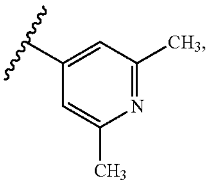

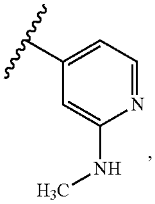
,

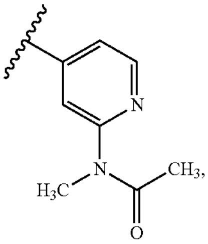

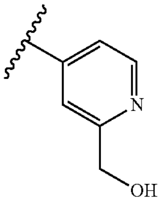
,

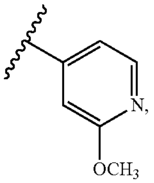

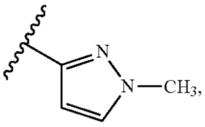

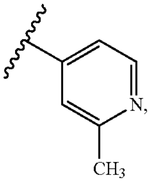

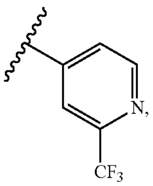

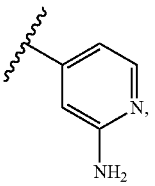

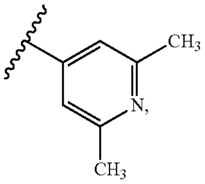

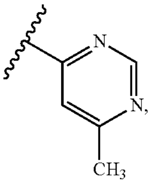
or

-continued

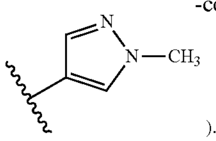

).

In some embodiments, $R^{23}$ is optionally substituted $C_2$-$C_9$ heterocyclyl (e.g.,

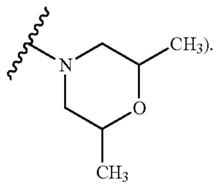

In some embodiments, $R^{23}$ is optionally substituted $C_6$-$C_{10}$ aryl (e.g., 3,5-di-cyano-phenyl, 3-hydroxymethyl-5-trifluoromethyl-phenyl, 3-chloro-phenyl, 3-cyano-phenyl, 3,5-di-chloro-phenyl, or 3-hydroxymethyl-5-cyano-phenyl).

In some embodiments, r is 0. In some embodiments, $R^{23}$ combines with an $R^{22}$ and the carbons to which they are attached to form an optionally substituted $C_2$-$C_9$ heterocyclyl.

In some embodiments the compound has the structure:

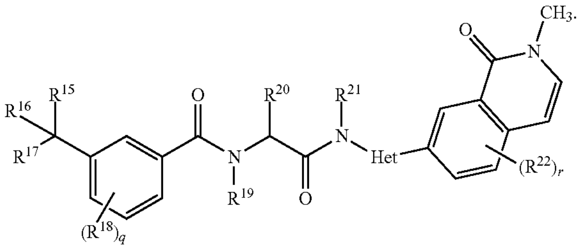

In some embodiments, the compound is any one of compounds 48-109 in Table 3a. In some embodiments, the compound is any one of compounds 132-268 in Table 3b. In some embodiments, the compound is any one of compounds 269-444 in Table 3c.

TABLE 3a

| Compounds of the invention | |
|---|---|
| # | Compound |
| 48 | 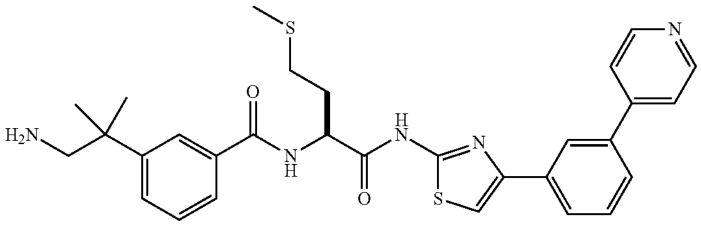 [SMILES: CSCC[C@H](NC(=O)c1cccc(C(C)(C)CN)c1)C(=O)Nc1nc(-c2cccc(-c3ccncc3)c2)cs1] |
| 49 | 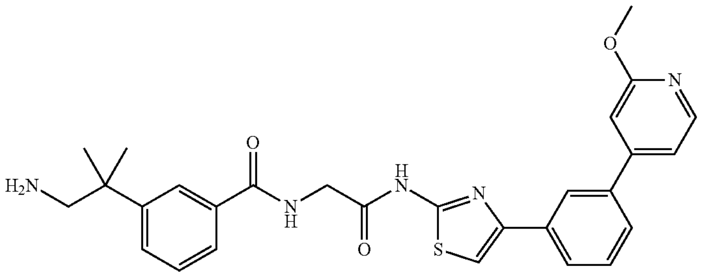 [SMILES: COc1cc(-c2cccc(-c3csc(NC(=O)CNC(=O)c4cccc(C(C)(C)CN)c4)n3)c2)ccn1] |
| 50 | 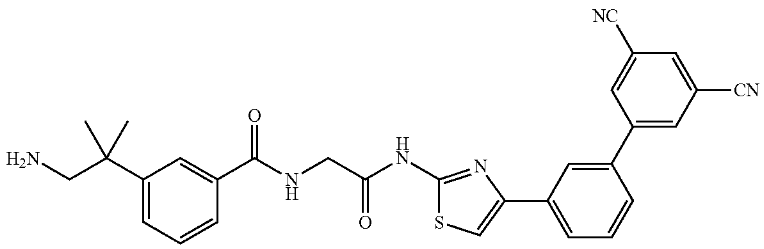 [SMILES: CC(C)(CN)c1cccc(C(=O)NCC(=O)Nc2nc(-c3cccc(-c4cc(C#N)cc(C#N)c4)c3)cs2)c1] |

TABLE 3a-continued
| Compounds of the invention | |
|---|---|
| # | Compound |
| 51 | 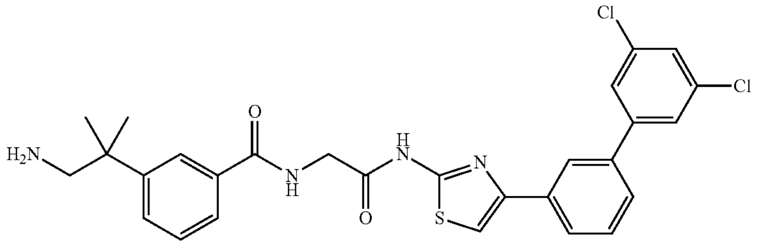 [SMILES: CC(C)(CN)c1cccc(C(=O)NCC(=O)Nc2nc(-c3cccc(-c4cc(Cl)cc(Cl)c4)c3)cs2)c1] |
| 52 | 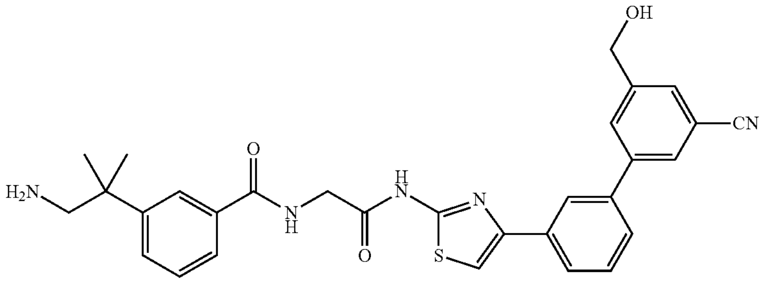 [SMILES: CC(C)(CN)c1cccc(C(=O)NCC(=O)Nc2nc(-c3cccc(-c4cc(C#N)cc(CO)c4)c3)cs2)c1] |
| 53 | 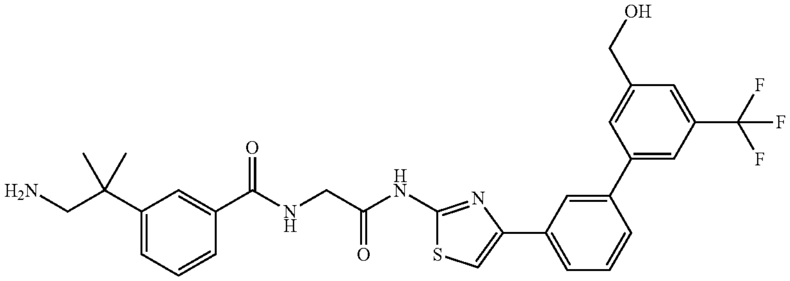 [SMILES: CC(C)(CN)c1cccc(C(=O)NCC(=O)Nc2nc(-c3cccc(-c4cc(CO)cc(C(F)(F)F)c4)c3)cs2)c1] |
| 54 | 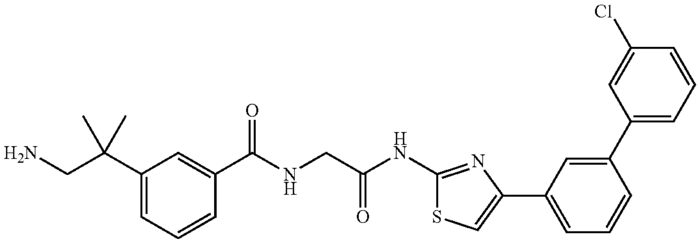 [SMILES: CC(C)(CN)c1cccc(C(=O)NCC(=O)Nc2nc(-c3cccc(-c4cccc(C#N)c4)c3)cs2)c1] |
| 55 | 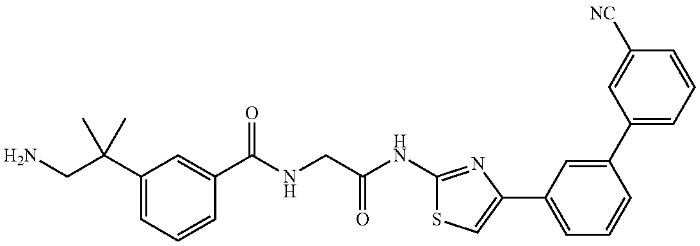 |

TABLE 3a-continued
| Compounds of the invention | |
|---|---|
| # | Compound |
| 56 | 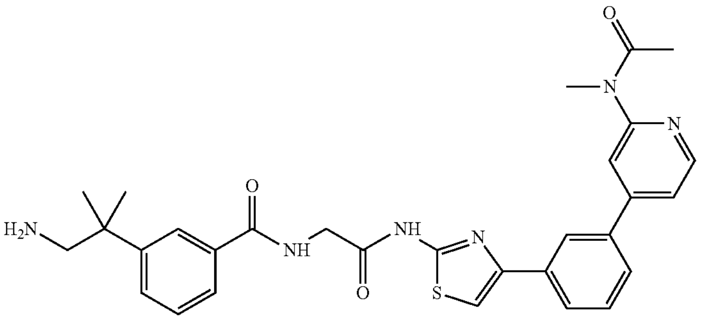 [SMILES: CC(=O)N(C)c1cc(-c2cccc(-c3csc(NC(=O)CNC(=O)c4cccc(C(C)(C)CN)c4)n3)c2)ccn1] |
| 57 | 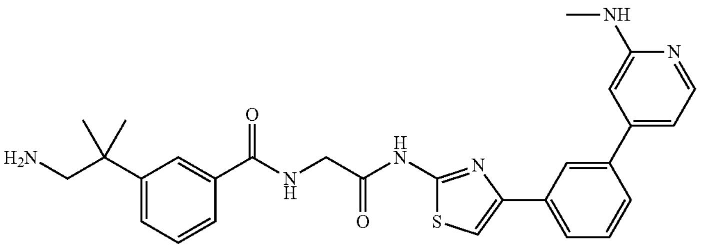 [SMILES: CNc1cc(-c2cccc(-c3csc(NC(=O)CNC(=O)c4cccc(C(C)(C)CN)c4)n3)c2)ccn1] |
| 58 | 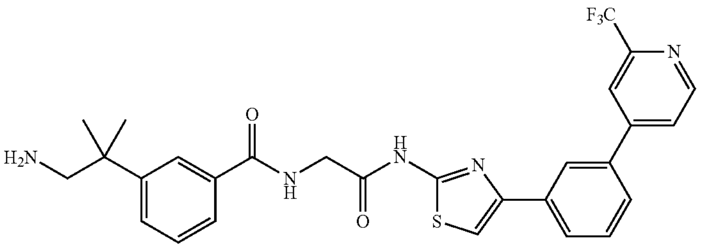 [SMILES: CC(C)(CN)c1cccc(C(=O)NCC(=O)Nc2nc(-c3cccc(-c4ccnc(C(F)(F)F)c4)c3)cs2)c1] |
| 59 | 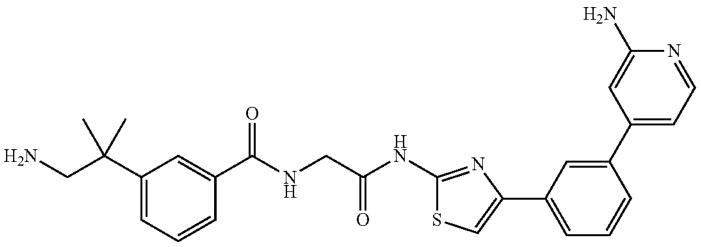 [SMILES: CC(C)(CN)c1cccc(C(=O)NCC(=O)Nc2nc(-c3cccc(-c4ccnc(N)c4)c3)cs2)c1] |
| 60 | 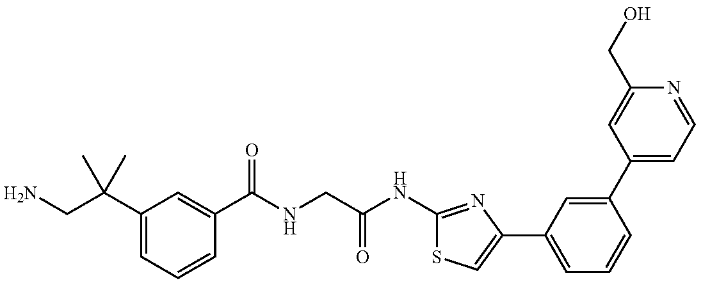 [SMILES: CC(C)(CN)c1cccc(C(=O)NCC(=O)Nc2nc(-c3cccc(-c4ccnc(CO)c4)c3)cs2)c1] |

TABLE 3a-continued
| Compounds of the invention | |
|---|---|
| # | Compound |
| 61 | 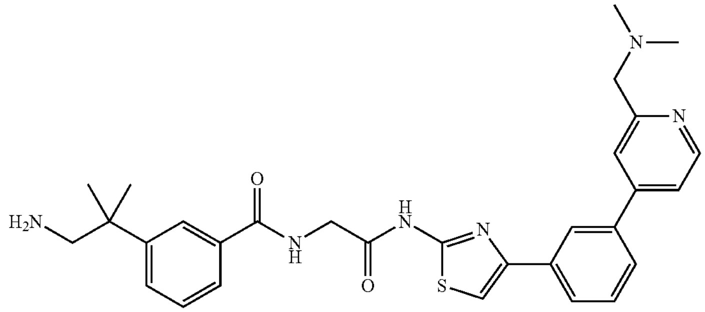 [SMILES: CN(C)Cc1cc(-c2cccc(-c3csc(NC(=O)CNC(=O)c4cccc(C(C)(C)CN)c4)n3)c2)ccn1] |
| 62 | 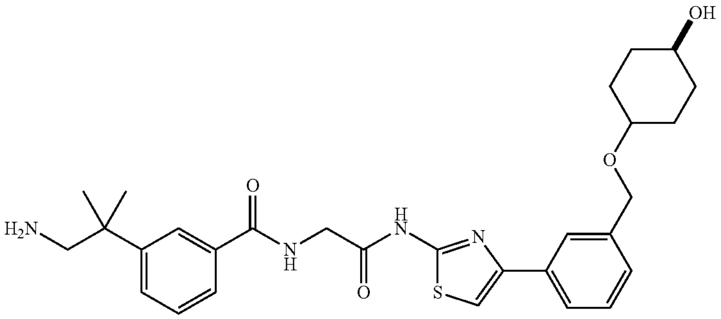 |
| 63 | 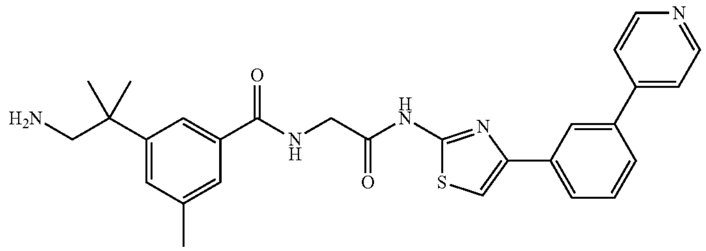 [SMILES: Cc1cc(C(=O)NCC(=O)Nc2nc(-c3cccc(-c4ccncc4)c3)cs2)cc(C(C)(C)CN)c1] |
| 64 | 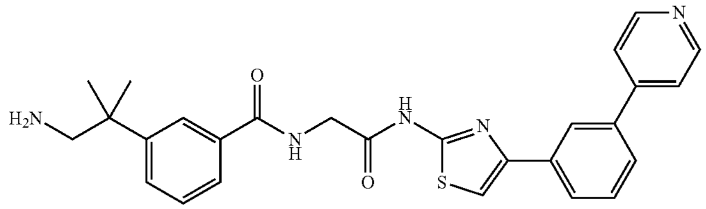 [SMILES: CC(C)(CN)c1cccc(C(=O)NCC(=O)Nc2nc(-c3cccc(-c4ccncc4)c3)cs2)c1] |
| 65 | 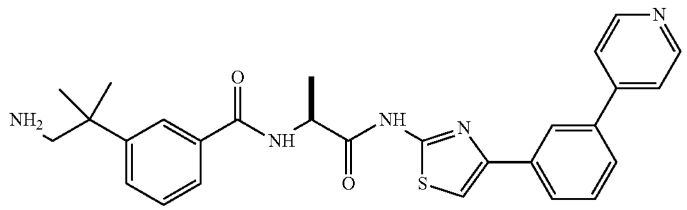 [SMILES: C[C@H](NC(=O)c1cccc(C(C)(C)CN)c1)C(=O)Nc1nc(-c2cccc(-c3ccncc3)c2)cs1] |

TABLE 3a-continued
| Compounds of the invention | |
|---|---|
| # | Compound |
| 66 | 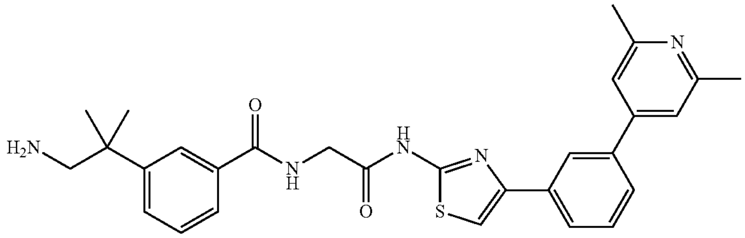 [SMILES: Cc1cc(-c2cccc(-c3csc(NC(=O)CNC(=O)c4cccc(C(C)(C)CN)c4)n3)c2)cc(C)n1] |
| 67 | 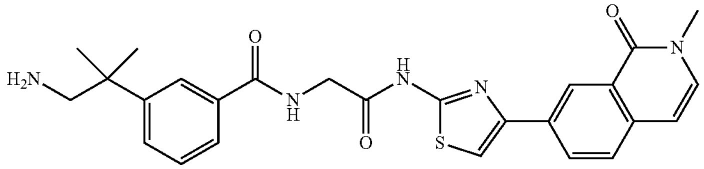 [SMILES: Cn1ccc2ccc(-c3csc(NC(=O)CNC(=O)c4cccc(C(C)(C)CN)c4)n3)cc2c1=O] |
| 68 | 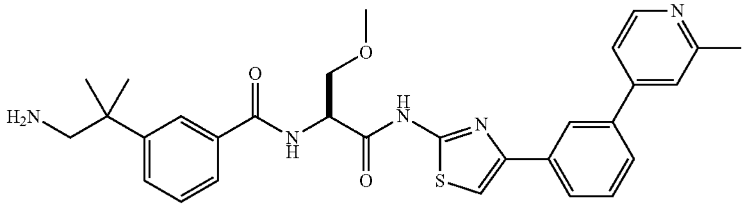 [SMILES: COC[C@H](NC(=O)c1cccc(C(C)(C)CN)c1)C(=O)Nc1nc(-c2cccc(-c3ccnc(C)c3)c2)cs1] |
| 69 | 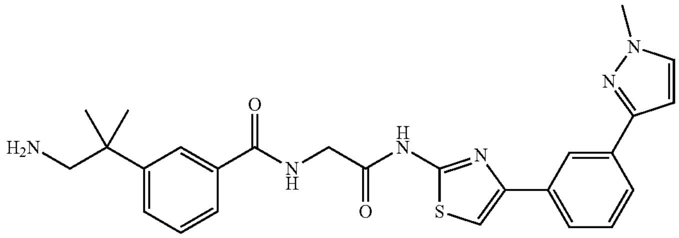 [SMILES: Cn1ccc(-c2cccc(-c3csc(NC(=O)CNC(=O)c4cccc(C(C)(C)CN)c4)n3)c2)n1] |
| 70 | 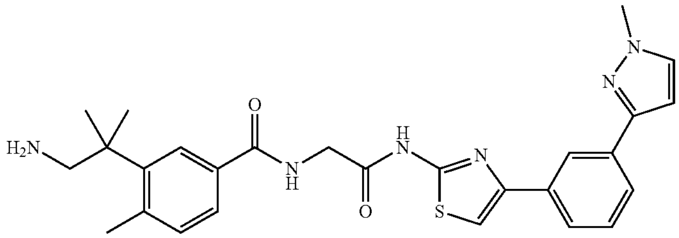 [SMILES: Cc1ccc(C(=O)NCC(=O)Nc2nc(-c3cccc(-c4ccn(C)n4)c3)cs2)cc1C(C)(C)CN] |
| 71 | 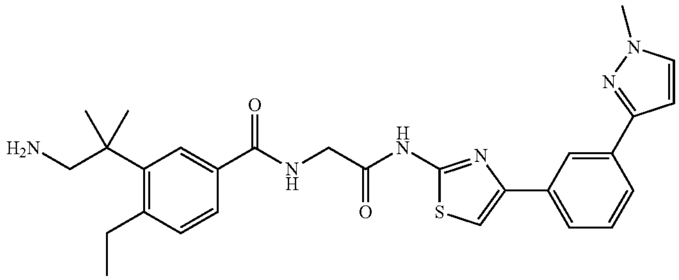 [SMILES: CCc1ccc(C(=O)NCC(=O)Nc2nc(-c3cccc(-c4ccn(C)n4)c3)cs2)cc1C(C)(C)CN] |

TABLE 3a-continued
| Compounds of the invention | |
|---|---|
| # | Compound |
| 72 | 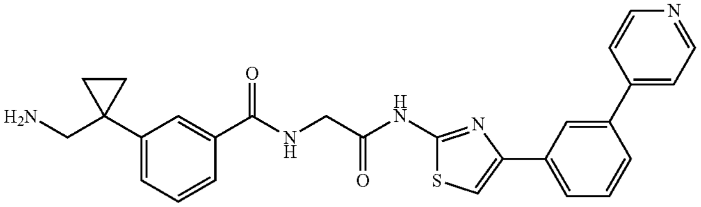 [SMILES: NCC1(c2cccc(C(=O)NCC(=O)Nc3nc(-c4cccc(-c5ccncc5)c4)cs3)c2)CC1] |
| 73 | 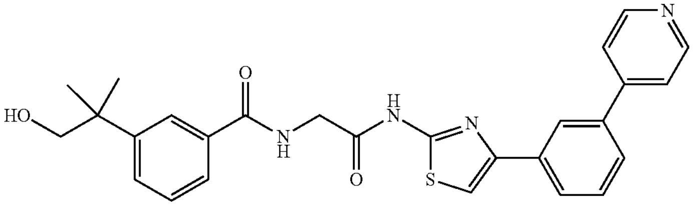 [SMILES: CC(C)(CO)c1cccc(C(=O)NCC(=O)Nc2nc(-c3cccc(-c4ccncc4)c3)cs2)c1] |
| 74 | 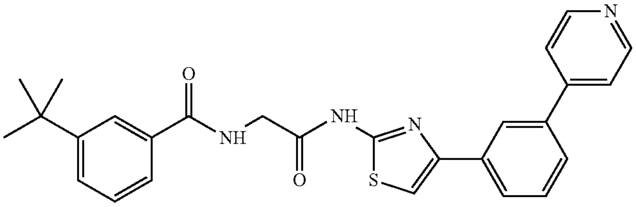 [SMILES: CC(C)(C)c1cccc(C(=O)NCC(=O)Nc2nc(-c3cccc(-c4ccncc4)c3)cs2)c1] |
| 75 | 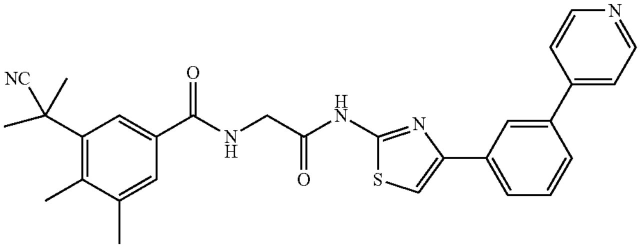 [SMILES: Cc1cc(C(=O)NCC(=O)Nc2nc(-c3cccc(-c4ccncc4)c3)cs2)cc(C(C)(C)C#N)c1C] |
| 76 | 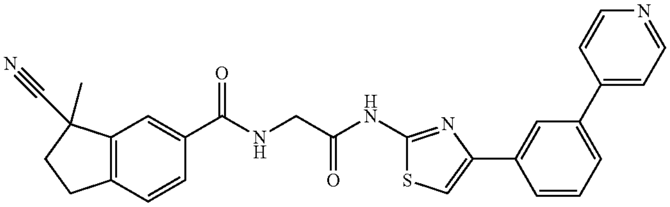 [SMILES: CC1(C#N)CCc2ccc(C(=O)NCC(=O)Nc3nc(-c4cccc(-c5ccncc5)c4)cs3)cc21] |
| 77 | 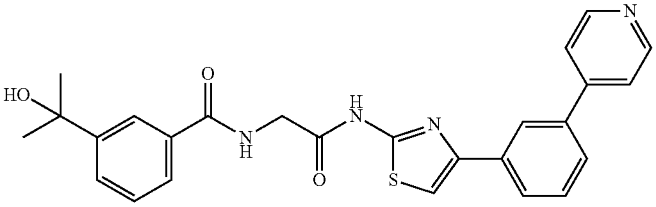 [SMILES: CC(C)(O)c1cccc(C(=O)NCC(=O)Nc2nc(-c3cccc(-c4ccncc4)c3)cs2)c1] |
| 78 | 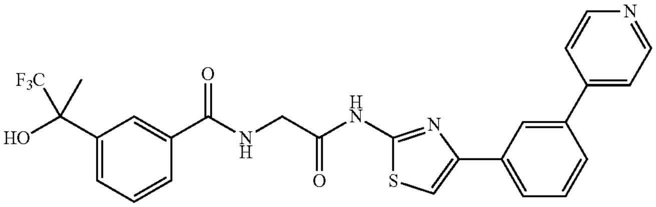 [SMILES: CC(O)(c1cccc(C(=O)NCC(=O)Nc2nc(-c3cccc(-c4ccncc4)c3)cs2)c1)C(F)(F)F] |

TABLE 3a-continued
| Compounds of the invention | |
|---|---|
| # | Compound |
| 79 | 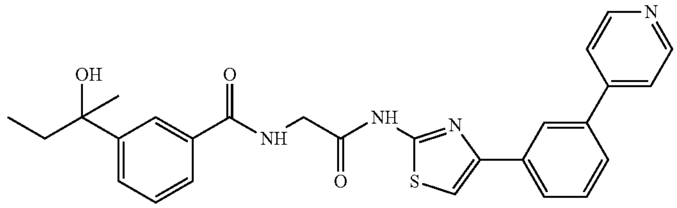 [SMILES: CCC(C)(O)c1cccc(C(=O)NCC(=O)Nc2nc(-c3cccc(-c4ccncc4)c3)cs2)c1] |
| 80 | 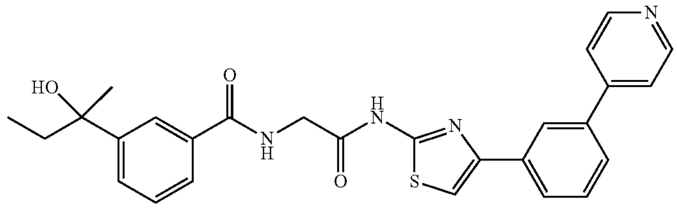 [SMILES: CCC(C)(O)c1cccc(C(=O)NCC(=O)Nc2nc(-c3cccc(-c4ccncc4)c3)cs2)c1] Enantiomer-1 |
| 81 | 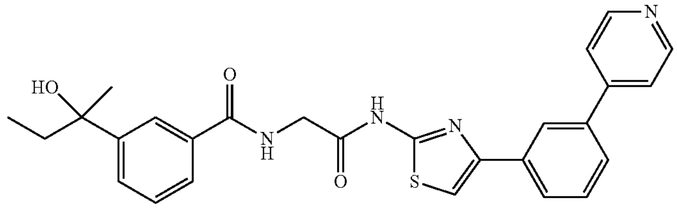 [SMILES: CCC(C)(O)c1cccc(C(=O)NCC(=O)Nc2nc(-c3cccc(-c4ccncc4)c3)cs2)c1] Enantiomer-2 |
| 82 | 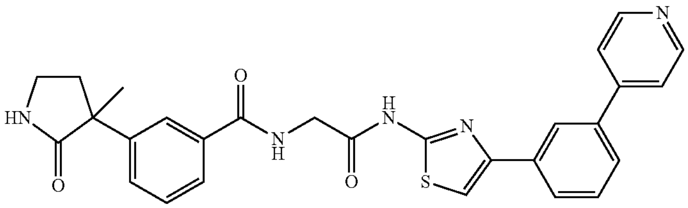 [SMILES: CC1(c2cccc(C(=O)NCC(=O)Nc3nc(-c4cccc(-c5ccncc5)c4)cs3)c2)CCNC1=O] |
| 83 | 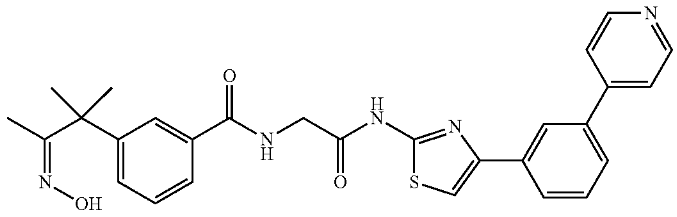 [SMILES: C/C(=N/O)C(C)(C)c1cccc(C(=O)NCC(=O)Nc2nc(-c3cccc(-c4ccncc4)c3)cs2)c1] |
| 84 | 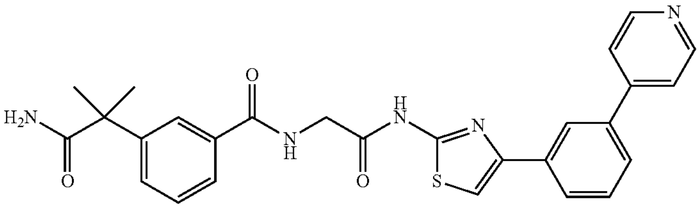 [SMILES: CC(C)(C(N)=O)c1cccc(C(=O)NCC(=O)Nc2nc(-c3cccc(-c4ccncc4)c3)cs2)c1] |

TABLE 3a-continued
| Compounds of the invention | |
|---|---|
| # | Compound |
| 85 | 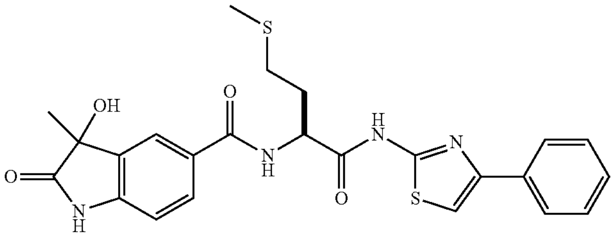 [SMILES: CSCC[C@H](NC(=O)c1ccc2c(c1)C(C)(O)C(=O)N2)C(=O)Nc1nc(-c2ccccc2)cs1] |
| 86 | 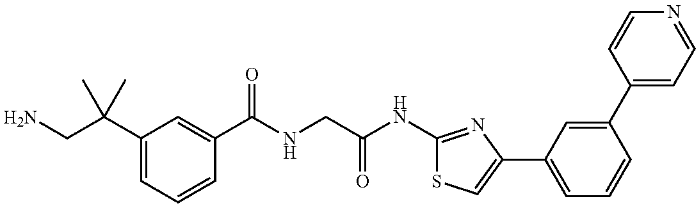 [SMILES: CC(C)(CN)c1cccc(C(=O)NCC(=O)Nc2nc(-c3cccc(-c4ccncc4)c3)cs2)c1] |
| 87 | 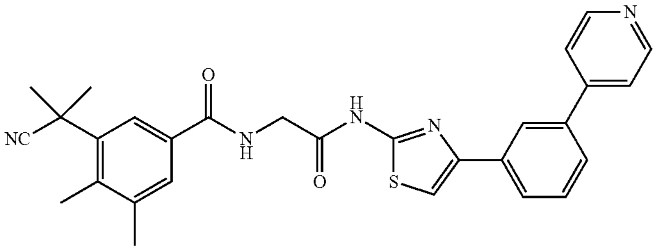 [SMILES: Cc1cc(C(=O)NCC(=O)Nc2nc(-c3cccc(-c4ccncc4)c3)cs2)cc(C(C)(C)C#N)c1C] |
| 88 | 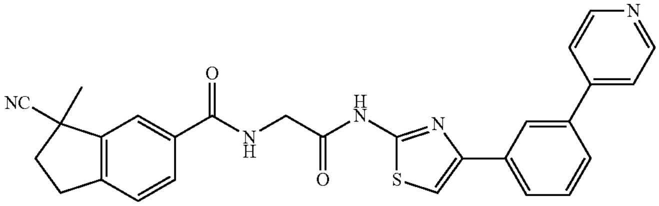 [SMILES: CC1(C#N)CCc2ccc(C(=O)NCC(=O)Nc3nc(-c4cccc(-c5ccncc5)c4)cs3)cc21] Enantiomer-1 |
| 89 | 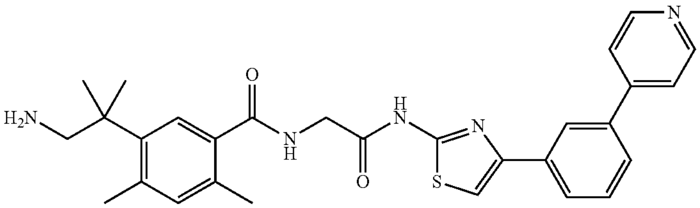 [SMILES: Cc1cc(C)c(C(C)(C)CN)cc1C(=O)NCC(=O)Nc1nc(-c2cccc(-c3ccncc3)c2)cs1] |
| 90 | 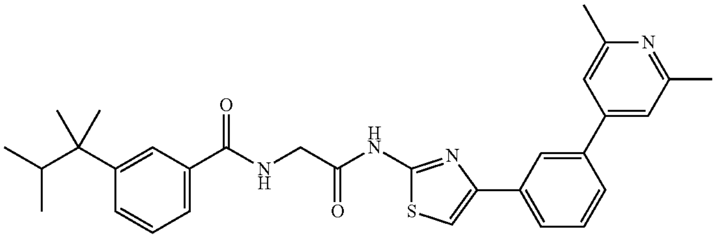 [SMILES: Cc1cc(-c2cccc(-c3csc(NC(=O)CNC(=O)c4cccc(C(C)(C)C(C)C)c4)n3)c2)cc(C)n1] |

TABLE 3a-continued
| Compounds of the invention | |
|---|---|
| # | Compound |
| 91 | 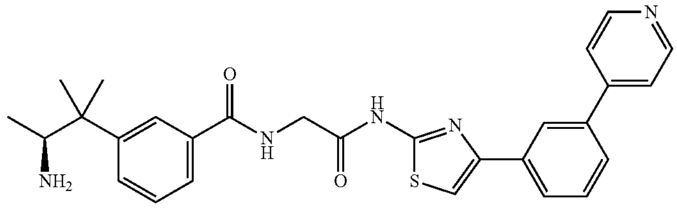 [SMILES: C[C@H](N)C(C)(C)c1cccc(C(=O)NCC(=O)Nc2nc(-c3cccc(-c4ccncc4)c3)cs2)c1] |
| 92 | 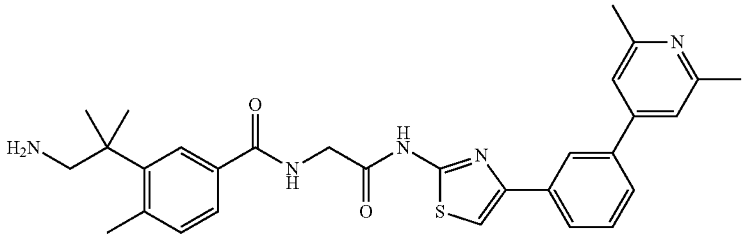 [SMILES: Cc1cc(-c2cccc(-c3csc(NC(=O)CNC(=O)c4ccc(C)c(C(C)(C)CN)c4)n3)c2)cc(C)n1] |
| 93 | 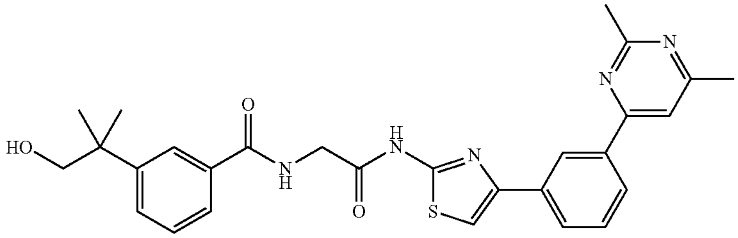 [SMILES: Cc1cc(-c2cccc(-c3csc(NC(=O)CNC(=O)c4cccc(C(C)(C)CO)c4)n3)c2)nc(C)n1] |
| 94 | 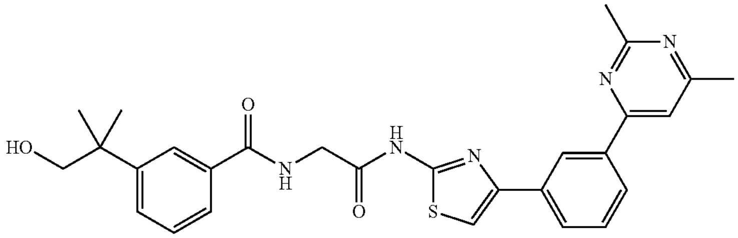 [SMILES: Cc1cc(-c2cccc(-c3csc(NC(=O)CNC(=O)c4cccc(C(C)(C)CO)c4)n3)c2)nc(C)n1] |
| 95 | 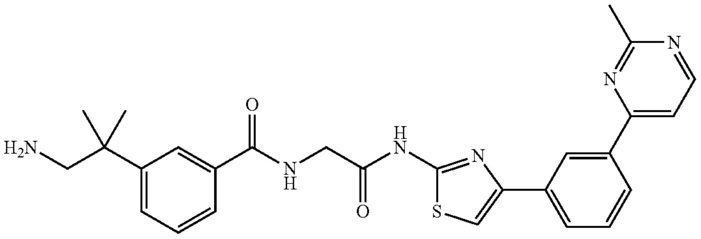 [SMILES: Cc1nccc(-c2cccc(-c3csc(NC(=O)CNC(=O)c4cccc(C(C)(C)CN)c4)n3)c2)n1] |
| 96 | 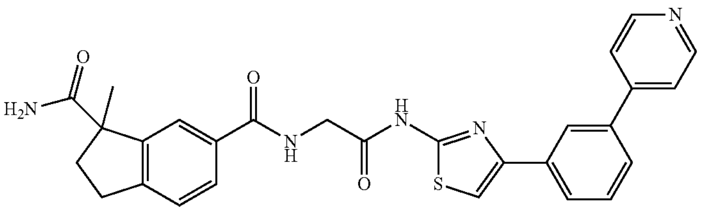 [SMILES: CC1(C(N)=O)CCc2ccc(C(=O)NCC(=O)Nc3nc(-c4cccc(-c5ccncc5)c4)cs3)cc21] |

TABLE 3a-continued
| Compounds of the invention | |
|---|---|
| # | Compound |
| 97 | 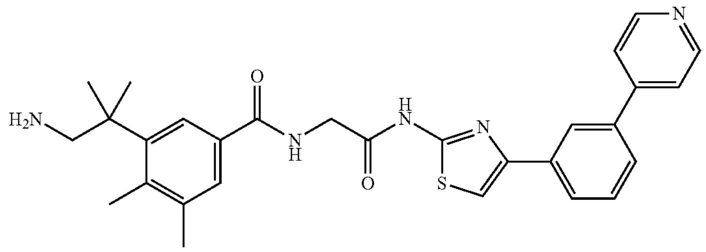 [SMILES: Cc1cc(C(=O)NCC(=O)Nc2nc(-c3cccc(-c4ccncc4)c3)cs2)cc(C(C)(C)CN)c1C] |
| 98 | 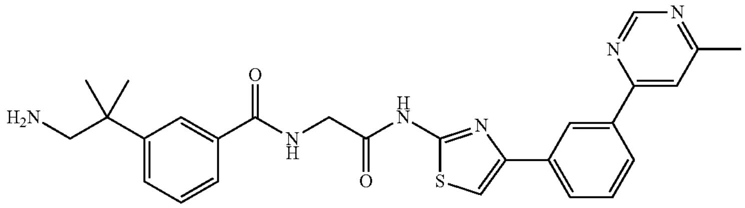 [SMILES: Cc1cc(-c2cccc(-c3csc(NC(=O)CNC(=O)c4cccc(C(C)(C)CN)c4)n3)c2)ncn1] |
| 99 | 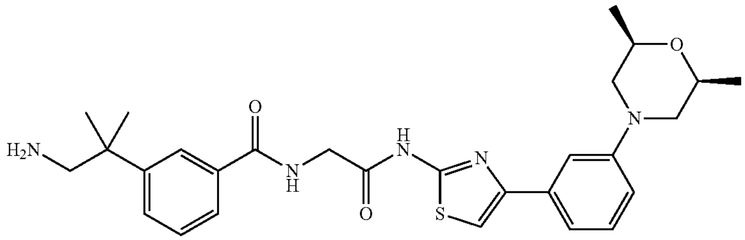 [SMILES: C[C@@H]1CN(c2cccc(-c3csc(NC(=O)CNC(=O)c4cccc(C(C)(C)CN)c4)n3)c2)C[C@H](C)O1] |
| 100 | 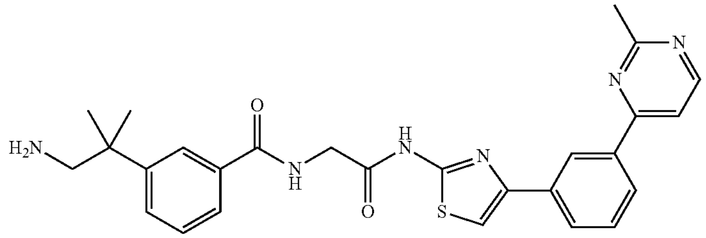 [SMILES: Cc1nccc(-c2cccc(-c3csc(NC(=O)CNC(=O)c4cccc(C(C)(C)CN)c4)n3)c2)n1] |
| 101 | 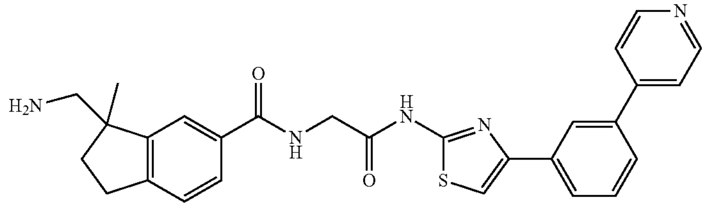 [SMILES: CC1(CN)CCc2ccc(C(=O)NCC(=O)Nc3nc(-c4cccc(-c5ccncc5)c4)cs3)cc21] |
| 102 | 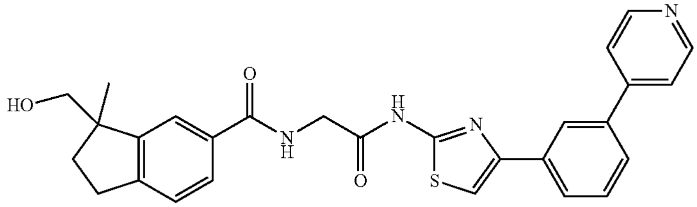 [SMILES: CC1(CO)CCc2ccc(C(=O)NCC(=O)Nc3nc(-c4cccc(-c5ccncc5)c4)cs3)cc21] |

TABLE 3a-continued
| Compounds of the invention | |
|---|---|
| # | Compound |
| 103 | 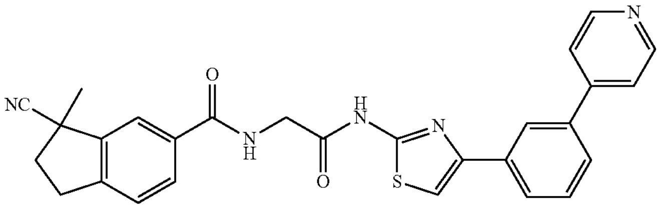 [SMILES: CC1(C#N)CCc2ccc(C(=O)NCC(=O)Nc3nc(-c4cccc(-c5ccncc5)c4)cs3)cc21] Enantiomer-2 |
| 104 | 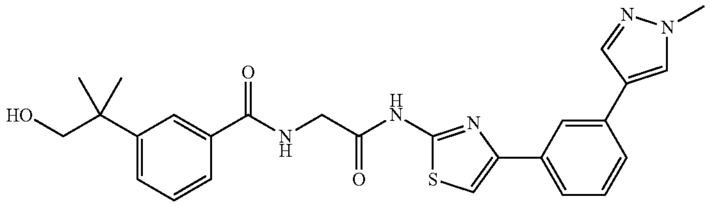 [SMILES: Cn1cc(-c2cccc(-c3csc(NC(=O)CNC(=O)c4cccc(C(C)(C)CO)c4)n3)c2)cn1] |
| 105 | 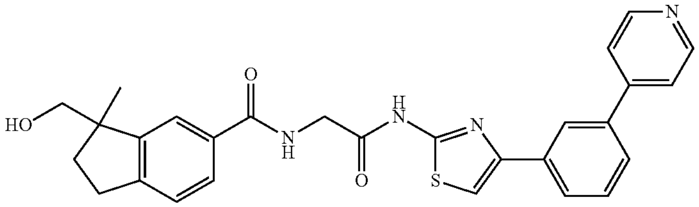 [SMILES: CC1(CO)CCc2ccc(C(=O)NCC(=O)Nc3nc(-c4cccc(-c5ccncc5)c4)cs3)cc21] Enantiomer-1 |
| 106 | 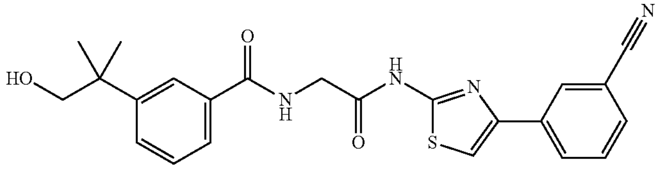 [SMILES: CC(C)(CO)c1cccc(C(=O)NCC(=O)Nc2nc(-c3cccc(C#N)c3)cs2)c1] |
| 107 | 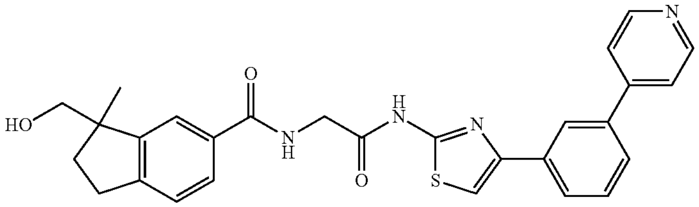 [SMILES: CC1(CO)CCc2ccc(C(=O)NCC(=O)Nc3nc(-c4cccc(-c5ccncc5)c4)cs3)cc21] Enantiomer-2 |
| 108 | 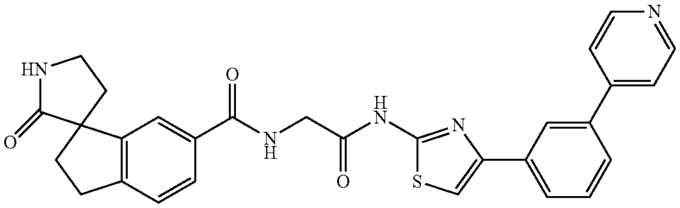 [SMILES: O=C(CNC(=O)c1ccc2c(c1)C1(CCNC1=O)CC2)Nc1nc(-c2cccc(-c3ccncc3)c2)cs1] |

TABLE 3a-continued
| Compounds of the invention | |
|---|---|
| # | Compound |
| 109 | 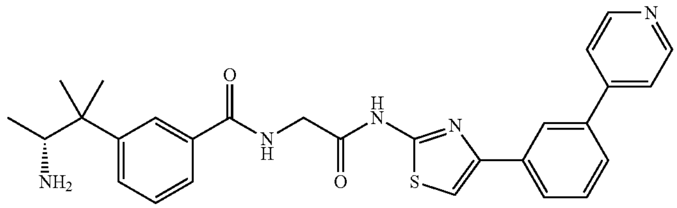 [SMILES: C[C@@H](N)C(C)(C)c1cccc(C(=O)NCC(=O)Nc2nc(-c3cccc(-c4ccncc4)c3)cs2)c1] |
TABLE 3b
| Compounds of the Invention | |
|---|---|
| # | Compound |
| 132 | 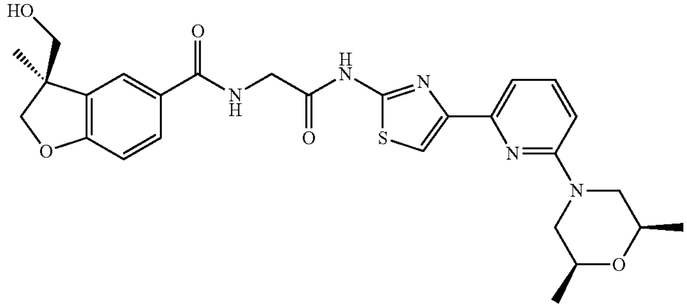 |
| 133 | 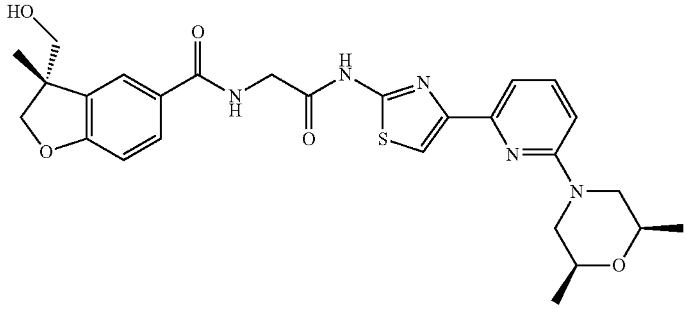 |
| 134 | 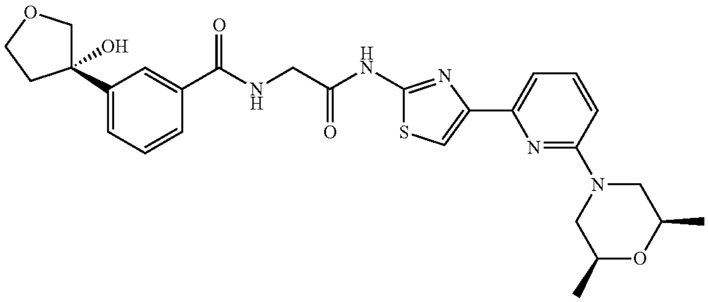 [SMILES: C[C@@H]1CN(c2cccc(-c3csc(NC(=O)CNC(=O)c4cccc([C@@]5(O)CCOC5)c4)n3)n2)C[C@H](C)O1] |

TABLE 3b-continued
| Compounds of the Invention | |
|---|---|
| # | Compound |
| 135 | 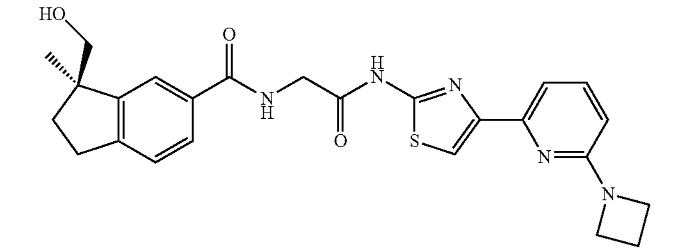 [SMILES: C[C@@]1(CO)CCc2ccc(C(=O)NCC(=O)Nc3nc(-c4cccc(N5CCC5)n4)cs3)cc21] |
| 136 | 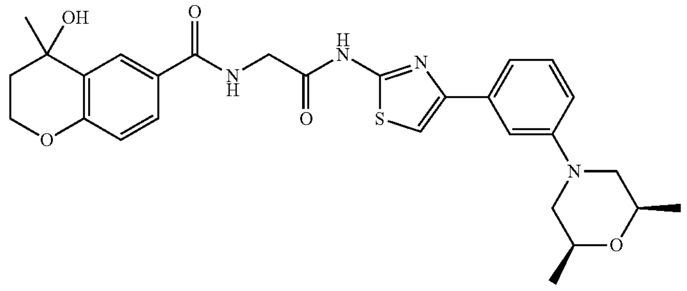 [SMILES: C[C@@H]1CN(c2cccc(-c3csc(NC(=O)CNC(=O)c4ccc5c(c4)C(C)(O)CCO5)n3)c2)C[C@H](C)O1] |
| 137 | 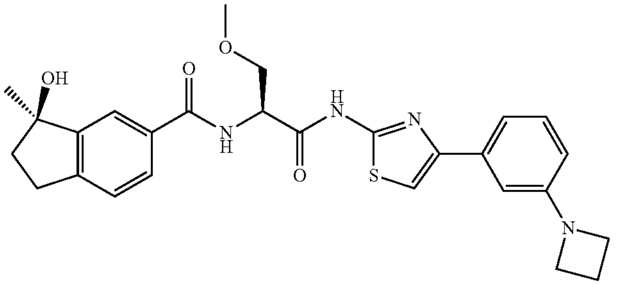 [SMILES: COC[C@H](NC(=O)c1ccc2c(c1)[C@](C)(O)CC2)C(=O)Nc1nc(-c2cccc(N3CCC3)c2)cs1] |
| 138 | 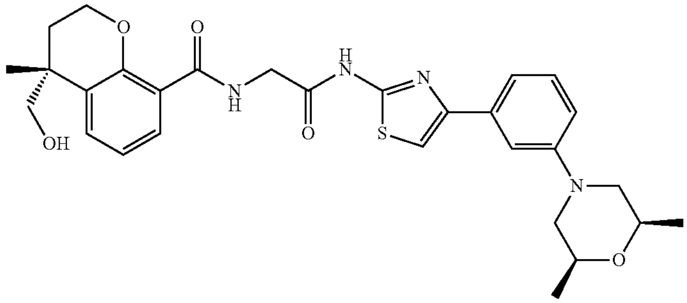 |
| 139 | 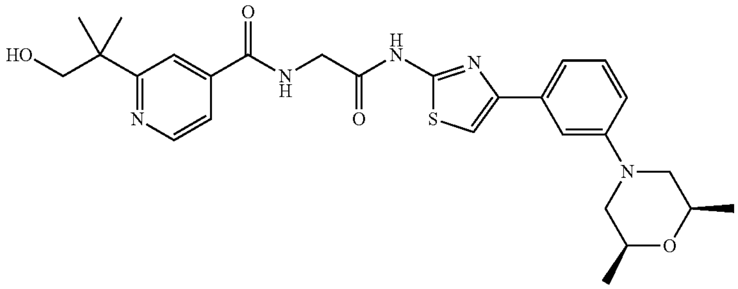 [SMILES: C[C@@H]1CN(c2cccc(-c3csc(NC(=O)CNC(=O)c4ccnc(C(C)(C)CO)c4)n3)c2)C[C@H](C)O1] |

TABLE 3b-continued
| Compounds of the Invention | |
|---|---|
| # | Compound |
| 140 | 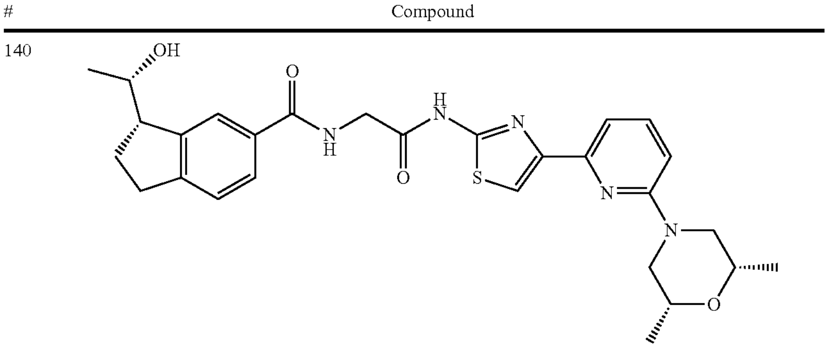 |
| 141 | 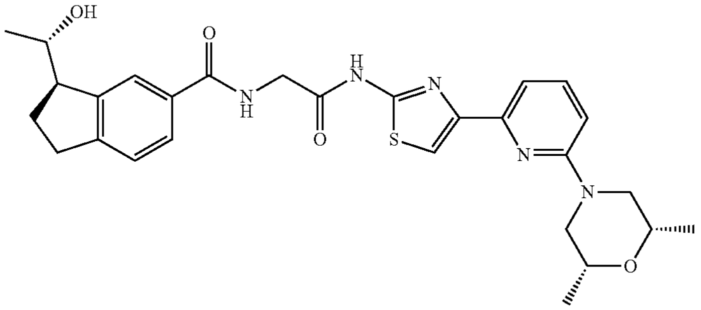 [SMILES: C[C@@H]1CN(c2cccc(-c3csc(NC(=O)CNC(=O)c4ccc5c(c4)[C@H]([C@H](C)O)CC5)n3)n2)C[C@H](C)O1] |
| 142 | 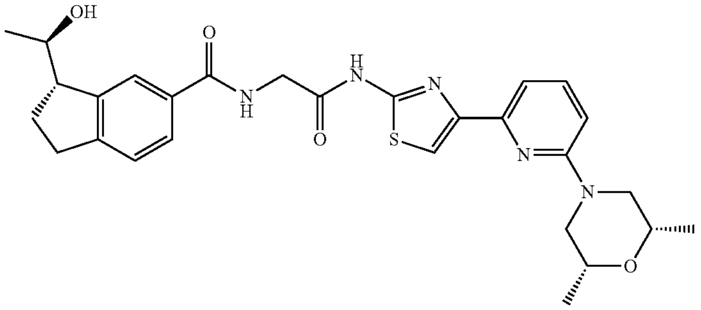 [SMILES: C[C@@H]1CN(c2cccc(-c3csc(NC(=O)CNC(=O)c4ccc5c(c4)[C@@H]([C@@H](C)O)CC5)n3)n2)C[C@H](C)O1] |
| 143 | 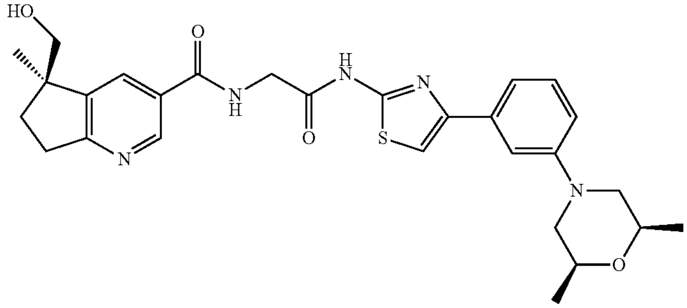 |
| 144 | 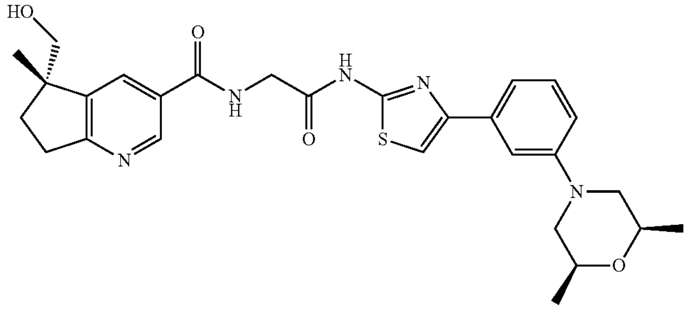 |

TABLE 3b-continued
| Compounds of the Invention | |
|---|---|
| # | Compound |
| 145 | 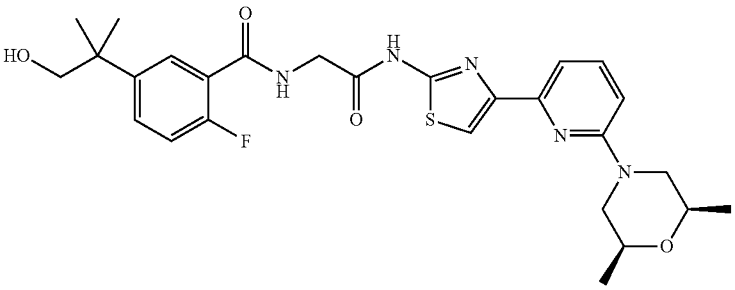 [SMILES: C[C@@H]1CN(c2cccc(-c3csc(NC(=O)CNC(=O)c4cc(C(C)(C)CO)ccc4F)n3)n2)C[C@H](C)O1] |
| 146 | 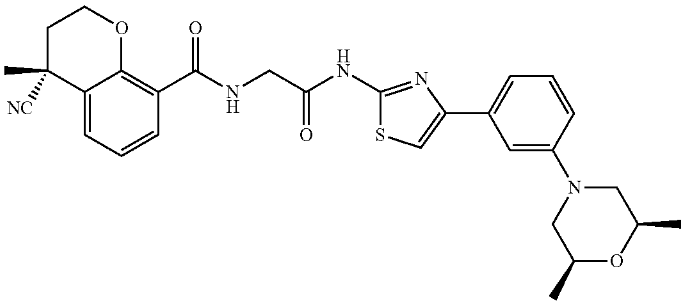 |
| 147 | 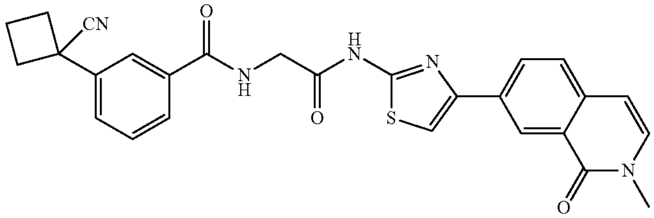 [SMILES: Cn1ccc2ccc(-c3csc(NC(=O)CNC(=O)c4cccc(C5(C#N)CCC5)c4)n3)cc2c1=O] |
| 148 | 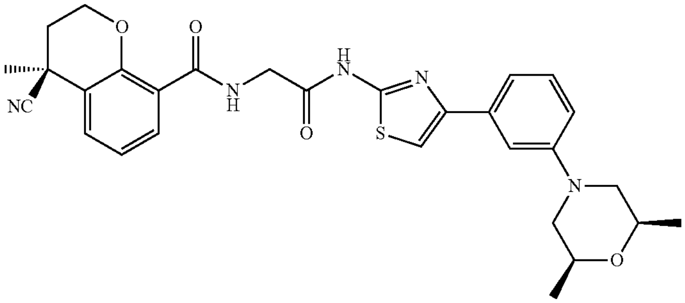 |
| 149 | 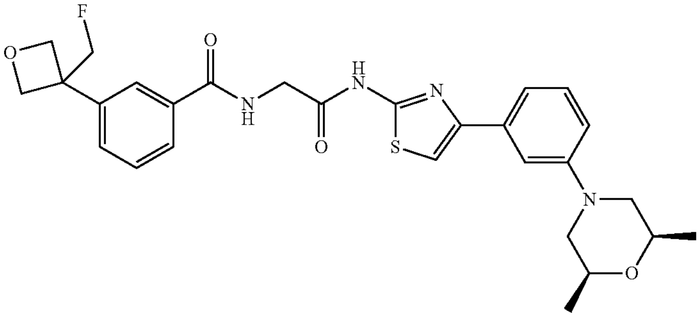 [SMILES: C[C@@H]1CN(c2cccc(-c3csc(NC(=O)CNC(=O)c4cccc(C5(CF)COC5)c4)n3)c2)C[C@H](C)O1] |

TABLE 3b-continued
| Compounds of the Invention | |
|---|---|
| # | Compound |
| 150 | 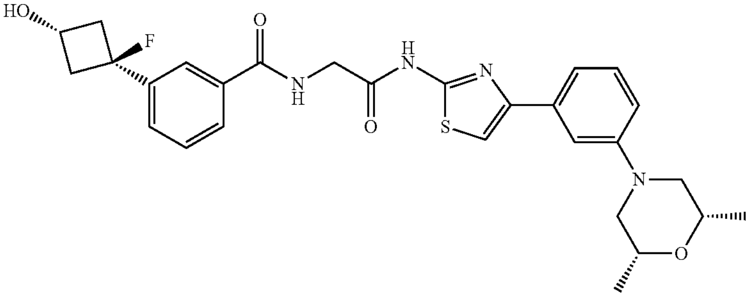 [SMILES: C[C@@H]1CN(c2cccc(-c3csc(NC(=O)CNC(=O)c4cccc([C@]5(F)C[C@H](O)C5)c4)n3)c2)C[C@H](C)O1] |
| 151 | 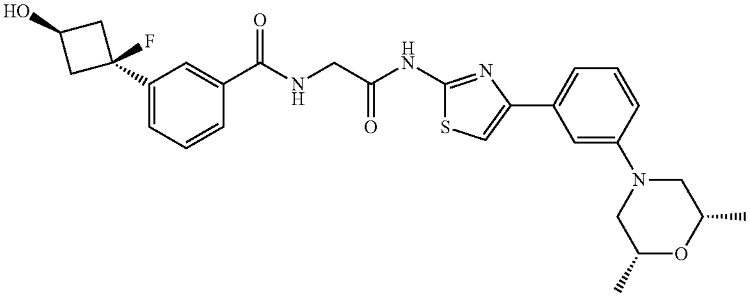 [SMILES: C[C@@H]1CN(c2cccc(-c3csc(NC(=O)CNC(=O)c4cccc([C@]5(F)C[C@@H](O)C5)c4)n3)c2)C[C@H](C)O1] |
| 152 | 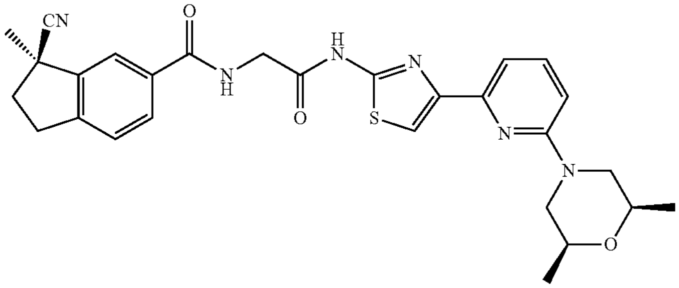 |
| 153 | 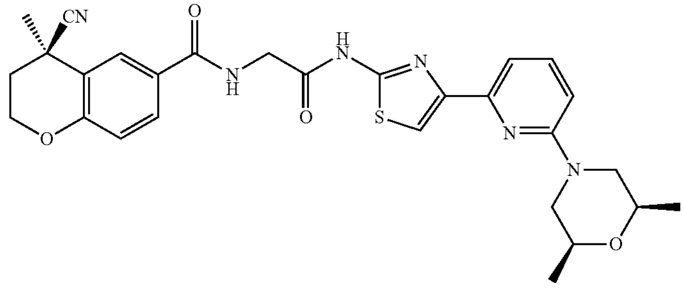 [SMILES: C[C@@H]1CN(c2cccc(-c3csc(NC(=O)CNC(=O)c4ccc5c(c4)[C@](C)(C#N)CCO5)n3)n2)C[C@H](C)O1] |
| 154 | 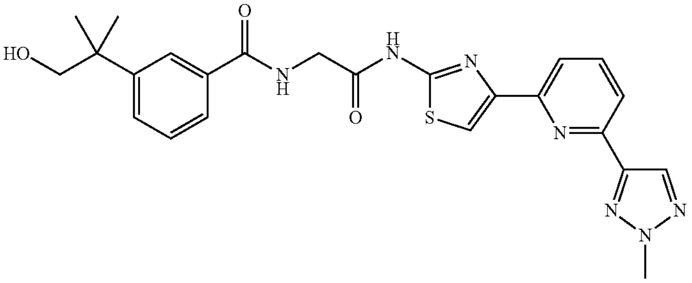 [SMILES: Cn1ncc(-c2cccc(-c3csc(NC(=O)CNC(=O)c4cccc(C(C)(C)CO)c4)n3)n2)n1] |

TABLE 3b-continued
Compounds of the Invention
| # | Compound |
| --- | --- |
| 155 | 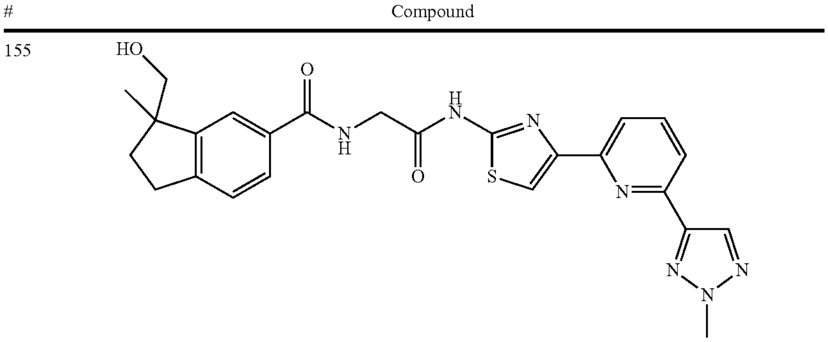 |
| 156 | 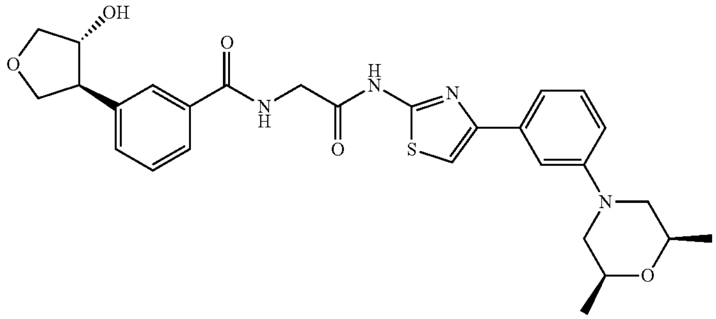 [SMILES: C[C@@H]1CN(c2cccc(-c3csc(NC(=O)CNC(=O)c4cccc([C@H]5COC[C@@H]5O)c4)n3)c2)C[C@H](C)O1] |
| 157 | 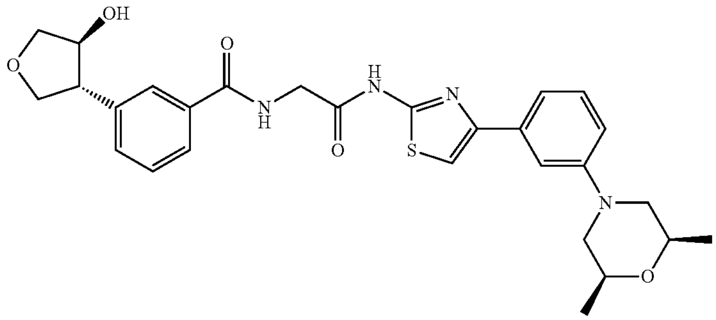 |
| 158 | 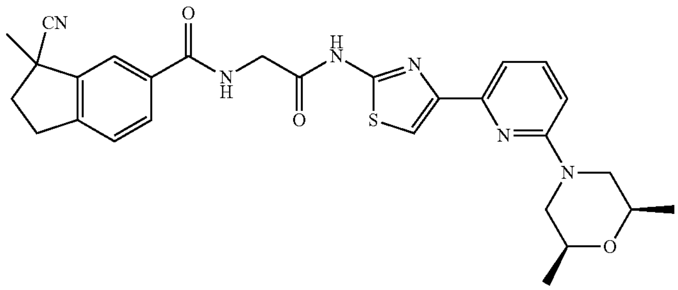 |
| 159 | 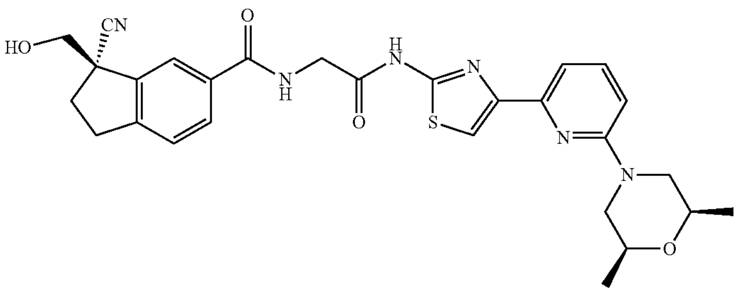 [SMILES: C[C@@H]1CN(c2cccc(-c3csc(NC(=O)CNC(=O)c4ccc5c(c4)[C@](C#N)(CO)CC5)n3)n2)C[C@H](C)O1] |

TABLE 3b-continued
| Compounds of the Invention | |
|---|---|
| # | Compound |
| 160 | 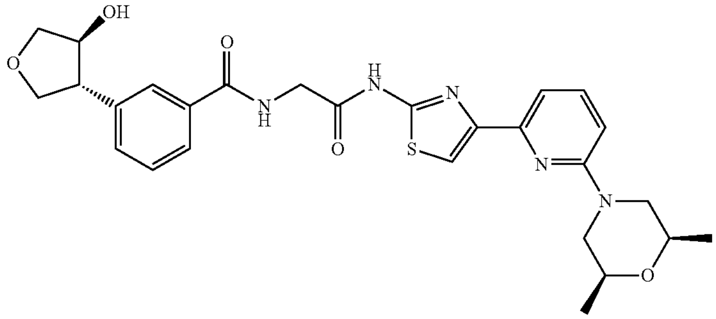 [SMILES: C[C@@H]1CN(c2cccc(-c3csc(NC(=O)CNC(=O)c4cccc([C@@H]5COC[C@H]5O)c4)n3)n2)C[C@H](C)O1] |
| 161 | 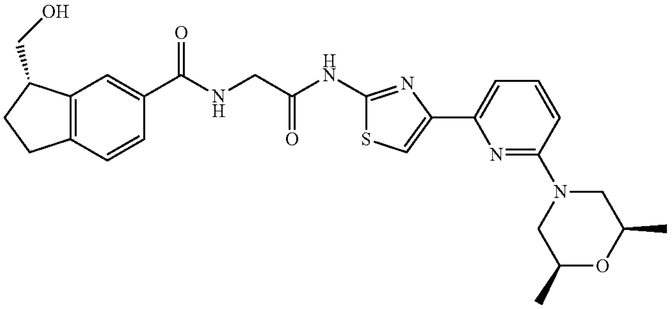 [SMILES: C[C@@H]1CN(c2cccc(-c3csc(NC(=O)CNC(=O)c4ccc5c(c4)[C@@H](CO)CC5)n3)n2)C[C@H](C)O1] |
| 162 | 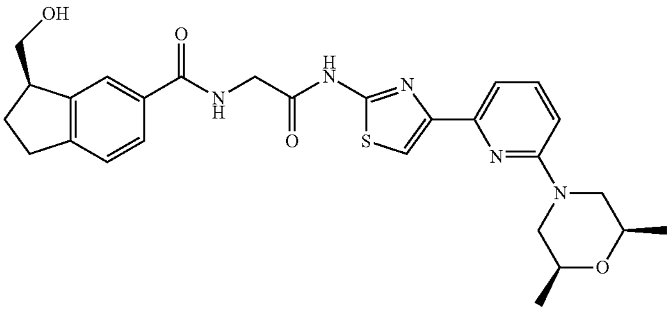 [SMILES: C[C@@H]1CN(c2cccc(-c3csc(NC(=O)CNC(=O)c4ccc5c(c4)[C@H](CO)CC5)n3)n2)C[C@H](C)O1] |
| 163 | 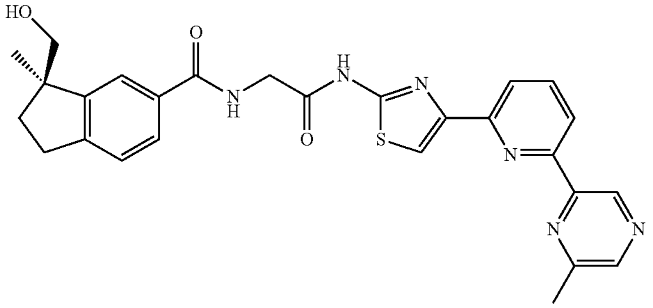 [SMILES: Cc1cncc(-c2cccc(-c3csc(NC(=O)CNC(=O)c4ccc5c(c4)[C@](C)(CO)CC5)n3)n2)n1] |

TABLE 3b-continued
| Compounds of the Invention | |
|---|---|
| # | Compound |
| 164 | 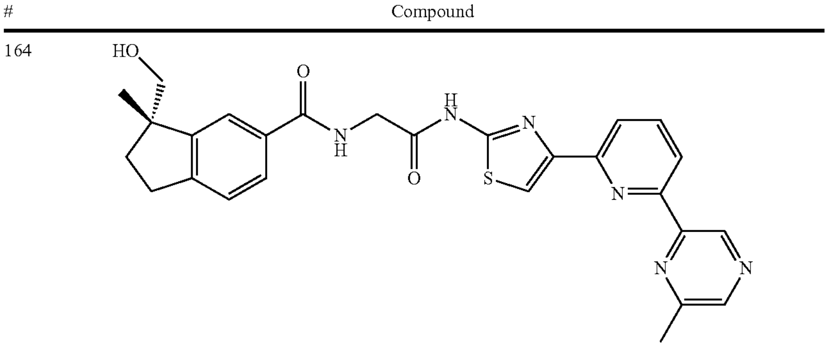 |
| 165 | 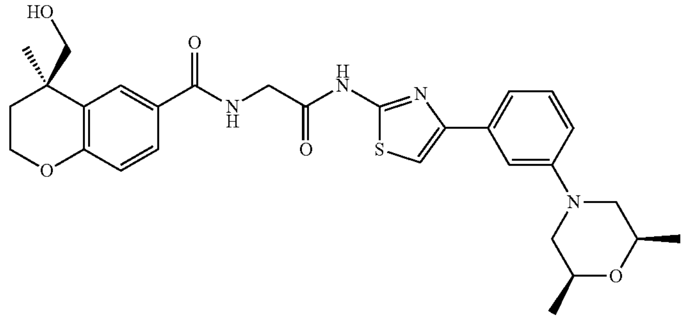 [SMILES: C[C@@H]1CN(c2cccc(-c3csc(NC(=O)CNC(=O)c4ccc5c(c4)[C@](C)(CO)CCO5)n3)c2)C[C@H](C)O1] |
| 166 | 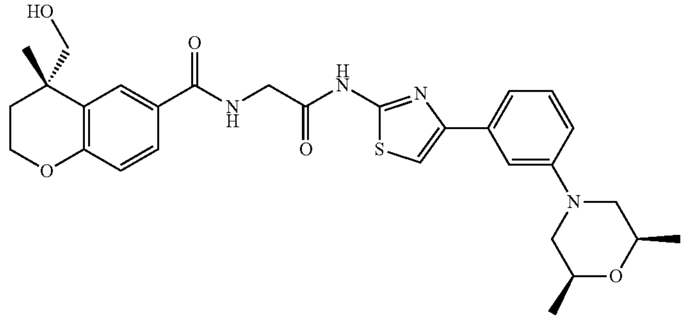 [SMILES: C[C@@H]1CN(c2cccc(-c3csc(NC(=O)CNC(=O)c4ccc5c(c4)[C@@](C)(CO)CCO5)n3)c2)C[C@H](C)O1] |
| 167 | 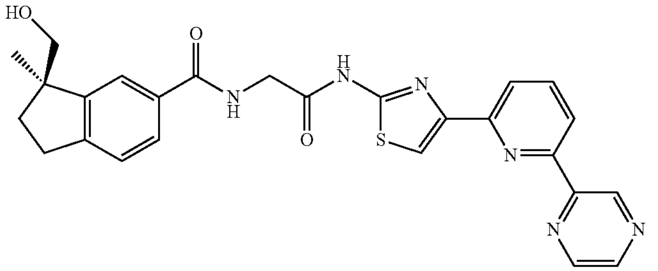 [SMILES: C[C@@]1(CO)CCc2ccc(C(=O)NCC(=O)Nc3nc(-c4cccc(-c5cnccn5)n4)cs3)cc21] |
| 168 | 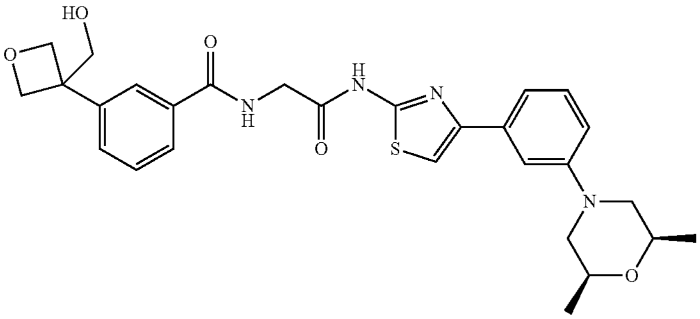 |

TABLE 3b-continued
| Compounds of the Invention | |
|---|---|
| # | Compound |
| 169 | 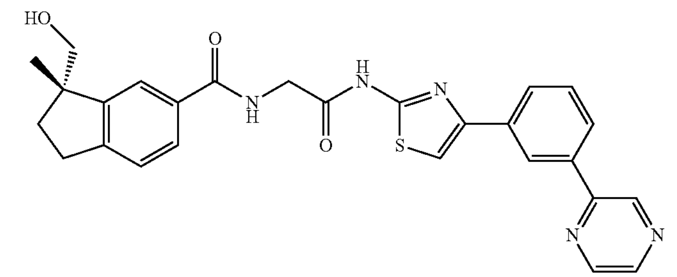 [SMILES: C[C@]1(CO)CCc2ccc(C(=O)NCC(=O)Nc3nc(-c4cccc(-c5cnccn5)c4)cs3)cc21] |
| 170 | 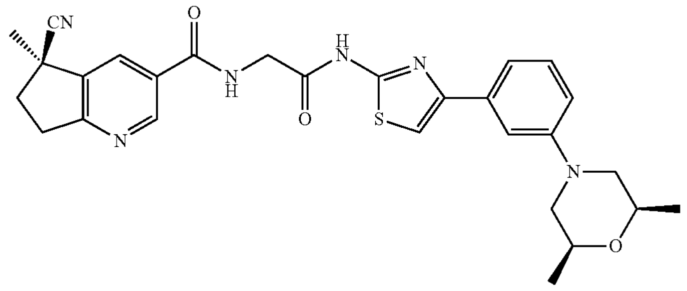 |
| 171 | 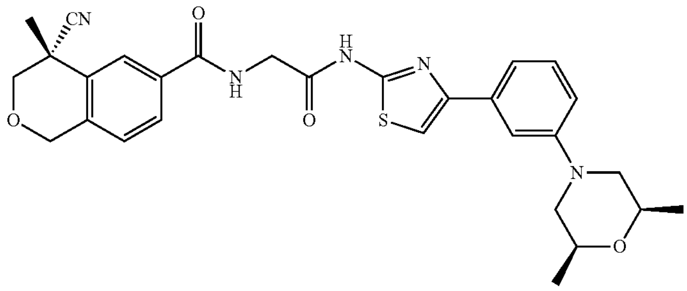 [SMILES: C[C@@H]1CN(c2cccc(-c3csc(NC(=O)CNC(=O)c4ccc5c(c4)[C@@](C)(C#N)COC5)n3)c2)C[C@H](C)O1] |
| 172 | 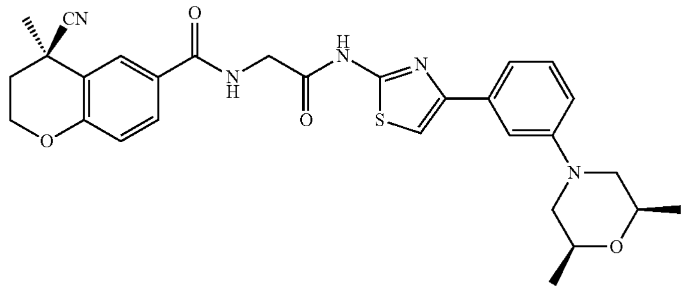 [SMILES: C[C@@H]1CN(c2cccc(-c3csc(NC(=O)CNC(=O)c4ccc5c(c4)[C@](C)(C#N)CCO5)n3)c2)C[C@H](C)O1] |
| 173 | 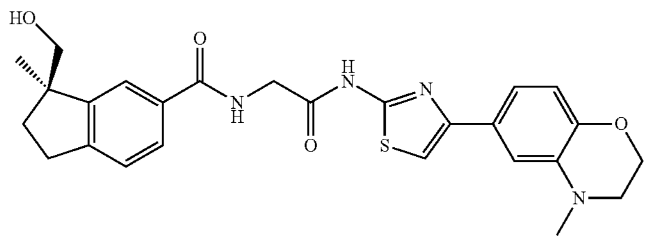 [SMILES: CN1CCOc2ccc(-c3csc(NC(=O)CNC(=O)c4ccc5c(c4)[C@](C)(CO)CC5)n3)cc21] |

TABLE 3b-continued
| Compounds of the Invention | |
|---|---|
| # | Compound |
| 174 | 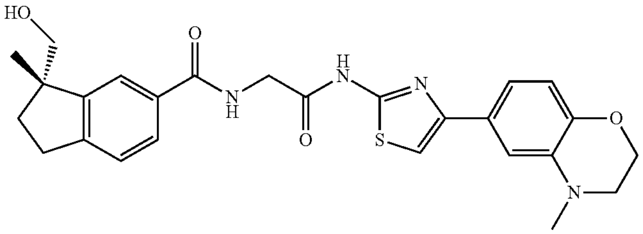 [SMILES: CN1CCOc2ccc(-c3csc(NC(=O)CNC(=O)c4ccc5c(c4)[C@@](C)(CO)CC5)n3)cc21] |
| 175 | 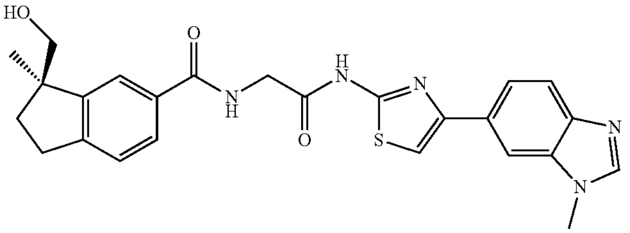 [SMILES: Cn1cnc2ccc(-c3csc(NC(=O)CNC(=O)c4ccc5c(c4)[C@](C)(CO)CC5)n3)cc21] |
| 176 | 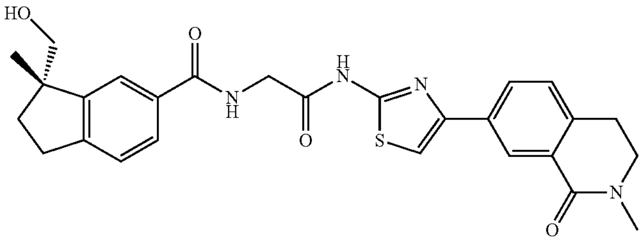 |
| 177 | 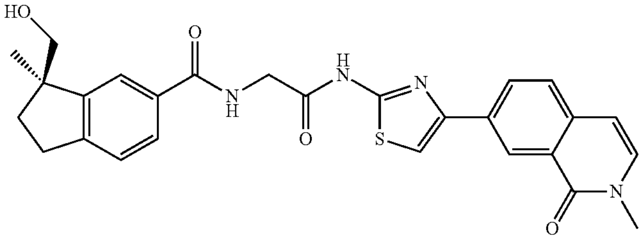 |
| 178 | 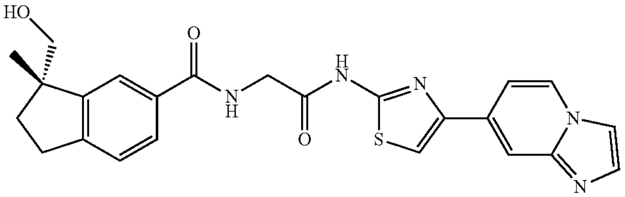 [SMILES: C[C@]1(CO)CCc2ccc(C(=O)NCC(=O)Nc3nc(-c4ccn5ccnc5c4)cs3)cc21] |
| 179 | 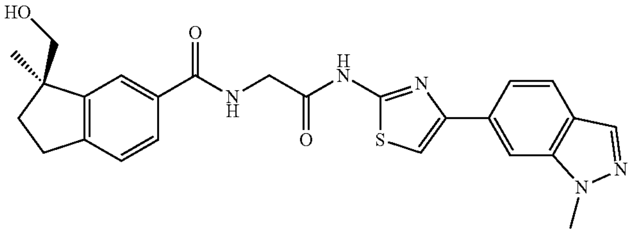 [SMILES: Cn1ncc2ccc(-c3csc(NC(=O)CNC(=O)c4ccc5c(c4)[C@](C)(CO)CC5)n3)cc21] |

TABLE 3b-continued
| Compounds of the Invention | |
|---|---|
| # | Compound |
| 180 | 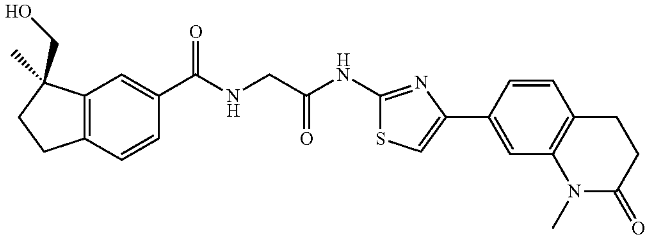 [SMILES: CN1C(=O)CCc2ccc(-c3csc(NC(=O)CNC(=O)c4ccc5c(c4)[C@](C)(CO)CC5)n3)cc21] |
| 181 | 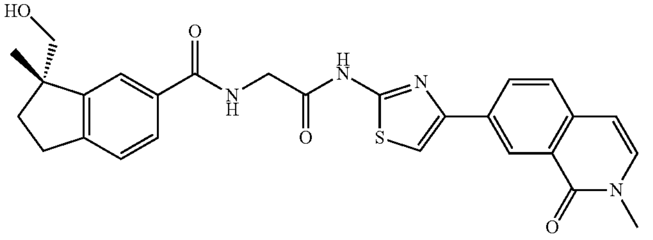 |
| 182 | 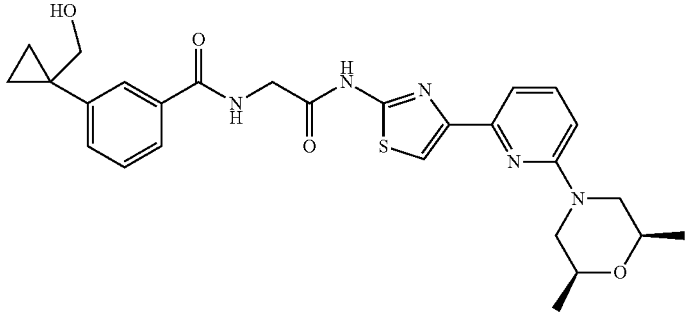 [SMILES: C[C@@H]1CN(c2cccc(-c3csc(NC(=O)CNC(=O)c4cccc(C5(CO)CC5)c4)n3)n2)C[C@H](C)O1] |
| 183 | 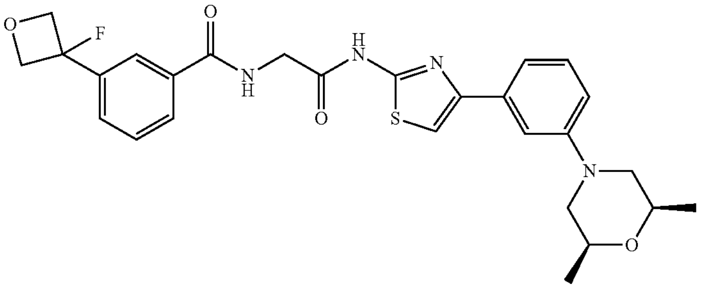 [SMILES: C[C@@H]1CN(c2cccc(-c3csc(NC(=O)CNC(=O)c4cccc(C5(F)COC5)c4)n3)c2)C[C@H](C)O1] |
| 184 | 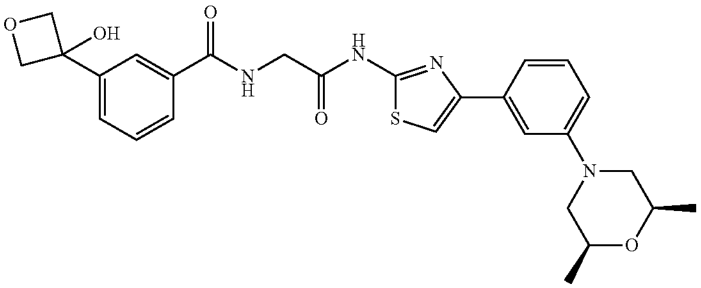 [SMILES: C[C@@H]1CN(c2cccc(-c3csc(NC(=O)CNC(=O)c4cccc(C5(O)COC5)c4)n3)c2)C[C@H](C)O1] |

TABLE 3b-continued
| Compounds of the Invention | |
|---|---|
| # | Compound |
| 185 | 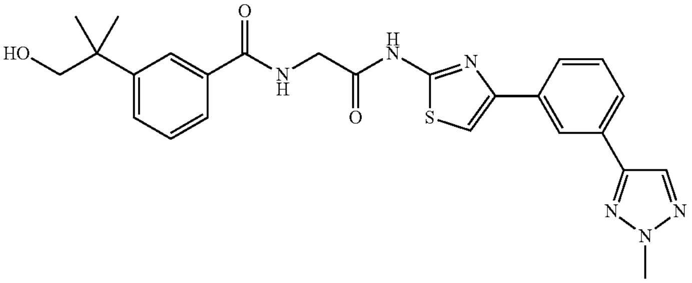 [SMILES: Cn1ncc(-c2cccc(-c3csc(NC(=O)CNC(=O)c4cccc(C(C)(C)CO)c4)n3)c2)n1] |
| 186 | 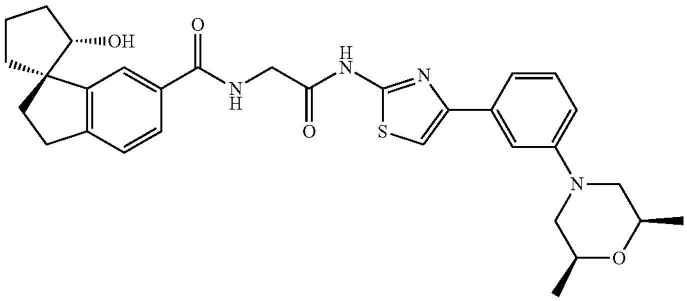 [SMILES: C[C@@H]1CN(c2cccc(-c3csc(NC(=O)CNC(=O)c4ccc5c(c4)[C@@]4(CCC[C@@H]4O)CC5)n3)c2)C[C@H](C)O1] |
| 187 | 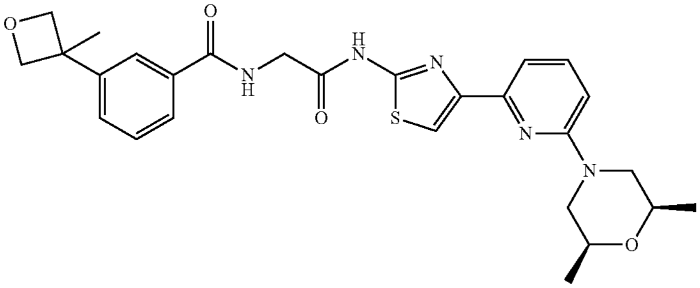 [SMILES: C[C@@H]1CN(c2cccc(-c3csc(NC(=O)CNC(=O)c4cccc(C5(C)COC5)c4)n3)n2)C[C@H](C)O1] |
| 188 | 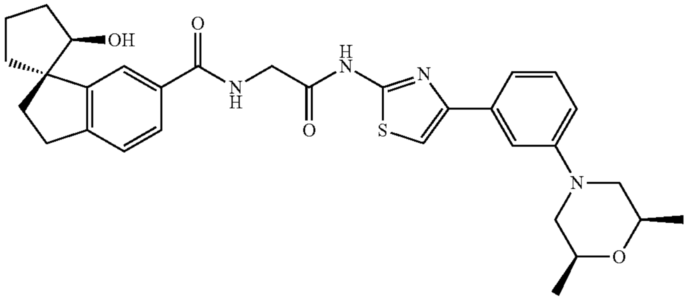 [SMILES: C[C@@H]1CN(c2cccc(-c3csc(NC(=O)CNC(=O)c4ccc5c(c4)[C@@]4(CCC[C@H]4O)CC5)n3)c2)C[C@H](C)O1] |
| 189 | 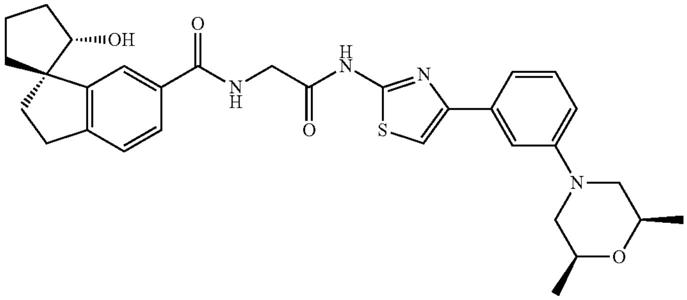 [SMILES: C[C@@H]1CN(c2cccc(-c3csc(NC(=O)CNC(=O)c4ccc5c(c4)[C@]4(CCC[C@@H]4O)CC5)n3)c2)C[C@H](C)O1] |

TABLE 3b-continued
| Compounds of the Invention | |
|---|---|
| # | Compound |
| 190 | 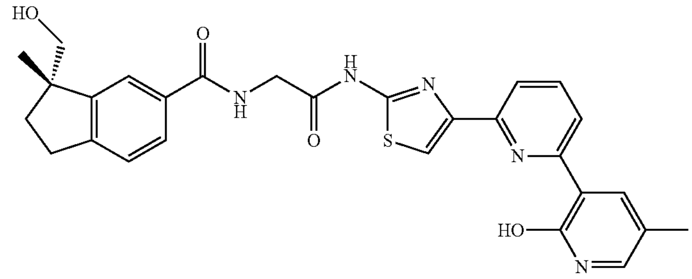 |
| 191 | 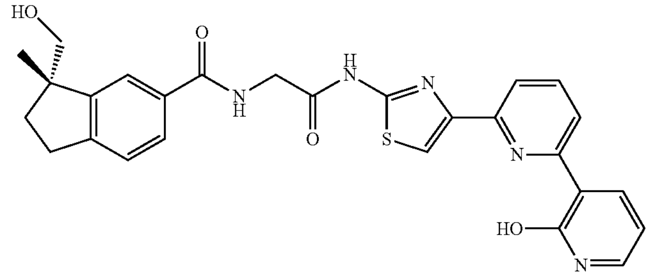 [SMILES: C[C@]1(CO)CCc2ccc(C(=O)NCC(=O)Nc3nc(-c4cccc(-c5cccnc5O)n4)cs3)cc21] |
| 192 | 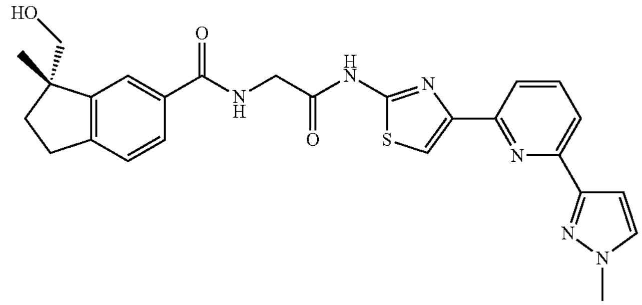 [SMILES: Cn1ccc(-c2cccc(-c3csc(NC(=O)CNC(=O)c4ccc5c(c4)[C@@](C)(CO)CC5)n3)n2)n1] |
| 193 | 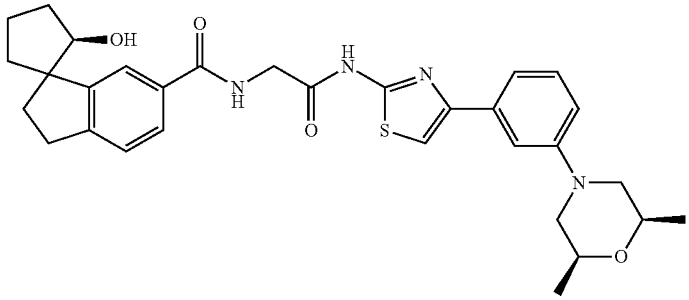 [SMILES: C[C@@H]1CN(c2cccc(-c3csc(NC(=O)CNC(=O)c4ccc5c(c4)C4(CCC[C@H]4O)CC5)n3)c2)C[C@H](C)O1] |
| 194 | 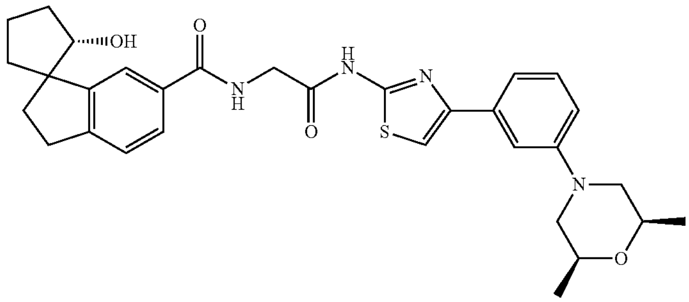 [SMILES: C[C@@H]1CN(c2cccc(-c3csc(NC(=O)CNC(=O)c4ccc5c(c4)C4(CCC[C@@H]4O)CC5)n3)c2)C[C@H](C)O1] |

TABLE 3b-continued
| Compounds of the Invention | |
|---|---|
| # | Compound |
| 195 | 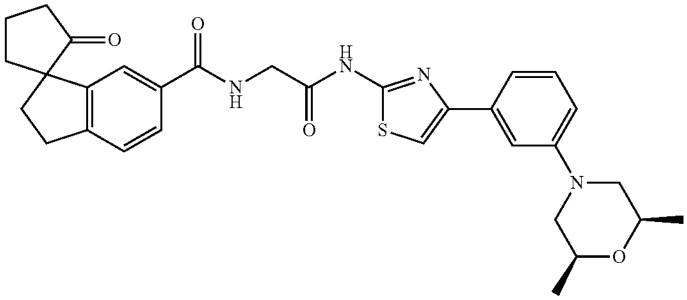 [SMILES: C[C@@H]1CN(c2cccc(-c3csc(NC(=O)CNC(=O)c4ccc5c(c4)C4(CCCC4=O)CC5)n3)c2)C[C@H](C)O1] |
| 196 | 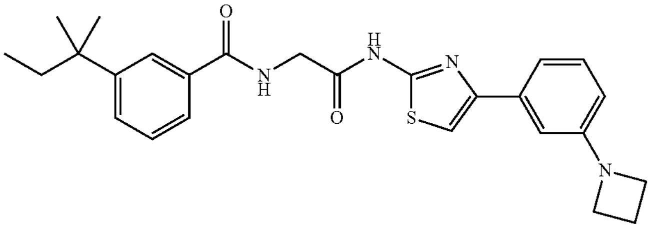 [SMILES: CCC(C)(C)c1cccc(C(=O)NCC(=O)Nc2nc(-c3cccc(N4CCC4)c3)cs2)c1] |
| 197 | 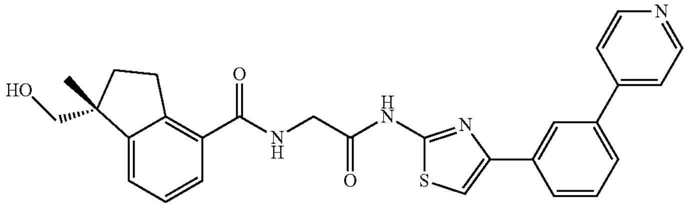 [SMILES: C[C@@]1(CO)CCc2c(C(=O)NCC(=O)Nc3nc(-c4cccc(-c5ccncc5)c4)cs3)cccc21] |
| 198 | 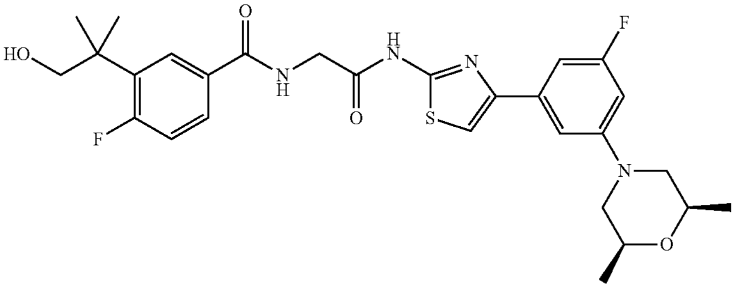 [SMILES: C[C@@H]1CN(c2cc(F)cc(-c3csc(NC(=O)CNC(=O)c4ccc(F)c(C(C)(C)CO)c4)n3)c2)C[C@H](C)O1] |
| 199 | 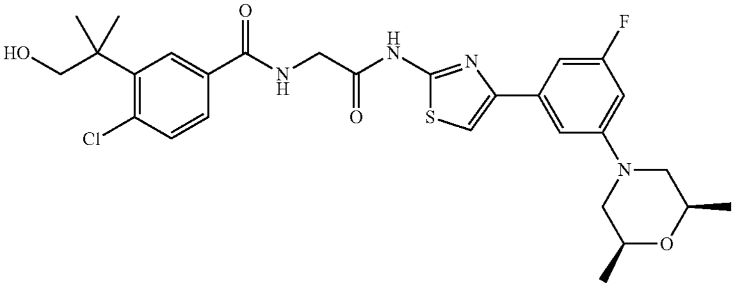 [SMILES: C[C@@H]1CN(c2cc(F)cc(-c3csc(NC(=O)CNC(=O)c4ccc(Cl)c(C(C)(C)CO)c4)n3)c2)C[C@H](C)O1] |

TABLE 3b-continued
| Compounds of the Invention | |
|---|---|
| # | Compound |
| 200 | 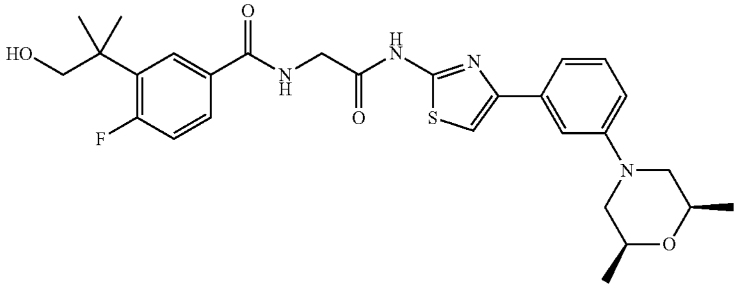 [SMILES: C[C@@H]1CN(c2cccc(-c3csc(NC(=O)CNC(=O)c4ccc(F)c(C(C)(C)CO)c4)n3)c2)C[C@H](C)O1] |
| 201 | 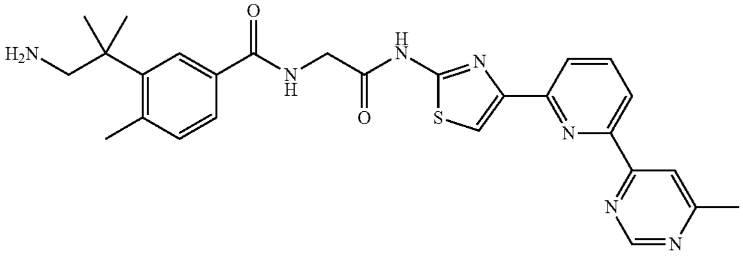 [SMILES: Cc1cc(-c2cccc(-c3csc(NC(=O)CNC(=O)c4ccc(C)c(C(C)(C)CN)c4)n3)n2)ncn1] |
| 202 | 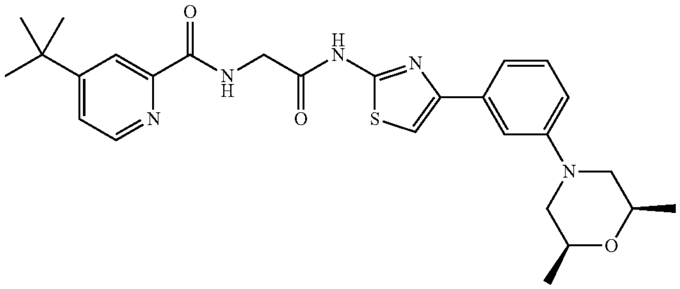 [SMILES: C[C@@H]1CN(c2cccc(-c3csc(NC(=O)CNC(=O)c4cc(C(C)(C)C)ccn4)n3)c2)C[C@H](C)O1] |
| 203 | 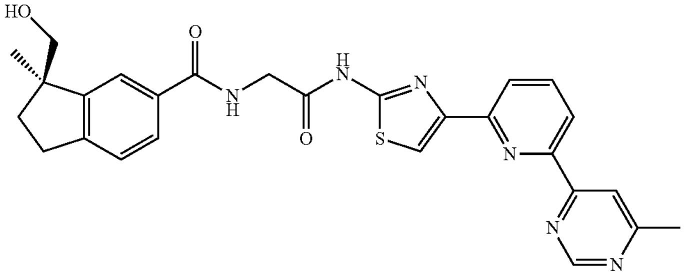 |
| 204 | 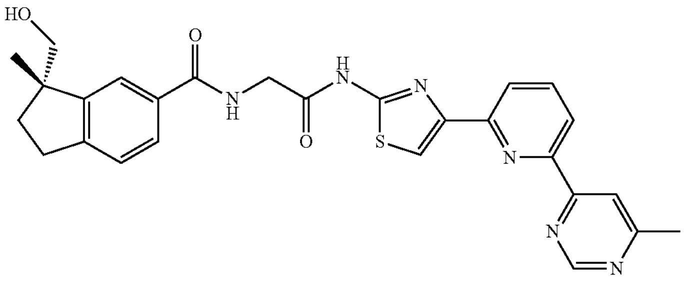 |

TABLE 3b-continued
| Compounds of the Invention | |
|---|---|
| # | Compound |
| 205 | 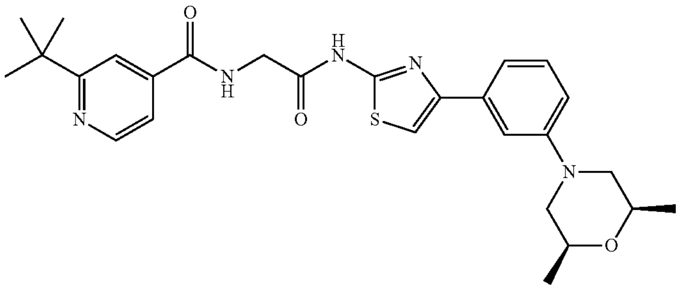 [SMILES: C[C@@H]1CN(c2cccc(-c3csc(NC(=O)CNC(=O)c4ccnc(C(C)(C)C)c4)n3)c2)C[C@H](C)O1] |
| 206 | 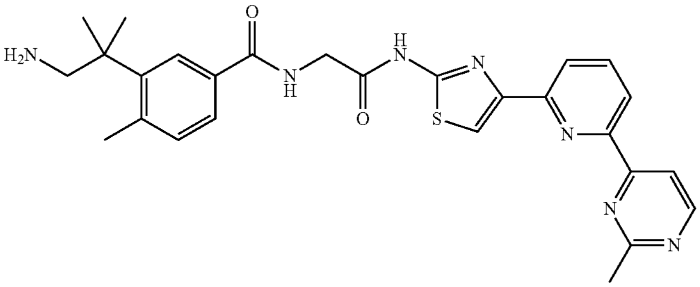 [SMILES: Cc1nccc(-c2cccc(-c3csc(NC(=O)CNC(=O)c4ccc(C)c(C(C)(C)CN)c4)n3)n2)n1] |
| 207 | 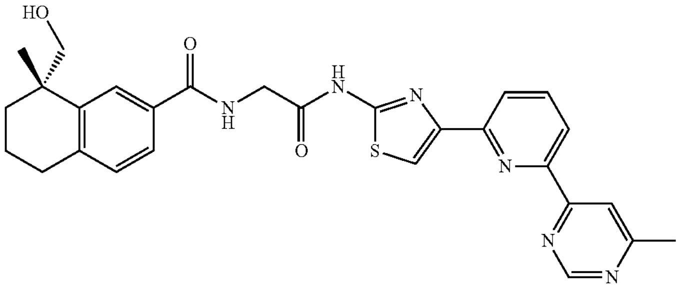 [SMILES: Cc1cc(-c2cccc(-c3csc(NC(=O)CNC(=O)c4ccc5c(c4)[C@@](C)(CO)CCC5)n3)n2)ncn1] |
| 208 | 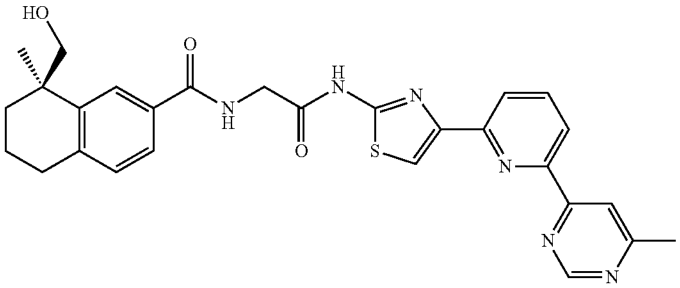 [SMILES: Cc1cc(-c2cccc(-c3csc(NC(=O)CNC(=O)c4ccc5c(c4)[C@](C)(CO)CCC5)n3)n2)ncn1] |
| 209 | 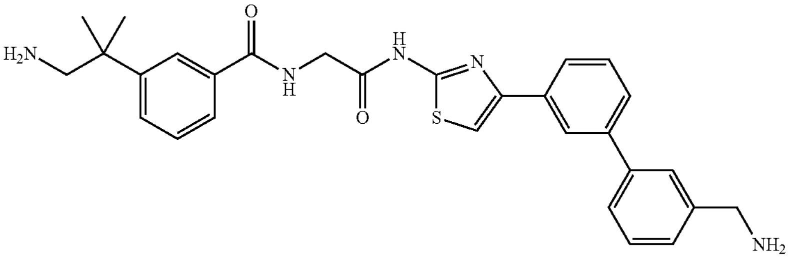 [SMILES: CC(C)(CN)c1cccc(C(=O)NCC(=O)Nc2nc(-c3cccc(-c4cccc(CN)c4)c3)cs2)c1] |

TABLE 3b-continued
| Compounds of the Invention | |
|---|---|
| # | Compound |
| 210 | 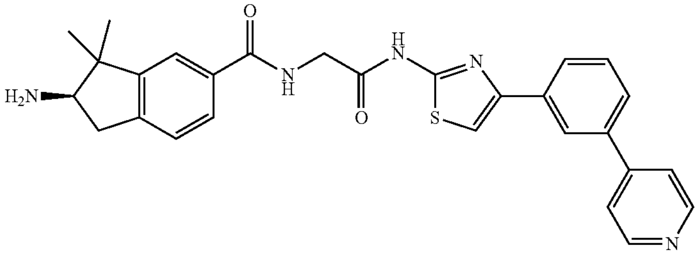 [SMILES: CC1(C)c2cc(C(=O)NCC(=O)Nc3nc(-c4cccc(-c5ccncc5)c4)cs3)ccc2C[C@H]1N] |
| 211 | 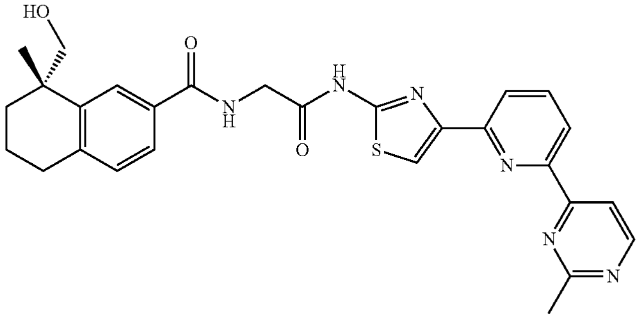 [SMILES: Cc1nccc(-c2cccc(-c3csc(NC(=O)CNC(=O)c4ccc5c(c4)[C@@](C)(CO)CCC5)n3)n2)n1] |
| 212 | 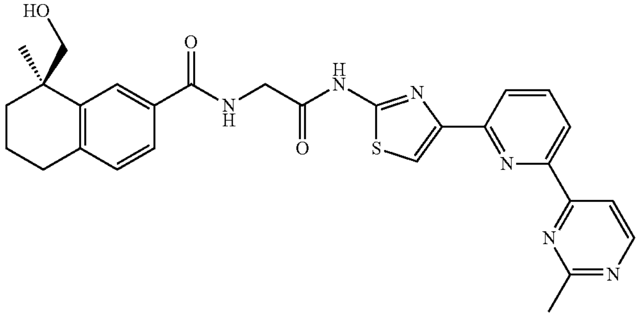 [SMILES: Cc1nccc(-c2cccc(-c3csc(NC(=O)CNC(=O)c4ccc5c(c4)[C@](C)(CO)CCC5)n3)n2)n1] |
| 213 | 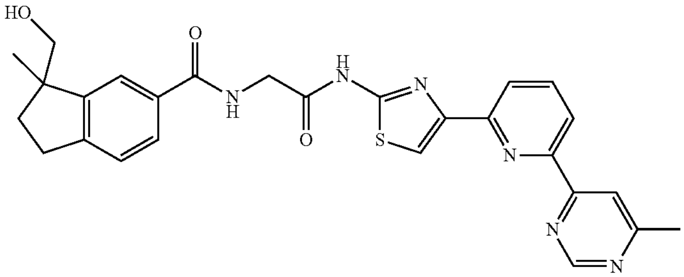 |
| 214 | 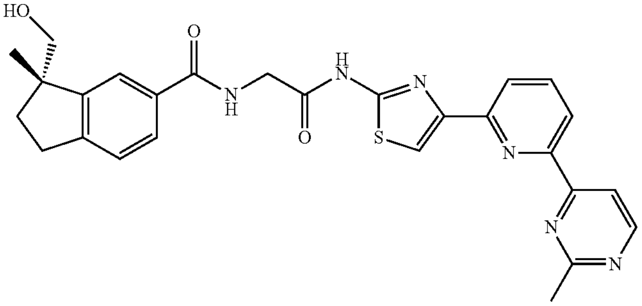 [SMILES: Cc1nccc(-c2cccc(-c3csc(NC(=O)CNC(=O)c4ccc5c(c4)[C@@](C)(CO)CC5)n3)n2)n1] |

TABLE 3b-continued
| Compounds of the Invention | |
|---|---|
| # | Compound |
| 215 | 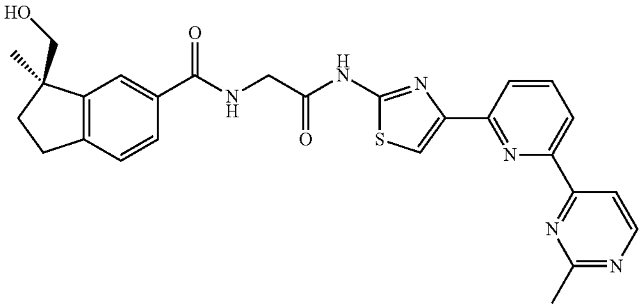 [SMILES: Cc1nccc(-c2cccc(-c3csc(NC(=O)CNC(=O)c4ccc5c(c4)[C@](C)(CO)CC5)n3)n2)n1] |
| 216 | 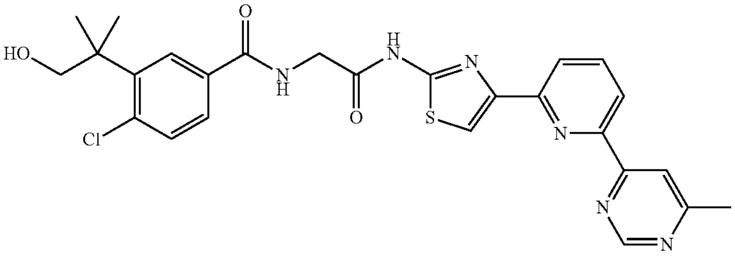 [SMILES: Cc1cc(-c2cccc(-c3csc(NC(=O)CNC(=O)c4ccc(Cl)c(C(C)(C)CO)c4)n3)n2)ncn1] |
| 217 | 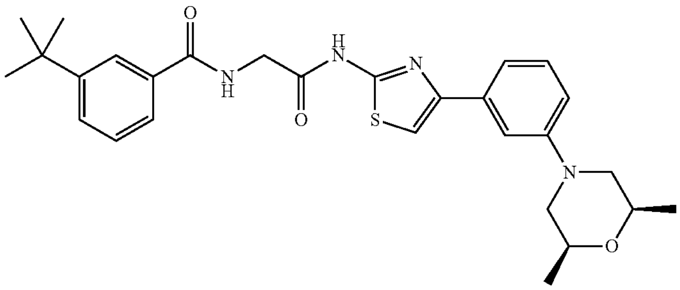 |
| 218 | 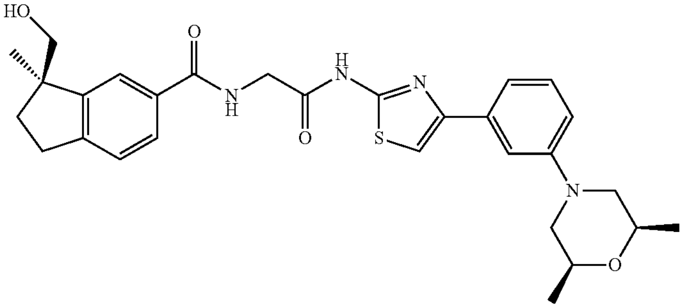 |
| 219 | 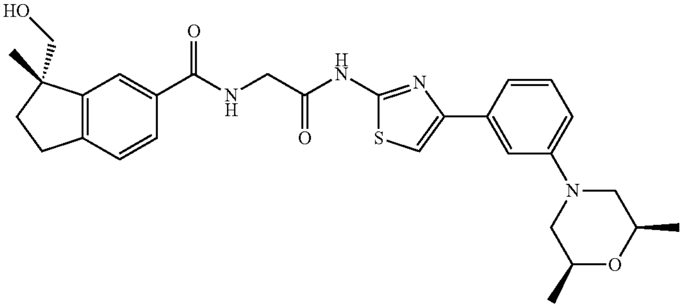 |

TABLE 3b-continued
| Compounds of the Invention | |
|---|---|
| # | Compound |
| 220 | 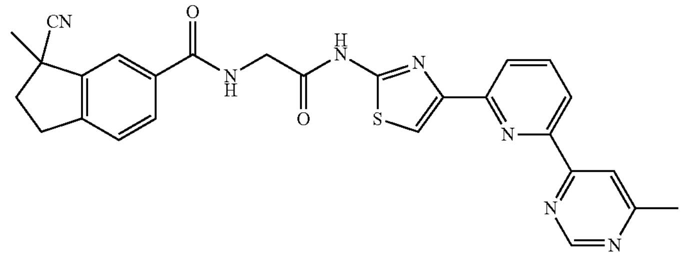 |
| 221 | 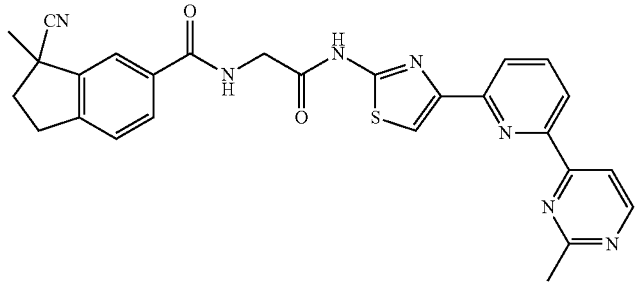 [SMILES: Cc1nccc(-c2cccc(-c3csc(NC(=O)CNC(=O)c4ccc5c(c4)C(C)(C#N)CC5)n3)n2)n1] |
| 222 | 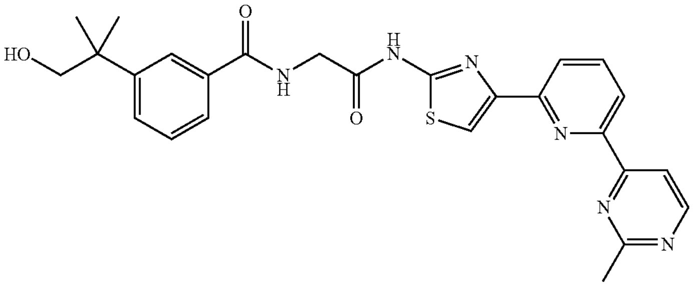 [SMILES: Cc1nccc(-c2cccc(-c3csc(NC(=O)CNC(=O)c4cccc(C(C)(C)CO)c4)n3)n2)n1] |
| 223 | 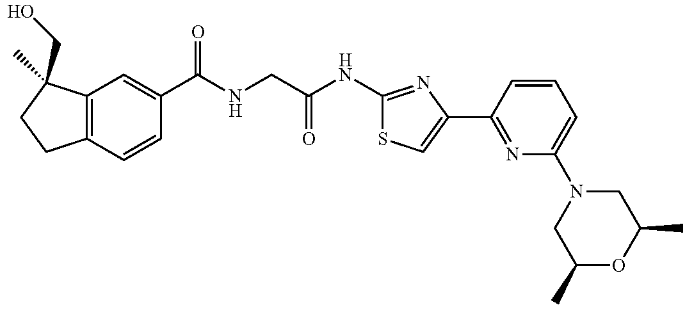 |
| 224 | 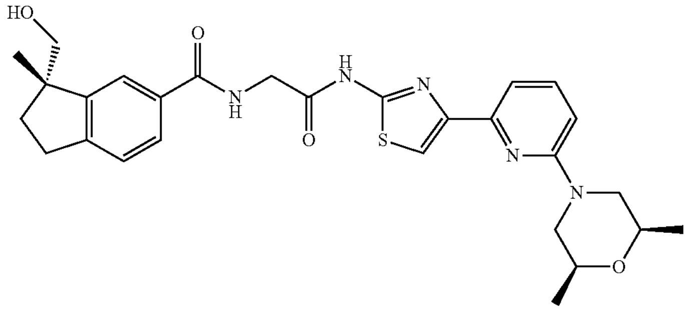 |

TABLE 3b-continued
| Compounds of the Invention | |
|---|---|
| # | Compound |
| 225 | 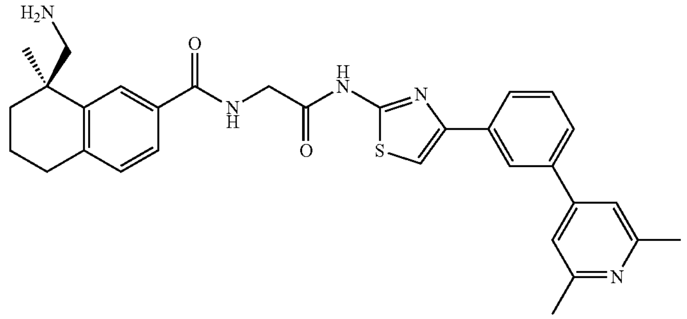 [SMILES: Cc1cc(-c2cccc(-c3csc(NC(=O)CNC(=O)c4ccc5c(c4)[C@](C)(CN)CCC5)n3)c2)cc(C)n1] |
| 226 | 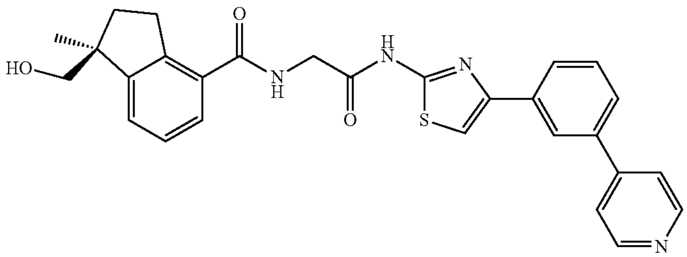 [SMILES: C[C@]1(CO)CCc2c(C(=O)NCC(=O)Nc3nc(-c4cccc(-c5ccncc5)c4)cs3)cccc21] |
| 227 | 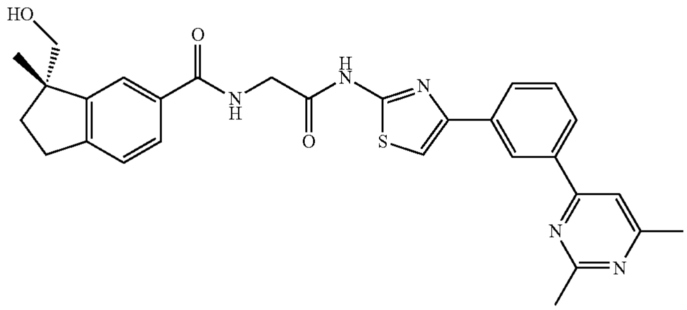 |
| 228 | 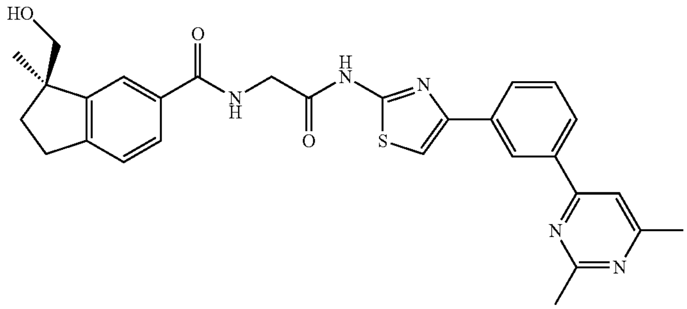 |
| 229 | 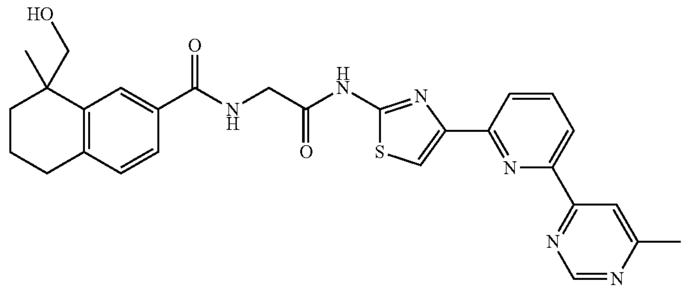 [SMILES: Cc1cc(-c2cccc(-c3csc(NC(=O)CNC(=O)c4ccc5c(c4)C(C)(CO)CCC5)n3)n2)ncn1] |

TABLE 3b-continued
| Compounds of the Invention | |
|---|---|
| # | Compound |
| 230 | 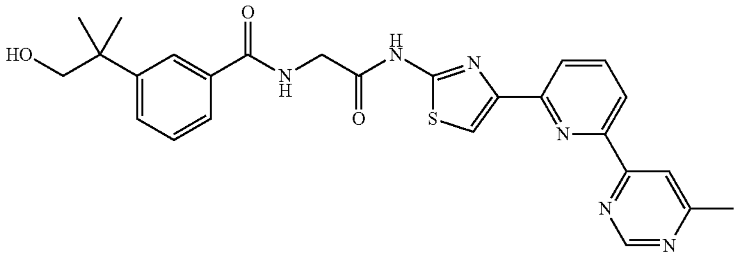 [SMILES: Cc1cc(-c2cccc(-c3csc(NC(=O)CNC(=O)c4cccc(C(C)(C)CO)c4)n3)n2)ncn1] |
| 231 | 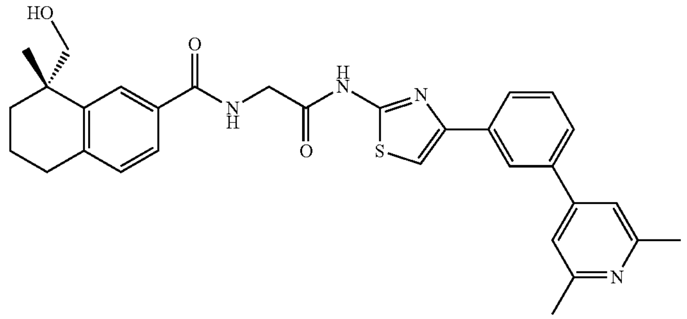 [SMILES: Cc1cc(-c2cccc(-c3csc(NC(=O)CNC(=O)c4ccc5c(c4)[C@@](C)(CO)CCC5)n3)c2)cc(C)n1] |
| 232 | 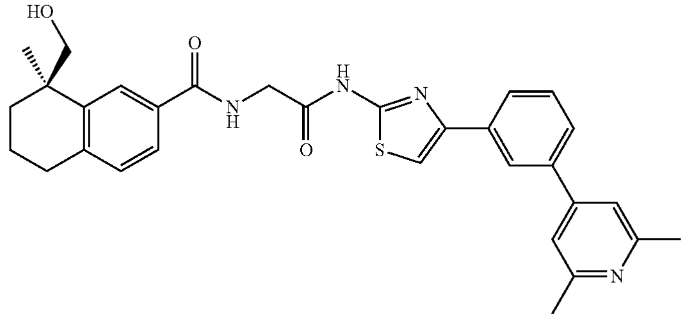 [SMILES: Cc1cc(-c2cccc(-c3csc(NC(=O)CNC(=O)c4ccc5c(c4)[C@](C)(CO)CCC5)n3)c2)cc(C)n1] |
| 233 | 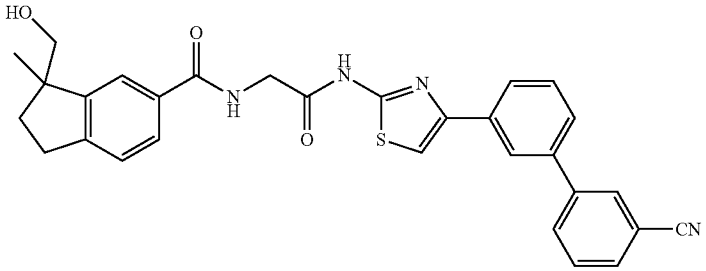 [SMILES: CC1(CO)CCc2ccc(C(=O)NCC(=O)Nc3nc(-c4cccc(-c5cccc(C#N)c5)c4)cs3)cc21] |
| 234 | 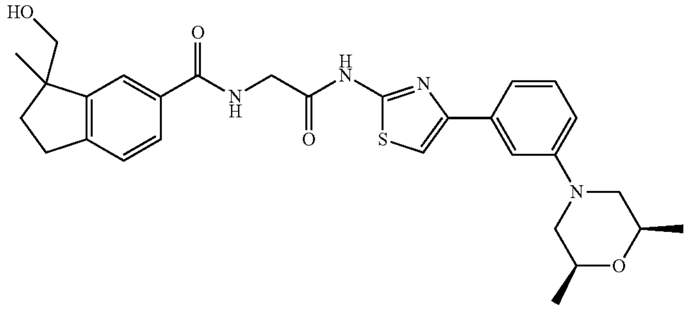 |

TABLE 3b-continued
| Compounds of the Invention | |
|---|---|
| # | Compound |
| 235 | 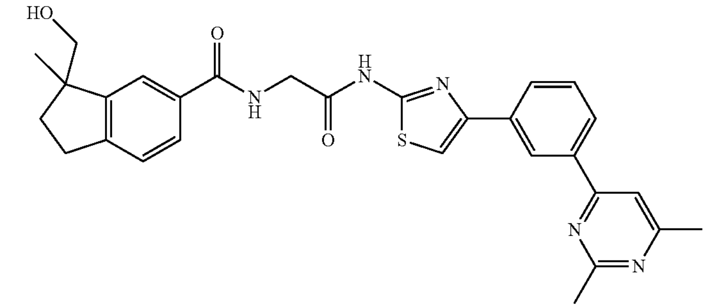 |
| 236 | 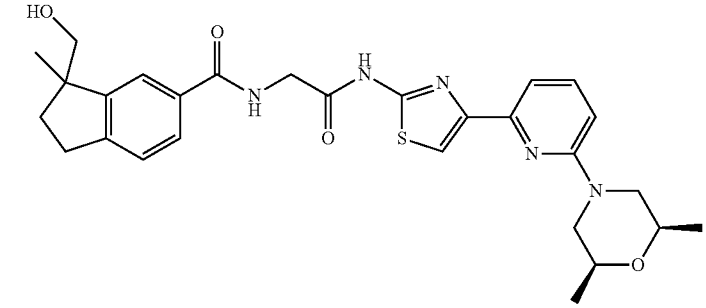 |
| 237 | 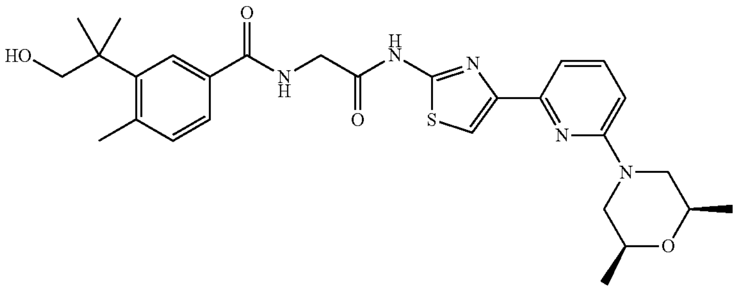 [SMILES: Cc1ccc(C(=O)NCC(=O)Nc2nc(-c3cccc(N4C[C@@H](C)O[C@@H](C)C4)n3)cs2)cc1C(C)(C)CO] |
| 238 | 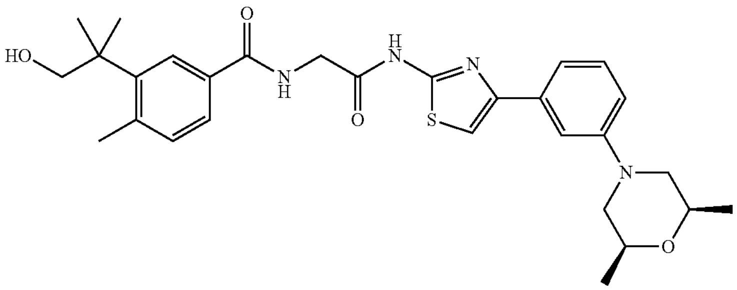 [SMILES: Cc1ccc(C(=O)NCC(=O)Nc2nc(-c3cccc(N4C[C@@H](C)O[C@@H](C)C4)c3)cs2)cc1C(C)(C)CO] |
| 239 | 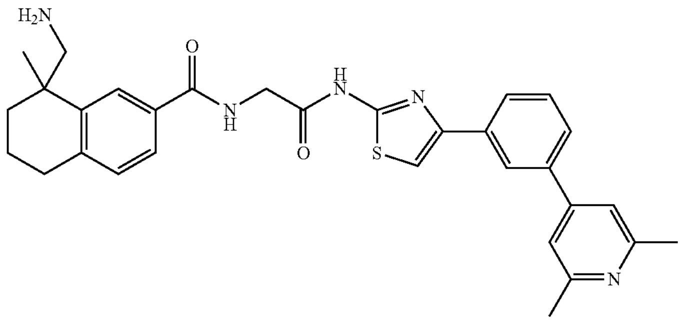 |

TABLE 3b-continued
| Compounds of the Invention | |
|---|---|
| # | Compound |
| 240 | 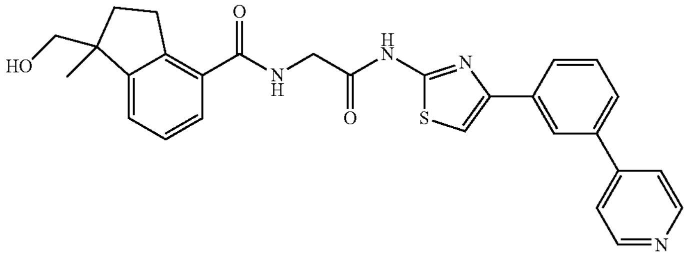 [SMILES: CC1(CO)CCc2c(C(=O)NCC(=O)Nc3nc(-c4cccc(-c5ccncc5)c4)cs3)cccc21] |
| 241 | 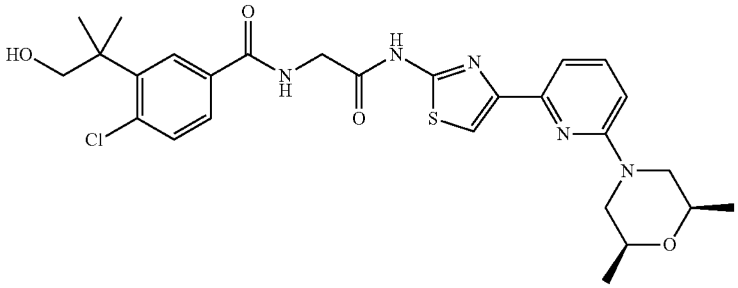 [SMILES: C[C@@H]1CN(c2cccc(-c3csc(NC(=O)CNC(=O)c4ccc(Cl)c(C(C)(C)CO)c4)n3)n2)C[C@H](C)O1] |
| 242 | 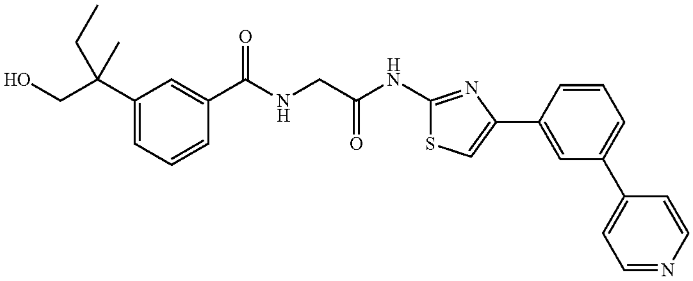 [SMILES: CCC(C)(CO)c1cccc(C(=O)NCC(=O)Nc2nc(-c3cccc(-c4ccncc4)c3)cs2)c1] |
| 243 | 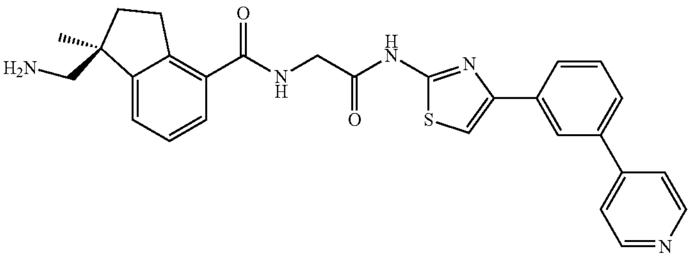 [SMILES: C[C@]1(CN)CCc2c(C(=O)NCC(=O)Nc3nc(-c4cccc(-c5ccncc5)c4)cs3)cccc21] |
| 244 | 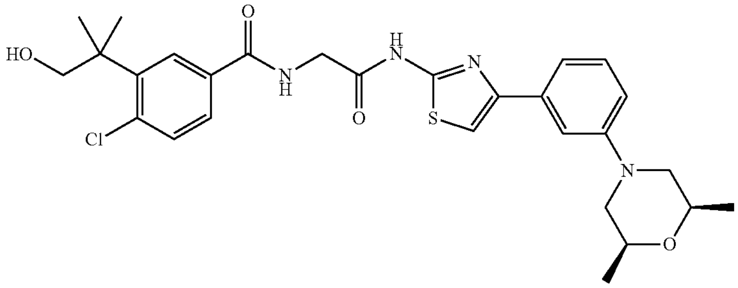 [SMILES: C[C@@H]1CN(c2cccc(-c3csc(NC(=O)CNC(=O)c4ccc(Cl)c(C(C)(C)CO)c4)n3)c2)C[C@H](C)O1] |

TABLE 3b-continued
| Compounds of the Invention | |
|---|---|
| # | Compound |
| 245 | 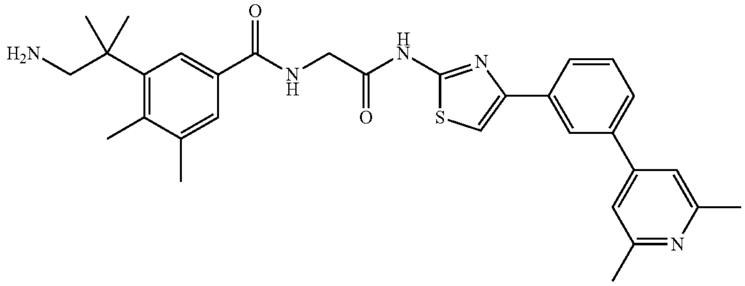 [SMILES: Cc1cc(-c2cccc(-c3csc(NC(=O)CNC(=O)c4cc(C)c(C)c(C(C)(C)CN)c4)n3)c2)cc(C)n1] |
| 246 | 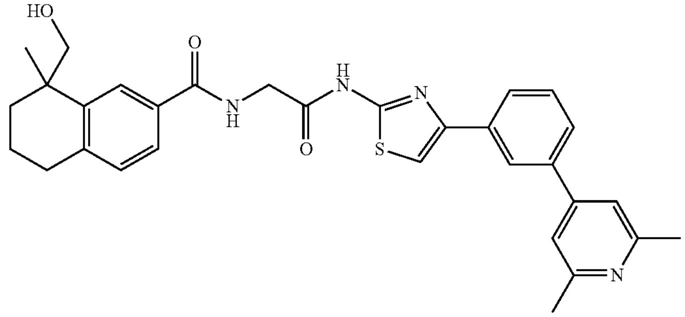 [SMILES: Cc1cc(-c2cccc(-c3csc(NC(=O)CNC(=O)c4ccc5c(c4)C(C)(CO)CCC5)n3)c2)cc(C)n1] |
| 247 | 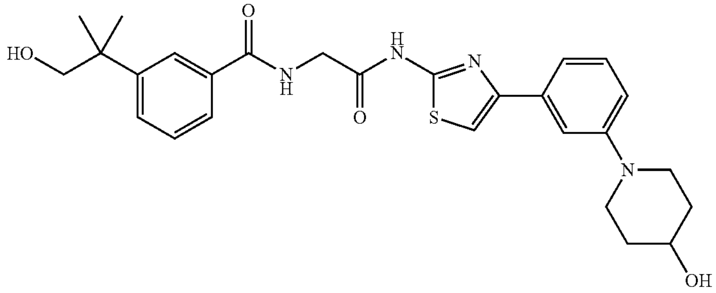 [SMILES: CC(C)(CO)c1cccc(C(=O)NCC(=O)Nc2nc(-c3cccc(N4CCC(O)CC4)c3)cs2)c1] |
| 248 | 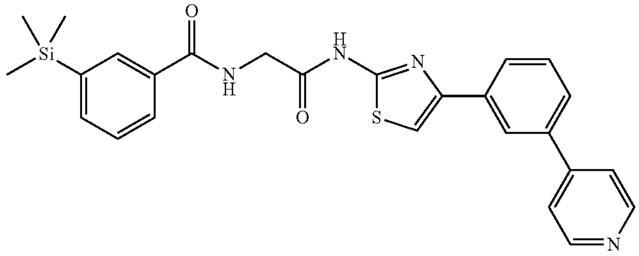 [SMILES: C[Si](C)(C)c1cccc(C(=O)NCC(=O)Nc2nc(-c3cccc(-c4ccncc4)c3)cs2)c1] |
| 249 | 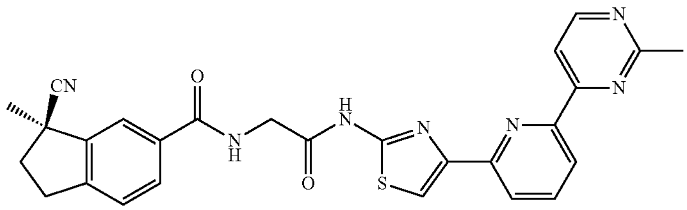 |

TABLE 3b-continued
| Compounds of the Invention | |
|---|---|
| # | Compound |
| 250 | 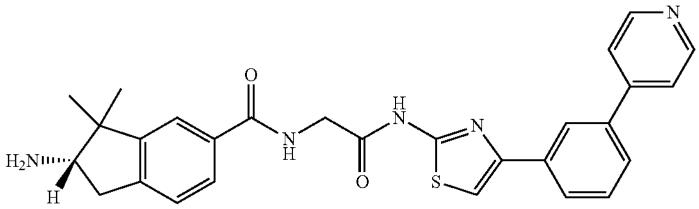 [SMILES: CC1(C)c2cc(C(=O)NCC(=O)Nc3nc(-c4cccc(-c5ccncc5)c4)cs3)ccc2C[C@@H]1N] |
| 251 | 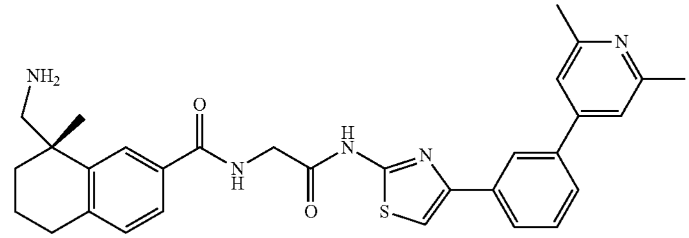 [SMILES: Cc1cc(-c2cccc(-c3csc(NC(=O)CNC(=O)c4ccc5c(c4)[C@@](C)(CN)CCC5)n3)c2)cc(C)n1] |
| 252 | 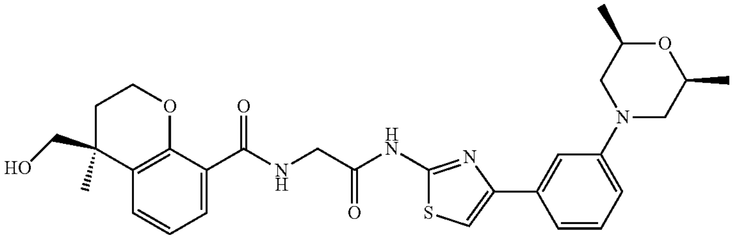 [SMILES: C[C@@H]1CN(c2cccc(-c3csc(NC(=O)CNC(=O)c4cccc5c4OCC[C@]5(C)CO)n3)c2)C[C@H](C)O1] |
| 253 | 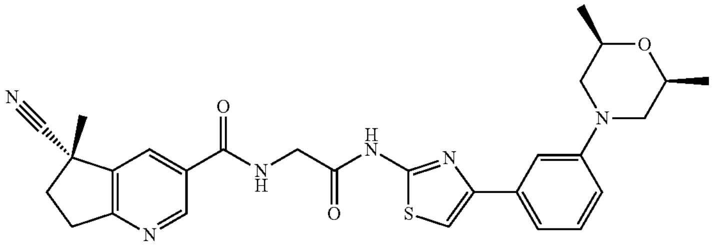 [SMILES: C[C@@H]1CN(c2cccc(-c3csc(NC(=O)CNC(=O)c4cnc5c(c4)[C@@](C)(C#N)CC5)n3)c2)C[C@H](C)O1] |
| 254 | 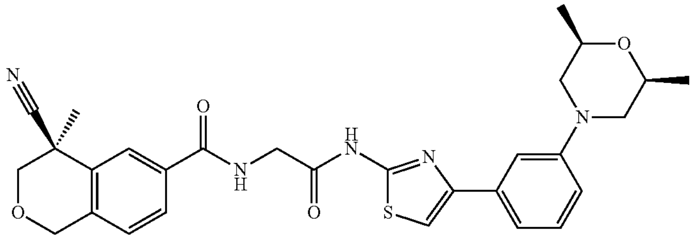 [SMILES: C[C@@H]1CN(c2cccc(-c3csc(NC(=O)CNC(=O)c4ccc5c(c4)[C@](C)(C#N)COC5)n3)c2)C[C@H](C)O1] |
| 255 | 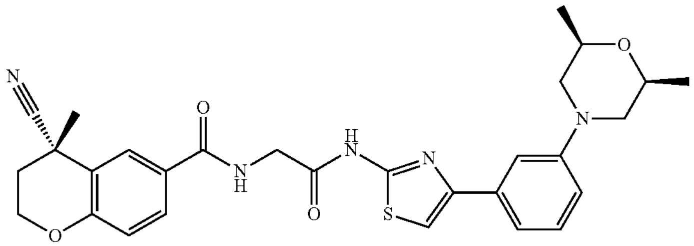 [SMILES: C[C@@H]1CN(c2cccc(-c3csc(NC(=O)CNC(=O)c4ccc5c(c4)[C@@](C)(C#N)CCO5)n3)c2)C[C@H](C)O1] |

TABLE 3b-continued
| Compounds of the Invention | |
|---|---|
| # | Compound |
| 256 | 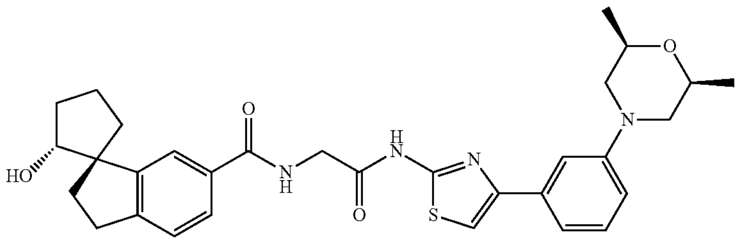 [SMILES: C[C@@H]1CN(c2cccc(-c3csc(NC(=O)CNC(=O)c4ccc5c(c4)[C@]4(CCC[C@H]4O)CC5)n3)c2)C[C@H](C)O1] |
| 257 | 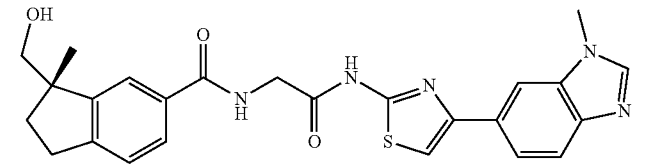 [SMILES: Cn1cnc2ccc(-c3csc(NC(=O)CNC(=O)c4ccc5c(c4)[C@@](C)(CO)CC5)n3)cc21] |
| 258 | 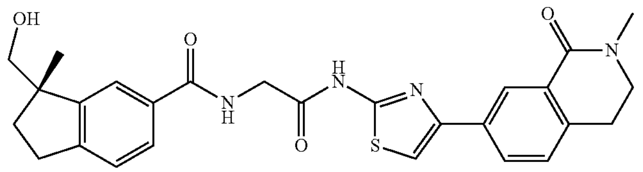 [SMILES: CN1CCc2ccc(-c3csc(NC(=O)CNC(=O)c4ccc5c(c4)[C@@](C)(CO)CC5)n3)cc2C1=O] |
| 259 | 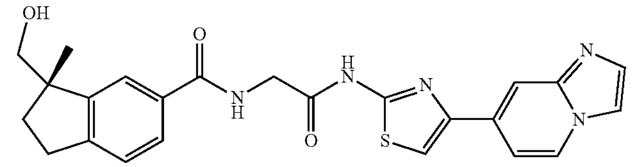 [SMILES: C[C@]1(CO)CCc2ccc(C(=O)NCC(=O)Nc3nc(-c4ccn5ccnc5c4)cs3)cc21] |
| 260 | 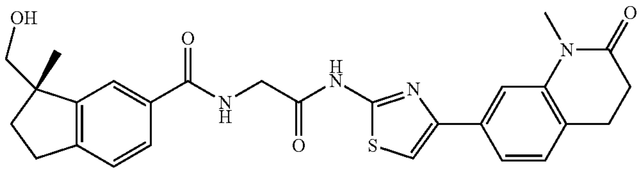 [SMILES: CN1C(=O)CCc2ccc(-c3csc(NC(=O)CNC(=O)c4ccc5c(c4)[C@@](C)(CO)CC5)n3)cc21] |
| 261 | 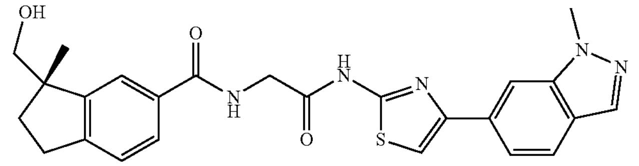 [SMILES: Cn1ncc2ccc(-c3csc(NC(=O)CNC(=O)c4ccc5c(c4)[C@@](C)(CO)CC5)n3)cc21] |
| 262 | 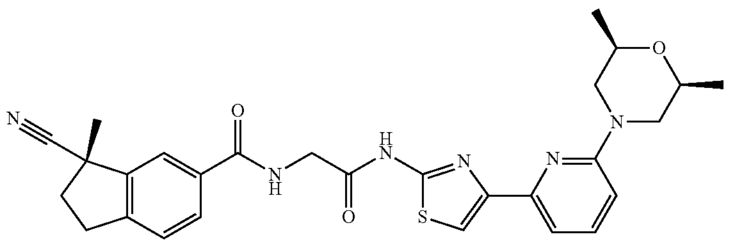 [SMILES: C[C@@H]1CN(c2cccc(-c3csc(NC(=O)CNC(=O)c4ccc5c(c4)[C@@](C)(C#N)CC5)n3)n2)C[C@H](C)O1] |

TABLE 3b-continued
| Compounds of the Invention | |
|---|---|
| # | Compound |
| 263 | 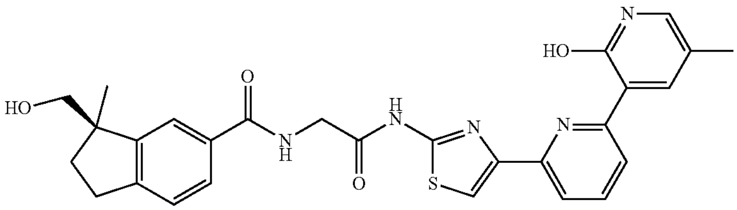 [SMILES: Cc1cnc(O)c(-c2cccc(-c3csc(NC(=O)CNC(=O)c4ccc5c(c4)[C@](C)(CO)CC5)n3)n2)c1] |
| 264 | 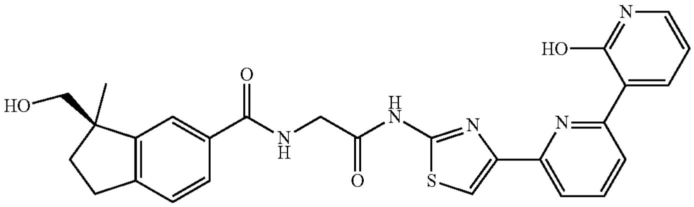 [SMILES: C[C@@]1(CO)CCc2ccc(C(=O)NCC(=O)Nc3nc(-c4cccc(-c5cccnc5O)n4)cs3)cc21] |
| 265 | 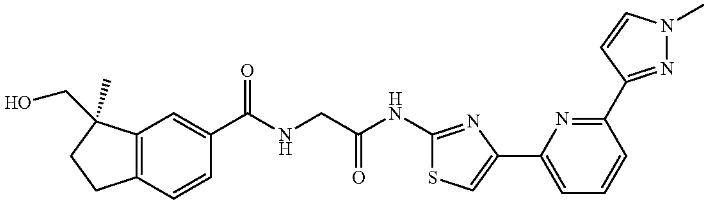 [SMILES: Cn1ccc(-c2cccc(-c3csc(NC(=O)CNC(=O)c4ccc5c(c4)[C@](C)(CO)CC5)n3)n2)n1] |
| 266 | 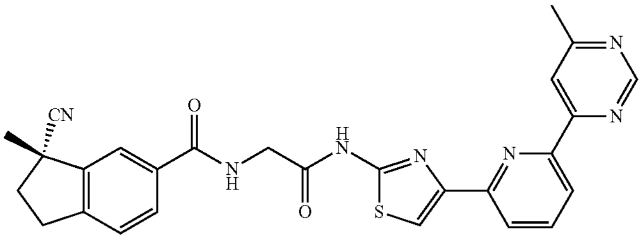 [SMILES: Cc1cc(-c2cccc(-c3csc(NC(=O)CNC(=O)c4ccc5c(c4)[C@@](C)(C#N)CC5)n3)n2)ncn1] |
| 267 | 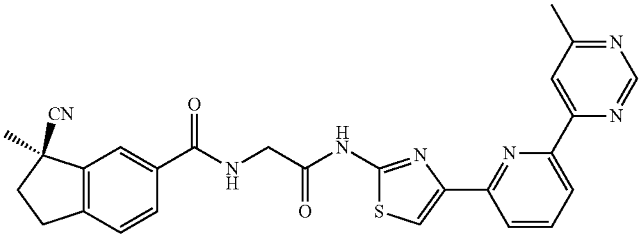 [SMILES: Cc1cc(-c2cccc(-c3csc(NC(=O)CNC(=O)c4ccc5c(c4)[C@](C)(C#N)CC5)n3)n2)ncn1] |
| 268 | 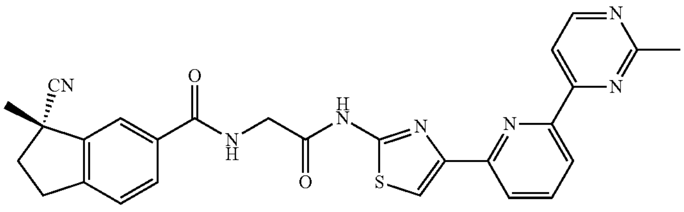 |

TABLE 3b-continued
| Compounds of the Invention | |
|---|---|
| # | Compound |
| 269 | 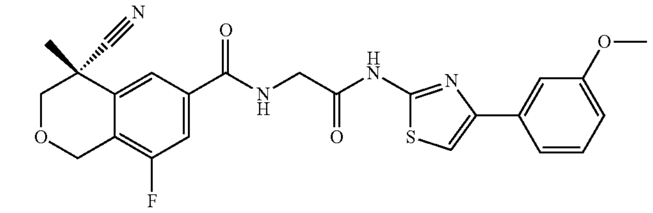 [SMILES: COc1cccc(-c2csc(NC(=O)CNC(=O)c3cc(F)c4c(c3)[C@@](C)(C#N)COC4)n2)c1] |
| 270 | 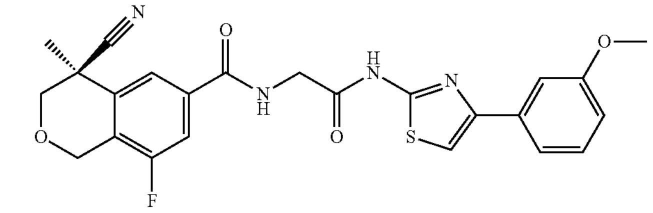 [SMILES: COc1cccc(-c2csc(NC(=O)CNC(=O)c3cc(F)c4c(c3)[C@](C)(C#N)COC4)n2)c1] |
| 271 | 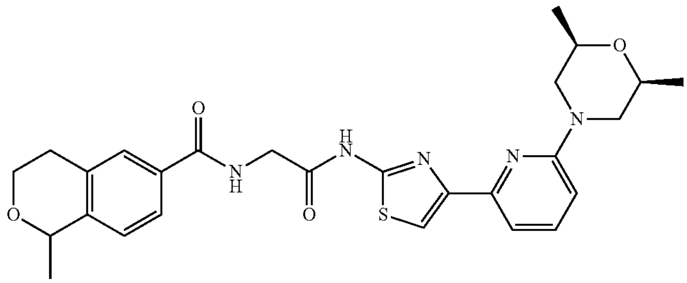 [SMILES: CC1OCCc2cc(C(=O)NCC(=O)Nc3nc(-c4cccc(N5C[C@@H](C)O[C@@H](C)C5)n4)cs3)ccc21] |
| 272 | 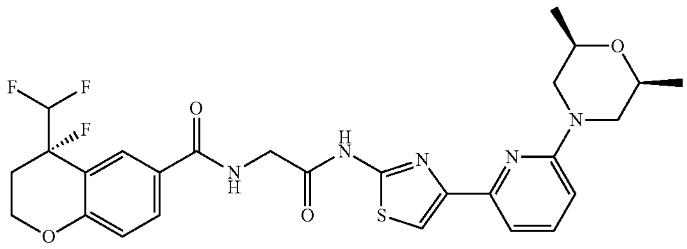 [SMILES: C[C@@H]1CN(c2cccc(-c3csc(NC(=O)CNC(=O)c4ccc5c(c4)[C@](F)(C(F)F)CCO5)n3)n2)C[C@H](C)O1] |
| 273 | 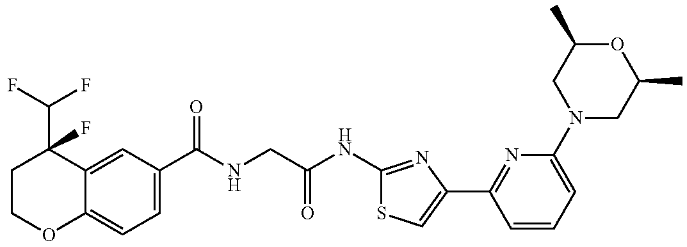 [SMILES: C[C@@H]1CN(c2cccc(-c3csc(NC(=O)CNC(=O)c4ccc5c(c4)[C@@](F)(C(F)F)CCO5)n3)n2)C[C@H](C)O1] |
| 274 | 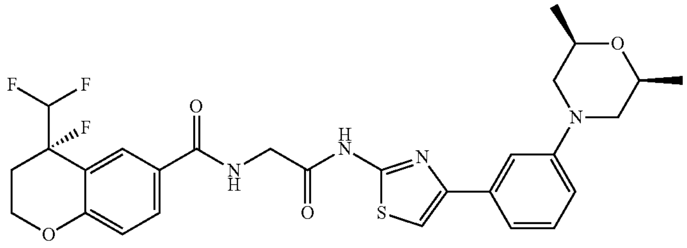 [SMILES: C[C@@H]1CN(c2cccc(-c3csc(NC(=O)CNC(=O)c4ccc5c(c4)[C@](F)(C(F)F)CCO5)n3)c2)C[C@H](C)O1] |

TABLE 3b-continued
Compounds of the Invention
| # | Compound |
|---|---|
| 275 | 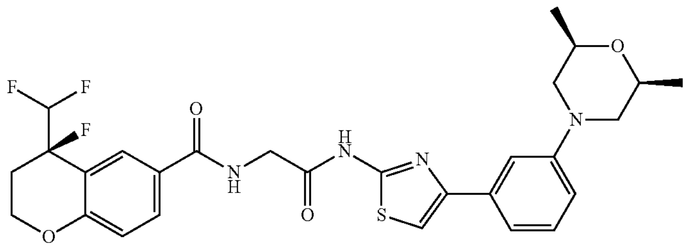 [SMILES: C[C@@H]1CN(c2cccc(-c3csc(NC(=O)CNC(=O)c4ccc5c(c4)[C@@](F)(C(F)F)CCO5)n3)c2)C[C@H](C)O1] |
| 276 | 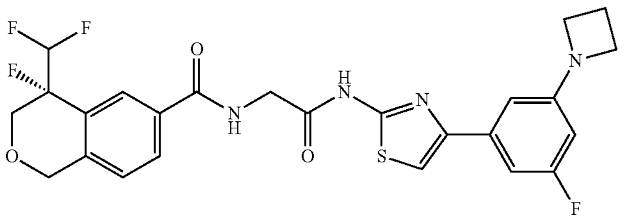 [SMILES: O=C(CNC(=O)c1ccc2c(c1)[C@](F)(C(F)F)COC2)Nc1nc(-c2cc(F)cc(N3CCC3)c2)cs1] |
| 277 | 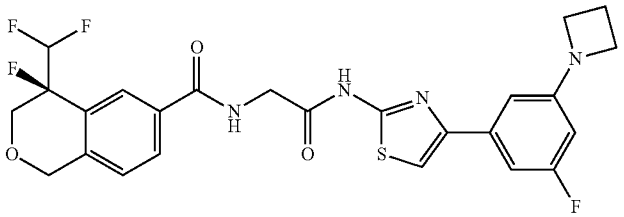 [SMILES: O=C(CNC(=O)c1ccc2c(c1)[C@@](F)(C(F)F)COC2)Nc1nc(-c2cc(F)cc(N3CCC3)c2)cs1] |
| 278 | 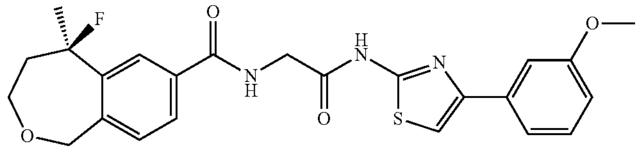 [SMILES: COc1cccc(-c2csc(NC(=O)CNC(=O)c3ccc4c(c3)[C@](C)(F)CCOC4)n2)c1] |
| 279 | 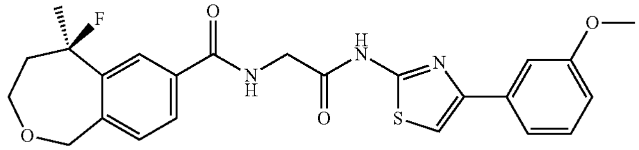 [SMILES: COc1cccc(-c2csc(NC(=O)CNC(=O)c3ccc4c(c3)[C@](C)(F)CCOC4)n2)c1] |
| 280 | 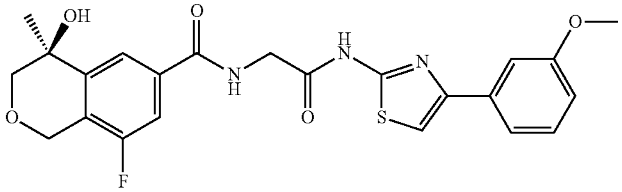 [SMILES: COc1cccc(-c2csc(NC(=O)CNC(=O)c3cc(F)c4c(c3)[C@](C)(O)COC4)n2)c1] |
| 281 | 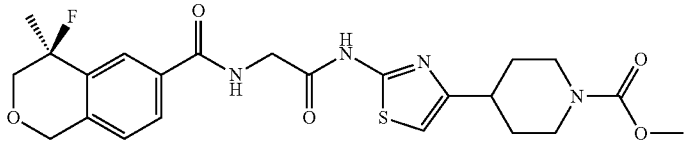 [SMILES: COC(=O)N1CCC(c2csc(NC(=O)CNC(=O)c3ccc4c(c3)[C@](C)(F)COC4)n2)CC1] |

TABLE 3b-continued
| Compounds of the Invention | |
|---|---|
| # | Compound |
| 282 | 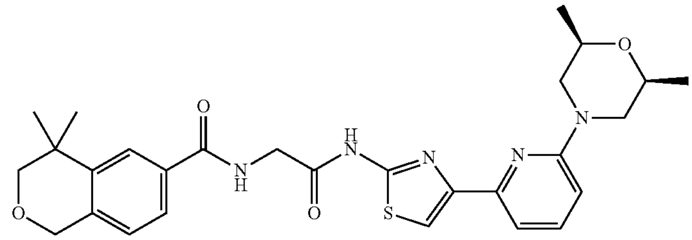 [SMILES: C[C@@H]1CN(c2cccc(-c3csc(NC(=O)CNC(=O)c4ccc5c(c4)C(C)(C)COC5)n3)n2)C[C@H](C)O1] |
| 283 | 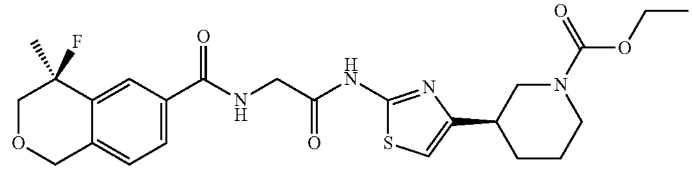 [SMILES: CCOC(=O)N1CCC[C@@H](c2csc(NC(=O)CNC(=O)c3ccc4c(c3)[C@](C)(F)COC4)n2)C1] |
| 284 | 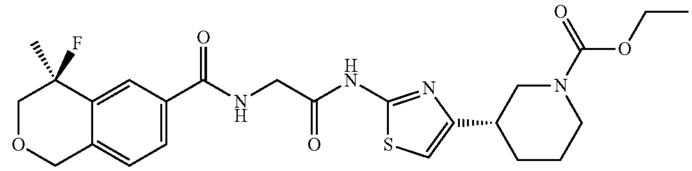 [SMILES: CCOC(=O)N1CCC[C@H](c2csc(NC(=O)CNC(=O)c3ccc4c(c3)[C@](C)(F)COC4)n2)C1] |
| 285 | 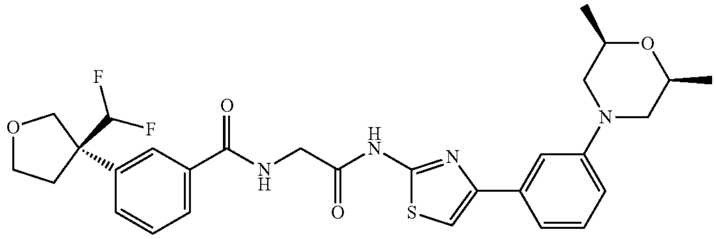 [SMILES: C[C@@H]1CN(c2cccc(-c3csc(NC(=O)CNC(=O)c4cccc([C@]5(C(F)F)CCOC5)c4)n3)c2)C[C@H](C)O1] |
| 286 | 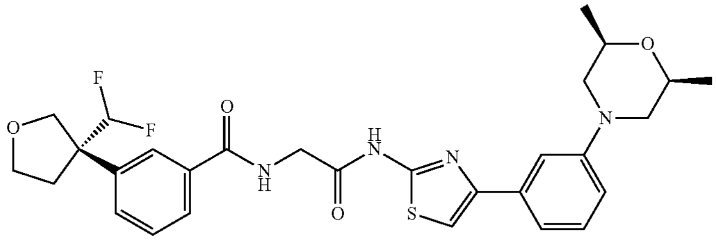 [SMILES: C[C@@H]1CN(c2cccc(-c3csc(NC(=O)CNC(=O)c4cccc([C@@]5(C(F)F)CCOC5)c4)n3)c2)C[C@H](C)O1] |
| 287 | 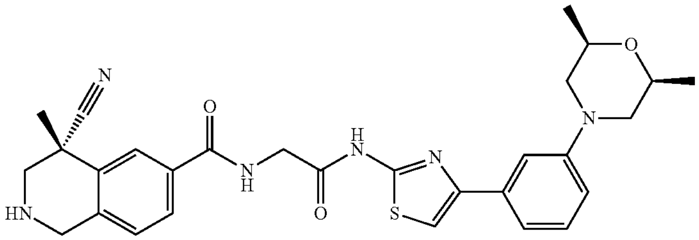 [SMILES: C[C@@H]1CN(c2cccc(-c3csc(NC(=O)CNC(=O)c4ccc5c(c4)[C@@](C)(C#N)CNC5)n3)c2)C[C@H](C)O1] |

TABLE 3b-continued
| Compounds of the Invention | |
|---|---|
| # | Compound |
| 288 | 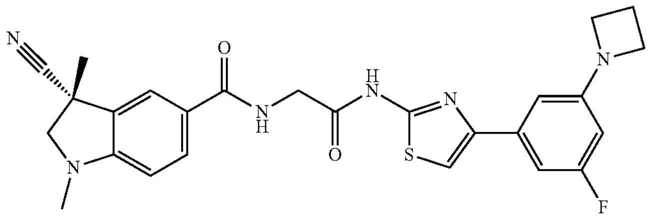 [SMILES: CN1C[C@](C)(C#N)c2cc(C(=O)NCC(=O)Nc3nc(-c4cc(F)cc(N5CCC5)c4)cs3)ccc21] |
| 289 | 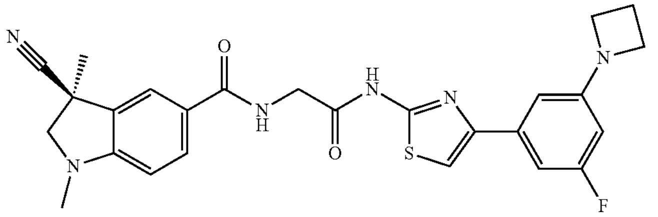 [SMILES: CN1C[C@@](C)(C#N)c2cc(C(=O)NCC(=O)Nc3nc(-c4cc(F)cc(N5CCC5)c4)cs3)ccc21] |
| 290 | 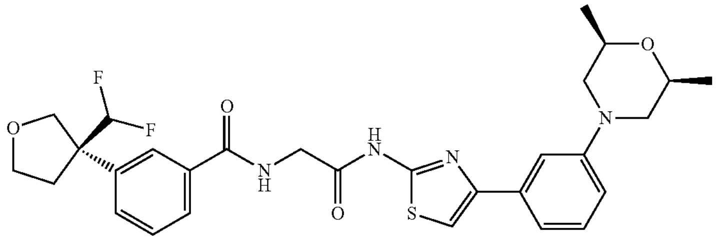 [SMILES: C[C@@H]1CN(c2cccc(-c3csc(NC(=O)CNC(=O)c4cccc([C@]5(C(F)F)CCOC5)c4)n3)c2)C[C@H](C)O1] |
| 291 | 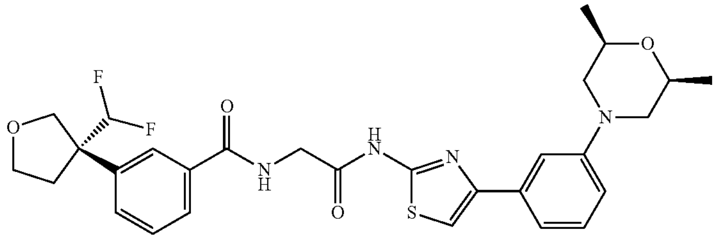 [SMILES: C[C@@H]1CN(c2cccc(-c3csc(NC(=O)CNC(=O)c4cccc([C@@]5(C(F)F)CCOC5)c4)n3)c2)C[C@H](C)O1] |
| 292 | 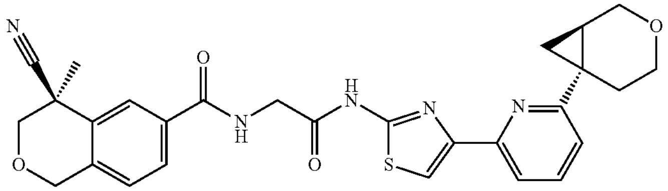 [SMILES: C[C@@]1(C#N)COCc2ccc(C(=O)NCC(=O)Nc3nc(-c4cccc([C@@]56CCOC[C@@H]5C6)n4)cs3)cc21] |
| 293 | 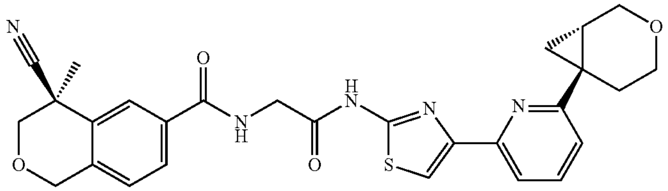 [SMILES: C[C@@]1(C#N)COCc2ccc(C(=O)NCC(=O)Nc3nc(-c4cccc([C@]56CCOC[C@H]5C6)n4)cs3)cc21] |
| 294 | 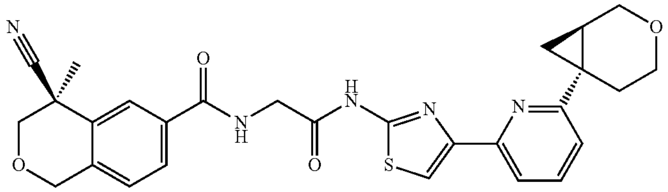 [SMILES: C[C@@]1(C#N)COCc2ccc(C(=O)NCC(=O)Nc3nc(-c4cccc([C@@]56CCOC[C@@H]5C6)n4)cs3)cc21] |

TABLE 3b-continued
Compounds of the Invention
| # | Compound |
|---|---|
| 295 | 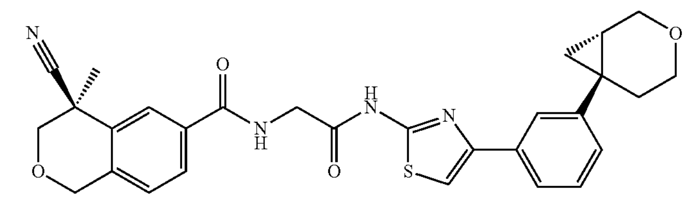 [SMILES: C[C@@]1(C#N)COCc2ccc(C(=O)NCC(=O)Nc3nc(-c4cccc([C@]56CCOC[C@H]5C6)c4)cs3)cc21] |
| 296 | 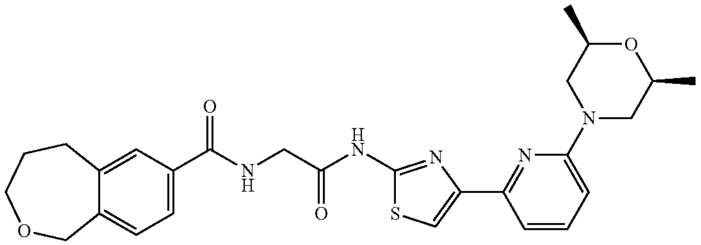 [SMILES: C[C@@H]1CN(c2cccc(-c3csc(NC(=O)CNC(=O)c4ccc5c(c4)CCCOC5)n3)n2)C[C@H](C)O1] |
| 297 | 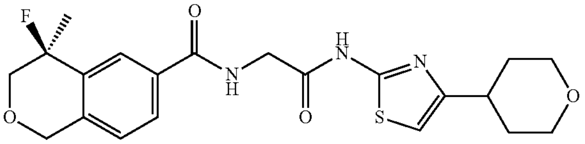 [SMILES: C[C@@]1(F)COCc2ccc(C(=O)NCC(=O)Nc3nc(C4CCOCC4)cs3)cc21] |
| 298 | 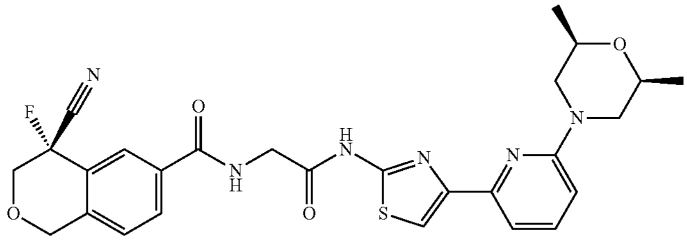 [SMILES: C[C@@H]1CN(c2cccc(-c3csc(NC(=O)CNC(=O)c4ccc5c(c4)[C@](F)(C#N)COC5)n3)n2)C[C@H](C)O1] |
| 299 | 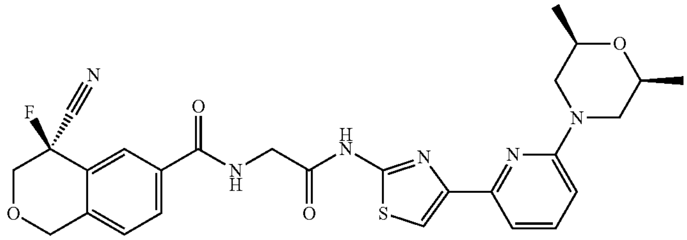 [SMILES: C[C@@H]1CN(c2cccc(-c3csc(NC(=O)CNC(=O)c4ccc5c(c4)[C@@](F)(C#N)COC5)n3)n2)C[C@H](C)O1] |
| 300 | 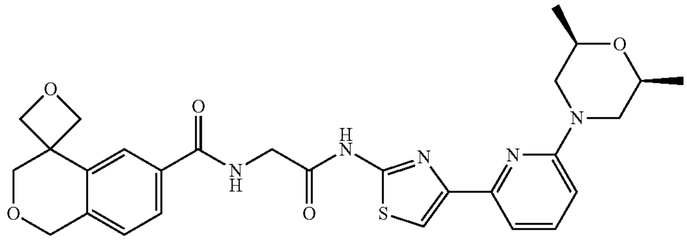 |
| 301 | 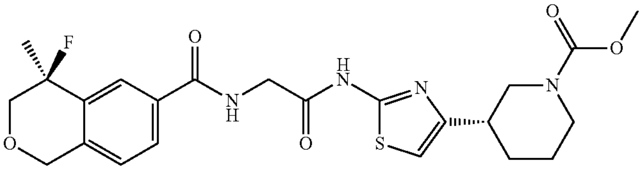 [SMILES: COC(=O)N1CCC[C@H](c2csc(NC(=O)CNC(=O)c3ccc4c(c3)[C@](C)(F)COC4)n2)C1] |

TABLE 3b-continued
| Compounds of the Invention | |
|---|---|
| # | Compound |
| 302 | 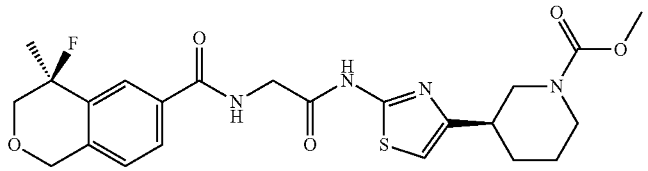 [SMILES: COC(=O)N1CCC[C@@H](c2csc(NC(=O)CNC(=O)c3ccc4c(c3)[C@](C)(F)COC4)n2)C1] |
| 303 | 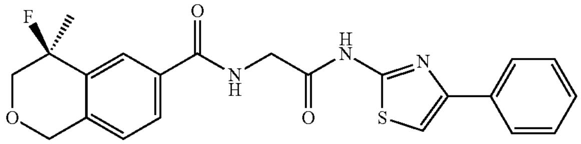 [SMILES: C[C@@]1(F)COCc2ccc(C(=O)NCC(=O)Nc3nc(-c4ccccc4)cs3)cc21] |
| 304 | 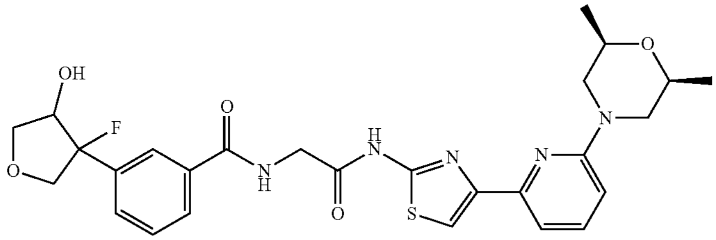 [SMILES: C[C@@H]1CN(c2cccc(-c3csc(NC(=O)CNC(=O)c4cccc(C5(F)COCC5O)c4)n3)n2)C[C@H](C)O1] |
| 305 | 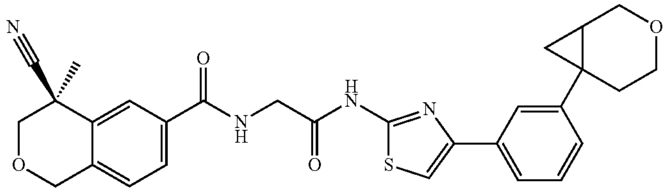 [SMILES: C[C@@]1(C#N)COCc2ccc(C(=O)NCC(=O)Nc3nc(-c4cccc(C56CCOCC5C6)c4)cs3)cc21] |
| 306 | 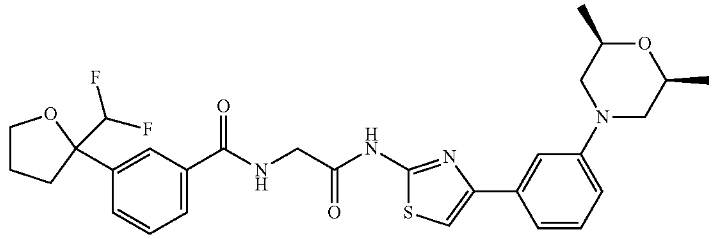 [SMILES: C[C@@H]1CN(c2cccc(-c3csc(NC(=O)CNC(=O)c4cccc(C5(C(F)F)CCCO5)c4)n3)c2)C[C@H](C)O1] |
| 307 | 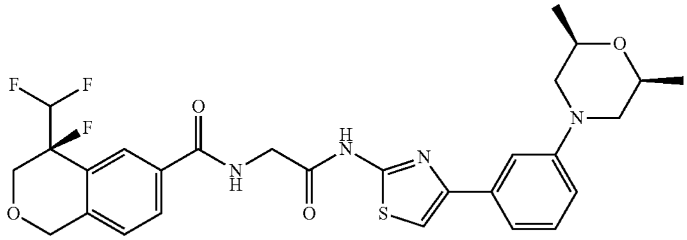 [SMILES: C[C@@H]1CN(c2cccc(-c3csc(NC(=O)CNC(=O)c4ccc5c(c4)[C@@](F)(C(F)F)COC5)n3)c2)C[C@H](C)O1] |
| 308 | 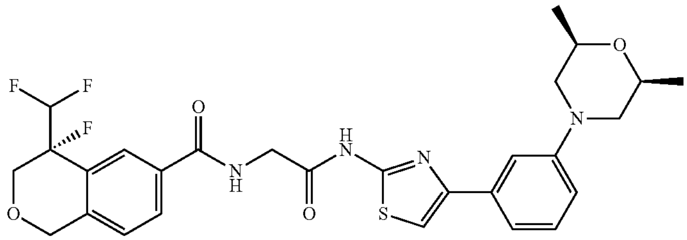 |

TABLE 3b-continued
Compounds of the Invention
| # | Compound |
|---|---|
| 309 | 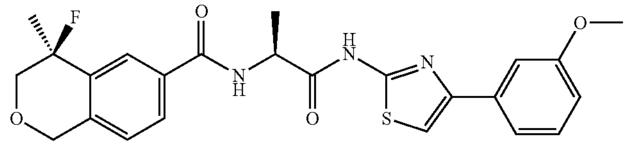 [SMILES: COc1cccc(-c2csc(NC(=O)[C@H](C)NC(=O)c3ccc4c(c3)[C@](C)(F)COC4)n2)c1] |
| 310 | 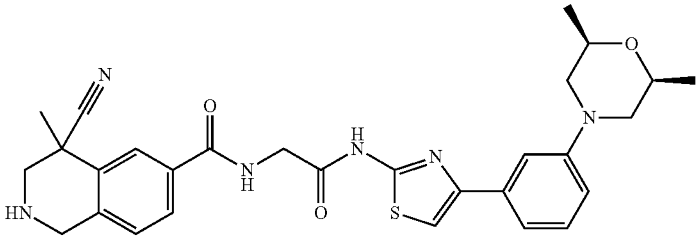 [SMILES: C[C@@H]1CN(c2cccc(-c3csc(NC(=O)CNC(=O)c4ccc5c(c4)C(C)(C#N)CNC5)n3)c2)C[C@H](C)O1] |
| 311 | 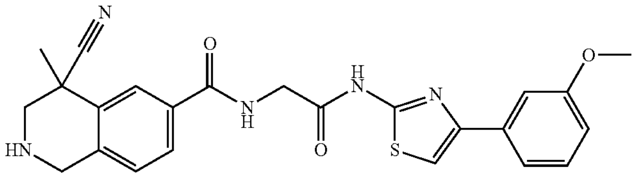 [SMILES: COc1cccc(-c2csc(NC(=O)CNC(=O)c3ccc4c(c3)C(C)(C#N)CNC4)n2)c1] |
| 312 | 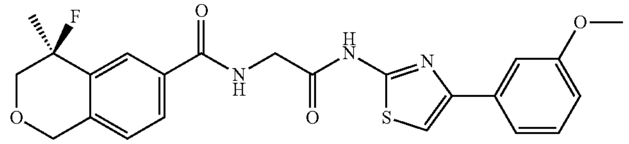 [SMILES: COc1cccc(-c2csc(NC(=O)CNC(=O)c3ccc4c(c3)[C@](C)(F)COC4)n2)c1] |
| 313 | 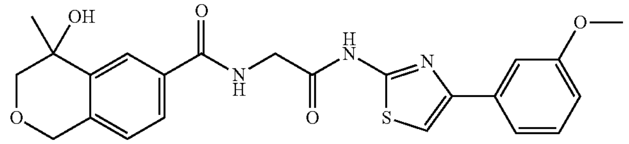 [SMILES: COc1cccc(-c2csc(NC(=O)CNC(=O)c3ccc4c(c3)C(C)(O)COC4)n2)c1] |
| 314 | 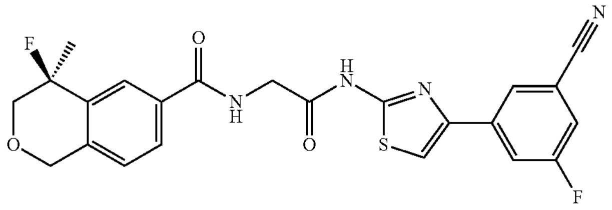 [SMILES: C[C@@]1(F)COCc2ccc(C(=O)NCC(=O)Nc3nc(-c4cc(F)cc(C#N)c4)cs3)cc21] |
| 315 | 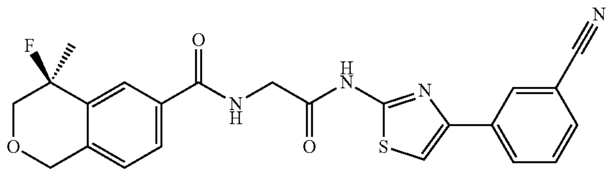 [SMILES: C[C@@]1(F)COCc2ccc(C(=O)NCC(=O)Nc3nc(-c4cccc(C#N)c4)cs3)cc21] |
| 316 | 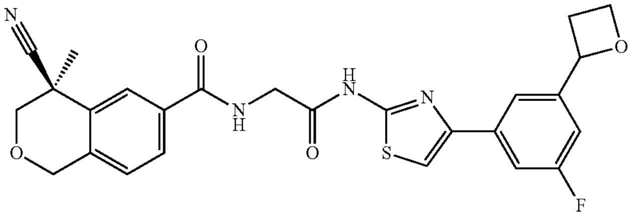 [SMILES: C[C@@]1(C#N)COCc2ccc(C(=O)NCC(=O)Nc3nc(-c4cc(F)cc(C5CCO5)c4)cs3)cc21] |

TABLE 3b-continued
| Compounds of the Invention | |
|---|---|
| # | Compound |
| 317 | 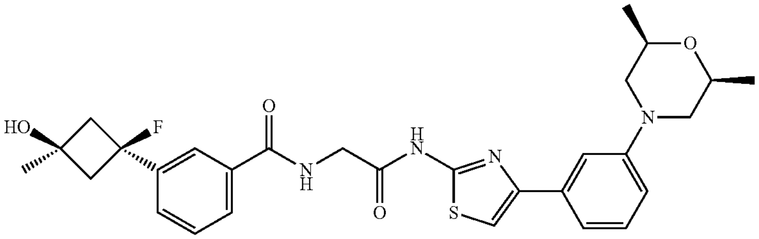 |
| 318 | 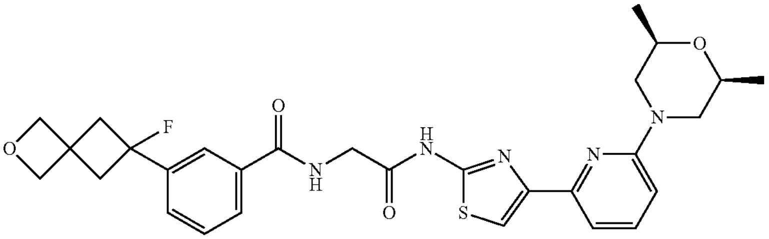 [SMILES: C[C@@H]1CN(c2cccc(-c3csc(NC(=O)CNC(=O)c4cccc(C5(F)CC6(COC6)C5)c4)n3)n2)C[C@H](C)O1] |
| 319 | 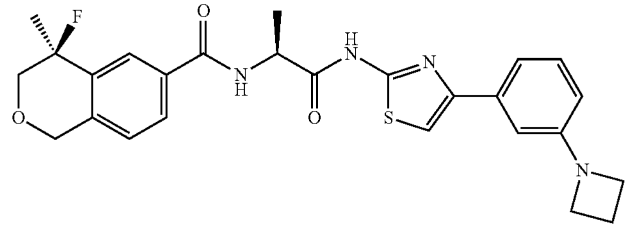 [SMILES: C[C@H](NC(=O)c1ccc2c(c1)[C@](C)(F)COC2)C(=O)Nc1nc(-c2cccc(N3CCC3)c2)cs1] |
| 320 | 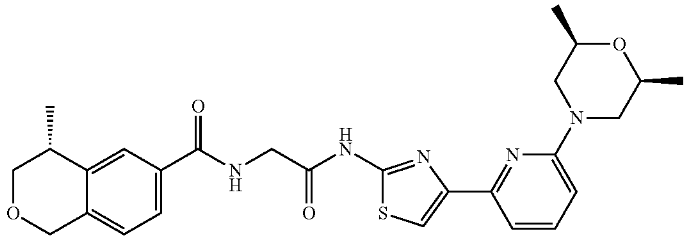 |
| 321 | 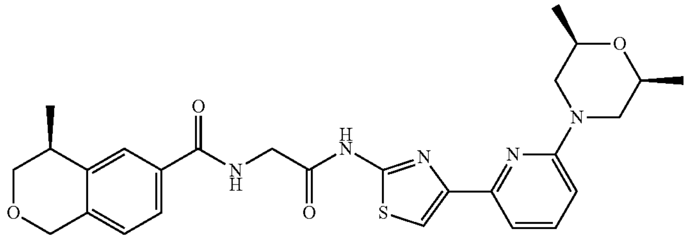 [SMILES: C[C@@H]1CN(c2cccc(-c3csc(NC(=O)CNC(=O)c4ccc5c(c4)[C@H](C)COC5)n3)n2)C[C@H](C)O1] |
| 322 | 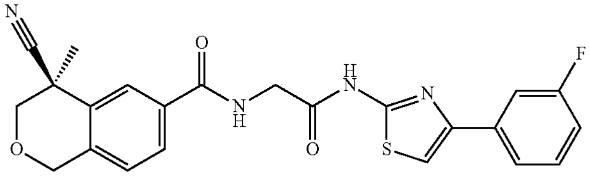 [SMILES: C[C@@]1(C#N)COCc2ccc(C(=O)NCC(=O)Nc3nc(-c4cccc(F)c4)cs3)cc21] |

TABLE 3b-continued
| # | Compounds of the Invention<br>Compound |
|---|---|
| 323 | 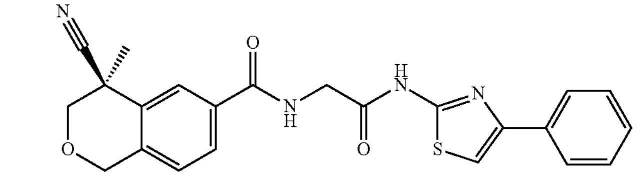 [SMILES: C[C@@]1(C#N)COCc2ccc(C(=O)NCC(=O)Nc3nc(-c4ccccc4)cs3)cc21] |
| 324 | 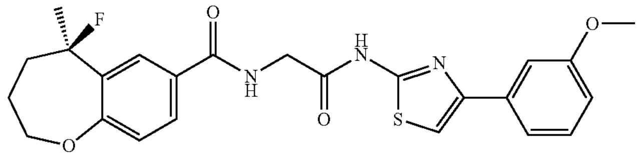 [SMILES: COc1cccc(-c2csc(NC(=O)CNC(=O)c3ccc4c(c3)[C@](C)(F)CCCO4)n2)c1] |
| 325 | 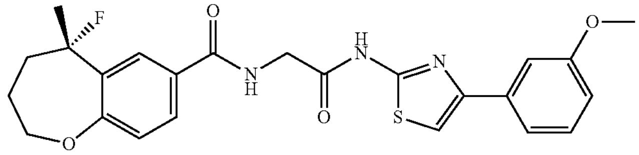 [SMILES: COc1cccc(-c2csc(NC(=O)CNC(=O)c3ccc4c(c3)[C@@](C)(F)CCCO4)n2)c1] |
| 326 | 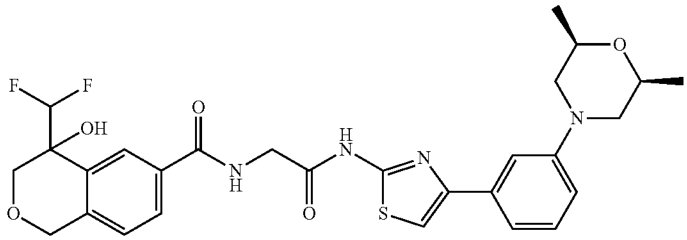 [SMILES: C[C@@H]1CN(c2cccc(-c3csc(NC(=O)CNC(=O)c4ccc5c(c4)C(O)(C(F)F)COC5)n3)c2)C[C@H](C)O1] |
| 327 | 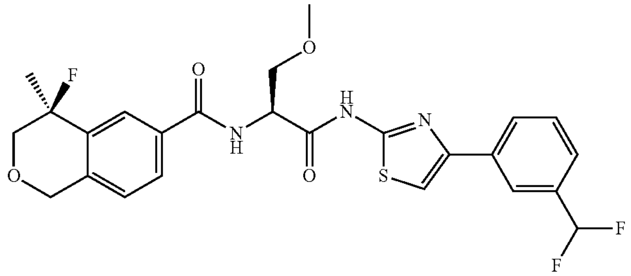 [SMILES: COC[C@H](NC(=O)c1ccc2c(c1)[C@](C)(F)COC2)C(=O)Nc1nc(-c2cccc(C(F)F)c2)cs1] |
| 328 | 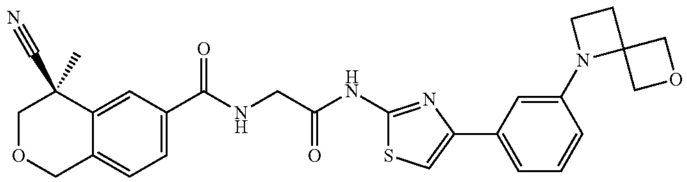 [SMILES: C[C@@]1(C#N)COCc2ccc(C(=O)NCC(=O)Nc3nc(-c4cccc(N5CCC56COC6)c4)cs3)cc21] |
| 329 | 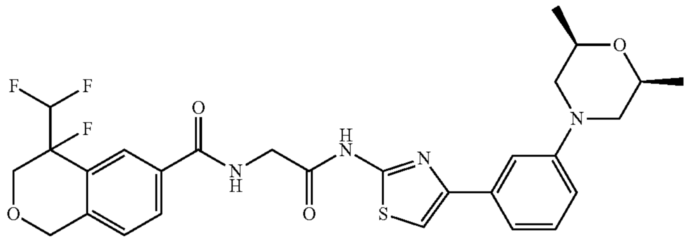 [SMILES: C[C@@H]1CN(c2cccc(-c3csc(NC(=O)CNC(=O)c4ccc5c(c4)C(F)(C(F)F)COC5)n3)c2)C[C@H](C)O1] |

TABLE 3b-continued
| Compounds of the Invention | |
|---|---|
| # | Compound |
| 330 | 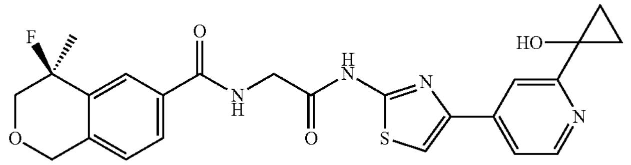 [SMILES: C[C@@]1(F)COCc2ccc(C(=O)NCC(=O)Nc3nc(-c4ccnc(C5(O)CC5)c4)cs3)cc21] |
| 331 | 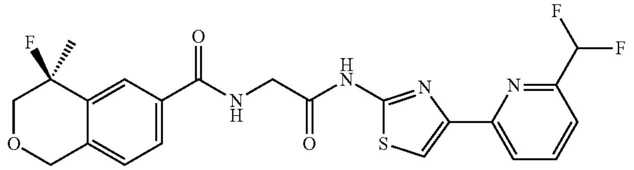 [SMILES: C[C@@]1(F)COCc2ccc(C(=O)NCC(=O)Nc3nc(-c4cccc(C(F)F)n4)cs3)cc21] |
| 332 | 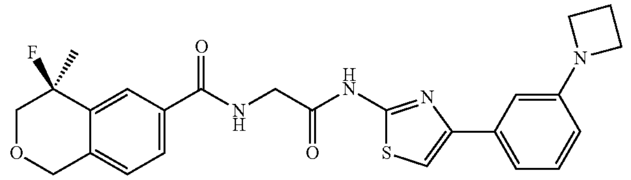 [SMILES: C[C@@]1(F)COCc2ccc(C(=O)NCC(=O)Nc3nc(-c4cccc(N5CCC5)c4)cs3)cc21] |
| 333 | 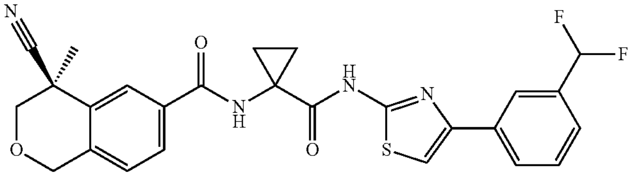 [SMILES: C[C@@]1(C#N)COCc2ccc(C(=O)NC3(C(=O)Nc4nc(-c5cccc(C(F)F)c5)cs4)CC3)cc21] |
| 334 | 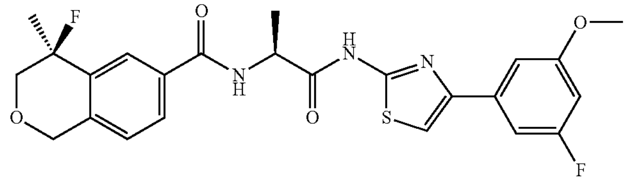 [SMILES: COc1cc(F)cc(-c2csc(NC(=O)[C@H](C)NC(=O)c3ccc4c(c3)[C@](C)(F)COC4)n2)c1] |
| 335 | 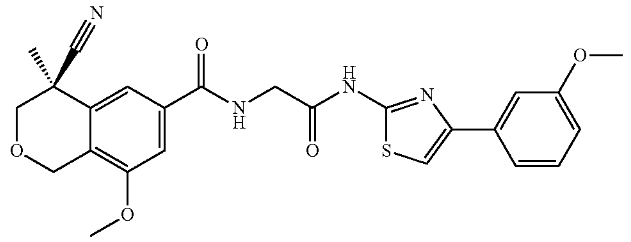 [SMILES: COc1cccc(-c2csc(NC(=O)CNC(=O)c3cc(OC)c4c(c3)[C@](C)(C#N)COC4)n2)c1] |
| 336 | 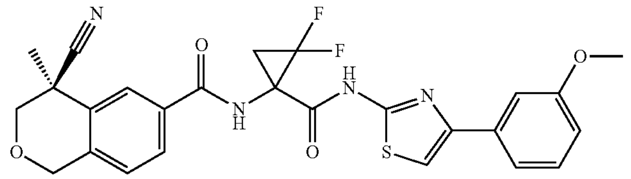 [SMILES: COc1cccc(-c2csc(NC(=O)C3(NC(=O)c4ccc5c(c4)[C@](C)(C#N)COC5)CC3(F)F)n2)c1] |
| 337 | 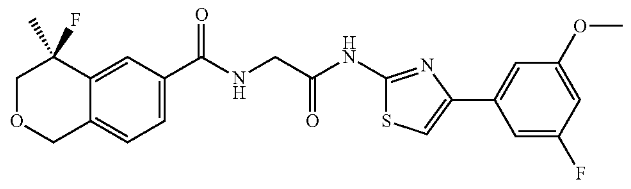 [SMILES: COc1cc(F)cc(-c2csc(NC(=O)CNC(=O)c3ccc4c(c3)[C@](C)(F)COC4)n2)c1] |

TABLE 3b-continued
| Compounds of the Invention | |
|---|---|
| # | Compound |
| 338 | 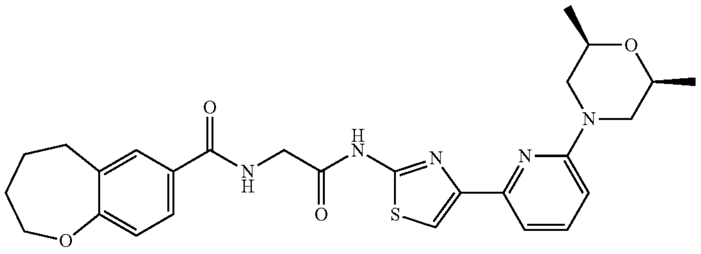 [SMILES: C[C@@H]1CN(c2cccc(-c3csc(NC(=O)CNC(=O)c4ccc5c(c4)CCCCO5)n3)n2)C[C@H](C)O1] |
| 339 | 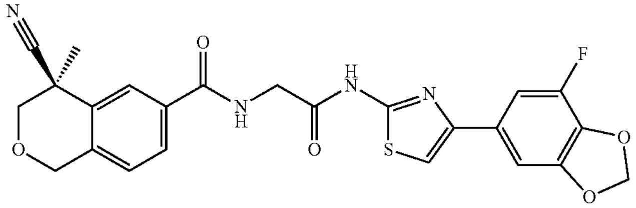 [SMILES: C[C@@]1(C#N)COCc2ccc(C(=O)NCC(=O)Nc3nc(-c4cc(F)c5c(c4)OCO5)cs3)cc21] |
| 340 | 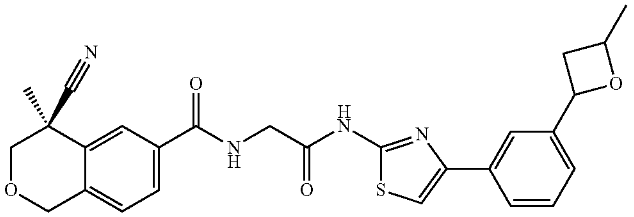 [SMILES: CC1CC(c2cccc(-c3csc(NC(=O)CNC(=O)c4ccc5c(c4)[C@](C)(C#N)COC5)n3)c2)O1] |
| 341 | 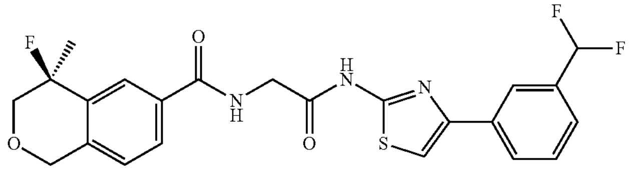 |
| 342 | 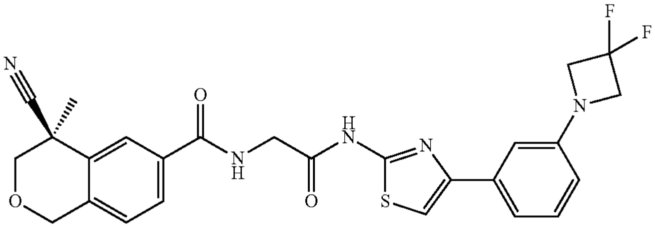 [SMILES: C[C@@]1(C#N)COCc2ccc(C(=O)NCC(=O)Nc3nc(-c4cccc(N5CC(F)(F)C5)c4)cs3)cc21] |
| 343 | 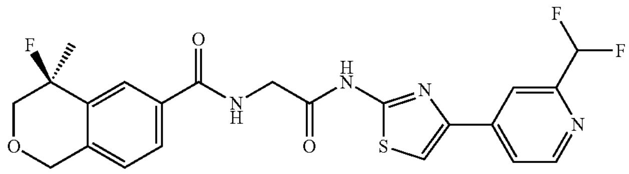 [SMILES: C[C@@]1(F)COCc2ccc(C(=O)NCC(=O)Nc3nc(-c4ccnc(C(F)F)c4)cs3)cc21] |
| 344 | 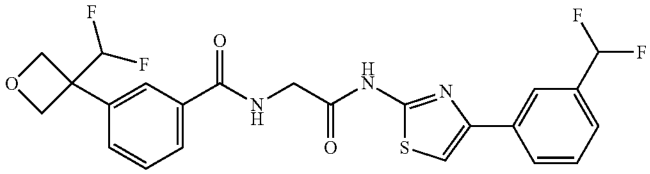 [SMILES: O=C(CNC(=O)c1cccc(C2(C(F)F)COC2)c1)Nc1nc(-c2cccc(C(F)F)c2)cs1] |

TABLE 3b-continued
| Compounds of the Invention | |
|---|---|
| # | Compound |
| 345 | 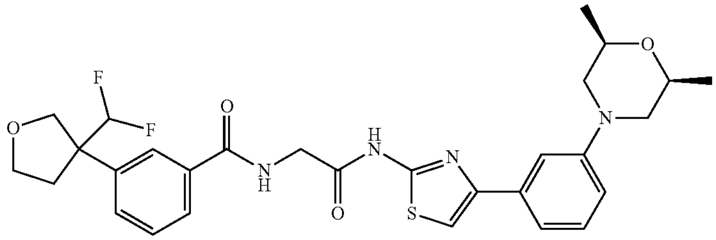 [SMILES: C[C@@H]1CN(c2cccc(-c3csc(NC(=O)CNC(=O)c4cccc(C5(C(F)F)CCOC5)c4)n3)c2)C[C@H](C)O1] |
| 346 | 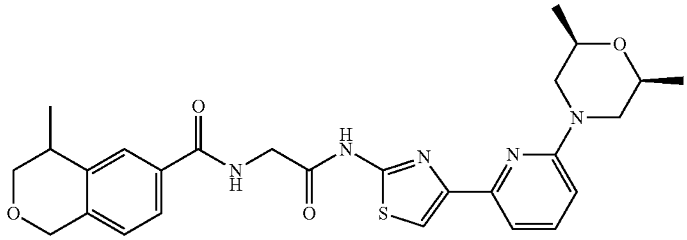 [SMILES: CC1COCc2ccc(C(=O)NCC(=O)Nc3nc(-c4cccc(N5C[C@@H](C)O[C@@H](C)C5)n4)cs3)cc21] |
| 347 | 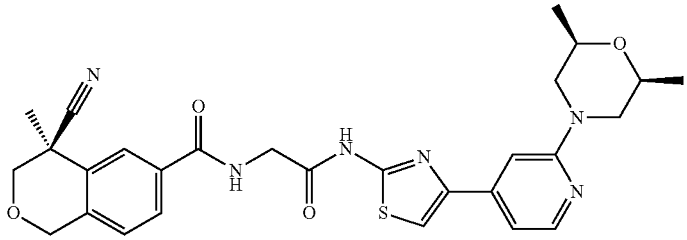 [SMILES: C[C@@H]1CN(c2cc(-c3csc(NC(=O)CNC(=O)c4ccc5c(c4)[C@](C)(C#N)COC5)n3)ccn2)C[C@H](C)O1] |
| 348 | 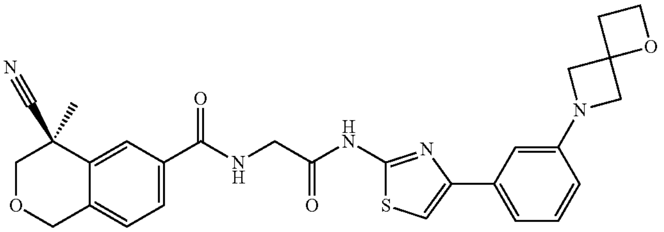 [SMILES: C[C@@]1(C#N)COCc2ccc(C(=O)NCC(=O)Nc3nc(-c4cccc(N5CC6(CCO6)C5)c4)cs3)cc21] |
| 349 | 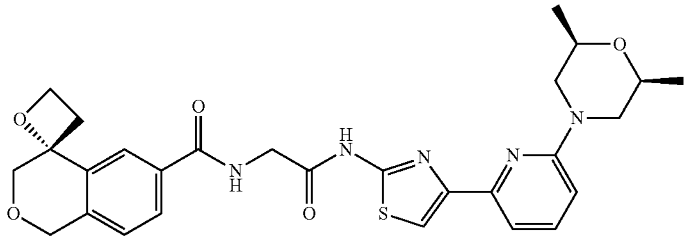 [SMILES: C[C@@H]1CN(c2cccc(-c3csc(NC(=O)CNC(=O)c4ccc5c(c4)[C@]4(CCO4)COC5)n3)n2)C[C@H](C)O1] |
| 350 | 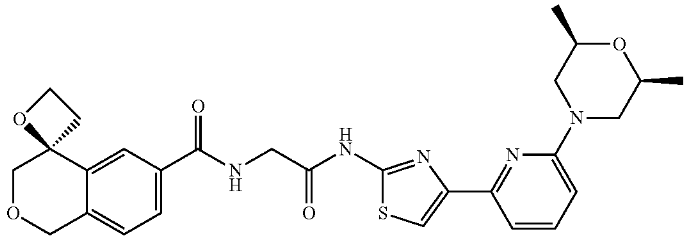 [SMILES: C[C@@H]1CN(c2cccc(-c3csc(NC(=O)CNC(=O)c4ccc5c(c4)[C@@]4(CCO4)COC5)n3)n2)C[C@H](C)O1] |

TABLE 3b-continued
| Compounds of the Invention | |
|---|---|
| # | Compound |
| 351 | 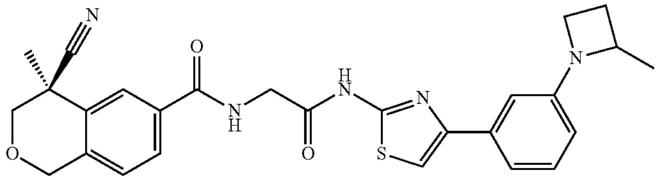 [SMILES: CC1CCN1c1cccc(-c2csc(NC(=O)CNC(=O)c3ccc4c(c3)[C@](C)(C#N)COC4)n2)c1] |
| 352 | 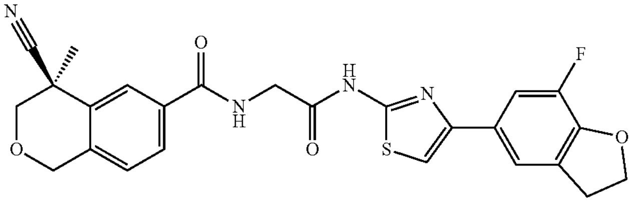 [SMILES: C[C@@]1(C#N)COCc2ccc(C(=O)NCC(=O)Nc3nc(-c4cc(F)c5c(c4)CCO5)cs3)cc21] |
| 353 | 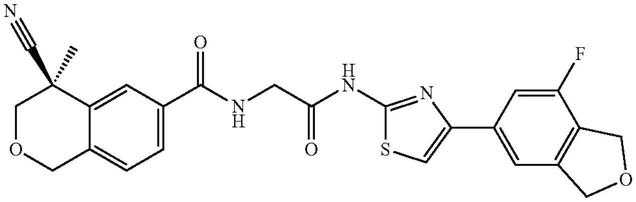 [SMILES: C[C@@]1(C#N)COCc2ccc(C(=O)NCC(=O)Nc3nc(-c4cc(F)c5c(c4)COC5)cs3)cc21] |
| 354 | 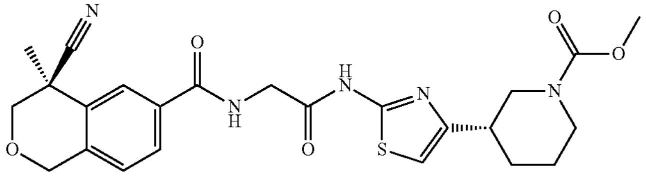 [SMILES: COC(=O)N1CCC[C@H](c2csc(NC(=O)CNC(=O)c3ccc4c(c3)[C@](C)(C#N)COC4)n2)C1] |
| 355 | 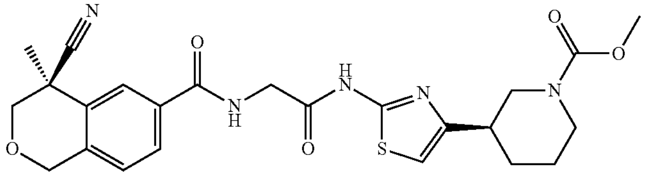 [SMILES: COC(=O)N1CCC[C@@H](c2csc(NC(=O)CNC(=O)c3ccc4c(c3)[C@](C)(C#N)COC4)n2)C1] |
| 356 | 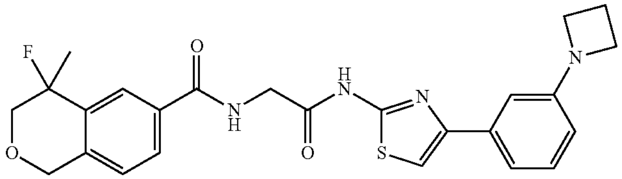 [SMILES: CC1(F)COCc2ccc(C(=O)NCC(=O)Nc3nc(-c4cccc(N5CCC5)c4)cs3)cc21] |
| 357 | 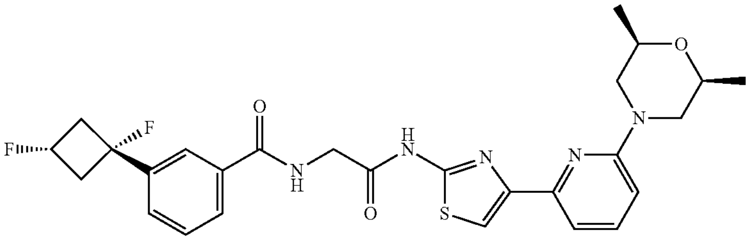 [SMILES: C[C@@H]1CN(c2cccc(-c3csc(NC(=O)CNC(=O)c4cccc([C@]5(F)C[C@@H](F)C5)c4)n3)n2)C[C@H](C)O1] |

TABLE 3b-continued
| Compounds of the Invention | |
|---|---|
| # | Compound |
| 358 | 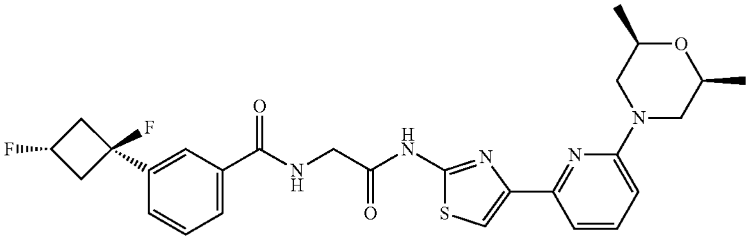 [SMILES: C[C@@H]1CN(c2cccc(-c3csc(NC(=O)CNC(=O)c4cccc([C@]5(F)C[C@H](F)C5)c4)n3)n2)C[C@H](C)O1] |
| 359 | 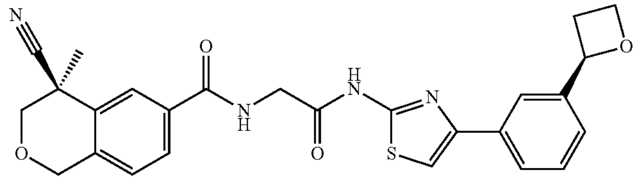 [SMILES: C[C@@]1(C#N)COCc2ccc(C(=O)NCC(=O)Nc3nc(-c4cccc([C@H]5CCO5)c4)cs3)cc21] |
| 360 | 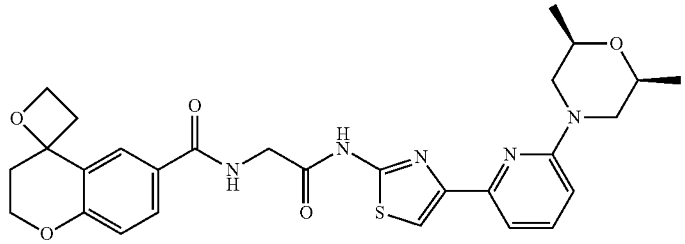 [SMILES: C[C@@H]1CN(c2cccc(-c3csc(NC(=O)CNC(=O)c4ccc5c(c4)C4(CCO5)CCO4)n3)n2)C[C@H](C)O1] |
| 360 | 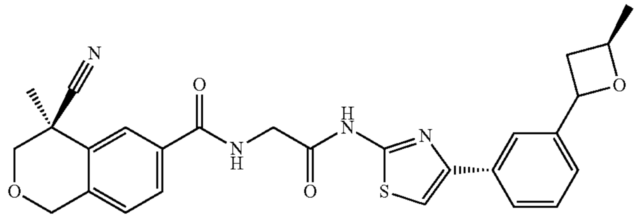 |
| 361 | 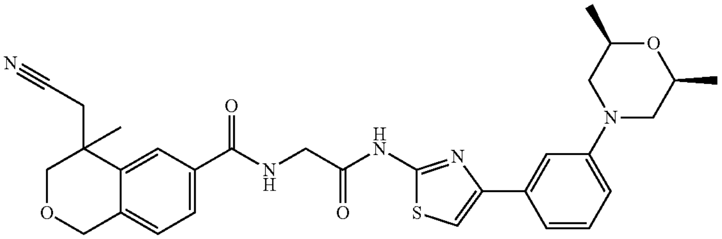 [SMILES: C[C@@H]1CN(c2cccc(-c3csc(NC(=O)CNC(=O)c4ccc5c(c4)C(C)(CC#N)COC5)n3)c2)C[C@H](C)O1] |
| 362 | 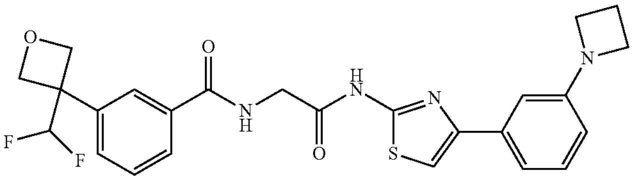 [SMILES: O=C(CNC(=O)c1cccc(C2(C(F)F)COC2)c1)Nc1nc(-c2cccc(N3CCC3)c2)cs1] |
| 363 | 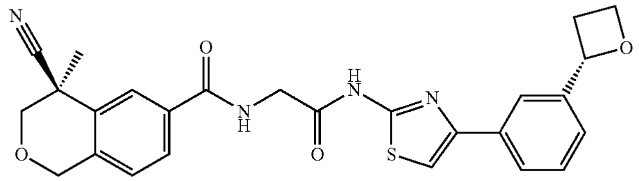 [SMILES: C[C@@]1(C#N)COCc2ccc(C(=O)NCC(=O)Nc3nc(-c4cccc([C@@H]5CCO5)c4)cs3)cc21] |

TABLE 3b-continued
| Compounds of the Invention | |
|---|---|
| # | Compound |
| 364 | 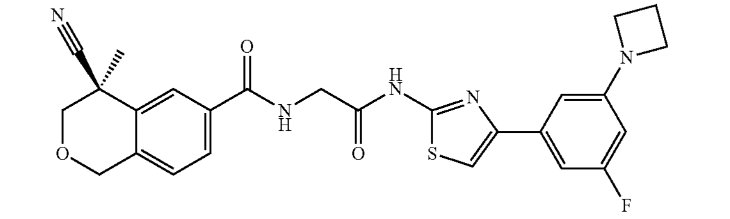 [SMILES: C[C@@]1(C#N)COCc2ccc(C(=O)NCC(=O)Nc3nc(-c4cc(F)cc(N5CCC5)c4)cs3)cc21] |
| 366 | 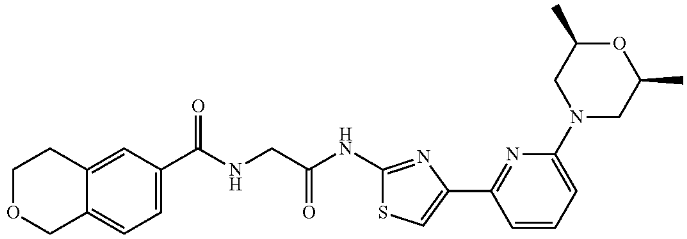 [SMILES: C[C@@H]1CN(c2cccc(-c3csc(NC(=O)CNC(=O)c4ccc5c(c4)CCOC5)n3)n2)C[C@H](C)O1] |
| 367 | 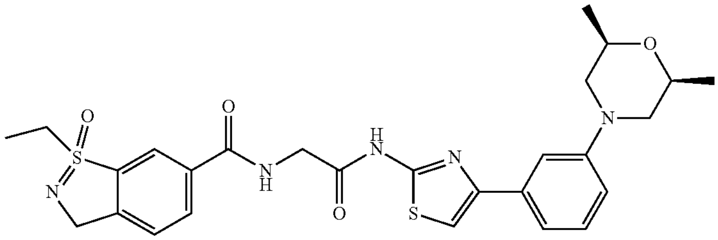 [SMILES: CCS1(=O)=NCc2ccc(C(=O)NCC(=O)Nc3nc(-c4cccc(N5C[C@@H](C)O[C@@H](C)C5)c4)cs3)cc21] |
| 368 | 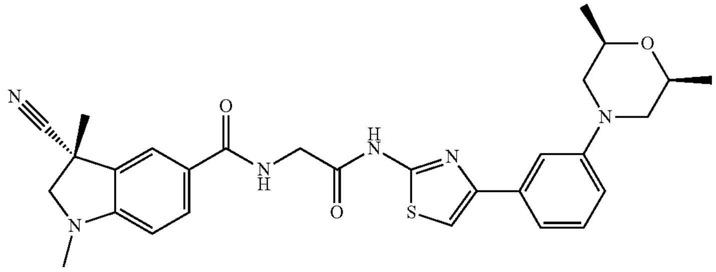 [SMILES: C[C@@H]1CN(c2cccc(-c3csc(NC(=O)CNC(=O)c4ccc5c(c4)[C@@](C)(C#N)CN5C)n3)c2)C[C@H](C)O1] |
| 369 | 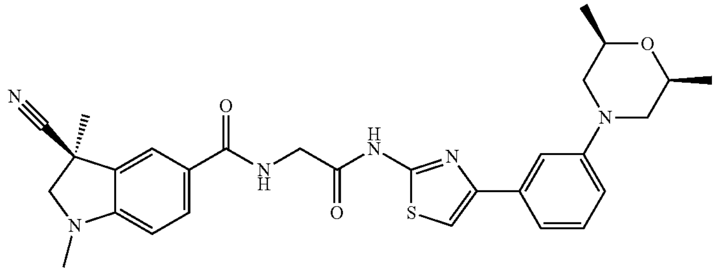 [SMILES: C[C@@H]1CN(c2cccc(-c3csc(NC(=O)CNC(=O)c4ccc5c(c4)[C@](C)(C#N)CN5C)n3)c2)C[C@H](C)O1] |
| 370 | 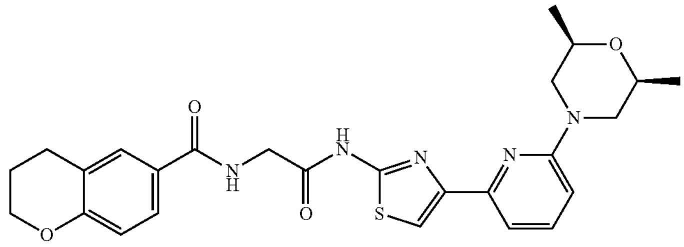 [SMILES: C[C@@H]1CN(c2cccc(-c3csc(NC(=O)CNC(=O)c4ccc5c(c4)CCCO5)n3)n2)C[C@H](C)O1] |

TABLE 3b-continued
| Compounds of the Invention | |
|---|---|
| # | Compound |
| 371 | 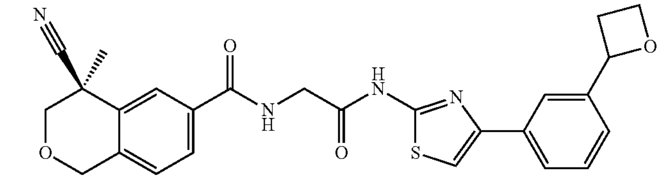 |
| 372 | 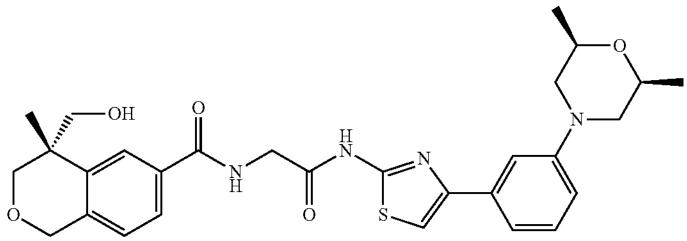 [SMILES: C[C@@H]1CN(c2cccc(-c3csc(NC(=O)CNC(=O)c4ccc5c(c4)[C@@](C)(CO)COC5)n3)c2)C[C@H](C)O1] |
| 373 | 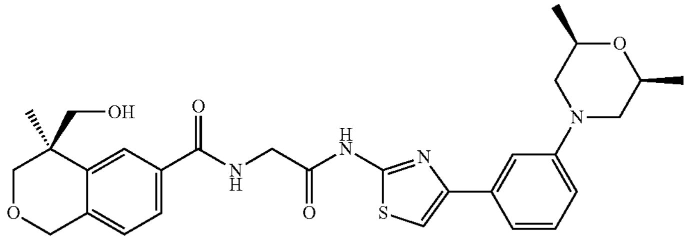 [SMILES: C[C@@H]1CN(c2cccc(-c3csc(NC(=O)CNC(=O)c4ccc5c(c4)[C@](C)(CO)COC5)n3)c2)C[C@H](C)O1] |
| 374 | 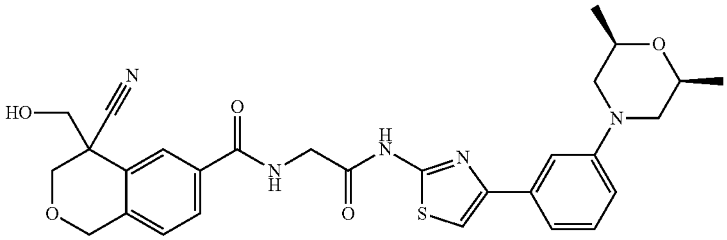 [SMILES: C[C@@H]1CN(c2cccc(-c3csc(NC(=O)CNC(=O)c4ccc5c(c4)C(C#N)(CO)COC5)n3)c2)C[C@H](C)O1] |
| 375 | 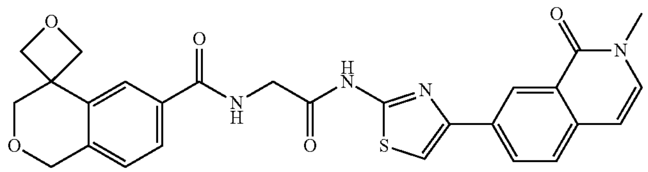 [SMILES: Cn1ccc2ccc(-c3csc(NC(=O)CNC(=O)c4ccc5c(c4)C4(COC5)COC4)n3)cc2c1=O] |
| 376 | 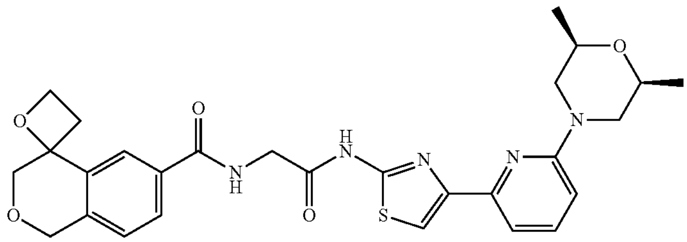 [SMILES: C[C@@H]1CN(c2cccc(-c3csc(NC(=O)CNC(=O)c4ccc5c(c4)C4(CCO4)COC5)n3)n2)C[C@H](C)O1] |

TABLE 3b-continued
| # | Compound |
|---|---|
| 377 | 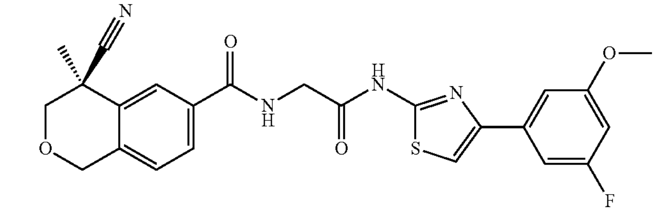 [SMILES: COc1cc(F)cc(-c2csc(NC(=O)CNC(=O)c3ccc4c(c3)[C@](C)(C#N)COC4)n2)c1] |
| 378 | 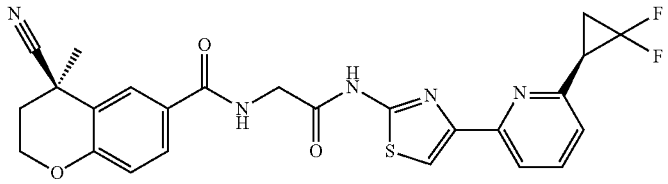 [SMILES: C[C@@]1(C#N)CCOc2ccc(C(=O)NCC(=O)Nc3nc(-c4cccc([C@H]5CC5(F)F)n4)cs3)cc21] |
| 379 | 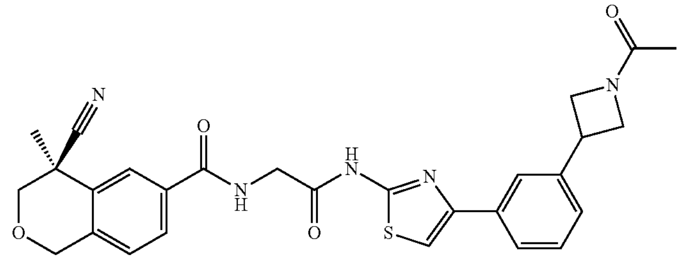 [SMILES: CC(=O)N1CC(c2cccc(-c3csc(NC(=O)CNC(=O)c4ccc5c(c4)[C@](C)(C#N)COC5)n3)c2)C1] |
| 380 | 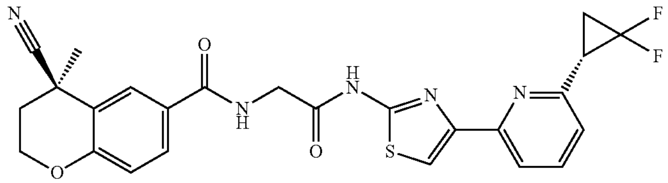 [SMILES: C[C@@]1(C#N)CCOc2ccc(C(=O)NCC(=O)Nc3nc(-c4cccc([C@@H]5CC5(F)F)n4)cs3)cc21] |
| 381 | 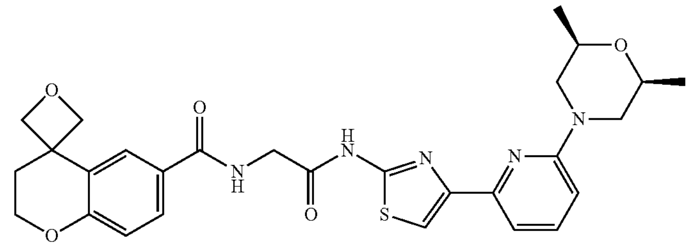 |
| 382 | 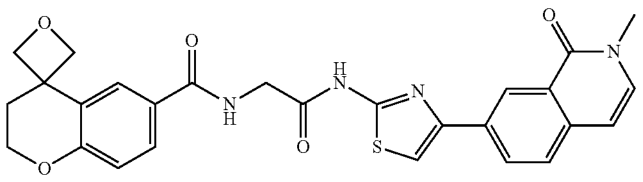 [SMILES: Cn1ccc2ccc(-c3csc(NC(=O)CNC(=O)c4ccc5c(c4)C4(CCO5)COC4)n3)cc2c1=O] |
| 383 | 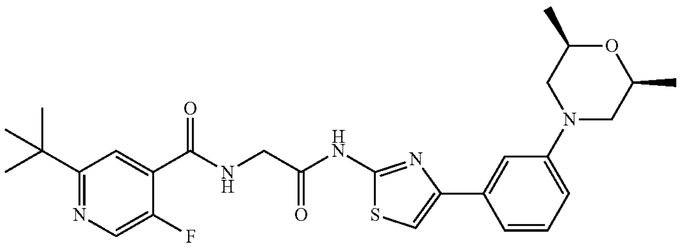 [SMILES: C[C@@H]1CN(c2cccc(-c3csc(NC(=O)CNC(=O)c4cc(C(C)(C)C)ncc4F)n3)c2)C[C@H](C)O1] |
Compounds of the Invention TABLE 3b-continued
| Compounds of the Invention | |
|---|---|
| # | Compound |
| 384 | 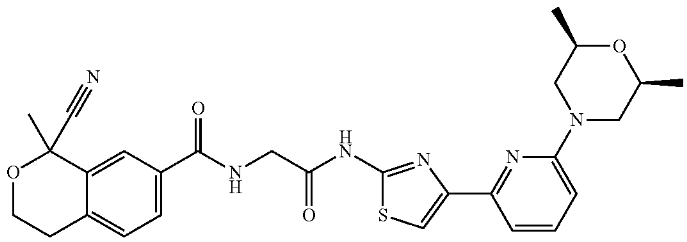 [SMILES: C[C@@H]1CN(c2cccc(-c3csc(NC(=O)CNC(=O)c4ccc5c(c4)C(C)(C#N)OCC5)n3)n2)C[C@H](C)O1] |
| 385 | 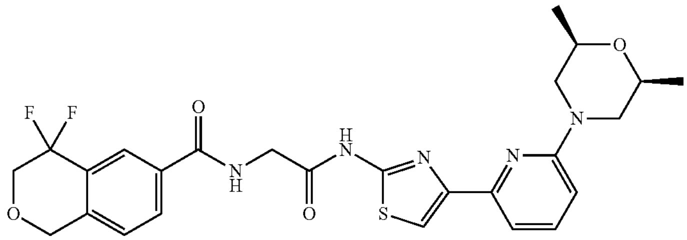 |
| 386 | 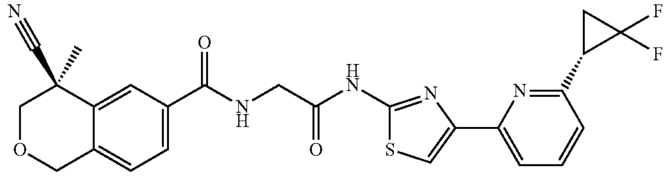 [SMILES: C[C@@]1(C#N)COCc2ccc(C(=O)NCC(=O)Nc3nc(-c4cccc([C@@H]5CC5(F)F)n4)cs3)cc21] |
| 387 | 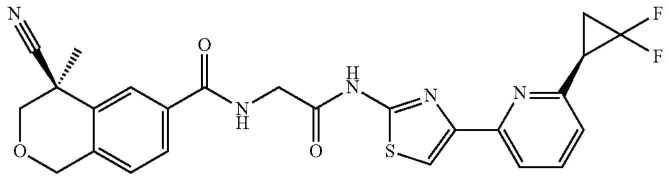 [SMILES: C[C@@]1(C#N)COCc2ccc(C(=O)NCC(=O)Nc3nc(-c4cccc([C@H]5CC5(F)F)n4)cs3)cc21] |
| 388 | 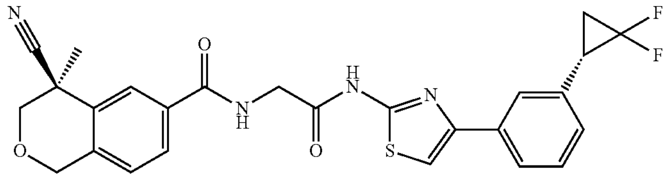 [SMILES: C[C@@]1(C#N)COCc2ccc(C(=O)NCC(=O)Nc3nc(-c4cccc([C@@H]5CC5(F)F)c4)cs3)cc21] |
| 389 | 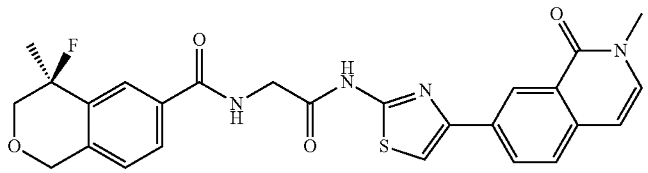 [SMILES: Cn1ccc2ccc(-c3csc(NC(=O)CNC(=O)c4ccc5c(c4)[C@](C)(F)COC5)n3)cc2c1=O] |
| 390 | 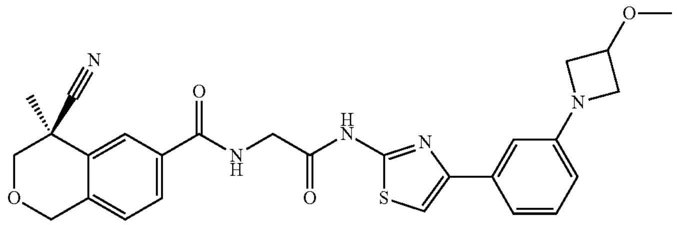 [SMILES: COC1CN(c2cccc(-c3csc(NC(=O)CNC(=O)c4ccc5c(c4)[C@](C)(C#N)COC5)n3)c2)C1] |

TABLE 3b-continued
| Compounds of the Invention | |
|---|---|
| # | Compound |
| 391 | 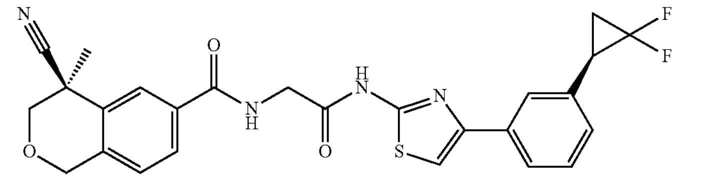 [SMILES: C[C@@]1(C#N)COCc2ccc(C(=O)NCC(=O)Nc3nc(-c4cccc([C@H]5CC5(F)F)c4)cs3)cc21] |
| 392 | 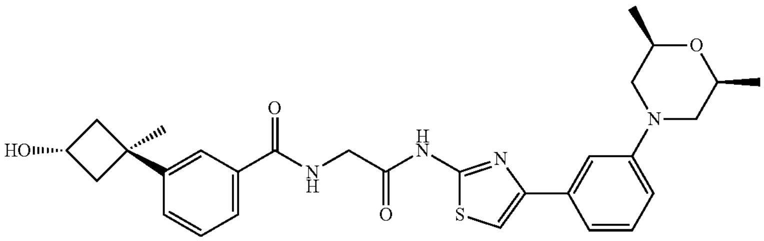 [SMILES: C[C@@H]1CN(c2cccc(-c3csc(NC(=O)CNC(=O)c4cccc([C@]5(C)C[C@@H](O)C5)c4)n3)c2)C[C@H](C)O1] |
| 393 | 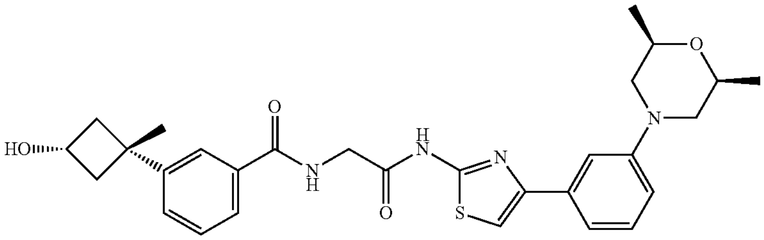 [SMILES: C[C@@H]1CN(c2cccc(-c3csc(NC(=O)CNC(=O)c4cccc([C@]5(C)C[C@H](O)C5)c4)n3)c2)C[C@H](C)O1] |
| 394 | 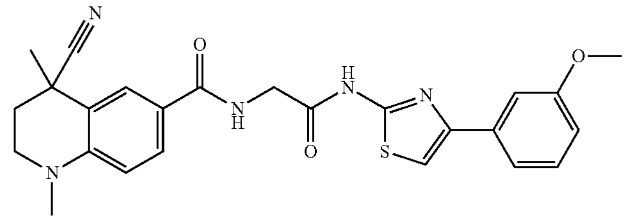 [SMILES: COc1cccc(-c2csc(NC(=O)CNC(=O)c3ccc4c(c3)C(C)(C#N)CCN4C)n2)c1] |
| 395 | 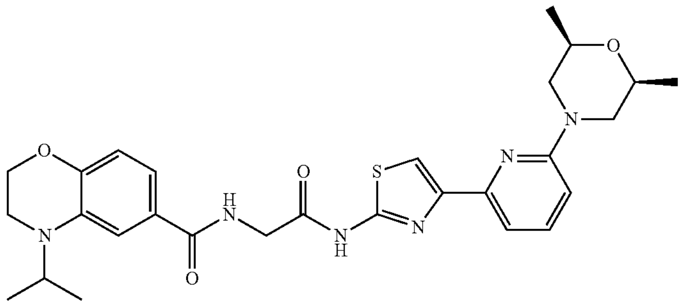 [SMILES: CC(C)N1CCOc2ccc(C(=O)NCC(=O)Nc3nc(-c4cccc(N5C[C@@H](C)O[C@@H](C)C5)n4)cs3)cc21] |
| 396 | 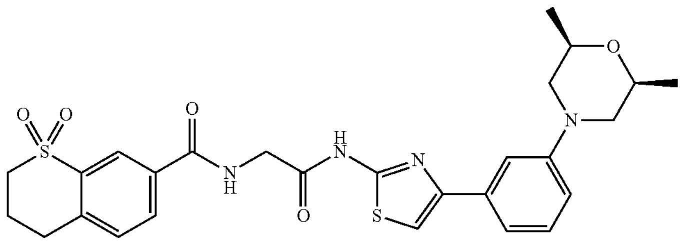 [SMILES: C[C@@H]1CN(c2cccc(-c3csc(NC(=O)CNC(=O)c4ccc5c(c4)S(=O)(=O)CCC5)n3)c2)C[C@H](C)O1] |

TABLE 3b-continued
| # | Compound |
| --- | --- |
| 397 | 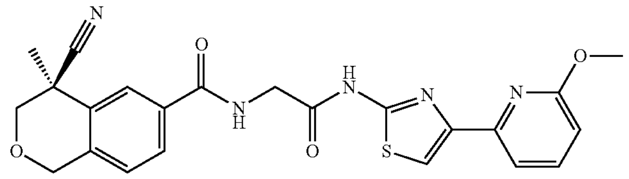 [SMILES: COc1cccc(-c2csc(NC(=O)CNC(=O)c3ccc4c(c3)[C@](C)(C#N)COC4)n2)n1] |
| 398 | 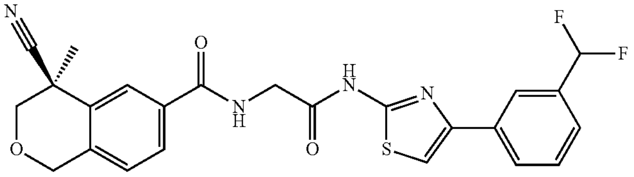 [SMILES: C[C@@]1(C#N)COCc2ccc(C(=O)NCC(=O)Nc3nc(-c4cccc(C(F)F)c4)cs3)cc21] |
| 399 | 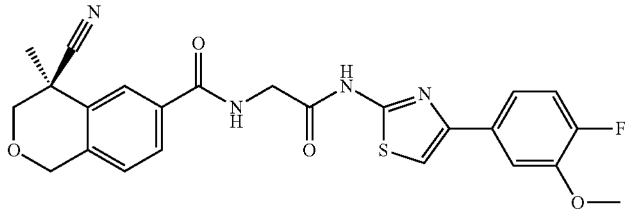 [SMILES: COc1cc(-c2csc(NC(=O)CNC(=O)c3ccc4c(c3)[C@](C)(C#N)COC4)n2)ccc1F] |
| 400 | 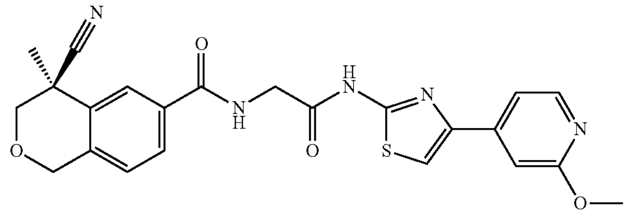 [SMILES: COc1cc(-c2csc(NC(=O)CNC(=O)c3ccc4c(c3)[C@](C)(C#N)COC4)n2)ccn1] |
| 401 | 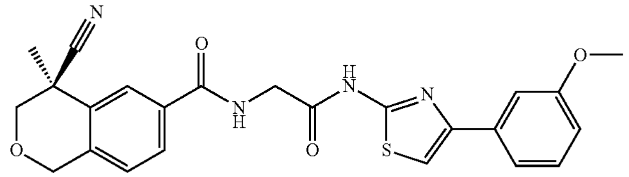 [SMILES: COc1cccc(-c2csc(NC(=O)CNC(=O)c3ccc4c(c3)[C@](C)(C#N)COC4)n2)c1] |
| 402 | 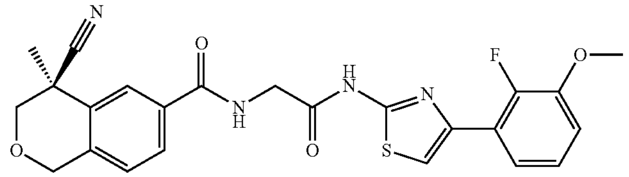 [SMILES: COc1cccc(-c2csc(NC(=O)CNC(=O)c3ccc4c(c3)[C@](C)(C#N)COC4)n2)c1F] |
| 403 | 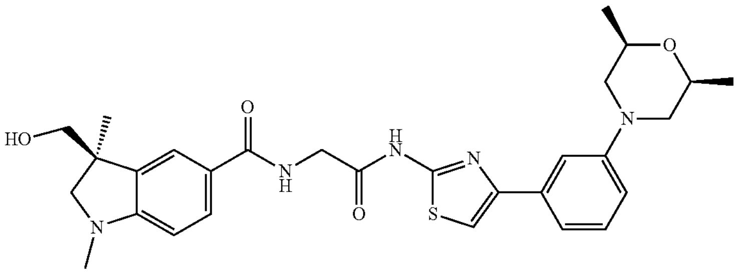 [SMILES: C[C@@H]1CN(c2cccc(-c3csc(NC(=O)CNC(=O)c4ccc5c(c4)[C@](C)(CO)CN5C)n3)c2)C[C@H](C)O1] |

TABLE 3b-continued
| # | Compounds of the Invention<br>Compound |
|---|---|
| 404 | 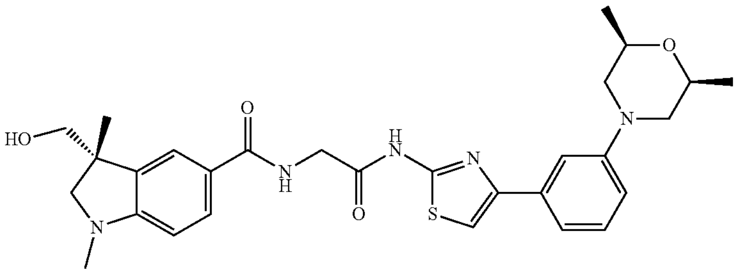 [SMILES: C[C@@H]1CN(c2cccc(-c3csc(NC(=O)CNC(=O)c4ccc5c(c4)[C@@](C)(CO)CN5C)n3)c2)C[C@H](C)O1] |
| 405 | 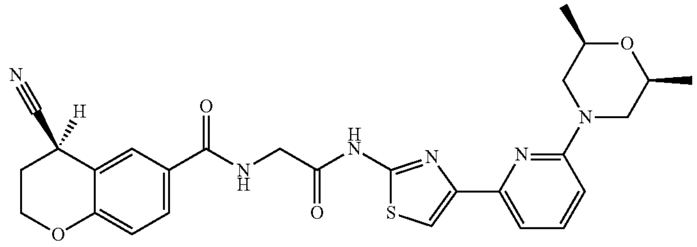 [SMILES: C[C@@H]1CN(c2cccc(-c3csc(NC(=O)CNC(=O)c4ccc5c(c4)[C@H](C#N)CCO5)n3)n2)C[C@H](C)O1] |
| 406 | 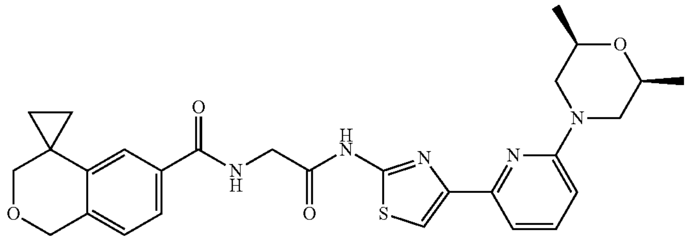 [SMILES: C[C@@H]1CN(c2cccc(-c3csc(NC(=O)CNC(=O)c4ccc5c(c4)C4(CC4)COC5)n3)n2)C[C@H](C)O1] |
| 407 | 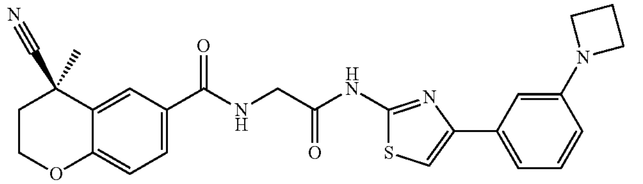 [SMILES: C[C@@]1(C#N)CCOc2ccc(C(=O)NCC(=O)Nc3nc(-c4cccc(N5CCC5)c4)cs3)cc21] |
| 408 | 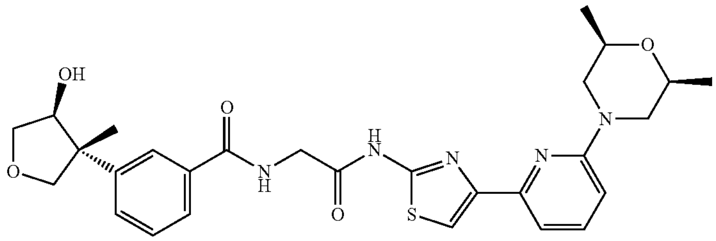 [SMILES: C[C@@H]1CN(c2cccc(-c3csc(NC(=O)CNC(=O)c4cccc([C@]5(C)COC[C@H]5O)c4)n3)n2)C[C@H](C)O1] |
| 409 | 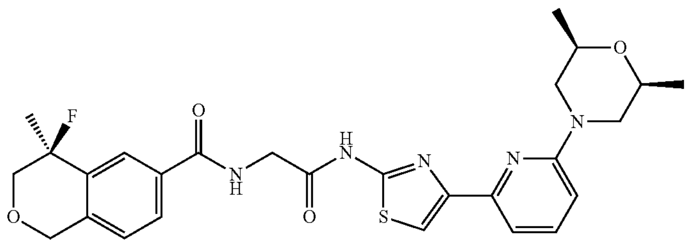 [SMILES: C[C@@H]1CN(c2cccc(-c3csc(NC(=O)CNC(=O)c4ccc5c(c4)[C@](C)(F)COC5)n3)n2)C[C@H](C)O1]

TABLE 3b-continued
| Compounds of the Invention | |
|---|---|
| # | Compound |
| 410 | 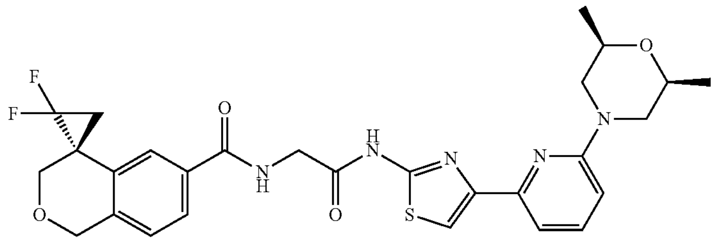 [SMILES: C[C@@H]1CN(c2cccc(-c3csc(NC(=O)CNC(=O)c4ccc5c(c4)[C@@]4(COC5)CC4(F)F)n3)n2)C[C@H](C)O1] |
| 411 | 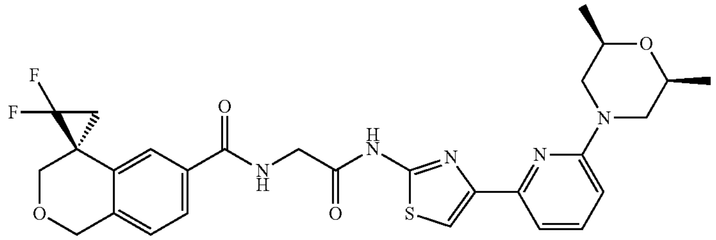 [SMILES: C[C@@H]1CN(c2cccc(-c3csc(NC(=O)CNC(=O)c4ccc5c(c4)[C@]4(COC5)CC4(F)F)n3)n2)C[C@H](C)O1] |
| 412 | 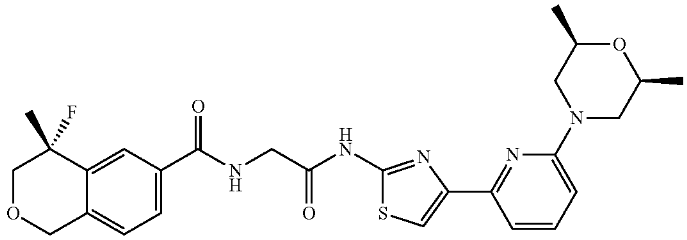 [SMILES: C[C@@H]1CN(c2cccc(-c3csc(NC(=O)CNC(=O)c4ccc5c(c4)[C@@](C)(F)COC5)n3)n2)C[C@H](C)O1] |
| 413 | 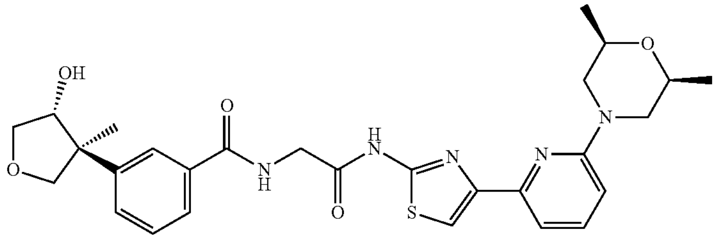 [SMILES: C[C@@H]1CN(c2cccc(-c3csc(NC(=O)CNC(=O)c4cccc([C@@]5(C)COC[C@@H]5O)c4)n3)n2)C[C@H](C)O1] |
| 414 | 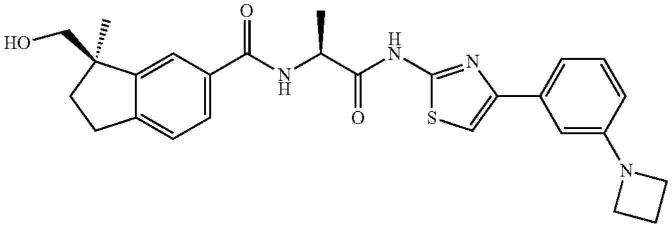 [SMILES: C[C@H](NC(=O)c1ccc2c(c1)[C@](C)(CO)CC2)C(=O)Nc1nc(-c2cccc(N3CCC3)c2)cs1] |
| 415 | 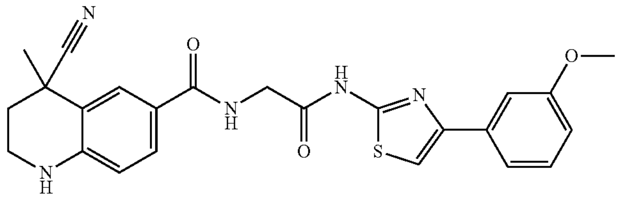 [SMILES: COc1cccc(-c2csc(NC(=O)CNC(=O)c3ccc4c(c3)C(C)(C#N)CCN4)n2)c1] |

TABLE 3b-continued
| Compounds of the Invention | |
|---|---|
| # | Compound |
| 416 | 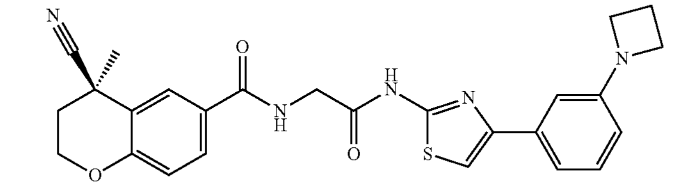 [SMILES: C[C@@]1(C#N)CCOc2ccc(C(=O)NCC(=O)Nc3nc(-c4cccc(N5CCC5)c4)cs3)cc21] |
| 417 | 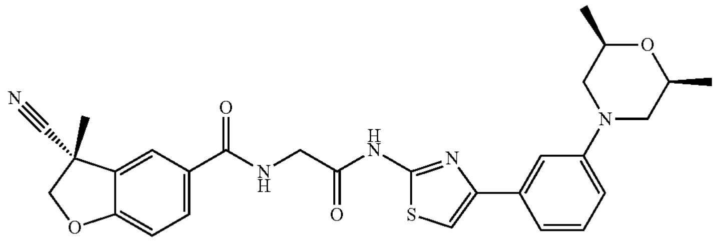 [SMILES: C[C@@H]1CN(c2cccc(-c3csc(NC(=O)CNC(=O)c4ccc5c(c4)[C@@](C)(C#N)CO5)n3)c2)C[C@H](C)O1] |
| 418 | 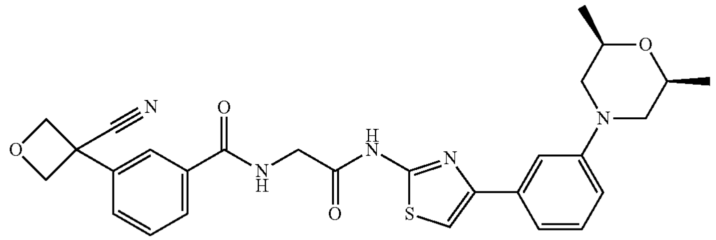 [SMILES: C[C@@H]1CN(c2cccc(-c3csc(NC(=O)CNC(=O)c4cccc(C5(C#N)COC5)c4)n3)c2)C[C@H](C)O1] |
| 419 | 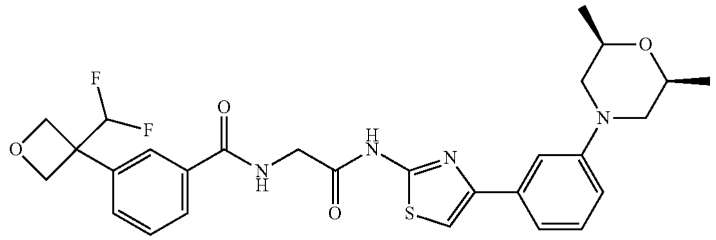 [SMILES: C[C@@H]1CN(c2cccc(-c3csc(NC(=O)CNC(=O)c4cccc(C5(C(F)F)COC5)c4)n3)c2)C[C@H](C)O1] |
| 420 | 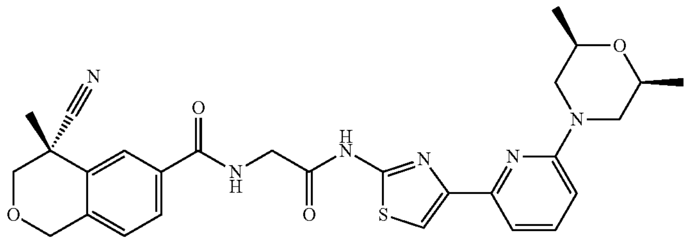 [SMILES: C[C@@H]1CN(c2cccc(-c3csc(NC(=O)CNC(=O)c4ccc5c(c4)[C@@](C)(C#N)COC5)n3)n2)C[C@H](C)O1] |
| 421 | 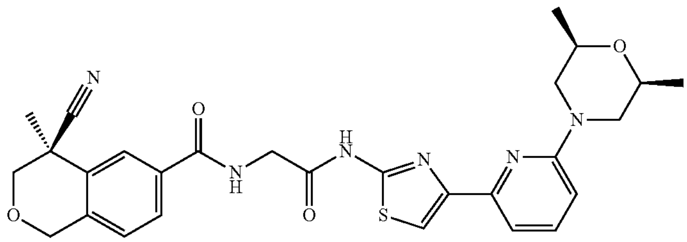 [SMILES: C[C@@H]1CN(c2cccc(-c3csc(NC(=O)CNC(=O)c4ccc5c(c4)[C@](C)(C#N)COC5)n3)n2)C[C@H](C)O1] |

TABLE 3b-continued
| Compounds of the Invention | |
|---|---|
| # | Compound |
| 422 | 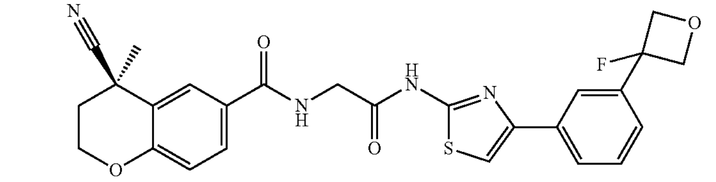 [SMILES: C[C@@]1(C#N)CCOc2ccc(C(=O)NCC(=O)Nc3nc(-c4cccc(C5(F)COC5)c4)cs3)cc21] |
| 423 | 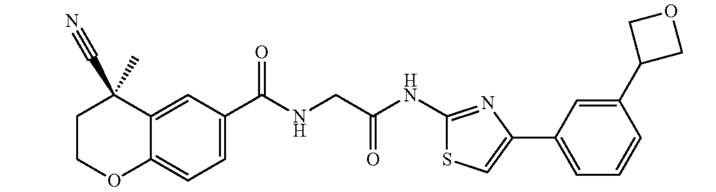 [SMILES: C[C@@]1(C#N)CCOc2ccc(C(=O)NCC(=O)Nc3nc(-c4cccc(C5COC5)c4)cs3)cc21] |
| 424 | 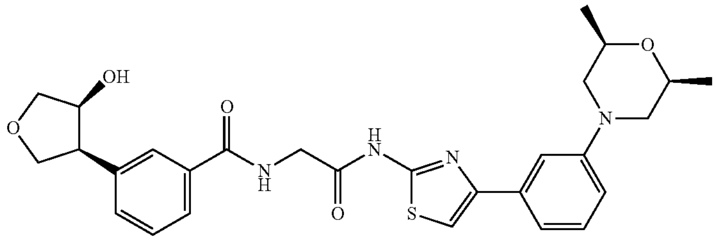 [SMILES: C[C@@H]1CN(c2cccc(-c3csc(NC(=O)CNC(=O)c4cccc([C@H]5COC[C@H]5O)c4)n3)c2)C[C@H](C)O1] |
| 425 | 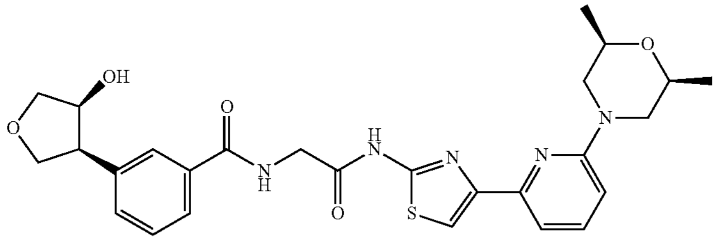 [SMILES: C[C@@H]1CN(c2cccc(-c3csc(NC(=O)CNC(=O)c4cccc([C@H]5COC[C@H]5O)c4)n3)n2)C[C@H](C)O1] |
| 426 | 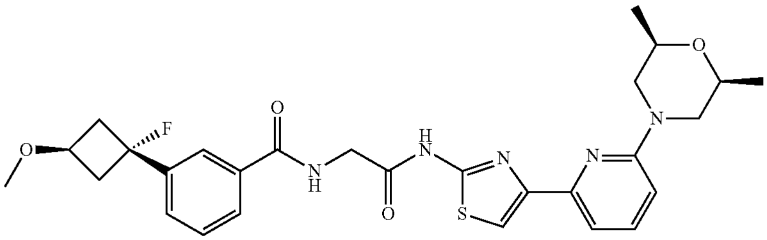 |
| 427 | 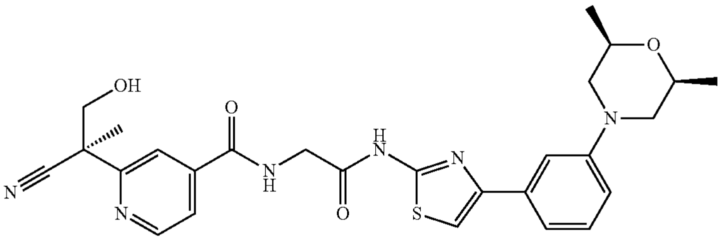 [SMILES: C[C@@H]1CN(c2cccc(-c3csc(NC(=O)CNC(=O)c4ccnc([C@@](C)(C#N)CO)c4)n3)c2)C[C@H](C)O1] |

TABLE 3b-continued
Compounds of the Invention
| # | Compound |
|---|---|
| 428 | 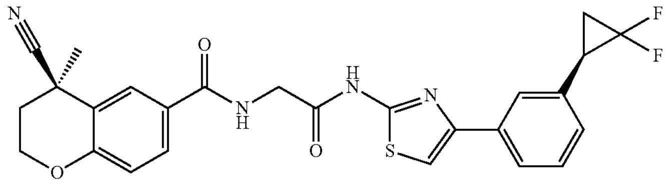 [SMILES: C[C@@]1(C#N)CCOc2ccc(C(=O)NCC(=O)Nc3nc(-c4cccc([C@H]5CC5(F)F)c4)cs3)cc21] |
| 429 | 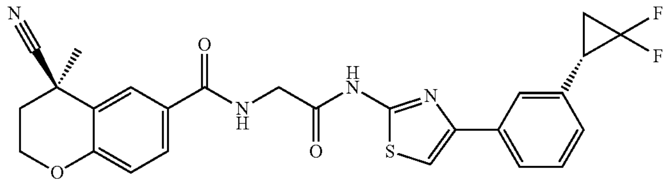 [SMILES: C[C@@]1(C#N)CCOc2ccc(C(=O)NCC(=O)Nc3nc(-c4cccc([C@@H]5CC5(F)F)c4)cs3)cc21] |
| 430 | 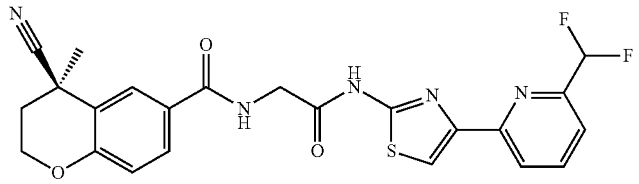 [SMILES: C[C@@]1(C#N)CCOc2ccc(C(=O)NCC(=O)Nc3nc(-c4cccc(C(F)F)n4)cs3)cc21] |
| 431 | 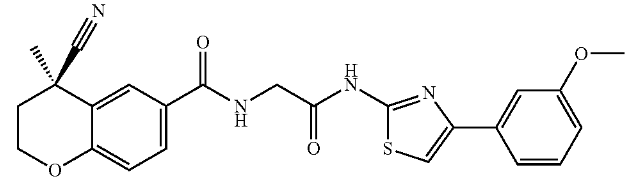 [SMILES: COc1cccc(-c2csc(NC(=O)CNC(=O)c3ccc4c(c3)[C@](C)(C#N)CCO4)n2)c1] |
| 432 | 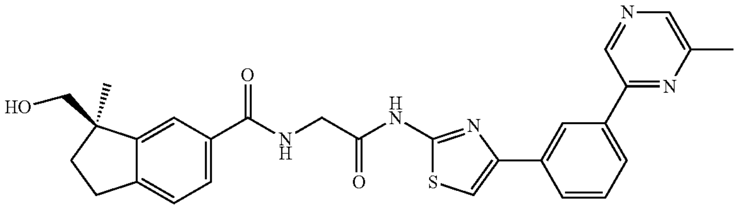 [SMILES: Cc1cncc(-c2cccc(-c3csc(NC(=O)CNC(=O)c4ccc5c(c4)[C@](C)(CO)CC5)n3)c2)n1] |
| 433 | 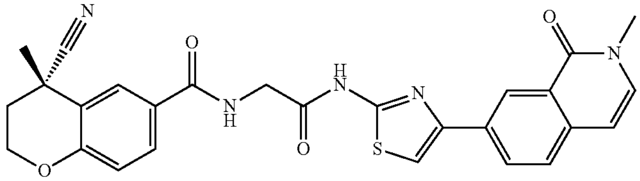 [SMILES: Cn1ccc2ccc(-c3csc(NC(=O)CNC(=O)c4ccc5c(c4)[C@@](C)(C#N)CCO5)n3)cc2c1=O] |
| 434 | 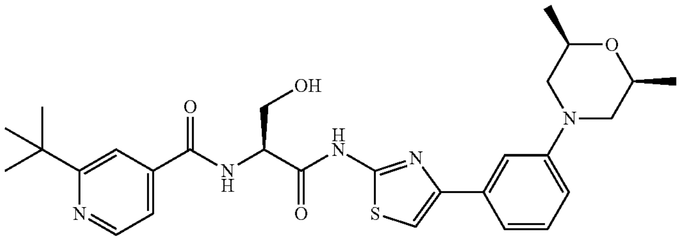 [SMILES: C[C@@H]1CN(c2cccc(-c3csc(NC(=O)[C@H](CO)NC(=O)c4ccnc(C(C)(C)C)c4)n3)c2)C[C@H](C)O1] |

TABLE 3b-continued
| # | Compounds of the Invention<br>Compound |
|---|---|
| 435 | 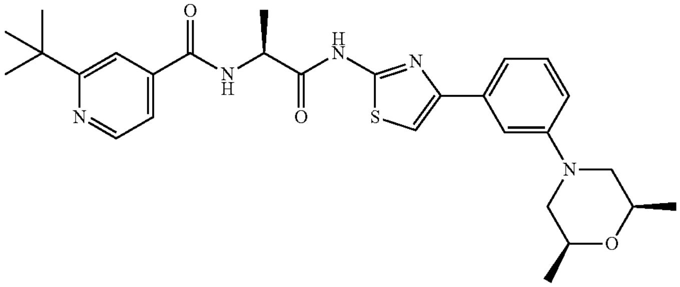 [SMILES: C[C@@H]1CN(c2cccc(-c3csc(NC(=O)[C@H](C)NC(=O)c4ccnc(C(C)(C)C)c4)n3)c2)C[C@H](C)O1] |
| 436 | 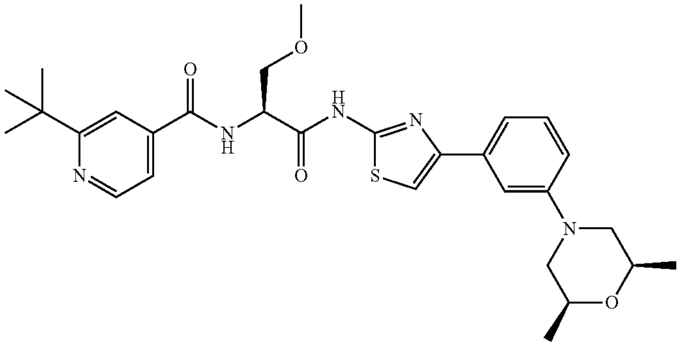 [SMILES: COC[C@H](NC(=O)c1ccnc(C(C)(C)C)c1)C(=O)Nc1nc(-c2cccc(N3C[C@@H](C)O[C@@H](C)C3)c2)cs1] |
| 437 | 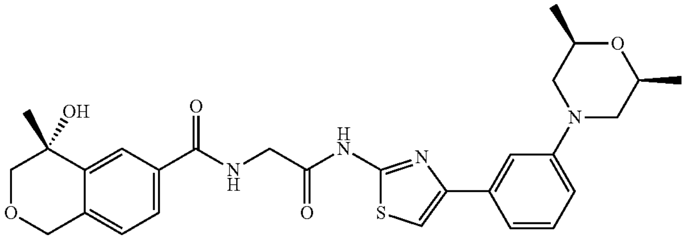 [SMILES: C[C@@H]1CN(c2cccc(-c3csc(NC(=O)CNC(=O)c4ccc5c(c4)[C@@](C)(O)COC5)n3)c2)C[C@H](C)O1] |
| 438 | 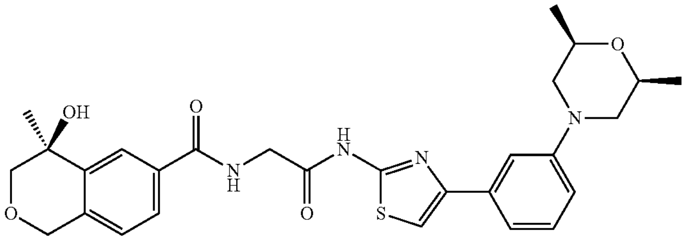 [SMILES: C[C@@H]1CN(c2cccc(-c3csc(NC(=O)CNC(=O)c4ccc5c(c4)[C@](C)(O)COC5)n3)c2)C[C@H](C)O1] |
| 439 | 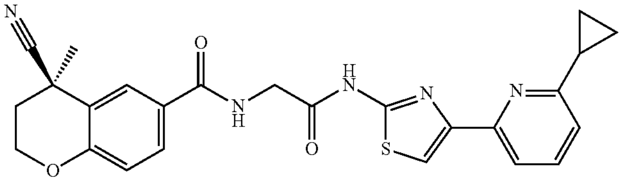 [SMILES: C[C@@]1(C#N)CCOc2ccc(C(=O)NCC(=O)Nc3nc(-c4cccc(C5CC5)n4)cs3)cc21] |
| 440 | 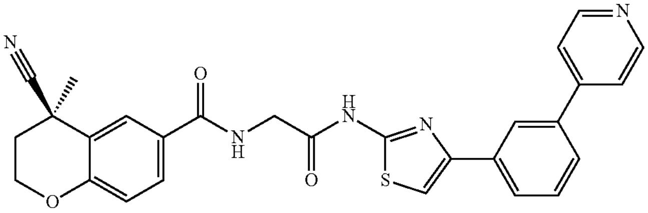 [SMILES: C[C@@]1(C#N)CCOc2ccc(C(=O)NCC(=O)Nc3nc(-c4cccc(-c5ccncc5)c4)cs3)cc21] |

TABLE 3b-continued

| Compounds of the Invention | |
|---|---|
| # | Compound |
| 441 | 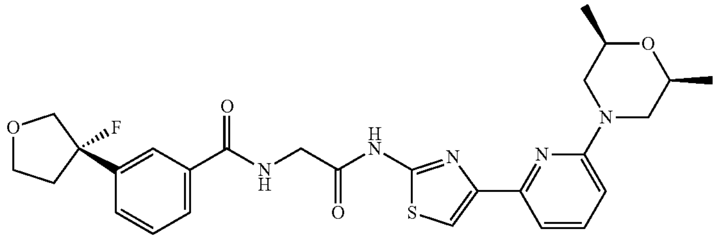 [SMILES: C[C@@H]1CN(c2cccc(-c3csc(NC(=O)CNC(=O)c4cccc([C@@]5(F)CCOC5)c4)n3)n2)C[C@H](C)O1] |
| 442 | 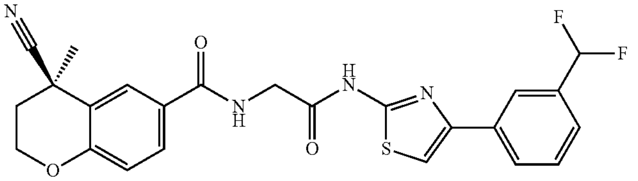 [SMILES: C[C@@]1(C#N)CCOc2ccc(C(=O)NCC(=O)Nc3nc(-c4cccc(C(F)F)c4)cs3)cc21] |
| 443 | 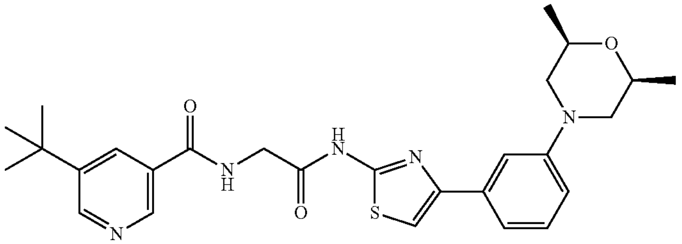 [SMILES: C[C@@H]1CN(c2cccc(-c3csc(NC(=O)CNC(=O)c4cncc(C(C)(C)C)c4)n3)c2)C[C@H](C)O1] |
| 444 | 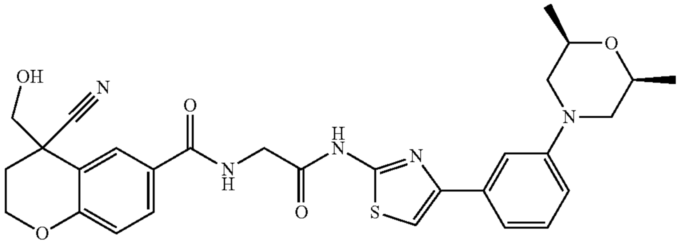 [SMILES: C[C@@H]1CN(c2cccc(-c3csc(NC(=O)CNC(=O)c4ccc5c(c4)C(C#N)(CO)CCO5)n3)c2)C[C@H](C)O1] |

In an aspect, the invention features a pharmaceutical composition comprising any of the foregoing compounds and a pharmaceutically acceptable excipient.

In another aspect, the invention features a method of decreasing the activity of a BAF complex in a cell, the method involving contacting the cell with an effective amount of any of the foregoing compounds or a pharmaceutical composition thereof.

In some embodiments, the cell is a cancer cell.

In another aspect, the invention features a method of treating a BAF complex-related disorder in a subject in need thereof, the method involving administering to the subject an effective amount of any of the foregoing compounds (e.g., a BRM/BRG1 dual inhibitor compound or a BRM-selective compound) or a pharmaceutical composition thereof.

In some embodiments, the BAF complex-related disorder is cancer.

In a further aspect, the invention features a method of inhibiting BRM, the method involving contacting a cell with an effective amount of any of the foregoing compounds (e.g., a BRM/BRG1 dual inhibitor compound or a BRM-selective compound) or a pharmaceutical composition thereof.

In some embodiments, the cell is a cancer cell.

In another aspect, the invention features a method of inhibiting BRG1, the method involving contacting the cell with an effective amount of any of the foregoing compounds or a pharmaceutical composition thereof.

In some embodiments, the cell is a cancer cell.

In a further aspect, the invention features a method of inhibiting BRM and BRG1, the method involving contacting the cell with an effective amount of any of the foregoing compounds or a pharmaceutical composition thereof.

In some embodiments, the cell is a cancer cell.

In another aspect, the invention features a method of treating a disorder related to a BRG1 loss of function mutation in a subject in need thereof, the method involving administering to the subject an effective amount of any of the foregoing compounds (e.g., a BRM/BRG1 dual inhibitor compound or a BRM-selective compound) or a pharmaceutical composition thereof.

In some embodiments, the disorder related to a BRG1 loss of function mutation is cancer. In other embodiments, the subject is determined to have a BRG1 loss of function disorder, for example, is determined to have a BRG1 loss of function cancer (for example, the cancer has been determined to include cancer cells with loss of BRG1 function).

In another aspect, the invention features a method of inducing apoptosis in a cell, the method involving contacting the cell with an effective amount of any of the foregoing compounds (e.g., a BRM/BRG1 dual inhibitor compound or a BRM-selective compound) or a pharmaceutical composition thereof.

In some embodiments, the cell is a cancer cell.

In a further aspect, the invention features a method of treating cancer in a subject in need thereof, the method including administering to the subject an effective amount of any of the foregoing compounds (e.g., a BRM/BRG1 dual inhibitor compound or a BRM-selective compound) or a pharmaceutical composition thereof.

In some embodiments of any of the foregoing methods, the cancer is non-small cell lung cancer, colorectal cancer, bladder cancer, cancer of unknown primary, glioma, breast cancer, melanoma, non-melanoma skin cancer, endometrial cancer, esophagogastric cancer, pancreatic cancer, hepatobiliary cancer, soft tissue sarcoma, ovarian cancer, head and neck cancer, renal cell carcinoma, bone cancer, non-Hodgkin lymphoma, small-cell lung cancer, prostate cancer, embryonal tumor, germ cell tumor, cervical cancer, thyroid cancer, salivary gland cancer, gastrointestinal neuroendocrine tumor, uterine sarcoma, gastrointestinal stromal tumor, CNS cancer, thymic tumor, Adrenocortical carcinoma, appendiceal cancer, small bowel cancer, or penile cancer.

In some embodiments of any of the foregoing methods, the cancer is non-small cell lung cancer, colorectal cancer, bladder cancer, cancer of unknown primary, glioma, breast cancer, melanoma, non-melanoma skin cancer, endometrial cancer, or penile cancer.

In some embodiments of any of the foregoing methods, the cancer is a drug resistant cancer or has failed to respond to a prior therapy (e.g., vemurafenib, dacarbazine, a CTLA4 inhibitor, a PD1 inhibitor, interferon therapy, a BRAF inhibitor, a MEK inhibitor, radiotherapy, temozolomide, irinotecan, a CAR-T therapy, Herceptin®, Perjeta®, tamoxifen, Xeloda®, docetaxol, platinum agents such as carboplatin, taxanes such as paclitaxel and docetaxel, ALK inhibitors, MET inhibitors, Alimta®, Abraxane®, Adriamycin®, gemcitabine, Avastin®, Halaven®, neratinib, a PARP inhibitor, ARN810, an mTOR inhibitor, topotecan, Gemzar®, a VEGFR2 inhibitor, a folate receptor antagonist, demcizumab, fosbretabulin, or a PDL1 inhibitor).

In some embodiments of any of the foregoing methods, the cancer has or has been determined to have BRG1 mutations. In some embodiments of any of the foregoing methods, the BRG1 mutations are homozygous. In some embodiments of any of the foregoing methods, the cancer does not have, or has been determined not to have, an epidermal growth factor receptor (EGFR) mutation. In some embodiments of any of the foregoing methods, the cancer does not have, or has been determined not to have, an anaplastic lymphoma kinase (ALK) driver mutation. In some embodiments of any of the foregoing methods, the cancer has, or has been determined to have, a KRAS mutation. In some embodiments of any of the foregoing methods, the BRG1 mutation is in the ATPase catalytic domain of the protein. In some embodiments of any of the foregoing methods, the BRG1 mutation is a deletion at the C-terminus of BRG1.

In another aspect, the disclosure provides a method treating a disorder related to BAF (e.g., cancer or viral infections) in a subject in need thereof. This method includes contacting a cell with an effective amount of any of the foregoing compounds (e.g., a BRM/BRG1 dual inhibitor compound or a BRM-selective compound), or pharmaceutically acceptable salts thereof, or any of the foregoing pharmaceutical compositions. In some embodiments, the disorder is a viral infection is an infection with a virus of the Retroviridae family such as the lentiviruses (e.g., Human immunodeficiency virus (HIV) and deltaretroviruses (e.g., human T cell leukemia virus I (HTLV-I), human T cell leukemia virus II (HTLV-II)), Hepadnaviridae family (e.g., hepatitis B virus (HBV)), Flaviviridae family (e.g., hepatitis C virus (HCV)), Adenoviridae family (e.g., Human Adenovirus), Herpesviridae family (e.g., Human cytomegalovirus (HCMV), Epstein-Barr virus, herpes simplex virus 1 (HSV-1), herpes simplex virus 2 (HSV-2), human herpesvirus 6 (HHV-6), Herpesvitus K*, CMV, varicella-zoster virus), Papillomaviridae family (e.g., Human Papillomavirus (HPV, HPV E1)), Parvoviridae family (e.g., Parvovirus B19), Polyomaviridae family (e.g., JC virus and BK virus), Paramyxoviridae family (e.g., Measles virus), Togaviridae family (e.g., Rubella virus). In some embodiments, the disorder is Coffin Siris, Neurofibromatosis (e.g., NF-1, NF-2, or Schwannomatosis), or Multiple Meningioma.

In another aspect, the disclosure provides a method for treating a viral infection in a subject in need thereof. This method includes administering to the subject an effective amount of any of the foregoing compounds (e.g., a BRM/BRG1 dual inhibitor compound or a BRM-selective compound), or pharmaceutically acceptable salts thereof, or any of the foregoing pharmaceutical compositions. In some embodiments, the viral infection is an infection with a virus of the Retroviridae family such as the lentiviruses (e.g., Human immunodeficiency virus (HIV) and deltaretroviruses (e.g., human T cell leukemia virus I (HTLV-1), human T cell leukemia virus II (HTLV-II)), Hepadnaviridae family (e.g., hepatitis B virus (HBV)), Flaviviridae family (e.g., hepatitis C virus (HCV)), Adenoviridae family (e.g., Human Adenovirus), Herpesviridae family (e.g., Human cytomegalovirus (HCMV), Epstein-Barr virus, herpes simplex virus 1 (HSV-1), herpes simplex virus 2 (HSV-2), human herpesvirus 6 (HHV-6), Herpesvitus K*, CMV, varicella-zoster virus), Papillomaviridae family (e.g., Human Papillomavirus (HPV, HPV E1)), Parvoviridae family (e.g., Parvovirus B19), Polyomaviridae family (e.g., JC virus and BK virus), Paramyxoviridae family (e.g., Measles virus), or Togaviridae family (e.g., Rubella virus).

In some embodiments of any of the foregoing aspects, the compound is a BRM-selective compound. In some embodiments, the BRM-selective compound inhibits the level and/or activity of BRM at least 10-fold greater than the compound inhibits the level and/or activity of BRG1 and/or the compound binds to BRM at least 10-fold greater than the compound binds to BRG1. For example, in some embodiments, a BRM-selective compound has an $IC_{50}$ or $IP_{50}$ that is at least 10-fold lower than the $IC_{50}$ or $IP_{50}$ against BRG1. In some embodiments of any of the foregoing aspects, the compound is a BRM/BRG1 dual inhibitor compound. In some embodiments, the BRM/BRG1 dual inhibitor compound has similar activity against both BRM and BRG1 (e.g., the activity of the compound against BRM and BRG1 with within 10-fold (e.g., less than 5-fold, less than 2-fold). In some embodiments, the activity of the BRM/BRG1 dual inhibitor compound is greater against BRM. In some embodiments, the activity of the BRM/BRG1 dual inhibitor compound is greater against BRG1. For example, in some embodiments, a BRM/BRG1 dual inhibitor compound has an $IC_{50}$ or $IP_{50}$ against BRM that is within 10-fold of the $IC_{50}$ or $IP_{50}$ against BRG1.

In another aspect, the invention features a method of treating melanoma, prostate cancer, breast cancer, bone cancer, renal cell carcinoma, or a hematologic cancer in a subject in need thereof, the method including administering to the subject an effective amount of any of the foregoing compounds or pharmaceutical compositions thereof.

In another aspect, the invention features a method of reducing tumor growth of melanoma, prostate cancer, breast cancer, bone cancer, renal cell carcinoma, or a hematologic cancer in a subject in need thereof, the method including administering to the subject an effective amount of any of the foregoing compounds or pharmaceutical compositions thereof.

In another aspect, the invention features a method of suppressing metastatic progression of melanoma, prostate cancer, breast cancer, bone cancer, renal cell carcinoma, or a hematologic cancer in a subject, the method including administering an effective amount of any of the foregoing compounds or pharmaceutical compositions thereof.

In another aspect, the invention features a method of suppressing metastatic colonization of melanoma, prostate cancer, breast cancer, bone cancer, renal cell carcinoma, or a hematologic cancer in a subject, the method including administering an effective amount of any of the foregoing compounds or pharmaceutical compositions thereof.

In another aspect, the invention features a method of reducing the level and/or activity of BRG1 and/or BRM in a melanoma, prostate cancer, breast cancer, bone cancer, renal cell carcinoma, or hematologic cancer cell, the method including contacting the cell with an effective amount of any of the foregoing compounds or pharmaceutical compositions thereof.

In some embodiments of any of the above aspects, the melanoma, prostate cancer, breast cancer, bone cancer, renal cell carcinoma, or hematologic cell is in a subject.

In some embodiments of any of the above aspects, the effective amount of the compound reduces the level and/or activity of BRG1 by at least 5% (e.g., 6%, 7%, 8%, 9%, 10%, 15%, 20%, 25%, 30%, 35%, 40%, 45%, 50%, 55%, 60%, 65%, 70%, 75%, 80%, 85%, 90%, or 95%) as compared to a reference. In some embodiments, the effective amount of the compound that reduces the level and/or activity of BRG1 by at least 50% (e.g., 55%, 60%, 65%, 70%, 75%, 80%, 85%, 90%, or 95%) as compared to a reference. In some embodiments, the effective amount of the compound that reduces the level and/or activity of BRG1 by at least 90% (e.g., 91%, 92%, 93%, 94%, 95%, 96%, 97%, 98%, or 99%).

In some embodiments, the effective amount of the compound reduces the level and/or activity of BRG1 by at least 5% (e.g., 6%, 7%, 8%, 9%, 10%, 15%, 20%, 25%, 30%, 35%, 40%, 45%, 50%, 55%, 60%, 65%, 70%, 75%, 80%, 85%, 90%, or 95%) as compared to a reference for at least 12 hours (e.g., 14 hours, 16 hours, 18 hours, 20 hours, 22 hours, 24 hours, 30 hours, 36 hours, 48 hours, 72 hours, or more). In some embodiments, the effective amount of the compound that reduces the level and/or activity of BRG1 by at least 5% (e.g., 6%, 7%, 8%, 9%, 10%, 15%, 20%, 25%, 30%, 35%, 40%, 45%, 50%, 55%, 60%, 65%, 70%, 75%, 80%, 85%, 90%, or 95%) as compared to a reference for at least 4 days (e.g., 5 days, 6 days, 7 days, 14 days, 28 days, or more).

In some embodiments of any of the above aspects, the effective amount of the compound reduces the level and/or activity of BRM by at least 5% (e.g., 6%, 7%, 8%, 9%, 10%, 15%, 20%, 25%, 30%, 35%, 40%, 45%, 50%, 55%, 60%, 65%, 70%, 75%, 80%, 85%, 90%, or 95%) as compared to a reference. In some embodiments, the effective amount of the compound that reduces the level and/or activity of BRM by at least 50% (e.g., 55%, 60%, 65%, 70%, 75%, 80%, 85%, 90%, or 95%) as compared to a reference. In some embodiments, the effective amount of the compound that reduces the level and/or activity of BRM by at least 90% (e.g., 91%, 92%, 93%, 94%, 95%, 96%, 97%, 98%, or 99%).

In some embodiments, the effective amount of the compound reduces the level and/or activity of BRM by at least 5% (e.g., 6%, 7%, 8%, 9%, 10%, 15%, 20%, 25%, 30%, 35%, 40%, 45%, 50%, 55%, 60%, 65%, 70%, 75%, 80%, 85%, 90%, or 95%) as compared to a reference for at least 12 hours (e.g., 14 hours, 16 hours, 18 hours, 20 hours, 22 hours, 24 hours, 30 hours, 36 hours, 48 hours, 72 hours, or more). In some embodiments, the effective amount of the compound that reduces the level and/or activity of BRM by at least 5% (e.g., 6%, 7%, 8%, 9%, 10%, 15%, 20%, 25%, 30%, 35%, 40%, 45%, 50%, 55%, 60%, 65%, 70%, 75%, 80%, 85%, 90%, or 95%) as compared to a reference for at least 4 days (e.g., 5 days, 6 days, 7 days, 14 days, 28 days, or more).

In some embodiments, the subject has cancer. In some embodiments, the cancer expresses BRG1 and/or BRM protein and/or the cell or subject has been identified as expressing BRG1 and/or BRM. In some embodiments, the cancer expresses BRG1 protein and/or the cell or subject has been identified as expressing BRG1. In some embodiments, the cancer expresses BRM protein and/or the cell or subject has been identified as expressing BRM. In some embodiments, the cancer is melanoma (e.g., uveal melanoma, mucosal melanoma, or cutaneous melanoma). In some embodiments, the cancer is prostate cancer. In some embodiments, the cancer is a hematologic cancer, e.g., multiple myeloma, large cell lymphoma, acute T-cell leukemia, acute myeloid leukemia, myelodysplastic syndrome, immunoglobulin A lambda myeloma, diffuse mixed histiocytic and lymphocytic lymphoma, B-cell lymphoma, acute lymphoblastic leukemia (e.g., T-cell acute lymphoblastic leukemia or B-cell acute lymphoblastic leukemia), diffuse large cell lymphoma, or non-Hodgkin's lymphoma. In some embodiments, the cancer is breast cancer (e.g., an ER positive breast cancer, an ER negative breast cancer, triple positive breast cancer, or triple negative breast cancer). In some embodiments, the cancer is a bone cancer (e.g., Ewing's sarcoma). In some embodiments, the cancer is a renal cell carcinoma (e.g., a Microphthalmia Transcription Factor (MITF) family translocation renal cell carcinoma (tRCC)). In some embodiments, the cancer is metastatic (e.g., the cancer has spread to the liver). The metastatic cancer can include cells exhibiting migration and/or invasion of migrating cells and/or include cells exhibiting endothelial recruitment and/or angiogenesis. In other embodiments, the migrating cancer is a cell migration cancer. In still other embodiments, the cell migration cancer is a non-metastatic cell migration cancer. The metastatic cancer can be a cancer spread via seeding the surface of the peritoneal, pleural, pericardial, or subarachnoid spaces. Alternatively, the metastatic cancer can be a cancer spread via the lymphatic system, or a cancer spread hematogenously. In some embodiments, the effective amount of an agent that reduces the level and/or activity of BRG1 and/or BRM is an amount effective to inhibit metastatic colonization of the cancer to the liver.

In some embodiments the cancer harbors a mutation in GNAQ. In some embodiments the cancer harbors a mutation in GNA11. In some embodiments the cancer harbors a mutation in PLCB4. In some embodiments the cancer harbors a mutation in CYSLTR2. In some embodiments the cancer harbors a mutation in BAP1. In some embodiments the cancer harbors a mutation in SF3B1. In some embodiments the cancer harbors a mutation in EIF1AX. In some embodiments the cancer harbors a TFE3 translocation. In some embodiments the cancer harbors a TFEB translocation. In some embodiments the cancer harbors a MITF translocation. In some embodiments the cancer harbors an EZH2 mutation. In some embodiments the cancer harbors a SUZ12 mutation. In some embodiments the cancer harbors an EED mutation.

In some embodiments, the method further includes administering to the subject or contacting the cell with an anticancer therapy, e.g., a chemotherapeutic or cytotoxic agent, immunotherapy, surgery, radiotherapy, thermotherapy, or photocoagulation. In some embodiments, the anticancer therapy is a chemotherapeutic or cytotoxic agent, e.g., an antimetabolite, antimitotic, antitumor antibiotic, asparagine-specific enzyme, bisphosphonates, antineoplastic, alkylating agent, DNA-Repair enzyme inhibitor, histone deacetylase inhibitor, corticosteroid, demethylating agent, immunomodulatory, janus-associated kinase inhibitor, phosphinositide 3-kinase inhibitor, proteasome inhibitor, or tyrosine kinase inhibitor.

In some embodiments, the compound of the invention is used in combination with another anti-cancer therapy used for the treatment of uveal melanoma such as surgery, a MEK inhibitor, and/or a PKC inhibitor. For example, in some embodiments, the method further comprises performing surgery prior to, subsequent to, or at the same time as administration of the compound of the invention. In some embodiments, the method further comprises administration of a MEK inhibitor and/or a PKC inhibitor prior to, subsequent to, or at the same time as administration of the compound of the invention.

In some embodiments, the anticancer therapy and the compound of the invention are administered within 28 days of each other and each in an amount that together are effective to treat the subject.

In some embodiments, the subject or cancer has and/or has been identified as having a BRG1 loss of function mutation. In some embodiments, the subject or cancer has and/or has been identified as having a BRM loss of function mutation.

In some embodiments, the cancer is resistant to one or more chemotherapeutic or cytotoxic agents (e.g., the cancer has been determined to be resistant to chemotherapeutic or cytotoxic agents such as by genetic markers, or is likely to be resistant, to chemotherapeutic or cytotoxic agents such as a cancer that has failed to respond to a chemotherapeutic or cytotoxic agent). In some embodiments, the cancer has failed to respond to one or more chemotherapeutic or cytotoxic agents. In some embodiments, the cancer is resistant or has failed to respond to dacarbazine, temozolomide, cisplatin, treosulfan, fotemustine, IMCgp100, a CTLA-4 inhibitor (e.g., ipilimumab), a PD-1 inhibitor (e.g., Nivolumab or pembrolizumab), a PD-L1 inhibitor (e.g., atezolizumab, avelumab, or durvalumab), a mitogen-activated protein kinase (MEK) inhibitor (e.g., selumetinib, binimetinib, or tametinib), and/or a protein kinase C (PKC) inhibitor (e.g., sotrastaurin or IDE196).

In some embodiments, the cancer is resistant to or failed to respond to a previously administered therapeutic used for the treatment of uveal melanoma such as a MEK inhibitor or PKC inhibitor. For example, in some embodiments, the cancer is resistant to or failed to respond to a mitogen-activated protein kinase (MEK) inhibitor (e.g., selumetinib, binimetinib, or tametinib), and/or a protein kinase C (PKC) inhibitor (e.g., sotrastaurin or IDE196).

Chemical Terms

The terminology employed herein is for the purpose of describing particular embodiments and is not intended to be limiting.

For any of the following chemical definitions, a number following an atomic symbol indicates that total number of atoms of that element that are present in a particular chemical moiety. As will be understood, other atoms, such as H atoms, or substituent groups, as described herein, may be present, as necessary, to satisfy the valences of the atoms. For example, an unsubstituted $C_2$ alkyl group has the formula $—CH_2CH_3$. When used with the groups defined herein, a reference to the number of carbon atoms includes the divalent carbon in acetal and ketal groups but does not include the carbonyl carbon in acyl, ester, carbonate, or carbamate groups. A reference to the number of oxygen, nitrogen, or sulfur atoms in a heteroaryl group only includes those atoms that form a part of a heterocyclic ring.

The term "acyl," as used herein, represents a H or an alkyl group that is attached to a parent molecular group through a carbonyl group, as defined herein, and is exemplified by formyl (i.e., a carboxaldehyde group), acetyl, trifluoroacetyl, propionyl, and butanoyl. Exemplary unsubstituted acyl groups include from 1 to 6, from 1 to 11, or from 1 to 21 carbons.

The term "alkyl," as used herein, refers to a branched or straight-chain monovalent saturated aliphatic hydrocarbon radical of 1 to 20 carbon atoms (e.g., 1 to 16 carbon atoms, 1 to 10 carbon atoms, 1 to 6 carbon atoms, or 1 to 3 carbon atoms).

An alkylene is a divalent alkyl group. The term "alkenyl," as used herein, alone or in combination with other groups, refers to a straight chain or branched hydrocarbon residue having a carbon-carbon double bond and having 2 to 20 carbon atoms (e.g., 2 to 16 carbon atoms, 2 to 10 carbon atoms, 2 to 6 carbon atoms, or 2 carbon atoms).

The term "alkynyl," as used herein, alone or in combination with other groups, refers to a straight chain or branched hydrocarbon residue having a carbon-carbon triple bond and having 2 to 20 carbon atoms (e.g., 2 to 16 carbon atoms, 2 to 10 carbon atoms, 2 to 6 carbon atoms, or 2 carbon atoms).

The term "amino," as used herein, represents $—N(R^{N1})_2$, wherein each $R^{N1}$ is, independently, H, OH, $NO_2$. $N(R^{N2})_2$, $SO_2OR^{N2}$, $SO_2R^{N2}$, $SOR^{N2}$, an N-protecting group, alkyl, alkoxy, aryl, arylalkyl, cycloalkyl, acyl (e.g., acetyl, trifluoroacetyl, or others described herein), wherein each of these recited $R^{N1}$ groups can be optionally substituted; or two $R^{N1}$ combine to form an alkylene or heteroalkylene, and wherein each $R^{N2}$ is, independently, H, alkyl, or aryl. The amino groups of the invention can be an unsubstituted amino (i.e., $—NH_2$) or a substituted amino (i.e., $—N(R^{N1})_2$).

The term "aryl," as used herein, refers to an aromatic mono- or polycarbocyclic radical of 6 to 12 carbon atoms having at least one aromatic ring. Examples of such groups include, but are not limited to, phenyl, naphthyl, 1,2,3,4-tetrahydronaphthyl, 1,2-dihydronaphthyl, indanyl, and 1H-indenyl.

The term "arylalkyl," as used herein, represents an alkyl group substituted with an aryl group. Exemplary unsubstituted arylalkyl groups are from 7 to 30 carbons (e.g., from 7 to 16 or from 7 to 20 carbons, such as $C_1$-$C_6$ alkyl $C_6$-$C_{10}$ aryl, $C_1$-$C_{10}$ alkyl $C_6$-$C_{10}$ aryl, or $C_1$-$C_{20}$ alkyl $C_6$-$C_{10}$ aryl), such as, benzyl and phenethyl. In some embodiments, the alkyl and the aryl each can be further substituted with 1, 2, 3, or 4 substituent groups as defined herein for the respective groups.

The term "azido," as used herein, represents a —$N_3$ group.

The term "bridged polycycloalkyl," as used herein, refers to a bridged polycyclic group of 5 to 20 carbons, containing from 1 to 3 bridges.

The term "cyano," as used herein, represents a —CN group.

The term "carbocyclyl," as used herein, refers to a non-aromatic $C_3$-$C_{12}$ monocyclic, bicyclic, or tricyclic structure in which the rings are formed by carbon atoms. Carbocyclyl structures include cycloalkyl groups and unsaturated carbocyclyl radicals.

The term "cycloalkyl." as used herein, refers to a saturated, non-aromatic, and mono- or polycarbocyclic radical of 3 to 10, preferably 3 to 6 carbon atoms. Cycloalkyl may be monovalent or divalent. This term is further exemplified by radicals such as cyclopropyl, cyclobutyl, cyclopentyl, cyclohexyl, cycloheptyl, norbornyl, and adamantyl. The term cycloalkyl," as used herein, may also refer to a non-aromatic and mono- or polycarbocyclic ring system fused to an aromatic ring, when so specified.

The term "halo," as used herein, means a fluorine (fluoro), chlorine (chloro), bromine (bromo), or iodine (iodo) radical.

The term "heteroalkyl," as used herein, refers to an alkyl group, as defined herein, in which one or more of the constituent carbon atoms have been replaced by nitrogen, oxygen, or sulfur. In some embodiments, the heteroalkyl group can be further substituted with 1, 2, 3, or 4 substituent groups as described herein for alkyl groups. Examples of heteroalkyl groups are an "alkoxy" which, as used herein, refers alkyl-O— (e.g., methoxy and ethoxy). A heteroalkylene is a divalent heteroalkyl group. The term "heteroalkenyl," as used herein, refers to an alkenyl group, as defined herein, in which one or more of the constituent carbon atoms have been replaced by nitrogen, oxygen, or sulfur. In some embodiments, the heteroalkenyl group can be further substituted with 1, 2, 3, or 4 substituent groups as described herein for alkenyl groups. Examples of heteroalkenyl groups are an "alkenoxy" which, as used herein, refers alkenyl-O—. A heteroalkenylene is a divalent heteroalkenyl group. The term "heteroalkynyl," as used herein, refers to an alkynyl group, as defined herein, in which one or more of the constituent carbon atoms have been replaced by nitrogen, oxygen, or sulfur. In some embodiments, the heteroalkynyl group can be further substituted with 1, 2, 3, or 4 substituent groups as described herein for alkynyl groups. Examples of heteroalkynyl groups are an "alkynoxy" which, as used herein, refers alkynyl-O—. A heteroalkynylene is a divalent heteroalkynyl group.

The term "heteroaryl," as used herein, refers to an aromatic mono- or polycyclic radical of 5 to 12 atoms having at least one aromatic ring containing 1, 2, or 3 ring atoms selected from nitrogen, oxygen, and sulfur, with the remaining ring atoms being carbon. One or two ring carbon atoms of the heteroaryl group may be replaced with a carbonyl group. Examples of heteroaryl groups are pyridyl, pyrazolyl, benzooxazolyl, benzoimidazolyl, benzothiazolyl, imidazolyl, oxazolyl, and thiazolyl.

The term "heteroarylalkyl," as used herein, represents an alkyl group substituted with a heteroaryl group. Exemplary unsubstituted heteroarylalkyl groups are from 7 to 30 carbons (e.g., from 7 to 16 or from 7 to 20 carbons, such as $C_1$-$C_6$ alkyl $C_2$-$C_9$ heteroaryl, $C_1$-$C_{10}$ alkyl $C_2$-$C_9$ heteroaryl, or $C_1$-$C_{20}$ alkyl $C_2$-$C_9$ heteroaryl). In some embodiments, the alkyl and the heteroaryl each can be further substituted with 1, 2, 3, or 4 substituent groups as defined herein for the respective groups.

The terms "heterocycle" and "heterocyclyl," as used interchangeably herein, refers a mono- or polycyclic radical having 3 to 12 atoms having at least one ring containing 1, 2, 3, or 4 ring atoms selected from N, O, and S. A heterocyclyl may be non-aromatic, wherein no ring is aromatic. Alternatively, a heterocyclyl may be aromatic. An aromatic heterocyclyl may be referred to as a heteroaryl as described herein. Examples of heterocyclyl groups include, but are not limited to, morpholinyl, thiomorpholinyl, furyl, piperazinyl, piperidinyl, pyranyl, pyrrolidinyl, tetrahydropyranyl, tetrahydrofuranyl, and 1,3-dioxanyl.

The term "heterocyclylalkyl," as used herein, represents an alkyl group substituted with a heterocyclyl group. Exemplary unsubstituted heterocyclylalkyl groups are from 7 to 30 carbons (e.g., from 7 to 16 or from 7 to 20 carbons, such as $C_1$-$C_6$ alkyl $C_2$-$C_9$ heterocyclyl, $C_1$-$C_{10}$ alkyl $C_2$-$C_9$ heterocyclyl, or $C_1$-$C_{20}$ alkyl $C_2$-$C_9$ heterocyclyl). In some embodiments, the alkyl and the heterocyclyl each can be further substituted with 1, 2, 3, or 4 substituent groups as defined herein for the respective groups.

The term "hydroxyalkyl," as used herein, represents alkyl group substituted with an —OH group.

The term "hydroxyl," as used herein, represents an —OH group.

The term "N-protecting group," as used herein, represents those groups intended to protect an amino group against undesirable reactions during synthetic procedures. Commonly used N-protecting groups are disclosed in Greene, "Protective Groups in Organic Synthesis," 3rd Edition (John Wiley & Sons, New York, 1999). N-protecting groups include, but are not limited to, acyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries such as protected or unprotected D, L, or D, L-amino acids such as alanine, leucine, and phenylalanine; sulfonyl-containing groups such as benzenesulfonyl, and p-toluenesulfonyl; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-20 dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, and phenylthiocarbonyl, arylalkyl groups such as benzyl, triphenylmethyl, and benzyloxymethyl, and silyl groups, such as trimethylsilyl. Preferred N-protecting groups are alloc, formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "nitro," as used herein, represents an —$NO_2$ group.

The term “thiol,” as used herein, represents an —SH group.

The alkyl, alkenyl, alkynyl, heteroalkyl, heteroalkenyl, heteroalkynyl, carbocyclyl (e.g., cycloalkyl), aryl, heteroaryl, and heterocyclyl groups may be substituted or unsubstituted. When substituted, there will generally be 1 to 4 substituents present, unless otherwise specified. Substituents include, for example: alkyl (e.g., unsubstituted and substituted, where the substituents include any group described herein, e.g., aryl, halo, hydroxy), aryl (e.g., substituted and unsubstituted phenyl), carbocyclyl (e.g., substituted and unsubstituted cycloalkyl), halo (e.g., fluoro), hydroxyl, heteroalkyl (e.g., substituted and unsubstituted methoxy, ethoxy, or thioalkoxy), heteroaryl, heterocyclyl, amino (e.g., $NH_2$ or mono- or dialkyl amino), azido, cyano, nitro, or thiol. Aryl, carbocyclyl (e.g., cycloalkyl), heteroaryl, and heterocyclyl groups may also be substituted with alkyl (unsubstituted and substituted such as arylalkyl (e.g., substituted and unsubstituted benzyl)).

Compounds of the invention can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates, or mixtures of diastereoisomeric racemates. The optically active forms can be obtained for example by resolution of the racemates, by asymmetric synthesis or asymmetric chromatography (chromatography with a chiral adsorbents or eluant). That is, certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. “Enantiomer” means one of a pair of molecules that are mirror images of each other and are not superimposable. Diastereomers are stereoisomers that are not related as mirror images, most commonly because they contain two or more asymmetrically substituted carbon atoms and represent the configuration of substituents around one or more chiral carbon atoms. Enantiomers of a compound can be prepared, for example, by separating an enantiomer from a racemate using one or more well-known techniques and methods, such as, for example, chiral chromatography and separation methods based thereon. The appropriate technique and/or method for separating an enantiomer of a compound described herein from a racemic mixture can be readily determined by those of skill in the art. “Racemate” or “racemic mixture” means a compound containing two enantiomers, wherein such mixtures exhibit no optical activity; i.e., they do not rotate the plane of polarized light. “Geometric isomer” means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on 25 opposite sides of the carbon-carbon double bond) or Z (substituents are oriented on the same side) configuration. “R,” “S,” “S*.” “R*,” “E,” “Z,” “cis,” and “trans,” indicate configurations relative to the core molecule. Certain of the disclosed compounds may exist in atropisomeric forms. Atropisomers are stereoisomers resulting from hindered rotation about single bonds where the steric strain barrier to rotation is high enough to allow for the isolation of the conformers. The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide 35 of each of the isomers of an isomeric pair using an optically pure acid, amine or alcohol (followed by chromatographic separation and removal of the chiral auxiliary), or resolving an isomeric mixture of either a starting material or a final product using various well known chromatographic methods. When the stereochemistry of a disclosed compound is named or depicted by structure, the named or depicted stereoisomer is at least 60%, 70%, 80%, 90%, 99%, or 99.9% by weight relative to the other stereoisomers. When a single enantiomer is named or depicted by structure, the depicted or named enantiomer is at least 60%, 70%, 80%, 90%, 99%, or 99.9% by weight optically pure. When a single diastereomer is named or depicted by structure, the depicted or named diastereomer is at least 60%, 70%, 80%, 90%, 99%, or 99.9% by weight pure. Percent optical purity is the ratio of the weight of the enantiomer or over the weight of the enantiomer plus the weight of its optical isomer. Diastereomeric purity by weight is the ratio of the weight of one diastereomer or over the weight of all the diastereomers. When the stereochemistry of a disclosed compound is named or depicted by structure, the named or depicted stereoisomer is at least 60%, 70%, 80%, 90%, 99%, or 99.9% by mole fraction pure relative to the other stereoisomers. When a single enantiomer is named or depicted by structure, the depicted or named enantiomer is at least 60%, 70%, 80%, 90%, 99%, or 99.9% by mole fraction pure. When a single diastereomer is named or depicted by structure, the depicted or named diastereomer is at least 60%, 70%, 80%, 90%, 99%, or 99.9% by mole fraction pure. Percent purity by mole fraction is the ratio of the moles of the enantiomer or over the moles of the enantiomer plus the moles of its optical isomer. Similarly, percent purity by moles fraction is the ratio of the moles of the diastereomer or over the moles of the diastereomer plus the moles of its isomer. When a disclosed compound is named or depicted by structure without indicating the stereochemistry, and the compound has at least one chiral center, it is to be understood that the name or structure encompasses either enantiomer of the compound free from the corresponding optical isomer, a racemic mixture of the compound, or mixtures enriched in one enantiomer relative to its corresponding optical isomer. When a disclosed compound is named or depicted by structure without indicating the stereochemistry and has two or more chiral centers, it is to be understood that the name or structure encompasses a diastereomer free of other diastereomers, a number of diastereomers free from other diastereomeric pairs, mixtures of diastereomers, mixtures of diastereomeric pairs, mixtures of diastereomers in which one diastereomer is enriched relative to the other diastereomer(s), or mixtures of diastereomers in which one or more diastereomer is enriched relative to the other diastereomers. The invention embraces all of these forms.

Unless otherwise defined, all technical and scientific terms used herein have the same meaning as commonly understood by one of ordinary skill in the art to which this invention belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Definitions

In this application, unless otherwise clear from context, (i) the term "a" may be understood to mean "at least one"; (ii) the term "or" may be understood to mean "and/or"; and (iii) the terms "comprising" and "including" may be understood to encompass itemized components or steps whether presented by themselves or together with one or more additional components or steps.

As used herein, the terms "about" and "approximately" refer to a value that is within 10% above or below the value being described. For example, the term "about 5 nM" indicates a range of from 4.5 to 5.5 nM.

As used herein, the term "administration" refers to the administration of a composition (e.g., a compound or a preparation that includes a compound as described herein) to a subject or system. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intratumoral, intravenous, intraventricular, mucosal, nasal, oral, rectal, subcutaneous, sublingual, topical, tracheal (including by intratracheal instillation), transdermal, vaginal, and vitreal.

As used herein, the term "BAF complex" refers to the BRG1- or HRBM-associated factors complex in a human cell.

As used herein, the term "BAF complex-related disorder" refers to a disorder that is caused or affected by the level of activity of a BAF complex.

As used herein, the term "BRG1 loss of function mutation" refers to a mutation in BRG1 that leads to the protein having diminished activity (e.g., at least 1% reduction in BRG1 activity, for example 2%, 5%, 10%, 25%, 50%, or 100% reduction in BRG1 activity). Exemplary BRG1 loss of function mutations include, but are not limited to, a homozygous BRG1 mutation and a deletion at the C-terminus of BRG1.

As used herein, the term "BRG1 loss of function disorder" refers to a disorder (e.g., cancer) that exhibits a reduction in BRG1 activity (e.g., at least 1% reduction in BRG1 activity, for example 2%, 5%, 10%, 25%, 50%, or 100% reduction in BRG1 activity).

The term "cancer" refers to a condition caused by the proliferation of malignant neoplastic cells, such as tumors, neoplasms, carcinomas, sarcomas, leukemias, and lymphomas.

As used herein, a "combination therapy" or "administered in combination" means that two (or more) different agents or treatments are administered to a subject as part of a defined treatment regimen for a particular disease or condition. The treatment regimen defines the doses and periodicity of administration of each agent such that the effects of the separate agents on the subject overlap. In some embodiments, the delivery of the two or more agents is simultaneous or concurrent and the agents may be co-formulated. In some embodiments, the two or more agents are not co-formulated and are administered in a sequential manner as part of a prescribed regimen. In some embodiments, administration of two or more agents or treatments in combination is such that the reduction in a symptom, or other parameter related to the disorder is greater than what would be observed with one agent or treatment delivered alone or in the absence of the other. The effect of the two treatments can be partially additive, wholly additive, or greater than additive (e.g., synergistic). Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination may be administered by intravenous injection while a second therapeutic agent of the combination may be administered orally.

By "determining the level" of a protein or RNA is meant the detection of a protein or an RNA, by methods known in the art, either directly or indirectly. "Directly determining" means performing a process (e.g., performing an assay or test on a sample or "analyzing a sample" as that term is defined herein) to obtain the physical entity or value. "Indirectly determining" refers to receiving the physical entity or value from another party or source (e.g., a third party laboratory that directly acquired the physical entity or value). Methods to measure protein level generally include, but are not limited to, western blotting, immunoblotting, enzyme-linked immunosorbent assay (ELISA), radioimmunoassay (RIA), immunoprecipitation, immunofluorescence, surface plasmon resonance, chemiluminescence, fluorescent polarization, phosphorescence, immunohistochemical analysis, matrix-assisted laser desorption/ionization time-of-flight (MALDI-TOF) mass spectrometry, liquid chromatography (LC)-mass spectrometry, microcytometry, microscopy, fluorescence activated cell sorting (FACS), and flow cytometry, as well as assays based on a property of a protein including, but not limited to, enzymatic activity or interaction with other protein partners. Methods to measure RNA levels are known in the art and include, but are not limited to, quantitative polymerase chain reaction (qPCR) and Northern blot analyses.

By a "decreased level" or an "increased level" of a protein or RNA is meant a decrease or increase, respectively, in a protein or RNA level, as compared to a reference (e.g., a decrease or an increase by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 150%, about 200%, about 300%, about 400%, about 500%, or more; a decrease or an increase of more than about 10%, about 15%, about 20%, about 50%, about 75%, about 100%, or about 200%, as compared to a reference; a decrease or an increase by less than about 0.01-fold, about 0.02-fold, about 0.1-fold, about 0.3-fold, about 0.5-fold, about 0.8-fold, or less; or an increase by more than about 1.2-fold, about 1.4-fold, about 1.5-fold, about 1.8-fold, about 2.0-fold, about 3.0-fold, about 3.5-fold, about 4.5-fold, about 5.0-fold, about 10-fold, about 15-fold, about 20-fold, about 30-fold, about 40-fold, about 50-fold, about 100-fold, about 1000-fold, or more). A level of a protein may be expressed in mass/vol (e.g., g/dL, mg/mL, μg/mL, ng/mL) or percentage relative to total protein in a sample.

By "decreasing the activity of a BAF complex" is meant decreasing the level of an activity related to a BAF complex, or a related downstream effect. A non-limiting example of decreasing an activity of a BAF complex is Sox2 activation. The activity level of a BAF complex may be measured using any method known in the art, e.g., the methods described in Kadoch et al. Cell, 2013, 153, 71-85, the methods of which are herein incorporated by reference.

As used herein, the term "inhibiting BRM" refers to blocking or reducing the level or activity of the ATPase catalytic binding domain or the bromodomain of the protein. BRM inhibition may be determined using methods known in the art, e.g., a BRM ATPase assay, a Nano DSF assay, or a BRM Luciferase cell assay.

The term "pharmaceutical composition," as used herein, represents a composition containing a compound described herein formulated with a pharmaceutically acceptable excipient and appropriate for administration to a mammal, for example a human. Typically, a pharmaceutical composition is manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other pharmaceutically acceptable formulation.

A "pharmaceutically acceptable excipient," as used herein, refers to any ingredient other than the compounds described herein (for example, a vehicle capable of suspending or dissolving the active compound) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

As used herein, the term "pharmaceutically acceptable salt" means any pharmaceutically acceptable salt of a compound, for example, any compound of Formula I-III. Pharmaceutically acceptable salts of any of the compounds described herein may include those that are within the scope of sound medical judgment, suitable for use in contact with the tissues of humans and animals without undue toxicity, irritation, allergic response and are commensurate with a reasonable benefit/risk ratio. Pharmaceutically acceptable salts are well known in the art. For example, pharmaceutically acceptable salts are described in: Berge et al., J. Pharmaceutical Sciences 66:1-19, 1977 and in Pharmaceutical Salts: Properties, Selection, and Use, (Eds. P. H. Stahl and C. G. Wermuth), Wiley-VCH, 2008. The salts can be prepared in situ during the final isolation and purification of the compounds described herein or separately by reacting a free base group with a suitable organic acid.

The compounds of the invention may have ionizable groups so as to be capable of preparation as pharmaceutically acceptable salts. These salts may be acid addition salts involving inorganic or organic acids or the salts may, in the case of acidic forms of the compounds of the invention be prepared from inorganic or organic bases. Frequently, the compounds are prepared or used as pharmaceutically acceptable salts prepared as addition products of pharmaceutically acceptable acids or bases. Suitable pharmaceutically acceptable acids and bases and methods for preparation of the appropriate salts are well-known in the art. Salts may be prepared from pharmaceutically acceptable non-toxic acids and bases including inorganic and organic acids and bases. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, and valerate salts. Representative alkali or alkaline earth metal salts include sodium, lithium, potassium, calcium, and magnesium, as well as nontoxic ammonium, quaternary ammonium, and amine cations, including, but not limited to ammonium, tetramethylammonium, tetraethylammonium, methylamine, dimethylamine, trimethylamine, triethylamine, and ethylamine.

By a "reference" is meant any useful reference used to compare protein or RNA levels. The reference can be any sample, standard, standard curve, or level that is used for comparison purposes. The reference can be a normal reference sample or a reference standard or level. A "reference sample" can be, for example, a control, e.g., a predetermined negative control value such as a "normal control" or a prior sample taken from the same subject; a sample from a normal healthy subject, such as a normal cell or normal tissue; a sample (e.g., a cell or tissue) from a subject not having a disease; a sample from a subject that is diagnosed with a disease, but not yet treated with a compound of the invention; a sample from a subject that has been treated by a compound of the invention; or a sample of a purified protein or RNA (e.g., any described herein) at a known normal concentration. By "reference standard or level" is meant a value or number derived from a reference sample. A "normal control value" is a pre-determined value indicative of non-disease state, e.g., a value expected in a healthy control subject. Typically, a normal control value is expressed as a range ("between X and Y"), a high threshold ("no higher than X"), or a low threshold ("no lower than X"). A subject having a measured value within the normal control value for a particular biomarker is typically referred to as "within normal limits" for that biomarker. A normal reference standard or level can be a value or number derived from a normal subject not having a disease or disorder (e.g., cancer); a subject that has been treated with a compound of the invention. In preferred embodiments, the reference sample, standard, or level is matched to the sample subject sample by at least one of the following criteria: age, weight, sex, disease stage, and overall health. A standard curve of levels of a purified protein or RNA, e.g., any described herein, within the normal reference range can also be used as a reference.

As used herein, the term "subject" refers to any organism to which a composition in accordance with the invention may be administered, e.g., for experimental, diagnostic, prophylactic, and/or therapeutic purposes. Typical subjects include any animal (e.g., mammals such as mice, rats, rabbits, non-human primates, and humans). A subject may seek or be in need of treatment, require treatment, be receiving treatment, be receiving treatment in the future, or be a human or animal who is under care by a trained professional for a particular disease or condition.

As used herein, the terms "treat," "treated," or "treating" mean therapeutic treatment or any measures whose object is to slow down (lessen) an undesired physiological condition, disorder, or disease, or obtain beneficial or desired clinical results. Beneficial or desired clinical results include, but are not limited to, alleviation of symptoms; diminishment of the extent of a condition, disorder, or disease; stabilized (i.e., not worsening) state of condition, disorder, or disease; delay in onset or slowing of condition, disorder, or disease progression; amelioration of the condition, disorder, or disease state or remission (whether partial or total); an amelioration of at least one measurable physical parameter, not necessarily discernible by the patient; or enhancement or improvement of condition, disorder, or disease. Treatment includes eliciting a clinically significant response without excessive levels of side effects. Treatment also includes prolonging survival as compared to expected survival if not receiving treatment. Compounds of the invention may also be used to "prophylactically treat" or "prevent" a disorder, for example, in a subject at increased risk of developing the disorder.

As used herein, the terms "variant" and "derivative" are used interchangeably and refer to naturally-occurring, synthetic, and semi-synthetic analogues of a compound, peptide, protein, or other substance described herein. A variant or derivative of a compound, peptide, protein, or other substance described herein may retain or improve upon the biological activity of the original material. The details of one or more embodiments of the invention are set forth in the description below. Other features, objects, and advantages of the invention will be apparent from the description and from the claims.

DETAILED DESCRIPTION

Figure 1:
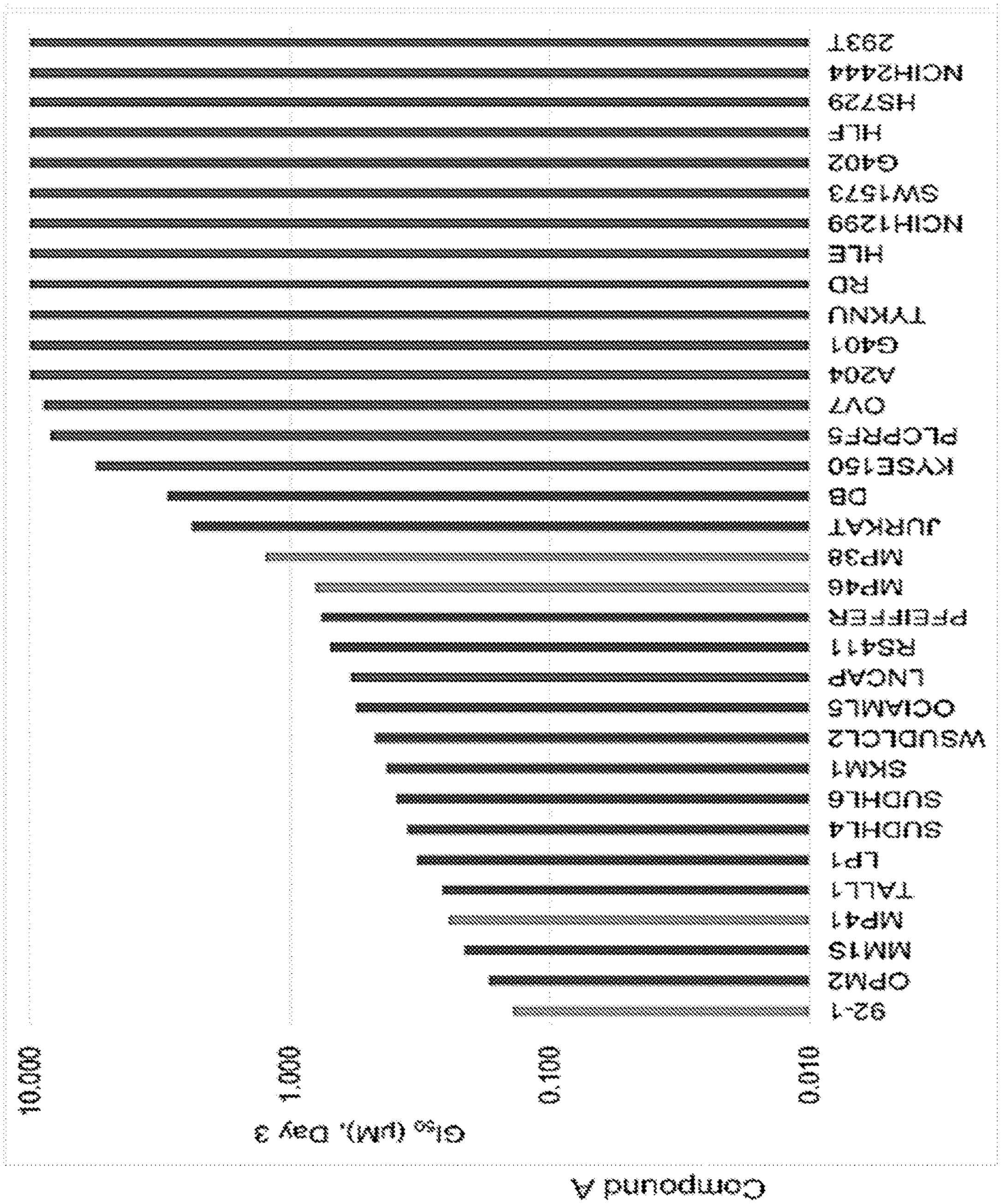
FIG. 1 is a graph illustrating inhibition of cell proliferation of several cancer cell lines by a BRG1/BRM inhibitor (Compound A).

The present disclosure features compounds useful for the inhibition of BRG1 and/or BRM. These compounds may be used to modulate the activity of a BAF complex, for example, for the treatment of a BAF-related disorder, such as cancer. Exemplary compounds described herein include compounds having a structure according to Formula I-IIIa:

Formula I

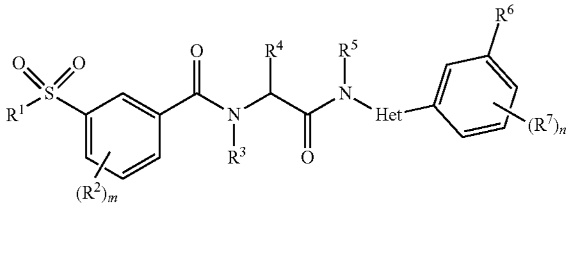

wherein m is 0, 1, 2, 3, or 4;

n is 0, 1, 2, 3, or 4;

$R^1$ is optionally substituted $C_3$-$C_6$ branched alkyl;

each $R^2$ is, independently, optionally substituted $C_1$-$C_6$ alkyl, optionally substituted $C_1$-$C_6$ heteroalkyl, or optionally substituted amino;

$R^3$ and $R^5$ are, independently, hydrogen or optionally substituted $C_1$-$C_6$ alkyl;

$R^4$ is hydrogen, optionally substituted $C_1$-$C_6$ alkyl, or optionally substituted $C_1$-$C_6$ heteroalkyl;

Het is 5- or 6-membered heterocycle;

$R^6$ is hydrogen, cyano, optionally substituted $C_1$-$C_6$ heteroalkyl, carboxyl, optionally substituted $C_2$-$C_9$ heteroaryl, optionally substituted $C_2$-$C_9$ heterocyclyl, or optionally substituted $C_6$-$C_{10}$ aryl; and $R^7$ is cyano, optionally substituted $C_1$-$C_6$ alkyl or optionally substituted $C_1$-$C_6$ heteroalkyl;

Formula II

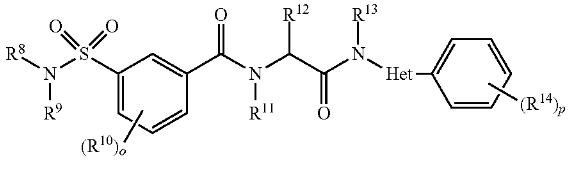

wherein o is 0, 1, 2, 3, or 4;

p is 0, 1, 2, 3, 4, or 5;

$R^8$ and $R^9$ are, independently, hydrogen or optionally substituted $C_1$-$C_6$ alkyl, or $R^9$ combines with an $R^{10}$ and the atoms to which they are attached to form a 5- to 8-membered ring;

each $R^{10}$ is, independently, halo, optionally substituted $C_1$-$C_6$ alkyl, or optionally substituted $C_1$-$C_6$ heteroalkyl or an $R^{10}$ combines with $R^9$ and the atoms to which they are attached to form a 5- to 8-membered ring;

$R^{11}$ and $R^{13}$ are, independently, hydrogen or optionally substituted $C_1$-$C_6$alkyl;

$R^{12}$ is hydrogen, optionally substituted $C_1$-$C_6$ alkyl, or optionally substituted $C_1$-$C_6$ heteroalkyl; Het is optionally substituted $C_2$-$C_9$ heteroaryl; and each $R^{14}$ is, independently, optionally substituted amide, cyano, optionally substituted $C_1$-$C_6$ heteroalkyl, carboxyl, optionally substituted $C_2$-$C_9$ heteroaryl, optionally substituted $C_2$-$C_9$ heterocyclyl, or $C_6$-$C_{10}$ aryl;

Formula III

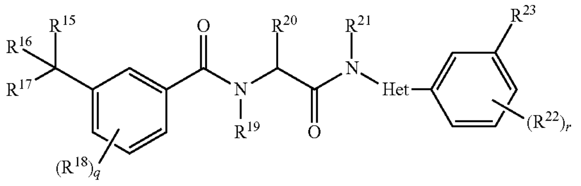

wherein q and r are, independently, 0, 1, 2, 3, or 4;

$R^{15}$ is optionally substituted $C_1$-$C_6$ alkyl or halo, or $R^{15}$ combines with $R^{17}$ and the carbon to which they are attached to form an optionally substituted $C_3$-$C_8$ cycloalkyl or optionally substituted $C_2$-$C_9$ heterocyclyl;

$R^{16}$ is optionally substituted $C_1$-$C_6$ alkyl, optionally substituted $C_1$-$C_6$ perfluoroalkyl, or $R^{18}$ combines with an $R^{18}$ and the carbons to which they are attached to form an optionally substituted $C_3$-$C_8$ cycloalkyl or optionally substituted $C_2$-$C_9$ heterocyclyl, or $R^{16}$ combines with $R^{15}$ and the carbons to which they are attached to form an optionally substituted $C_3$-$C_8$ cycloalkyl or optionally substituted $C_2$-$C_9$ heterocyclyl;

$R^{17}$ is cyano, optionally substituted amino, hydroxy, optionally substituted $C_1$-$C_6$ alkyl, optionally substituted $C_1$-$C_6$ hydroxyalkyl, optionally substituted $C_1$-$C_6$ aminoalkyl, or

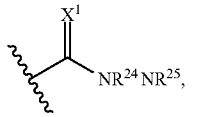

or $R^{17}$ combines with an $R^{18}$ and the carbons to which they are attached to form an optionally substituted $C_3$-$C_8$cycloalkyl or optionally substituted $C_2$-$C_9$ heterocyclyl;

$X^1$ is O or —N—OH;

each $R^{18}$ is, independently, halo, optionally substituted $C_1$-$C_6$ alkyl, or optionally substituted $C_1$-$C_6$ heteroalkyl, or an $R^{18}$ combines with $R^{18}$ and the carbons to which they are attached to form an optionally substituted $C_3$-$C_8$cycloalkyl or optionally substituted $C_2$-$C_9$ heterocyclyl or an $R^{18}$ combines with an $R^{17}$ and the carbons to which they are attached to form an optionally substituted $C_3$-$C_8$cycloalkyl or optionally substituted $C_2$-$C_9$ heterocyclyl;

$R^{19}$, $R^{21}$, $R^{24}$, and $R^{25}$ are, independently, hydrogen or optionally substituted $C_1$-$C_6$ alkyl;

$R^{20}$ is hydrogen, optionally substituted $C_1$-$C_6$ alkyl, or optionally substituted $C_1$-$C_6$ heteroalkyl;

Het is optionally substituted $C_2$-$C_9$ heteroaryl; and each $R^{22}$ is, independently, hydroxy, halo, optionally substituted $C_1$-$C_6$ alkyl, or optionally substituted $C_1$-$C_6$ heteroalkyl, or an $R^2$ combines with $R^2$ and the carbons to which they are attached to form an optionally substituted $C_2$-$C_9$ heterocyclyl;

$R^{23}$ is, independently, hydrogen, cyano, optionally substituted $C_1$-$C_6$ heteroalkyl, optionally substituted $C_2$-$C_9$ heteroaryl, optionally substituted $C_2$-$C_9$ heterocyclyl, or optionally substituted $C_6$-$C_{10}$ aryl, or $R^{23}$ combines with an $R^{22}$ and the carbons to which they are attached to form an optionally substituted $C_2$-$C_9$ heterocyclyl; or Formula IIIa

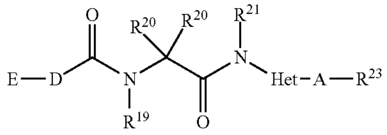

wherein E is hydrogen, hydroxy, amino, cyano, optionally substituted $C_1$-$C_6$ alkyl, optionally substituted $C_1$-$C_6$ hydroxyalkyl, optionally substituted $C_1$-$C_6$ aminoalkyl, optionally substituted silyl, optionally substituted $C_2$-$C_9$ heterocyclyl, or optionally substituted $C_3$-$C_8$ cycloalkyl;

D is optionally substituted $C_6$-$C_{10}$ aryl or optionally substituted $C_2$-$C_9$ heteroaryl;

$R^{19}$ and $R^{21}$ are, independently, hydrogen or optionally substituted $C_1$-$C_6$ alkyl;

each $R^{20}$ is, independently, hydrogen, optionally substituted $C_1$-$C_6$ alkyl, or optionally substituted $C_1$-$C_6$ heteroalkyl, or two $R^{20}$ groups combine with the carbon to which they are attached to form an optionally substituted $C_3$-$C_8$cycloalkyl;

Het is optionally substituted $C_2$-$C_9$ heteroaryl;

A is optionally substituted $C_6$-$C_{10}$ aryl or optionally substituted $C_2$-$C_9$ heteroaryl; and $R^{23}$ is, independently, hydrogen, cyano, optionally substituted $C_1$-$C_6$ alkyl, optionally substituted $C_1$-$C_6$ alkoxy, optionally substituted amide, optionally substituted $C_1$-$C_6$ heteroalkyl, optionally substituted $C_3$-$C_8$cycloalkyl, optionally substituted $C_2$-$C_9$ heteroaryl, optionally substituted $C_2$-$C_9$ heterocyclyl, or optionally substituted $C_6$-$C_{10}$ aryl, or $R^{23}$ combines with an $R^{22}$ and the carbons to which they are attached to form an optionally substituted $C_2$-$C_9$ heterocyclyl;

or a pharmaceutically acceptable salt thereof.

In some embodiments, the compound, or pharmaceutically acceptable salt thereof, has the structure of any one of compounds 1-11 in Table 2, 12-47 in Table 1a, 48-109 in Table 3a, 110-129 of Table 1b, 130 or 131 of Table 2b, 132-268 of Table 3b, or 269-444 of Table 3c.

Other embodiments, as well as exemplary methods for the synthesis of production of these compounds, are described herein.

Pharmaceutical Uses

The compounds described herein are useful in the methods of the invention and, while not bound by theory, are believed to exert their ability to modulate the level, status, and/or activity of a BAF complex, i.e., by inhibiting the activity of the BRG1 and/or BRM proteins within the BAF complex in a mammal. BAF complex-related disorders include, but are not limited to, BRG1 loss of function mutation-related disorders.

An aspect of the present invention relates to methods of treating disorders related to BRG1 loss of function mutations such as cancer (e.g., non-small cell lung cancer, colorectal cancer, bladder cancer, cancer of unknown primary, glioma, breast cancer, melanoma, non-melanoma skin cancer, endometrial cancer, or penile cancer) in a subject in need thereof. In some embodiments, the compound is administered in an amount and for a time effective to result in one or more (e.g., two or more, three or more, four or more) of: (a) reduced tumor size, (b) reduced rate of tumor growth, (c) increased tumor cell death (d) reduced tumor progression, (e) reduced number of metastases, (f) reduced rate of metastasis, (g) decreased tumor recurrence (h) increased survival of subject, (i) increased progression free survival of subject.

Treating cancer can result in a reduction in size or volume of a tumor. For example, after treatment, tumor size is reduced by 5% or greater (e.g., 10%, 20%, 30%, 40%, 50%, 60%, 70%, 80%, 90%, or greater) relative to its size prior to treatment. Size of a tumor may be measured by any reproducible means of measurement. For example, the size of a tumor may be measured as a diameter of the tumor.

Treating cancer may further result in a decrease in number of tumors. For example, after treatment, tumor number is reduced by 5% or greater (e.g., 10%, 20%, 30%, 40%, 50%, 60%, 70%, 80%, 90%, or greater) relative to number prior to treatment. Number of tumors may be measured by any reproducible means of measurement, e.g., the number of tumors may be measured by counting tumors visible to the naked eye or at a specified magnification (e.g., 2×, 3×, 4×, 5×, 10×, or 50×).

Treating cancer can result in a decrease in number of metastatic nodules in other tissues or organs distant from the primary tumor site. For example, after treatment, the number of metastatic nodules is reduced by 5% or greater (e.g., 10%, 20%, 30%, 40%, 50%, 60%, 70%, 80%, 90% or greater) relative to number prior to treatment. The number of metastatic nodules may be measured by any reproducible means of measurement. For example, the number of metastatic nodules may be measured by counting metastatic nodules visible to the naked eye or at a specified magnification (e.g., 2×, 10×, or 50×).

Treating cancer can result in an increase in average survival time of a population of subjects treated according to the present invention in comparison to a population of untreated subjects. For example, the average survival time is increased by more than 30 days (more than 60 days, 90 days, or 120 days). An increase in average survival time of a population may be measured by any reproducible means. An increase in average survival time of a population may be measured, for example, by calculating for a population the average length of survival following initiation of treatment with the compound of the invention. An increase in average survival time of a population may also be measured, for example, by calculating for a population the average length of survival following completion of a first round of treatment with a pharmaceutically acceptable salt of the invention.

Treating cancer can also result in a decrease in the mortality rate of a population of treated subjects in comparison to an untreated population. For example, the mortality rate is decreased by more than 2% (e.g., more than 5%, 10%, or 25%). A decrease in the mortality rate of a population of treated subjects may be measured by any reproducible means, for example, by calculating for a population the average number of disease-related deaths per unit time following initiation of treatment with a pharmaceutically acceptable salt of the invention. A decrease in the mortality rate of a population may also be measured, for example, by calculating for a population the average number of disease-related deaths per unit time following completion of a first round of treatment with a pharmaceutically acceptable salt of the invention.

Exemplary cancers that may be treated by the invention include, but are not limited to, non-small cell lung cancer, small-cell lung cancer, colorectal cancer, bladder cancer, glioma, breast cancer, melanoma, non-melanoma skin cancer, endometrial cancer, esophagogastric cancer, pancreatic cancer, hepatobiliary cancer, soft tissue sarcoma, ovarian cancer, head and neck cancer, renal cell carcinoma, bone cancer, non-Hodgkin lymphoma, prostate cancer, embryonal tumor, germ cell tumor, cervical cancer, thyroid cancer, salivary gland cancer, gastrointestinal neuroendocrine tumor, uterine sarcoma, gastrointestinal stromal tumor, CNS cancer, thymic tumor, Adrenocortical carcinoma, appendiceal cancer, small bowel cancer and penile cancer.

Combination Formulations and Uses Thereof

The compounds of the invention can be combined with one or more therapeutic agents. In particular, the therapeutic agent can be one that treats or prophylactically treats any cancer described herein.

Combination Therapies

A compound of the invention can be used alone or in combination with an additional therapeutic agent, e.g., other agents that treat cancer or symptoms associated therewith, or in combination with other types of treatment to treat cancer. In combination treatments, the dosages of one or more of the therapeutic compounds may be reduced from standard dosages when administered alone. For example, doses may be determined empirically from drug combinations and permutations or may be deduced by isobolographic analysis (e.g., Black et al., Neurology 65:S3-S6, 2005). In this case, dosages of the compounds when combined should provide a therapeutic effect.

In some embodiments, the second therapeutic agent is a chemotherapeutic agent (e.g., a cytotoxic agent or other chemical compound useful in the treatment of cancer). These include alkylating agents, antimetabolites, folic acid analogs, pyrimidine analogs, purine analogs and related inhibitors, vinca alkaloids, epipodopyyllotoxins, antibiotics, L-Asparaginase, topoisomerase inhibitors, interferons, platinum coordination complexes, anthracenedione substituted urea, methyl hydrazine derivatives, adrenocortical suppressant, adrenocorticosteroides, progestins, estrogens, antiestrogen, androgens, antiandrogen, and gonadotropin-releasing hormone analog. Also included is 5-fluorouracil (5-FU), leucovorin (LV), renotecan, oxaliplatin, capecitabine, paclitaxel and doxetaxel. Non-limiting examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammall and calicheamicin omegall (see, e.g., Agnew, Chem. Intl. Ed Engl. 33:183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, Adriamycin® (doxorubicin, including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 8-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., Taxol® paclitaxel (Bristol-Myers Squibb Oncology, Princeton, N.J.), ABraxane®, cremophor-free, albumin-engineered nanoparticle formulation of paclitaxel (American Pharmaceutical Partners, Schaumberg, Ill.), and Taxotere® doxetaxel (Rhone-Poulenc Rorer, Antony, France); chloranbucil; Gemzar4® gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; Navelbine® vinorelbine; novantrone; teniposide; edatrexate; daunomycin; aminopterin; xeloda; ibandronate; irinotecan (e.g., CPT-11); topoisomerase inhibitor RFS 2000; difluoromethylomithine (DMFO); retinoids such as retinoic acid; capecitabine; and pharmaceutically acceptable salts, acids or derivatives of any of the above. Two or more chemotherapeutic agents can be used in a cocktail to be administered in combination with the first therapeutic agent described herein. Suitable dosing regimens of combination chemotherapies are known in the art and described in, for example, Saltz et al. (1999) Proc ASCO 18:233a and Douillard et al. (2000) Lancet 355:1041-7.

In some embodiments, the second therapeutic agent is a therapeutic agent which is a biologic such a cytokine (e.g., interferon or an interleukin (e.g., IL-2)) used in cancer treatment. In some embodiments the biologic is an anti-angiogenic agent, such as an anti-VEGF agent, e.g., bevacizumab (Avastin). In some embodiments the biologic is an immunoglobulin-based biologic, e.g., a monoclonal antibody (e.g., a humanized antibody, a fully human antibody, an Fc fusion protein or a functional fragment thereof) that agonizes a target to stimulate an anti-cancer response, or antagonizes an antigen important for cancer. Such agents include Rituxan (Rituximab); Zenapax (Daclizumab); Simulect (Basiliximab); Synagis (Palivizumab); Remicade (Infliximab); Herceptin (Trastuzumab); Mylotarg (Gemtuzumab ozogamicin); Campath (Alemtuzumab); Zevalin (Ibritumomab tiuxetan); Humira (Adalimumab); Xolair (Omalizumab); Bexxar (Tositumomab-I-131); Raptiva (Efalizumab); Erbitux (Cetuximab); Avastin (Bevacizumab); Tysabri (Natalizumab); Actemra (Tocilizumab); Vectibix (Panitumumab); Lucentis (Ranibizumab); Soliris (Eculizumab); Cimzia (Certolizumab pegol); Simponi (Golimumab); Ilaris (Canakinumab); Stelara (Ustekinumab); Arzerra (Ofatumumab); Prolia (Denosumab); Numax (Motavizumab); ABThrax (Raxibacumab); Benlysta (Belimumab); Yervoy (Ipilimumab); Adcetris (Brentuximab Vedotin); Perjeta (Pertuzumab); Kadcyla (Ado-trastuzumab emtansine); and Gazyva (Obinutuzumab). Also included are antibody-drug conjugates.

The second agent may be a therapeutic agent which is a non-drug treatment. For example, the second therapeutic agent is radiation therapy, cryotherapy, hyperthermia and/or surgical excision of tumor tissue.

The second agent may be a checkpoint inhibitor. In one embodiment, the inhibitor of checkpoint is an inhibitory antibody (e.g., a monospecific antibody such as a monoclonal antibody). The antibody may be, e.g., humanized or fully human. In some embodiments, the inhibitor of checkpoint is a fusion protein, e.g., an Fc-receptor fusion protein. In some embodiments, the inhibitor of checkpoint is an agent, such as an antibody, that interacts with a checkpoint protein. In some embodiments, the inhibitor of checkpoint is an agent, such as an antibody, that interacts with the ligand of a checkpoint protein. In some embodiments, the inhibitor of checkpoint is an inhibitor (e.g., an inhibitory antibody or small molecule inhibitor) of CTLA-4 (e.g., an anti-CTLA4 antibody such as ipilimumab/Yervoy or tremelimumab). In some embodiments, the inhibitor of checkpoint is an inhibitor (e.g., an inhibitory antibody or small molecule inhibitor) of PD-1 (e.g., nivolumab/Opdivo®; pembrolizumab/Keytruda®; pidilizumab/CT-011). In some embodiments, the inhibitor of checkpoint is an inhibitor (e.g., an inhibitory antibody or small molecule inhibitor) of PDL1 (e.g., MPDL3280A/RG7446: MED14736; MSB0010718C; BMS 936559). In some embodiments, the inhibitor of checkpoint is an inhibitor (e.g., an inhibitory antibody or Fc fusion or small molecule inhibitor) of PDL2 (e.g., a PDL2/Ig fusion protein such as AMP 224). In some embodiments, the inhibitor of checkpoint is an inhibitor (e.g., an inhibitory antibody or small molecule inhibitor) of B7-H3 (e.g., MGA271), B7-H4, BTLA, HVEM, TIM3, GAL9, LAG3, VISTA, KIR, 2B4, CD160, CGEN-15049, CHK 1, CHK2, A2aR, B-7 family ligands, or a combination thereof.

In any of the combination embodiments described herein, the first and second therapeutic agents are administered simultaneously or sequentially, in either order. The first therapeutic agent may be administered immediately, up to 1 hour, up to 2 hours, up to 3 hours, up to 4 hours, up to 5 hours, up to 6 hours, up to 7 hours, up to, 8 hours, up to 9 hours, up to 10 hours, up to 11 hours, up to 12 hours, up to 13 hours, 14 hours, up to hours 16, up to 17 hours, up 18 hours, up to 19 hours up to 20 hours, up to 21 hours, up to 22 hours, up to 23 hours up to 24 hours or up to 1-7, 1-14, 1-21 or 1-30 days before or after the second therapeutic agent.

Pharmaceutical Compositions

The compounds of the invention are preferably formulated into pharmaceutical compositions for administration to a mammal, preferably, a human, in a biologically compatible form suitable for administration in vivo. Accordingly, in an aspect, the present invention provides a pharmaceutical composition comprising a compound of the invention in admixture with a suitable diluent, carrier, or excipient.

The compounds of the invention may be used in the form of the free base, in the form of salts, solvates, and as prodrugs. All forms are within the scope of the invention. In accordance with the methods of the invention, the described compounds or salts, solvates, or prodrugs thereof may be administered to a patient in a variety of forms depending on the selected route of administration, as will be understood by those skilled in the art. The compounds of the invention may be administered, for example, by oral, parenteral, buccal, sublingual, nasal, rectal, patch, pump, or transdermal administration and the pharmaceutical compositions formulated accordingly. Parenteral administration includes intravenous, intraperitoneal, subcutaneous, intramuscular, transepithelial, nasal, intrapulmonary, intrathecal, rectal, and topical modes of administration. Parenteral administration may be by continuous infusion over a selected period of time.

A compound of the invention may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, a compound of the invention may be incorporated with an excipient and used in the form of ingestible tablets, buccal tablets, troches, capsules, elixirs, suspensions, syrups, and wafers. A compound of the invention may also be administered parenterally. Solutions of a compound of the invention can be prepared in water suitably mixed with a surfactant, such as hydroxypropylcellulose. Dispersions can also be prepared in glycerol, liquid polyethylene glycols, DMSO, and mixtures thereof with or without alcohol, and in oils. Under ordinary conditions of storage and use, these preparations may contain a preservative to prevent the growth of microorganisms. Conventional procedures and ingredients for the selection and preparation of suitable formulations are described, for example, in Remington's Pharmaceutical Sciences (2003, 20th ed.) and in The United States Pharmacopeia: The National Formulary (USP 24 NF19), published in 1999. The pharmaceutical forms suitable for injectable use include sterile aqueous solutions or dispersions and sterile powders for the extemporaneous preparation of sterile injectable solutions or dispersions. In all cases the form must be sterile and must be fluid to the extent that may be easily administered via syringe. Compositions for nasal administration may conveniently be formulated as aerosols, drops, gels, and powders. Aerosol formulations typically include a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device, such as a single dose nasal inhaler or an aerosol dispenser fitted with a metering valve which is intended for disposal after use. Where the dosage form comprises an aerosol dispenser, it will contain a propellant, which can be a compressed gas, such as compressed air or an organic propellant, such as fluorochlorohydrocarbon. The aerosol dosage forms can also take the form of a pump-atomizer. Compositions suitable for buccal or sublingual administration include tablets, lozenges, and pastilles, where the active ingredient is formulated with a carrier, such as sugar, acacia, tragacanth, gelatin, and glycerine. Compositions for rectal administration are conveniently in the form of suppositories containing a conventional suppository base, such as cocoa butter. A compound described herein may be administered intratumorally, for example, as an intratumoral injection. Intratumoral injection is injection directly into the tumor vasculature and is specifically contemplated for discrete, solid, accessible tumors. Local, regional, or systemic administration also may be appropriate. A compound described herein may advantageously be contacted by administering an injection or multiple injections to the tumor, spaced for example, at approximately, 1 cm intervals. In the case of surgical intervention, the present invention may be used preoperatively, such as to render an inoperable tumor subject to resection. Continuous administration also may be applied where appropriate, for example, by implanting a catheter into a tumor or into tumor vasculature.

The compounds of the invention may be administered to an animal, e.g., a human, alone or in combination with pharmaceutically acceptable carriers, as noted herein, the proportion of which is determined by the solubility and chemical nature of the compound, chosen route of administration, and standard pharmaceutical practice.

Dosages

The dosage of the compounds of the invention, and/or compositions comprising a compound of the invention, can vary depending on many factors, such as the pharmacodynamic properties of the compound; the mode of administration; the age, health, and weight of the recipient; the nature and extent of the symptoms; the frequency of the treatment, and the type of concurrent treatment, if any; and the clearance rate of the compound in the animal to be treated. One of skill in the art can determine the appropriate dosage based on the above factors. The compounds of the invention may be administered initially in a suitable dosage that may be adjusted as required, depending on the clinical response. In general, satisfactory results may be obtained when the compounds of the invention are administered to a human at a daily dosage of, for example, between 0.05 mg and 3000 mg (measured as the solid form). Dose ranges include, for example, between 10-1000 mg (e.g., 50-800 mg). In some embodiments, 50, 100, 150, 200, 250, 300, 350, 400, 450, 500, 550, 600, 650, 700, 750, 800, 850, 900, 950, or 1000 mg of the compound is administered.

Alternatively, the dosage amount can be calculated using the body weight of the patient. For example, the dose of a compound, or pharmaceutical composition thereof, administered to a patient may range from 0.1-50 mg/kg (e.g., 0.25-25 mg/kg). In exemplary, non-limiting embodiments, the dose may range from 0.5-5.0 mg/kg (e.g., 0.5, 1.0, 1.5, 2.0, 2.5, 3.0, 3.5, 4.0, 4.5, or 5.0 mg/kg) or from 5.0-20 mg/kg (e.g., 5.5, 6.0, 6.5, 7.0, 7.5, 8.0, 8.5, 9.0, 9.5, 10, 11, 12, 13, 14, 15, 16, 17, 18, 19, or 20 mg/kg).

EXAMPLES

Example 1. Preparation 3-(dimethylsulfamoyl)benzoic acid (Intermediate B) and 2-[[3-(dimethylsulfamoyl)benzoyl]amino]acetic acid (Intermediate E)

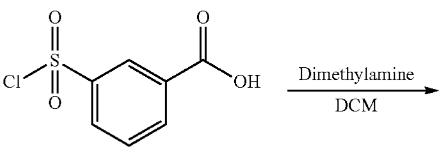

A

-continued

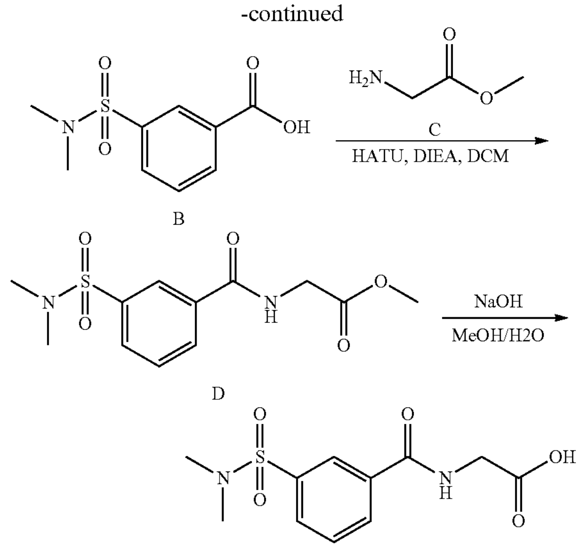

B

D

E

Step 1: Preparation of 3-(dimethylsulfamoyl)benzoic acid (Intermediate B)

B

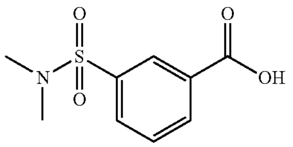

To a solution of 3-chlorosulfonylbenzoic acid (10 g, 45.32 mmol) in DCM (80 mL) was added dimethylamine (2 M, 74.79 mL) at 0° C. The mixture was stirred at 20° C. for 1 hr. The mixture was poured into water (50 mL) and extracted with EA (100 mL). The organic layer was discarded. To the water phase was added aqueous HCl (1N) to adjust pH=4, then extracted with EA (100 mL×3), washed with brine (50 mL), dried over $Na_2SO_4$, filtered and concentrated. The crude product was washed with 2-methoxy-2-methylpropane (20 mL), then filtered and dried in vacuum to give Intermediate B (8.1 g, 35.33 mmol, 77.95% yield) as a pink solid. LCMS (ESI) m/z $[M+H]^+$=230.1. $^1H$ NMR (400 MHz, DMSO-$d_6$) δ=13.56 (s, 1H), 8.24 (d, J=8.0 Hz, 1H), 8.19 (s, 1H), 7.99 (d, J=8.4 Hz, 1H), 7.82-7.78 (m, 1H), 2.62 (s, 6H) ppm.

Step 2: Preparation of methyl 2-[[3-(dimethylsulfamoyl)benzoyl]amino]acetate (Intermediate D)

D

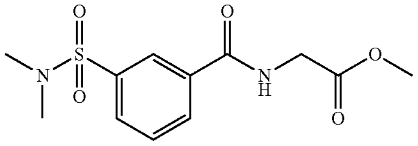

To a solution of Intermediate B (2.5 g, 10.91 mmol) in DCM (25 mL) were added HATU (4.56 g, 12.00 mmol) and DIPEA (4.23 g, 32.72 mmol, 5.70 mL) at 20° C., the mixture was stirred for 0.5 hr. Then methyl 2-aminoacetate (1.64 g, 13.09 mmol, HCl salt) was added and the mixture was stirred at 20° C. for 1.5 hr. The reaction mixture was poured into water (30 mL) and extracted with EA (30 mL×3). The combined organic layer was washed with brine (20 mL), dried over $Na_2SO_4$, filtered and concentrated. The residue was purified by column chromatography ($SiO_2$, PE:EA=5:1 to 1:1) and concentrated in vacuum to give Intermediate D (3.4 g, 10.53 mmol, 96.55% yield) as yellow oil. LCMS (ESI) m/z $[M+H]^4$=301.0. $^1H$ NMR (400 MHz, DMSO-$d_6$) δ=9.31-9.28 (m, 1H), 8.22-8.18 (m, 2H), 7.94-7.92 (m, 1H), 7.92-7.79 (m, 1H), 4.06-4.05 (m, 2H), 3.67 (s, 3H), 2.64 (s, 6H).

Step 3: Preparation of 2-[[3-(dimethylsulfamoyl)benzoyl]amino]acetic acid (Intermediate E)

E

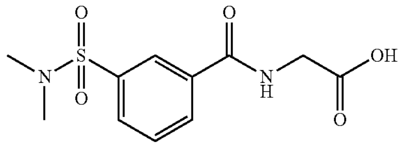

To a solution of Intermediate D (3.4 g, 11.32 mmol) in MeOH (23 mL) was added a solution of NaOH (905.60 mg, 22.64 mmol) in $H_2O$ (11 mL) at 20° C. The mixture was stirred at 20° C. for 3 hr. To the reaction mixture was added aqueous HCl (1 N) to adjust pH=5 and then extracted with EA (30 mL×3). The organic phase was washed with brine (20 mL), dried over $Na_2SO_4$, filtered and concentrated. The crude product was triturated with 2-methoxy-2-methylpropane (15 mL), then filtered and dried in vacuum to give Intermediate E (1.8 g, 6.22 mmol, 54.98% yield) as a white solid. LCMS (ESI) m/z $[M+H]^+$=287.0. $^1H$ NMR (400 MHz, DMSO-$d_6$) δ=12.66 (br.s, 1H), 9.21-9.19 (m, 1H), 8.22-8.18 (m, 2H), 7.93-7.91 (m, 1H), 7.80-7.78 (m, 1H), 3.95 (d, J=5.6 Hz, 2H), 2.64 (s, 6H).

Example 2. Preparation of tert-butyl N-[2-[[4-(3-bromophenyl)thiazol-2-yl]amino]-2-oxo-ethyl]carbamate (Intermediate D) and preparation of 2-amino-N-(4-(3-bromophenyl)thiazol-2-yl)acetamide (Intermediate E)

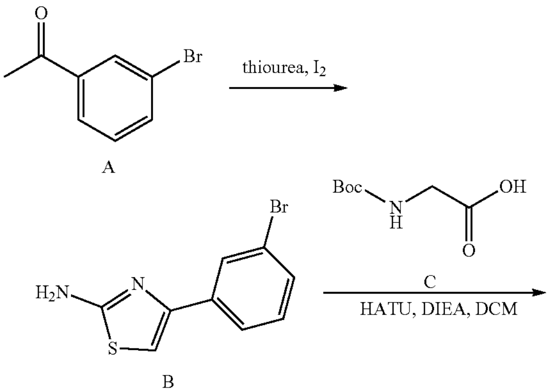

A

B

-continued

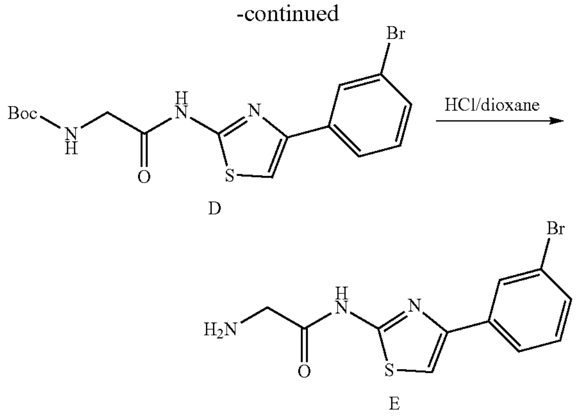

D

E

Step 1: Preparation of 4-(3-bromophenyl)thiazol-2-amine (Intermediate B)

B

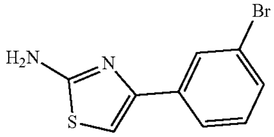

To a mixture of 1-(3-bromophenyl)ethanone (473 g, 2.38 mol, 313.25 mL) and thiourea (361.78 g, 4.75 mol) was added 12 (603.14 g, 2.38 mol, 478.68 mL, 1 eq). The mixture was stirred at 110° C. for 16 hr. After cooling, the reaction mixture was triturated with MTBE (5 L), and then filtered to remove any unreacted iodine and acetophenone. The filter cake was put in ice water (4 L) and treated with 25% $NH_3 \cdot H_2O$ to pH=9-10. The suspension was stirred at 25° C. for 15 min, then filtered and washed with water (1 L) to give wet solid. The wet solid was dissolved in EA (4 L) and washed with sat.$NaHCO_3$ (1 L×2) and brine (1 L). The EA layer was dried over $Na_2SO_4$, filtered and concentrated under reduced pressure to give a residue. The residue was triturated with PE/EA=100:1 (4 L) at 25° C. for 3 h, then the suspension was filtered, the filter cake was washed with PE (1 L) and dried in vacuum to give intermediate B (450 g, 1.69 mol, 71.20% yield, 95.93% purity) as a pink solid. LCMS (ESI) m/z [$^{79}$BrM+H$^+$]=254.9. $^1$H NMR (400 MHz, DMSO-$d_6$) δ=7.98-7.97 (m, 1H), 7.80-7.77 (m, 1H), 7.43-7.42 (m, 1H), 7.34-7.30 (m, 1H), 7.15 (s, 1H), 7.10 (s, 2H).

Step 2: Preparation of tert-butyl N-[2-[[4-(3-bromophenyl)thiazol-2-yl]amino]-2-oxo-ethyl]carbamate (Intermediate D)

D

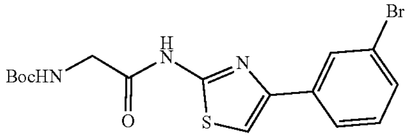

To a solution of 2-(tert-butoxycarbonylamino)acetic acid (82.40 g, 470.34 mmol), HATU (178.84 g, 470.34 mmol) and DIEA (151.97 g, 1.18 mol, 204.81 mL) in DCM (1000.00 mL) was added intermediate B (100.00 g, 391.95 mmol), the mixture was stirred at 30° C. for 16 hr. The reaction mixture was washed with sat. citric acid (500 mL×4) and brine (500 mL), dried over $Na_2SO_4$, filtered and concentrated under reduced pressure to give a residue. The residue was triturated with MeOH (200.0 mL), filtered and dried in vacuum to give Intermediate D (100 g, 241.89 mmol, 61.71% yield) as a white solid. LCMS (ESI) m/z [$^{81}$BrM+H]$^+$=413.8. $^1$H NMR (400 MHz, DMSO-$d_6$) δ=12.29 (s, 1H), 8.09-8.09 (m, 1H), 7.89 (d, J=7.6 Hz, 1H), 7.76 (s, 1H), 7.52-7.49 (m, 1H), 7.41-7.37 (m, 1H), 7.16-7.13 (m, 1H), 3.87-3.81 (m, 2H), 1.39 (s, 9H) ppm.

Step 3: Preparation of 2-amino-N-(4-(3-bromophenyl)thiazol-2-yl)acetamide (Intermediate E)

E

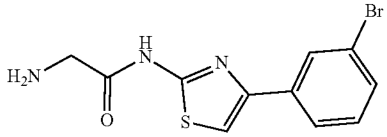

A mixture of intermediate D (10 g, 24.25 mmol) in HCl/dioxane (100 mL) was stirred at 30° C. for 2 hr. The reaction mixture was concentrated in vacuum to give intermediate E (8.4 g, crude, HCl) as a white solid, which was used for next step directly. LCMS (ESI) m/z [M+H]$^+$=313.8.

Example 3. Preparation of 2-amino-N-[4-[3-(4-pyridyl)phenyl]thiazol-2-yl]acetamide (Intermediate F)

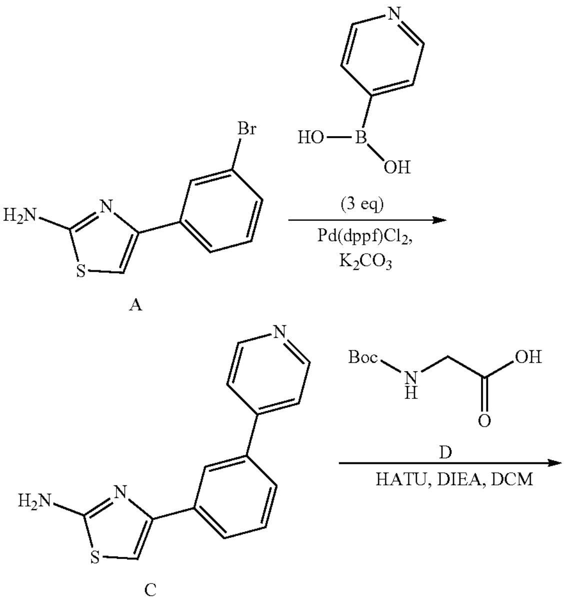

A

C

-continued

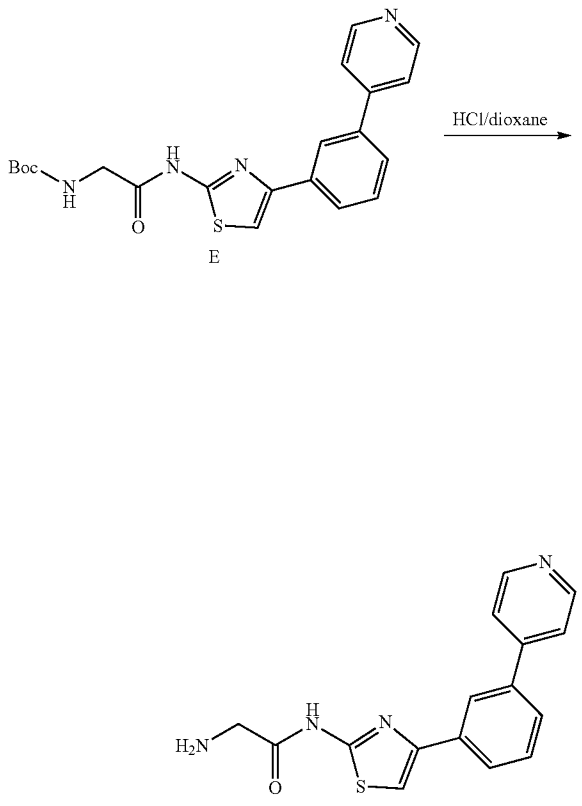

E

F

Step 1: Preparation of 4-[3-(4-pyridyl)phenyl]thiazol-2-amine (intermediate C)

C

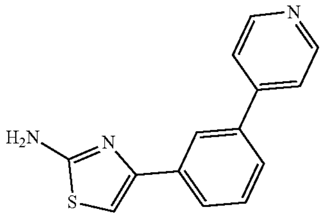

To a solution of 4-(3-bromophenyl)thiazol-2-amine (10 g, 39.20 mmol), 4-pyridylboronic acid (14.45 g, 117.59 mmol) and $K_2CO_3$ (16.25 g, 117.59 mmol) in dioxane (120 mL) and Water (30 mL) was added Pd(dppf)$Cl_2$ (1 g, 1.37 mmol) under $N_2$, the mixture was stirred at 100° C. for 4 hr. The reaction mixture was diluted with water (500 mL), extracted with EA (500 mL) and concentrated under reduced pressure to give a residue. The residue was purified by crystallization from DCM/MTBE=1:20 (200 mL) and filtered to give intermediate C (9.5 g, 36.33 mmol, 92.69% yield) as a brown solid. LCMS (ESI) m/z $[M+H]^+$=254.2. $^1H$ NMR (400 MHz, DMSO-$d_6$) δ 8.66 (d, J=6.0 Hz, 2H), 8.19 (s, 1H), 7.90 (d, J=8.0 Hz, 1H), 7.76-7.70 (m, 2H), 7.68 (d, J=8.0 Hz, 1H), 7.52 (t, J=8.0 Hz, 1H), 7.21 (s, 1H), 7.11 (s, 2H) ppm.

Step 2: Preparation of tert-butyl N-[2-oxo-2-[[4-[3-(4-pyridyl)phenyl]thiazol-2-yl]amino]ethyl]carbamate (Intermediate E)

E

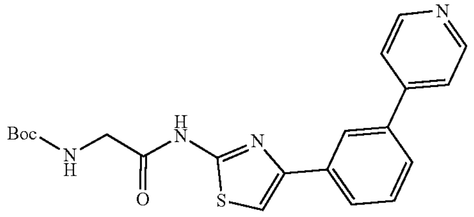

To a solution of 2-(tert-butoxycarbonylamino)acetic acid (9.85 g, 56.25 mmol), HATU (21.39 g, 56.25 mmol) and DIPEA (14.54 g, 112.51 mmol) in DCM (200 mL) was added int C (9.5 g, 37.50 mmol, 1 eq), the mixture was stirred at 30° C. for 16 hr. A precipitate was formed. The reaction mixture was filtered to give a yellow solid. The crude product was triturated with EA (300.0 mL) and MeOH (50.0 mL) and dried in vacuum to give intermediate E (11 g, 25.89 mmol, 69.03% yield) as a white solid. LCMS (ESI) m/z $[M+H]^+$=411.3. $^1H$ NMR (400 MHz, DMSO-$d_6$) δ 12.32 (br s, 1H), 8.69-8.67 (m, 2H), 8.30 (s, 1H), 8.01 (d, J=7.8 Hz, 1H), 7.83 (s, 1H), 7.80-7.76 (m, 3H), 7.64-7.60 (m, 1H), 7.20-7.15 (m, 1H), 3.88 (d, J=6.4 Hz, 2H), 1.44 (s, 9H) ppm.

Step 3: Preparation of 2-amino-N-[4-[3-(4-pyridyl)phenyl]thiazol-2-yl]acetamide (Intermediate F)

F

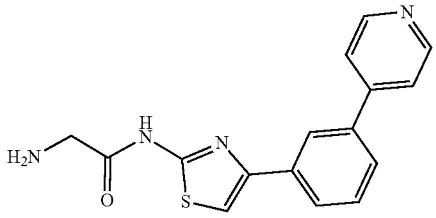

To a solution of Intermediate E (11 g, 26.80 mmol) in MeOH (20 mL) was added 4 M HCl/EtOAc (20 mL). The mixture was stirred at 20° C. for 2 hr. The reaction mixture was concentrated under reduced pressure to give a residue. The residue was purified by triturated with EA (200 mL) and MTBE (50 mL) and dried in vacuum to give intermediate F (12 g, HCl salt) a light yellow solid. LCMS (ESI) m/z $[M+H]^+$=311.3. $^1H$ NMR (400 MHz, methanol-d4) δ8.92 (d, J=6.8 Hz, 2H), 8.52-8.47 (m, 3H), 8.22 (d, J=8.0 Hz, 1H), 7.94 (m, J=8.4 Hz, 1H), 7.75-7.66 (m, 2H), 4.04 (s, 2H) ppm.

Example 4. Preparation of 3-[2-[[2-[[3-(dimethylsulfamoyl)benzoyl]amino]acetyl]amino]thiazol-4-yl]-N,N-dimethyl-benzamide (Compound 1)

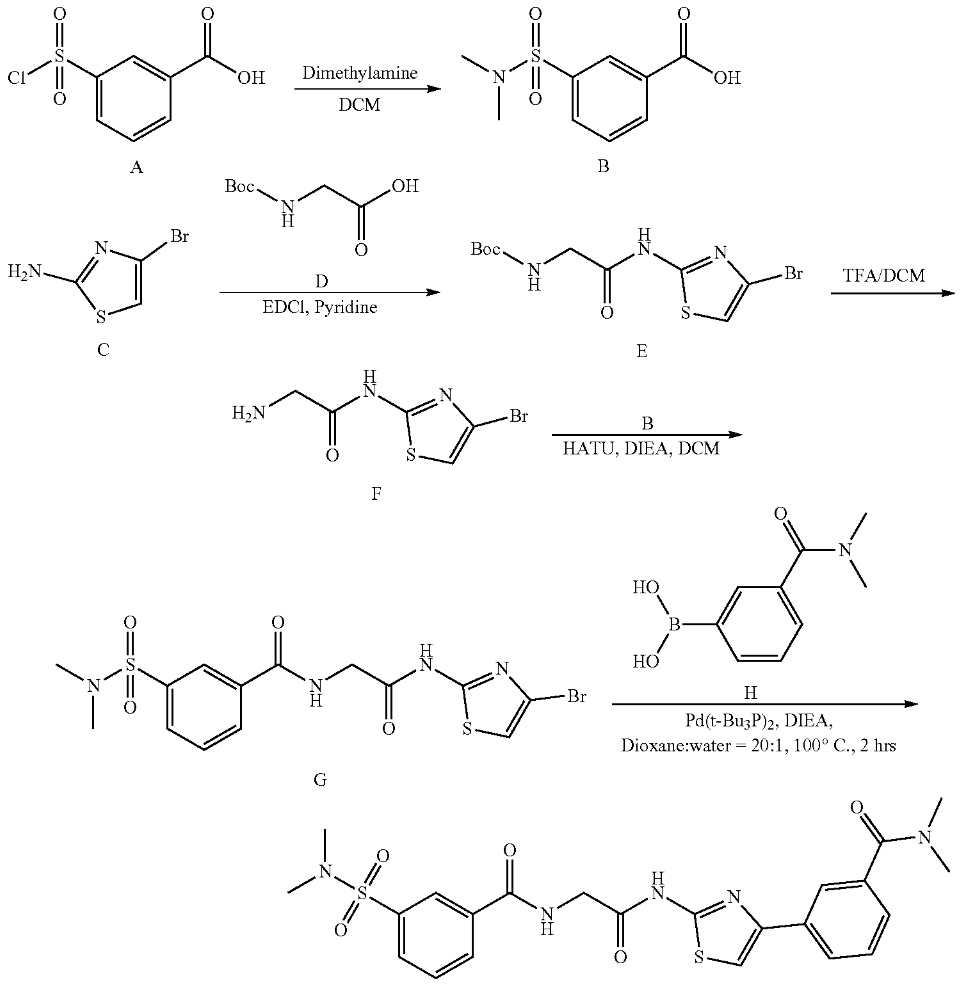

Compound 1

Step 1: Preparation of 3-(dimethylsulfamoyl)benzoic acid (Intermediate B)

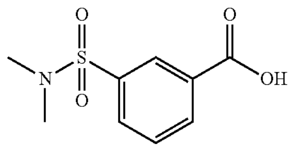

B

To a solution of 3-chlorosulfonylbenzoic acid (10 g, 45.32 mmol) in DCM (80 mL) was added dimethylamine (2 M, 74.79 mL) at 0° C. The mixture was stirred at 20° C. for 1 hr. The mixture was poured into water (50 mL) and extracted with EA (100 mL). The organic layer was discarded. To the water phase was added aqueous HCl (1 N) to adjust pH=4, then extracted with EA (100 mL×3), washed with brine (50 mL), dried over $Na_2SO_4$, filtered and concentrated. The crude product was washed with 2-methoxy-2-methylpropane (20 mL), then filtered and dried in vacuum to give Intermediate B (8.1 g, 35.33 mmol, 77.95% yield) as a pink solid. LCMS (ESI) m/z $[M+H]^+$=230.1. $^1H$ NMR (400 MHz, DMSO-$d_6$) δ=13.56 (s, 1H), 8.24 (d, J=8.0 Hz, 1H), 8.19 (s, 1H), 7.99 (d, J=8.4 Hz, 1H), 7.82-7.78 (m, 1H), 2.62 (s, 6H) ppm.

Step 2: Preparation of tert-butyl N-[2-[(4-bromothiazol-2-yl)amino]-2-oxo-ethyl]carbamate (Intermediate E)

E

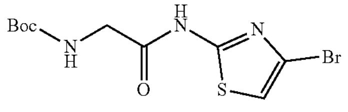

To a solution of 4-bromothiazol-2-amine (3 g, 16.76 mmol) and 2-(tert-butoxycarbonylamino)acetic acid (4.40 g, 25.13 mmol) in pyridine (30 mL) was added EDCl (16.06 g, 83.78 mmol). The mixture was stirred at 15° C. for 16 hr. The reaction mixture was concentrated under reduced pressure to remove pyridine. The residue was diluted with 0.5N HCl (100 mL) and extracted with EA (50 mL×3). The combined organic layers were washed with $NaHCO_3$ (50 mL) and brine (50 ml), dried over $Na_2SO_4$, filtered and concentrated under reduced pressure to give a residue. The residue was purified by column chromatography ($SiO_2$, Petroleum ether/Ethyl acetate=7/1 to 3:1) to give Intermediate E (2.2 g, 6.44 mmol, 38.40% yield) as a white solid. LCMS (ESI) m/z $[^{79}BrM+23]^+$=358.1.

Step 3: Preparation of 2-amino-N-(4-bromothiazol-2-yl)acetamide (Intermediate F)

F

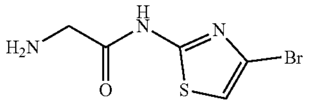

To a solution of Intermediate E (1.28 g, 3.80 mmol) in DCM (13 mL) was added TFA (1.3 mL). The mixture was stirred at 25° C. for 1 hr. The reaction mixture was concentrated under reduced pressure to give a residue. The residue was triturated with MTBE (10 mL). The solid was collected by filtered and dried in vacuum to give Intermediate F (800 mg, 2.28 mmol, 60.09% yield, TFA salt) as a white solid. LCMS (ESI) m/z $[^{79}BrM+23]^+$=258.1.

Step 4: Preparation of N-[2-[(4-bromothiazol-2-yl)amino]-2-oxo-ethyl]-3-(dimethylsulfamoyl)benzamide_(Intermediate G)

G

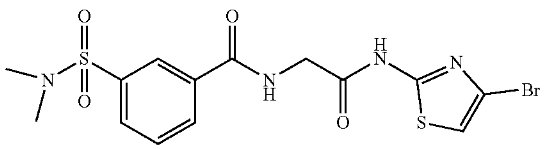

To a solution of Intermediate B (576.22 mg, 2.51 mmol) in DCM (15 mL) were added HATU (1.30 g, 3.43 mmol) and DIEA (1.77 g, 13.71 mmol, 2.39 mL). The mixture was stirred at 25° C. for 0.5 h. Then Intermediate F (800 mg, 2.28 mmol, TFA salt) was added and the mixture was stirred at 25° C. for 16 h. The reaction mixture was concentrated under reduced pressure to give a residue. The residue was purified by column chromatography ($SiO_2$, Petroleum ether/Ethyl acetate=1/1 to 0/1) and concentrated in vacuum to give Intermediate G (850 mg, 1.90 mmol, 83.16% yield) as a yellow solid. LCMS (ESI) m/z $[^{81}BrM+H]^+$=449.1. $^1H$ NMR (400 MHz, DMSO-$d_6$) δ=12.61 (s, 1H), 9.31-9.28 (m, 1H), 8.25-8.21 (m, 2H), 7.94 (d, J=8.0 Hz, 1H), 7.81-7.77 (m, 1H), 7.30 (s, 1H), 4.20-4.19 (m, 1H), 2.64 (s, 6H) ppm.

Step 5: Preparation of 3-[2-[[2-[[3-(dimethylsulfamoyl)benzoyl] amino]acetyl]amino]thiazol-4-yl]-N,N-dimethyl-benzamide (Compound 1)

Compound 1

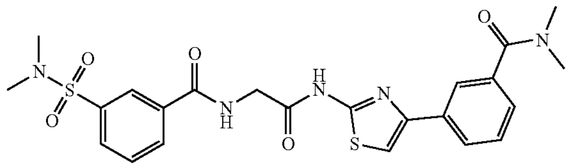

To a solution of Intermediate G (50 mg, 111.78 μmol) and Intermediate H (64.72 mg, 335.33 μmol) in dioxane (3 mL) and $H_2O$ (0.3 mL) was added $Pd(t\text{-}Bu_3P)_2$ (28.56 mg, 55.89 μmol) and DIEA (72.23 mg, 558.88 μmol, 97.34 μL) under protect of $N_2$. The mixture was stirred at 100° C. for 2 hrs. Lots of solid was appeared after cooled to 30° C. The mixture was filtered and triturated in EA (3 mL) to afford crude product. The crude product was dissolved in MeOH (1 mL) and DMSO (1 mL) and purified by Pre-HPLC (column: Phenomenex Synergi C18 150×25×10 μm; mobile phase: [water (0.1% TFA)-ACN]; B %: 30%-60%, 9 min) and lyophilized to give Compound 1 (14.46 mg, 27.69 μmol, 24.77% yield) as white solid. LCMS (ESI) m/z $[M+H]^+$=516.0. $^1H$ NMR (400 MHz, DMSO-$d_6$) δ=12.47 (s, 1H), 9.30-9.29 (m, 1H), 8.23-8.27 (m, 2H), 7.98-7.93 (m, 3H), 7.81-7.79 (m, 1H), 7.76 (s, 1H), 7.52-7.50 (m, 1H), 7.35-7.33 (m, 1H), 4.25 (d, J=5.6 Hz, 2H), 3.01-2.94 (m, 6H), 2.67 (s, 6H) ppm.

Example 5. Preparation of 3-(N,N-dimethylsulfamoyl)-N-(2-oxo-2-((4-(3-(pyridin-4-yl)phenyl)thiazol-2-yl)amino)ethyl)benzamide (Compound 2)

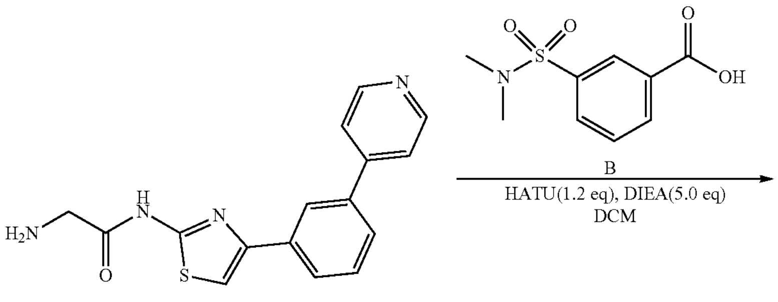

A

-continued

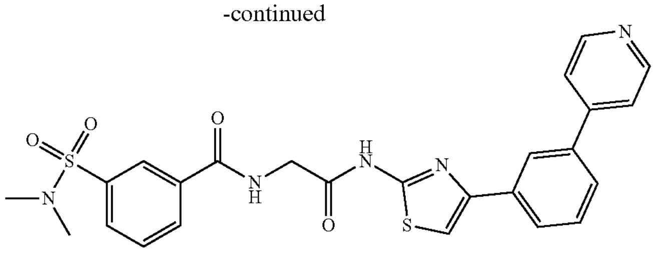

Compound 2

To a solution of 2-amino-N-[4-[3-(4-pyridyl)phenyl]thiazol-2-yl]acetamide (prepared according to the method in Example 3) (50 mg, 144.16 μmol, HCl salt) and 3-(dimethylsulfamoyl)benzoic acid (33.05 mg, 144.16 μmol) in DCM (2 mL) were added HATU (65.78 mg, 172.99 μmol) and DIEA (93.16 mg, 720.81 μmol, 125.55 μL). The mixture was stirred at 30° C. for 16 hr. The reaction mixture was filtered to give a residue. The residue was triturated with MeOH (2 mL). The mixture was filtered and the solid was dried in vacuum to give Compound 2 (48.80 mg, 92.79 μmol, 64.36% yield) as a white solid. LCMS (ESI) m/z $[M+H]^+$ =522.2. $^1H$ NMR (400 MHz, DMSO) 5=12.49 (br s, 1H), 9.30-9.28 (m, 1H), 8.67-8.66 (m, 2H), 8.29 (s, 1H), 8.26-8.25 (m, 2H), 8.01 (d, J=8.0 Hz, 1H), 7.94-7.92 (m, 1H), 7.83 (s, 1H), 7.797 (s, 1H), 7.76-7.74 (m, 3H), 7.59 (s, 1H), 4.23 (d, J=5.6 Hz, 2H), 2.64 (s, 6H) ppm.

Example 6. Preparation of 3-(dimethylsulfamoyl)-N-[2-oxo-2-[[4-[2-(1H-pyrazol-4-yl)phenyl]thiazol-2-yl]amino]ethyl]benzamide (Compound 3)

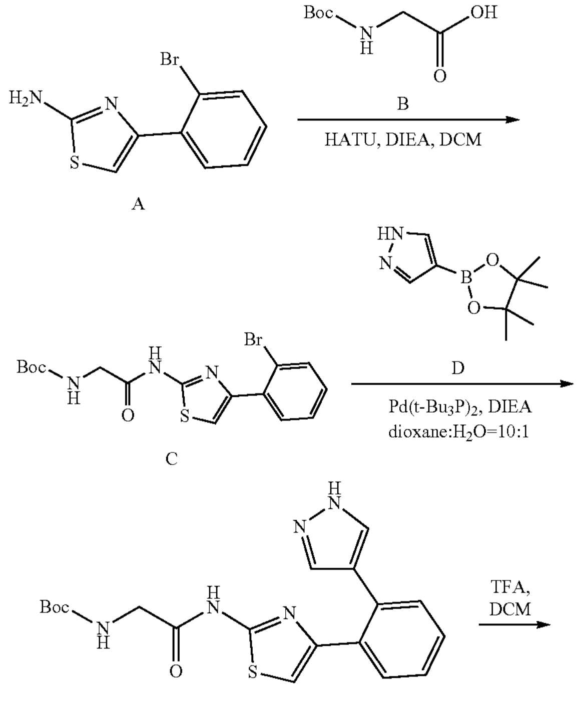

-continued

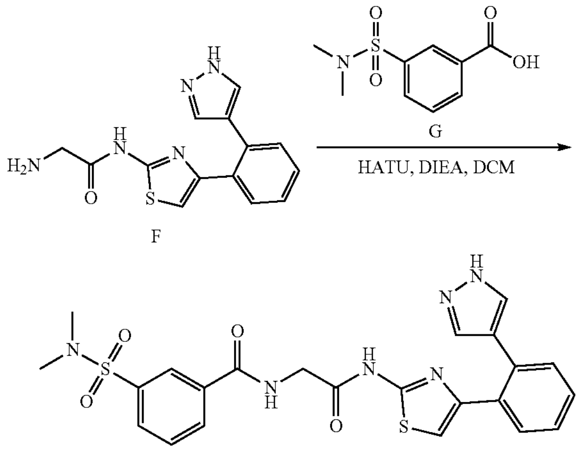

Compound 3

Step 1: Preparation of tert-butyl N-[2-[[4-(2-bromophenyl)thiazol-2-yl]amino]-2-oxo-ethyl]carbamate (Intermediate C)

C

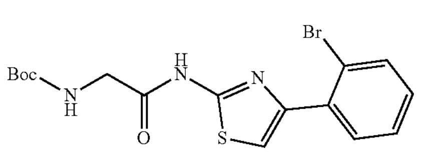

To a solution of 2-(tert-butoxycarbonylamino)acetic acid (1.65 g, 9.41 mmol) in DCM (100 mL) was added HATU (4.47 g, 11.76 mmol) and DIEA (3.04 g, 23.52 mmol, 4.10 mL) and the mixture was stirred at 30° C. for 30 min. Then 4-(2-bromophenyl)thiazol-2-amine (2 g, 7.84 mmol) was added. The mixture was stirred at 30° C. for another 12 hrs. The mixture was diluted with DCM (50 mL) and washed with water (10 mL×3) and brine (10 mL×2), then dried over $Na_2SO_4$, filtered and concentrated under vacuum. The crude product was purified by column chromatography ($SiO_2$,PE:EA=100:1-10:1) and concentrated to give Intermediate C (2.80 g, 6.79 mmol, 86.63% yield) as yellow oil. $^1H$ NMR (400 MHz, DMSO-$d_6$) δ=12.10 (s, 1H), 7.56-7.48 (m, 2H), 7.33 (s, 1H), 7.32-7.26 (m, 1H), 7.11-7.09 (m, 1H), 3.68 (br d, J=6.0 Hz, 2H), 1.23-1.10 (m, 9H) ppm.

Step 2: Preparation of tert-butyl N-[2-oxo-2-[[4-[2-(1H-pyrazol-4-yl)phenyl] thiazol-2-yl]amino]ethyl] carbamate (Intermediate E)

E

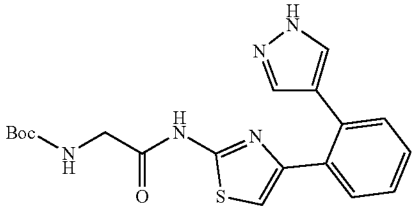

To a solution of Intermediate C (25.00 mg, 60.64 μmol) and tert-butyl 4-(4,4,5,5-tetramethyl-1,3,2-dioxaborolan-2-yl)pyrazole-1-carboxylate (53.51 mg, 181.92 μmol) in dioxane (2 mL) and water (0.4 mL) was added $Pd(t-Bu_3P)_2$ (6.20 mg, 12.13 μmol) and DIEA (23.51 mg, 181.92 μmol, 31.68 μL) under protect of $N_2$. The mixture was stirred at 100° C. for 2 hr. The combined reaction mixture was diluted with EA (30 mL) then filtered through silica. The filtrate was washed with water (5 mL×3) and brine (5 mL×2), dried over $Na_2SO_4$, filtered and concentrated under vacuum to give Intermediate E (110 mg, crude) as yellow oil which was used to next step directly. LCMS (ESI) m/z $[M+H]^+$=400.0.

Step 3: Preparation of 2-amino-N-[4-[2-(1H-pyrazol-4-yl)phenyl] thiazol-2-yl]acetamide (Intermediate F)

F

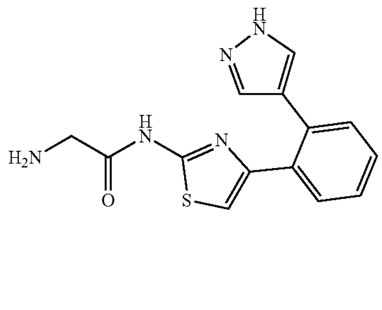

A solution of Intermediate E (100 mg, 250.33 μmol) in HCl/dioxane (4 M, 10 mL) was stirred at 25° C. for 2 hr. The mixture was concentrated under vacuum. The residue was purified by Prep-HPLC (column: Phenomenex Synergi C18 150×25×10 μm; mobile phase: [water (0.05% HCl)-ACN]; B %: 5%-25%, 10 min) and lyophilized to give Intermediate F (40 mg, 119.11 μmol, 47.58% yield, HCl salt) as light yellow solid which was used to next step directly.

Step 4: Preparation of 3-(dimethylsulfamoyl)-N-[2-oxo-2-[[4-[2-(1H-pyrazol-4-yl)phenyl]thiazol-2-yl] amino]ethyl]benzamide (Compound 3)

Compound 3

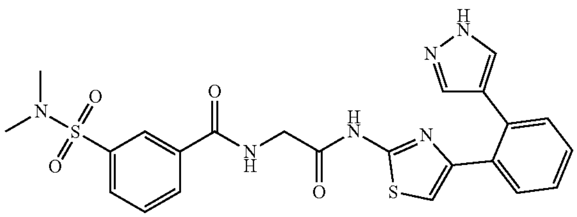

To a solution of Intermediate F (20.00 mg, 59.56 μmol, HCl salt) and 3-(dimethylsulfamoyl)benzoic acid (prepared according to the method in Example 1) (15.02 mg, 65.51 μmol) in DCM (1 mL) was added DIEA (23.09 mg, 178.67 μmol, 31.12 μL) and HATU (33.97 mg, 89.34 μmol). The mixture was stirred at 30° C. for 16 hr. The reaction mixture was diluted with DCM (20 mL) and washed with saturated $NaHCO_3$ solution (5 mL×3), saturated critic acid solution (5 mL×3), water (5 mL×3) and brine (5 mL×3). Then dried over $Na_2SO_4$, filtered and concentrated under vacuum. The residue was purified by Pre-HPLC (column: Boston Prime C18 150×30 mm×5 μm; mobile phase: [water (0.1% TFA)-ACN]; B %: 37%-57%, 8 min) and lyophilized to give Compound 3 (4.22 mg, 8.26 μmol, 13.88% yield) as white solid. LCMS (ESI) m/z [M+H]+=511.2. $^1H$ NMR (400 MHz, DMSO-$d_6$) δ=12.40 (s, 1H), 9.31-9.28 (m, 1H), 8.26-8.23 (m, 2H), 7.94 (d, J=7.6 Hz, 1H), 7.82-7.78 (m, 1H), 7.52 (d, J=7.2 Hz, 1H), 7.45-7.38 (m, 3H), 7.32-7.28 (m, 2H), 6.96 (s, 1H), 4.20 (d, J=5.6 Hz, 2H), 2.66 (s, 6H) ppm.

Example 7. Preparation of 3-(dimethylsulfamoyl)-N-[2-oxo-2-[[4-[3-(1H-pyrazol-4-yl)phenyl]thiazol-2-yl]amino]ethyl]benzamide (Compound 4)

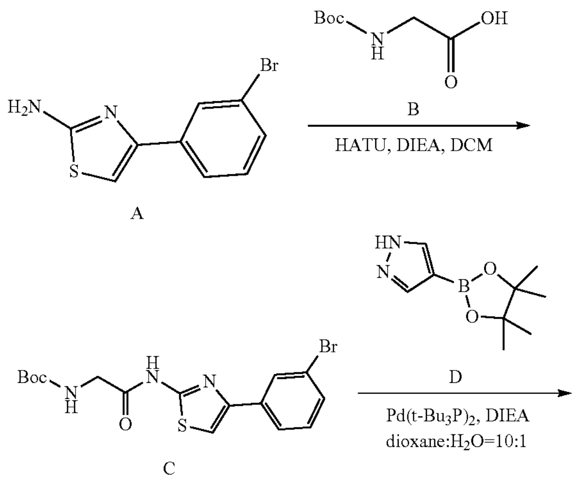

-continued

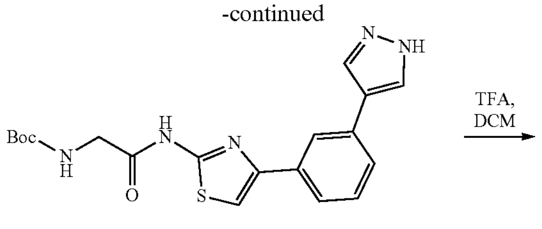

E

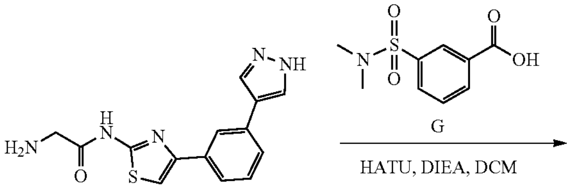

F

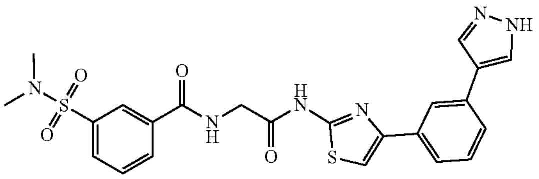

Compound 4

Step 1: Preparation of tert-butyl N-[2-[[4-(3-bromophenyl)thiazol-2-yl] amino]-2-oxo-ethyl]carbamate (Intermediate C)

C

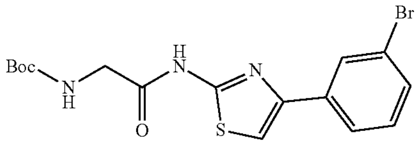

To a solution of 2-(tert-butoxycarbonylamino)acetic acid (1.65 g, 9.41 mmol) in DCM (100 mL) was added HATU (4.47 g, 11.76 mmol) and DIEA (3.04 g, 23.52 mmol, 4.10 mL) and the mixture was stirred at 30° C. for 30 min. Then 4-(3-bromophenyl)thiazol-2-amine (2 g, 7.84 mmol) was added. The mixture was stirred at 30° C. for another 12 hrs. The mixture was diluted with DCM (200 mL) and washed with $H_2O$ (50 mL×3) and brine (50 mL×2), then dried over $Na_2SO_4$, filtered and concentrated under vacuum. The crude product was purified by column chromatography ($SiO_2$, PE:EA=100:1-10:1) and concentrated to give Intermediate C (1.6 g, 3.88 mmol, 49.50% yield) as yellow oil. $^1$H NMR (400 MHz, methanol-$d_4$) δ=8.10 (d, J=1.6 Hz, 1H), 7.87 (br d, J=7.8 Hz, 1H), 7.48-7.45 (m, 2H), 7.33-7.30 (m, 1H), 4.00 (s, 2H), 1.51-1.47 (m, 9H) ppm.

Step 2: Preparation of tert-butyl N-[2-oxo-2-[[4-[3-(1H-pyrazol-4-yl)phenyl] thiazol-2-yl]amino]ethyl] carbamate (Intermediate E)

E

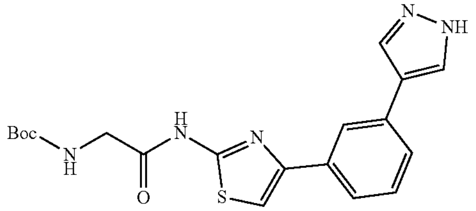

To a solution of Intermediate C (100.00 mg, 242.54 μmol) and 4-(4,4,5,5-tetramethyl-1,3,2-dioxaborolan-2-yl)-1H-pyrazole (141.19 mg, 727.62 μmol) in dioxane (3 mL) and water (0.3 mL) was added Pd(t-$Bu_3P)_2$ (24.79 mg, 48.51 μmol) and DIEA (94.04 mg, 727.62 μmol, 126.74 μL) under protect of $N_2$. The mixture was stirred at 100° C. for 2 hr. The mixture was diluted by EA (50 mL) and filter through silica. Then washed with water (10 mL×3) and brine (10 mL×2), dried over $Na_2SO_4$, filtered and concentrated under reduced pressure to give Intermediate E (100 mg, crude) as gray solid, which was used to next step directly. LCMS (ESI) m/z $[M+H]^+$=400.0.

Step 3: Preparation of 2-amino-N-[4-[3-(1H-pyrazol-4-yl)phenyl]thiazol-2-yl]acetamide (Intermediate F)

F

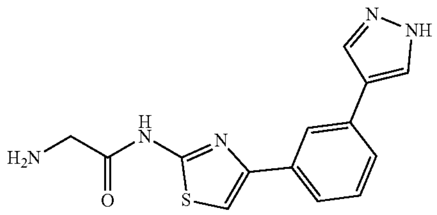

A mixture of Intermediate E (100.00 mg, 250.33 μmol) in DCM (3 mL) and TFA (0.5 mL) was stirred at 25° C. for 2 hr. The mixture was poured into water (20 mL) and treated with saturated $NaHCO_3$ solution to pH was 7-8, then extracted with EA (5 mL×5). The combined organic layer was washed with water (5 mL×3) and brine (5 mL×2), dried over $Na_2SO_4$, filtered and concentrated under vacuum. The solid was purified by Pre-HPLC (column: Phenomenex Synergi C18 150×25×10 μm; mobile phase: [water (0.05% HCl)-ACN]; B %: 5%-25%, 10 min) and lyophilized to give Intermediate F (30 mg, 100.22 μmol, 30.00% yield) as a light yellow solid. $^1$H NMR (400 MHz, DMSO-$d_6$) δ=12.83 (br s, 1H), 8.44 (br s, 2H), 8.19-8.17 (m, 3H), 7.88 (s, 1H), 7.79 (d, J=7.6 Hz, 1H), 7.65 (d, J=8.0 Hz, 1H), 7.51-7.47 (m, 1H), 3.99-3.97 (m, 2H) ppm.

Step 4: Preparation of 3-(dimethylsulfamoyl)-N-[2-oxo-2-[[4-[3-(1H-pyrazol-4-yl)phenyl]thiazol-2-yl]amino]ethyl]benzamide (Compound 4)

Compound 4

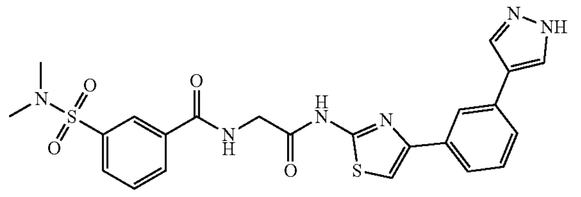

To a solution of Intermediate F (20.00 mg, 59.56 μmol) and 3-(dimethylsulfamoyl)benzoic acid (prepared according to the method in Example 1) (15.48 mg, 65.51 μmol) in DCM (3 mL) was added DIEA (23.09 mg, 178.67 μmol, 31.12 μL) and HATU (33.97 mg, 89.34 μmol). The mixture was stirred at 30° C. for 16 hr. The reaction mixture was diluted with DCM (20 mL) and washed with saturated $NaHCO_3$ solution (5 mL×3), saturated critic solution (5 mL×3), water (5 mL×3) and brine (5 mL×3), then dried over $Na_2SO_4$, filtered and concentrated under vacuum. The residue was purified by Prep-HPLC (column: Phenomenex Synergi C18 150×25×10 μm; mobile phase: [water (0.1% TFA)-ACN]; B %: 28%-58%, 9 min) and lyophilized to give Compound 4 (7.76 mg, 15.20 μmol, 25.52% yield) as white solid. LCMS (ESI) m/z $[M+H]^+$=511.1. $^1$H NMR (400 MHz, DMSO-$d_6$) δ=12.50 (s, 1H), 9.33-9.30 (m, 1H), 8.28-8.24 (m, 2H), 8.11 (br d, J=5.0 Hz, 3H), 7.95 (d, J=8.0 Hz, 1H), 7.83-7.79 (m, 1H), 7.74-7.72 (m, 2H), 7.57 (d, J=7.8 Hz, 1H), 7.44-7.40 (m, 1H), 4.25 (d, J=5.6 Hz, 2H), 2.66 (s, 6H) ppm.

Example 8. Preparation of compound N-(2-((4-(4-(1H-pyrazol-4-yl)phenyl)thiazol-2-yl)amino)-2-oxoethyl)-3-(N,N-dimethylsulfamoyl)benzamide (Compound 5)

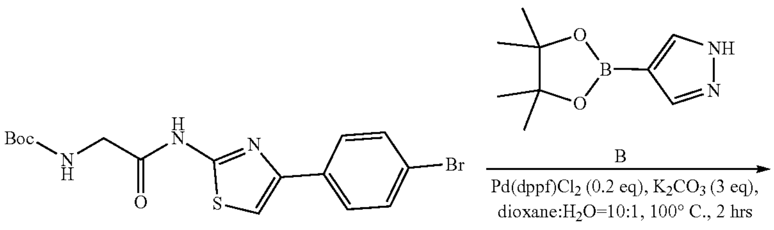

A

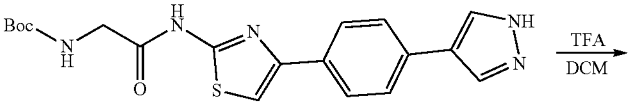

C

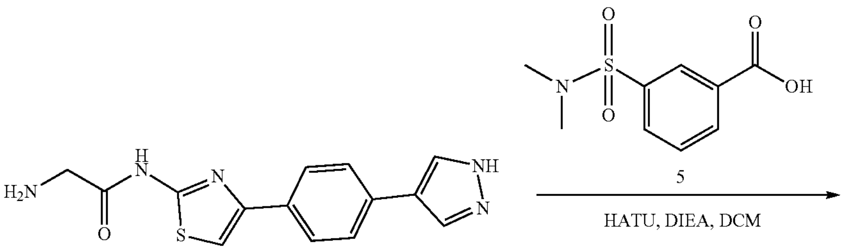

D

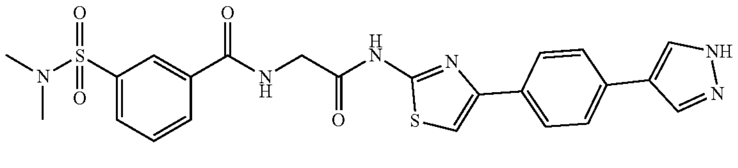

Compound 5

Step 1: Preparation of tert-butyl (2-((4-(4-(1H-pyrazol-4-yl)phenyl)thiazol-2-yl)amino)-2-oxoethyl) carbamate (Intermediate C)

C

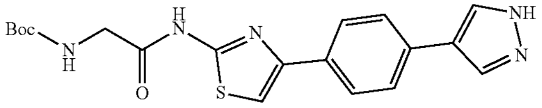

To a solution of tert-butyl N-[2-[[4-(4-bromophenyl)thiazol-2-yl]amino]-2-oxo-ethyl]carbamate (Prepared according to the method in FG-A518) (300 mg, 691.97 μmol) in dioxane (4 mL) and $H_2O$ (0.4 mL) was added 4-(4,4,5,5-tetramethyl-1,3,2-dioxaborolan-2-yl)-1H-pyrazole (402.81 mg, 2.08 mmol), DIEA (268.30 mg, 2.08 mmol, 361.59 μL) and palladium;tritert-butylphosphane (176.82 mg, 345.99 μmol) under $N_2$. The reaction mixture was stirred at 100° C. for 2 hr. The reaction mixture was poured into water (10 mL) and EA (10 mL). The mixture was filtered and the filter cake was dried in vacuum to give Intermediate C (200 mg, 432.08 μmol, 62.44% yield) as a white solid. LCMS (ESI) m/z $[M+H]^+$=400.03. $^1H$ NMR (400 MHz, DMSO-$d_6$) δ=12.95 (s, 1H), 12.26 (s, 1H), 8.23 (s, 1H), 7.96 (s, 1H), 7.87 (d, J=8.4 Hz, 2H), 7.67 (d, J=8.4 Hz, 2H), 7.59 (s, 1H), 7.16-7.14 (m, 1H), 3.87 (d, J=6.0 Hz, 2H), 1.40 (s, 9H) ppm.

Step 2: Preparation of N-(4-(4-(1H-pyrazol-4-yl)phenyl)thiazol-2-yl)-2-aminoacetamide (Intermediate D)

D

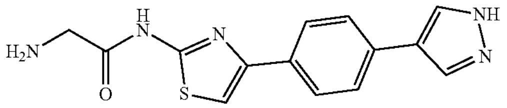

To a solution of Intermediate C (180 mg, 388.87 μmol) in MeOH (2 mL) was added HCl/dioxane (4 M, 2 mL). The mixture was stirred at 30° C. for 1 hr. The reaction mixture was concentrated to give a residue. The residue was triturated with MTBE (2 mL) then filtered and the solid was dried under vacuum to give Intermediate D (120 mg, 339.80 μmol, 87.38% yield, HCl salt) as a white solid. LCMS (ESI) m/z $[M+Na]^+$=322.3.

Step 3: Preparation of N-(2-((4-(4-(1H-pyrazol-4-yl)phenyl)thiazol-2-yl)amino)-2-oxoethyl)-3-(N,N-dimethylsulfamoyl)benzamide (Compound 5)

Compound 5

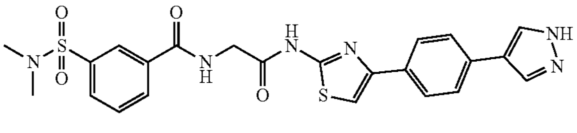

To a solution of 3-(dimethylsulfamoyl)benzoic acid (prepared according to the method in Example 1) (12.81 mg, 55.87 μmol) in DCM (0.5 mL) was added HATU (25.49 mg, 67.04 μmol), DIEA (36.10 mg, 279.35 μmol, 48.66 μL) and Intermediate D (20 mg, 55.87 μmol, HCl salt). The mixture was stirred at 30° C. for 2 hr and a solid was formed. The reaction mixture was filtered to give a solid. The solid was triturated with MeOH (2 mL), then filtered and the solid was dried in vacuum to give Compound 5 (9.72 mg, 18.49 μmol, 33.09% yield) as a white solid. LCMS (ESI) m/z [M+H]+ =511.3. $^1H$ NMR (400 MHz, DMSO-$d_6$) δ=12.97 (s, 1H), 12.47 (s, 1H), 9.31-9.29 (m, 1H), 8.27-8.23 (m, 3H), 7.93 (d, J=7.8 Hz, 2H), 7.89 (d, J=8.4 Hz, 2H), 7.81-7.79 (m, 1H), 7.67 (d, J=8.4 Hz, 2H), 7.62 (s, 1H), 4.24 (d, J=6.0 Hz, 2H), 2.65 (m, 6H) ppm.

Example 9. Preparation of 3-(N,N-dimethylsulfamoyl)-N-(2-((4-(3-(1-methyl-1H-pyrazol-3-yl)phenyl)thiazol-2-yl)amino)-2-oxoethyl)benzamide (Compound 6)

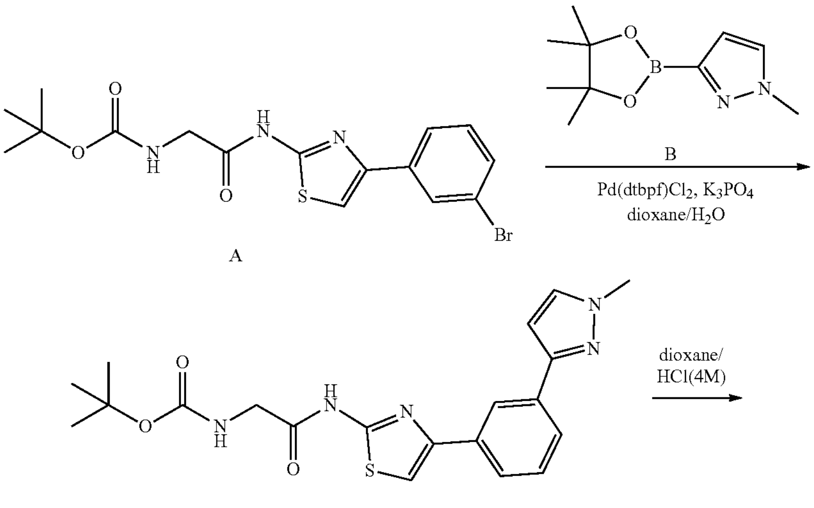

C

-continued

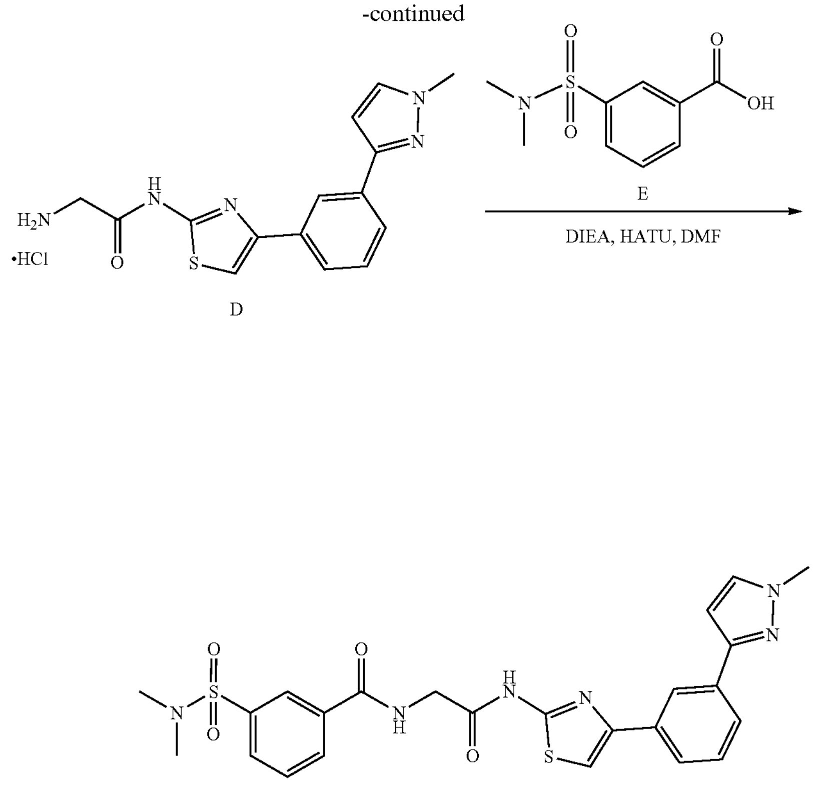

Compound 6

Step 1: Preparation of tert-butyl (2-((4-(3-(1-methyl-1H-pyrazol-3-yl)phenyl)thiazol-2-yl)amino)-2-oxoethyl)carbamate (Intermediate C)

C

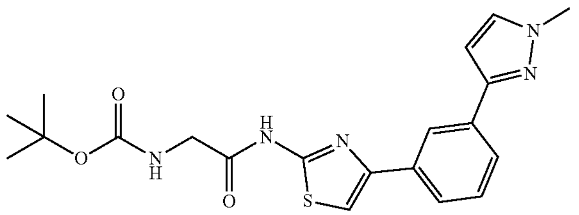

To a solution of tert-butyl N-[2-[[4-(3-bromophenyl)thiazol-2-yl]amino]-2-oxo-ethyl]carbamate (prepared according to the method in Example 2) (100 mg, 242.54 μmol), 1-methyl-3-(4,4,5,5-tetramethyl-1,3,2-dioxaborolan-2-yl) pyrazole (60.56 mg, 291.05 μmol) and $K_3PO_4$ (154.45 mg, 727.62 μmol) in dioxane (1 mL) and $H_2O$ (0.2 mL) was added ditert-butyl(cyclopentyl)phosphane;dichloropalladium;iron (15.81 mg, 24.25 μmol). The mixture was stirred under $N_2$ at 75° C. for 16 hr. The reaction mixture was filtered and concentrated under reduced pressure to give a residue. The residue was purified by reversed phase HPLC (0.1% FA condition) and lyophilized to give Intermediate C (100 mg, 209.68 μmol, 86% yield) as a yellow solid. LCMS (ESI) m/z $[M+H]^+$=414.1. $^1$H NMR (400 MHz, $CDCl_3$) δ=9.93 (br s, 1H), 8.26 (s, 1H), 7.76-7.74 (m, 2H), 7.46-7.40 (m, 2H), 7.24 (s, 1H), 6.60 (d, J=2.4 Hz, 1H), 4.05 (br s, 2H), 3.98 (s, 3H), 1.48 (s, 9H) ppm.

Step 2: Preparation of 2-amino-N-(4-(3-(1-methyl-1H-pyrazol-3-yl)phenyl)thiazol-2-yl)acetamide hydrochloride (Intermediate D)

D

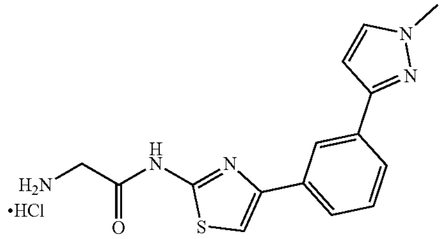

To a solution of Intermediate C (100 mg, 209.68 μmol) in dioxane (1 mL) was added dioxane/HCl (4 M, 0.5 mL). The mixture was stirred at 30° C. for 3 hr. The precipitate was collected by filtration, the filter cake was washed with EA (5 mL) and dried under high vacuum to afford Intermediate D (90 mg, crude, HCl, salt) as a white solid. LCMS (ESI) m/z $[M+H]^+$=314.2. $^1$H NMR (400 MHz, $D_2O$) δ=8.08-7.33 (m, 6H), 6.71-6.11 (m, 1H), 4.10-4.08 (m, 2H), 3.89-3.87 (m, 3H) ppm.

Step 3: Preparation of 3-(N,N-dimethylsulfamoyl)-N-(2-((4-(3-(1-methyl-1H-pyrazol-3-yl)phenyl)thiazol-2-yl)amino)-2-oxoethyl)benzamide (Compound 6)

Compound 6

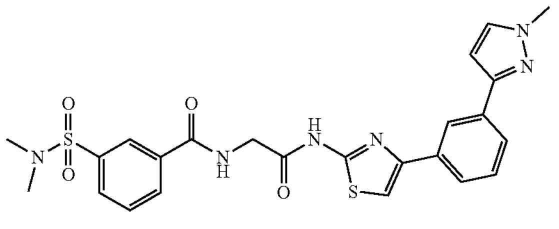

To a solution of Intermediate D (90 mg, 257.26 μmol, HCl, salt) 3-(dimethylsulfamoyl)benzoic acid (prepared according to the method in Example 1) (58.98 mg, 257.26 μmol) in DMF (1 mL) were added DIEA (224.05 μL, 1.29 mmol) and HATU (146.73 mg, 385.89 μmol), and then the mixture was stirred at 40° C. for 16 hr. The reaction mixture was diluted with $H_2O$ (2 mL) and extracted with EA (3 mL×2). The combined organic layers were washed with brine (3 mL), dried over anhydrous $Na_2SO_4$, filtered and concentrated under reduced pressure to give a residue. The residue was purified by reversed-phase (0.1% FA condition) and lyophilized to give Compound 6 (48.43 mg, 92.32 μmol, 36% yield) as a white solid. LCMS (ESI) m/z [M+H]+=525.0. $^1H$ NMR (400 MHz, MeOD) δ=8.36 (d, J=1.6 Hz, 2H), 8.22-8.00 (m, 1H), 8.00-7.85 (m, 1H), 7.85-7.78 (m, 1H), 7.78-7.71 (m, 2H), 7.71-7.64 (m, 1H), 7.64-7.62 (m, 2H), 7.46-7.44 (m, 1H), 6.69-6.67 (m, 1H), 4.37 (s, 1H), 3.97 (s, 3H), 2.76 (s, 6H) ppm.

Example 10. Preparation of 3-(dimethylsulfamoyl)-N-[2-[[4-[3-(1-methylpyrazol-4-yl)phenyl]thiazol-2-yl]amino]-2-oxo-ethyl]benzamide (Compound 7)

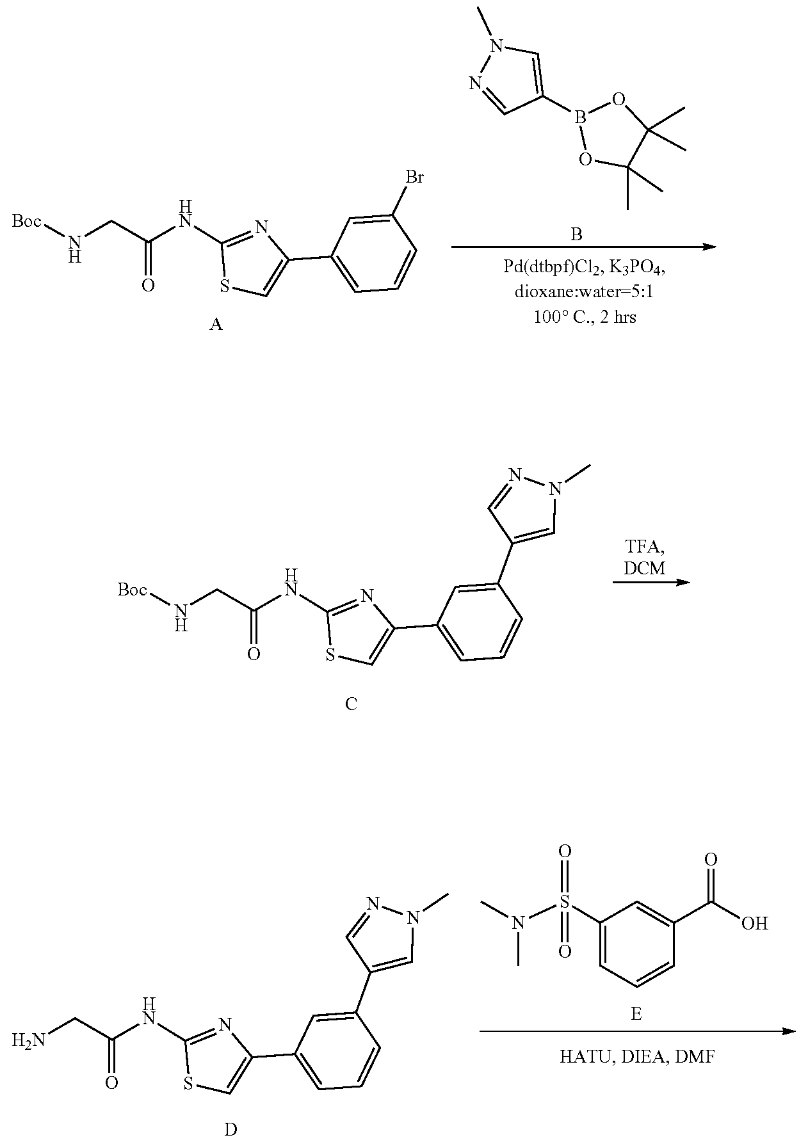

-continued

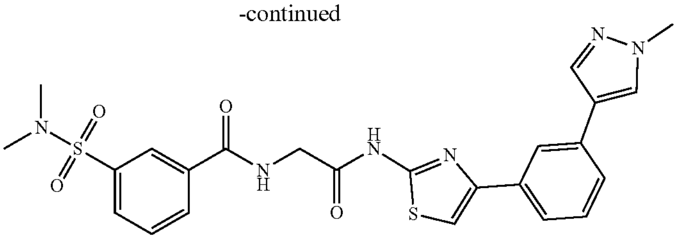

Compound 7

Step 1: Preparation of tert-butyl N-[2-[[4-[3-(1-methylpyrazol-4-yl)phenyl] thiazol-2-yl]amino]-2-oxo-ethyl]carbamate (Intermediate C)

C

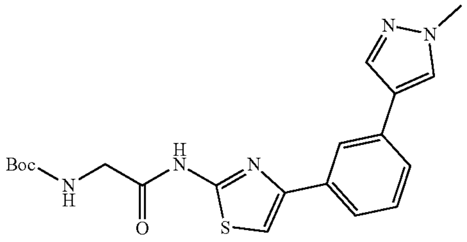

To a solution of tert-butyl N-[2-[[4-(3-bromophenyl)thiazol-2-yl]amino]-2-oxo-ethyl]carbamate (prepared according to the method in Example 2) (100.00 mg, 242.54 μmol) and 1-methyl-4-(4,4,5,5-tetramethyl-1,3,2-dioxaborolan-2-yl)pyrazole (75.70 mg, 363.81 μmol) in dioxane (8 mL) and water (2 mL) was added Pd(dtbpf)$Cl_2$ (15.81 mg, 24.25 μmol) and $K_3PO_4$ (15.44 mg, 72.76 μmol) under protect of $N_2$. The mixture was stirred at 100° C. for 2 hr. The reaction mixture was diluted with EA (50 mL) and washed with water (10 mL×3) and brine (10 mL×2), then dried over $Na_2SO_4$, filtered and concentrated under vacuum to give Intermediate C (100.00 mg, crude) as yellow solid, which was used to next step directly. LCMS (ESI) m/z $[M+H]^+$=413.9.

Step 2: Preparation of 2-amino-N-[4-[3-(1-methylpyrazol-4-yl)phenyl] thiazol-2-yl]acetamide (Intermediate D)

D

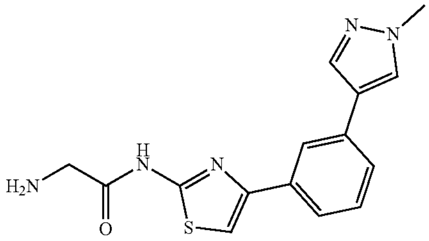

To a solution of Intermediate C (100 mg, 241.84 μmol) in DCM (5 mL) was added TFA (1 mL). The mixture was stirred at 30° C. for 2 hr. The mixture was diluted with DCM (20 mL) and concentrated under vacuum and this operation was repeated three times. The residue was washed by MTBE (5 mL*2) and dried in vacuum to give Intermediate D (95.00 mg, crude, TFA salt) as yellow oil, which was used to next step directly.

Step 3: Preparation of 3-(dimethylsulfamoyl)-N-[2-[[4-[3-(1-methylpyrazol-4-yl)phenyl]thiazol-2-yl] amino]-2-oxo-ethyl]benzamide (Compound 7)

Compound 7

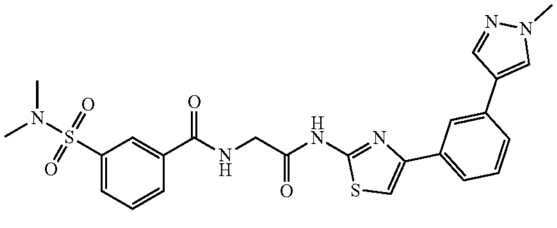

To a solution of Intermediate D (80.00 mg, 187.18 μmol, TFA salt) and 3-(dimethylsulfamoyl) benzoic acid (47.20 mg, 205.90 μmol) in DCM (6 mL) was added DIEA (72.57 mg, 561.53 μmol, 97.81 μL) and HATU (106.76 mg, 280.77 μmol). The mixture was stirred at 30° C. for 16 hr. The mixture was poured into water (30 mL) and extracted with EA (5 mL×3). The combined organic layer was washed with water (5 mL×2) and brine (5 mL), dried over $Na_2SO_4$, filtered and concentrated under vacuum. The residue was purified by Prep-HPLC (column: Phenomenex luna C18 150×25×10 u; mobile phase: [water (0.1% TFA)-ACN]; B %: 34%-61%, 10 min) and lyophilized to give Compound 7 (11.30 mg, 19.71 μmol, 10.53% yield) as yellow solid. LCMS (ESI) m/z $[M+H]^+$=525.2. $^1$H NMR (400 MHz, DMSO-$d_6$) δ=12.48 (s, 1H), 9.30-9.27 (m, 1H), 8.28-8.24 (m, 2H), 8.16 (s, 1H), 8.08 (s, 1H), 7.95 (d, J=8.0 Hz, 1H), 7.89 (s, 1H), 7.83-7.79 (m, 1H), 7.74-7.71 (m, 2H), 7.52 (d, J=7.6 Hz, 1H), 7.43-7.39 (m, 1H), 4.25 (d, J=5.6 Hz, 2H), 3.89 (s, 3H), 2.66 (s, 6H) ppm.

Example 11. Preparation of 4-[2-[[2-[[3-(dimethylsulfamoyl)benzoyl]amino]acetyl]amino]thiazol-4-yl] benzoic acid (Compound 8)

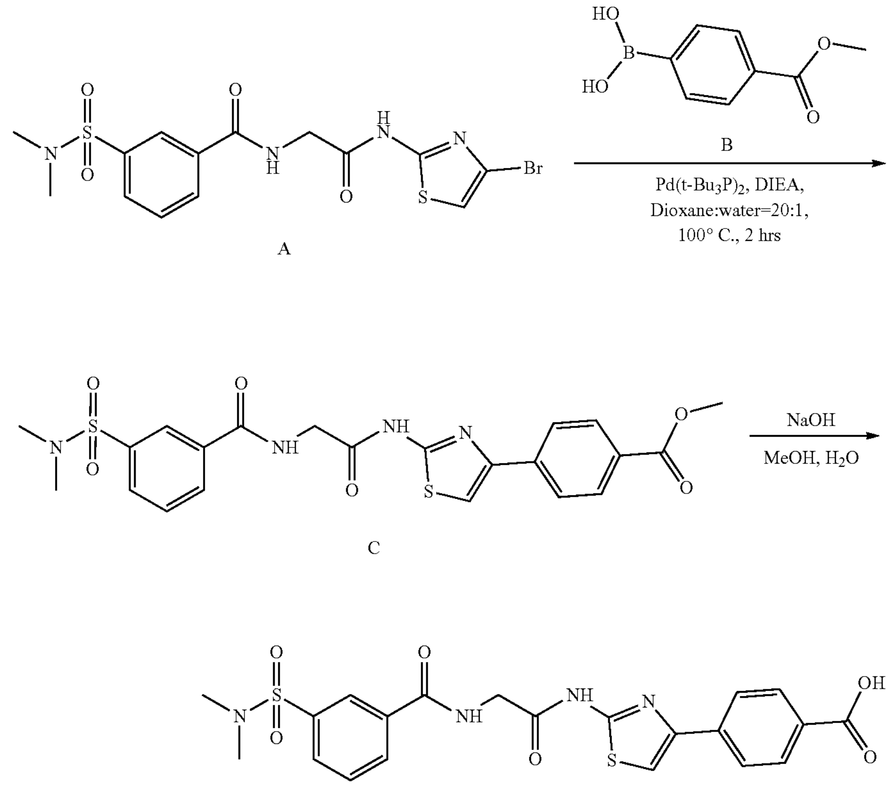

Compound 8

Step 1: Preparation of methyl 4-[2-[[2-[[3-(dimethylsulfamoyl)benzoyl]amino]acetyl]amino]thiazol-4-yl]benzoate (Intermediate C)

C

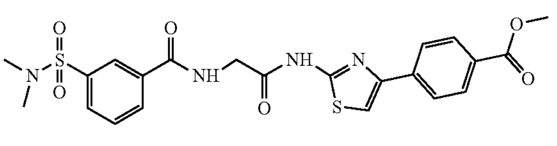

To a solution of N-[2-[(4-bromothiazol-2-yl)amino]-2-oxo-ethyl]-3-(dimethylsulfamoyl)benzamide (prepared according to the method in Example 4) (50 mg, 111.78 µmol) and (4-methoxycarbonylphenyl)boronic acid (60.35 mg, 335.33 µmol) in Dioxane (3 mL) and $H_2O$ (0.2 mL) were added palladium;tritert-butylphosphane (28.56 mg, 55.89 µmol) and DIEA (28.89 mg, 223.55 µmol, 38.94 µL, 2 eq) under protect of $N_2$. The mixture was stirred at 100° C. for 2 hrs. Lots of solid was formed after cooled to 30° C. The mixture was filtered and the solid was triturated in EA (3 mL), then filtered and dried in vacuum to give Intermediate C (25 mg, crude) as a gray solid, which was used to next step directly.

LCMS (ESI) m/z $[M+H]^+$=502.9.

Step 2: Preparation of 4-[2-[[2-[[3-(dimethylsulfamoyl) benzoyl]amino]acetyl]amino]thiazol-4-yl] benzoic acid (Compound 8)

Compound 8

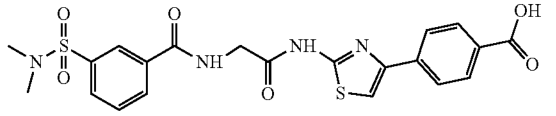

To a solution of Intermediate C (20.00 mg, 39.80 µmol) in MeOH (2 mL) was added water (1 mL) and NaOH (1.59 mg, 39.80 µmol). The mixture was stirred at 30° C. for 2 hr. The reaction mixture was adjusted pH to 5-6 with HCl (1 M) and a heavy solid formed. The solid was filtered and dried under reduced pressure to give Compound 8 (9.08 mg, 18.59 µmol, 46.70% yield) as white solid. LCMS (ESI) m/z $[M+H]^+$=489.0. $^1H$ NMR (400 MHz, DMSO-$d_6$) δ=12.54 (br s, 1H), 9.31-9.28 (m, 1H), 8.27-8.24 (m, 2H), 8.04-7.99 (m, 4H), 7.95 (br d, J=7.6 Hz, 1H), 7.83-7.79 (m, 2H), 4.25 (br d, J=5.6 Hz, 2H), 2.67 (s, 6H) ppm.

Example 12. Preparation of compound N-(2-((4-(4-(1H-pyrazol-3-yl)phenyl)thiazol-2-yl)amino)-2-oxo-ethyl)-3-(N,N-dimethylsulfamoyl)benzamide (Compound 9)

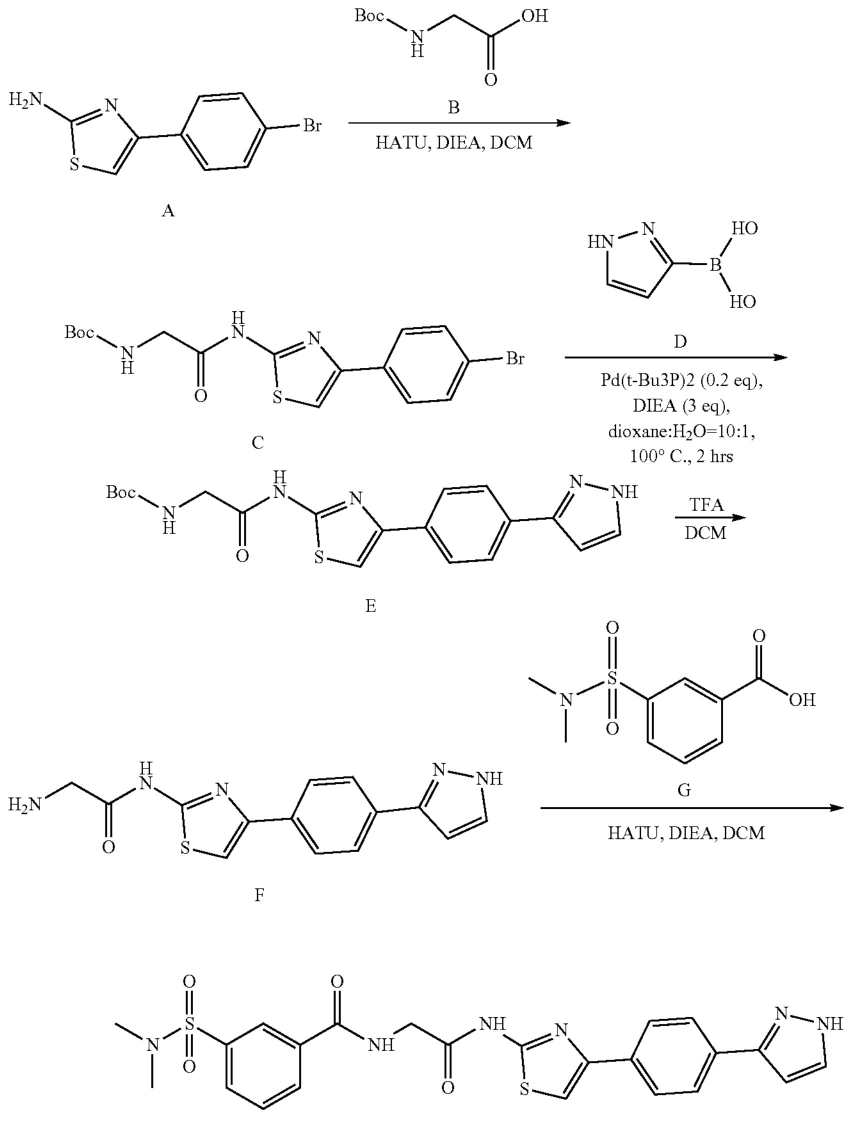

A, B, C, D, E, F, G

Compound 9

Step 1: Preparation of tert-butyl N-[2-[[4-(4-bromophenyl)thiazol-2-yl]amino]-2-oxo-ethyl]carbamate (Intermediate C)

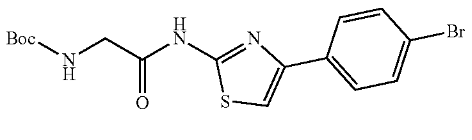

C

To a solution of 2-(tert-butoxycarbonylamino)acetic acid (1.65 g, 9.41 mmol) in DCM (20 mL) were added HATU (4.47 g, 11.76 mmol), DIEA (3.04 g, 23.52 mmol) and 4-(4-bromophenyl)thiazol-2-amine (2 g, 7.84 mmol). The reaction mixture was stirred at 30° C. for 12 hr. The reaction mixture was poured into water (20 ml), then extracted with EA (20 mL×3). The combined organic layer was washed with brine (50 ml), dried over $Na_2SO_4$ and filtered. The filtrate was concentrated to give a residue. The residue was purified by column chromatography ($SiO_2$, PE:EA=100:1-80:1-50:1-10:1-1:1) then concentrated to give a residue. The residue was triturated with MTBE (2 ml), then filtered and dried in vacuum to give Intermediate C (1.2 g, 2.90 mmol, 36.97% yield) as a white solid. LCMS (ESI) m/z [$^{81}$BrM+H]$^+$=414.1. $^1$H NMR (400 MHz, DMSO-$d_6$) δ=12.28 (s, 1H), 7.84 (d, J=8.8 Hz, 2H), 7.69 (s, 1H), 7.63 (d, J=8.4 Hz, 2H), 3.86 (d, J=6.0 Hz, 2H), 1.40 (s, 9H) ppm.

Step 2: Preparation of tert-butyl N-[2-oxo-2-[[4-[4-(1H-pyrazol-3-yl)phenyl]thiazol-2-yl]amino]ethyl] carbamate (Intermediate E)

E

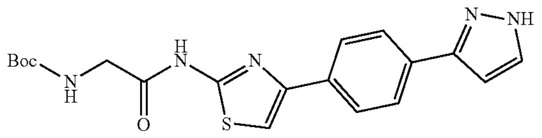

To a solution of Intermediate C (100 mg, 241.52 μmol) in dioxane (5 mL) and H2O (0.5 mL) were added 1H-pyrazol-3-ylboronic acid (81.08 mg, 724.57 μmol), DIEA (93.65 mg, 724.57 μmol, 126.21 μL) and $Pd(t\text{-}Bu_3P)_2$ (24.69 mg, 48.30 μmol) under $N_2$. The reaction mixture was stirred at 100° C. for 2 hr. The reaction mixture was poured into water (5 mL). The solution was extracted with EA (5 mL×3). The combined organic layer was washed with brine (10 mL), dried over $Na_2SO_4$ and filtered. The filtrate was concentrated to give a residue. The residue was triturated with EA (2 mL), then filtered and dried in vacuum to give Intermediate E (40 mg, 99.45 μmol, 41.18% yield) as a white solid. LCMS (ESI) m/z $[M+H]^+$=400.0.

Step 3: Preparation of 2-amino-N-[4-[4-(1H-pyrazol-3-yl)phenyl]thiazol-2-yl]acetamide (Intermediate F)

F

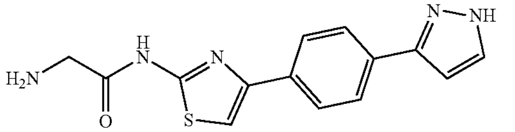

To a solution of Intermediate E (40 mg, 99.45 μmol, 1 eq) in DCM (5 mL) was added TFA (1 mL). The mixture was stirred at 30° C. for 2 hr. The mixture was concentrated to give a residue under vacuum. The residue was triturated with MTBE (1 mL) then filtered and dried in vacuum to give Intermediate F (30 mg, 70.86 μmol, 71.25% yield, 97.64% purity, TFA) as a yellow solid. LCMS (ESI) m/z $[M+H]^+$=300.2.

Step 4: Preparation of N-(2-((4-(4-(1H-pyrazol-3-yl)phenyl)thiazol-2-yl)amino)-2-oxoethyl)-3-(N,N-dimethylsulfamoyl)benzamide (Compound 9)

Compound 9

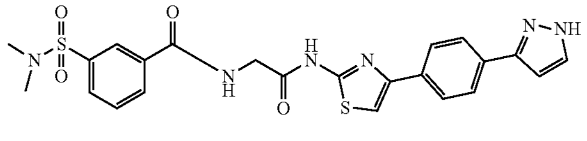

To a solution of 3-(dimethylsulfamoyl)benzoic acid (prepared according to the method in Example 1) (16.63 mg, 72.55 μmol) in DMF (3 mL) was added HATU (33.11 mg, 87.07 μmol), DIEA (46.90 mg, 362.85 μmol, 63.20 μL) and 2-amino-N-[4-[4-(1H-pyrazol-3-yl)phenyl]thiazol-2-yl] acetamide (30 mg, 69.78 μmol, TFA salt). The mixture was stirred at 30° C. for 12 hr. The reaction mixture was poured into water (5 mL). The solution was extracted with EA (5 mL×3), the combined organic layer was washed with brine (10 mL), dried over $Na_2SO_4$ and filtered. The filtrate was concentrated to give a residue. The residue was purified by Prep-HPLC (column: Phenomenex Synergi C18 150×25×10 μm; mobile phase: [water (0.225% FA)-ACN]; B %: 32%-53%, 7 min). The solution was lyophilized to give a solid. The solid was triturated with EA (1 mL) then filtered and dried in vacuum to give Compound 9 (2.62 mg, 5.13 μmol, 7.35% yield) as a white solid. LCMS (ESI) m/z $[M+H]^+$=511.3. $^1H$ NMR (400 MHz, DMSO-$d_6$) δ=12.88 (s, 1H), 12.44 (s, 1H), 9.27-9.25 (m, 1H), 8.25 (s, 2H), 7.93-7.87 (m, 5H), 7.80-7.76 (m, 2H), 7.62 (s, 1H), 6.73 (s, 1H), 4.22 (d, J=6.0 Hz, 2H), 2.63 (s, 6H) ppm.

Example 13. Preparation of 3-(dimethylsulfamoyl)-N-[2-oxo-2-[[4-[3-(1H-pyrazol-3-yl)phenyl]thiazol-2-yl]amino]ethyl]benzamide (Compound 10)

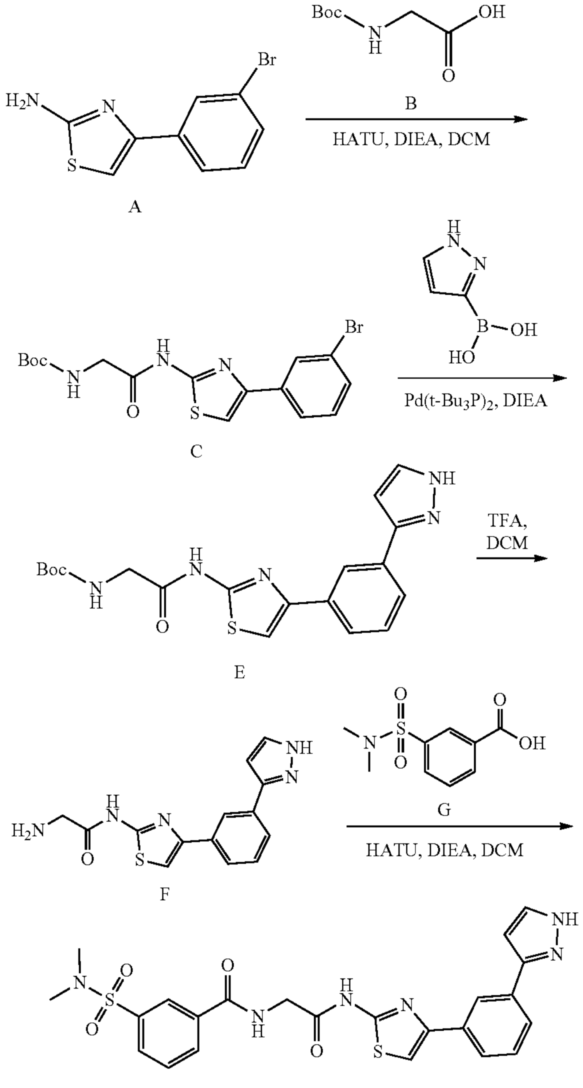

Compound 10

Step 1: Preparation of tert-butyl N-[2-[[4-(3-bromophenyl)thiazol-2-yl] amino]-2-oxo-ethyl]carbamate (Intermediate C)

C

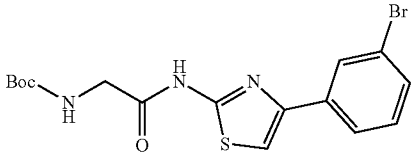

To a solution of 2-(tert-butoxycarbonylamino)acetic acid (82.40 mg, 470.34 μmol) in DCM (10 mL) were added HATU (223.55 mg, 587.93 μmol) and DIEA (151.97 mg, 1.18 mmol, 204.81 μL) and the mixture was stirred at 30° C. for 30 min. Then 4-(3-bromophenyl)thiazol-2-amine (100.00 mg, 391.95 μmol) was added. The mixture was stirred at 30° C. for another 12 hrs then diluted with DCM (50.0 mL). The solution was washed with $H_2O$ (10.0 mL×3) and brine (10 mL×2), then dried over $Na_2SO_4$, filtered and concentrated under vacuum to give Intermediate C (150 mg, crude) as yellow oil which was used to next step directly. LCMS (ESI) m/z $[M+H]^+$=412.3.

Step 2: Preparation of tert-butyl N-[2-oxo-2-[[4-[3-(1H-pyrazol-3-yl) phenyl]thiazol-2-yl]amino]ethyl] carbamate (Intermediate E)

E

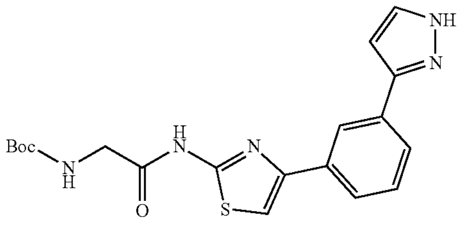

To a solution of Intermediate C (25.00 mg, 60.64 μmol) and 1H-pyrazol-3-ylboronic acid (20.36 mg, 181.92 μmol) in dioxane (2 mL) and $H_2O$ (0.2 mL) was added $Pd(t\text{-}Bu_3P)_2$ (9.30 mg, 18.19 μmol) and DIEA (23.51 mg, 181.92 μmol, 31.68 μL) under protect of $N_2$. The mixture was stirred at 100° C. for 2 hr. The mixture was poured into water (30 mL) and extracted with EA (5 mL×5). The combined organic layer was washed with water (5 mL×3) and brine (5 mL×2), dried over $Na_2SO_4$, filtered and concentrated under reduced pressure to give Intermediate E (65.00 mg, crude) as yellow solid, which was used to next step directly. LCMS (ESI) m/z $[M+H]^+$=399.9.

Step 3: Preparation of 2-amino-N-[4-[3-(1H-pyrazol-3-yl)phenyl]thiazol-2-yl] acetamide (Intermediate F)

F

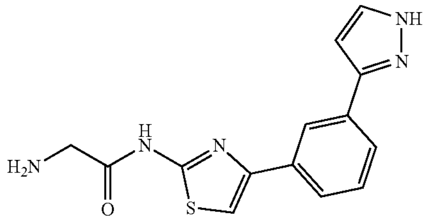

A mixture of Intermediate E (65 mg, 162.72 μmol) in DCM (3 mL) and TFA (0.3 mL) was stirred at 25° C. for 2 hr. The mixture was diluted with DCM (20 ml) and concentrated under vacuum. This operation was repeated for three times. Then the residue was washed by MTBE (5 mL×2) and concentrated in vacuum to give Intermediate F (70.00 mg, crude, TFA salt) as yellow oil which was used to next step directly. LCMS (ESI) m/z $[M+H]^+$=300.1.

Step 4: Preparation of 3-(dimethylsulfamoyl)-N-[2-oxo-2-[[4-[3-(1H-pyrazol-3-yl)phenyl]thiazol-2-yl] amino]ethyl]benzamide (Compound 10)

Compound 10

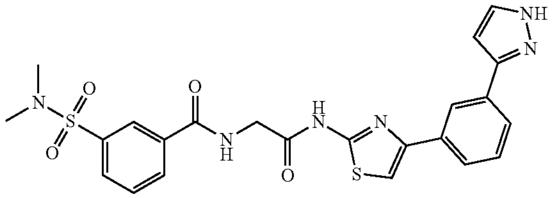

To a solution of Intermediate F (70.00 mg, 169.34 μmol, TFA salt) and 3-(dimethylsulfamoyl) benzoic acid (prepared according to the method in Example 1) (42.70 mg, 186.27 μmol) in DCM (10 mL) was added DIEA (65.66 mg, 508.02 μmol, 88.49 μL) and HATU (96.58 mg, 254.01 μmol). The mixture was stirred at 30° C. for 16 hr. The mixture was diluted with DCM (20 mL) and washed with water (10 mL×3) and brine (10 mL×2), dried over $Na_2SO_4$, filtered and concentrated in reduced pressure. The residue was purified by Pre-HPLC (column: Phenomenex Synergi C18 150×25×10 μm; mobile phase: [water (0.1% TFA)-ACN]; B %: 28%-58%, 9 min) and lyophilized to give Compound 10 (21.26 mg, 41.64 μmol, 24.59% yield) as off-white solid. LCMS (ESI) m/z [M+H]+=510.9. $^1H$ NMR (400 MHz, DMSO-$d_6$) δ=12.52 (s, 1H), 9.30-9.28 (m, 1H), 8.39 (s, 1H), 8.28-8.24 (m, 2H), 7.95 (d, J=7.6 Hz, 1H), 7.84-7.81 (m, 2H), 7.76-7.74 (m, 2H), 7.71 (s, 1H), 7.49-7.45 (m, 1H), 6.75 (d, J=2.0 Hz, 1H), 4.25 (d, J=6.0 Hz, 2H), 2.67 (s, 6H) ppm.

Example 14. Preparation of 3-[2-[[2-[[3-(dimethylsulfamoyl)benzoyl]amino]acetyl]amino]thiazol-4-yl] benzoic acid (Compound 11)

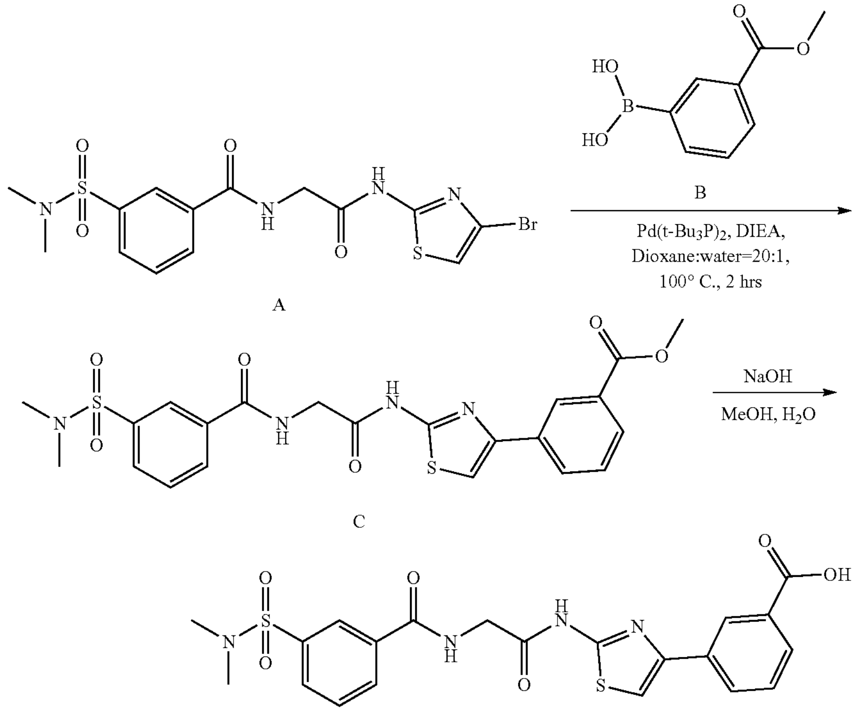

Compound 11

Step 1: Preparation of methyl 3-[2-[[2-[[3-(dimethylsulfamoyl)benzoyl] amino]acetyl]amino]thiazol-4-yl]benzoate (Intermediate C)

C

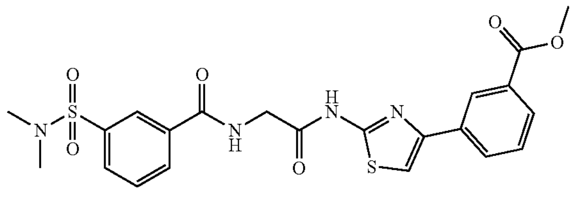

To a solution of N-[2-[(4-bromothiazol-2-yl)amino]-2-oxo-ethyl]-3-(dimethylsulfamoyl)benzamide (prepared according to the method in Example 4) (30 mg, 67.07 μmol) and (3-methoxycarbonylphenyl) boronic acid (36.21 mg, 201.21 μmol) in dioxane (2 mL) and $H_2O$ (0.1 mL) was added $Pd(t-Bu_3P)_2$ (17.14 mg, 33.53 μmol) and DIEA (43.34 mg, 335.35 μmol, 58.41 μL) under protect of $N_2$. The mixture was stirred at 100° C. for 2 hrs. Lots of solid was formed after cooled to 30° C. The mixture was filtered and the solid was triturated in EA (3 mL), then filtered and dried in vacuum to give Intermediate C (15 mg, 29.85 μmol) as a light yellow solid, which was used to next step directly. LCMS (ESI) m/z $[M+H]^+$=502.9.

Step 2: Preparation of 3-[2-[[2-[[3-(dimethylsulfamoyl) benzoyl]amino]acetyl]amino]thiazol-4-yl] benzoic acid (Compound 11)

Compound 11

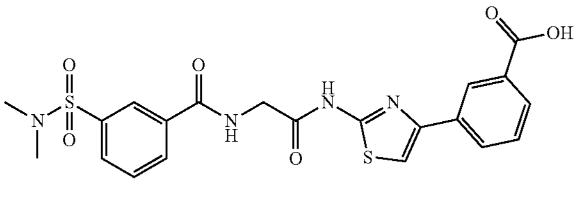

To a solution of Intermediate C (15.00 mg, 29.85 μmol) in MeOH (2 mL) was added $H_2O$ (1 mL) and NaOH (1.19 mg, 29.85 μmol). The mixture was stirred at 30° C. for 12 hr then diluted with MeOH (10 mL) and treated with HCl (1 M) to pH was 5-6, concentrated under vacuum to give crude product. The residue was diluted by MeOH (1 mL) and purified by Prep-HPLC (column: Phenomenex Synergi C18 150×25×10 μm; mobile phase: [water (0.1% TFA)-ACN]; B %: 28%-58%, 9 min) and lyophilized to give Compound 11 (9.21 mg, 18.85 μmol, 63.16% yield) as off-white solid. LCMS (ESI) m/z $[M+H]^+$=488.9. $^1H$ NMR (400 MHz, DMSO-$d_6$) δ=13.02 (br s, 1H), 12.53 (s, 1H), 9.31-9.29 (m, 1H), 8.55 (s, 1H), 8.54-8.24 (m, 2H), 8.13 (br d, J=7.8 Hz, 1H), 7.94 (d, J=7.6 Hz, 1H), 7.89 (d, J=7.6 Hz, 1H), 7.85-7.83 (m, 2H), 7.81-7.77 (m, 1H), 4.25 (d, J=5.6 Hz, 2H), 2.67 (s, 6H) ppm.

Example 15. Preparation of tert-butyl N-[2-[[4-(3-bromophenyl)thiazol-2-yl]amino]-2-oxo-ethyl]carbamate (Intermediate D) and 2-amino-N-(4-(3-bromophenyl)thiazol-2-yl)acetamide (Intermediate E)

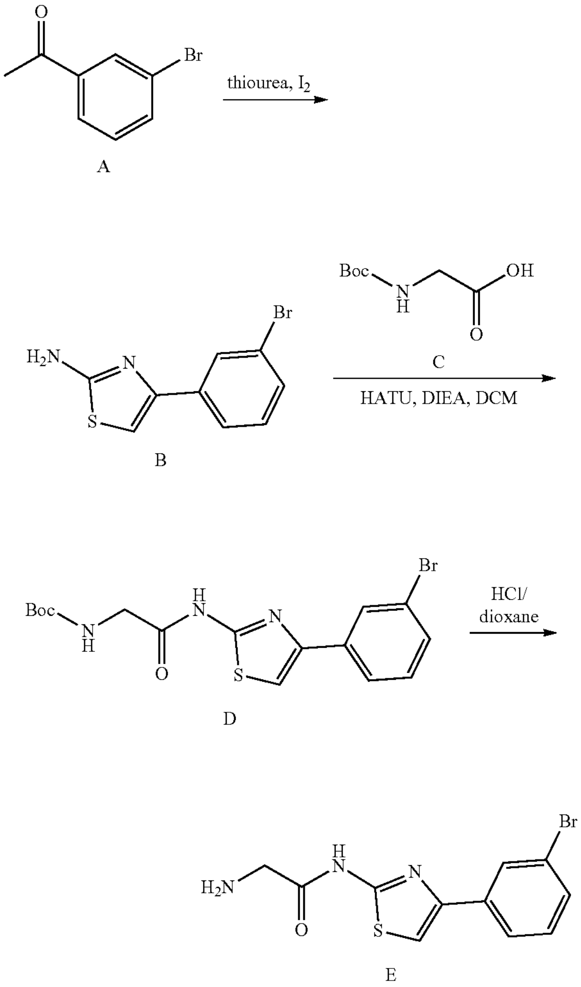

Step 1: Preparation of 4-(3-bromophenyl)thiazol-2-amine (Intermediate B)

B

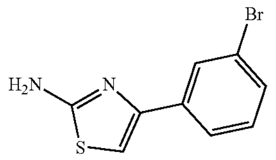

To a mixture of 1-(3-bromophenyl)ethanone (473 g, 2.38 mol, 313.25 mL) and thiourea (361.78 g, 4.75 mol) was added 12 (603.14 g, 2.38 mol, 478.68 mL, 1 eq). The mixture was stirred at 110° C. for 16 hr. After cooling, the reaction mixture was triturated with MTBE (5 L), and then filtered to remove any unreacted iodine and acetophenone. The filter cake was put in ice water (4 L) and treated with 25% $NH_3 \cdot H_2O$ to pH=9-10. The suspension was stirred at 25° C. for 15 min, then filtered and washed with water (1 L) to give wet solid. The wet solid was dissolved in EA (4 L) and washed with sat. $NaHCO_3$ (1 L×2) and brine (1 L). The EA layer was dried over $Na_2SO_4$, filtered and concentrated under reduced pressure to give a residue. The residue was triturated with PE/EA=100:1 (4 L) at 25° C. for 3 h, then the suspension was filtered, the filter cake was washed with PE (1 L) and dried in vacuum to give intermediate B (450 g, 1.69 mol, 71.20% yield, 95.93% purity) as a pink solid. LCMS (ESI) m/z [$^{79}$BrM+H$^+$]=254.9. $^1$H NMR (400 MHz, DMSO-$d_6$) δ=7.98-7.97 (m, 1H), 7.80-7.77 (m, 1H), 7.43-7.42 (m, 1H), 7.34-7.30 (m, 1H), 7.15 (s, 1H), 7.10 (s, 2H).

Step 2: Preparation of tert-butyl N-[2-[[4-(3-bromophenyl)thiazol-2-yl]amino]-2-oxo-ethyl]carbamate (Intermediate D)

D

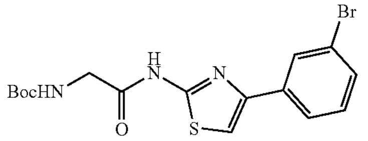

To a solution of 2-(tert-butoxycarbonylamino)acetic acid (82.40 g, 470.34 mmol), HATU (178.84 g, 470.34 mmol) and DIEA (151.97 g, 1.18 mol, 204.81 mL) in DCM (1000.00 mL) was added intermediate B (100.00 g, 391.95 mmol), the mixture was stirred at 30° C. for 16 hr. The reaction mixture was washed with sat. citric acid (500 mL×4) and brine (500 mL), dried over $Na_2SO_4$, filtered and concentrated under reduced pressure to give a residue. The residue was triturated with MeOH (200.0 mL), filtered and dried in vacuum to give Intermediate D (100 g, 241.89 mmol, 61.71% yield) as a white solid. LCMS (ESI) m/z [$^{81}$BrM+H]$^+$=413.8. $^1$H NMR (400 MHz, DMSO-$d_6$) δ=12.29 (s, 1H), 8.09-8.09 (m, 1H), 7.89 (d, J=7.6 Hz, 1H), 7.76 (s, 1H), 7.52-7.49 (m, 1H), 7.41-7.37 (m, 1H), 7.16-7.13 (m, 1H), 3.87-3.81 (m, 2H), 1.39 (s, 9H) ppm.

Step 3: Preparation of 2-amino-N-(4-(3-bromophenyl)thiazol-2-yl)acetamide (Intermediate E)

E

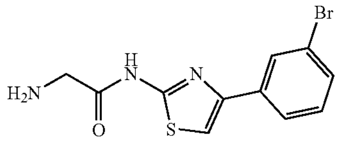

A mixture of intermediate D (10 g, 24.25 mmol) in HCl/dioxane (100 mL) was stirred at 30° C. for 2 hr. The reaction mixture was concentrated in vacuum to give intermediate E (8.4 g, crude, HCl) as a white solid. LCMS (ESI) m/z [M+H]$^+$=313.8.

Example 16. Preparation of 2-amino-N-[4-[3-(4-pyridyl)phenyl]thiazol-2-yl]acetamide (Intermediate F)

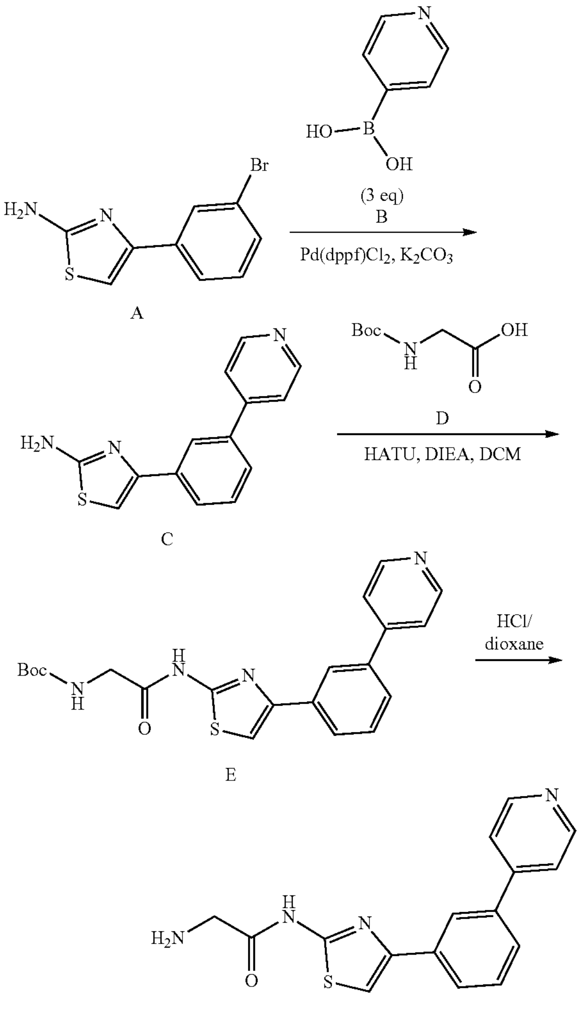

F

Step 1: Preparation of 4-[3-(4-pyridyl)phenyl]thiazol-2-amine (Intermediate C)

C

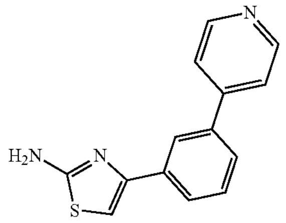

To a solution of 4-(3-bromophenyl)thiazol-2-amine (10 g, 39.20 mmol), 4-pyridylboronic acid (14.45 g, 117.59 mmol) and $K_2CO_3$ (16.25 g, 117.59 mmol) in dioxane (120 mL) and Water (30 mL) was added Pd(dppf)$Cl_2$ (1 g, 1.37 mmol) under $N_2$, the mixture was stirred at 100° C. for 4 hr. The reaction mixture was diluted with water (500 mL), extracted with EA (500 mL) and concentrated under reduced pressure to give a residue. The residue was purified by crystallization from DCM/MTBE=1:20 (200 mL) and filtered to give intermediate C (9.5 g, 36.33 mmol, 92.69% yield) as a brown solid. LCMS (ESI) m/z $[M+H]^+$=254.2. $^1H$ NMR (400 MHz, DMSO-$d_6$) δ 8.66 (d, J=6.0 Hz, 2H), 8.19 (s, 1H), 7.90 (d, J=8.0 Hz, 1H), 7.76-7.70 (m, 2H), 7.68 (d, J=8.0 Hz, 1H), 7.52 (t, J=8.0 Hz, 1H), 7.21 (s, 1H), 7.11 (s, 2H) ppm.

Step 2: Preparation of tert-butyl N-[2-oxo-2-[[4-[3-(4-pyridyl)phenyl]thiazol-2-yl]amino]ethyl]carbamate (Intermediate E)

E

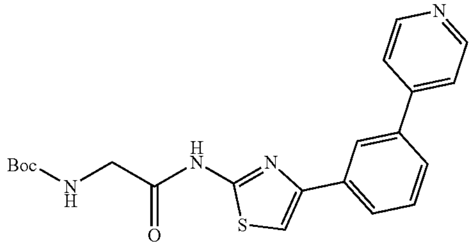

To a solution of 2-(tert-butoxycarbonylamino)acetic acid (9.85 g, 56.25 mmol), HATU (21.39 g, 56.25 mmol) and DIPEA (14.54 g, 112.51 mmol) in DCM (200 mL) was added int C (9.5 g, 37.50 mmol, 1 eq), the mixture was stirred at 30° C. for 16 hr. A precipitate was formed. The reaction mixture was filtered to give a yellow solid. The crude product was triturated with EA (300.0 mL) and MeOH (50.0 mL) and dried in vacuum to give intermediate E (11 g, 25.89 mmol, 69.03% yield) as a white solid. LCMS (ESI) m/z $[M+H]^+$=411.3. $^1H$ NMR (400 MHz, DMSO-$d_6$) δ 12.32 (br s, 1H), 8.69-8.67 (m, 2H), 8.30 (s, 1H), 8.01 (d, J=7.8 Hz, 1H), 7.83 (s, 1H), 7.80-7.76 (m, 3H), 7.64-7.60 (m, 1H), 7.20-7.15 (m, 1H), 3.88 (d, J=6.4 Hz, 2H), 1.44 (s, 9H) ppm.

Step 3: Preparation of 2-amino-N-[4-[3-(4-pyridyl)phenyl]thiazol-2-yl]acetamide (Intermediate F)

F

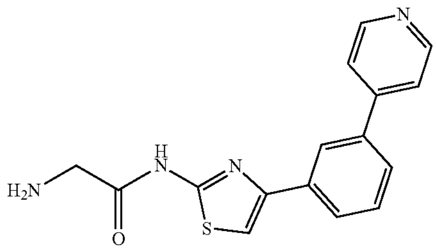

To a solution of Intermediate E (11 g, 26.80 mmol) in MeOH (20 mL) was added 4 M HCl/EtOAc (20 mL). The mixture was stirred at 20° C. for 2 hr. The reaction mixture was concentrated under reduced pressure to give a residue. The residue was purified by triturated with EA (200 mL) and MTBE (50 mL) and dried in vacuum to give intermediate F (12 g, HCl salt) a light yellow solid. LCMS (ESI) m/z $[M+H]^+$=311.3. $^1H$ NMR 1H NMR (400 MHz, methanol-d4) δ8.92 (d, J=6.8 Hz, 2H), 8.52-8.47 (m, 3H), 8.22 (d, J=8.0 Hz, 1H), 7.94 (m, J=8.4 Hz, 1H), 7.75-7.66 (m, 2H), 4.04 (s, 2H) ppm.

Example 17. Preparation of methyl 3-(2-(2-(3-(isopropylsulfonyl)benzamido)acetamido)thiazol-4-yl) benzoate (Compound 12)

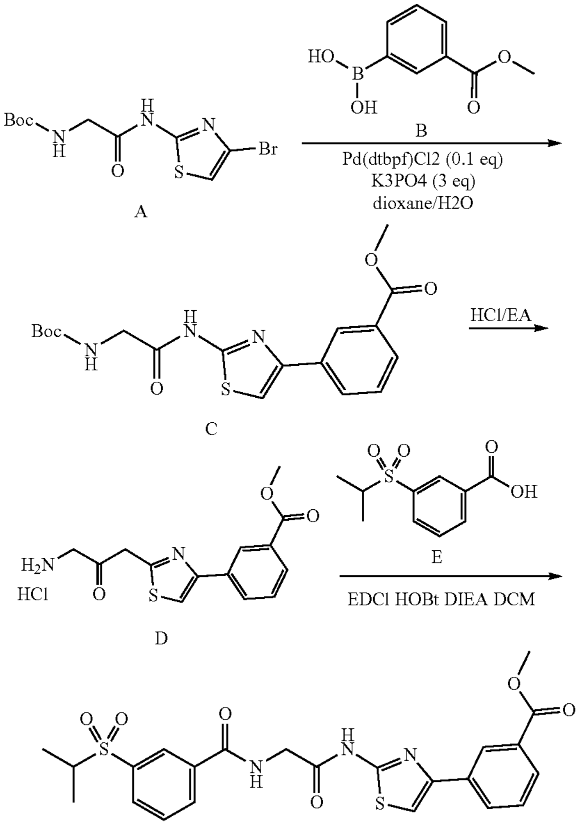

Compound 12

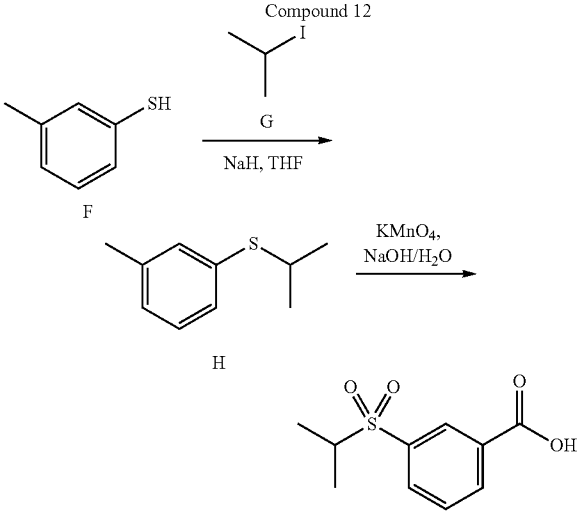

E

Step 1: Preparation of methyl 3-(2-(2-((tert-butoxycarbonyl)amino)acetamido)thiazol-4-yl)benzoate (Intermediate C)

C

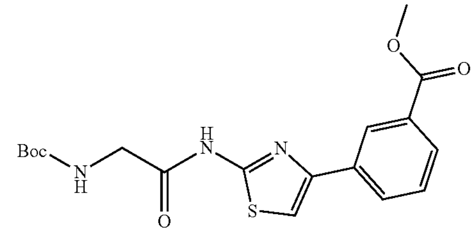

To a solution of tert-butyl (2-((4-bromothiazol-2-yl) amino)-2-oxoethyl)carbamate (400 mg, 1.19 mmol), (3-methoxycarbonylphenyl)boronic acid (428.23 mg, 2.38 mmol), $H_3PO_4$ (349.77 mg, 3.57 mmol, 208.20 μL) in dioxane (5 mL) and $H_2O$ (1 mL) was added ditert-butyl (cyclopentyl)phosphane;dichloropalladium;iron (155.08 mg, 237.95 μmol). Then the mixture was stirred at 70° C. for 2 hr under $N_2$. The reaction mixture was poured into water (20 mL) and extracted with EA (10 mL×2), the organic layer was wished with brine (20 mL) and dried over $Na_2SO_4$, concentrated to get the crude product. The crude product was purified by flash silica gel chromatography (PE: EA=10:1 to 3:1) and concentrated in vacuum to give Intermediate C (300 mg, 759.96 μmol, 63.88% yield) as off-white solid. LCMS (ESI) m/z $[M+H]^+$=392.1. $^1H$ NMR (400 MHz, chloroform-d) δ=10.08 (br s, 1H), 8.48 (s, 1H), 8.00-7.98 (m, 2H), 7.49-7.45 (m, 1H), 7.24 (s, 1H), 5.53-5.12 (m, 1H), 4.15-4.10 (m, 2H), 3.95 (s, 3H), 1.50 (s, 9H) ppm.

Step 2: Preparation of methyl 3-(2-(2-aminoacetamido)thiazol-4-yl)benzoate (Intermediate D)

D

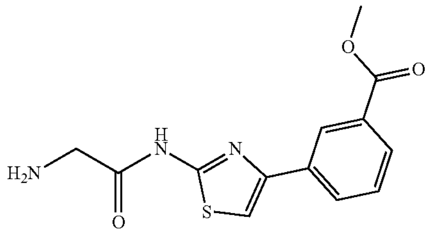

A solution of Intermediate C (300 mg, 766.40 μmol) in HCl/EtOAc (4 M, 3 mL) was stirred at 25° C. for 1 hr. The reaction mixture was concentrated to give Intermediate C (240 mg, 719.74 μmol, 93.91% yield, HCl, salt) as a white solid, which was used for next step without farther purification. LCMS (ESI) m/z $[M+H]^+$=292.1. $^1H$ NMR (400 MHz, DMSO-$d_6$) δ=12.83 (br s, 1H), 8.55-8.53 (m, 1H), 8.38 (br s, 2H), 8.19 (d, J=7.8 Hz, 1H), 7.93 (d, J=7.8 Hz, 1H), 7.88 (s, 1H), 7.63-7.61 (m, 1H), 3.98-3.85 (m, 5H) ppm.

Step 3: Preparation of 1-isopropylsulfanyl-3-methyl-benzene (Intermediate H)

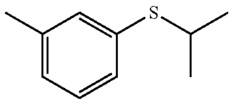

H

To a solution of 3-methylbenzenethiol (10.0 g, 80.51 mmol, 9.62 mL) in THE (100.0 mL) was added NaH (3.86 g, 96.62 mmol, 60% purity) at 0° C., then 2-iodopropane (16.42 g, 96.62 mmol, 9.66 mL) was added to the mixture, the reaction mixture was stirred at 20° C. for 1 hr. The reaction mixture was poured into aq. $NH_4Cl$ (400.0 mL), extracted with EtOAc (400.0 mL×3). The combined organic layers were washed with brine (500.0 mL), dried over [$Na_2SO_4$], filtered and concentrated under reduced pressure to give Intermediate H (14.0 g, crude) as light yellow oil. The residue was used to the next step without further purification. $^1H$ NMR (400 MHz, DMSO-$d_6$) δ 7.27-7.12 (m, 3H), 7.04 (br d, J=7.2 Hz, 1H), 3.48-3.42 (m, 1H), 2.28 (s, 3H), 1.22 (d, J=6.8 Hz, 6H) ppm.

Step 4: Preparation of 3-isopropylsulfonylbenzoic acid (Intermediate E)

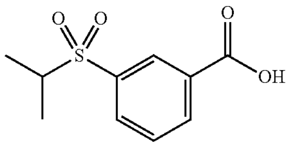

E

To a solution of Intermediate H (14.0 g, 84.19 mmol) and $KMnO_4$ (53.22 g, 336.78 mmol) in water (400.0 mL) was added NaOH (1.68 g, 42.10 mmol), the mixture was stirred at 90° C. for 6 hr. The reaction mixture was poured into saturation $Na_2SO_3$ (500.0 mL), then 1 N HCl (100.0 mL) was added. The mixture was extracted with EtOAc (500.0 mL×3). The combined organic layers were washed with aq. $NaHCO_3$ (500 mL×2). The water layers were acidized with 1 N HCl to pH=3.0, then extracted with EtOAc (500.0 mL×3). The combined organic layers were washed with brine (500.0 mL), dried over [$Na_2SO_4$], filtered and concentrated under reduced pressure to give Intermediate E (13.0 g, 54.30 mmol, 64.49% yield) as a white solid. LCMS (ESI) m/z $[M+H]^+$=229.0. $^1H$ NMR (400 MHz, DMSO-$d_6$) δ 13.58 (s, 1H), 8.32-8.27 (m, 2H), 8.11-8.08 (m, 1H), 7.83-7.79 (m, 1H), 3.53-3.46 (m, 1H), 1.15 (d, J=6.8 Hz, 6H) ppm.

Step 5: Preparation of methyl 3-(2-(2-(3-(isopropylsulfonyl)benzamido)acetamido)thiazol-4-yl)benzoate (Compound 12)

Compound 12

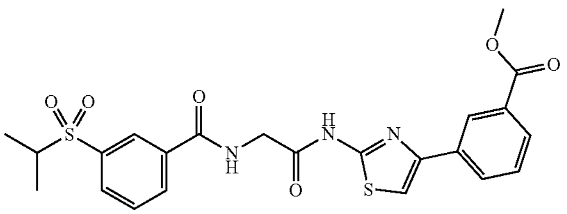

To a solution of Intermediate C (70 mg, 213.55 μmol, HCl salt), Intermediate E (48.75 mg, 213.55 μmol), EDCl (81.88 mg, 427.11 μmol), HOBt (57.71 mg, 427.11 μmol) in DCM (1 mL) was added DIEA (138.00 mg, 1.07 mmol, 185.99 μL). Then the mixture was stirred at 25° C. for 16 hr. The reaction mixture was concentrated to get the crude product. The crude product was purified by Prep-HPLC (FA) and lyophilized to afford Compound 12 (65.25 mg, 118.51 μmol, 55.50% yield) as white solid. LCMS (ESI) m/z $[M+H]^+$ =501.9. $^1H$ NMR (400 MHz, DMSO-$d_6$) δ=12.58 (s, 1H), 9.32 (s, 1H), 8.56 (m, 1H), 8.39 (s, 1H), 8.28 (d, J=8.0 Hz, 1H), 8.19 (d, J=8.0 Hz, 1H), 8.06 (d, J=8.0 Hz, 1H), 7.92 (d, J=7.6 Hz, 1H), 7.87-7.79 (m, 2H), 7.61-7.59 (m, 1H), 4.25 (d, J=5.6 Hz, 2H), 3.90 (s, 3H), 3.58-3.46 (m, 1H), 1.19 (d, J=6.6 Hz, 6H) ppm.

Example 18. Preparation of 3-(isopropylsulfonyl)-N-(2-((4-(3-(2-methylpyrimidin-4-yl)phenyl)thiazol-2-yl)amino)-2-oxoethyl)benzamide (Compound 13)

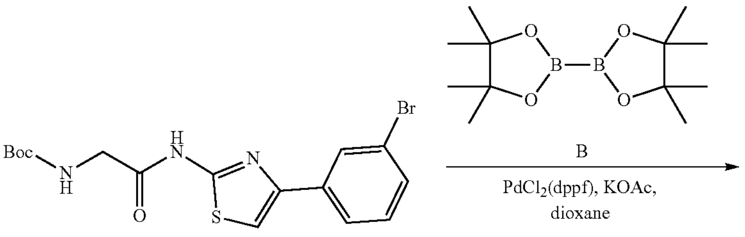

A

-continued

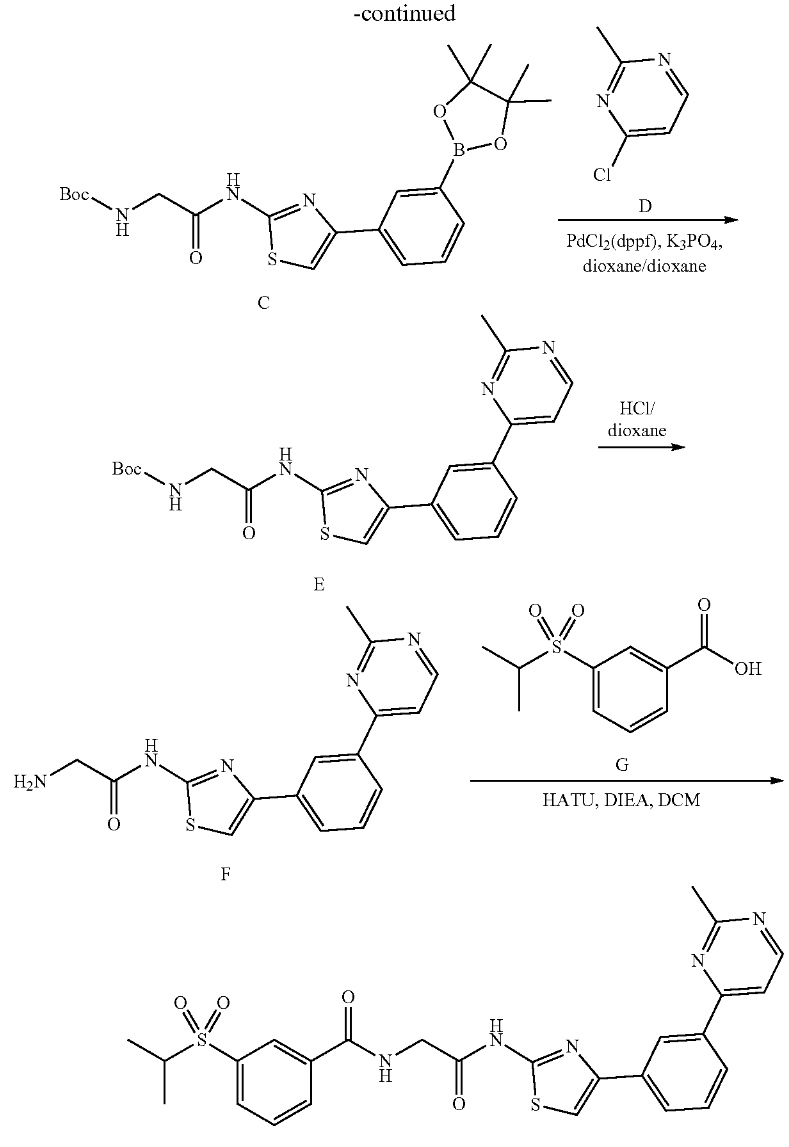

Compound 13

Step 1: Preparation of tert-butyl N-[2-oxo-2-[[4-[3-(4,4,5,5-tetramethyl-1,3,2-dioxaborolan-2-yl)phenyl]thiazol-2-yl]amino]ethyl]carbamate (Intermediate C)

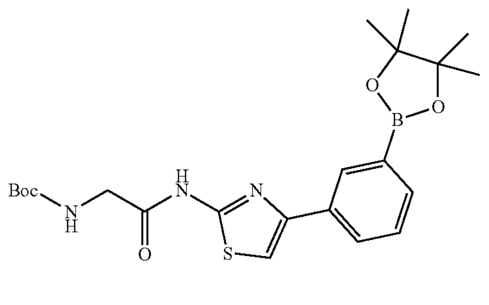

C

To a solution of tert-butyl N-[2-[[4-(3-bromophenyl)thiazol-2-yl]amino]-2-oxo-ethyl]carbamate (prepared according to the method in Example 15) (14.5 g, 35.17 mmol), 4,4,5,5-tetramethyl-2-(4,4,5,5-tetramethyl-1,3,2-dioxaborolan-2-yl)-1,3,2-dioxaborolane (26.79 g, 105.51 mmol) and Pd(dppf)Cl2 (2.57 g, 3.52 mmol) in dioxane (150 mL) was added KOAc (10.35 g, 105.51 mmol) under $N_2$, the mixture was stirred at 80° C. for 2 hr. The reaction mixture was concentrated under reduced pressure to give a residue. The residue was purified by column chromatography ($SiO_2$, Petroleum ether/Ethyl acetate=1/1) and concentrated under reduced pressure to give Intermediate C (11.5 g, 24.03 mmol, 68.34% yield) as a white solid. LCMS (ESI) m/z $[M+H]^+$=460.4. $^1H$ NMR (400 MHz, DMSO-$d_6$) δ=12.33 (s, 1H), 8.29 (s, 1H), 8.00 (d, J=8.0 Hz, 1H), 7.65 (s, 1H), 7.61 (d, J=8.0 Hz, 1H), 7.45-7.42 (m, 1H), 7.16-7.13 (m, 1H), 3.85 (d, J=6.0 Hz, 2H), 1.40 (s, 9H), 1.31 (s, 12H) ppm.

Step 2: Preparation of tert-butyl N-[2-[[4-[3-(2-methylpyrimidin-4-yl)phenyl]thiazol-2-yl]amino]-2-oxo-ethyl]carbamate (Intermediate E)

E

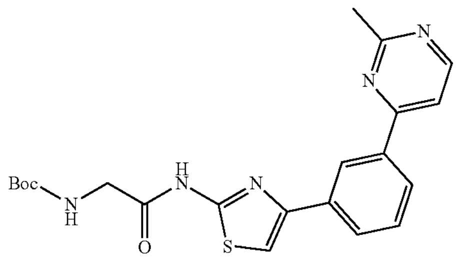

To a solution of Intermediate C (1.5 g, 3.27 mmol), 4-chloro-2-methyl-pyrimidine (420.39 mg, 3.27 mmol) and ditert-butyl(cyclopentyl)phosphane;dichloropalladium;iron (213.12 mg, 327.00 μmol) in dioxane (15 mL) and Water (3 mL) was added $K_3PO_4$ (2.08 g, 9.81 mmol) under $N_2$, the mixture was stirred at 80° C. for 2 hr. The reaction mixture was diluted with water (100 mL) and extracted with EtOAc (100 mL×3). The combined organic layers were washed with brine (300 mL), dried over $Na_2SO_4$, filtered and concentrated under reduced pressure to give Intermediate E (1.2 g, 2.82 mmol, 86.24% yield) as a brown solid, which was used to the next step without further purification. LCMS (ESI) m/z $[M+H]^+$=426.1.

Step 3: Preparation of 2-amino-N-[4-[3-(2-methylpyrimidin-4-yl)phenyl]thiazol-2-yl]acetamide (Intermediate F)

F

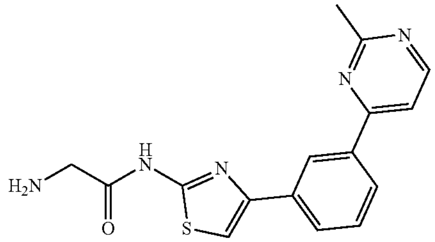

The solution of Intermediate E (1.2 g, 2.82 mmol) in HCl/dioxane (20 mL) was stirred at 30° C. for 1 hr. The reaction mixture was concentrated under reduced pressure to give a residue. The residue was triturated with MTBE (10.0 mL), then filtered and dried in vacuum to give Intermediate F (1 g, 2.76 mmol, 97.99% yield, HCl) as a red solid. LCMS (ESI) m/z $[M+H]^+$=326.1.

Step 4: Preparation of 3-(isopropylsulfonyl)-N-(2-((4-(3-(2-methylpyrimidin-4-yl)phenyl)thiazol-2-yl)amino)-2-oxoethyl)benzamide (Compound 13)

Compound 13

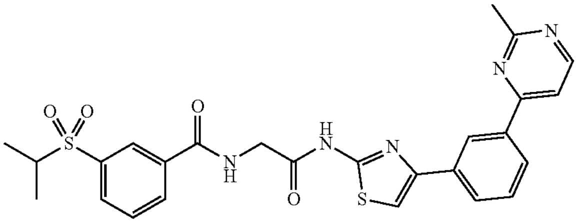

To a solution of 3-isopropylsulfonylbenzoic acid (50.47 mg, 221.09 μmol), HATU (100.88 mg, 265.30 μmol) and DIEA (142.87 mg, 1.11 mmol, 192.55 μL) in DCM (1 mL) was added Intermediate F (80 mg, 221.09 μmol, HCl), the mixture was stirred at 30° C. for 2 hr. The reaction mixture was concentrated under reduced pressure to give a residue. The residue was triturated with MeOH (5.0 mL) and MTBE (5.0 mL), then filtered and dried in vacuum to give Compound 13 (52.65 mg, 96.21 μmol, 43.52% yield) as a white solid. LCMS (ESI) m/z $[M+H]^+$=536.3. $^1H$ NMR (400 MHz, DMSO-$d_6$) δ=12.55 (br s, 1H), 9.30-9.28 (m, 1H), 8.79-8.72 (m, 2H), 8.38 (s, 1H), 8.27 (d, J=8.0 Hz, 1H), 8.13-8.04 (m, 3H), 7.92 (d, J=5.6 Hz, 1H), 7.84-7.80 (m, 2H), 7.63-7.59 (m, 1H), 4.25 (d, J=5.6 Hz, 2H), 3.53-3.46 (m, 1H), 2.71 (s, 3H), 1.18 (d, J=6.8 Hz, 6H) ppm.

Example 19. Preparation of N-(2-((4-(3-((2S,6R)-2,6-dimethylmorpholino)phenyl)thiazol-2-yl)amino)-2-oxoethyl)-3-(isopropylsulfonyl)benzamide (Compound 14)

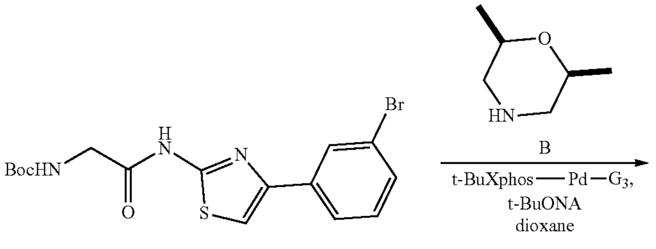

A

-continued

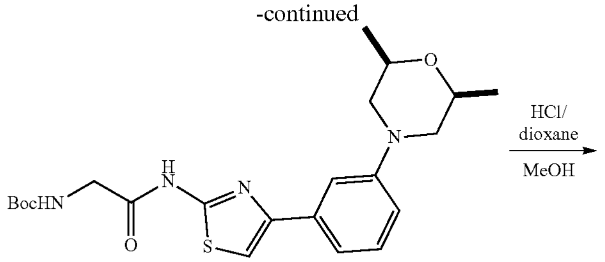

C

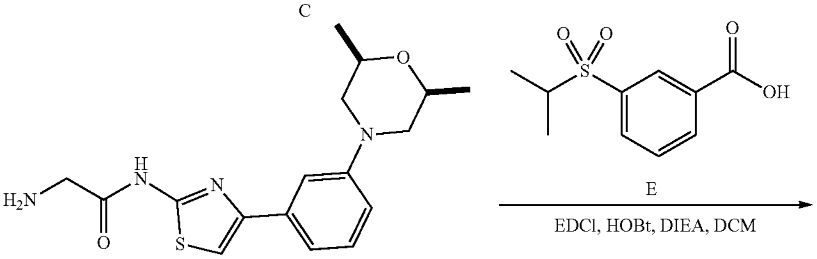

D

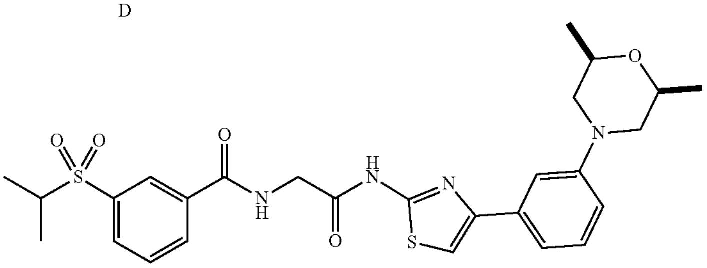

Compound 14

Step 1: Preparation of tert-butyl (2-((4-(3-((2S,6R)-2,6-dimethylmorpholino)phenyl)thiazol-2-yl)amino)-2-oxoethyl)carbamate (Intermediate C)

C

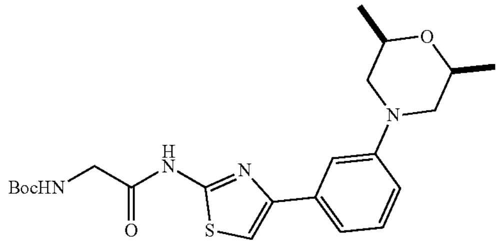

A mixture of tert-butyl N-[2-[[4-(3-bromophenyl)thiazol-2-yl]amino]-2-oxo-ethyl]carbamate (prepared according to the method in Example 15) (1.5 g, 3.64 mmol), (2S,6R)-2,6-dimethylmorpholine (628.52 mg, 5.46 mmol), [2-(2-aminophenyl)phenyl]-methylsulfonyloxy-palladium;ditert-butyl-[2-(2,4,6-triisopropylphenyl)phenyl]phosphane (289.00 mg, 363.81 μmol) and t-BuONa (1.05 g, 10.91 mmol) in dioxane (15 mL) was degassed and purged with $N_2$ for 3 times, and then the mixture was stirred at 60° C. for 5 hr under $N_2$ atmosphere. Water (40 mL) was added and the reaction mixture was extracted with EA (100 mL×2). The combined organic layers were washed with brine (40 mL), dried over $Na_2SO_4$, filtered and concentrated under reduced pressure to give a residue. The residue was purified by flash silica gel chromatography (ISCO®; 40 g SepaFlash® Silica Flash Column, Eluent of 10-60% Ethylacetate/Petroleum ether gradient at 50 mL/min) and concentrated in vacuum to give Intermediate C (800 mg, 1.61 mmol, 44.32% yield) as a white solid. LCMS (ESI) m/z $[M+H]^+$=447.4.

Step 2: Preparation of 2-amino-N-(4-(3-((2S,6R)-2,6-dimethylmorpholino)phenyl)thiazol-2-yl)acetamide (Intermediate D)

D

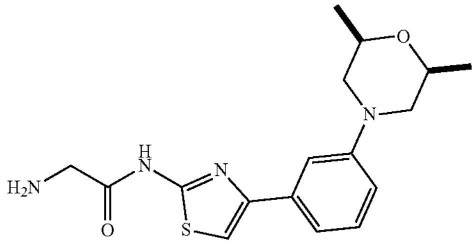

To a solution of Intermediate C (700 mg, 1.57 mmol) in MeOH (5 mL) was added HCl/dioxane (5 mL). The mixture was stirred at 25° C. for 2 hr. The reaction mixture was concentrated under reduced pressure to give Intermediate D (700 mg, crude, HCl) as a yellow solid, which was used into the next step without further purification. LCMS (ESI) m/z $[M+H]^+$=347.2.

Step 3: Preparation of N-(2-((4-(3-((2S,6R)-2,6-dimethylmorpholino)phenyl)thiazol-2-yl)amino)-2-oxoethyl)-3-(isopropylsulfonyl)benzamide (Compound 14)

Compound 14

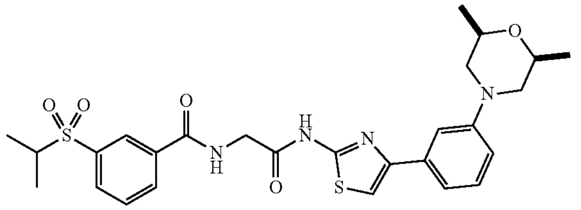

To a solution of 3-isopropylsulfonylbenzoic acid (54.25 mg, 237.66 μmol) in DCM (2 mL) was added EDCl (52.57 mg, 274.22 μmol), DIEA (70.88 mg, 548.44 μmol, 95.53 μL) and HOBt (37.05 mg, 274.22 μmol), then Intermediate D (70 mg, 182.81 μmol, HCl) was added. The mixture was stirred at 25° C. for 2 hr. The reaction mixture was concentrated under reduced pressure to remove DCM. The residue was purified by prep-HPLC (TFA condition; column: Luna C18 150×25 5 u; mobile phase: [water (0.075% TFA)-ACN]; B %: 35%-65%, 2 min) and lyophilized to give a product, which was re-purified by prep-TLC ($SiO_2$, DCM: MeOH=10:1) to give Compound 14 (17 mg, 30.28 μmol, 16.56% yield, 99.16% purity) as a white solid. LCMS (ESI) m/z $[M+H]^+$=557.3. $^1H$ NMR (400 MHz, methanol-$d_4$) δ=8.44 (s, 1H), 8.27 (d, J=8.0 Hz, 1H), 8.09 (d, J=7.6 Hz, 1H), 7.81-7.77 (m, 1H), 7.55 (s, 1H), 7.38-7.36 (m, 2H), 7.29-7.25 (m, 1H), 6.93 (d, J=7.6 Hz, 1H), 4.34 (s, 2H), 3.85-3.80 (m, 2H), 3.58 (d, J=10.8 Hz, 2H), 3.44-3.37 (m, 1H), 2.39-2.33 (m, 2H), 1.29 (d, J=6.8 Hz, 6H), 1.24 (d, J=6.0 Hz, 6H) ppm. Chiral HPLC: Cellucoat-MeOH (DEA)-40-3 mL-35T·lcm, Rt=1.816 min, ee %=100%.

Example 20. Preparation of 3-(hydroxymethyl)-5-(isopropylsulfonyl)-N-(2-oxo-2-((4-(3-(pyridin-4-yl)phenyl)thiazol-2-yl)amino)ethyl)benzamide (Compound 15)

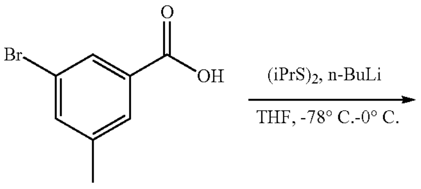

A

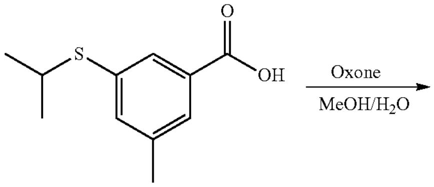

B

-continued

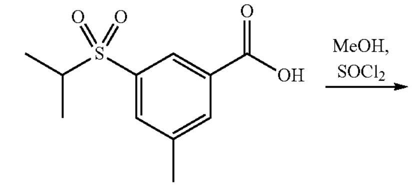

C

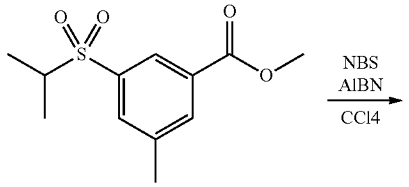

D

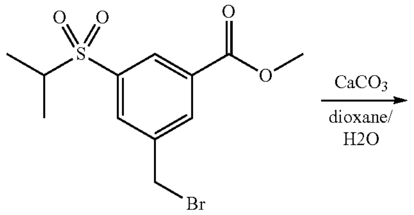

E

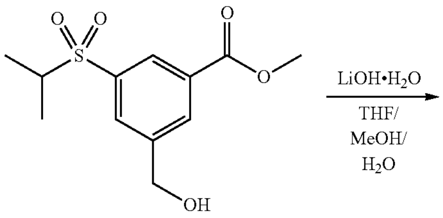

F

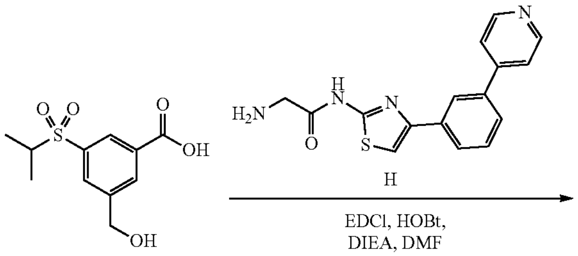

G

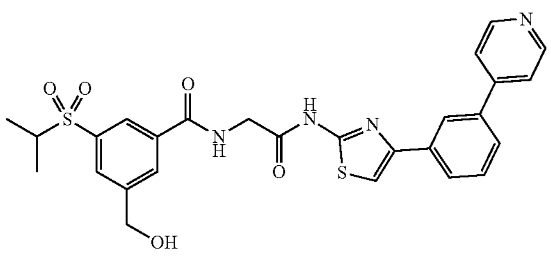

Compound 15

Step 1: Preparation of 3-(isopropylthio)-5-methylbenzoic acid (Intermediate B)

B

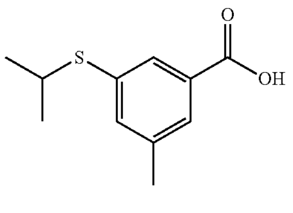

To a mixture of 3-bromo-5-methyl-benzoic acid (4 g, 18.60 mmol) in THF (50 mL) was added n-BuLi (2.5 M, 16.37 mL) drop wise at −78° C. under $N_2$. The mixture was stirred at −78° C. for 30 min, then 2-(isopropyldisulfanyl) propane (2.94 g, 19.53 mmol, 3.11 mL) was added to the mixture at −78° C. The mixture was stirred at 25° C. for 10 hour. The mixture was treated with aqueous $NH_4Cl$ (300 mL) and extracted with ethyl acetate (100 mL×2). The combined organic phase was washed with brine (100 mL×1), dried with anhydrous $Na_2SO_4$, filtered and concentrated in vacuum. The residue was purified by column chromatography ($SiO_2$, Petroleum ether/Ethyl acetate to DCM/MeOH=5/1 to 5/1) to give Intermediate B (2.9 g, 13.79 mmol, 74.14% yield) as a yellow solid. LCMS (ESI) m/z $[M+H]^+$=211.1. $^1$H NMR (400 MHz, chloroform-d) δ=7.89-7.80 (m, 1H), 7.74-7.63 (m, 1H), 7.37-7.31 (m, 1H), 3.48-3.30 (m, 1H), 2.58-2.52 (m, 1H), 2.49-2.43 (m, 1H), 2.33-2.26 (m, 1H), 2.36-2.25 (m, 2H), 1.26-1.17 (m, 7H) ppm.

Step 2: Preparation of 3-(isopropylsulfonyl)-5-methylbenzoic acid (Intermediate C)

C

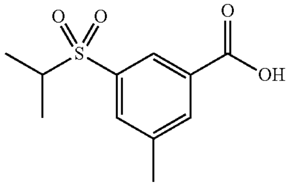

To a solution of Intermediate B (2.3 g, 10.94 mmol) in MeOH (25 mL) and $H_2O$ (25 mL) was added oxone (10.09 g, 16.41 mmol). Then the mixture was stirred at 25° C. for 3 hr. The reaction mixture was diluted with water (60 mL) and extracted with EA (60 mL×2). The combined organic phase was washed with brine (60 mL×1), dried with anhydrous $Na_2SO_4$, filtered and concentrated in vacuum. The crude product was triturated with MTBE/PE=2/1 (20 mL) at 25° C. for 5 min, filtered and dried in vacuum to give Intermediate C (1.7 g, 7.02 mmol, 64.15% yield) as a white solid. LCMS (ESI) m/z $[M+H]^+$=243.0.

Step 3: Preparation of methyl 3-(isopropylsulfonyl)-5-methylbenzoate (Intermediate D)

D

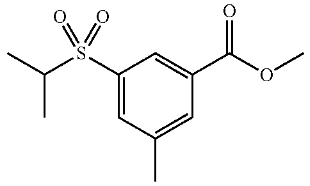

To a solution of Intermediate C (800 mg, 3.30 mmol) in MeOH (8 mL) was added thionyl chloride (785.63 mg, 6.60 mmol, 479.05 μL) at 0° C. Then the mixture solution was stirred at 80° C. for 12 hr. The mixture was adjusted to pH=9 with $NaHCO_3$ (10 mL) then extracted with EA (15 mL×3), the combined organic phase was dried over anhydrous $Na_2SO_4$, filtered and concentrated under reduced pressure to give Intermediate D (880 mg, crude) as a yellow solid, which was used into the next step without further purification. $^1$H NMR (400 MHz, methanol-$d_4$) δ=8.17 (s, 1H), 8.09 (s, 1H), 7.84 (s, 1H), 3.86 (s, 3H), 3.32-3.24 (m, 1H), 2.43 (s, 3H), 1.16 (d, J=6.8 Hz, 6H) ppm.

Step 4: Preparation of methyl 3-(bromomethyl)-5-(isopropylsulfonyl)benzoate (Intermediate E)

E

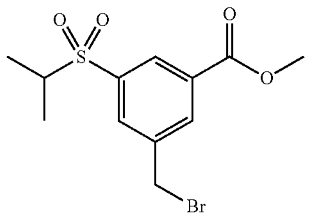

To a solution of methyl Intermediate D (880 mg, 3.43 mmol) in $CCl_4$ (10 mL) was added AIBN (16.91 mg, 103.00 μmol) and NBS (763.83 mg, 4.29 mmol) at 25° C. Then the mixture was stirred at 80° C. for 16 hr. The reaction mixture was poured into $H_2O$ (15 mL) and extracted with DCM (15 mL×3), the combined organic phase was dried over anhydrous $Na_2SO_4$, filtered and concentrated under reduced pressure to afford a residue. The residue was purified by Prep-TLC (PE/EA=3/1) to give Intermediate E (540 mg, 1.61 mmol, 46.92% yield) as a yellow solid. LCMS (ESI) m/z $[^{81}BrM+H]^+$=337.0. $^1$H NMR (400 MHz, METHANOL-$d_4$) δ=8.40-8.39 (m, J=4 Hz, 1H), 8.38-8.37 (m, J=4 Hz, 1H), 8.18-8.16 (m, 1H), 4.74 (s, 2H), 3.98 (s, 3H), 3.42-3.34 (m, 1H), 1.28-1.26 (d, J=8.0 Hz, 6H) ppm.

Step 5: Preparation of methyl 3-(hydroxymethyl)-5-(isopropylsulfonyl)benzoate (Intermediate F)

F

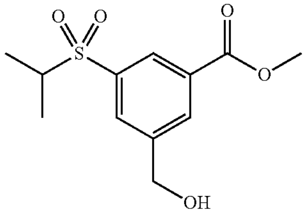

To a solution Intermediate E (240 mg, 715.96 μmol) in dioxane (2 mL) and $H_2O$ (2 mL) was added $CaCO_3$ (286.64 mg, 2.86 mmol). Then the mixture was stirred at 100° C. for 8 hr. To the reaction mixture was added water (5 mL) and extracted with EA (5 mL×3), the combined organic phase was dried over anhydrous $Na_2SO_4$, filtered and concentrated under reduced pressure to afford a residue. The residue was purified by column chromatography ($SiO_2$, Petroleum ether/Ethyl acetate to PE/EA=10/1 to 5/1) to give Intermediate F (100 mg, 367.22 μmol, 51.29% yield) as yellow oil. LCMS (ESI) m/z $[M+H]^+$=272.9. $^1H$ NMR (400 MHz, DMSO-$d_6$) δ=8.26-8.21 (m, 1H), 8.21-8.19 (m, 1H), 8.19-8.06 (m, 1H), 5.63-5.60 (m, 1H), 4.68 (d, J=8.0 Hz, 2H), 3.92 (s, 3H), 3.92-3.51 (m, 1H), 1.18 (d, J=6.8 Hz, 6H) ppm.

Step 6: Preparation of 3-(hydroxymethyl)-5-(isopropylsulfonyl)benzoic acid (Intermediate G)

G

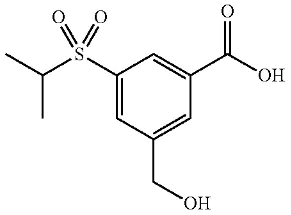

To a solution of Intermediate F (100 mg, 367.22 μmol) in THF (1 mL) and MeOH (0.5 mL) was added a solution of $LiOH \cdot H_2O$ (77.05 mg, 1.84 mmol) in $H_2O$ (0.5 mL) at 25° C. Then the mixture was stirred at 25° C. for 1 hr. The mixture was adjusted to pH=6 with HCl (1 M) then extracted with EA (5 mL×3), the combined organic phase was dried over anhydrous $Na_2SO_4$, filtered and concentrated under reduced pressure to give Intermediate G (60 mg, 232.30 μmol, 63.26% yield) as a yellow solid, which was used into the next step without further purification. LCMS (ESI) m/z $[^{81}BrM+H]^+$=337.0. $^1H$ NMR (400 MHz, DMSO-$d_6$) δ=8.23 (s, 1H), 8.18 (s, 1H), 8.02 (s, 1H), 4.68 (s, 2H), 3.52-3.43 (m, 1H), 1.19-1.15 (m, 6H) ppm.

Step 7: Preparation of 3-(hydroxymethyl)-5-isopropylsulfonyl-N-[2-oxo-2-[[4-[3-(4-pyridyl)phenyl]thiazol-2-yl]amino]ethyl]benzamide (Compound 15)

Compound 15

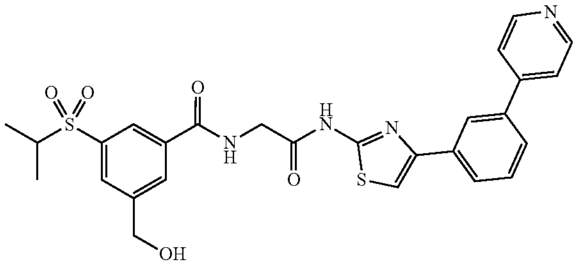

To a solution of Intermediate G (40 mg, 154.86 μmol) and 2-amino-N-[4-[3-(4-pyridyl)phenyl]thiazol-2-yl]acetamide (prepared according to the method in Example 16) (53.71 mg, 154.86 μmol, HCl) in DMF (2 mL) was added DIEA (100.08 mg, 774.32 μmol, 134.87 μL) and HATU (88.33 mg, 232.30 μmol). The mixture was stirred at 25° C. for 8 hr. To the reaction mixture was added water (5 mL) and extracted with EA (5 mL×3), the combined organic phase was dried over anhydrous $Na_2SO_4$, filtered and concentrated under reduced pressure to afford a residue. The crude product was purified by reversed-phase column (FA condition) and lyophilized to give Compound 15 (29.46 mg, 49.37 μmol, 31.88% yield, 100% purity, FA) as a white solid. LCMS (ESI) m/z $[M+H]^+$=551.1. $^1H$ NMR (400 MHz, DMSO-$d_6$) δ=12.53 (s, 1H), 9.30-9.27 (m, 1H), 8.71 (d, J=6.4 Hz, 2H), 8.33 (s, 1H), 8.24 (d, J=12.8 Hz, 2H), 8.10-7.99 (m, 2H), 7.86-7.84 (m, 3H), 7.83-7.82 (m, 1H), 7.63-7.61 (m, 1H), 5.63-5.58 (br s, 1H), 4.69 (s, 2H), 4.24 (m, 2H), 3.50-3.45 (m, 1H), 1.19 (d, J=6.8 Hz, 6H) ppm.

Example 21. Preparation of 3-(isopropylsulfonyl)-4,5-dimethyl-N-(2-oxo-2-((4-(3-(pyridin-4-yl)phenyl)thiazol-2-yl)amino)ethyl)benzamide (Compound 16)

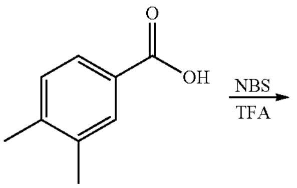

A

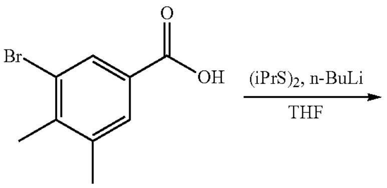

B

-continued

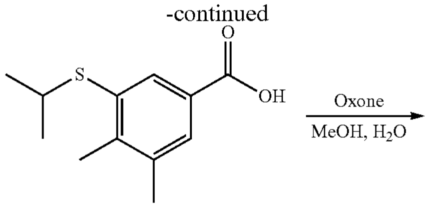

C

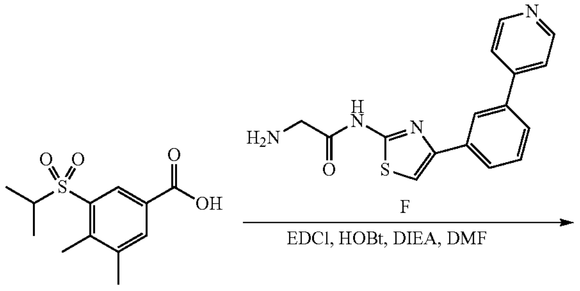

D

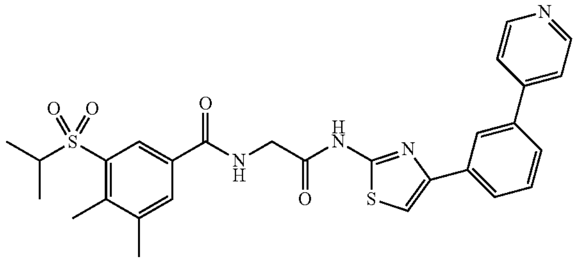

Compound 16

Step 1: Preparation of 3-bromo-4,5-dimethylbenzoic acid (Intermediate B)

B

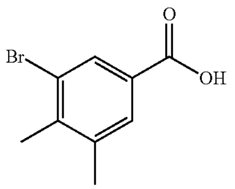

To a solution of 3,4-dimethylbenzoic acid (2 g, 13.32 mmol) in TFA (50 mL) was added NBS (2.37 g, 13.32 mmol). The mixture was stirred at 50° C. for 16 hr. The reaction mixture was concentrated under reduced pressure to give a residue. The residue was diluted with EA (15 mL), then filtered and concentrated under reduced pressure to give Intermediate B (0.773 g, 2.90 mmol, 21.80% yield) as a white solid, which was used into the next step without further purification. LCMS (ESI) m/z $[^{81}BrM+H]^+$=231.0. $^1H$ NMR (400 MHz, DMSO-$d_6$) δ=11.20-10.95 (m, 1H), 7.91 (s, 1H), 7.73 (s, 1H), 2.57 (s, 3H), 2.37 (s, 10H) ppm.

Step 2: Preparation of 3-(isopropylthio)-4,5-dimethylbenzoic acid (Intermediate C)

C

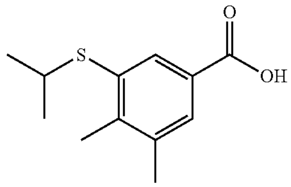

To a solution of Intermediate B (300 mg, 1.31 mmol) in THE (4 mL) was added n-BμLi (2.5 M, 1.05 mL) at −78° C. and the mixture was stirred for 0.5 h under $N_2$ atmosphere. Then to the mixture was added 2-(isopropyldisulfanyl)propane (236.21 mg, 1.57 mmol, 250.49 μL), the reaction mixture was wormed to 0° C. and stirred at 0° C. for 1 h. The mixture was quenched with water (5 mL) and extracted with MTBE (5 mL×2). The organic layer was discarded and then aqueous phase was adjusted the pH=5 with 2N HCl and extracted with EA (10 mL×3), the combined organic layers were washed with brine (10 mL×2), dried over $Na_2SO_4$, filtered and concentrated in vacuum to give Intermediate C (230 mg, 842.19 μmol, 64.31% yield, 82.139% purity) as a light yellow solid, which was used into next step without purification. LCMS (ESI) m/z $[M+H]^+$=225.2. $^1H$ NMR (400 MHz, DMSO-$d_6$) δ=12.91-12.70 (m, 2H), 7.78 (d, J=1.2 Hz, 1H), 7.72 (s, 1H), 7.69-7.65 (m, 1H), 7.64 (s, 1H), 7.57 (d, J=4.4 Hz, 1H), 7.26 (d, J=8.0 Hz, 1H), 3.44-3.37 (m, 1H), 2.36-2.33 (m, 3H), 2.32 (s, 3H), 2.29 (s, 3H), 2.28 (s, 2H), 1.26 (d, J=6.4 Hz, 6H) ppm.

Step 3: Preparation of 3-(isopropylsulfonyl)-4,5-dimethylbenzoic acid (Intermediate D)

D

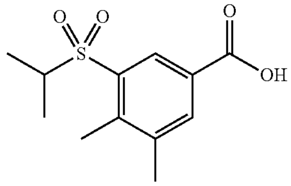

To a solution of Intermediate C (230 mg, 1.03 mmol) in MeOH (2 mL) and $H_2O$ (2 mL) was added Oxone (1.26 g, 2.05 mmol). The mixture was stirred at 20° C. for 16 h. Water (10 mL) was added into the mixture and then extracted with EA (15 mL×3). The combined organic layers were washed with brine (10 mL×2), dried over $Na_2SO_4$, filtered and concentrated in vacuum to give Intermediate D (230 mg, 897.32 μmol, 87.52% yield) as a white solid, which was used into next step without purification. LCMS (ESI) m/z $[M+H]^+$=257.1.

Step 4: Preparation of 3-(isopropylsulfonyl)-4,5-dimethyl-N-(2-oxo-2-((4-(3-(pyridin-4-yl)phenyl)thiazol-2-yl)amino)ethyl)benzamide (Compound 16)

Compound 16

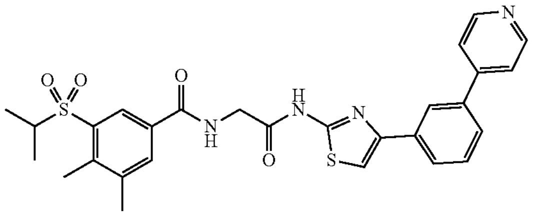

To a solution of Intermediate D (100 mg, 390.14 μmol), EDCl (112.19 mg, 585.21 μmol), HOBt (79.08 mg, 585.21 μmol) and DIEA (252.12 mg, 1.95 mmol, 339.78 μL) in DMF (1 mL) was added 2-amino-N-[4-[3-(4-pyridyl)phenyl]thiazol-2-yl]acetamide (prepared according to the method in Example 16) (142.08 mg, 409.65 μmol, HCl). The mixture was stirred at 20° C. for 2 h. The mixture was added into water (10 mL) and filtered. The solid was washed with MeOH (5 mL), and then dried in vacuum to give Compound 16 (104.26 mg, 180.05 μmol, 46.15% yield) as a white solid. LCMS (ESI) m/z $[M+H]^+$=549.2. $^1$H NMR (400 MHz, DMSO-$d_6$) δ=9.16 (s, 1H), 8.72-8.65 (m, 2H), 8.30 (m, 2H), 8.08 (s, 1H), 8.02 (m, 1H), 7.85 (s, 1H), 7.77 (m, 3H), 7.61 (m, 1H), 4.23 (m, 2H), 3.59-3.41 (m, 1H), 2.61 (s, 3H), 2.42 (s, 3H), 1.19 (m, 6H) ppm.

Example 22. Preparation of N-(2-((4-(3-((((1R,4R)-4-hydroxycyclohexyl)oxy)methyl)phenyl)thiazol-2-yl)amino)-2-oxoethyl)-3-(isopropylsulfonyl)benzamide (Compound 17)

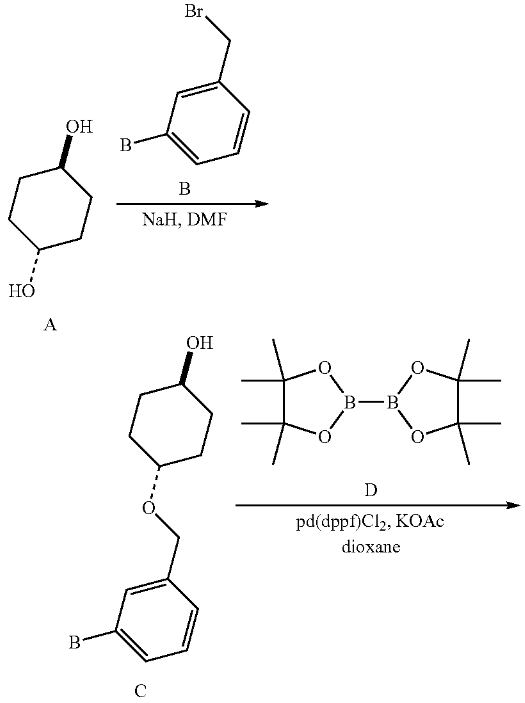

-continued

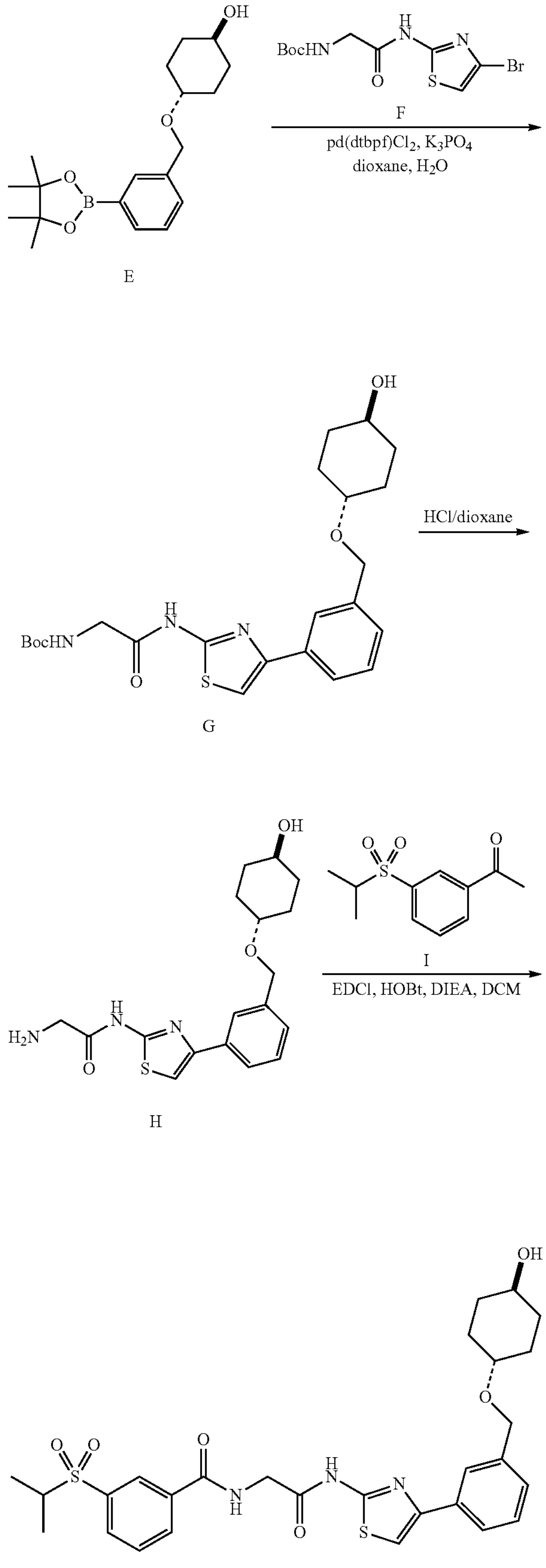

Compound 17

Step 1: Preparation of (1R,4R)-4-((3-bromobenzyl)oxy)cyclohexanol (Intermediate C)

C

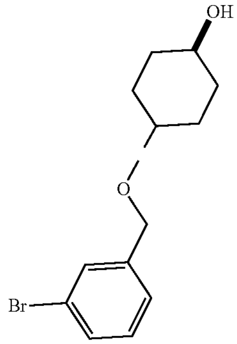

To a solution of cyclohexane-1,4-diol (2.0 g, 17.22 mmol) and NaH (826.38 mg, 20.66 mmol, 60% purity) in DMF (40 mL) was added 1-bromo-3-(bromomethyl)benzene (5.16 g, 20.66 mmol) at 0° C., the mixture was stirred at 30° C. for 16 hr. The reaction mixture was poured into $NH_4Cl$ solution (20 mL), the solution was extracted with EA (20 mL×3), the combined organic layer was washed with brine (50 mL), dried over $Na_2SO_4$, filtered and concentrated to give a residue in vacuum. The residue was purified by column chromatography ($SiO_2$, PE:EA=10:1-3:1), the solution was concentrated in vacuum to give Intermediate C (1.0 g, 3.51 mmol, 20.37% yield) as yellow oil. $^1H$ NMR (400 MHz, METHANOL-$d_4$) δ=7.50 (s, 1H), 7.41 (br d, J=7.6 Hz, 1H), 7.30-7.23 (m, 2H), 4.51 (s, 2H), 3.64-3.54 (m, 1H), 3.43-3.35 (m, 1H), 2.05 (br d, J=11.7 Hz, 2H), 1.96-1.89 (m, 2H), 1.38-1.28 (m, 4H) ppm.

Step 2: Preparation of (1R,4R)-4-((3-(4,4,5,5-tetramethyl-1,3,2-dioxaborolan-2-yl)benzyl)oxy)cyclohexanol (Intermediate E)

E

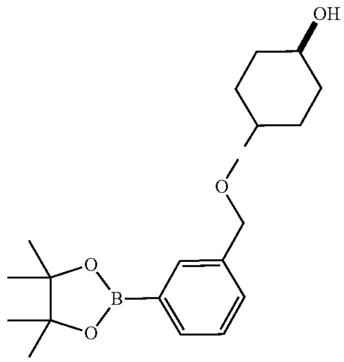

To a solution of Intermediate C (1 g, 3.51 mmol), 4,4,5,5-tetramethyl-2-(4,4,5,5-tetramethyl-1,3,2-dioxaborolan-2-yl)-1,3,2-dioxaborolane (1.16 g, 4.56 mmol) in dioxane (10 mL) were added ditertbutyl(cyclopentyl)phosphane;dichloropalladium;iron (228.54 mg, 350.66 μmol) and KOAc (1.03 g, 10.52 mmol) at 25° C. under $N_2$. The mixture was stirred at 80° C. for 3 h. The reaction mixture was concentrated under reduced pressure to give a residue. The residue was purified by column chromatography (PE/EA=1:1, Rf=0.5, $SiO_2$, Petroleum ether/Ethyl acetate=1/0 to 1:1) to give Intermediate E (1.16 g, crude) as brown oil. LCMS (ESI) m/z $[M-115]^+$=217.1.

Step 3: Preparation of tert-butyl (2-((4-(3-((((1R,4R)-4-hydroxycyclohexyl)oxy)methyl)phenyl)thiazol-2-yl)amino)-2-oxoethyl)carbamate (Intermediate G)

G

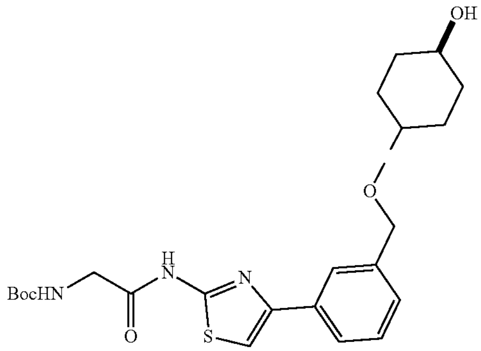

To a solution of tert-butyl N-[2-[(4-bromothiazol-2-yl)amino]-2-oxo-ethyl]carbamate (prepared according to the method in Example 4) (435.13 mg, 1.29 mmol), Intermediate E (860 mg, 2.59 mmol) in dioxane (15 mL) and $H_2O$ (1.5 mL) were added $K_3PO_4$ (824.19 mg, 3.88 mmol) and ditertbutyl(cyclopentyl)phosphane;dichloropalladium;iron (84.35 mg, 129.42 μmol) under $N_2$. The mixture was stirred at 100° C. for 4 h. The reaction mixture was diluted with water (20 mL) and extracted with EA (30 mL×3), the combined organic layers were washed with brine (40 mL×2) and dried over anhydrous $Na_2SO_4$. The mixture was filtered and concentrated under reduced pressure to give a residue. The residue was purified by column chromatography (PE/EA=1:2, Rf=0.35, $SiO_2$, Petroleum ether/Ethyl acetate=5/1 to 3/1) and then concentrated in vacuum to give Intermediate G (650 mg, 1.27 mmol, 98.04% yield, 90.106% purity) as a brown solid. LCMS (ESI) m/z $[M+H]^+$=462.1.

Step 4: Preparation of 2-amino-N-(4-(3-((((1R,4R)-4-hydroxycyclohexyl)oxy)methyl)phenyl)thiazol-2-yl)acetamide (Intermediate H)

H

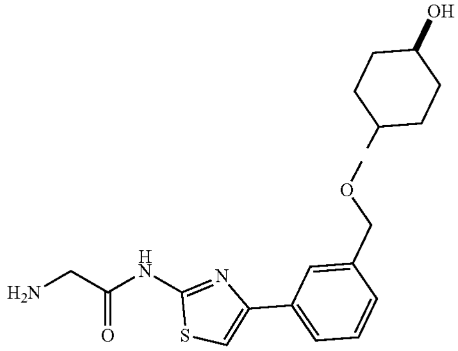

A solution of Intermediate G (650.00 mg, 1.41 mmol) in HCl/dioxane (7 mL) was stirred at 20° C. for 1 h. The reaction mixture was concentrated under reduced pressure to give a residue. The residue was triturated with MTBE (10 mL) at 20° C. for 5 min. Then the mixture was filtered, the solid was washed with MTBE (5 mL×3), dried in vacuum to give Intermediate H (500 mg, crude, HCl) as a brown solid. LCMS (ESI) m/z $[M+H]^+$=361.9.

Step 5: Preparation of N-(2-((4-(3-((((1r,4r)-4-hydroxycyclohexyl)oxy)methyl)phenyl)thiazol-2-yl)amino)-2-oxoethyl)-3-(isopropylsulfonyl)benzamide (Compound 17)

Compound 17

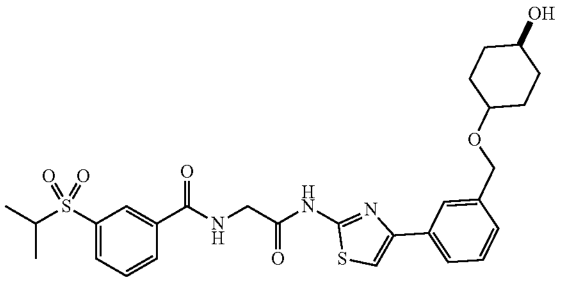

To a solution of 3-isopropylsulfonylbenzoic acid (75.78 mg, 331.99 μmol), Intermediate H (100.00 mg, 276.66 μmol, 1 eq), DIEA (178.78 mg, 1.38 mmol, 240.94 μL) in DCM (1 mL) were added EDCl (63.64 mg, 331.99 μmol), HOBt (44.86 mg, 331.99 μmol). The mixture was stirred at 20° C. for 16 h. The reaction mixture was concentrated under reduced pressure to give a residue. The residue was purified by reversed-phase HPLC (0.1% FA condition) and then lyophilized to give Compound 17 (16.94 mg, 28.04 μmol, 10.13% yield, 94.621% purity) as a yellow solid. LCMS (ESI) m/z $[M+H]^+$=572.1. $^1$H NMR (400 MHz, DMSO-$d_6$) δ=12.46-12.44 (m, 1H), 9.29-9.26 (m, 1H), 8.37 (s, 1H), 8.27 (d, J=7.6 Hz, 1H), 8.05 (d, J=8.0 Hz, 1H), 7.85-7.78 (m, 3H), 7.62 (s, 1H), 7.40-7.37 (m, 1H), 7.27 (d, J=7.6 Hz, 1H), 4.52 (s, 2H), 4.49 (d, J=4.4 Hz, 1H), 4.24 (d, J=5.6 Hz, 2H), 3.53-3.42 (m, 3H), 1.98-1.94 (m, 2H), 1.82-1.78 (m, 2H), 1.28-1.16 (m, 8H) ppm.

Example 23. Preparation of N-(2-((4-(3-(2,6-dimethylpyridin-4-yl)phenyl)thiazol-2-yl)amino)-2-oxoethyl)-3-(isopropylsulfonyl)benzamide (Compound 18)

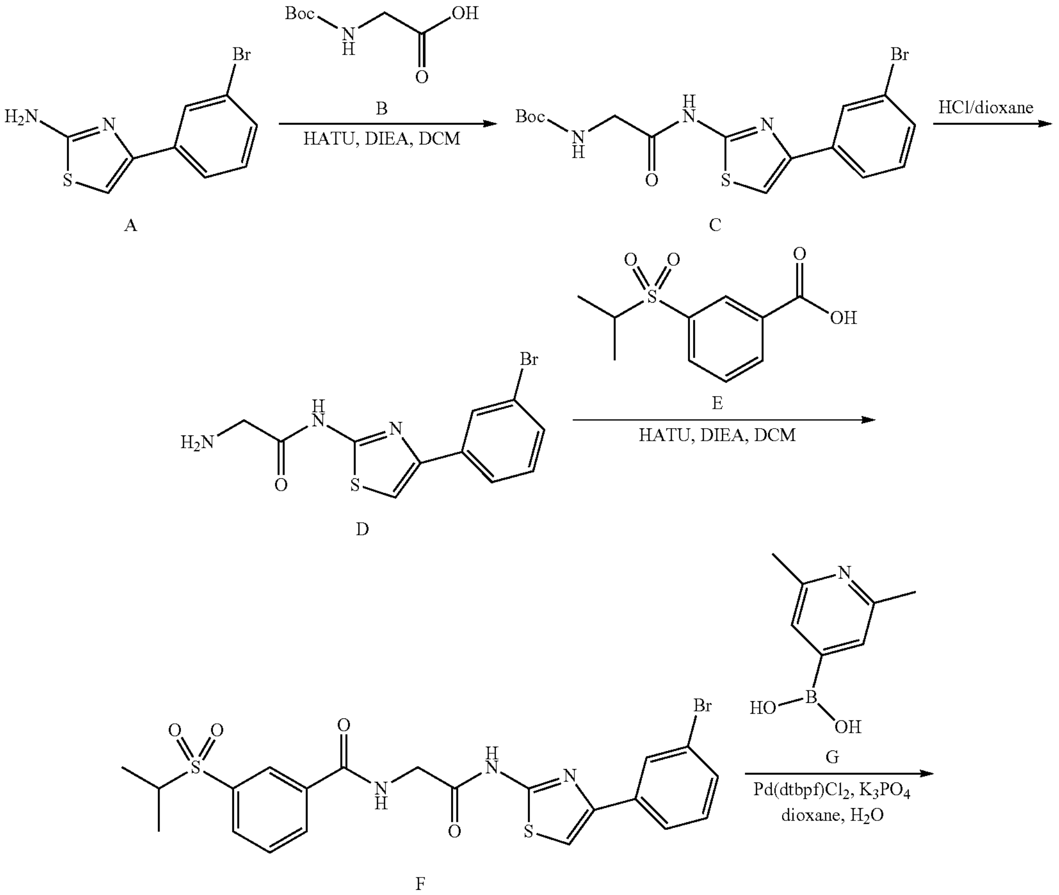

-continued

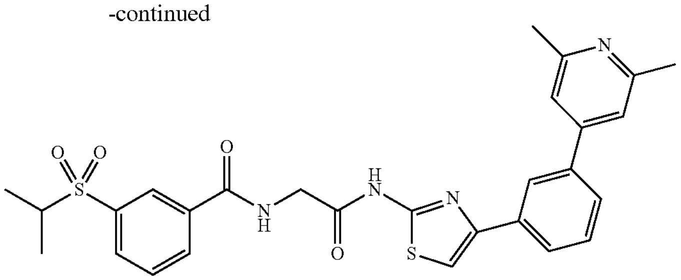

Compound 18

Step 1: Preparation of tert-butyl N-[2-[[4-(3-bromophenyl)thiazol-2-yl]amino]-2-oxo-ethyl]carbamate (Intermediate C)

C

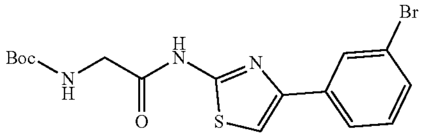

To a solution of 2-(tert-butoxycarbonylamino)acetic acid (41.20 g, 235.17 mmol), HATU (89.42 g, 235.17 mmol) and DIEA (75.99 g, 587.93 mmol, 102.41 mL) in DCM (500 mL) was added 4-(3-bromophenyl)thiazol-2-amine (50 g, 195.98 mmol), the mixture was stirred at 30° C. for 4 hr. The reaction mixture was washed with sat. citric acid (500 mL×4) and then washed with brine (500 mL), dried over $Na_2SO_4$, filtered and concentrated under reduced pressure to give a residue. The residue was triturated with MeOH (200 mL) and filtered to give a solid, the solid was re-triturated with PE/EA (200 mL, 10:1) and dried in vacuum to give Intermediate C (70 g, 166.38 mmol, 84.90% yield) as a white solid. LCMS (ESI) m/z $[M+H]^+$=412.2. $^1H$ NMR (400 MHz, DMSO-$d_6$) δ=12.29 (s, 1H), 8.09 (s, 1H), 7.90 (d, J=8.0 Hz, 1H), 7.77 (s, 1H), 7.50 (s, 1H), 7.41-7.37 (m, 1H), 7.16-7.15 (m, 1H), 3.86 (d, J=6.4 Hz, 2H) 1.39 (s, 9H) ppm.

Step 2: Preparation of 2-amino-N-[4-(3-bromophenyl)thiazol-2-yl]acetamide (Intermediate D)

D

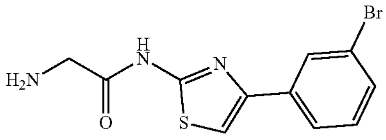

A solution of Intermediate C (14 g, 33.96 mmol) in 4 M HCl/dioxane (50 mL) was stirred at 30° C. for 2 hr. The residue was concentrated under reduced pressure to give a residue. The residue was triturated with MTBE (100 mL), filtered and dried in vacuum to give Intermediate D (12.1 g, crude, HCl) a white solid. LCMS (ESI) m/z $[M+H]^+$=312.2.

Step 3: Preparation of N-[2-[[4-(3-bromophenyl)thiazol-2-yl]amino]-2-oxo-ethyl]-3-isopropylsulfonyl-benzamide (Intermediate F)

F

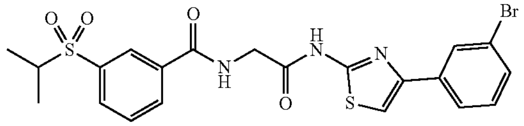

To a solution of 3-isopropylsulfonylbenzoic acid (prepared according to the method in Example 17) (1.96 g, 8.60 mmol), EDCl (2.75 g, 14.34 mmol), HOBt (1.94 g, 14.34 mmol) and DIEA (4.63 g, 35.85 mmol, 6.24 mL) in DCM (30 mL) was added Intermediate D (2.5 g, 7.17 mmol, HCl), the mixture was stirred at 30° C. for 4 hr. The reaction mixture was concentrated under reduced pressure to give a residue. The residue was diluted with EtOAc (200 mL) and washed with sat. citric acid (200 mL×3) and brine (200 mL), dried over $Na_2SO_4$, filtered and concentrated under reduced pressure to give a residue. The residue was purified was triturated with MeOH (20 mL), filtered and dried in vacuum to give Intermediate F (2.8 g, 5.31 mmol, 74.00% yield, 99% purity) a white solid. LCMS (ESI) m/z $[M+H]^+$=521.9. $^1H$ NMR (400 MHz, DMSO-$d_6$) δ=12.49 (s, 1H), 9.31-9.28 (m, 1H), 8.38 (s, 1H), 8.21-8.30 (m, 1H), 8.11 (s, 1H), 8.04-8.03 (m, 1H), 7.90-7.89 (d, J=8.0 Hz, 1H), 7.83-7.79 (m, 2H), 7.50-7.49 (d, J=7.6 Hz, 1H), 7.40-7.31 (m, 1H), 4.23 (d, J=6.0 Hz, 2H), 3.53-3.46 (m, 1H), 2.52-2.51 (m, 6H), 1.18 (d, J=6.8 Hz, 6H) ppm.

Step 4: Preparation of N-(2-((4-(3-(2,6-dimethylpyridin-4-yl)phenyl)thiazol-2-yl)amino)-2-oxo-ethyl)-3-(isopropylsulfonyl)benzamide (Compound 18)

Compound 18

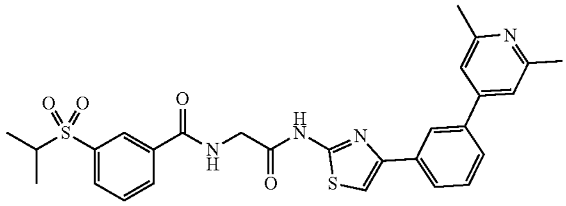

Intermediate F (75 mg, 143.56 μmol), (2,6-dimethyl-4-pyridyl)boronic acid (43.35 mg, 287.12 μmol), ditertbutyl(cyclopentyl)phosphane;dichloropalladium;iron (9.36 mg, 14.36 μmol) and $K_3PO_4$ (91.42 mg, 430.68 μmol) were taken up in dioxane (1 mL) and $H_2O$ (0.2 mL), the mixture was purged with $N_2$ three times. Then the resulting mixture was stirred at 80° C. for 2 hr. The residue was slurried in MeOH/$H_2O$ (2/1, 5 mL) and stirred for 5 min. The precipitate was collected by filtration and washed with MeOH (3 mL), then dried in vacuum to give Compound 18 (59.64 mg, 106.74 μmol, 74.35% yield, 98.2% purity) as a brown solid. LCMS (ESI) m/z $[M+H]^+$=549.4. $^1H$ NMR (400 MHz, DMSO-$d_6$) δ=12.51 (s, 1H), 9.31-9.28 (m, 1H), 8.38 (s, 1H), 8.28-8.26 (m, 2H), 8.05 (d, J=7.6 Hz, 1H), 7.98 (d, J=8.0 Hz, 1H), 7.84-7.80 (m, 2H), 7.71 (d, J=7.6 Hz, 1H), 7.58-7.54 (m, 1H), 7.41 (s, 2H), 4.25 (d, J=6.0 Hz, 2H), 3.53-3.46 (m, 1H), 2.52-2.51 (m, 6H), 1.19 (d, J=6.8 Hz, 6H) ppm.

Example 24. Preparation of 3-(isopropylsulfonyl)-N-(2-oxo-2-((4-(3-(2-(trifluoromethyl)pyridin-4-yl)phenyl)thiazol-2-yl)amino)ethyl)benzamide (Compound 19)

A mixture of N-[2-[[4-(3-bromophenyl)thiazol-2-yl]amino]-2-oxo-ethyl]-3-isopropylsulfonyl-benzamide (prepared according to the method in Example 23) (75 mg, 143.56 μmol), 4-(4,4,5,5-tetramethyl-1,3,2-dioxaborolan-2-yl)-2-(trifluoromethyl)pyridine (39.20 mg, 143.56 μmol), ditertbutyl(cyclopentyl)phosphane;dichloropalladium;iron (4.68 mg, 7.18 μmol), $K_3PO_4$ (121.89 mg, 574.23 μmol) in dioxane (4 mL) and $H_2O$ (0.08 mL) was degassed with $N_2$ for 3 times, then the reaction mixture was stirred at 80° C. for 2 hr under $N_2$. The reaction mixture was filtered with column chromatography ($SiO_2$, 100% Ethyl acetate), the organic phase was concentrated under vacuum to give residue. The residue was purified by pre-HPLC (TFA condition: column: Phenomenex luna C18 150×25 10 u; mobile phase: [water (0.1% TFA)-ACN]; B %: 44%-74%, 10 min) and then lyophilized to give Compound 19 (33.86 mg, 56.37 μmol, 39.27% yield, 98% purity, TFA) as an off-white solid. LCMS (ESI) m/z $[M+H]^+$=589.0. $^1H$ NMR (400 MHz, DMSO-$d_6$) δ=12.53 (s, 1H), 9.32-9.30 (m, 1H), 8.87 (d, J=5.2 Hz, 1H), 8.39 (d, J=1.6 Hz, 2H), 8.31-8.22 (m, 2H), 8.14-8.01 (m, 3H), 7.93-7.78 (m, 3H), 7.65-7.63 (m, 1H), 4.25 (d, J=5.6 Hz, 2H), 3.49 (s, 1H), 1.19 (d, J=6.8 Hz, 6H) ppm.

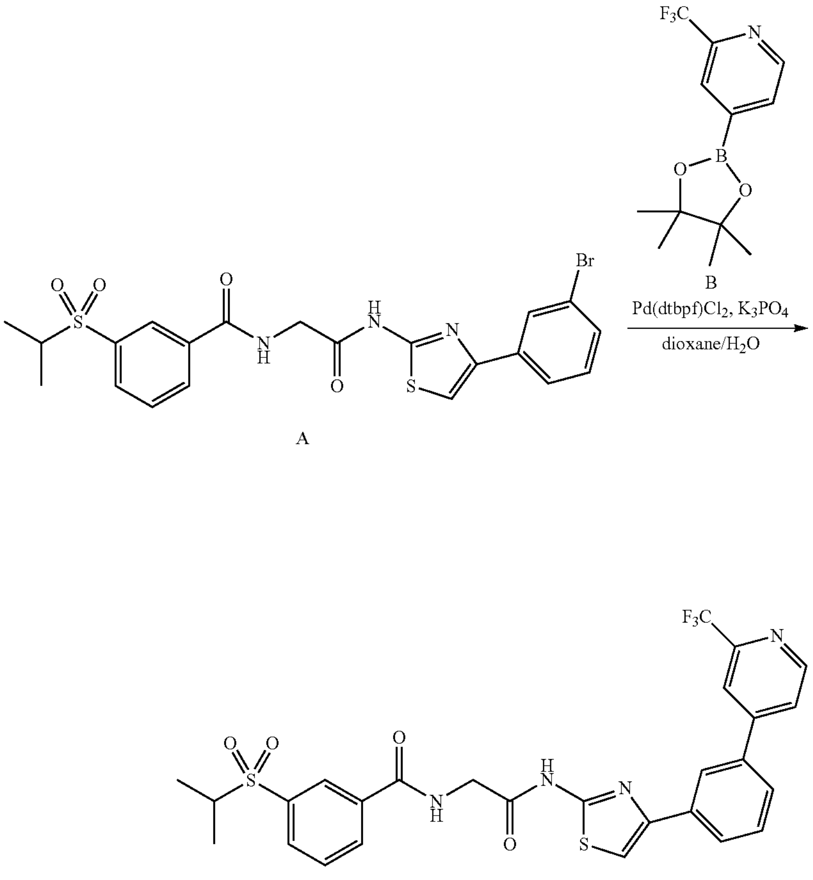

A

B

Compound 19

Example 25. Preparation of 3-(isopropylsulfonyl)-5-methyl-N-(2-oxo-2-((4-(3-(pyridin-4-yl)phenyl)thiazol-2-yl)amino)ethyl)benzamide (Compound 20)

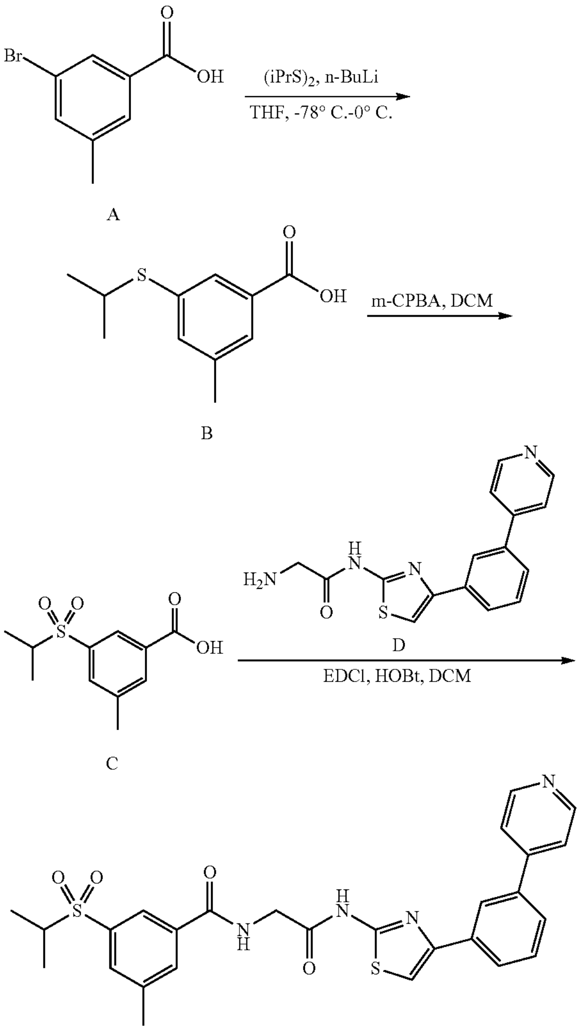

Compound 20

Step 1: Preparation of 3-isopropylsulfanyl-5-methyl-benzoic acid (Intermediate B)

B

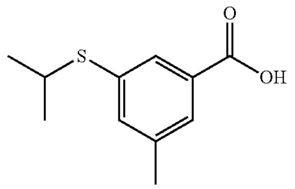

To a mixture of 3-bromo-5-methyl-benzoic acid (1 g, 4.65 mmol) in THE (25 mL) was added n-BμLi (2.5 M, 4.09 mL) dropwise at −78° C. under $N_2$. The mixture was stirred at −78° C. for 30 min, then 2-(isopropyldisulfanyl)propane (698.95 mg, 4.65 mmol, 741.20 μL) was added. The mixture was stirred at 25° C. for 1 hour. The mixture was quenched with aqueous $NH_4Cl$ (100 mL) and extracted with ethyl acetate (50 mL×2). The combined organic phase was washed with brine (50 mL×1), dried with anhydrous $Na_2SO_4$, filtered and concentrated in vacuum to give Intermediate B (800 mg, 3.80 mmol, 81.81% yield) as light yellow oil. LCMS (ESI) m/z $[M+H]^+$=211.1.

Step 2: Preparation of 3-isopropylsulfonyl-5-methyl-benzoic acid (Intermediate C)

C

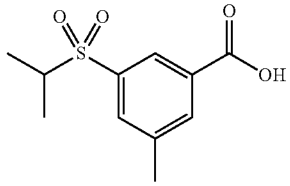

To a mixture of Intermediate B (800 mg, 3.80 mmol) in DCM (10 mL) was added m-CPBA (1.93 g, 9.51 mmol, 85% purity) in one portion at 10° C. The mixture was stirred at 25° C. for 1 hours. The reaction solution was poured into H2O (20 mL) and extracted with DCM (20 mL×2). The combined organic phase was washed with brine (10 mL×1), dried with anhydrous $Na_2SO_4$, filtered and concentrated in vacuum. The residue was purified by prep-TLC (DCM/MeOH=20/1) to give Intermediate C (100 mg, 412.73 μmol, 10.85% yield) as a white solid. LCMS (ESI) m/z $[M+H]^+$=243.1. $^1$H NMR (400 MHz, MEOD) δ=8.16 (s, 1H), 8.07 (s, 1H), 7.81 (s, 1H), 3.27-3.20 (m, 1H), 2.42 (s, 3H), 1.16 (d, J=6.8 Hz, 6H) ppm.

Step 3: Preparation of 3-(isopropylsulfonyl)-5-methyl-N-(2-oxo-2-((4-(3-(pyridin-4-yl)phenyl)thiazol-2-yl)amino)ethyl)benzamide (Compound 20)

Compound 20

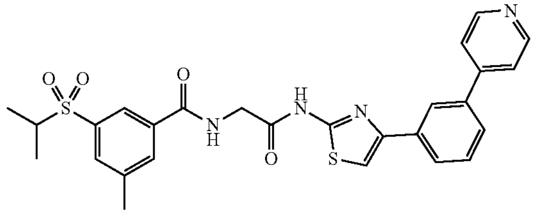

To a solution of Intermediate C (40 mg, 165.09 μmol), HOBt (33.46 mg, 247.64 μmol), EDCl (47.47 mg, 247.64 μmol) and 2-amino-N-[4-[3-(4-pyridyl)phenyl]thiazol-2-yl]acetamide (prepared according to the method in Example 3) (57.26 mg, 165.09 μmol, HCl) in DMF (2 mL) was added DIEA (106.68 mg, 825.45 μmol, 143.78 μL). Then the mixture was stirred at 25° C. for 12 hr. To the reaction mixture was added water (5 mL) and a precipitate was formed. The crude product was filtered and the solid was purified by reversed-phase column (FA condition) and lyophilized to give Compound 20 (16.7 mg, 28.76 μmol, 17.42% yield, 100% purity, FA) as a white solid. LCMS (ESI) m/z $[M+H]^+$=535.2. $^1$H NMR (400 MHz, DMSO-$d_6$) δ=8.65-8.64 (m, 2H), 8.27 (s, 1H), 8.13 (s, 1H), 8.06 (s, 1H), 8.00 (d, J=7.6 Hz, 1H), 7.85 (s, 1H), 7.78 (s, 1H), 7.76-7.60 (m, 4H), 4.20 (s, 2H), 3.49-3.41 (m, 1H), 2.49 (s, 3H), 1.17 (d, J=6.8 Hz, 6H) ppm.

Example 26. Preparation of N-(2-((4-(3',5'-dicyano-[1,1'-biphenyl]-3-yl)thiazol-2-yl)amino)-2-oxo-ethyl)-3-(isopropylsulfonyl)benzamide (Compound 21)

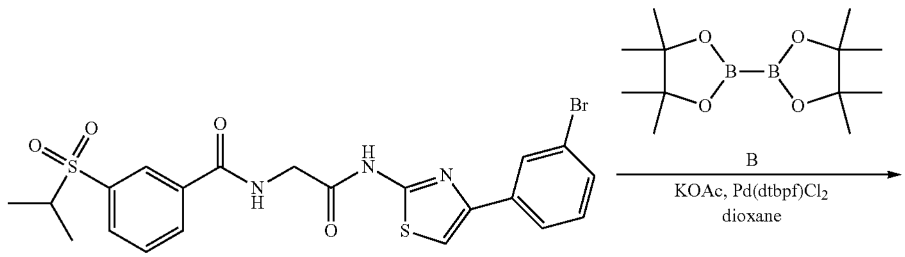

A

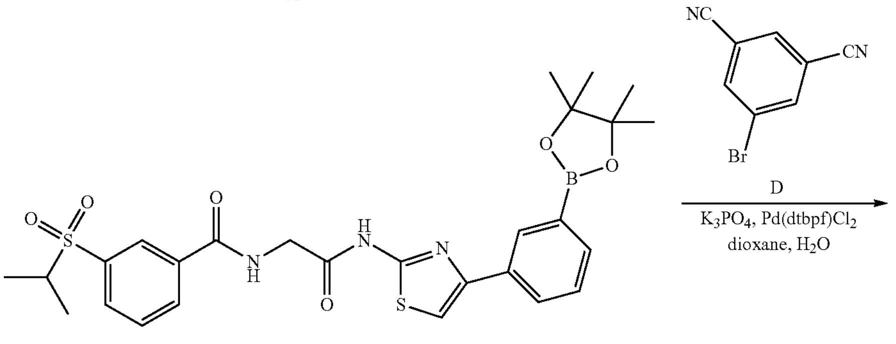

C

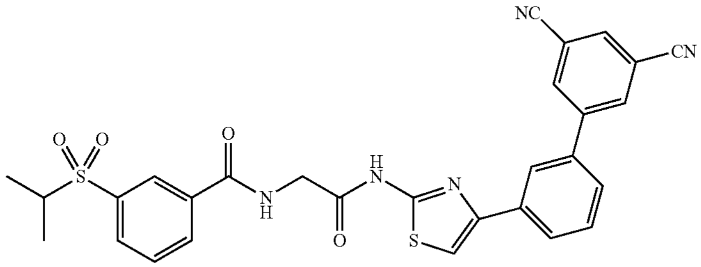

Compound 21

Step 1: Preparation of 3-isopropylsulfonyl-N-[2-oxo-2-[[4-[3-(4,4,5,5-tetramethyl-1,3,2-dioxaborolan-2-yl)phenyl]thiazol-2-yl]amino]ethyl]benzamide (Intermediate C)

C

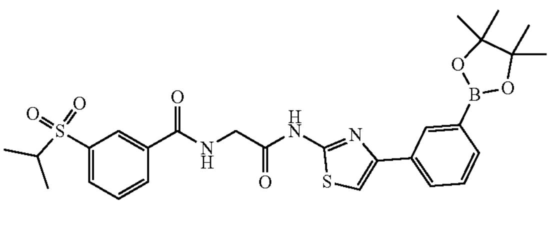

To a solution of N-[2-[[4-(3-bromophenyl)thiazol-2-yl]amino]-2-oxo-ethyl]-3-isopropylsulfonyl-benzamide (prepared according to the method in Example 23) (1.4 g, 2.68 mmol), 4,4,5,5-tetramethyl-2-(4,4,5,5-tetramethyl-1,3,2-dioxaborolan-2-yl)-1,3,2-dioxaborolane (2.04 g, 8.04 mmol) and Pd(dppf)$Cl_2$ (196.08 mg, 267.98 μmol) in dioxane (14 mL) was added KOAc (788.99 mg, 8.04 mmol), the mixture was stirred at 80° C. for 1 hr. The reaction mixture was concentrated under reduced pressure to give a residue. The residue was purified by column chromatography ($SiO_2$, Petroleum ether/Ethyl acetate=1/1 to 4/1) and concentrated under reduced pressure to give Intermediate C (1.2 g, 2.04 mmol, 76.27% yield, 97% purity) as a pink solid. LCMS (ESI) m/z=$[M+H]^+$=570.1. $^1H$ NMR (400 MHz, DMSO-$d_6$) δ=12.56 (s, 1H), 9.33-9.31 (m, 1H), 8.39 (s, 1H), 8.31-8.27 (m, 2H), 8.11-8.02 (m, 2H), 7.84-7.82 (m, 1H), 7.69 (s, 1H), 7.63-7.61 (m, 1H), 7.45-7.42 (m, 1H), 4.24 (d, J=5.2 Hz, 2H), 3.54-3.47 (m, 1H), 1.32 (s, 12H), 1.19 (d, J=6.8 Hz, 6H) ppm.

Step 2: Preparation of N-(2-((4-(3',5'-dicyano-[1,1'-biphenyl]-3-yl)thiazol-2-yl)amino)-2-oxoethyl)-3-(isopropylsulfonyl)benzamide (Compound 21)

Compound 21

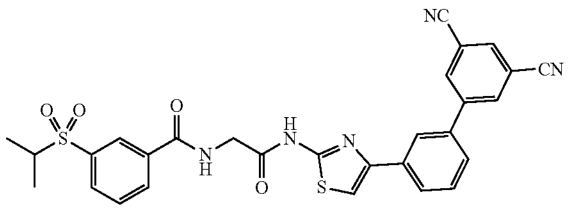

To a solution of Intermediate C (50 mg, 87.80 μmol) and 5-bromobenzene-1,3-dicarbonitrile (27.26 mg, 131.69 μmol) in dioxane (1 mL) and $H_2O$ (0.1 mL) were added $K_3PO_4$ (55.91 mg, 263.39 μmol) and ditertbutyl(cyclopentyl)phosphane;dichloropalladium;iron (5.72 mg, 8.78 μmol). The mixture was stirred at 75° C. for 12 hours under $N_2$. The reaction mixture was partitioned between water (10 mL) and ethyl acetate (5 mL×3). The organic phase was concentrated under reduced pressure. The residue was purified by column chromatography ($SiO_2$, Petroleum ether/Ethyl acetate=10/1 to 1/2) to give a crude product, which was purified by prep-HPLC (column: Phenomenex Synergi C18 150×25×10 um; mobile phase: [water (0.225% FA)-ACN]; B %: 50%-80%, 9 min) and lyophilized to give Compound 21 (10.02 mg, 17.41 μmol, 19.83% yield, 98.998% purity) as a white solid. LCMS (ESI) m/z=$[M+H]^+$=570.3. $^1H$ NMR (400 MHz, DMSO-$d_6$) δ=12.66-12.35 (m, 1H), 9.37-9.18 (m, 1H), 8.63 (d, J=1.2 Hz, 2H), 8.48 (s, 1H), 8.37 (d, J=19.2 Hz, 2H), 8.28 (d, J=7.6 Hz, 1H), 8.04 (m, 2H), 7.89-7.79 (m, 3H), 7.62-7.60 (m, 1H), 4.25 (d, J=5.2 Hz, 2H), 3.52-3.50 (m, 1H), 1.20 (d, J=6.8 Hz, 6H) ppm.

Example 27. Preparation of N-(2-((4-(3-(2-amino-pyridin-4-yl)phenyl)thiazol-2-yl)amino)-2-oxo-ethyl)-3-(isopropylsulfonyl)benzamide (Compound 22)

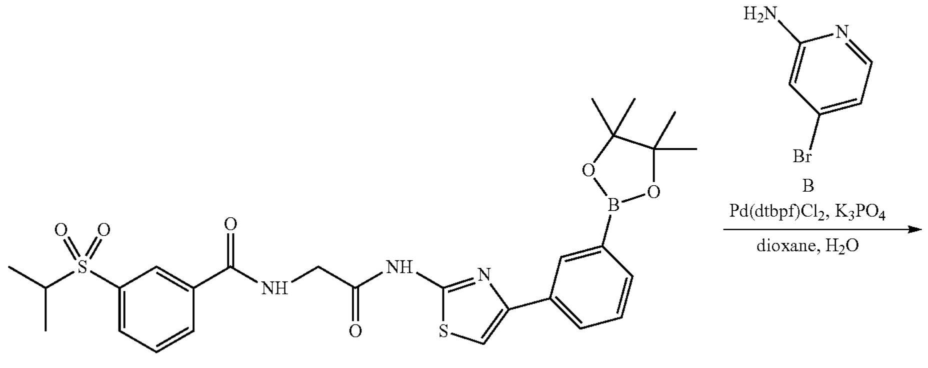

A

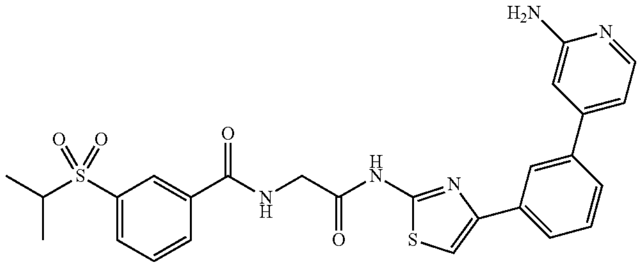

Compound 22

To a solution of 4-bromopyridin-2-amine (25 mg, 144.50 μmol), 3-isopropylsulfonyl-N-[2-oxo-2-[[4-[3-(4,4,5,5-tetramethyl-1,3,2-dioxaborolan-2-yl)phenyl]thiazol-2-yl]amino]ethyl]benzamide (prepared according to the method in Example 26) (82.29 mg, 144.50 μmol), $K_3PO_4$ (122.69 mg, 578.00 μmol) in dioxane (4 mL) and $H_2O$ (0.8 mL) was added ditertbutyl(cyclopentyl) phosphane;dichloropalladium;iron (4.71 mg, 7.22 μmol), the mixture was degassed and purged with $N_2$ for 3 times, and then the mixture was stirred at 80° C. for 2 hr under $N_2$ atmosphere. The reaction mixture was filtered with column chromatography ($SiO_2$, Ethyl acetate), the organic phase was concentrated under vacuum to give residue. The residue was re-purified by pre-HPLC (TFA condition, column: Phenomenex luna C18 150×25 10 u; mobile phase: [water (0.1% TFA)-ACN]; B %: 15%-45%, 10 min) and lyophilized to give Compound 22 (49.42 mg, 73.79 μmol, 51.06% yield, 97% purity, TFA) as an off-white solid. LCMS (ESI) m/z $[M+H]^+$=536.1. $^1H$ NMR (400 MHz, DMSO-$d_6$) δ=12.54 (s, 1H), 9.33-9.30 (m, 1H), 8.38-8.26 (m, 3H), 8.11-8.04 (m, 5H), 7.85-7.80 (m, 2H), 7.73-7.63 (m, 2H), 7.28-7.25 (m, 2H), 4.24 (d, J=5.6 Hz, 2H), 3.52-3.48 (m, 1H), 1.18 (d, J=6.8 Hz, 6H) ppm.

Example 28. Preparation of N-(2-((4-(3'-cyano-5'-(hydroxymethyl)-[1,1'-biphenyl]-3-yl)thiazol-2-yl)amino)-2-oxoethyl)-3-(isopropylsulfonyl)benzamide (Compound 23)

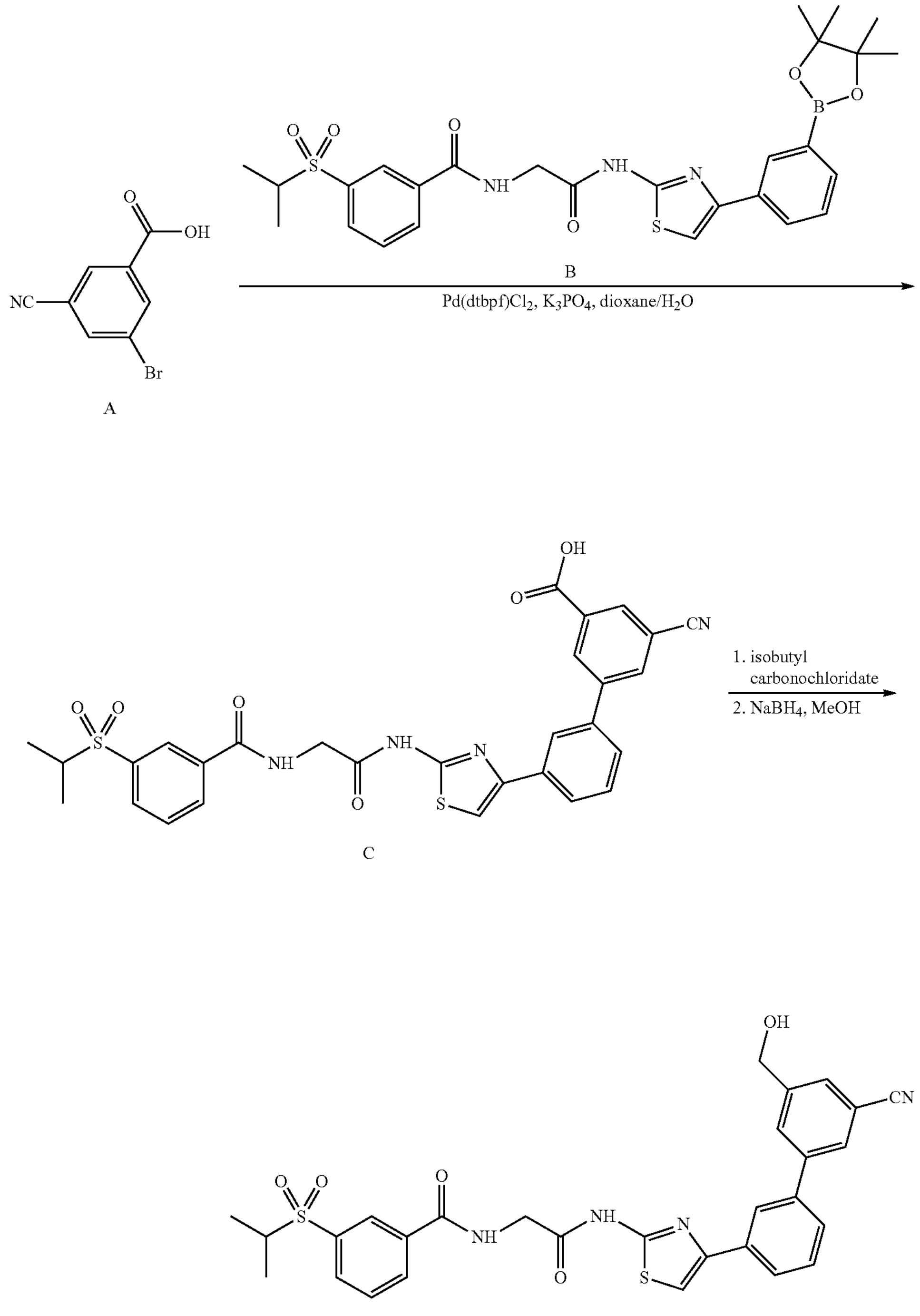

A

B

C

Compound 23

Step 1: Preparation of 5-cyano-3'-(2-(2-(3-(isopropylsulfonyl)benzamido)acetamido)thiazol-4-yl)-[1,1'-biphenyl]-3-carboxylic acid (Intermediate C)

C

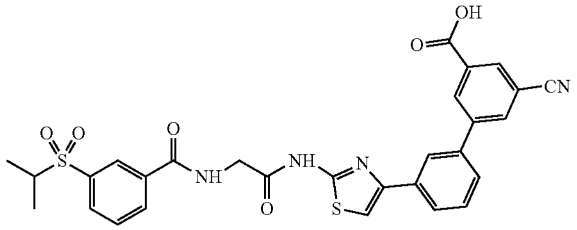

To a solution of 3-isopropylsulfonyl-N-[2-oxo-2-[[4-[3-(4,4,5,5-tetramethyl-1,3,2-dioxaborolan-2-yl)phenyl]thiazol-2-yl]amino]ethyl]benzamide (prepared according to the method in Example 26) (125.98 mg, 221.21 μmol), 3-bromo-5-cyano-benzoic acid (50 mg, 221.21 μmol) and $K_3PO_4$ (140.87 mg, 663.64 μmol) in dioxane (0.8 mL) and $H_2O$ (0.2 mL) was added ditertbutyl(cyclopentyl)phosphane;dichloropalladium;iron (14.42 mg, 22.12 μmol) at 25° C. under $N_2$. The reaction mixture was stirred at 80° C. under $N_2$ for 16 hours. The reaction mixture was diluted with water (10 mL) and washed with EA (10 mL×3). The aqueous layers was added HCl (1 M) to adjust pH to 4, and then extracted with EA (10 mL×2), the combined organic layers were concentrated to give Intermediate C (100 mg, 162.42 μmol, 73.42% yield, 95.61% purity) as yellow solid. LCMS (ESI) m/z $[M+H]^+$=589.3. $^1H$ NMR (400 MHz, DMSO-$d_6$) δ=14.60-12.96 (m, 1H), 12.53 (s, 1H), 9.29-9.29 (m, 1H), 8.50 (d, J=4.4 Hz, 2H), 8.38 (s, 1H), 8.34-8.24 (m, 3H), 8.03-7.99 (m, 2H), 7.89-7.75 (m, 3H), 7.63-7.56 (m, 1H), 4.25 (d, J=5.2 Hz, 2H), 3.52-3.48 (m, 1H), 1.19 (d, J=6.4 Hz, 6H) ppm.

Step 2: Preparation of N-(2-((4-(3'-cyano-5'-(hydroxymethyl)-[1,1'-biphenyl]-3-yl)thiazol-2-yl)amino)-2-oxoethyl)-3-(isopropylsulfonyl)benzamide (Compound 23)

Compound 23

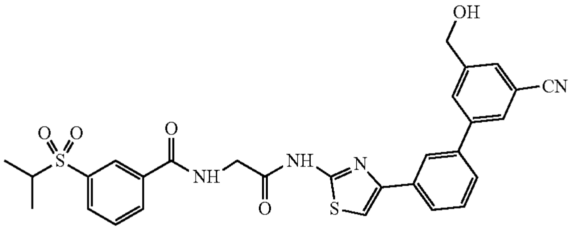

To a solution of Intermediate C (80 mg, 135.90 μmol) and $Et_3N$ (20.63 mg, 203.86 μmol, 28.37 μL) in THE (1 mL) was added isobutyl carbonochloridate (22.27 mg, 163.08 μmol, 21.42 μL) dropwise at 0° C. The reaction mixture was stirred at 25° C. for 1 hour. Then MeOH (0.2 mL), and $NaBH_4$ (46.27 mg, 1.22 mmol) was added in turn at 0° C. The reaction mixture was warmed to 25° C. and stirred at 25° C. for 1 hour. The reaction mixture was quenched with water (10 mL) and extracted with EA (10 mL×2), the combined organic layers was concentrated in vacuum. The residue was purified by flash silica gel chromatography (ISCO®; 20 g SepaFlash® Silica Flash Column, Eluent of 0~100% Ethylacetate/Petroleum ether gradient at 35 mL/min) and concentrated to give Compound 23 (49.36 mg, 85.89 μmol, 63.20% yield, 100% purity) as colorless oil. LCMS (ESI) m/z $[M+H]^+$=575.4. $^1H$ NMR (400 MHz, DMSO-$d_6$) δ=12.51 (br s, 1H), 9.29-9.27 (m, 1H), 8.39 (s, 1H), 8.30-8.24 (m, 2H), 8.10 (s, 1H), 8.08-7.94 (m, 3H), 7.86-7.79 (m, 2H), 7.76 (s, 1H), 7.71 (d, J=7.6 Hz, 1H), 7.60-7.54 (m, 1H), 5.50-5.48 (m, 1H), 4.65 (d, J=4.8 Hz, 2H), 4.25 (d, J=5.6 Hz, 2H), 3.50-3.45 (m, 1H), 1.19 (d, J=6.8 Hz, 6H) ppm.

Example 29. Preparation of N-(2-((4-(3'-cyano-[1,1'-biphenyl]-3-yl)thiazol-2-yl)amino)-2-oxoethyl)-3-(isopropylsulfonyl)benzamide (Compound 24)

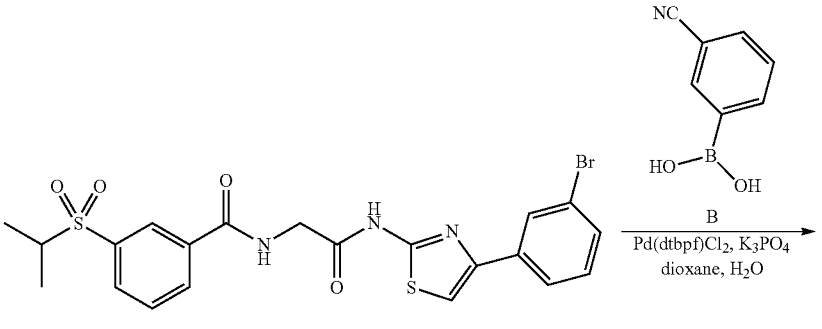

A

-continued

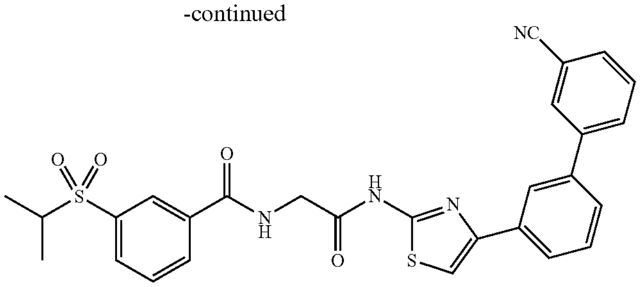

Compound 24

To a solution of N-[2-[[4-(3-bromophenyl)thiazol-2-yl]amino]-2-oxo-ethyl]-3-isopropylsulfonyl-benzamide (prepared according to the method in Example 23) (50 mg, 95.71 μmol) and (3-cyanophenyl)boronic acid (21.09 mg, 143.56 μmol) in dioxane (1 mL) and $H_2O$ (0.1 mL) was added $K_3PO_4$ (60.95 mg, 287.12 μmol) and ditert-butyl(cyclopentyl)phosphane;dichloropalladium;iron (6.24 mg, 9.57 μmol). The mixture was stirred at 80° C. for 12 hr under $N_2$. The reaction mixture was partitioned between water (10 mL) and ethyl acetate (30 mL). The organic phase was concentrated under reduced pressure. The residue was purified by reversed phase-HPLC (FA condition) and lyophilized to give the crude product, which was re-purified by prep-HPLC (column: Phenomenex luna C18 150×25×10 u; mobile phase: [water (0.1% TFA)-ACN]; B %: 44%-74%, 10 min) and lyophilized to give Compound 24 (11.80 mg, 20.73 μmol, 21.66% yield, 95.70% purity) as a white solid. LCMS (ESI) m/z=$[M+H]^+$=545.3. $^1H$ NMR (400 MHz, DMSO+$D_2O$) δ=8.36 (s, 1H), 8.28-8.24 (m, 2H), 8.20 (s, 1H), 8.07-8.05 (m, 2H), 7.97 (d, J=7.6 Hz, 1H), 7.87-7.80 (m, 3H), 7.73-7.68 (m, 2H), 7.60-7.55 (m, 1H), 4.24 (s, 2H), 3.49-3.44 (m, 1H), 1.18 (d, J=6.8 Hz, 6H) ppm.

Example 30. Preparation of 3-(isopropylsulfonyl)-N-(2-((4-(3-(2-(N-methylacetamido)pyridin-4-yl)phenyl)thiazol-2-yl)amino)-2-oxoethyl)benzamide (Compound 25)

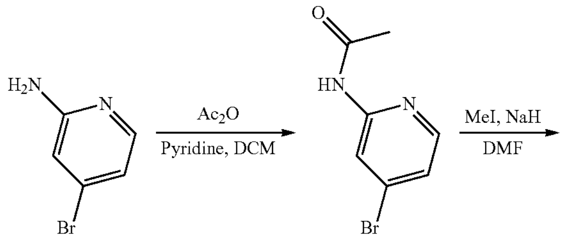

A B

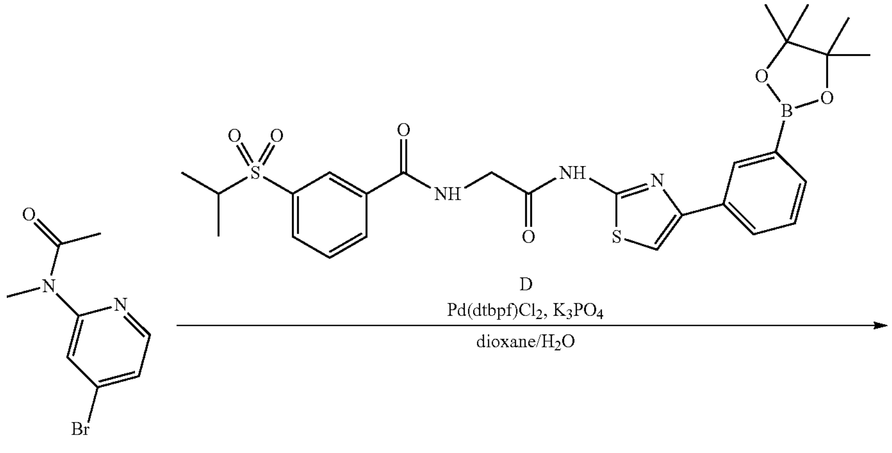

C

-continued

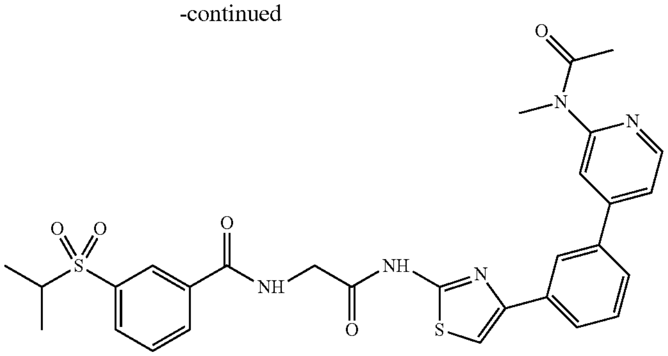

Compound 25

Step 1: Preparation of N-(4-bromopyridin-2-yl)acetamide (Intermediate B)

B

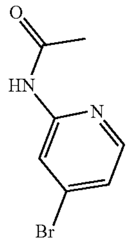

To a solution of 4-bromopyridin-2-amine (1 g, 5.78 mmol) in DCM (7.5 mL) and pyridine (7.5 mL) was added $Ac_2O$ (885.11 mg, 8.67 mmol, 812.03 μL), the mixture was stirred at 30° C. for 24 hr. The reaction mixture was concentrated under reduced pressure to give a residue. The residue was diluted with water (20 mL) and extracted with EtOAc (20 mL×3). The combined organic layers were washed with brine (40 mL), dried over $Na_2SO_4$, filtered and concentrated under reduced pressure to give Intermediate B (1 g, crude) as a light yellow solid, which was used to the next step without further purification. LCMS (ESI) m/z $[^{81}BrM+H]^+$=217.1.

Step 2: Preparation of N-(4-bromopyridin-2-yl)-N-methylacetamide (Intermediate C)

C

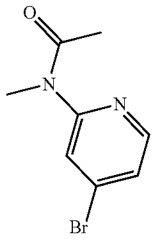

To a solution of Intermediate B (0.5 g, 2.33 mmol) in DMF (10 mL) was added NaH (139.49 mg, 3.49 mmol, 60% purity) under $N_2$ at 0° C. and stirred at 0° C. for 0.5 h, then MeI (495.03 mg, 3.49 mmol, 217.12 μL) was added to the mixture at 0° C., the mixture was warmed to 25° C. and stirred at 25° C. for 1 hr. The reaction mixture was quenched by addition water (20 mL), and extracted with EtOAc (20 mL×3). The combined organic layers were washed with brine (50 mL), dried over $Na_2SO_4$, filtered and concentrated under reduced pressure to give a residue. The residue was purified by column chromatography ($SiO_2$, Petroleum ether/Ethyl acetate=1/1) and concentrated under reduced pressure to give Intermediate C (300 mg, 1.30 mmol, 55.76% yield, 99% purity) as a light yellow oil. LCMS (ESI) m/z $[^{79}BrM+H]^+$=229.1.

Step 3: Preparation of 3-(isopropylsulfonyl)-N-(2-((4-(3-(2-(N-methylacetamido)pyridin-4-yl)phenyl)thiazol-2-yl)amino)-2-oxoethyl)benzamide (Compound 25)

Compound 25

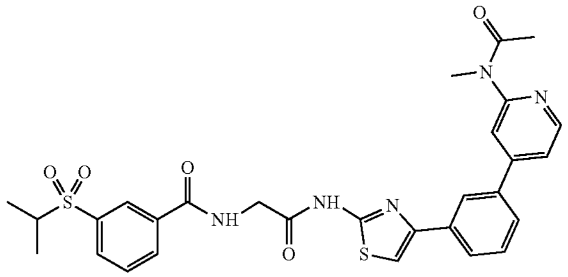

To a solution of Intermediate C (40 mg, 174.62 μmol), 3-isopropylsulfonyl-N-[2-oxo-2-[[4-[3-(4,4,5,5-tetramethyl-1,3,2-dioxaborolan-2-yl)phenyl]thiazol-2-yl]amino]ethyl]benzamide (prepared according to the method in Example 26) (99.44 mg, 174.62 μmol) and ditert-butyl(cyclopentyl)phosphane;dichloropalladium;iron (11.38 mg, 17.46 μmol) in dioxane (1.2 mL) and Water (0.3 mL) was added $K_3PO_4$ (111.20 mg, 523.85 μmol) under $N_2$, the mixture was stirred at 80° C. for 1 hr. The reaction mixture was diluted with water (5.0 mL) and extracted with EtOAc (10 mL×3). The combined organic layers were washed with brine (20 mL), dried over $Na_2SO_4$, filtered and concentrated under reduced pressure to give a residue. The residue was purified by reverse phase (FA) and lyophilized to give Compound 25 (38.77 mg, 60.30 μmol, 34.53% yield, 99.18% purity, FA) as an off-white solid. LCMS (ESI) m/z $[M+H]^+$=592.2. $^1$H NMR (400 MHz, DMSO-$d_6$) δ=12.52 (s, 1H), 9.31-9.28 (m, 1H), 8.57 (d, J=5.2 Hz, 1H), 8.38 (s, 1H), 8.32-8.27 (m, 2H), 8.07-8.02 (m, 2H), 7.89-7.78 (m, 4H), 7.69 (br d, J=4.8 Hz, 1H), 7.63-7.59 (m, 1H), 4.31-4.22 (m, 2H), 3.54-3.49 (m, 1H), 3.34 (br s, 3H), 2.08 (s, 3H), 1.19 (d, J=6.8 Hz, 6H) ppm.

Example 31. Preparation of N-(2-((4-(3-(2-(hydroxymethyl)pyridin-4-yl)phenyl)thiazol-2-yl)amino)-2-oxoethyl)-3-(isopropylsulfonyl)benzamide (Compound 26)

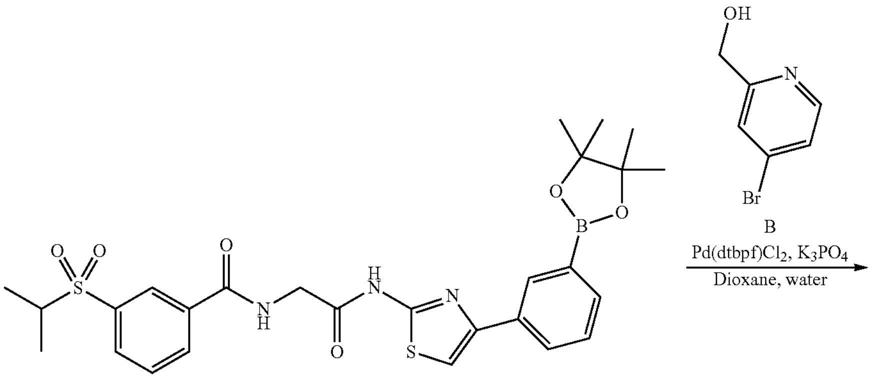

A

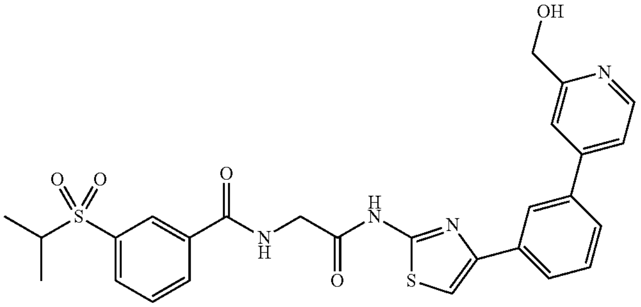

Compound 26

To a mixture of 3-isopropylsulfonyl-N-[2-oxo-2-[[4-[3-(4,4,5,5-tetramethyl-1,3,2-dioxaborolan-2-yl)phenyl]thiazol-2-yl]amino]ethyl]benzamide (prepared according to the method in Example 26) (50 mg, 87.80 μmol), (4-bromo-2-pyridyl)methanol (24.76 mg, 131.70 μmol) in Dioxane (2 mL) and Water (0.5 mL) were added ditert-butyl(cyclopentyl)phosphane;dichloropalladium;iron (11.44 mg, 17.56 μmol) and $K_3PO_4$ (55.91 mg, 263.40 μmol). The mixture was stirred at 100° C. for 2 hr. The mixture was poured into water (20 mL) then extracted with EA (5 mL×3). The combined organic layer was washed with water (10 mL×3) and brine (10 mL×2), then dried over $Na_2SO_4$, filtered and concentrated under vacuum. The residue was purified by Pre-HPLC (column: Luna C18 150×25 5 u; mobile phase: [water (0.075% TFA)-ACN]; B %: 15%-45%, 9 min) and lyophilized to give Compound 26 (20.18 mg, 29.06 μmol, 33.09% yield, 95.7% purity, TFA) as a white solid. LCMS (ESI) m/z $[M+H]^+$=551.1. $^1$H NMR (400 MHz, DMSO-$d_6$) δ=12.55 (s, 1H), 9.32-9.29 (m, 1H), 8.74 (d, J=5.6 Hz, 1H), 8.40 (d, J=5.6 Hz, 2H), 8.28 (d, J=7.6 Hz, 1H), 8.14-8.04 (m, 3H), 8.00 (d, J=3.6 Hz, 1H), 7.90-7.79 (m, 3H), 7.69-7.65 (m, 1H), 4.82 (s, 2H), 4.26 (d, J=5.6 Hz, 2H), 1.19 (d, J=6.8 Hz, 6H) ppm.

Example 32. Preparation of N-(2-((4-(3'-(hydroxymethyl)-5'-(trifluoromethyl)-[1,1'-biphenyl]-3-yl)thiazol-2-yl)amino)-2-oxoethyl)-3-(isopropylsulfonyl)benzamide (Compound 27)

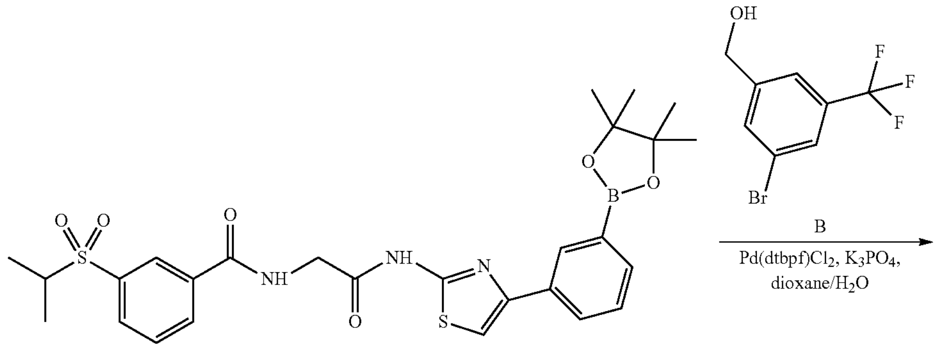

A

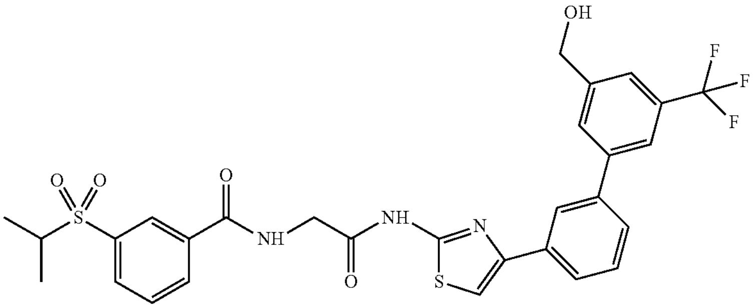

Compound 27

To a solution of 3-isopropylsulfonyl-N-[2-oxo-2-[[4-[3-(4,4,5,5-tetramethyl-1,3,2-dioxaborolan-2-yl)phenyl]thiazol-2-yl]amino]ethyl]benzamide (prepared according to the method in Example 26) (122.82 mg, 215.66 μmol), [3-bromo-5-(trifluoromethyl)phenyl]methanol (50.00 mg, 196.05 μmol) and $K_3PO_4$ (124.85 mg, 588.16 μmol) in dioxane (0.8 mL) and $H_2O$ (0.2 mL) was added ditertbutyl (cyclopentyl)phosphane;dichloropalladium;iron (12.78 mg, 19.61 μmol) at 25° C. under $N_2$. The reaction mixture was stirred at 80° C. for 16 hours. The reaction mixture was diluted with water (10 mL) and extracted with EA (10 mL×3), the combined organic layers was concentrated to afford a black brown oil. The oil was purified by flash silica gel chromatography (ISCO®; 12 g SepaFlash® Silica Flash Column, Eluent of 0~100% Ethylacetate/Petroleum ether gradient at 30 mL/min), concentrated in vacuum to give Compound 27 (34.05 mg, 51.36 μmol, 26.20% yield, 93.17% purity) as a white solid. LCMS (ESI) m/z $[M+H]^+$ =618.0. $^1H$ NMR (400 MHz, DMSO-$d_6$) δ=12.51 (s, 1H), 9.29-9.28 (m, 1H), 8.38 (s, 1H), 8.30-8.23 (m, 2H), 8.05 (d, J=7.8 Hz, 1H), 8.00-7.94 (m, 2H), 7.89 (s, 1H), 7.86-7.79 (m, 2H), 7.73-7.67 (m, 2H), 7.61-7.54 (m, 1H), 5.49-5.48 (m, 1H), 4.69 (d, J=5.6 Hz, 2H), 4.25 (d, J=5.6 Hz, 2H), 3.50-3.46 (m, 1H), 1.17 (d, J=6.8 Hz, 6H) ppm.

Example 33. Preparation of N-(2-((4-(3'-chloro-[1, 1'-biphenyl]-3-yl)thiazol-2-yl)amino)-2-oxoethyl)-3-(isopropylsulfonyl)benzamide (Compound 28)

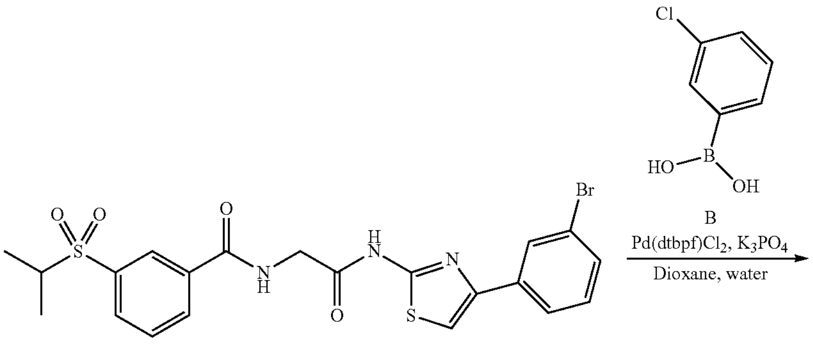

A

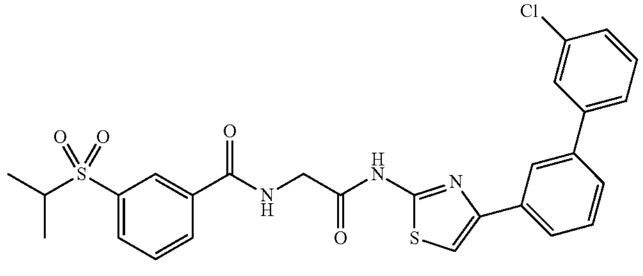

Compound 28

To a solution of N-[2-[[4-(3-bromophenyl)thiazol-2-yl]amino]-2-oxo-ethyl]-3-isopropylsulfonyl-benzamide (prepared according to the method in Example 23) (50 mg, 95.71 μmol) and (3-chlorophenyl)boronic acid (29.93 mg, 191.41 μmol) in dioxane (1 mL) and $H_2O$ (0.1 mL) was added $K_3PO_4$ (60.95 mg, 287.12 μmol) and ditert-butyl(cyclopentyl)phosphane;dichloropalladium;iron (6.24 mg, 9.57 μmol) under $N_2$. Then the reaction mixture was heated to 80° C. and stirred at 80° C. for 12 hrs. To the reaction mixture were added water (10 mL×1) and EtOAc (15 mL) and stirred for 10 min, the organic layer was concentrated under vacuum. The residue was purified by flash silica gel chromatography (ISCO®; 10 g SepaFlash® Silica Flash Column, Eluent of 0~55% Ethylacetate/Petroleum ether gradient at 40 mL/min) to give a crude product, which was re-purified by reverse flash (0.1% FA condition) and lyophilized to give Compound 28 (8.29 mg, 14.95 μmol, 15.62% yield, 99.9% purity) as a white solid. LCMS (ESI) m/z $[M+H]^+$=554.3. $^1$H NMR (400 MHz, CHLOROFORM-d) δ=10.88 (br s, 1H), 8.41 (s, 1H), 8.29 (d, J=8.0 Hz, 1H), 8.07-8.02 (m, 2H), 7.85-7.79 (m, 1H), 7.82 (d, J=7.2 Hz, 1H), 7.75 (m, 1H), 7.78-7.72 (m, 1H), 7.66-7.61 (m, 1H), 7.67-7.61 (m, 1H), 7.54 (m, 2H), 7.59-7.49 (m, 1H), 7.44-7.36 (m, 2H), 7.34 (s, 1H), 4.52 (d, J=5.6 Hz, 2H), 3.30 (m, 1H), 1.35 (d, J=7.2 Hz, 6H) ppm.

Example 34. Preparation of 3-(isopropylsulfonyl)-N-(2-((4-(3-(2-methoxypyridin-4-yl)phenyl)thiazol-2-yl)amino)-2-oxoethyl)benzamide (Compound 29)

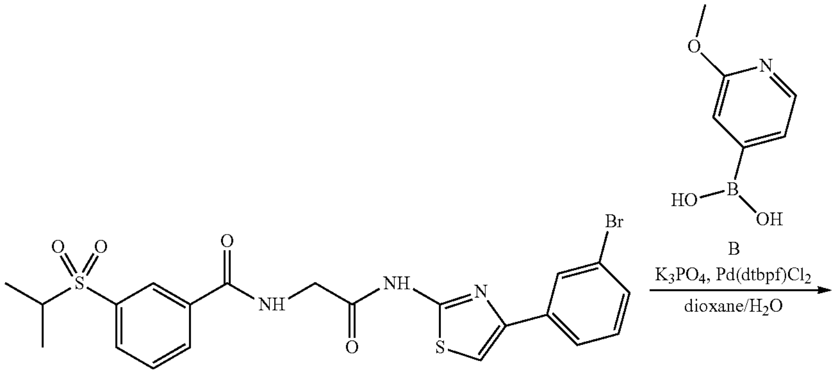

A

-continued

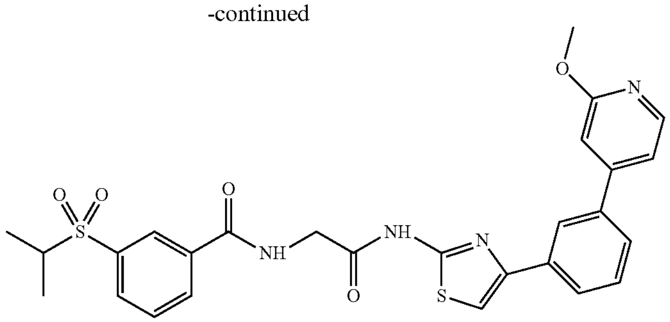

Compound 29

To a solution of N-[2-[[4-(3-bromophenyl)thiazol-2-yl] amino]-2-oxo-ethyl]-3-isopropylsulfonyl-benzamide (prepared according to the method in Example 23) (50 mg, 95.71 μmol), (2-methoxy-4-pyridyl)boronic acid (29.28 mg, 191.41 μmol), $K_3PO_4$ (60.95 mg, 287.12 μmol) in dioxane (1 mL) and $H_2O$ (0.2 mL) was added ditert-butyl(cyclopentyl) phosphane;dichloropalladium;iron (6.24 mg, 9.57 μmol). Then the mixture was stirred at 70° C. for 0.5 hr under $N_2$. The reaction mixture was concentrated to get the crude product. The crude product was purified by reverse phase column (FA) and lyophilized to give Compound 29 (24.15 mg, 40.31 μmol, 42.12% yield, 99.6% purity, FA) as a white solid. LCMS (ESI) m/z $[M+H]^+$=551.2. $^1H$ NMR (400 MHz, DMSO-$d_6$) δ=12.53 (br s, 1H), 9.32 (s, 1H), 8.39 (s, 1H), 8.29 (d, J=6.4 Hz, 3H), 8.11-7.97 (m, 2H), 7.90-7.80 (m, 2H), 7.74 (d, J=7.6 Hz, 1H), 7.58 (m, 1H), 7.37 (d, J=4.8 Hz, 1H), 7.17 (s, 1H), 4.25 (d, J=5.2 Hz, 2H), 3.92 (s, 3H), 3.57-3.47 (m, 1H), 1.19 (d, J=6.4 Hz, 6H) ppm.

Example 35. Preparation of N-(2-((4-(3',5'-dichloro-[1,1'-biphenyl]-3-yl)thiazol-2-yl)amino)-2-oxo-ethyl)-3-(isopropylsulfonyl)benzamide (Compound 30)

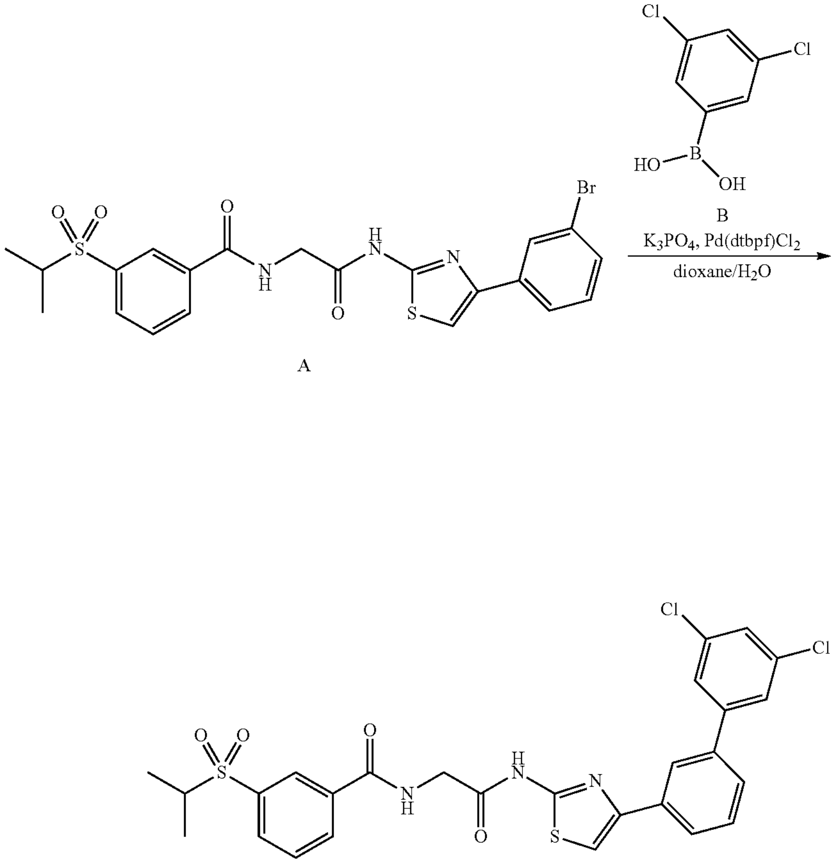

Compound 30

To a solution of N-[2-[[4-(3-bromophenyl)thiazol-2-yl]amino]-2-oxo-ethyl]-3-isopropylsulfonyl-benzamide (prepared according to the method in Example 23) (50 mg, 95.71 μmol), (3,5-dichlorophenyl)boronic acid (36.53 mg, 191.41 μmol), $K_3PO_4$ (60.95 mg, 287.12 μmol) in dioxane (1 mL) and $H_2O$ (0.2 mL) was added ditert-butyl(cyclopentyl)phosphane;dichloropalladium;iron (6.24 mg, 9.57 μmol). Then the mixture was stirred at 70° C. for 0.5 hr under $N_2$. The reaction mixture was concentrated to get the crude product. The crude product was purified by reverse phase column (FA) and lyophilized to give Compound 30 (10.27 mg, 17.45 μmol, 18.23% yield, 100% purity) as a white solid. LCMS (ESI) m/z [$^{35}$ClM+H]$^+$=588.1. $^1$H NMR (400 MHz, DMSO-$d_6$) δ=12.52 (br s, 1H), 9.35 (s, 1H), 8.41 (s, 1H), 8.33-8.25 (m, 2H), 8.08 (d, J=7.6 Hz, 1H), 8.01 (d, J=7.6 Hz, 1H), 7.90 (s, 1H), 7.88-7.81 (m 3H), 7.74 (d, J=7.6 Hz, 1H), 7.67 (s, 1H), 7.58 (m, 1H), 4.27 (d, J=5.6 Hz, 2H), 3.53 (m, 1H), 1.21 (d, J=6.8 Hz, 6H) ppm.

Example 36. Preparation of N-(2-((4-(3'-(aminomethyl)-[1,1'-biphenyl]-3-yl)thiazol-2-yl)amino)-2-oxoethyl)-3-(isopropylsulfonyl)benzamide (Compound 31)

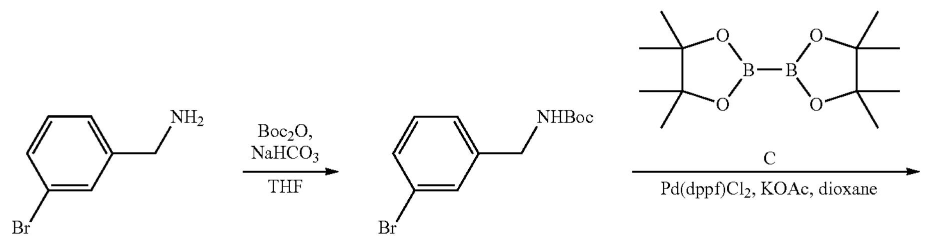

A B

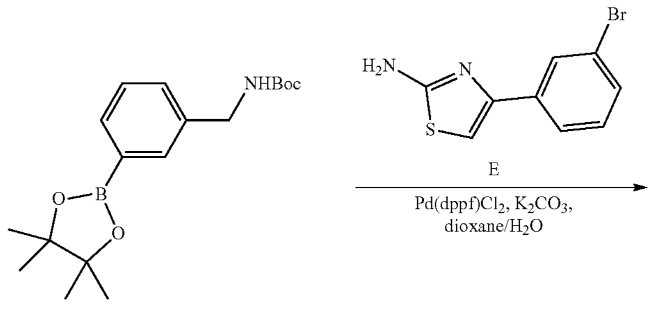

D

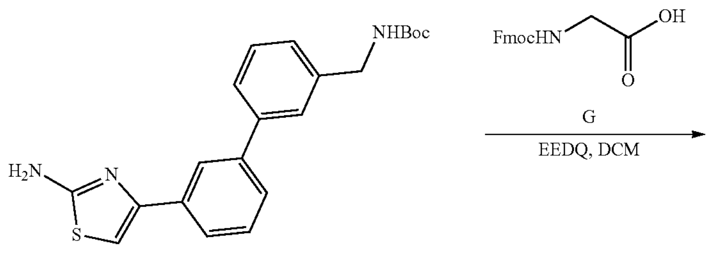

F

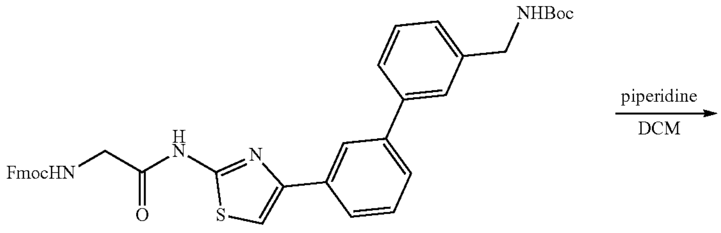

H

-continued

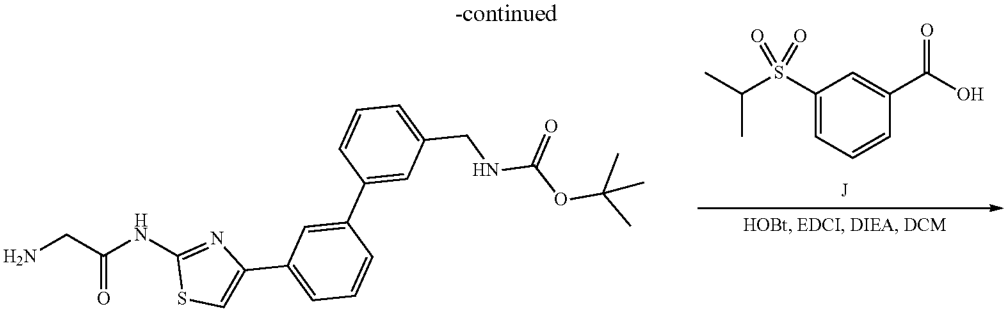

I

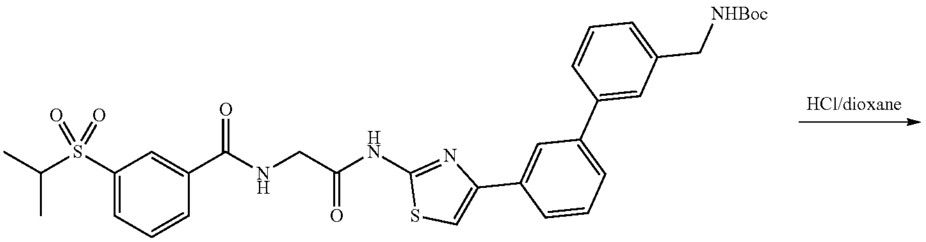

K

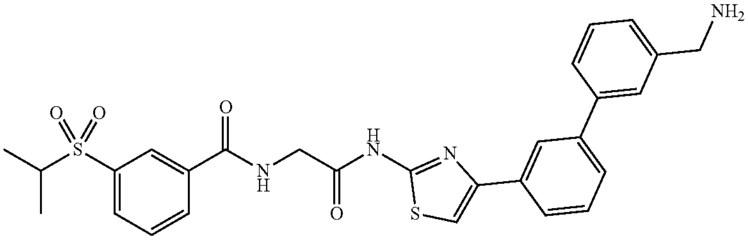

Compound 31

Step 1: Preparation of tert-butyl N-[(3-bromophenyl)methyl]carbamate (Intermediate B)

B

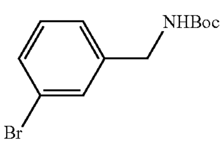

To a solution of (3-bromophenyl)methanamine (50 g, 268.75 mmol) in THE (500 mL) was added $NaHCO_3$ (45.15 g, 537.49 mmol) and $Boc_2O$ (64.52 g, 295.62 mmol), the mixture was stirred at 30° C. for 16 hr. The reaction mixture was filtered and the filtrate was concentrated to give Intermediate B (76 g, crude) as colorless oil, which was used for next step directly. LCMS (ESI) m/z=$[^{81}BrM+H-56]^+$=232.1.

Step 2: Preparation of tert-butyl N-[[3-(4,4,5,5-tetramethyl-1,3,2-dioxaborolan-2-yl)phenyl]methyl] carbamate (Intermediate D)

D

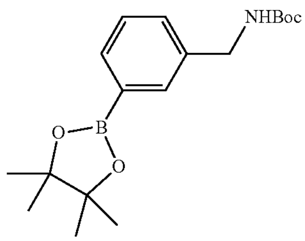

To a solution of Intermediate B (76 g, 265.58 mmol) and 4,4,5,5-tetramethyl-2-(4,4,5,5-tetramethyl-1,3,2-dioxaborolan-2-yl)-1,3,2-dioxaborolane (80.93 g, 318.70 mmol) in dioxane (800 mL) was added KOAc (78.19 g, 796.75 mmol) and $Pd(dppf)Cl_2$ (19.43 g, 26.56 mmol) under $N_2$, the mixture was stirred at 80° C. for 2 hr. The reaction mixture was poured into water (1000 mL), the solution was extracted with EA (1000 mL×3), the combined organic layers were washed with brine (2000 mL), dried over $Na_2SO_4$ and filtered. The filtrate was concentrated in vacuum to give Intermediate D (88 g, crude) as black oil, which was used for the next step directly. LCMS (ESI) m/z=$[M+H-56]^+$=278.3.

Step 3: Preparation of tert-butyl N-[[3-[3-(2-aminothiazol-4-yl)phenyl]phenyl]methyl]carbamate (Intermediate F)

F

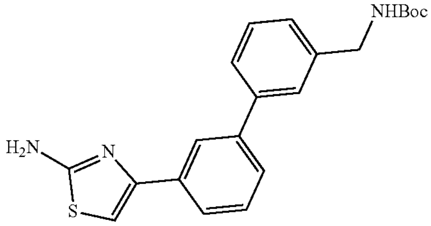

To a solution of Intermediate D (78.37 g, 235.17 mmol) and 4-(3-bromophenyl)thiazol-2-amine (40 g, 156.78 mmol) in dioxane (900 mL) and H2O (90 mL) was added $K_2CO_3$ (65.00 g, 470.34 mmol) and Pd(dppf)$Cl_2$ (5.74 g, 7.84 mmol), the mixture was stirred at 80° C. for 2 hr. The reaction mixture was concentrated to give a residue. The residue was purified by column chromatography ($SiO_2$, Petroleum ether/Ethyl acetate=5:1-3:1). The solution was concentrated in vacuum to give Intermediate F (26 g, 67.74 mmol, 43.21% yield) as a brown solid. $^1H$ NMR (400 MHz, DMSO-$d_6$) δ=8.06 (s, 1H), 7.79 (d, J=8.0 Hz, 1H), 7.55-7.45 (m, 6H), 7.25 (d, J=8.0 Hz, 1H), 7.11-7.10 (m, 3H), 4.22 (br d, J=5.6 Hz, 2H), 1.40 (s, 9H) ppm. LCMS (ESI) m/z=$[M+H-56]^+$=382.3.

Step 4: Preparation of 9H-fluoren-9-ylmethyl N-[2-[[4-[3-[3-[(tert-butoxycarbonylamino)methyl]phenyl]phenyl]thiazol-2-yl]amino]-2-oxo-ethyl]carbamate (Intermediate H)

H

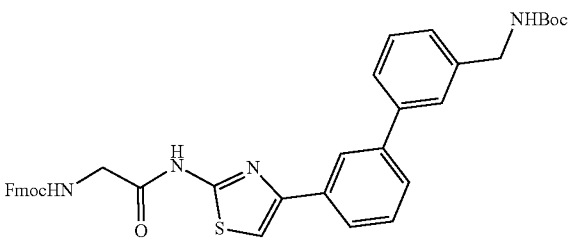

To a solution of Intermediate F (1 g, 2.62 mmol) and 2-(9H-fluoren-9-ylmethoxycarbonylamino)acetic acid (935.19 mg, 3.15 mmol) in DCM (10 mL) was added HATU (1.20 g, 3.15 mmol) and DIEA (1.69 g, 13.11 mmol, 2.28 mL), the mixture was stirred at 30° C. for 16 hr. The reaction mixture was poured into water (10 mL), extracted with EA (10 mL×3), the combined organic layers were washed with brine (20 mL), dried over $Na_2SO_4$ and filtered. The filtrate was concentrated in vacuum to give Intermediate H (1.7 g, crude) as yellow oil, which was used for next step directly. LCMS (ESI) m/z=$[M+H-56]^+$=605.1.

Step 5: Preparation of tert-butyl N-[[3-[3-[2-[(2-aminoacetyl)amino]thiazol-4-yl]phenyl]phenyl]methyl]carbamate (Intermediate I)

I

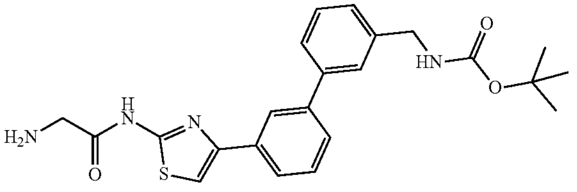

A mixture of Intermediate H (1 g, 1.51 mmol) in DCM (10 mL) was added piperidine (2 mL), the mixture was stirred at 30° C. for 1 hr. The reaction mixture was concentrated to give a residue. The crude product was purified by reversed-phase HPLC (0.1% FA condition). The elute was adjusted to pH=9 with $NaHCO_3$, extracted with EA (100 mL×3), the combined organic layer was washed with brine (200 mL), dried over $Na_2SO_4$ and filtered. The filtrate was concentrated to give Intermediate I (200 mg, 439.87 μmol, 29.07% yield) as yellow oil. LCMS (ESI) m/z=$[M+H-56]^+$=439.3.

Step 6: Preparation of tert-butyl ((3'-(2-(2-(3-(isopropylsulfonyl)benzamido)acetamido)thiazol-4-yl)-[1,1'-biphenyl]-3-yl)methyl)carbamate (Intermediate K)

K

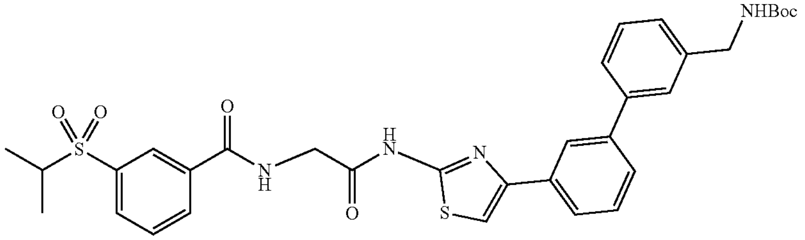

To a solution of Intermediate I (200 mg, 456.06 μmol) and 3-isopropylsulfonylbenzoic acid (156.15 mg, 684.08 μmol) in DCM (4 mL) was added EDCl (104.91 mg, 547.27 μmol), HOBt (73.95 mg, 547.27 μmol) and DIEA (294.71 mg, 2.28 mmol, 397.18 μL), the mixture was stirred at 30° C. for 16 hr.

The reaction mixture was poured into water (5 mL), the solution was extracted with EA (5 mL×3), the combined organic layers were washed with brine (20 mL), dried over $Na_2SO_4$ and filtered. The filtrate was concentrated to give Intermediate K (290 mg, 446.99 μmol, 98.01% yield) as yellow oil. LCMS (ESI) m/z=$[M+H-56]^+$=593.3.

Step 7: Preparation of N-(2-((4-(3'-(aminomethyl)-[1,1'-biphenyl]-3-yl)thiazol-2-yl)amino)-2-oxoethyl)-3-(isopropylsulfonyl)benzamide (Compound 31)

Compound 31

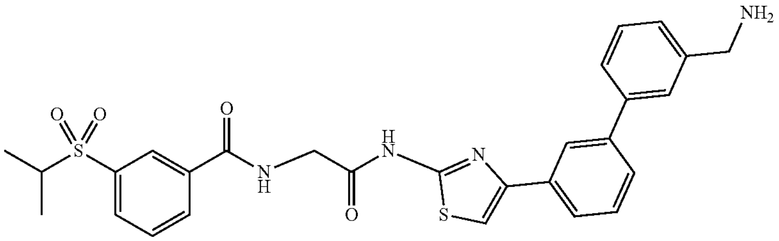

A mixture of Intermediate K (290 mg, 446.99 μmol) in HCl/dioxane (3 mL) was stirred at 30° C. for 1 hr. The reaction mixture was concentrated to give a residue (250 mg). The residue (50 mg) was purified by Prep-HPLC (column: Xtimate C18 150×25 mm×5 um; mobile phase: [water (0.05% ammonia hydroxide v/v)-ACN]; B %: 32%-62%, 10 min), the solution was lyophilized to give Compound 31 (10.45 mg, 19.05 μmol, 4.26% yield) as a white solid. LCMS (ESI) m/z=$[M+H]^+$=549.2. $^1$H NMR (400 MHz, DMSO) δ=9.33-9.26 (m, 1H), 8.38 (s, 1H), 8.28 (d, J=8.0 Hz, 1H), 8.20 (s, 1H), 8.04 (s, 1H), 7.90 (br d, J=7.6 Hz, 1H), 7.84-7.82 (m, 1H), 7.75 (br s, 1H), 7.70 (s, 1H), 7.63-7.61 (m, 1H), 7.56-7.52 (m, 2H), 7.44-7.42 (m, 1H), 7.36 (s, 1H), 4.24 (br d, J=5.6 Hz, 2H), 3.83-3.79 (m, 2H), 3.54-3.47 (m, 1H), 1.19 (d, J=6.8 Hz, 6H) ppm.

Example 37. Preparation of (S)-3-(isopropylsulfonyl)-N-(3-methoxy-1-((4-(3-(2-methylpyridin-4-yl)phenyl)thiazol-2-yl)amino)-1-oxopropan-2-yl)benzamide (Compound 32)

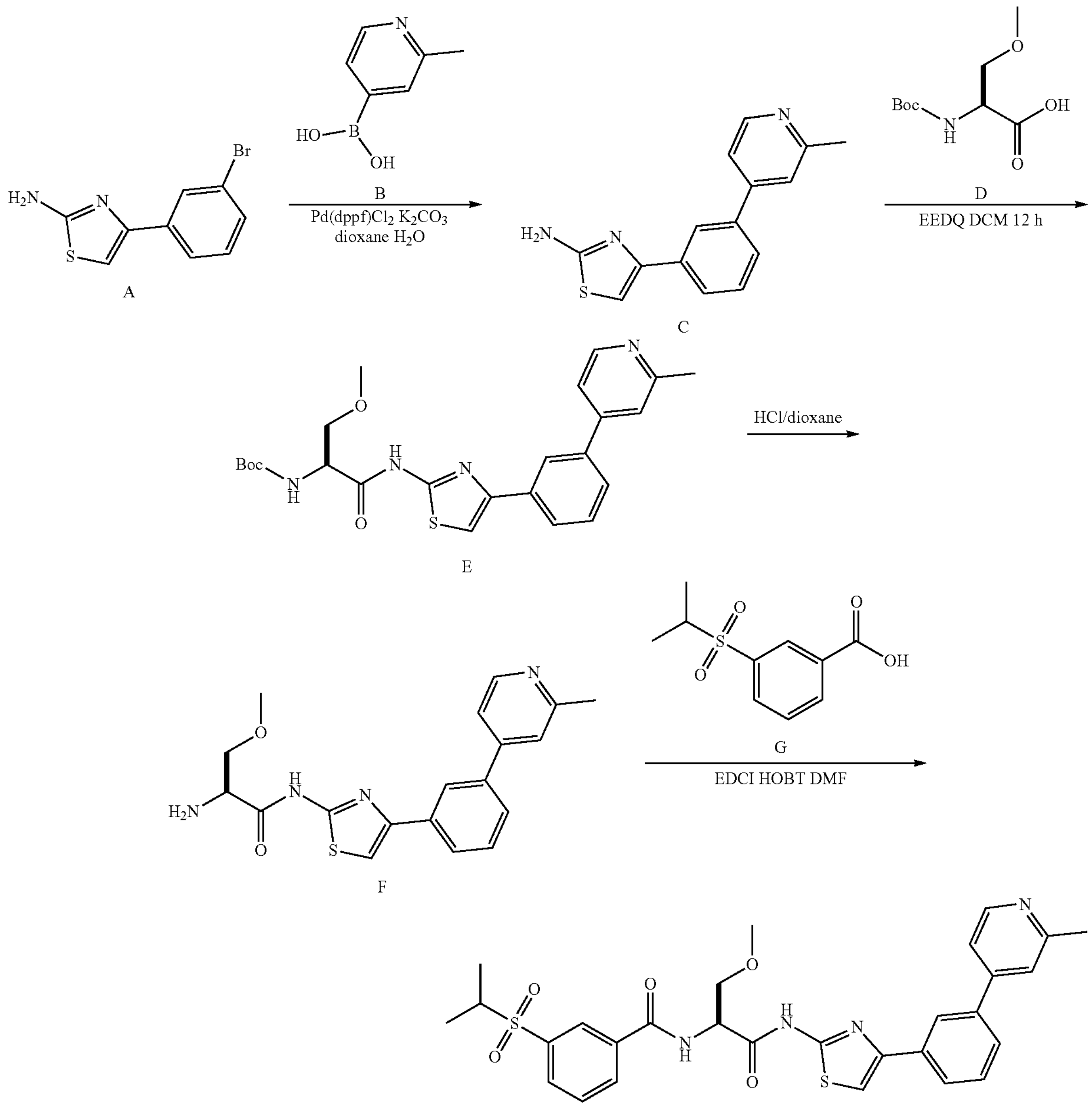

Compound 32

Step 1: Preparation of 4-(3-(2-methylpyridin-4-yl)phenyl)thiazol-2-amine (Intermediate C)

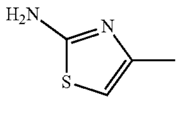

A mixture of 4-(3-bromophenyl)thiazol-2-amine (1 g, 3.92 mmol), (2-methyl-4-pyridyl)boronic acid (805.13 mg, 5.88 mmol), $K_2CO_3$ (1.63 g, 11.76 mmol), Pd(dppf)$Cl_2$ (286.79 mg, 391.95 μmol) in dioxane (10 mL), H2O (3 mL) was degassed and purged with $N_2$ for 3 times, and then the mixture was stirred at 80° C. for 2 hr under $N_2$ atmosphere. The reaction mixture was poured into water (30 mL), and extracted with EA (20 mL×3), dried over $Na_2SO_4$, filtered and concentrated under reduced pressure to give a residue. The residue was purified by column chromatography ($SiO_2$, Petroleum ether/Ethyl acetate=10/1 to 1:1) and concentrated in vacuum to give Intermediate C (1 g, 3.74 mmol, 95.43% yield) as a yellow solid. LCMS (ESI) m/z $[M+H]^+$=268.3. 1H NMR (400 MHz, DMSO) δ=8.56-8.49 (m, 1H), 8.18-8.16 (m, 1H), 7.89 (d, J=8.0 Hz, 1H), 7.71-7.63 (m, 1H), 7.60 (s, 1H), 7.54-7.48 (m, 2H), 7.20 (s, 1H), 7.11 (s, 2H), 2.55 (s, 3H) ppm.

Step 2: Preparation of (S)-tert-butyl (3-methoxy-1-((4-(3-(2-methylpyridin-4-yl)phenyl)thiazol-2-yl) amino)-1-oxopropan-2-yl)carbamate (Intermediate E)

E

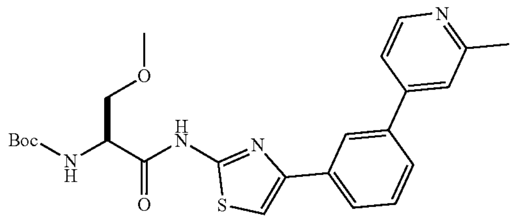

A mixture of Intermediate C (950 mg, 3.55 mmol), 2-(tert-butoxycarbonylamino)-3-methoxy-propanoic acid (934.84 mg, 4.26 mmol), EEDQ (1.76 g, 7.11 mmol) in DCM (10 mL) was degassed and purged with $N_2$ for 3 times, and then the mixture was stirred at 25° C. for 12 hr under $N_2$ atmosphere. The reaction mixture was poured into water (20 mL), and extracted with EA (20 mL×3). The combined organic layers were washed with NaCl (10 mL×3), dried over $Na_2SO_4$, filtered and concentrated under reduced pressure to give a residue. The residue was purified by reversed phase (base) and lyophilized to give Intermediate E (1.3 g, 2.77 mmol, 78.08% yield) as a yellow solid. LCMS (ESI) m/z $[M+H]^+$=469.4. 1H NMR (400 MHz, DMSO) δ=12.43 (s, 1H), 8.54 (d, J=5.2 Hz, 1H), 8.29 (s, 1H), 8.00 (d, J=7.8 Hz, 1H), 7.83 (s, 1H), 7.74 (d, J=7.8 Hz, 1H), 7.67-7.48 (m, 3H), 7.17 (br d, J=7.6 Hz, 1H), 4.52 (br d, J=6.6 Hz, 1H), 3.58 (br d, J=5.6 Hz, 2H), 3.27 (s, 3H), 2.56 (s, 3H), 1.44-1.25 (m, 9H) ppm.

Step 3: Preparation of (S)-2-amino-3-methoxy-N-(4-(3-(2-methylpyridin-4-yl)phenyl)thiazol-2-yl) propanamide (Intermediate F)

F

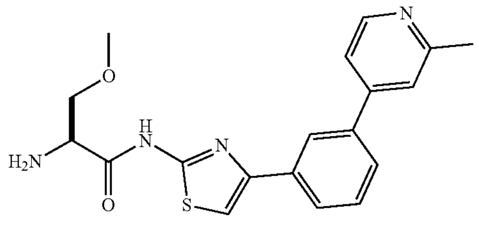

A mixture of Intermediate E (300 mg, 640.25 μmol) in HCl/dioxane (4 M, 1.60 mL) was degassed and purged with $N_2$ for 3 times, and then the mixture was stirred at 25° C. for 2 hr under $N_2$ atmosphere. The mixture was concentrated to give Intermediate F (350 mg, crude, HCl salt) as a yellow solid. LCMS (ESI) m/z $[M+H]^+$=369.2.

Step 4: Preparation of (S)-3-(isopropylsulfonyl)-N-(3-methoxy-1-((4-(3-(2-methylpyridin-4-yl)phenyl) thiazol-2-yl)amino)-1-oxopropan-2-yl)benzamide (Compound 32)

Compound 32

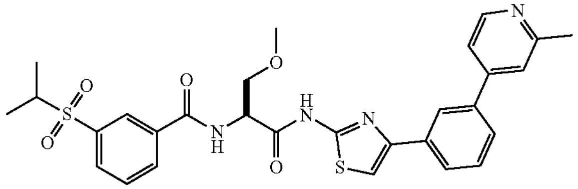

A mixture of Intermediate F (90 mg, 222.27 μmol, HCl salt), 3-isopropylsulfonylbenzoic acid (101.47 mg, 444.54 μmol), DIEA (114.90 mg, 889.08 μmol, 154.86 μL), HOBt (60.07 mg, 444.54 μmol) and EDCl (85.22 mg, 444.54 μmol) in DMF (1 mL) was degassed and purged with $N_2$ for 3 times, and then the mixture was stirred at 25° C. for 12 hr under $N_2$ atmosphere. The reaction mixture was poured into water (10 mL), extracted with EA (10 mL×3). The combined organic layers were washed with brine (10 mL×3), dried over $Na_2SO_4$, filtered and concentrated under reduced pressure to give a residue. The residue was purified by reversed phase (FA) and lyophilized to give Compound 32 (73 mg, 115.50 μmol, 51.96% yield, FA salt) as a yellow solid. LCMS (ESI) m/z=$[M+H]^+$=579.3. $^1$H NMR (400 MHz, DMSO+$D_2O$) δ=8.51 (d, J=5.2 Hz, 1H), 8.39-8.37 (m, 1H), 8.29-8.25 (m, 2H), 8.14 (s, 1H), 8.06-7.97 (m, 2H), 7.83-7.78 (m, 2H), 7.75-7.71 (m, 1H), 7.65-7.53 (m, 3H), 5.02-4.95 (m, 1H), 3.85-3.75 (m, 2H), 3.48 (m, 1H), 3.33 (s, 3H), 2.54 (s, 3H), 1.17 (d, J=6.8 Hz, 6H) ppm.

Example 38. Preparation of N-[2-[[4-[3-[4-(aminomethyl)phenyl]-5-cyano-phenyl]thiazol-2-yl]amino]-2-oxo-ethyl]-3-isopropylsulfonyl-benzamide (Compound 33)
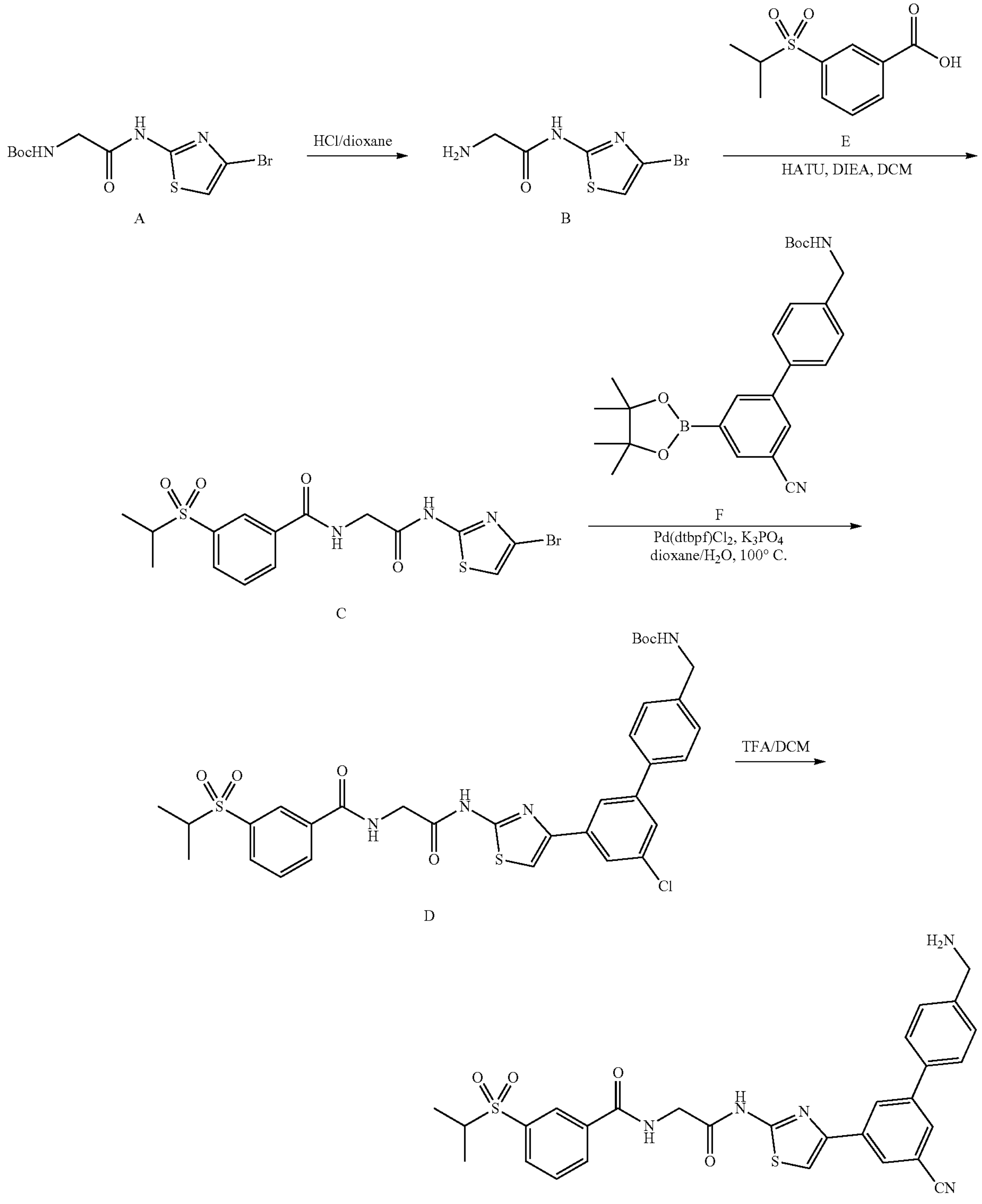
A
B
E
F
C
D
Compound 33

-continued

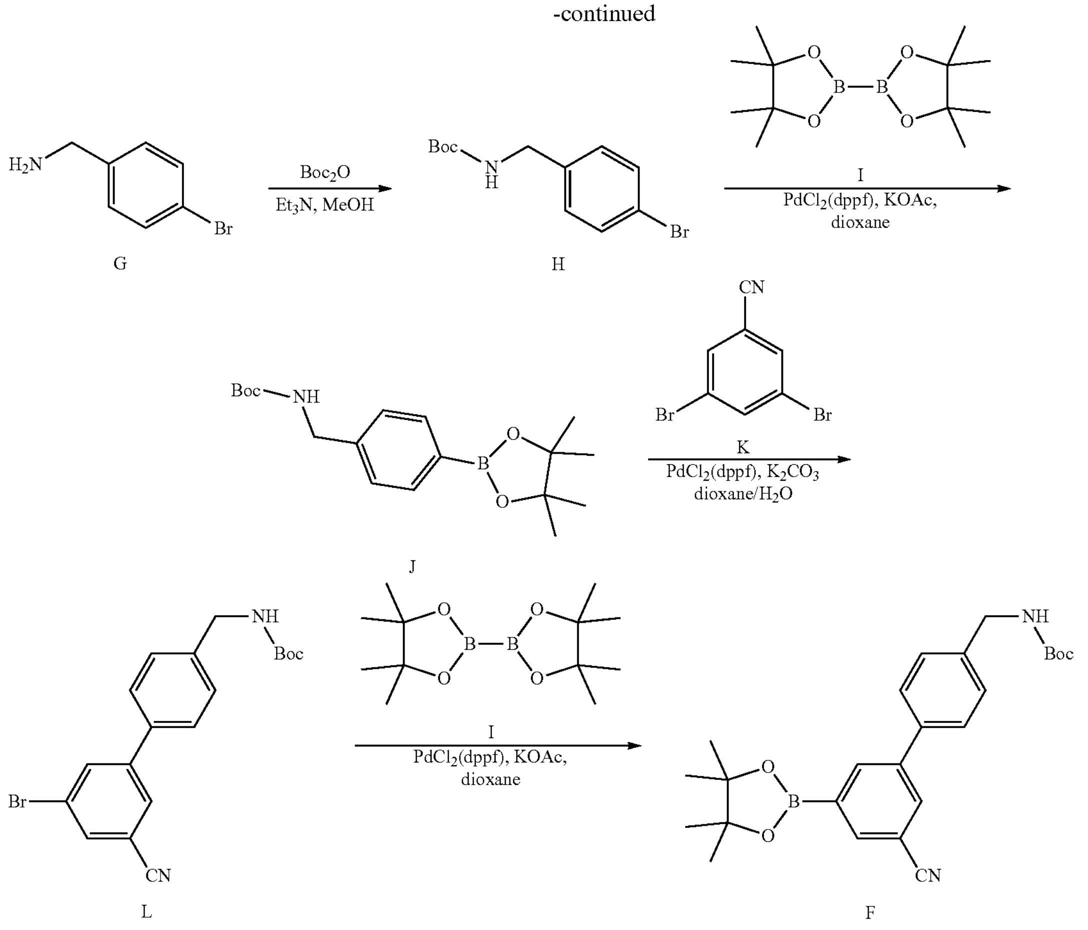

Step 1: Preparation of 2-amino-N-(4-bromothiazol-2-yl)acetamide (Intermediate B)

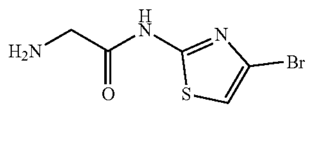

B

To a mixture of tert-butyl N-[2-[(4-bromothiazol-2-yl)amino]-2-oxo-ethyl]carbamate (200 mg, 594.88 μmol) in dioxane (1 mL) was added HCl/dioxane (4 M, 5 mL) in one portion at 20° C. under $N_2$.

The mixture was stirred at 20° C. for 1 hour. The reaction mixture was concentrated under reduced pressure to give Intermediate B (162 mg, 594.39 μmol, 99.92% yield, HCl salt) as a white solid, which was used into next step without further purification. LCMS (ESI) m/z [M+H]+=237.8.

Step 2: Preparation of N-[2-[(4-bromothiazol-2-yl)amino]-2-oxo-ethyl]-3-isopropylsulfonyl-benzamide (Intermediate C)

C

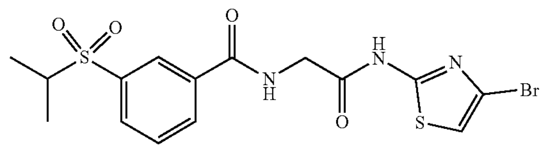

To a mixture of 3-isopropylsulfonylbenzoic acid (201.00 mg, 880.57 μmol) and DIEA (303.49 mg, 2.35 mmol) in DCM (2 mL) was added HATU (446.43 mg, 1.17 mmol) in one portion at 20° C. under $N_2$. The mixture was stirred at 20° C. for 15 min, then Intermediate B (160 mg, 587.05 μmol, HCl salt) was added and the mixture was stirred for 2 hours. The reaction mixture was concentrated under reduced pressure to give a residue. The residue was purified by prep-HPLC (TFA condition; column: Phenomenex Synergi C18 150×25×10 um; mobile phase: [water (0.1% TFA)-ACN]; B %: 30%-60%, 4 min) and concentrated to get Intermediate C (120 mg, 268.85 μmol, 45.80% yield) as a white solid. $^1$H NMR (400 MHz, MeOD) δ=8.43-8.42 (m, 1H), 8.27-8.25 (m, 1H), 8.11-8.09 (m, 1H), 7.82-7.78 (m, 1H), 7.70 (s, 1H), 4.33 (s, 2H), 3.44-3.39 (m, 1H), 1.30-1.24 (m, 7H) ppm.

Step 3: Preparation of tert-butyl N-[(4-bromophenyl)methyl]carbamate (Intermediate H)

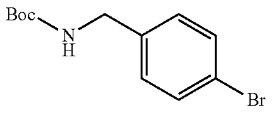

H

To a mixture of (4-bromophenyl)methanamine (10 g, 53.75 mmol) and tert-butoxycarbonyl tert-butyl carbonate (23.46 g, 107.50 mmol) in MeOH (50 mL) was added $Et_3N$ (10.88 g, 107.50 mmol) in one portion at 20° C. under $N_2$. The mixture was stirred at 20° C. for 12 hours. The reaction mixture was concentrated under reduced pressure to give a residue. The residue was purified by column chromatography ($SiO_2$, Petroleum ether/Ethyl acetate=10/1) and concentrated in vacuum to give Intermediate H (12 g, 41.93 mmol, 78.02% yield) as a white solid. LCMS (ESI) m/z [M−55]+=229.9.

Step 4: Preparation of tert-butyl N-[[4-(4,4,5,5-tetramethyl-1,3,2-dioxaborolan-2-yl)phenyl]methyl]carbamate (Intermediate J)

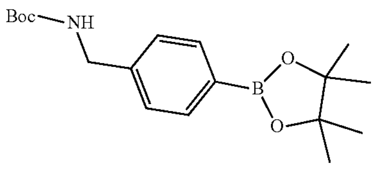

J

To a mixture of Intermediate H (5 g, 17.47 mmol) and 4,4,5,5-tetramethyl-2-(4,4,5,5-tetramethyl-1,3,2-dioxaborolan-2-yl)-1,3,2-dioxaborolane (5.32 g, 20.97 mmol) in dioxane (30 mL) was added Pd(dppf)$Cl_2$ (255.69 mg, 349.45 μmol) and KOAc (5.14 g, 52.42 mmol) in one portion at 20° C. under $N_2$. The mixture was heated to 100° C. and stirred for 12 hours. The reaction mixture was concentrated under reduced pressure to give a residue. The residue was purified by column chromatography ($SiO_2$, Petroleum ether/Ethyl acetate=10/1) and concentrated in vacuum to give Intermediate J (5.6 g, 16.81 mmol, 96.18% yield) as a white solid. LCMS (ESI) m/z [M−55]+=278.1.

Step 5: Preparation of tert-butyl N-[[4-(3-bromo-5-cyano-phenyl)phenyl]methyl]carbamate (Intermediate L)

L

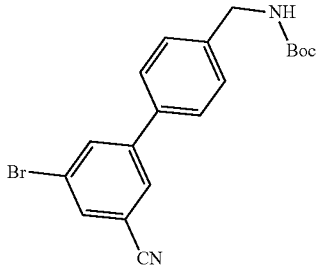

The mixture of 3,5-dibromobenzonitrile (6.58 g, 25.21 mmol), Intermediate J (5.6 g, 16.81 mmol), Pd(dppf)$Cl_2$ (245.93 mg, 336.11 μmol) and $K_2CO_3$ (6.97 g, 50.42 mmol) in dioxane (20 mL) and $H_2O$ (5 mL) was de-gassed and then heated to 100° C. for 2 hours under $N_2$. The reaction mixture was concentrated under reduced pressure to give a residue. The residue was purified by column chromatography ($SiO_2$, Petroleum ether/Ethyl acetate=10/1) and concentrated in vacuum to give Intermediate L (1.3 g, 3.36 mmol, 19.97% yield) as a white solid. $^1H$ NMR (400 MHz, $CDCl_3$) δ=7.85 (s, 1H), 7.70-7.67 (m, 2H), 7.43 (d, J=8.0 Hz, 2H), 7.33 (d, J=8.0 Hz, 2H), 4.31-4.30 (m, 2H), 1.38 (s, 9H) ppm.

Step 6: Preparation of tert-butyl N-[[4-[3-cyano-5-(4,4,5,5-tetramethyl-1,3,2-dioxaborolan-2-yl)phenyl]phenyl]methyl]carbamate (Intermediate F)

F

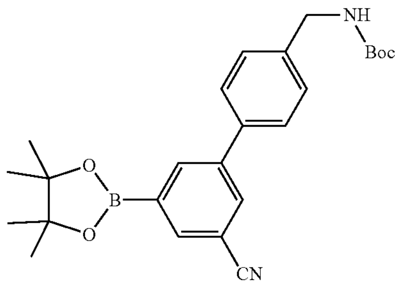

The mixture of Intermediate L (1.2 g, 3.10 mmol), 4,4,5,5-tetramethyl-2-(4,4,5,5-tetramethyl-1,3,2-dioxaborolan-2-yl)-1,3,2-dioxaborolane (1.57 g, 6.20 mmol), Pd(dppf)$Cl_2 \cdot CH_2Cl_2$ (126.52 mg, 154.93 μmol) and KOAc (912.32 mg, 9.30 mmol) in dioxane (10 mL) was de-gassed and then heated to 100° C. and stirred for 2 hours under $N_2$. The reaction mixture was concentrated under reduced pressure to give a residue. The residue was purified by column chromatography ($SiO_2$, Petroleum ether/Ethyl acetate=10/1) and concentrated in vacuum to give Intermediate F (1.1 g, 2.53 mmol, 81.73% yield) as a white solid.

Step 7: Preparation of tert-butyl N-[[4-[3-cyano-5-[2-[[2-[(3-isopropylsulfonylbenzoyl)amino]acetyl]amino]thiazol-4-yl]phenyl]phenyl]methyl]carbamate (Intermediate D)

D

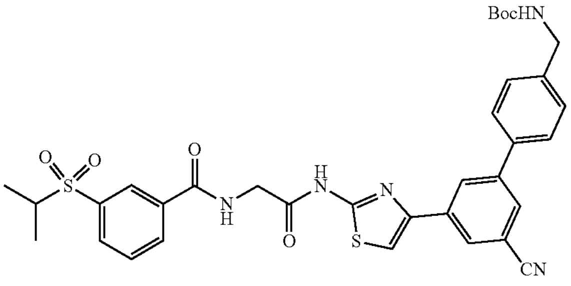

The mixture of Intermediate F, Intermediate C (100 mg, 224.04 μmol), $K_3PO_4$ (142.67 mg, 672.13 μmol), cyclopentyl(diphenyl)phosphane;ditert-butyl(cyclopentyl)phosphane;iron (23.05 mg, 44.81 μmol) in dioxane (4 mL) and $H_2O$ (1 mL) was de-gassed and then heated to 100° C. for 12 hours under $N_2$. The reaction mixture was concentrated under reduced pressure to give a residue. The residue was purified by column chromatography ($SiO_2$, Petroleum ether/Ethyl acetate=1/1) and concentrated to give Intermediate D (70 mg, 88.31 μmol, 39.41% yield) as a yellow solid. LCMS (ESI) m/z [M+Na]+=696.1.

Step 8: Preparation of N-[2-[[4-[3-[4-(aminomethyl)phenyl]-5-cyano-phenyl]thiazol-2-yl]amino]-2-oxo-ethyl]-3-isopropylsulfonyl-benzamide (Compound 33)

Compound 33

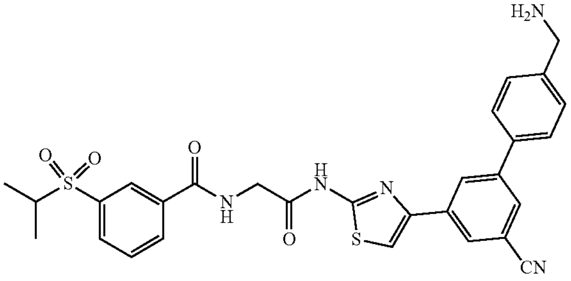

To Intermediate D (70 mg, 88.31 μmol) in DCM (10 mL) was added TFA (1 mL) in one portion at 20° C. under $N_2$. The mixture was stirred at 20° C. for 1 hour. The reaction mixture was concentrated under reduced pressure to give a residue. The residue was purified by prep-HPLC (TFA condition; column: Phenomenex Synergi C18 150×25×10 um; mobile phase: [water (0.1% TFA)-ACN]; B %: 27%-51%, 10 min) and lyophilized to give Compound 33 (42.28 mg, 61.48 μmol, 69.62% yield, TFA salt) as a pink solid. LCMS (ESI) m/z [M+H]+=574.3. $^1H$ NMR (400 MHz, DMSO-$d^6$) δ=12.54 (brs, 1H), 9.33-9.31 (m, 1H) 8.53-8.52 (m, 1H), 8.39-8.28 (m, 1H), 8.35-8.34 (m, 1H), 8.29-8.27 (m, 1H), 8.16-8.15 (m, 3H), 8.07-8.05 (m, 2H), 7.90 (d, J=8.0 Hz, 2H), 7.85-7.81 (m, 1H), 7.61 (d, J=8.0 Hz, 2H), 4.26 (d, J=8.0 Hz, 2H), 4.12 (s, 2H), 3.54-3.47 (m, 1H), 1.19 (d, J=8.0 Hz, 6H) ppm.

Example 39. Preparation of (S)—N-(1-((4-(4-cyanophenyl)thiazol-2-yl)amino)-4-(methylthio)-1-oxobutan-2-yl)-3-(isopropylsulfonyl)benzamide (Compound 34)

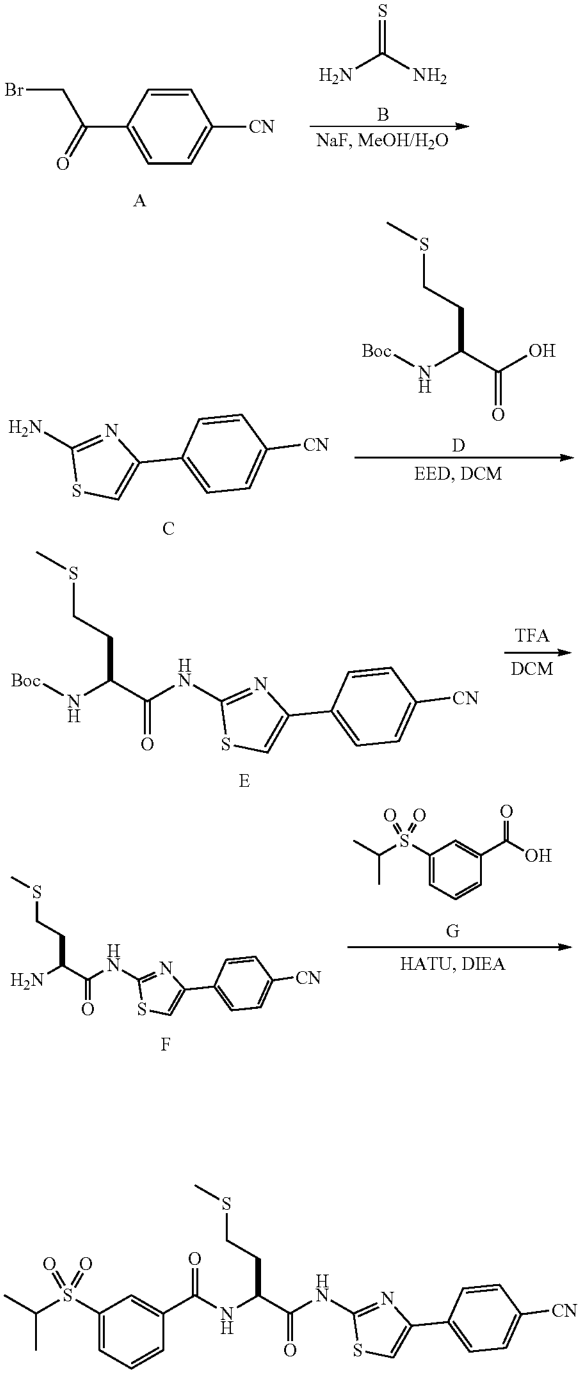

Compound 34

Step 1: Preparation of 4-(2-aminothiazol-4-yl)benzonitrile (Intermediate C)

C

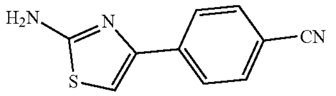

A mixture of 4-(2-bromoacetyl)benzonitrile (10 g, 44.63 mmol), thiourea (3.74 g, 49.10 mmol) in $H_2O$ (150 mL)/MeOH (150 mL) was added NaF (93.70 mg, 2.23 mmol, 93.70 μL), and then the mixture was stirred at 25° C. for 2 hr under $N_2$ atmosphere. The reaction mixture was diluted with water (50 mL) and extracted with EtOAc (100 mL×2). The combined organic layers were washed with brine (40 mL×2), dried over $Na_2SO_4$, filtered and concentrated under reduced pressure to give Intermediate C (8.9 g, crude) as a yellow solid, and used into the next step without further purification. LCMS (ESI) m/z $[M+H]^+$=202.1.

Step 2: Preparation of (S)-tert-butyl (1-((4-(4-cyanophenyl)thiazol-2-yl)amino)-4-(methylthio)-1-oxobutan-2-yl)carbamate (Intermediate E)

E

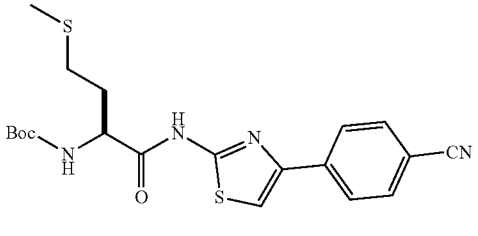

A mixture of Intermediate C (1 g, 4.97 mmol), (S)-2-((tert-butoxycarbonyl)amino)-4-(methylthio)butanoic acid (1.86 g, 7.45 mmol) and EEDQ (1.84 g, 7.45 mmol) in DCM (20 mL) was degassed and purged with $N_2$ for 3 times, and then the mixture was stirred at 25° C. for 10 hr. The reaction mixture was diluted with water (20 mL) and extracted with EtOAc (20 mL×2). The combined organic layers were washed with brine (20 mL×2), dried over $Na_2SO_4$, filtered and concentrated under reduced pressure to give a residue. The residue was purified by column chromatography ($SiO_2$, Petroleum ether/Ethyl acetate=100/1 to 20:1) and concentrated to give Intermediate E (1.22 g, 2.54 mmol, 51.08% yield) as yellow oil. LCMS (ESI) m/z$[M+H]^+$=433.1. SFC: OJ-3-MeOH (DEA)-5-40-3 mL-35 T, Rt: 2.019 min, ee %=100%.

Step 3: Preparation of (S)-2-amino-N-(4-(4-cyanophenyl)thiazol-2-yl)-4-(methylthio)butanamide (Intermediate F)

F

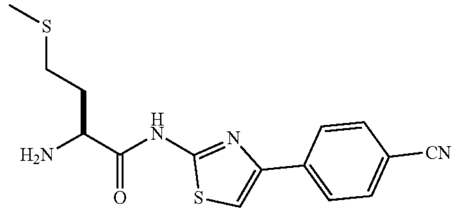

A mixture of Intermediate E (1.2 g, 2.77 mmol) in DCM (10 mL) was added TFA (2.31 g, 20.26 mmol, 1.5 mL), and then the mixture was stirred at 25° C. for 10 hr under $N_2$ atmosphere. The reaction mixture was diluted with $NaHCO_3$ (15 mL) and extracted with EtOAc (10 mL×2). The combined organic layers were washed with brine (20 mL×2), dried over $Na_2SO_4$, filtered and concentrated under reduced pressure to give Intermediate F (715.00 mg, 1.83 mmol, 65.90% yield) as yellow oil. LCMS (ESI) m/z$[M+H]^+$=333.0.

Step 4: Preparation of (S)—N-(1-((4-(4-cyanophenyl)thiazol-2-yl)amino)-4-(methylthio)-1-oxobutan-2-yl)-3-(isopropylsulfonyl)benzamide (Compound 34)

Compound 34

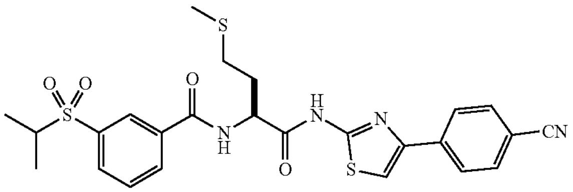

To a solution of 3-(isopropylsulfonyl)benzoic acid (128.40 mg, 562.50 μmol) in DCM (5 mL) were added HATU (291.65 mg, 767.05 μmol), DIEA (198.27 mg, 1.53 mmol, 267.21 μL) and Intermediate F (200 mg, 511.37 μmol) in turn. The mixture was stirred at 25° C. for 10 hr. The reaction mixture was diluted with water (10 mL) and extracted with EtOAc (15 mL×2). The combined organic layers were washed with brine (10 mL×2), dried over $Na_2SO_4$, filtered and concentrated under reduced pressure to give a residue. The residue was purified by column chromatography ($SiO_2$, Petroleum ether/Ethyl acetate=50/1 to 2:1) and concentrated to give Compound 34 (240 mg, 424.55 μmol, 83.02% yield) as an off-white solid. LCMS (ESI) m/z=$[M+H]^+$=543.2. $^1H$ NMR (400 MHz, DMSO-$d_6$) δ=12.65 (s, 1H), 9.12 (d, J=7.2 Hz, 1H), 8.39 (s, 1H), 8.30 (d, J=8.0 Hz, 1H), 8.10-8.03 (m, 3H), 7.95 (s, 1H), 7.94-7.89 (m, 2H), 7.82-7.79 (m, 1H), 4.83-4.78 (m, 1H), 3.53-3.46 (m, 1H), 2.67-2.63 (m, 1H), 2.59-2.54 (m, 1H), 2.21-2.11 (m, 2H), 2.09-1.98 (m, 3H), 1.19-1.17 (m, 6H) ppm. SFC: Cellucoat-MeOH (DEA)-40-3 mL-35T, Rt: 0.979 min, ee %=100%.

Example 40. Preparation of (S)—N-(1-((4-(4-cyanophenyl)thiazol-2-yl)amino)-1-oxopropan-2-yl)-3-(isopropylsulfonyl)benzamide (Compound 35)

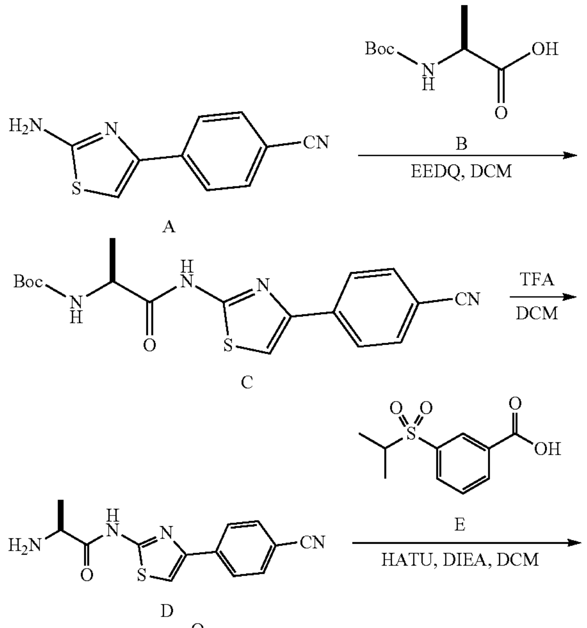

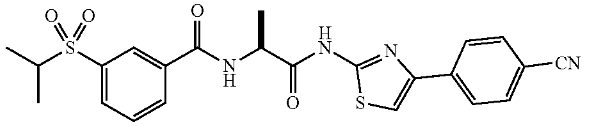

Compound 35

Step 1: Preparation of (S)-tert-butyl (1-((4-(4-cyanophenyl)thiazol-2-yl)amino)-1-oxopropan-2-yl) carbamate (Intermediate C)

C

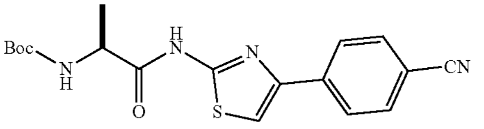

To a solution of (S)-2-((tert-butoxycarbonyl)amino)propanoic acid (705.13 mg, 3.73 mmol) in DCM (10 mL) was added EEDQ (921.59 mg, 3.73 mmol) and 4-(2-aminothiazol-4-yl)benzonitrile (prepared according to the method in Example 39) (500 mg, 2.48 mmol). The mixture was stirred at 25° C. for 10 hr. The reaction mixture was filtered to remove the solid, and the filtrate was diluted with water 10 mL and extracted with EtOAc (10 mL×2). The combined organic layers were washed with brine (10 mL×2), dried over $Na_2SO_4$, filtered and concentrated under reduced pressure to give a residue. The residue was purified by column chromatography ($SiO_2$, Petroleum ether/Ethyl acetate=50/1 to 20:1) and concentrated to get Intermediate C (914 mg, 2.23 mmol, 89.89% yield) as yellow oil. LCMS (ESI) m/z $[M+H]^+$=373.1. SFC: OD-3_5CM_MEOH (DEA)_5_40_3ML_AT35.M, ee %=100%, Rt: 1.407 min.

Step 2: Preparation of (S)-2-amino-N-(4-(4-cyanophenyl)thiazol-2-yl)propanamide (Intermediate D)

D

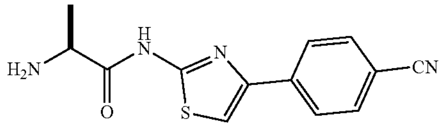

To a solution of Intermediate C (900 mg, 2.42 mmol) in DCM (10 mL) was added TFA (3.08 g, 27.01 mmol, 2 mL). The mixture was stirred at 25° C. for 10 hr. The reaction mixture was diluted with $NaHCO_3$ (15 mL) and extracted with EtOAc (10 mL×2). The combined organic layers were washed with brine (20 mL×2), dried over $Na_2SO_4$, filtered and concentrated under reduced pressure to give Intermediate D (375 mg, 1.20 mmol, 49.58% yield) as yellow oil. LCMS (ESI) m/z$[M+H]^+$=273.0.

Step 3: Preparation of (S)—N-(1-((4-(4-cyanophenyl)thiazol-2-yl)amino)-1-oxopropan-2-yl)-3-(isopropylsulfonyl)benzamide (Compound 35)

Compound 35

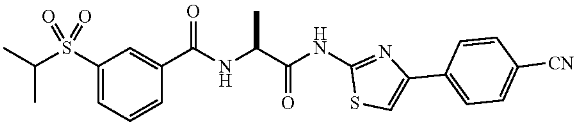

To a solution of 3-(isopropylsulfonyl)benzoic acid (120.32 mg, 527.13 μmol) in DCM (4 mL) was added HATU (273.31 mg, 718.81 μmol), DIEA (185.80 mg, 1.44 mmol, 250.41 μL) and Intermediate D (150 mg, 479.21 μmol) in turn. The mixture was stirred at 25° C. for 10 hr. The reaction mixture was diluted with water (10 mL) and extracted with EtOAc (15 mL×2). The combined organic layers were washed with brine (10 mL×2), dried over $Na_2SO_4$, filtered and concentrated under reduced pressure to give a residue. The residue was purified by column chromatography ($SiO_2$, Petroleum ether/Ethyl acetate=20/1 to 3:1) and concentrated to give Compound 35 (200 mg, 410.30 μmol, 85.62% yield) as a white solid. LCMS (ESI) m/z=$[M+H]^+$=483.1. $^1H$ NMR (400 MHz, DMSO-$d_6$) δ=12.56 (s, 1H), 9.14 (d, J=6.4 Hz, 1H), 8.41 (s, 1H), 8.28 (d, J=8.0 Hz, 1H), 8.09 (d, J=8.4 Hz, 2H), 8.04 (d, 1H), 7.94 (s, 1H), 7.90 (d, J=8.4 Hz, 2H), 7.82-7.78 (m, 1H), 4.77-4.70 (m, 1H), 3.53-3.46 (m, 1H), 1.49 (d, J=7.2 Hz, 3H), 1.19-1.17 (m, 6H) ppm. SFC: OJ-3-MeOH (DEA)-5-40-3 mL-35T·lcm, ee %=100%, Rt: 2.359 min.

Example 41. Preparation of 3-isopropylsulfonyl-N-[2-[[4-[3-(1,3,4-oxadiazol-2-yl)phenyl]thiazol-2-yl]amino]-2-oxo-ethyl]benzamide (Compound 36)

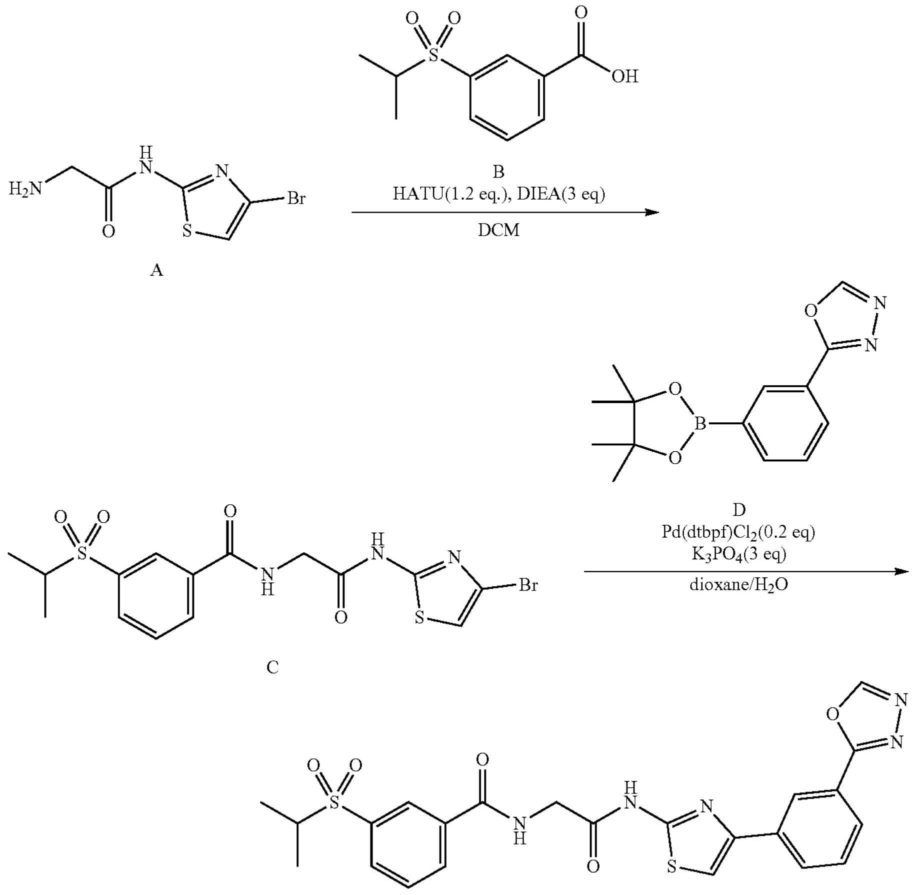

Compound 36

Step 1: Preparation of N-[2-[(4-bromothiazol-2-yl)amino]-2-oxo-ethyl]-3-isopropylsulfonyl-benzamide (Intermediate C)

C

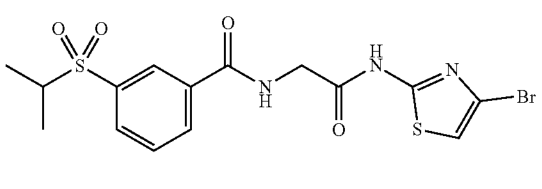

To a mixture of 3-isopropylsulfonylbenzoic acid (45.23 mg, 198.13 μmol) in DCM (1 mL) was added HATU (90.40 mg, 237.75 μmol) and DIEA (102.43 mg, 792.51 μmol) and the mixture was stirred at 20° C. for 5 min. Then 2-amino-N-(4-bromothiazol-2-yl)acetamide (54 mg, 198.13 μmol) was added and the mixture was stirred at 30° C. for 1 hr. Water (30 mL) was added and the mixture was extracted with EtOAc (40 mL×2). The combined organic phase was washed with brine, dried over anhydrous $Na_2SO_4$, filtered and concentrated under vacuum. The residue was slurried in MeOH (4 mL) and stirred for 10 min and the precipitate was collected by filtration, washed with MTBE (2 mL) and dried in vacuum to give Intermediate C (45 mg, 98.88 μmol, 49.91% yield) as a white solid. LCMS (ESI) m/z $[M+H]^+$=448.0.

Step 2: Preparation of 3-isopropylsulfonyl-N-[2-[[4-[3-(1,3,4-oxadiazol-2-yl)phenyl]thiazol-2-yl]amino]-2-oxo-ethyl]benzamide (Compound 36)

Compound 36

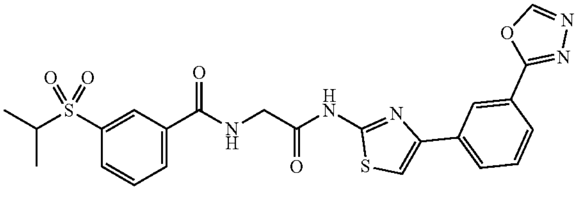

Intermediate C (45 mg, 100.82 μmol), 2-[3-(4,4,5,5-tetramethyl-1,3,2-dioxaborolan-2-yl)phenyl]-1,3,4-oxadiazole (54.87 mg, 201.64 μmol), ditert-butyl(cyclopentyl)phosphane;dichloro palladium;iron (13.14 mg, 20.16 μmol) and $K_3PO_4$ (64.20 mg, 302.46 μmol) were taken up in dioxane (2 mL) and $H_2O$ (0.2 mL) and the mixture was purged with $N_2$ for three times. The resulting mixture was stirred at 100° C. for 3 hr. Another 2-[3-(4,4,5,5-tetramethyl-1,3,2-dioxaborolan-2-yl)phenyl]-1,3,4-oxadiazole (54.87 mg, 201.64 μmol) and ditert-butyl(cyclopentyl) phosphane;dichloropalladium; iron (13.14 mg, 20.16 μmol) were added and the mixture was stirred at 100° C. for another 2 hr. Then the mixture was filtered through column chromatography ($SiO_2$, PE:EtOAc=20:1-1:1, DCM:MeOH=10:1) and the eluent was concentrated under vacuum. The residue was purified by Prep-HPLC (column: Phenomenex Gemini 150×25 mm×10 um; mobile phase: [water (0.04% $NH_3H_2O$+10 mM NH4HCO3)-ACN]; B %: 26%-59%, 10 min). The eluent was concentrated under vacuum and then extracted with EtOAc (40 mL×2) and the combined organic phase was washed with brine, dried over anhydrous $Na_2SO_4$, filtered and concentrated under vacuum. The residue was further purified by Prep-HPLC (column: Waters Xbridge 150×25 5 u; mobile phase: [water (0.05% ammonia hydroxide v/v)-ACN]; B %: 18%-48%, 10 min) and lyophilized to give Compound 36 (2.95 mg, 5.77 μmol, 5.72% yield) as a yellow solid. LCMS (ESI) m/z $[M+H]^+$=512.2. $^1$H NMR (400 MHz, DMSO) δ=12.50 (s, 1H), 9.37 (s, 1H), 9.17 (s, 1H), 8.59 (s, 1H), 8.39-8.38 (m, 1H), 8.29-8.26 (m, 1H), 8.16-8.13 (m, 1H), 8.06-8.03 (m, 1H), 7.95 (d, J=7.6 Hz, 1H), 7.83-7.79 (m, 1H), 7.77-7.63 (m, 2H), 4.17 (s, 2H), 3.54-3.47 (m, 1H), 1.18 (d, J=6.8 Hz, 6H) ppm.

Example 42. Preparation of N-[2-[[4-[3-cyano-5-(4-pyridyl)phenyl]thiazol-2-yl]amino]-2-oxo-ethyl]-3-isopropylsulfonyl-benzamide (Compound 37)

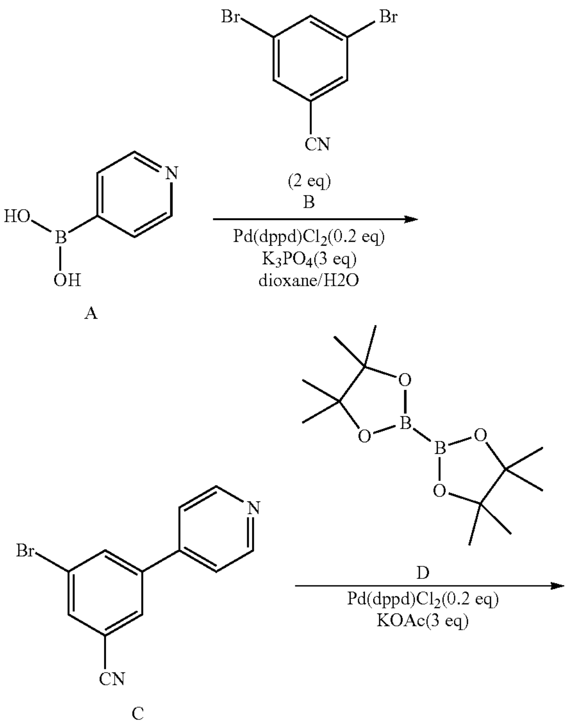

-continued

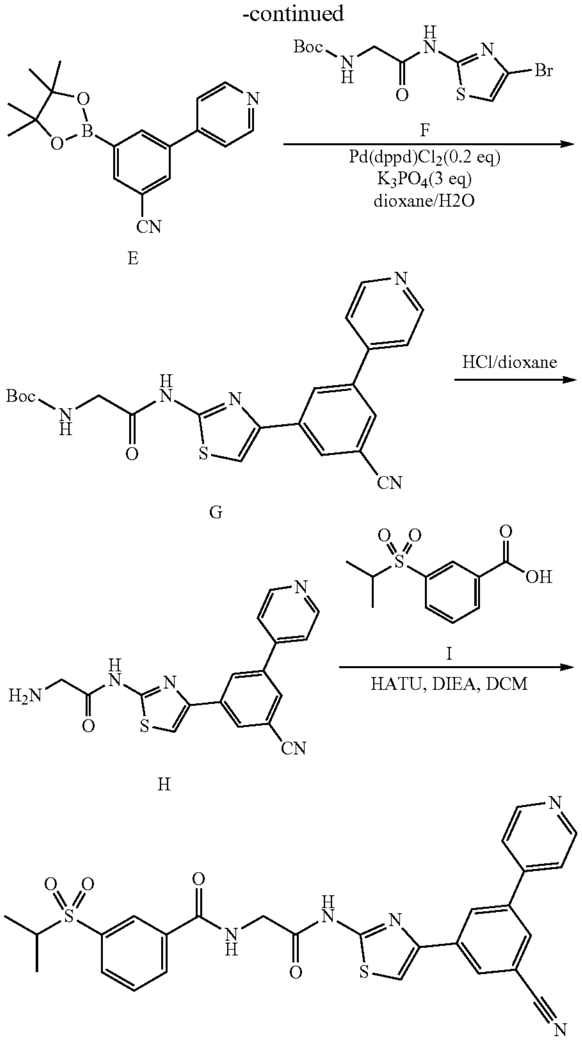

Compound 37

Step 1: Preparation of 3-bromo-5-(4-pyridyl)benzonitrile (Intermediate C)

C

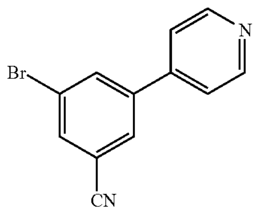

4-pyridylboronic acid (0.5 g, 4.07 mmol), 3,5-dibromobenzonitrile (2.12 g, 8.14 mmol), Pd(dppf)$Cl_2$ (595.28 mg, 813.55 μmol) and $K_3PO_4$ (2.59 g, 12.20 mmol) were taken up in dioxane (10 mL) and $H_2O$ (1 mL) and the mixture was purged with $N_2$ three times. Then the mixture was stirred at 100° C. for 3 hr. Water (30 mL) was added and the mixture was extracted with EtOAc (30 mL×2). The combined organic phase was washed with brine, dried over anhydrous $Na_2SO_4$, filtered and concentrated under vacuum and the residue was purified by column chromatography ($SiO_2$, PE:EtOAc=50:1-2:1). Then the solid was slurried in EtOAc (5 mL) and stirred for 5 min. The precipitate was collected through filtration and washed with MTBE (2 mL), dried in vacuum to give Intermediate C (450 mg, 1.74 mmol, 42.70% yield) as a white solid. LCMS (ESI) m/z $[M+H]^+$=258.9. $^1H$ NMR (400 MHz, $CDCl_3$) δ=8.75-8.74 (m, 2H), 7.99-7.98 (m, 1H), 7.86-7.83 (m, 2H), 7.46-7.45 (m, 2H) ppm.

Step 2: Preparation of 3-(4-pyridyl)-5-(4,4,5,5-tetramethyl-1,3,2-dioxaborolan-2-yl)benzonitrile (Intermediate E)

E

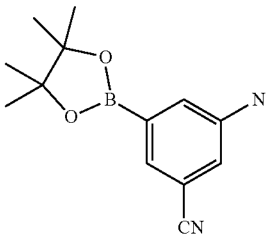

Intermediate C (200 mg, 771.90 μmol), 4,4,5,5-tetramethyl-2-(4,4,5,5-tetramethyl-1,3,2-dioxa borolan-2-yl)-1,3,2-dioxaborolane (235.22 mg, 926.28 μmol), Pd(dppf)$Cl_2$ (112.96 mg, 154.38 μmol) and KOAc (227.27 mg, 2.32 mmol) were taken up in dioxane (2 mL) and the mixture was purged with $N_2$ three times. Then the resulting mixture was stirred at 100° C. for 2 hr. The reaction mixture was concentrated in vacuum to give Intermediate E (236 mg, crude) as a black oil, which was used for the next step without purification.

Step 3: Preparation of tert-butyl N-[2-[[4-[3-cyano-5-(4-pyridyl)phenyl]thiazol-2-yl]amino]-2-oxo-ethyl]carbamate (Intermediate G)

G

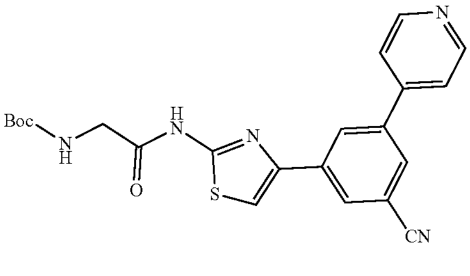

Tert-butyl N-[2-[(4-bromothiazol-2-yl)amino]-2-oxo-ethyl]carbamate (125 mg, 371.80 μmol), Intermediate E (227.66 mg, 743.59 μmol), ditert-butyl(cyclopentyl)phosphane;dichloro palladium;iron (48.46 mg, 74.36 μmol) and $K_3PO_4$ (236.76 mg, 1.12 mmol) were taken up in dioxane (4 mL) and $H_2O$ (0.4 mL) and the mixture was purged with $N_2$ three times. The resulting mixture was stirred at 100° C. for 3 hr. Water (40 mL) was added and the mixture was extracted with EtOAc (40 mL×3). Then the combined organic phase was washed with brine, dried over anhydrous $Na_2SO_4$, filtered and concentrated under vacuum. The residue was slurried in MeOH (3 mL) and stirred for 5 min. Finally, the precipitate was collected through filtration, washed with MTBE (2 mL) and dried in vacuum to give Intermediate G (45 mg, 103.33 μmol, 27.79% yield) as a white solid. LCMS (ESI) m/z $[M+H]^+$=436.3.

Step 4: Preparation of 2-amino-N-[4-[3-cyano-5-(4-pyridyl)phenyl]thiazol-2-yl]acetamide (Intermediate H)

H

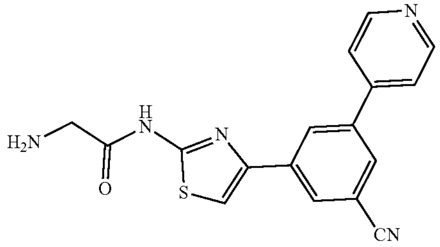

To a solution of Intermediate G (55 mg, 126.29 μmol) in DCM (5 mL) was added HCl/dioxane (4 M, 1 mL) and the mixture was stirred at 20° C. for 1 hr. Then the solvent was removed under reduced pressure to give the Intermediate H (46 mg, crude, HCl salt) as a white solid, which was used for the next step without further purification. LCMS (ESI) m/z $[M+Na]^+$=359.2.

Step 5: Preparation of N-[2-[[4-[3-cyano-5-(4-pyridyl)phenyl]thiazol-2-yl]amino]-2-oxo-ethyl]-3-isopropylsulfonyl-benzamide (Compound 37)

Compound 37

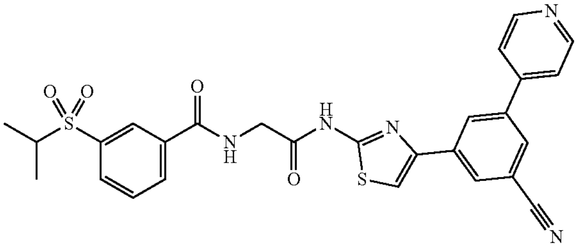

To a mixture of 3-isopropylsulfonylbenzoic acid (22.10 mg, 96.81 μmol) in DCM (1 mL) was added HATU (44.17 mg, 116.18 μmol) and DIEA (50.05 mg, 387.26 μmol) and the mixture was stirred at 20° C. for 5 min. Then Intermediate H (36 mg, 96.81 μmol) was added and the mixture was stirred at 30° C. for another 2 hr. The precipitate was collected through filtration and the solid was slurried in DMSO (1 mL) and MeOH (4 mL) and stirred for 10 min. Then the precipitate was collected by filtration and then washed with MTBE (3 mL) and lyophilized to give Compound 37 (17.62 mg, 31.48 μmol, 25.40% yield) as a grey solid. LCMS (ESI) m/z $[M+H]^+$=546.3. $^1H$ NMR (400 MHz, DMSO) δ=12.58 (s, 1H), 9.34-9.31 (m, 1H), 8.73-8.71 (m, 2H), 8.61-8.59 (m, 1H), 8.43-8.38 (m, 2H), 8.27-8.26 (m, 2H), 8.07-8.04 (m, 2H), 7.85-7.80 (m, 3H), 4.25 (d, J=5.6 Hz, 2H), 3.53-3.47 (m, 1H), 1.18 (d, J=6.8 Hz, 6H) ppm.

Example 43. Preparation of N-[2-[[4-(4-cyanophenyl)thiazol-2-yl]amino]-2-oxo-ethyl]-3-isopropylsulfonyl-benzamide (Compound 38)

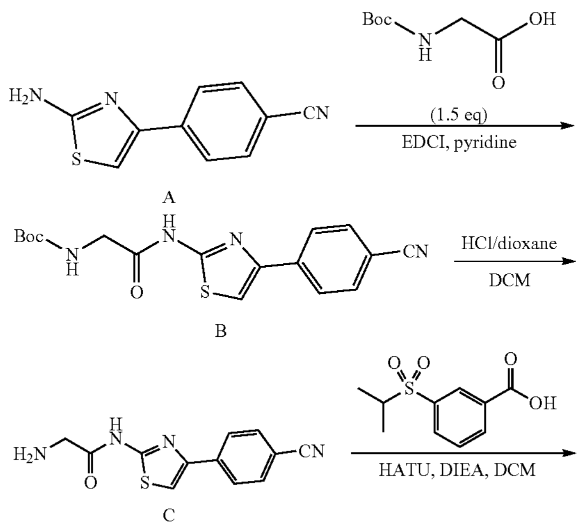

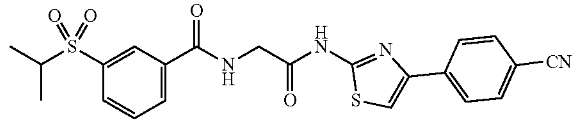

Compound 38

Step 1: Preparation of tert-butyl N-[2-[[4-(4-cyanophenyl)thiazol-2-yl]amino]-2-oxo-ethyl]carbamate (Intermediate B)

B

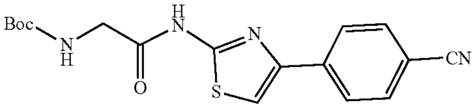

To a solution of 4-(2-aminothiazol-4-yl)benzonitrile (prepared according to the method in Example 39) (400 mg, 1.99 mmol) in pyridine (10 mL) was added EDCl (1.14 g, 5.96 mmol) and 2-(tert-butoxycarbonylamino)acetic acid (417.83 mg, 2.39 mmol). The mixture was stirred at 25° C. for 10 hr. The reaction mixture was concentrated under vacuum to remove the solvent, then diluted with water (50 mL) and extracted with EtOAc (30 mL×2). The combined organic layers were washed with citric acid solution (20 mL) and brine (25 mL×2), dried over $Na_2SO_4$, filtered and concentrated under reduced pressure to give a residue. The residue was purified by column chromatography ($SiO_2$, Petroleum ether/Ethyl acetate=100/1 to 20:1) and concentrated to give Intermediate B (500 mg, 1.35 mmol, 68.08% yield) as a white solid. LCMS (ESI) m/z $[M+H]^+$=359.1.

Step 2: Preparation of 2-amino-N-[4-(4-cyanophenyl)thiazol-2-yl]acetamide (Intermediate C)

C

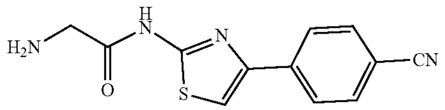

To a solution of Intermediate B (500 mg, 1.40 mmol) in DCM (4 mL) was added HCl/dioxane (4 M, 4.17 mL). The mixture was stirred at 25° C. for 2 hr. The reaction mixture was filtered to remove solvent, the solid was washed with MBTE (10 mL), dried in the vacuum to give Intermediate C (400 mg, crude, HCl salt) as a white solid, which was used into the next step without further purification. LCMS (ESI) m/z $[M+H]^+$=259.1.

Step 3: Preparation of N-[2-[[4-(4-cyanophenyl)thiazol-2-yl]amino]-2-oxo-ethyl]-3-isopropylsulfonyl-benzamide (Compound 38)

Compound 38

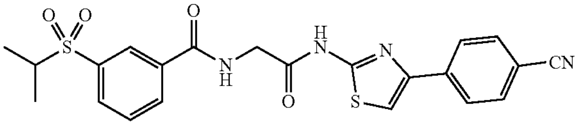

To a solution of 3-isopropylsulfonylbenzoic acid (185.86 mg, 814.22 μmol) in DCM (5 mL) was added HATU (309.59 mg, 814.22 μmol), DIEA (526.16 mg, 4.07 mmol) and Intermediate C (200 mg, 678.52 μmol, HCl salt) in turn. The mixture was stirred at 25° C. for 12 hr. The reaction mixture was filtered to remove the solvent, and the filter cake was washed by MTBE (10 mL), dried in the vacuum to give Compound 38 (230 mg, 456.52 μmol, 67.28% yield) as a white solid. LCMS (ESI) m/z $[M+H]^+$=469.1. $^1H$ NMR (400 MHz, DMSO-$d_6$) δ=12.54 (s, 1H), 9.32-9.29 (m, 1H), 8.37 (s, 1H), 8.26 (d, J=7.6, 1H), 8.09-8.04 (m, 3H), 7.94-7.89 (m, 3H), 7.83-7.79 (m, 1H), 4.25 (d, J=5.6 Hz, 2H), 3.53-3.46 (m, 1H), 1.18 (d, J=6.8 Hz, 6H) ppm.

Example 44. Preparation of 3-isopropylsulfonyl-N-[2-oxo-2-[[4-[3-(3-pyridyl)phenyl]thiazol-2-yl]amino]ethyl]benzamide (Compound 39)

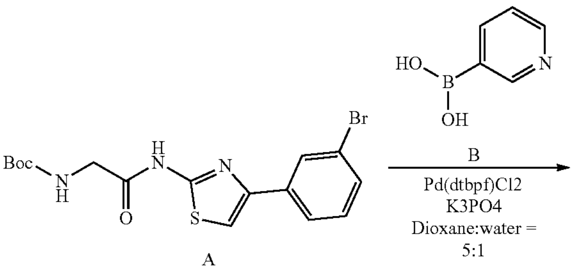

-continued

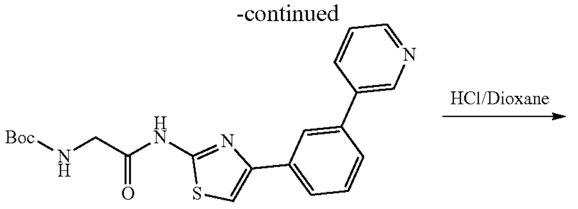

C

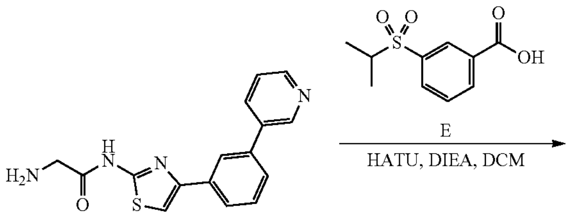

D

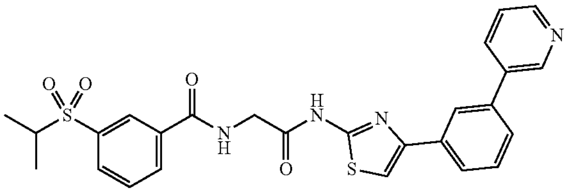

Compound 39

Step 1: Preparation of tert-butyl N-[2-oxo-2-[[4-[3-(3-pyridyl)phenyl] thiazol-2-yl]amino]ethyl]carbamate (Intermediate C)

C

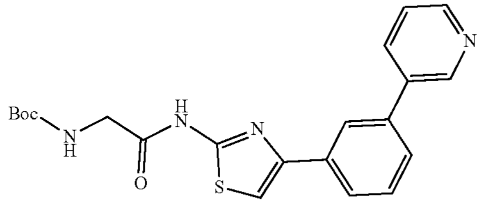

To a solution of tert-butyl N-[2-[[4-(3-bromophenyl)thiazol-2-yl]amino]-2-oxo-ethyl]carbamate (prepared according to the method in Example 2) (100 mg, 242.54 μmol) and 3-pyridylboronic acid (89.44 mg, 727.62 μmol) in dioxane (10 mL) and water (2 mL) was added Pd(dtbpf)$Cl_2$ (31.62 mg, 48.51 μmol) and $K_3PO_4$ (154.45 mg, 727.62 μmol). The reaction mixture was degassed with $N_2$ for three times and stirred for 2 hrs at 100° C. The mixture was diluted with EA (30 mL) and filtered through silica, then washed with water (10 mL×3) and brine (10 mL×2), dried over $Na_2SO_4$, filtered and concentrated under vacuum to give Intermediate C (125 mg, crude) as yellow oil, which was used to next step directly. LCMS (ESI) m/z $[M+H]^+$=411.1.

Step 2: Preparation of 2-amino-N-[4-[3-(3-pyridyl)phenyl]thiazol-2-yl]acetamide (Intermediate D)

D

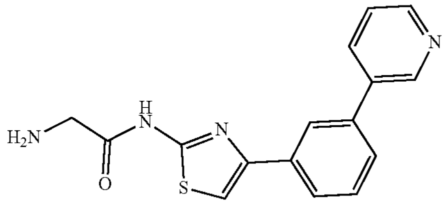

A solution of Intermediate C (120.00 mg, 292.33 μmol) in HCl/dioxane (4 M, 10 mL) was stirred at 30° C. for 2 hr. The mixture was diluted with DCM (20 mL) and concentrated under vacuum. This operation was repeated three times. The residue was washed by MTBE (5 mL×2) and dried in vacuum to give Intermediate D (120 mg, crude, HCl salt) as yellow solid, which was used to next step directly. LCMS (ESI) m/z $[M+H]^+$=311.0.

Step 3: Preparation of 3-isopropylsulfonyl-N-[2-oxo-2-[[4-[3-(3-pyridyl)phenyl]thiazol-2-yl]amino]ethyl]benzamide (Compound 39)

Compound 39

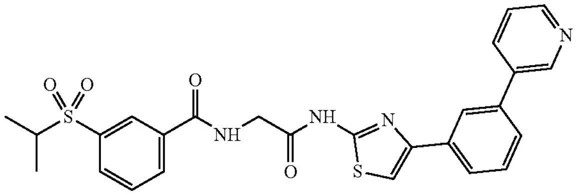

To a solution of 3-isopropylsulfonylbenzoic acid (7.35 mg, 32.20 μmol) in DCM (1 mL) was added HATU (18.38 mg, 48.34 μmol), DIEA (12.49 mg, 96.64 μmol, 16.83 μL). Then Intermediate D (10 mg, 28.83 μmol, HCl salt) was added and the mixture was stirred at 30° C. for 2 hrs. Combined the mixture of 3 batches and diluted with DCM (50 mL) and washed with saturated $NaHCO_3$ solution (5 mL×2), water (5 mL×3) and brine (5 mL×2), dried over $Na_2SO_4$, filtered and concentrated under vacuum. The residue was purified by Prep-HPLC (column: Phenomenex Synergi C18 150×25×10 um; mobile phase: [water (0.1% TFA)-ACN]; B %: 20%-40%, 10 min) and lyophilized to give Compound 39 (5.86 mg, 9.23 μmol, 10.67% yield, TFA salt) as yellow solid. LCMS (ESI) m/z $[M+H]^+$=521.1. $^1H$ NMR (400 MHz, DMSO-$d_6$) δ=12.51 (s, 1H), 9.32-9.30 (m, 1H), 9.07 (s, 1H), 8.70 (br d, J=5.6 Hz, 1H), 8.38-8.27 (m, 4H), 8.07-7.99 (m, 2H), 7.85-7.81 (m, 2H), 7.75-7.73 (m, 2H), 7.63-7.59 (m, 1H), 4.25 (br d, J=5.6 Hz, 2H), 1.19 (d, J=6.8 Hz, 6H) ppm.

Example 45. Preparation of 3-(isopropylsulfonyl)-N-(2-oxo-2-((4-(3-(pyridin-4-yl)phenyl)thiazol-2-yl)amino)ethyl)benzamide (Compound 40)

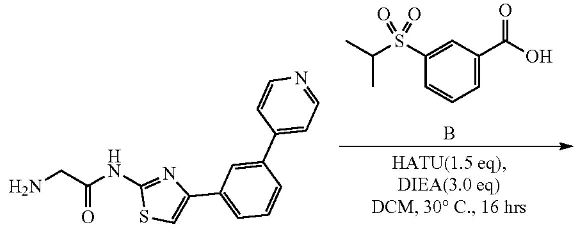

A

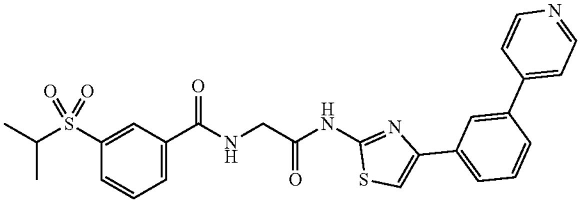

Compound 40

To a solution of 3-isopropylsulfonylbenzoic acid (294.00 mg, 1.29 mmol) in DCM (20 mL) was added HATU (735.20 mg, 1.93 mmol), DIEA (499.60 mg, 3.87 mmol, 673.32 μL). Then 2-amino-N-[4-[3-(4-pyridyl)phenyl]thiazol-2-yl]acetamide (400 mg, 1.15 mmol, HCl salt) was added and the mixture was stirred at 30° C. for 2 hrs. The mixture was diluted with DCM (50 mL) and washed with saturated $NaHCO_3$ solution (5 mL×2), water (5 mL×3) and brine (5 mL×2), dried over $Na_2SO_4$, filtered and concentrated under vacuum. The residue was purified by column chromatography ($SiO_2$, DCM:MeOH=100:1-10:1) and concentrated to give white solid which was recrystallized in DMSO (2 mL) and MeOH (200 mL) to get Compound 40 (132 mg, 253.54 μmol, 21.98% yield) as white solid. LCMS (ESI) m/z $[M+H]^+$=521.2. $^1H$ NMR (400 MHz, DMSO) δ=12.51 (br s, 1H), 9.31-9.28 (m, 1H), 8.68 (d, J=6.0 Hz, 2H), 8.39 (s, 1H), 8.33-8.25 (m, 2H), 8.07-8.01 (m, 2H), 7.87-7.80 (m, 2H), 7.77 (d, J=6.2 Hz, 3H), 7.65-7.56 (m, 1H), 4.26 (d, J=5.6 Hz, 2H), 3.54-3.48 (m, 1H), 1.19 (d, J=6.8 Hz, 6H) ppm.

Example 46. Preparation of 4-amino-N-(2-((4-(3-(aminomethyl)phenyl)thiazol-2-yl)amino)-2-oxoethyl)-3-(isopropylsulfonyl)benzamide (Compound 41)

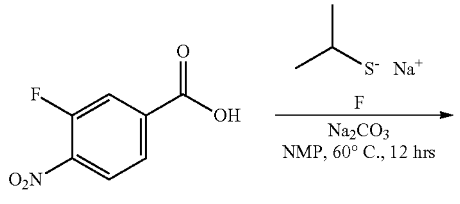

A

-continued

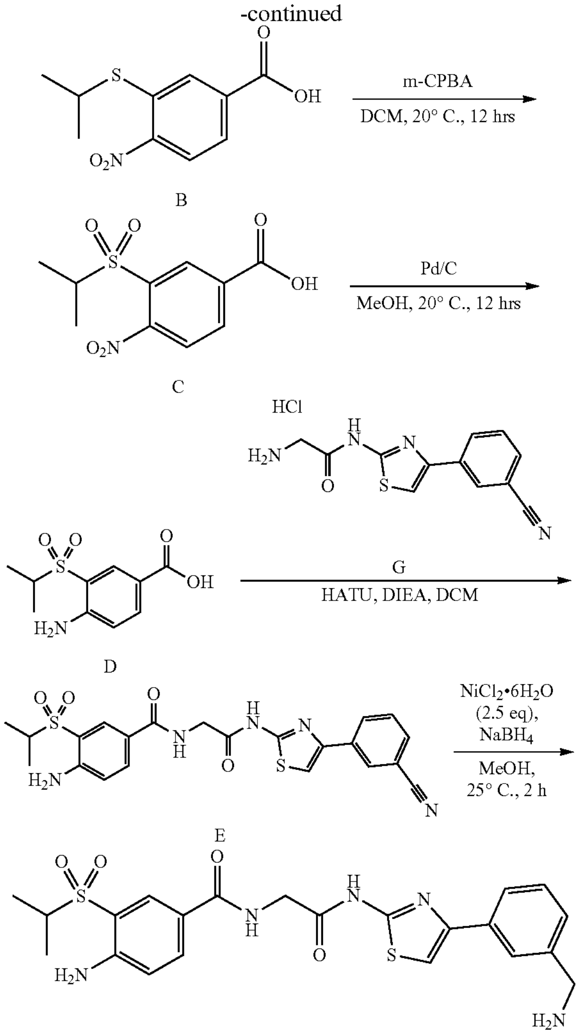

Compound 41

Step 1: Preparation of 3-(isopropylthio)-4-nitrobenzoic acid (Intermediate B)

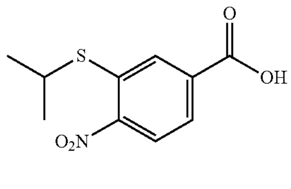

B

A solution of 3-fluoro-4-nitro-benzoic acid (2 g, 10.80 mmol), $Na_2CO_3$ (1.15 g, 10.80 mmol) and sodium propane-2-thiolate (1.27 g, 12.97 mmol) in NMP (20 mL) was stirred at 60° C. for 12 hours. The reaction solution was cooled to 20° C. and then water (30 mL) was added. The reaction solution was extracted with ethyl acetate (2×40 mL). The organic layers were discarded and the aqueous layer was treated with 1 N HCl solution to pH=3. A precipitate was formed. The precipitate was collected by filtration, washed with EA and dried under reduced pressure to afford Intermediate B (2.4 g, 8.06 mmol, 74.58% yield) as a yellow solid. LCMS (ESI) m/z $[M+H]^+$=242.0. $^1H$ NMR (400 MHz, DMSO-$d_6$) δ=13.82 (br s, 1H), 8.19 (d, J=8.8 Hz, 1H), 8.09 (d, J=1.2 Hz, 1H), 7.87-7.86 (m, 1H), 3.75-3.74 (m, 1H), 1.32 (s, 3H), 1.30 (s, 3H) ppm.

Step 2: Preparation of 3-(isopropylsulfonyl)-4-nitrobenzoic acid (Intermediate C)

C

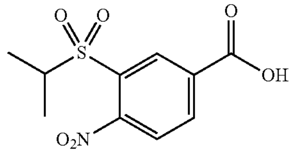

To a solution of Intermediate B (617.28 mg, 2.07 mmol) in DCM (5 mL) was added m-CPBA (1.07 g, 5.27 mmol, 85% purity). The reaction was stirred at 20° C. for 12 hrs. The reaction mixture was diluted with water (5 mL) and extracted with DCM (3×8 mL). The combined organic layers were washed with brine (10 mL), dried over $Na_2SO_4$, filtered and concentrated in vacuum. The residue was purified by silica gel chromatography ($SiO_2$, PE:EA=20:1 to 2:1) and concentrated to afford Intermediate C (180 mg, 658.71 μmol, 31.78% yield) as a white solid. LCMS (ESI) m/z $[M+H]^+$=274.0. $^1H$ NMR (400 MHz, DMSO-$d_6$) δ=14.10 (br s, 1H), 8.47-8.46 (m, 1H), 8.43 (d, J=1.6 Hz, 1H), 8.23 (d, J=8.0 Hz, 1H), 3.82-3.81 (m, 1H), 1.29 (s, 3H), 1.27 (s, 3H) ppm.

Step 3: Preparation of 4-amino-3-(isopropylsulfonyl)benzoic acid (Intermediate D)

D

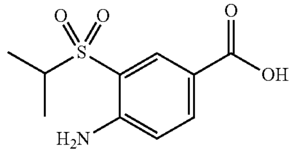

To a solution of Intermediate C (160 mg, 585.52 μmol) in MeOH (1 mL) was added Pd/C (80 mg, 10% purity) under $N_2$ atmosphere. The suspension was degassed and purged with $H_2$ for 3 times. The mixture was stirred under $H_2$ (15 Psi) at 20° C. for 12 hr. The reaction mixture filtered through a piece of celite. The filter cake was washed with methanol (3×5 mL). The combined organic layers were concentrated under reduced pressure to afford Intermediate D (130 mg, 432.84 μmol, 73.92% yield) as a white solid. LCMS (ESI) m/z $[M+H]^+$=244.1. $^1H$ NMR (400 MHz, DMSO-$d_6$) δ=13.36-11.59 (m, 1H), 8.04 (d, J=2.0 Hz, 1H), 7.85-7.84 (m, 1H), 6.89 (d, J=8.8 Hz, 1H), 6.76 (br s, 2H), 3.41-3.32 (m, 1H), 1.18 (s, 3H), 1.17 (s, 3H) ppm.

Step 4: Preparation of 4-amino-N-(2-((4-(3-cyanophenyl)thiazol-2-yl)amino)-2-oxoethyl)-3-(isopropylsulfonyl)benzamide Intermediate E)

E

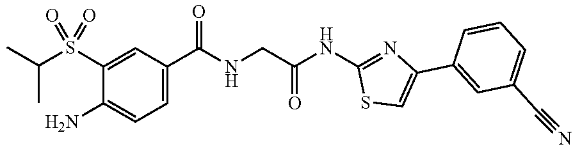

To a solution of Intermediate D (100 mg, 411.05 μmol) in DMF (1.2 mL) was added HATU (234.44 mg, 616.58 μmol) and DIEA (286.38 μL, 1.64 mmol). The mixture was stirred at this temperature for 15 min. Then 2-amino-N-[4-(3-cyanophenyl)thiazol-2-yl]acetamide (prepared according to the method in Example 47) (121.16 mg, 411.05 μmol, HCl salt) was added to the solution. The reaction was stirred at 30° C. for 1.75 hrs. The reaction solution was diluted with water (2 mL) and extracted with EA (3×3 mL). The combined organic layers were washed with brine (6 mL) dried over $Na_2SO_4$, filtered and concentrated under reduced pressure to give a residue. The residue was purified by reverse phase-HPLC (FA condition) and lyophilized to afford Intermediate E (90 mg, 184.26 μmol, 44.83% yield) as a white solid. LCMS (ESI) m/z $[M+H]^+$=484.2.

Step 5: Preparation of 4-amino-N-(2-((4-(3-(aminomethyl)phenyl)thiazol-2-yl)amino)-2-oxoethyl)-3-(isopropylsulfonyl)benzamide (Compound 41)

Compound 41

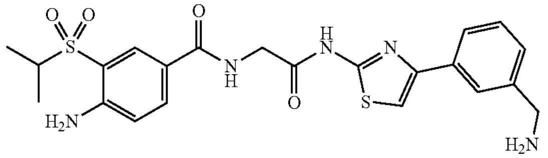

To a solution of Intermediate E (50 mg, 103.40 μmol) in MeOH (0.5 mL) was added dichloronickel;hexahydrate (61.44 mg, 258.50 μmol) and $NaBH_4$ (39.12 mg, 1.03 mmol) at 0° C. The reaction was stirred at 20° C. for 2 hrs. Water (0.1 mL) was added to the reaction mixture. The mixture was filtered through a piece of celite. The filter cake was washed with DMSO (1 mL) and MeOH (3×5 mL). The combined filtrate was concentrated under reduced pressure to give a residue. The residue was purified by reverse phase-HPLC (FA condition) and lyophilized to afford Compound 41 (11 mg, 20.61 μmol, 19.94% yield, FA salt) as a white solid. LCMS (ESI) m/z $[M+H]^+$=488.3. $^1H$ NMR (400 MHz, methanol-$d_4$) δ=8.51 (br s, 1H), 8.19 (d, J=2.4 Hz, 1H), 8.00-7.99 (m, 2H), 7.91-7.90 (m, 1H), 7.52-7.46 (m, 1H), 7.45 (s, 1H), 7.40 (d, J=7.6 Hz, 1H), 6.91 (d, J=8.4 Hz, 1H), 4.27 (s, 2H), 4.16 (s, 2H), 3.41-3.40 (m, 1H), 1.31 (s, 3H), 1.29 (s, 3H) ppm.

Example 47. Preparation of 4-amino-N-(2-((4-(3-cyanophenyl)thiazol-2-yl)amino)-2-oxoethyl)-3-(isopropylsulfonyl)benzamide (Compound 42)

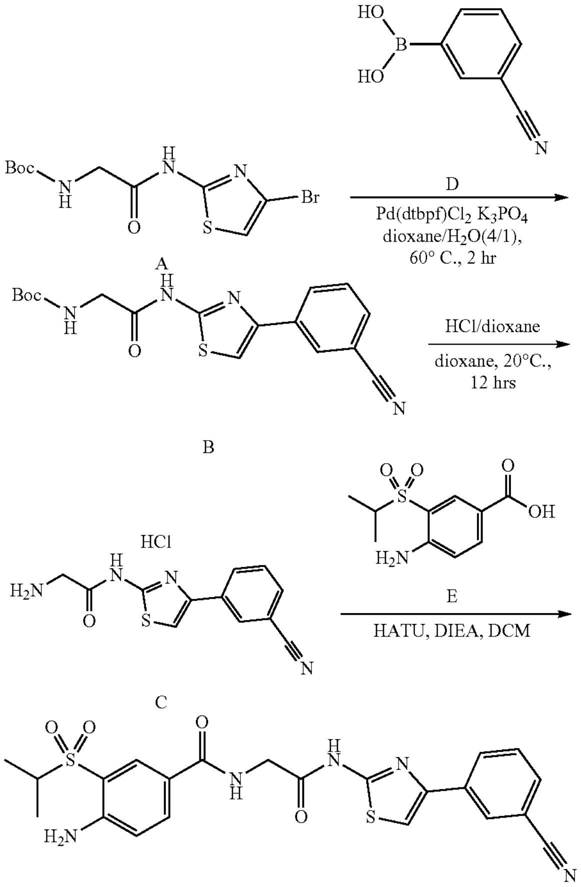

Compound 42

Step 1: Preparation of tert-butyl (2-((4-(3-cyanophenyl)thiazol-2-yl)amino)-2-oxoethyl)carbamate (Intermediate B)

B

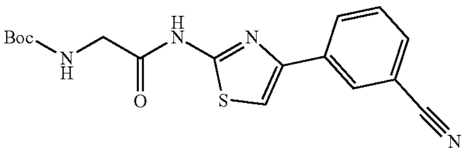

To a solution of tert-butyl N-[2-[(4-bromothiazol-2-yl)amino]-2-oxo-ethyl]carbamate (prepared according to the method in Example 4) (200 mg, 594.88 μmol) in dioxane (2 mL) and $H_2O$ (0.5 mL) was added (3-cyanophenyl)boronic acid (131.12 mg, 892.31 μmol), $K_3PO_4$ (378.82 mg, 1.78 mmol) and ditert-butyl(cyclopentyl)phosphane;dichloropalladium;iron (38.77 mg, 59.49 μmol). The reaction mixture was stirred at 120° C. for 2 hr under $N_2$. The mixture was filtered and the filtrate was concentrated in vacuum to give a residue. The residue was purified by reversed phase HPLC (FA) and lyophilized to afford Intermediate B (178 mg, 471.80 μmol, 79.31% yield) as yellow gum. LCMS (ESI) m/z $[M+H]^+$=359.1. $^1H$ NMR (400 MHz, chloroform-d) δ=9.81 (br s, 1H), 8.16 (s, 1H), 8.03 (d, J=8.0 Hz, 1H), 7.63-7.58 (m, 1H), 7.55-7.48 (m, 1H), 7.25 (s, 1H), 5.24 (br s, 1H), 4.11 (d, J=6.4 Hz, 2H), 1.53 (s, 9H) ppm.

Step 2: Preparation of 2-amino-N-(4-(3-cyanophenyl)thiazol-2-yl)acetamide hydrochloride (Intermediate C)

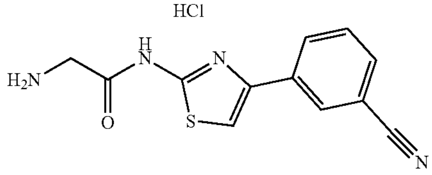 [SMILES: Cl ; N#Cc1cccc(-c2csc(NC(=O)CN)n2)c1]

To a solution of Intermediate B (170 mg, 474.31 μmol) in dioxane (2 mL) was added HCl/dioxane (4 M, 2 mL). The reaction was stirred at 20° C. for 12 hrs. The reaction mixture was concentrated in vacuum to afford Intermediate C (138 mg, crude, HCl salt) as a white solid, which was used into next step directly. LCMS (ESI) m/z $[M+H]^+$=259.1. $^1H$ NMR (400 MHz, deuterium oxide) δ=7.84 (m, 2H), 7.56 (br d, J=7.6 Hz, 1H), 7.44 (m, 1H), 7.32 (s, 1H), 4.12 (s, 2H), 4.17-4.08 (m, 1H) ppm.

Step 3: Preparation of 4-amino-N-(2-((4-(3-cyanophenyl)thiazol-2-yl)amino)-2-oxoethyl)-3-(isopropylsulfonyl)benzamide (Compound 42)

Compound 42

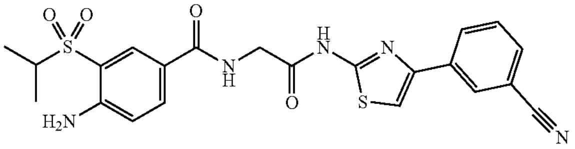

To a solution of 4-amino-3-isopropylsulfonyl-benzoic acid (prepared according to the method in Example 47) (100 mg, 411.05 μmol) in DMF (1.2 mL) was added HATU (234.44 mg, 616.58 μmol) and DIEA (286.38 μL, 1.64 mmol). The mixture was stirred at this temperature for 15 min. Then Intermediate C (121.16 mg, 411.05 μmol, HCl salt) was added. The reaction was stirred at 30° C. for 1.75 hrs. The reaction solution was diluted with water (2 mL) and extracted with EA (3x3 mL). The combined organic layers were washed with brine (6 mL), dried over anhydrous $Na_2SO_4$, filtered and concentrated under reduced pressure to give a residue. The residue was purified by reverse phase-HPLC (FA condition) and lyophilized to give Compound 42 (90 mg, 184.26 μmol, 44.83% yield) as a white solid. LCMS (ESI) m/z $[M+H]^+$=484.1. $^1H$ NMR (400 MHz, DMSO-$d_6$) δ=12.54-12.33 (m, 1H), 8.81-8.80 (m, 1H), 8.33-8.32 (m, 1H), 8.24-8.23 (m, 1H), 8.08 (d, J=2.4 Hz, 1H), 7.90-7.85 (m, 2H), 7.80-7.79 (m, 1H), 7.69-7.63 (m, 1H), 6.90 (d, J=8.8 Hz, 1H), 6.61 (s, 2H), 4.15 (d, J=5.6 Hz, 2H), 3.42-3.36 (m, 1H), 1.21 (s, 3H), 1.19 (s, 3H) ppm.

Example 48. Preparation of 3-(2-(2-(3-(isopropylsulfonyl)benzamido)acetamido)thiazol-4-yl)benzoic acid (Compound 43)

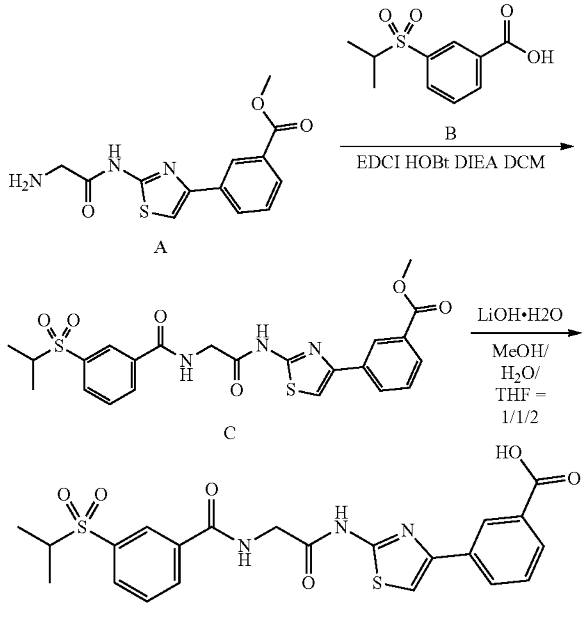

Step 1: Preparation of methyl 3-(2-(2-(3-(isopropylsulfonyl)benzamido)acetamido)thiazol-4-yl)benzoate (Intermediate C)

C

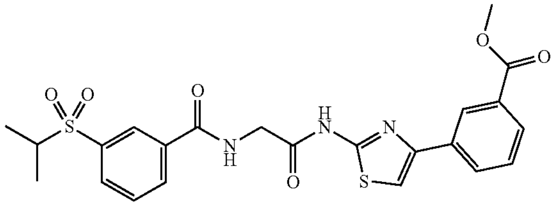

To a solution of methyl 3-[2-[(2-aminoacetyl)amino]thiazol-4-yl]benzoate (60 mg, 183.05 μmol, HCl) in DCM (1 mL) was added 3-isopropylsulfonylbenzoic acid (41.78 mg, 183.05 μmol), DIEA (159.41 μL, 915.23 μmol), then EDCl (52.63 mg, 274.57 μmol) and HOBt (37.10 mg, 274.57 μmol) was added to the mixture, and the mixture was stirred at 30° C. for 2 hr. The reaction mixture was concentrated under reduced pressure to give a residue. The residue was purified by reversed-phase (0.1% FA condition) and lyophilized to afford Intermediate C (60 mg, 117.23 μmol, 64% yield) as a white solid. LCMS (ESI) m/z [M+H]+=502.1. $^1$H NMR (400 MHz, DMSO-$d_6$) δ=12.55 (brs, 1H), 9.30-9.27 (m, 1H), 8.55 (s, 1H), 8.38 (s, 1H), 8.27-8.25 (m, 1H), 8.17-8.15 (m, 1H), 8.05-8.03 (m, 1H), 7.91-7.89 (m, 1H), 7.84-7.82 (m, 2H), 7.79-7.59 (m, 1H), 4.24 (d, J=5.6 Hz, 2H), 3.88 (s, 3H), 3.50-3.48 (m, 1H), 1.19 (d, J=6.8 Hz, 6H) ppm.

Step 2: Preparation of 3-(2-(2-(3-(isopropylsulfonyl)benzamido)acetamido)thiazol-4-yl)benzoic acid (Compound 43)

Compound 43

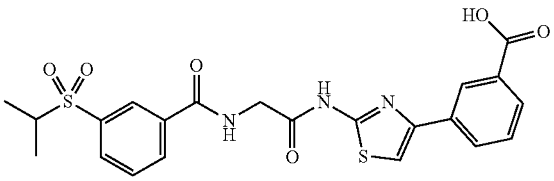

To a solution of Intermediate C (60 mg, 119.62 μmol) in MeOH/$H_2O$/THF=1/1/2 (1 mL) was added LiOH·$H_2O$ (10.04 mg, 239.25 μmol). The mixture was stirred at 30° C. for 1 hr. To the reaction mixture was added HCl (1 N) to adjust the pH=4, white precipitate was formed. The precipitate was collected by filtration and dried in vacuum to give Compound 43 (35.68 mg, 72.94 μmol, 61% yield) as a white solid. LCMS (ESI) m/z $[M+H]^+$=488.0. $^1$H NMR (400 MHz, DMSO-$d_6$) δ=13.06 (br s, 1H), 12.55 (br s, 1H), 9.34-9.32 (m, 1H), 8.55 (s, 1H), 8.39 (s, 1H), 8.29-8.27 (d, J=8.0 Hz, 1H), 8.14-8.13 (m, 1H), 8.05-8.04 (m, 1H), 7.90 (d, J=7.6 Hz, 1H), 7.88-7.82 (m, 1H), 7.78 (s, 1H), 7.56 (m, 1H), 4.25-4.24 (m, 2H), 3.56-3.46 (m, 1H), 1.20 (d, J=6.8 Hz, 6H) ppm.

Example 49. Preparation of N-(2-((4-(3-cyanophenyl)thiazol-2-yl)amino)-2-oxoethyl)-3-(isopropylsulfonyl)benzamide (Compound 44)

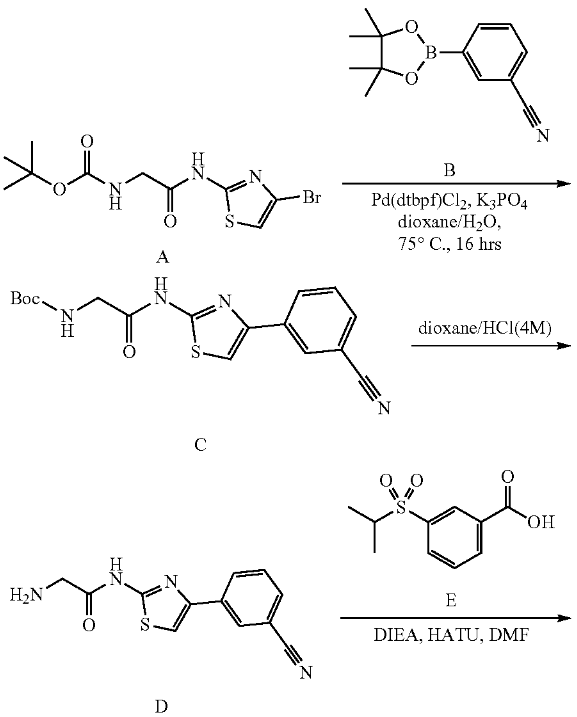

-continued

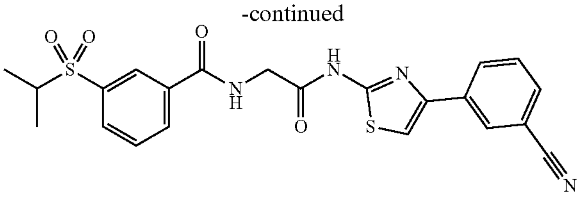

Compound 44

Step 1: Preparation of tert-butyl (2-((4-(3-cyanophenyl)thiazol-2-yl)amino)-2-oxoethyl)carbamate (Intermediate C)

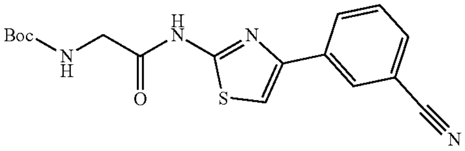

C

To a mixture of tert-butyl N-[2-[(4-bromothiazol-2-yl)amino]-2-oxo-ethyl]carbamate (prepared according to the method in Example 4) (150 mg, 446.16 μmol) and 3-(4,4,5,5-tetramethyl-1,3,2-dioxaborolan-2-yl)benzonitrile (122.65 mg, 535.39 μmol) in dioxane (3 mL) and $H_2O$ (0.5 mL) was added $K_3PO_4$ (284.11 mg, 1.34 mmol) and ditert-butyl(cyclopentyl)phosphane;dichloropalladium;iron (58.16 mg, 89.23 μmol) in one portion at 25° C. under $N_2$. The mixture was stirred at 120° C. for 1 hr. The mixture was concentrated. The residue was purified by reverse phase column (FA) and lyophilized to afford Intermediate C (110 mg, 306.91 μmol, 68.79% yield) as a yellow solid. LCMS (ESI) m/z $[M+H]^+$=359.0. $^1$H NMR (400 MHz, $CDCl_3$) δ=9.82 (br s, 1H), 8.16 (s, 1H), 8.03 (d, J=7.8 Hz, 1H), 7.61-7.59 (m, 1H), 7.53-7.49 (m, 1H), 7.24 (s, 1H), 5.25-5.22 (m, 1H), 4.11 (d, J=5.6 Hz, 2H), 1.52 (s, 9H) ppm.

Step 2: Preparation of 2-amino-N-(4-(3-cyanophenyl)thiazol-2-yl)acetamide (Intermediate D)

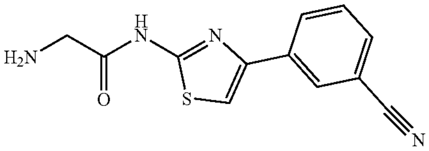

D

To a mixture of Intermediate C (110 mg, 306.91 μmol) in dioxane (1 mL) was added HCl/dioxane (4 M, 383.63 μL) in one portion at 25° C. The mixture was stirred at 25° C. for 12 hours. The suspension was filtered and the filter cake was dried in vacuum to give Intermediate D (60 mg, 196.00 μmol, 63.86% yield, HCl salt) as yellow solid. LCMS (ESI) m/z $[M+H]^+$=259.1.

Step 3: Preparation of N-(2-((4-(3-cyanophenyl)thiazol-2-yl)amino)-2-oxoethyl)-3-(isopropylsulfonyl)benzamide (Compound 44)

Compound 44

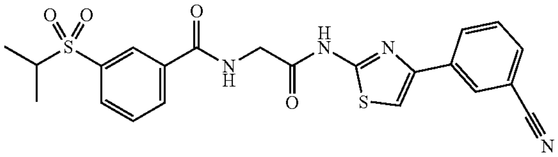

To a mixture of 3-isopropylsulfonylbenzoic acid (prepared according to the method in Example 17) (37.28 mg, 163.34 μmol) in DMF (0.5 mL) was added DIEA (63.33 mg, 490.01 μmol, 85.35 μL) and HATU (93.16 mg, 245.00 μmol) in one portion at 25° C. The mixture was stirred at 25° C. for 30 min, then Intermediate D (50 mg, 163.34 μmol, HCl salt) was added. The mixture was stirred at 25° C. for 0.5 hours and then concentrated in vacuum. The residue was purified by reverse phase column (FA) and lyophilized to afford Compound 44 (47.33 mg, 99.97 μmol, 61.21% yield) as a white solid. LCMS (ESI) m/z $[M+H]^+$=469.1. $^1$H NMR (400 MHz, DMSO-$d_6$) δ=9.29 (br s, 1H), 8.35 (d, J=19.4 Hz, 2H), 8.25-8.22 (m, 2H), 8.05 (J=7.8 Hz, 1H), 7.88 (s, 1H), 7.82-7.78 (m, 2H), 7.78-7.66 (m, 1H), 4.25 (d, J=5.6 Hz, 2H), 3.50-3.48 (m, 1H), 1.19 (d, J=6.8 Hz, 6H) ppm.

Example 50. Preparation of N-(2-((4-(3-(2-((dimethylamino)methyl)pyridin-4-yl)phenyl)thiazol-2-yl)amino)-2-oxoethyl)-3-(isopropylsulfonyl)benzamide (Compound 45)

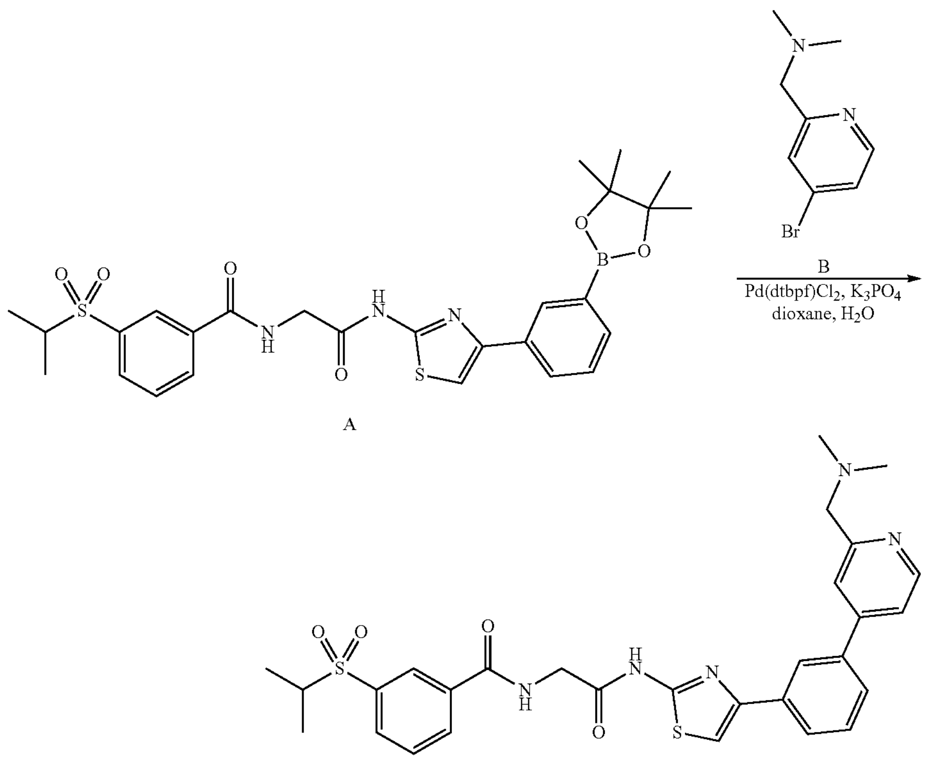

A

Compound 45

A mixture of 3-isopropylsulfonyl-N-[2-oxo-2-[[4-[3-(4,4,5,5-tetramethyl-1,3,2-dioxaborolan-2-yl)phenyl]thiazol-2-yl]amino]ethyl]benzamide (prepared according to the method in Example 26) (60 mg, 105.36 μmol), 1-(4-bromo-2-pyridyl)-N,N-dimethyl-methanamine (prepared according to the method in FG-A1629) (27.19 mg, 126.43 μmol), ditert-butyl(cyclopentyl)phosphane;dichloropalladium;iron (6.87 mg, 10.54 μmol) and $K_3PO_4$ (22.36 mg, 105.36 μmol) in dioxane (2 mL) and $H_2O$ (0.5 mL) was degassed and purged with $N_2$ for 3 times, and then the mixture was stirred at 80° C. for 2 hr under $N_2$ atmosphere. Water (20 mL) was added and the reaction mixture was extracted with EA (50 mL×2). The combined organic layers were washed with brine (20 mL), dried over $Na_2SO_4$, filtered and concentrated under reduced pressure to give a residue. The crude product was purified by reversed-phase HPLC (0.1% FA condition) and lyophilized to give Compound 45 (20 mg, 32.06 μmol, 30.43% yield, 100% purity, FA) as a yellow solid. LCMS (ESI) m/z $[M+H]^+$=578.3. $^1H$ NMR (400 MHz, DMSO-$d_6$) δ=12.54 (s, 1H), 9.31-928 (m, 1H), 8.58 (d, J=5.2 Hz, 1H), 8.38 (s, 1H), 8.28-8.26 (m, 2H), 8.18 (s, 1H), 8.18 (s, 1H), 8.05 (d, J=8.0 Hz, 1H), 8.01 (d, J=8.0 Hz, 1H) 7.84-7.80 (m, 2H), 7.74 (s, 2H), 7.64-7.57 (m, 2H), 4.25 (d, J=5.6 Hz, 2H), 3.61 (s, 2H), 2.24 (s, 6H), 1.19 (d, J=6.4 Hz, 6H) ppm.

Example 51. Preparation of 3-(isopropylsulfonyl)-4-methyl-N-(2-((4-(3-(1-methyl-1H-pyrazol-3-yl)phenyl)thiazol-2-yl)amino)-2-oxoethyl)benzamide (Compound 46)

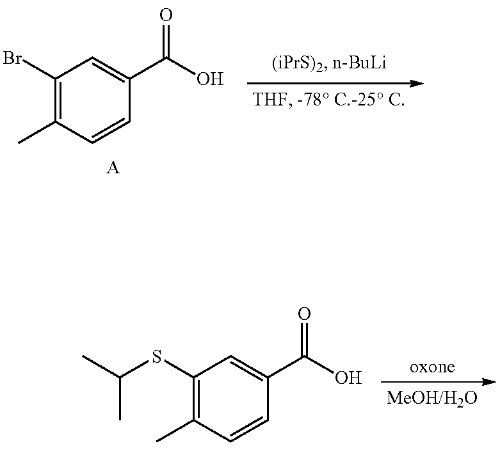

A

B

-continued

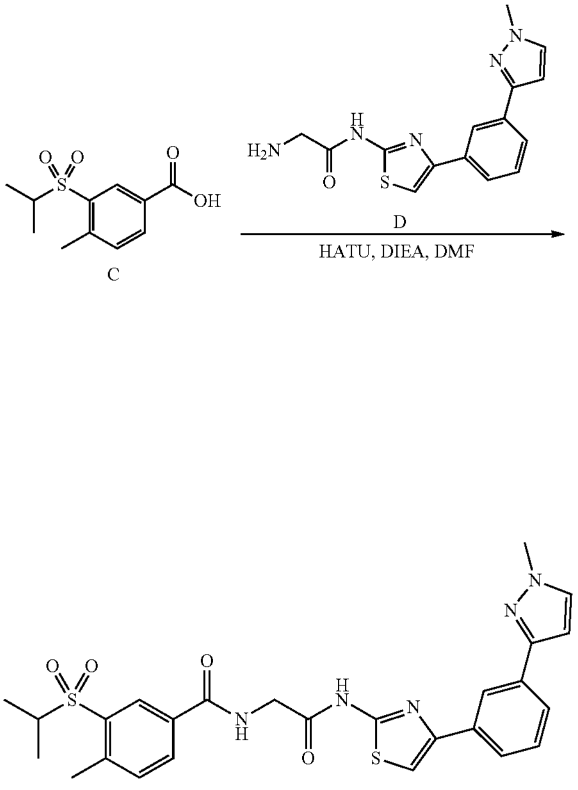

Compound 46

Step 1: Preparation of 3-(isopropylthio)-4-methylbenzoic acid (Intermediate B)

B

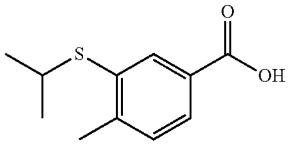

To a solution of 3-bromo-4-methyl-benzoic acid (1 g, 4.65 mmol) in THF (25 mL) was added n-BμLi (2.5 M, 4.09 mL) dropwise at −78° C. under $N_2$ and the mixture was stirred at −78° C. for 30 min. Then 2-isopropylsulfanylpropane (549.84 mg, 4.65 mmol, 675.56 μL) dissolved in THF (1 mL) was added dropwise at −78° C. The resulting mixture was allowed to stir at −78° C. for 30 min and then at 25° C. for another 30 min. The reaction mixture was diluted with 1 N NaOH (30 mL) and washed with EtOAc (40 mL). The organic layer was discarded and the aqueous layer was adjusted pH to ~3 with 4M HCl and then extracted with EtOAc (40 mL×2). The combined organic phase was washed with brine, dried over anhydrous $Na_2SO_4$, filtered and concentrated under vacuum to give Intermediate B (900 mg, 4.28 mmol, 92.03% yield) as a yellow solid, which was used for the next step without further purification. LCMS (ESI) m/z $[M+H]^+$=211.2.

Step 2: Preparation of 3-(isopropylsulfonyl)-4-methylbenzoic acid (Intermediate C)

C

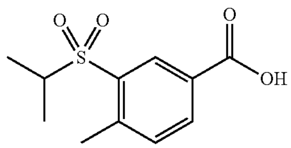

To a solution of Intermediate B (200 mg, 951.06 μmol) in MeOH (1 mL) was added Oxone (877.02 mg, 1.43 mmol) in $H_2O$ (1 mL) at 0° C. and then the mixture was stirred at 25° C. for 2 hr. The mixture was poured into saturated $Na_2SO_3$ (50 mL) and stirred for 30 min and then was extracted with EtOAc (30 mL). The organic layer was discarded and the aqueous layer was adjusted pH to ~4 with 2N HCl and then extracted with EtOAc (40 mL×2). The combined organic phase was washed with brine, dried over anhydrous $Na_2SO_4$, filtered and concentrated under vacuum to give Intermediate C (160 mg, 621.73 μmol, 65.37% yield) as a yellow solid, which was used for the next step without further purification. LCMS (ESI) m/z $[M+H]^+$=242.9.

Step 3: Preparation of 3-(isopropylsulfonyl)-4-methyl-N-(2-((4-(3-(1-methyl-1H-pyrazol-3-yl)phenyl)thiazol-2-yl)amino)-2-oxoethyl)benzamide (Compound 46)

Compound 46

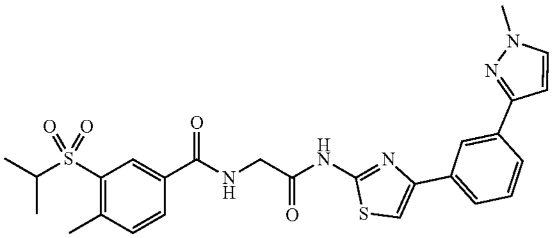

To a solution of Intermediate C (80 mg, 330.18 μmol) in DCM (1 mL) was added HATU (150.65 mg, 396.22 μmol) and DIEA (128.02 mg, 990.54 μmol, 172.53 μL) and the mixture was stirred at 25° C. for 10 min. Then 2-amino-N-[4-[3-(1-methylpyrazol-3-yl)phenyl]thiazol-2-yl]acetamide (115.51 mg, 330.18 μmol, HCl salt) was added and the mixture was stirred at 25° C. for another 1 hr. Water (10 mL) was added and the mixture was extracted with EtOAc (10 mL×2). The combined organic phase was washed with brine, dried over anhydrous $Na_2SO_4$, filtered and concentrated under vacuum. The residue was purified by Prep-HPLC (column: Phenomenex luna C18 150×25 10 u; mobile phase: [water (0.1% TFA)-ACN]; B %: 33%-63%, 10 min) and lyophilized to give Compound 46 (87.88 mg, 163.45 μmol, 49.50% yield) as a white solid. LCMS (ESI) m/z $[M+H]^+$=538.0. $^1H$ NMR (400 MHz, DMSO) δ=8.34-8.33 (m, 1H), 7.96 (d, J=1.6 Hz, 1H), 7.85-7.83 (m, 1H), 7.72-7.67 (m, 2H), 7.62 (d, J=1.6 Hz, 1H), 7.45-7.41 (m, 2H), 7.34 (d, J=7.6 Hz, 1H), 6.66 (d, J=2.0 Hz, 1H), 4.31 (s, 2H), 3.95 (s, 3H), 3.56-3.49 (m, 1H), 2.44 (s, 3H), 1.32 (d, J=6.4 Hz, 6H) ppm.

Example 52. Preparation of 3-(isopropylsulfonyl)-N-(2-oxo-2-((4-(3-(pyridin-4-yl)phenyl)thiazol-2-yl)amino)ethyl)benzamide (Compound 47)

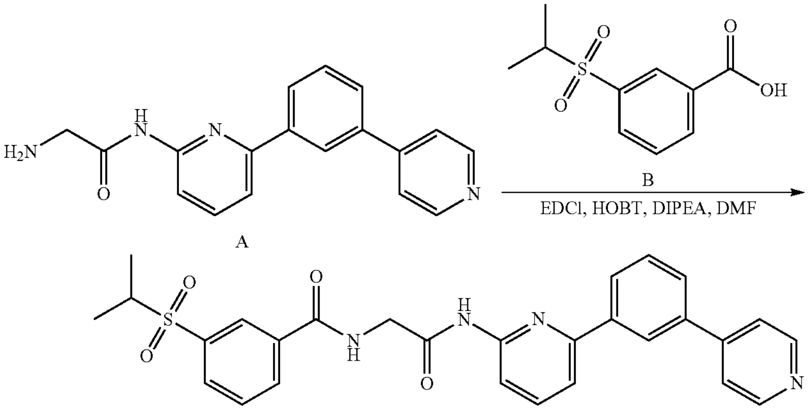

Compound 47

To a solution of 3-(isopropylsulfonyl)benzoic acid (30 mg, 131.43 μmol) and 2-amino-N-(6-(3-(pyridin-4-yl)phenyl)pyridin-2-yl)acetamide (44.79 mg, 131.43 μmol, HCl salt) in DMF (1 mL) was added EDCl (50.39 mg, 262.85 μmol), HOBt (35.52 mg, 262.85 μmol) and DIEA (84.93 mg, 657.13 μmol, 114.46 μL) at 25° C. The mixture was stirred at 25-30° C. for 16 hrs. The reaction mixture was concentrated in vacuum. The residue was purified by reversed-phase HPLC (0.1% $NH_3 \cdot H_2O$) and lyophilized to give Compound 47 (35.60 mg, 67.54 μmol, 51.39% yield) as a white solid. LCMS (ESI) m/z $[M+H]^+$=515.4. $^1H$ NMR (400 MHz, MeOD) δ=8.63 (d, J=6.0 Hz, 2H), 8.48-8.47 (m, 2H), 8.28-8.27 (m, 1H), 8.15-8.14 (m, 1H), 8.10-8.09 (m, 1H), 7.88-7.87 (m, 1H), 7.84-7.76 (m, 5H), 7.74-7.73 (m, 1H), 7.66-7.60 (m, 1H), 4.34 (br s, 2H), 3.40-3.36 (m, 1H), 1.28 (d, J=6.8 Hz, 6H) ppm.

Example 53. Preparation of tert-butyl N-[2-[[4-(3-bromophenyl)thiazol-2-yl]amino]-2-oxo-ethyl]carbamate (Intermediate D) and 2-amino-N-(4-(3-bromophenyl)thiazol-2-yl)acetamide (Intermediate E)

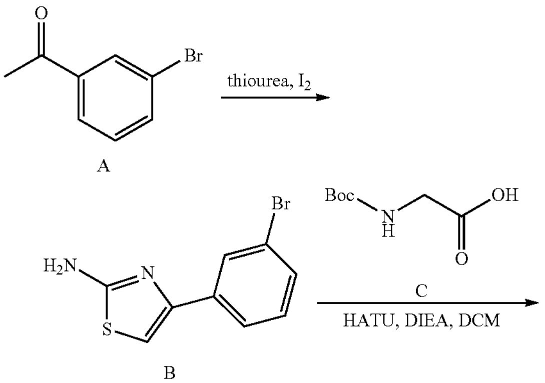

-continued

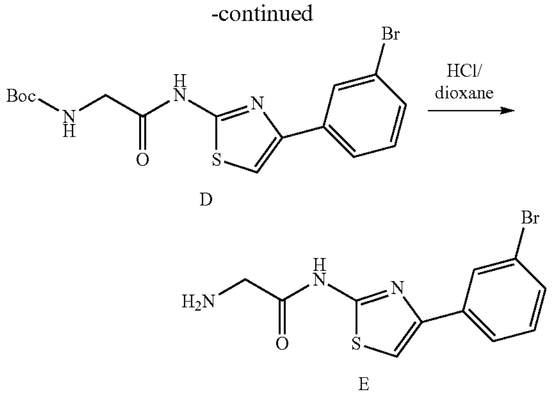

Step 1: Preparation of 4-(3-bromophenyl)thiazol-2-amine (Intermediate B)

B

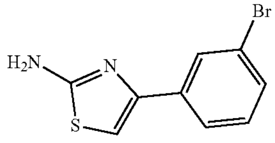

To a mixture of 1-(3-bromophenyl)ethanone (473 g, 2.38 mol, 313.25 mL) and thiourea (361.78 g, 4.75 mol) was added 12 (603.14 g, 2.38 mol, 478.68 mL, 1 eq). The mixture was stirred at 110° C. for 16 hr. After cooling, the reaction mixture was triturated with MTBE (5 L), and then filtered to remove any unreacted iodine and acetophenone. The filter cake was put in ice water (4 L) and treated with 25% $NH_3 \cdot H_2O$ to pH=9-10. The suspension was stirred at 25° C. for 15 min, then filtered and washed with water (1 L) to give wet solid. The wet solid was dissolved in EA (4 L) and washed with sat.$NaHCO_3$ (1 L×2) and brine (1 L). The EA layer was dried over $Na_2SO_4$, filtered and concentrated under reduced pressure to give a residue. The residue was triturated with PE/EA=100:1 (4 L) at 25° C. for 3 h, then the suspension was filtered, the filter cake was washed with PE (1 L) and dried in vacuum to give intermediate B (450 g, 1.69 mol, 71.20% yield, 95.93% purity) as a pink solid. LCMS (ESI) m/z [$^{79}$BrM+H$^+$]=254.9. $^1$H NMR (400 MHz, DMSO-$d_6$) δ=7.98-7.97 (m, 1H), 7.80-7.77 (m, 1H), 7.43-7.42 (m, 1H), 7.34-7.30 (m, 1H), 7.15 (s, 1H), 7.10 (s, 2H)

Step 2: Preparation of tert-butyl N-[2-[[4-(3-bromophenyl)thiazol-2-yl]amino]-2-oxo-ethyl]carbamate (Intermediate D)

D

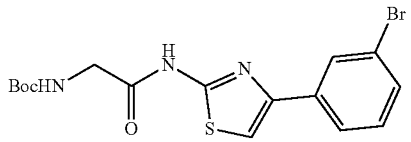

To a solution of 2-(tert-butoxycarbonylamino)acetic acid (82.40 g, 470.34 mmol), HATU (178.84 g, 470.34 mmol) and DIEA (151.97 g, 1.18 mol, 204.81 mL) in DCM (1000.00 mL) was added intermediate B (100.00 g, 391.95 mmol), the mixture was stirred at 30° C. for 16 hr. The reaction mixture was washed with sat. citric acid (500 mL×4) and brine (500 mL), dried over $Na_2SO_4$, filtered and concentrated under reduced pressure to give a residue. The residue was triturated with MeOH (200.0 mL), filtered and dried in vacuum to give Intermediate D (100 g, 241.89 mmol, 61.71% yield) as a white solid. LCMS (ESI) m/z [$^{81}$BrM+H]$^+$=413.8. $^1$H NMR (400 MHz, DMSO-$d_6$) δ=12.29 (s, 1H), 8.09-8.09 (m, 1H), 7.89 (d, J=7.6 Hz, 1H), 7.76 (s, 1H), 7.52-7.49 (m, 1H), 7.41-7.37 (m, 1H), 7.16-7.13 (m, 1H), 3.87-3.81 (m, 2H), 1.39 (s, 9H) ppm.

Step 3: Preparation of 2-amino-N-(4-(3-bromophenyl)thiazol-2-yl)acetamide (Intermediate E)

E

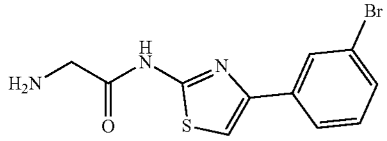

A mixture of intermediate D (10 g, 24.25 mmol) in HCl/dioxane (100 mL) was stirred at 30° C. for 2 hr. The reaction mixture was concentrated in vacuum to give intermediate E (8.4 g, crude, HCl) as a white solid, which was used for next step directly. LCMS (ESI) m/z [M+H]$^+$=313.8.

Example 54. Preparation of 2-amino-N-[4-[3-(4-pyridyl)phenyl]thiazol-2-yl]acetamide (Intermediate F)

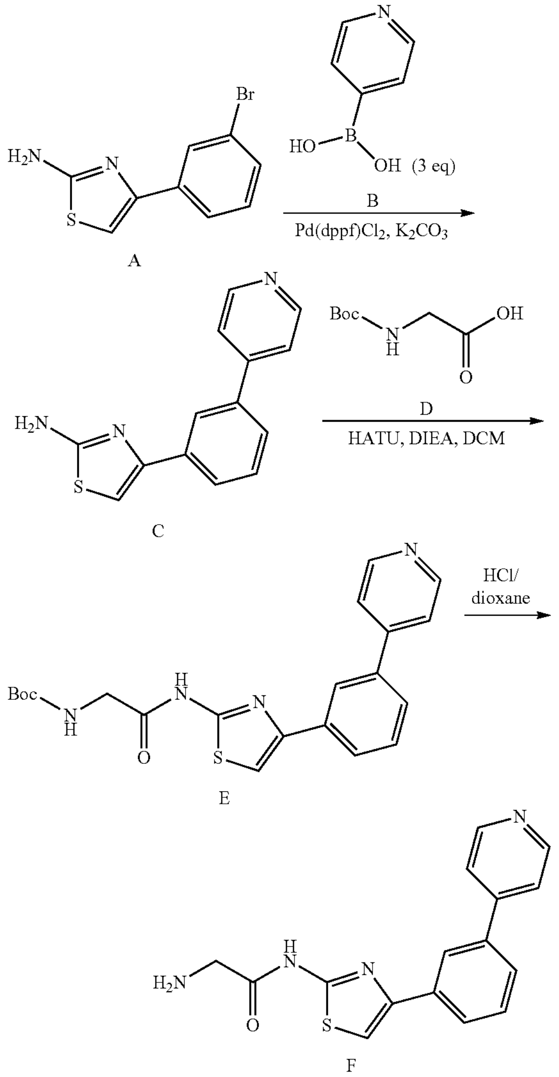

Step 1: Preparation of 4-[3-(4-pyridyl)phenyl]thiazol-2-amine (Intermediate C)

C

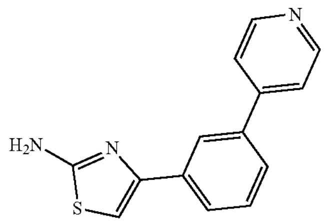

To a solution of 4-(3-bromophenyl)thiazol-2-amine (10 g, 39.20 mmol), 4-pyridylboronic acid (14.45 g, 117.59 mmol) and $K_2CO_3$ (16.25 g, 117.59 mmol) in dioxane (120 mL) and Water (30 mL) was added Pd(dppf)$Cl_2$ (1 g, 1.37 mmol) under $N_2$, the mixture was stirred at 100° C. for 4 hr. The reaction mixture was diluted with water (500 mL), extracted with EA (500 mL) and concentrated under reduced pressure to give a residue. The residue was purified by crystallization from DCM/MTBE=1:20 (200 mL) and filtered to give intermediate C (9.5 g, 36.33 mmol, 92.69% yield) as a brown solid. $^1$H NMR (400 MHz, DMSO-$d_6$) δ 8.66 (d, J=6.0 Hz, 2H), 8.19 (s, 1H), 7.90 (d, J=8.0 Hz, 1H), 7.76-7.70 (m, 2H), 7.68 (d, J=8.0 Hz, 1H), 7.52 (t, J=8.0 Hz, 1H), 7.21 (s, 1H), 7.11 (s, 2H) ppm. LCMS (ESI) m/z $[M+H]^+$=254.2.

Step 2: Preparation of tert-butyl N-[2-oxo-2-[[4-[3-(4-pyridyl)phenyl]thiazol-2-yl]amino]ethyl]carbamate (Intermediate E)

E

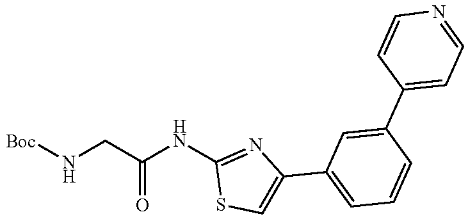

To a solution of 2-(tert-butoxycarbonylamino)acetic acid (9.85 g, 56.25 mmol), HATU (21.39 g, 56.25 mmol) and DIPEA (14.54 g, 112.51 mmol) in DCM (200 mL) was added Intermediate C (9.5 g, 37.50 mmol, 1 eq), the mixture was stirred at 30° C. for 16 hr. A precipitate was formed. The reaction mixture was filtered to give a yellow solid. The crude product was triturated with EA (300.0 mL) and MeOH (50.0 mL) and dried in vacuum to give Intermediate E (11 g, 25.89 mmol, 69.03% yield) as a white solid. LCMS (ESI) m/z $[M+H]^+$=411.3. $^1$H NMR (400 MHz, DMSO-$d_6$) δ 12.32 (br s, 1H), 8.69-8.67 (m, 2H), 8.30 (s, 1H), 8.01 (d, J=7.8 Hz, 1H), 7.83 (s, 1H), 7.80-7.76 (m, 3H), 7.64-7.60 (m, 1H), 7.20-7.15 (m, 1H), 3.88 (d, J=6.4 Hz, 2H), 1.44 (s, 9H) ppm.

Step 3: Preparation of 2-amino-N-[4-[3-(4-pyridyl)phenyl]thiazol-2-yl]acetamide (Intermediate F)

F

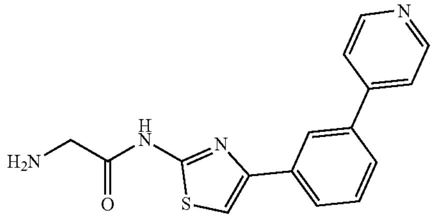

To a solution of Intermediate E (11 g, 26.80 mmol) in MeOH (20 mL) was added 4 M HCl/EtOAc (20 mL). The mixture was stirred at 20° C. for 2 hr. The reaction mixture was concentrated under reduced pressure to give a residue. The residue was purified by triturated with EA (200 mL) and MTBE (50 mL) and dried in vacuum to give intermediate F (12 g, HCl salt) a light yellow solid. LCMS (ESI) m/z $[M+H]^+$=311.3. $^1$H NMR (400 MHz, methanol-d4) δ8.92 (d, J=6.8 Hz, 2H), 8.52-8.47 (m, 3H), 8.22 (d, J=8.0 Hz, 1H), 7.94 (m, J=8.4 Hz, 1H), 7.75-7.66 (m, 2H), 4.04 (s, 2H) ppm.

Example 55. Preparation of (S)-3-(1-amino-2-methylpropan-2-yl)-N-(4-(methylthio)-1-oxo-1-((4-(3-(pyridin-4-yl)phenyl)thiazol-2-yl)amino)butan-2-yl)benzamide (Compound 48)

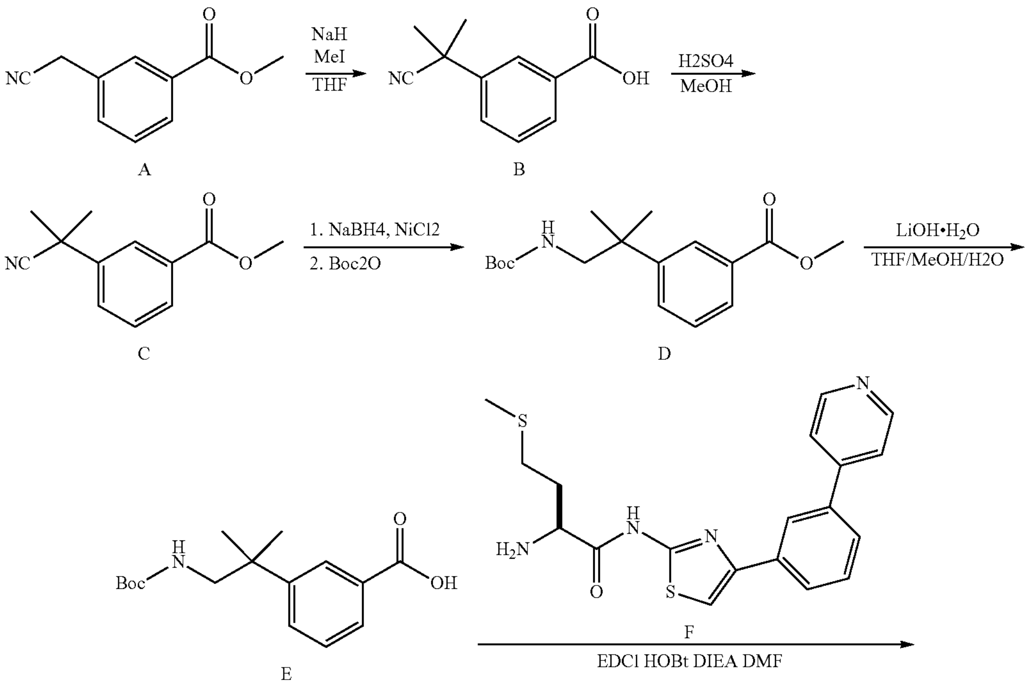

-continued

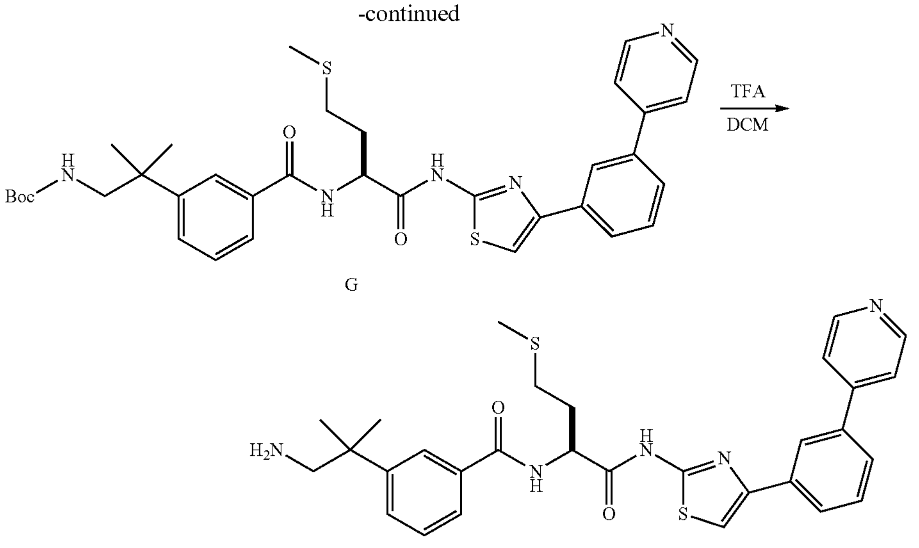

G

Compound 48

Step 1: Preparation of 3-(2-cyanopropan-2-yl)benzoic acid (Intermediate B)

B

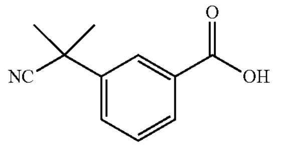

To a solution of methyl 3-(cyanomethyl)benzoate (5 g, 28.54 mmol) in THE (50 mL) was added NaH (3.42 g, 85.62 mmol, 60% purity) at 0° C. and stirred at 25° C. for 0.5 hr. Then MeI (12.15 g, 85.62 mmol, 5.33 mL) was added at 0° C. The mixture was stirred at 25° C. for 16 hr. The reaction mixture was quenched with $H_2O$ (50 mL) at 0° C. and extracted with EA (50 mL×2). The organic layer was discarded and the aqueous phase was added 1 N HCl to adjust the pH=5 and extracted with EA (50 mL×2). The combined organic layers were dried over anhydrous $Na_2SO_4$, filtered and concentrated under reduced pressure to give Intermediate B (5 g, 26.43 mmol, 92.59% yield) as colorless oil, which used directly in the next step. LCMS (ESI) m/z $[M+H]^+$ =190.1. $^1H$ NMR (400 MHz, $CDCl_3$) δ=8.20-8.10 (m, 1H), 8.10-8.08 (m, 1H), 7.81-7.79 (m, 1H), 7.56-7.52 (m, 1H), 1.84-1.75 (m, 6H) ppm.

Step 2: Preparation of methyl 3-(2-cyanopropan-2-yl)benzoate (Intermediate C)

C

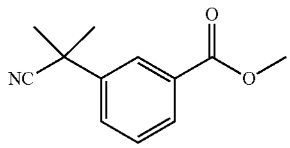

To a solution of Intermediate B (5 g, 26.43 mmol) in MeOH (50 mL) was added $H_2SO_4$ (920.00 mg, 9.38 mmol, 0.5 mL). The mixture was stirred at 60° C. for 8 hr. The reaction mixture was concentrated to remove MeOH and diluted with aq. $NaHCO_3$ (20 mL) and extracted with EA (20 mL×2). The combined organic layers were dried over anhydrous $Na_2SO_4$, filtered and concentrated under reduced pressure to give the residue. The residue was purified by flash silica gel chromatography (ISCO; 80 g SepaFlash Silica Flash Column, Eluent of 0~50% Ethylacetate/Petroleum ether gradient 60 mL/min) and concentrated to afford Intermediate C (5 g, 24.60 mmol, 93.10% yield) as colorless oil. LCMS (ESI) m/z $[M+H]^+$=204.1. $^1H$ NMR (400 MHz, $CDCl_3$) δ=8.12-8.01 (m, 1H), 8.01-7.99 (m, 1H), 7.52-7.50 (m, 1H), 7.48-7.46 (m, 1H), 3.94 (s, 3H), 1.76 (s, 6H) ppm.

Step 3: Preparation of methyl 3-(1-((tert-butoxycarbonyl)amino)-2-methylpropan-2-yl)benzoate (Intermediate D)

D

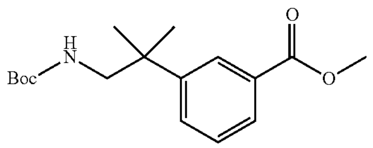

To a solution of Intermediate C (3 g, 14.76 mmol) in MeOH (30 mL) was added $NiCl_2·6H_2O$ (8.77 g, 36.90 mmol) and $NaBH_4$ (5.58 g, 147.61 mmol) at 0° C. and stirred at 30° C. for 16 hr. Then di-tert-butyl dicarbonate (9.66 g, 44.28 mmol, 10.17 mL) was added and stirred for another 2 hr. The reaction mixture was diluted with $H_2O$ (40 mL) and extracted with EA (40 mL×2). The combined organic layers were dried over anhydrous $Na_2SO_4$, filtered and concentrated under reduced pressure to give Intermediate D (7 g, crude) as colorless oil, which was used directly for the next step. LCMS (ESI) m/z=$[M+H-Boc]^+$=208.1. $^1H$ NMR (400 MHz, $CDCl_3$) δ=8.03-7.91 (m, 1H), 7.90-7.88 (m, 1H), 7.57-7.56 (m, 1H), 7.43-7.41 (m, 1H), 3.95-3.92 (m, 3H), 3.36-3.35 (m, 2H), 1.41-1.39 (m, 9H), 1.37-1.35 (m, 6H) ppm.

Step 4: Preparation of 3-(1-((tert-butoxycarbonyl) amino)-2-methylpropan-2-yl)benzoic acid (Intermediate E)

E

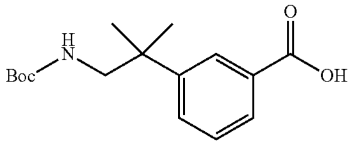

To a solution of Intermediate D (7 g, 22.77 mmol) in THF/MeOH/$H_2O$ (50 mL) was added LiOH·$H_2O$ (1.91 g, 45.55 mmol). The mixture was stirred at 30° C. for 16 hr. The reaction mixture was diluted with $H_2O$ (30 mL) and extracted with EA (30 mL×2). The organic layer was discarded and the aqueous was adjusted pH=5 with 1 N HCl, then extracted with EA (50 mL×2). The combined organic layers were dried over anhydrous $Na_2SO_4$, filtered and concentrated under reduced pressure to give Intermediate E (2.5 g, 8.52 mmol, 37.42% yield) as a yellow solid, which was used directly in the next step. LCMS (ESI) m/z=[M+H−55]$^+$=238.1. $^1$H NMR (400 MHz, $CDCl_3$) δ=8.06-8.06 (m, 1H), 7.98-7.91 (m, 1H), 7.63-7.61 (m, 1H), 7.47-7.43 (m, 2H), 3.43-3.31 (m, 2H), 1.42 (s, 9H), 1.37 (s, 6H) ppm.

Step 5: Preparation of (S)-tert-butyl (2-methyl-2-(3-((4-(methylthio)-1-oxo-1-((4-(3-(pyridin-4-yl)phenyl)thiazol-2-yl)amino)butan-2-yl)carbamoyl)phenyl)propyl)carbamate (Intermediate G)

G

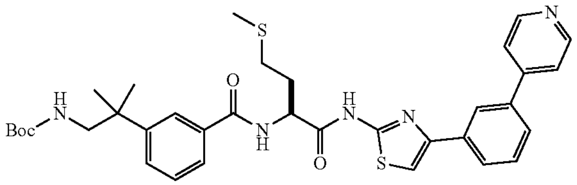

To a solution of (2S)-2-amino-4-methylsulfanyl-N-[4-[3-(4-pyridyl)phenyl]thiazol-2-yl]butanamide (100 mg, 237.54 μmol, HCl salt) in DMF (1 mL) was added Intermediate E (69.68 mg, 237.54 μmol) and DIEA (153.50 mg, 1.19 mmol, 206.87 μL) then EDCl (68.31 mg, 356.31 μmol) and HOBt (38.52 mg, 285.05 μmol) was added to the mixture. The mixture was stirred at 30° C. for 16 hr. The reaction mixture was diluted with $H_2O$ (2 mL) and extracted with EA (2 mL×2). The combined organic layers were dried over anhydrous $Na_2SO_4$, filtered and concentrated under reduced pressure to give a residue. The reaction was purified by reversed phase (0.1% FA condition) and concentrated to remove the ACN and extracted with EA (10 mL×2), the organic layers were dried over anhydrous $Na_2SO_4$, filtered and concentrated to afford Intermediate G (90 mg, 136.39 μmol, 57.42% yield) as a white solid. LCMS (ESI) m/z=[M+H]$^+$=660.1. Chiral SFC: Rt=2.386 min, ee value=100%, OJ-3_5CM_MEOH (DEA)_5_40_3ML_AT35.M Step 6: Preparation of (S)-3-(1-amino-2-methylpropan-2-yl)-N-(4-(methylthio)-1-oxo-1-((4-(3-(pyridin-4-yl)phenyl)thiazol-2-yl)amino)butan-2-yl)benzamide (Compound 48)

Compound 48

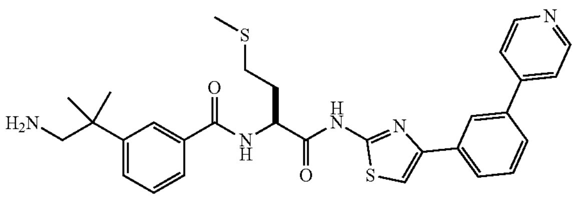

Intermediate G (90 mg, 136.39 μmol) was added to a solution of TFA (1.54 g, 13.51 mmol, 1 mL) in DCM (4 mL), then the mixture was stirred at 30° C. for 16 hr. The mixture was concentrated and dissolved in DMSO (2 mL) and purified by Prep-HPLC (column: Luna C18 150×25 5 u; mobile phase: [water (0.075% TFA)-ACN]; B %: 12%-42%, 9 min) and lyophilized to afford Compound 48 (21.86 mg, 38.98 μmol, 28.58% yield) as yellow oil. LCMS (ESI) m/z=[M+H]$^+$=560.3. $^1$H NMR (400 MHz, DMSO+$D_2O$) δ=8.85-8.83 (m, 2H), 8.40-8.33 (m, 1H), 8.32-8.30 (m, 2H), 8.13-8.11 (m, 1H), 7.89-7.86 (m, 1H), 7.85-7.81 (m, 1H), 7.80-7.79 (m, 1H), 7.78-7.70 (m, 1H), 7.69-7.68 (m, 1H), 7.67-7.49 (m, 1H), 7.48-7.46 (m, 1H), 4.77-4.74 (m, 1H), 3.07-2.66 (m, 2H), 2.65-2.50 (m, 2H), 2.49-2.14 (m, 2H), 2.12-2.06 (m, 3H), 1.35-1.32 (m, 6H) ppm.

Chiral SFC: Rt=2.360 min, ee value=100%, OJ-3-MeOH (DEA)-5-40-3ML-35T·lcm

Example 56. Preparation of 3-(1-amino-2-methylpropan-2-yl)-N-(2-((4-(3-(2-methoxypyridin-4-yl)phenyl)thiazol-2-yl)amino)-2-oxoethyl)benzamide (Compound 49)

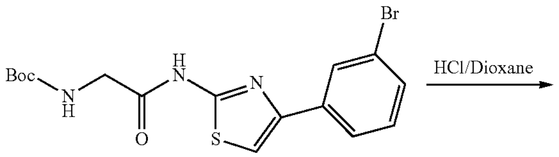

A

-continued

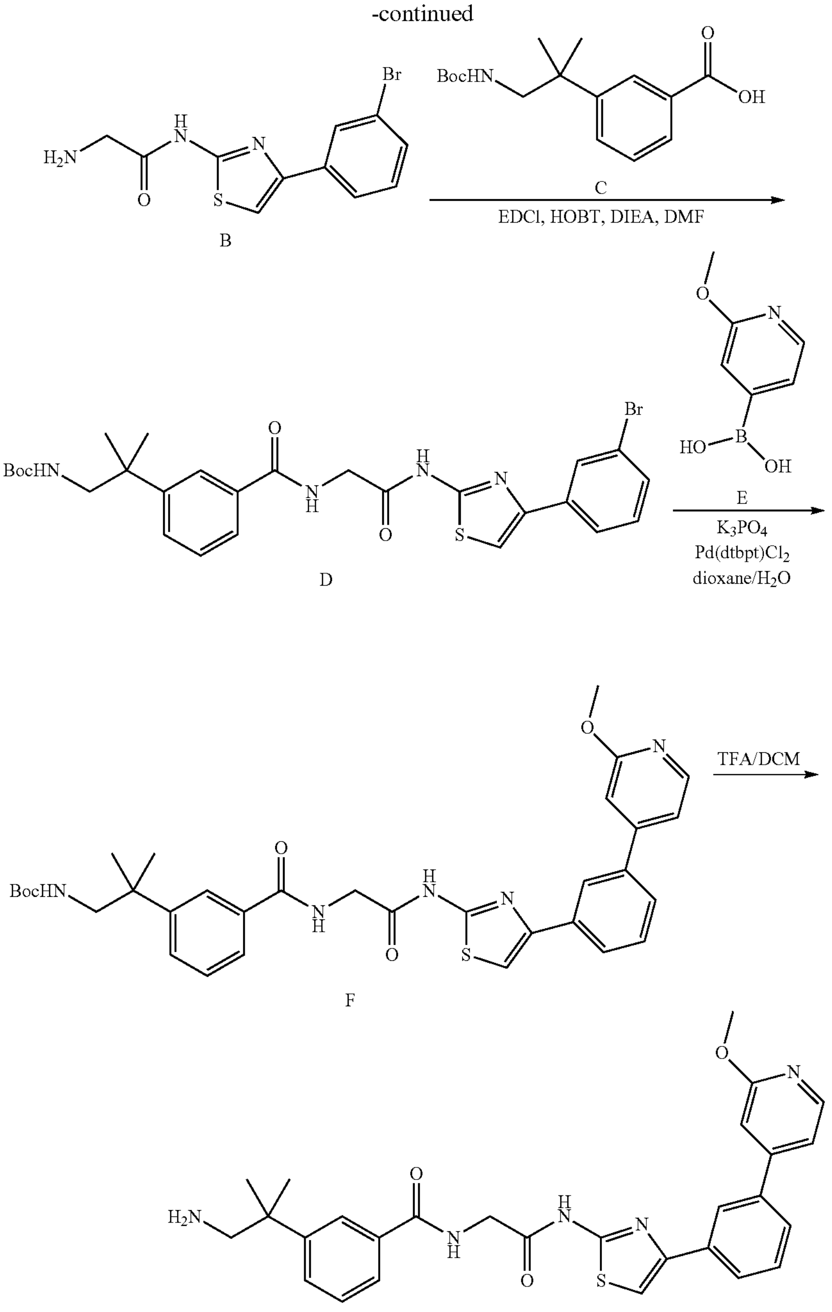

Compound 49

Step 1: Preparation of 2-amino-N-(4-(3-bromophenyl)thiazol-2-yl)acetamide (Intermediate B)

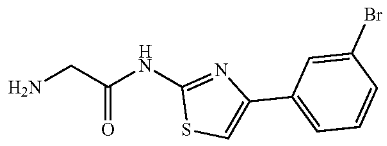

B

A mixture of tert-butyl N-[2-[[4-(3-bromophenyl)thiazol-2-yl]amino]-2-oxo-ethyl]carbamate (prepared according to the method in Example 2) (5 g, 12.13 mmol), HCl/dioxane (4 M, 15.16 mL) in dioxane (20 mL) was stirred at 25° C. for 2 hr under $N_2$ atmosphere. The solid was filtered off and washed with MTBE (10 mL×3). Then dried in vacuum to give Intermediate B (4 g, 11.47 mmol, 94.61% yield, HCl salt) as a white solid, which was used to next step directly. $^1H$ NMR (400 MHz, DMSO) δ=13.10-12.62 (m, 1H), 8.58 (br s, 3H), 8.10-8.09 (m, 1H), 7.99-7.77 (m, 2H), 7.56-7.32 (m, 2H), 3.93-3.92 (m, 2H) ppm.

Step 2: Preparation of tert-butyl (2-(3-((2-((4-(3-bromophenyl)thiazol-2-yl)amino)-2-oxo-ethyl)carbamoyl)phenyl)-2-methylpropyl)carbamate (Intermediate D)

D

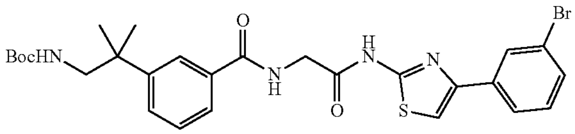

A mixture of Intermediate B (4 g, 11.47 mmol, HCl salt), 3-[2-(tertbutoxycarbonylamino)-1,1-dimethyl-ethyl]benzoic acid (prepared according to the method in Example 55) (3.37 g, 11.47 mmol), EDCl (3.30 g, 17.21 mmol), HOBt (2.33 g, 17.21 mmol) and DIEA (7.41 g, 57.36 mmol, 9.99 mL) in DMF (40 mL) was degassed and purged with $N_2$ for 3 times, and then the mixture was stirred at 25° C. for 12 hr under $N_2$ atmosphere. The reaction mixture was poured into water (80 mL), and extracted with EA (30 mL×2). The combined organic layers were washed with brine (30 mL×2), dried over $Na_2SO_4$, filtered and concentrated under reduced pressure to give a residue. The residue was purified by flash silica gel chromatography (ISCO; 120 g SepaFlash Silica Flash Column, Eluent of 0~50% Ethylacetate/Petroleum ether gradient 80 mL/min) and concentrated to give Intermediate D (5 g, 8.51 mmol, 74.18% yield) as a yellow solid. LCMS (ESI) m/z=$[M+H]^+$=589.3.

Step 3: Preparation of tert-butyl (2-(3-((2-((4-(3-(2-methoxypyridin-4-yl)phenyl)thiazol-2-yl)amino)-2-oxoethyl)carbamoyl)phenyl)-2-methylpropyl)carbamate (Intermediate F)

F

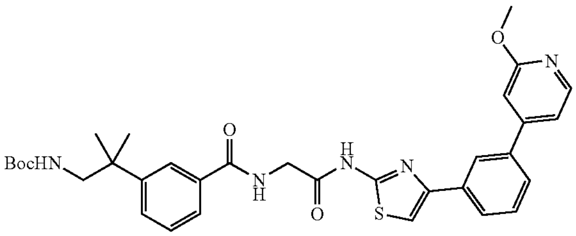

A mixture of Intermediate D (100 mg, 170.20 μmol), ditert-butyl(cyclopentyl)phosphane;dichloropalladium;iron (11.09 mg, 17.02 μmol), $K_3PO_4$ (108.39 mg, 510.60 μmol) and (2-methoxypyridin-4-yl)boronic acid (39.05 mg, 255.30 μmol) in dioxane (1 mL) and $H_2O$ (0.2 mL) was degassed and purged with $N_2$ for 3 times, and then the mixture was stirred at 80° C. for 1.5 hr under $N_2$ atmosphere. The reaction mixture was partitioned between EA (50 mL) and saturated aqueous $NH_4Cl$ (50 mL). The organic phase was separated, washed with brine (50 mL), dried over $Na_2SO_4$, filtered and concentrated under reduced pressure to give a residue. The residue was purified by flash silica gel chromatography (ISCO; 20 SepaFlash Silica Flash Column, Eluent of 0~60% Ethylacetate/Petroleum ether gradient 35 mL/min) and concentrated to give Intermediate F (100 mg, 160.78 μmol, 94.47% yield) as a white solid. LCMS (ESI) m/z=$[M+H]^+$=616.3.

Step 4: Preparation of 3-(1-amino-2-methylpropan-2-yl)-N-(2-((4-(3-(2-methoxypyridin-4-yl)phenyl)thiazol-2-yl)amino)-2-oxoethyl)benzamide (Compound 49)

Compound 49

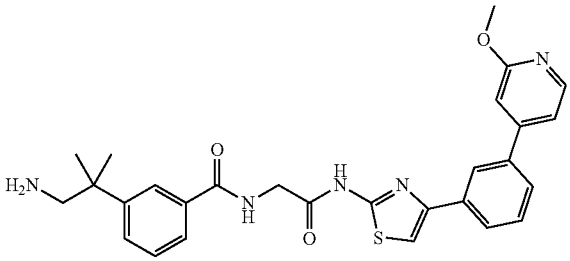

To a solution of Intermediate F (100 mg, 160.78 μmol) in DCM (2 mL) was added TFA (952.87 mg, 8.36 mmol, 618.75 μL). The mixture was stirred at 25° C. for 1 hr. The reaction mixture was concentrated under reduced pressure to remove solvent to get the residue. The residue was diluted with $H_2O$ (10 mL) and then lyophilized to give Compound 49 (99.07 mg, 156.36 μmol, 97.25% yield, TFA salt) as a yellow solid. LCMS (ESI) m/z=$[M+H]^+$=516.4. $^1H$ NMR (400 MHz, DMSO+$D_2O$) δ=8.31-8.25 (m, 2H), 8.01 (br d, J=8.0 Hz, 1H), 7.95 (s, 1H), 7.85-7.80 (m, 2H), 7.74 (br d, J=8.0 Hz, 1H), 7.64 (br d, J=8.0 Hz, 1H), 7.59-7.57 (m, 1H), 7.55-7.47 (m, 1H), 7.37 (dd, J=1.6, 5.6 Hz, 1H), 7.17 (s, 1H), 4.22 (s, 2H), 3.92 (s, 3H), 3.11 (s, 2H), 1.39 (s, 6H) ppm.

Example 57. Preparation of 3-(1-amino-2-methyl-propan-2-yl)-N-(2-((4-(3',5'-dicyano-[1,1'-biphenyl]-3-yl)thiazol-2-yl)amino)-2-oxoethyl)benzamide (Compound 50)

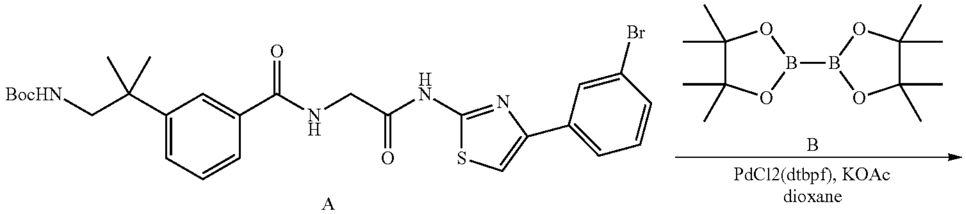

A

-continued

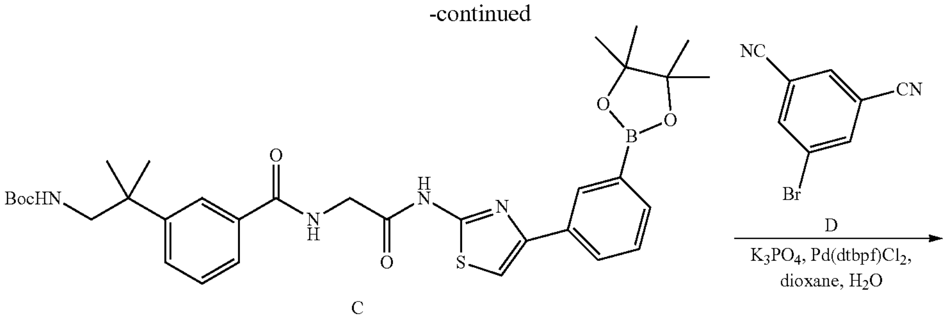

C

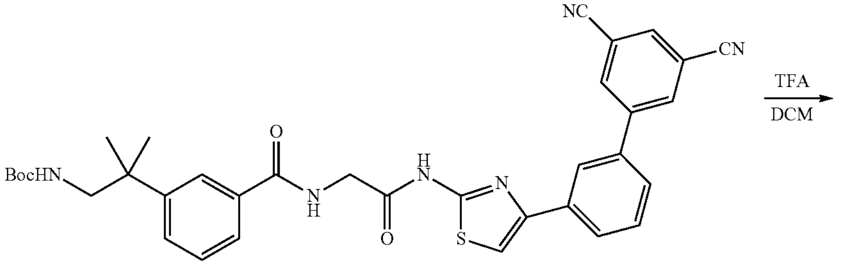

E

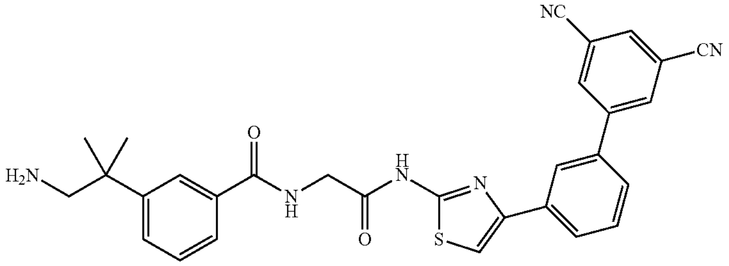

Compound 50

Step 1: Preparation of tert-butyl N-[2-methyl-2-[3-[[2-oxo-2-[[4-[3-(4,4,5,5-tetramethyl-1,3,2-dioxaborolan-2-yl)phenyl]thiazol-2-yl]amino]ethyl]carbamoyl]phenyl]propyl]carbamate (Intermediate C)

C

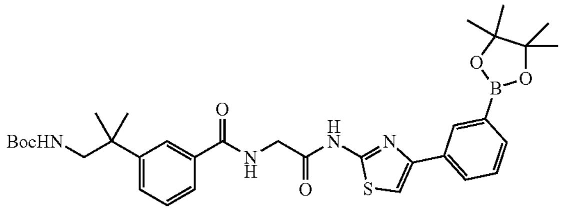

A mixture of tert-butyl N-[2-[3-[[2-[[4-(3-bromophenyl)thiazol-2-yl]amino]-2-oxo-ethyl]carbamoyl]phenyl]-2-methylpropyl]carbamate (prepared according to the method in Example 56) (2 g, 3.40 mmol), KOAc (1.00 g, 10.21 mmol), ditertbutyl(cyclopentyl)phosphane;dichloropalladium;iron (443.72 mg, 680.82 μmol) and 4,4,4',4',5,5,5',5'-octamethyl-2,2'-bi(1,3,2-dioxaborolane) (1.30 g, 5.11 mmol) in dioxane (20 mL) was degassed and purged with $N_2$ for 3 times, and then the mixture was stirred at 80° C. for 2 hr under $N_2$ atmosphere. The reaction mixture was poured into aq. $NH_4Cl$ (150 mL) and EA (150 mL) and extracted with EA (150 mL×2). The combined organic layers were washed with brine (150 mL), dried over $Na_2SO_4$, filtered and concentrated under reduced pressure to give a residue. The residue was purified by flash silica gel chromatography (ISCO®; 80 g SepaFlash® Silica Flash Column, Eluent of 0~60% Ethylacetate/Petroleum ether gradient at 60 mL/min) and concentrated in vacuum to give Intermediate C (2 g, 2.68 mmol, 78.70% yield) as a red solid. LCMS (ESI) m/z=$[M+H]^+$=635.2. $^1H$ NMR (400 MHz, DMSO-$d_6$) δ=12.51 (s, 1H), 8.96-8.93 (m, 1H), 8.31 (s, 1H), 8.03 (d, J=7.6 Hz, 1H), 7.89 (s, 1H), 7.73 (m, 1H), 7.68 (s, 2H), 7.63-7.61 (m, 1H), 7.47-7.44 (m, 1H), 7.43-7.42 (m, 2H), 6.78-6.75 (m, 1H), 4.21 (d, J=5.6 Hz, 2H), 3.16 (d, J=6.4 Hz, 2H), 1.34 (s, 12H), 1.19 (s, 6H) ppm.

Step 2: Preparation of tert-butyl (2-(3-((2-((4-(3',5'-dicyano-[1,1'-biphenyl]-3-yl)thiazol-2-yl)amino)-2-oxoethyl)carbamoyl)phenyl)-2-methylpropyl)carbamate (Intermediate E)

E

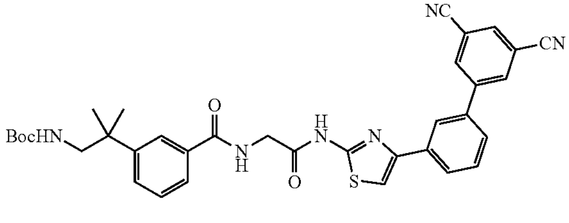

To a solution of Intermediate C (480 mg, 756.39 μmol) and 5-bromobenzene-1,3-dicarbonitrile (156.59 mg, 756.39 μmol) in dioxane (5 mL) and $H_2O$ (0.5 mL) was added $K_3PO_4$ (481.67 mg, 2.27 mmol) and ditert-butyl(cyclopentyl)phosphane;dichloropalladium;iron (49.30 mg, 75.64 μmol). The mixture was stirred at 70° C. for 2 hr. The reaction mixture was partitioned between water (10 mL) and Ethyl acetate (15 mL). The organic phase was separated and concentrated under reduced pressure to give a residue. The residue was purified by flash silica gel chromatography (ISCO®; 40 g SepaFlash® Silica Flash Column, Eluent of 0~60% Ethylacetate/Petroleum ether gradient at 40 mL/min) and concentrated to give Intermediate E (270 mg, 425.37 μmol, 56.24% yield) as a yellow oil. LCMS (ESI) m/z=[M+H]$^+$=635.2.

Step 3: Preparation of 3-(1-amino-2-methylpropan-2-yl)-N-(2-((4-(3',5'-dicyano-[1,1'-biphenyl]-3-yl)thiazol-2-yl)amino)-2-oxoethyl)benzamide (Compound 50)

Compound 50

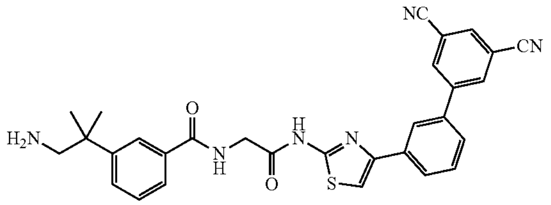

To a solution of Intermediate E (270 mg, 425.37 μmol) in DCM (6.75 mL) was added TFA (1.35 mL). The mixture was stirred at 16° C. for 2 hrs. The reaction mixture was concentrated under reduced pressure to give a residue. The residue was purified by prep-HPLC (column: Phenomenex Synergi C18 150×25×10 um; mobile phase: [water (0.1% TFA)-ACN]; B %: 28%-58%, 10 min) and lyophilized to give Compound 50 (138.24 mg, 212.54 μmol, 49.97% yield, 99.73% purity, TFA) as a white solid. LCMS (ESI) m/z=[M+H]$^+$=535.1. $^1$H NMR (400 MHz, DMSO-$d_6$) δ=12.49 (s, 1H), 8.98 (s, 1H), 8.62 (d, J=1.6 Hz, 2H), 8.49 (s, 1H), 8.34 (s, 1H), 8.03 (d, J=7.6 Hz, 1H), 7.96 (s, 1H), 7.88 (s, 1H), 7.85-7.83 (m, 2H), 7.63-7.58 (m, 2H), 7.55-7.49 (m, 1H), 4.24 (d, J=5.6 Hz, 2H), 3.16-3.08 (m, 2H), 1.40 (s, 6H) ppm. $^{19}$F NMR (377 MHz, DMSO-$d_6$) δ=−73.64-−73.79 (m, 1F)

Example 58. Preparation of 3-(1-amino-2-methylpropan-2-yl)-N-(2-((4-(3',5'-dichloro-[1,1'-biphenyl]-3-yl)thiazol-2-yl)amino)-2-oxoethyl)benzamide (Compound 51)

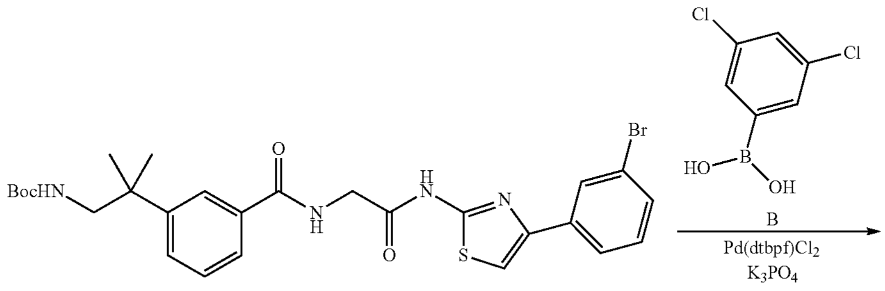

A

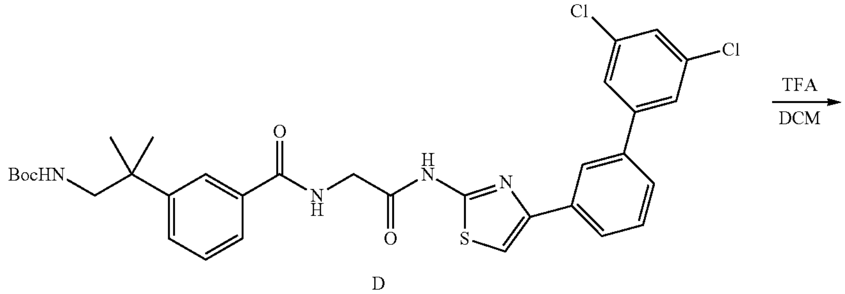

D

-continued

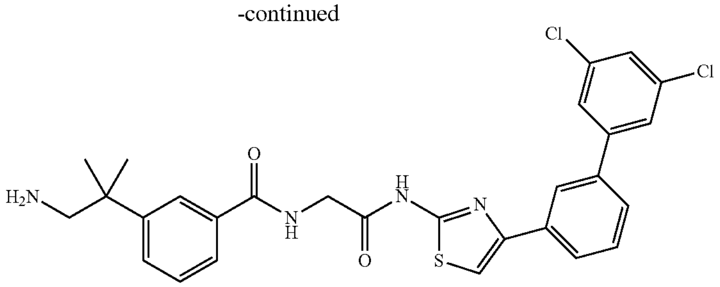

Compound 51

Step 1: Preparation of tert-butyl (2-(3-((2-((4-(3',5'-dichloro-[1,1'-biphenyl]-3-yl)thiazol-2-yl)amino)-2-oxoethyl)carbamoyl)phenyl)-2-methylpropyl)carbamate (Intermediate C)

C

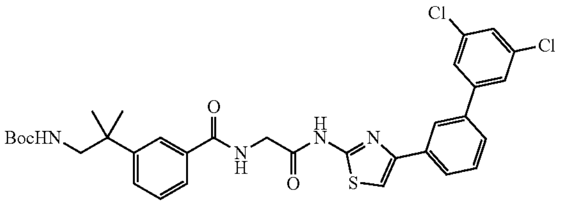

A mixture of tert-butyl N-[2-[3-[[2-[[4-(3-bromophenyl) thiazol-2-yl]amino]-2-oxo-ethyl]carbamoyl]phenyl]-2-methylpropyl]carbamate (100 mg, 170.20 μmol) (prepared according to the method in Example 56), (3,5-dichlorophenyl)boronic acid (48.72 mg, 255.31 μmol), ditertbutyl(cyclopentyl)phosphane;dichloropalladium;iron (11.09 mg, 17.02 μmol) and $K_3PO_4$ (108.39 mg, 510.61 μmol) in dioxane (1 mL) and $H_2O$ (0.2 mL) was degassed and purged with $N_2$ for 3 times, and then the mixture was stirred at 80° C. for 2 hr under $N_2$ atmosphere. The reaction mixture was partitioned between saturated aqueous $NH_4Cl$ (5 mL) and EA (5 mL). The organic phase was separated, washed with brine (5 mL). The organic layers were concentrated under reduced pressure to give a residue. The residue was purified by flash silica gel chromatography (ISCO; SepaFlash Silica Flash Column, Eluent of 0~60% Ethylacetate/Petroleum ether gradient 35 mL/min) and concentrated to give Intermediate C (80 mg, 99.14 μmol, 58.25% yield) as a yellow solid. LCMS (ESI) m/z=$[M+H]^+$=653.2/655.1.

Step 2: Preparation of 3-(1-amino-2-methylpropan-2-yl)-N-(2-((4-(3',5'-dichloro-[1,1'-biphenyl]-3-yl) thiazol-2-yl)amino)-2-oxoethyl)benzamide (Compound 51)

Compound 51

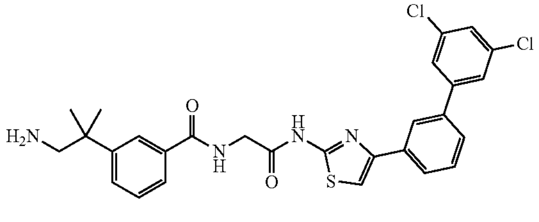

To a solution of Intermediate C (65.19 mg, 80.78 μmol) in DCM (2 mL) was added TFA (616.00 mg, 5.40 mmol, 0.4 mL). The mixture was stirred at 25° C. for 1.5 hr. The reaction mixture was concentrated under reduced pressure to remove solvent. The residue was purified by Prep-HPLC (FA condition: column: Phenomenex Synergi C18 150×25×10 um; mobile phase: [water (0.225% FA)-ACN]; B %: 26%-56%, 10 min) and lyophilized to give Compound 51 (30.5 mg, 50.87 μmol, 62.98% yield, FA salt) as a white solid. LCMS (ESI) m/z=$[M+H]^+$=553.4. $^1H$ NMR (400 MHz, DMSO) δ=9.06-9.04 (m, 1H), 8.26 (d, J=10.6 Hz, 2H), 7.99 (br d, J=8.0 Hz, 1H), 7.92 (s, 1H), 7.88 (s, 1H), 7.82 (d, J=1.6 Hz, 2H), 7.78 (br d, J=7.6 Hz, 1H), 7.72 (br d, J=7.2 Hz, 1H), 7.68-7.63 (m, 1H), 7.62-7.53 (m, 2H), 7.51-7.43 (m, 1H), 4.22 (br d, J=5.6 Hz, 2H), 2.87 (s, 2H), 1.32 (s, 6H) ppm.

Example 59. Preparation of 3-(1-amino-2-methyl-propan-2-yl)-N-(2-((4-(3'-cyano-5'-(hydroxymethyl)-[1,1'-biphenyl]-3-yl)thiazol-2-yl)amino)-2-oxoethyl) benzamide (Compound 52)

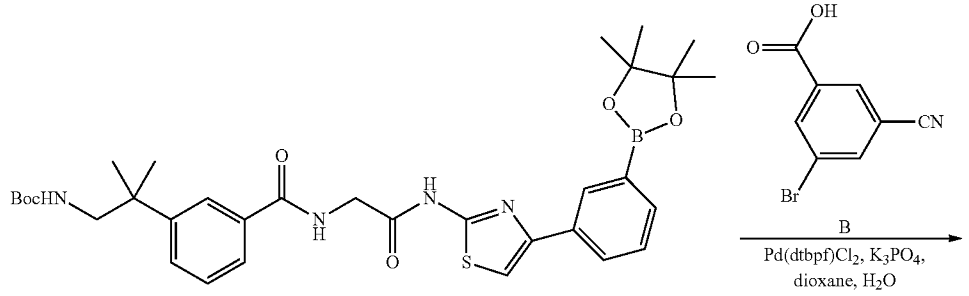

A

-continued

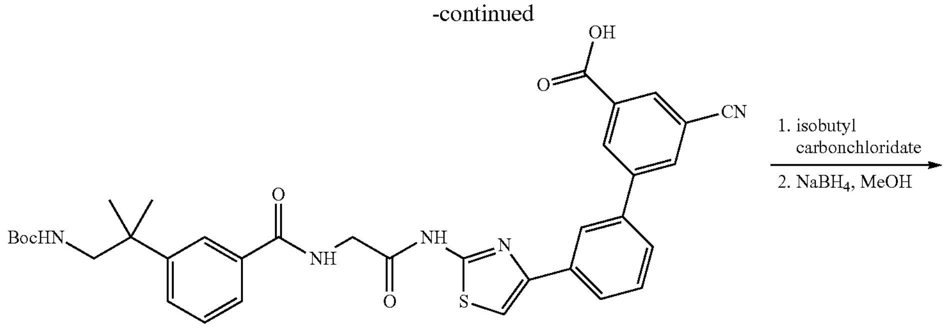

C

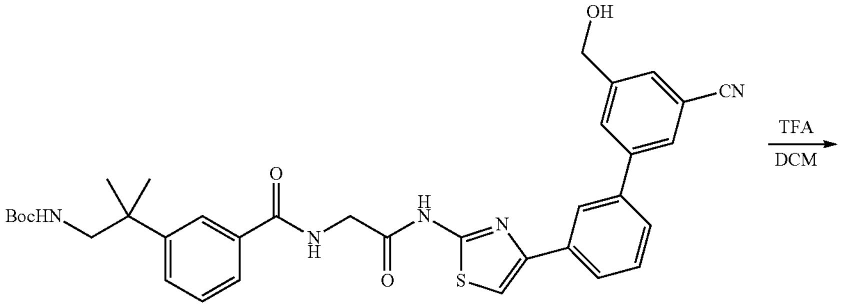

D

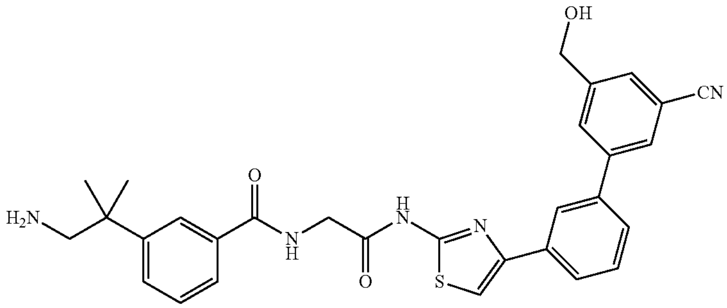

Compound 52

Step 1: Preparation of 3'-(2-(2-(3-(1-((tert-butoxycarbonyl)amino)-2-methylpropan-2-yl)benzamido)acetamido)thiazol-4-yl)-5-cyano-[1,1'-biphenyl]-3-carboxylic acid (Intermediate C)

C

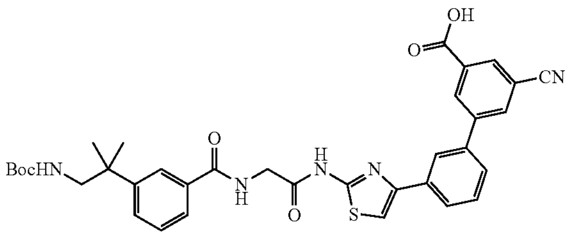

To a solution of tert-butyl N-[2-methyl-2-[3-[[2-oxo-2-[[4-[3-(4,4,5,5-tetramethyl-1,3,2-dioxaborolan-2-yl)phenyl]thiazol-2-yl]amino]ethyl]carbamoyl]phenyl]propyl]carbamate (prepared according to the method in Example 57) (100 mg, 157.58 μmol), 3-bromo-5-cyano-benzoic acid (35.62 mg, 157.58 μmol) and $K_3PO_4$ (100.35 mg, 472.74 μmol) in dioxane (0.8 mL) and $H_2O$ (0.2 mL) was added ditertbutyl (cyclopentyl)phosphane;dichloropalladium;iron (10.27 mg, 15.76 μmol) at 25° C. under $N_2$. The reaction mixture was stirred at 80° C. under $N_2$ for 5 hours. The reaction mixture was diluted with water (10 mL) and extracted with EA (10 mL×3). The organic layers were discarded and the aqueous layers was adjust pH to 4 with HCl (1 M), and then extracted with EA (10 mL×2), the combine organic layers was concentrated in vacuum to give Intermediate C (100 mg, 114.72 μmol, 72.80% yield, 75% purity) as brown oil. LCMS (ESI) m/z $[M+H]^+$=654.4. $^1$H NMR (400 MHz, DMSO-$d_6$) δ=13.75-13.57 (m, 1H), 12.51-12.43 (m, 1H), 8.93-8.91 (m, 1H), 8.44-8.44 (m, 1H), 8.30-8.29 (m, 1H), 8.01 (d, J=8.0 Hz, 1H), 7.92-7.89 (m, 1H), 7.86 (s, 1H), 7.81-7.71 (m, 3H), 7.60-7.60 (m, 1H), 7.55 (d, J=9.2 Hz, 1H), 7.43-7.42 (m, 1H), 6.77-6.68 (m, 1H), 4.21 (d, J=5.6 Hz, 2H), 3.92 (s, 1H), 3.16 (d, J=6.4 Hz, 2H), 1.34 (s, 9H), 1.26 (s, 6H) ppm.

Step 2: Preparation of tert-butyl (2-(3-((2-((4-(3'-cyano-5'-(hydroxymethyl)-[1,1'-biphenyl]-3-yl)thiazol-2-yl)amino)-2-oxoethyl)carbamoyl)phenyl)-2-methylpropyl)carbamate (Intermediate D)

D

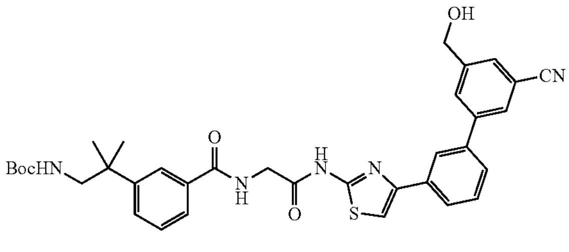

To a solution of Intermediate C (100 mg, 114.72 μmol) and $Et_3N$ (17.41 mg, 172.09 μmol, 23.95 u) in THE (1 mL) was added isobutyl carbonochloridate (18.80 mg, 137.67 μmol, 18.08 μL) dropwise at 0° C. The reaction mixture was stirred at 25° C. for 1 hour. Then MeOH (0.2 mL), and $NaBH_4$ (39.06 mg, 1.03 mmol) were added in turn at 0° C. The reaction mixture was warmed to 25° C. and stirred at 25° C. for 1 hour. The reaction mixture was quenched with water (10 mL) and extracted with EA (10 mL×2), the combined organic layers were concentrated to give a yellow residue. The residue was purified by flash silica gel chromatography (ISCO®; 12 g SepaFlash® Silica Flash Column, Eluent of 0~100% Ethylacetate/Petroleum ether gradient at 35 mL/min), concentrated to give Intermediate D (30 mg, 44.59 μmol, 38.86% yield, 95.08% purity) as a light yellow oil. LCMS (ESI) m/z [M+H]+=640.5. $^1$H NMR (400 MHz, DMSO-$d_6$) δ=12.47 (br s, 1H), 8.93-8.92 (m, 1H), 8.26 (s, 1H), 8.10 (s, 1H), 8.03-7.96 (m, 2H), 7.88 (s, 1H), 7.83 (s, 1H), 7.79-7.68 (m, 3H), 7.61-7.52 (m, 2H), 7.47-7.37 (m, 1H), 6.77-6.68 (m, 1H), 5.55-5.46 (m, 1H), 4.65 (d, J=5.6 Hz, 2H), 4.20 (d, J=5.6 Hz, 2H), 3.16 (d, J=6.0 Hz, 2H), 1.33 (s, 9H), 1.25 (s, 6H) ppm.

Step 3: Preparation of 3-(1-amino-2-methylpropan-2-yl)-N-(2-((4-(3'-cyano-5'-(hydroxymethyl)-[1,1'-biphenyl]-3-yl)thiazol-2-yl)amino)-2-oxoethyl)benzamide (Compound 52)

Compound 52

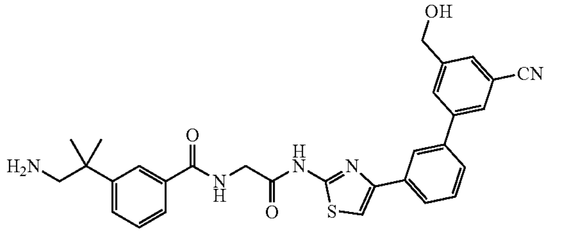

The solution of Intermediate D (30 mg, 46.89 μmol) in DCM (1 mL) and TFA (0.5 mL) was stirred at 25° C. for 2 hours. The reaction mixture was concentrated in vacuum. The residue was diluted with MeOH and $H_2O$, then lyophilized to give Compound 52 (22.47 mg, 31.30 μmol, 66.75% yield, 91.05% purity, TFA) as a gray solid. LCMS (ESI) m/z [M+H]+=540.1. $^1$H NMR (400 MHz, DMSO-$d_6$) δ=12.49 (s, 1H), 8.99-8.98 (m, 1H), 8.26 (s, 1H), 8.10 (s, 1H), 8.01 (s, 1H), 7.99-7.94 (m, 2H), 7.86-7.81 (m, 2H), 7.76 (s, 1H), 7.71 (d, J=8.0 Hz, 1H), 7.69-7.61 (m, 4H), 7.60-7.55 (m, 1H), 7.54-7.49 (m, 1H), 4.65 (s, 2H), 4.23 (d, J=6.0 Hz, 2H), 3.12 (d, J=6.0 Hz, 2H), 1.39 (s, 6H) ppm.

Example 60. Preparation of 3-(1-amino-2-methylpropan-2-yl)-N-(2-((4-(3'-(hydroxymethyl)-5'-(trifluoromethyl)-[1,1'-biphenyl]-3-yl)thiazol-2-yl)amino)-2-oxoethyl)benzamide (Compound 53)

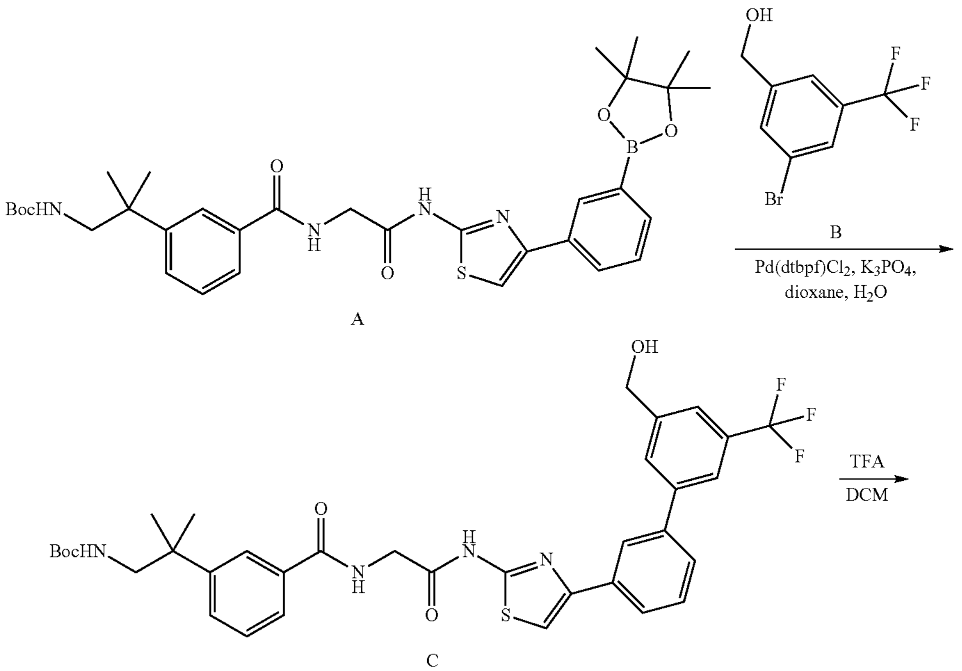

-continued

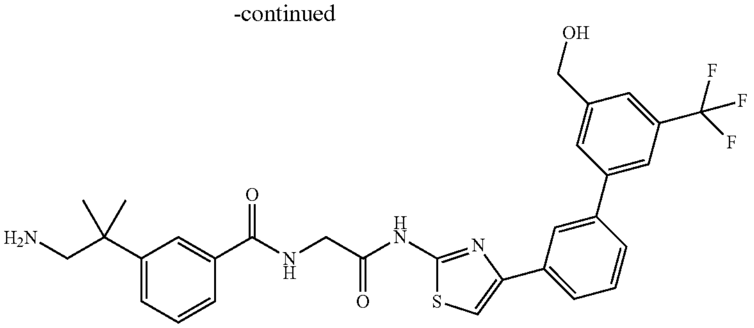

Compound 53

Step 1: Preparation of tert-butyl (2-(3-((2-((4-(3'-(hydroxymethyl)-5'-(trifluoromethyl)-[1,1'-biphenyl]-3-yl)thiazol-2-yl)amino)-2-oxoethyl)carbamoyl)phenyl)-2-methylpropyl)carbamate (Intermediate C)

C

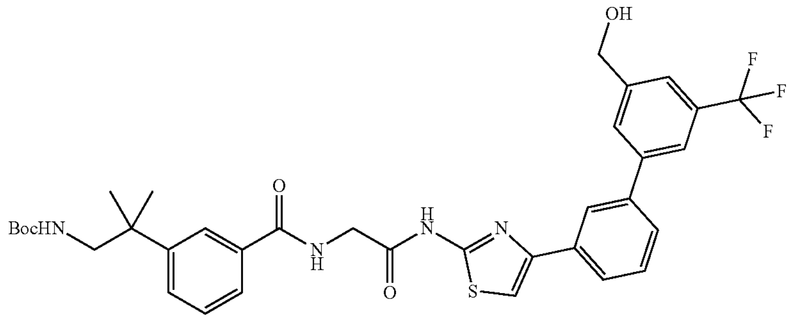

To a solution of [3-bromo-5-(trifluoromethyl)phenyl]methanol (100 mg, 392.11 μmol), tert-butyl N-[2-methyl-2-[3-[[2-oxo-2-[[4-[3-(4,4,5,5-tetramethyl-1,3,2-dioxaborolan-2-yl)phenyl]thiazol-2-yl]amino]ethyl]carbamoyl]phenyl]propyl]carbamate (prepared according to the method in Example 57) (248.83 mg, 392.11 μmol) and $K_3PO_4$ (249.69 mg, 1.18 mmol) in dioxane (2 mL) and $H_2O$ (0.2 mL) was added ditert-butyl(cyclopentyl)phosphane;dichloropalladium;iron (25.56 mg, 39.21 μmol). Then the mixture was stirred at 80° C. for 12 hours under $N_2$. The reaction mixture was diluted with water (10 mL) and extracted with Ethyl acetate (5 mL×3). The combined organic phase was concentrated under reduced pressure to give a residue. The residue was purified by flash silica gel chromatography (ISCO®; 40 g SepaFlash® Silica Flash Column, Eluent of 0~50% Ethylacetate/Petroleum ether gradient at 40 mL/min) and concentrated to give Intermediate C (70 mg, 102.53 μmol, 26.15% yield) as a yellow oil. LCMS (ESI) m/z=$[M+H]^+$=683.5

.

Step 2: Preparation of 3-(1-amino-2-methylpropan-2-yl)-N-(2-((4-(3'-(hydroxymethyl)-5'-(trifluoromethyl)-[1,1'-biphenyl]-3-yl)thiazol-2-yl)amino)-2-oxoethyl)benzamide (Compound 53)

Compound 53

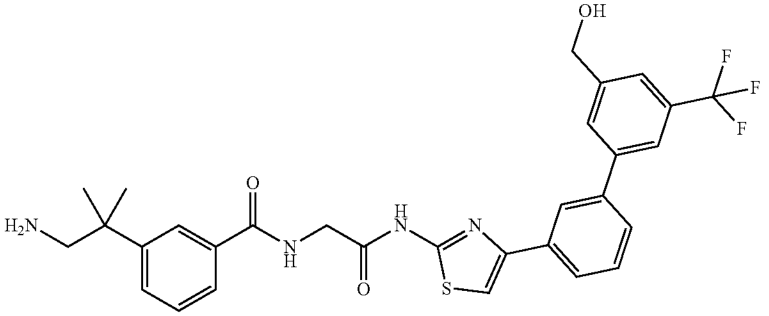

To a solution of Intermediate C (90 mg, 131.82 μmol) in DCM (1 mL) was added TFA (1 mL). The mixture was stirred at 25° C. for 12 hrs. The reaction mixture was concentrated under reduced pressure to give a residue. The residue was purified by reversed phase (FA condition) and lyophilized to give Compound 53 (32.99 mg, 46.84 μmol, 35.53% yield, 98.91% purity, TFA) as a pink solid. LCMS (ESI) m/z=$[M+H]^+$=583.4. $^1H$ NMR (400 MHz, DMSO-$d_6$) δ=8.96 (s, 1H), 8.26 (s, 2H), 8.00-7.95 (m, 2H), 7.90 (m, 2H), 7.83 (s, 1H), 7.77 (d, J=7.6 Hz, 1H), 7.73-7.68 (m, 2H), 7.61-7.56 (m, 2H), 7.49-7.44 (m, 1H), 4.70 (s, 2H), 4.22 (d, J=5.6 Hz, 2H), 2.87-2.87 (m, 1H), 2.86 (s, 1H), 2.87-2.83 (m, 1H), 1.32 (s, 6H) ppm.

Example 61. Preparation of 3-(1-amino-2-methyl-propan-2-yl)-N-(2-((4-(3'-chloro-[1,1'-biphenyl]-3-yl)thiazol-2-yl)amino)-2-oxoethyl)benzamide (Compound 54)

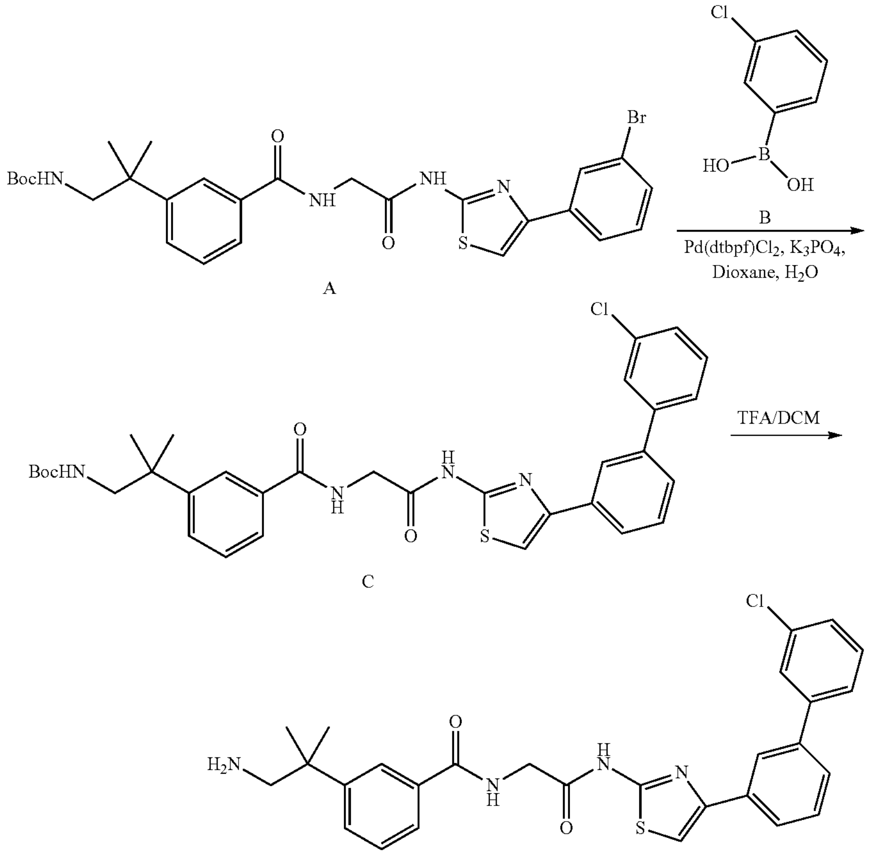

Compound 54

Step 1: Preparation of tert-butyl (2-(3-((2-((4-(3'-chloro-[1,1'-biphenyl]-3-yl)thiazol-2-yl)amino)-2-oxoethyl)carbamoyl)phenyl)-2-methylpropyl)carbamate (Intermediate C)

C

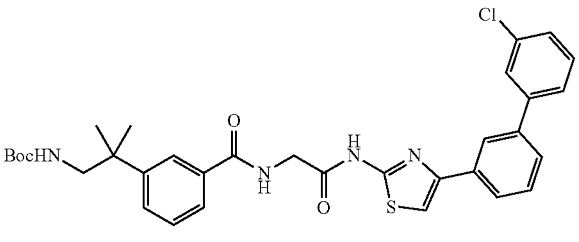

To a solution of tert-butyl N-[2-[3-[[2-[[4-(3-bromophenyl)thiazol-2-yl]amino]-2-oxo-ethyl]carbamoyl]phenyl]-2-methylpropyl]carbamate (prepared according to the method in Example 56) (100 mg, 170.20 μmol) and (3-chlorophenyl) boronic acid (53.23 mg, 340.40 μmol) in dioxane (1 mL) and water (0.1 mL) were added $K_3PO_4$ (108.39 mg, 510.60 μmol) and ditertbutyl(cyclopentyl)phosphane;dichloropalladium;iron (11.09 mg, 17.02 μmol) under $N_2$. Then the reaction mixture was heated to 80° C. and stirred at 80° C. for 12 hrs. The reaction mixture was added water (5 mL×1) and extracted with EtOAc (3 mL×3), the combined organic layers were concentrated under vacuum. The residue was purified by flash silica gel chromatography (ISCO; 40 g SepaFlash Silica Flash Column, Eluent of 0~94% Ethylacetate/Petroleum ether gradient 40 mL/min) and concentrated to give Intermediate C (40 mg, 63.12 μmol, 37.08% yield) as a yellow solid. LCMS (ESI) m/z=[M+H]+=619.4.

Step 2: Preparation of 3-(1-amino-2-methylpropan-2-yl)-N-(2-((4-(3'-chloro-[1,1'-biphenyl]-3-yl)thiazol-2-yl)amino)-2-oxoethyl)benzamide (Compound 54)

Compound 54

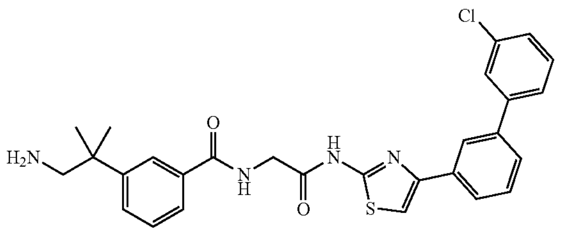

To a solution of Intermediate C (40 mg, 64.60 μmol) in DCM (3.5 mL) was added TFA (1.54 g, 13.51 mmol, 1 mL) at 0° C., then the reaction mixture was stirred at 25° C. for 12 hrs. The reaction mixture was concentrated under vacuum to remove DCM and TFA. The residue was purified by reverse phase (FA condition) and lyophilized to give Compound 54 (23.39 mg, 38.78 μmol, 60.04% yield, FA salt) a white solid. LCMS (ESI) m/z=[M+H]+=519.0. $^1H$ NMR (400 MHz, DMSO) δ=9.00-8.96 (m, 1H), 8.34-8.28 (m, 1H), 8.23-8.21 (m, 1H), 7.96-7.91 (m, 2H), 7.83 (s, 1H), 7.79-7.76 (m, 2H), 7.71-7.65 (m, 2H), 7.59-7.52 (m, 3H), 7.48-7.44 (m, 2H), 4.22-4.21 (d, J=5.6 Hz, 2H), 2.89-2.85 (m, 2H), 1.32 (s, 6H) ppm.

Example 62. Preparation of 3-(1-amino-2-methylpropan-2-yl)-N-(2-((4-(3'-cyano-[1,1'-biphenyl]-3-yl)thiazol-2-yl)amino)-2-oxoethyl)benzamide (Compound 55)

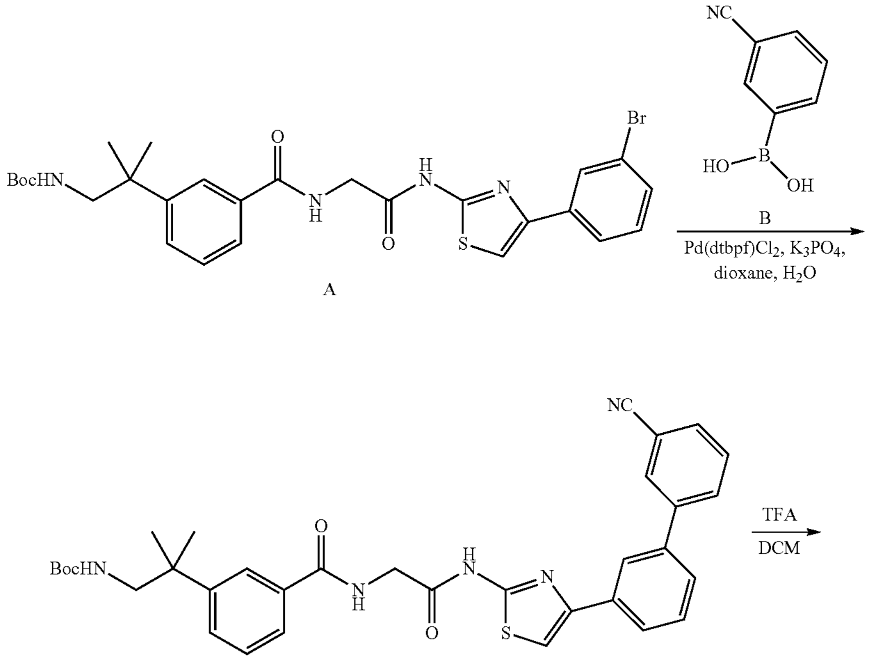

A

C

-continued

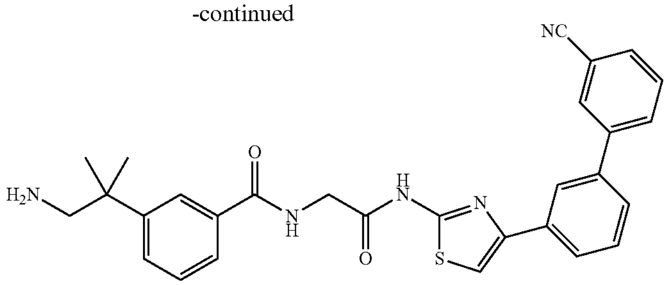

Compound 55

Step 1: Preparation of tert-butyl (2-(3-((2-((4-(3'-cyano-[1,1'-biphenyl]-3-yl)thiazol-2-yl)amino)-2-oxoethyl)carbamoyl)phenyl)-2-methylpropyl)carbamate (Intermediate C)

C

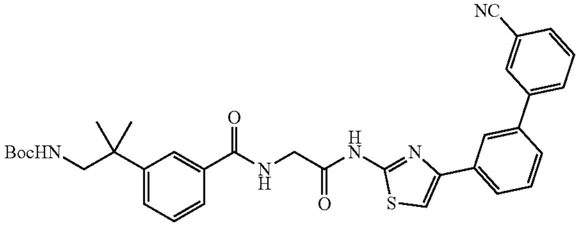

To a solution of tert-butyl N-[2-[3-[[2-[[4-(3-bromophenyl)thiazol-2-yl]amino]-2-oxo-ethyl]carbamoyl]phenyl]-2-methylpropyl] carbamate (prepared according to the method in Example 56) (100 mg, 170.20 μmol) and (3-isocyanophenyl)boronic acid (37.51 mg, 255.30 μmol) in dioxane (1.5 mL) and $H_2O$ (0.1 mL) was added $K_3PO_4$ (108.39 mg, 510.60 μmol) and ditertbutyl (cyclopentyl)phosphane;dichloropalladium;iron (11.09 mg, 17.02 μmol). The mixture was stirred at 75° C. for 12 hr under $N_2$. The reaction mixture was diluted with water (10 mL) and extracted with ethyl acetate (10 mL×3). The organic phase was concentrated under reduced pressure to give the residue. The residue was purified by column chromatography ($SiO_2$, Petroleum ether/Ethyl acetate=20/1 to 1:1) and concentrated in vacuum to give Intermediate C (90 mg, 147.60 μmol, 86.72% yield) as a yellow solid. LCMS (ESI) m/z=$[M+H]^+$=610.1. $^1H$ NMR (400 MHz, DMSO-$d_6$) δ=12.44 (s, 1H), 8.94-8.92 (m, 1H), 8.25 (d, J=12.8 Hz, 2H), 8.12-8.05 (m, 1H), 7.97 (d, J=7.6 Hz, 1H), 7.91-7.82 (m, 3H), 7.78-7.67 (m, 3H), 7.61-7.51 (m, 2H), 7.46-7.37 (m, 1H), 6.75-6.66 (m, 1H), 4.21 (d, J=5.6 Hz, 2H), 3.16 (d, J=6.4 Hz, 2H), 1.38-1.22 (m, 18H) ppm.

Step 2: Preparation of 3-(1-amino-2-methylpropan-2-yl)-N-(2-((4-(3'-cyano-[1,1'-biphenyl]-3-yl)thiazol-2-yl)amino)-2-oxoethyl)benzamide (Compound 55)

Compound 55

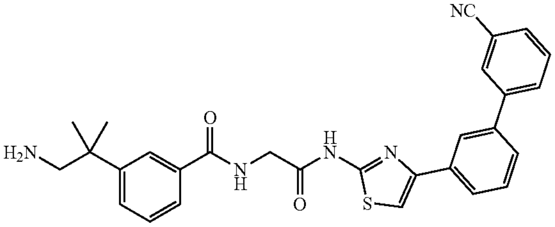

To a solution of Intermediate C (90.00 mg, 147.60 μmol) in DCM (2.25 mL) was added TFA (0.45 mL). Then the mixture was stirred at 30° C. for 2 hours. The reaction mixture was concentrated under reduced pressure to give a residue and lyophilized to give Compound 55 (94.85 mg, 145.98 μmol, 98.90% yield, 95.98% purity, TFA) as an off-white solid. LCMS (ESI) m/z=$[M+H]^+$=510.4. $^1H$ NMR (400 MHz, DMSO-$d_6$) δ=12.54 (s, 1H), 9.06-9.01 (m, 1H), 8.31 (d, J=12.8 Hz, 2H), 8.15 (bd, J=8.0 Hz, 1H), 8.06-8.00 (m, 2H), 7.96-7.88 (m, 3H), 7.81-7.75 (m, 2H), 7.72-7.57 (m, 5H), 4.29 (d, J=5.6 Hz, 2H), 3.22-3.15 (m, 2H), 1.46 (s, 6H) ppm.

Example 63. Preparation of 3-(1-amino-2-methylpropan-2-yl)-N-(2-((4-(3-(2-(N-methylacetamido)pyridin-4-yl)phenyl)thiazol-2-yl)amino)-2-oxoethyl)benzamide (Compound 56)

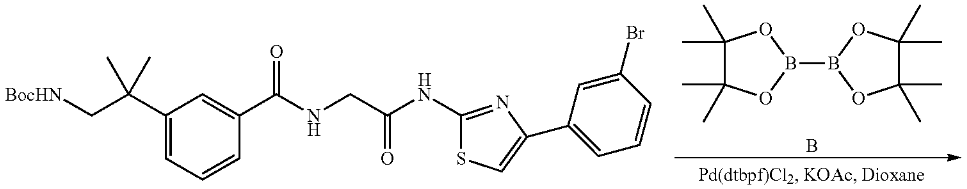

A

-continued

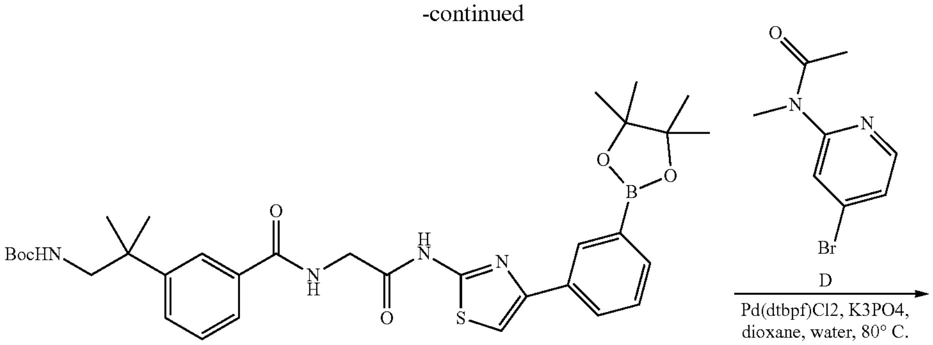

C

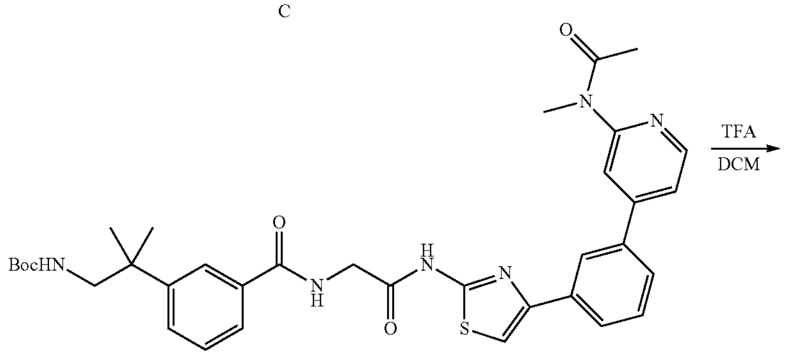

E

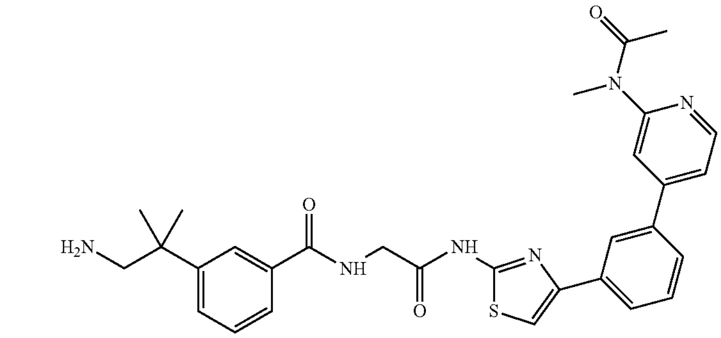

Compound 56

Step 1: Preparation of tert-butyl (2-methyl-2-(3-((2-oxo-2-((4-(3-(4,4,5,5-tetramethyl-1,3,2-dioxaborolan-2-yl)phenyl)thiazol-2-yl)amino)ethyl)carbamoyl)phenyl)propyl)carbamate (Intermediate C)

C

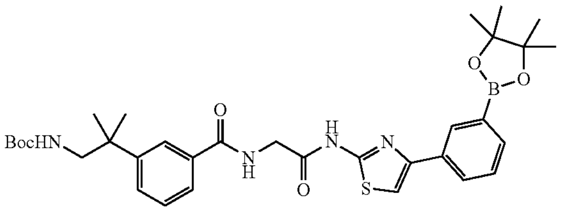

A mixture of tert-butyl N-[2-[3-[[2-[[4-(3-bromophenyl)thiazol-2-yl]amino]-2-oxo-ethyl]carbamoyl]phenyl]-2-methylpropyl]carbamate (2 g, 3.40 mmol) (prepared according to the method in Example 56), KOAc (1.00 g, 10.21 mmol), ditertbutyl(cyclopentyl)phosphane;dichloropalladium;iron (443.72 mg, 680.82 μmol) and 4,4,4',4',5,5,5',5'-octamethyl-2,2'-bi(1,3,2-dioxaborolane) (1.30 g, 5.11 mmol) in dioxane (20 mL) was degassed and purged with $N_2$ for 3 times, and then the mixture was stirred at 80° C. for 2 hr under $N_2$ atmosphere. The reaction mixture was quenched by addition aq. $NH_4Cl$ (150 mL), and then diluted with EA (150 mL) and extracted with EA (150 mL×2). The combined organic layers were washed with brine (150 mL), dried over $Na_2SO_4$, filtered and concentrated under reduced pressure to give a residue. The residue was purified by flash silica gel chromatography (ISCO; 80 g SepaFlash Silica Flash Column, Eluent of 0~60% Ethylacetate/Petroleum ether gradient 60 mL/min) and concentrated to give Intermediate C (2 g, 2.68 mmol, 78.70% yield) as a red solid. LCMS (ESI) m/z $[M+H]^+$=635.5.

Step 2: Preparation of tert-butyl (2-methyl-2-(3-((2-((4-(3-(2-(N-methylacetamido)pyridin-4-yl)phenyl)thiazol-2-yl)amino)-2-oxoethyl)carbamoyl)phenyl)propyl)carbamate (Intermediate E)

E

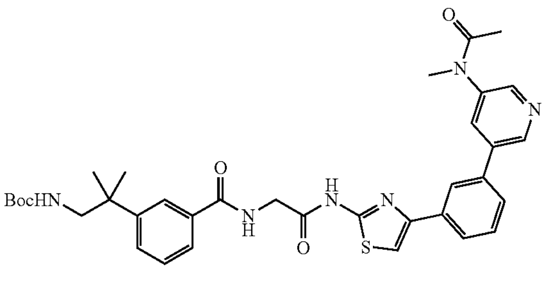

To a solution of N-(4-bromo-2-pyridyl)-N-methyl-acetamide (50 mg, 218.27 μmol) (prepared according to the method in FG-A1639), Intermediate C (138.51 mg, 218.27 μmol) and ditert-butyl(cyclopentyl)phosphane;dichloropalladium;iron (14.23 mg, 21.83 μmol) in dioxane (1.2 mL) and Water (0.3 mL) was added $K_3PO_4$ (138.99 mg, 654.81 μmol) under $N_2$, the mixture was stirred at 80° C. for 2 hr. The reaction mixture was diluted with water (10 mL) and extracted with EtOAc (10 mL×3). The combined organic layers were washed with brine (20 mL), dried over $Na_2SO_4$, filtered and concentrated under reduced pressure to give a residue. The residue was purified by reverse phase (FA) and concentrated under reduced pressure to remove MeCN, and extracted with EtOAc (50 mL×2). The combined organic layers were washed with brine (50 mL), dried over $Na_2SO_4$, filtered and concentrated under reduced pressure to give Intermediate E (80 mg, 105.84 μmol, 48.49% yield) as brown oil. LCMS (ESI) m/z $[M+H]^+$=657.6.

Step 3: Preparation of 3-(1-amino-2-methylpropan-2-yl)-N-(2-((4-(3-(2-(N-methylacetamido)pyridin-4-yl)phenyl)thiazol-2-yl)amino)-2-oxoethyl)benzamide (Compound 56)

Compound 56

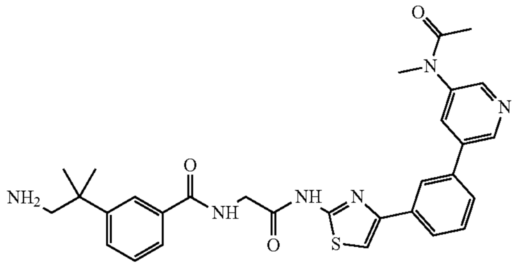

To a solution of Intermediate E (60 mg, 79.38 μmol) in DCM (1 mL) was added TFA (90.51 mg, 793.77 μmol, 58.77 μL) and stirred at 30° C. for 2 hr. The reaction mixture was concentrated under reduced pressure to give a residue. The residue was purified by reverse phase (FA) and lyophilized to give Compound 56 (15.47 mg, 24.98 μmol, 31.47% yield, FA salt) as a white solid. LCMS (ESI) m/z $[M+H]^+$=557.3. $^1$H NMR (400 MHz, MeOD) δ=8.56-8.54 (m, 2H), 8.33 (s, 1H), 8.04-7.99 (m, 2H), 7.83-7.81 (m, 2H), 7.75-7.73 (m, 2H), 7.67 (d, J=8.4 Hz, 1H), 7.59-7.51 (m, 3H), 4.34 (s, 2H), 3.40 (s, 3H), 3.13 (s, 2H), 2.09 (s, 3H), 1.46 (s, 6H) ppm.

Example 64. Preparation of 3-(1-amino-2-methylpropan-2-yl)-N-(2-((4-(3-(2-(methylamino)pyridin-4-yl)phenyl)thiazol-2-yl)amino)-2-oxoethyl)benzamide (Compound 57)

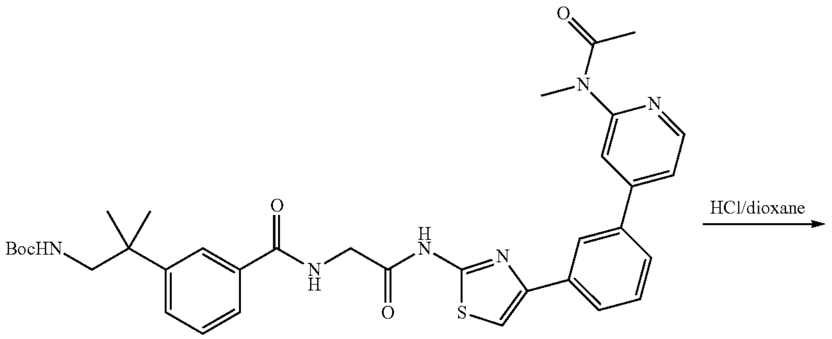

A

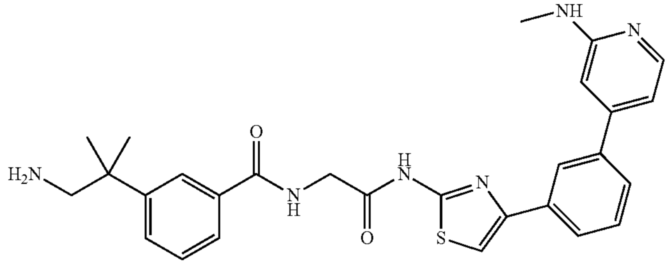

Compound 57

The solution of tert-butyl N-[2-[3-[[2-[[4-[3-[2-[acetyl (methyl)amino]-4-pyridyl]phenyl]thiazol-2-yl]amino]-2-oxoethyl] carbamoyl]phenyl]-2-methyl-propyl]carbamate (60 mg, 91.35 μmol) in 4 M HCl/dioxane (2 mL) was stirred at 30° C. for 1 hr. The reaction mixture was concentrated under reduced pressure to give a residue. The residue was purified by reverse phase (FA) and lyophilized to give Compound 57 (13.66 mg, 24.12 μmol, 26.40% yield, 99% purity, FA) as a white solid. LCMS (ESI) m/z $[M+H]^+$= 515.3. $^1$H NMR (400 MHz, DMSO-$d_6$) δ=9.05-9.02 (m, 1H), 8.29 (s, 2H), 8.17 (s, 1H), 8.07 (d, J=5.2 Hz, 1H), 7.96-7.92 (m, 2H), 7.79-7.77 (m, 2H), 7.61-7.45 (m, 4H), 6.82-6.80 (m, 1H), 6.70 (s, 1H), 6.56 (d, J=4.8 Hz, 1H), 4.21 (d, J=5.6 Hz, 2H), 2.93 (s, 2H), 2.82 (d, J=4.4 Hz, 3H), 1.33 (s, 6H) ppm.

Example 65. Preparation of 3-(1-amino-2-methyl-propan-2-yl)-N-(2-oxo-2-((4-(3-(2-(trifluoromethyl) pyridin-4-yl)phenyl)thiazol-2-yl)amino)ethyl)benz-amide (Compound 58)

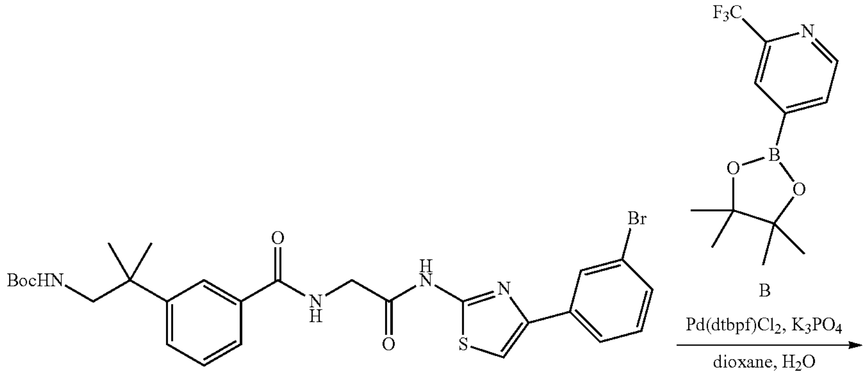

B

A

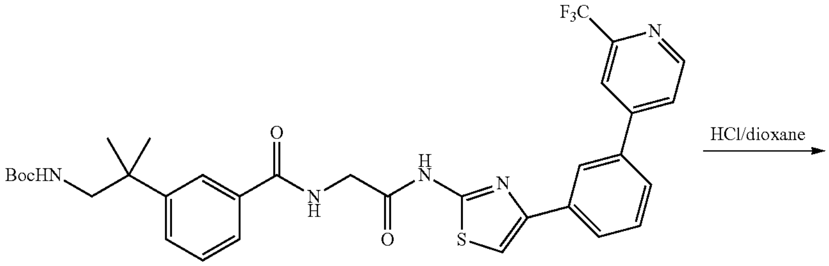

C

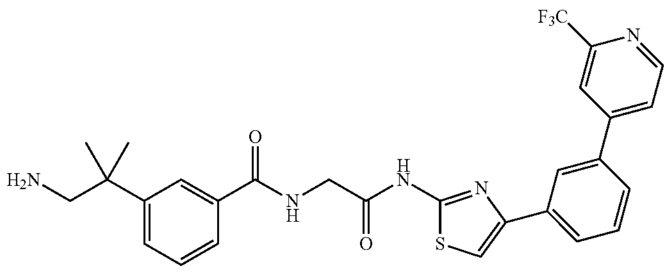

Compound 58

Step 1: Preparation of tert-butyl (2-methyl-2-(3-((2-oxo-2-((4-(3-(2-(trifluoromethyl)pyridin-4-yl)phenyl)thiazol-2-yl)amino)ethyl)carbamoyl)phenyl)propyl)carbamate (Intermediate C)

C

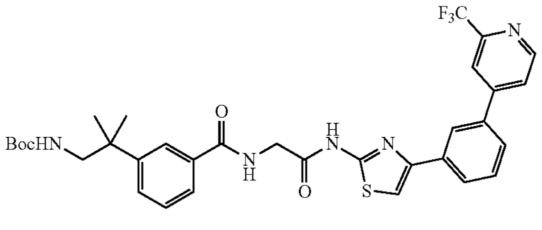

To a mixture of 4-(4,4,5,5-tetramethyl-1,3,2-dioxaborolan-2-yl)-2-(trifluoromethyl)pyridine (60.00 mg, 219.73 μmol), tert-butyl N-[2-[3-[[2-[[4-(3-bromophenyl)thiazol-2-yl]amino]-2-oxo-ethyl]carbamoyl]phenyl]-2-methyl-propyl]carbamate (prepared according to the method in Example 56) (107.58 mg, 183.11 μmol) in dioxane (3 mL) and $H_2O$ (0.3 mL) was added $K_3PO_4$ (155.47 mg, 732.44 μmol) and ditert-butyl(cyclopentyl)phosphane;dichloropalladium;iron (11.93 mg, 18.31 μmol), the mixture was degassed with $N_2$ for 3 times, then stirred at 85° C. for 2 hr under $N_2$. The reaction mixture was concentrated under vacuum to give residue, then diluted with water (20 mL), extracted with EA (35 mL×3), the combined organic phase was washed with brine (25 mL×2), dried over $Na_2SO_4$, filtered and concentrated under reduced pressure to give a residue. The residue was purified by reversed phase HPLC (0.1% FA condition), fraction was lyophilized to give Intermediate C (75 mg, 105.04 μmol, 57.36% yield, 98% purity, FA) as a white solid. LCMS (ESI) m/z $[M+H]^+$=654.6.

Step 2: Preparation of 3-(1-amino-2-methylpropan-2-yl)-N-(2-oxo-2-((4-(3-(2-(trifluoromethyl)pyridin-4-yl)phenyl)thiazol-2-yl)amino)ethyl)benzamide (Compound 58)

Compound 58

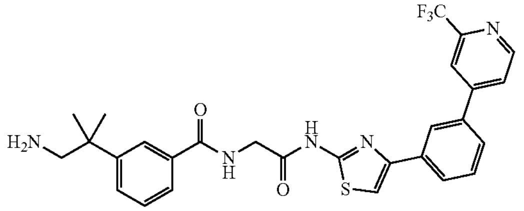

A mixture of Intermediate C (70 mg, 100.04 μmol, FA) in HCl/dioxane (4 M, 2.80 mL) was stirred at 25° C. for 0.5 hr under $N_2$. The reaction mixture was concentrated under vacuum to give residue. The crude product was triturated with MTBE (20 mL) at 25° C. for 15 min, filtered and the solid was dried in the vacuum to give Compound 58 (56.10 mg, 95.08 μmol, 95.04% yield, 100% purity, HCl) as a yellow solid. LCMS (ESI) m/z $[M+H]^+$=554.4. $^1H$ NMR (400 MHz, methanol-$d_4$) δ=8.78 (d, J=5.2 Hz, 1H), 8.37-8.37 (m, 1H), 8.13 (s, 1H), 8.08-8.05 (m, 1H), 8.01-8.00 (m, 2H), 7.86-7.84 (m, 1H), 7.78-7.76 (m, 1H), 7.71-7.68 (m, 1H), 7.62-7.54 (m, 3H), 4.34 (s, 2H), 3.25 (s, 2H), 1.50 (s, 6H) ppm.

Example 66. Preparation of 3-(1-amino-2-methylpropan-2-yl)-N-(2-((4-(3-(2-aminopyridin-4-yl)phenyl)thiazol-2-yl)amino)-2-oxoethyl)benzamide (Compound 59)

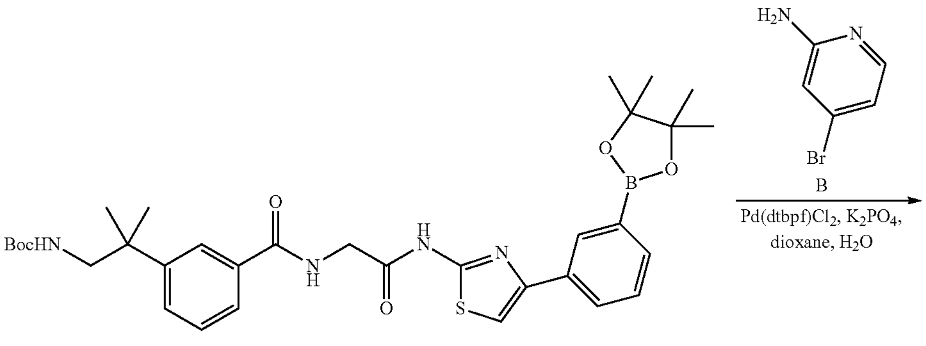

A

-continued

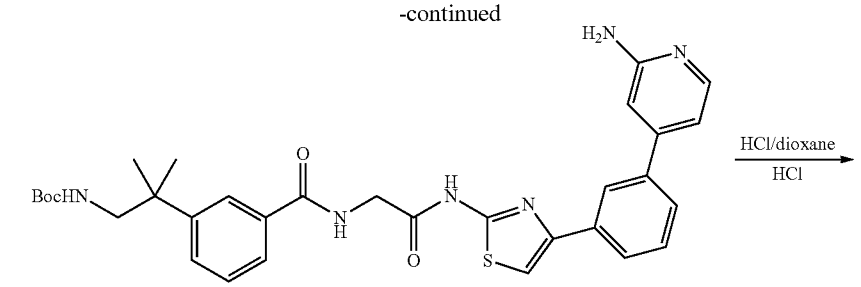

C

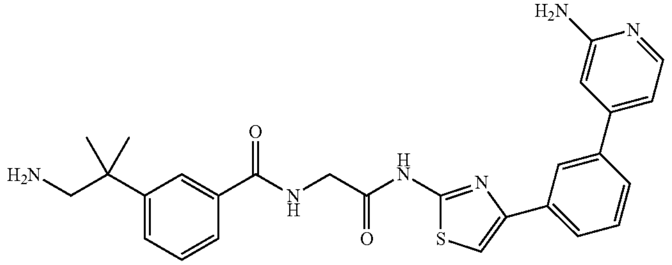

Compound 59

Step 1: Preparation of tert-butyl (2-(3-((2-((4-(3-(2-aminopyridin-4-yl)phenyl)thiazol-2-yl)amino)-2-oxoethyl)carbamoyl)phenyl)-2-methylpropyl)carbamate (Intermediate C)

C

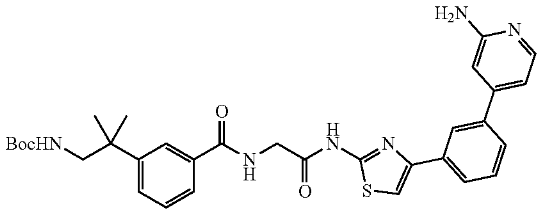

To a mixture of 4-bromopyridin-2-amine (35.99 mg, 208.01 μmol), tert-butyl N-[2-methyl-2-[3-[[2-oxo-2-[[4-[3-(4,4,5,5-tetramethyl-1,3,2-dioxaborolan-2-yl)phenyl]thiazol-2-yl]amino]ethyl]carbamoyl]phenyl]propyl]carbamate (prepared according to the method in Example 57) (110 mg, 173.34 μmol) in dioxane (4 mL) and $H_2O$ (0.4 mL) were added $K_3PO_4$ (147.18 mg, 693.36 μmol) and ditertbutyl (cyclopentyl)phosphane;dichloropalladium;iron (11.30 mg, 17.33 μmol), the mixture was degassed with $N_2$ for 3 times and then stirred at 85° C. for 2 hr under $N_2$. The reaction mixture was concentrated under vacuum, the residue was diluted with water (20 mL), extracted with EA (35 mL×3), the combined organic phase was washed with brine (25 mL×2), dried over $Na_2SO_4$ filtered and concentrated under reduced pressure to give a residue. The residue was purified by reversed phase HPLC (0.1% FA condition) and lyophilized to give Intermediate C (80 mg, 122.46 μmol, 70.65% yield, 99% purity, FA) as a white solid. LCMS (ESI) m/z $[M+H]^+$=601.6.

Step 2: Preparation of 3-(1-amino-2-methylpropan-2-yl)-N-(2-((4-(3-(2-aminopyridin-4-yl)phenyl)thiazol-2-yl)amino)-2-oxoethyl)benzamide (Compound 59)

Compound 59

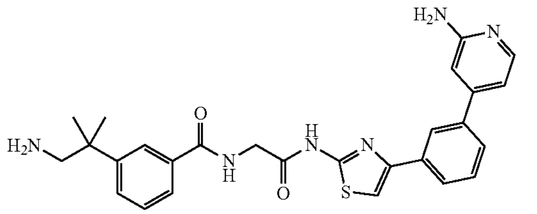

A mixture of Intermediate C (80 mg, 123.69 μmol, FA) in HCl/dioxane (4 M, 3 mL) was stirred at 25° C. for 0.5 hr under $N_2$. The reaction was concentrated under vacuum to give a crude product. The crude product was triturated with MTBE (15 mL) at 25° C. for 15 min, filtered and the solid was dried in vacuum to give Compound 59 (63.25 mg, 115.41 μmol, 93.30% yield, 98% purity, HCl) as a yellow solid. LCMS (ESI) m/z $[M+H]^+$=501.4. $^1H$ NMR (400 MHz, methanol-$d_4$) δ=8.30-8.29 (m, 1H), 8.12 (d, J=7.6, 1H), 8.01-8.00 (m, 1H), 7.94-7.92 (m, 1H), 7.86-7.84 (m, 1H), 7.72-7.68 (m, 2H), 7.63-7.54 (m, 3H), 7.29-7.28 (m, 2H), 4.35 (s, 2H), 3.26 (s, 2H), 1.50 (s, 6H) ppm.

Example 67. Preparation of 3-(1-amino-2-methylpropan-2-yl)-N-(2-((4-(3-(2-(hydroxymethyl)pyridin-4-yl)phenyl)thiazol-2-yl)amino)-2-oxoethyl)benzamide (Compound 60)
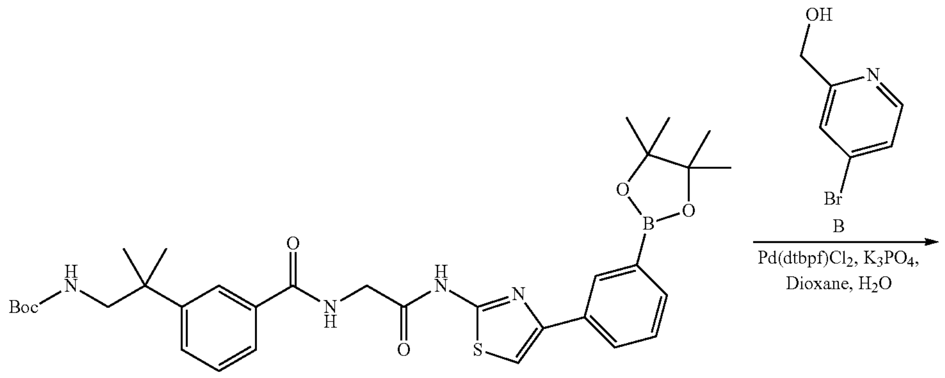
A
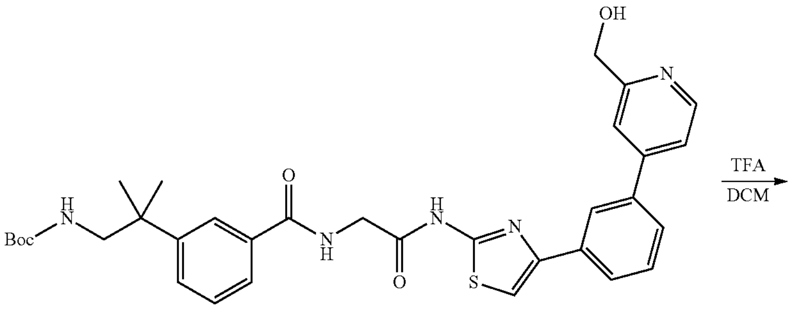
C
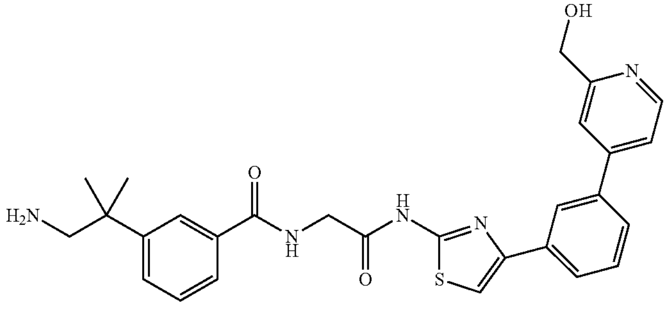
Compound 60

Step 1: Preparation of tert-butyl (2-(3-((2-((4-(3-(2-(hydroxymethyl)pyridin-4-yl)phenyl)thiazol-2-yl) amino)-2-oxoethyl)carbamoyl)phenyl)-2-methylpropyl)carbamate (Intermediate C)

C

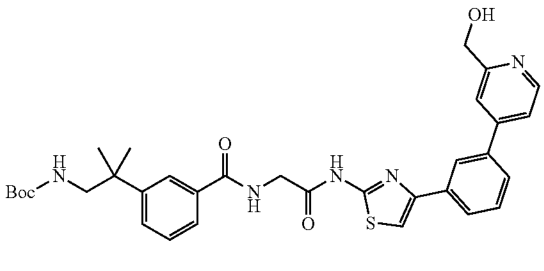

To a mixture of (4-bromo-2-pyridyl)methanol (44.44 mg, 236.37 μmol), tert-butyl N-[2-methyl-2-[3-[[2-oxo-2-[[4-[3-(4,4,5,5-tetramethyl-1,3,2-dioxaborolan-2-yl)phenyl]thiazol-2-yl]amino]ethyl]carbamoyl]phenyl]propyl]carbamate (prepared according to the method in Example 57) (100 mg, 157.58 μmol) in dioxane (2 mL) were added Water (0.5 mL), ditert-butyl(cyclopentyl)phosphane;dichloropalladium;iron (20.54 mg, 31.52 μmol) and $K_3PO_4$ (100.35 mg, 472.74 μmol). The mixture was stirred at 100° C. for 2 hr. The mixture was poured into water (20 mL) then extracted with EA (5 mL×3). The combined organic layers were washed with water (10 mL×3) and brine (10 mL×2), then dried over $Na_2SO_4$, filtered and concentrated under vacuum to give Intermediate C (95 mg, 154.29 μmol, 97.91% yield) as light yellow solid, which was used to next step directly without further purification. LCMS (ESI) m/z=$[M+H]^+$=616.4. $^1H$ NMR (400 MHz, chloroform-d) δ=8.72-8.60 (m, 1H), 8.14 (s, 1H), 7.96 (s, 1H), 7.90-7.81 (m, 1H), 7.76 (d, J=3.6 Hz, 1H), 7.67-7.47 (m, 6H), 7.46-7.37 (m, 1H), 7.24 (s, 1H), 4.91 (s, 2H), 4.62-4.36 (m, 3H), 3.55-3.11 (m, 2H), 1.35 (s, 13H) ppm.

Step 2: Preparation of 3-(1-amino-2-methylpropan-2-yl)-N-(2-((4-(3-(2-(hydroxymethyl)pyridin-4-yl) phenyl)thiazol-2-yl)amino)-2-oxoethyl)benzamide (Compound 60)

Compound 60

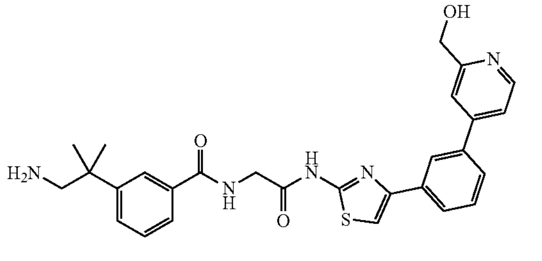

The mixture of Intermediate C (90 mg, 146.17 μmol) in DCM (3 mL) and TFA (1 mL) was stirred at 30° C. for 2 hr. The mixture was concentrated under reduced pressure. The residue was purified by Pre-HPLC (column: Luna C18 150×25 5 u; mobile phase: [water (0.075% TFA)-ACN]; B %: 5%-35%, 9 min) and lyophilized to give Compound 60 (32.60 mg, 51.03 μmol, 34.91% yield, 98.56% purity, TFA) as a yellow solid. LCMS (ESI) m/z=$[M+H]^+$=516.3. $^1H$ NMR (400 MHz, DMSO-$d_6$) δ=12.54 (s, 1H), 9.01-8.98 (m, 1H), 8.74 (d, J=5.6 Hz, 1H), 8.40 (s, 1H), 8.14-8.07 (m, 2H), 8.02-7.94 (m, 2H), 7.90-7.81 (m, 3H), 7.75-7.62 (m, 5H), 7.56-7.49 (m, 1H), 4.82 (s, 2H), 4.24 (d, J=5.6 Hz, 2H), 3.13 (d, J=5.6 Hz, 2H), 1.40 (s, 6H) ppm.

Example 68. Preparation of 3-(1-amino-2-methyl-propan-2-yl)-N-(2-((4-(3-(2-((dimethylamino) methyl)pyridin-4-yl)phenyl)thiazol-2-yl)amino)-2-oxoethyl)benzamide (Compound 61)

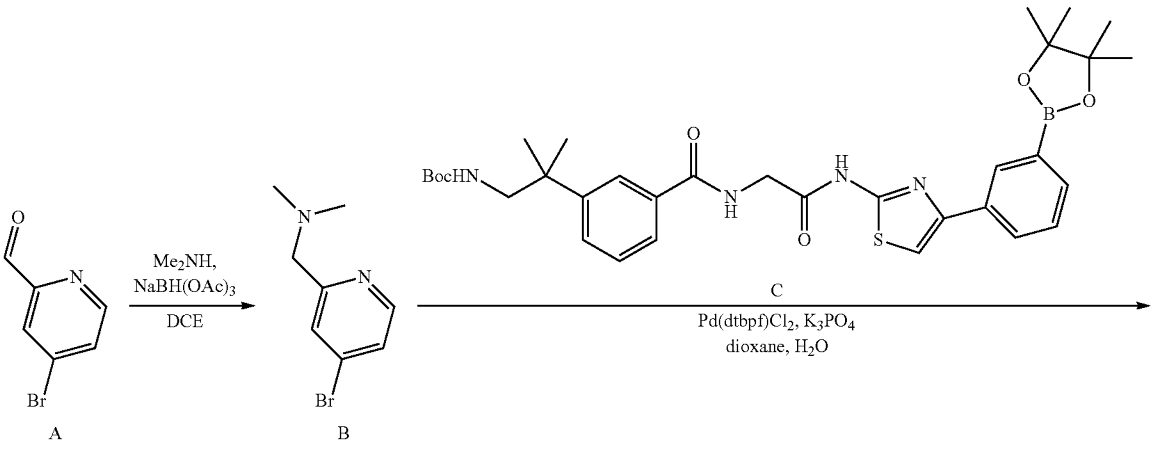

-continued

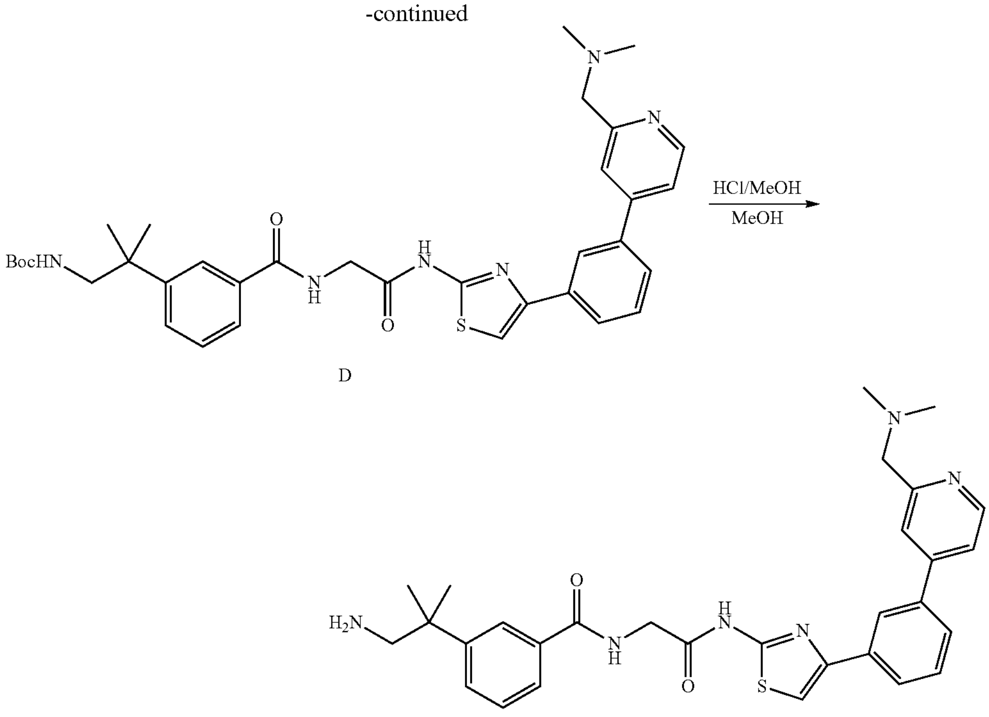

D

Compound 61

Step 1: Preparation of 1-(4-bromopyridin-2-yl)-N,N-dimethylmethanamine (Intermediate B)

B

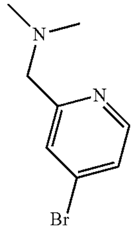

To a solution of 4-bromopyridine-2-carbaldehyde (500 mg, 2.69 mmol) in DCE (5 mL) was added $Me_2NH$ (2 M, 1.61 mL) at 0° C., then $NaBH(OAc)_3$ (1.71 g, 8.06 mmol) was added. The mixture was stirred at 25° C. for 12 hr. Sat. $NaHCO_3$ (20 mL) was added and the reaction mixture was extracted with EA (50 mL×2). The combined organic layers were washed with brine (20 mL), dried over $Na_2SO_4$, filtered and concentrated under reduced pressure to give Intermediate B (400 mg, 1.62 mmol, 60.19% yield) as a white solid. LCMS (ESI) m/z $[M+H]^+$=215.0.

Step 2: Preparation of tert-butyl (2-(3-((2-((4-(3-(2-((dimethylamino)methyl)pyridin-4-yl)phenyl)thiazol-2-yl)amino)-2-oxoethyl)carbamoyl)phenyl)-2-methylpropyl)carbamate (Intermediate D)

D

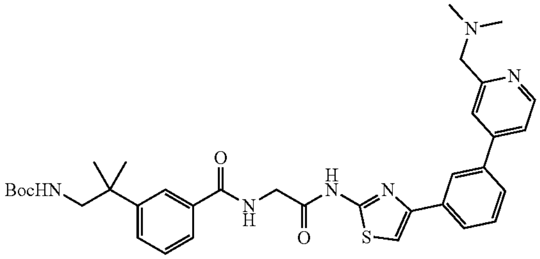

A mixture of tert-butyl N-[2-methyl-2-[3-[[2-oxo-2-[[4-[3-(4,4,5,5-tetramethyl-1,3,2-dioxaborolan-2-yl)phenyl]thiazol-2-yl]amino]ethyl]carbamoyl]phenyl]propyl]carbamate (prepared according to the method in Example 57) (100 mg, 157.58 μmol), Intermediate B (40.67 mg, 189.10 μmol), ditert-butyl(cyclopentyl)phosphane;dichloropalladium;iron (10.27 mg, 15.76 μmol) and $K_3PO_4$ (100.35 mg, 472.74 μmol) in dioxane (2 mL) and $H_2O$ (0.5 mL) was degassed and purged with $N_2$ for 3 times, and then the mixture was stirred at 80° C. for 2 hr under $N_2$ atmosphere. Water (20 mL) was added and the reaction mixture was extracted with EA (50 mL×2). The combined organic layers were washed with brine (20 mL), dried over $Na_2SO_4$, filtered and concentrated under reduced pressure to give a residue. The crude product was purified by reversed-phase HPLC (0.1% FA condition) and lyophilized to give Intermediate D (30 mg, 41.54 μmol, 26.36% yield, 89% purity) as a white solid. LCMS (ESI) m/z $[M+H]^+$=643.6.

Step 3: Preparation of 3-(1-amino-2-methylpropan-2-yl)-N-(2-((4-(3-(2-((dimethylamino)methyl)pyridin-4-yl)phenyl)thiazol-2-yl)amino)-2-oxoethyl) benzamide (Compound 61)

Compound 61

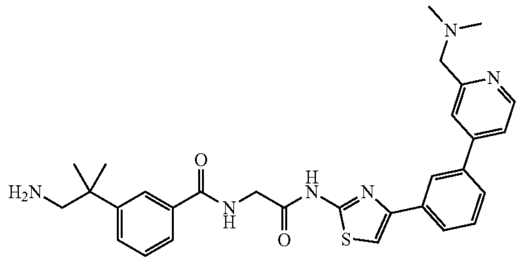

To a solution of Intermediate D (30 mg, 46.67 μmol) in MeOH (2 mL) was added HCl/MeOH (2 mL). The mixture was stirred at 25° C. for 2 hr. The reaction mixture was concentrated under reduced pressure to remove MeOH. The crude product was triturated with MTBE (20 mL) at 25° C. for 10 min, filtered and dried in vacuum to give Compound 61 (25.57 mg, 43.27 μmol, 92.71% yield, 98% purity, HCl) as a yellow solid. LCMS (ESI) m/z $[M+H]^+$=543.3. $^1$H NMR (400 MHz, DMSO-$d_6$) δ=12.50 (s, 1H), 10.51 (s, 1H), 9.07 (s, 1H), 8.76 (d, J=5.2 Hz, 1H), 8.37 (s, 1H), 8.09-8.03 (m, 2H), 7.98 (s, 1H), 7.87 (d, J=3.2 Hz, 2H), 7.82 (d, J=6.4 Hz, 4H), 7.65-7.62 (m, 2H), 7.51-7.47 (m, 1H), 4.53 (s, 2H), 4.23 (d, J=5.6 Hz, 2H), 3.10 (d, J=5.6 Hz, 2H), 2.84 (s, 6H), 1.40 (s, 6H) ppm.

Example 69. Preparation of 3-(1-amino-2-methylpropan-2-yl)-N-(2-((4-(3-((((1R,4R)-4-hydroxycyclohexyl)oxy)methyl)phenyl)thiazol-2-yl)amino)-2-oxoethyl)benzamide (Compound 62)

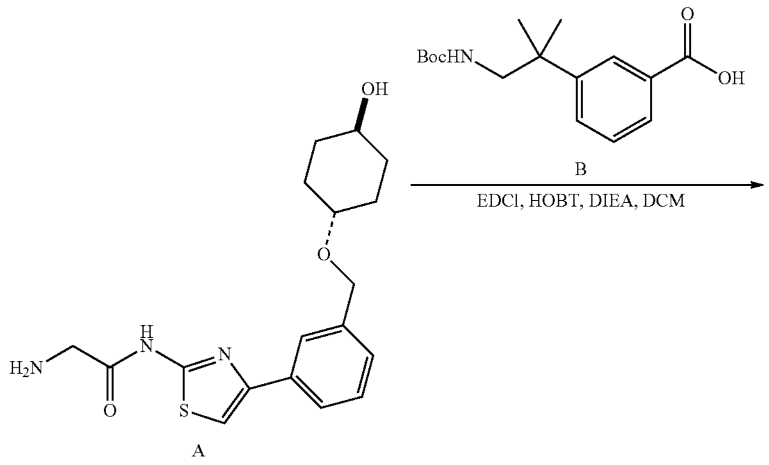

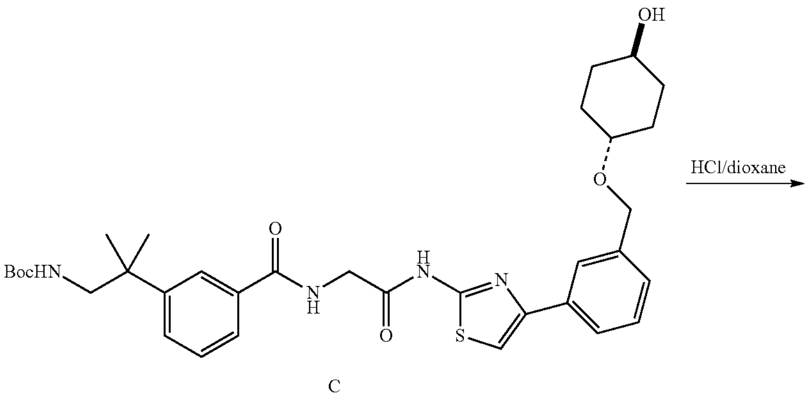

-continued

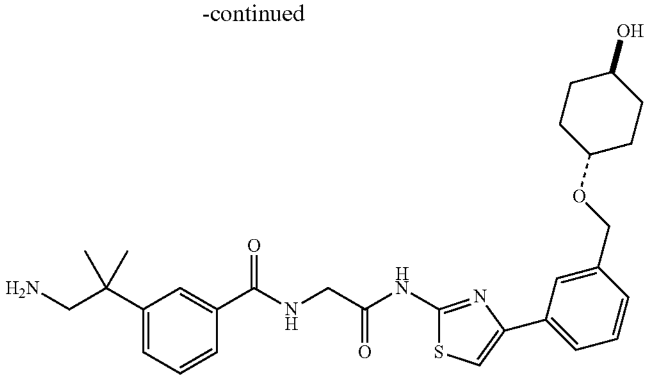

Compound 62

Step 1: Preparation of tert-butyl (2-(3-((2-((4-(3-((((1r,4r)-4-hydroxycyclohexyl)oxy)methyl)phenyl)thiazol-2-yl)amino)-2-oxoethyl)carbamoyl)phenyl)-2-methylpropyl)carbamate (Intermediate C)

C

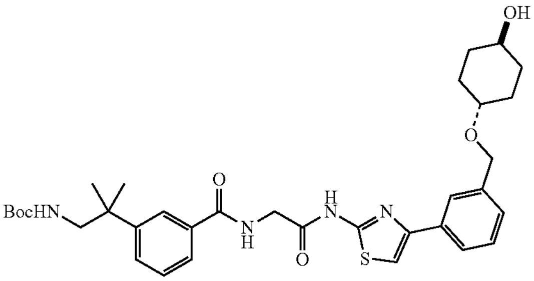

To a solution of 2-amino-N-[4-[3-[(4-hydroxycyclohexoxy)methyl]phenyl]thiazol-2-yl]acetamide (prepared according to the method in Example 22) (100.00 mg, 276.66 μmol), 3-[2-(tert-butoxycarbonylamino)-1,1-dimethyl-ethyl]benzoic acid (97.39 mg, 331.99 μmol), DIEA (178.78 mg, 1.38 mmol, 240.94 μL) in DCM (1 mL) were added EDCl (63.64 mg, 331.99 μmol) and HOBt (44.86 mg, 331.99 μmol). The mixture was stirred at 20° C. for 16 h. The reaction mixture was diluted with water (2 mL) and extracted with EA (3 mL×3). The combined organic layers were washed with brine (4 mL×2) and dried over anhydrous $Na_2SO_4$. The mixture was filtered and concentrated under reduced pressure to give a residue. The residue was purified by reversed-phase HPLC (0.1% FA condition). The solution was extracted with EA (15 mL×3). The combined organic layers were washed with brine (20 mL×3) and dried over anhydrous $Na_2SO_4$, filtered and concentrated under reduced pressure to give Intermediate C (20 mg, 27.21 μmol, 9.84% yield, 86.65% purity) as a white solid. LCMS (ESI) m/z $[M+H]^+$=637.3.

Step 2: Preparation of 3-(1-amino-2-methylpropan-2-yl)-N-(2-((4-(3-((((1r,4r)-4-hydroxycyclohexyl)oxy)methyl)phenyl)thiazol-2-yl)amino)-2-oxoethyl)benzamide (Compound 62)

Compound 62

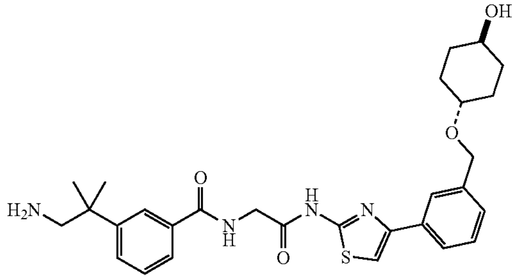

A solution of Intermediate C (20.00 mg, 31.41 μmol) in HCl/dioxane (0.2 mL) was stirred at 20° C. for 1 h. The reaction mixture was triturated with MTBE (2 mL) at 20° C. for 5 min. Then, the mixture was filtered and washed with MTBE (3 mL×3) to give a residue. The residue was purified by reversed-phase HPLC (0.1% FA condition) and lyophilized to give Compound 62 (15 mg, 25.19 μmol, 80.21% yield, 97.865% purity, FA) as a white solid. LCMS (ESI) m/z $[M+H]^+$=537.3. $^1$H NMR (400 MHz, METHANOL-$d_4$) δ=8.50 (s, 1H), 8.00 (s, 1H), 7.91 (s, 1H), 7.85-7.81 (m, 2H), 7.69 (J=8.8 Hz, 1H), 7.57-7.53 (m, 1H), 7.40-7.36 (m, 2H), 7.30-7.28 (m, 1H), 4.59 (s, 2H), 4.34 (s, 2H), 3.64-3.57 (m, 1H), 3.49-3.41 (m, 1H), 3.24 (s, 2H), 2.10-2.07 (m, 2H), 1.97-1.94 (m, 2H), 1.50 (s, 6H), 1.44-1.30 (m, 4H) ppm.

Example 70. Preparation of 3-(1-amino-2-methyl-propan-2-yl)-5-methyl-N-(2-oxo-2-((4-(3-(pyridin-4-yl)phenyl)thiazol-2-yl)amino)ethyl)benzamide (Compound 63)
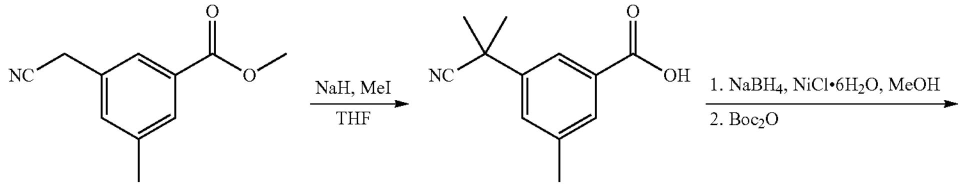
A B
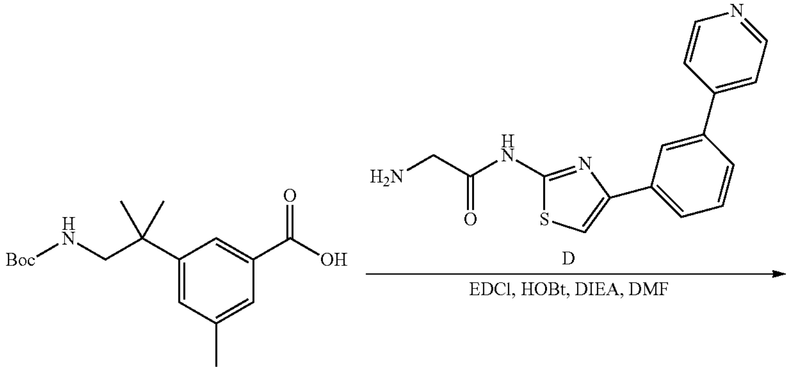
D
C
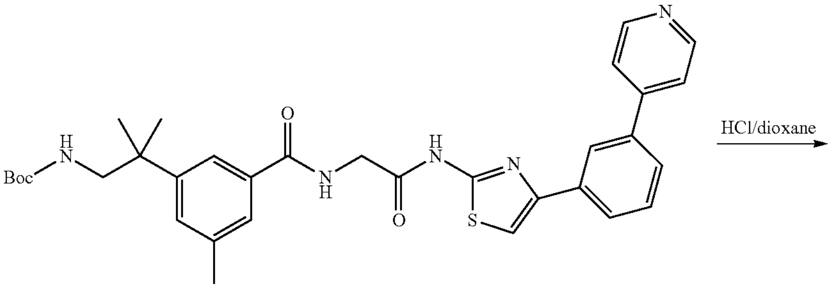
E
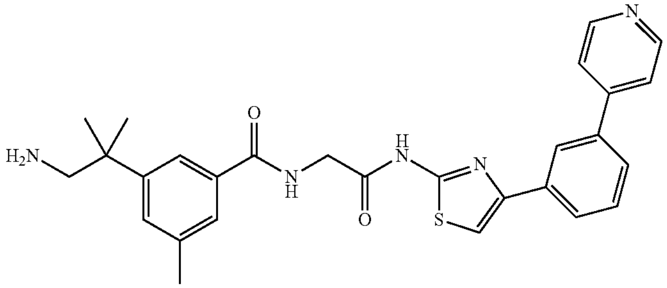
Compound 63

Step 1: Preparation of 3-(2-cyanopropan-2-yl)-5-methylbenzoic acid (Intermediate B)

B

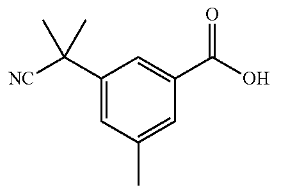

To a solution of methyl 3-(cyanomethyl)-5-methyl-benzoate (3.45 g, 18.23 mmol) in THE (40 mL) was added NaH (4.38 g, 109.40 mmol, 60% purity) at 0° C. and stirred at 25° C. for 0.5 hr. Then MeI (12.94 g, 91.17 mmol, 5.68 mL) was added to the mixture at 0° C. The mixture was stirred at 25° C. for 16 hr. The reaction mixture was quenched with aq citric acid (50 mL) at 0° C. and extracted with EA (100 mL×2). The combined organic layers were dried over anhydrous $Na_2SO_4$, filtered and concentrated under reduced pressure to give the residue. The residue was purified by column chromatography ($SiO_2$, Petroleum ether/Ethyl acetate=1/0 to 1/1), and then concentrated in vacuum to give Intermediate B (1.5 g, 7.38 mmol, 40.48% yield) as yellow oil. LCMS (ESI) m/z $[M+H]^+$=204.1. $^1H$ NMR (400 MHz, DMSO-$d_6$) δ=13.08 (br s, 1H), 7.86 (s, 1H), 7.73 (s, 1H), 7.60 (s, 1H), 2.40 (s, 3H), 1.69 (s, 6H) ppm.

Step 2: Preparation of 3-(1-((tert-butoxycarbonyl) amino)-2-methylpropan-2-yl)-5-methylbenzoic acid (Intermediate C)

C

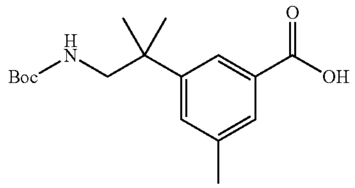

To a solution of Intermediate B (1.5 g, 7.38 mmol) in MeOH (30 mL) was added $NiCl_2 \cdot 6H_2O$ (4.39 g, 18.45 mmol) and $NaBH_4$ (2.79 g, 73.81 mmol) at 0° C. and stirred at 30° C. for 2 hr. Then di-tertbutyl dicarbonate (4.83 g, 22.14 mmol, 5.09 mL) was added to the mixture and stirred for another 16 hr. The reaction mixture was diluted with MeOH/$H_2O$=1/1 (30 mL), filtered and concentrated to remove MeOH and then extracted with EA (40 mL×2). The organic layer was discarded and the aqueous was adjusted the pH=4 with 1 M HCl and then extracted with EA (50 mL×2). The combined organic layers were dried over anhydrous $Na_2SO_4$, filtered and concentrated under reduced pressure to give the crude. The crude was purified by reversed phase (0.1% FA condition), then the elute was concentrated to remove ACN and extracted with EA (40 mL×2), the combined organic layers were dried over anhydrous $Na_2SO_4$, filtered and concentrated under reduced pressure to give Intermediate C (550 mg, 1.79 mmol, 24.24% yield) as a white solid. LCMS (ESI) m/z $[M+Na]^+$=330.1. $^1H$ NMR (400 MHz, DMSO-$d_6$) δ=12.77 (brs, 1H), 7.71 (s, 1H), 7.58 (s, 1H), 7.41 (s, 1H), 6.74-6.71 (m, 1H), 3.12 (d, J=6.0 Hz, 2H), 2.35 (s, 3H), 1.32-1.22 (m, 15H) ppm.

Step 3: Preparation of tert-butyl (2-methyl-2-(3-methyl-5-((2-oxo-2-((4-(3-(pyridin-4-yl)phenyl)thiazol-2-yl)amino)ethyl)carbamoyl)phenyl)propyl) carbamate (Intermediate E)

E

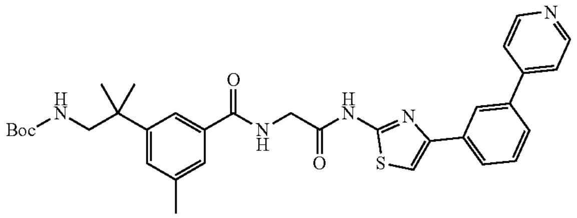

To a solution of Intermediate C (150 mg, 487.99 μmol) and 2-amino-N-[4-[3-(4-pyridyl)phenyl]thiazol-2-yl]acetamide (prepared according to the method in Example 3) (169.25 mg, 487.99 μmol, HCl) in DMF (2 mL) was added DIEA (315.34 mg, 2.44 mmol, 424.98 μL), then EDCl (140.32 mg, 731.98 μmol) and HOBt (79.12 mg, 585.59 μmol) were added to the mixture. The mixture was stirred at 30° C. for 16 hr. To the reaction mixture was added $H_2O$ (0.5 mL) and a white precipitate was formed. The precipitate was collected by filtration, the filter cake was washed with $CH_3CN$ (5 mL) and dried under high vacuum to give Intermediate E (210 mg, 350.15 μmol, 71.75% yield) as a white solid. LCMS (ESI) m/z $[M+H]^+$=600.2. $^1H$ NMR (400 MHz, DMSO-$d_6$) δ=12.44 (s, 1H), 8.88-8.86 (m, 1H), 8.68-8.67 (m, 2H), 8.30 (s, 1H), 8.00 (d, J=8.0 Hz, 1H), 7.83 (s, 1H), 7.77-7.75 (m, 3H), 7.59 (s, 1H), 7.59-7.55 (m, 2H), 7.36 (s, 1H), 6.72-6.69 (m, 1H), 4.20 (d, J=5.6 Hz, 2H), 3.16 (d, J=6.4 Hz, 2H), 2.36 (s, 3H), 1.34-1.24 (m, 15H) ppm.

Step 4: Preparation of 3-(1-amino-2-methylpropan-2-yl)-5-methyl-N-(2-oxo-2-((4-(3-(pyridin-4-yl)phenyl)thiazol-2-yl)amino)ethyl)benzamide (Compound 63)

Compound 63

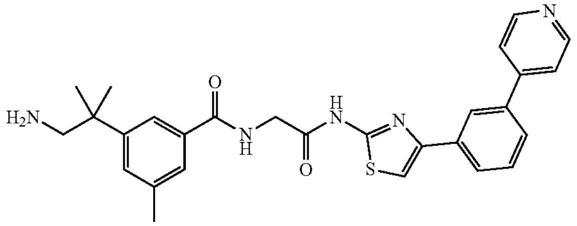

A solution of Intermediate E (210 mg, 350.15 μmol) in HCl/dioxane (4 M, 5 mL) was stirred at 25° C. for 1 hr. The precipitate was collected by filtration; the filter cake was washed with MTBE (5 mL) and then lyophilized to give Compound 63 (169.39 mg, 310.95 μmol, 88.80% yield, 98.41% purity, HCl) as a yellow solid. LCMS (ESI) m/z

[M+H]$^+$=500.1. $^1$H NMR (400 MHz, MeOD) δ=8.92-8.90 (m, 2H), 8.52-8.47 (m, 3H), 8.20-8.15 (m, 1H), 7.94 (d, J=6.8 Hz, 1H), 7.82-7.80 (m, 1H), 7.69-7.67 (m, 3H), 7.51 (s, 1H), 4.36 (d, J=5.6 Hz, 2H), 3.25 (s, 2H), 2.46 (d, J=2.0 Hz, 3H), 1.48 (s, 6H) ppm.
Example 71. Preparation of 3-(1-amino-2-methylpropan-2-yl)-N-(2-oxo-2-((4-(3-(pyridin-4-yl)phenyl)thiazol-2-yl)amino)ethyl)benzamide (Compound 64)
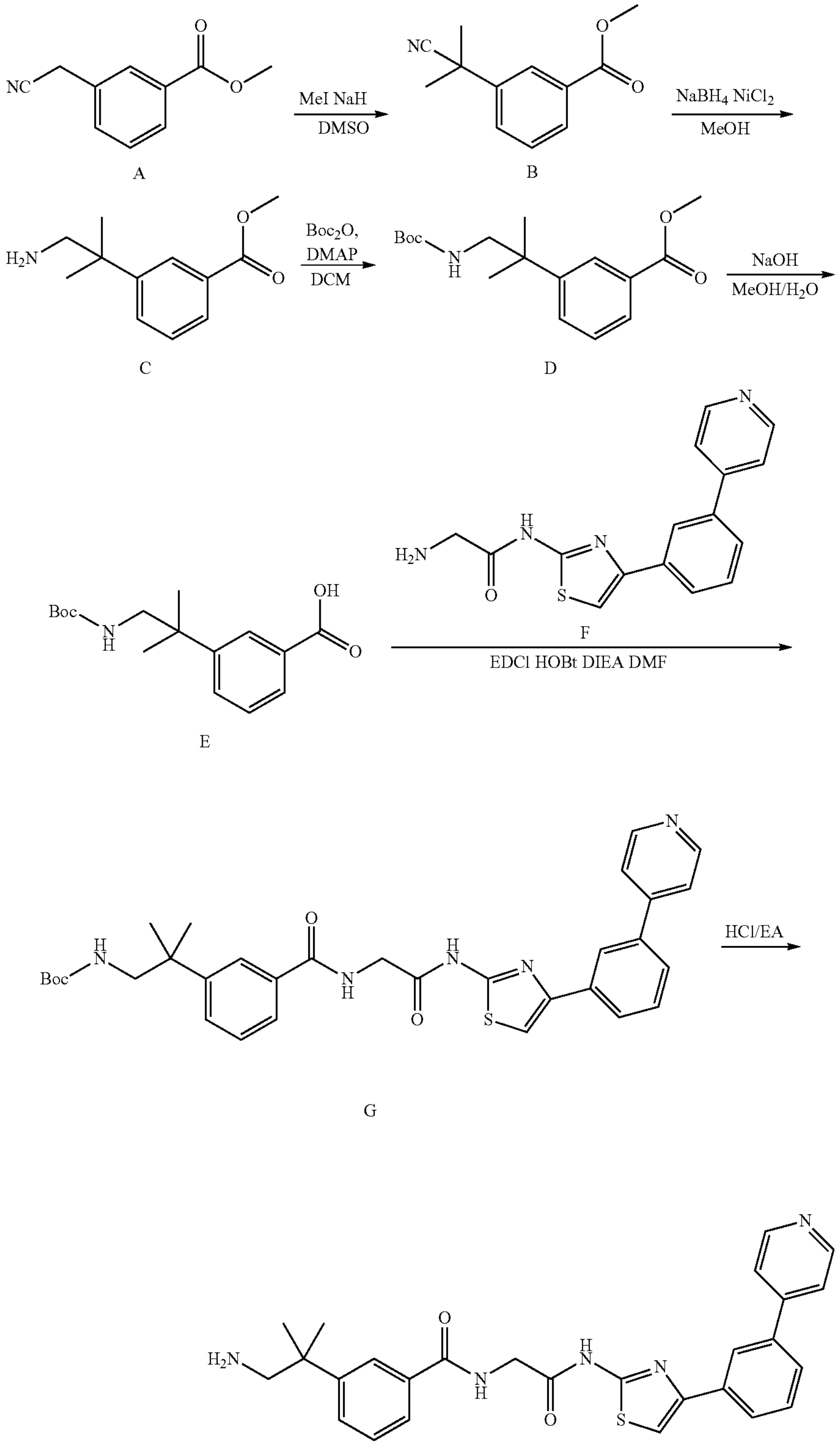
Compound 64

Step 1: Preparation of methyl 3-(2-cyanopropan-2-yl)benzoate (Intermediate B)

B

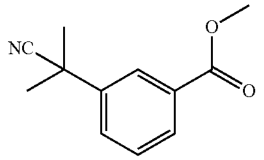

To a solution of methyl 3-(cyanomethyl)benzoate (5.00 g, 28.54 mmol) in anhydrous THE (50 mL) was added NaH (2.85 g, 71.35 mmol, 60% purity) at 0° C. The mixture was stirred at 0° C. for 0.5 hr. Then MeI (10.13 g, 71.35 mmol, 4.44 mL) was added. The mixture was stirred at 0° C. for 1.5 hr. The reaction mixture was poured into water (50 mL), then extracted with EA (50 mL×2). The combined organic layers were washed with brine, dried over anhydrous sodium sulfate, filtered and concentrated to give a residue. The residue was purified by flash silica gel chromatography (ISCO; 20 g SepaFlash Silica Flash Column, Eluent of 0~30% Ethylacetate/Petroleum ether gradient 40 mL/min) to give Intermediate B (2.5 g, 10.68 mmol, 37.41% yield) as colorless oil. LCMS (ESI) m/z $[M+H]^+$=204.1. $^1H$ NMR (400 MHz, DMSO) δ=8.08-8.07 (m, 1H), 7.95-7.93 (m, 1H), 7.83-7.81 (m, 1H), 7.63-7.58 (m, 1H), 3.88 (s, 3H), 1.72 (s, 6H) ppm.

Step 2: Preparation of methyl 3-(1-amino-2-methylpropan-2-yl)benzoate (Intermediate C)

C

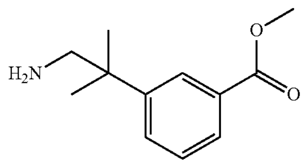

To a solution of Intermediate B (1.00 g, 4.92 mmol) in MeOH (10 mL) was added $NiCl_2 \cdot 6H_2O$ (2.92 g, 12.30 mmol) and $NaBH_4$ (3.72 g, 98.41 mmol) under ice-bath. The reaction mixture was stirred at 30° C. for 17 hr and then diluted with EA (50 mL) and filtered to remove the solid. The organic layer was poured into saturation $NaHCO_3$ aq (50 mL), then extracted by EA (50 mL×4). The combined organic layers were washed with brine, dried over anhydrous sodium sulfate, filtered and concentrated to give Intermediate C (800 mg, 3.38 mmol, 68.65% yield) as yellow oil, which was used for next step directly. LCMS (ESI) m/z $[M+H]^+$=208.1.

Step 3: Preparation of methyl 3-(1-((tert-butoxycarbonyl)amino)-2-methylpropan-2-yl)benzoate (Intermediate D)

D

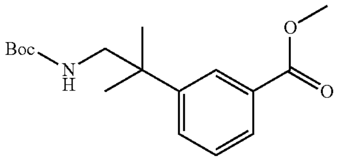

To a solution of Intermediate C (300.00 mg, 1.45 mmol) in DCM (3 mL) was added DMAP (35.37 mg, 289.48 μmol) and $Boc_2O$ (631.78 mg, 2.89 mmol, 665.03 μL). The reaction mixture was stirred at 30° C. for 17 hr. The reaction mixture was poured into water (10 mL), then extracted with EA (10 mL×2). The combined organic layers were washed with brine, dried over anhydrous sodium sulfate, filtered and concentrated to give crude product Intermediate D (300 mg, 370.87 μmol, 25.62% yield) as a yellow oil, which was used for next step directly. LCMS (ESI) m/z $[M+H-56]^+$=252.1.

Step 4: Preparation of 3-(1-((tert-butoxycarbonyl)amino)-2-methylpropan-2-yl)benzoic acid (Intermediate E)

E

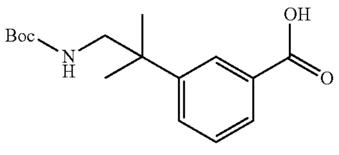

To a solution of Intermediate D (300.00 mg, 370.87 μmol) in THE (2 mL) was added $H_2O$ (1 mL), MeOH (1 mL) and NaOH (29.67 mg, 741.74 μmol). The reaction mixture was stirred at 30° C. for 2 hr. The reaction mixture was adjusted to pH=7 with 1 M HCl aq. The mixture was purified by reversed phased HPLC (FA) to give Intermediate E (100 mg, 285.56 μmol, 77.00% yield) as yellow oil. LCMS (ESI) m/z $[M+H-56]^+$=238.1.

Step 5: Preparation of tert-butyl (2-methyl-2-(3-((2-oxo-2-((4-(3-(pyridin-4-yl)phenyl)thiazol-2-yl)amino)ethyl)carbamoyl)phenyl)propyl)carbamate (Intermediate G)

G

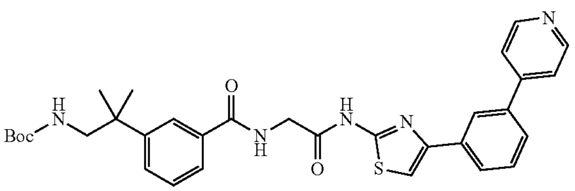

To a solution of Intermediate E (90 mg, 306.79 μmol) in DMF (1 mL) was added EDCI (73.52 mg, 383.49 μmol), HOBt (51.82 mg, 383.49 μmol) and DIPEA (99.13 mg, 766.98 μmol, 133.59 μL). The reaction mixture was stirred at 30° C. for 5 min. Then 2-amino-N-(4-(3-(pyridin-4-yl)phenyl)thiazol-2-yl)acetamide hydrochloride (88.67 mg, 255.66 μmol) was added. The reaction mixture was stirred at 30° C. for 17 hr. The reaction mixture was poured into water (10 mL), White solid was formed. The white solid was filtered and dried in vacuum to give Intermediate G (100 mg, 129.76 μmol, 50.75% yield) as white solid. LCMS (ESI) m/z $[M+H]^+$=586.2.

Step 6: Preparation of 3-(1-amino-2-methylpropan-2-yl)-N-(2-oxo-2-((4-(3-(pyridin-4-yl)phenyl)thiazol-2-yl)amino)ethyl)benzamide (Compound 64)

Compound 64

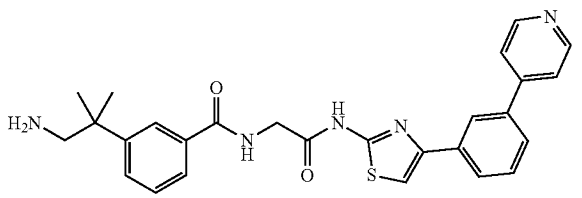

The solution of Intermediate G (100 mg, 170.73 μmol) in HCl/EtOAc (1 mL) was stirred at 25° C. for 3 hours. The reaction mixture was concentrated to afford a yellow residue. The residue was dissolved with DMSO (3 mL), then purified by Prep-HPLC (Xtimate C18 150×25 mm×5 um; mobile phase: [water (0.05% ammonia hydroxide v/v)-ACN]; B %: 29%-59%, 1 min), concentrated, then lyophilized to give Compound 64 (34.28 mg, 70.59 μmol, 41.35% yield) as an off-white solid. LCMS (ESI) m/z $[M+H]^+$=486.3. $^1$H NMR (400 MHz, MeOD) δ=8.93-8.91 (m, 1H), 8.70-8.65 (m, 2H), 8.30 (s, 1H), 8.01 (d, J=8.0 Hz, 1H), 7.88 (s, 1H), 7.82 (s, 1H), 7.78-7.73 (m, 3H), 7.72 (s, 1H), 7.61-7.60 (m, 1H), 7.56-7.52 (m, 1H), 7.47-7.40 (m, 1H), 4.20 (d, J=5.6 Hz, 2H), 2.71 (s, 2H), 1.27 (s, 6H) ppm.

Example 72. Preparation of (S)-3-(1-amino-2-methylpropan-2-yl)-N-(1-oxo-1-((4-(3-(pyridin-4-yl)phenyl)thiazol-2-yl)amino)propan-2-yl)benzamide (Compound 65)

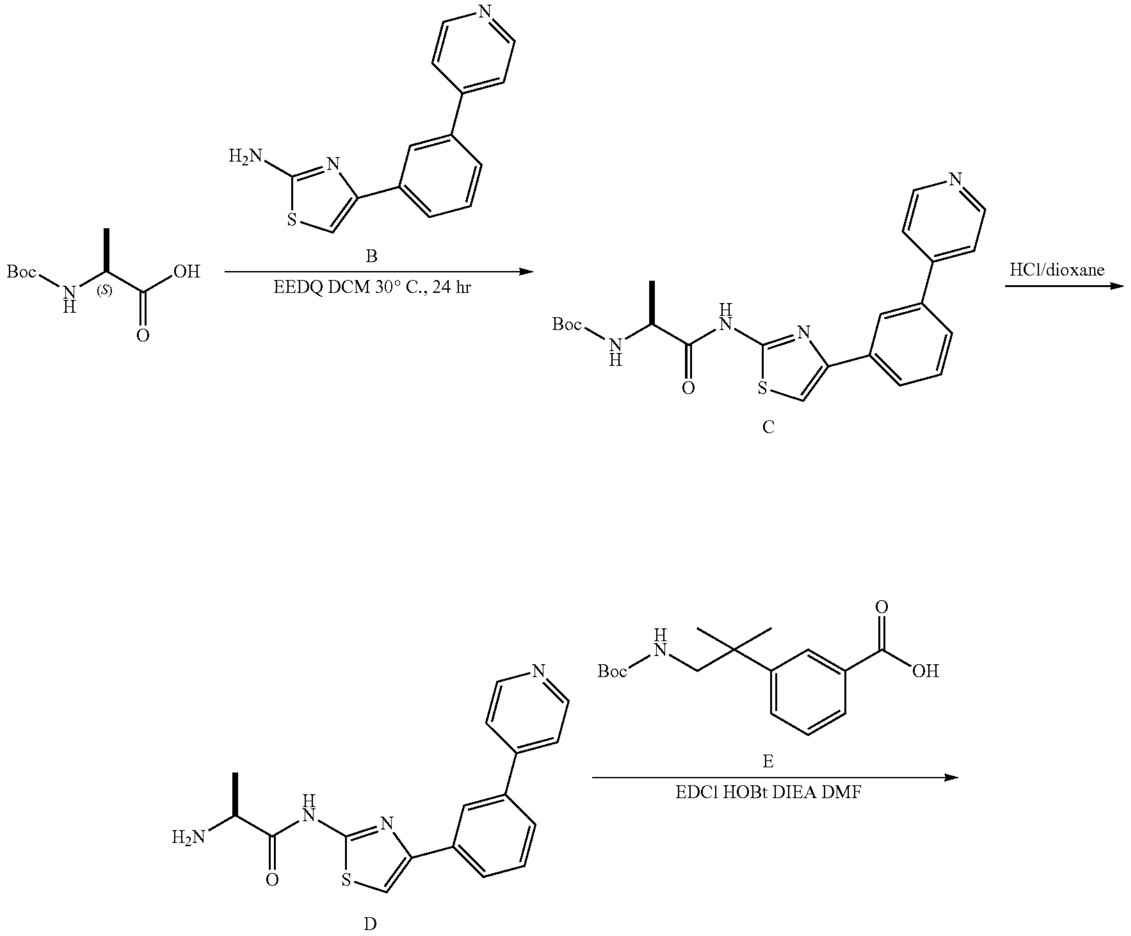

-continued

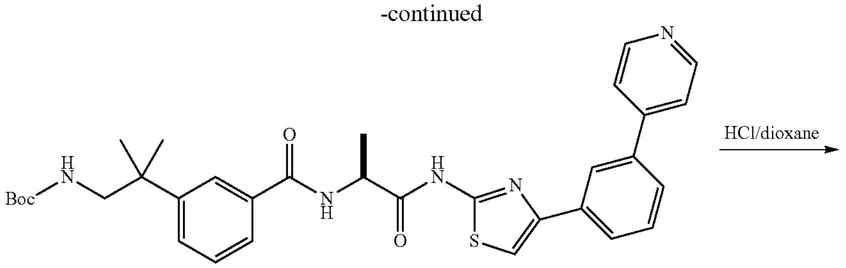

F

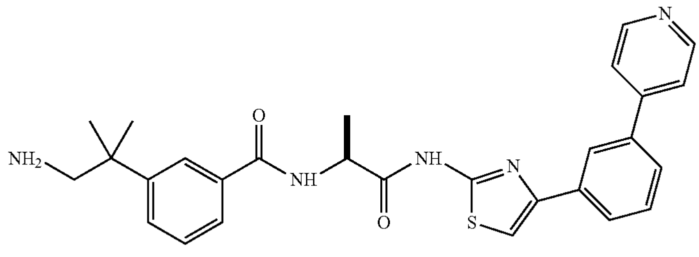

Compound 65

Step 1: Preparation of (S)-tert-butyl (1-oxo-1-((4-(3-(pyridin-4-yl)phenyl)thiazol-2-yl)amino)propan-2-yl)carbamate (Intermediate C)

C

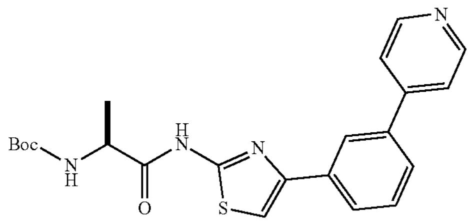

To a solution of 4-[3-(4-pyridyl)phenyl]thiazol-2-amine (prepared according to the method in Example 16) (200 mg, 789.51 μmol) and (2S)-2-(tertbutoxycarbonylamino) propanoic acid (224.07 mg, 1.18 mmol) in DCM (20 mL) was added EEDQ (390.48 mg, 1.58 mmol), the mixture was stirred at 30° C. for 16 hr. The reaction mixture was diluted with $H_2O$ (10 mL) and extracted with EA (10 mL×2). The combined organic layers were dried over anhydrous $Na_2SO_4$, filtered and concentrated under reduced pressure to give the residue. The residue was slurried in MTBE (5 mL), filtered and dried in vacuum to give Intermediate C (180 mg, 424.01 μmol, 53.71% yield) as a yellow solid. LCMS (ESI) m/z $[M+H]^+$=425.3. $^1$H NMR (400 MHz, DMSO) δ=12.31 (br s, 1H), 8.68-8.66 (m, 2H), 8.30 (s, 1H), 8.01 (d, J=8.0 Hz, 1H), 7.76-7.74 (m, 4H), 7.60-7.59 (m, 1H), 7.20 (m, 1H), 4.30-4.20 (m, 1H), 2.46-2.45 (m, 3H), 1.39 (s, 9H) ppm. Chiral SFC_racemate (EW9897-424-P1A_3): Rt=1.704, 2.354 min, ee value=8.27%, OJ-3_5CM_MEOH(DEA)_5_40_3ML_AT35.M. Chiral SFC (EW9897-424-P1A1_1): Rt=1.702 min, ee value=100%, OJ-3_5CM_MEOH(DEA)_5_40_3ML_AT35.M Step 2: Preparation of (S)-2-amino-N-(4-(3-(pyridin-4-yl)phenyl)thiazol-2-yl)propanamide (Intermediate D)

D

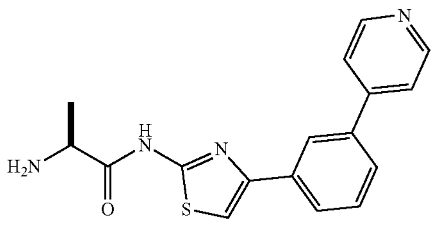

A solution of Intermediate C (180 mg, 424.01 μmol) in HCl/dioxane (4 M, 5 mL) was stirred at 30° C. for 2 hr. The reaction mixture was concentrated in vacuum to give Intermediate D (220 mg, crude, HCl salt) as a yellow solid, which was used directly in the next step. $^1$H NMR (400 MHz, DMSO) δ=12.90 (br s, 1H), 9.01 (br d, J=6.4 Hz, 2H), 8.59-8.42 (m, 6H), 8.16 (br d, J=8.0 Hz, 1H), 8.02-7.99 (m, 2H), 7.73-7.71 (m, 1H), 4.05-3.98 (m, 1H), 1.58-1.45 (m, 3H) ppm.

Step 3: Preparation of (S)-tert-butyl (2-methyl-2-(3-((1-oxo-1-((4-(3-(pyridin-4-yl)phenyl)thiazol-2-yl)amino)propan-2-yl)carbamoyl)phenyl)propyl)carbamate (Intermediate F)

F

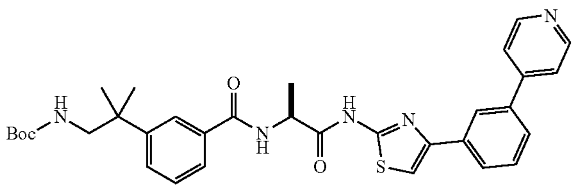

To a solution of Intermediate D (170 mg, 471.10 μmol, HCl salt) in DMF (2 mL) was added 3-[2-(tert-butoxycarbonylamino)-1,1-dimethyl-ethyl]benzoic acid (prepared according to the method in Example 55) (138.20 mg, 471.10 μmol) and DIEA (304.42 mg, 2.36 mmol, 410.27 μL), then EDCl (135.46 mg, 706.64 μmol) and HOBt (76.39 mg, 565.32 μmol) was added to the mixture. The mixture was stirred at 30° C. for 16 hr. The reaction mixture was diluted with $H_2O$ (2 mL) and extracted with EA (2 mL×2). The combined organic layers were dried over anhydrous $Na_2SO_4$, filtered and concentrated under reduced pressure to give a residue. The reaction was purified by reversed phase (0.1% FA condition) and lyophilized to give Intermediate F (40 mg, 66.70 μmol, 14.16% yield) as a white solid. $^1H$ NMR (400 MHz, MeOD) δ=8.61-8.60 (m, 2H), 8.31 (s, 1H), 8.03 (d, J=8.0 Hz, 1H), 7.95 (s, 1H), 7.79-7.77 (m, 2H), 7.69-7.58 (m, 2H), 7.63-7.53 (m, 3H), 7.56-7.43 (m, 1H), 4.81-4.77 (m, 2H), 4.58 (s, 2H), 1.62 (d, J=7.2 Hz, 3H), 1.35 (s, 15H) ppm. Chiral SFC (EW9897-432-P1A_1): Rt=2.006 min, ee value=97.46%, AS-3-MeOH (DEA)-5-40-3 mL-35T·lcm. Chiral SFC_racemate (EW9897-432-P1B_5): Rt=1.704, 1.991 min, ee value=32.80%, AS-3-MeOH (DEA)-5-40-3 mL-35T·lcm.

Step 4: Preparation of (S)-3-(1-amino-2-methylpropan-2-yl)-N-(1-oxo-1-((4-(3-(pyridin-4-yl)phenyl)thiazol-2-yl)amino)propan-2-yl)benzamide (Compound 65)

Compound 65

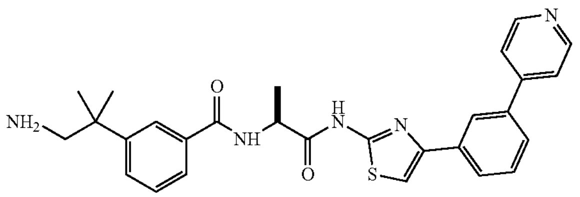

A solution of Intermediate F (40 mg, 66.70 μmol) in HCl/dioxane (4 M, 2 mL) was stirred at 30° C. for 2 hr. The reaction mixture was concentrated to remove the solvent to afford the residue. The residue was purified by reversed phase (0.1% FA condition) and lyophilized to give Compound 65 (19.85 mg, 35.48 μmol, 53.20% yield, FA salt) as a white solid. LCMS (ESI) m/z $[M+H]^+$=500.1. $^1H$ NMR (400 MHz, MeOD) δ=8.61-8.60 (m, 2H), 8.53 (s, 1H), 8.32-8.31 (m, 1H), 8.01-7.98 (m, 2H), 7.97-7.79 (m, 1H), 7.78-7.76 (m, 2H), 7.58-7.56 (m, 2H), 7.55-7.53 (m, 3H), 4.83-4.77 (m, 1H), 3.22 (s, 2H), 1.62-1.60 (m, 3H), 1.52-1.43 (m, 6H) ppm. Chiral SFC_racemate (EW9897-435-P1A_13): Rt=1.814, 3.136 min, ee value=7.98%, AD-3-IPA (DEA)-40-3ML-7MIN-35T·lcm. Chiral SFC (EW9897-435-P1B_3): Rt=1.779 min, ee value=100%, AD-3-IPA (DEA)-40-3ML-7MIN-35T·lcm.

Example 73. Preparation of 3-(1-amino-2-methylpropan-2-yl)-N-(2-((4-(3-(2,6-dimethylpyridin-4-yl)phenyl)thiazol-2-yl)amino)-2-oxoethyl)benzamide (Compound 66)

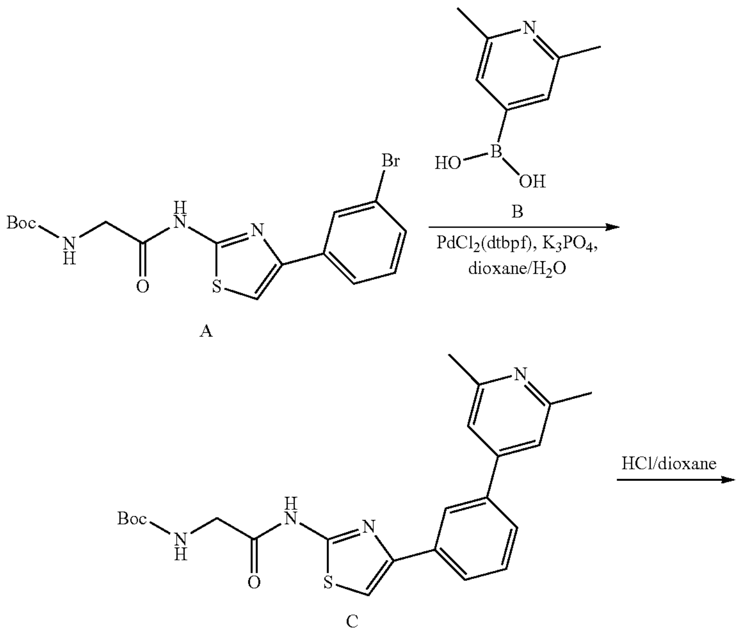

-continued

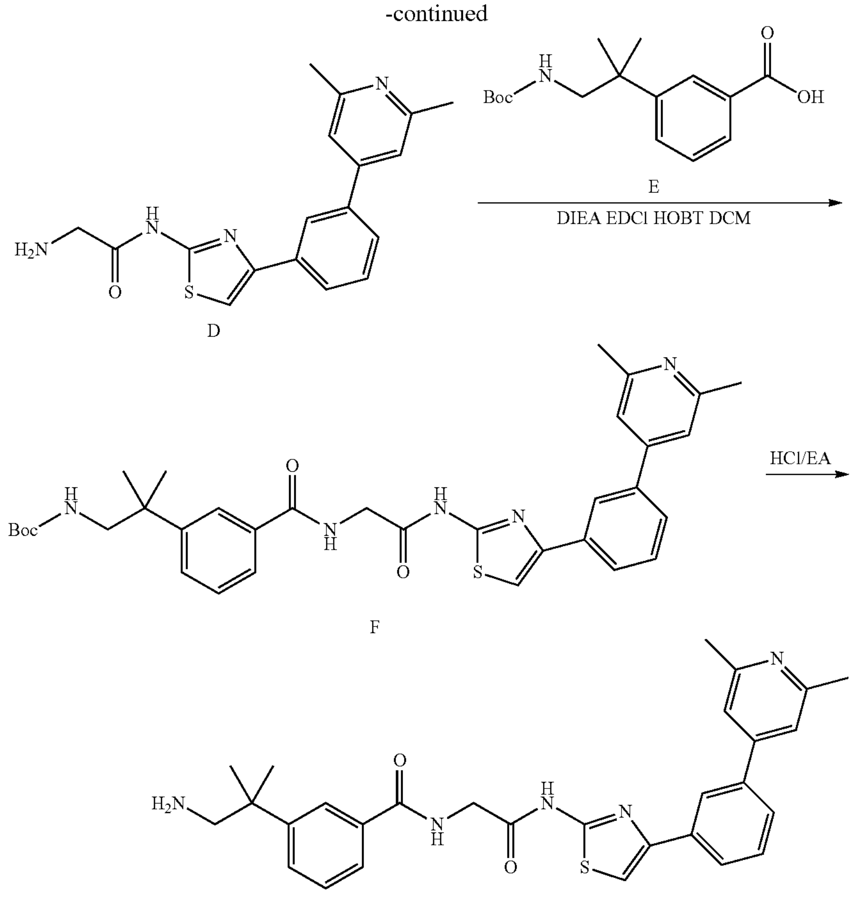

Compound 66

Step 1: Preparation of tert-butyl N-[2-[[4-[3-(2,6-dimethyl-4-pyridyl)phenyl]thiazol-2-yl]amino]-2-oxo-ethyl]carbamate (Intermediate C)

C

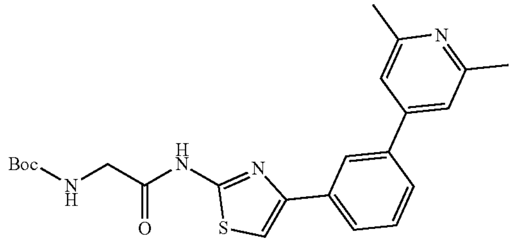

A mixture of tert-butyl N-[2-[[4-(3-bromophenyl)thiazol-2-yl]amino]-2-oxo-ethyl]carbamate (prepared according to the method in Example 2) (1 g, 2.43 mmol), (2,6-dimethyl-4-pyridyl)boronic acid (549.25 mg, 3.64 mmol), ditert-butyl (cyclopentyl)phosphane;dichloropalladium;iron (158.08 mg, 242.54 μmol), $K_3PO_4$ (1.54 g, 7.28 mmol) in dioxane (18 mL) and $H_2O$ (2 mL) was degassed and purged with $N_2$ for 3 times, and then the mixture was stirred at 80° C. for 2 hr under $N_2$ atmosphere. The reaction mixture was concentrated under reduced pressure to give a residue. The residue was purified by column chromatography ($SiO_2$, Petroleum ether/Ethyl acetate=1/1 to 0/1), then the fraction was concentrated in vacuum to give Intermediate C (0.96 g, 2.19 mmol, 90.26% yield) as a yellow solid. LCMS (ESI) m/z=$[M+H]^+$=439.2. $^1$H NMR (400 MHz, MeOD) δ=8.26 (s, 1H) 7.97 (d, J=8.0 Hz, 1H), 7.65 (d, J=8.0 Hz, 1H), 7.54-7.50 (m, 2H), 7.42 (s, 2H), 3.99 (s, 2H), 2.57 (s, 6H), 1.48 (s, 9H) ppm.

Step 2: Preparation of 2-amino-N-[4-[3-(2,6-dimethyl-4-pyridyl)phenyl]thiazol-2-yl]acetamide (Intermediate D)

D

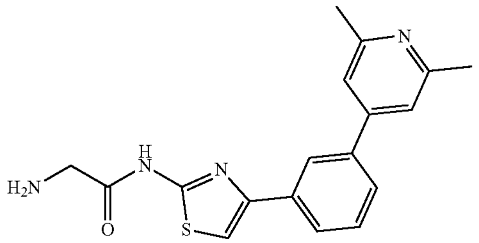

A mixture of Intermediate C (0.96 g, 2.19 mmol) in HCl/MeOH (4 M, 20 mL) was stirred at 25° C. for 2 hr. The reaction mixture was concentrated under reduced pressure to give a residue. The residue was triturated with MTBE:

MeOH=20:1 (20 mL) at 25° C. for 0.5 h, then the solid was collected by filtered, washed with MTBE (10 mL) and dried in vacuum to give Intermediate D (900 mg, crude, HCl) as a white solid, which was used into the next step without further purification. LCMS (ESI) m/z=$[M+H]^+$=339.3.

Step 3: Preparation of tert-butyl (2-(3-((2-((4-(3-(2,6-dimethylpyridin-4-yl)phenyl)thiazol-2-yl)amino)-2-oxoethyl)carbamoyl)phenyl)-2-methylpropyl)carbamate (Intermediate F)

F

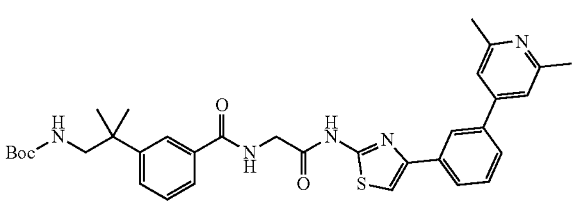

To a solution of Intermediate D (100 mg, 266.75 μmol, HCl salt) in DCM (1 mL) was added 3-[2-(tert-butoxycarbonylamino)-1,1-dimethyl-ethyl]benzoic acid (prepared according to the method in Example 55) (78.25 mg, 266.75 μmol) and DIEA (206.85 mg, 1.60 mmol, 278.77 μL), then EDCI (76.70 mg, 400.12 μmol) and HOBt (43.25 mg, 320.10 μmol) was added. The mixture was stirred at 30° C. for 2 hr. The reaction mixture was diluted with $H_2O$ (2 mL) and extracted with EA (2 mL×2). The combined organic layers were dried over anhydrous $Na_2SO_4$, filtered and concentrated under reduced pressure to give a residue. The residue was purified by reversed phase (0.1% FA condition) and concentrated to remove the ACN, then extracted with EA (10 mL×2), the organic layers were dried over anhydrous $Na_2SO_4$, filtered and concentrated to afford Intermediate F (85 mg, 138.49 μmol, 51.92% yield) as a white solid. LCMS (ESI) m/z=$[M+H]^+$=614.3.

Step 4: Preparation of 3-(1-amino-2-methylpropan-2-yl)-N-(2-((4-(3-(2,6-dimethylpyridin-4-yl)phenyl)thiazol-2-yl)amino)-2-oxoethyl)benzamide (Compound 66)

Compound 66

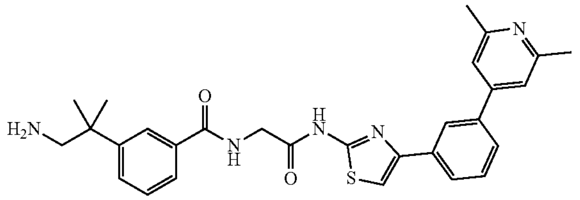

A solution of Intermediate F (85 mg, 138.49 μmol) in HCl/EA (4 M, 5 mL) was stirred at 30° C. for 0.5 hr. The reaction mixture was concentrated in vacuum. The residue was purified by reversed phase (0.1% FA condition) and lyophilized to give Compound 66 (30.92 mg, 58.93 μmol, 42.55% yield) as an off-white solid. LCMS (ESI) m/z=$[M+H]^+$=514.3. $^1H$ NMR (400 MHz, MeOD) δ=8.39 (s, 1H), 8.29 (s, 1H), 8.02-8.00 (m, 2H), 7.88 (d, J=8.0 Hz, 1H), 7.70-7.68 (m, 2H), 7.59-7.55 (m, 3H), 7.46 (s, 2H), 4.36 (s, 2H), 3.27 (s, 2H), 2.60 (s, 6H), 1.51 (s, 6H) ppm.

Example 74. Preparation 3-(1-amino-2-methylpropan-2-yl)-N-(2-((4-(2-methyl-1-oxo-1,2-dihydroisoquinolin-7-yl)thiazol-2-yl)amino)-2-oxoethyl)benzamide (Compound 67)

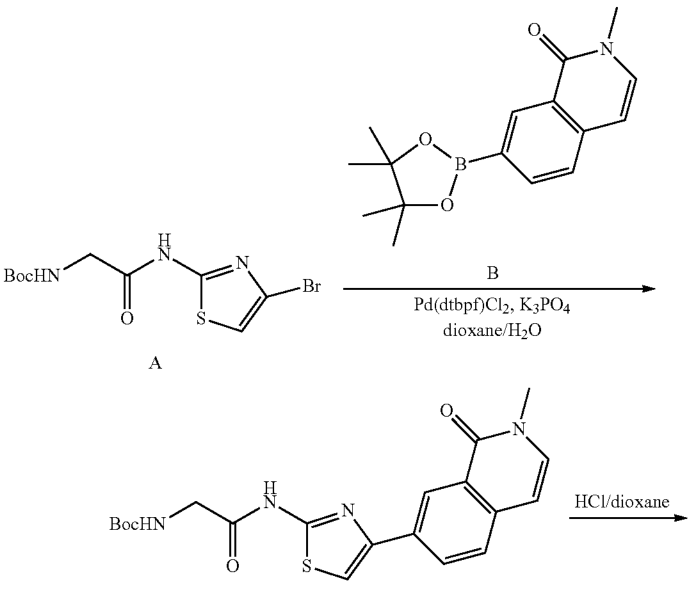

-continued

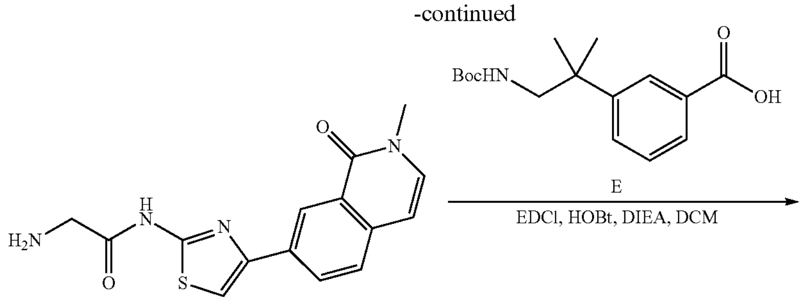

D

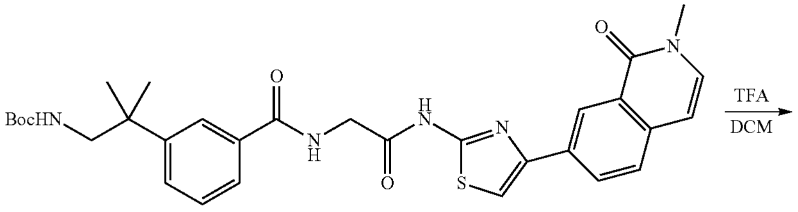

F

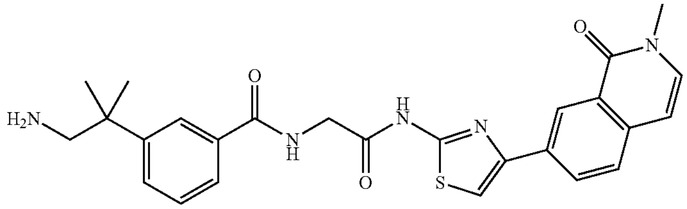

Compound 67

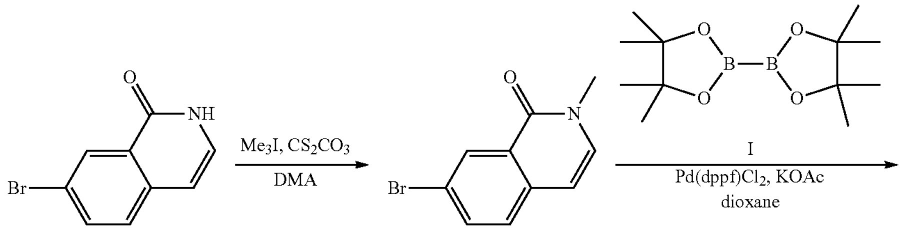

G H

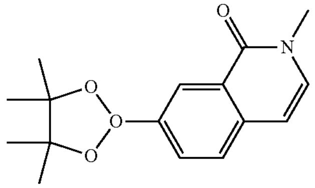

B

Step 1: Preparation of 7-bromo-2-methylisoquinolin-1(2H)-one (Intermediate H)

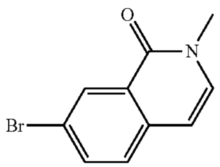

H

To a solution of 7-bromo-2H-isoquinolin-1-one (22 g, 98.19 mmol) and $Cs_2CO_3$ (47.99 g, 147.29 mmol) in DMA (400 mL) was added MeI (20.91 g, 147.29 mmol, 9.17 mL) at 25° C. The mixture was stirred at 60° C. for 4 hr. The reaction mixture was pour into ice water (500 mL). The crude product was triturated with $H_2O$ (500 mL) at 0° C. for 10 min, then filtered and dried in vacuum to give Intermediate H (23 g, 96.61 mmol, 98.39% yield) as a white solid. LCMS (ESI) m/z $[M+H]^+$=240.0. $^1H$ NMR (400 MHz, chloroform-d) δ=8.55 (d, J=2.0 Hz, 1H), 7.68 (d, J=2.0 Hz, 1H), 7.38-7.36 (m, 1H), 7.09-7.07 (m, 1H), 6.44 (d, J=7.2 Hz, 1H), 3.60 (s, 3H) ppm.

Step 2: Preparation of 2-methyl-7-(4,4,5,5-tetramethyl-1,3,2-dioxaborolan-2-yl)isoquinolin-1(2H)-one (Intermediate B)

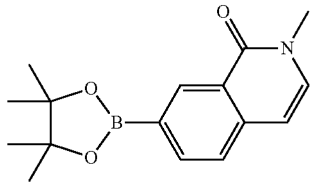

B

A mixture of Intermediate H (23 g, 96.61 mmol), 4,4,5,5-tetramethyl-2-(4,4,5,5-tetramethyl-1,3,2-dioxaborolan-2-yl)-1,3,2-dioxaborolane (26.99 g, 106.27 mmol), AcOK (28.44 g, 289.82 mmol) and Pd(dppf)$Cl_2$ (3 g, 4.10 mmol) in dioxane (300 mL) was degassed and purged with $N_2$ for 3 times, and then the mixture was stirred at 80° C. for 2 hr under $N_2$ atmosphere. Water (20 mL) was added and the reaction mixture was extracted with EA (50 mL×2). The combined organic layers were washed with brine (20 mL), dried over $Na_2SO_4$, filtered and concentrated under reduced pressure to give Intermediate B (30 g, crude) as a brown solid, which was used into the next step without further purification. LCMS (ESI) m/z $[M+H]^+$=286.3.

Step 3: Preparation of tert-butyl (2-((4-(2-methyl-1-oxo-1,2-dihydroisoquinolin-7-yl)thiazol-2-yl) amino)-2-oxoethyl)carbamate (Intermediate C)

C

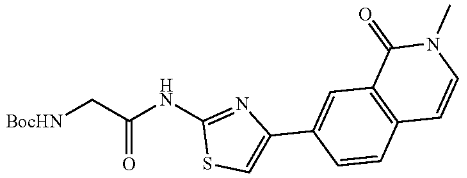

A mixture of tert-butyl N-[2-[(4-bromothiazol-2-yl) amino]-2-oxo-ethyl]carbamate (300 mg, 892.31 μmol), Intermediate B (381.66 mg, 1.34 mmol), ditertbutyl(cyclopentyl)phosphane;dichloropalladium;iron (29.08 mg, 44.62 μmol) and $K_3PO_4$ (568.22 mg, 2.68 mmol) in dioxane (3 mL) and $H_2O$ (0.5 mL) was de-gassed and then heated to 100° C. for 2 hours under $N_2$. The reaction mixture was diluted with $H_2O$ (2 mL) and EA (2 mL), then filtered, and the filter cake was washed with EA (2 mL) and dried in vacuum to give Intermediate C (200 mg, 479.11 μmol, 53.69% yield) as a gray solid. LCMS (ESI) m/z $[M+H]^+$=415.1.

Step 4: Preparation of 2-amino-N-(4-(2-methyl-1-oxo-1,2-dihydroisoquinolin-7-yl)thiazol-2-yl)acetamide (Intermediate D)

D

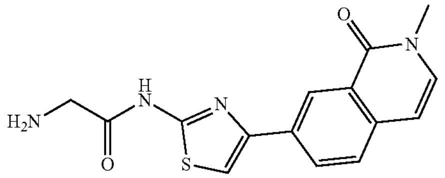

To a solution of Intermediate C (200 mg, 482.54 μmol) in MeOH (1 mL) was added HCl/dioxane (4 M, 2 mL). The mixture was stirred at 25° C. for 1 hr. The reaction mixture was diluted with MTBE (10 mL), then filtered, and the filter cake was washed with MTBE (2 mL) and dried in vacuum to give Intermediate D (180 mg, crude, HCl salt) as gray solid, which was used into the next step without further purification. LCMS (ESI) m/z $[M+H]^+$=315.2.

Step 5: Preparation of tert-butyl (2-methyl-2-(3-((2-((4-(2-methyl-1-oxo-1,2-dihydroisoquinolin-7-yl) thiazol-2-yl)amino)-2-oxoethyl)carbamoyl)phenyl) propyl)carbamate (Intermediate E)

E

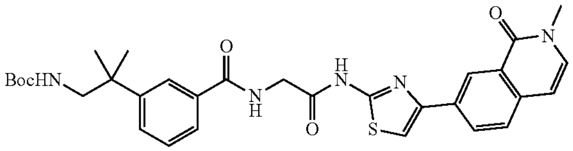

To a solution of 3-[2-(tert-butoxycarbonylamino)-1,1-dimethyl-ethyl]benzoic acid (prepared according to the method in Example 55) (90.31 mg, 307.85 μmol), EDCl (59.02 mg, 307.85 μmol), HOBt (41.60 mg, 307.85 μmol) and DIEA (198.94 mg, 1.54 mmol, 268.11 μL) in DCM (2 mL) was added Intermediate D (90 mg, 256.54 μmol, HCl salt). The mixture was stirred at 25° C. for 16 hr. To the reaction mixture was added sat. citric acid (5 mL) and extracted with EA (3 mL×3). The combined organic layers were washed with brine (3 mL), dried over $Na_2SO_4$, filtered and concentrated under reduced pressure to give Intermediate E (150 mg, crude) as yellow solid, which was used into the next step without further purification. LCMS (ESI) m/z $[M+H]^+$=590.3.

Step 6: Preparation of 3-(1-amino-2-methylpropan-2-yl)-N-(2-((4-(2-methyl-1-oxo-1,2-dihydroisoquinolin-7-yl)thiazol-2-yl)amino)-2-oxoethyl)benzamide (Compound 67)

Compound 67

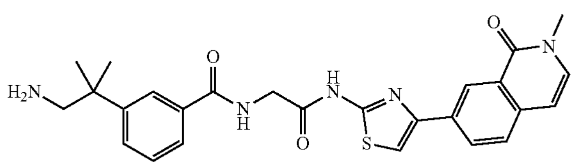

A mixture of Intermediate E (150 mg, 254.37 μmol) in TFA (0.3 mL) and DCM (1.5 mL) was stirred at 25° C. for 1 hr under $N_2$ atmosphere. The reaction mixture was concentrated under reduced pressure to give a residue. The residue was purified by Prep-HPLC (column: Luna C18 150×25 5 u; mobile phase: [water (0.075% TFA)-ACN]; B %: 20%-50%, 9 min). The fraction was concentrated under reduced pressure to remove $CH_3CN$, adjusted with sat. $NaHCO_3$ to pH=8 and extracted with EA (20 mL×5). The combined organic layers were washed with brine (30 mL), dried over $Na_2SO_4$, filtered and concentrated under reduced pressure to give a solid. The solid was triturated with MTBE (1 mL) for 10 min, then filtered and the filter cake was washed MTBE (1 mL) and dried in vacuum to give Compound 67 (7.8 mg, 15.60 μmol, 6.13% yield) as a yellow solid. LCMS (ESI) m/z $[M+H]^+$=490.3. $^1H$ NMR (400 MHz, MeOD) δ=8.89 (d, J=1.6 Hz, 1H), 8.24-8.22 (m, 1H), 7.97-7.96 (m, 1H), 7.79 (d, J=7.6 Hz, 1H), 7.68-7.62 (m, 2H), 7.54 (s, 1H), 7.51-7.47 (m, 1H), 7.36 (d, J=7.2 Hz, 1H), 6.70 (d, J=7.2 Hz, 1H), 4.34 (s, 2H), 3.64 (s, 3H), 2.99-2.89 (m, 2H), 1.40 (s, 6H) ppm.

Example 75. Preparation of (S)-3-(1-amino-2-methylpropan-2-yl)-N-(3-methoxy-1-((4-(3-(2-methylpyridin-4-yl)phenyl)thiazol-2-yl)amino)-1-oxopropan-2-yl)benzamide (Compound 68)

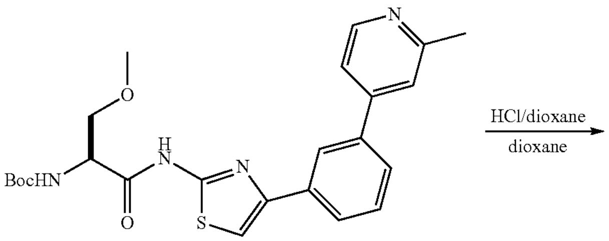

A

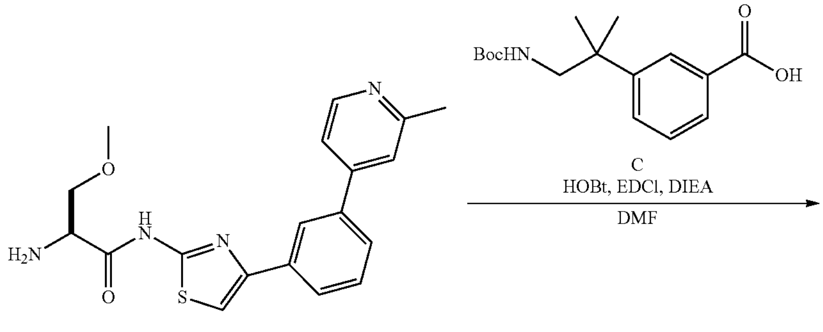

B

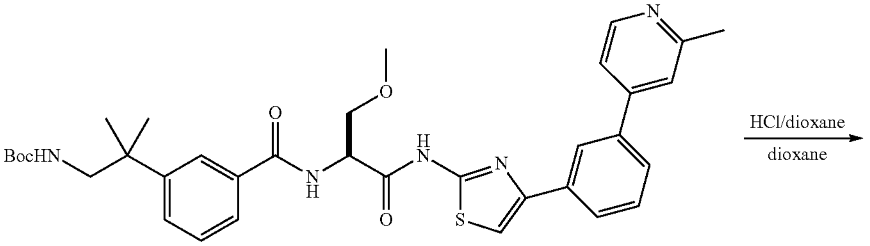

D

-continued

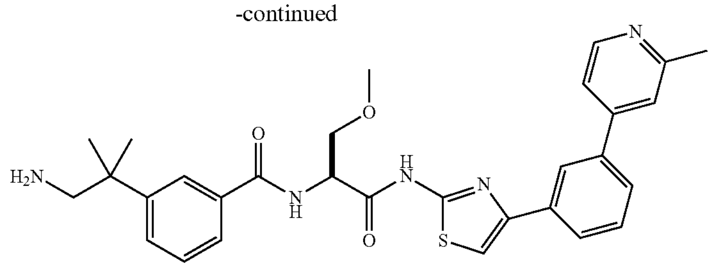

Compound 68

Step 1: Preparation of (S)-2-amino-3-methoxy-N-(4-(3-(2-methylpyridin-4-yl)phenyl)thiazol-2-yl) propanamide (Intermediate B)

B

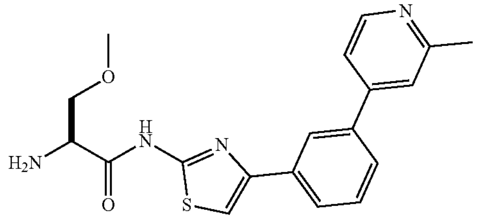

To a mixture of tert-butyl N-[1-(methoxymethyl)-2-[[4-[3-(2-methyl-4-pyridyl)phenyl]thiazol-2-yl]amino]-2-oxo-ethyl]carbamate (200 mg, 426.83 μmol) in dioxane (1 mL) was added HCl/dioxane (4 M, 1.07 mL), and then the mixture was stirred at 25° C. for 1 hr. The reaction mixture was concentrated under reduced pressure to give Intermediate B (450 mg, crude, HCl salt) as white solid, which was used into the next step without further purification. LCMS (ESI) m/z=[M+H]$^+$=369.2.

Step 2: Preparation of (S)-tert-butyl (2-(3-((3-methoxy-1-((4-(3-(2-methylpyridin-4-yl)phenyl) thiazol-2-yl)amino)-1-oxopropan-2-yl)carbamoyl) phenyl)-2-methylpropyl)carbamate (Intermediate D)

D

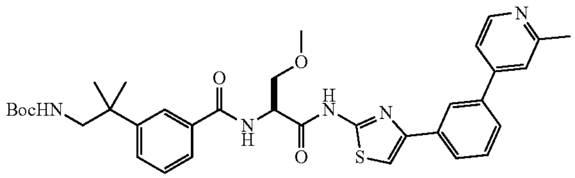

A mixture of Intermediate B (130 mg, 321.06 μmol, HCl salt), 3-[2-(tert-butoxycarbonylamino)-1,1-dimethyl-ethyl] benzoic acid (prepared according to the method in Example 55) (141.28 mg, 481.59 μmol), DIEA (124.48 mg, 963.17 μmol, 167.76 μL), HOBt (86.76 mg, 642.11 μmol) and EDCl (123.09 mg, 642.11 μmol) in DMF (6 mL) was degassed and purged with $N_2$ for 3 times, and then the mixture was stirred at 25° C. for 12 hr under $N_2$ atmosphere. The reaction mixture was diluted with $H_2O$ (3 mL), and extracted with EA (3 mL×3). The combined organic layers were washed with brine (6 mL×1), dried over $Na_2SO_4$, filtered and concentrated under reduced pressure to give a residue. The residue was purified by Prep-HPLC (basic condition) and concentrated to remove ACN, then extracted with EA (3 mL×3), dried over $Na_2SO_4$, filtered and concentrated under reduced pressure to give Intermediate D (130 mg, 161.06 μmol, 50.16% yield) as an off-white gum. LCMS (ESI) m/z=[M+H]$^+$=644.4.

Step 3: Preparation of (S)-3-(1-amino-2-methylpropan-2-yl)-N-(3-methoxy-1-((4-(3-(2-methylpyridin-4-yl)phenyl)thiazol-2-yl)amino)-1-oxopropan-2-yl) benzamide (Compound 68)

Compound 68

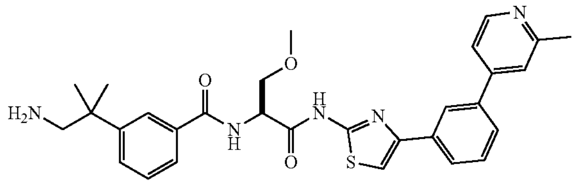

To a mixture of Intermediate D (121.89 mg, 189.33 μmol) in dioxane (1 mL) was added HCl/dioxane (4 M, 473.34 μL), and then the mixture was stirred at 25° C. for 1 hr. The reaction mixture was concentrated under reduced pressure. The residue was purified by Prep-HPLC (neutral condition) and lyophilized to give Compound 68 (24 mg, 44.14 μmol, 23.32% yield) as a white solid. LCMS (ESI) m/z=[M+H]$^+$=544.3. $^1$H NMR (400 MHz, DMSO+$D_2O$) δ=8.52 (d, J=5.2 Hz, 1H), 8.28 (s, 1H), 8.00 (d, J=8.4 Hz, 1H), 7.86 (s, 1H), 7.80-7.71 (m, 3H), 7.64 (s, 1H), 7.62-7.53 (m, 3H), 7.46-7.41 (m, 1H), 5.01-4.90 (m, 1H), 3.82-3.75 (m, 2H), 3.33 (s, 3H), 2.72 (s, 2H), 2.55 (s, 3H), 1.27 (s, 6H) ppm. SFC: AD-RH-0-30-1ML·lcm, Rt=8.647 min, 100% ee value.

Example 76. Preparation of 3-(1-amino-2-methyl-propan-2-yl)-N-(2-((4-(3-(1-methyl-1H-pyrazol-3-yl)phenyl)thiazol-2-yl)amino)-2-oxoethyl)benzamide (Compound 69)
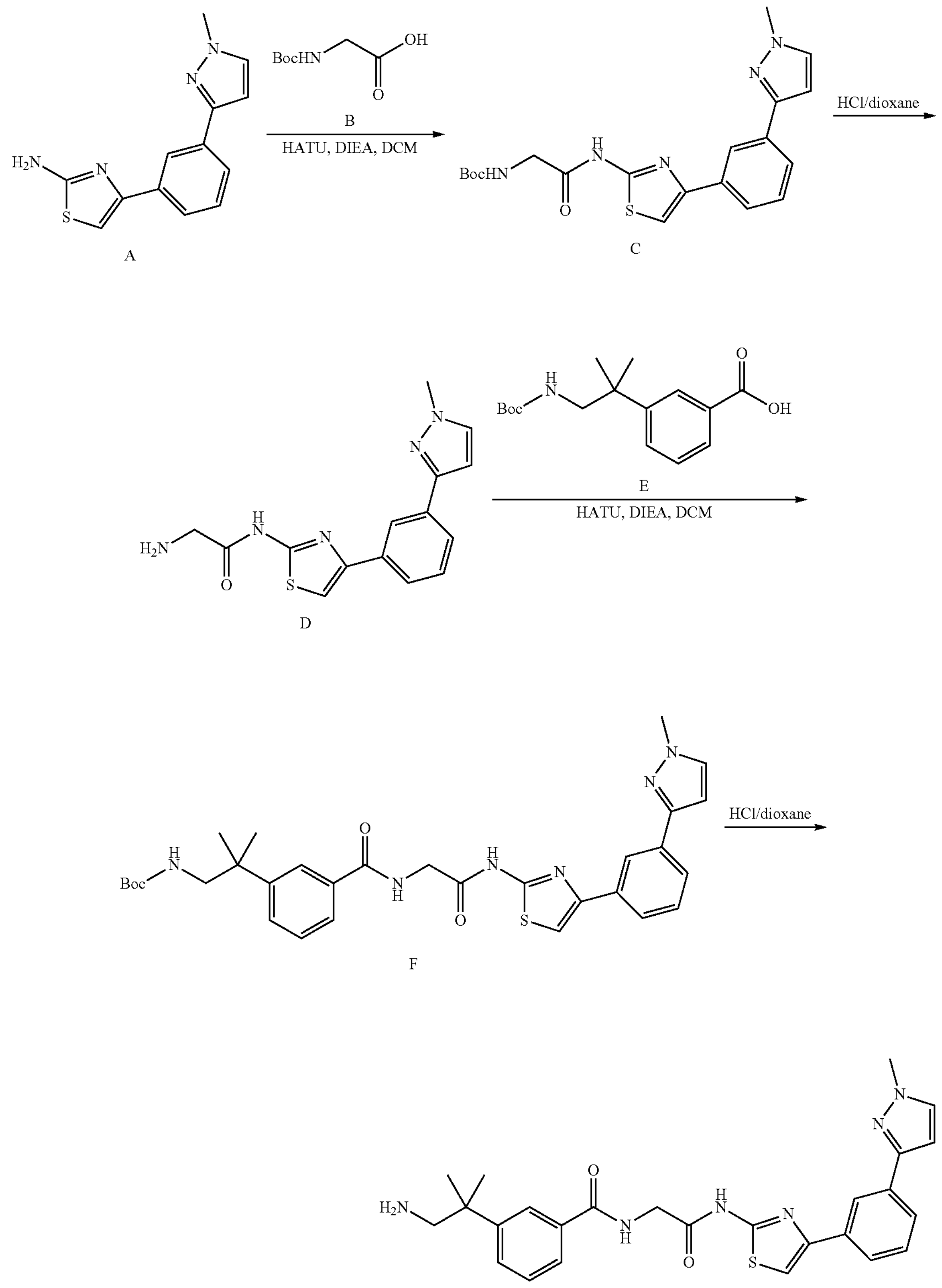
Compound 69

Step 1: Preparation of tert-butyl (2-((4-(3-(1-methyl-1H-pyrazol-3-yl)phenyl)thiazol-2-yl)amino)-2-oxoethyl)carbamate (Intermediate C)

C

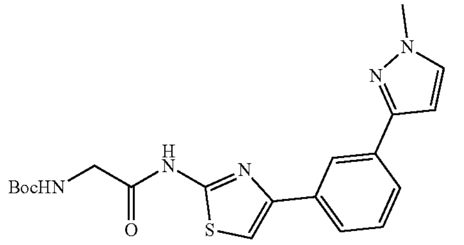

To a solution of 2-(tert-butoxycarbonylamino)acetic acid (4.10 g, 23.41 mmol), DIEA (6.05 g, 46.82 mmol, 8.15 mL) and HATU (8.90 g, 23.41 mmol) in DCM (40 mL) was added 4-[3-(1-methylpyrazol-3-yl)phenyl]thiazol-2-amine (4 g, 15.61 mmol), the mixture was stirred at 30° C. for 2 hr. The mixture was concentrated under reduced pressure to give a residue. The residue was purified by reverse phase (FA) and lyophilized to give Intermediate C (2 g, 4.44 mmol, 28.45% yield) as a brown solid. LCMS (ESI) m/z $[M+H]^+$=414.1.

Step 2: Preparation of 2-amino-N-(4-(3-(1-methyl-1H-pyrazol-3-yl)phenyl)thiazol-2-yl)acetamide (Intermediate D)

D

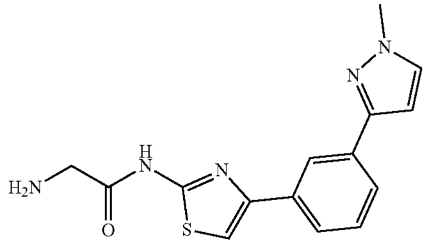

A solution of Intermediate C (2 g, 4.84 mmol) in 4 M HCl/dioxane (20 mL) was stirred at 30° C. for 1 hr. The reaction mixture was concentrated under reduced pressure to give a residue. The residue was triturated with MTBE (50.0 mL), then filtered and concentrated under reduced pressure to give Intermediate D (2 g, crude, HCl salt) as a brown solid. LCMS (ESI) m/z $[M+H]^+$=313.9. $^1$H NMR (400 MHz, DMSO) δ=12.80 (s, 1H), 8.51 (s, 3H), 8.39 (s, 1H), 7.82-7.72 (m, 4H), 7.47-7.43 (m, 1H), 6.74-6.73 (m, 1H), 3.93-3.90 (m, 5H) ppm.

Step 3: Preparation of tert-butyl (2-methyl-2-(3-((2-((4-(3-(1-methyl-1H-pyrazol-3-yl)phenyl)thiazol-2-yl)amino)-2-oxoethyl)carbamoyl)phenyl)propyl) carbamate (Intermediate F)

F

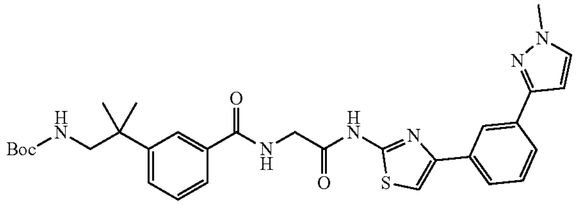

To a solution of 3-[2-(tert-butoxycarbonylamino)-1,1-dimethyl-ethyl]benzoic acid (prepared according to the method in Example 55) (80 mg, 272.71 μmol), DIEA (176.23 mg, 1.36 mmol, 237.50 μL) and HATU (155.54 mg, 409.06 μmol) in DCM (1 mL) was added Intermediate D (95.40 mg, 272.71 μmol, HCl salt), the mixture was stirred at 30° C. for 1 hr. The reaction mixture was concentrated under reduced pressure to give a residue. The residue was diluted with water (10 mL) and extracted with EtOAc (10 mL×3). The combined organic layers were washed with brine (20 mL), dried over $Na_2SO_4$, filtered and concentrated under reduced pressure to give Intermediate F (120 mg, crude) as a light yellow oil, which was used to the next step without further purification. LCMS (ESI) m/z $[M+H]^+$=589.6.

Step 4: Preparation of 3-(1-amino-2-methylpropan-2-yl)-N-(2-((4-(3-(1-methyl-1H-pyrazol-3-yl)phenyl)thiazol-2-yl)amino)-2-oxoethyl)benzamide (Compound 69)

Compound 69

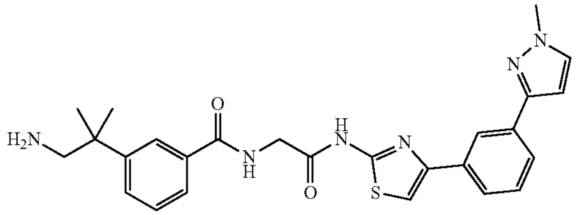

A solution of Intermediate F (120 mg, 203.83 μmol) in 4 M HCl/dioxane (2 mL) was stirred at 30° C. for 1 hr. The reaction mixture was concentrated under reduced pressure to give a residue. The residue was purified by Prep-HPLC (column: Luna C18 150×25 5 u; mobile phase: [water (0.075% TFA)-ACN]; B %: 15%-45%, 9 min) and lyophilized to give Compound 69 (26.64 mg, 44.21 μmol, 21.69% yield, TFA salt) as a yellow solid. LCMS (ESI) m/z $[M+H]^+$=489.3. 1 H NMR (400 MHz, MeOD) δ=8.34-8.32 (m, 1H), 8.00-7.98 (m, 1H), 7.85 (d, J=8.0 Hz, 2H), 7.72-7.68 (m, 2H), 7.63 (d, J=1.8 Hz, 1H), 7.58-7.54 (m, 1H), 7.46-7.41 (m, 2H), 6.67 (d, J=1.8 Hz, 1H), 4.34 (s, 2H), 3.95 (m, 3H), 3.25 (s, 2H), 1.50 (m, 6H) ppm.

Example 77. Preparation of 3-(1-amino-2-methylpropan-2-yl)-4-methyl-N-(2-((4-(3-(1-methyl-1H-pyrazol-3-yl)phenyl)thiazol-2-yl)amino)-2-oxoethyl)benzamide (Compound 70)
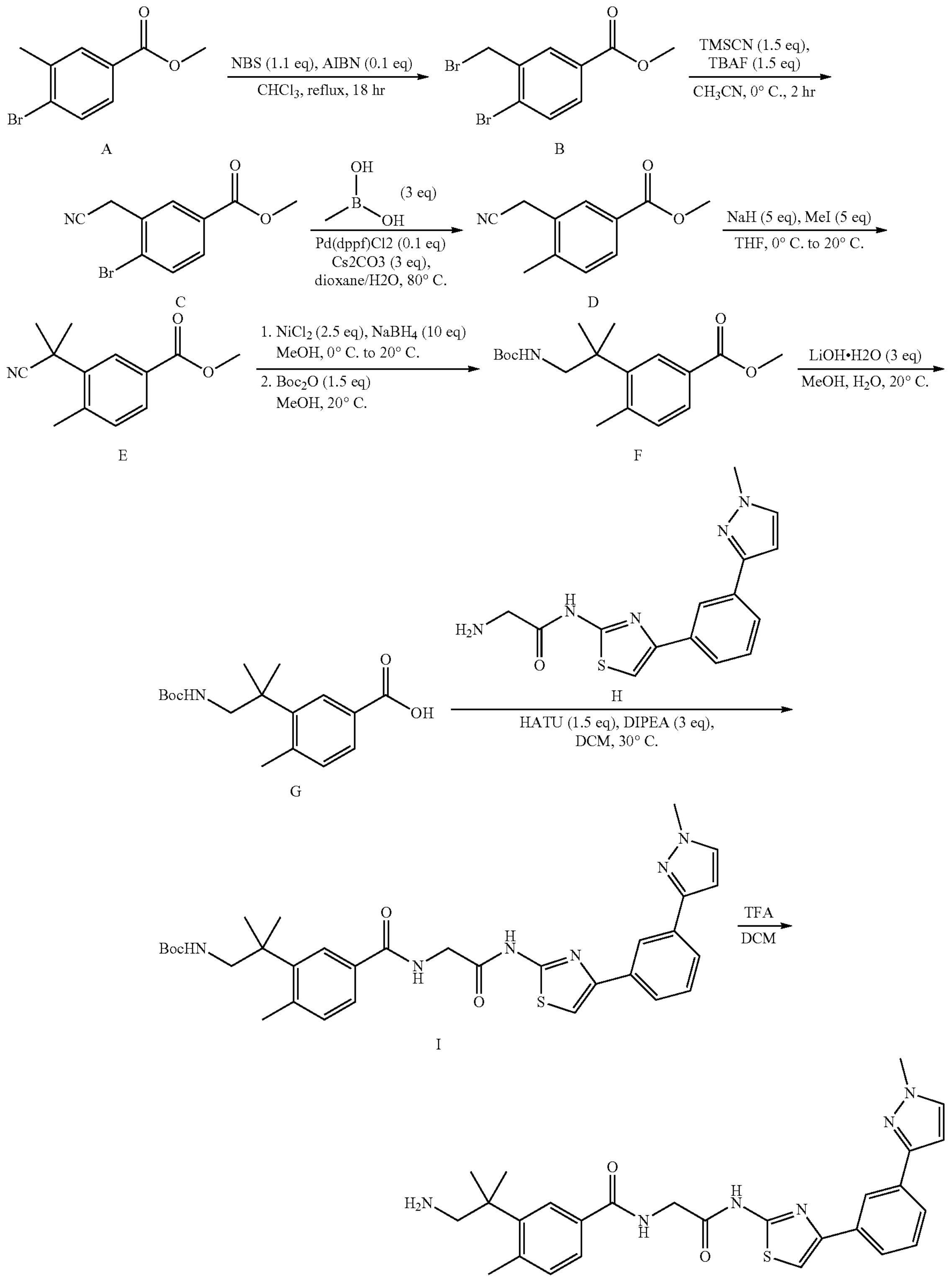
Compound 70

Step 1: Preparation of methyl 4-bromo-3-(bromomethyl)benzoate (Intermediate B)

B

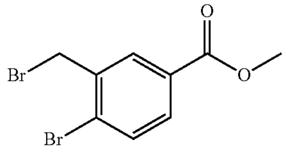

To a solution of methyl 4-bromo-3-methyl-benzoate (4 g, 17.46 mmol) in $CHCl_3$ (15 mL) was added AIBN (286.74 mg, 1.75 mmol) and NBS (3.42 g, 19.21 mmol). The mixture was stirred at 90° C. for 24 hr. The reaction mixture was quenched by addition water 10 mL at 25° C., and extracted with ethyl acetate (10 mL*3). The combined organic layers were washed with brine 10 mL, dried over $Na_2SO_4$, filtered and concentrated under reduced pressure to give a residue. The residue was purified column chromatography ($SiO_2$, Petroleum ether:Ethyl acetate=5:1) and concentrated to give Intermediate B (3.6 g, 11.69 mmol, 66.94% yield) as white solid. $^1H$ NMR (400 MHz, $CDCl_3$) δ=8.14 (d, J=2.0 Hz, 1H), 7.84 (dd, J=8.4 Hz, 2.0 Hz, 1H), 7.69 (d, J=8.4 Hz, 1H), 4.65 (s, 2H), 3.95 (s, 3H) ppm.

Step 2: Preparation of methyl 4-bromo-3-(cyanomethyl)benzoate (Intermediate C)

C

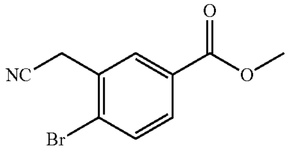

To a solution of Intermediate B (1.5 g, 4.87 mmol) in $CH_3CN$ (15 mL) were added TMSCN (724.83 mg, 7.31 mmol, 914.03 μL) and TBAF (1 M, 7.31 mL) at 0° C. The mixture was stirred at 25° C. for 2 hr. The reaction mixture was poured into water (60 mL), a pink precipitate was formed. The mixture were filtered and the cake was washed with water and dried in vacuum to give Intermediate C (1.6 g, crude) as a pink solid. $^1H$ NMR (400 MHz, $CDCl_3$) δ=8.20 (d, J=2.0 Hz, 1H), 7.91 (dd, J=8.4 Hz, 2.0 Hz, 1H), 7.73 (d, J=8.4 Hz, 1H), 3.96 (s, 3H), 3.91 (s, 2H) ppm.

Step 3: Preparation of methyl 3-(cyanomethyl)-4-methylbenzoate (Intermediate D)

D

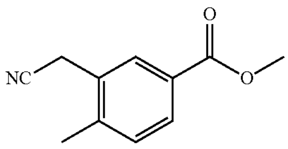

A mixture of Intermediate C (1.5 g, 5.90 mmol), methylboronic acid (1.06 g, 17.71 mmol), $Cs_2CO_3$ (5.77 g, 17.71 mmol), Pd(dppf)$Cl_2$ (431.98 mg, 590.37 μmol) in dioxane (10 mL) and $H_2O$ (3 mL) was degassed and purged with $N_2$ for 3 times, and then the mixture was stirred at 90° C. for 3 hr under $N_2$ atmosphere. The reaction mixture was concentrated under reduced pressure to give a residue. The residue was purified by column chromatography ($SiO_2$, Petroleum ether:Ethyl acetate=3:1) and concentrated to give Intermediate D (1 g, 5.29 mmol, 89.52% yield) as yellow oil. LCMS (ESI) m/z $[M+H]^+$=190.0. $^1H$ NMR (400 MHz, $CDCl_3$) δ=8.04 (s, 1H), 7.96 (dd, J=8.0 Hz, 1.6 Hz, 1H), 7.33 (d, J=8.0 Hz, 1H), 3.97-3.91 (m, 3H) 3.73 (s, 2H), 2.45 (s, 3H) ppm.

Step 4: Preparation of methyl 3-(2-cyanopropan-2-yl)-4-methylbenzoate (Intermediate E)

E

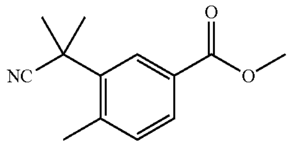

To a solution of Intermediate D (0.4 g, 2.11 mmol) in THE (6 mL) was added NaH (253.69 mg, 6.34 mmol, 60% purity) at 0° C. The mixture was stirred at 0° C. for 30 min. MeI (1.50 g, 10.57 mmol, 658.04 μL) was added and the mixture was stirred at 25° C. for 2 hr. The reaction mixture was quenched by addition water (10 mL) at 25° C., and extracted with ethyl acetate (10 mL*3). The combined organic layers were washed with brine (10 mL), dried over $Na_2SO_4$, filtered and concentrated under reduced pressure to give a residue. The residue was purified by column chromatography ($SiO_2$, Petroleum ether:Ethyl acetate=3:1) and to give Intermediate E (0.16 g, 736.43 μmol, 34.84% yield) as white solid. $^1H$ NMR (400 MHz, $CDCl_3$) δ=8.00 (d, J=1.6 Hz, 1H), 7.90 (dd, J=8.0 Hz, 1.6 Hz, 1H), 7.32 (d, J=8.0 Hz, 1H), 3.93 (s, 3H), 2.73 (s, 3H), 1.83 (s, 6H) ppm.

Step 5: Preparation of methyl 3-(1-((tert-butoxycarbonyl)amino)-2-methylpropan-2-yl)-4-methylbenzoate (Intermediate F)

F

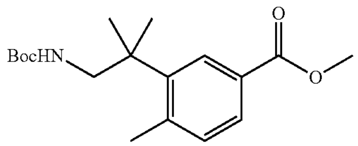

To a solution of Intermediate E (0.15 g, 690.41 μmol) in MeOH (5 mL) was added $NiCl_2 \cdot 6H_2O$ (410.26 mg, 1.73 mmol) and $NaBH_4$ (261.18 mg, 6.90 mmol) at 0° C. The mixture was stirred at 0° C. for 1 hr. $Boc_2O$ (226.02 mg, 1.04 mmol, 237.92 μL) was added and the mixture was stirred at 25° C. for 17 hr. The reaction mixture was quenched by addition water (10 mL) at 25° C., and extracted with ethyl acetate (10 mL*3). The combined organic layers were washed with brine (10 mL), dried over $Na_2SO_4$, filtered and concentrated under reduced pressure to give Intermediate F (0.26 g, crude) as yellow oil, which was used in next step without further purification. LCMS (ESI) m/z $[M+Na]^+$ =344.3.

Step 6: Preparation of 3-(1-((tert-butoxycarbonyl) amino)-2-methylpropan-2-yl)-4-methylbenzoic acid (Intermediate G)

G

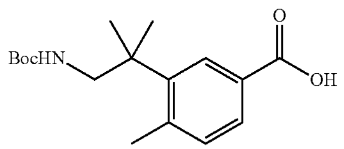

To a solution of Intermediate F (0.25 g, 777.82 μmol) in MeOH (2 mL) and $H_2O$ (2 mL) was added $LiOH \cdot H_2O$ (97.91 mg, 2.33 mmol). The mixture was stirred at 25° C. for 2 hr. The reaction mixture was poured into water (10 mL), and extracted with ethyl acetate (10 mL*3). The organic layers were discarded and the aqueous layers were adjusted pH to 4 with 1 N HCl solution and extracted with ethyl acetate (10 mL*3). The combined organic phases were washed with brine (10 mL), dried over $Na_2SO_4$, filtered and concentrated under reduced pressure to give Intermediate G (0.2 g, 650.65 μmol, 83.65% yield) as yellow oil. LCMS (ESI) m/z $[M+Na]^+$=330.0. $^1$H NMR (400 MHz, DMSO) δ=12.76 (br s, 1H), 7.88 (s, 1H), 7.67 (br d, J=7.6 Hz, 1H), 7.23 (br d, J=7.6 Hz, 1H), 6.78 (br s, 1H), 3.28 (s, 2H), 2.61-2.60 (m, 3H), 1.42-1.26 (m, 15H) ppm.

Step 7: Preparation of tert-butyl (2-methyl-2-(2-methyl-5-((2-((4-(3-(1-methyl-1H-pyrazol-3-yl)phenyl)thiazol-2-yl)amino)-2-oxoethyl)carbamoyl)phenyl)propyl)carbamate (Intermediate I)

I

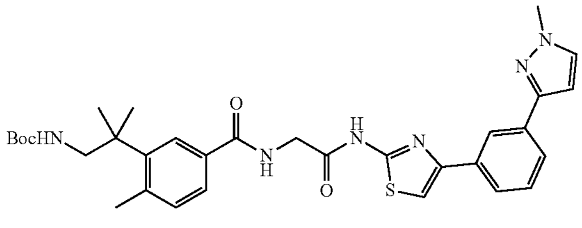

To a solution of Intermediate G (57.99 mg, 188.66 μmol) in DCM (2 mL) was added 2-amino-N-[4-[3-(1-methylpyrazol-3-yl)phenyl]thiazol-2-yl]acetamide (60 mg, 171.51 μmol, HCl salt), DIPEA (66.50 mg, 514.52 μmol, 89.62 μL) and HATU (78.25 mg, 205.81 μmol). The mixture was stirred at 20° C. for 2 hr. The reaction mixture was concentrated to give a residue. The residue was purified by column chromatography ($SiO_2$, Petroleum ether/Ethyl acetate=1/1) to give Intermediate I (53 mg, 87.93 μmol, 51.27% yield) as yellow solid. LCMS (ESI) m/z $[M+H]^+$=603.1. $^1$H NMR (400 MHz, DMSO) δ=12.48 (brs, 1H), 8.86-8.85 (m, 1H), 8.40 (s, 1H), 7.86-7.62 (m, 6H), 7.46-7.45 (m, 1H), 7.24 (d, J=8.0 Hz, 1H), 6.85-6.68 (m, 2H), 4.20-4.19 (m, 2H), 3.91 (s, 3H), 2.62-2.56 (m, 3H), 1.41-1.27 (m, 15H) ppm.

Step 8: Preparation of 3-(1-amino-2-methylpropan-2-yl)-4-methyl-N-(2-((4-(3-(1-methyl-1H-pyrazol-3-yl)phenyl)thiazol-2-yl)amino)-2-oxoethyl)benzamide (Compound 70)

Compound 70

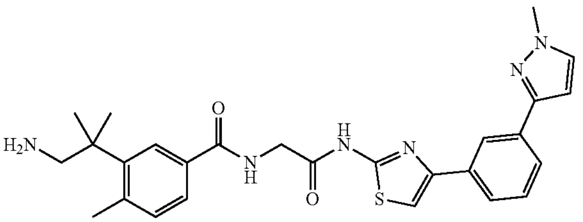

To a solution of Intermediate I (40 mg, 66.36 μmol) in DCM (2 mL) was added TFA (22.70 mg, 199.09 μmol, 14.74 μL). The mixture was stirred at 20° C. for 1 hr. The reaction mixture was concentrated to give a residue. The residue was purified by Prep-HPLC (column: Luna C18 150*25 5 u; mobile phase: [water (0.075% TFA)-ACN]; B %: 18%-48%, 9 min) and lyophilized to give Compound 70 (35.73 mg, 57.94 μmol, 87.31% yield, TFA salt) as white solid. LCMS (ESI) m/z $[M+H]^+$=503.1. $^1$H NMR (400 MHz, DMSO) δ=12.52 (s, 1H), 8.93-8.92 (m, 1H), 8.40 (s, 1H), 7.87 (s, 1H), 7.82 (br d, J=8.0 Hz, 1H), 7.78-7.70 (m, 4H), 7.64 (br s, 2H), 7.45 (m, 1H), 7.33 (d, J=8.0 Hz, 1H), 6.73 (d, J=2.0 Hz, 1H), 4.22-4.21 (m, 2H), 3.91 (s, 3H), 3.22-3.21 (m, 2H), 2.56 (s, 3H), 1.48 (s, 6H) ppm.

Example 78. Preparation of 3-(1-amino-2-methyl-propan-2-yl)-4-ethyl-N-(2-((4-(3-(1-methyl-1H-pyrazol-3-yl)phenyl)thiazol-2-yl)amino)-2-oxoethyl) benzamide (Compound 71)

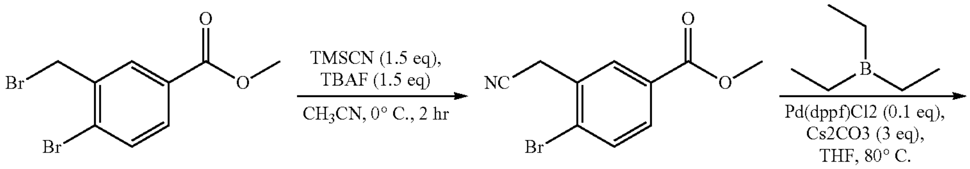

A B

-continued
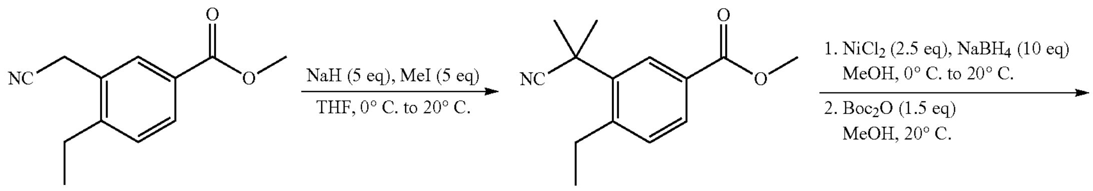
C D
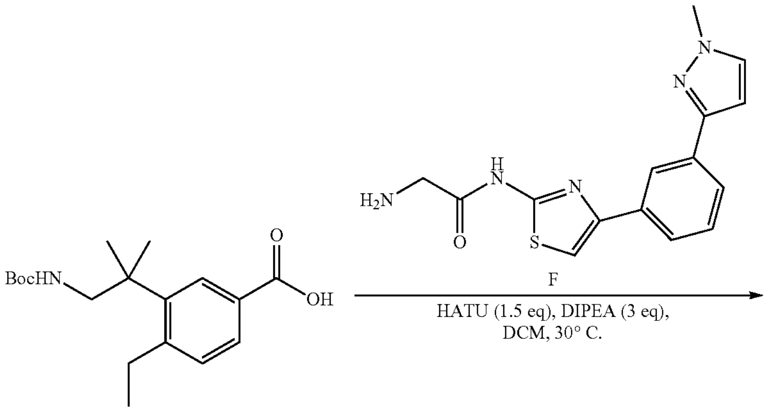
F
E
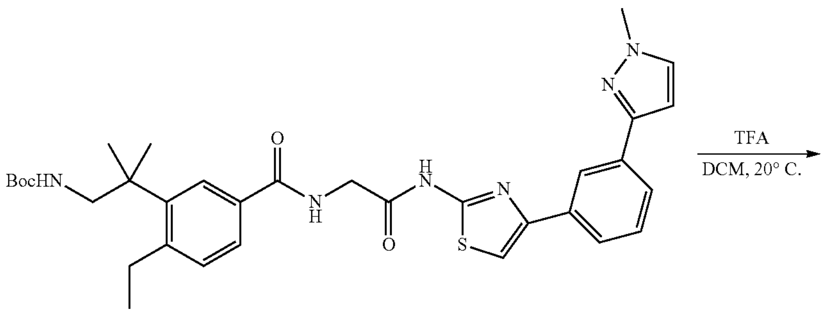
G
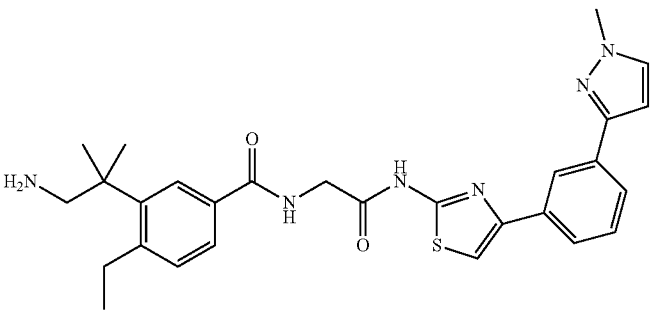
Compound 71

Step 1: Preparation of methyl 4-bromo-3-(cyanomethyl)benzoate (Intermediate B)

B

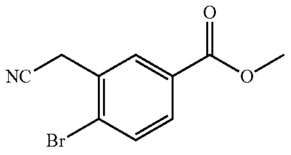

To a solution of methyl 4-bromo-3-(bromomethyl)benzoate (2 g, 6.49 mmol) in $CH_3CN$ (15 mL) were added TMSCN (966.44 mg, 9.74 mmol, 1.22 mL) and TBAF (1 M, 9.74 mL) at 0° C. The mixture was stirred at 25° C. for 2 hr. The reaction mixture was poured into water (60 mL). A pink precipitate was formed. The mixture were filtered and the cake was washed with water and dried in vacuum to give Intermediate B (1.5 g, crude) as pink solid, which was used in next step without further purification.

Step 2: Preparation of methyl 3-(cyanomethyl)-4-ethylbenzoate (Intermediate C)

C

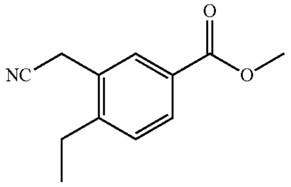

A mixture of Intermediate B (0.6 g, 2.36 mmol), triethylborane (1 M, 7.08 mL), $Cs_2CO_3$ (2.31 g, 7.08 mmol), Pd(dppf)$Cl_2$ (172.79 mg, 236.15 μmol) in THF (2 mL) was degassed and purged with $N_2$ for 3 times, and then the mixture was stirred at 80° C. for 1 hr under $N_2$ atmosphere. The reaction mixture was concentrated under reduced pressure to give a residue. The residue was purified by column chromatography ($SiO_2$, Petroleum ether:Ethyl acetate=3:1) and concentrated to give Intermediate C (0.44 g, 2.16 mmol, 91.68% yield) as yellow oil. LCMS (ESI) m/z $[M+H]^+$=204.1. $^1$H NMR (400 MHz, $CDCl_3$) δ=8.12-7.91 (m, 2H), 7.44-7.20 (m, 1H), 3.94 (br s, 3H), 3.77 (br s, 2H), 2.76-2.75 (m, 2H), 1.39-1.22 (m, 3H) ppm.

Step 3: Preparation of 3-(2-cyanopropan-2-yl)-4-ethylbenzoic acid (Intermediate D)

D

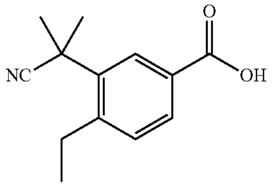

To a solution of Intermediate C (429.65 mg, 2.11 mmol) in THE (6 mL) was added NaH (422.81 mg, 10.57 mmol, 60% purity) at 0° C. The mixture was stirred at 0° C. for 30 min. MeI (2.40 g, 16.91 mmol, 1.05 mL) was added and the mixture was stirred at 25° C. for 16 hr. The reaction mixture was quenched by addition water (10 mL) at 25° C., and extracted with ethyl acetate (10 mL*3). The organic layers were discarded and the aqueous layers were adjusted pH to 5 with 1 N HCl solution and the mixture was extracted with ethyl acetate (10 mL*3). The combined organic phase was washed with brine (10 mL), dried over $Na_2SO_4$, filtered and concentrated under reduced pressure to give Intermediate D (0.32 g, 1.47 mmol, 69.67% yield) as yellow oil. LCMS (ESI) m/z $[M+42]^+$=259.0. $^1$H NMR (400 MHz, DMSO) δ=13.04 (br s, 1H), 7.95-7.84 (m, 2H), 7.49 (d, J=8.0 Hz, 1H), 2.97 (m, 2H), 1.77 (s, 6H), 1.29 (m, 3H) ppm.

Step 4: Preparation of 3-(1-((tert-butoxycarbonyl)amino)-2-methylpropan-2-yl)-4-ethylbenzoic acid (Intermediate E)

E

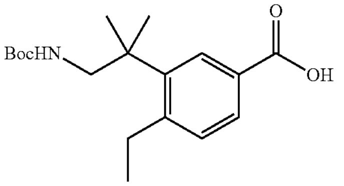

To a solution of Intermediate D (0.3 g, 1.38 mmol) in MeOH (5 mL) was added $NiCl_2·6H_2O$ (820.51 mg, 3.45 mmol) and $NaBH_4$ (522.36 mg, 13.81 mmol) at 0° C. The mixture was stirred at 0° C. for 1 hr. $Boc_2O$ (452.04 mg, 2.07 mmol, 475.84 μL) was added and the mixture was stirred at 20° C. for 2 hr. The reaction mixture was quenched by addition water (20 mL) at 25° C., filtered and the filtrate was adjusted pH to 4 with 1 N HCl solution. The resulting mixture was extracted with ethyl acetate (20 mL*3). The combined organic layers were washed with brine (20 mL), dried over $Na_2SO_4$, filtered and concentrated under reduced pressure to give Intermediate E (0.22 g, crude) as yellow oil, which was used in next step without further purification. LCMS (ESI) m/z $[M+Na]^+$=344.3.

Step 5: Preparation of tert-butyl (2-(2-ethyl-5-((2-((4-(3-(1-methyl-1H-pyrazol-3-yl)phenyl)thiazol-2-yl)amino)-2-oxoethyl)carbamoyl)phenyl)-2-methylpropyl)carbamate (Intermediate G)

G

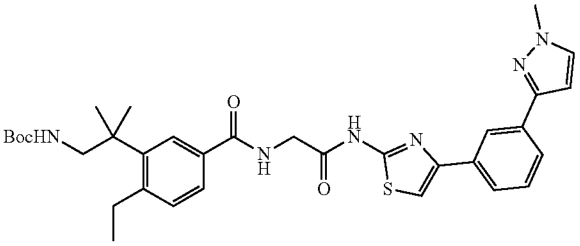

To a solution of Intermediate E (60.64 mg, 188.66 μmol) in DCM (2 mL) was added 2-amino-N-[4-[3-(1-methylpyrazol-3-yl)phenyl]thiazol-2-yl]acetamide (60 mg, 171.51 μmol, HCl salt), DIPEA (66.50 mg, 514.53 μmol, 89.62 μL) and HATU (78.25 mg, 205.81 μmol). The mixture was stirred at 20° C. for 16 hr. The reaction mixture was concentrated to give a residue. The residue was purified by column chromatography ($SiO_2$, Petroleum ether/Ethyl acetate=1/1) and concentrated in vacuum to give Intermediate G (52 mg, crude) as yellow oil. LCMS (ESI) m/z $[M+H]^+$=617.1.

Step 6: Preparation of 3-(1-amino-2-methylpropan-2-yl)-4-ethyl-N-(2-((4-(3-(1-methyl-1H-pyrazol-3-yl)phenyl)thiazol-2-yl)amino)-2-oxoethyl)benzamide (Compound 71)

Compound 71

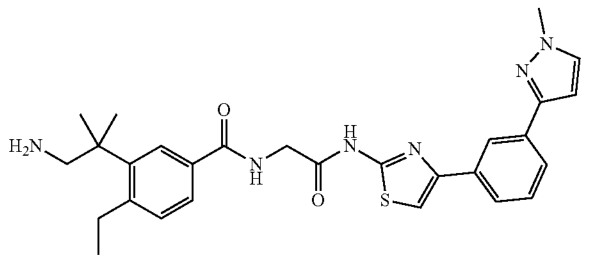

To a solution of Intermediate G (50 mg, 81.07 μmol) in DCM (2 mL) was added TFA (27.73 mg, 243.20 μmol, 18.01 μL). The mixture was stirred at 20° C. for 2 hr. The reaction mixture was concentrated to give a residue. The residue was purified by Prep-HPLC (column: Phenomenex Synergi C18 150*25*10 um; mobile phase: [water (0.1% TFA)-ACN]; B %: 24%-44%, 10 min) and lyophilized to give Compound 71 (21.87 mg, 33.01 μmol, 40.72% yield, TFA salt) as white solid. LCMS (ESI) m/z $[M+H]^+$=517.1. $^1H$ NMR (400 MHz, DMSO) δ=12.50 (s, 1H), 8.89 (s, 1H), 8.40 (s, 1H), 7.86-7.78 (m, 3H), 7.76 (d, J=2.4 Hz, 1H), 7.73 (br d, J=7.6 Hz, 1H), 7.70 (s, 1H), 7.66 (br s, 2H), 7.39-7.50 (m, 2H), 6.73 (d, J=2.4 Hz, 1H), 4.22-4.21 (m, 2H), 3.91 (s, 3H), 3.19-3.18 (m, 2H), 2.88-2.87 (m, 2H), 1.49 (s, 6H), 1.26-1.25 (m, 3H) ppm.

Example 79. Preparation of 3-(1-(aminomethyl)cyclopropyl)-N-(2-oxo-2-((4-(3-(pyridin-4-yl)phenyl)thiazol-2-yl)amino)ethyl)benzamide (Compound 72)

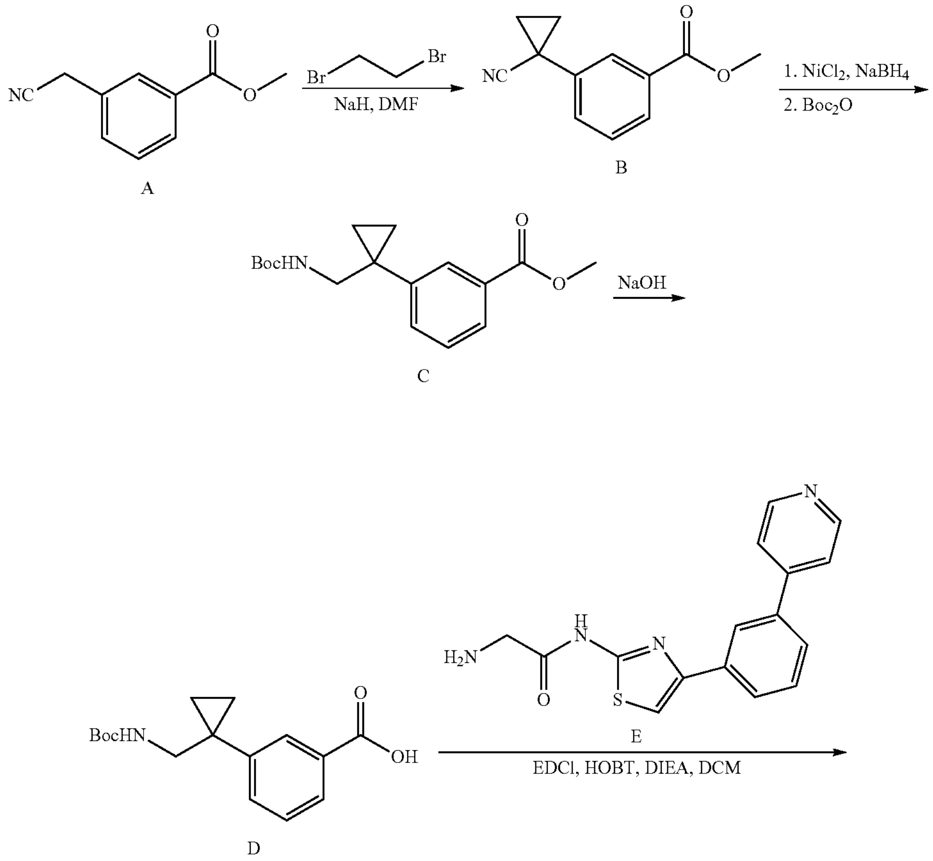

-continued

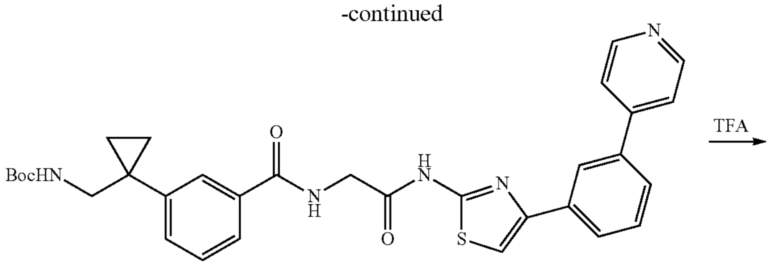

F

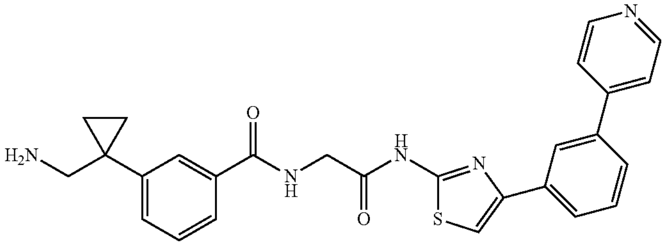

Compound 72

Step 1: Preparation of methyl 3-(1-cyanocyclopropyl)benzoate (Intermediate B)

B

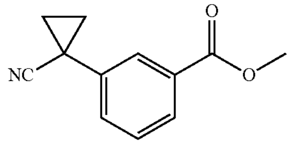

A mixture of methyl 3-(cyanomethyl)benzoate (1 g, 5.71 mmol) in DMF (10 mL) was degassed and purged with $N_2$ for 3 times, and then NaH (570.77 mg, 14.27 mmol, 60% purity) was added at 0° C. The mixture was stirred at 0° C. for 0.5 hr under $N_2$ atmosphere. 1,2-dibromoethane (1.07 g, 5.71 mmol, 430.67 μL) was added. The mixture was stirred at 25° C. for 3 hr. The reaction mixture was quenched by addition water (20 mL) at 25° C., and then extracted with EA (50 mL*2). The combined organic layers were washed with brine (20 mL), dried over $Na_2SO_4$, filtered and concentrated under reduced pressure to give a residue. The residue was purified by flash silica gel chromatography (ISCO; 40 g SepaFlash Silica Flash Column, Eluent of 0~60% Ethylacetate/Petroleum ether gradient 60 mL/min) and concentrated to give Intermediate B (500 mg, 2.48 mmol, 43.53% yield) as a yellow oil. LCMS (ESI) m/z $[M+H]^+$=202.2. $^1H$ NMR (400 MHz, $CDCl_3$) δ=7.97-7.95 (m, 1H), 7.88-7.87 (m, 1H), 7.60-7.57 (m, 1H), 7.46-7.42 (m, 1H), 3.93 (s, 3H), 1.79-1.76 (m, 2H), 1.48-1.45 (m, 2H) ppm.

Step 2: Preparation of methyl 3-(1-(((tert-butoxy-carbonyl)amino)methyl)cyclopropyl)benzoate (Intermediate C)

C

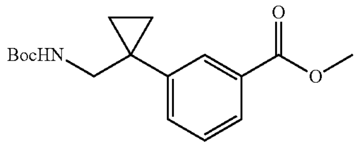

To a solution of Intermediate B (500 mg, 2.48 mmol) and $NiCl_2 \cdot 6H_2O$ (1.48 g, 6.21 mmol) in MeOH (5 mL) was added $NaBH_4$ (940.08 mg, 24.85 mmol) at 0° C. and then the mixture was stirred for 1 hr, then $Boc_2O$ (1.08 g, 4.97 mmol, 1.14 mL) and $Et_3N$ (754.32 mg, 7.45 mmol, 1.04 mL) was added. The mixture was stirred at 25° C. for 1 hr. 4N HCl (10 mL) and water (10 mL) was added and the reaction mixture was extracted with EA (50 mL*2). The combined organic layers were washed with brine (20 mL), dried over $Na_2SO_4$, filtered and concentrated under reduced pressure to give a residue. The residue was purified by flash silica gel chromatography (ISCO; 40 g SepaFlash Silica Flash Column, Eluent of 10-70% Ethylacetate/Petroleum ether gradient 50 mL/min) and concentrated to give Intermediate C (600 mg, 1.59 mmol, 64.05% yield) as a colorless oil. LCMS (ESI) m/z $[M+H-56]^+$=250.2.

Step 3: Preparation of 3-(1-(((tert-butoxycarbonyl)amino)methyl)cyclopropyl)benzoic acid (Intermediate D)

D

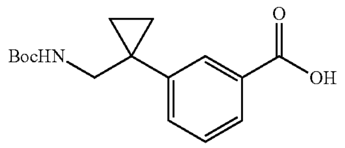

To a solution of Intermediate C (200 mg, 530.51 μmol) in MeOH (1 mL) was added a solution of NaOH (78.59 mg, 1.96 mmol) in $H_2O$ (0.5 mL). The mixture was stirred at 30° C. for 2.5 hr. Water (20 mL) was added and the reaction mixture was extracted with EA (50 mL). The organic layer was discarded and the aqueous phase was adjusted pH=4 with 4N HCl, and the reaction mixture was extracted with EA (50 mL). The combined organic layers were washed with brine (20 mL), dried over $Na_2SO_4$, filtered and concentrated under reduced pressure to give Intermediate D (120 mg, 411.89 μmol, 77.64% yield) as colorless oil. LCMS (ESI) m/z=$[M+Na]^+$=314.2.

Step 4: Preparation of tert-butyl ((1-(3-((2-oxo-2-((4-(3-(pyridin-4-yl)phenyl)thiazol-2-yl)amino)ethyl)carbamoyl)phenyl)cyclopropyl)methyl)carbamate (Intermediate F)

F

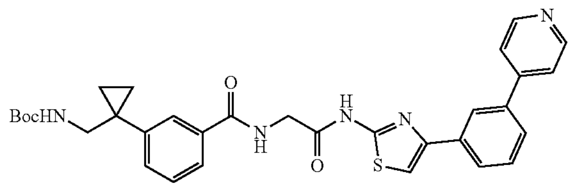

To a solution of Intermediate D (60.48 mg, 207.59 μmol) in DCM (2 mL) was added EDCI (49.74 mg, 259.49 μmol), DIEA (89.43 mg, 691.97 μmol, 120.53 μL) and HOBt (35.06 mg, 259.49 μmol). Then 2-amino-N-[4-[3-(4-pyridyl)phenyl]thiazol-2-yl]acetamide (prepared according to the method in Example 3) (60 mg, 172.99 μmol, HCl salt) was added. The mixture was stirred at 25° C. for 2 hr. Water (20 mL) was added and the reaction mixture was extracted with EA (2*50 mL). The combined organic layers were washed with brine (20 mL), dried over $Na_2SO_4$, filtered and concentrated under reduced pressure to give a residue. The crude product was purified by reversed-phase HPLC (0.1% FA condition) and lyophilized to give Intermediate F (60 mg, 59.62 μmol, 34.46% yield) as a white solid. LCMS (ESI) m/z=$[M+H]^+$=584.4.

Step 5: Preparation of 3-(1-(aminomethyl)cyclopropyl)-N-(2-oxo-2-((4-(3-(pyridin-4-yl)phenyl)thiazol-2-yl)amino)ethyl)benzamide (Compound 72)

Compound 72

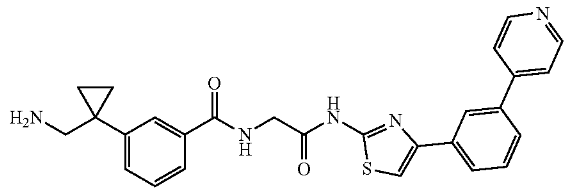

To a solution of Intermediate F (60 mg, 102.79 μmol) in DCM (3 mL) was added TFA (2 mL). The mixture was stirred at 25° C. for 0.5 hr. The reaction mixture was concentrated under reduced pressure to remove DCM and TFA. The residue was purified by Prep-HPLC (TFA condition; column: Phenomenex luna C18 150*25 10 u; mobile phase: [water (0.1% TFA)-ACN]; B %: 5%-35%, 10 min) and lyophilized to give Compound 72 (20.44 mg, 34.20 μmol, 33.27% yield, TFA salt) as a white solid. LCMS (ESI) m/z=$[M+H]^+$=484.2. $^1H$ NMR (400 MHz, MeOD) δ=12.49 (s, 1H), 8.94-8.92 (m, 1H), 8.78 (s, 2H), 8.35 (s, 1H), 8.06 (d, J=7.2 Hz, 1H), 7.97 (s, 2H), 7.89 (s, 1H), 7.85-7.86 (m, 1H), 7.83-7.79 (m, 2H), 7.74 (s, 3H), 7.65-7.61 (m, 1H), 7.58 (d, J=8.0 Hz, 1H), 7.49-7.46 (m, 1H), 4.22 (d, J=5.6 Hz, 2H), 3.12 (d, J=5.6 Hz, 2H), 1.05-1.00 (m, 2H), 0.99-0.97 (m, 2H) ppm.

Example 80. Preparation of 3-(1-hydroxy-2-methylpropan-2-yl)-N-(2-oxo-2-((4-(3-(pyridin-4-yl)phenyl)thiazol-2-yl)amino)ethyl)benzamide (Compound 73)

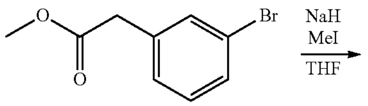

A

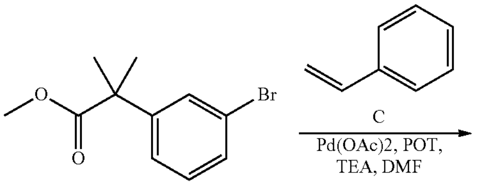

B

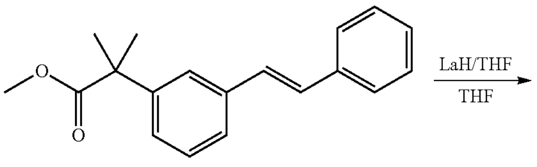

D

-continued

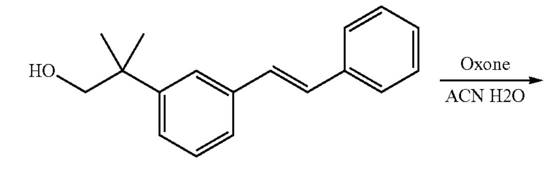

E

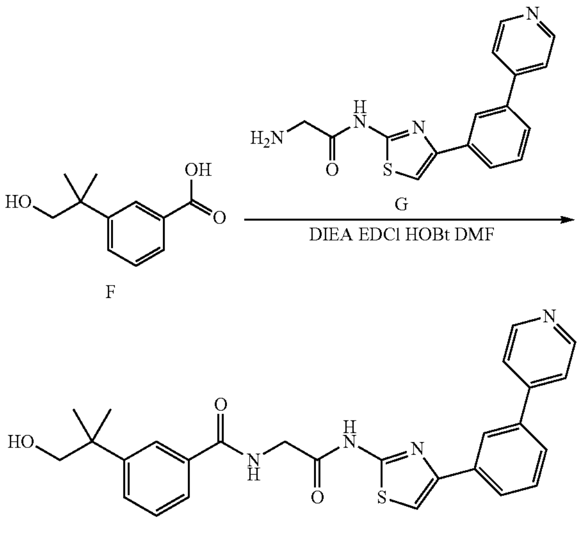

F

Compound 73

Step 1: Preparation of methyl 2-(3-bromophenyl)-2-methylpropanoate (Intermediate B)

B

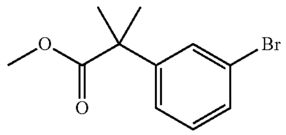

To a solution of methyl 2-(3-bromophenyl)acetate (10 g, 43.65 mmol) in THF (100 mL) was added NaH (10.48 g, 261.93 mmol, 60% purity) at 0° C. and stirred for 0.5 hr, then MeI (30.98 g, 218.27 mmol, 13.59 mL) was added to the mixture at 0° C. The mixture was stirred at 30° C. for 4 hr. The reaction mixture was diluted with aq. $NH_4Cl$ (200 mL) at 0° C. and extracted with EA (200 mL×2). The combined organic layers were dried over anhydrous $Na_2SO_4$, filtered and concentrated under reduced pressure to afford the residue. The residue was purified by reversed phase (0.1% FA condition) and concentrated to remove the ACN. The mixture was extracted with EA (20 mL×2), the organic layers were dried over anhydrous $Na_2SO_4$, filtered and concentrated to give Intermediate B (4.4 g, 17.11 mmol, 39.20% yield) as colorless oil. LCMS (ESI) m/z $[M+H]^+$=257.0/259.0. $^1H$ NMR (400 MHz, $CDCl_3$) δ=7.49-7.48 (m, 1H), 7.37-7.27 (m, 1H), 7.26-7.25 (m, 1H), 7.22-7.20 (m, 1H), 3.67 (s, 3H), 1.57 (s, 6H) ppm.

Step 2: Preparation of (E)-methyl 2-methyl-2-(3-styrylphenyl)propanoate (Intermediate D)

D

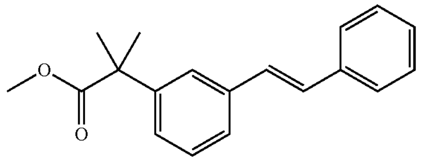

To a solution of Intermediate B (2 g, 7.78 mmol) and styrene (1.62 g, 15.56 mmol) in DMF (20 mL) was added TEA (1.57 g, 15.56 mmol, 2.17 mL), tris-o-tolylphosphane (473.50 mg, 1.56 mmol) and $Pd(OAc)_2$ (174.63 mg, 777.84 μmol). The mixture was stirred at 130° C. under $N_2$ for 16 hr. The reaction mixture was diluted with $H_2O$ (20 mL) and extracted with EA (20 mL×2). The combined organic layers were dried over anhydrous $Na_2SO_4$, filtered and concentrated under reduced pressure to give a residue. The residue was purified by column chromatography ($SiO_2$, Petroleum ether/Ethyl acetate=1/0 to 3:1) and concentrated to give Intermediate D (1.3 g, 4.64 mmol, 59.61% yield) as yellow oil. LCMS (ESI) m/z $[M+H]^+$=281.1. $^1H$ NMR (400 MHz, $CDCl_3$) δ=7.54-7.52 (m, 2H), 7.52-7.46 (m, 2H), 7.37-7.25 (m, 6H), 7.12 (s, 2H), 3.68 (s, 3H), 1.63 (s, 6H) ppm.

Step 3: Preparation of (E)-2-methyl-2-(3-styrylphenyl)propan-1-ol (Intermediate E)

E

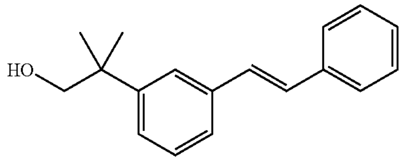

E To a solution of Intermediate D (1.28 g, 4.57 mmol) in THE (5 mL) was added $LiAlH_4$/THF (1 M, 13.70 mL) at 0° C. and stirred at 25° C. for 2 hr. This reaction mixture was quenched by addition $H_2O$ (0.52 mL), and then diluted with 15% NaOH solution (1.56 mL). The mixture was filtered and the filtrate was concentrated under reduced pressure to give Intermediate E (1.1 g, 4.36 mmol, 95.48% yield) as a white solid, which was used directly for the next step. LCMS (ESI) m/z $[M-OH]^+$=235.1. $^1H$ NMR (400 MHz, DMSO) δ=7.62-7.60 (m, 2H), 7.60 (s, 1H), 7.37-7.29 (m, 1H), 7.29-7.28 (m, 2H), 7.28-7.24 (m, 5H), 4.70-4.67 (m, 1H), 3.46 (d, J=5.2 Hz, 2H), 1.25 (s, 6H) ppm.

Step 4: Preparation of 3-(1-hydroxy-2-methylpropan-2-yl)benzoic acid (Intermediate F)

F

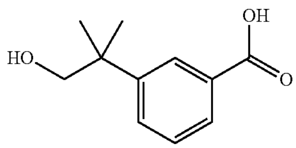

To a solution of Intermediate E (500 mg, 1.98 mmol) in ACN/$H_2O$=1/1 (5 mL) was added Oxone (2.44 g, 3.96 mmol) at 100° C. and stirred for 2 hr. The reaction mixture was cooled and diluted with aq $NaHCO_3$ (10 mL), extracted with EA (10 mL×2). The organic layer was discarded and the aqueous phase was adjusted the pH=4 with 1 N HCl, then extracted with EA (20 mL×2). The combined organic layers were dried over anhydrous $Na_2SO_4$, filtered and concentrated under reduced pressure to give a residue. The residue was purified by Prep-TLC (EA) and concentrated to give Intermediate F (30 mg, 154.46 μmol, 7.80% yield) as a yellow solid, which was used directly for the next step.

Step 5: Preparation of 3-(1-hydroxy-2-methylpropan-2-yl)-N-(2-oxo-2-((4-(3-(pyridin-4-yl)phenyl) thiazol-2-yl)amino)ethyl)benzamide (Compound 73)

Compound 73

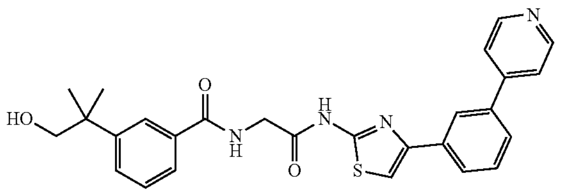

To a solution of Intermediate F (20 mg, 102.97 μmol) and 2-amino-N-[4-[3-(4-pyridyl)phenyl]thiazol-2-yl]acetamide (prepared according to the method in Example 3) (35.71 mg, 102.97 μmol, HCl salt) in DMF (1 mL) was added DIEA (66.54 mg, 514.86 μmol, 89.68 μL), then EDCl (29.61 mg, 154.46 μmol) and HOBt (16.70 mg, 123.57 μmol) were added to the mixture. The mixture was stirred at 30° C. for 16 hr. This reaction mixture was concentrated in vacuum. The residue was purified by reversed phase (0.1% FA condition) and lyophilized to give Compound 73 (21.51 mg, 40.39 μmol, 39.22% yield, FA salt) as a white solid. LCMS (ESI) m/z $[M+H]^+$=487.3. $^1H$ NMR (400 MHz, DMSO) δ=12.45 (br s, 1H), 8.92-8.91 (m, 1H), 8.68 (d, J=6.0 Hz, 2H), 8.30 (s, 1H), 8.02 (d, J=7.6 Hz, 1H), 7.90 (s, 1H), 7.83 (s, 1H), 7.76-7.75 (m, 4H), 7.59-7.57 (m, 2H), 7.51-7.41 (m, 1H), 4.71-4.68 (m, 1H), 4.21 (d, J=5.6 Hz, 2H), 3.47 (d, J=5.2 Hz, 2H), 1.26 (s, 6H) ppm.

Example 81. Preparation of 3-(tert-butyl)-N-(2-oxo-2-((4-(3-(pyridin-4-yl)phenyl)thiazol-2-yl)amino) ethyl)benzamide (Compound 74)

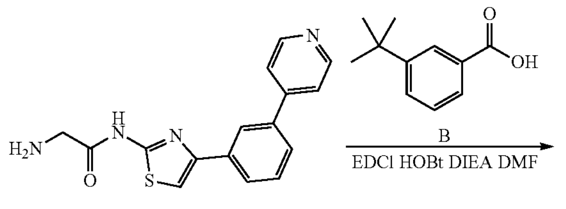

-continued

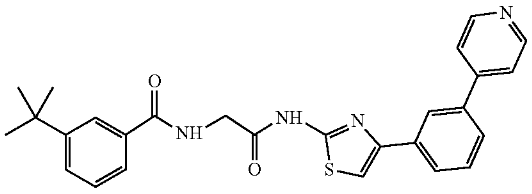

Compoun d74

To a solution of 2-amino-N-[4-[3-(4-pyridyl)phenyl]thiazol-2-yl]acetamide (100 mg, 288.32 μmol, HCl salt) and 3-tertbutylbenzoic acid (61.66 mg, 345.99 μmol) in DMF (1 mL) was added EDCl (82.91 mg, 432.48 μmol), HOBt (58.44 mg, 432.48 μmol) and DIEA (111.79 mg, 864.97 μmol, 150.66 μL), then the reaction mixture was stirred at 5° C. for 2 hrs. To the reaction mixture was added water (2 mL×1), then the mixture was filtered. The filter cake was triturated with MeOH (5 mL×1), filtered and the filter cake was lyophilized to give Compound 74 (34.81 mg, 73.16 μmol, 25.37% yield) as a white solid. LCMS (ESI) m/z $[M+H]^+$=471.2. $^1H$ NMR (400 MHz, DMSO) δ=12.49 (s, 1H), 8.98-8.95 (m, 1H), 8.69-8.67 (m, 2H), 8.32-8.31 (m, 1H), 8.03-8.00 (m, 1H), 7.94-7.93 (m, 1H), 7.84 (s, 1H), 7.77-7.76 (m, 3H), 7.74-7.71 (m, 1H), 7.62-7.58 (m, 2H), 7.44-7.41 (m, 1H), 4.21-4.20 (d, J=6 Hz, 2H), 1.33 (s, 9H) ppm.

Example 82. Preparation of 3-(2-cyanopropan-2-yl)-4,5-dimethyl-N-(2-oxo-2-((4-(3-(pyridin-4-yl)phenyl)thiazol-2-yl)amino)ethyl)benzamide (Compound 75)

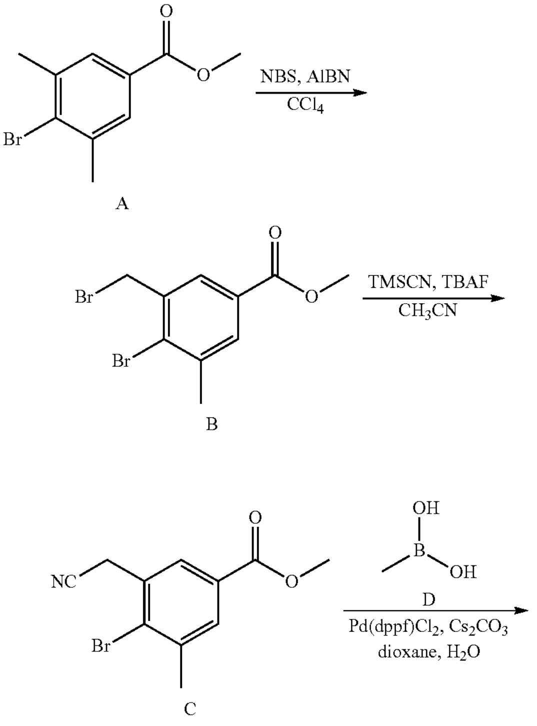

-continued

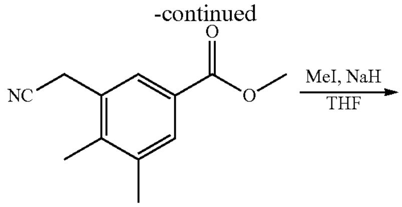

E

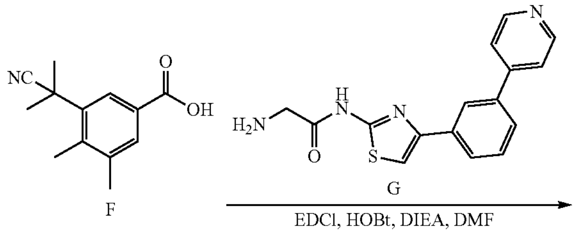

F

G

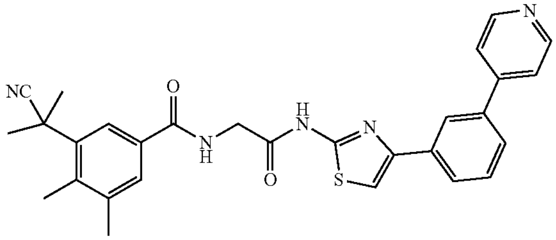

Compound 75

Step 1: Preparation of methyl 4-bromo-3-(bromomethyl)-5-methylbenzoate (Intermediate B)

B

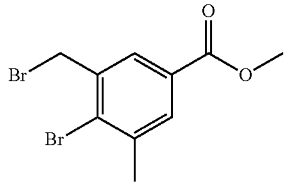

To a solution of methyl 4-bromo-3,5-dimethyl-benzoate (2 g, 8.23 mmol) in $CCl_4$ (10 mL) was added NBS (1.46 g, 8.23 mmol) and AIBN (40.53 mg, 246.82 μmol) at 25° C. The reaction mixture was stirred at 80° C. for 16 hours. The reaction mixture was extracted with DCM (3 mL×3), the combined organic layers was concentrated to afford a yellow oil. The oil was purified by flash silica gel chromatography (ISCO®; 120 g SepaFlash® Silica Flash Column, Eluent of 0~10% Ethylacetate/Petroleum ether gradient at 85 mL/min) and then concentrated to give Intermediate B (1.9 g, 4.72 mmol, 57.38% yield, 80% purity) as a white solid. LCMS (ESI) m/z $[^{81}BrM+H]^+$=322.9. $^1H$ NMR (400 MHz, DMSO-$d_6$) δ=8.05-8.00 (m, 1H), 7.88 (d, J=1.6 Hz, 1H), 4.86 (s, 2H), 3.87 (s, 3H), 2.45 (s, 3H) ppm.

Step 2: Preparation of methyl 4-bromo-3-(cyanomethyl)-5-methylbenzoate (Intermediate C)

C

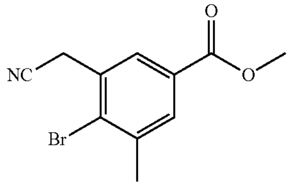

To a solution of Intermediate B (1.8 g, 5.59 mmol) in $CH_3CN$ (1 mL) was added TMSCN (831.87 mg, 8.39 mmol, 1.05 mL) and TBAF (1 M, 8.39 mL) at 0° C. The reaction mixture was stirred at 10° C. for 16 hours and then stirred at 30° C. for another 2 hours. The reaction mixture was diluted with water (30 mL) and extracted with EA (15 mL×2), the combined organic layers was dried over anhydrous $Na_2SO_4$ and concentrated to afford a yellow residue. The residue was dissolved with DCM (5 mL) and purified by flash silica gel chromatography (ISCO®; 40 g SepaFlash® Silica Flash Column, Eluent of 0~25% Ethylacetate/Petroleum ether gradient at 40 mL/min), concentrated to give Intermediate C (1 g, 3.39 mmol, 60.68% yield, 90.94% purity) as a white solid. LCMS (ESI) m/z $[^{81}BrM+H]^+$= 269.9. $^1H$ NMR (400 MHz, DMSO-$d_6$) δ=7.96 (s, 1H), 7.91 (s, 1H), 4.19 (s, 2H), 3.90-3.85 (m, 3H), 2.46 (s, 3H) ppm.

Step 3: Preparation of methyl 3-(cyanomethyl)-4,5-dimethylbenzoate (Intermediate E)

E

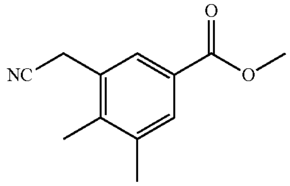

To a solution of Intermediate C (900 mg, 3.36 mmol), methylboronic acid (602.83 mg, 10.07 mmol) and $Cs_2CO_3$ (3.28 g, 10.07 mmol) in dioxane (6 mL) and $H_2O$ (3 mL) was added Pd(dppf)$Cl_2$ (245.63 mg, 335.69 μmol) at 10° C. under $N_2$. The mixture was stirred at 90° C. under $N_2$ for 4 hours. The reaction mixture was diluted with water (15 mL) and extracted with EA (15 mL×3), the combined organic layers was dried over anhydrous $Na_2SO_4$ and concentrated to afford a black brown residue. The residue was dissolved with DCM (5 mL) and purified by flash silica gel chromatography (ISCO®; 20 g SepaFlash® Silica Flash Column, Eluent of 0~25% Ethylacetate/Petroleum ether gradient at 35 mL/min), concentrated to give Intermediate E (700 mg, 2.84 mmol, 84.62% yield, 82.47% purity) as a white solid. LCMS (ESI) m/z $[M+H]^+$=204.0. $^1H$ NMR (400 MHz, DMSO-$d_6$) δ=7.83 (s, 1H), 7.75 (s, 1H), 4.11 (s, 2H), 3.84 (s, 3H), 2.33 (s, 3H), 2.25 (s, 3H) ppm.

Step 4: Preparation of 3-(2-cyanopropan-2-yl)-4,5-dimethylbenzoic acid (Intermediate F)

F

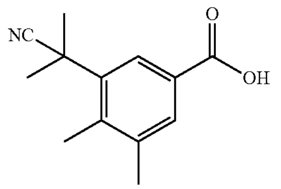

To a solution of Intermediate E (700 mg, 3.44 mmol) in THF (15 mL) was added NaH (825.52 mg, 20.64 mmol, 60% purity) at 0° C. The reaction mixture was stirred at 0° C. for 30 minutes, then MeI (2.44 g, 17.20 mmol, 1.07 mL, 5 eq) was added at 0° C. The reaction mixture was stirred at 10° C. for 1.5 hours. more NaH (825.52 mg, 20.64 mmol, 60% purity, 6 eq) was added at 0° C. After stirred at 0° C. for 30 minutes, more MeI (2.44 g, 17.20 mmol, 1.07 mL, 5 eq) was added at 0° C. Then the mixture was stirred at 10° C. for 3 hours. The reaction mixture was quenched with $H_2O$ (30 mL) and stirred for 30 min and then extracted with EA (15 mL×3), the combined organic layers were dried over anhydrous $Na_2SO_4$, concentrated to afford a yellow solid. The aqueous was adjusted pH to 6 with HCl (2 M), then extracted with EA (10 mL×3), concentrated to afford a yellow solid. The two batches of solid was dissolved in MeOH (5 mL) and purified by reversed-phase HPLC (FA) and lyophilized to give Intermediate F (450 mg, 1.65 mmol, 48.02% yield, 79.75% purity) as a light yellow solid. LCMS (ESI) m/z $[M+H]^+$=218.1. $^1H$ NMR (400 MHz, DMSO+$D_2O$) δ=7.77 (s, 1H), 7.75 (s, 1H), 2.48 (s, 3H), 2.31 (s, 3H), 1.75 (s, 6H) ppm.

Step 5: Preparation of 3-(2-cyanopropan-2-yl)-4,5-dimethyl-N-(2-oxo-2-((4-(3-(pyridin-4-yl)phenyl)thiazol-2-yl)amino)ethyl)benzamide (Compound 75)

Compound 75

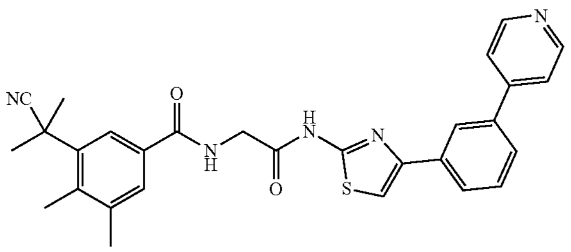

To a solution of Intermediate F (50 mg, 230.14 μmol, 1 eq), EDCl (66.18 mg, 345.20 μmol), HOBt (46.64 mg, 345.20 μmol) and DIEA (89.23 mg, 690.41 μmol, 120.26 μL) in DMF (0.5 mL) was added 2-amino-N-[4-[3-(4-pyridyl)phenyl]thiazol-2-yl]acetamide (71.43 mg, 230.14 μmol) at 10° C. The reaction mixture was stirred at 30° C. for 4 hours. The reaction mixture was poured into water (3 mL), light yellow precipitate was formed, the mixture was filtered to afford a light yellow solid. The solid was triturated with PE/EA (1/1, 3 mL), filtered and the solid was dispersed into $H_2O$ (20 mL) and lyophilized to give Compound 75 (54.19 mg, 106.09 μmol, 46.10% yield, 99.77% purity) as an off-white solid. LCMS (ESI) m/z $[M+H]^+$=510.1. $^1H$ NMR (400 MHz, DMSO-$d_6$) δ=12.47 (s, 1H), 8.95-8.94 (m, 1H), 8.69-8.66 (m, 2H), 8.31 (s, 1H), 8.01 (d, J=7.6 Hz, 1H), 7.84 (s, 1H), 7.78-7.75 (m, 4H), 7.73 (s, 1H), 7.63-7.57 (m, 1H), 4.20 (d, J=5.6 Hz, 2H), 2.52 (s, 3H), 2.35 (s, 3H), 1.79 (s, 6H) ppm.

Example 83. Preparation of 3-cyano-3-methyl-N-(2-oxo-2-((4-(3-(pyridin-4-yl)phenyl)thiazol-2-yl)amino)ethyl)-2,3-dihydro-1H-indene-5-carboxamide (Compound 76)

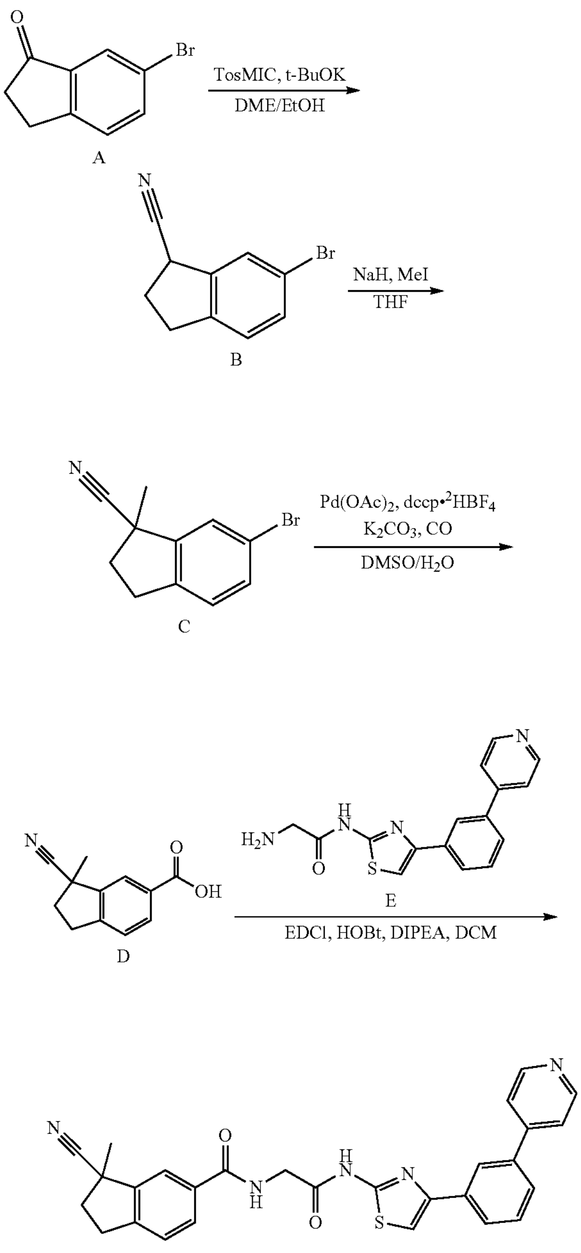

Compound 76

Step 1: Preparation of 6-bromo-2,3-dihydro-1H-indene-1-carbonitrile (Intermediate B)

B

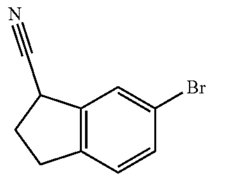

To a solution of 6-bromoindan-1-one (5 g, 23.69 mmol) and 1-(isocyanomethylsulfonyl)-4-methyl-benzene (6.94 g, 35.54 mmol) in DME (250 mL) and EtOH (10 mL) was added tBuOK (5.32 g, 47.38 mmol) at 0° C. The reaction mixture was stirred at 25° C. for 16 hr. The reaction mixture was poured into water (500 mL) and extracted with EA (400 mL×2). The combined organic layer was dried over anhydrous $Na_2SO_4$ and concentrated in vacuum. The residue was purified by silica gel chromatography column (PE-PE/EA=2/1) and concentrated in vacuum to give Intermediate B (3 g, 12.70 mmol, 53.60% yield, 94% purity) as a white solid. LCMS (ESI) m/z $[^{81}BrM+H]^+$=223.9. $^1H$ NMR (400 MHz, DMSO-$d_6$) δ=7.59 (s, 1H), 7.48 (m, 1H), 7.29 (d, J=8.0 Hz, 1H), 4.49-4.47 (m, 1H), 3.02-2.93 (m, 1H), 2.92-2.82 (m, 1H), 2.58-2.52 (m, 1H), 2.30-2.19 (m, 1H) ppm.

Step 2: Preparation of 6-bromo-1-methyl-2,3-dihydro-1H-indene-1-carbonitrile (Intermediate C)

C

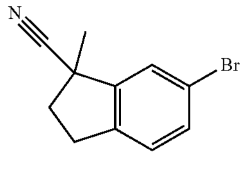

To a solution of Intermediate B (1 g, 4.50 mmol) in THE (10 mL) was added NaH (216.12 mg, 5.40 mmol, 60% purity) at 0° C. and the mixture was stirred at 0° C. for 0.5 hr. Then $CH_3I$ (3.20 g, 22.51 mmol, 1.40 mL) was added at 0° C. The mixture was stirred at 25° C. for 2 hr. The reaction was diluted with aq. $NH_4Cl$ (30 mL), extracted with EA (15 mL×3). The combined organic layers were dried over $Na_2SO_4$, filtered and concentrated under reduced pressure to give a residue. The residue was purified by column chromatography ($SiO_2$, PE:EA=50:1 to 10:1) and concentrated in vacuum to give Intermediate C (800 mg, 3.05 mmol, 67.72% yield, 90% purity) as a light yellow solid. $^1H$ NMR (400 MHz, DMSO-$d_6$) δ=7.69 (d, J=1.6 Hz, 1H), 7.50-7.47 (m, 1H), 7.28 (d, J=8.0 Hz, 1H), 2.97-2.93 (m, 2H), 2.62-2.52 (m, 1H), 2.21-2.14 (m, 1H), 1.63 (s, 3H) ppm.

Step 3: Preparation of 3-cyano-3-methyl-2,3-dihydro-1H-indene-5-carboxylic acid (Intermediate D)

D

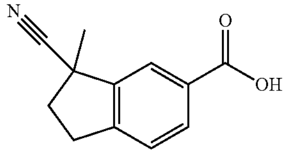

A mixture of Intermediate C (400 mg, 1.69 mmol) in DMSO (4 mL) was added $K_2CO_3$ (351.21 mg, 2.54 mmol), $H_2O$ (61.04 mg, 3.39 mmol, 61.04 μL), dicyclohexyl(3-dicyclohexylphosphaniumylpropyl)phosphonium;ditetrafluoroborate (103.73 mg, 169.41 μmol) and $Pd(OAc)_2$ (38.03 mg, 169.41 μmol), purged with CO for 3 times, and then the mixture was stirred at 100° C. for 14 hr under CO (15 psi) atmosphere. The reaction mixture was diluted with $H_2O$ (10 mL), and then extracted with EA (5 mL×2). The organic layer was discarded and the aqueous phase was adjusted pH=4 with aq. HCl and then extracted with EA (10 mL×3). The combined organic layers were dried over anhydrous $Na_2SO_4$, filtered and concentrated under reduced pressure to give a residue. The residue was purified by reversed-phase HPLC (FA) and lyophilized to give Intermediate D (200 mg, 911.73 μmol, 53.82% yield, 91.73% purity) as a white solid. LCMS (ESI) m/z $[M+H]^+$=202.1. $^1H$ NMR (400 MHz, DMSO-$d_6$) δ=13.70-12.34 (m, 1H), 7.95 (d, J=1.2 Hz, 1H), 7.90-7.88 (m, 1H), 7.44 (d, J=8.0 Hz, 1H), 3.09-3.01 (m, 2H), 2.62-2.56 (m, 1H), 2.28-2.18 (m, 1H), 1.64 (s, 3H) ppm.

Step 4: Preparation of 3-cyano-3-methyl-N-(2-oxo-2-((4-(3-(pyridin-4-yl)phenyl)thiazol-2-yl)amino)ethyl)-2,3-dihydro-1H-indene-5-carboxamide (Compound 76)

Compound 76

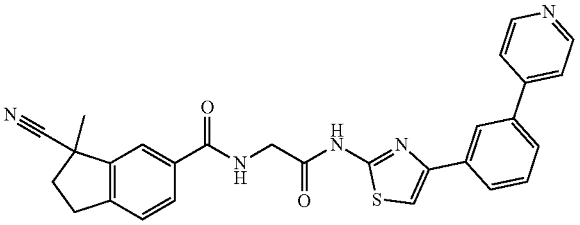

To a solution of Intermediate D (63.82 mg, 317.15 μmol) in DCM (1 mL) was added EDCl (82.91 mg, 432.48 μmol), HOBt (58.44 mg, 432.48 μmol), DIEA (186.32 mg, 1.44 mmol, 251.10 μL) and 2-amino-N-[4-[3-(4-pyridyl)phenyl]thiazol-2-yl]acetamide (prepared according to the method in Example 3) (100 mg, 288.32 μmol, HCl). The mixture was stirred at 25° C. for 2 hr. MeOH (1 mL) was added into the mixture, heavy precipitate was formed, the mixture was filtered and the solid was washed with MeOH (2 mL×2) and dried in vacuum to give Compound 76 (110 mg, 221.77 μmol, 76.92% yield, 99.51% purity) as a white solid. LCMS (ESI) m/z $[M+H]^+$=494.3. $^1H$ NMR (400 MHz, DMSO-$d_6$)

δ=13.10-12.03 (m, 1H), 9.12-9.09 (m, 1H), 8.72-8.65 (m, 2H), 8.32-8.31 (m, 1H), 8.06-7.99 (m, 2H), 7.91-7.89 (m, 1H), 7.85 (s, 1H), 7.81-7.73 (m, 3H), 7.66-7.56 (m, 1H), 7.45 (d, J=7.6 Hz, 1H), 4.24-4.22 (m, 2H), 3.08-3.04 (m, 2H), 2.69-2.56 (m, 1H), 2.28-2.21 (m, 1H), 1.67 (s, 3H) ppm.

Example 84. Preparation of N-(2-((4-(3-cyanophenyl)thiazol-2-yl)amino)-2-oxoethyl)-1,2,3,4-tetrahydroisoquinoline-7-carboxamide (Compound 77)

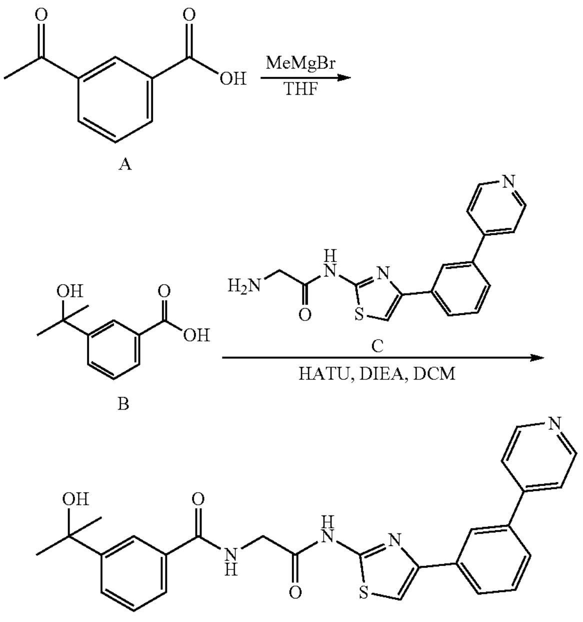

Compound 77

Step 1: Preparation of 3-(2-hydroxypropan-2-yl)benzoic acid (Intermediate B)

B

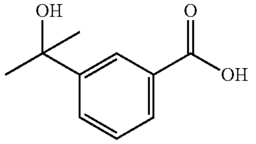

To a solution of 3-acetylbenzoic acid (100 mg, 609.17 μmol) in THE (4 mL) was added MeMgBr (3 M, 1.02 mL) drop-wise at 0° C. and then the reaction mixture stirred at 70° C. for 2 hours. The reaction mixture was quenched by addition HCl (2 N) solution (3 mL). The above solution was diluted with NaOH (4 N) solution (4 mL) and extracted with EtOAc (8 mL). The organic layer was discarded and the water layers were acidified by addition HCl (4 N) solution to pH=4, and then extracted with EtOAc (4 mL×2). The combined organic layers were washed with brine (5 mL×2), dried over $Na_2SO_4$, filtered and concentrated under reduced pressure to give Intermediate B (93 mg, 464.48 μmol, 76.25% yield) as a colorless oil. LCMS (ESI) m/z $[M-OH]^+$= 163.1.

Step 2: Preparation of N-(2-((4-(3-cyanophenyl)thiazol-2-yl)amino)-2-oxoethyl)-1,2,3,4-tetrahydroisoquinoline-7-carboxamide (Compound 77)

Compound 77

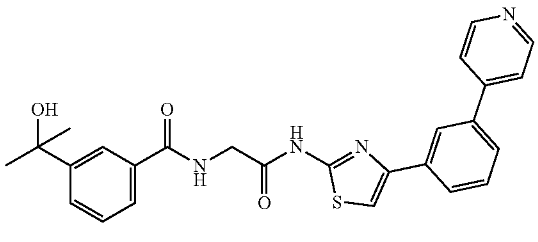

A mixture of Intermediate B (45 mg, 249.72 μmol), 2-amino-N-[4-[3-(4-pyridyl)phenyl]thiazol-2-yl]acetamide (prepared according to the method in Example 3) (86.61 mg, 249.72 μmol, HCl salt), DIEA (161.37 mg, 1.25 mmol, 217.49 μL) in DCM (2 mL) was added HATU (104.45 mg, 274.69 μmol), and then the mixture was stirred at 25° C. for 2 hr under $N_2$ atmosphere. The reaction mixture was concentrated in vacuum. The residue was purified by Prep-HPLC (TFA condition, column: Phenomenex luna C18 250×50 mm×10 μm; mobile phase: [water (0.1% TFA)-ACN]; B %: 22%-39%, 7 min) and lyophilized to give Compound 77 (27.71 mg, 47.24 μmol, 18.92% yield, TFA salt) as a white solid. LCMS (ESI) m/z $[M+H]^+$=473.0. $^1H$ NMR (400 MHz, DMSO) δ=12.47 (s, 1H), 8.92-8.84 (m, 3H), 8.40 (s, 1H), 8.12-8.08 (m, 3H), 8.02 (s, 1H), 7.88-7.86 (m, 2H), 7.74 (d, J=8.0 Hz, 1H), 7.68-7.64 (m, 2H), 7.44-7.40 (m, 1H), 4.21 (d, J=6 Hz, 2H), 1.47 (s, 6H) ppm.

Example 85. Preparation of N-(2-oxo-2-((4-(3-(pyridin-4-yl)phenyl)thiazol-2-yl)amino)ethyl)-3-(1,1,1-trifluoro-2-hydroxypropan-2-yl)benzamide (Compound 78)

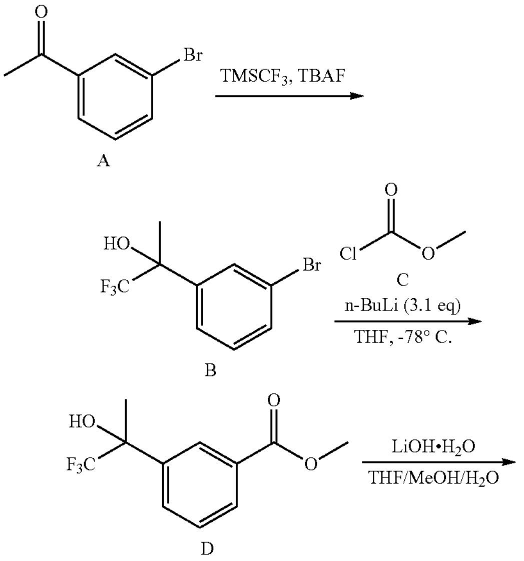

-continued

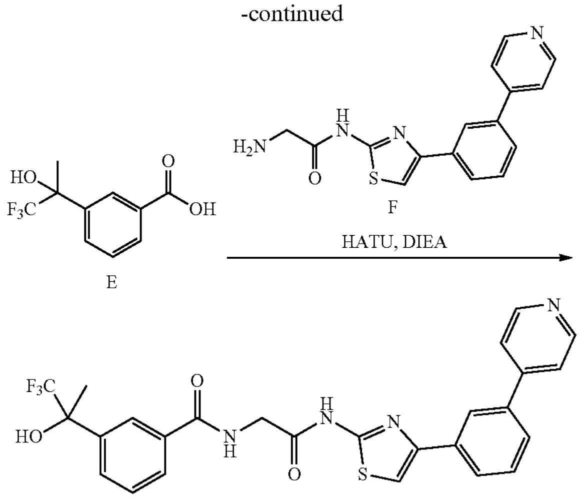

E

F

Compound 78

Step 1: Preparation of 2-(3-bromophenyl)-1,1,1-trifluoropropan-2-ol (Intermediate B)

B

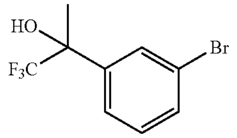

To a mixture of 1-(3-bromophenyl)ethanone (1 g, 5.02 mmol, 662.25 μL) and TMS-$CF_3$ (857.26 mg, 6.03 mmol) in THE (10 mL) was added TBAF (1 M, 100.48 μL) at 0° C. under $N_2$. The resulting mixture was stirred at 25° C. for 2 hr. The reaction mixture was quenched with 1 N HCl (10 mL). Then water (30 mL) and EtOAc (30 mL) was added. The two layers were separated and the aqueous layer was extracted with EtOAc (30 mL). The combined organic phase was washed with brine, dried over anhydrous $Na_2SO_4$, filtered and concentrated under vacuum. The residue was purified by column chromatography ($SiO_2$, PE:EtOAc=80:1-30:1) and concentrated to give Intermediate B (650 mg, 2.42 mmol, 48.09% yield) as a white solid. $^1H$ NMR (400 MHz, $CDCl_3$) δ=7.75 (s, 1H), 7.51-7.49 (m, 2H), 7.29-7.25 (m, 1H), 2.57 (s, 1H), 1.77-1.76 (m, 3H) ppm.

Step 2: Preparation of methyl 3-(1,1,1-trifluoro-2-hydroxypropan-2-yl)benzoate (Intermediate E)

D

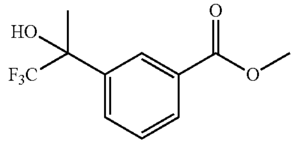

To a solution of Intermediate B (100 mg, 371.67 μmol) in THE (2 mL) was added n-BμLi (2.5 M, 460.87 μL) at −78° C. under $N_2$ and the mixture was stirred at −78° C. for 30 min. Then methyl carbonochloridate (38.63 mg, 408.83 μmol, 31.67 μL) was added and the mixture was stirred at 25° C. for 30 min. The mixture was quenched with water (10 mL) and then was extracted with EtOAc (30 mL×2). The combined organic phase was washed with brine, dried over anhydrous $Na_2SO_4$, filtered and concentrated under vacuum. The residue was purified by Prep-HPLC (FA condition). The eluent was extracted with EtOAc (40 mL×2). The combined organic phase was washed with brine, dried over anhydrous $Na_2SO_4$, filtered and concentrated under vacuum to give Intermediate E (28 mg, 112.81 μmol, 30.35% yield) as yellow oil. LCMS (ESI) m/z $[M+H]^+$=249.0.

Step 3: Preparation of 3-(1,1,1-trifluoro-2-hydroxypropan-2-yl)benzoic acid (Intermediate E)

E

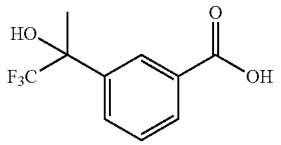

To a mixture of Intermediate E (28 mg, 112.81 μmol) in THE (0.4 mL), MeOH (0.4 mL) and $H_2O$ (0.2 mL) was added LiOH·$H_2O$ (14.20 mg, 338.44 μmol) and the mixture was stirred at 25° C. for 3 hr. The mixture was adjusted pH to ~5 with 1 N HCl and diluted with water (10 mL). Then the mixture was extracted with EtOAc (20 mL×2). The combined organic phase was washed with brine, dried over anhydrous $Na_2SO_4$, filtered and concentrated under vacuum to give Intermediate E (24 mg, 102.49 μmol, 90.85% yield) as yellow oil, which was used for the next step without further purification. LCMS (ESI) m/z $[M+H]^+$=235.0.

Step 4: Preparation of N-(2-oxo-2-((4-(3-(pyridin-4-yl)phenyl)thiazol-2-yl)amino)ethyl)-3-(1,1,1-trifluoro-2-hydroxypropan-2-yl)benzamide (Compound 78)

Compound 78

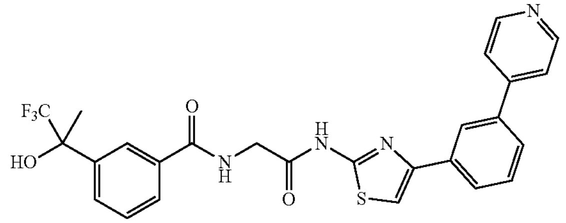

To a mixture of 2-amino-N-[4-[3-(4-pyridyl)phenyl]thiazol-2-yl]acetamide (prepared according to the method in Example 3) (34.07 mg, 98.22 μmol, HCl salt) and Intermediate E (23 mg, 98.22 μmol) in DCM (1 mL) were added EDCl (28.24 mg, 147.33 μmol), HOBt (19.91 mg, 147.33 μmol) and DIEA (50.78 mg, 392.87 μmol, 68.43 μL). The resulting mixture was stirred at 25° C. for 2 hr. The solvent was removed under reduced pressure. The residue was purified by Prep-HPLC (column: Phenomenex Synergi C18

150×25×10 um; mobile phase: [water (0.1% TFA)-ACN]; B %: 18%-48%, 10 min) and lyophilized to give Compound 78 (11.10 mg, 17.33 μmol, 17.64% yield, TFA salt) as a white solid. LCMS (ESI) m/z $[M+H]^+$=527.0. $^1H$ NMR (400 MHz, DMSO) δ=12.48 (s, 1H), 9.02-9.00 (m, 1H), 8.85-8.81 (m, 2H), 8.40-8.38 (m, 1H), 8.13-8.07 (m, 4H), 7.92-7.85 (m, 3H), 7.79-7.77 (m, 1H), 7.68-7.63 (m, 1H), 7.58-7.52 (m, 1H), 7.73 (s, 1H), 4.21 (d, J=5.6 Hz, 2H), 1.73 (s, 3H) ppm.

Example 86. Preparation of 3-(2-hydroxybutan-2-yl)-N-(2-oxo-2-((4-(3-(pyridin-4-yl)phenyl)thiazol-2-yl)amino)ethyl)benzamide (Compound 79)

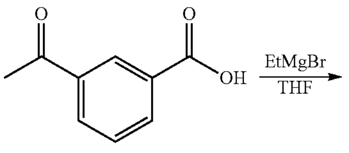

A

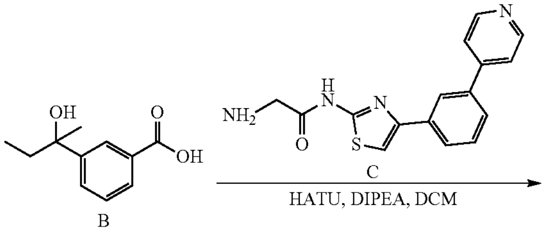

B

Compound 79

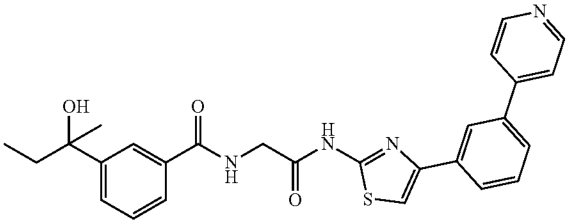

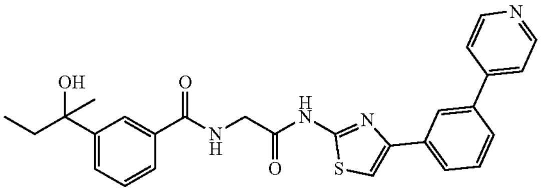

Compound 79

Step 1: Preparation of 2-((4-bromopyridin-2-yl)amino)-N-(4-phenylthiazol-2-yl)acetamide (Intermediate B)

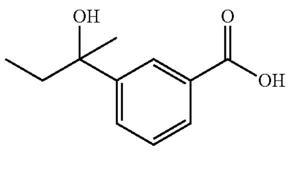

B

To a solution of 3-acetylbenzoic acid (100 mg, 609.17 μmol) in THF (2 mL) was added EtMgBr (3 M, 1.02 mL) at 0° C. under $N_2$. The mixture was stirred at 30° C. for 2 hr. The reaction mixture was quenched by addition water (20 mL) at 0° C., and then extracted with EA (50 mL×2). The organic layer were discarded and the aqueous was adjusted pH=4 with 2M HCl, and then the mixture was extracted with EA (50 mL×2). The combined organic layers were washed with brine (20 mL), dried over $Na_2SO_4$, filtered and concentrated under reduced pressure to give Intermediate B (85 mg, 437.63 μmol, 71.84% yield) as a colorless oil, which was used into the next step without further purification. $^1H$ NMR (400 MHz, DMSO) δ=12.79 (s, 1H), 8.03-8.02 (m, 1H), 7.78-7.75 (m, 1H), 7.64-7.61 (m, 1H), 7.43-7.39 (m, 1H), 4.94 (s, 1H), 1.70-1.65 (m, 2H), 1.42 (s, 3H), 0.68-0.65 (m, 3H) ppm.

Step 2: Preparation of 3-(2-hydroxybutan-2-yl)-N-(2-oxo-2-((4-(3-(pyridin-4-yl)phenyl)thiazol-2-yl)amino)ethyl)benzamide (Compound 79)

To a solution of Intermediate B (40 mg, 205.94 μmol) and 2-amino-N-[4-[3-(4-pyridyl)phenyl]thiazol-2-yl]acetamide (prepared according to the method in Example 3) (63.92 mg, 184.29 μmol, HCl salt) in DCM (2 mL) was added DIPEA (79.85 mg, 617.83 μmol, 107.62 μL), and then HATU (117.46 mg, 308.92 μmol) was added. The mixture was stirred at 25° C. for 2 hr. The reaction mixture was concentrated under reduced pressure to remove DCM. The crude product was triturated with MeOH to give a crude product. The crude product was purified by reversed-phase HPLC (0.1% FA condition) and lyophilized to give Compound 79 (30 mg, 56.33 μmol, 27.35% yield, FA salt) as a white solid. LCMS (ESI) m/z $[M+H]^+$=487.2. $^1H$ NMR (400 MHz, DMSO) δ=12.44 (s, 1H), 8.89-8.87 (m, 1H) 8.68-8.66 (m, 2H), 8.30 (s, 1H), 8.01 (d, J=7.6 Hz, 1H), 7.96 (s, 1H), 7.82 (s, 1H), 7.76-7.72 (m, 4H), 7.61-7.57 (m, 2H), 7.43-7.40 (m, 1H), 4.93 (s, 1H), 4.20 (d, J=6.0 Hz, 2H), 1.78-1.66 (m, 2H), 1.44 (s, 3H), 0.71-0.67 (m, 3H) ppm.

Example 87. Preparation of (R)-3-(2-hydroxybutan-2-yl)-N-(2-oxo-2-((4-(3-(pyridin-4-yl)phenyl)thiazol-2-yl)amino)ethyl)benzamide (Compound 80) and (S)-3-(2-hydroxybutan-2-yl)-N-(2-oxo-2-((4-(3-(pyridin-4-yl)phenyl)thiazol-2-yl)amino)ethyl)benzamide (Compound 81)

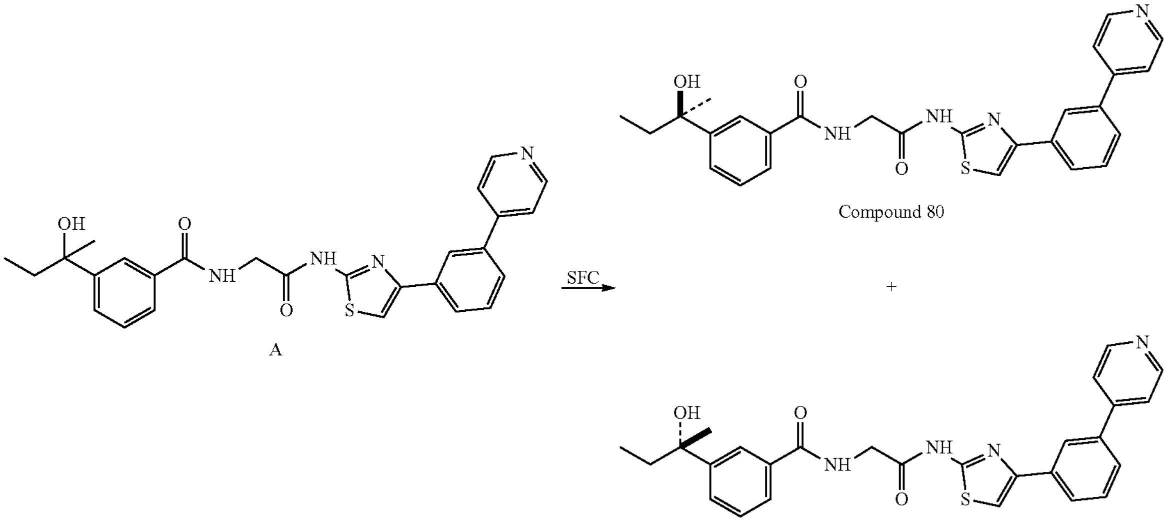

A

Compound 80

+

Compound 81

3-(1-hydroxy-1-methyl-propyl)-N-[2-oxo-2-[[4-[3-(4-pyridyl)phenyl]thiazol-2-yl]amino]ethyl]benzamide (40 mg, 82.21 μmol) was separated by SFC (column: DAICEL CHIRALPAK IC (250 mm×30 mm, 10 um); mobile phase: [0.1% $NH_3H_2O$ MEOH]; B %: 55%-55%, 3.55 min; 100 min) to give product 1 and product 2, and then product 1 and product 2 was re-purified by Pre-HPLC (TFA condition; column: Phenomenex Synergi C18 150×25×10 μm; mobile phase: [water (0.1% TFA)-ACN]; B %: 21%-45%, 8 min) and reversed-phase HPLC (0.1% FA condition) and lyophilized to give Compound 80 (5.14 mg, 10.56 μmol, 12.85% yield) as a white solid and Compound 81 (1.35 mg, 2.77 μmol, 3.37% yield) as a white solid.

Compound 80: LCMS (ESI) m/z $[M+H]^+$=487.2. $^1H$ NMR (400 MHz, DMSO) δ=8.90-8.87 (m, 1H) 8.68 (d, J=6.0 Hz, 2H), 8.42 (s, 1H), 8.31 (s, 1H), 8.01 (d, J=8.0 Hz, 1H), 7.97 (s, 1H), 7.83 (s, 1H), 7.77-7.72 (m, 4H), 7.61-7.58 (m, 2H), 7.43-7.40 (m, 1H), 4.93 (s, 1H), 4.20 (d, J=5.6 Hz, 2H), 1.74-1.70 (m, 2H), 1.44 (s, 3H), 0.71-0.67 (m, 3H) ppm. SFC: IC-3-MeOH+CAN (DEA)-40-7 min-3 mL-35T·lcm; Rt: 2.757 min, ee %=100%.

Compound 81: LCMS (ESI) m/z $[M+H]^+$=487.2. $^1H$ NMR (400 MHz, DMSO) δ=8.87 (s, 1H), 8.68 (d, J=6.0 Hz, 2H), 8.46 (s, 1H), 8.31 (s, 1H), 8.01 (d, J=7.2 Hz, 1H), 7.97 (s, 1H), 7.81 (s, 1H), 7.77-7.72 (m, 4H), 7.61-7.57 (m, 2H), 7.43-7.39 (m, 1H), 4.93 (s, 1H), 4.19 (d, J=5.2 Hz, 2H), 1.74-1.71 (m, 2H), 1.44 (s, 3H), 0.71-0.67 (m, 3H) ppm. SFC: IC-3-MeOH+CAN (DEA)-40-7 min-3 mL-35T·lcm; Rt: 3.383 min, ee %=100%.

Example 88. Preparation of 3-(3-methyl-2-oxopyrrolidin-3-yl)-N-(2-oxo-2-((4-(3-(pyridin-4-yl)phenyl)thiazol-2-yl)amino)ethyl)benzamide (Compound 82)

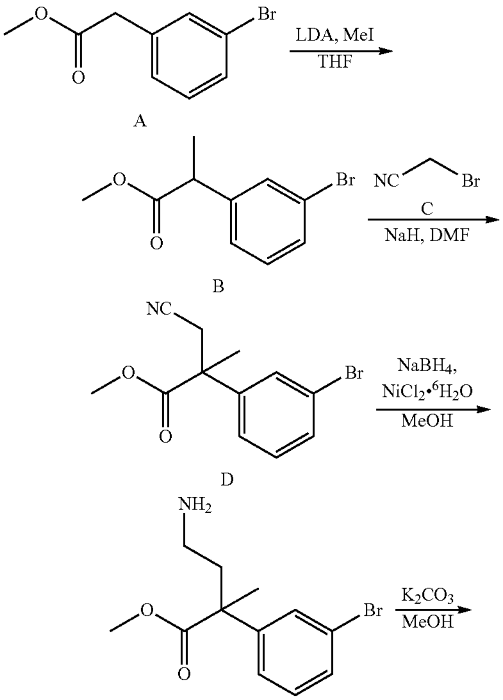

A

B

D

E

-continued

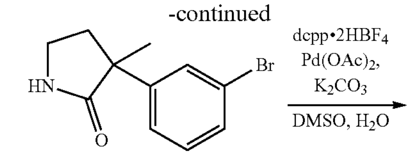

F

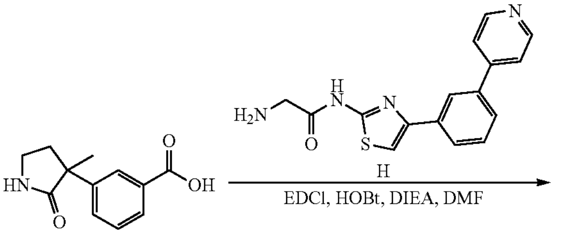

G

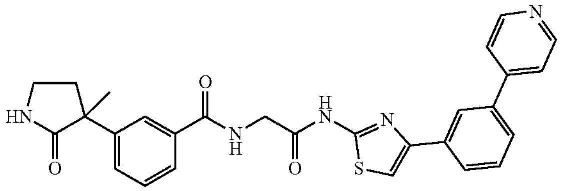

Compound 82

Step 1: Preparation of methyl 2-(3-bromophenyl)propanoate (Intermediate B)

B

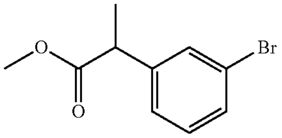

To a solution of methyl 2-(3-bromophenyl)acetate (5 g, 21.83 mmol) in THE (50 mL) was added LDA (2 M, 10.91 mL) at −60° C. Then the mixture was stirred at −60° C. for 1 hr. Then to the mixture was added MeI (2.79 g, 19.64 mmol, 1.22 mL) at −60° C. and then stirred at 25° C. for 1 hr. The reaction mixture was poured into water (50 mL) and extracted with EA (50 mL×2), the organic layer was washed with brine (50 mL) and dried over $Na_2SO_4$ and concentrated to get the crude product. The crude product was purified by column chromatography ($SiO_2$, PE:EA=100:1 to 10:1) and concentrated in vacuum to give Intermediate B (4.5 g, 18.01 mmol, 82.52% yield, 97.3% purity) as a colorless oil. LCMS (ESI) m/z $[^{79}BrM+H]^+$=242.9. $^1H$ NMR (400 MHz, chloroform-d) δ=7.38 (s, 1H), 7.32 (m, 1H), 7.18-7.09 (m, 2H), 3.64-3.57 (m, 4H), 1.42 (d, J=7.2 Hz, 3H) ppm.

Step 2: Preparation of methyl 2-(3-bromophenyl)-3-cyano-2-methylpropanoate (Intermediate D)

D

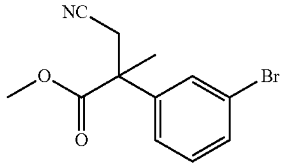

To a solution of Intermediate B (2.5 g, 10.28 mmol in DMF (50 mL) was added NaH (822.64 mg, 20.57 mmol, 60% purity) at 0° C. Then the mixture was stirred at 25° C. for 1 hr. Then to the mixture was added 2-bromoacetonitrile (2.47 g, 20.57 mmol, 1.37 mL) and the solution was stirred at 25° C. for 1 hr. The reaction mixture was quenched by water (10 mL) and then concentrated to get the crude product. The crude product was purified by reverse phase column (FA) to give Intermediate D (600 mg, 1.92 mmol, 18.69% yield) as colorless oil. LCMS (ESI) m/z $[^{79}BrM+H]^+$=282.0. $^1H$ NMR (400 MHz, chloroform-d) δ=7.45-7.37 (m, 2H), 7.19-7.14 (m, 2H), 3.67 (s, 3H), 3.03-2.90 (m, 1H), 2.86-2.77 (m, 1H), 1.74 (s, 3H) ppm.

Step 3: Preparation of methyl 4-amino-2-(3-bromophenyl)-2-methylbutanoate (Intermediate E)

E

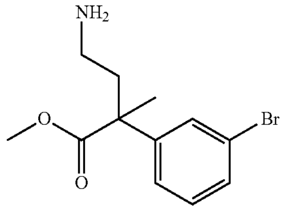

To a solution of Intermediate D (400 mg, 1.42 mmol), $NiCl_2·6H_2O$ (842.48 mg, 3.54 mmol) in MeOH (5 mL) was added $NaBH_4$ (536.38 mg, 14.18 mmol) at 0° C. Then the mixture was stirred at 0° C. for 1 hr. The reaction mixture was concentrated to give the crude product. The crude product was purified by reverse phase column (FA), the elute was adjusted pH to 8 and then extracted with EA (100 mL), the organic layer was concentrated in vacuum to give Intermediate E (150 mg, 263.66 μmol, 18.60% yield, 50.3% purity) as a colorless oil. LCMS (ESI) m/z $[^{81}BrM+H]^+$=288.0.

Step 4: Preparation of 3-(3-bromophenyl)-3-methylpyrrolidin-2-one (Intermediate F)

F

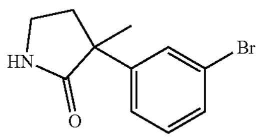

To a solution of Intermediate E (150 mg, 524.17 μmol) in MeOH (1 mL) was added $K_2CO_3$ (217.33 mg, 1.57 mmol). Then the mixture was stirred at 60° C. for 1 hr. The reaction mixture was filtered and the filtrate was concentrated to give the crude product. The crude product was purified by reverse phase (FA) and lyophilized to give Intermediate F (70 mg, 226.43 μmol, 43.20% yield, 82.2% purity) as a white solid. LCMS (ESI) m/z $[^{81}BrM+Na]^+$=256.0. $^1H$ NMR (400 MHz, chloroform-d) δ=7.51 (m, 1H), 7.34-7.29 (m, 2H), 7.17-7.12 (m, 1H), 3.37-3.19 (m, 2H), 2.43 (m, 1H), 2.20 (m, 1H), 1.48 (s, 3H) ppm.

Step 5: Preparation of 3-(3-methyl-2-oxopyrrolidin-3-yl)benzoic acid (Intermediate G)

G

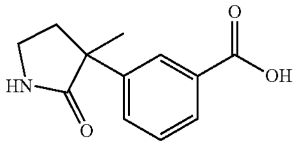

To a solution of Intermediate F (60 mg, 236.11 μmol), dicyclohexyl(3-dicyclohexylphosphaniumylpropyl)phosphonium;ditetrafluoroborate (14.46 mg, 23.61 μmol), $Pd(OAc)_2$ (2.65 mg, 11.81 μmol), $K_2CO_3$ (48.95 mg, 354.16 μmol) in DMSO (1 mL) was added $H_2O$ (8.51 mg, 472.21 μmol, 8.51 μL). Then the mixture was stirred at 100° C. for 16 hr under CO (15 psi). The reaction mixture was concentrated in vacuum. The residue was purified by reverse phase column (FA) to give Intermediate G (20 mg, 82.56 μmol, 34.97% yield, 90.5% purity) as a white solid. LCMS (ESI) m/z $[M+H]^+$=220.1.

Step 6: Preparation of 3-(3-methyl-2-oxopyrrolidin-3-yl)-N-(2-oxo-2-((4-(3-(pyridin-4-yl)phenyl)thiazol-2-yl)amino)ethyl)benzamide (Compound 82)

Compound 82

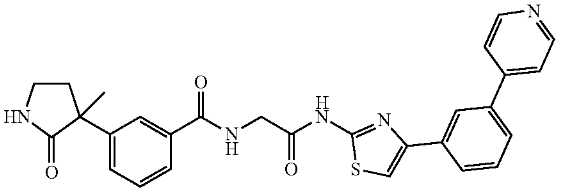

To a solution of Intermediate G (20 mg, 91.23 μmol), 2-amino-N-[4-[3-(4-pyridyl)phenyl]thiazol-2-yl]acetamide (prepared according to the method in Example 3) (34.80 mg, 100.35 μmol, HCl), EDCl (34.98 mg, 182.45 μmol), HOBt (24.65 mg, 182.45 μmol) in DMF (0.5 mL) was added DIEA (58.95 mg, 456.13 μmol, 79.45 μL). Then the mixture was stirred at 25° C. for 0.5 hr. The reaction mixture was concentrated to get the crude product. The crude product was purified by reverse phase column (FA) and lyophilized to give Compound 82 (21.38 mg, 38.34 μmol, 42.03% yield, 100% purity, FA) as a white solid. LCMS (ESI) m/z $[M+H]^+$=512.3. $^1H$ NMR (400 MHz, DMSO-$d_6$) δ=12.47 (br s, 1H), 8.97 (m, 1H), 8.74-8.63 (m, 2H), 8.32 (s, 1H), 8.02 (d, J=8.0 Hz, 1H), 7.94 (s, 1H), 7.88-7.83 (m, 2H), 7.81-7.74 (m, 4H), 7.64-7.58 (m, 2H), 7.50-7.42 (m, 1H), 4.22 (d, J=5.6 Hz, 2H), 3.29-3.26 (m, 1H), 3.19-3.11 (m, 1H), 2.44 (m, 1H), 2.25-2.14 (m, 1H), 1.45 (s, 3H) ppm.

Example 89. Preparation of (E)-3-(1-amino-1-(hydroxyimino)-2-methylpropan-2-yl)-N-(2-oxo-2-((4-(3-(pyridin-4-yl)phenyl)thiazol-2-yl)amino)ethyl)benzamide (Compound 83) and 3-(1-amino-2-methyl-1-oxopropan-2-yl)-N-(2-oxo-2-((4-(3-(pyridin-4-yl)phenyl)thiazol-2-yl)amino)ethyl)benzamide (Compound 84)

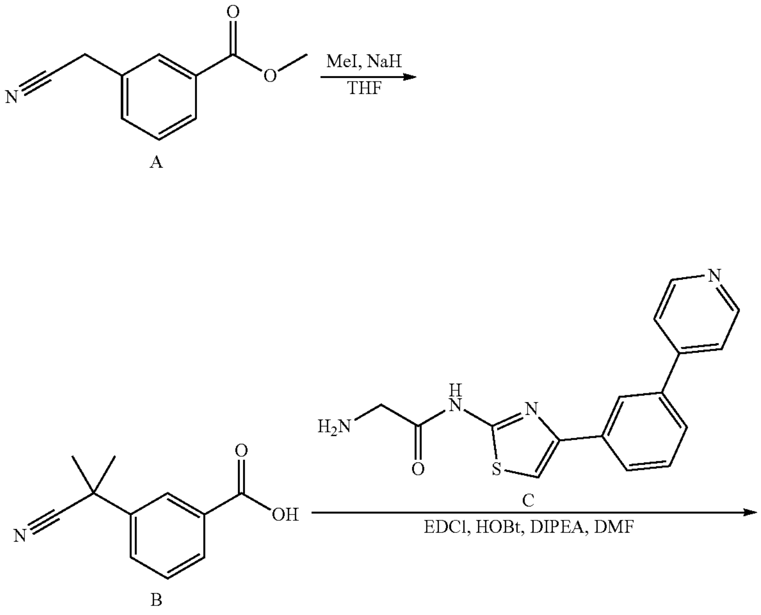

-continued

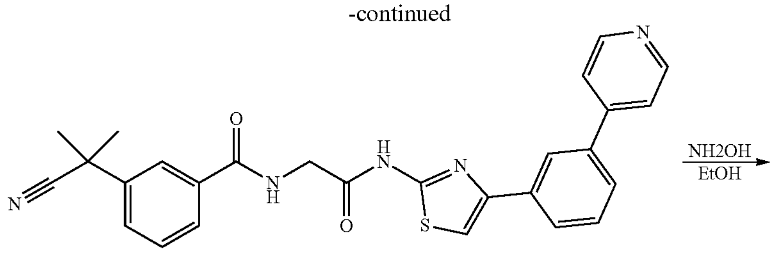

D

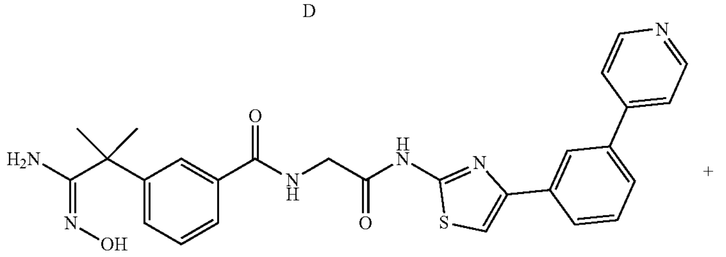

Compound 83

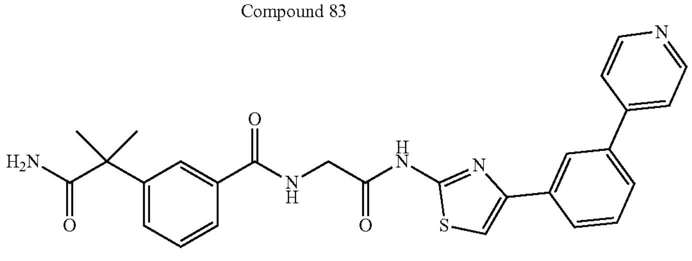

Compound 84

Step 1: Preparation of 3-(1-cyano-1-methyl-ethyl)benzoic acid (Intermediate B)

B

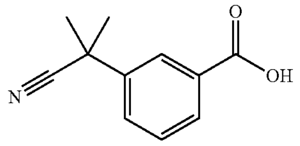

To a solution of methyl 3-(cyanomethyl)benzoate (5 g, 28.54 mmol) in THE (50 mL) was added NaH (3.42 g, 85.62 mmol, 60% purity) at 0° C. and stirred at 25° C. for 0.5 hr. Then MeI (12.15 g, 85.62 mmol, 5.33 mL) was added at 0° C. The mixture was stirred at 25° C. for 16 hr. The reaction mixture was quenched with H2O (50 mL) at 0° C. and stirred at 25° C. for 1 h and then extracted with EA (50 mL). The organic layer was discarded and the aqueous phase was adjusted pH=5 with 1N HCl, then extracted with EA (50 mL×2). The combined organic layers were dried over anhydrous $Na_2SO_4$, filtered and concentrated under reduced pressure to give Intermediate B (5 g, 26.43 mmol, 92.59% yield) as colorless oil, which used directly for the next step. $^1$H NMR (400 MHz, $CDCl_3$) δ=8.20-8.10 (m, 1H), 8.10-8.08 (m, 1H), 7.81-7.79 (m, 1H), 7.56-7.52 (m, 1H), 1.84-1.75 (m, 6H)

Step 2: Preparation of 3-(2-cyanopropan-2-yl)-N-(2-oxo-2-((4-(3-(pyridin-4-yl)phenyl)thiazol-2-yl)amino)ethyl)benzamide (Intermediate D)

D

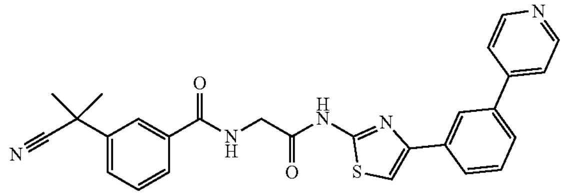

To a solution of 2-amino-N-[4-[3-(4-pyridyl)phenyl]thiazol-2-yl]acetamide (prepared according to the method in Example 3) (250 mg, 720.81 μmol, HCl salt) and Intermediate B (150.02 mg, 792.89 μmol) in DCM (2 mL) was added EDCI (207.27 mg, 1.08 mmol), HOBt (146.09 mg, 1.08 mmol) and DIPEA (465.78 mg, 3.60 mmol, 627.74 μL). The reaction mixture was stirred at 25° C. for 16 hr. To the reaction mixture was added MeOH (2 mL), a precipitate was formed and the mixture was filtered. The filter cake was washed with MeOH (2 mL) and dried in vacuum to give Intermediate D (250 mg, 460.99 μmol, 63.96% yield) as a white solid. LCMS (ESI) m/z $[M+H]^+$=482.1. $^1$H NMR (400 MHz, DMSO) δ=12.50 (s, 1H), 9.09-9.07 (m, 1H), 8.73-8.63 (m, 2H), 8.31 (s, 1H), 8.06-7.99 (m, 2H), 7.89 (d, J=8.0 Hz, 1H), 7.84 (s, 1H), 7.79-7.71 (m, 4H), 7.59-7.57 (m, 2H), 4.23 (d, J=5.6 Hz, 2H), 1.74 (s, 6H) ppm.

Step 3: Preparation of (E)-3-(1-amino-1-(hydroxy-imino)-2-methylpropan-2-yl)-N-(2-oxo-2-((4-(3-(pyridin-4-yl)phenyl)thiazol-2-yl)amino)ethyl)benzamide (Compound 83) and 3-(1-amino-2-methyl-1-oxopropan-2-yl)-N-(2-oxo-2-((4-(3-(pyridin-4-yl)phenyl)thiazol-2-yl)amino)ethyl)benzamide (Compound 84)

Compound 83

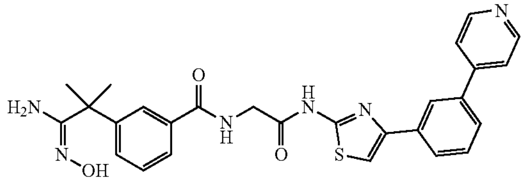

+

Compound 84

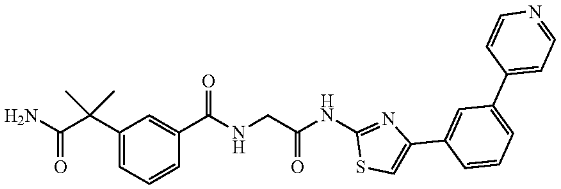

To a solution of Intermediate D (50 mg, 103.83 μmol) in EtOH (0.5 mL) was added hydroxylamine (27.44 mg, 415.31 μmol, 50% purity). The reaction mixture was stirred at 50° C. for 16 hr. More hydroxylamine (13.72 mg, 415.31 μmol) was added. The reaction mixture was stirred at 50° C. for another 24 hr. The reaction mixture concentrated in vacuum. The residue was dissolved in DMSO (1 mL) and purified by reverse phase flash (FA) and lyophilized to get Compound 83 (6 mg, 10.50 μmol, 10.11% yield, FA salt) as white solid and Compound 84 (FG-A1541A) (2 mg, 3.30 μmol, 3.18% yield, FA salt) as white solid.

Compound 83: LCMS (ESI) m/z $[M+H]^+$=515.1. $^1H$ NMR (400 MHz, DMSO) δ=9.14 (brs, 1H), 8.91-8.89 (m, 1H), 8.71-8.65 (m, 2H), 8.31-8.30 (m, 1H), 8.20 (s, 1H), 8.01 (d, J=8.0 Hz, 1H), 7.89 (s, 1H), 7.83 (s, 1H), 7.79-7.73 (m, 5H), 7.63-7.57 (m, 1H), 7.53-7.48 (m, 1H), 7.46-7.38 (m, 1H), 5.09 (s, 2H), 4.21 (d, J=6.0 Hz, 2H), 1.47 (s, 6H) ppm.

Compound 84: LCMS (ESI) m/z $[M+H]^+$=500.3. $^1H$ NMR (400 MHz, DMSO) δ=8.93-8.91 (m, 1H), 8.70-8.66 (m, 2H), 8.42 (s, 1H), 8.31-8.30 (m, 1H), 8.01 (d, J=8.0 Hz, 1H), 7.91-7.87 (m, 1H), 7.83 (s, 1H), 7.80-7.72 (m, 5H), 7.63-7.57 (m, 1H), 7.54-7.49 (m, 1H), 7.47-7.42 (m, 1H), 6.91 (br d, J=11.2 Hz, 2H), 4.20 (d, J=5.6 Hz, 2H), 1.48 (s, 6H) ppm.

Example 90. Preparation of 3-hydroxy-3-methyl-N—((S)-4-(methylthio)-1-oxo-1-((4-phenylthiazol-2-yl)amino)butan-2-yl)-2-oxoindoline-5-carboxamide (Compound 85)

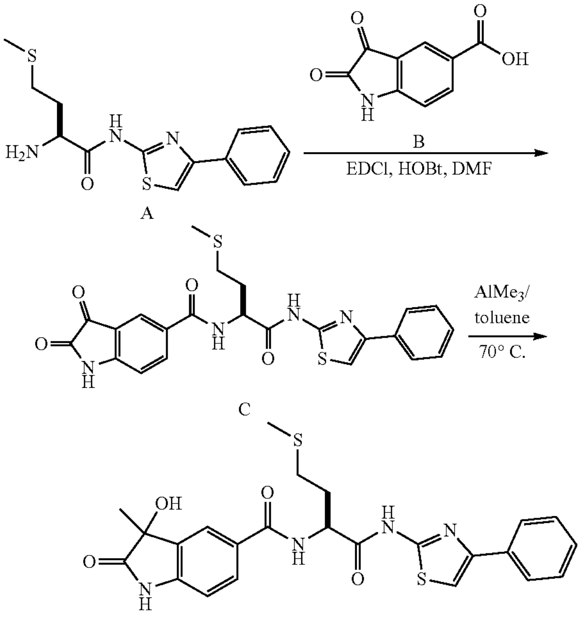

Compound 85

Step 1: Preparation of N-[(1S)-3-methylsulfanyl-1-[(4-phenylthiazol-2-yl)carbamoyl]propyl]-2,3-dioxo-indoline-5-carboxamide (Intermediate C)

C

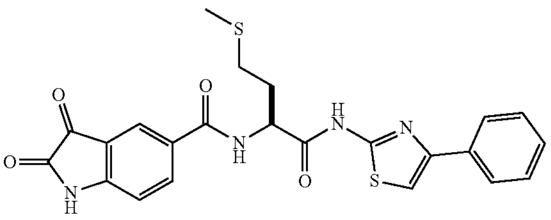

To a mixture of 2,3-dioxoindoline-5-carboxylic acid (49.89 mg, 261.00 μmol), DIPEA (122.66 mg, 949.09 μmol, 165.31 μL), HOBt (48.09 mg, 355.91 μmol) and EDCl (68.23 mg, 355.91 μmol) in DMF (1.5 mL) was added (S)-2-amino-4-(methylthio)-N-(4-phenylthiazol-2-yl)butanamide (100 mg, 237.27 μmol), then the reaction mixture was stirred at 30° C. for 2 hr. The reaction mixture was diluted with $H_2O$ (10 mL) and extracted with EA (20 mL×3). The combined organic layers were dried over $Na_2SO_4$, filtered and concentrated under reduced pressure to give a residue. The residue was purified by column chromatography ($SiO_2$, DCM:MeOH=20:1 to 10:1) and concentrated to give Intermediate C (30 mg, 41.83 μmol, 17.63% yield) as a red solid, which was used for next step directly. LCMS (ESI) m/z $[M+H]^+$=481.1.

Step 2: Preparation of 3-hydroxy-3-methyl-N—((S)-4-(methylthio)-1-oxo-1-((4-phenylthiazol-2-yl)amino)butan-2-yl)-2-oxoindoline-5-carboxamide (Compound 85)

Compound 85

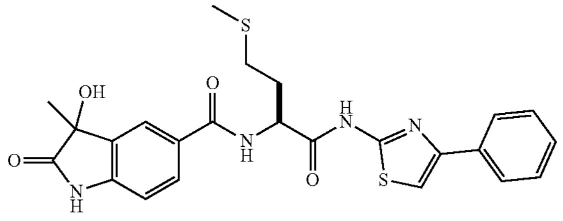

To a mixture of Intermediate C (15 mg, 31.21 μmol) in toluene (0.2 mL) was added trimethylalumane (2 M, 31.21 μL) under $N_2$ at 30° C., then the reaction mixture was stirred at 70° C. for 2 h. The reaction mixture was quenched by addition $H_2O$ (30.0 mL), then extracted with EA (20 mL×3). The combined organic layers were dried over $Na_2SO_4$, filtered and concentrated under reduced pressure to give a residue. The residue was purified by Prep-HPLC (column: Waters Xbridge 150×25 5 u; mobile phase: [water (0.05% ammonia hydroxide v/v)-ACN]; B %: 22%-52%, 10 min) and lyophilized to give Compound 85 (4.72 mg, 9.50 μmol, 30.45% yield) as a white solid. LCMS (ESI) m/z $[M+H]^+$=497.2. $^1H$ NMR (400 MHz, MeOD-$d_4$) δ=7.96 (s, 1H), 7.90-7.87 (m, 3H), 7.40-7.36 (m, 3H), 7.31-7.26 (m, 1H), 6.98 (d, J=8.4 Hz, 1H), 4.92 (m, 1H), 2.71-2.64 (m, 2H), 2.30-2.22 (m, 2H), 2.14 (s, 3H), 1.55 (d, J=2.4 Hz, 3H) ppm.

Example 91. Preparation of 3-(2-aminopropan-2-yl)-N-(2-oxo-2-((4-(3-(pyridin-4-yl)phenyl)thiazol-2-yl)amino)ethyl)benzamide (Compound 86)

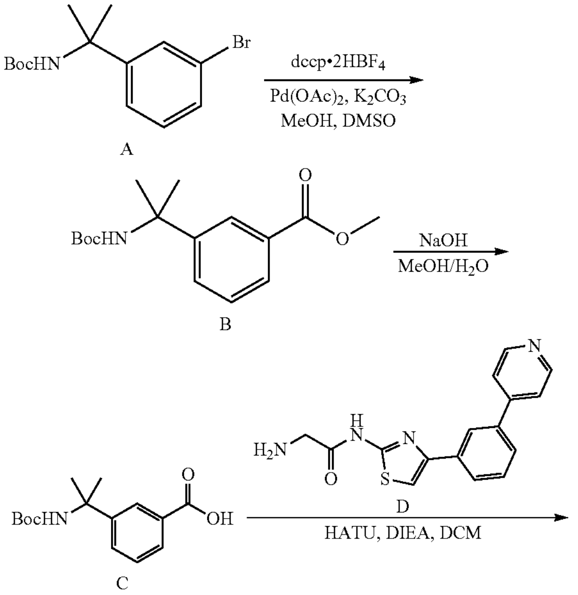

-continued

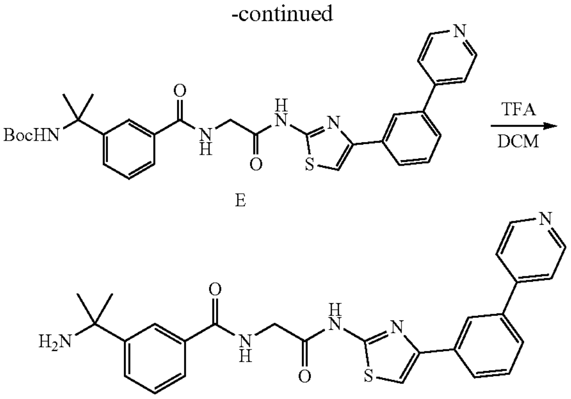

Compound 86

Step 1: Preparation of methyl 3-(2-((tert-butoxycarbonyl)amino)propan-2-yl)benzoate (Intermediate B)

B

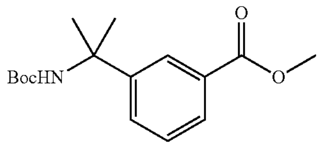

A mixture of tert-butyl N-[1-(3-bromophenyl)-1-methyl-ethyl]carbamate (1 g, 3.18 mmol), $Pd(OAc)_2$ (35.72 mg, 159.13 μmol), $K_2CO_3$ (659.76 mg, 4.77 mmol), MeOH (203.95 mg, 6.37 mmol, 257.57 μL) and dicyclohexyl(3-dicyclohexylphosphaniumylpropyl)phosphonium;ditetrafluoroborate (97.43 mg, 159.13 μmol) in DMSO (10 mL) was degassed and purged with $N_2$ for 3 times, and then the mixture was stirred at 100° C. for 16 hr under CO (50 psi). The reaction mixture was poured into water (20 mL), the solution was extracted with EA (20 mL×3), the combined organic layer was washed with brine (50 mL), dried over $Na_2SO_4$ and filtered. The filtrate was concentrated to give a residue. The filtrate was purified by reversed-phase HPLC (0.1% FA condition). The solution was extracted with EA (5 mL), the combined organic layer was washed with (10 mL), dried over $Na_2SO_4$ and filtrated. The filtrate was concentrated to give Intermediate B (400 mg, 1.36 mmol, 42.77% yield) as yellow oil. LCMS (ESI) m/z $[M+H-56]^+$=238.2.

Step 2: Preparation of 3-(2-((tert-butoxycarbonyl)amino)propan-2-yl)benzoic acid (Intermediate C)

C

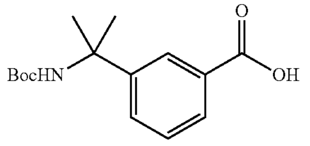

To a solution of Intermediate B (150 mg, 511.32 μmol) in MeOH (2 mL) and $H_2O$ (1 mL) was added NaOH (30.68 mg, 766.98 μmol), the reaction mixture was stirred at 30° C. for 1 hr. The reaction mixture was adjusted to pH=6 with 1

N HCl solution, the solution was extracted with EA (5 mL×3), the combined organic layer was washed with brine (10 mL), dried over $Na_2SO_4$, and filtered. The filtrate was concentrated to give Intermediate C (140 mg, 488.67 μmol, 95.57% yield) as a white solid which was used for next step directly. LCMS (ESI) m/z $[M+Na]^+$=302.2.

Step 3: Preparation of tert-butyl (2-(3-((2-oxo-2-((4-(3-(pyridin-4-yl)phenyl)thiazol-2-yl)amino)ethyl)carbamoyl)phenyl)propan-2-yl)carbamate (Intermediate E)

E

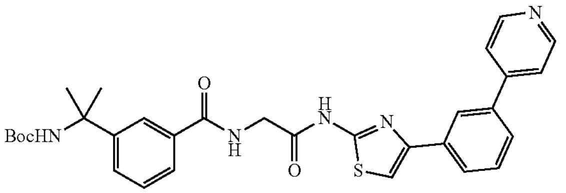

To a solution of Intermediate C (140 mg, 501.20 μmol) and 2-amino-N-[4-[3-(4-pyridyl)phenyl]thiazol-2-yl]acetamide (prepared according to the method in Example 3) (86.92 mg, 250.60 μmol, HCl salt) in DCM (2 mL) was added HATU (114.34 mg, 300.72 μmol) and DIEA (161.94 mg, 1.25 mmol, 218.25 μL), the mixture was stirred at 30° C. for 1.5 hr. The reaction mixture was extracted with EA (5 mL×3), the combined organic layer was washed with brine (10 mL), dried over $Na_2SO_4$ and filtered. The filtrate was concentrated to give Intermediate E (140 mg, 210.14 μmol, 83.86% yield) as a white solid which was used for next step directly. LCMS (ESI) m/z $[M+H]^+$=572.3.

Step 4: Preparation of 3-(2-aminopropan-2-yl)-N-(2-oxo-2-((4-(3-(pyridin-4-yl)phenyl)thiazol-2-yl)amino)ethyl)benzamide (Compound 86)

Compound 86

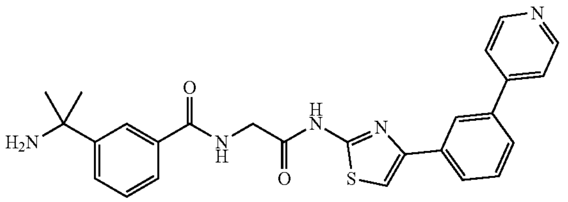

A mixture of Intermediate E (130 mg, 195.13 μmol) in HCl/dioxane (2 mL) was stirred at 30° C. for 1 hr. The reaction mixture was concentrated to give a residue. The residue was purified by Prep-HPLC (column: Phenomenex Synergi C18 150×25×10 um; mobile phase: [water (0.225% FA)-ACN]; B %: 4%-34%, 10 min) and lyophilized to give Compound 86 (18.47 mg, 35.68 μmol, 18.29% yield, FA salt) as a white solid. LCMS (ESI) m/z $[M+H]^+$=472.3. $^1H$ NMR (400 MHz, DMSO) δ=9.01-9.00 (m, 1H), 8.67-8.66 (m, 2H), 8.33-8.29 (m, 2H), 8.08 (br s, 1H), 8.00 (d, J=8.0 Hz, 1H), 7.82-7.71 (m, 6H), 7.61-7.56 (m, 1H), 7.49-7.45 (m, 1H), 4.21 (br d, J=6.0 Hz, 2H), 1.51-1.47 (m, 6H) ppm.

Example 92. Preparation of 3-(2-cyanopropan-2-yl)-N-(2-oxo-2-((4-(3-(pyridin-4-yl)phenyl)thiazol-2-yl)amino)ethyl)benzamide (Compound 87)

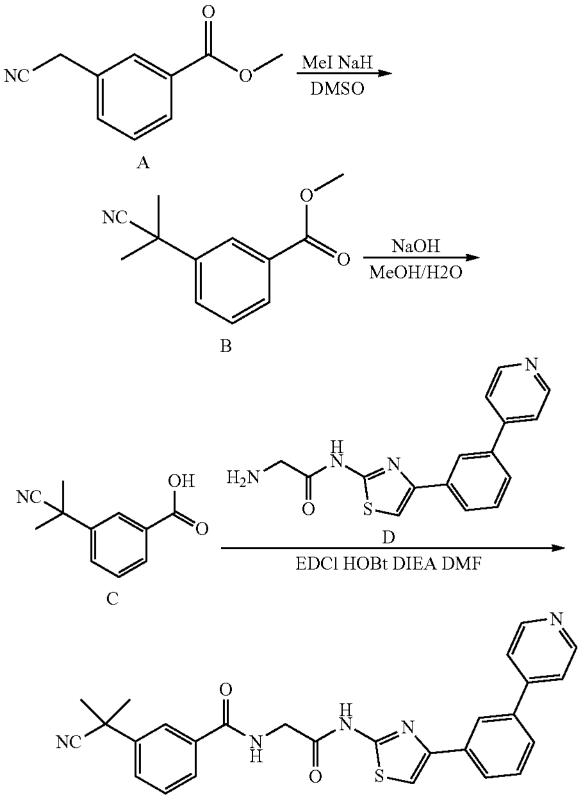

Compound 87

Step 1: Preparation of methyl 3-(2-cyanopropan-2-yl)benzoate (Intermediate B)

B

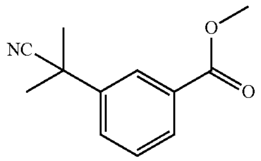

To a solution of methyl 3-(cyanomethyl)benzoate (1 g, 5.71 mmol) in anhydrous THE (10 mL) was added NaH (570.83 mg, 14.27 mmol, 60% purity) at 0° C. The mixture was stirred at 0° C. for 0.5 hr. Then MeI (2.03 g, 14.27 mmol, 888.41 μL) was added. The mixture was stirred at 0° C. for 1.5 hr. The reaction mixture was poured into water (50 mL), then extracted with EA (50 mL×2). The combined organic layer was washed with brine, dried over anhydrous sodium sulfate, filtered and concentrated to give residue. The residue was purified by flash silica gel chromatography (ISCO; 20 g SepaFlash Silica Flash Column, Eluent of 0~30% Ethylacetate/Petroleum ether gradient 40 mL/min) and concentrated to give Intermediate B (900 mg, 3.85 mmol, 67.49% yield) as yellow oil. LCMS (ESI) m/z $[M+H]^+$=204.1. $^1$H NMR (400 MHz, $CDCl_3$) δ=8.14-8.10 (m, 1H), 8.01-7.99 (m, 1H), 7.76-7.69 (m, 1H), 7.49-7.47 (m, 1H), 3.95 (s, 3H), 1.77 (s, 6H) ppm.

Step 2: Preparation of 3-(2-cyanopropan-2-yl)benzoic acid (Intermediate C)

C

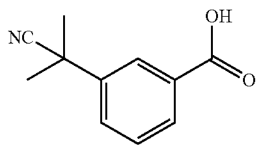

To a solution of Intermediate B (100 mg, 492.04 μmol) in THE (1 mL) were added $H_2O$ (0.5 mL), EtOH (0.5 mL) and NaOH (39.36 mg, 984.07 μmol). The reaction mixture was stirred at 30° C. for 2 hr.

The reaction mixture was diluted with water (5 mL), then washed by EA (10 mL×1). The aqueous phase was acidified by 1M HCl to pH=3, then extracted by EA (10 mL×2). The combined organic layer was washed with brine, dried over anhydrous sodium sulfate, filtered and concentrated to give Intermediate C (60 mg, 251.40 μmol, 51.09% yield) as yellow oil, which was used for next step directly. LCMS (ESI) m/z $[M+H]^+$=190.1. $^1$H NMR (400 MHz, DMSO) δ=8.07-8.06 (m, 1H), 7.92-7.90 (m, 1H), 7.79-7.75 (m, 1H), 7.61-7.54 (m, 1H), 1.71 (s, 6H) ppm.

Step 3: Preparation of 3-(2-cyanopropan-2-yl)-N-(2-oxo-2-((4-(3-(pyridin-4-yl)phenyl)thiazol-2-yl)amino)ethyl)benzamide (Compound 87)

Compound 87

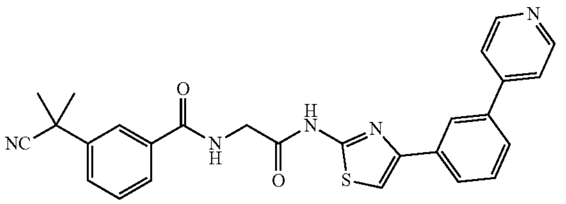

To a solution of Intermediate C (60 mg, 251.40 μmol) in DMF (2 mL) was added EDCl (60.24 mg, 314.25 μmol), HOBt (42.46 mg, 314.25 μmol), DIPEA (81.23 mg, 628.51 μmol, 109.47 μL) and 2-amino-N-[4-[3-(4-pyridyl)phenyl]thiazol-2-yl]acetamide (prepared according to the method in Example 3) (72.66 mg, 209.50 μmol, HCl salt). The reaction mixture was stirred at 30° C. for 17 hr. The reaction mixture was triturated with water (10 mL). The suspension was filtered to give a white solid. The solid was dissolved into DMSO (2 mL) and purified by reversed phased HPLC (FA) and lyophilized to give Compound 87 (30.23 mg, 56.48 μmol, 26.96% yield, FA salt) as off-white solid. LCMS (ESI) m/z $[M+H]^+$=482.4. $^1$H NMR (400 MHz, DMSO) δ=12.31 (br s, 1H), 8.40 (s, 1H), 7.67-7.58 (m, 3H), 7.51 (s, 1H), 7.41-7.36 (m, 1H), 7.33-7.27 (m, 1H), 7.02-6.95 (m, 1H), 6.56 (d, J=8.8 Hz, 2H), 5.66 (s, 2H), 4.10 (d, J=5.6 Hz, 2H), 3.81 (br s, 4H), 3.16 (br s, 4H) ppm.

Example 93. Preparation of 2-amino-N-(4-(6-((cis)-2,6-dimethylmorpholino)pyridin-2-yl)thiazol-2-yl) acetamide hydrochloride salt

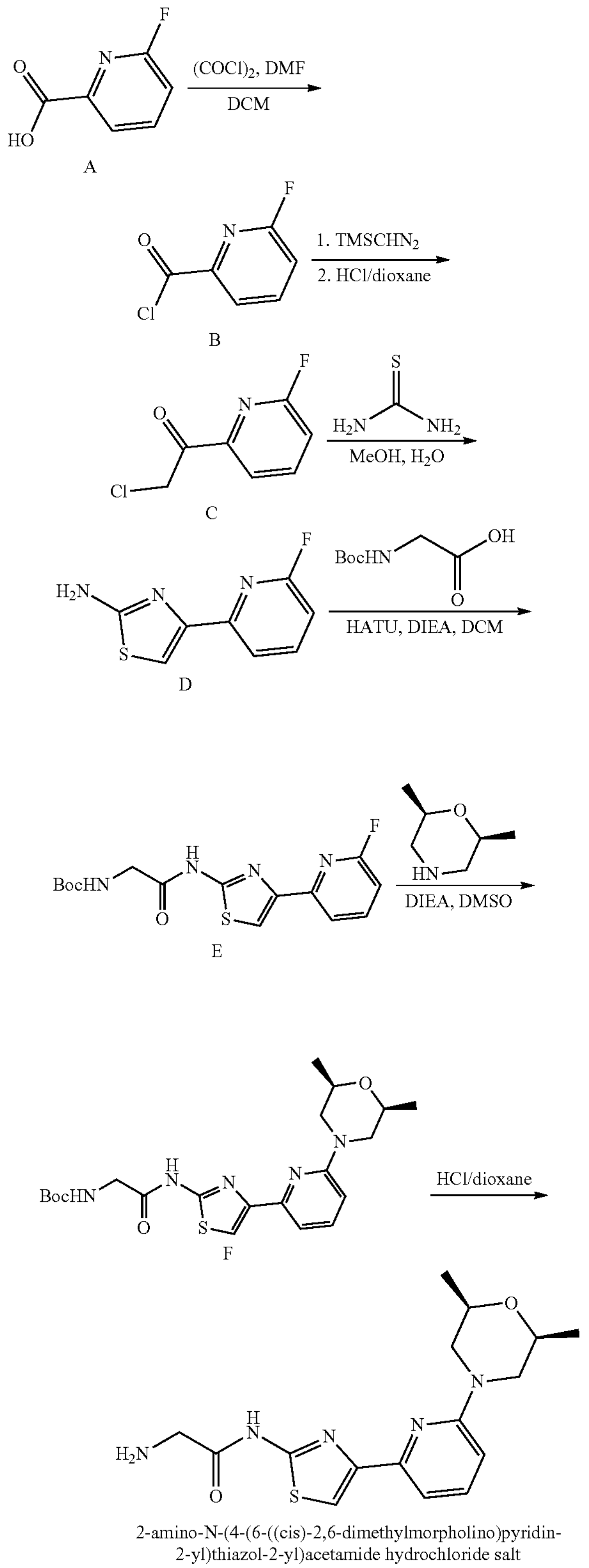

2-amino-N-(4-(6-((cis)-2,6-dimethylmorpholino)pyridin-2-yl)thiazol-2-yl)acetamide hydrochloride salt Step 1: Preparation of 6-fluoropyridine-2-carbonyl chloride

B

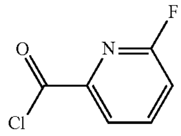

To a mixture of 6-fluoropyridine-2-carboxylic acid (24 g, 170.09 mmol) and DMF (124.32 mg, 1.70 mmol, 130.86 uL) in DCM (240 mL) was added $(COCl)_2$ (107.95 g, 850.46 mmol, 74.45 mL) at 0° C., then the reaction mixture was stirred at 25° C. 0.5 hr. The mixture was concentrated under vacuum to give Intermediate B (27 g, crude) as a white solid which was used to next step without further purification.

Step 2: Preparation of 2-chloro-1-(6-fluoro-2-pyridyl)ethanone

C

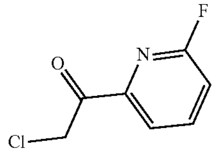

To a mixture of Intermediate B (27 g, 169.23 mmol) in dioxane (300 mL) was added $TMSCHN_2$ (2 M, 169.23 mL) drop wise at 0° C., then the reaction mixture was stirred at 25° C. 10 hrs. The reaction mixture was quenched with HCl/dioxane (4 M, 300 mL) and stirred at 25° C. for 2 hrs. Then mixture the concentrated under vacuum to give a residue, the residue was diluted with $NaHCO_3$ (450 mL), extracted with EA (300 mL*3). The combined organic layers were washed with brine (200 mL*2), dried over $Na_2SO_4$, filtered and concentrated under reduced pressure to give Intermediate C (29 g, crude) as a white solid, which was used to next step directly. LCMS (ESI) m/z: [M+H]+=174.1.

Step 3: Preparation of 4-(6-fluoro-2-pyridyl)thiazol-2-amine

D

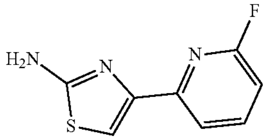

A mixture of Intermediate C (29 g, 167.08 mmol), thiourea (12.72 g, 167.08 mmol) in MeOH (250 mL) and H2O (250 mL) was stirred at 25° C. 10 hrs. The mixture was diluted with $NaHCO_3$ (100 mL), then concentrated under vacuum to removed MeOH, then filtered to give a crude product. The residue was triturated with PE (100 mL) at 25° C. for 10 min, filtered and the solid was dried in vacuum to give Intermediate D (27 g, 83% yield) as a white solid. LCMS (ESI) m/z: [M+H]+=195.8.

Step 4: Preparation of tert-butyl N-[2-[[4-(6-fluoro-2-pyridyl)thiazol-2-yl]amino]-2-oxo-ethyl]carbamate

E

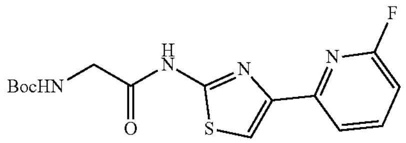

To a solution of 2-(tert-butoxycarbonylamino)acetic acid (26.92 g, 153.68 mmol), HATU (58.43 g, 153.68 mmol) and DIEA (66.20 g, 512.25 mmol, 89.23 mL) in DCM (250 mL) was added Intermediate D (25 g, 128.06 mmol). The reaction mixture was stirred at 25° C. for 4 hrs. The reaction mixture was concentrated under vacuum, then diluted with water (200 mL) and extracted with EtOAc (300 mL*4). The combined organic layers were washed with brine (300 mL*2), dried over $Na_2SO_4$, filtered and concentrated under reduced pressure to give a residue. The crude product was triturated with MeOH (50 mL) at 25° C. for 15 min, then filtered to give filter cake, the filter cake was washed with MTBE (50 mL*2), dried in vacuum to give Intermediate E (25 g, 55% yield) as a white solid. LCMS (ESI) m/z: [M+H]+=352.9. $^1H$ NMR (400 MHz, DMSO-$d_6$) δ=12.35 (s, 1H), 8.10-8.04 (m, 1H), 7.85-7.82 (m, 2H), 7.17-7.10 (m, 2H), 3.88-3.81 (m, 2H), 1.39 (s, 8H) ppm.

Step 5: Preparation of tert-butyl N-[2-[[4-[6-[(cis)-2,6-dimethylmorpholin-4-yl]-2-pyridyl]thiazol-2-yl]amino]-2-oxo-ethyl]carbamate

F

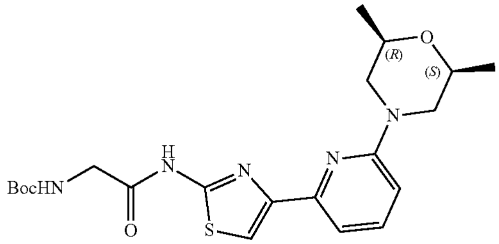

To a solution of (cis)-2,6-dimethylmorpholine (16.34 g, 141.89 mmol), DIEA (11.00 g, 85.13 mmol, 14.83 mL) in DMSO (200 mL) was added Intermediate E (10 g, 28.38 mmol). The reaction mixture was stirred at 120° C. for 2 hrs at a seal tube. The reaction mixture was concentrated under vacuum, then diluted with water (600 mL) and extracted with EtOAc (300 mL*3). The combined organic layers were washed with brine (200 mL*2), dried over $Na_2SO_4$, filtered and concentrated under reduced pressure to give a residue. The residue was purified by column chromatography (Petroleum ether/Ethyl acetate=50/1 to 1/1), the fraction was concentrated under vacuum to give a crude product. The crude product was triturated with MeOH (30 mL) at 25° C. for 15 min, filtered and dried in vacuum to give Intermediate F (6.4 g, 76% yield) as a white solid. LCMS (ESI) m/z: [M+H]+=448.1.

Step 6: Preparation of 2-amino-N-[4-[6-[(cis)-2,6-dimethylmorpholin-4-yl]-2-pyridyl]thiazol-2-yl] acetamide hydrochloride salt

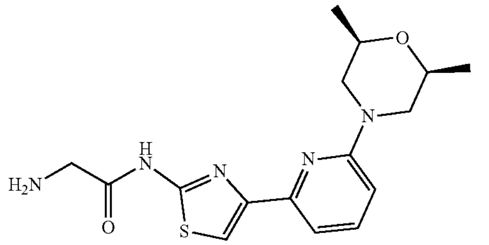

2-amino-N-(4-(6-((cis)-2,6-dimethylmorpholino)pyridin-2-yl)thiazol-2yl)acetamide hydrochloride salt A solution of Intermediate F (3.6 g, 8.04 mmol) in HCl/dioxane (4 M, 72.00 mL) was stirred at 25° C. for 1 hr. The mixture was concentrated under vacuum to give residue as a crude product, and crude product was triturated with MTBE (100 mL) at 25° C. for 15 min, filtered and dried in the vacuum to afford the title compound (4.4 g, crude, HCl salt) as a white solid. LCMS (ESI) m/z: [M+H]+=348.0. $^1$H NMR (400 MHz, METHANOL-d4) δ=8.17 (s, 1H), 8.11-8.07 (m, 1H), 7.54 (d, J=7.2 Hz, 1H), 7.36 (d, J=9.2 Hz, 1H), 4.08 (d, J=8.8 Hz, 4H), 3.85-3.81 (m, 2H), 2.98-2.92 (m, 2H), 1.30 (d, J=6.4 Hz, 6H) ppm.

Example 94. Preparation of 3-(hydroxymethyl)-3-methyl-2,3-dihydrobenzofuran-5-carboxylic acid

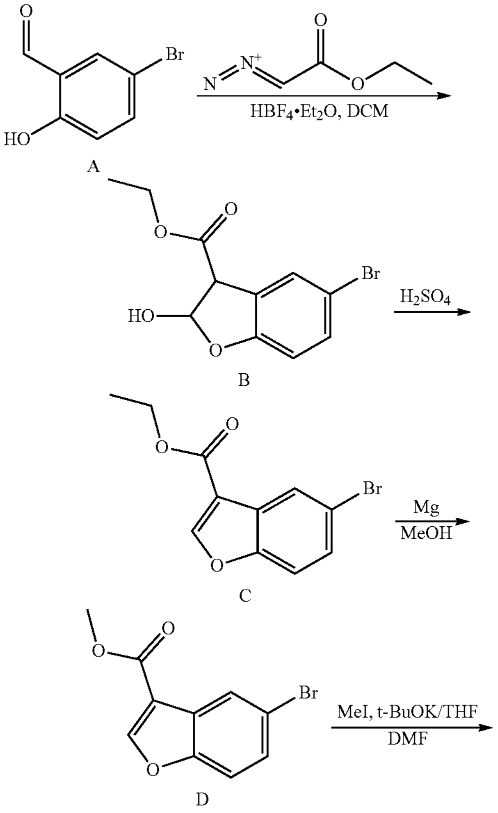

-continued

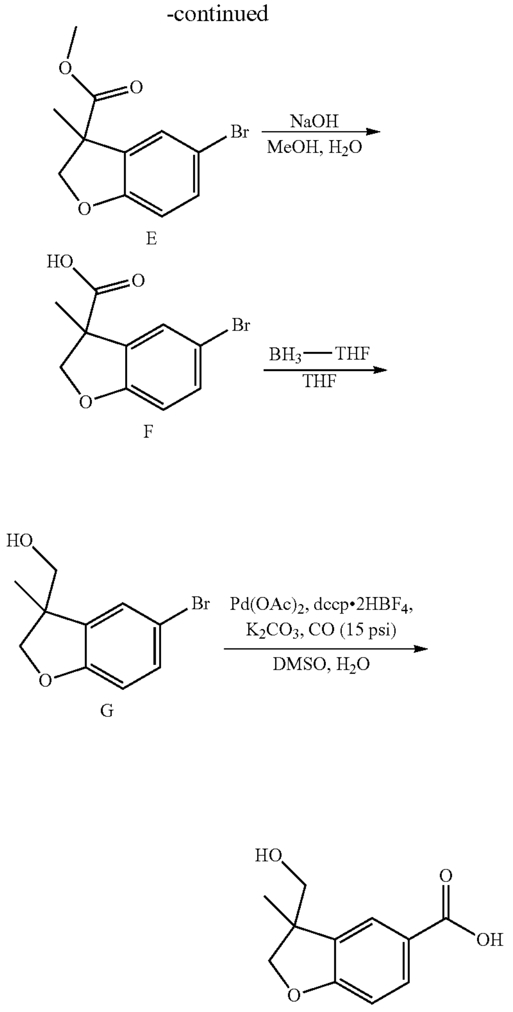

3-(hydroxymethyl)-3-methyl-2,3-dihydrobenzofuran-5-carboxylic acid

Step 1: Preparation of ethyl 5-bromo-2-hydroxy-2,3-dihydrobenzofuran-3-carboxylate

B

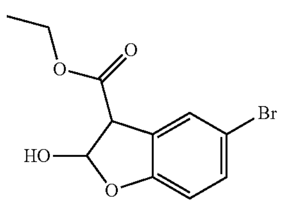

To a solution of 5-bromo-2-hydroxy-benzaldehyde (10 g, 49.75 mmol) and ethoxyethane;trifluoroborane;hydrofluoride (805.57 mg, 4.97 mmol, 682.69 uL) in DCM (25 mL) was added the ethyl 2-diazoacetate (9.08 g, 79.60 mmol) in DCM (25 mL). The mixture was stirred at 30° C. for 0.5 hr. The reaction mixture was concentrated under reduced pressure to give Intermediate B (15 g, crude) as a brown liquid, which was used to the next step without further purification.

Step 2: Preparation of ethyl 5-bromobenzofuran-3-carboxylate

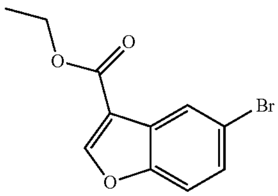

C

A mixture of Intermediate B (15 g, 52.25 mmol) in $H_2SO_4$ (67.97 g, 679.19 mmol, 36.94 mL, 98% purity) was stirred at 20° C. for 1 hr. The reaction mixture was diluted with DCM (200 mL) and neutralized with solid $Na_2CO_3$ (50 g). Then the suspension was filtered, and the filtrate was concentrated under reduced pressure to give a residue. The residue was purified by reverse phase (0.1% FA) and concentrated under reduced pressure to give Intermediate C (5.5 g, 39% yield) as a light yellow solid. $^1$H NMR (400 MHz, DMSO-$d_6$) δ=8.82 (s, 1H), 8.06 (d, J=2.0 Hz, 1H), 7.72 (d, J=8.4 Hz, 1H), 7.60-7.57 (m, 1H), 4.38-4.32 (m, 2H), 1.36-1.32 (m, 3H) ppm.

Step 3: Preparation of methyl 5-bromo-2,3-dihydrobenzofuran-3-carboxylate

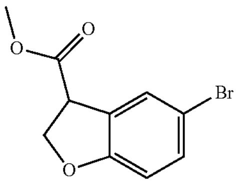

D

To a solution of Intermediate C (5 g, 18.58 mmol) in MeOH (250 mL) was added Mg (2.38 g, 97.92 mmol) at 20° C. The mixture was stirred at 30° C. for 4 hrs. The reaction mixture was quenched with 1 N HCl (50 mL), then diluted with water (200 mL) and extracted with EtOAc (200 mL*2). The combined organic layers were washed with brine (200 mL), dried over $Na_2SO_4$, filtered and concentrated under reduced pressure to give a residue. The residue was purified by reverse phase (0.1% FA) and concentrated under reduced pressure to give Intermediate D (3 g, 63% yield) as a light-yellow oil. LCMS (ESI) m/z: [81 BrM+H]+=259.0. $^1$H NMR (400 MHz, DMSO-$d_6$) δ=7.46-7.45 (m, 1H), 7.36-7.33 (m, 1H), 6.81 (d, J=8.8 Hz, 1H), 4.80-4.69 (m, 2H), 4.56-4.52 (m, 1H), 3.72 (s, 3H) ppm.

Step 4: Preparation of methyl 5-bromo-3-methyl-2H-benzofuran-3-carboxylate

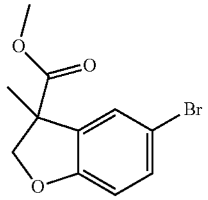

E

To a solution of Intermediate D (2500 mg, 9.72 mmol) and MeI (1.38 g, 9.72 mmol, 605.40 uL) in DMF (45 mL) was added t-BuOK (1 M, 14.59 mL) under $N_2$ at 0° C., then the mixture was stirred at 0° C. for 1 hr. The reaction mixture was quenched by addition 1 N HCl (30 mL), and then diluted with water (100 mL) and extracted with MTBE (100 mL*2). The combined organic layers were washed with brine (100 mL), dried over $Na_2SO_4$, filtered and concentrated under reduced pressure to give a residue. The reaction mixture was purified by column chromatography ($SiO_2$, PE/EA=6:1) and concentrated under reduced pressure to give Intermediate E (800 mg, 28% yield) as a light-yellow oil. LCMS (ESI) m/z: [BrM+H]+=271.0. $^1$H NMR (400 MHz, CHLOROFORM-d) δ=7.43-7.72 (m, 1H), 7.29-7.27 (m, 1H), 6.70 (d, J=8.4 Hz, 1H), 5.07 (d, J=9.2 Hz, 1H), 4.27 (d, J=9.2 Hz, 1H), 3.76 (s, 3H), 1.61 (s, 3H) ppm.

Step 5: Preparation of 5-bromo-3-methyl-2H-benzofuran-3-carboxylic acid

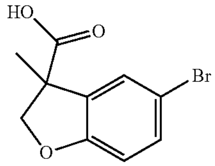

F

To a solution of Intermediate E (800 mg, 2.95 mmol) in MeOH (8 mL) and Water (8 mL) was added NaOH (236.07 mg, 5.90 mmol). The mixture was stirred at 30° C. for 2 hrs. The reaction mixture was concentrated under reduced pressure to remove MeOH. Then the residue was diluted with water (30 mL) and acidized with 1 N HCl to pH 4.0, then extracted with EtOAc (50 mL*3). The combined organic layers were dried over $Na_2SO_4$, filtered and concentrated under reduced pressure to give a residue. The residue was used to the next step without further purification. Intermediate F (800 mg, crude) as a light yellow solid, which was used to the next step without further purification. $^1$H NMR (400 MHz, CHLOROFORM-d) δ=7.46 (d, J=2.0 Hz, 1H), 7.31-7.28 (m, 1H), 6.71 (d, J=8.8 Hz, 1H), 5.05 (d, J=8.8 Hz, 1H), 4.28 (d, J=9.2 Hz, 1H), 1.64 (s, 3H) ppm.

Step 6: Preparation of (5-bromo-3-methyl-2H-benzofuran-3-yl)methanol

G

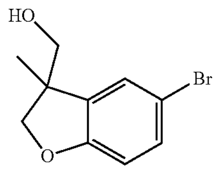

To a solution of Intermediate F (800 mg, 3.11 mmol) in THE (8 mL) was added $BH_3$-THF (1 M, 4.67 mL) at 0° C. under $N_2$, then the mixture was stirred at 30° C. for 2 hrs. The reaction mixture was poured into 1N HCl (20 mL) and diluted with water (50 mL) and extracted with EtOAc (100 mL*2). The combined organic layers were washed with brine (100 mL), dried over $Na_2SO_4$, filtered and concentrated under reduced pressure to give Intermediate G (740 mg, 98% yield) as a light-yellow oil, which was used to the next step without further purification. LCMS (ESI) m/z: [81 BrM+H]+=245.0.

Step 7: Preparation of 3-(hydroxymethyl)-3-methyl-2H-benzofuran-5-carboxylic acid

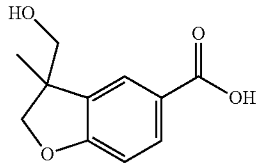

3-(hydroxymethyl)-3-methyl-2,3-dihydrobenzofuran-5-carboxylic acid

To a solution of Intermediate G (740 mg, 3.04 mmol), $Pd(OAc)_2$ (34.17 mg, 152.20 umol) and dicyclohexyl(3-dicyclohexylphosphaniumylpropyl)phosphonium;ditetrafluoroborate (186.38 mg, 304.41 umol) in DMSO (15 mL) and Water (1 mL) was added $K_2CO_3$ (631.06 mg, 4.57 mmol) and stirred at 100° C. for 4 hr under CO (15 psi). The reaction mixture was diluted with water (100 mL) and extracted with MTBE (100 mL*2). The aqueous phase was acidized with 1 N HCl to pH 4.0 and extracted with EtOAc (100 mL*2). The combined organic layers were washed with brine (100 mL), dried over $Na_2SO_4$, filtered and concentrated under reduced pressure to give 3-(hydroxymethyl)-3-methyl-2H-benzofuran-5-carboxylic acid (500 mg, crude) as a light yellow solid, which was used without further purification. LCMS (ESI) m/z: [M+H]+=209.1. $^1H$ NMR (400 MHz, DMSO-$d_6$) δ=12.50 (s, 1H), 7.77-7.74 (m, 2H), 6.81 (d, J=8.0 Hz, 1H), 5.05-5.02 (m, 1H), 4.56 (d, J=8.8 Hz, 1H), 4.19 (d, J=8.8 Hz, 1H), 3.47-3.42 (m, 2H), 2.54 (s, 1H), 1.28 (s, 3H) ppm.

Example 95. Preparation of 3-(hydroxymethyl)-3-methyl-2,3-dihydrobenzofuran-5-carboxylic acid

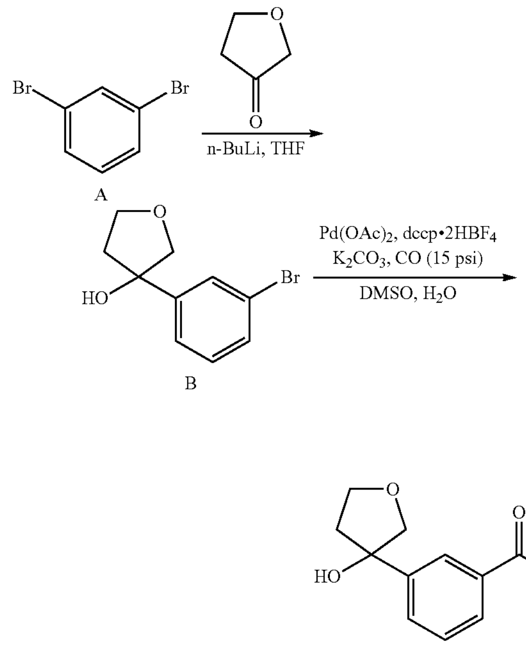

3-(hydroxymethyl)-3-methyl-2,3-dihydrobenzofuran-5-carboxylic acid

Step 1: Preparation of 3-(3-bromophenyl)tetrahydrofuran-3-ol

B

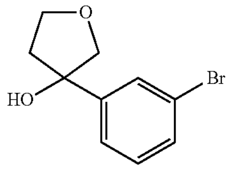

A solution of 1,3-dibromobenzene (4 g, 16.96 mmol, 2.04 mL) in THE (40 mL) was added n-BuLi (2.5 M, 6.78 mL) dropwise at −70° C. under $N_2$. The mixture was stirred at −70° C. for 30 min and then was added a solution of tetrahydrofuran-3-one (1.46 g, 16.96 mmol) in THE (3 mL) dropwise at −70° C. The mixture was stirred at −70° C. for 1 h. The reaction mixture was poured into saturated $NH_4Cl$ solution (50 mL). The solution was extracted with EA (30 mL*3), the combined organic layers were dried over $Na_2SO_4$ and concentrated in vacuo to give a residue. The residue was purified by column chromatography (PE:EA=5:1, Rf=0.3, $SiO_2$, Petroleum ether/Ethyl acetate=100/1 to 5/1). The solution was concentrated in vacuo to give Intermediate B (4 g, 73% yield) as a colorless oil. LCMS (ESI) m/z: [81 BrM−18]+=227.0. $^1H$ NMR (400 MHz, DMSO-$d_6$) δ=7.69-7.68 (m, 1H), 7.50-7.42 (m, 2H), 7.35-7.28 (m, 1H), 5.55-5.38 (m, 1H), 4.01-3.97 (m, 2H), 3.81-3.70 (m, 2H), 2.27-2.20 (m, 1H), 2.13-2.08 (m, 1H) ppm.

Step 2: Preparation of 3-(3-hydroxytetrahydrofuran-3-yl)benzoic acid

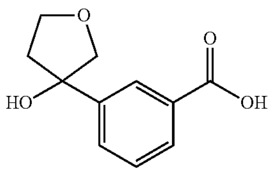

3-(hydroxymethyl)-3-methyl-2,3-dihydrobenzofuran-5-carboxylic acid

To a solution of Intermediate B (300 mg, 1.23 mmol) in DMSO (3 mL) was added dicyclohexyl(3-dicyclohexylphosphaniumylpropyl)phosphonium;ditetrafluoroborate (75.56 mg, 123.41 umol), $Pd(OAc)_2$ (27.71 mg, 123.41 umol), $K_2CO_3$ (255.84 mg, 1.85 mmol), $H_2O$ (44.46 mg, 2.47 mmol, 44.46 uL) under CO atmosphere (15 psi). The mixture was stirred at 100° C. for 16 hrs under CO atmosphere (15 psi). The reaction mixture was diluted with MeOH (3 mL). The mixture was filtered and washed with MeOH (3 mL*3) and concentrated under reduced pressure to give a residue. The residue was purified by reversed-phase HPLC (0.1% FA condition). The solution was extracted with EA (20 mL*3). The combined organic layers were washed with brine (30 mL), dried over $Na_2SO_4$, filtered and concentrated under reduced pressure to give 3-(hydroxymethyl)-3-methyl-2,3-dihydrobenzofuran-5-carboxylic acid (100 mg, 39% yield) as a white solid. LCMS (ESI) m/z: [M−17]+=191.1.

Example 96. Preparation of 3-(1-hydroxyethyl)-2,3-dihydro-1H-indene-5-carboxylic acid

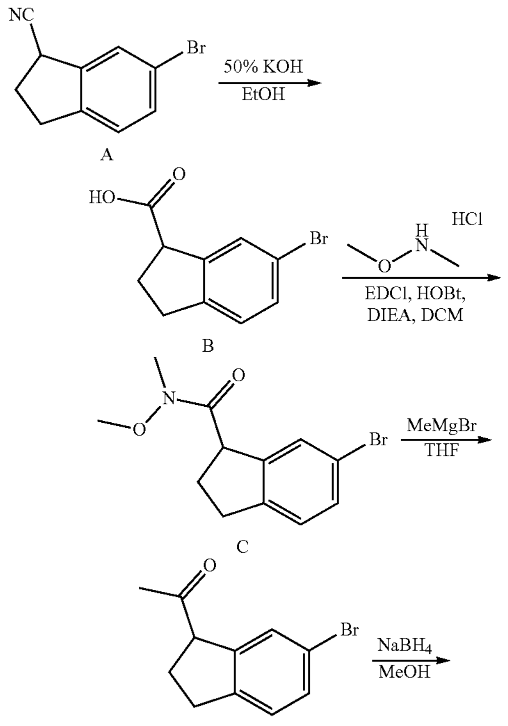

-continued

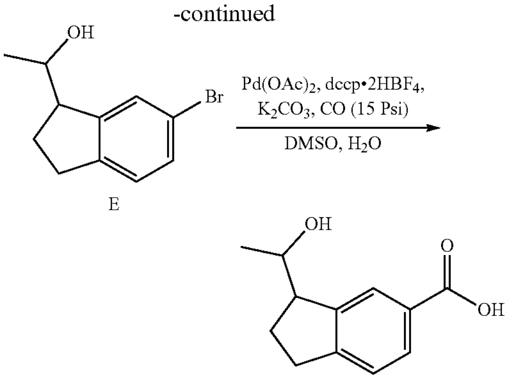

3-(1-hydroxyethyl)-2,3-dihydro-1H-indene-5-carboxylic acid

Step 1: Preparation of 6-bromo-2,3-dihydro-1H-indene-1-carboxylic acid

B

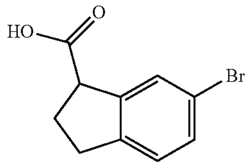

To a solution of 6-bromo-2,3-dihydro-1H-indene-1-carbonitrile (1 g, 4.50 mmol) in EtOH (60 mL) was added KOH (20 g, 178.24 mmol, 20 mL, 50% purity), the mixture was stirred at 100° C. for 16 hrs.

The mixture was concentrated to give a solution, the solution was extracted with MTBE (100 mL), the aqueous phase was adjusted to pH=3 with 1 N HCl, the solution was extracted with EA (100 mL*3), the combined organic layer was washed with brine (200 mL), dried over $Na_2SO_4$, filtered and concentrated to give Intermediate B (1.09 g, 100% yield) as a yellow oil. $^1$H NMR (400 MHz, DMSO-$d_6$) δ=13.12-11.89 (m, 1H), 7.48 (s, 1H), 7.38-7.35 (m, 1H), 7.21 (d, J=8.0 Hz, 1H), 4.03-3.99 (m, 1H), 2.91-2.79 (m, 2H), 2.28-2.22 (m, 2H) ppm.

Step 2: Preparation of 6-bromo-N-methoxy-N-methyl-2,3-dihydro-1H-indene-1-carboxamide

C

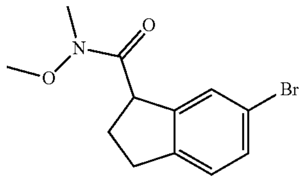

To a solution of Intermediate B (1.09 g, 4.52 mmol) and N-methoxymethanamine (485.13 mg, 4.97 mmol) in DCM (10 mL) was added EDCl (1.04 g, 5.43 mmol), HOBt (733.12 mg, 5.43 mmol) and DIEA (2.92 g, 22.61 mmol, 3.94 mL), the mixture was stirred at 30° C. for 16 hrs. The reaction mixture was concentrated to give a residue. The residue was purified by reversed-phase HPLC (0.1% FA condition). The solution was extracted with EA (20 mL*3), the combined organic layer was dried over $Na_2SO_4$, filtered and concentrated to give Intermediate C (900 mg, 70% yield) as a yellow oil. LCMS (ESI) m/z: [M+H]+=283.9. $^1$H NMR (400 MHz, CHLOROFORM-d) δ=7.38 (s, 1H), 7.31-7.29 (m, 1H), 7.11 (d, J=8.0 Hz, 1H), 4.46 (d, J=7.6 Hz, 1H), 3.78 (s, 3H), 3.28 (s, 3H), 3.16-3.02 (m, 1H), 2.90-2.88 (m, 1H), 2.46-2.25 (m, 2H) ppm.

Step 3: Preparation of 1-(6-bromoindan-1-yl)ethanone

D

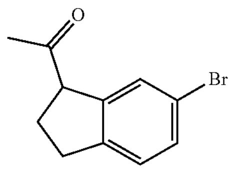

To a solution of Intermediate C (800 mg, 2.82 mmol) in THE (1 mL) was added MeMgBr (3 M, 1.13 mL) at 0° C., the mixture was stirred at 30° C. for 1 hr. The reaction mixture was poured into $NH_4Cl$ (10 mL), the solution was extracted with EA (10 mL*3), the combined organic layer was washed with brine (20 mL), dried over $Na_2SO_4$, filtered and concentrated to give Intermediate D (600 mg, 89% yield) as a yellow oil. LCMS (ESI) m/z: [M+H]+=239.1. $^1$H NMR (400 MHz, CHLOROFORM-d) δ=7.41 (s, 1H), 7.34-7.32 (m, 1H), 7.13-7.11 (m, 1H), 4.09-4.05 (m, 1H), 3.05-2.92 (m, 1H), 2.90-2.83 (m, 1H), 2.37-2.32 (m, 2H), 2.21 (s, 3H) ppm.

Step 4: Preparation of 1-(6-bromo-2,3-dihydro-1H-inden-1-yl)ethanol

E

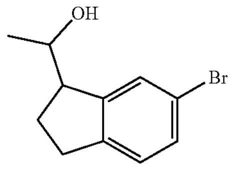

To a solution of Intermediate D (600 mg, 2.51 mmol) in MeOH (6 mL) was added $NaBH_4$ (189.87 mg, 5.02 mmol) at 0° C., the mixture was stirred at 0° C. for 1 hr. The reaction mixture was poured into $NH_4Cl$ (10 mL), the solution was extracted with EA (10 mL), the combined organic layer was washed with brine (20 mL), dried over $Na_2SO_4$, filtered and concentrated to give a residue. The residue was combined with another batch. The crude product was purified by reversed-phase HPLC (0.1% FA condition). The solution was extracted with EA (20 mL*3), the combined organic layer was dried over $Na_2SO_4$, filtered and concentrated to give Intermediate E (380 mg, 1.58 mmol, 62.80% yield, N/A purity) as a yellow oil. LCMS (ESI) m/z: [M−17]+=223.1. $^1$H NMR (400 MHz, CHLOROFORM-d) δ=7.57 (s, 1H), 7.41 (s, 1H), 7.30 (d, J=8.0 Hz, 1H), 7.11-7.08 (m, 1H), 4.25-3.89 (m, 1H), 3.25-3.14 (m, 1H), 2.95-2.76 (m, 2H), 2.25-1.85 (m, 2H), 1.95-1.84 (m, 1H), 1.26-1.22 (m, 3H) ppm.

Step 5: Preparation of 3-(1-hydroxyethyl)-2,3-dihydro-1H-indene-5-carboxylic acid

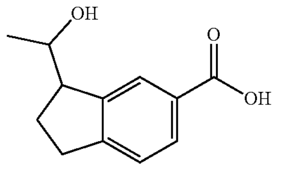

3-(1-hydroxyethyl)-2,3-dihydro-1H-indene-5-carboxylic acid

To a solution of Intermediate E (300 mg, 1.24 mmol) in DMSO (3 mL) was added dicyclohexyl(3-dicyclohexylphosphaniumylpropyl)phosphonium;ditetrafluoroborate (76.18 mg, 124.42 umol), $Pd(OAc)_2$ (27.93 mg, 124.42 umol), $K_2CO_3$ (343.90 mg, 2.49 mmol) and $H_2O$ (2.24 mg, 124.42 umol, 2.24 uL), the mixture was stirred at 100° C. for 2 hrs. The reaction mixture was filtered to give a solution. The solution was purified by reversed-phase HPLC (0.1% FA condition). The solution was extracted with EA (10 mL*3), the combined organic layer was dried over $Na_2SO_4$, filtered and concentrated to give 3-(1-hydroxyethyl)-2,3-dihydro-1H-indene-5-carboxylic acid (50 mg, 19% yield) as a yellow oil. LCMS (ESI) m/z: [M−17]+=189.2.

Example 97. Preparation of 4-cyano-4-methylchromane-6-carboxylic acid

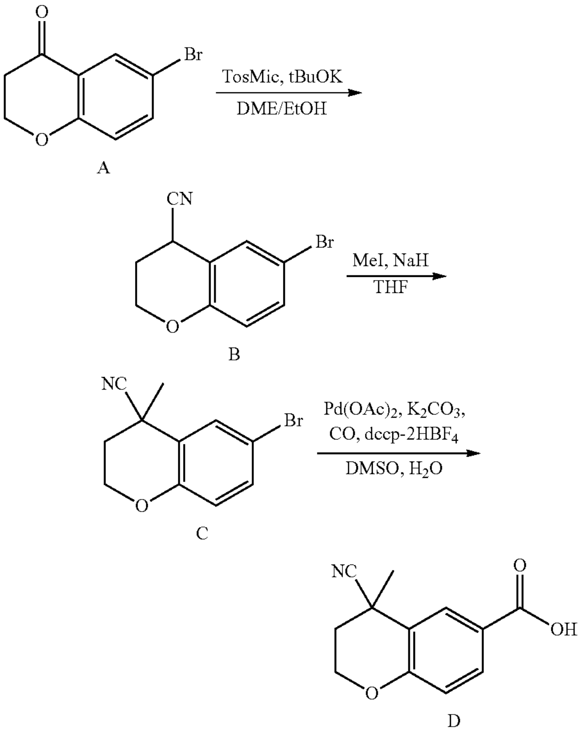

A

B

C

D

Step 1: Preparation of 6-bromochromane-4-carbonitrile

B

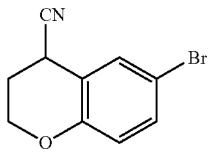

To a solution of 6-bromochroman-4-one (50 g, 220.21 mmol) and 1-(isocyanomethylsulfonyl)-4-methyl-benzene (64.49 g, 330.32 mmol) in DME (2500 mL) and EtOH (100 mL) was added tBuOK (54.36 g, 484.47 mmol) at 0° C. The reaction mixture was stirred at 25° C. for 16 hrs. The reaction mixture was poured into water (2 L) and adjusted to pH=6-7 with $NH_4Cl$ (56.9 g, 1.1 eq of tBuOK). The mixture was concentrated in vacuum to remove DME and EtOH. The aqueous phase was extracted with EA (1.5 L*2). The combined organic layer was dried over anhydrous $Na_2SO_4$ and concentrated in vacuum. The residue was purified by flash silica gel chromatography (PE-PE/EA=20/1), desired spot was collected from PE/EA=35/1. The fraction was concentrated in vacuum. The residue combined with another batch was triturated with MTBE (150 mL). The solid was filtered and concentrated in vacuum to give Intermediate B (40 g, 34% yield) as a white solid. $^1H$ NMR (400 MHz, CHLOROFORM-d) δ=7.43-7.42 (m, 1H), 7.33-7.31 (m, 1H), 6.76 (d, J=8.8 Hz, 1H), 4.36-4.30 (m, 1H), 4.26-4.21 (m, 1H), 4.01-3.98 (m, 1H), 2.35-2.31 (m, 2H) ppm.

Step 2: Preparation of 6-bromo-4-methyl-chromane-4-carbonitrile

C

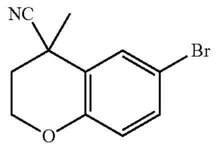

To a solution of Intermediate B (25 g, 105.01 mmol) in THF (250 mL) was added NaH (8.40 g, 210.01 mmol, 60% purity) at 0° C. The reaction mixture was stirred at 0° C. for 0.5 hr. Then MeI (74.52 g, 525.03 mmol, 32.69 mL) was added. The reaction mixture was stirred at 25° C. for 2 hrs. The reaction mixture was diluted with aq·$NH_4Cl$ (800 mL), extracted with EA (800 mL*3). The combined organic layer was dried over anhydrous $Na_2SO_4$, filtered and concentrated under reduced pressure to get the residue. The residue was purified by flash silica gel chromatography (PE:EA=1:0 to 5:1), the fraction was concentrated under reduced pressure to get Intermediate C (18 g, 66% yield) as a light yellow solid. $^1H$ NMR (400 MHz, DMSO-$d_6$) δ=7.69 (d, J=2.4 Hz, 1H), 7.41-7.38 (m, 1H), 6.83 (d, J=8.8 Hz, 1H), 4.33-4.25 (m, 1H), 4.24-4.15 (m, 1H), 2.41-2.35 (m, 1H), 2.17-2.11 (m, 1H), 1.75 (s, 3H) ppm.

Step 3: Preparation of 4-cyano-4-methyl-chromane-6-carboxylic acid

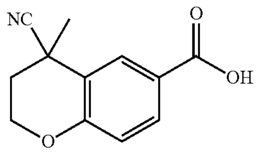

4-cyano-4-methyl-chromane-6-carboxylic acid

A mixture of Intermediate C (8.5 g, 33.72 mmol), dicyclohexyl(3-dicyclohexylphosphaniumylpropyl)phosphonium;ditetrafluoroborate (2.06 g, 3.37 mmol), $K_2CO_3$ (6.99 g, 50.57 mmol), $Pd(OAc)_2$ (756.95 mg, 3.37 mmol) and H2O (1.22 g, 67.43 mmol, 1.22 mL) in DMSO (85 mL) was degassed and purged with CO for 3 times, and then the mixture was stirred at 100° C. for 14 hrs under CO (15 psi) atmosphere. The reaction mixture combined with another batch was filtered to move off the black solid, and then diluted with water (60 mL), extracted with EA (60 mL*2). The organic layer was discarded, and the aqueous phase was adjusted pH=4 with aq. HCl, heavy precipitate was formed, the mixture was filtered and the solid was dried in vacuum to give the white solid. The white solid was washed with water (40 mL*2), filtered and dried in vacuum to give 4-cyano-4-methyl-chromane-6-carboxylic acid (12 g, 76% yield) as a white solid. LCMS (ESI) m/z: [M+H]+=218.1. $^1H$ NMR (400 MHz, DMSO-$d_6$) δ=8.02 (d, J=2.0 Hz, 1H), 7.81-7.78 (m, 1H), 6.95 (d, J=8.4 Hz, 1H), 4.40-4.24 (m, 2H), 2.46-2.40 (m, 1H), 2.24-2.17 (m, 1H), 1.76 (s, 3H) ppm.

Example 98. Preparation of 3-cyano-3-(hydroxymethyl)-2,3-dihydro-1H-indene-5-carboxylic acid

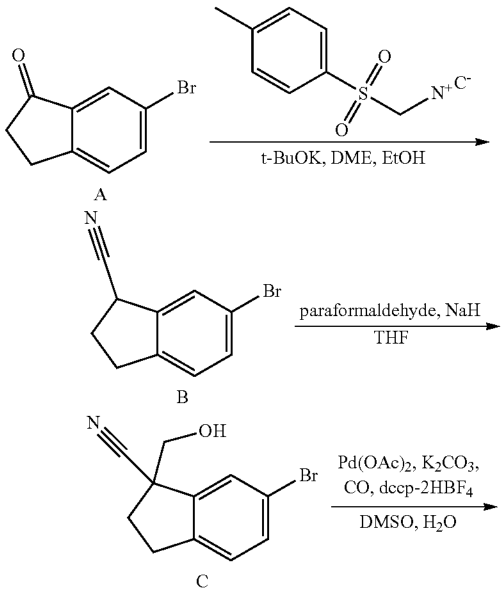

-continued

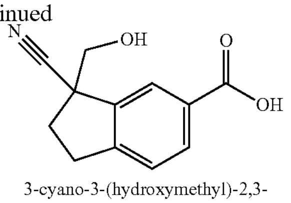

3-cyano-3-(hydroxymethyl)-2,3-dihydro-1H-indene-5-carboxylic acid

Step 1: Preparation of 6-bromo-2,3-dihydro-1H-indene-1-carbonitrile

B

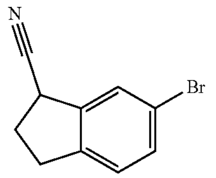

To a solution of 6-bromoindan-1-one (50 g, 236.91 mmol) and 1-(isocyanomethylsulfonyl)-4-methyl-benzene (69.38 g, 355.36 mmol) in DME (2500 mL) and EtOH (100 mL) was added t-BuOK (53.17 g, 473.81 mmol) at 0° C. The reaction mixture was stirred at 25° C. for 16 hrs. The reaction mixture becomes muddy. The reaction mixture (each batch) was poured into water (2000 mL) and extracted with EA (2000 mL*2). The combined organic layer (contained water) was concentrated in vacuum to removed DME&EtOH. Then diluted with EA (500 mL), washed with brine (500 mL), dried over anhydrous $Na_2SO_4$ and concentrated in vacuum. The residue was purified by silica gel chromatography column (1000 g of 100 #silica gel, PE-PE/EA=20/1, desired spot collected from PE/EA=30/1). The fraction was concentrated in vacuum and triturated with MTBE (100 mL) to give Intermediate B (58 g, 55% yield) as a white solid. $^1H$ NMR (400 MHz, CHLOROFORM-d) δ=7.58 (s, 1H), 7.42-7.40 (m, 1H), 7.16 (d, J=8.4 Hz, 1H), 4.12-4.08 (m, 1H), 3.10-3.00 (m, 1H), 2.97-2.86 (m, 1H), 2.65-2.55 (m, 1H), 2.43-2.37 (m, 1H) ppm.

Step 2: Preparation of 6-bromo-1-(hydroxymethyl)-2,3-dihydro-1H-indene-1-carbonitrile

C

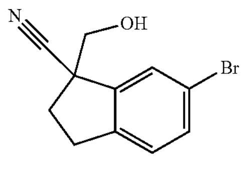

To a solution of Intermediate B (2 g, 9.01 mmol) in THE (10 mL) was added NaH (720.46 mg, 18.01 mmol, 60% purity) at 0~10° C. The reaction mixture was stirred at 25° C. for 0.5 hr. Then paraformaldehyde (313.62 mg, 10.81 mmol) was added at 25° C. The reaction mixture was stirred at 25° C. for 2 hrs. The reaction mixture was poured into saturation aq. $NH_4Cl$ (100 mL) and extracted with EA (100 mL*3). The combined organic layer was dried over anhydrous $Na_2SO_4$ and concentrated in vacuum. The residue was purified by flash silica gel chromatography (PE-PE/EA=3/1). The fraction was concentrated in vacuum to give Intermediate C (2 g, 85% yield) as a colorless oil. $^1H$ NMR (400 MHz, DMSO-$d_6$) δ=7.62 (d, J=1.6 Hz, 1H), 7.51-7.48 (m 1H), 7.28 (d, J=8.0 Hz, 1H), 5.76-5.73 (m, 1H), 3.69-3.59 (m, 2H), 2.94-2.91 (m, 2H), 2.42-2.37 (m, 2H) ppm.

Step 3: Preparation of 3-cyano-3-(hydroxymethyl)-2,3-dihydro-1H-indene-5-carboxylic acid

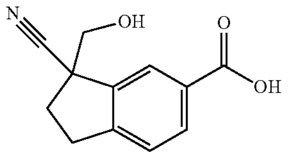

3-cyano-3-(hydroxymethyl)-2,3-dihydro-1*H*-indene-5carboxylic acid

A mixture of Intermediate C (2 g, 7.93 mmol), dicyclohexyl(3-dicyclohexylphosphaniumylpropyl)phosphonium; ditetrafluoroborate (485.71 mg, 793.31 umol), $Pd(OAc)_2$ (178.11 mg, 793.31 umol), $K_2CO_3$ (3.29 g, 23.80 mmol) and $H_2O$ (285.91 mg, 15.87 mmol, 285.91 uL) in DMSO (30 mL) was degassed and purged with CO for 3 times, and then the mixture was stirred at 100° C. for 14 hrs under CO (15 Psi) atmosphere. The reaction mixture was filtered and washed with EA (200 mL) & H2O (200 mL). The organic layer was separated and discarded. The aqueous phase was adjusted to pH=4 with HCl (2M) and then extracted with EA (150 mL*3). The combined organic layer was dried over anhydrous $Na_2SO_4$, filtered and concentrated under reduced pressure to get the residue. The residue was purified by reverse phase flash (FA). The fraction was concentrated to remover MeCN and lyophilized to give 3-cyano-3-(hydroxymethyl)-2,3-dihydro-1H-indene-5-carboxylic acid (1 g, 54% yield) as a white solid. LCMS (ESI) m/z: $[M+H]^+$=218.1. $^1H$ NMR (400 MHz, DMSO-$d_6$) δ=14.06-12.13 (m, 1H), 7.98 (d, J=1.2 Hz, 1H), 7.91-7.88 (m, 1H), 7.43 (d, J=7.6 Hz, 1H), 5.75-5.72 (m, 1H), 3.64 (d, J=4.4 Hz, 2H), 3.04-3.01 (m, 2H), 2.45-2.41 (m, 2H) ppm.

Example 99. Preparation of 3-((trans)-4-hydroxytetrahydrofuran-3-yl)benzoic acid

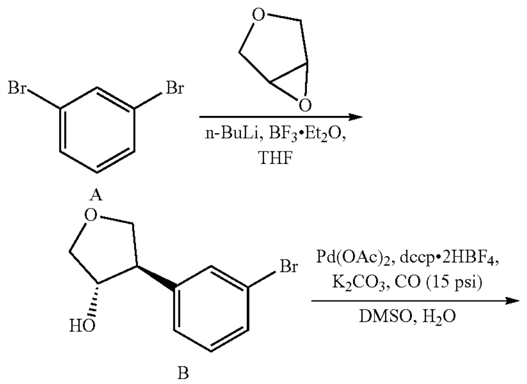

-continued

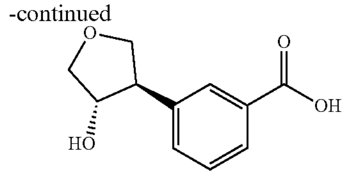

3-((trans)-4-hydroxytetrahydrofuran-3-yl)benzoic acid

Step 1: Preparation of trans-4-(3-bromophenyl)tetrahydrofuran-3-ol

B

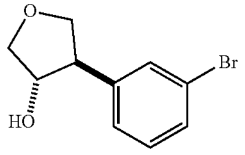

To a solution of 1,3-dibromobenzene (5 g, 21.20 mmol, 2.55 mL) in THE (50 mL) was added n-BuLi (2.5 M, 8.48 mL) at −70° C., the mixture was stirred at −70° C. for 30 min, then to the solution was added 3,6-dioxabicyclo[3.1.0]hexane (912.33 mg, 10.60 mmol) and $BF_3 \cdot Et_2O$ (3.01 g, 21.20 mmol, 2.62 mL) at −70° C., the mixture was stirred at −70° C. for 2 hrs. The reaction mixture was poured into $NH_4Cl$ (50 mL), the solution was extracted with EA (50 mL*3), the combined organic layer was washed with brine (100 mL), dried over $Na_2SO_4$, filtered and concentrated to give a residue. The crude product was purified by reversed-phase HPLC (0.1% FA condition). The solution was extracted with EA (30 mL*3), the combined organic layer was dried over $Na_2SO_4$, filtered and concentrated to give Intermediate B (1 g, 39% yield) as a yellow oil. $^1H$ NMR (400 MHz, CHLOROFORM-d) δ=7.36-7.28 (m, 2H), 7.15-7.09 (m, 2H), 4.34-4.20 (m, 2H), 4.07-4.00 (m, 1H), 3.85-3.83 (m, 1H), 3.74-3.72 (m, 1H), 3.20-3.18 (m, 1H) ppm.

Step 2: Preparation of 3-((trans)-4-hydroxytetrahydrofuran-3-yl)benzoic acid

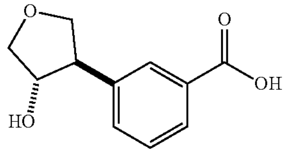

3-((trans)-4-hydroxytetrahydrofuran-3-yl)benzoic acid

To a solution of Intermediate B (200.00 mg, 822.72 umol) in DMSO (1 mL) was added dicyclohexyl(3-dicyclohexylphosphaniumylpropyl)phosphonium;ditetrafluoroborate (25.19 mg, 41.14 umol), $Pd(OAc)_2$ (18.47 mg, 82.27 umol), $K_2CO_3$ (170.56 mg, 1.23 mmol), and $H_2O$ (29.64 mg, 1.65 mmol, 29.64 uL), the mixture was stirred under CO (15 psi) at 100° C. for 16 hrs. The reaction mixture was poured into water (5 mL), the solution was adjusted to pH=4 with 1 N HCl, the solution was extracted with EA (5 mL*3), the combined organic layer was washed with brine (10 mL), dried over $Na_2SO_4$, filtered and concentrated to give a residue. The crude product was purified by reversed-phase HPLC (0.1% FA condition). The solution was extracted with EA (20 mL), the combined organic later was dried over $Na_2SO_4$, filtered and concentrated to give of 3-((trans)-4-hydroxytetrahydrofuran-3-yl)benzoic acid (40 mg, 22% yield) as a yellow oil. $^1H$ NMR (400 MHz, CHLOROFORM-d) δ=8.07-7.96 (m, 2H), 7.58-7.52 (m, 1H), 7.50-7.43 (m, 1H), 4.46 (d, J=3.6 Hz, 1H), 4.40 (d, J=7.2 Hz, 1H), 4.19-4.12 (m, 1H), 3.98 (d, J=5.6, 1H), 3.86 (d, J=3.2, 1H), 3.43-3.42 (m, 1H) ppm.

Example 100. Preparation of 3-(1-fluoro-3-hydroxycyclobutyl)benzoic acid

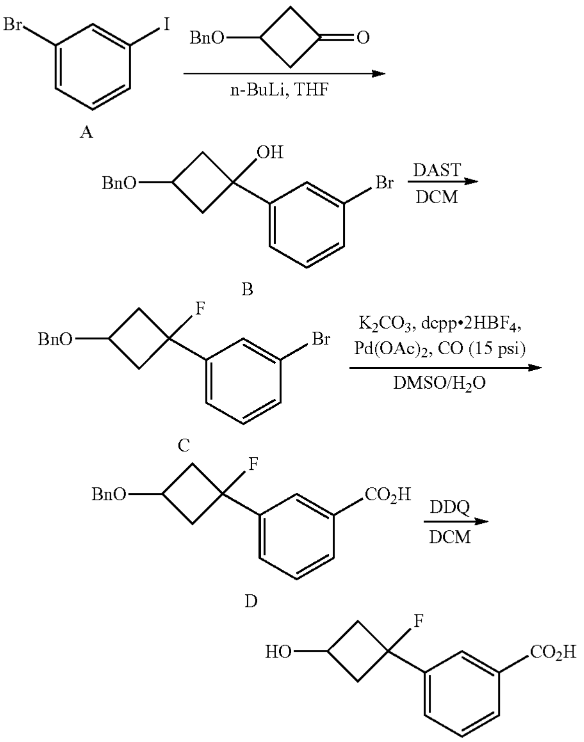

3-(1-fluoro-3-hydroxycyclobutyl)benzoic acid

Step 1: Preparation of 3-(benzyloxy)-1-(3-bromophenyl)cyclobutanol

B

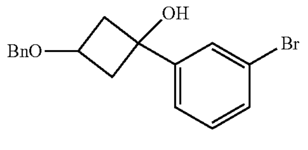

To a solution of 1-bromo-3-iodo-benzene (10 g, 35.35 mmol, 4.50 mL) in THE (200 mL) was added n-BuLi (2.5 M, 15.55 mL) at −70° C. at $N_2$ atmosphere, after stirred for 30 min, 3-benzyloxycyclobutanone (7.47 g, 42.42 mmol)

was added and stirred for 1 h at 25° C. The mixture was quenched with saturated aqueous $NH_4Cl$ (1 mL), extracted with EA (5 mL*3) and concentrated to give a residue. The residue was purified by column chromatography ($SiO_2$, Petroleum ether/Ethyl acetate=100/1 to 1/100) and concentrated to give Intermediate B (8 g, 61% yield) as a brown oil. $^1H$ NMR (400 MHz, CHLOROFORM-d) δ=7.53-7.52 (m, 1H), 7.36-7.27 (m, 4H), 7.27 (s, 3H), 7.19-7.12 (m, 1H), 4.39 (s, 2H), 3.84-3.77 (m, 1H), 2.89-2.70 (m, 2H), 2.42-2.36 (m, 2H) ppm.

Step 2: Preparation of 1-(3-(benzyloxy)-1-fluorocyclobutyl)-3-bromobenzene

C

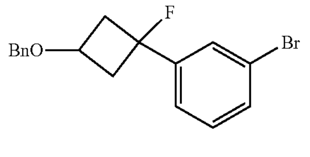

To a solution of Intermediate B (4 g, 12.00 mmol) in DCM (80 mL) was added DAST (9.67 g, 60.02 mmol, 7.93 mL) at −70° C. at $N_2$ atmosphere. Then the mixture was stirred for 1 h at −70° C. The mixture was quenched with saturated aqueous $NH_4Cl$ (30 mL) and extracted with EA (100 mL*3), concentrated to give a residue. The residue was purified by column chromatography ($SiO_2$, Petroleum ether/Ethyl acetate=100/1 to 30/1) and concentrated to give Intermediate C (3.5 g, 70% yield) as a brown oil. $^1H$ NMR (400 MHz, CHLOROFORM-d) δ=7.51-7.43 (m, 1H), 7.35-7.34 (m, 1H), 7.32-7.27 (m, 2H), 7.26-7.13 (m, 4H), 4.41 (s, 2H), 4.40-4.34 (m, 1H), 2.87-2.75 (m, 2H), 2.52-2.30 (m, 2H) ppm.

Step 3: Preparation of 3-(3-(benzyloxy)-1-fluorocyclobutyl)benzoic acid

D

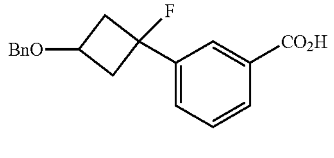

To a solution of Intermediate C (2.3 g, 6.86 mmol) in DMSO (20 mL) and $H_2O$ (10 mL) was added dicyclohexyl (3-dicyclohexylphosphaniumylpropyl)phosphonium;ditetrafluoroborate (420.09 mg, 686.14 umol), $K_2CO_3$ (1.42 g, 10.29 mmol), $Pd(OAc)_2$ (77.02 mg, 343.07 umol) at 25° C., then the mixture was degassed and purged with CO for 3 times, and then the mixture was stirred at 100° C. for 16 hrs under CO atmosphere (15 psi). The mixture was filtered. The filtrate was purified by prep-HPLC (column: Shim-pack C18 150*25*10 um; mobile phase: [water (0.2% FA)-ACN]; B %: 44%-74%, 10 min) and concentrated to give Intermediate D (1.8 g, 79% yield) as a white solid. LCMS (ESI) m/z: [M+18]*=318.1. $^1H$ NMR (400 MHz, DMSO-$d_6$) δ=13.49-12.53 (m, 1H), 8.03-7.88 (m, 2H), 7.70 (d, J=7.6 Hz, 1H), 7.63-7.51 (m, 1H), 7.36 (d, J=4.4 Hz, 4H), 7.33-7.27 (m, 1H), 4.47 (s, 2H), 4.46-4.40 (m, 1H), 3.04-2.82 (m, 2H), 2.71-2.54 (m, 2H) ppm.

Step 4: Preparation of 3-(1-fluoro-3-hydroxycyclobutyl)benzoic acid

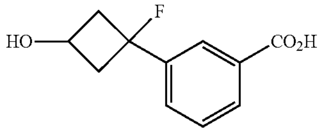

3-(1-fluoro-3-hydroxycyclobutyl)benzoic acid

To a solution of Intermediate D (450 mg, 1.50 mmol) in DCM (5 mL) was added DDQ (680.27 mg, 3.00 mmol). The suspension was stirred for 16 h at 25° C. The mixture was washed with saturated aqueous $Na_2SO_3$ (5 mL), extracted with EA (10 mL*3) and concentrated to give a residue. The residue was purified by reverse-phase (FA) to give 3-(1-fluoro-3-hydroxycyclobutyl)benzoic acid (100 mg, 22% yield) as a brown oil. $^1H$ NMR (400 MHz, CHLOROFORM-d) δ=8.24-8.14 (m, 1H), 8.08-8.07 (m, 1H), 7.77-7.66 (m, 1H), 7.60-7.49 (m, 1H), 4.87-4.83 (m, 1H), 4.38-4.22 (m, 1H), 3.15-2.96 (m, 2H), 2.86-2.67 (m, 1H), 2.66-2.47 (m, 1H) ppm.

Example 101. Preparation of 2-hydroxy-2',3'-dihydrospiro[cyclopentane-1,1'-indene]-6'-carboxylic acid

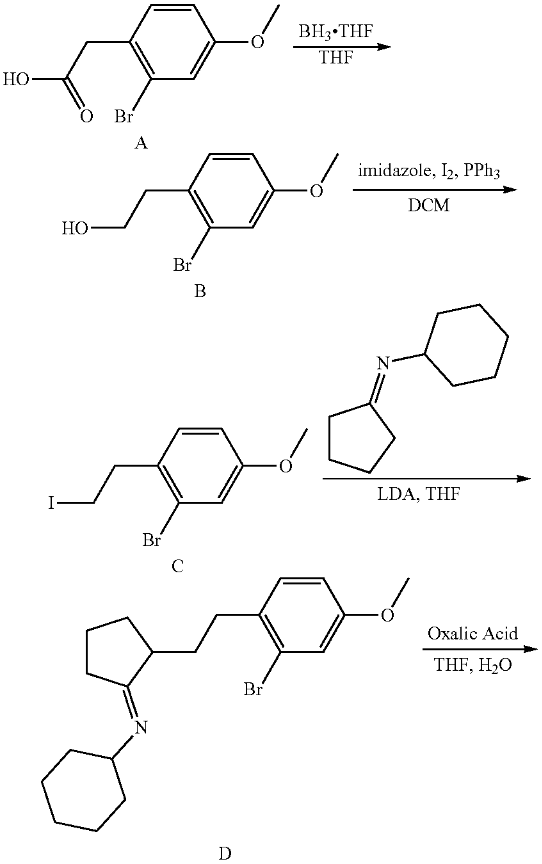

-continued

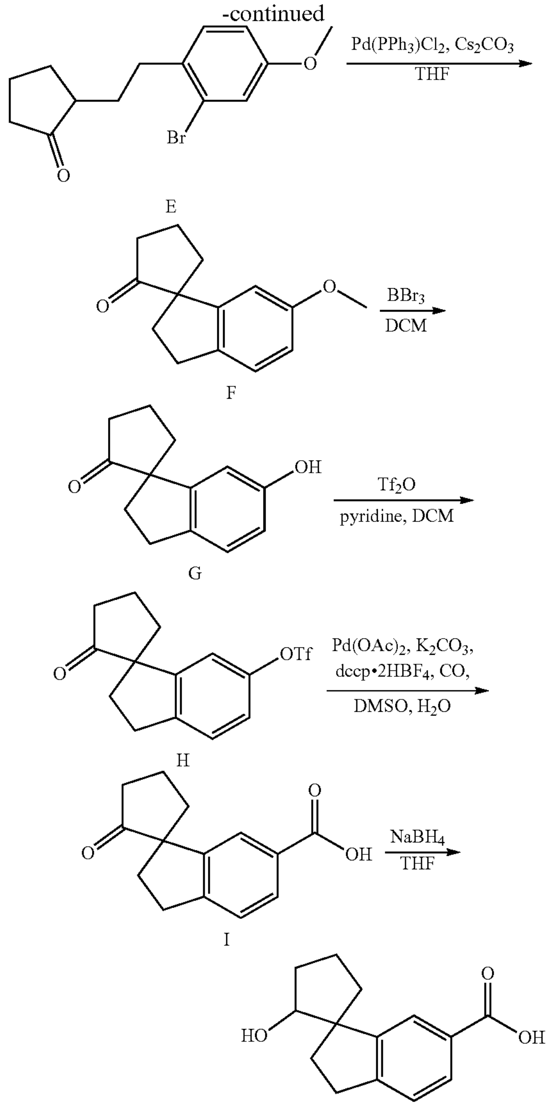

2-hydroxy-2′,3′-dihydrospiro[cyclopentane-1,1′-indene]-6′-carboxylic acid

Step 1: Preparation of 2-(2-bromo-4-methoxyphenyl)ethanol

B

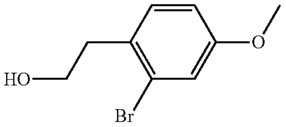

To a solution of 2-(2-bromo-4-methoxy-phenyl)acetic acid (24 g, 97.93 mmol) in THF (200 mL) was added $BH_3$·THF (1 M, 293.79 mL) at 0° C. under $N_2$. The reaction mixture was stirred at 25° C. for 12 hrs. The reaction mixture was quenched by the addition MeOH (300 mL), The resulting mixture was concentrated under reduced pressure. The residue was redissolved in EA (300 mL). The resulting solution was washed with water (100 mL*3). The organic phase was dried over anhydrous $Na_2SO_4$, filtered and concentrated under reduced pressure to give Intermediate B (27 g, crude) as a colorless oil. LCMS (ESI) m/z: $[M-17]^+$=215.0. $^1H$ NMR (400 MHz, CHLOROFORM-d) δ=7.20-7.15 (m, 1H), 7.14-7.09 (m, 1H), 6.85-6.79 (m, 1H), 3.85 (m, 1H), 3.84-3.81 (m, 1H), 3.79 (s, 3H), 2.97 (m, 2H) ppm.

Step 2: Preparation of Intermediate 3 2-bromo-1-(2-iodoethyl)-4-methoxybenzene

C

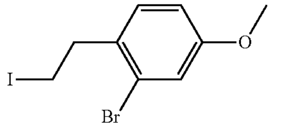

To a solution of $PPh_3$ (32.69 g, 124.63 mmol) and imidazole (8.48 g, 124.63 mmol) in DCM (200 mL) was added 12 (31.63 g, 124.63 mmol, 25.10 mL) in portions at 0° C. under $N_2$ (Caution exothermic). Then a solution of Intermediate B (24 g, 103.86 mmol) in DCM (30 mL) was added drop wise at 0° C. under $N_2$. The reaction mixture was stirred at 0° C. for 3 hrs. The reaction mixture was concentrated under reduced pressure to give the residue. The residue was purified by column chromatography ($SiO_2$, Petroleum ether/Ethyl acetate=100/1 to 10/1) to give Intermediate C (33.3 g, 94% yield) as a colorless oil. $^1H$ NMR (400 MHz, CHLOROFORM-d) δ=7.15 (d, J=8.4 Hz, 1H), 7.11 (d, J=2.4 Hz, 1H), 7.12-7.09 (m, 1H), 6.83 (m, 1H), 3.80 (s, 3H), 3.39-3.31 (m, 2H), 3.28-3.19 (m, 2H) ppm.

Step 3: Preparation of N-(2-(2-bromo-4-methoxyphenethyl)cyclopentylidene)cyclohexanamine

D

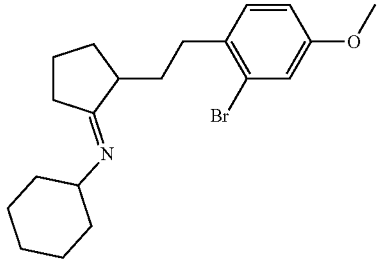

To a solution of Intermediate C (14.54 g, 87.98 mmol) in THF (200 mL) was added LDA (2 M, 43.99 mL) drop wise at 0° C. under $N_2$. The reaction mixture was stirred at 0° C. for 30 min. The mixture was cooled to −5° C. and a solution of N-cyclohexylcyclopentanimine (25 g, 73.32 mmol) in THF (25 mL) was added drop wise at −5° C. The reaction mixture was stirred at −5° C. for 1 hr. The reaction mixture was quenched with sat $NH_4Cl$ (200 mL). The resulting mixture was extracted with EA (200 mL*3). The organic phase was combined with another batch. The combined organic phase was dried over $Na_2SO_4$, filtered and concentrated under reduced pressure to give Intermediate D (41 g, crude) as a yellow oil.

LCMS (ESI) m/z: $[M+H]^+$=378.1.

Step 4: Preparation of 2-(2-bromo-4-methoxyphenethyl)cyclopentanone

E

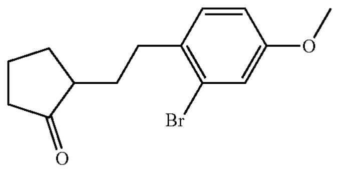

To a solution of Intermediate D (41 g, 108.37 mmol) in THE (150 mL) and $H_2O$ (30 mL) was added oxalic acid (14.64 g, 162.55 mmol, 792.93 uL) at 25° C. The reaction mixture was stirred at 25° C. for 2 hrs. The resulting mixture was quenched with water (200 mL) and extracted with DCM (250 mL*3). The combined organic phase was washed with sat $NaHCO_3$ (100 mL*3). The organic phase was dried over $Na_2SO_4$, filtered and concentrated under reduced pressure. The crude product was purified by column chromatography ($SiO_2$, Petroleum ether/Ethyl acetate=100/1 to 5/1, Rf=0.29) to give the crude. The crude was purified by reversed-phase HPLC (0.1% FA condition). The separated solution was concentrated under reduced pressure and adjusted pH~8 by sat $NaHCO_3$. The resulting solution was extracted with EA (200 mL*3). The combined organic phase was dried over $Na_2SO_4$, filtered and concentrated under reduced pressure to give Intermediate E (7 g, 23.55 mmol, 50.00% yield) as a yellow oil. LCMS (ESI) m/z: $[M+H]^+$=297.1. $^1$H NMR (400 MHz, CHLOROFORM-d) δ=7.06 (d, J=8.4 Hz, 1H), 6.73 (d, J=2.8 Hz, 1H), 6.74-6.69 (m, 1H), 3.70 (s, 3H), 2.67 (m, 2H), 2.30-2.18 (m, 2H), 2.12-1.90 (m, 4H), 1.80-1.62 (m, 1H), 1.56-1.47 (m, 2H) ppm.

Step 5: Preparation of 6'-methoxy-2',3'-dihydrospiro [cyclopentane-1,1'-inden]-2-one

F

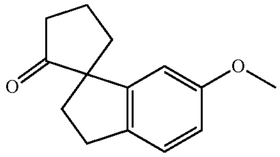

To a solution of Intermediate E (2 g, 6.73 mmol) in THE (200 mL) was added $Cs_2CO_3$ (6.58 g, 20.19 mmol), $Pd(PPh_3)_2Cl_2$ (472.36 mg, 672.98 umol) at 25° C. under $N_2$. The reaction mixture was stirred at 100° C. for 12 hrs. The reaction mixture was combined with another batch. Water (200 mL) was added. The resulting mixture was extracted with EA (200 mL*3). The combined organic phase was dried over $Na_2SO_4$, filtered and concentrated under reduced pressure to give the residue. The residue was purified by purified by column chromatography (petroleum ether/ethyl acetate=10/1 to 2/1) to give Intermediate F (1 g, 69% yield) as a yellow oil. LCMS (ESI) m/z: $[M+H]^+$=217.1. $^1$H NMR (400 MHz, CHLOROFORM-d) δ=7.16 (d, J=8.4 Hz, 1H), 6.78 (d, J=2.4 Hz, 1H), 6.80-6.75 (m, 1H), 6.58 (d, J=2.4 Hz, 1H), 3.80-3.77 (s, 3H), 3.05-2.97 (m, 1H), 2.94-2.86 (m, 1H), 2.53-2.33 (m, 3H), 2.30-2.14 (m, 3H), 2.07-1.97 (m, 2H) ppm.

Step 6: Preparation of 6'-hydroxy-2',3'-dihydrospiro [cyclopentane-1,1'-inden]-2-one

G

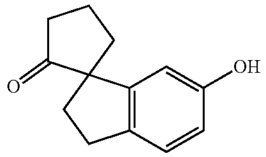

To a solution of Intermediate F (200 mg, 924.75 umol) in DCM (10 mL) was added $BBr_3$ (463.34 mg, 1.85 mmol, 178.21 uL) drop wise at −78° C. under $N_2$. Then the reaction mixture was stirred at 0° C. for 3 hrs. The reaction mixture was quenched with sat $NH_4Cl$ (20 mL). The resulting mixture was extracted with EA (10 mL*3). The combined organic phase was dried over $Na_2SO_4$, filtered and concentrated under reduced pressure to give Intermediate G (200 mg, crude) was obtained as a yellow oil. LCMS (ESI) m/z: $[M+H]^+$=203.1. $^1$H NMR (400 MHz, CHLOROFORM-d) δ=6.98 (d, J=8.0 Hz, 1H), 6.56 (m, 1H), 6.39 (d, J=2.4 Hz, 1H), 2.92-2.82 (m, 1H), 2.82-2.72 (m, 1H), 2.43-2.19 (m, 3H), 2.14-2.00 (m, 3H), 1.95-1.83 (m, 2H) ppm.

Step 7: Preparation of 2-oxo-2',3'-dihydrospiro[cyclopentane-1,1'-inden]-6'-yl trifluoromethanesulfonate

H

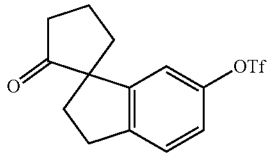

To a solution of Intermediate G (200 mg, 988.88 umol) in DCM (4 mL) was added pyridine (117.33 mg, 1.48 mmol, 119.72 uL) at 0° C. under $N_2$. Then trifluoromethylsulfonyl trifluoromethanesulfonate (418.50 mg, 1.48 mmol, 244.74 uL) was added drop wise at 0° C. The reaction mixture was stirred at 0° C. for 1 hr. The reaction mixture was quenched with sat $NaHCO_3$. The resulting mixture was extracted with EA (10 mL*3). The combined organic phase was dried over $Na_2SO_4$, filtered and concentrated under reduced pressure to give Intermediate H (330 mg, crude) as a yellow oil. LCMS (ESI) m/z: $[M+H]^+$=335.1. $^1$H NMR (400 MHz, CHLOROFORM-d) δ=7.22 (d, J=8.4 Hz, 1H), 7.02 (m, 1H), 6.83 (d, J=2.4 Hz, 1H), 3.05-2.96 (m, 1H), 2.93-2.83 (m, 1H), 2.47-2.29 (m, 3H), 2.17-2.07 (m, 3H), 2.02-1.95 (m, 2H) ppm.

Step 8: Preparation of 2-oxo-2',3'-dihydrospiro[cyclopentane-1,1'-indene]-6'-carboxylic acid

I

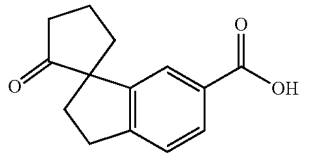

To a solution of Intermediate H (230 mg, 687.98 umol) in DMSO (3 mL) was added $Pd(OAc)_2$ (15.45 mg, 68.80 umol), $K_2CO_3$ (285.25 mg, 2.06 mmol), dicyclohexyl(3-dicyclohexylphosphaniumylpropyl)phosphonium;ditetrafluoroborate (8.42 mg, 13.76 umol), $H_2O$ (24.79 mg, 1.38 mmol, 24.79 uL) at 25° C. Then the reaction mixture was stirred at 100° C. for 2 hrs under CO atmosphere (15 psi). The reaction mixture was combined with another batch. The resulting mixture was diluted with water (3 mL) and extracted with MTBE (5 mL*3). The water phase was adjusted to pH=6 with 1 N HCl solution and extracted with EA (10 mL*3). The combined organic layers were dried over $Na_2SO_4$, filtered and concentrated under reduced pressure to give Intermediate I (160 mg, crude) as a yellow solid. LCMS (ESI) m/z: $[M+H]^+$=231.1. $^1H$ NMR (400 MHz, CHLOROFORM-d) δ=7.89 (m, 1H), 7.69 (m, 1H), 7.27 (m, 1H), 3.11-3.02 (m, 1H), 2.93 (m, 1H), 2.44-2.28 (m, 3H), 2.28-2.21 (m, 1H), 2.18-2.07 (m, 2H), 2.01-1.91 (m, 3H) ppm.

Step 9: Preparation of 2-hydroxy-2',3'-dihydrospiro[cyclopentane-1,1'-indene]-6'-carboxylic acid

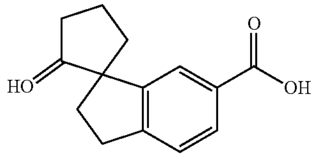

2-hydroxy-2',3'-dihydrospiro[cyclopentane-1,1'-indene]-6'-carboxylic acid

To a solution of Intermediate I (60 mg, 260.58 umol) in THE (2 mL) was added $NaBH_4$ (49.29 mg, 1.30 mmol) at 25° C., the reaction mixture was stirred at 25° C. for 1 hr. The reaction mixture was quenched with sat $NH_4Cl$ (10 ml) and adjust pH~5 by 1 N HCl. The resulting mixture was extracted with EA (10 mL*3). The combined organic phase was dried over $Na_2SO_4$, filtered and concentrated under reduced pressure to give 2-hydroxy-2',3'-dihydrospiro[cyclopentane-1,1'-indene]-6'-carboxylic acid (60 mg, crude) as a yellow oil. LCMS (ESI) m/z: $[M-17]^+$=214.9. $^1H$ NMR (400 MHz, CHLOROFORM-d) δ=7.36-7.28 (m, 2H), 7.15-7.09 (m, 2H), 4.34-4.20 (m, 2H), 4.07-4.00 (m, 1H), 3.85-3.83 (m, 1H), 3.74-3.72 (m, 1H), 3.20-3.18 (m, 1H) ppm.

Example 102. Preparation of 2,3,4,5-tetrahydrobenzo[b]thiepine-8-carboxylic acid 1,1-dioxide

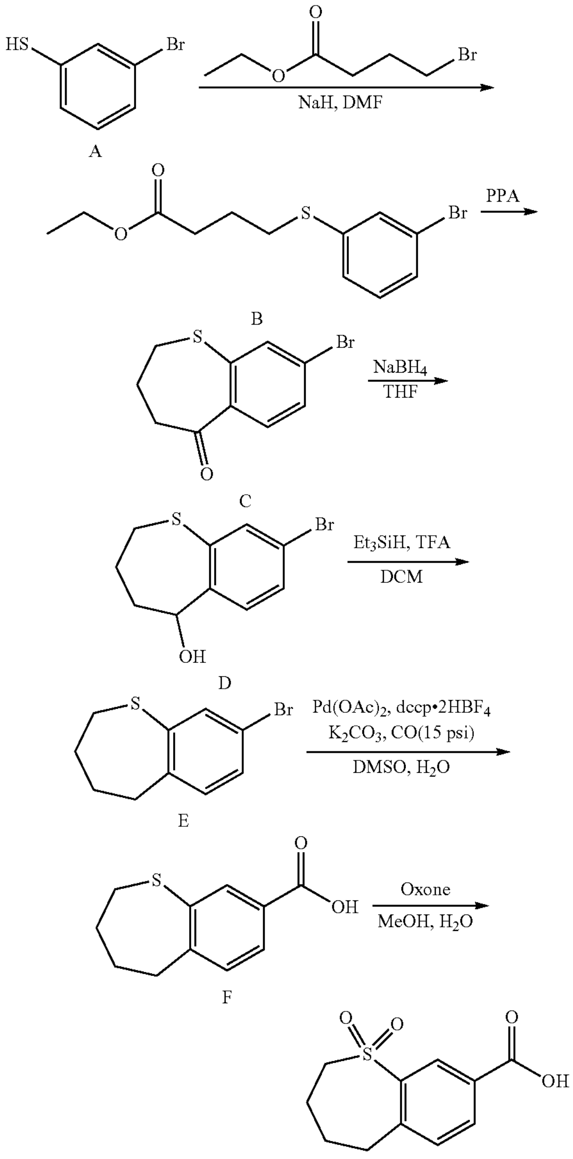

2,3,4,5-tetrahydrobenzo[b]thiepine-8-caboxylic acid 1,1-dioxide

Step 1: Preparation of ethyl 4-(3-bromophenyl)sulfanylbutanoate

B

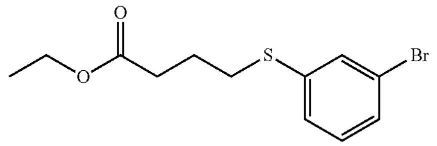

To a mixture of 3-bromobenzenethiol (10 g, 52.89 mmol, 5.46 mL) in DMF (40 mL) was added NaH (3.17 g, 79.33 mmol, 60% purity) at 0° C. The mixture was stirred at 0° C. for 30 min, followed by addition of ethyl 4-bromobutanoate (12.38 g, 63.47 mmol, 9.10 mL). The mixture was allowed to warm to 30° C. and stirred for 16 hrs. The reaction was quenched by addition of saturated $NH_4Cl$ solution (10 mL) then poured into water (400 mL). The mixture was extracted with EA (50 mL*3). The combined organic layer was washed with water (30 mL*1) and brine (30 mL*1), then dried over $Na_2SO_4$, filtered and concentrated under vacuum to give Intermediate B (8.3 g, 52% yield) as a yellow oil which was used to next step directly without further purification.

Step 2: Preparation of 8-bromo-3,4-dihydro-2H-1-benzothiepin-5-one

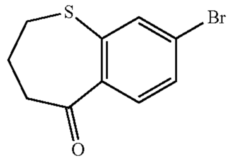

C

To pre-heated PPA (10 mL) at 150° C. was added Intermediate B (6 g, 19.79 mmol). The mixture was stirred at 150° C. for 0.5 hrs. The reaction mixture was poured onto ice (50 mL) and then extracted with DCM (10 mL*3). The combined organic layer was washed with brine (10 mL), dried over anhydrous $Na_2SO_4$, filtered and concentrated under vacuum. The residue was purified by column chromatography (PE:EA=20:1-3:1) and the eluent was concentrated under vacuum to give Intermediate C (2.6 g, 51% yield) as a yellow oil. $^1H$ NMR (400 MHz, CHLOROFORM-d) δ=7.72 (d, J=8.4 Hz, 1H), 7.67 (d, J=1.6 Hz, 1H), 7.40-7.38 (m, 1H), 3.07-2.98 (m, 2H), 3.02-2.98 (m, 2H), 2.32-2.26 (m, 2H) ppm.

Step 3: Preparation of 8-bromo-2,3,4,5-tetrahydro-1-benzothiepin-5-ol

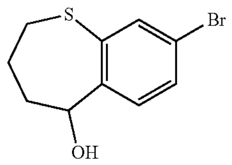

D

To a mixture of Intermediate C (2.5 g, 9.72 mmol) in THE (50 mL) was added $NaBH_4$ (1.84 g, 48.61 mmol) in portions at 0° C. The mixture was allowed to warm to 30° C. and stirred at 30° C. for 2 hrs. The combined reaction mixture was quenched by addition saturated $NH_4Cl$ solution (10 mL) and then poured into water (300 mL). The mixture was extracted with EA (50 mL*3). The combined organic layer was washed with brine (30 mL), dried over anhydrous $Na_2SO_4$, filtered and concentrated under vacuum to give Intermediate D (2.2 g, 87% yield) as a light-yellow solid which was used to next step directly without further purification.

$^1H$ NMR (400 MHz, CHLOROFORM-d) δ=7.57 (d, J=1.6 Hz, 1H), 7.37-7.33 (m, 1H), 7.33-7.28 (m, 1H), 2.73-2.70 (m, 1H), 2.58-2.47 (m, 2H), 2.12-1.90 (m, 4H), 1.70-1.66 (m, 1H) ppm.

Step 4: Preparation of Intermediate 6 8-bromo-2,3,4,5-tetrahydro-1-benzothiepine

E

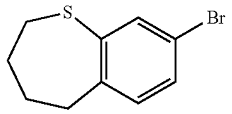

To a mixture of Intermediate D (2.1 g, 8.10 mmol) in DCM (30 mL) was added triethylsilane (2.83 g, 24.31 mmol, 3.88 mL) and TFA (4.62 g, 40.52 mmol, 3.00 mL) at 0° C. The mixture was allowed to warm to 30° C. and stirred at 30° C. for 2 hrs. The reaction was quenched by addition of saturated $NH_4Cl$ solution (3 mL) and then poured into water (30 mL). The mixture was extracted with DCM (15 mL*3). The combined organic phase was washed with brine (10 mL), dried over anhydrous $Na_2SO_4$, filtered and concentrated under vacuum to give Intermediate E (1.2 g, 61% yield) as light-yellow oil which was used to next step directly without further purification. $^1H$ NMR (400 MHz, CHLOROFORM-d) δ=7.60 (d, J=2.0 Hz, 1H), 7.23-7.18 (m, 1H), 6.98 (d, J=8.0 Hz, 1H), 2.93-2.85 (m, 2H), 2.69-2.61 (m, 2H), 2.05-1.94 (m, 2H), 1.61 (d, J=4.4 Hz, 2H) ppm.

Step 5: Preparation of Intermediate 7 2,3,4,5-tetrahydro-1-benzothiepine-8-carboxylic acid

F

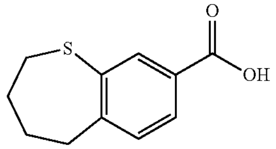

To a mixture of Intermediate E (500 mg, 2.06 mmol) in DMSO (5 mL) was added $Pd(OAc)_2$ (9.23 mg, 41.12 umol), dicyclohexyl(3-dicyclohexylphosphaniumylpropyl)phosphonium;ditetrafluoro borate (50.36 mg, 82.25 umol), $H_2O$ (74.09 mg, 4.11 mmol, 74.09 uL) and $K_2CO_3$ (426.28 mg, 3.08 mmol). The mixture was purged three times with CO and stirred at 100° C. for 2 hrs under CO (15 psi). Water (50 mL) was added and the mixture was extracted with EA (10 mL*3). The combined organic phase was washed with brine (5 mL), dried over anhydrous $Na_2SO_4$, filtered and concentrated under vacuum to give Intermediate F (410 mg, 96% yield) as a yellow oil which was used to next step directly without further purification. $^1H$ NMR (400 MHz, CHLOROFORM-d) δ=8.22 (d, J=1.6 Hz, 1H), 7.87-7.85 (m, 1H), 7.26-7.23 (m, 1H), 3.10-3.02 (m, 2H), 2.75-2.68 (m, 2H), 2.11-2.02 (m, 2H), 1.69 (s, 2H) ppm.

Step 6: Preparation of 2,3,4,5-tetrahydrobenzo[b]thiepine-8-carboxylic acid 1,1-dioxide

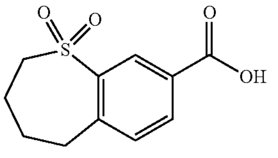

2,3,4,5-tetrahydrobenzo[b]thiepine-8-carboxylic acid 1,1-dioxide

To a mixture of Intermediate F (200 mg, 960.26 umol) in MeOH (2 mL) was added the mixture of Oxone (1.18 g, 1.92 mmol) in $H_2O$ (2 mL) dropwise. The mixture was stirred at 30° C. for 16 hrs. The combined reaction mixture (two batches) was quenched by saturated $Na_2SO_3$ solution (5 mL) then poured into water (50 mL). The mixture was extracted with EA (10 mL*3). The combined organic layer was washed by brine (5 mL*1), dried over $Na_2SO_4$, filtered and concentrated under vacuum to give of 2,3,4,5-tetrahydrobenzo[b]thiepine-8-carboxylic acid 1,1-dioxide (450 mg, crude) as a light-yellow oil. LCMS (ESI) m/z: [M+H]+ =240.9. $^1$H NMR (400 MHz, CHLOROFORM-d) 7=8.70 (d, J=1.6 Hz, 1H), 8.16-8.14 (m, 1H), 7.35 (d, J=8.0 Hz, 1H), 3.34-3.11 (i, 4H), 2.23 (s, 2H), 1.78 (d, J=2.4 Hz, 2H) ppm.

Example 103. Preparation of Compounds of the Invention

The following compounds in Table 4 were prepared using standard chemical manipulations and procedures similar to those used for the preparation of Compound 13.

TABLE 4

| # | Name | LC-MS (m/z) | 1H NMR |
|---|---|---|---|
| 185 | 3-(1-hydroxy-2-methylpropan-2-yl)-N-(2-((4-(3-(2-methyl-2H-1,2,3-triazol-4-yl)phenyl)thiazol-2-yl)amino)-2-oxoethyl)benzamide | 491.1 | $^1$H NMR (400 MHz, DMSO-d6) δ = 12.51 (s, 1H), 8.97-8.87 (m, 1H), 8.45-8.37 (m, 1H), 8.27 (s, 1H),7.96-7.85 (m, 2H), 7.83-7.69 (m, 3H), 7.63-7.48 (m, 2H), 7.46-7.37 (m, 1H), 4.71 (d, J = 5.6 Hz, 1H), 4.23 (s, 3H), 4.21 (d, J = 6.0 Hz, 2H), 3.47 (d, J = 5.2 Hz, 2H), 1.28 (s, 6H) ppm |
| 197 | 2-oxo-N-(2-oxo-2-((4-(3-(pyridin-4-yl)phenyl)thiazol-2-yl)amino)ethyl)-2',3'-dihydrospiro[cyclopentane-1,1'-indene]-6'-carboxamide | 523.0 | $^1$H NMR (400 MHz, DMSO-d6) δ = 12.64-12.19 (m, 1H), 8.85 (m, 1H), 8.72-8.65 (m, 2H), 8.31 (m, 1H), 8.02 (m, 1H), 7.84 (s, 1H), 7.79-7.74 (m, 4H), 7.65-7.57 (m, 2H), 7.36 (d, J = 8.0 Hz, 1H), 4.19 (m, 2H), 2.97 (m, 2H), 2.44 (m, 2H), 2.31-2.21 (m, 2H), 2.18-2.09 (m, 2H), 2.05-1.92 (m, 2H) ppm |
| 209 | 3-(2-amino-1,1-dimethyl-ethyl)-N-[2-[[4-[3-[3-(aminomethyl)phenyl]phenyl] thiazol-2-yl]amino]-2-oxo-ethyl]benzamide | 514.5 | $^1$H NMR (400 MHz, DMSO-d6) δ = 8.95-8.92 (m, 1H), 8.20 (s, 1H), 7.90-7.87 (m, 2H), 7.75-7.70 (m, 3H), 7.63-7.61 (m, 1H), 7.54-7.52 (m, 3H), 7.44-7.41 (m, 2H), 7.36-7.34 (m, 1H), 4.20 (d, J = 5.6 Hz, 2H), 3.81 (s, 2H), 2.70 (s, 2H), 1.27 (s, 6H) ppm |
| 210 | (R)-2-amino-3,3-dimethyl-N-(2-oxo-2-((4-(3-(pyridin-4-yl)phenyl)thiazol-2-yl)amino)ethyl)-2,3-dihydro-1H-indene-5-carboxamide | 498.1 | $^1$H NMR (400 MHz, METHANOL-d4) δ = 8.86 (d, J = 5.4 Hz, 2H), 8.48 (s, 1H), 8.37 (d, J = 4.8 Hz, 2H), 8.18 (d, J = 8.0 Hz, 1H), 7.89 (d, J = 7.6 Hz, 1H), 7.83-7.80 (m, 2H), 7.69-7.65 (m, 1H), 7.63 (s, 1H), 7.41 (d, J = 8.4 Hz, 1H), 4.33 (s, 2H), 3.78-3.74 (m, 1H), 3.53-3.44 (m, 1H), 3.07-3.02 (m, 1H), 1.45 (s, 3H), 1.36 (s, 3H) ppm |
| 250 | (S)-2-amino-3,3-dimethyl-N-(2-oxo-2-((4-(3-(pyridin-4-yl)phenyl)thiazol-2-yl)amino)ethyl)-2,3-dihydro-1H-indene-5-carboxamide | 498.1 | $^1$H NMR (400 MHz, METHANOL-d4) δ = 8.85 (d, J = 5.2 Hz, 2H), 8.46 (s, 1H), 8.35 (s, 2H), 8.17 (d, J = 7.2 Hz, 1H), 7.88 (d, J = 8.0 Hz, 1H), 7.83-7.81 (m, 2H), 7.68-7.62 (m, 2H), 7.41 (d, J = 8.4 Hz, 1H), 4.33 (s, 2H), 3.78-3.74 (m, 1H), 3.52-3.46 (m, 1H), 3.08-3.02 (m, 1H), 1.45 (s, 3H), 1.36 (s, 3H) ppm |
| 111 | N-(2-((4-(3'-(acetamidomethyl)-[1,1'-biphenyl]-3-yl)thiazol-2-yl)amino)-2-oxoethyl)-3-(isopropylsulfonyl) benzamide | 591.3 | $^1$H NMR (400 MHz, DMSO-d6) δ = 12.50 (s, 1H), 9.30-9.27 (m, 1H), 8.40-8.37 (m, 2H), 8.27 (d, J = 8.0 Hz, 1H), 8.17 (s, 1H), 8.05 (d, J = 8.0 Hz, 1H), 7.90 (d, J = 8.0 Hz, 1H), 7.84-7.77 (m, 2H), 7.60-7.51 (m, 4H), 7.47-7.43 (m, 1H), 7.28 (d, J = 7.6 Hz, 1H), 4.34 (d, J = 5.6 Hz, 2H), 4.25 (d, J = 5.6 Hz, 2H), 3.53-3.46 (m, 1H), 1.88 (s, 3H), 1.18 (d, J = 7.2 Hz, 6H) ppm |
| 225 | (4R)-4-(aminomethyl)-N-[2-[[4-[3-(2,6-dimethyl-4-pyridyl)phenyl]thiazol-2-yl]amino]-2-oxo-ethyl]-4-methyl-tetralin-6-carboxamide | 539.9 | $^1$H NMR (400 MHz, METHANOL-d4) δ = 8.44-8.41 (m, 2H), 8.29 (s, 1H), 8.01 (d, J = 8.0 Hz, 1H), 7.92 (d, J = 1.6 Hz, 1H), 7.75-7.71 (m, 2H), 7.58-7.55 (m, 2H), 7.46 (s, 2H), 7.30 (d, J = 8.0 Hz, 1H), 4.35 (s, 2H), 3.42 (d, J = 13.2 Hz, 1H), 3.17 (d, J = 13.2 Hz, 1H), 2.93-2.91 (m, 2H), 2.60 (s, 6H), 1.96-1.94 (m, 3H), 1.80-1.76 (m, 1H), 1.44 (s, 3H) ppm |
| 251 | (4S)-4-(aminomethyl)-N-[2-[[4-[3-(2,6-dimethyl-4-pyridyl)phenyl]thiazol-2-yl]amino]-2-oxo-ethyl]-4-methyl-tetralin-6-carboxamide | 539.9 | $^1$H NMR (400 MHz, METHANOL-d4) δ 8.41 (s, 2H), 8.30 (s, 1H), 8.01 (d, J = 8.0 Hz, 1H), 7.92 (d, J = 1.6 Hz, 1H), 7.74-7.68 (m, 2H), 7.58-7.55 (m, 2H), 7.46 (s, 2H), 7.30 (d, J = 8.0 Hz, 1H), 4.35 (s, 2H), 3.42 (d, J = 13.6 Hz, 1H), 3.17 (d, J = 13.2 Hz, 1H), 2.93-2.89 (m, 2H), 2.60 (s, 6H), 1.96-1.93 (m, 3H), 1.80-1.76 (m, 1H), 1.44 (s, 3H) ppm |
| 226 | (S)-1-(hydroxymethyl)-1-methyl-N-(2-oxo-2-((4-(3- | 499.3 | $^1$H NMR (400 MHz, DMSO-d6) δ = 8.68 (d, J = 6.0 Hz, 2H), 8.56-8.53 (m, 1H), 8.31 (s, 1H), 8.01 (d, |

TABLE 4-continued

| # | Name | LC-MS (m/z) | 1H NMR |
|---|---|---|---|
| | (pyridin-4-yl)phenyl)thiazol-2-yl)amino)ethyl)-2,3-dihydro-1H-indene-4-carboxamide | | J = 8.0 Hz, 1H), 7.84 (s, 1H), 7.77 (d, J = 6.0 Hz, 3H), 7.60-7.58 (m, 1H), 7.49-7.47 (m, 1H), 7.32-7.31 (m, 1H), 7.27-7.25 (m, 1H), 4.76-4.73 (m, 1H), 4.18-4.16 (m, 2H), 3.39-3.38 (m, 2H), 3.08-3.03 (m, 2H), 2.16-2.10 (m, 1H), 1.70-1.65 (m, 1H), 1.21 (s, 3H) ppm |
| 197 | (R)-1-(hydroxymethyl)-1-methyl-N-(2-oxo-2-((4-(3-(pyridin-4-yl)phenyl)thiazol-2-yl)amino)ethyl)-2,3-dihydro-1H-indene-4-carboxamide | 499.3 | $^1$H NMR (400 MHz, DMSO-d6) δ = 8.68 (d, J = 6.0 Hz, 2H), 8.54-8.53 (m, 1H), 8.31 (s, 1H), 8.01 (d, J = 8.0 Hz, 1H), 7.84 (s, 1H), 7.77 (d, J = 6.0 Hz, 3H), 7.61-7.60 (m, 1H), 7.48 (d, J = 7.2 Hz, 1H), 7.34-7.30 (m, 1H), 7.27-7.25 (m, 1H), 4.76-4.73(m, 1H), 4.18 (d, J = 5.6 Hz, 2H), 3.38-3.37 (m, 2H), 3.08-3.03 (m, 2H), 2.14-2.10 (m, 1H), 1.70-1.65 (m, 1H), 1.20 (s, 3H) ppm |
| 227 | (3S)-N-[2-[[4-[3-(2,6-dimethylpyrimidin-4-yl)phenyl]thiazol-2-yl]amino]-2-oxo-ethyl]-3-(hydroxymethyl)-3-methylindane-5-carboxamide | 528.1 | $^1$H NMR (400 MHz, DMSO-d6 + D2O) δ = 8.60 (s, 1H), 8.03-8.00 (m, 2H), 7.74 (s, 1H), 7.65 (d, J = 12.0 Hz, 3H), 7.60-7.56 (m, 1H), 7.28 (d, J = 8.4 Hz, 1H), 4.17 (s, 2H), 3.36 (s, 2H), 2.87-2.83 (m, 2H), 2.62 (s, 3H), 2.47 (s, 3H), 2.18-2.08 (m, 1H), 1.76-1.65 (m, 1H), 1.19 (s, 3H) ppm |
| 228 | (3R)-N-[2-[[4-[3-(2,6-dimethylpyrimidin-4-yl)phenyl]thiazol-2-yl]amino]-2-oxo-ethyl]-3-(hydroxymethyl)-3-methyl-indane-5-carboxamide | 528.1 | $^1$H NMR (400 MHz, DMSO-d6 + D2O) δ = 8.64 (s, 1H), 8.39 (s, 1H), 8.04 (d, J = 2.0 Hz, 2H), 7.77 (s, 1H), 7.70-7.64 (m, 3H), 7.60-7.56 (m, 1H), 7.28 (d, J = 8.4 Hz, 1H), 4.16 (s, 2H), 3.36 (s, 2H), 2.88-2.84 (m, 2H), 2.63 (s, 3H), 2.48 (s, 3H), 2.20-2.11 (m, 1H), 1.75-1.68 (m, 1H), 1.21 (s, 3H) ppm |
| 113 | N-(2-oxo-2-((4-(3-(pyridin-4-yl)phenyl)thiazol-2-yl)amino)ethyl)-3-((1,1,1-trifluoropropan-2-yl)sulfonyl)benzamide | 574.8 | $^1$H NMR (400 MHz, DMSO-d6) δ = 12.52(s, 1H), 9.34-9.31 (m, 1H), 8.68-8.67 (m, 2H), 8.46-8.45 (m, 1H), 8.34-8.31 (m, 2H), 8.14 (d, J = 8.0 Hz, 1H), 8.01 (d, J = 7.6 Hz, 1H), 7.89-7.85 (m, 2H), 7.77-7.75 (m, 3H), 7.62-7.58 (m, 1H), 5.06-4.98(m, 1H), 4.25 (d, J = 6.0 Hz, 2H), 1.46 (d, J = 6.8 Hz, 3H) ppm |
| 114 | 3-((1-aminopropan-2-yl)sulfonyl)-N-(2-((4-(3-(2,6-dimethylpyridin-4-yl)phenyl)thiazol-2-yl)amino)-2-oxoethyl)benzamide | 563.9 | $^1$H NMR (400 MHz, DMSO-d6) δ = 12.54 (br s, 1H), 9.37-9.34 (m, 1H), 8.42-8.41 (m, 1H), 8.35-8.31 (m, 2H), 8.13-8.12(m, 2H), 8.08-8.02 (m, 3H), 7.90-7.86 (m, 1H), 7.85 (s, 1H), 7.78 (d, J = 7.6 Hz, 1H), 7.69-7.59 (m, 3H), 4.26 (d, J = 6.0 Hz, 2H), 3.72-3.67 (m, 1H), 3.25-3.20 (m, 1H), 3.01-2.95 (m, 1H), 2.57 (s, 6H), 1.29-1.26 (m, 3H) |
| 115 | (S)-3-((1-hydroxypropan-2-yl)sulfonyl)-N-(2-oxo-2-((4-(3-(pyridin-4-yl)phenyl)thiazol-2-yl)amino)ethyl)benzamide | 537.2 | $^1$H NMR (400 MHz, DMSO-d6) δ = 12.51 (s, 1H), 9.29-9.26 (m, 1H), 8.67 (d, J = 5.6 Hz, 2H), 8.38-8.24 (m, 3H), 8.06-8.00 (m, 2H), 7.84-7.75 (m, 5H), 7.61-7.58 (m, 1H), 4.99-4.96 (m, 1H), 4.25 (d, J = 5.6 Hz, 2H), 3.74-3.69 (m, 1H), 3.51-3.43 (m, 2H), 1.24-1.21 (m, 3H) ppm |
| 116 | (R)-3-((1-hydroxypropan-2-yl)sulfonyl)-N-(2-oxo-2-((4-(3-(pyridin-4-yl)phenyl)thiazol-2-yl)amino)ethyl)benzamide | 537.2 | $^1$H NMR (400 MHz, DMSO-d6) δ = 12.48 (s, 1H), 9.29-9.26 (m, 1H), 8.68-8.67 (m, 2H), 8.38-8.24 (m, 3H), 8.04-8.00 (m, 2H), 7.84-7.76 (m, 5H), 7.75-7.59(m, 1H), 4.99-4.96 (m, 1H), 4.24 (d, J = 5.6 Hz, 2H), 3.73-3.71 (m, 1H), 3.51-3.42 (m, 2H), 1.24 (d, J = 6.8 Hz, 3H) ppm |
| 231 | (S)-N-(2-((4-(3-(2,6-dimethylpyridin-4-yl)phenyl)thiazol-2-yl)amino)-2-oxoethyl)-8-(hydroxymethyl)-8-methyl-5,6,7,8-tetrahydronaphthalene-2-carboxamide | 541.2 | $^1$H NMR (400 MHz, METHANOL-d4) δ = 8.27 (s, 1H), 7.98 (d, J = 7.6 Hz, 1H), 7.91 (d, J = 1.6 Hz, 1H), 7.69-7.59 (m, 2H), 7.57-7.50 (m, 2H), 7.42 (s, 2H), 7.19 (d, J = 8.0 Hz, 1H), 4.31 (s, 2H), 3.73 (d, J = 11.2 Hz, 1H), 3.55 (d, J = 11.2 Hz, 1H), 2.83 (d, J = 6.4 Hz, 2H), 2.57 (s, 6H), 2.12-2.01 (m, 1H), 1.93-1.74 (m, 2H), 1.62-1.52 (m, 1H), 1.30 (s, 3H) ppm |
| 232 | (R)-N-(2-((4-(3-(2,6-dimethylpyridin-4-yl)phenyl)thiazol-2-yl)amino)-2-oxoethyl)-8-(hydroxymethyl)-8-methyl-5,6,7,8-tetrahydronaphthalene-2-carboxamide | 541.2 | $^1$H NMR (400 MHz, METHANOL-d4) δ = 8.27 (s, 1H), 8.02-7.96 (m, 1H), 7.91 (d, J = 1.6 Hz, 1H), 7.66 (d, J = 7.2 Hz, 1H), 7.63-7.62 (m, 1H), 7.56-7.50 (m, 2H), 7.42 (s, 2H), 7.19 (d, J = 8.0 Hz, 1H), 4.31 (s, 2H), 3.73 (d, J = 11.2 Hz, 1H), 3.55 (d, J = 11.2 Hz, 1H), 2.83 (d, J = 6.4 Hz, 2H), 2.58 (s, 6H), 2.12-2.02 (m, 1H), 1.94-1.76 (m, 2H), 1.61-1.52 (m, 1H), 1.30 (s, 3H) ppm |
| 130 | 2-methyl-1,1-dioxo-N-[2-oxo-2-[[4-[3-(4-pyridyl)phenyl]thiazol-2-yl]amino]ethyl]-3H-1,2-benzothiazepine-8-carboxamide | 545.9 | $^1$H NMR (400 MHz, DMSO-d6) δ = 12.57-12.48 (m, 1H), 9.31-9.30 (m, 1H), 8.69-8.67 (m, 2H), 8.43 (d, J = 2.0 Hz, 1H), 8.38 (s, 1H), 8.34-8.31 (m, 1H), 8.18-8.15 (m, 1H), 8.02 (d, J = 8.0 Hz, 1H), 7.85 (s, 1H), 7.78-7.76 (m, 3H), 7.62-7.58 (m, 1H), 6.72 (d, J = 12.8 Hz, 1H), 6.13-6.08 (m, 1H), 4.24-4.21 (m, 4H), 2.57 (s, 3H) ppm |
| 131 | 2-methyl-1,1-dioxo-N-[2-oxo-2-[[4-[3-(4-pyridyl)phenyl]thiazol- | 547.9 | $^1$H NMR (400 MHz, DMSO-d6) δ = 12.50 (s, 1H), 9.22-9.20 (m, 1H), 8.68-8.67 (m, 2H), 8.31-8.30 (m, |

TABLE 4-continued

| # | Name | LC-MS (m/z) | 1H NMR |
|---|---|---|---|
| | 2-yl]amino]ethyl]-4,5-dihydro-3H-1,2-benzothiazepine-8-carboxamide | | 2H), 8.07-8.00 (m, 2H), 7.84 (s, 1H), 7.77-7.75 (m, 3H), 7.61-7.59 (m, 2H), 4.22 (d, J = 5.6 Hz, 2H), 3.66-3.61 (m, 2H), 3.23 (s, 2H), 2.57 (s, 3H), 1.79-1.76 (m, 2H) ppm |
| 233 | N-[2-[[4-[3-(3-cyanophenyl)phenyl]thiazol-2-yl]amino]-2-oxo-ethyl]-3-(hydroxymethyl)-3-methyl-indane-5-carboxamide | 523.2 | $^1$H NMR (400 MHz, DMSO-d6) δ = 12.35-12.28 (m, 1H), 8.83-8.80 (m, 1H), 8.25 (d, J = 11.2 Hz, 2H), 8.09 (d, J = 7.6 Hz, 1H), 7.97 (d, J = 8.0 Hz, 1H), 7.87-7.83 (m, 2H), 7.73-7.69 (m, 4H), 7.59-7.55 (m, 1H), 7.28 (d, J = 7.6 Hz, 1H), 4.77-4.76(m, 1H), 4.18 (d, J = 5.6 Hz, 2H), 3.37 (s, 2H), 2.89-2.86 (m, 2H), 2.20-2.16 (m, 1H), 1.76-1.69 (m, 1H), 1.23 (s, 3H) ppm |
| 129 | 1,1-dioxo-N-[2-oxo-2-[[4-[3-(4-pyridyl)phenyl]thiazol-2-yl]amino]ethyl]-2,3,4,5-tetrahydro-1benzothiepine-8-carboxamide | 533.1 | $^1$H NMR (400 MHz, DMSO-d6) δ = 9.24-9.22 (m, 1H), 8.69 (d, J = 6.0 Hz, 2H), 8.44 (d, J = 1.6 Hz, 1H), 8.32 (s, 1H), 8.12 (d, J = 6.0 Hz, 1H), 8.02 (d, J = 8.0 Hz, 1H), 7.85 (s, 1H), 7.77 (d, J = 6.0 Hz, 3H), 7.65-7.56 (m, 2H), 4.23 (d, J = 5.6 Hz, 2H), 3.45-3.39 (m, 2H), 3.18 (d, J = 5.6 Hz, 2H), 2.17-2.07 (m, 2H), 1.89-1.59 (m, 2H) ppm |
| 242 | 3-[1-(hydroxymethyl)-1-methyl-propyl]-N-[2-oxo-2-[[4-[3-(4-pyridyl)phenyl]thiazol-2-yl]amino]ethyl]benzamide | 501.1 | $^1$H NMR (400 MHz, METHANOL-d4) δ = 8.85 (d, J = 6.8 Hz, 2H), 8.48-8.47 (m, 1H), 8.41-8.35 (m, 2H), 8.19-8.17 (m, 1H), 7.96-7.86 (m, 2H), 7.76-7.74 (m, 1H), 7.69-7.65 (m, 1H), 7.63 (s, 1H), 7.61-7.57 (m, 1H), 7.48-7.43 (m, 1H), 4.33 (s,2H), 3.77-3.69 (m, 1H), 3.61 (d, J = 11.2 Hz, 1H), 1.90-1.85 (m, 1H), 1.68-1.63 (m, 1H), 1.38 (s, 3H), 0.73-0.69 (m, 3H) ppm |
| 243 | (1S)-1-(aminomethyl)-1-methyl-N-[2-oxo-2-[[4-[3-(4-pyridyl)phenyl]thiazol-2-yl]amino]ethyl]indane-4-carboxamide | 498.2 | $^1$H NMR (400 MHz, METHANOL-d4) δ = 8.85 (d, J = 6.8 Hz, 2H), 8.47 (s, 1H), 8.34 (d, J = 6.8 Hz, 2H), 8.18 (d, J = 8.0 Hz, 1H), 7.90-7.88 (m, 1H), 7.70-7.62 (m, 3H), 7.44-7.36 (m, 2H), 4.32 (s, 2H), 3.28-3.24 (m, 2H), 3.15 (d, J = 5.2 Hz, 2H), 2.26-2.16 (m, 1H), 2.06-1.96 (m, 1H), 1.40 (s, 3H) ppm |
| 245 | 3-(2-amino-1,1-dimethyl-ethyl)-N-[2-[[4-[3-(2,6-dimethyl-4-pyridyl)phenyl]thiazol-2-yl]amino]-2-oxo-ethyl]-4,5-dimethyl-benzamide | 542.3 | $^1$H NMR (400 MHz, DMSO-d6) δ = 12.50 (br s, 1H), 8.93-8.91 (m, 1H), 8.45 (s, 1H), 8.19 (s, 2H), 8.15 (d, J = 7.6 Hz, 1H), 7.93 (d, J = 7.6 Hz, 1H), 7.89 (s, 1H), 7.80 (s, 2H), 7.75-7.67 (m, 3H), 4.20 (d, J = 5.2 Hz, 2H), 3.21 (d, J = 5.6 Hz, 2H), 2.77(s, 6H), 2.39 (s, 3H), 2.31 (s, 3H), 1.49 (s, 6H) ppm |
| 122 | 3-isopropylsulfonyl-N-[2-[[4-[3-(2-methoxy-6-methyl-pyrimidin-4-yl)phenyl]thiazol-2-yl]amino]-2-oxoethyl] benzamide | 566.4 | $^1$H NMR (400 MHz, METHANOL-d4) δ = 8.71-8.69 (m, 1H), 8.47-8.45 (m, 1H), 8.30-8.28 (m, 1H), 8.14-8.06 (m, 3H), 7.84-7.79 (m, 1H), 7.60-7.54 (m, 3H), 4.38 (s, 2H), 4.13 (s, 3H), 3.46-3.39 (m, 1H), 2.55 (s, 3H), 1.31 (d, J = 6.8 Hz, 6H) ppm |
| 123 | 3-isopropylsulfonyl-N-[2-[[4-[3-(6-methoxy-2-methyl-pyrimidin-4-yl)phenyl]thiazol-2-yl]amino]-2-oxo-ethyl]benzamide | 566.3 | $^1$H NMR (400 MHz, DMSO-d6) δ = 12.55 (s, 1H), 9.35-9.26 (m, 1H), 8.73-8.67 (m, 1H), 8.43-8.37 (m, 1H), 8.32-8.24 (m, 1 H), 8.13-8.02 (m, 3H), 7.87-7.79 (m, 2H), 7.62-7.54 (m, 1H), 7.35 (s, 1H), 4.30-4.22(m, 2H), 3.98 (s, 3H), 3.54-3.48 (m, 1H), 2.63 (s, 3H), 1.21-1.19 (d, J = 6.8 Hz, 6H) ppm |
| 248 | N-[2-oxo-2-[[4-[3-(4-pyridyl)phenyl]thiazol-2-yl]amino]ethyl]-3-trimethylsilyl-benzamide | 487.3 | $^1$H NMR (400 MHz, DMSO-d6) δ = 12.81-12.11 (m, 1H), 8.98-8.95 (m, 1H), 8.69-8.67 (m, 2H), 8.31 (d, J = 1.6 Hz, 1H), 8.05 (s, 1H), 8.02 (d, J = 8.0 Hz, 1H), 7.91-7.88 (m, 1H), 7.84 (s, 1H), 7.77-7.75 (m, 3H), 7.71 (d, J = 7.2 Hz, 1H), 7.62-7.58 (m, 1H), 7.51-7.47 (m, 1H), 4.22 (d, J = 6.0 Hz, 2H), 0.30 (s, 9H) ppm |
| 124 | N-[2-[[4-[3-[2-(aminomethyl)-4-pyridyl]phenyl]thiazol-2-yl]amino]-2-oxo-ethyl]-3-isopropylsulfonyl-benzamide | 550.1 | $^1$H NMR (400 MHz, DMSO-d6) δ = 12.50 (s, 1H), 9.01-8.99(m, 1H), 8.73 (d, J = 5.2 Hz, 1H), 8.38 (s, 2H), 8.33 (s, 1H), 8.05 (d, J = 7.6 Hz, 1H), 7.94 (d, J = 15.2 Hz, 2H), 7.85-7.81 (m, 3H), 7.71 (s, 2H), 7.67-7.62 (m, 2H), 7.54-7.48 (m, 1H), 4.30 (d, J = 5.2 Hz, 2H), 3.13 (d, J = 6.0 Hz, 2H), 2.53-2.52 (m, 1H), 1.40 (s, 6H) ppm |
| 127 | 3-isopropylsulfonyl-N-[2-[[4-[3-(6-methylpyrimidin-4-yl)phenyl]thiazol-2-yl]amino]-2-oxoethyl] benzamide | 536.0 | $^1$H NMR (400 MHz, DMSO-d6) δ = 12.58 (s, 1H), 9.31-9.30(m, 1H), 9.14 (d, J = 1.2 Hz, 1H), 8.80 (s, 1H), 8.39 (s, 1H), 8.28 (d, J = 7.6 Hz, 1H), 8.17-8.03(m, 4H), 7.89-7.76(m, 2H), 7.63-7.61(m, 1H), 4.26 (d, J = 5.6 Hz, 2H), 3.55-3.49(m, 1H), 2.56 (s, 3H), 1.20 (d, J = 6.8 Hz, 6H) ppm |
| 274 | (S)-4-(difluoromethyl)-N-(2-((4-(3-((cis)-2,6-dimethylmorpholino)phenyl) thiazol-2-yl)amino)-2-oxoethyl)-4-fluorochromane-6-carboxamide | 575.1 | $^1$H NMR (400 MHz, DMSO-d6) δ = 12.40 (s, 1H), 8.91-8.90 (m, 1H), 8.23-8.14 (m, 1H), 7.95 (d, J = 8.8 Hz, 1H), 7.63 (s, 1H), 7.46 (s, 1H), 7.37-7.31 (m, 1H), 7.31-7.23 (m, 1H), 7.08 (d, J = 8.8 Hz, 1H), 6.99-6.63 (m, 2H), 4.51-4.37 (m, 1H), 4.29-4.12 (m, 3H), 3.81-3.68 (m, 2H), 3.63 (d, J = 10.8 Hz, 2H), 2.47-2.35 (m, 2H), 2.32-2.27 (m, 2H), 1.19 (s, 3H), 1.17 (s, 3H) ppm |

TABLE 4-continued

| # | Name | LC-MS (m/z) | 1H NMR |
|---|---|---|---|
| 275 | (R)-4-(difluoromethyl)-N-(2-((4-(3-((cis)-2,6-dimethylmorpholino)phenyl) thiazol-2-yl)amino)-2-oxoethyl)-4-fluorochromane-6-carboxamide | 575.1 | $^1$H NMR (400 MHz, DMSO-d6) δ = 12.42 (s, 1H), 8.91-8.90 (m, 1H), 8.18 (s, 1H), 7.95 (d, J = 8.8 Hz, 1H), 7.63 (s, 1H), 7.46 (s, 1H), 7.38-7.32 (m, 1H), 7.31-7.22 (m, 1H), 7.07 (d, J = 8.8 Hz, 1H), 6.98-6.65 (m, 2H), 4.51-4.40 (m, 1H), 4.27-4.15(m, 3H), 3.79-3.56 (m, 4H), 2.46-2.35 (m, 2H), 2.32-2.27 (m, 2H), 1.19 (s, 3H), 1.17 (s, 3H) ppm |
| 276 | (R)-N-(2-((4-(3-(azetidin-1-yl)-5-fluorophenyl)thiazol-2-yl)amino)-2-oxoethyl)-4-(difluoromethyl)-4-fluoroisochromane-6-carboxamide | 535.2 | $^1$H NMR (400 MHz, DMSO-d6) δ = 12.59-12.23 (m, 1H), 9.06-9.02 (m, 1H), 8.20 (s, 1H), 7.99 (d, J = 8.0 Hz, 1H), 7.68 (s, 1H), 7.41 (d, J = 8.0 Hz, 1H), 6.97 (d, J = 10.0 Hz, 1H), 6.88-6.53 (m, 2H), 6.19-6.14 (m, 1H), 4.95-4.75 (m, 2H), 4.30-4.09 (m, 4H), 3.89-3.84 (m, 4H), 2.38-2.29 (m, 2H) ppm |
| 277 | (S)-N-(2-((4-(3-(azetidin-1-yl)-5-fluorophenyl)thiazol-2-yl)amino)-2-oxoethyl)-4-(difluoromethyl)-4-fluoroisochromane-6-carboxamide | 535.2 | $^1$H NMR (400 MHz, DMSO-d6) δ = 12.62-12.30 (m, 1H), 9.06-9.02 (m, 1H), 8.20 (s, 1H), 7.99 (d, J = 8.0 Hz, 1H), 7.68 (s, 1H), 7.41 (d, J = 8.4 Hz, 1H), 6.97 (d, J = 10.0 Hz, 1H), 6.87-6.54 (m, 2H), 6.20-6.10 (m, 1H), 4.95-4.74 (m, 2H), 4.30-4.10 (m, 4H), 3.89-3.84 (m, 4H), 2.38-2.30 (m, 2H) ppm |
| 285 | 3-(R)-3-(difluoromethyl)tetrahydrofuran-3-yl)-N-(2-((4-(3-((cis)-2,6-dimethylmorpholino)phenyl) thiazol-2-yl)amino)-2-oxoethyl)benzamide | 571.2 | $^1$H NMR (400 MHz, MeOD-d4) δ = 7.95-7.83 (m, 2H), 7.60-7.49 (m, 3H), 7.41-7.36 (m, 2H), 7.28 (m, 1H), 6.94 (m, 1H), 6.20-5.86 (m, 1H), 4.48 (d, J = 9.2 Hz, 1H), 4.34-4.30 (m, 2H), 4.07 (m, 1H), 4.00 (m, 1H), 3.97-3.89 (m, 1H), 3.82 (m, 2H), 3.58 (d, J = 10.8 Hz, 2H), 2.66 (m, 1H), 2.48-2.34 (m, 3H), 1.24 (d, J = 6.0 Hz, 6H) ppm |
| 286 | 3-((S)-3-(difluoromethyl)tetrahydrofuran-3-yl)-N-(2-((4-(3-((cis)-2,6-dimethylmorpholino)phenyl) thiazol-2-yl)amino)-2-oxoethyl)benzamide | 571.2 | $^1$H NMR (400 MHz, MeOD-d4) δ = 7.91-7.85 (m, 2H), 7.56-7.51 (m, 3H), 7.40-7.35 (m, 2H), 7.30-7.25 (m, 1H), 6.93 (m, 1H), 6.20-5.86 (m, 1H), 4.48 (d, J = 9.2 Hz, 1H), 4.32 (s, 2H), 4.11-4.04 (m, 1H), 4.03-3.98 (m, 1H), 3.94 (m, 1H), 3.87-3.77 (m, 2H), 3.58 (d, J = 10.4 Hz, 2H), 2.71-2.61 (m, 1H), 2.48-2.41 (m, 1H), 2.37 (m, 2H), 1.24 (d, J = 6.0 Hz, 6H) ppm |
| 287 | (S)-4-cyano-N-(2-((4-(3-((cis)-2,6-dimethylmorpholino)phenyl) thiazol-2-yl)amino)-2-oxoethyl)-4-methyl-1,2,3,4-tetrahydroisoquinoline-6-carboxamide | 545.3 | $^1$H NMR (400 MHz, DMSO-d6) δ = 12.42 (s, 1H), 9.06-9.04 (m, 1H), 8.09 (d, J = 1.2 Hz, 1H), 7.84-7.82 (m, 1H), 7.62 (s, 1H), 7.45 (s, 1H), 7.35-7.23 (m, 3H), 6.94-6.93 (m, 1H), 4.21-4.19 (m, 2H), 4.06 (d, J = 4.0 Hz, 2H), 3.77-3.67 (m, 2H), 3.62 (d, J = 11.6 Hz, 2H), 3.50 (d, J = 12.4 Hz, 1H), 3.20 (d, J = 12.4 Hz, 1H), 2.31-2.25 (m, 2H), 1.74 (s, 3H), 1.17 (d, J = 6.4 Hz, 6H) ppm |
| 288 | (R)-N-(2-((4-(3-(azetidin-1-yl)-5-fluorophenyl)thiazol-2-yl)amino)-2-oxoethyl)-3-cyano-1,3-dimethylindoline-5-carboxamide | 505.1 | $^1$H NMR (400 MHz, DMSO-d6) δ = 12.58-12.22 (m, 1H), 8.69-8.66 (m, 1H), 8.82-8.59 (m, 1H), 7.85 (d, J = 1.6 Hz, 1H), 7.80-7.78 (m, 1H), 7.66 (s, 1H), 6.96 (d, J = 9.6 Hz, 1H), 6.76 (d, J = 1.6 Hz, 1H), 6.70 (d, J = 8.4 Hz, 1H), 6.16-6.13 (m, 1H), 4.15-4.13 (m, 2H), 3.88-3.82 (m, 5H), 3.40 (s, 1H), 2.82 (s, 3H), 2.34-2.30 (m, 2H), 1.69 (s, 3H) ppm |
| 289 | (S)-N-(2-((4-(3-(azetidin-1-yl)-5-fluorophenyl)thiazol-2-yl)amino)-2-oxoethyl)-3-cyano-1,3-dimethylindoline-5-carboxamide | 505.1 | $^1$H NMR (400 MHz, DMSO-d6) δ = 12.39 (s, 1H), 8.68-8.67 (m, 1H), 7.88-7.76 (m, 2H), 7.66 (s, 1H), 7.00-6.92 (m, 1H), 6.78-6.74 (m, 1H), 6.70 (d, J = 8.4 Hz, 1H), 6.16-6.13 (m, 1H), 4.14-4.12 (m, 2H), 3.90-3.80 (m, 5H), 3.41 (d, J = 9.6 Hz, 1H), 2.82 (s, 3H), 2.33-2.29 (m, 2H), 1.68 (s, 3H) ppm |
| 290 | 3-((R)-2-(difluoromethyl)tetrahydrofuran-2-yl)-N-(2-((4-(3-((cis)-2,6-dimethylmorpholino)phenyl) thiazol-2-yl)amino)-2-oxoethyl)benzamide | 571.3 | $^1$H NMR (400 MHz, DMSO-d6) δ = 12.40 (s, 1H), 8.98-8.96 (m, 1H), 7.99 (s, 1H), 7.87 (d, J = 7.7 Hz, 1H), 7.68-7.57 (m, 2H), 7.56-7.48 (m, 1H), 7.45 (s, 1H), 7.38-7.30 (m, 1H), 7.30-7.21 (m, 1H), 6.94-6.93 (m, 1H), 6.36-5.89 (m, 1H), 4.20 (d, J = 5.6 Hz, 2H), 4.07-3.97 (m, 1H), 3.94-3.91 (m, 1H), 3.78-3.67 (m, 2H), 3.67-3.56 (m, 2H), 2.46-2.44 (m, 1H), 2.32-2.18 (m, 3H), 2.08-1.97 (m, 1H), 1.87-1.74 (m, 1H), 1.17 (d, J = 6.4 Hz, 6H) ppm |
| 291 | 3-((S)-2-(difluoromethyl)tetrahydrofuran-2-yl)-N-(2-((4-(3-((cis)-2,6-dimethylmorpholino)phenyl) thiazol-2-yl)amino)-2-oxoethyl)benzamide | 571.3 | $^1$H NMR (400 MHz, DMSO-d6) δ = 12.40 (s, 1H), 8.98-8.96 (m, 1H), 7.99 (s, 1H), 7.87 (d, J = 7.6 Hz, 1H), 7.68-7.57 (m, 2H), 7.55-7.48 (m, 1H), 7.45 (s, 1H), 7.38-7.30 (m, 1H), 7.30-7.21 (m, 1H), 6.94-6.93 (m, 1H), 6.32-5.94 (m, 1H), 4.19 (d, J = 5.6 Hz, 2H), 4.02-4.00 (m, 1H), 3.94-3.92 (m, 1H), 3.78-3.66 (m, 2H), 3.66-3.55 (m, 2H), 2.46-2.44 (m, 1H), 2.32-2.18 (m, 3H), 2.09-1.96 (m, 1H), 1.85-1.75 (m, 1H), 1.17 (d, J = 6.4 Hz, 6H) ppm |
| 306 | 3-(2-(difluoromethyl)tetrahydrofuran-2-yl)-N-(2-((4-(3-((cis)-2,6-dimethylmorpholino)phenyl) | 571.3 | $^1$H NMR (400 MHz, DMSO-d6) δ = 12.68-11.99 (m, 1H), 8.98-8.96 (m, 1H), 8.44 (s, 1H), 7.99 (s, 1H), 7.87 (d, J = 7.6 Hz, 1H), 7.68-7.58 (m, 2H), 7.56-7.48 (m, 1H), 7.45 (s, 1H), 7.38-7.30 (m, 1H), 7.30- |

TABLE 4-continued

| # | Name | LC-MS (m/z) | 1H NMR |
|---|---|---|---|
| | thiazol-2-yl)amino)-2-oxoethyl)benzamide | | 7.22 (m, 1H), 6.94-6.93 (m, 1H), 6.27-5.99 (m, 1H), 4.20 (d, J = 5.6 Hz, 2H), 4.02-4.00 (m, 1H), 3.97-3.88 (m, 1H), 3.77-3.67 (m, 2H), 3.66-3.58 (m, 2H), 2.48-2.43 (m, 1H), 2.32-2.17 (m, 3H), 2.09-1.97 (m, 1H), 1.86-1.76 (m, 1H), 1.17 (d, J = 6.4 Hz, 6H) ppm |
| 307 | (R)-4-(difluoromethyl)-N-(2-((4-(3-((cis)-2,6-dimethylmorpholino)phenyl) thiazol-2-yl)amino)-2-oxoethyl)-4-fluoroisochromane-6-carboxamide | 575.2 | $^1$H NMR (400 MHz, DMSO-d6) δ = 12.42 (s, 1H), 9.05-9.02 (m, 1H), 8.19 (s, 1H), 7.99 (d, J = 8.0 Hz, 1H), 7.62 (s, 1H), 7.45 (s, 1H), 7.40 (d, J = 8.4 Hz, 1H), 7.35-7.31 (m, 1H), 7.30-7.23 (m, 1H), 6.94-6.92 (m, 1H), 6.71-6.56 (m, 1H), 4.92-4.76 (m, 2H), 4.24-4.13 (m, 4H), 3.71 (d, J = 8.0 Hz, 2H), 3.61 (s, 2H), 2.32-2.25 (m, 2H), 1.17 (d, J = 6.4 Hz, 6H) ppm |
| 308 | (S)-4-(difluoromethyl)-N-(2-((4-(3-((cis)-2,6-dimethylmorpholino)phenyl) thiazol-2-yl)amino)-2-oxoethyl)-4-fluoroisochromane-6-carboxamide | 575.2 | $^1$H NMR (400 MHz, DMSO-d6) δ = 12.42 (s, 1H), 9.05-9.02 (m, 1H), 8.19 (s, 1H), 7.99 (d, J = 8.0 Hz, 1H), 7.62 (s, 1H), 7.45 (s, 1H), 7.40 (d, J = 8.4 Hz, 1H), 7.35-7.31 (m, 1H), 7.30-7.23 (m, 1H), 6.94-6.92 (m, 1H), 6.71-6.56 (m, 1H), 4.92-4.76 (m, 2H), 4.24-4.13 (m, 4H), 3.71 (d, J = 8.0 Hz, 2H), 3.61 (s, 2H), 2.32-2.25 (m, 2H), 1.17 (d, J = 6.4 Hz, 6H) ppm |
| 310 | 4-cyano-N-(2-((4-(3-((cis)-2,6-dimethylmorpholino)phenyl) thiazol-2-yl)amino)-2-oxoethyl)-4-methyl-1,2,3,4-tetrahydroisoquinoline-6-carboxamide | 545.2 | $^1$H NMR (400 MHz, DMSO-d6) 6 = 12.44 (s, 1H), 9.79-9.49 (m, 1H), 9.16-9.13 (m, 1H), 8.21 (d, J = 1.2 Hz, 1H), 7.94-7.92(m, 1H), 7.62 (s, 1H), 7.50-7.43 (m, 2H), 7.36-7.22 (m, 2H), 6.94-6.92 (m, 1H), 4.39 (d, J = 3.6 Hz, 2H), 4.23-4.21 (m, 2H), 4.02 (d, J = 13.2 Hz, 1H), 3.64-3.60 (m, 5H), 2.31-2.24 (m, 2H), 1.87 (s, 3H), 1.17 (d, J = 6.0 Hz, 6H) ppm |
| 317 | N-(2-((4-(3-((cis)-2,6-dimethylmorpholino)phenyl) thiazol-2-yl)amino)-2-oxoethyl)-3-((1s,3s)-1-fluoro-3-hydroxy-3-methylcyclobutyl)benzamide | 553.4 | $^1$H NMR (400 MHz, MeOD) δ = 8.09-8.02 (m, 1H), 7.95-7.86 (m, 1H), 7.74-7.67 (m, 1H), 7.57-7.50 (m, 2H), 7.40-7.32 (m, 2H), 7.30-7.22 (m, 1H), 6.96-6.89 (m, 1H), 4.31 (s, 2H), 3.87-3.74 (m, 2H), 3.61-3.53 (m, 2H), 2.97-2.71 (m, 4H), 2.41-2.29 (m, 2H), 1.24 (s, 3H), 1.22 (m, 6H) ppm |
| 319 | (S)-N-((R)-1-((4-(3-(azetidin-1-yl)phenyl)thiazol-2-yl)amino)-1-oxopropan-2-yl)-4-fluoro-4-methylisochromane-6-carboxamide | 495.1 | $^1$H NMR (400 MHz, DMSO-d6) δ = 12.44 (s, 1H), 8.85 (d, J = 6.8 Hz, 1H), 8.25 (s, 1H), 7.92 (d, J = 8.0 Hz, 1H), 7.55 (s, 1H), 7.27 (d, J = 8.0 Hz, 1H), 7.20 (d, J = 4.8 Hz, 2H), 6.95 (s, 1H), 6.46-6.26 (m, 1H), 4.90-4.77 (m, 1H), 4.77-4.65 (m, 2H), 4.13-4.00 (m, 1H), 3.88-3.78 (m, 5H), 2.37-2.24 (m, 2H), 1.76-1.61 (m, 3H), 1.48 (d, J = 6.8 Hz, 3H) ppm |
| 326 | 4-(difluoromethyl)-N-(2-((4-(3-((cis)-2,6-dimethylmorpholino)phenyl) thiazol-2-yl)amino)-2-oxoethyl)-4-hydroxyisochromane-6-carboxamide | 573.1 | $^1$H NMR (400 MHz, DMSO-d6) δ = 12.41 (s, 1H), 8.92 (s, 1H), 8.17 (s, 1H), 7.92-7.79 (m, 1H), 7.62 (s, 1H), 7.46 (s, 1H), 7.36-7.32 (m, 1H), 7.30-7.23 (m, 2H), 6.94 (d, J = 7.6 Hz, 1H), 6.34-5.97 (m, 2H), 4.80 (d, J = 1.6 Hz, 2H), 4.20 (d, J = 6.0 Hz, 2H), 4.12 (d, J = 11.6 Hz, 1H), 3.73-3.71 (m, 2H), 3.68-3.57 (m, 3H), 2.33-2.23 (m, 2H), 1.18 (d, J = 6.0 Hz, 6H) ppm |
| 328 | (R)-N-(2-((4-(3-(6-oxa-1-azaspiro[3.3]heptan-1-yl)phenyl)thiazol-2-yl)amino)-2-oxoethyl)-4-cyano-4-methylisochromane-6-carboxamide | 530.4 | $^1$H NMR (400 MHz, CDCl3) δ = 10.89-10.41 (m, 1H), 7.98 (d, J = 1.6 Hz, 1H), 7.82-7.73 (m, 1H), 7.45-7.28 (m, 1H), 7.26 (s, 1H), 7.23 (m, 1H), 7.19 (d, J = 8.0 Hz, 1H), 7.16-7.14 (m, 1H), 7.12-7.05 (m, 1H), 6.74 (m, 1H), 5.32 (m, 2H), 4.88-4.82 (m, 2H), 4.78 (d, J = 8.0 Hz, 2H), 4.40-4.31 (m, 2H), 4.13 (d, J = 11.2 Hz, 1H), 3.97-3.89 (m, 1H), 3.71 (m, 2H), 2.53 (m, 2H), 1.73 (s, 3H) ppm |
| 329 | 4-(difluoromethyl)-N-(2-((4-(3-((cis)-2,6-dimethylmorpholino)phenyl) thiazol-2-yl)amino)-2-oxoethyl)-4-fluoroisochromane-6-carboxamide | 575.1 | $^1$H NMR (400 MHz, DMSO-d6) δ = 12.42 (s, 1H), 9.05-9.02 (m, 1H), 8.19 (s, 1H), 7.99 (d, J = 8.0 Hz, 1H), 7.62 (s, 1H), 7.45 (s, 1H), 7.40 (d, J = 8.4 Hz, 1H), 7.35-7.31 (m, 1H), 7.30-7.23 (m, 1H), 6.94-6.92 (m, 1H), 6.71-6.56 (m, 1H), 4.96-4.73 (m, 2H), 4.32-4.07 (m, 4H), 3.78-3.67 (m, 2H), 3.63-3.60 (m, 2H), 2.31-2.26 (m, 2H), 1.17 (d, J = 6.4 Hz, 6H)ppm |
| 332 | (S)-N-(2-((4-(3-(azetidin-1-yl)phenyl)thiazol-2-yl)amino)-2-oxoethyl)-4-fluoro-4-methylisochromane-6-carboxamide | 481.1 | $^1$H NMR (400 MHz, DMSO-d6) δ = 12.43 (br s, 1H), 9.06-9.03 (m, 1H), 8.20 (s, 1H), 7.89 (d, J = 8.0 Hz, 1H), 7.55 (s, 1H), 7.28 (d, J = 8.4 Hz, 1H), 7.20 (d, J = 4.8 Hz, 2H), 6.95 (s, 1H), 6.39-6.36 (m, 1H), 4.88-4.83 (m, 1H), 4.76-4.70 (m, 1H), 4.27-4.15 (m, 2H), 4.11-4.04 (m), 3.89-3.79 (m, 5H), 2.36-2.28 (m, 2H), 1.71-1.65 (m, 3H) ppm |
| 342 | (R)-4-cyano-N-(2-((4-(3-(3,3-difluoroazetidin-1-yl)phenyl)thiazol-2-yl)amino)-2-oxoethyl)-4-methylisochromane-6-carboxamide | 524.2 | $^1$H NMR (400 MHz, DMSO-d6) δ = 12.48 (s, 1H), 9.07 (m, 1H), 8.13 (d, J=1.2 Hz, 1H), 7.88 (m, 1H), 7.62 (s, 1H), 7.38-7.33 (m, 1H), 7.32-7.27 (m, 2H), 7.09 (s, 1H), 6.55 (m, 1H), 4.95-4.79 (m, 2H), 4.31 (m, 4H), 4.26-4.19 (m, 3H), 3.87 (d, J = 11.6 Hz, 1H), 1.70 (s, 3H) ppm |

TABLE 4-continued

| # | Name | LC-MS (m/z) | 1H NMR |
|---|---|---|---|
| 345 | 3-(3-(difluoromethyl)tetrahydrofuran-3-yl)-N-(2-((4-(3-((cis)-2,6-dimethylmorpholino)phenyl) thiazol-2-yl)amino)-2-oxoethyl)benzamide | 571.1 | $^1$H NMR (400 MHz, DMSO-d6) δ = 12.16-11.95 (m, 1H), 8.73-8.65 (m, 1H), 7.93-7.84 (m, 2H), 7.59-7.48 (m, 3H), 7.45 (s, 1H), 7.34-7.30 (m, 1H), 7.29-7.24 (m, 1H), 6.93-6.88 (m, 1H), 6.34 (s, 1H), 6.22-6.18 (m, 1H), 6.07-6.05 (m, 1H), 4.33 (d, J = 9.2 Hz, 1H), 4.23 (d, J = 5.6 Hz, 2H), 4.01-3.94 (m, 2H), 3.88-3.82 (m, 1H), 3.74 (m, 2H), 3.62-3.57 (m, 2H), 2.57-2.54 (m, 1H), 2.37 (s, 1H), 2.35-2.32 (m, 2H), 1.19 (d, J = 6.0 Hz, 6H) ppm |
| 347 | (R)-4-cyano-N-(2-((4-(2-((cis)-2,6-dimethylmorpholino)pyridin-4-yl)thiazol-2-yl)amino)-2-oxoethyl)-4-methylisochromane-6-carboxamide | 547.2 | $^1$H NMR (400 MHz, DMSO-d6) δ = 12.52 (s, 1H), 9.08 (m, 1H), 8.23-8.10 (m, 2H), 7.93 (s, 1H), 7.88 (m, 1H), 7.33-7.22 (m, 2H), 7.16 (m, 1H), 4.93-4.80 (m, 2H), 4.30-4.13 (m, 5H), 3.92-3.84 (m, 1H), 3.65 (m, 2H), 2.43 (m, 2H), 1.73-1.67 (m, 3H), 1.18 (d, J = 6.0 Hz, 6H) ppm |
| 348 | (R)-N-(2-((4-(3-(1-oxa-6-azaspiro[3.3]heptan-6-yl)phenyl)thiazol-2-yl)amino)-2-oxoethyl)-4-cyano-4-methylisochromane-6-carboxamide | 530.2 | $^1$H NMR (400 MHz, DMSO-d6) δ = 9.07 (m, 1H), 8.12 (d, J = 1.6 Hz, 1H), 7.89-7.85 (m, 1H), 7.57 (s, 1H), 7.29 (d, J = 8.0 Hz, 1H), 7.26-7.16 (m, 2H), 6.96 (d, J = 1.6 Hz, 1H), 6.43-6.39 (m, 1H), 4.99-4.76 (m, 2H), 4.46 (m, 2H), 4.28-4.18 (m, 3H), 4.11 (d, J = 9.6 Hz, 2H), 3.91-3.83 (m, 3H), 2.89 (m, 2H), 1.69 (s, 3H) ppm |
| 351 | (4R)-4-cyano-4-methyl-N-(2-((4-(3-(2-methylazetidin-1-yl)phenyl)thiazol-2-yl)amino)-2-oxoethyl)isochromane-6-carboxamide | 502.1 | $^1$H NMR (400 MHz, DMSO-d6) δ = 12.42 (s, 1H), 9.08-9.04 (m, 1H), 8.12 (d, J = 1.6 Hz, 1H), 7.88-7.85 (m, 1H), 7.55 (s, 1H), 7.29 (d, J = 8.0 Hz, 1H), 7.20 (d, J = 4.8 Hz, 2H), 6.98 (s, 1H), 6.45-6.42 (m, 1H), 4.93-4.81 (m, 2H), 4.24-4.20 (m, 3H), 4.13-4.07 (m, 1H), 3.91-3.85 (m, 2H), 3.55-3.52 (m, 1H), 2.41-2.37 (m, 1H), 2.06-1.96 (m, 1H), 1.69 (s, 3H), 1.44 (d, J = 6.0 Hz, 3H) ppm |
| 356 | N-(2-((4-(3-(azetidin-1-yl)phenyl)thiazol-2-yl)amino)-2-oxoethyl)-4-fluoro-4-methylisochromane-6-carboxamide | 481.2 | $^1$H NMR (400 MHz, DMSO-d6) δ = 12.44 (s, 1H), 9.06-9.03 (m, 1H), 8.19 (s, 1H), 7.89 (d, J = 8.0 Hz, 1H), 7.56 (s, 1H), 7.28 (d, J = 8.0 Hz, 1H), 7.20 (d, J = 5.2 Hz, 2H), 6.95 (s, 1H), 6.39-6.35 (m, 1H), 4.88-4.83 (m, 1H), 4.76-4.70 (m, 1H), 4.22-4.19 (m, 2H), 4.11-4.04 (m, 1H), 3.89-3.79 (m, 5H), 2.36-2.28 (m, 2H), 1.71-1.65 (m, 3H) ppm |
| 362 | N-(2-((4-(3-(azetidin-1-yl)phenyl)thiazol-2-yl)amino)-2-oxoethyl)-3-(3-(difluoromethyl)oxetan-3-yl)benzamide | 499.4 | $^1$H NMR (400 MHz, DMSO-d6) δ = 12.43 (s, 1H), 8.99 (s, 1H), 7.89 (d, J = 8.0 Hz, 1H), 7.74 (s, 1H), 7.61-7.50 (m, 2H), 7.42 (d, J = 7.6 Hz, 1H), 7.20 (d, J = 4.8 Hz, 2H), 6.95 (s, 1H), 6.71-6.40 (m, 1H), 6.37-6.37 (m, 1H), 4.96-4.92 (m, 4H), 4.20 (d, J = 5.6 Hz, 2H), 3.84-3.81 (m, 4H), 2.35-2.26 (m, 2H) ppm |
| 363 | 4-(cyanomethyl)-N-(2-((4-(3-((cis)-2,6-dimethylmorpholino)phenyl) thiazol-2-yl)amino)-2-oxoethyl)-4-methylisochromane-6-carboxamide | 560.3 | $^1$H NMR (400 MHz, DMSO-d6) δ = 12.41 (brs, 1H), 8.95-8.88 (m, 1H), 8.02 (d, J = 1.6 Hz, 1H), 7.78-7.73 (m, 1H), 7.62 (s, 1H), 7.45 (s, 1H), 7.36-7.31 (m, 1H), 7.29-7.24 (m, 1H), 7.20 (d, J = 8.0 Hz, 1H), 6.96-6.89 (m, 1H), 4.87-4.75 (m, 2H), 4.21 (d, J = 5.6 Hz, 2H), 3.82 (d, J = 11.6 Hz, 1H), 3.77-3.68 (m, 2H), 3.68-3.57 (m, 3H), 3.01-2.86 (m, 2H), 2.33-2.24 (m, 2H), 1.35 (s, 3H), 1.17 (d, J = 6.0 Hz, 6H) ppm |
| 364 | (R)-N-(2-((4-(3-(azetidin-1-yl)-5-fluorophenyl)thiazol-2-yl)amino)-2-oxoethyl)-4-cyano-4-methylisochromane-6-carboxamide | 506.1 | $^1$H NMR (400 MHz, DMSO-d6) δ = 12.73-12.22 (m, 1H), 9.08- 9.05 (m, 1H), 8.12 (d, J = 0.8 Hz, 1H), 7.87-7.85 (m, 1H), 7.68 (s, 1H), 7.29 (d, J = 8.0 Hz, 1H), 6.97 (d, J = 9.6 Hz, 1H),6.77(s, 1H), 6.17-6.13 (m, 1H), 4.97-4.77 (m, 2H), 4.31-4.16 (m, 3H), 3.91-3.80 (m, 5H), 2.36-2.29 (m, 2H), 1.69 (s, 3H) ppm |
| 367 | N-(2-((4-(3-((cis)-2,6-dimethylmorpholino)phenyl) thiazol-2-yl)amino)-2-oxoethyl)-1-ethyl-3H-1I4-benzo[d]isothiazole-6-carboxamide 1-oxide | 554.2 | $^1$H NMR (400 MHz, DMSO-d6) δ = 12.47 (s, 1H), 9.30-9.27 (m, 1H), 8.73 (s, 1H), 8.34-8.32 (m, 1H), 7.89 (d, J = 8.4 Hz, 1H), 7.63 (s, 1H), 7.45 (s, 1H), 7.35-7.25 (m, 2H), 6.95-6.92 (m, 1H), 5.04-5.00 (m, 1H), 4.87 (d, J = 17.2 Hz, 1H), 4.31-4.23 (m, 3H), 4.10-4.06 (m, 1H), 3.74-3.60 (m, 4H), 2.32-2.26 (m, 2H), 1.17-1.10 (m, 9H) ppm |
| 368 | (R)-3-cyano-N-(2-((4-(3-((cis)-2,6-dimethylmorpholino)phenyl) thiazol-2-yl)amino)-2-oxoethyl)-1,3-dimethylindoline-5-carboxamide | 545.2 | $^1$H NMR (400 MHz, DMSO-d6) δ = 7.90-7.82 (m, 2H), 7.54 (s, 1H), 7.41-7.34 (m, 2H), 7.31-7.23 (m, 1H), 6.94-6.92 (m, 1H), 6.67 (d, J = 9.2 Hz, 1H), 4.28 (s, 2H), 3.90-3.76 (m, 3H), 3.59 (d, J = 10.4 Hz, 2H), 3.47 (d, J = 9.2 Hz, 1H), 2.89 (s, 3H), 2.43-2.30 (m, 2H), 1.73 (s, 3H), 1.24 (d, J = 6.0 Hz, 6H) ppm |
| 369 | (S)-3-cyano-N-(2-((4-(3-((cis)-2,6-dimethylmorpholino)phenyl) thiazol-2-yl)amino)-2-oxoethyl)- | 545.2 | $^1$H NMR (400 MHz, DMSO-d6) δ = 12.35 (br s, 1H), 8.68-8.66 (m, 1H), 7.85 (d, J = 1.6 Hz, 1H), 7.80-7.88 (m, 1H), 7.60 (s, 1H), 7.44 (s, 1H), 7.35-7.30 (m, 1H), 7.29-7.22 (m, 1H), 6.93-6.90 (m, 1H), |

TABLE 4-continued

| # | Name | LC-MS (m/z) | 1H NMR |
|---|---|---|---|
| | 1,3-dimethylindoline-5-carboxamide | | 6.70 (d, J = 8.4 Hz, 1H), 4.20-4.11 (m, 2H), 3.84 (d, J = 9.6 Hz, 1H), 3.72-3.70 (m, 2H), 3.61 (d, J = 10.4 Hz, 2H), 3.41 (d, J = 9.6 Hz, 1H), 2.82 (s, 3H), 2.35-2.22 (m, 2H), 1.68 (s, 3H), 1.16 (d, J = 6.0 Hz, 6H) ppm |
| 372 | (R)-N-(2-((4-(3-((cis)-2,6-dimethylmorpholino)phenyl) thiazol-2-yl)amino)-2-oxoethyl)-4-(hydroxymethyl)-4-methylisochromane-6-carboxamide | 551.2 | $^1$H NMR (400 MHz, DMSO-d6) δ 12.39 (s, 1H), 8.91-8.88 (m, 1H), 7.89 (s, 1H), 7.70-7.68 (m, 1H), 7.62-7.61 (m, 1H), 7.44 (s, 1H), 7.32-7.31 (m, 1H), 7.28-7.26 (m, 1H), 7.13 (d, J = 8.0 Hz, 1H), 6.93 (d, J = 8.0 Hz, 1H), 4.89 (t, J = 5.6 Hz, 1H), 4.74-4.73 (m, 2H), 4.18 (d, J = 6.0 Hz, 2H), 3.94 (d, J = 11.6 Hz, 1H), 3.72-3.71 (m, 2H), 3.62 (d, J = 11.6 Hz, 2H), 3.56-3.55(m, 1H), 3.40 (d, J = 11.2 Hz, 2H), 2.31-2.26 (m, 2H), 1.18-1.16 (m, 9H) ppm |
| 373 | (S)-N-(2-((4-(3-((cis)-2,6-dimethylmorpholino)phenyl) thiazol-2-yl)amino)-2-oxoethyl)-4-(hydroxymethyl)-4-methylisochromane-6-carboxamide | 551.2 | $^1$H NMR (400 MHz, DMSO-d6) δ 12.39 (s, 1H), 8.91-8.88 (m, 1H), 7.89 (d, J = 1.6 Hz, 1H), 7.69 7.68 (m, 1H), 7.61 (s, 1H), 7.44 (s, 1H), 7.32-7.31 (m, 1H), 7.28-7.26 (m, 1H), 7.13 (d, J = 8.0 Hz, 1H), 6.93 (d, J = 9.6 Hz, 1H), 4.89 (t, J = 5.6 Hz, 1H), 4.74-4.73 (m, 2H), 4.18 (d, J = 5.6 Hz, 2H), 3.94 (d, J = 11.2 Hz, 1H), 3.72-3.70 (m, 2H), 3.62 (d, J = 10.4 Hz, 2H), 3.56 (d, J = 5.2 Hz, 1H), 3.39 (s, 2H), 2.31-2.26 (m, 2H), 1.18-1.16 (m, 9H) ppm |
| 374 | 4-cyano-N-(2-((4-(3-((cis)-2,6-dimethylmorpholino)phenyl) thiazol-2-yl)amino)-2-oxoethyl)-4-(hydroxymethyl)isochromane-6-carboxamide | 562.2 | $^1$H NMR (400 MHz, DMSO-d6) δ = 12.71-12.13 (m, 1H), 9.06-9.03 (m, 1H), 8.05 (s, 1H), 7.88-7.86 (m, 1H), 7.62 (s, 1H), 7.45 (s, 1H), 7.34-7.24 (m, 3H), 6.94-6.92 (m, 1H), 5.99-5.89 (m, 1H), 4.91-4.79 (m, 2H), 4.31-4.17 (m, 3H), 4.04 (d, J = 11.2 Hz, 1H), 3.86-3.82 (m, 1H), 3.76-3.68 (m, 3H), 3.65-3.59 (m, 2H), 2.31-2.26 (m, 2H), 1.18 (s, 3H), 1.17 (s, 3H) ppm |
| 383 | 2-(tert-butyl)-N-(2-((4-(3-((cis)-2,6-dimethylmorpholino)phenyl) thiazol-2-yl)amino)-2-oxoethyl)-5-fluoroisonicotinamide | 526.3 | $^1$H NMR (400 MHz, DMSO-d6) δ 12.42 (s, 1H), 8.96 (s, 1H), 8.64 (d, J = 1.2 Hz, 1H), 7.63-7.61 (m, 2H), 7.44 (s, 1H), 7.34-7.32 (m, 1H), 7.28-7.24 (m, 1H), 6.93 (d, J = 8.0 Hz, 1H), 4.23 (d, J = 5.6 Hz, 2H), 3.73-3.69 (m, 2H), 3.62 (d, J = 11.2 Hz, 2H), 2.29-2.26 (m, 2H), 1.33 (s, 9H), 1.17 (d, J = 6.4 Hz, 6H) ppm |
| 390 | (R)-4-cyano-N-(2-((4-(3-(3-methoxyazetidin-1-yl)phenyl)thiazol-2-yl)amino)-2-oxoethyl)-4-methylisochromane-6-carboxamide | 518.2 | $^1$H NMR (400 MHz, DMSO-d6) δ = 12.45 (br s, 1H), 9.08- 9.05 (m, 1H), 8.13 (s, 1H), 7.88-7.86 (m, 1H), 7.57(s, 1H), 7.30 (d, J = 8.0 Hz, 1H), 7.25-7.19 (m, 2H), 6.98 (s, 1H), 6.43-6.41 (m, 1H), 4.94-4.81 (m, 2H), 4.38-4.31(m, 1H), 4.26-4.19 (m, 3H), 4.09-4.07 (m, 2H), 3.88-3.86 (m, 1H), 3.64-3.61 (m, 2H), 3.26 (s, 2H), 1.70 (s, 3H) ppm |
| 392 | N-(2-((4-(3-((cis)-2,6-dimethylmorpholino)phenyl) thiazol-2-yl)amino)-2-oxoethyl)-3-((1r,3r)-3-hydroxy-1-methylcyclobutyl)benzamide | 535.2 | $^1$H NMR (400 MHz, DMSO-d6) δ = 12.40 (s, 1H), 9.02-8.91 (m, 1H), 7.85 (s, 1H), 7.76-7.69 (m, 1H), 7.62 (s, 1H), 7.55-7.39 (m, 3H), 7.37-7.23 (m, 2H), 7.00-6.89 (m, 1H), 5.08-5.00 (m, 1H), 4.25-4.15 (m, 2H), 3.96-3.86 (m, 1H), 3.78-3.70 (m, 2H), 3.68-3.58 (m, 2H), 2.82-2.70 (m, 2H), 2.35-2.24 (m, 2H), 2.08-1.97 (m, 2H), 1.43 (s, 3H), 1.23-1.14 (m, 6H) ppm |
| 393 | N-(2-((4-(3-((cis)-2,6-dimethylmorpholino)phenyl) thiazol-2-yl)amino)-2-oxoethyl)-3-((1s,3s)-3-hydroxy-1-methylcyclobutyl)benzamide | 535.2 | $^1$H NMR (400 MHz, DMSO-d6)δ = 12.46-12.37 (m, 1H), 8.97-8.89 (m, 1H), 7.73-7.67 (m, 2H), 7.64-7.61 (m, 1H), 7.48-7.39 (m, 2H), 7.37-7.31 (m, 2H), 7.30-7.24 (m, 1H), 6.98-6.88 (m, 1H), 5.01-4.95 (m, 1H), 4.36-4.27 (m, 1H), 4.24-4.09(m, 2H), 3.78-3.69 (m, 2H), 3.66-3.59 (m, 2H), 2.34-2.26 (m, 2H), 2.16-2.06 (m, 2H), 1.39-1.32 (m, 3H), 1.22-1.12 (m, 6H) ppm |
| 396 | N-(2-((4-(3-((cis)-2,6-dimethylmorpholino)phenyl) thiazol-2-yl)amino)-2-oxoethyl)thiochromane-7-carboxamide 1,1-dioxide | 555.1 | $^1$H NMR (400 MHz, DMSO-d6) δ = 9.24 (m, 1H), 8.36 (d, J = 1.6 Hz, 1H), 8.07-8.03 (m, 1H), 7.62 (s, 1H), 7.52 (d, J = 8.4 Hz, 1H), 7.45 (s, 1H), 7.36-7.30 (m, 1H), 7.30-7.23 (m, 1H), 6.95-6.91 (m, 1H), 4.20 (d, J = 5.6 Hz, 2H), 3.76-3.68 (m, 2H), 3.64-3.60 (m, 2H), 3.59-3.55 (m, 2H), 3.08 (m, 2H), 2.38-2.33 (m, 2H), 2.32-2.26 (m, 2H), 1.17 (d, J = 6.4 Hz, 6H) ppm |
| 403 | (S)-N-(2-((4-(3-((cis)-2,6-dimethylmorpholino)phenyl) thiazol-2-yl)amino)-2-oxoethyl)-3-(hydroxymethyl)-1,3-dimethylindoline-5-carboxamide | 550.3 | $^1$H NMR (400 MHz, DMSO-d6) δ = 12.35 (s, 1H), 8.51-8.50 (m, 1H), 7.71-7.60 (m, 2H), 7.62 (s, 1H), 7.54 (d, J = 1.6 Hz, 1H), 7.45 (s, 1H), 7.37-7.31 (m, 1H), 7.31-7.22 (m, 1H), 6.95-6.94 (m, 1H), 6.49 (d, J = 8.4 Hz, 1H), 4.95-4.92 (m, 1H), 4.13 (d, J = 5.6 Hz, 2H), 3.79-3.68 (m, 2H), 3.63 (d, J = 11.2 Hz, 2H), 3.48 (d, J = 9.2 Hz, 1H), 3.37 (s, 2H), 3.00 (d, J = 9.2 Hz, 1H), 2.79 (s, 3H), 2.33-2.22 (m, 2H), 1.27 (s, 3H), 1.18 (d, J = 6.4 Hz, 6H) ppm |

TABLE 4-continued

| # | Name | LC-MS (m/z) | 1H NMR |
|---|---|---|---|
| 404 | (R)-N-(2-((4-(3-((cis)-2,6-dimethylmorpholino)phenyl) thiazol-2-yl)amino)-2-oxoethyl)-3-(hydroxymethyl)-1,3-dimethylindoline-5-carboxamide | 550.2 | $^1$H NMR (400 MHz, DMSO-d6) δ = 12.35 (s, 1H), 8.51-8.50 (m, 1H), 7.67-7.65 (m, 1H), 7.62 (s, 1H), 7.54 (d, J = 1.6 Hz, 1H), 7.45 (s, 1H), 7.37-7.31 (m, 1H), 7.31-7.23 (m, 1H), 6.95 (d, J = 2.0 Hz, 1H), 6.49 (d, J = 8.4 Hz, 1H), 4.95-4.92 (m, 1H), 4.13 (d, J = 5.6 Hz, 2H), 3.78-3.68 (m, 2H), 3.63 (d, J = 11.2 Hz, 2H), 3.48 (d, J = 9.2 Hz, 1H), 3.38-3.36 (m, 2H), 3.00 (d, J = 9.2 Hz, 1H), 2.79 (s, 3H), 2.29 (t, J = 11.2 Hz, 2H), 1.27 (s, 3H), 1.18 (d, J = 6.0 Hz, 6H) ppm |
| 407 | (R)-N-(2-((4-(3-(azetidin-1-yl)phenyl)thiazol-2-yl)amino)-2-oxoethyl)-4-cyano-4-methylisochromane-6-carboxamide | 488.2 | $^1$H NMR (400 MHz, DMSO-d6) δ = 9.06 (d, J = 5.6 Hz, 1H), 8.12 (s, 1H), 7.87 (m, 1H), 7.56 (s, 1H), 7.29 (s, 1H), 7.23-7.17 (m, 2H), 6.95 (s, 1H), 6.40-6.33 (m, 1H), 4.95-4.79 (m, 2H), 4.28-4.15 (m, 3H), 3.88-3.80 (m, 5H), 2.35-2.27 (m, 2H), 1.69 (s, 3H) ppm |
| 414 | (S)-N-((S)-1-((4-(3-(azetidin-1-yl)phenyl)thiazol-2-yl)amino)-1-oxopropan-2-yl)-3-(hydroxymethyl)-3-methyl-2,3-dihydro-1H-indene-5-carboxamide | 491.2 | $^1$H NMR (400 MHz, DMSO-d6) δ = 12.38 (d, J = 2.0 Hz, 1H), 8.60 (d, J = 6.4 Hz, 1H), 8.40 (s, 1H), 7.73-7.71 (m, 2H), 7.54 (s, 1H), 7.26 (d, J = 8.4 Hz, 1H), 7.20 (d, J = 4.8 Hz, 2H), 6.94 (s, 1H), 6.37-6.35 (m, 1H), 4.74-4.66 (m, 2H), 3.84-3.81 (m, 4H), 3.37 (s, 2H), 2.88-2.85 (m, 2H), 2.35-2.28 (m, 2H), 2.21-2.14 (m, 1H), 1.75-1.68 (m, 1H), 1.46 (d, J = 7.2 Hz, 3H), 1.23 (s, 3H) ppm |
| 416 | (S)-N-(2-((4-(3-(azetidin-1-yl)phenyl)thiazol-2-yl)amino)-2-oxoethyl)-4-cyano-4-methylchromane-6-carboxamide | 488.2 | $^1$H NMR (400 MHz, DMSO-d6) δ = 12.43 (s, 1H), 8.92-8.91 (m, 1H), 8.08 (d, J = 2.0 Hz, 1H), 7.81-7.79 (m, 1H), 7.55 (s, 1H), 7.20 (d, J = 4.8 Hz, 2H), 7.02-6.87 (m, 2H), 6.46-6.28 (m, 1H), 4.45-4.07 (m, 4H), 3.84-3.80 (m, 4H), 2.44-2.40 (m, 1H), 2.36-2.27 (m, 2H), 2.21-2.20 (m, 1H), 1.79 (s, 3H) ppm |
| 417 | (R)-3-cyano-N-(2-((4-(3-((cis)-2,6-dimethylmorpholino)phenyl) thiazol-2-yl)amino)-2-oxoethyl)-3-methyl-2,3-dihydrobenzofuran-5-carboxamide | 532.2 | $^1$H NMR (400 MHz, DMSO-d6) δ = 12.39 (s, 1H), 8.90-8.86 (m, 1H), 8.09 (d, J = 1.6 Hz, 1H), 7.91-7.88 (m, 1H), 7.62 (s, 1H), 7.45 (s, 1H), 7.37-7.31 (m, 1H), 7.30-7.24 (m, 1H), 7.05 (d, J = 8.8 Hz, 1H), 6.95-6.91 (m, 1H), 5.01 (d, J = 9.6 Hz, 1H), 4.55 (d, J = 9.6 Hz, 1H), 4.20-4.17 (m, 2H), 3.77-3.67 (m, 2H), 3.62 (d, J = 10.8 Hz, 2H), 2.32-2.25 (m, 2H), 1.77 (s, 3H), 1.17 (d, J = 6.4 Hz, 6H) ppm |
| 418 | 3-(3-cyanooxetan-3-yl)-N-(2-((4-(3-((cis)-2,6-dimethylmorpholino)phenyl) thiazol-2-yl)amino)-2-oxoethyl)benzamide | 532.2 | $^1$H NMR (400 MHz, DMSO-d6) δ = 12.44 (s, 1H), 9.16-9.07 (m, 1H), 8.16-8.12 (m, 1H), 8.00-7.92 m, 1H), 7.84-7.78 (m,1 H), 7.68-7.61 (m, 2H), 7.48-7.44 (m, 1H), 7.36-7.31 (m, 1H), 7.30-7.24 (m, 1H), 6.98-6.91 (m, 1H), 5.24-5.20 (m, 2H),4.99-4.94 (m, 2H), 4.31-4.18 (m, 2H), 3.77-3.69 (m, 2H), 3.67-3.58 (m, 2H), 2.33-2.25 (m, 2H), 1.22-1.13 (m, 6H) ppm |
| 419 | 3-(3-(difluoromethyl)oxetan-3-yl)-N-(2-((4-(3-((cis)-2,6-dimethylmorpholino)phenyl) thiazol-2-yl)amino)-2-oxoethyl)benzamide | 557 | $^1$H NMR (400 MHz, CDCl3) δ = 10.62-10.12 (m, 1H), 7.72-7.66 (m, 1H), 7.54 (s, 1H), 7.45-7.39 (m, 1H), 7.30 (s, 1H), 7.26-7.19 (m,3H), 7.07 (s, 1H), 7.01-6.95 (m, 1H), 6.84-6.78 (m, 1H), 6.31-5.99 (m, 1H), 4.97-4.90 (m, 4H), 4.31-4.23 (m, 2H), 3.79-3.67 (m, 2H), 3.45-3.38 (m, 2H), 2.42-2.33 (m, 2H), 1.21-1.16 (m, 6H) ppm |
| 424 | N-(2-((4-(3-((cis)-2,6-dimethylmorpholino)phenyl) thiazol-2-yl)amino)-2-oxoethyl)-3-((cis)-4-hydroxytetrahydrofuran-3-yl)benzamide | 537.2 | $^1$H NMR (400 MHz, DMSO-d6) δ = 12.40 (br s, 1H), 8.88-8.86 (m, 1H), 7.82 (s, 1H), 7.75 (d, J = 7.6 Hz, 1H), 7.61 (s, 1H), 7.48-7.39 (m, 3H), 7.34-7.32 (m, 1H), 7.28-7.24 (m, 1H), 6.94-6.92 (m, 1H), 4.92 (d, J = 4.8 Hz, 1H), 4.39-4.36 (m, 1H), 4.19 (d, J = 5.6 Hz, 2H), 4.10-4.06 (m, 1H), 4.02-3.96 (m, 2H), 3.74-3.69 (m, 3H), 3.62 (d, J = 11.6 Hz, 2H), 3.39-3.37 (m, 1H),2.31-2.26 (m, 2H), 1.17 (d, J = 6.0 Hz, 6H) ppm |
| 427 | 2-((R)-2-cyano-1-hydroxypropan-2-yl)-N-(2-((4-(3-((cis)-2,6-dimethylmorpholino)phenyl) thiazol-2-yl)amino)-2-oxoethyl)isonicotinamide | 535.2 | $^1$H NMR (400 MHz, DMSO-d6) δ = 12.45 (br s, 1H), 9.36-9.33 (m, 1H), 8.79 (d, J = 4.8 Hz, 1H), 7.97 (s, 1H), 7.82-7.80 (m, 1H), 7.63 (s, 1H), 7.45 (s, 1H), 7.35-7.25 (m, 2H), 6.95-6.92 (m, 1H), 5.67-5.64 (m, 1H), 4.25 (d, J = 5.6 Hz, 2H), 3.90-3.61 (m, 6H), 2.32-2.26 (m, 2H), 1.68 (s, 3H), 1.18 (d, J = 6.4 Hz, 6H) ppm |
| 432 | (S)-3-(hydroxymethyl)-3-methyl-N-(2-((4-(3-(6-methylpyrazin-2-yl)phenyl)thiazol-2-yl)amino)-2-oxoethyl)-2,3-dihydro-1H-indene-5-carboxamide | 514 | $^1$H NMR (400 MHz, DMSO-d6) δ = 9.11 (s, 1H), 8.83-8.81 (m, 1H), 8.67 (s, 1H), 8.54 (s, 1H), 8.06-8.01 (m, 2H), 7.80 (s, 1H), 7.72-7.69 (m, 2H), 7.61-7.57 (m, 1H), 7.28 (d, J = 8.0 Hz, 1H), 4.77 (s, 1H), 4.20 (d, J = 5.6 Hz, 2H), 3.38 (s, 2H), 2.89-2.86 (m, 2H), 2.60 (s, 3H), 2.21-2.15 (m, 1H), 1.74-1.71 (m, 1H), 1.24 (s, 3H) ppm |

TABLE 4-continued

| # | Name | LC-MS (m/z) | 1H NMR |
|---|---|---|---|
| 434 | 2-(tert-butyl)-N-((S)-1-((4-(3-((cis)-2,6-dimethylmorpholino)phenyl) thiazol-2-yl)amino)-3-hydroxy-1-oxopropan-2-yl)isonicotinamide | 538.2 | $^1$H NMR (400 MHz, METHANOL-d4) δ = 8.64 (d, J = 5.2 Hz, 1H), 7.92 (s, 1H), 7.66-7.64 (m, 1H), 7.54 (d, J = 2.0 Hz, 1H), 7.39-7.35 (m, 2H), 7.28-7.25 (m, 1H), 6.94-6.91 (m, 1H), 4.91-4.88 (m, 1H), 4.04 (d, J = 5.6 Hz, 2H), 3.85-3.77 (m, 2H), 3.58 (d, J = 10.8 Hz, 2H), 2.39-2.33 (m, 2H), 1.41-1.39 (m, 9H), 1.24 (d, J = 6.0 Hz, 6H) ppm |
| 435 | 2-(tert-butyl)-N-((S)-1-((4-(3-((cis)-2,6-dimethylmorpholino)phenyl) thiazol-2-yl)amino)-1-oxopropan-2-yl)isonicotinamide | 522.2 | $^1$H NMR (400 MHz, MeOD) δ = 8.63 (d, J = 5.2 Hz, 1H), 7.91 (s, 1H), 7.64-7.62 (m, 1H), 7.55 (d, J = 1.2 Hz, 1H), 7.38-7.36 (m, 2H), 7.29-7.25 (m, 1H), 6.93 (d, J = 8.4 Hz, 1H), 4.85-4.78 (m, 1H), 3.83-3.79 (m, 2H), 3.58 (d, J = 12.0 Hz, 2H), 2.39-2.33 (m, 2H), 1.60 (d, J = 7.2 Hz, 3H), 1.41 (s, 9H), 1.24 (d, J = 6.4 Hz, 6H) ppm |
| 436 | 2-(tert-butyl)-N-((S)-1-((4-(3-((cis)-2,6-dimethylmorpholino)phenyl) thiazol-2-yl)amino)-3-methoxy-1-oxopropan-2-yl)isonicotinamide | 552.2 | $^1$H NMR (400 MHz, MeOD) δ = 8.64 (d, J = 5.2 Hz, 1H), 7.91-7.90 (m, 1H), 7.64-7.63 (m, 1H), 7.54 (s, 1H), 7.39-7.36 (m, 2H), 7.29-7.25 (m, 1H), 6.94-6.92 (m, 1H), 5.00 (s, 1H), 3.91-3.79 (m, 4H), 3.58 (d, J = 10.8 Hz, 2H), 3.44 (s, 3H), 2.39-2.33 (m, 2H), 1.41 (s, 9H), 1.24 (d, J = 6.4 Hz, 6H) ppm |
| 437 | (R)-N-(2-((4-(3-((cis)-2,6-dimethylmorpholino)phenyl) thiazol-2-yl)amino)-2-oxoethyl)-4-hydroxy-4-methylisochromane-6-carboxamide | 537.2 | $^1$H NMR (400 MHz, DMSO-d6) δ = 12.63-12.15 (m, 1H), 8.93-8.90 (m, 1H), 8.14 (s, 1H), 7.74-7.71 (m, 1H), 7.62 (s, 1H), 7.46 (s, 1H), 7.37-7.31 (m, 1H), 7.31-7.24 (m, 1H), 7.14 (d, J = 8.0 Hz, 1H), 6.98-6.90 (m, 1H), 5.31 (s, 1H), 4.83-4.68 (m, 2H), 4.27-4.12 (m, 2H), 3.82-3.55 (m, 6H), 2.33-2.26 (m, 2H), 1.44 (s, 3H), 1.18 (d, J = 6.4 Hz, 6H) ppm |
| 438 | (S)-N-(2-((4-(3-((cis)-2,6-dimethylmorpholino)phenyl) thiazol-2-yl)amino)-2-oxoethyl)-4-hydroxy-4-methylisochromane-6-carboxamide | 537.2 | $^1$H NMR (400 MHz, DMSO-d6) δ = 12.39 (s, 1H), 8.92-8.89 (m, 1H), 8.13 (d, J = 1.6 Hz, 1H), 7.73-7.70 (m, 1H), 7.62 (s, 1H), 7.45 (s, 1H), 7.36-7.31 (m, 1H), 7.30- 7.24 (m, 1H), 7.13 (d, J = 8.0 Hz, 1H), 6.94-6.91 (m, 1H), 5.30 (s, 1H), 4.82-4.68 (m, 2H), 4.20-4.17 (m, 2H), 3.78-3.56 (m, 6H), 2.32-2.25 (m, 2H), 1.43 (s, 3H), 1.17 (d, J = 6.4 Hz, 6H) ppm |
| 443 | 5-(tert-butyl)-N-(2-((4-(3-((cis)-2,6-dimethylmorpholino)phenyl) thiazol-2-yl)amino)-2-oxoethyl)nicotinamide | 508.3 | $^1$H NMR (400 MHz, DMSO-d6) δ = 12.71-12.01 (m, 1H), 9.19-9.16 (m, 1H), 8.90 (d, J = 2.0 Hz, 1H), 8.82 (d, J = 2.4 Hz, 1H), 8.24-8.25 (m, 1H), 7.63 (s, 1H), 7.46 (s, 1H), 7.36-7.31 (m, 1H), 7.30-7.23 (m, 1H), 6.95-6.92 (m, 1H), 4.23 (d, J = 5.6 Hz, 2H), 3.78-3.67 (m, 2H), 3.63 (d, J = 10.4 Hz, 2H), 2.32-2.26 (m, 2H), 1.37 (s, 9H), 1.18 (d, J = 6.0 Hz, 6H) ppm |
| 444 | 4-cyano-N-(2-((4-(3-((cis)-2,6-dimethylmorpholino)phenyl) thiazol-2-yl)amino)-2-oxoethyl)-4-(hydroxymethyl)chromane-6-carboxamide | 562.2 | $^1$H NMR (400 MHz, DMSO-d6) δ = 12.40 (s, 1H), 8.92-8.90 (m, 1H), 8.05 (d, J = 2.0 Hz, 1H), 7.83-7.81 (m, 1H), 7.63 (s, 1H), 7.45 (s, 1H), 7.33-7.27 (m, 2H), 6.98-6.93 (m, 2H), 5.91-5.89 (m, 1H), 4.30-4.27 (m, 2H), 4.19-4.17 (m, 2H), 3.98-3.94 (m, 1H), 3.78-3.70 (m, 3H), 3.64-3.61 (m, 2H), 3.47-3.41 (m, 1H), 2.42-2.36 (m, 1H), 2.33-2.26 (m, 2H), 1.18 (d, J = 6.4 Hz, 6H) ppm |

Example 104. Preparation of Compounds of the Invention

The following compounds in Table 5 were prepared using standard chemical manipulations and procedures similar to those used for the preparation of Compound 14.

TABLE 5

| # | Name | LC-MS (m/z) | 1H NMR |
|---|---|---|---|
| 136 | N-[2-[[4-[3-[(cis)-2,6-dimethylmorpholin-4-yl]phenyl]thiazol-2-yl]amino]-2-oxo-ethyl]-4-hydroxy-4-methylchromane-6-carboxamide | 537.2 | $^1$H NMR (400 MHz, METHANOL-d4) δ = 8.46 (br s,, 1H), 8.17 (s, 1H), 7.75-7.73 (m, 1H), 7.56 (s, 1H), 7.41-7.36 (m, 2H), 7.30-7.28 (m, 1H), 6.96-6.95 (m, 1H), 6.87 (d, J = 8.6 Hz, 1H), 4.42-4.34 (m, 1H), 4.33-4.26 (m, 3H), 3.91-3.77 (m, 2H), 3.63-3.56 (m, 2H), 2.43-2.33 (m, 2H), 2.16-2.05 (m, 2H), 1.66 (s, 3H), 1.26 (d, J = 6.4 Hz, 6H) ppm |
| 252 | (S)-N-(2-((4-(3-((cis)-2,6-dimethylmorpholino)phenyl)thiazol-2-yl)amino)-2-oxoethyl)-4-(hydroxymethyl)-4- | 551.2 | $^1$H NMR (400 MHz, DMSO-d6) δ = 12.30 (br s, 1H), 8.69-8.65(m, 1H), 7.69-7.66(m, 1H), 7.62 (s, 1H), 7.50-7.47(m, 1H), 7.44 (s, 1H), 7.36-7.30 (m, 1H), 7.30-7.22 (m, 1H), 7.01-6.88 (m, 2H), 4.92-4.88(m, 1H), 4.40-4.27 (m, 2H), 4.23 (d, J = 5.6 Hz, 2H), 3.78-3.67 (m, 2H), 3.62 (d, J = |

TABLE 5-continued

| # | Name | LC-MS (m/z) | 1H NMR |
|---|---|---|---|
| | methylchroman-8-carboxamide | | 10.8 Hz, 2H), 3.57-3.53(m, 1H), 3.47-3.43(m, 1H), 2.32-2.26(m, 2H), 2.19-2.06 (m, 1H), 1.71-1.64(m, 1H), 1.25 (s, 3H), 1.17 (d, J = 6.0 Hz, 6H) ppm |
| 138 | (R)-N-(2-((4-(3-((cis)-2,6-dimethylmorpholino)phenyl)thiazol-2-yl)amino)-2-oxoethyl)-4-(hydroxymethyl)-4-methylchroman-8-carboxamide | 551.2 | $^1$H NMR (400 MHz, DMSO-d6) δ = 12.31 (br s, 1H), 8.70-8.66(m, 1H), 7.70-7.67(m, 1H), 7.63 (s, 1H), 7.51-7.48(m, 1H), 7.45 (s, 1H), 7.37-7.31 (m, 1H), 7.31-7.24 (m, 1H), 7.03-6.90 (m, 2H), 4.92-4.89(m, 1H), 4.40-4.28 (m, 2H), 4.24 (d, J = 5.6 Hz, 2H), 3.77-3.68 (m, 2H), 3.63 (b d, J = 11.6 Hz, 2H), 3.58-3.54(m, 1H), 3.48-3.44(m, 1H), 2.32-2.26(m, 2H), 2.17-2.09 (m, 1H), 1.72-1.65(m, 1H), 1.26 (s, 3H), 1.18 (d, J = 6.0 Hz, 6H) ppm |
| 139 | N-[2-[[4-[3-[(cis)-2,6-dimethylmorpholin-4-yl]phenyl]thiazol-2-yl]amino]-2-oxo-ethyl]-2-(2-hydroxy-1,1-dimethyl-ethyl)pyridine-4-carboxamide | 524.3 | $^1$H NMR (400 MHz, DMSO-d6) δ = 12.43 (br s, 1H), 9.23-9.21 (m, 1H), 8.68 (d, J = 4.8 Hz, 1H), 7.81 (s, 1H), 7.62-7.60 (m, 2H), 7.45 (s, 1H), 7.34-7.32 (m, 1H), 7.28-7.26 (m, 1H), 6.96-6.94 (m, 1H), 4.68-4.65 (m, 1H), 4.23 (d, J = 5.6 Hz, 2H), 3.71-3.70 (m, 2H), 3.67-3.60 (m, 2H), 3.59 (d, J = 5.2 Hz, 2H), 2.31-2.26 (m, 2H), 1.29 (s, 6H), 1.18(d, J = 6.0 Hz, 6H) ppm |
| 143 | (R)-N-(2-((4-(3-((cis)-2,6-dimethylmorpholino)phenyl)thiazol-2-yl)amino)-2-oxoethyl)-5-(hydroxymethyl)-5-methyl-6,7-dihydro-5H-cyclopenta[b]pyridine-3-carboxamide | 536.2 | $^1$H NMR (400 MHz, DMSO-d6) δ = 9.01-8.98 (m, 1H), 8.83 (d, J = 2.0 Hz, 1H), 8.03 (d, J = 2.0 Hz, 1H), 7.58 (s, 1H), 7.46 (s, 1H), 7.36-7.31 (m, 1H), 7.30-7.23 (m, 1H), 6.93 (d, J = 6.4 Hz, 1H), 4.89 (s, 1H), 4.19 (d, J = 5.6 Hz, 2H), 3.77-3.69 (m, 2H), 3.63 (d, J = 11.2 Hz, 2H), 3.44-3.40 (m, 2H), 3.01-2.91 (m, 2H), 2.32-2.26 (m, 2H), 2.23-2.13 (m, 1H), 1.85-1.74 (m, 1H), 1.26 (s, 3H), 1.19 (s, 3H), 1.17 (s, 3H) ppm |
| 144 | (S)-N-(2-((4-(3-((cis)-2,6-dimethylmorpholino)phenyl)thiazol-2-yl)amino)-2-oxoethyl)-5-(hydroxymethyl)-5-methyl-6,7-dihydro-5H-cyclopenta[b]pyridine-3-carboxamide | 536.2 | $^1$H NMR (400 MHz, DMSO-d6) δ = 12.40 (d, J = 6.0 Hz, 1H), 9.03-9.00 (m, 1H), 8.82 (d, J = 2.0 Hz, 1H), 8.02 (d, J = 2.0 Hz, 1H), 7.62 (s, 1H), 7.45 (s, 1H), 7.36-7.31 (m, 1H), 7.30-7.23 (m, 1H), 6.94-6.92 (m, 1H), 4.89-4.86 (m, 1H), 4.20 (d, J = 5.6 Hz, 2H), 3.76-3.67 (m, 2H), 3.62 (d, J = 10.4 Hz, 2H), 3.45-3.39 (m, 2H), 3.00-2.92 (m, 2H), 2.31-2.25 (m, 2H), 2.21-2.13 (m, 1H), 1.81-1.79 (m, 1H), 1.25 (s, 3H), 1.18 (s, 3H), 1.16 (s, 3H) ppm |
| 146 | (R)-4-cyano-N-(2-((4-(3-((cis)-2,6-dimethylmorpholino)phenyl)thiazol-2-yl)amino)-2-oxoethyl)-4-methylchroman-8-carboxamide | 546.0 | $^1$H NMR (400 MHz, DMSO-d6) δ = 12.33 (s, 1H), 8.66-8.62(m, 1H), 7.80-7.77(m, 1H), 7.70-7.62(m, 1H), 7.62 (s, 1H), 7.44 (s, 1H), 7.37-7.30 (m, 1H), 7.30-7.23 (m, 1H), 7.12-7.08(m, 1H), 6.94-6.91(m, 1H), 4.53-4.34 (m, 2H), 4.23 (d, J = 5.6 Hz, 2H), 3.78-3.67 (m, 2H), 3.62 (d, J = 11.6 Hz, 2H), 2.46-2.44(m, 1H), 2.32-2.20 (m, 3H), 1.79 (s, 3H), 1.17 (d, J = 6.4 Hz, 6H) ppm |
| 148 | (S)-4-cyano-N-(2-((4-(3-((cis)-2,6-dimethylmorpholino)phenyl)thiazol-2-yl)amino)-2-oxoethyl)-4-methylchroman-8-carboxamide | 546.0 | $^1$H NMR (400 MHz, DMSO-d6) δ = 12.33 (s, 1H), 8.67-8.63(m, 1H), 7.81-7.78(m, 1H), 7.71-7.69(m, 1H), 7.63 (s, 1H), 7.45 (s, 1H), 7.37-7.31 (m, 1H), 7.31-7.24 (m, 1H), 7.13-7.09(m, 1H), 6.95-6.92(m, 1H), 4.57-4.35 (m, 2H), 4.24 (d, J = 5.6 Hz, 2H), 3.80-3.68 (m, 2H), 3.63 (d, J = 10.4 Hz, 2H), 2.49-2.45 (m, 1H), 2.37-2.19 (m, 3H), 1.80 (s, 3H), 1.18 (d, J = 6.4 Hz, 6H) ppm |
| 149 | N-(2-((4-(3-((cis)-2,6-dimethylmorpholino)phenyl)thiazol-2-yl)amino)-2-oxoethyl)-3-(3-(fluoromethyl)oxetan-3-yl)benzamide | 539.2 | $^1$H NMR (400 MHz, METHANOL-d4) δ = 8.07-7.67 (m, 2H), 7.58-7.34 (m, 5H), 7.32-7.23 (m, 1H), 6.98-6.87 (m, 1H), 5.07-4.89 (m, 2H), 4.84-4.57 (m, 4H), 4.31 (s, 2H), 3.87-3.75 (m, 2H), 3.60-3.51 (m, 2H), 2.44-2.28 (m, 2H), 1.24 (d, J = 6.4 Hz, 6H) ppm. |
| 150 | N-(2-((4-(3-((cis)-2,6-dimethylmorpholino)phenyl)thiazol-2-yl)amino)-2-oxoethyl)-3-((1r,3r)-1-fluoro-3-hydroxycyclobutyl)benzamide | 539.2 | $^1$H NMR (400 MHz, DMSO-d6) δ = 12.40 (s, 1H), 9.05 (d, J = 5.6 Hz, 1H), 7.97 (s, 1H), 7.89 (d, J = 7.6 Hz, 1H), 7.69-7.59(m, 2H), 7.59-7.51 (m, 1H), 7.46 (s, 1H), 7.37-7.24 (m, 2H), 6.94 (d, J = 7.6 Hz, 1H), 5.43 (d, J = 6.4 Hz, 1H), 4.56-4.45 (m, 1H), 4.21 (d, J = 5.6 Hz, 2H), 3.75-3.68 (m, 2H), 3.63 (d, J = 11.6 Hz, 2H), 2.92-2.82 (m, 2H), 2.48-2.38 (m, 2H), 2.30 (d, J = 11.2 Hz, 2H), 1.18 (d, J = 6.4 Hz, 6H) ppm |
| 151 | N-(2-((4-(3-((cis)-2,6-dimethylmorpholino)phenyl)thiazol-2-yl)amino)-2-oxoethyl)-3-((1s,3s)-1-fluoro-3-hydroxycyclobutyl)benzamide | 539.2 | $^1$H NMR (400 MHz, DMSO-d6) δ = 12.33 (s, 1H), 8.99 (d, J = 5.6 Hz, 1H), 7.93-7.80 (m, 2H), 7.61-7.53 (m, 2H), 7.52-7.45(m, 1H), 7.39 (s, 1H), 7.32-7.24 (m, 1H), 7.24-7.17 (m, 1H), 6.87 (d, J = 7.6 Hz, 1H), 5.38 (d, J = 6.0 Hz, 1H), 4.14 (d, J = 5.6 Hz, 2H), 3.96-3.83 (m, 1H), 3.70-3.62 (m, 2H), 3.56 (d, J = 11.2 Hz, 2H), 2.96-2.85 (m, 2H), 2.55-2.50 (m, 2H), 2.23(d, J = 11.2 Hz, 2H), 1.11 (d, J = 6.0 Hz, 6H) ppm |
| 156 | N-(2-((4-(3-((cis)-2,6-dimethylmorpholino)phenyl)thiazol-2-yl)amino)-2-oxoethyl)-3-((3S,4R)-4-hydroxytetrahydrofuran-3-yl)benzamide | 537.2 | $^1$H NMR (400 MHz, DMSO-d6) δ = 12.47-12.37 (m, 1H), 8.93-8.90 (m, 1H), 7.84-7.75 (m, 2H), 7.61 (s, 1H), 7.46-7.44 (m, 3H), 7.34-7.32 (m, 1H), 7.28-7.24 (m, 1H), 6.94-6.91 (m, 1H), 5.33-5.32 (m, 1H), 4.28-4.24 (m, 1H), 4.20-4.16 (m, 3H), 4.01-3.96 (m, 1H), 3.78-3.70 (m, 3H), 3.69-3.56 (m, 3H), 3.22 (s, 1H), 2.31-2.26 (m, 2H), 1.18-1.13 (m, 6H) ppm |

TABLE 5-continued

| # | Name | LC-MS (m/z) | 1H NMR |
|---|---|---|---|
| 157 | N-(2-((4-(3-((cis)-2,6-dimethylmorpholino)phenyl)thiazol-2-yl)amino)-2-oxoethyl)-3-((3R,4S)-4-hydroxytetrahydrofuran-3-yl)benzamide | 537.2 | $^1$H NMR (400 MHz, DMSO-d6) δ = 12.74-12.37 (m, 1H), 8.93-8.90 (m, 1H), 8.49-8.32 (m, 1H), 7.82-7.75 (m, 2H), 7.75-7.61 (s, 1H), 7.45-7.42 (m, 3H), 7.34-7.32 (m, 1H), 7.28-7.24 (m, 1H), 6.97-6.91 (m, 1H), 5.34-5.30 (m, 1H), 4.29-4.24(m, 1H), 4.20-4.16 (m, 3H), 4.00-3.96 (m, 1H), 3.78-3.69 (m, 3H), 3.63-3.52 (m, 3H), 3.26-3.24 (m, 1H), 2.31-2.25 (m, 2H), 1.18-1.14 (m, 6H) ppm |
| 165 | (R)-N-(2-((4-(3-((cis)-2,6-dimethylmorpholino)phenyl)thiazol-2-yl)amino)-2-oxoethyl)-4-(hydroxymethyl)-4-methylchroman-6-carboxamide | 551.2 | $^1$H NMR (400 MHz, DMSO-d6) δ = 12.49-12.16 (m, 1H), 8.76-8.73 (m, 1H), 7.88 (d, J = 1.6 Hz, 1H), 7.67-7.59 (m, 2H), 7.45 (s, 1H), 7.36-7.31 (m, 1H), 7.30-7.23 (m, 1H), 6.93 (d, J = 8.0 Hz, 1H), 6.81 (d, J = 8.4 Hz, 1H), 4.90-4.88 (m, 1H), 4.25-4.12 (m, 4H), 3.77-3.67 (m, 2H), 3.62 (d, J = 11.6 Hz, 2H), 3.57-3.53 (m, 1H), 3.48-3.44 (m, 1H), 2.31-2.26 (m, 2H), 2.10-2.04 (m, 1H), 1.66-1.60 (m, 1H), 1.26 (s, 3H), 1.18 (s, 3H), 1.17 (s, 3H) ppm |
| 166 | (S)-N-(2-((4-(3-((cis)-2,6-dimethylmorpholino)phenyl)thiazol-2-yl)amino)-2-oxoethyl)-4-(hydroxymethyl)-4-methylchroman-6-carboxamide | 551.2 | $^1$H NMR (400 MHz, DMSO-d6) δ = 12.63-12.15 (m, 1H), 8.75 (s, 1H), 7.88 (s, 1H), 7.67-7.59 (m, 2H), 7.45 (s, 1H), 7.36-7.31 (m, 1H), 7.30-7.23 (m, 1H), 6.93 (d, J = 7.6 Hz, 1H), 6.81 (d, J = 8.4 Hz, 1H), 4.90-4.88 (m, 1H), 4.26-4.12 (m, 4H), 3.73 (d, J = 6.4 Hz, 2H), 3.62 (d, J = 11.2 Hz, 2H), 3.58-3.45 (m, 2H), 2.31-2.26 (m, 2H), 2.13-2.04 (m, 1H), 1.69-1.59(m, 1H), 1.26 (s, 3H), 1.18 (s, 3H), 1.17 (s, 3H) ppm |
| 168 | N-(2-((4-(3-((cis)-2,6-dimethylmorpholino)phenyl)thiazol-2-yl)amino)-2-oxoethyl)-3-(3-(hydroxymethyl)oxetan-3-yl)benzamide | 537.0 | $^1$H NMR (400 MHz, DMSO-d6) δ = 12.40 (s, 1H), 8.98-8.90 (m, 1H), 8.13 (s, 1H), 7.81-7.75 (m, 1H), 7.69-7.65 (m, 1H), 7.62 (s, 1H), 7.53-7.42 (m, 2H), 7.36-7.30 (m, 2H), 7.30-7.23 (m, 1H), 6.97-6.90 (m, 1H), 4.81-4.70 (m, 4H), 4.19 (d, J = 6.0 Hz, 2H), 3.79-3.66 (m, 5H), 3.64-3.59 (m, 2H), 2.33-2.25 (m, 2H), 1.17 (d, J = 6.0 Hz, 6H) ppm |
| 170 | (R)-5-cyano-N-(2-((4-(3-((cis)-2,6-dimethylmorpholino)phenyl)thiazol-2-yl)amino)-2-oxoethyl)-5-methyl-6,7-dihydro-5H-cyclopenta[b]pyridine-3-carboxamide | 531.2 | $^1$H NMR (400 MHz, METHANOL-d4) δ = 8.99 (d, J = 1.6 Hz, 1H), 8.38 (d, J = 2.0 Hz, 1H), 7.54 (s, 1H), 7.41-7.34 (m, 2H), 7.28-7.24 (m, 1H), 6.94-6.91 (m, 1H), 4.34 (s, 2H), 3.88-3.75 (m, 2H), 3.57 (d, J = 10.8 Hz, 2H), 3.23-3.19 (m, 2H), 2.79-2.72 (m, 1H), 2.45-2.29 (m, 3H), 1.75 (s, 3H), 1.25 (s, 3H), 1.23 (s, 3H) ppm |
| 253 | (S)-5-cyano-N-(2-((4-(3-((cis)-2,6-dimethylmorpholino)phenyl)thiazol-2-yl)amino)-2-oxoethyl)-5-methyl-6,7-dihydro-5H-cyclopenta[b]pyridine-3-carboxamide | 531.2 | $^1$H NMR (400 MHz, METHANOL-d4) δ = 8.98 (d, J = 1.6 Hz, 1H), 8.37 (d, J = 1.6 Hz, 1H), 7.53 (s, 1H), 7.39-7.34 (m, 2H), 7.30-7.23 (m, 1H), 6.93 (d, J = 8.0 Hz, 1H), 4.34 (s, 2H), 3.88-3.76 (m, 2H), 3.57 (d, J = 11.6 Hz, 2H), 3.22-3.18 (m, 2H), 2.80-2.71 (m, 1H), 2.41-2.32 (m, 3H), 1.74 (s, 3H), 1.24 (s, 3H), 1.23 (s, 3H) ppm |
| 171 | (S)-4-cyano-N-(2-((4-(3-((cis)-2,6-dimethylmorpholino)phenyl)thiazol-2-yl)amino)-2-oxoethyl)-4-methylisochroman-6-carboxamide | 546.2 | $^1$H NMR (400 MHz, DMSO-d6) δ = 12.42 (s, 1H), 9.07-9.04(m, 1H), 8.12 (d, J = 1.6 Hz, 1H), 7.88-7.85(m, 1H), 7.62 (s, 1H), 7.45 (s, 1H), 7.32-7.26(m, 3H), 6.94-6.93(m, 1H), 4.92-4.81 (m, 2H), 4.23-4.20(m, 3H), 3.87(d, J = 11.6 Hz, 1H), 3.77-3.71(m, 2H), 3.62 (d, J = 10.8 Hz, 2H), 2.31-2.26 (m, 2H), 1.69 (s, 3H), 1.17 (d, J = 6.0 Hz, 6H) ppm |
| 254 | (R)-4-cyano-N-(2-((4-(3-((cis)-2,6-dimethylmorpholino)phenyl)thiazol-2-yl)amino)-2-oxoethyl)-4-methylisochroman-6-carboxamide | 546.2 | $^1$H NMR (400 MHz, DMSO-d6) δ = 12.42 (s, 1H), 9.06 (s, 1H), 8.12 (d, J = 1.6 Hz, 1H), 7.88-7.85(m, 1H), 7.62 (s, 1H), 7.45 (s, 1H), 7.32-7.26(m, 3H), 6.93 (d, J = 5.6 Hz, 1H), 4.92-4.81(m, 2H), 4.23-4.20(m, 3H), 3.87 (d, J = 11.6 Hz, 1H), 3.77-3.71(m, 2H), 3.62 (d, J = 10.5 Hz, 2H), 2.31-2.26(m, 2H), 1.69 (s, 3H), 1.17 (d, J = 6.0 Hz, 6H) |
| 172 | (4R)-4-cyano-N-[2-[[4-[3-[(cis)-2,6-dimethylmorpholin-4-yl]phenyl]thiazol-2-yl]amino]-2-oxo-ethyl]-4-methyl-chromane-6-carboxamide | 546.0 | $^1$H NMR (400 MHz, DMSO-d6) δ = 12.40 (s, 1H), 8.95-8.92 (m, 1H), 8.09 (d, J = 1.6 Hz, 1H), 7.82-7.79 (m, 1H), 7.62 (s, 1H), 7.45 (s, 1H), 7.37-7.31 (m, 1H), 7.30-7.23 (m, 1H), 7.03-6.88 (m, 2H), 4.41-4.33 (m, 1H), 4.32-4.23 (m, 1H), 4.22-4.12 (m, 2H), 3.76-3.66 (m, 2H), 3.62 (d, J = 11.2 Hz, 2H), 2.45-2.41 (m, 1H), 2.32-2.17 (m, 3H), 1.80 (s, 3H), 1.18 (s, 3H), 1.16 (s, 3H) ppm |
| 255 | (4S)-4-cyano-N-[2-[[4-[3-[(cis)-2,6-dimethylmorpholin-4-yl]phenyl]thiazol-2-yl]amino]-2-oxo-ethyl]-4-methyl-chromane-6-carboxamide | 546.0 | $^1$H NMR (400 MHz, DMSO-d6) δ = 12.42 (s, 1H), 8.95-8.92 (m, 1H), 8.09 (d, J = 2.0 Hz, 1H), 7.82-7.79 (m, 1H), 7.62 (s, 1H), 7.45 (s, 1H), 7.36-7.31 (m, 1H), 7.29-7.24 (m, 1H), 6.99-6.91 (m, 2H), 4.41-4.22 (m, 2H), 4.21-4.13 (m, 2H), 3.77-3.66 (m, 2H), 3.62 (d, J = 10.8 Hz, 2H), 2.45-2.41 (m, 1H), 2.33-2.15 (m, 3H), 1.80 (s, 3H), 1.18 (s, 3H), 1.16 (s, 3H) ppm |
| 183 | N-(2-((4-(3-((cis)-2,6-dimethylmorpholino)phenyl)thiazol-2-yl)amino)-2-oxoethyl)-3-(3-fluorooxetan-3-yl)benzamide | 525.0 | $^1$H NMR (400 MHz, DMSO-d6) δ = 12.43 (s, 1H), 9.09 (d, J = 5.6 Hz, 1H), 8.11 (s, 1H), 7.96 (d, J = 8.0 Hz, 1H), 7.80-7.71 m, 1H), 7.68-7.57 (m, 2H), 7.46 (s, 1H), 7.37-7.22 (m, 2H), 6.95-6.92 (m, 1H), 5.10-4.90 (m, 4H), 4.23 (d, J = 6.0 Hz, 2H), 3.74-3.70 (m, 2H), 3.67-3.56 (m, 2H), 2.32-2.26 (m, 2H), 1.18 (d, J = 6.4 Hz, 6H) ppm |

TABLE 5-continued

| # | Name | LC-MS (m/z) | 1H NMR |
|---|---|---|---|
| 184 | N-(2-((4-(3-((2R,6S)-2,6-dimethylmorpholino)phenyl)thiazol-2-yl)amino)-2-oxoethyl)-3-(3-hydroxyoxetan-3-yl)benzamide | 523.1 | $^1$H NMR (400 MHz, DMSO-d6) δ = 12.44 (s, 1H), 9.03-9.02 (m, 1H), 8.17 (s, 1H), 7.90-7.76 (m, 2H), 7.63 (s, 1H), 7.54 (d, J = 8.0 Hz, 1H), 7.46 (s, 1H), 7.37-7.21 (m, 2H), 6.95-6.94 (m, 1H), 6.51 (s, 1H), 4.84-4.79 (m, 2H), 4.77-4.72 (m, 2H), 4.21 (d, J = 5.6 Hz, 2H), 3.74-3.71 (m, 2H), 3.64-3.61 (m, 2H), 2.29 (d, J = 11.2 Hz, 2H), 1.18 (d, J = 6.4 Hz, 6H) ppm |
| 186 | (1R,2S)-N-(2-((4-(3-((cis)-2,6-dimethylmorpholino)phenyl)thiazol-2-yl)amino)-2-oxoethyl)-2-hydroxy-2',3'-dihydrospiro[cyclopentane-1,1'-indene]-6'-carboxamide | 561.3 | $^1$H NMR (400 MHz, DMSO-d6) δ = 12.38-12.37 (m, 1H), 8.78-8.73 (m, 1H), 7.84 (s, 1H), 7.69-7.67 (m, 1H), 7.61 (s, 1H), 7.44 (s, 1H), 7.34-7.32 (m, 1H), 7.28-7.24 (m, 2H), 6.94-6.91 (m, 1H), 4.48 (d, J = 4.4 Hz, 1H), 4.17 (d, J = 5.6 Hz, 2H), 3.78-3.77 (m, 1H), 3.74-3.69 (m, 2H), 3.62 (d, J = 12.0 Hz, 2H), 2.90-2.82 (m, 2H), 2.32-2.28 (m, 2H), 2.19-2.14 (m, 1H), 2.04-1.99 (m, 1H), 1.93-1.87 (m, 2H), 1.80-1.77 (m, 1H), 1.61-1.59 (m, 2H), 1.24-1.23 (m, 1H), 1.17 (d, J = 6.4 Hz, 6H) ppm |
| 256 | (1S,2R)-N-(2-((4-(3-((cis)-2,6-dimethylmorpholino)phenyl)thiazol-2-yl)amino)-2-oxoethyl)-2-hydroxy-2',3'-dihydrospiro[cyclopentane-1,1'-indene]-6'-carboxamide | 561.3 | $^1$H NMR (400 MHz, DMSO-d6) δ = 12.46-12.29 (m, 1H), 8.77-8.74 (m, 1H), 7.84 (s, 1H), 7.69-7.67 (m, 1H), 7.61 (s, 1H), 7.44 (s, 1H), 7.34-7.32 (m, 1H), 7.28-7.24 (m, 2H), 6.94-6.91 (m, 1H), 4.48 (d, J = 4.4 Hz, 1H), 4.17 (d, J = 5.6 Hz, 2H), 3.78 (d, J = 1.6 Hz, 1H), 3.74-3.69 (m, 2H), 3.62 (d, J = 11.2 Hz, 2H), 2.92-2.84 (m, 2H), 2.32-2.28 (m, 2H), 2.19-2.16 (m, 1H), 2.02-1.98 (m, 1H), 1.95-1.86 (m, 2H), 1.80-1.77 (m, 1H), 1.63-1.56 (m, 2H), 1.23 (s, 1H), 1.17 (d, J = 6.4 Hz, 6H) ppm |
| 188 | (1R,2R)-N-(2-((4-(3-((cis)-2,6-dimethylmorpholino)phenyl)thiazol-2-yl)amino)-2-oxoethyl)-2-hydroxy-2',3'-dihydrospiro[cyclopentane-1,1'-indene]-6'-carboxamide | 561.1 | $^1$H NMR (400 MHz, DMSO-d6) δ = 12.39 (br s, 1H), 8.84-8.83 (m, 1H), 7.73-7.67 (m, 2H), 7.62 (s, 1H), 7.46 (s, 1H), 7.36-7.32 (m, 1H), 7.27 (d, J = 3.2 Hz, 2H), 6.94 (d, J = 8.0 Hz, 1H), 4.71 (d, J = 5.2 Hz, 1H), 4.21-4.14 (m, 2H), 4.09-4.03 (m, 1H), 3.76-3.70 (m, 2H), 3.65-3.60 (m, 2H), 2.94-2.81 (m, 2H), 2.47-2.43 (m, 1H), 2.30 (d, J = 11.2 Hz, 2H), 2.01 (d, J = 4.4, 1H), 1.83-1.66 (m, 5H), 1.62-1.53 (m, 1H), 1.18 (d, J = 6.0 Hz, 6H) ppm |
| 189 | (1S,2S)-N-(2-((4-(3-((cis)-2,6-dimethylmorpholino)phenyl)thiazol-2-yl)amino)-2-oxoethyl)-2-hydroxy-2',3'-dihydrospiro[cyclopentane-1,1'-indene]-6'-carboxamide | 561.1 | $^1$H NMR (400 MHz, DMSO-d6) δ = 12.53-12.25 (m, 1H), 8.84-8.82 (m, 1H), 7.76-7.66 (m, 2H), 7.62 (s, 1H), 7.45 (s, 1H), 7.36-7.31 (m, 1H), 7.27 (d, J = 7.6 Hz, 2H), 6.94 (d, J = 1.6, Hz, 1H), 4.71 (d, J = 5.2 Hz, 1H), 4.18 (d, J = 5.6 Hz, 2H), 4.05 (d, J = 5.2 Hz, 1H), 3.76-3.70 (m, 2H), 3.63 (d, J = 11.8 Hz, 2H), 2.92-2.83 (m, 2H), 2.46-2.43(m, 1H), 2.33-2.30 (m, 2H), 2.05-1.96 (m, 1H), 1.84-1.68 (m, 5H), 1.61-1.54 (m, 1H), 1.18 (d, J = 6.0 Hz, 6H) ppm |
| 195 | N-(2-((4-(3-((cis)-2,6-dimethylmorpholino)phenyl)thiazol-2-yl)amino)-2-oxoethyl)-2-oxo-2',3'-dihydrospiro[cyclopentane-1,1'-indene]-6'-carboxamide | 559.3 | $^1$H NMR (400 MHz, DMSO-d6) δ = 12.38 (s, 1H), 8.88-8.78 (m, 1H), 7.76 (m, 1H), 7.66-7.56 (m, 2H), 7.45 (s, 1H), 7.38-7.32 (m, 2H), 7.30-7.24 (m, 1H), 6.94 (m, 1H), 4.18 (m, 2H), 3.76-3.69(m, 2H), 3.63 (d, J = 10.8 Hz, 2H), 2.97 (m, 2H), 2.44 (m, 2H), 2.32-2.21 (m, 4H), 2.17-2.08 (m, 2H), 2.04-1.95 (m, 2H), 1.18 (d, J = 6.4 Hz, 6H) ppm |
| 196 | N-(2-((4-(3-(azetidin-1-yl)phenyl)thiazol-2-yl)amino)-2-oxoethyl)-3-(tert-butyl)benzamide | 449.4 | $^1$H NMR (400 MHz, DMSO-d6) δ = 12.44 (s, 1H), 8.95-8.94 (m, 1H), 7.94-7.93 (m, 1H), 7.77-7.67 (m, 1H), 7.64-7.54 (m, 2H), 7.43-7.22 (m, 1H), 7.21 (d, J = 4.8 Hz, 2H), 6.96 (s, 1H), 6.39-6.38 (m, 1H), 4.19 (d, J = 5.6 Hz, 2H), 3.84-3.83 (m, 4H), 2.38-2.28 (m, 2H), 1.33 (s, 9H) ppm |
| 198 | N-(2-((4-(3-((cis)-2,6-dimethylmorpholino)-5-fluorophenyl)thiazol-2-yl)amino)-2-oxoethyl)-4-fluoro-3-(1-hydroxy-2-methylpropan-2-yl)benzamide | 559.1 | $^1$H NMR (400 MHz, DMSO-d6) δ = 12.42 (s, 1H), 9.08-8.85 (m, 1H), 7.91-7.85 (m, 1H), 7.84-7.78 (m, 1H), 7.74 (s, 1H), 7.31-7.19 (m, 2H), 7.09 (d, J = 9.2 Hz, 1H), 6.76 (d, J = 12.8 Hz, 1H), 4.80-4.73 (m, 1H), 4.18 (d, J = 5.6 Hz, 2H), 3.73-3.64 (m, 4H), 3.58 (d, J = 5.6 Hz, 2H), 2.39-2.27 (m, 2H), 1.31 (s, 6H), 1.17 (d, J = 6.0 Hz, 6H) ppm |
| 199 | 4-chloro-N-[2-[[4-[3-[(cis)-2,6-dimethylmorpholin-4-yl]-5-fluoro-phenyl]thiazol-2-yl]amino]-2-oxo-ethyl]-3-(2-hydroxy-1,1-dimethyl-ethyl)benzamide | 575.1 | $^1$H NMR (400 MHz, DMSO-d6) δ = 12.48-12.41 (m, 1H), 9.03-9.01 (m, 1H), 7.96 (d, J = 2.4 Hz, 1H), 7.74-7.72 (m, 2H), 7.51 (d, J = 8.0 Hz, 1H), 7.28 (s, 1H), 7.09-7.07 (m, 1H), 6.76 (d, J = 12.4 Hz, 1H), 4.79-4.76 (m, 1H), 4.18 (d, J = 5.6 Hz, 2H), 3.77 (d, J = 5.6 Hz, 2H), 3.70-3.66 (m, 4H), 2.57-2.56 (m, 2H), 1.40 (s, 6H), 1.17 (d, J = 6.0 Hz, 6H) ppm |
| 200 | N-(2-((4-(3-((cis)-2,6-dimethylmorpholino)phenyl)thiazol-2-yl)amino)-2-oxoethyl)-4-fluoro-3-(1-hydroxy-2-methylpropan-2-yl)benzamide | 541.1 | $^1$H NMR (400 MHz, METHANOL-d4) δ = 8.00-7.95 (m, 1H), 7.85-7.79 (m, 1H), 7.57-7.53 (m, 1H), 7.40-7.35 (m, 2H), 7.30-7.24 (m, 1H), 7.21-7.11 (m, 1H), 6.96-6.89 (m, 1H), 4.30 (s, 2H), 3.86-3.79 (m, 2H), 3.76 (s, 2H), 3.58 (d, J = 10.4 Hz, 2H), 2.41-2.32 (m, 2H), 1.41 (s, 6H), 1.24 (d, J = 6.0 Hz, 6H) ppm |
| 202 | 4-tert-butyl-N-[2-[[4-[3-[(cis)-2,6- | 508.1 | $^1$H NMR (400 MHz, DMSO-d6) δ = 12.40 (s, 1H), 9.10-9.07(m, 1H), 8.60(d, J = 5.2 Hz, 1H), 8.05 (d, J = 1.6 Hz, |

TABLE 5-continued

| # | Name | LC-MS (m/z) | 1H NMR |
|---|---|---|---|
| | dimethylmorpholin-4-yl]phenyl]thiazol-2-yl]amino]-2-oxo-ethyl]pyridine-2-carboxamide | | 1H), 7.67-7.65(m, 1H), 7.62 (s, 1H), 7.45 (s, 1H), 7.34(d, J = 8.0 Hz, 1H), 7.29-7.25(m, 1H), 6.95-6.92(m, 1H), 4.25(d, J = 6.0 Hz, 2H), 3.74-3.70 (m, 2H), 3.62 (d, J = 11.2 Hz, 2H), 2.29-2.27(m, 2H), 1.33 (s, 9H), 1.17(d, J = 6.0 Hz, 6H) ppm |
| 205 | 2-(tert-butyl)-N-(2-((4-(3-((cis)-2,6-dimethylmorpholino)phenyl)thiazol-2-yl)amino)-2-oxoethyl)isonicotinamide | 508.4 | $^1$H NMR (400 MHz, DMSO-d6) δ = 12.40 (br s, 1H), 9.24-9.21 (m, 1H), 8.68 (d, J = 4.8 Hz, 1H), 7.85 (s, 1H), 7.62-7.61 (m, 2H), 7.45 (s, 1H), 7.34-7.32 (m, 1H), 7.28-7.24 (m, 1H), 6.94-6.93 (m, 1H), 4.23 (d, J = 5.6 Hz, 2H), 3.73-3.69 (m, 2H), 3.63 (d, J = 11.2 Hz, 2H), 2.31-2.26 (m, 2H), 1.35 (s, 9H), 1.18 (d, J = 6.4 Hz, 6H) ppm |
| 128 | N-(2-((4-(3-((cis)-2,6-dimethylmorpholino)phenyl)thiazol-2-yl)amino)-2-oxoethyl)-2,3,4,5-tetrahydrobenzo[b]thiepine-8-carboxamide 1,1-dioxide | 569.5 | $^1$H NMR (400 MHz, DMSO-d6) δ = 12.53-12.28 (m, 1H), 9.19-9.17(m, 1H), 8.43 (d, J = 2.0 Hz, 1H), 8.12-8.09(m, 1H), 7.65-7.55 (m, 2H), 7.45 (d, J = 2.0 Hz, 1H), 7.36-7.32 (m, 1H), 7.30-7.24 (m, 1H), 6.95-6.92(m, 1H), 4.22 (d, J = 5.6 Hz, 2H), 3.78-3.67 (m, 2H), 3.63 (d, J = 10.2 Hz, 2H), 3.46-3.39 (m, 2H), 3.22-3.15 (m, 2H), 2.33-2.23 (m, 2H), 2.16-2.08 (m, 2H), 1.76 (s, 2H), 1.18 (d, J = 6.0 Hz, 6H) ppm |
| 217 | 3-tert-butyl-N-[2-[[4-[3-[(cis)-2,6-dimethylmorpholin-4-yl]phenyl]thiazol-2-yl]amino]-2-oxo-ethyl]benzamide | 507.2 | $^1$H NMR (400 MHz, DMSO-d6) δ = 12.38 (s, 1H), 8.93-8.91(m, 1H), 7.93-7.92(m, 1H), 7.72 (d, J = 7.2 Hz, 1H), 7.63-7.61(m, 2H), 7.44-7.42(m, 2H), 7.36-7.32(m, 1H), 7.8-7.26(m, 1H), 6.94-6.90 (m, 1H), 4.20-4.18(m, 2H), 3.73-3.69 (m, 2H), 3.62 (d, J = 11.2 Hz, 2H), 2.29-2.26 (m, 2H), 1.32(s, 9H), 1.17 (d, J = 6.0 Hz, 6H) ppm |
| 218 | (R)-N-(2-((4-(3-((cis)-2,6-dimethylmorpholino)phenyl)thiazol-2-yl)amino)-2-oxoethyl)-3-(hydroxymethyl)-3-methyl-2,3-dihydro-1H-indene-5-carboxamide | 535.2 | $^1$H NMR (400 MHz, DMSO-d6) δ = 8.81-8.78 (m, 1H), 7.72-7.69 (m, 2H), 7.61 (s, 1H), 7.45 (s, 1H), 7.34-7.33 (m, 1H), 7.28 (d, J = 8.0 Hz, 2H), 6.94 (d, J = 7.2 Hz, 1H), 4.78-4.76 (m, 1H), 4.18 (d, J = 5.6 Hz, 2H), 3.74-3.70 (m, 2H), 3.63 (d, J = 11.2 Hz, 2H), 3.39 (d, J = 4.8 Hz, 2H), 2.90-2.86 (m, 2H), 2.32-2.27 (m, 2H), 2.20-2.17 (m, 1H), 1.77-1.71(m, 1H), 1.24 (s, 3H), 1.18 (s, 3H), 1.17 (s, 3H) ppm |
| 219 | (S)-N-(2-((4-(3-((cis)-2,6-dimethylmorpholino)phenyl)thiazol-2-yl)amino)-2-oxoethyl)-3-(hydroxymethyl)-3-methyl-2,3-dihydro-1H-indene-5-carboxamide | 535.2 | $^1$H NMR (400 MHz, DMSO-d6) δ = 8.81-8.78 (m, 1H), 7.70-7.69 (m, 2H), 7.61 (s, 1H), 7.47 (s, 1H), 7.34-7.33 (m, 1H), 7.28 (d, J = 8.0 Hz, 2H), 6.94 (d, J = 7.6 Hz, 1H), 4.78-4.76 (m, 1H), 4.18 (d, J = 5.2 Hz, 2H), 3.74-3.70 (m, 2H), 3.63 (d, J = 11.6 Hz, 2H), 3.38 (s, 2H), 2.88-2.86 (m, 2H), 2.32-2.27(m, 2H), 2.22-2.17 (m, 1H), 1.77-1.71(m, 1H), 1.24 (s, 3H), 1.18 (s, 3H), 1.17(s, 3H) ppm |
| 238 | N-(2-((4-(3-((cis)-2,6-dimethylmorpholino)phenyl)thiazol-2-yl)amino)-2-oxoethyl)-3-(1-hydroxy-2-methylpropan-2-yl)-4-methylbenzamide | 537.0 | $^1$H NMR (400 MHz, DMSO-d6) δ = 12.42-12.26 (m, 1H), 12.47-12.24 (m, 1H), 8.85-8.76 (m, 1H), 8.47-8.36 (m, 1H), 7.85(d, J = 1.4 Hz, 1H), 7.67-7.57 (m, 2H), 7.45 (s, 1H), 7.36-7.32 (m, 1H), 7.30-7.24 (m, 1H), 7.21 (d, J = 8.0 Hz, 1H), 6.99-6.88 (m, 1H), 4.70 (d, J = 5.4 Hz, 1H), 4.17 d, J = 5.8 Hz, 2H), 3.75-3.69 (m, 2H), 3.63 (d, J = 5.6 Hz, 4H), 2.53-2.53(m, 3H), 2.33-2.25 (m, 1H), 1.35 (s, 6H), 1.18 (d, J = 6.1 Hz, 6H) ppm |
| 244 | 4-chloro-N-[2-[[4-[3-[(cis)-2,6-dimethylmorpholin-4-yl]phenyl]thiazol-2-yl]amino]-2-oxo-ethyl]-3-(2-hydroxy-1,1-dimethyl-ethyl)benzamide | 557.1 | $^1$H NMR (400 MHz, DMSO-d6) δ = 12.39 (s, 1H), 9.00-8.97(m, 1H), 7.96(d, J = 2.0 Hz, 1H), 7.75-7.73(m, 1H), 7.61(s, 1H), 7.50 (d, J = 8.4 Hz, 1H), 7.44(s, 1H), 7.36-7.31 (m, 1H), 7.30-7.24 (m, 1H), 6.94-6.93(m, 1H), 4.76-4.73(m, 1H), 4.18 (d, J = 6.0 Hz, 2H), 3.77 (d, J = 6.0 Hz, 2H), 3.74-3.71(m, 2H), 3.62 (d, J = 12.0 Hz, 2H), 2.32-2.26 (m, 2H), 1.41 (s, 6H), 1.17 (d, J = 6.0 Hz, 6H) ppm |
| 247 | 3-(2-hydroxy-1,1-dimethyl-ethyl)-N-[2-[[4-[3-(4-hydroxy-1-piperidyl)phenyl]thiazol-2-yl]amino]-2-oxo-ethyl]benzamide | 509.2 | $^1$H NMR (400 MHz, METHANOL-d4) δ = 8.13 (s, 1H), 8.02 (d, J = 8.0 Hz, 1H), 7.97-7.97(m, 1H), 7.74 (d, J = 7.6 Hz, 1H), 7.64-7.57(m, 3H), 7.53-7.50 (m, 1H), 7.46-7.42 (m, 1H), 4.32 (s, 2H), 4.11-4.06(m, 1H), 3.90-3.84(m, 2H), 3.62-3.56(m, 4H), 2.26-2.19(m, 2H), 2.04-1.97(m, 2H), 1.35(s, 6H) ppm |
| 125 | N-(2-((4-(3-((cis)-2,6-dimethylmorpholino)phenyl)thiazol-2-yl)amino)-2-oxoethyl)-3-(isopropylsulfonyl)-4-methylbenzamide | 571.1 | $^1$H NMR (400 MHz, DMSO-d6) δ = 12.41(s, 1H), 9.20-9.17(m, 1H), 8.38 (d, J = 2.0 Hz, 1H), 8.14-8.11(m, 1H), 7.63-7.61(m, 2H), 7.45 (s, 1H), 7.34-7.31 (m, 1H), 7.28-7.24 (m, 1H), 6.94-6.92(m, 1H), 4.21 (d, J = 5.6 Hz, 2H), 3.75-3.68(m, 2H), 3.62 (d, J = 11.6 Hz, 2H), 3.53 (s, 1H), 2.68(s, 3H), 2.32-2.26 (m, 2H), 1.19-1.16(m, 12H) ppm |
| 126 | 3-isopropylsulfonyl-N-[2-[[4-(3-morpholinophenyl)thiazol-2-yl]amino]-2-oxoethyl]benzamide | 529.1 | $^1$H NMR (400 MHz, DMSO-d6) δ = 12.56-12.37 (m, 1H), 9.29-9.26 (m, 1H), 8.42-8.35 (m, 1H), 8.27 (d, J = 8.0 Hz, 1H), 8.05 (d, J = 8.0 Hz, 1H), 7.90-7.76 (m, 1H), 7.62 (s, 1H), 7.47 (s, 1H), 7.41-7.34 (m, 1H), 7.32-7.22 (m, 1H), 6.94-6.91 (m, 1H), 4.23 (d, J = 5.6 Hz, 2H), 3.85-3.71 (m, 4H), 3.56-3.46 (m, 1H), 3.19-3.12 (m, 4H), 1.19 (d, J = 6.8 Hz, 6H) ppm |

Example 105. Preparation of Compounds of the Invention

The following compounds in Table 6 were prepared using standard chemical manipulations and procedures similar to those used for the preparation of Compound 67.

TABLE 6

| # | Name | LC-MS (m/z) | 1H NMR |
|---|---|---|---|
| 147 | 3-(1-cyanocyclobutyl)-N-(2-((4-(2-methyl-1-oxo-1,2-dihydroisoquinolin-7-yl)thiazol-2-yl)amino)-2-oxoethyl)benzamide | 498.3 | $^1$H NMR (400 MHz, DMSO-d6) δ = 12.77-12.38 (m, 1H), 9.10-9.08(m, 1H), 8.83 (d, J = 1.8 Hz, 1H), 8.23-8.20(m, 1H), 8.01-7.96 (m, 1H), 7.93-7.88 (m, 1H), 7.79 (s, 1H), 7.72 (d, J = 8.4 Hz, 1H), 7.69-7.65 (m, 1H), 7.62-7.56 (m, 1H), 7.49 (d, J = 7.6 Hz, 1H), 6.68-6.61 (m, 1H), 4.24 (d, J = 5.6 Hz, 2H), 3.53 (s, 3H), 2.84-2.75 (m, 2H), 2.73-2.67 (m, 2H), 2.34-2.32(m, 1H), 2.10-2.00 (m, 1H) ppm |
| 173 | (R)-3-(hydroxymethyl)-3-methyl-N-(2-((4-(4-methyl-3,4-dihydro-2H-benzo[b][1,4]oxazin-6-yl)thiazol-2-yl)amino)-2-oxoethyl)-2,3-dihydro-1H-indene-5-carboxamide | 493.0 | $^1$H NMR (400 MHz, DMSO-d6) δ = 12.34 (br s, 1H), 8.79-8.77 (m, 1H), 7.71-7.68 (m, 2H), 7.40 (s, 1H), 7.28 (d, J = 7.6 Hz, 1H), 7.20 (d, J = 2.0 Hz, 1H), 7.13-7.10 (m, 1H), 6.70 (d, J = 8.4 Hz, 1H), 4.78-4.75 (m, 1H), 4.25-4.23 (m, 2H), 4.16 (d, J = 5.6 Hz, 2H), 3.37 (d, J = 6.0 Hz, 2H), 3.26-3.24 (m, 2H), 2.88-2.86 (m, 5H), 2.21-2.14 (m, 1H), 1.76-1.68 (m, 1H), 1.23 (s, 3H) ppm |
| 174 | (S)-3-(hydroxymethyl)-3-methyl-N-(2-((4-(4-methyl-3,4-dihydro-2H-benzo[b][1,4]oxazin-6-yl)thiazol-2-yl)amino)-2-oxoethyl)-2,3-dihydro-1H-indene-5-carboxamide | 493.0 | $^1$H NMR (400 MHz, DMSO-d6) δ = 12.33 (br d, J = 5.6 Hz, 1H), 8.80-8.77 (m, 1H), 7.74-7.68 (m, 2H), 7.40 (s, 1H), 7.28-7.26(m, 1H), 7.20 (d, J = 2.0 Hz, 1H), 7.13-7.10 (m, 1H), 6.70 (d, J = 8.4 Hz, 1H), 4.78-4.76 (m, 1H), 4.25-4.23 (m, 2H), 4.16 (d, J = 5.6 Hz, 2H), 3.38-3.36(m, 2H), 3.26-3.24 (m, 2H), 2.88 (s, 5H), 2.21-2.14 (m, 1H), 1.76-1.68 (m, 1H), 1.23(s, 3H) ppm |
| 175 | (R)-3-(hydroxymethyl)-3-methyl-N-(2-((4-(1-methyl-1H-benzo[d]imidazol-6-yl)thiazol-2-yl)amino)-2-oxoethyl)-2,3-dihydro-1H-indene-5-carboxamide | 476.1 | $^1$H NMR (400 MHz, DMSO-d6) δ = 12.43 (s, 1H), 8.82-8.80(m, 1H), 8.21 (s, 1H), 8.08 (d, J = 1.6 Hz, 1H), 7.81-7.80 (m, 1H), 7.74-7.70 (m, 2H), 7.68 (d, J = 8.4 Hz, 1H), 7.62 (s, 1H), 7.29 (d, J = 7.6 Hz, 1H), 4.79-4.77 (m, 1H), 4.20-4.18(m, 2H), 3.88 (s, 3H), 3.39-3.38 (m, 2H), 2.94-2.83 (m, 2H), 2.23-2.13 (m, 1H), 1.77-1.72 (m, 1H), 1.25 (s, 3H) ppm |
| 257 | (S)-3-(hydroxymethyl)-3-methyl-N-(2-((4-(1-methyl-1H-benzo[d]imidazol-6-yl)thiazol-2-yl)amino)-2-oxoethyl)-2,3-dihydro-1H-indene-5-carboxamide | 476.1 | $^1$H NMR (400 MHz, DMSO-d6) δ = 8.82 (s, 1H), 8.21 (s, 1H), 8.08 (s, 1H), 7.80-7.79 (m, 1H), 7.75-7.58 (m, 4H), 7.29-7.28 (m, 1H), 4.93-4.62 (m, 1H), 4.20-4.19 (m, 2H), 3.88 (s, 3H), 3.37-3.32 (m, 2H), 2.88-2.87 (m, 2H), 2.19-2.18 (m, 1H), 1.74-1.73 (m, 1H), 1.24 (s, 3H) ppm |
| 176 | (R)-3-(hydroxymethyl)-3-methyl-N-(2-((4-(2-methyl-1-oxo-1,2,3,4-tetrahydroisoquinolin-7-yl)thiazol-2-yl)amino)-2-oxoethyl)-2,3-dihydro-1H-indene-5-carboxamide | 505.1 | $^1$H NMR (400 MHz, DMSO-d6) δ = 12.53-12.38 (m, 1H), 8.81-8.78(m, 1H), 8.46 (d, J = 1.6 Hz, 1H), 7.98-7.96(m, 1H), 7.71-7.66(m, 3H), 7.35 (d, J = 8.0 Hz, 1H), 7.28 (d, J = 7.6 Hz, 1H), 4.78-4.75(m, 1H), 4.17 (d, J = 6.0 Hz, 2H), 3.58-3.55(m, 2H), 3.38 (d, J = 5.6 Hz, 2H), 3.04(s, 3H), 3.01-2.98(m, 2H), 2.90-2.86(m, 2H), 2.21-2.15(m, 1H), 1.76-1.69(m, 1H), 1.23 (s, 3H) ppm |
| 258 | (S)-3-(hydroxymethyl)-3-methyl-N-(2-((4-(2-methyl-1-oxo-1,2,3,4-tetrahydroisoquinolin-7-yl)thiazol-2-yl)amino)-2-oxoethyl)-2,3-dihydro-1H-indene-5-carboxamide | 505.1 | $^1$H NMR (400 MHz, DMSO-d6) δ = 12.49 (br s, 1H), 8.82 (t, J = 5.6 Hz, 1H), 8.46 (d, J = 1.9 Hz, 1H), 7.98 (dd, J = 2.0, 7.9 Hz, 1H), 7.73-7.66 (m, 3H), 7.35 (d, J = 8.0 Hz, 1H), 7.28 (d, J = 7.6 Hz, 1H), 4.78 (t, J = 5.4 Hz, 1H), 4.17 (d, J = 5.8 Hz, 2H), 3.57 (t, J = 6.7 Hz, 2H), 3.37 (br d, J = 6.4 Hz, 2H), 3.05 (s, 3H), 3.00 (t, J = 6.6 Hz, 2H), 2.91-2.85 (m, 2H), 2.22-2.14 (m, 1H), 1.72 (td, J = 8.1, 12.7 Hz, 1H), 1.23 (s, 3H) ppm |
| 177 | (R)-3-(hydroxymethyl)-3-methyl-N-(2-((4-(2-methyl-1-oxo-1,2-dihydroisoquinolin-7-yl)thiazol-2-yl)amino)-2-oxoethyl)-2,3-dihydro-1H-indene-5-carboxamide | 503.3 | $^1$H NMR (400 MHz, DMSO-d6) δ = 12.52(br s, 1H), 8.83-8.80(m, 2H), 8.22-8.19(m, 1H), 7.78(s, 1H), 7.71-7.69(m, 3H), 7.49 (d, J = 7.2 Hz, 1H), 7.28 (d, J = 8.0 Hz, 1H), 6.63 (d, J = 7.6 Hz, 1H), 4.80-4.76(m, 1H), 4.19 (d, J = 5.6 Hz, 2H), 3.52(s, 3H), 3.38-3.37(m, 2H), 2.90-2.86(m, 2H), 2.21-2.15(m, 1H), 1.76-1.69(m, 1H), 1.23(s, 3H) ppm |

TABLE 6-continued

| # | Name | LC-MS (m/z) | 1H NMR |
|---|---|---|---|
| 181 | (S)-3-(hydroxymethyl)-3-methyl-N-(2-((4-(2-methyl-1-oxo-1,2-dihydroisoquinolin-7-yl)thiazol-2-yl)amino)-2-oxoethyl)-2,3-dihydro-1H-indene-5-carboxamide | 503.3 | $^1$H NMR (400 MHz, DMSO-d6) δ = 12.52 (s, 1H), 8.82-8.80(m, 2H), 8.22-8.20(m, 1H), 7.78 (s, 1H), 7.71-7.69 (m, 3H), 7.48 (d, J = 7.2 Hz, 1H), 7.28 (d, J = 7.6 Hz, 1H), 6.63 (d, J = 7.2 Hz, 1H), 4.78-4.75(m, 1H), 4.19 (d, J = 6.0 Hz, 2H), 3.52(s, 3H), 3.38 (d, J = 6.0 Hz, 2H), 2.89-2.86(m, 2H), 2.20-2.15(m, 1H), 1.76-7.71(m, 1H), 1.23(s, 3H) ppm |
| 178 | (R)-3-(hydroxymethyl)-N-(2-((4-(imidazo[1,2-a]pyridin-7-yl)thiazol-2-yl)amino)-2-oxoethyl)-3-methyl-2,3-dihydro-1H-indene-5-carboxamide | 461.9 | $^1$H NMR (400 MHz, DMSO-d6) δ = 12.60-12.35 (m, 1H), 8.89-8.77 (m, 1H), 8.58 (d, J = 7.2 Hz, 1H), 8.04 (s, 1H), 7.95 (s, 1H), 7.83 (s, 1H), 7.76-7.67 (m, 2H), 7.59 (d, J = 0.8 Hz, 1H), 7.48-7.39 (m, 1H), 7.28 (d, J = 7.6 Hz, 1H), 4.77 (s, 1H), 4.20(d, J = 5.6 Hz, 2H), 3.38 (s, 2H), 2.93-2.85 (m, 2H), 2.23-2.14 (m, 1H), 1.78-1.68 (m, 1H), 1.24 (s, 3H) ppm |
| 259 | (S)-3-(hydroxymethyl)-N-(2-((4-(imidazo[1,2-a]pyridin-7-yl)thiazol-2-yl)amino)-2-oxoethyl)-3-methyl-2,3-dihydro-1H-indene-5-carboxamide | 461.9 | $^1$H NMR (400 MHz, DMSO-d6) δ = 12.46 (s, 1H), 8.86-8.79 (m, 1H), 8.61-8.56 (m, 1H), 8.13 (s, 1H), 8.04 (s, 1H), 7.95 (s, 1H), 7.84 (s, 1H), 7.74-7.67 (m, 2H), 7.60 (d, J = 1.2 Hz, 1H), 7.47-7.40 (m, 1H), 7.28 (d, J = 8.0 Hz, 1H), 4.81-4.73 (m, 1H), 4.20 (d, J = 5.8 Hz, 2H), 3.38 (d, J = 4.4 Hz, 2H), 2.94-2.83 (m, 2H), 2.23-2.14 (m, 1H), 1.78-1.68 (m, 1H), 1.24 (s, 3H) ppm |
| 179 | (R)-3-(hydroxymethyl)-3-methyl-N-(2-((4-(1-methyl-1H-indazol-6-yl)thiazol-2-yl)amino)-2-oxoethyl)-2,3-dihydro-1H-indene-5-carboxamide | 476.1 | $^1$H NMR (400 MHz, DMSO-d6) δ = 12.47 (s, 1H), 8.83-8.82(m, 1H), 8.11 (s, 1H), 8.04 (d, J = 1.2 Hz, 1H), 7.82-7.67 (m, 5H), 7.28 (d, J = 8.0 Hz, 1H), 4.79-4.77(m, 1H), 4.19 (d, J = 5.6 Hz, 2H), 4.07 (s, 3H), 3.38 (d, J = 6.4 Hz, 2H), 2.93-2.81(m, 2H), 2.25-2.12 (m, 1H), 1.77-1.69 (m, 1H), 1.24 (s, 3H) ppm |
| 261 | (S)-3-(hydroxymethyl)-3-methyl-N-(2-((4-(1-methyl-1H-indazol-6-yl)thiazol-2-yl)amino)-2-oxoethyl)-2,3-dihydro-1H-indene-5-carboxamide | 476.1 | $^1$H NMR (400 MHz, DMSO-d6) δ = 12.62-12.12 (m, 1H), 8.83-8.80 (m, 1H), 8.11 (s, 1H), 8.04 (s, 1H), 7.81-7.77 (m, 1H), 7.75-7.69 (m, 4H), 7.29-7.27 (d, J = 8.0 Hz, 1H), 4.78-4.76 (m, 1H), 4.19-4.18 (d, J = 5.6 Hz, 2H), 4.07 (s, 3H), 3.38-3.37 (d, J = 4.8 Hz, 2H), 2.94-2.81 (m, 2H), 2.21-2.15(m, 1H), 1.81-1.65 (m, 1H), 1.24 (s, 3H) ppm |
| 180 | (R)-3-(hydroxymethyl)-3-methyl-N-(2-((4-(1-methyl-2-oxo-1,2,3,4-tetrahydroquinolin-7-yl)thiazol-2-yl)amino)-2-oxoethyl)-2,3-dihydro-1H-indene-5-carboxamide | 505.0 | $^1$H NMR (400 MHz, DMSO-d6) δ = 8.84-8.81(m, 1H), 7.76-7.65 (m, 3H), 7.62-7.53 (m, 2H), 7.29-7.27(m, 2H), 4.79 (s, 1H), 4.19-4.17(m, 2H), 4.13-4.05 (m, 1H), 3.38 (s, 1H), 3.17 (s, 3H), 2.91-2.87(m, 4H), 2.59-2.57(m, 2H), 2.26-2.11 (m, 1H), 1.75-1.71(m, 1H), 1.24 (s, 3H) ppm |
| 260 | (S)-3-(hydroxymethyl)-3-methyl-N-(2-((4-(1-methyl-2-oxo-1,2,3,4-tetrahydroquinolin-7-yl)thiazol-2-yl)amino)-2-oxoethyl)-2,3-dihydro-1H-indene-5-carboxamide | 505.0 | $^1$H NMR (400 MHz, DMSO-d6) δ = 12.69-11.99 (m, 1H), 8.81-8.80 (m, 1H), 7.75-7.65 (m, 3H), 7.61-7.53 (m, 2H), 7.28-7.27 (m, 2H), 4.78-4.77 (m, 1H), 4.18-4.17(m, 2H), 4.14-4.05 (m, 1H), 3.38-3.37 (m, 3H), 3.18-3.17 (m, 1H), 2.89-2.88 (m, 4H), 2.57-2.56 (m, 2H), 2.26-2.13 (m, 1H), 1.73-1.72 (m, 1H), 1.24 (s, 3H) ppm |

Example 106. Preparation of (S)—N-(2-((4-(6-((cis)-2,6-dimethylmorpholino)pyridin-2-yl)thiazol-2-yl)amino)-2-oxoethyl)-3-(hydroxymethyl)-3-methyl-2,3-dihydrobenzofuran-5-carboxamide (Compound 133) and (R)—N-(2-((4-(6-((cis)-2,6-dimethylmorpholino)pyridin-2-yl)thiazol-2-yl)amino)-2-oxoethyl)-3-(hydroxymethyl)-3-methyl-2,3-dihydrobenzofuran-5-carboxamide (Compound 132)

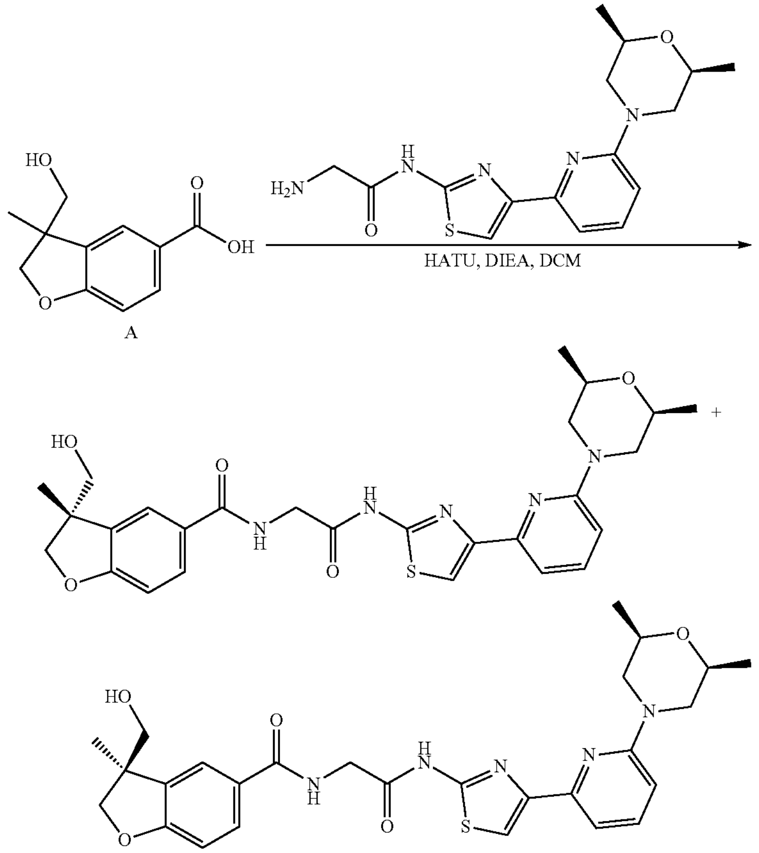

To a solution of 2-amino-N-[4-[6-[(cis)-2,6-dimethylmorpholin-4-yl]-2-pyridyl]thiazol-2-yl]acetamide hydrochloride salt (200 mg, 520.98 umol), 3-(hydroxymethyl)-3-methyl-2,3-dihydrobenzofuran-5-carboxylic acid (162.71 mg, 781.46 umol) and HATU (297.14 mg, 781.46 umol) in DCM (3 mL) was added DIEA (336.66 mg, 2.60 mmol, 453.72 uL). The mixture was stirred at 30° C. for 2 hrs. The reaction mixture was concentrated under reduced pressure to give a residue. The residue was triturated with MeOH (3.0 mL) and MTBE (3.0 mL), the solid was collected by filtered and concentrated under reduced pressure to give an off-white solid. The crude product was separated by SFC (column: DAICEL CHIRALCEL OD (250 mm*30 mm, 10 um); mobile phase: [0.1% $NH_3H2O$ IPA]; B %: 40%-40%, 3.55 min; 150 min) to give peak 1 and peak 2. Peak 1 was concentrated under reduced pressure and lyophilized to give Compound 133 (27.53 mg, 9.7% yield) as an off-white solid. Peak 2 was concentrated under reduced pressure and lyophilized to give Compound 132 (39.55 mg, 14% yield) as a white solid.

Compound 133:

LCMS (ESI) m/z: $[M+H]^+$=538.2.

$^1H$ NMR (400 MHz, DMSO-$d_6$) δ=12.35 (s, 1H), 8.72-8.69 (m, 1H), 7.76-7.72 (m, 3H), 7.71-7.60 (m, 1H), 7.25 (d, J=7.2 Hz, 1H), 6.83-6.78 (m, 2H), 5.07-5.04 (m, 1H), 4.57 (d, J=9.2 Hz, 1H), 4.26-4.14 (m, 5H), 3.65-3.61 (m, 2H), 3.60-3.42 (m, 2H), 2.44-2.38 (m, 2H), 1.31 (s, 3H), 1.18 (d, J=6.0 Hz, 6H) ppm.

Chiral SFC: OD-3-IPA (DEA)-40-3ML-35T·lcm; Rt=1.614 min

Compound 132:

LCMS (ESI) m/z: $[M+H]^+$=538.2.

$^1H$ NMR (400 MHz, DMSO-$d_6$) δ=12.35 (s, 1H), 8.72-8.69 (m, 1H), 7.76-7.73 (m, 3H), 7.62-7.60 (m, 1H), 7.25 (d, J=7.2 Hz, 1H), 6.83-6.78 (m, 2H), 5.07-5.04 (m, 1H), 4.57 (d, J=9.2 Hz, 1H), 4.26-4.14 (m, 5H), 3.65-3.61 (m, 2H), 3.60-3.42 (m, 2H), 2.44-2.38 (m, 2H), 1.30 (s, 3H), 1.18 (d, J=6.4 Hz, 6H) ppm.

Chiral SFC: OD-3-IPA (DEA)-40-3ML-35T·lcm; Rt=2.052 min.

Example 107. Preparation of Compounds of the Invention

The following compounds in Table 7 were prepared using standard chemical manipulations and procedures similar to those used for the preparation of Compound 133 and Compound 132.

TABLE 7

| # | Name | LC-MS (m/z) | 1H NMR |
|---|---|---|---|
| 134 | N-[2-[[4-[6-[(cis)-2,6-dimethylmorpholin-4-yl]-2-pyridyl]thiazol-2-yl]amino]-2-oxo-ethyl]-3-[(3S)-3-hydroxytetrahydrofuran-3-yl]benzamide | 538.0 | $^1$H NMR (400 MHz, DMSO-d6) δ = 12.55-12.25 (m, 1H), 8.95-8.93 (m, 1H), 8.03 (s, 1H), 7.79-7.76 (m, 2H), 7.69 (d, J = 8.0 Hz, 1H), 7.64-7.60 (m, 1H), 7.48-7.44 (m, 1H), 7.25 (d, J = 7.2 Hz, 1H), 6.80 (d, J = 8.4 Hz, 1H), 5.52 (s, 1H), 4.25 (br d, J = 11.6 Hz, 2H), 4.19 (d, J = 5.6 Hz, 2H), 4.04-4.01 (m, 2H), 3.84-3.77 (m, 2H), 3.66-3.59 (m, 2H), 2.44-2.38 (m, 2H), 2.31-2.27 (m, 1H), 2.18-2.12 (m, 1H), 1.18 (d, J = 6.0 Hz, 6H) ppm |
| 140 | (3S)-N-[2-[[4-[6-[(cis)-2,6-dimethylmorpholin-4-yl]-2-pyridyl]thiazol-2-yl]amino]-2-oxo-ethyl]-3-[(1S)-1-hydroxyethyl]indane-5-carboxamide | 536.2 | $^1$H NMR (400 MHz, DMSO-d6) δ = 12.40-12.36 (m, 1H), 8.79-8.74 (m, 1H), 8.47-8.46 (m, 1H), 7.93 (s, 1H), 7.76 (s, 1H), 7.71-7.60 (m, 2H), 7.29-7.24 (m, 2H), 6.80 (d, J = 8.4 Hz, 1H), 4.73 (d, J = 4.8 Hz, 1H), 4.25 (br d, J = 13.2 Hz, 2H), 4.16 (br d, J = 6.0 Hz, 2H), 3.85-3.81 (m, 1H), 3.66-3.59 (m, 2H), 3.20-3.14 (m, 1H), 2.94-2.79 (m, 2H), 2.44-2.38 (m, 2H), 2.12-2.06 (m, 1H), 1.88-1.83 (m, 1H), 1.18 (d, J = 6.0 Hz, 6H), 1.02 (d, J = 6.4 Hz, 3H) ppm |
| 141 | (3R)-N-[2-[[4-[6-[(cis)-2,6-dimethylmorpholin-4-yl]-2-pyridyl]thiazol-2-yl]amino]-2-oxo-ethyl]-3-[(1S)-1-hydroxyethyl]indane-5-carboxamide | 536.3 | $^1$H NMR (400 MHz, DMSO-d6) δ = 12.38 (br s, 1H), 8.80-8.77 (m, 1H), 7.83 (s, 1H), 7.77 (s, 1H), 7.69 (d, J = 8.0 Hz, 1H), 7.65-7.61 (m, 1H), 7.29-7.25 (m, 2H), 6.81 (d, J = 8.4 Hz, 1H), 4.52 (d, J = 4.8 Hz, 1H), 4.26 (br d, J = 11.6 Hz, 2H), 4.18 (d, J = 5.6 Hz, 2H), 4.01-3.97 (m, 1H), 3.67-3.59 (m, 2H), 3.17-3.13 (m, 1H), 2.96-2.88 (m, 1H), 2.84-2.77 (m, 1H), 2.45-2.39 (m, 2H), 2.09-2.04 (m, 2H), 1.19 (d, J = 6.0 Hz, 6H), 1.10 (d, J = 6.0 Hz, 3H) ppm |
| 142 | (3S)-N-[2-[[4-[6-[(cis)-2,6-dimethylmorpholin-4-yl]-2-pyridyl]thiazol-2-yl]amino]-2-oxo-ethyl]-3-[(1R)-1-hydroxyethyl]indane-5-carboxamide | 536.2 | $^1$H NMR (400 MHz, DMSO-d6) δ = 12.45-12.24 (m, 1H), 8.79-8.76 (m, 1H), 7.81-7.76 (m, 2H), 7.68-7.59 (m, 2H), 7.28-7.24 (m, 2H), 6.79 (d, J = 8.8 Hz, 1H), 4.52 (d, J = 4.8 Hz, 1H), 4.25 (br d, J = 11.6 Hz, 2H), 4.16 (d, J = 6.0 Hz, 2H), 4.01-3.95 (m, 1H), 3.64-3.60 (m, 2H), 3.16-3.13 (m, 1H), 2.95-2.87 (m, 1H), 2.83-2.75 (m, 1H), 2.43-2.37 (m, 2H), 2.08-2.02(m, 2H), 1.18 (d, J = 6.0 Hz, 6H), 1.09 (d, J = 6.0 Hz, 3H) ppm |
| 145 | N-[2-[[4-[6-[(cis)-2,6-dimethylmorpholin-4-yl]-2-pyridyl]thiazol-2-yl]amino]-2-oxo-ethyl]-2-fluoro-5-(2-hydroxy-1,1-dimethyl-ethyl)benzamide | 542.2 | $^1$H NMR (400 MHz, DMSO-d6) δ = 12.40 (s, 1H), 8.60-8.51 (m, 1H), 7.80-7.77 (m, 1H), 7.71 (dd, J = 2.5, 7.2 Hz, 1H), 7.66-7.60 (m, 1H), 7.59-7.54 (m, 1H), 7.28-7.21 (m, 2H), 6.81 (d, J = 8.4 Hz, 1H), 4.26 (br d, J = 11.7 Hz, 2H), 4.22 (br d, J = 5.9 Hz, 2H), 3.68-3.59 (m, 2H), 3.43 (s, 2H), 2.42 (br s, 2H), 1.24 (s, 6H), 1.19 (d, J = 6.1 Hz, 6H) ppm |
| 152 | (R)-3-cyano-N-(2-((4-(6-((cis)-2,6-dimethylmorpholino)pyridin-2-yl)thiazol-2-yl)amino)-2-oxoethyl)-3-methyl-2,3-dihydro-1H-indene-5-carboxamide | 531.2 | $^1$H NMR (400 MHz, DMSO-d6) δ = 12.58-12.21 (m, 1H), 8.99 (t, J = 5.8 Hz, 1H), 8.00 (d, J = 1.1 Hz, 1H), 7.87 (dd, J = 1.6, 7.9 Hz, 1H), 7.77 (s, 1H), 7.62 (dd, J = 7.5, 8.4 Hz, 1H), 7.45 (d, J = 7.9 Hz, 1H), 7.26 (d, J = 7.2 Hz, 1H), 6.80 (d, J = 8.6 Hz, 1H), 4.25 (br d, J = 11.2 Hz, 2H), 4.20 (dd, J = 1.9, 5.7 Hz, 2H), 3.68-3.57 (m, 2H), 3.13-2.97 (m, 2H), 2.65-2.57 (m, 1H), 2.41 (dd, J = 10.6, 12.7 Hz, 2H), 2.24 (td, J = 7.2, 13.1 Hz, 1H), 1.66 (s, 3H), 1.18 (d, J = 6.2 Hz, 6H) ppm |
| 262 | (S)-3-cyano-N-(2-((4-(6-((cis)-2,6-dimethylmorpholino)pyridin-2-yl)thiazol-2-yl)amino)-2-oxoethyl)-3-methyl-2,3-dihydro-1H-indene-5-carboxamide | 531.2 | $^1$H NMR (400 MHz, DMSO-d6) δ = 12.41 (s, 1H), 8.99 (t, J = 5.7 Hz, 1H), 7.99 (d, J = 1.1 Hz, 1H), 7.86 (dd, J = 1.5, 7.9 Hz, 1H), 7.76 (s, 1H), 7.61 (dd, J = 7.5, 8.4 Hz, 1H), 7.44 (d, J = 7.8 Hz, 1H), 7.25 (d, J = 7.2 Hz, 1H), 6.79 (d, J = 8.6 Hz, 1H), 4.30-4.16 (m, 4H), 3.69-3.56 (m, 2H), 3.05 (br t, J = 7.0 Hz, 2H), 2.63-2.60 (m, 1H), 2.41 (dd, J = 10.8, 12.7 Hz, 2H), 2.24 (td, J = 7.2, 13.1 Hz, 1H), 1.65 (s, 3H), 1.17 (d, J = 6.2 Hz, 6H), 1.03 (d, J = 6.1 Hz, 1H) ppm |
| 153 | (R)-4-cyano-N-(2-((4-(6-((cis)-2,6-dimethylmorpholino)pyridin-2-yl)thiazol-2-yl)amino)-2-oxoethyl)-4-methylchroman-6-carboxamide | 547.3 | $^1$H NMR (400 MHz, DMSO-d6) δ = 12.41 (s, 1H), 8.94-8.92 (m, 1H), 8.09 (d, J = 2.0 Hz, 1H), 7.82-7.77 (m, 2H), 7.64-7.62 (m, 1H), 7.26 (d, J = 7.2 Hz, 1H), 6.96 (d, J = 8.8 Hz, 1H), 6.80 (d, J = 8.4 Hz, 1H), 4.39-4.33 (m, 1H), 4.31-4.22 (m, 3H), 4.21-4.16 (m, 2H), 3.68-3.58 (m, 2H), 2.45-2.38 (m, 3H), 2.24-2.17 (m, 1H), 1.80 (s, 3H), 1.19 (s, 3H), 1.17 (s, 3H) ppm |
| 159 | (R)-3-cyano-N-(2-((4-(6-((cis)-2,6-dimethylmorpholino)pyridin-2-yl)thiazol-2- | 547.3 | $^1$H NMR (400 MHz, DMSO-d6) δ = 12.91-11.88 (m, 1H), 8.99-8.96 (m, 1H), 7.98 (d, J = 1.2 Hz, 1H), 7.88-7.86 (m, 1H), 7.77 (s, 1H), 7.64-7.60 (m, 1H), 7.43 (d, J = 8.0 Hz, 1H), 7.26 (d, J = 7.2 Hz, 1H), 6.80 (d, J = 8.4 Hz, 1H), |

TABLE 7-continued

| # | Name | LC-MS (m/z) | 1H NMR |
|---|---|---|---|
| | yl)amino)-2-oxoethyl)-3-(hydroxymethyl)-2,3-dihydro-1H-indene-5-carboxamide | | 5.80-5.72 (m, 1H), 4.29-4.17 (m, 4H), 3.73-3.57 (m, 4H), 3.05-3.01 (m, 2H), 2.48-2.38 (m, 4H), 1.19 (s, 3H), 1.17 (s, 3H) ppm |
| 160 | N-(2-((4-(6-((cis)-2,6-dimethylmorpholino)pyridin-2-yl)thiazol-2-yl)amino)-2-oxoethyl)-3-((3R,4S)-4-hydroxytetrahydrofuran-3-yl)benzamide | 538.2 | $^1$H NMR (400 MHz, DMSO-d6) δ = 12.40 (br d, J = 1.6 Hz, 1H), 8.94-8.91 (m, 1H), 7.80-7.75 (m, 3H), 7.64-7.60 (m, 1H), 7.46-7.42 (m, 2H), 7.25 (d, J = 7.2 Hz, 1H), 6.80 (d, J = 8.4 Hz, 1H), 5.32 (d, J = 4.8 Hz, 1H), 4.29-4.23 (m, 3H), 4.20-4.16 (m, 3H), 4.00-3.96 (m, 1H), 3.78-3.63 (m, 1H), 3.62-3.56 (m, 3H), 3.28-3.23 (m, 1H), 2.44-2.38 (m, 2H), 1.18 (d, J = 6.0 Hz, 6H) ppm |
| 161 | (3S)-N-[2-[[4-[6-[(cis)-2,6-dimethylmorpholin-4-yl]-2-pyridyl]thiazol-2-yl]amino]-2-oxo-ethyl]-3-(hydroxymethyl)indane-5-carboxamide | 522.2 | $^1$H NMR (400 MHz, DMSO-d6) δ = 12.41-12.32 (m, 1H), 8.79-8.77 (m, 1H), 8.48-8.44 (m, 1H), 7.82 (s, 1H), 7.76 (s, 1H), 7.70-7.68 (m, 1H), 7.64-7.60 (m, 1H), 7.30 (d, J = 8.0 Hz, 1H), 7.25 (d, J = 7.6 Hz, 1H), 6.80 (d, J = 8.8 Hz, 1H), 4.78-4.75 (m, 1H), 4.25 (br d, J = 11.6 Hz, 2H), 4.16 (br d, J = 6.0 Hz, 2H), 3.67-3.61 (m, 3H), 3.52-3.49 (m, 1H), 3.25-3.22 (m, 1H), 2.91-2.86 (m, 2H), 2.44-2.41 (m, 2H), 2.20-2.16 (m, 1H), 1.90-1.85 (m, 1H), 1.18 (d, J = 6.0 Hz, 6H) ppm |
| 162 | (3R)-N-[2-[[4-[6-[(cis)-2,6-dimethylmorpholin-4-yl]-2-pyridyl]thiazol-2-yl]amino]-2-oxo-ethyl]-3-(hydroxymethyl)indane-5-carboxamide | 522.2 | $^1$H NMR (400 MHz, DMSO-d6) δ = 12.35-12.12 (m, 1H), 8.80-8.77 (m, 1H), 8.43 (s, 1H), 7.82 (s, 1H), 7.76 (s, 1H), 7.70-7.68 (m, 1H), 7.64-7.60 (m, 1H), 7.30 (d, J = 8.0 Hz, 1H), 7.25 (d, J = 7.2 Hz, 1H), 6.80 (d, J = 8.8 Hz, 1H), 4.78-4.75 (m, 1H), 4.25 (br d, J = 11.6 Hz, 2H), 4.16 (d, J = 5.6 Hz, 2H), 3.66-3.60 (m, 3H), 3.51-3.49 (m, 1H), 3.25-3.22 (m, 1H), 2.92-2.84 (m, 2H), 2.44-2.38 (m, 2H), 2.22-2.13 (m, 1H), 1.92-1.83 (m, 1H), 1.18 (d, J = 6.4 Hz, 6H) ppm |
| 182 | N-[2-[[4-[6-[(cis)-2,6-dimethylmorpholin-4-yl]-2-pyridyl]thiazol-2-yl]amino]-2-oxo-ethyl]-3-[1-(hydroxymethyl)cyclo-propyl]benzamide | 522.0 | $^1$H NMR (400 MHz, DMSO-d6) δ = 12.40 (br d, J = 3.7 Hz, 1H), 8.97-8.82 (m, 1H), 7.81 (s, 1H), 7.77 (s, 1H), 7.70 (d, J = 7.9 Hz, 1H), 7.65-7.59 (m, 1H), 7.50 (d, J = 7.8 Hz, 1H), 7.43-7.36 (m, 1H), 7.25 (d, J = 7.2 Hz, 1H), 6.80 (d, J = 8.6 Hz, 1H), 4.70 (t, J = 5.7 Hz, 1H), 4.29-4.22 (m, 2H), 4.18 (br d, J = 5.6 Hz, 2H), 3.68-3.60 (m, 2H), 3.57 (d, J = 5.6 Hz, 2H), 2.44-2.38 (m, 2H), 1.18 (d, J = 6.2 Hz, 6H), 0.90-0.85 (m, 2H), 0.81-0.76 (m, 2H) ppm |
| 187 | N-[2-[[4-[6-[(cis)-2,6-dimethylmorpholin-4-yl]-2-pyridyl]thiazol-2-yl]amino]-2-oxo-ethyl]-3-(3-methyloxetan-3-yl)benzamide | 522.1 | $^1$H NMR (400 MHz, DMSO-d6) δ = 12.40 (s, 1H), 8.98-8.95 (m, 1H), 7.78-7.77 (m, 3H), 7.64-7.60 (m, 1H), 7.50-7.42 (m, 2H), 7.26 (d, J = 7.6 Hz, 1H), 6.80 (d, J = 8.4 Hz, 1H), 4.86 (d, J = 5.6 Hz, 2H), 4.58 (d, J = 5.6 Hz, 2H), 4.25 (br d, J = 12.0 Hz, 2H), 4.20 (br d, J = 5.6 Hz, 2H), 3.64-3.61 (m, 2H), 2.44-2.38 (m, 2H), 1.66 (s, 3H), 1.18 (br d, J = 6.0 Hz, 6H) ppm |
| 223 | (R)-N-(2-((4-(6-((cis)-2,6-dimethylmorpholino)pyridin-2-yl)thiazol-2-yl)amino)-2-oxoethyl)-3-(hydroxymethyl)-3-methyl-2,3-dihydro-1H-indene-5-carboxamide | 536.4 | $^1$H NMR (400 MHz, DMSO-d6) δ = 12.36 (br s, 1H), 8.88-8.68 (m, 1H), 7.76 (s, 1H), 7.72-7.67 (m, 2H), 7.64-7.59 (m, 1H), 7.30-7.22 (m, 2H), 6.79 (d, J = 8.4 Hz, 1H), 4.79-4.73 (m, 1H), 4.25 (br d, J = 11.6 Hz, 2H), 4.16 (d, J = 5.6 Hz, 2H), 3.68-3.59 (m, 2H), 3.37 (br d, J = 5.6 Hz, 2H), 2.91-2.84 (m, 2H), 2.45-2.38 (m, 2H), 2.22-2.14 (m, 1H), 1.77-1.68 (m, 1H), 1.23 (s, 3H), 1.18 (d, J = 6.0 Hz, 6H) ppm |
| 224 | (3S)-N-[2-[[4-[6-[(cis)-2,6-dimethylmorpholin-4-yl]-2-pyridyl]thiazol-2-yl]amino]-2-oxo-ethyl]-3-(hydroxymethyl)-3-methyl-indane-5-carboxamide | 536.0 | $^1$H NMR (400 MHz, DMSO-d6) δ = 12.54-12.26 (m, 1H), 8.92-8.66 (m, 1H), 7.76 (s, 1H), 7.73-7.68 (m, 2H), 7.65-7.59 (m, 1H), 7.31-7.23 (m, 2H), 6.80 (d, J = 8.4 Hz, 1H), 4.79-4.73 (m, 1H), 4.25 (br d, J = 11.6 Hz, 2H), 4.17 (d, J = 5.6 Hz, 2H), 3.68-3.58 (m, 2H), 3.38 (br d, J = 5.6 Hz, 2H), 2.92-2.84 (m, 2H), 2.45-2.38 (m, 2H), 2.23-2.14 (m, 1H), 1.78-1.68 (m, 1H), 1.23 (s, 3H), 1.18 (d, J = 6.4 Hz, 6H) ppm |
| 237 | N-(2-((4-(6-((cis)-2,6-dimethylmorpholino)pyridin-2-yl)thiazol-2-yl)amino)-2-oxoethyl)-3-(1-hydroxy-2-methylpropan-2-yl)-4-methylbenzamide | 538.0 | $^1$H NMR (400 MHz, DMSO-d6) δ = 12.59-12.19 (m, 1H), 8.82 (t, J = 5.7 Hz, 1H), 7.85 (d, J = 1.6 Hz, 1H), 7.78 (s, 1H), 7.67-7.59 (m, 2H), 7.26 (d, J = 7.2 Hz, 1H), 7.22 (d, J = 8.1 Hz, 1H), 6.81 (d, J = 8.6 Hz, 1H), 6.83-6.78 (m, 1H), 4.71 (t, J = 5.4 Hz, 1H), 4.26 (br d, J = 12.2 Hz, 2H), 4.17 (br d, J = 5.7 Hz, 2H), 4.20-4.14 (m, 1H), 3.63 (br d, J = 5.5 Hz, 4H), 2.54-2.53 (m, 3H), 2.43-2.39 (m, 2H), 1.35 (s, 5H), 1.36 (br s, 1H), 1.19 (d, J = 6.2 Hz, 6H) ppm |
| 241 | 4-chloro-N-[2-[[4-[6-[(cis)-2,6-dimethylmorpholin-4-yl]-2-pyridyl]thiazol-2-yl]amino]-2-oxo-ethyl]-3-(2-hydroxy-1,1-dimethyl-ethyl)benzamide | 558.2 | $^1$H NMR (400 MHz, DMSO-d6) δ = 12.43 (br s, 1H), 9.03 (t, J = 5.9 Hz, 1H), 7.96 (d, J = 2.0 Hz, 1H), 7.78 (s, 1H), 7.74 (dd, J = 2.0, 8.3 Hz, 1H), 7.62 (dd, J = 7.4, 8.4 Hz, 1H), 7.51 (d, J = 8.3 Hz, 1H), 7.25 (d, J = 7.4 Hz, 1H), 6.80 (d, J = 8.6 Hz, 1H), 4.78 (t, J = 5.3 Hz, 1H), 4.26 (br d, J = 11.5 Hz, 2H), 4.18 (d, J = 5.8 Hz, 2H), 3.77 (d, J = 5.4 Hz, 2H), 3.63 (ddd, J = 2.5, 6.3, 10.2 Hz, 2H), 2.44-2.38 (m, 2H), 1.41 (s, 6H), 1.18 (d, J = 6.1 Hz, 6H) ppm |

TABLE 7-continued

| # | Name | LC-MS (m/z) | 1H NMR |
|---|---|---|---|
| 271 | N-(2-((4-(6-((cis)-2,6-dimethylmorpholino)pyridin-2-yl)thiazol-2-yl)amino)-2-oxoethyl)-1-methylisochromane-6-carboxamide | 522.3 | $^1$H NMR (400 MHz, DMSO-d6) δ = 12.32 (s, 1H), 8.88-8.85 (m, 1H), 7.77 (s, 1H), 7.73-7.66 (m, 2H), 7.69-7.60(m, 1H), 7.29-7.25 (m, 2H), 6.80 (d, J = 8.4 Hz, 1H), 4.83-4.80 (m, 1H), 4.26 (d, J = 11.2 Hz, 2H), 4.18 (d, J = 6.0 Hz, 2H), 4.09-4.04 (m, 1H), 3.75-3.71 (m, 1H), 3.66-3.61 (m, 2H), 3.03-2.88 (m, 1H), 2.76-2.71 (m, 1H), 2.45-2.39 (m, 2H), 1.47 (d, J = 6.4 Hz, 3H), 1.19 (d, J = 6.4 Hz, 6H) ppm |
| 272 | (R)-4-(difluoromethyl)-N-(2-((4-(6-((cis)-2,6-dimethylmorpholino)pyridin-2-yl)thiazol-2-yl)amino)-2-oxoethyl)-4-fluorochromane-6-carboxamide | 576.1 | $^1$H NMR (400 MHz, DMSO-d6) δ = 12.40 (s, 1H), 8.89 (s, 1H), 8.17 (s, 1H), 7.94 (d, J = 8.8 Hz, 1H), 7.77 (s, 1H), 7.62-7.60 (m, 1H), 7.25 (d, J = 7.2 Hz, 1H), 7.07 (d, J = 8.8 Hz, 1H), 6.98-6.64 (m, 2H), 4.50-4.35 (m, 1H), 4.32-4.08 (m, 5H), 3.64-3.61 (m, 2H), 2.44-2.38 (m, 4H), 1.19 (s, 3H), 1.17 (s, 3H) ppm |
| 273 | (S)-4-(difluoromethyl)-N-(2-((4-(6-((cis)-2,6-dimethylmorpholino)pyridin-2-yl)thiazol-2-yl)amino)-2-oxoethyl)-4-fluorochromane-6-carboxamide | 576.1 | $^1$H NMR (400 MHz, DMSO-d6) δ = 8.91-8.88 (m, 1H), 8.17 (s, 1H), 7.94 (d, J = 8.8 Hz, 1H), 7.77 (s, 1H), 7.64-7.60 (m, 1H), 7.25 (d, J = 7.2 Hz, 1H), 7.06 (d, J = 8.8 Hz, 1H), 6.97-6.61 (m, 2H), 4.52-4.38 (m, 1H), 4.29-4.16 (m, 5H), 3.68-3.56 (m, 2H), 2.46-2.35 (m, 4H), 1.19 (s, 3H), 1.17 (s, 3H) ppm |
| 282 | N-(2-((4-(6-((cis)-2,6-dimethylmorpholino)pyridin-2-yl)thiazol-2-yl)amino)-2-oxoethyl)-4,4-dimethylisochromane-6-carboxamide | 536.4 | $^1$H NMR (400 MHz, DMSO-d6) δ = 12.48-12.34 (m, 1H), 8.94-8.91 (m, 1H), 7.95 (d, J = 1.2 Hz, 1H), 7.78 (s, 1H), 7.73-7.57 (m, 2H), 7.26 (d, J = 7.2 Hz, 1H), 7.13 (d, J = 8.0 Hz, 1H), 6.81 (d, J = 8.8 Hz, 1H), 4.77 (s, 2H), 4.31-4.16 (m, 4H), 3.69-3.56 (m, 4H), 2.43-2.38 (m, 2H), 1.34-1.23 (m, 6H), 1.19 (d, J = 6.0 Hz, 6H) ppm |
| 296 | N-(2-((4-(6-((cis)-2,6-dimethylmorpholino)pyridin-2-yl)thiazol-2-yl)amino)-2-oxoethyl)-1,3,4,5-tetrahydrobenzo[c]oxepine-7-carboxamide | 522.4 | $^1$H NMR (400 MHz, DMSO-d6) δ 12.38 (s, 1H), 8.87-8.85 (t, J = 5.7 Hz, 1H), 7.77-7.73 (m, 2H), 7.67-7.60 (m, 2H), 7.31 (d, J = 8.0 Hz, 1H), 7.25 (d, J = 7.2 Hz, 1H), 6.80 (d, J = 8.4 Hz, 1H), 4.65 (s, 2H), 4.25 (d, J = 11.2 Hz, 2H), 4.17 (d, J = 6.0 Hz, 2H), 3.97-3.94 (m, 2H), 3.63-3.61 (m, 2H), 3.04-3.01 (m, 2H), 2.41 (br d, J = 2.0 Hz, 2H), 1.75-1.73 (m, 2H), 1.18 (d, J = 6.0 Hz, 6H) ppm |
| 300 | N-(2-((4-(6-((cis)-2,6-dimethylmorpholino)pyridin-2-yl)thiazol-2-yl)amino)-2-oxoethyl)spiro[isochromane-4,3'-oxetane]-6-carboxamide | 550.2 | $^1$H NMR (400 MHz, DMSO-d6) δ = 12.45 (d, J = 1.2 Hz, 1H), 9.10 (m, 1H), 8.47 (d, J = 1.6 Hz, 1H), 7.84-7.74 (m, 2H), 7.65-7.63 (m, 1H), 7.27 (d, J = 7.2 Hz, 1H), 7.19 (d, J = 8.0 Hz, 1H), 6.81 (d, J = 8.4 Hz, 1H), 4.80 (d, J = 6.4 Hz, 2H), 4.75 (s, 2H), 4.59 (d, J = 6.4 Hz, 2H), 4.30-4.20 (m, 4H), 4.16 (s, 2H), 3.73-3.57 (m, 2H), 2.45-2.39 (m, 2H), 1.19 (d, J = 6.4 Hz, 6H) ppm |
| 304 | N-(2-((4-(6-((cis)-2,6-dimethylmorpholino)pyridin-2-yl)thiazol-2-yl)amino)-2-oxoethyl)-3-(3-fluoro-4-hydroxytetrahydrofuran-3-yl)benzamide | 556.2 | $^1$H NMR (400 MHz, DMSO-d6) δ = 12.41 (s, 1H), 9.03-9.00 (m, 1H), 8.01 (s, 1H), 7.92 (d, J = 8.4 Hz, 1H), 7.77 (s, 1H), 7.66-7.60 (m, 2H), 7.56-7.52 (m, 1H), 7.26 (d, J = 7.6 Hz, 1H), 6.80 (d, J = 8.4 Hz, 1H), 5.58 (d, J = 5.2 Hz, 1H), 4.37-4.11 (m, 8H), 3.82 (d, J = 9.2 Hz, 1H), 3.65-3.60 (m, 2H), 2.44-2.38 (m, 2H), 1.21-1.14 (m, 6H) ppm |
| 318 | N-(2-((4-(6-((cis)-2,6-dimethylmorpholino)pyridin-2-yl)thiazol-2-yl)amino)-2-oxoethyl)-3-(6-fluoro-2-oxaspiro[3.3]heptan-6-yl)benzamide | 566.2 | $^1$H NMR (400 MHz, DMSO-d6) δ = 12.42 (s, 1H), 9.07-9.01 (m, 1H), 7.95 (s, 1H), 7.90 (d, J = 8.0 Hz, 1H), 7.78 (s, 1H), 7.66-7.60 (m, 2H), 7.58-7.53 (m, 1H), 7.26 (d, J = 7.2 Hz, 1H), 6.81 (d, J = 8.4 Hz, 1H), 4.73 (s, 2H), 4.57 (s, 2H), 4.26 (d, J = 11.6 Hz, 2H), 4.21 (d, J = 5.6 Hz, 2H), 3.67-3.60 (m, 2H), 3.00-2.91 (m, 2H), 2.87-2.78 (m, 2H), 2.42 (d, J = 2.0 Hz, 2H), 1.19 (d, J = 6.0 Hz, 6H) ppm |
| 320 | (R)-N-(2-((4-(6-((cis)-2,6-dimethylmorpholino)pyridin-2-yl)thiazol-2-yl)amino)-2-oxoethyl)-4-methylisochromane-6-carboxamide | 522.2 | $^1$H NMR (400 MHz, DMSO-d6) δ = 8.92-8.85 (m, 1H), 8.46 (s, 0.5H), 7.81 (s, 1H), 7.75 (s, 1H), 7.71-7.66 (m, 1H), 7.65-7.58 (m, 1H), 7.25 (d, J = 7.2 Hz, 1H), 7.14 (d, J = 8.0 Hz, 1H), 6.79 (d, J = 8.4 Hz, 1H), 4.81-4.65 (m, 2H), 4.25 (d, J = 11.6 Hz, 2H), 4.17 (d, J = 5.6 Hz, 2H), 3.93-3.86 (m, 1H), 3.64-3.57 (m, 3H), 2.98-2.88 (m, 1H), 2.45-2.36 (m, 2H), 1.26 (d, J = 7.2 Hz, 3H), 1.18 (d, J = 6.4 Hz, 6H) ppm |
| 321 | (S)-N-(2-((4-(6-((cis)-2,6-dimethylmorpholino)pyridin-2-yl)thiazol-2-yl)amino)-2-oxoethyl)-4-methylisochromane-6-carboxamide | 522.2 | $^1$H NMR (400 MHz, DMSO-d6) δ = 8.94-8.87 (m, 1H), 8.45 (s, 0.3H), 7.82 (s, 1H), 7.77 (s, 1H), 7.73-7.59 (m, 2H), 7.26 (d, J = 7.2 Hz, 1H), 7.15 (d, J = 8.0 Hz, 1H), 6.80 (d, J = 8.4 Hz, 1H), 4.81-4.68 (m, 2H), 4.26 (d, J = 11.6 Hz, 2H), 4.18 (d, J = 5.6 Hz, 2H), 3.95-3.88 (m, 1H), 3.66-3.58 (m, 3H), 3.03-2.87 (m, 1H), 2.46-2.38 (m, 2H), 1.27 (d, J = 7.2 Hz, 3H), 1.19 (d, J = 6.4 Hz, 6H) ppm |
| 338 | N-(2-((4-(6-((cis)-2,6-dimethylmorpholino)pyridin-2-yl)thiazol-2-yl)amino)-2-oxoethyl)-2,3,4,5- | 522.3 | $^1$H NMR (400 MHz, DMSO-d6) δ = 12.37 (s, 1H), 8.79-8.76 (m, 1H), 7.76-7.74 (m, 2H), 7.66-7.64 (m, 1H), 7.64-7.62 (m, 1H), 7.26 (d, J = 7.2 Hz, 1H), 7.01 (d, J = 8.4 Hz, 1H), 6.80 (d, J = 8.4 Hz, 1H), 4.26 (d, J = 11.6 Hz, 2H), 4.16 (d, J = 5.6 Hz, 2H), 4.00-3.97 (m, 2H), 3.63-3.62 |

TABLE 7-continued

| # | Name | LC-MS (m/z) | 1H NMR |
|---|---|---|---|
| | tetrahydrobenzo[b]oxepine-7-carboxamide | | (m, 2H), 2.82-2.79 (m, 2H), 2.44-2.38 (m, 2H), 1.91-1.89 (m, 2H), 1.69-1.62 (m, 2H), 1.18 (d, J = 6.4 Hz, 6H) ppm |
| 346 | N-(2-((4-(6-((cis)-2,6-dimethylmorpholino)pyridin-2-yl)thiazol-2-yl)amino)-2-oxoethyl)-4-methylisochromane-6-carboxamide | 522 | $^1$H NMR (400 MHz, DMSO-d6) δ = 12.40 (br s, 1H), 9.00-8.82 (m, 1H), 7.79 (d, J = 17.2 Hz, 2H), 7.73-7.57 (m, 2H), 7.25 (d, J = 7.2 Hz, 1H), 7.14 (d, J = 8.0 Hz, 1H), 6.80 (d, J = 8.4 Hz, 1H), 4.74 (d, J = 7.6 Hz, 2H), 4.32-4.15 (m, 4H), 3.95-3.85 (m, 1H), 3.70-3.55 (m, 3H), 2.94 (d, J = 5.6 Hz, 1H), 2.45-2.38 (m, 2H), 1.26 (d, J = 6.8 Hz, 3H), 1.18 (d, J = 6.0 Hz, 6H) ppm |
| 349 | (R)-N-(2-((4-(6-((cis)-2,6-dimethylmorpholino)pyridin-2-yl)thiazol-2-yl)amino)-2-oxoethyl)spiro[isochromane-4,2'-oxetane]-6-carboxamide | 550.5 | $^1$H NMR (400 MHz, DMSO-d6) δ = 12.41 (br s, 1H), 9.15-9.06 (m, 1H), 8.47 (s, 1H), 7.83-7.81 (m, 1H), 7.77 (s, 1H), 7.63-7.61 (m, 1H), 7.26 (d, J = 7.2 Hz, 1H), 7.18 (d, J = 8.0 Hz, 1H), 6.80 (d, J = 8.4 Hz, 1H), 4.78-4.56 (m, 4H), 4.30-4.18 (m, 4H), 4.14-4.07 (m, 1H), 3.98 (d, J = 11.6 Hz, 1H), 3.63-3.62 (m, 2H), 2.96-2.85 (m, 1H), 2.75-2.63 (m, 1H), 2.44-2.38 (m, 2H), 1.18 (d, J = 6.0 Hz, 6H) ppm |
| 350 | (S)-N-(2-((4-(6-((cis)-2,6-dimethylmorpholino)pyridin-2-yl)thiazol-2-yl)amino)-2-oxoethyl)spiro[isochromane-4,2'-oxetane]-6-carboxamide | 550.5 | $^1$H NMR (400 MHz, DMSO-d6) δ = 12.44 (br s, 1H), 9.11-9.08 (m, 1H), 8.47 (d, J = 1.2 Hz, 1H), 7.83-7.81 (m, 1H), 7.78 (s, 1H), 7.63-7.61 (m, 1H), 7.27-7.25 (m, 1H), 7.18 (d, J = 8.0 Hz, 1H), 6.80 (d, J = 8.4 Hz, 1H), 4.75-4.58 (m, 4H), 4.29-4.21 (m, 4H), 4.10 (d, J = 11.6 Hz, 1H), 3.98 (d, J = 11.6 Hz, 1H), 3.67-3.59 (m, 2H), 2.95-2.86 (m, 1H), 2.72-2.64 (m, 1H), 2.44-2.38 (m, 2H), 1.18 (d, J = 6.0 Hz, 6H) ppm |
| 357 | 3-((1S,3S)-1,3-difluorocyclobutyl)-N-(2-((4-(6-((cis)-2,6-dimethylmorpholino)pyridin-2-yl)thiazol-2-yl)amino)-2-oxoethyl)benzamide | 542.2 | $^1$H NMR (400 MHz, DMSO-d6) δ = 12.42 (s, 1H), 9.07 (m, 1H), 7.97 (s, 1H), 7.92 (d, J = 8.0 Hz, 1H), 7.78 (s, 1H), 7.70-7.48 (m, 3H), 7.26 (d, J = 7.2 Hz, 1H), 6.81 (d, J = 8.8 Hz, 1H), 5.27-5.00 (m, 1H), 4.26 (d, J = 11.6 Hz, 2H), 4.22 (d, J = 6.0 Hz, 2H), 3.64-3.62 (m, 2H), 3.26-3.11 (m, 2H), 3.01-2.79 (m, 2H), 2.45-2.39 (m, 2H), 1.19 (d, J = 6.0 Hz, 6H) ppm |
| 358 | 3-((1R,3R)-1,3-difluorocyclobutyl)-N-(2-((4-(6-((cis)-2,6-dimethylmorpholino)pyridin-2-yl)thiazol-2-yl)amino)-2-oxoethyl)benzamide | 542.2 | $^1$H NMR (400 MHz, DMSO-d6) δ = 12.55-12.26 (m, 1H), 9.08 (m, 1H), 8.00 (d, J = 1.2 Hz, 1H), 7.92 (d, J = 7.6 Hz, 1H), 7.77 (s, 1H), 7.70-7.54 (m, 3H), 7.26 (d, J = 7.6 Hz, 1H), 6.80 (d, J = 8.8 Hz, 1H), 5.67-5.36 (m, 1H), 4.25 (d, J = 11.6 Hz, 2H), 4.21 (d, J = 5.6 Hz, 2H), 3.67-3.59 (m, 2H), 3.18-2.99 (m, 2H), 2.97-2.77 (m, 2H), 2.44-2.38 (m, 2H), 1.18 (d, J = 6.0 Hz, 6H) ppm |
| 360 | N-(2-((4-(6-((cis)-2,6-dimethylmorpholino)pyridin-2-yl)thiazol-2-yl)amino)-2-oxoethyl)spiro[chromane-4,2'-oxetane]-6-carboxamide | 550.5 | $^1$H NMR (400 MHz, DMSO-d6) δ = 12.40 (s, 1H), 8.93 (m, 1H), 8.39 (d, J = 2.0 Hz, 1H), 7.83-7.73 (m, 2H), 7.63 (m, 1H), 7.27 (d, J = 7.2 Hz, 1H), 6.83 (m, 2H), 4.68-4.56 (m, 2H), 4.32-4.16 (m, 6H), 3.68-3.60 (m, 2H), 3.06-2.95 (m, 1H), 2.72-2.63 (m, 1H), 2.43-2.23 (m, 4H), 1.19 (d, J = 6.0 Hz, 6H) ppm |
| 366 | N-(2-((4-(6-((cis)-2,6-dimethylmorpholino)pyridin-2-yl)thiazol-2-yl)amino)-2-oxoethyl)isochromane-6-carboxamide | 508.2 | $^1$H NMR (400 MHz, DMSO-d6) δ = 12.41 (br s, 1H), 8.89-8.86 (m, 1H), 7.77 (s, 1H), 7.72-7.66 (m, 2H), 7.62-7.60 (m, 1H), 7.25 (d, J = 7.2 Hz, 1H), 7.15 (d, J = 7.6 Hz, 1H), 6.80 (d, J = 8.8 Hz, 1H), 4.73 (s, 2H), 4.26-4.23 (m, 2H), 4.17-4.16 (m, 2H), 3.91-3.90 (m, 2H), 3.69-3.56 (m, 2H), 2.85-2.83 (m, 2H), 2.43-2.38 (m, 2H), 1.18 (d, J = 6.0 Hz, 6H) ppm |
| 370 | N-(2-((4-(6-((cis)-2,6-dimethylmorpholino)pyridin-2-yl)thiazol-2-yl)amino)-2-oxoethyl)chromane-6-carboxamide | 508.1 | $^1$H NMR (400 MHz, DMSO-d6) δ = 12.26 (br s, 1H), 8.77-8.66 (m, 1H), 7.79-7.74 (m, 1H), 7.70-7.59 (m, 3H), 7.30-7.20 (m, 1H), 6.82-6.79 (m, 2H), 4.30-4.23 (m, 2H), 4.22-4.17 (m, 2H), 4.17-4.11 (m, 2H), 3.69-3.58 (m, 2H), 2.83-2.75 (m, 2H), 2.42-2.33 (m, 2H), 1.92-1.90 (m, 2H), 1.23-1.18 (m, 6H) ppm |
| 376 | N-(2-((4-(6-((cis)-2,6-dimethylmorpholino)pyridin-2-yl)thiazol-2-yl)amino)-2-oxoethyl)spiro[isochromane-4,2'-oxetane]-6-carboxamide | 550.4 | $^1$H NMR (400 MHz, DMSO-d6) δ = 12.43 (s, 1H), 9.08-9.05 (m, 1H), 8.46 (d, J = 1.6 Hz, 1H), 7.83-7.81 (m, 1H), 7.76 (s, 1H), 7.64-7.60 (m, 1H), 7.26 (d, J = 7.2 Hz, 1H), 7.18 (d, J = 8.0 Hz, 1H), 6.80 (d, J = 8.8 Hz, 1H), 4.77-4.59 (m, 4H), 4.29-4.19 (m, 4H), 4.10 (d, J = 11.6 Hz, 1H), 3.98 (d, J = 11.6 Hz, 1H), 3.70-3.56 (m, 2H), 2.95-2.85 (m, 1H), 2.72-2.65 (m, 1H), 2.44-2.38 (m, 2H), 1.18 (d, J = 6.0 Hz, 6H) ppm |
| 381 | N-(2-((4-(6-((cis)-2,6-dimethylmorpholino)pyridin-2-yl)thiazol-2-yl)amino)-2-oxoethyl)spiro[chromane-4,3'-oxetane]-6-carboxamide | 550.2 | $^1$H NMR (400 MHz, DMSO-d6) δ = 12.40 (s, 1H), 8.95-8.92 (m, 1H), 8.40 (d, J = 2.0 Hz, 1H), 7.77 (s, 1H), 7.73-7.71 (m, 1H), 7.64-7.60 (m, 1H), 7.26 (d, J = 7.2 Hz, 1H), 6.85 (d, J = 8.4 Hz, 1H), 6.80 (d, J = 8.4 Hz, 1H), 4.83 (d, J = 6.0 Hz, 2H), 4.56 (d, J = 6.0 Hz, 2H), 4.26 (d, J = 11.2 Hz, 2H), 4.19 (d, J = 5.6 Hz, 2H), 4.17-4.12 (m, 2H), 3.68-3.58 (m, 2H), 2.44-2.38 (m, 2H), 2.35-2.30 (m, 2H), 1.19 (s, 3H), 1.17 (s, 3H) ppm |

TABLE 7-continued

| # | Name | LC-MS (m/z) | 1H NMR |
|---|---|---|---|
| 384 | 1-cyano-N-(2-((4-(6-((cis)-2,6-dimethylmorpholino)pyridin-2-yl)thiazol-2-yl)amino)-2-oxoethyl)-1-methylisochromane-7-carboxamide | 547.2 | $^1$H NMR (400 MHz, DMSO-d6) δ = 12.43 (s, 1H), 9.08-9.04 (m, 1H), 8.03 (d, J = 1.2 Hz, 1H), 7.88-7.86 (m, 1H), 7.77 (s, 1H), 7.64-7.60 (m, 1H), 7.39 (d, J = 8.0 Hz, 1H), 7.25 (d, J = 7.2 Hz, 1H), 6.80 (d, J = 8.0 Hz, 1H), 4.27-4.20 (m, 5H), 3.94-3.88 (m, 1H), 3.65-3.62 (m, 2H), 3.11-3.10 (m, 1H), 2.85-2.81 (m, 1H), 2.41-2.38 (m, 2H), 1.94 (s, 3H), 1.18 (d, J = 6.0 Hz, 6H) ppm |
| 385 | N-(2-((4-(6-((cis)-2,6-dimethylmorpholino)pyridin-2-yl)thiazol-2-yl)amino)-2-oxoethyl)-4,4-difluoroisochromane-6-carboxamide | 544.2 | $^1$H NMR (400 MHz, DMSO-d6) δ = 12.42 (br s, 1H), 9.21-9.05 (m, 1H), 8.25 (s, 1H), 8.03 (d, J = 8.4 Hz, 1H), 7.77 (s, 1H), 7.68-7.54 (m, 1H), 7.41 (d, J = 8.4 Hz, 1H), 7.25 (d, J = 7.2 Hz, 1H), 6.79 (d, J = 8.4 Hz, 1H), 4.89 (s, 2H), 4.29-4.15 (m, 6H), 3.66-3.59 (m, 2H), 2.43-2.38 (m, 2H), 1.17 (d, J = 6.0 Hz, 6H) ppm |
| 395 | N-(2-((4-(6-((cis)-2,6-dimethylmorpholino)pyridin-2-yl)thiazol-2-yl)amino)-2-oxoethyl)-4-isopropyl-3,4-dihydro-2H-benzo[b][1,4]oxazine-6-carboxamide | 551.2 | $^1$H NMR (400 MHz, MeOD) δ = 7.68 (s, 1H), 7.63-7.55 (m, 1H), 7.42-7.32 (m, 2H), 7.16-7.15 (m, 1H), 6.80-6.70 (m, 2H), 5.17 (s, 2H), 4.31-4.20 (m, 7H), 3.80-3.68 (m, 2H), 2.51-2.45 (m, 2H), 1.26 (d, J = 6.0 Hz, 6H), 1.22 (d, J = 6.4 Hz, 6H)) ppm |
| 405 | rac-4-cyano-N-(2-((4-(6-((cis)-2,6-dimethylmorpholino)pyridin-2-yl)thiazol-2-yl)amino)-2-oxoethyl)chromane-6-carboxamide | 533.1 | $^1$H NMR (400 MHz, MeOD) δ = 7.94 (d, J = 1.2 Hz, 1H), 7.84-7.78 (m,, 1H), 7.68 (s, 1H), 7.62-7.55 (m, 1H), 7.35 (d, J = 7.2 Hz, 1H), 6.95 (d, J = 8.8 Hz, 1H), 6.73 (d, J = 8.4 Hz, 1H), 4.39-4.32 (m, 3H), 4.30-4.21 (m, 4H), 3.79-3.68 (m, 2H), 2.53-2.44 (m,, 2H), 2.43-2.28 (m, 2H), 1.26 (d, J = 6.4 Hz, 6H) ppm |
| 409 | (S)-N-(2-((4-(6-((cis)-2,6-dimethylmorpholino)pyridin-2-yl)thiazol-2-yl)amino)-2-oxoethyl)-4-fluoro-4-methylisochromane-6-carboxamide | 540.3 | $^1$H NMR (400 MHz, DMSO-d6) δ = 12.42 (s, 1H), 9.06 (m, 1H), 8.19 (s, 1H), 7.89 (d, J = 8.0 Hz, 1H), 7.77 (s, 1H), 7.62 (m, 1H), 7.32-7.22 (m, 2H), 6.80 (d, J = 8.4 Hz, 1H), 4.90-4.81 (m, 1H), 4.77-4.68 (m, 1H), 4.32-4.17 (m, 4H), 4.13-4.01 (m, 1H), 3.90-3.77 (m, 1H), 3.69-3.56 (m, 2H), 2.41 (m, 2H), 1.75-1.63 (m, 3H), 1.18 (d, J = 6.0 Hz, 6H) ppm |
| 410 | (R)-N-(2-((4-(6-((cis)-2,6-dimethylmorpholino)pyridin-2-yl)thiazol-2-yl)amino)-2-oxoethyl)-2,2-difluorospiro[cyclopropane-1,4'-isochromane]-6'-carboxamide | 570.3 | $^1$H NMR (400 MHz, DMSO-d6) δ = 12.43 (s, 1H), 8.97-8.95 (m, 1H), 7.86-7.74 (m, 2H), 7.67-7.59 (m, 2H), 7.28-7.26 (8, 2H), 6.81 (d, J = 8.8 Hz, 1H), 5.00-4.85 (m, 2H), 4.28-4.25 (m, 2H), 4.22-4.20 (m, 2H), 3.98-3.92 (m, 1H), 3.89-3.83 (m, 1H), 3.68-3.59 (m, 2H), 2.42 (br s, 3H), 1.95-1.87 (m, 1H), 1.19-1.17 (m, 6H) ppm |
| 411 | (S)-N-(2-((4-(6-((cis)-2,6-dimethylmorpholino)pyridin-2-yl)thiazol-2-yl)amino)-2-oxoethyl)-2,2-difluorospiro[cyclopropane-1,4'-isochromane]-6'-carboxamide | 570.3 | $^1$H NMR (400 MHz, DMSO-d6) δ = 12.43 (s, 1H), 8.97-8.95 (m, 1H), 7.86-7.74 (m, 2H), 7.67-7.59 (m, 2H), 7.28-7.26 (8, 2H), 6.81 (d, J = 8.8 Hz, 1H), 5.00-4.85 (m, 2H), 4.28-4.25 (m, 2H), 4.22-4.20 (m, 2H), 3.98-3.92 (m, 1H), 3.89-3.83 (m, 1H), 3.68-3.59 (m, 2H), 2.42 (s, 3H), 1.95-1.87 (m, 1H), 1.19-1.17 (m, 6H) ppm |
| 412 | (R)-N-(2-((4-(6-((cis)-2,6-dimethylmorpholino)pyridin-2-yl)thiazol-2-yl)amino)-2-oxoethyl)-4-fluoro-4-methylisochromane-6-carboxamide | 540.2 | $^1$H NMR (400 MHz, DMSO-d6) δ = 12.45 (br s, 1H), 9.09-9.06 (m, 1H), 8.20 (s, 1H), 7.89 (d, J = 8.0 Hz, 1H), 7.78 (s, 1H), 7.63-7.61 (m, 1H), 7.28-7.25 (m, 2H), 6.81 (d, J = 8.8 Hz, 1H), 4.91-4.69 (m, 2H), 4.31-4.18 (m, 4H), 4.08-4.06 (m, 1H), 3.93-3.77 (m, 1H), 3.64-3.60 (m, 2H), 2.44-2.39 (m, 2H), 1.75-1.62 (m, 3H), 1.19 (d, J = 6.0 Hz, 6H) ppm |
| 413 | N-(2-((4-(6-((cis)-2,6-dimethylmorpholino)pyridin-2-yl)thiazol-2-yl)amino)-2-oxoethyl)-3-((cis)-4-hydroxy-3-methyltetrahydrofuran-3-yl)benzamide | 552.2 | $^1$H NMR (400 MHz, DMSO-d6) δ = 12.43-12.36 (m, 1H), 8.95-8.92 (m, 1H), 7.89 (s, 1H), 7.77-7.74 (m, 2H), 7.64-7.57 (m, 2H), 7.46-7.42 (m, 1H), 7.25 (d, J = 7.6 Hz, 1H), 6.80 (d, J = 8.4 Hz, 1H), 5.33 (d, J = 5.2 Hz, 1H), 4.33-4.18 (m, 5H), 4.05 (d, J = 8.4 Hz, 1H), 3.87-3.81 (m, 2H), 3.64-3.61 (m, 2H), 3.55-3.52 (m, 1H), 2.44-2.38 (m, 2H), 1.32-1.31 (s, 3H), 1.18 (d, J = 6.4 Hz, 6H) ppm |
| 420 | (R)-4-cyano-N-(2-((4-(6-((cis)-2,6-dimethylmorpholino)pyridin-2-yl)thiazol-2-yl)amino)-2-oxoethyl)-4-methylisochromane-6-carboxamide | 547 | $^1$H NMR (400 MHz, DMSO-d6) δ = 12.45 (d, J = 6.0 Hz, 1H), 9.09 (d, J = 6.8 Hz, 1H), 8.13 (d, J = 6.0 Hz, 1H), 7.92-7.87 (m, 1H), 7.78 (d, J = 7.6 Hz, 1H), 7.63-7.62 (m, 1H), 7.31-7.26 (m, 2H), 6.82 (d, J = 8.0 Hz, 1H), 4.92-4.85 (m, 2H), 4.27-4.22 (m, 5H), 3.89-3.84 (m, 1H), 3.63 (s, 2H), 2.44 (d, J = 12.4 Hz, 2H), 1.70 (d, J = 6.8 Hz, 3H), 1.18-1.17 (m, 6H) ppm |
| 421 | (S)-4-cyano-N-(2-((4-(6-((cis)-2,6-dimethylmorpholino)pyridin-2-yl)thiazol-2-yl)amino)-2-oxoethyl)-4- | 547 | $^1$H NMR (400 MHz, DMSO-d6) δ = 12.44 (s, 1H), 9.09-9.06 (m, 1H), 8.12 (d, J = 1.6 Hz, 1H), 7.88-7.86 (m, 1H), 7.77 (s, 1H), 7.62-7.60 (m, 1H), 7.30-7.24 (m, 2H), 6.80 (d, J = 8.8 Hz, 1H), 4.92-4.85 (m, 2H), 4.27-4.20 (m, 5H), 3.86 (d, J = 11.6 Hz, 1H), 3.63-3.61 (m, 2H), 2.41-2.38 |

TABLE 7-continued

| # | Name | LC-MS (m/z) | 1H NMR |
|---|---|---|---|
| | methylisochromane-6-carboxamide | | (m, 2H), 1.69 (s, 3H), 1.18 (d, J = 6.0 Hz, 6H) ppm |
| 425 | N-(2-((4-(6-((cis)-2,6-dimethylmorpholino)pyridin-2-yl)thiazol-2-yl)amino)-2-oxoethyl)-3-((trans)-4-hydroxytetrahydrofuran-3-yl)benzamide | 538.2 | $^1$H NMR (400 MHz, DMSO-d6) δ = 12.53-12.24 (m, 1H), 8.95-8.82 (m, 1H), 7.82 (s, 1H), 7.76-7.74 (m, 2H), 7.64-7.60 (m, 1H), 7.48-7.46 (m, 1H), 7.43-7.39 (m, 1H), 7.25 (d, J = 7.6 Hz, 1H), 6.80 (d, J = 8.4 Hz, 1H), 4.92 (d, J = 4.8 Hz, 1H), 4.39-4.36 (m, 1H), 4.25 (d, J = 12.8 Hz, 2H), 4.18 (d, J = 5.6 Hz, 2H), 4.10-4.06 (m, 1H), 4.02-3.97 (m, 2H), 3.74-3.71 (m, 1H), 3.66-3.58 (m, 3H), 2.41 (s, 2H), 1.18 (d, J = 6.0 Hz, 6H) ppm |
| 426 | N-(2-((4-(6-((cis)-2,6-dimethylmorpholino)pyridin-2-yl)thiazol-2-yl)amino)-2-oxoethyl)-3-((cis)-1-fluoro-3-methoxycyclobutyl)benzamide | 554.1 | $^1$H NMR (400 MHz, DMSO-d6) δ = 12.57-12.29 (m, 1H), 9.22-8.97 (m, 1H), 7.97 (d, J = 0.8 Hz, 1H), 7.93-7.86 (m, 1H), 7.79 (s, 1H), 7.67-7.60 (m, 2H), 7.59-7.53 (m, 1H), 7.32-7.20 (m, 1H), 6.85-6.76 (m, 1H), 4.37-4.15 (m, 5H), 3.69-3.60 (m, 2H), 3.23 (s, 3H), 2.98-2.81 (m, 2H), 2.47-2.37 (m, 4H), 1.18 (s, 6H) ppm |
| 441 | N-(2-((4-(6-((cis)-2,6-dimethylmorpholino)pyridin-2-yl)thiazol-2-yl)amino)-2-oxoethyl)-3-((R)-3-fluorotetrahydrofuran-3-yl)benzamide | 540.2 | $^1$H NMR (400 MHz, DMSO-d6) δ = 9.06-9.03 (m, 1H), 8.01 (s, 1H), 7.90 (d, J = 7.6 Hz, 1H), 7.77 (s, 1H), 7.68 (d, J = 7.6 Hz, 1H), 7.64-7.60 (m, 1H), 7.58-7.54 (m, 1H), 7.25 (d, J = 7.2 Hz, 1H), 6.80 (d, J = 8.4 Hz, 1H), 4.29-4.04 (m, 7H), 3.97-3.85 (m, 1H), 3.66-3.59 (m, 2H), 2.62-2.59 (m, 2H), 2.44-2.38 (m, 2H), 1.18 (d, J = 6.4 Hz, 6H) ppm |
| 406 | N-(2-((4-(6-((cis)-2,6-dimethylmorpholino)pyridin-2-yl)thiazol-2-yl)amino)-2-oxoethyl)spiro[cyclopropane-1,4'-isochromane]-6'-carboxamide | 534.4 | $^1$H NMR (400 MHz, DMSO-d6) δ = 12.40 (br s, 1H), 8.90-8.87 (m, 1H), 7.77 (s, 1H), 7.66-7.59 (m, 2H), 7.31 (d, J = 1.2 Hz, 1H), 7.25 (d, J = 7.2 Hz, 1H), 7.14 (d, J = 8.0 Hz, 1H), 6.80 (d, J = 8.4 Hz, 1H), 4.85 (s, 2H), 4.25 (br d, J = 11.2 Hz, 2H), 4.16 (d, J = 6.0 Hz, 2H), 3.67 (s, 2H), 3.67-3.62 (m, 2H), 2.44-2.39 (m, 2H), 1.18 (d, J = 6.0 Hz, 6H), 1.10-1.04 (m, 2H), 0.99-0.91 (m, 2H) ppm |
| 134 | N-[2-[[4-[6-[(cis)-2,6-dimethylmorpholin-4-yl]-2-pyridyl]thiazol-2-yl]amino]-2-oxo-ethyl]-3-[(3S)-3-hydroxytetrahydrofuran-3-yl]benzamide | 538.0 | $^1$H NMR (400 MHz, DMSO-d6) δ = 12.55-12.25 (m, 1H), 8.95-8.93 (m, 1H), 8.03 (s, 1H), 7.79-7.76 (m, 2H), 7.69 (d, J = 8.0 Hz, 1H), 7.64-7.60 (m, 1H), 7.48-7.44 (m, 1H), 7.25 (d, J = 7.2 Hz, 1H), 6.80 (d, J = 8.4 Hz, 1H), 5.52 (s, 1H), 4.25 (br d, J = 11.6 Hz, 2H), 4.19 (d, J = 5.6 Hz, 2H), 4.04-4.01 (m, 2H), 3.84-3.77 (m, 2H), 3.66-3.59 (m, 2H), 2.44-2.38 (m, 2H), 2.31-2.27 (m, 1H), 2.18-2.12 (m, 1H), 1.18 (d, J = 6.0 Hz, 6H) ppm |
| 140 | (3S)-N-[2-[[4-[6-[(cis)-2,6-dimethylmorpholin-4-yl]-2-pyridyl]thiazol-2-yl]amino]-2-oxo-ethyl]-3-[(1S)-1-hydroxyethyl]indane-5-carboxamide | 536.2 | $^1$H NMR (400 MHz, DMSO-d6) δ = 12.40-12.36 (m, 1H), 8.79-8.74 (m, 1H), 8.47-8.46 (m, 1H), 7.93 (s, 1H), 7.76 (s, 1H), 7.71-7.60 (m, 2H), 7.29-7.24 (m, 2H), 6.80 (d, J = 8.4 Hz, 1H), 4.73 (d, J = 4.8 Hz, 1H), 4.25 (br d, J = 13.2 Hz, 2H), 4.16 (br d, J = 6.0 Hz, 2H), 3.85-3.81 (m, 1H), 3.66-3.59 (m, 2H), 3.20-3.14 (m, 1H), 2.94-2.79 (m, 2H), 2.44-2.38 (m, 2H), 2.12-2.06 (m, 1H), 1.88-1.83 (m, 1H), 1.18 (d, J = 6.0 Hz, 6H), 1.02 (d, J = 6.4 Hz, 3H) ppm |
| 141 | (3R)-N-[2-[[4-[6-[(cis)-2,6-dimethylmorpholin-4-yl]-2-pyridyl]thiazol-2-yl]amino]-2-oxo-ethyl]-3-[(1S)-1-hydroxyethyl]indane-5-carboxamide | 536.3 | $^1$H NMR (400 MHz, DMSO-d6) δ = 12.38 (br s, 1H), 8.80-8.77 (m, 1H), 7.83 (s, 1H), 7.77 (s, 1H), 7.69 (d, J = 8.0 Hz, 1H), 7.65-7.61 (m, 1H), 7.29-7.25 (m, 2H), 6.81 (d, J = 8.4 Hz, 1H), 4.52 (d, J = 4.8 Hz, 1H), 4.26 (br d, J = 11.6 Hz, 2H), 4.18 (d, J = 5.6 Hz, 2H), 4.01-3.97 (m, 1H), 3.67-3.59 (m, 2H), 3.17-3.13 (m, 1H), 2.96-2.88 (m, 1H), 2.84-2.77 (m, 1H), 2.45-2.39 (m, 2H), 2.09-2.04 (m, 2H), 1.19 (d, J = 6.0 Hz, 6H), 1.10 (d, J = 6.0 Hz, 3H) ppm |
| 142 | (3S)-N-[2-[[4-[6-[(cis)-2,6-dimethylmorpholin-4-yl]-2-pyridyl]thiazol-2-yl]amino]-2-oxo-ethyl]-3-[(1R)-1-hydroxyethyl]indane-5-carboxamide | 536.2 | $^1$H NMR (400 MHz, DMSO-d6) δ = 12.45-12.24 (m, 1H), 8.79-8.76 (m, 1H), 7.81-7.76 (m, 2H), 7.68-7.59 (m, 2H), 7.28-7.24 (m, 2H), 6.79 (d, J = 8.8 Hz, 1H), 4.52 (d, J = 4.8 Hz, 1H), 4.25 (br d, J = 11.6 Hz, 2H), 4.16 (d, J = 6.0 Hz, 2H), 4.01-3.95 (m, 1H), 3.64-3.60 (m, 2H), 3.16-3.13 (m, 1H), 2.95-2.87 (m, 1H), 2.83-2.75 (m, 1H), 2.43-2.37 (m, 2H), 2.08-2.02(m, 2H), 1.18 (d, J = 6.0 Hz, 6H), 1.09 (d, J = 6.0 Hz, 3H) ppm |
| 145 | N-[2-[[4-[6-[(cis)-2,6-dimethylmorpholin-4-yl]-2-pyridyl]thiazol-2-yl]amino]-2-oxo-ethyl]-2-fluoro-5-(2-hydroxy-1,1-dimethyl-ethyl)benzamide | 542.2 | $^1$H NMR (400 MHz, DMSO-d6) δ = 12.40 (s, 1H), 8.60-8.51 (m, 1H), 7.80-7.77 (m, 1H), 7.71 (dd, J = 2.5, 7.2 Hz, 1H), 7.66-7.60 (m, 1H), 7.59-7.54 (m, 1H), 7.28-7.21 (m, 2H), 6.81 (d, J = 8.4 Hz, 1H), 4.26 (br d, J = 11.7 Hz, 2H), 4.22 (br d, J = 5.9 Hz, 2H), 3.68-3.59 (m, 2H), 3.43 (s, 2H), 2.42 (br s, 2H), 1.24 (s, 6H), 1.19 (d, J = 6.1 Hz, 6H) ppm |
| 152 | (R)-3-cyano-N-(2-((4-(6-((cis)-2,6-dimethylmorpholino)pyridin-2-yl)thiazol-2-yl)amino)-2-oxoethyl)-3-methyl-2,3-dihydro-1H-indene-5-carboxamide | 531.2 | $^1$H NMR (400 MHz, DMSO-d6) δ = 12.58-12.21 (m, 1H), 8.99 (t, J = 5.8 Hz, 1H), 8.00 (d, J = 1.1 Hz, 1H), 7.87 (dd, J = 1.6, 7.9 Hz, 1H), 7.77 (s, 1H), 7.62 (dd, J = 7.5, 8.4 Hz, 1H), 7.45 (d, J = 7.9 Hz, 1H), 7.26 (d, J = 7.2 Hz, 1H), 6.80 (d, J = 8.6 Hz, 1H), 4.25 (br d, J = 11.2 Hz, 2H), 4.20 (dd, J = 1.9, 5.7 Hz, 2H), 3.68-3.57 (m, 2H), 3.13-2.97 (m, 2H), 2.65-2.57 (m, 1H), 2.41 (dd, J = 10.6, 12.7 Hz, 2H), 2.24 |

TABLE 7-continued

| # | Name | LC-MS (m/z) | 1H NMR |
|---|---|---|---|
| | | | (td, J = 7.2, 13.1 Hz, 1H), 1.66 (s, 3H), 1.18 (d, J = 6.2 Hz, 6H) ppm |
| 262 | (S)-3-cyano-N-(2-((4-(6-((cis)-2,6-dimethylmorpholino)pyridin-2-yl)thiazol-2-yl)amino)-2-oxoethyl)-3-methyl-2,3-dihydro-1H-indene-5-carboxamide | 531.2 | $^1$H NMR (400 MHz, DMSO-d6) δ = 12.41 (s, 1H), 8.99 (t, J = 5.7 Hz, 1H), 7.99 (d, J = 1.1 Hz, 1H), 7.86 (dd, J = 1.5, 7.9 Hz, 1H), 7.76 (s, 1H), 7.61 (dd, J = 7.5, 8.4 Hz, 1H), 7.44 (d, J = 7.8 Hz, 1H), 7.25 (d, J = 7.2 Hz, 1H), 6.79 (d, J = 8.6 Hz, 1H), 4.30-4.16 (m, 4H), 3.69-3.56 (m, 2H), 3.05 (br t, J = 7.0 Hz, 2H), 2.63-2.60 (m, 1H), 2.41 (dd, J = 10.8, 12.7 Hz, 2H), 2.24 (td, J = 7.2, 13.1 Hz, 1H), 1.65 (s, 3H), 1.17 (d, J = 6.2 Hz, 6H), 1.03 (d, J = 6.1 Hz, 1H) ppm |
| 153 | (R)-4-cyano-N-(2-((4-(6-((cis)-2,6-dimethylmorpholino)pyridin-2-yl)thiazol-2-yl)amino)-2-oxoethyl)-4-methylchroman-6-carboxamide | 547.3 | $^1$H NMR (400 MHz, DMSO-d6) δ = 12.41 (s, 1H), 8.94-8.92 (m, 1H), 8.09 (d, J = 2.0 Hz, 1H), 7.82-7.77 (m, 2H), 7.64-7.62 (m, 1H), 7.26 (d, J = 7.2 Hz, 1H), 6.96 (d, J = 8.8 Hz, 1H), 6.80 (d, J = 8.4 Hz, 1H), 4.39-4.33 (m, 1H), 4.31-4.22 (m, 3H), 4.21-4.16 (m, 2H), 3.68-3.58 (m, 2H), 2.45-2.38 (m, 3H), 2.24-2.17 (m, 1H), 1.80 (s, 3H), 1.19 (s, 3H), 1.17 (s, 3H) ppm |
| 159 | (R)-3-cyano-N-(2-((4-(6-((cis)-2,6-dimethylmorpholino)pyridin-2-yl)thiazol-2-yl)amino)-2-oxoethyl)-3-(hydroxymethyl)-2,3-dihydro-1H-indene-5-carboxamide | 547.3 | $^1$H NMR (400 MHz, DMSO-d6) δ = 12.91-11.88 (m, 1H), 8.99-8.96 (m, 1H), 7.98 (d, J = 1.2 Hz, 1H), 7.88-7.86 (m, 1H), 7.77 (s, 1H), 7.64-7.60 (m, 1H), 7.43 (d, J = 8.0 Hz, 1H), 7.26 (d, J = 7.2 Hz, 1H), 6.80 (d, J = 8.4 Hz, 1H), 5.80-5.72 (m, 1H), 4.29-4.17 (m, 4H), 3.73-3.57 (m, 4H), 3.05-3.01 (m, 2H), 2.48-2.38 (m, 4H), 1.19 (s, 3H), 1.17 (s, 3H) ppm |
| 160 | N-(2-((4-(6-((cis)-2,6-dimethylmorpholino)pyridin-2-yl)thiazol-2-yl)amino)-2-oxoethyl)-3-((3R,4S)-4-hydroxytetrahydrofuran-3-yl)benzamide | 538.2 | $^1$H NMR (400 MHz, DMSO-d6) δ = 12.40 (br d, J = 1.6 Hz, 1H), 8.94-8.91 (m, 1H), 7.80-7.75 (m, 3H), 7.64-7.60 (m, 1H), 7.46-7.42 (m, 2H), 7.25 (d, J = 7.2 Hz, 1H), 6.80 (d, J = 8.4 Hz, 1H), 5.32 (d, J = 4.8 Hz, 1H), 4.29-4.23 (m, 3H), 4.20-4.16 (m, 3H), 4.00-3.96 (m, 1H), 3.78-3.63 (m, 1H), 3.62-3.56 (m, 3H), 3.28-3.23 (m, 1H), 2.44-2.38 (m, 2H), 1.18 (d, J = 6.0 Hz, 6H) ppm |
| 161 | (3S)-N-[2-[[4-[6-[(cis)-2,6-dimethylmorpholin-4-yl]-2-pyridyl]thiazol-2-yl]amino]-2-oxo-ethyl]-3-(hydroxymethyl)indane-5-carboxamide | 522.2 | $^1$H NMR (400 MHz, DMSO-d6) δ = 12.41-12.32 (m, 1H), 8.79-8.77 (m, 1H), 8.48-8.44 (m, 1H), 7.82 (s, 1H), 7.76 (s, 1H), 7.70-7.68 (m, 1H), 7.64-7.60 (m, 1H), 7.30 (d, J = 8.0 Hz, 1H), 7.25 (d, J = 7.6 Hz, 1H), 6.80 (d, J = 8.8 Hz, 1H), 4.78-4.75 (m, 1H), 4.25 (br d, J = 11.6 Hz, 2H), 4.16 (br d, J = 6.0 Hz, 2H), 3.67-3.61 (m, 3H), 3.52-3.49 (m, 1H), 3.25-3.22 (m, 1H), 2.91-2.86 (m, 2H), 2.44-2.41 (m, 2H), 2.20-2.16 (m, 1H), 1.90-1.85 (m, 1H), 1.18 (d, J = 6.0 Hz, 6H) ppm |
| 162 | (3R)-N-[2-[[4-[6-[(cis)-2,6-dimethylmorpholin-4-yl]-2-pyridyl]thiazol-2-yl]amino]-2-oxo-ethyl]-3-(hydroxymethyl)indane-5-carboxamide | 522.2 | $^1$H NMR (400 MHz, DMSO-d6) δ = 12.35-12.12 (m, 1H), 8.80-8.77 (m, 1H), 8.43 (s, 1H), 7.82 (s, 1H), 7.76 (s, 1H), 7.70-7.68 (m, 1H), 7.64-7.60 (m, 1H), 7.30 (d, J = 8.0 Hz, 1H), 7.25 (d, J = 7.2 Hz, 1H), 6.80 (d, J = 8.8 Hz, 1H), 4.78-4.75 (m, 1H), 4.25 (br d, J = 11.6 Hz, 2H), 4.16 (d, J = 5.6 Hz, 2H), 3.66-3.60 (m, 3H), 3.51-3.49 (m, 1H), 3.25-3.22 (m, 1H), 2.92-2.84 (m, 2H), 2.44-2.38 (m, 2H), 2.22-2.13 (m, 1H), 1.92-1.83 (m, 1H), 1.18 (d, J = 6.4 Hz, 6H) ppm |
| 182 | N-[2-[[4-[6-[(cis)-2,6-dimethylmorpholin-4-yl]-2-pyridyl]thiazol-2-yl]amino]-2-oxo-ethyl]-3-[1-(hydroxymethyl)cyclopropyl]benzamide | 522.0 | $^1$H NMR (400 MHz, DMSO-d6) δ = 12.40 (br d, J = 3.7 Hz, 1H), 8.97-8.82 (m, 1H), 7.81 (s, 1H), 7.77 (s, 1H), 7.70 (d, J = 7.9 Hz, 1H), 7.65-7.59 (m, 1H), 7.50 (d, J = 7.8 Hz, 1H), 7.43-7.36 (m, 1H), 7.25 (d, J = 7.2 Hz, 1H), 6.80 (d, J = 8.6 Hz, 1H), 4.70 (t, J = 5.7 Hz, 1H), 4.29-4.22 (m, 2H), 4.18 (br d, J = 5.6 Hz, 2H), 3.68-3.60 (m, 2H), 3.57 (d, J = 5.6 Hz, 2H), 2.44-2.38 (m, 2H), 1.18 (d, J = 6.2 Hz, 6H), 0.90-0.85 (m, 2H), 0.81-0.76 (m, 2H) ppm |
| 187 | N-[2-[[4-[6-[(cis)-2,6-dimethylmorpholin-4-yl]-2-pyridyl]thiazol-2-yl]amino]-2-oxo-ethyl]-3-(3-methyloxetan-3-yl)benzamide | 522.1 | $^1$H NMR (400 MHz, DMSO-d6) δ = 12.40 (s, 1H), 8.98-8.95 (m, 1H), 7.78-7.77 (m, 3H), 7.64-7.60 (m, 1H), 7.50-7.42 (m, 2H), 7.26 (d, J = 7.6 Hz, 1H), 6.80 (d, J = 8.4 Hz, 1H), 4.86 (d, J = 5.6 Hz, 2H), 4.58 (d, J = 5.6 Hz, 2H), 4.25 (br d, J = 12.0 Hz, 2H), 4.20 (br d, J = 5.6 Hz, 2H), 3.64-3.61 (m, 2H), 2.44-2.38 (m, 2H), 1.66 (s, 3H), 1.18 (br d, J = 6.0 Hz, 6H) ppm |
| 223 | (R)-N-(2-((4-(6-((cis)-2,6-dimethylmorpholino)pyridin-2-yl)thiazol-2-yl)amino)-2-oxoethyl)-3-(hydroxymethyl)-3-methyl-2,3-dihydro-1H-indene-5-carboxamide | 536.4 | $^1$H NMR (400 MHz, DMSO-d6) δ = 12.36 (br s, 1H), 8.88-8.68 (m, 1H), 7.76 (s, 1H), 7.72-7.67 (m, 2H), 7.64-7.59 (m, 1H), 7.30-7.22 (m, 2H), 6.79 (d, J = 8.4 Hz, 1H), 4.79-4.73 (m, 1H), 4.25 (br d, J = 11.6 Hz, 2H), 4.16 (d, J = 5.6 Hz, 2H), 3.68-3.59 (m, 2H), 3.37 (br d, J = 5.6 Hz, 2H), 2.91-2.84 (m, 2H), 2.45-2.38 (m, 2H), 2.22-2.14 (m, 1H), 1.77-1.68 (m, 1H), 1.23 (s, 3H), 1.18 (d, J = 6.0 Hz, 6H) ppm |
| 224 | (3S)-N-[2-[[4-[6-[(cis)-2,6-dimethylmorpholin-4-yl]-2-pyridyl]thiazol-2-yl]amino]-2-oxo-ethyl]-3- | 536.0 | $^1$H NMR (400 MHz, DMSO-d6) δ = 12.54-12.26 (m, 1H), 8.92-8.66 (m, 1H), 7.76 (s, 1H), 7.73-7.68 (m, 2H), 7.65-7.59 (m, 1H), 7.31-7.23 (m, 2H), 6.80 (d, J = 8.4 Hz, 1H), 4.79-4.73 (m, 1H), 4.25 (br d, J = 11.6 Hz, 2H), 4.17 (d, |

TABLE 7-continued

| # | Name | LC-MS (m/z) | 1H NMR |
|---|---|---|---|
| | (hydroxymethyl)-3-methyl-indane-5-carboxamide | | J = 5.6 Hz, 2H), 3.68-3.58 (m, 2H), 3.38 (br d, J = 5.6 Hz, 2H), 2.92-2.84 (m, 2H), 2.45-2.38 (m, 2H), 2.23-2.14 (m, 1H), 1.78-1.68 (m, 1H), 1.23 (s, 3H), 1.18 (d, J = 6.4 Hz, 6H) ppm |
| 237 | N-(2-((4-(6-((cis)-2,6-dimethylmorpholino)pyridin-2-yl)thiazol-2-yl)amino)-2-oxoethyl)-3-(1-hydroxy-2-methylpropan-2-yl)-4-methylbenzamide | 538.0 | $^{1}$H NMR (400 MHz, DMSO-d6) δ = 12.59-12.19 (m, 1H), 8.82 (t, J = 5.7 Hz, 1H), 7.85 (d, J = 1.6 Hz, 1H), 7.78 (s, 1H), 7.67-7.59 (m, 2H), 7.26 (d, J = 7.2 Hz, 1H), 7.22 (d, J = 8.1 Hz, 1H), 6.81 (d, J = 8.6 Hz, 1H), 6.83-6.78 (m, 1H), 4.71 (t, J = 5.4 Hz, 1H), 4.26 (br d, J = 12.2 Hz, 2H), 4.17 (br d, J = 5.7 Hz, 2H), 4.20-4.14 (m, 1H), 3.63 (br d, J = 5.5 Hz, 4H), 2.54-2.53 (m, 3H), 2.43-2.39 (m, 2H), 1.35 (s, 5H), 1.36 (br s, 1H), 1.19 (d, J = 6.2 Hz, 6H) ppm |
| 241 | 4-chloro-N-[2-[[4-[6-[(cis)-2,6-dimethylmorpholin-4-yl]-2-pyridyl]thiazol-2-yl]amino]-2-oxo-ethyl]-3-(2-hydroxy-1,1-dimethyl-ethyl)benzamide | 558.2 | $^{1}$H NMR (400 MHz, DMSO-d6) δ = 12.43 (br s, 1H), 9.03 (t, J = 5.9 Hz, 1H), 7.96 (d, J = 2.0 Hz, 1H), 7.78 (s, 1H), 7.74 (dd, J = 2.0, 8.3 Hz, 1H), 7.62 (dd, J = 7.4, 8.4 Hz, 1H), 7.51 (d, J = 8.3 Hz, 1H), 7.25 (d, J = 7.4 Hz, 1H), 6.80 (d, J = 8.6 Hz, 1H), 4.78 (t, J = 5.3 Hz, 1H), 4.26 (br d, J = 11.5 Hz, 2H), 4.18 (d, J = 5.8 Hz, 2H), 3.77 (d, J = 5.4 Hz, 2H), 3.63 (ddd, J = 2.5, 6.3, 10.2 Hz, 2H), 2.44-2.38 (m, 2H), 1.41 (s, 6H), 1.18 (d, J = 6.1 Hz, 6H) ppm |
| 271 | N-(2-((4-(6-((cis)-2,6-dimethylmorpholino)pyridin-2-yl)thiazol-2-yl)amino)-2-oxoethyl)-1-methylisochromane-6-carboxamide | 522.3 | $^{1}$H NMR (400 MHz, DMSO-d6) δ = 12.32 (s, 1H), 8.88-8.85 (m, 1H), 7.77 (s, 1H), 7.73-7.66 (m, 2H), 7.69-7.60(m, 1H), 7.29-7.25 (m, 2H), 6.80 (d, J = 8.4 Hz, 1H), 4.83-4.80 (m, 1H), 4.26 (d, J = 11.2 Hz, 2H), 4.18 (d, J = 6.0 Hz, 2H), 4.09-4.04 (m, 1H), 3.75-3.71 (m, 1H), 3.66-3.61 (m, 2H), 3.03-2.88 (m, 1H), 2.76-2.71 (m, 1H), 2.45-2.39 (m, 2H), 1.47 (d, J = 6.4 Hz, 3H), 1.19 (d, J = 6.4 Hz, 6H) ppm |
| 272 | (R)-4-(difluoromethyl)-N-(2-((4-(6-((cis)-2,6-dimethylmorpholino)pyridin-2-yl)thiazol-2-yl)amino)-2-oxoethyl)-4-fluorochromane-6-carboxamide | 576.1 | $^{1}$H NMR (400 MHz, DMSO-d6) δ = 12.40 (s, 1H), 8.89 (s, 1H), 8.17 (s, 1H), 7.94 (d, J = 8.8 Hz, 1H), 7.77 (s, 1H), 7.62-7.60 (m, 1H), 7.25 (d, J = 7.2 Hz, 1H), 7.07 (d, J = 8.8 Hz, 1H), 6.98-6.64 (m, 2H), 4.50-4.35 (m, 1H), 4.32-4.08 (m, 5H), 3.64-3.61 (m, 2H), 2.44-2.38 (m, 4H), 1.19 (s, 3H), 1.17 (s, 3H) ppm |
| 273 | (S)-4-(difluoromethyl)-N-(2-((4-(6-((cis)-2,6-dimethylmorpholino)pyridin-2-yl)thiazol-2-yl)amino)-2-oxoethyl)-4-fluorochromane-6-carboxamide | 576.1 | $^{1}$H NMR (400 MHz, DMSO-d6) δ = 8.91-8.88 (m, 1H), 8.17 (s, 1H), 7.94 (d, J = 8.8 Hz, 1H), 7.77 (s, 1H), 7.64-7.60 (m, 1H), 7.25 (d, J = 7.2 Hz, 1H), 7.06 (d, J = 8.8 Hz, 1H), 6.97-6.61 (m, 2H), 4.52-4.38 (m, 1H), 4.29-4.16 (m, 5H), 3.68-3.56 (m, 2H), 2.46-2.35 (m, 4H), 1.19 (s, 3H), 1.17 (s, 3H) ppm |
| 282 | N-(2-((4-(6-((cis)-2,6-dimethylmorpholino)pyridin-2-yl)thiazol-2-yl)amino)-2-oxoethyl)-4,4-dimethylisochromane-6-carboxamide | 536.4 | $^{1}$H NMR (400 MHz, DMSO-d6) δ = 12.48-12.34 (m, 1H), 8.94-8.91 (m, 1H), 7.95 (d, J = 1.2 Hz, 1H), 7.78 (s, 1H), 7.73-7.57 (m, 2H), 7.26 (d, J = 7.2 Hz, 1H), 7.13 (d, J = 8.0 Hz, 1H), 6.81 (d, J = 8.8 Hz, 1H), 4.77 (s, 2H), 4.31-4.16 (m, 4H), 3.69-3.56 (m, 4H), 2.43-2.38 (m, 2H), 1.34-1.23 (m, 6H), 1.19 (d, J = 6.0 Hz, 6H) ppm |
| 296 | N-(2-((4-(6-((cis)-2,6-dimethylmorpholino)pyridin-2-yl)thiazol-2-yl)amino)-2-oxoethyl)-1,3,4,5-tetrahydrobenzo[c]oxepine-7-carboxamide | 522.4 | $^{1}$H NMR (400 MHz, DMSO-d6) δ 12.38 (s, 1H), 8.87-8.85 (t, J = 5.7 Hz, 1H), 7.77-7.73 (m, 2H), 7.67-7.60 (m, 2H), 7.31 (d, J = 8.0 Hz, 1H), 7.25 (d, J = 7.2 Hz, 1H), 6.80 (d, J = 8.4 Hz, 1H), 4.65 (s, 2H), 4.25 (d, J = 11.2 Hz, 2H), 4.17 (d, J = 6.0 Hz, 2H), 3.97-3.94 (m, 2H), 3.63-3.61 (m, 2H), 3.04-3.01 (m, 2H), 2.41 (br d, J = 2.0 Hz, 2H), 1.75-1.73 (m, 2H), 1.18 (d, J = 6.0 Hz, 6H) ppm |
| 300 | N-(2-((4-(6-((cis)-2,6-dimethylmorpholino)pyridin-2-yl)thiazol-2-yl)amino)-2-oxoethyl)spiro[isochromane-4,3'-oxetane]-6-carboxamide | 550.2 | $^{1}$H NMR (400 MHz, DMSO-d6) δ = 12.45 (d, J = 1.2 Hz, 1H), 9.10 (m, 1H), 8.47 (d, J = 1.6 Hz, 1H), 7.84-7.74 (m, 2H), 7.65-7.63 (m, 1H), 7.27 (d, J = 7.2 Hz, 1H), 7.19 (d, J = 8.0 Hz, 1H), 6.81 (d, J = 8.4 Hz, 1H), 4.80 (d, J = 6.4 Hz, 2H), 4.75 (s, 2H), 4.59 (d, J = 6.4 Hz, 2H), 4.30-4.20 (m, 4H), 4.16 (s, 2H), 3.73-3.57 (m, 2H), 2.45-2.39 (m, 2H), 1.19 (d, J = 6.4 Hz, 6H) ppm |
| 304 | N-(2-((4-(6-((cis)-2,6-dimethylmorpholino)pyridin-2-yl)thiazol-2-yl)amino)-2-oxoethyl)-3-(3-fluoro-4-hydroxytetrahydrofuran-3-yl)benzamide | 556.2 | $^{1}$H NMR (400 MHz, DMSO-d6) δ = 12.41 (s, 1H), 9.03-9.00 (m, 1H), 8.01 (s, 1H), 7.92 (d, J = 8.4 Hz, 1H), 7.77 (s, 1H), 7.66-7.60 (m, 2H), 7.56-7.52 (m, 1H), 7.26 (d, J = 7.6 Hz, 1H), 6.80 (d, J = 8.4 Hz, 1H), 5.58 (d, J = 5.2 Hz, 1H), 4.37-4.11 (m, 8H), 3.82 (d, J = 9.2 Hz, 1H), 3.65-3.60 (m, 2H), 2.44-2.38 (m, 2H), 1.21-1.14 (m, 6H) ppm |
| 318 | N-(2-((4-(6-((cis)-2,6-dimethylmorpholino)pyridin-2-yl)thiazol-2-yl)amino)-2-oxoethyl)-3-(6-fluoro-2-oxaspiro[3.3]heptan-6-yl)benzamide | 566.2 | $^{1}$H NMR (400 MHz, DMSO-d6) δ = 12.42 (s, 1H), 9.07-9.01 (m, 1H), 7.95 (s, 1H), 7.90 (d, J = 8.0 Hz, 1H), 7.78 (s, 1H), 7.66-7.60 (m, 2H), 7.58-7.53 (m, 1H), 7.26 (d, J = 7.2 Hz, 1H), 6.81 (d, J = 8.4 Hz, 1H), 4.73 (s, 2H), 4.57 (s, 2H), 4.26 (d, J = 11.6 Hz, 2H), 4.21 (d, J = 5.6 Hz, 2H), 3.67-3.60 (m, 2H), 3.00-2.91 (m, 2H), 2.87-2.78 (m, 2H), 2.42 (d, J = 2.0 Hz, 2H), 1.19 (d, J = 6.0 Hz, 6H) ppm |

TABLE 7-continued

| # | Name | LC-MS (m/z) | 1H NMR |
|---|---|---|---|
| 320 | (R)-N-(2-((4-(6-((cis)-2,6-dimethylmorpholino)pyridin-2-yl)thiazol-2-yl)amino)-2-oxoethyl)-4-methylisochromane-6-carboxamide | 522.2 | $^1$H NMR (400 MHz, DMSO-d6) δ = 8.92-8.85 (m, 1H), 8.46 (s, 0.5H), 7.81 (s, 1H), 7.75 (s, 1H), 7.71-7.66 (m, 1H), 7.65-7.58 (m, 1H), 7.25 (d, J = 7.2 Hz, 1H), 7.14 (d, J = 8.0 Hz, 1H), 6.79 (d, J = 8.4 Hz, 1H), 4.81-4.65 (m, 2H), 4.25 (d, J = 11.6 Hz, 2H), 4.17 (d, J = 5.6 Hz, 2H), 3.93-3.86 (m, 1H), 3.64-3.57 (m, 3H), 2.98-2.88 (m, 1H), 2.45-2.36 (m, 2H), 1.26 (d, J = 7.2 Hz, 3H), 1.18 (d, J = 6.4 Hz, 6H) ppm |
| 321 | (S)-N-(2-((4-(6-((cis)-2,6-dimethylmorpholino)pyridin-2-yl)thiazol-2-yl)amino)-2-oxoethyl)-4-methylisochromane-6-carboxamide | 522.2 | $^1$H NMR (400 MHz, DMSO-d6) δ = 8.94-8.87 (m, 1H), 8.45 (s, 0.3H), 7.82 (s, 1H), 7.77 (s, 1H), 7.73-7.59 (m, 2H), 7.26 (d, J = 7.2 Hz, 1H), 7.15 (d, J = 8.0 Hz, 1H), 6.80 (d, J = 8.4 Hz, 1H), 4.81-4.68 (m, 2H), 4.26 (d, J = 11.6 Hz, 2H), 4.18 (d, J = 5.6 Hz, 2H), 3.95-3.88 (m, 1H), 3.66-3.58 (m, 3H), 3.03-2.87 (m, 1H), 2.46-2.38 (m, 2H), 1.27 (d, J = 7.2 Hz, 3H), 1.19 (d, J = 6.4 Hz, 6H) ppm |
| 338 | N-(2-((4-(6-((cis)-2,6-dimethylmorpholino)pyridin-2-yl)thiazol-2-yl)amino)-2-oxoethyl)-2,3,4,5-tetrahydrobenzo[b]oxepine-7-carboxamide | 522.3 | $^1$H NMR (400 MHz, DMSO-d6) δ = 12.37 (s, 1H), 8.79-8.76 (m, 1H), 7.76-7.74 (m, 2H), 7.66-7.64 (m, 1H), 7.64-7.62 (m, 1H), 7.26 (d, J = 7.2 Hz, 1H), 7.01 (d, J = 8.4 Hz, 1H), 6.80 (d, J = 8.4 Hz, 1H), 4.26 (d, J = 11.6 Hz, 2H), 4.16 (d, J = 5.6 Hz, 2H), 4.00-3.97 (m, 2H), 3.63-3.62 (m, 2H), 2.82-2.79 (m, 2H), 2.44-2.38 (m, 2H), 1.91-1.89 (m, 2H), 1.69-1.62 (m, 2H), 1.18 (d, J = 6.4 Hz, 6H) ppm |
| 346 | N-(2-((4-(6-((cis)-2,6-dimethylmorpholino)pyridin-2-yl)thiazol-2-yl)amino)-2-oxoethyl)-4-methylisochromane-6-carboxamide | 522 | $^1$H NMR (400 MHz, DMSO-d6) δ = 12.40 (br s, 1H), 9.00-8.82 (m, 1H), 7.79 (d, J = 17.2 Hz, 2H), 7.73-7.57 (m, 2H), 7.25 (d, J = 7.2 Hz, 1H), 7.14 (d, J = 8.0 Hz, 1H), 6.80 (d, J = 8.4 Hz, 1H), 4.74 (d, J = 7.6 Hz, 2H), 4.32-4.15 (m, 4H), 3.95-3.85 (m, 1H), 3.70-3.55 (m, 3H), 2.94 (d, J = 5.6 Hz, 1H), 2.45-2.38 (m, 2H), 1.26 (d, J = 6.8 Hz, 3H), 1.18 (d, J = 6.0 Hz, 6H) ppm |
| 349 | (R)-N-(2-((4-(6-((cis)-2,6-dimethylmorpholino)pyridin-2-yl)thiazol-2-yl)amino)-2-oxoethyl)spiro[isochromane-4,2'-oxetane]-6-carboxamide | 550.5 | $^1$H NMR (400 MHz, DMSO-d6) δ = 12.41 (br s, 1H), 9.15-9.06 (m, 1H), 8.47 (s, 1H), 7.83-7.81 (m, 1H), 7.77 (s, 1H), 7.63-7.61 (m, 1H), 7.26 (d, J = 7.2 Hz, 1H), 7.18 (d, J = 8.0 Hz, 1H), 6.80 (d, J = 8.4 Hz, 1H), 4.78-4.56 (m, 4H), 4.30-4.18 (m, 4H), 4.14-4.07 (m, 1H), 3.98 (d, J = 11.6 Hz, 1H), 3.63-3.62 (m, 2H), 2.96-2.85 (m, 1H), 2.75-2.63 (m, 1H), 2.44-2.38 (m, 2H), 1.18 (d, J = 6.0 Hz, 6H) ppm |
| 350 | (S)-N-(2-((4-(6-((cis)-2,6-dimethylmorpholino)pyridin-2-yl)thiazol-2-yl)amino)-2-oxoethyl)spiro[isochromane-4,2'-oxetane]-6-carboxamide | 550.5 | $^1$H NMR (400 MHz, DMSO-d6) δ = 12.44 (br s, 1H), 9.11-9.08 (m, 1H), 8.47 (d, J = 1.2 Hz, 1H), 7.83-7.81 (m, 1H), 7.78 (s, 1H), 7.63-7.61 (m, 1H), 7.27-7.25 (m, 1H), 7.18 (d, J = 8.0 Hz, 1H), 6.80 (d, J = 8.4 Hz, 1H), 4.75-4.58 (m, 4H), 4.29-4.21 (m, 4H), 4.10 (d, J = 11.6 Hz, 1H), 3.98 (d, J = 11.6 Hz, 1H), 3.67-3.59 (m, 2H), 2.95-2.86 (m, 1H), 2.72-2.64 (m, 1H), 2.44-2.38 (m, 2H), 1.18 (d, J = 6.0 Hz, 6H) ppm |
| 357 | 3-((1S,3S)-1,3-difluorocyclobutyl)-N-(2-((4-(6-((cis)-2,6-dimethylmorpholino)pyridin-2-yl)thiazol-2-yl)amino)-2-oxoethyl)benzamide | 542.2 | $^1$H NMR (400 MHz, DMSO-d6) δ = 12.42 (s, 1H), 9.07 (m, 1H), 7.97 (s, 1H), 7.92 (d, J = 8.0 Hz, 1H), 7.78 (s, 1H), 7.70-7.48 (m, 3H), 7.26 (d, J = 7.2 Hz, 1H), 6.81 (d, J = 8.8 Hz, 1H), 5.27-5.00 (m, 1H), 4.26 (d, J = 11.6 Hz, 2H), 4.22 (d, J = 6.0 Hz, 2H), 3.64-3.62 (m, 2H), 3.26-3.11 (m, 2H), 3.01-2.79 (m, 2H), 2.45-2.39 (m, 2H), 1.19 (d, J = 6.0 Hz, 6H) ppm |
| 358 | 3-((1R,3R)-1,3-difluorocyclobutyl)-N-(2-((4-(6-((cis)-2,6-dimethylmorpholino)pyridin-2-yl)thiazol-2-yl)amino)-2-oxoethyl)benzamide | 542.2 | $^1$H NMR (400 MHz, DMSO-d6) δ = 12.55-12.26 (m, 1H), 9.08 (m, 1H), 8.00 (d, J = 1.2 Hz, 1H), 7.92 (d, J = 7.6 Hz, 1H), 7.77 (s, 1H), 7.70-7.54 (m, 3H), 7.26 (d, J = 7.6 Hz, 1H), 6.80 (d, J = 8.8 Hz, 1H), 5.67-5.36 (m, 1H), 4.25 (d, J = 11.6 Hz, 2H), 4.21 (d, J = 5.6 Hz, 2H), 3.67-3.59 (m, 2H), 3.18-2.99 (m, 2H), 2.97-2.77 (m, 2H), 2.44-2.38 (m, 2H), 1.18 (d, J = 6.0 Hz, 6H) ppm |
| 360 | N-(2-((4-(6-((cis)-2,6-dimethylmorpholino)pyridin-2-yl)thiazol-2-yl)amino)-2-oxoethyl)spiro[chromane-4,2'-oxetane]-6-carboxamide | 550.5 | $^1$H NMR (400 MHz, DMSO-d6) δ = 12.40 (s, 1H), 8.93 (m, 1H), 8.39 (d, J = 2.0 Hz, 1H), 7.83-7.73 (m, 2H), 7.63 (m, 1H), 7.27 (d, J = 7.2 Hz, 1H), 6.83 (m, 2H), 4.68-4.56 (m, 2H), 4.32-4.16 (m, 6H), 3.68-3.60 (m, 2H), 3.06-2.95 (m, 1H), 2.72-2.63 (m, 1H), 2.43-2.23 (m, 4H), 1.19 (d, J = 6.0 Hz, 6H) ppm |
| 366 | N-(2-((4-(6-((cis)-2,6-dimethylmorpholino)pyridin-2-yl)thiazol-2-yl)amino)-2-oxoethyl)isochromane-6-carboxamide | 508.2 | $^1$H NMR (400 MHz, DMSO-d6) δ = 12.41 (br s, 1H), 8.89-8.86 (m, 1H), 7.77 (s, 1H), 7.72-7.66 (m, 2H), 7.62-7.60 (m, 1H), 7.25 (d, J = 7.2 Hz, 1H), 7.15 (d, J = 7.6 Hz, 1H), 6.80 (d, J = 8.8 Hz, 1H), 4.73 (s, 2H), 4.26-4.23 (m, 2H), 4.17-4.16 (m, 2H), 3.91-3.90 (m, 2H), 3.69-3.56 (m, 2H), 2.85-2.83 (m, 2H), 2.43-2.38 (m, 2H), 1.18 (d, J = 6.0 Hz, 6H) ppm |
| 370 | N-(2-((4-(6-((cis)-2,6-dimethylmorpholino)pyridin-2-yl)thiazol-2- | 508.1 | $^1$H NMR (400 MHz, DMSO-d6) δ = 12.26 (br s, 1H), 8.77-8.66 (m, 1H), 7.79-7.74 (m, 1H), 7.70-7.59 (m, 3H), 7.30-7.20 (m, 1H), 6.82-6.79 (m, 2H), 4.30-4.23 (m, 2H), |

TABLE 7-continued

| # | Name | LC-MS (m/z) | 1H NMR |
|---|---|---|---|
| | yl)amino)-2-oxoethyl)chromane-6-carboxamide | | 4.22-4.17 (m, 2H), 4.17-4.11 (m, 2H), 3.69-3.58 (m, 2H), 2.83-2.75 (m, 2H), 2.42-2.33 (m, 2H), 1.92-1.90 (m, 2H), 1.23-1.18 (m, 6H) ppm |
| 376 | N-(2-((4-(6-((cis)-2,6-dimethylmorpholino)pyridin-2-yl)thiazol-2-yl)amino)-2-oxoethyl)spiro[isochromane-4,2'-oxetane]-6-carboxamide | 550.4 | $^1$H NMR (400 MHz, DMSO-d6) δ = 12.43 (s, 1H), 9.08-9.05 (m, 1H), 8.46 (d, J = 1.6 Hz, 1H), 7.83-7.81 (m, 1H), 7.76 (s, 1H), 7.64-7.60 (m, 1H), 7.26 (d, J = 7.2 Hz, 1H), 7.18 (d, J = 8.0 Hz, 1H), 6.80 (d, J = 8.8 Hz, 1H), 4.77-4.59 (m, 4H), 4.29-4.19 (m, 4H), 4.10 (d, J = 11.6 Hz, 1H), 3.98 (d, J = 11.6 Hz, 1H), 3.70-3.56 (m, 2H), 2.95-2.85 (m, 1H), 2.72-2.65 (m, 1H), 2.44-2.38 (m, 2H), 1.18 (d, J = 6.0 Hz, 6H) ppm |
| 381 | N-(2-((4-(6-((cis)-2,6-dimethylmorpholino)pyridin-2-yl)thiazol-2-yl)amino)-2-oxoethyl)spiro[chromane-4,3'-oxetane]-6-carboxamide | 550.2 | $^1$H NMR (400 MHz, DMSO-d6) δ = 12.40 (s, 1H), 8.95-8.92 (m, 1H), 8.40 (d, J = 2.0 Hz, 1H), 7.77 (s, 1H), 7.73-7.71 (m, 1H), 7.64-7.60 (m, 1H), 7.26 (d, J = 7.2 Hz, 1H), 6.85 (d, J = 8.4 Hz, 1H), 6.80 (d, J = 8.4 Hz, 1H), 4.83 (d, J = 6.0 Hz, 2H), 4.56 (d, J = 6.0 Hz, 2H), 4.26 (d, J = 11.2 Hz, 2H), 4.19 (d, J = 5.6 Hz, 2H), 4.17-4.12 (m, 2H), 3.68-3.58 (m, 2H), 2.44-2.38 (m, 2H), 2.35-2.30 (m, 2H), 1.19 (s, 3H), 1.17 (s, 3H) ppm |
| 384 | 1-cyano-N-(2-((4-(6-((cis)-2,6-dimethylmorpholino)pyridin-2-yl)thiazol-2-yl)amino)-2-oxoethyl)-1-methylisochromane-7-carboxamide | 547.2 | $^1$H NMR (400 MHz, DMSO-d6) δ = 12.43 (s, 1H), 9.08-9.04 (m, 1H), 8.03 (d, J = 1.2 Hz, 1H), 7.88-7.86 (m, 1H), 7.77 (s, 1H), 7.64-7.60 (m, 1H), 7.39 (d, J = 8.0 Hz, 1H), 7.25 (d, J = 7.2 Hz, 1H), 6.80 (d, J = 8.0 Hz, 1H), 4.27-4.20 (m, 5H), 3.94-3.88 (m, 1H), 3.65-3.62 (m, 2H), 3.11-3.10 (m, 1H), 2.85-2.81 (m, 1H), 2.41-2.38 (m, 2H), 1.94 (s, 3H), 1.18 (d, J = 6.0 Hz, 6H) ppm |
| 385 | N-(2-((4-(6-((cis)-2,6-dimethylmorpholino)pyridin-2-yl)thiazol-2-yl)amino)-2-oxoethyl)-4,4-difluoroisochromane-6-carboxamide | 544.2 | $^1$H NMR (400 MHz, DMSO-d6) δ = 12.42 (br s, 1H), 9.21-9.05 (m, 1H), 8.25 (s, 1H), 8.03 (d, J = 8.4 Hz, 1H), 7.77 (s, 1H), 7.68-7.54 (m, 1H), 7.41 (d, J = 8.4 Hz, 1H), 7.25 (d, J = 7.2 Hz, 1H), 6.79 (d, J = 8.4 Hz, 1H), 4.89 (s, 2H), 4.29-4.15 (m, 6H), 3.66-3.59 (m, 2H), 2.43-2.38 (m, 2H), 1.17 (d, J = 6.0 Hz, 6H) ppm |
| 395 | N-(2-((4-(6-((cis)-2,6-dimethylmorpholino)pyridin-2-yl)thiazol-2-yl)amino)-2-oxoethyl)-4-isopropyl-3,4-dihydro-2H-benzo[b][1,4]oxazine-6-carboxamide | 551.2 | $^1$H NMR (400 MHz, MeOD) δ = 7.68 (s, 1H), 7.63-7.55 (m, 1H), 7.42-7.32 (m, 2H), 7.16-7.15 (m, 1H), 6.80-6.70 (m, 2H), 5.17 (s, 2H), 4.31-4.20 (m, 7H), 3.80-3.68 (m, 2H), 2.51-2.45 (m, 2H), 1.26 (d, J = 6.0 Hz, 6H), 1.22 (d, J = 6.4 Hz, 6H)) ppm |
| 405 | rac-4-cyano-N-(2-((4-(6-((cis)-2,6-dimethylmorpholino)pyridin-2-yl)thiazol-2-yl)amino)-2-oxoethyl)chromane-6-carboxamide | 533.1 | $^1$H NMR (400 MHz, MeOD) δ = 7.94 (d, J = 1.2 Hz, 1H), 7.84-7.78 (m,, 1H), 7.68 (s, 1H), 7.62-7.55 (m, 1H), 7.35 (d, J = 7.2 Hz, 1H), 6.95 (d, J = 8.8 Hz, 1H), 6.73 (d, J = 8.4 Hz, 1H), 4.39-4.32 (m, 3H), 4.30-4.21 (m, 4H), 3.79-3.68 (m, 2H), 2.53-2.44 (m,, 2H), 2.43-2.28 (m, 2H), 1.26 (d, J = 6.4 Hz, 6H) ppm |
| 409 | (S)-N-(2-((4-(6-((cis)-2,6-dimethylmorpholino)pyridin-2-yl)thiazol-2-yl)amino)-2-oxoethyl)-4-fluoro-4-methylisochromane-6-carboxamide | 540.3 | $^1$H NMR (400 MHz, DMSO-d6) δ = 12.42 (s, 1H), 9.06 (m, 1H), 8.19 (s, 1H), 7.89 (d, J = 8.0 Hz, 1H), 7.77 (s, 1H), 7.62 (m, 1H), 7.32-7.22 (m, 2H), 6.80 (d, J = 8.4 Hz, 1H), 4.90-4.81 (m, 1H), 4.77-4.68 (m, 1H), 4.32-4.17 (m, 4H), 4.13-4.01 (m, 1H), 3.90-3.77 (m, 1H), 3.69-3.56 (m, 2H), 2.41 (m, 2H), 1.75-1.63 (m, 3H), 1.18 (d, J = 6.0 Hz, 6H) ppm |
| 410 | (R)-N-(2-((4-(6-((cis)-2,6-dimethylmorpholino)pyridin-2-yl)thiazol-2-yl)amino)-2-oxoethyl)-2,2-difluorospiro[cyclopropane-1,4'-isochromane]-6'-carboxamide | 570.3 | $^1$H NMR (400 MHz, DMSO-d6) δ = 12.43 (s, 1H), 8.97-8.95 (m, 1H), 7.86-7.74 (m, 2H), 7.67-7.59 (m, 2H), 7.28-7.26 (8, 2H), 6.81 (d, J = 8.8 Hz, 1H), 5.00-4.85 (m, 2H), 4.28-4.25 (m, 2H), 4.22-4.20 (m, 2H), 3.98-3.92 (m, 1H), 3.89-3.83 (m, 1H), 3.68-3.59 (m, 2H), 2.42 (br s, 3H), 1.95-1.87 (m, 1H), 1.19-1.17 (m, 6H) ppm |
| 411 | (S)-N-(2-((4-(6-((cis)-2,6-dimethylmorpholino)pyridin-2-yl)thiazol-2-yl)amino)-2-oxoethyl)-2,2-difluorospiro[cyclopropane-1,4'-isochromane]-6'-carboxamide | 570.3 | $^1$H NMR (400 MHz, DMSO-d6) δ = 12.43 (s, 1H), 8.97-8.95 (m, 1H), 7.86-7.74 (m, 2H), 7.67-7.59 (m, 2H), 7.28-7.26 (8, 2H), 6.81 (d, J = 8.8 Hz, 1H), 5.00-4.85 (m, 2H), 4.28-4.25 (m, 2H), 4.22-4.20 (m, 2H), 3.98-3.92 (m, 1H), 3.89-3.83 (m, 1H), 3.68-3.59 (m, 2H), 2.42 (s, 3H), 1.95-1.87 (m, 1H), 1.19-1.17 (m, 6H) ppm |
| 412 | (R)-N-(2-((4-(6-((cis)-2,6-dimethylmorpholino)pyridin-2-yl)thiazol-2-yl)amino)-2-oxoethyl)-4-fluoro-4-methylisochromane-6-carboxamide | 540.2 | $^1$H NMR (400 MHz, DMSO-d6) δ = 12.45 (br s, 1H), 9.09-9.06 (m, 1H), 8.20 (s, 1H), 7.89 (d, J = 8.0 Hz, 1H), 7.78 (s, 1H), 7.63-7.61 (m, 1H), 7.28-7.25 (m, 2H), 6.81 (d, J = 8.8 Hz, 1H), 4.91-4.69 (m, 2H), 4.31-4.18 (m, 4H), 4.08-4.06 (m, 1H), 3.93-3.77 (m, 1H), 3.64-3.60 (m, 2H), 2.44-2.39 (m, 2H), 1.75-1.62 (m, 3H), 1.19 (d, J = 6.0 Hz, 6H) ppm |

TABLE 7-continued

| # | Name | LC-MS (m/z) | 1H NMR |
|---|---|---|---|
| 413 | N-(2-((4-(6-((cis)-2,6-dimethylmorpholino)pyridin-2-yl)thiazol-2-yl)amino)-2-oxoethyl)-3-((cis)-4-hydroxy-3-methyltetrahydrofuran-3-yl)benzamide | 552.2 | $^1$H NMR (400 MHz, DMSO-d6) δ = 12.43-12.36 (m, 1H), 8.95-8.92 (m, 1H), 7.89 (s, 1H), 7.77-7.74 (m, 2H), 7.64-7.57 (m, 2H), 7.46-7.42 (m, 1H), 7.25 (d, J = 7.6 Hz, 1H), 6.80 (d, J = 8.4 Hz, 1H), 5.33 (d, J = 5.2 Hz, 1H), 4.33-4.18 (m, 5H), 4.05 (d, J = 8.4 Hz, 1H), 3.87-3.81 (m, 2H), 3.64-3.61 (m, 2H), 3.55-3.52 (m, 1H), 2.44-2.38 (m, 2H), 1.32-1.31 (s, 3H), 1.18 (d, J = 6.4 Hz, 6H) ppm |
| 420 | (R)-4-cyano-N-(2-((4-(6-((cis)-2,6-dimethylmorpholino)pyridin-2-yl)thiazol-2-yl)amino)-2-oxoethyl)-4-methylisochromane-6-carboxamide | 547 | $^1$H NMR (400 MHz, DMSO-d6) δ = 12.45 (d, J = 6.0 Hz, 1H), 9.09 (d, J = 6.8 Hz, 1H), 8.13 (d, J = 6.0 Hz, 1H), 7.92-7.87 (m, 1H), 7.78 (d, J = 7.6 Hz, 1H), 7.63-7.62 (m, 1H), 7.31-7.26 (m, 2H), 6.82 (d, J = 8.0 Hz, 1H), 4.92-4.85 (m, 2H), 4.27-4.22 (m, 5H), 3.89-3.84 (m, 1H), 3.63 (s, 2H), 2.44 (d, J = 12.4 Hz, 2H), 1.70 (d, J = 6.8 Hz, 3H), 1.18-1.17 (m, 6H) ppm |
| 421 | (S)-4-cyano-N-(2-((4-(6-((cis)-2,6-dimethylmorpholino)pyridin-2-yl)thiazol-2-yl)amino)-2-oxoethyl)-4-methylisochromane-6-carboxamide | 547 | $^1$H NMR (400 MHz, DMSO-d6) δ = 12.44 (s, 1H), 9.09-9.06 (m, 1H), 8.12 (d, J = 1.6 Hz, 1H), 7.88-7.86 (m, 1H), 7.77 (s, 1H), 7.62-7.60 (m, 1H), 7.30-7.24 (m, 2H), 6.80 (d, J = 8.8 Hz, 1H), 4.92-4.85 (m, 2H), 4.27-4.20 (m, 5H), 3.86 (d, J = 11.6 Hz, 1H), 3.63-3.61 (m, 2H), 2.41-2.38 (m, 2H), 1.69 (s, 3H), 1.18 (d, J = 6.0 Hz, 6H) ppm |
| 425 | N-(2-((4-(6-((cis)-2,6-dimethylmorpholino)pyridin-2-yl)thiazol-2-yl)amino)-2-oxoethyl)-3-((trans)-4-hydroxytetrahydrofuran-3-yl)benzamide | 538.2 | $^1$H NMR (400 MHz, DMSO-d6) δ = 12.53-12.24 (m, 1H), 8.95-8.82 (m, 1H), 7.82 (s, 1H), 7.76-7.74 (m, 2H), 7.64-7.60 (m, 1H), 7.48-7.46 (m, 1H), 7.43-7.39 (m, 1H), 7.25 (d, J = 7.6 Hz, 1H), 6.80 (d, J = 8.4 Hz, 1H), 4.92 (d, J = 4.8 Hz, 1H), 4.39-4.36 (m, 1H), 4.25 (d, J = 12.8 Hz, 2H), 4.18 (d, J = 5.6 Hz, 2H), 4.10-4.06 (m, 1H), 4.02-3.97 (m, 2H), 3.74-3.71 (m, 1H), 3.66-3.58 (m, 3H), 2.41 (s, 2H), 1.18 (d, J = 6.0 Hz, 6H) ppm |
| 426 | N-(2-((4-(6-((cis)-2,6-dimethylmorpholino)pyridin-2-yl)thiazol-2-yl)amino)-2-oxoethyl)-3-((cis)-1-fluoro-3-methoxycyclobutyl)benzamide | 554.1 | $^1$H NMR (400 MHz, DMSO-d6) δ = 12.57-12.29 (m, 1H), 9.22-8.97 (m, 1H), 7.97 (d, J = 0.8 Hz, 1H), 7.93-7.86 (m, 1H), 7.79 (s, 1H), 7.67-7.60 (m, 2H), 7.59-7.53 (m, 1H), 7.32-7.20 (m, 1H), 6.85-6.76 (m, 1H), 4.37-4.15 (m, 5H), 3.69-3.60 (m, 2H), 3.23 (s, 3H), 2.98-2.81 (m, 2H), 2.47-2.37 (m, 4H), 1.18 (s, 6H) ppm |
| 441 | N-(2-((4-(6-((cis)-2,6-dimethylmorpholino)pyridin-2-yl)thiazol-2-yl)amino)-2-oxoethyl)-3-((R)-3-fluorotetrahydrofuran-3-yl)benzamide | 540.2 | $^1$H NMR (400 MHz, DMSO-d6) δ = 9.06-9.03 (m, 1H), 8.01 (s, 1H), 7.90 (d, J = 7.6 Hz, 1H), 7.77 (s, 1H), 7.68 (d, J = 7.6 Hz, 1H), 7.64-7.60 (m, 1H), 7.58-7.54 (m, 1H), 7.25 (d, J = 7.2 Hz, 1H), 6.80 (d, J = 8.4 Hz, 1H), 4.29-4.04 (m, 7H), 3.97-3.85 (m, 1H), 3.66-3.59 (m, 2H), 2.62-2.59 (m, 2H), 2.44-2.38 (m, 2H), 1.18 (d, J = 6.4 Hz, 6H) ppm |
| 406 | N-(2-((4-(6-((cis)-2,6-dimethylmorpholino)pyridin-2-yl)thiazol-2-yl)amino)-2-oxoethyl)spiro[cyclopropane-1,4'-isochromane]-6'-carboxamide | 534.4 | $^1$H NMR (400 MHz, DMSO-d6) δ = 12.40 (br s, 1H), 8.90-8.87 (m, 1H), 7.77 (s, 1H), 7.66-7.59 (m, 2H), 7.31 (d, J = 1.2 Hz, 1H), 7.25 (d, J = 7.2 Hz, 1H), 7.14 (d, J = 8.0 Hz, 1H), 6.80 (d, J = 8.4 Hz, 1H), 4.85 (s, 2H), 4.25 (br d, J = 11.2 Hz, 2H), 4.16 (d, J = 6.0 Hz, 2H), 3.67 (s, 2H), 3.67-3.62 (m, 2H), 2.44-2.39 (m, 2H), 1.18 (d, J = 6.0 Hz, 6H), 1.10-1.04 (m, 2H), 0.99-0.91 (m, 2H) ppm |

Example 108. Preparation of 3-isopropylsulfonyl-N-[2-[[4-[6-(6-methylpyrimidin-4-yl)-2-pyridyl]thiazol-2-yl]amino]-2-oxo-ethyl]benzamide (Compound 117)

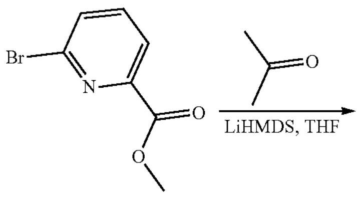

A

-continued

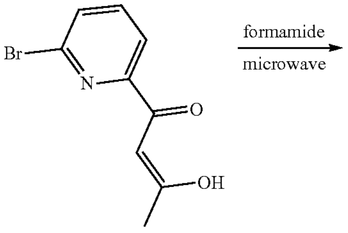

B

-continued

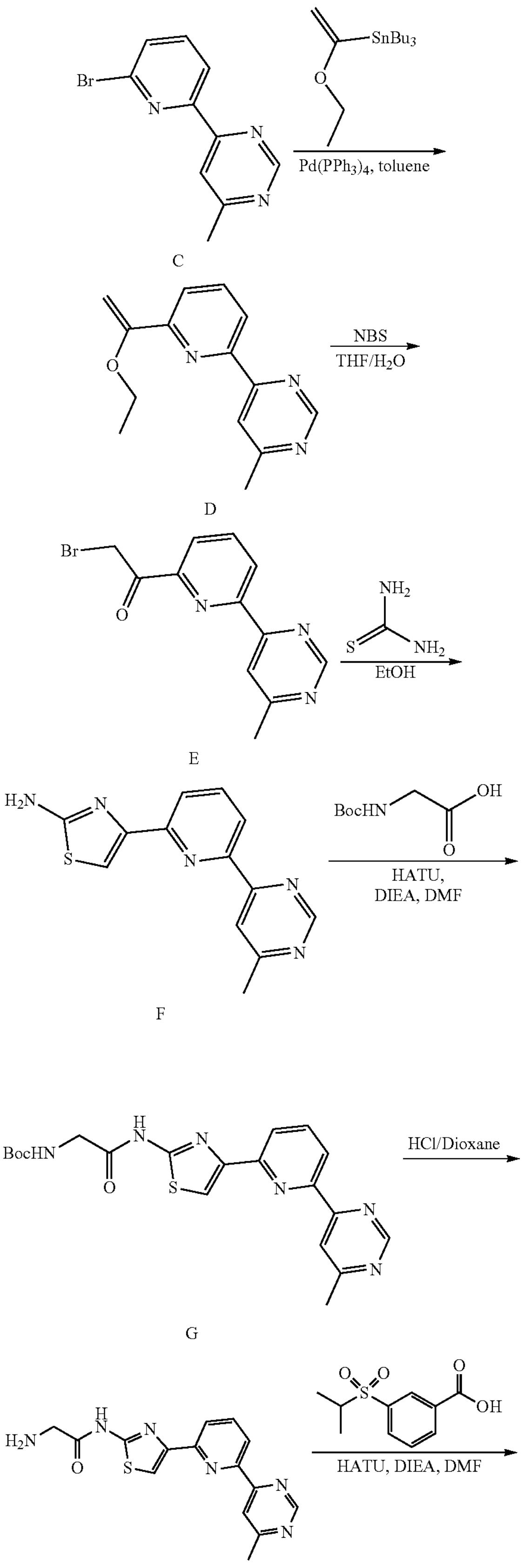

-continued

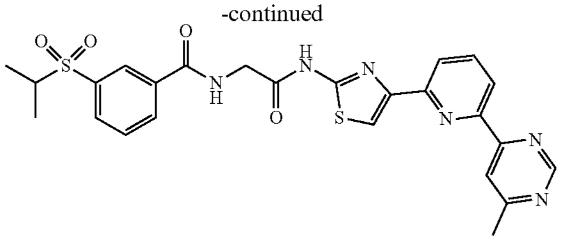

Step 1: Preparation of (Z)-1-(6-bromo-2-pyridyl)-3-hydroxy-but-2-en-1-one

B

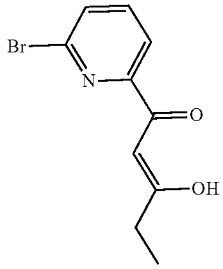

To a solution of acetone (1.75 g, 30.09 mmol, 2.21 mL) in THE (85 mL) at −78° C. was added LiHMDS (1 M, 30.09 mL), then the mixture was stirred at −78° C. for 1 h. A solution of methyl 6-bromopyridine-2-carboxylate (5.0 g, 23.14 mmol) in THE (30 mL) was added. The mixture was warmed to 25° C. and stirred for 11 hrs. The mixture was quenched with water (100 mL), extracted with EA (100 mL*3), the organic layer was separated and concentrated to give a residue. The residue was purified by column chromatography (Petroleum ether/Ethyl acetate=1/0 to 1/1). The eluant was concentrated to give Intermediate B (3.0 g, 51% yield) as a brown solid. LCMS (ESI) m/z: $[M+H]^+$=242.0. $^1H$ NMR (400 MHz, CHLOROFORM-d) δ=15.39 (s, 1H), 7.88-7.86 (m, 1H), 7.54 (d, J=7.6 Hz, 1H), 7.45-7.42 (m, 1H), 6.65 (s, 1H), 2.11 (s, 3H) ppm.

Step 2: Preparation of 4-(6-bromo-2-pyridyl)-6-methyl-pyrimidine

C

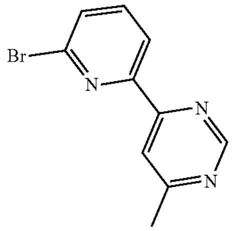

The mixture of Intermediate B (1.0 g, 4.13 mmol) in formamide (11.30 g, 250.88 mmol, 10 mL) was stirred for 3 hrs at 180° C. under microwave. The mixture was combined with another batch. The mixture was washed with water (5 mL) and extracted with EA (10 mL*3), the organic layer was separated and concentrated to give a residue. The residue was purified by column chromatography ($SiO_2$, Petroleum ether/Ethyl acetate=100/1 to 1/1), the eluant was concentrated to give Intermediate C (800 mg, 35% yield) as a brown solid. LCMS (ESI) m/z: $[M+H]^+$=250.0. $^1H$ NMR (400 MHz, CHLOROFORM-d) δ=9.15 (d, J=1.2 Hz, 1H), 8.46-8.44 (m, 1H), 8.23 (s, 1H), 7.73 (d, J=7.6 Hz, 1H), 7.59 (m, 1H), 2.64 (s, 3H) ppm.

Step 3: Preparation of 4-[6-(1-ethoxyvinyl)-2-pyridyl]-6-methyl-pyrimidine

D

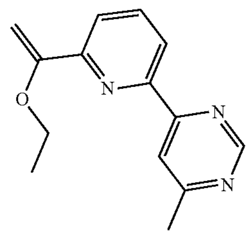

To a solution of Intermediate C (600 mg, 2.40 mmol) in toluene (6 mL) was added tributyl(1-ethoxyvinyl)stannane (1.30 g, 3.60 mmol, 1.21 mL) and Pd(PPh3)4 (554.46 mg, 479.82 umol) at 25° C. under nitrogen atmosphere. Then the mixture was heated to 100° C. and stirred for 12 hrs. The mixture was added saturated aqueous KF (10 mL) and stirred for 1 h, then extracted with EA (10 mL*3), the organic layer was separated and concentrated to give a residue. The residue was purified by column chromatography (petroleum ether/Ethyl acetate=100/1 to 1/1), the eluant was concentrated to give Intermediate D (500 mg, 82% yield) as a brown solid. LCMS (ESI) m/z: $[M+H]^+$=242.1. $^1$HNMR (400 MHz, CHLOROFORM-d) δ=9.07 (d, J=1.2 Hz, 1H), 8.33 (m, 1H), 8.25 (d, J=0.4 Hz, 1H), 7.83-7.71 (m, 2H), 5.57 (d, J=1.6 Hz, 1H), 4.37 (d, J=1.6 Hz, 1H), 3.95 (m, 2H), 2.57 (s, 3H), 1.40 (m, 3H) ppm.

Step 4: Preparation of 2-bromo-1-[6-(6-methylpyrimidin-4-yl)-2-pyridyl]ethanone

E

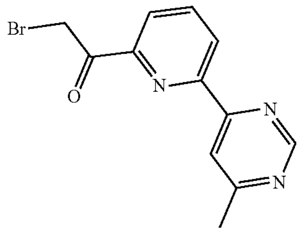

A mixture of Intermediate D (400 mg, 1.66 mmol) and NBS (354.06 mg, 1.99 mmol) in THF (2 mL) and H2O (0.2 mL) was stirred for 0.5 h at 25° C. The mixture was washed with water (2 mL) and extracted with EA (5 mL*3), the organic layer was separated and concentrated to afford a residue. The residue was purified by column chromatography ($SiO_2$, Petroleum ether/Ethyl acetate=100/1 to 1/1), the eluant was concentrated to give Intermediate E (400 mg, 74% yield) as a white solid. LCMS (ESI) m/z: $[M+H]^+$=292.0. $^1H$ NMR (400 MHz, CHLOROFORM-d) δ=9.20 (s, 1H), 8.75-8.73 (m, 1H), 8.26 (s, 1H), 8.22-8.20 (m, 1H), 8.11-8.04 (m, 1H), 4.96 (s, 2H), 2.70 (s, 3H) ppm.

Step 5: Preparation of 4-(6-(6-methylpyrimidin-4-yl)pyridin-2-yl)thiazol-2-amine

F

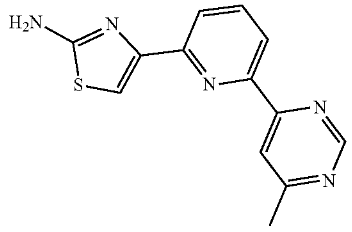

To a solution of Intermediate E (300 mg, 1.03 mmol) in EtOH (3 mL) was added thiourea (85.99 mg, 1.13 mmol) at 25° C. Then the mixture was heated to 70° C. and stirred for 1 hr. The mixture was washed with water (3 mL) and extracted with EA (5 mL*3), the organic layer was separated and concentrated to give Intermediate F (320 mg, crude) as a white solid. LCMS (ESI) m/z: $[M+H]^+$=270.1. $^1H$ NMR (400 MHz, DMSO-$d_6$) δ=9.19 (d, J=1.2 Hz, 1H), 8.61 (s, 1H), 8.43 (d, J=4.4 Hz, 1H), 8.14 (d, J=4.4 Hz, 2H), 7.77 (s, 1H), 2.64 (s, 3H) ppm.

Step 6: Preparation of tert-butyl N-[2-[[4-[6-(6-methylpyrimidin-4-yl)-2-pyridyl]thiazol-2-yl]amino]-2-oxo-ethyl]carbamate

G

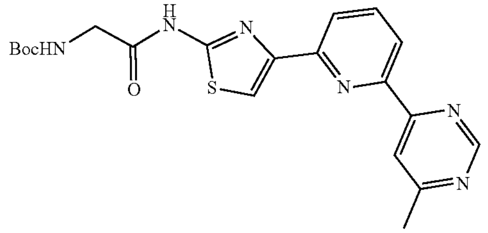

To a solution of Intermediate F (250 mg, 928.25 umol) in DMF (2.5 mL) was added HATU (705.90 mg, 1.86 mmol) and DIEA (359.90 mg, 2.78 mmol, 485.04 uL) at 25° C., then 2-(tertbutoxycarbonylamino) acetic acid (325.22 mg, 1.86 mmol) was added and stirred for 1 hr at 25° C. The mixture was washed with water (5 mL) and extracted with EA (10 mL*3), the organic layer was separated and concentrated to afford a residue. The residue was purified by column chromatography (petroleum ether/Ethyl acetate=100/1 to 1/10), the eluant was concentrated to give Intermediate G (350 mg, 80% yield) as a white solid. LCMS (ESI) m/z: $[M+H]^+$=427.1. $^1H$ NMR (400 MHz, CHLOROFORM-d) δ=9.19 (s, 1H), 8.41 (d, J=7.6 Hz, 1H), 8.35 (s, 1H), 8.05-7.99 (m, 1H), 7.97-7.91 (m, 1H), 7.89 (s, 1H), 7.26 (d, J=7.2 Hz, 1H), 7.20 (s, 1H), 4.15 (s, 2H), 2.68 (s, 3H), 1.52 (s, 9H) ppm.

Step 7: Preparation of 2-amino-N-(4-(6-(6-methylpyrimidin-4-yl)pyridin-2-yl)thiazol-2-yl)acetamide hydrochloride salt

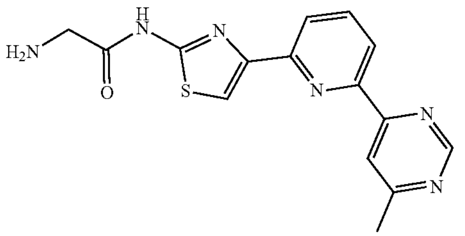

A mixture of Intermediate G (350 mg, 820.65 umol) in HCl/dioxane (4 M, 5 mL) was stirred for 30 min at 25° C. The mixture was concentrated to give Intermediate H (290 mg, crude) as a brown solid. LCMS (ESI) m/z: $[M+H]^+$ =327.3. $^1$H NMR (400 MHz, DMSO-6) δ=9.22 (d, J=1.2 Hz, 1H), 8.54-8.53 (m, 1H), 8.42-8.38 (m, 1H), 8.29 (s, 1H), 8.17-8.11 (m, 1H), 8.11-8.06 (m, 1H), 3.95 (d, J=5.6 Hz, 2H), 2.65 (s, 3H) ppm.

Step 8: Preparation of 3-isopropylsulfonyl-N-[2-[[4-[6-(6-methylpyrimidin-4-yl)-2-pyridyl]thiazol-2-yl]amino]-2-oxo-ethyl]benzamide (Compound 117)

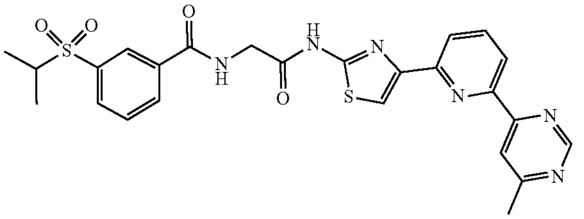 [SMILES: Cc1cc(-c2cccc(-c3csc(NC(=O)CNC(=O)c4cccc(S(=O)(=O)C(C)C)c4)n3)n2)ncn1]

To a solution of Intermediate H (100 mg, 275.61 umol) in DMF (1 mL) was added 3-isopropylsulfonylbenzoic acid (Prepared according to the method in FG-A796) (74.32 mg, 325.59 umol), HATU (190.45 mg, 500.88 umol), DIEA (161.84 mg, 1.25 mmol, 218.11 uL) at 25° C. Then the mixture was stirred for 1 h at 25° C. The mixture was washed with water (5 mL) and extracted with EA (5 mL*3), the organic layer was separated and concentrated to afford a residue. The residue was purified by prep-HPLC (column: Phenomenex Synergi C18 150*30 mm*4 um; mobile phase: [water (0.05% HCl)-ACN]; B %: 38%-58%, 12 min) and lyophilized to give Compound 117 (20 mg, 13% yield) as a yellow solid. LCMS (ESI) m/z: $[M+H]^+$=537.2. $^1$H NMR (400 MHz, METHANOL-d4) δ=9.48 (d, J=0.8 Hz, 1H), 9.01 (s, 1H), 8.63-8.61 (m, 1H), 8.46 (d, J=1.6 Hz, 1H), 8.46-8.39 (m, 1H), 8.33-8.22 (m, 3H), 8.13-8.10 (m, 1H), 7.82 (d, J=7.6 Hz, 1H), 4.40 (s, 2H), 3.50-3.39 (m, 1H), 2.91 (s, 3H), 1.32 (s, 3H), 1.30 (s, 3H) ppm.

Example 109. Preparation of Compounds of the Invention

The following compounds in Table 8 were prepared using standard chemical manipulations and procedures similar to those used for the preparation of Compound 117.

TABLE 8

| # | Name | LC-MS (m/z) | 1H NMR |
|---|---|---|---|
| 154 | 3-(1-hydroxy-2-methylpropan-2-yl)-N-(2-((4-(6-(2-methyl-2H-1,2,3-triazol-4-yl)pyridin-2-yl)thiazol-2-yl)amino)-2-oxoethyl)benzamide | 492.2 | $^1$H NMR (400 MHz, DMSO-d6) δ = 12.57-12.46 (m, 1H), 8.96-8.92 (m, 1H), 8.39 (s, 1H), 8.04 (s, 1H), 8.03-7.97 (m, 1H), 7.94-7.90 (m, 2H), 7.85-7.82 (m, 1H), 7.74 (d, J = 7.6 Hz, 1H), 7.57 (d, J = 8.4 Hz, 1H), 7.45-7.39 (m, 1H), 4.74-4.70 (m, 1H), 4.26 (s, 3H), 4.21 (d, J = 5.6 Hz, 2H), 3.47 (d, J = 4.8 Hz, 2H), 1.28 (s, 6H) ppm |
| 155 | 3-(hydroxymethyl)-3-methyl-N-(2-((4-(6-(2-methyl-2H-1,2,3-triazol-4-yl)pyridin-2-yl)thiazol-2-yl)amino)-2-oxoethyl)-2,3-dihydro-1H-indene-5-carboxamide | 504.2 | $^1$H NMR (400 MHz, DMSO-d6) δ = 12.50 (s, 1H), 8.85-8.81 (m, 1H), 8.39 (s, 1H), 8.04 (s, 1H), 8.02-7.97 (m, 1H), 7.94-7.89 (m, 1H), 7.85-7.82 (m, 1H), 7.75-7.69 (m, 2H), 7.29 (d, J = 8.0 Hz, 1H), 4.80-4.76 (m, 1H), 4.26 (s, 3H), 4.20 (d, J = 5.6 Hz, 2H), 3.39 (d, J = 5.2 Hz, 2H), 2.91-2.87 (m, 2H), 2.23-2.16 (m, 1H), 1.78-1.70 (m, 1H), 1.24 (s, 3H) ppm |
| 163 | (R)-3-(hydroxymethyl)-3-methyl-N-(2-((4-(6-(6-methylpyrazin-2-yl)pyridin-2-yl)thiazol-2-yl)amino)-2-oxoethyl)-2,3-dihydro-1H-indene-5-carboxamide | 515.2 | $^1$H NMR (400 MHz, DMSO-d6) δ = 12.50 (s, 1H), 9.57 (s, 1H), 8.84-8.82(m, 1H), 8.64 (s, 1H), 8.29 (d, J = 6.8 Hz, 1H), 8.18 (s, 1H), 8.08-8.02(m, 2H), 7.76-7.68 (m, 2H), 7.28 (d, J = 7.6 Hz, 1H), 4.20 (d, J = 5.6 Hz, 2H), 3.39-3.38 (m, 2H), 2.88-2.86(m, 2H), 2.61 (s, 3H), 2.26-2.17(m, 1H), 1.76-1.71 (m, 1H), 1.24 (s, 3H) ppm |
| 164 | (S)-3-(hydroxymethyl)-3-methyl-N-(2-((4-(6-(6-methylpyrazin-2-yl)pyridin-2-yl)thiazol-2-yl)amino)-2-oxoethyl)- | 515.2 | $^1$H NMR (400 MHz, DMSO-d6) δ = 12.48 (d, J = 16.8 Hz, 1H), 9.56(s, 1H), 8.84-8.82(m, 1H), 8.64 (s, 1H), 8.28-8.27(m, 1H), 8.18 (s, 1H), 8.08-8.02(m, 2H), 7.72-7.71(m, 2H), 7.28 (d, J = 7.6 Hz, 1H), 4.78-4.76(m, 1H), 4.20(d, J = 5.6 Hz, 2H), 3.38 (d, J = 6.0 Hz, 2H), 2.89-2.86(m, 2H), |

TABLE 8-continued

| # | Name | LC-MS (m/z) | 1H NMR |
|---|---|---|---|
| | 2,3-dihydro-1H-indene-5-carboxamide | | 2.61 (s, 3H), 2.20-2.16(m, 1H), 1.74-1.72(m, 1H), 1.23 (s, 3H) ppm |
| 167 | (R)-3-(hydroxymethyl)-3-methyl-N-(2-oxo-2-((4-(6-(pyrazin-2-yl)pyridin-2-yl)thiazol-2-yl)amino)ethyl)-2,3-dihydro-1H-indene-5-carboxamide | 501.3 | $^1$H NMR (400 MHz, DMSO-d6) δ = 9.79 (d, J = 1.6 Hz, 1H), 8.83 (s, 1H), 8.80-8.74 (m, 2H), 8.31-8.29(m, 1H), 8.20 (s, 1H), 8.15-8.03 (m, 2H), 7.76-7.68 (m, 2H), 7.29 (d, J = 7.6 Hz, 1H), 4.91-4.69 (m, 1H), 4.20 (d, J = 5.6 Hz, 2H), 3.39 (s, 2H), 2.96-2.82 (m, 2H), 2.25-2.13 (m, 1H), 1.77-1.70(m, 1H), 1.25 (s, 3H) ppm |
| 169 | (S)-3-(hydroxymethyl)-3-methyl-N-(2-oxo-2-((4-(6-(pyrazin-2-yl)pyridin-2-yl)thiazol-2-yl)amino)ethyl)-2,3-dihydro-1H-indene-5-carboxamide | 501.2 | $^1$H NMR (400 MHz, DMSO-d6) δ = 12.56-12.51(m, 1H), 9.78 (d, J = 1.2 Hz, 1H), 8.84 (s, 1H), 8.78-8.77 (m, 1H), 8.76-8.75(m, 1H), 8.30-8.29(m, 1H), 8.21 (s, 1H), 8.10-8.08 (m, 1H), 8.06-8.05(m, 1H), 7.72-7.71(m, 2H), 7.29 (d, J = 7.6 Hz, 1H), 4.80-4.78(m, 1H), 4.20 (d, J = 5.6 Hz, 2H), 3.38 (d, J = 6.4 Hz, 2H), 2.89-2.86(m, 2H), 2.21-2.17(m, 1H), 1.76-1.71 (m, 1H), 1.23(s, 3H) ppm |
| 190 | (S)-N-(2-((4-(2'-hydroxy-5'-methyl-[2,3'-bipyridin]-6-yl)thiazol-2-yl)amino)-2-oxoethyl)-3-(hydroxymethyl)-3-methyl-2,3-dihydro-1H-indene-5-carboxamide | 530.4 | $^1$H NMR (400 MHz, DMSO-d6) δ = 12.59-12.49 (m, 1H), 12.32-11.82 (m, 1H), 8.85 (d, J = 5.6 Hz, 1H), 8.65-8.55 (m, 2H), 8.10 (s, 1H), 8.06-7.92 (m, 2H), 7.76-7.69 (m, 2H), 7.44 (s, 1H), 7.29 (d, J = 7.8 Hz, 1H), 4.21 (d, J = 5.6 Hz, 2H), 3.39-3.39 (m, 2H), 2.92-2.86 (m, 2H), 2.22 (d, J = 7.6 Hz, 1H), 2.19 (s, 3H), 1.78-1.69 (m, 1H), 1.24 (s, 3H) ppm |
| 263 | (R)-N-(2-((4-(2'-hydroxy-5'-methyl-[2,3'-bipyridin]-6-yl)thiazol-2-yl)amino)-2-oxoethyl)-3-(hydroxymethyl)-3-methyl-2,3-dihydro-1H-indene-5-carboxamide | 530.4 | $^1$H NMR (400 MHz, DMSO-d6) δ = 12.49 (s, 1H), 11.84 (d, J = 0.8 Hz, 1H), 8.84 (d, J = 5.2 Hz, 1H), 8.60 (d, J = 7.6 Hz, 1H), 8.52 (d, J = 1.6 Hz, 1H), 8.03 (s, 1H), 7.96-7.82 (m, 2H), 7.76-7.66 (m, 2H), 7.36 (s, 1H), 7.29 (d, J = 8.0 Hz, 1H), 4.86-4.70 (m, 1H), 4.20 (d, J = 5.6 Hz, 2H), 3.39 (s, 2H), 2.92-2.87 (m, 2H), 2.23-2.15 (m, 4H), 1.77-1.73(m, 1H), 1.24 (s, 3H) ppm |
| 191 | (S)-N-(2-((4-(2'-hydroxy-[2,3'-bipyridin]-6-yl)thiazol-2-yl)amino)-2-oxoethyl)-3-(hydroxymethyl)-3-methyl-2,3-dihydro-1H-indene-5-carboxamide | 516.5 | $^1$H NMR (400 MHz, DMSO-d6) δ = 12.57 (s, 1H), 12.25 (s, 1H), 8.86-8.85(m, 1H), 8.71-8.69(m, 1H), 8.60-8.58(m, 1H), 8.08-7.98(m, 3H), 7.73-7.65(m, 3H), 7.29 (d, J = 7.6 Hz, 1H), 6.53-6.51 (m, 1H), 4.21 (d, J = 5.6 Hz, 2H), 3.41-3.35 (m, 2H), 2.90-2.87(m, 2H), 2.20-2.17(m, 1H), 1.75-1.69(m, 1H), 1.24 (s, 3H) ppm |
| 264 | (R)-N-(2-((4-(2'-hydroxy-[2,3'-bipyridin]-6-yl)thiazol-2-yl)amino)-2-oxoethyl)-3-(hydroxymethyl)-3-methyl-2,3-dihydro-1H-indene-5-carboxamide | 516.5 | $^1$H NMR (400 MHz, DMSO-d6) δ = 12.57 (s, 1H), 12.25 (s, 1H), 8.86-8.85(m, 1H), 8.71-8.69(m, 1H), 8.60-8.58(m, 1H), 8.08-7.98(m, 3H), 7.73-7.65(m, 3H), 7.29 (d, J = 7.6 Hz, 1H), 6.53-6.51(m, 1H), 4.21 (d, J = 5.6 Hz, 2H), 3.41-3.35 (m, 2H), 2.90-2.87(m, 2H), 2.20-2.17(m, 1H), 1.75-1.69(m, 1H), 1.24 (s, 3H) ppm |
| 192 | (3S)-3-(hydroxymethyl)-3-methyl-N-[2-[[4-[6-(1-methylpyrazol-3-yl)-2-pyridyl]thiazol-2-yl]amino]-2-oxo-ethyl]indane-5-carboxamide | 503.3 | $^1$H NMR (400 MHz, DMSO-d6) δ = 12.48 (s, 1H), 8.85-8.82 (m, 1H), 7.95 (s, 1H), 7.92-7.88 (m, 1H), 7.84-7.82 (m, 2H), 7.80 (d, J = 2.0 Hz, 1H), 7.72-7.69 (m, 2H), 7.28 (d, J = 7.6 Hz, 1H), 6.95 (d, J = 2.4 Hz, 1H), 4.80-4.77 (m, 1H), 4.19 (d, J = 5.6 Hz, 2H), 3.93 (s, 3H), 3.38 (d, J = 6.0 Hz, 2H), 2.89-2.86 (m, 2H), 2.21-2.15 (m, 1H), 1.76-1.69 (m, 1H), 1.23 (s, 3H) ppm |
| 265 | (3R)-3-(hydroxymethyl)-3-methyl-N-[2-[[4-[6-(1-methylpyrazol-3-yl)-2-pyridyl]thiazol-2-yl]amino]-2-oxo-ethyl]indane-5-carboxamide | 503.3 | $^1$H NMR (400 MHz, DMSO-d6) δ = 8.86-8.83 (m, 1H), 7.95 (s, 1H), 7.92-7.88 (m, 1H), 7.84-7.82 (m, 2H), 7.80 (d, J = 2.0 Hz, 1H), 7.72-7.69 (m, 2H), 7.28 (d, J = 7.6 Hz, 1H), 6.95 (d, J = 2.4 Hz, 1H), 4.82-4.75 (m, 1H), 4.19 (d, J = 6.0 Hz, 2H), 3.93 (s, 3H), 3.37 (s, 2H), 2.90-2.86 (m, 2H), 2.22-2.21 (m, 1H), 2.18-2.15 (m, 1H), 1.76-1.68 (m, 1H), 1.23 (s, 3H) ppm |
| 201 | 3-(2-amino-1,1-dimethyl-ethyl)-4-methyl-N-[2-[[4-[6-(6-methylpyrimidin-4-yl)-2-pyridyl]thiazol-2-yl]amino]-2-oxo-ethyl]benzamide | 516.3 | $^1$H NMR (400 MHz, DMSO-d6) δ = 9.17 (d, J = 0.8 Hz, 1H), 9.04-8.95 (m, 1H), 8.49 (d, J = 0.8 Hz, 1H), 8.43-8.29 (m, 2H), 8.20 (s, 1H), 8.16-8.04 (m, 2H), 7.84 (d, J = 1.6 Hz, 1H), 7.69 (m, 1H), 7.26 (d, J = 8.4 Hz, 1H), 4.23-4.18 (m, 2H), 3.06-2.96 (m, 2H), 2.61 (s, 3H), 2.55-2.52 (m, 3H), 1.41 (s, 6H) ppm |
| 203 | (3R)-3-(hydroxymethyl)-3-methyl-N-[2-[[4-[6-(6-methylpyrimidin-4-yl)-2-pyridyl]thiazol-2-yl]amino]-2-oxo-ethyl]indane-5-carboxamide | 515.4 | $^1$H NMR (400 MHz, DMSO-d6) δ = 12.56 (s, 1H), 9.21 (d, J = 1.2 Hz, 1H), 8.89 (d, J = 6.0 Hz, 1H), 8.54(s, 1H), 8.39 (d, J = 7.6 Hz, 1H), 8.23 (s, 1H), 8.17-8.06 (m, 2H), 7.77-7.66 (m, 2H), 7.29 (d, J = 8.0 Hz, 1H), 4.21 (d, J = 5.6 Hz, 2H), 3.39 (d, J = 5.6, 2H), 2.95-2.85 (m, 2H), 2.64 (s, 3H), 2.22-2.15 (m, 1H), 1.79-1.70 (m, 1H), 1.24 (s, 3H) ppm |
| 204 | (3S)-3-(hydroxymethyl)-3-methyl-N-[2-[[4-[6-(6-methylpyrimidin-4-yl)-2-pyridyl]thiazol-2-yl]amino]-2-oxo- | 515.4 | $^1$H NMR (400 MHz, DMSO-d6) δ = 12.53 (s, 1H), 9.18 (d, J = 1.2 Hz, 1H), 8.85 (d, J = 5.6 Hz, 1H), 8.50 (s, 1H), 8.39 (d, J = 7.6 Hz, 1H), 8.21 (s, 1H), 8.17-8.05 (m, 2H), 7.75-7.68 (m, 2H), 7.29 (d, J = 8.0 Hz, 1H), 4.78 (d, J = 5.6 Hz, 1H), 4.21 (d, J = 5.6 Hz, 2H), 3.39 (d, J = 6.0 Hz, 2H), 2.93-2.85 |

TABLE 8-continued

| # | Name | LC-MS (m/z) | 1H NMR |
|---|---|---|---|
| | ethyl]indane-5-carboxamide | | (m, 2H), 2.63 (s, 3H), 2.23-2.16 (m, 1H), 1.77-1.70 (m, 1H), 1.25 (s, 3H) ppm |
| 206 | 3-(2-amino-1,1-dimethyl-ethyl)-4-methyl-N-[2-[[4-[6-(2-methylpyrimidin-4-yl)-2-pyridyl]thiazol-2-yl]amino]-2-oxo-ethyl]benzamide | 516.2 | $^1$H NMR (400 MHz, DMSO-d6) δ = 12.57 (s, 1H), 9.04 (d, J = 5.6 Hz, 1H), 8.95 (d, J = 5.2 Hz, 1H), 8.45 (d, J = 5.2 Hz, 1H), 8.43-8.36 (m, 1H), 8.15 (s, 1H), 8.14-8.08 (m, 2H), 7.91 (s, 3H), 7.87 (d, J = 1.2 Hz, 1H), 7.77-7.72 (m, 1H), 7.31 (d, J = 8.0 Hz, 1H), 4.21 (d, J = 5.6 Hz, 2H), 3.22-3.13 (m, 2H), 2.77 (s, 3H), 2.55 (s, 3H), 1.49 (s, 6H) ppm |
| 207 | (S)-8-(hydroxymethyl)-8-methyl-N-(2-((4-(6-(6-methylpyrimidin-4-yl)pyridin-2-yl)thiazol-2-yl)amino)-2-oxoethyl)-5,6,7,8-tetrahydronaphthalene-2-carboxamide | 529.2 | $^1$H NMR (400 MHz, DMSO-d6) δ = 9.17 (s, 1H), 8.83-8.63 (m, 1H), 8.50 (s, 1H), 8.39-8.32 (m, 1H), 8.18-8.04 (m, 3H), 7.88 (s, 1H), 7.66-7.56 (m, 1H), 7.21-7.12 (m, 1H), 4.75 (d, J = 5.6 Hz, 1H), 4.13 (d, J = 3.6 Hz, 2H), 3.53-3.43 (m, 2H), 2.76 (d, J = 6.0 Hz, 2H), 2.62 (s, 3H), 2.05-1.93 (m, 1H), 1.82-1.67 (m, 2H), 1.49-1.39 (m, 1H), 1.22 (s, 3H) ppm |
| 208 | (R)-8-(hydroxymethyl)-8-methyl-N-(2-((4-(6-(6-methylpyrimidin-4-yl)pyridin-2-yl)thiazol-2-yl)amino)-2-oxoethyl)-5,6,7,8-tetrahydronaphthalene-2-carboxamide | 529.2 | $^1$H NMR (400 MHz, DMSO-d6) δ = 12.53 (s, 1H), 9.18 (d, J = 1.2 Hz, 1H), 8.94-8.83 (m, 1H), 8.50 (s, 1H), 8.39 (d, J = 7.2 Hz, 1H), 8.21 (s, 1H), 8.17-8.06 (m, 2H), 7.88 (d, J = 1.6 Hz, 1H), 7.62 (d, J = 8.0 Hz, 1H), 7.16 (d, J = 8.4 Hz, 1H), 4.74 (d, J = 5.6 Hz, 1H), 4.20 (d, J = 6.0 Hz, 2H), 3.54-3.41 (m, 1H), 2.76 (d, J = 6.4 Hz, 2H), 2.62 (s, 3H), 2.02-1.95(m, 1H), 1.86-1.64 (m, 2H), 1.49-1.41 (m, 1H), 1.22 (s, 3H) ppm |
| 211 | (4S)-4-(hydroxymethyl)-4-methyl-N-[2-[[4-[6-(2-methylpyrimidin-4-yl)-2-pyridyl]thiazol-2-yl]amino]-2-oxo-ethyl]tetralin-6-carboxamide | 529.1 | $^1$H NMR (400 MHz, DMSO-d6) δ = 12.55 (s, 1H), 8.91 (d, J = 5.2 Hz, 2H), 8.46-8.36 (m, 2H), 8.20-8.05 (m, 3H), 7.88 (d, J = 1.6 Hz, 1H), 7.63-7.61 (m, 1H), 7.16 (d, J = 8.0 Hz, 1H), 4.20 (d, J = 5.6 Hz, 2H), 3.52 (d, J = 10.8 Hz, 1H), 3.42 (s, 1H), 2.74 (s, 5H), 2.03-1.93 (m, 1H), 1.85-1.62 (m, 2H), 1.49-1.38 (m, 1H), 1.22 (s, 3H) ppm |
| 212 | (4R)-4-(hydroxymethyl)-4-methyl-N-[2-[[4-[6-(2-methylpyrimidin-4-yl)-2-pyridyl]thiazol-2-yl]amino]-2-oxo-ethyl]tetralin-6-carboxamide | 529.1 | $^1$H NMR (400 MHz, DMSO-d6) δ = 12.52 (s, 1H), 8.90 (d, J = 5.2 Hz, 1H), 8.89-8.84 (m, 1H), 8.45-8.35 (m, 2H), 8.19-8.06(m, 3H), 7.88 (d, J = 1.6 Hz, 1H), 7.64-7.62 (m, 1H), 7.16 (d, J = 8.0 Hz, 1H), 4.73 (d, J = 5.6 Hz, 1H), 4.21 (d, J = 5.6 Hz, 2H), 3.54-3.50 (m, 2H), 2.76-2.72 (m, 5H), 2.05-1.93 (m, 1H), 1.87-1.64 (m, 2H), 1.48-1.40 (m, 1H), 1.22 (s, 3H) ppm |
| 214 | (S)-N-(2-((4-(3-(2,6-dimethylpyridin-4-yl)phenyl)thiazol-2-yl)amino)-2-oxoethyl)-8-(hydroxymethyl)-8-methyl-5,6,7,8-tetrahydronaphthalene-2-carboxamide | 515.0 | $^1$H NMR (400 MHz, DMSO-d6) δ = 12.50 (s, 1H), 8.90 (d, J = 5.2 Hz, 1H), 8.84-8.83 (m, 1H), 8.45-8.34 (m, 2H), 8.17-8.08 (m, 3H), 7.77-7.68 (m, 2H), 7.29 (d, J = 7.6 Hz, 1H), 4.78-4.75(m, 1H), 4.21 (d, J = 5.6 Hz, 2H), 3.39 (d, J = 6.0 Hz, 2H), 2.98-2.83 (m, 2H), 2.75 (s, 3H), 2.20-2.18 (m, 1H), 1.75-1.73 (m, 1H), 1.25 (s, 3H) ppm |
| 215 | (R)-N-(2-((4-(3-(2,6-dimethylpyridin-4-yl)phenyl)thiazol-2-yl)amino)-2-oxoethyl)-8-(hydroxymethyl)-8-methyl-5,6,7,8-tetrahydronaphthalene-2-carboxamide | 515.0 | $^1$H NMR (400 MHz, DMSO-d6) δ = 12.51 (s, 1H), 8.90 (d, J = 5.2 Hz, 1H), 8.84-8.83 (m, 1H), 8.44-8.36 (m, 2H), 8.24-8.02 (m, 3H), 7.76-7.68 (m, 2H), 7.29 (d, J = 7.6 Hz, 1H), 4.78-4.75(m, 1H), 4.21 (d, J = 5.6 Hz, 2H), 3.39 (d, J = 6.0 Hz, 2H), 2.95-2.85 (m, 2H), 2.75 (s, 3H), 2.24-2.15 (m, 1H), 1.75-1.73 (m, 1H), 1.25 (s, 3H) ppm |
| 110 | 3-isopropylsulfonyl-4-methyl-N-[2-[[4-[6-(6-methylpyrimidin-4-yl)-2-pyridyl]thiazol-2-yl]amino]-2-oxo-ethyl]benzamide | 551.1 | $^1$H NMR (400 MHz, DMSO-d6) δ = 12.59 (s, 1H), 9.26-9.24 (m, 1H), 9.17 (d, J = 1.2 Hz, 1H), 8.49 (s, 1H), 8.38-8.37 (m, 2H), 8.21 (s, 1H), 8.15-8.06 (m, 3H), 7.64 (d, J = 8.0 Hz, 1H), 4.24 (d, J = 4.0 Hz, 2H), 3.58-3.49 (m, 1H), 2.68 (s, 3H), 2.61(s, 3H), 1.19 (d, J = 6.8 Hz, 6H) ppm |
| 216 | 4-chloro-3-(2-hydroxy-1,1-dimethyl-ethyl)-N-[2-[[4-[6-(6-methylpyrimidin-4-yl)-2-pyridyl]thiazol-2-yl]amino]-2-oxo-ethyl]benzamide | 537.2 | $^1$H NMR (400 MHz, DMSO-d6) δ = 12.60-12.53 (m, 1H), 9.17 (d, J = 8.0 Hz, 1H), 9.08-9.05 (m, 1H), 8.49 (s, 1H), 8.39-8.36 (m, 1H), 8.21 (s, 1H), 8.13-8.06 (m, 2H), 7.97 (d, J = 2.0 Hz, 1H), 7.76-7.73 (m, 1H), 7.52 (d, J = 8.4 Hz, 1H), 4.79 (s, 1H), 4.21 (d, J = 5.2 Hz, 2H), 3.76 (s, 2H), 2.61 (s, 3H), 1.41 (s, 6H) ppm |
| 266 | (3S)-3-cyano-3-methyl-N-[2-[[4-[6-(6-methylpyrimidin-4-yl)-2-pyridyl]thiazol-2-yl]amino]-2-oxo-ethyl]indane-5-carboxamide | 510.2 | $^1$H NMR (400 MHz, DMSO-d6) δ = 9.17 (d, J = 0.8 Hz, 1H), 9.02 (d, J = 5.6 Hz, 1H), 8.50 (s, 1H), 8.38 (d, J = 7.2 Hz, 1H), 8.20 (s, 1H), 8.15-8.06 (m, 2H), 8.02 (s, 1H), 7.89 (d, J = 1.6 Hz, 1H), 7.46 (d, J = 8.0 Hz, 1H), 4.23 (d, J = 4.0 Hz, 2H), 3.07 (d, J = 7.2 Hz, 2H), 2.70-2.65 (m, 1H), 2.62 (s, 3H), 2.28-2.23 (m, 1H), 1.68 (s, 3H) ppm |
| 267 | (3R)-3-cyano-3-methyl-N-[2-[[4-[6-(6-methylpyrimidin-4-yl)-2- | 510.2 | $^1$H NMR (400 MHz, DMSO-d6) δ = 9.18 (d, J = 0.8 Hz, 1H), 9.01 (d, J = 5.6 Hz, 1H), 8.56-8.46 (m, 1H), 8.38 (d, J = 7.2 Hz, 1H), 8.20 (s, 1H), 8.16-8.07 (m, 2H), 8.02 (s, 1H), 7.95- |

TABLE 8-continued

| # | Name | LC-MS (m/z) | 1H NMR |
|---|---|---|---|
| | pyridyl]thiazol-2-yl]amino]-2-oxo-ethyl]indane-5-carboxamide | | 7.83 (m, 1H), 7.46 (d, J = 8.0 Hz, 1H), 4.23 (d, J = 3.6 Hz, 2H), 3.07 (d, J = 7.2 Hz, 2H), 2.69-2.66 (m, 1H), 2.63 (s, 3H), 2.31-2.20 (m, 1H), 1.68 (s, 3H) ppm |
| 268 | (3S)-3-cyano-3-methyl-N-[2-[[4-[6-(2-methylpyrimidin-4-yl)-2-pyridyl]thiazol-2-yl]amino]-2-oxo-ethyl]indane-5-carboxamide | 510.1 | $^1$H NMR (400 MHz, DMSO-d6) δ = 12.57 (s, 1H), 9.06-9.04 (m, 1H), 8.90 (d, J = 5.2 Hz, 1H), 8.40-8.37 (m, 2H), 8.14-8.13(m, 1H), 8.11-8.08 (m, 2H), 8.01 (d, J = 1.2 Hz, 1H), 7.88-7.87 (m, 1H), 7.46 (d, J = 8.0 Hz, 1H), 4.23-4.21 (m, 2H), 3.06-3.04 (m, 2H), 2.73 (s, 3H), 2.63-2.50 (m, 1H), 2.26-2.23 (m, 1H), 1.66 (s, 3H) ppm |
| 249 | (3R)-3-cyano-3-methyl-N-[2-[[4-[6-(2-methylpyrimidin-4-yl)-2-pyridyl]thiazol-2-yl]amino]-2-oxo-ethyl]indane-5-carboxamide | 510.1 | $^1$H NMR (400 MHz, DMSO-d6) δ = 8.84 (d, J = 5.2 Hz, 1H), 8.36 (d, J = 5.2 Hz, 2H), 8.08 (d, J = 3.2 Hz, 3H), 7.93 (s, 1H), 7.83 (d, J = 7.6 Hz, 1H), 7.45 (d, J = 8.0 Hz, 1H), 4.20 (s, 2H), 3.05-3.02 (m, 2H), 2.70 (s, 3H), 2.62-2.58 (m, 1H), 2.25-2.20 (m, 1H), 1.63 (s, 3H) ppm |
| 222 | 3-(2-hydroxy-1,1-dimethyl-ethyl)-N-[2-[[4-[6-(2-methylpyrimidin-4-yl)-2-pyridyl]thiazol-2-yl]amino]-2-oxo-ethyl]benzamide | 502.9 | $^1$H NMR (400 MHz, DMSO-d6) δ = 12.53 (s, 1H), 8.95-8.89 (m, 2H), 8.41-8.37 (m, 2H), 8.15-8.10 (m, 3H), 7.92 (s, 1H), 7.74 (d, J = 8.0 Hz, 1H), 7.58 (d, J = 8.0 Hz, 1H), 7.44-7.42 (m, 1H), 4.73-4.70 (m, 1H), 4.23 (d, J = 5.6 Hz, 2H), 3.47 (d, J = 5.2 Hz, 2H), 2.75 (s, 3H), 1.28 (s, 6H) ppm |
| 230 | 3-(2-hydroxy-1,1-dimethyl-ethyl)-N-[2-[[4-[6-(6-methylpyrimidin-4-yl)-2-pyridyl]thiazol-2-yl]amino]-2-oxo-ethyl]benzamide | 503.2 | $^1$H NMR (400 MHz, DMSO-d6) δ = 12.56-12.53 (m, 1H), 9.18 (s, 1H), 8.94 (d, J = 5.6 Hz, 1H), 8.50 (s, 1H), 8.39 (d, J = 6.0 Hz, 1H), 8.21 (s, 1H), 8.17-8.06 (m, 2H), 7.92 (s, 1H), 7.74 (d, J = 7.6 Hz, 1H), 7.58 (d, J = 8.0 Hz, 1H), 7.46-7.39 (m, 1H), 4.77-4.65 (m, 1H), 4.22 (d, J = 5.6 Hz, 2H), 3.47 (d, J = 4.8 Hz, 2H), 2.63 (s, 3H), 1.28 (s, 6H)ppm. |
| 118 | N-[2-[[4-[6-(6-cyano-2-pyridyl)-2-pyridyl]thiazol-2-yl]amino]-2-oxo-ethyl]-3-isopropylsulfonyl-benzamide | 547.0 | $^1$H NMR (400 MHz, DMSO-d6) δ = 12.58 (br s, 1H), 9.33-9.30 (m, 1H), 8.90 (d, J = 8.0 Hz, 1H), 8.39 (s, 1H), 8.33-8.31 (m, 1H), 8.30-8.24 (m, 2H), 8.16-8.04 (m, 5H), 7.86-7.81 (m, 1H), 4.27 (d, J = 5.6 Hz, 2H), 3.54-3.47 (m, 1H), 1.20 (d, J = 6.8 Hz, 6H) ppm |
| 119 | 3-isopropylsulfonyl-N-[2-[[4-[6-(2-methoxypyrimidin-4-yl)-2-pyridyl]thiazol-2-yl]amino]-2-oxo-ethyl]benzamide | 553.1 | $^1$H NMR (400 MHz, DMSO-d6) δ = 12.60 (s, 1H), 9.35-9.30 (m, 1H), 8.82 (d, J = 4.8 Hz, 1H), 8.40-8.37 (m, 2H), 8.30-8.27(m, 1H), 8.22 (d, J = 5.2 Hz, 1H), 8.16-8.05 (m, 4H), 7.86-7.81 (m, 1H), 4.27 (d, J = 5.6 Hz, 2H), 4.05 (s, 3H), 3.55-3.48 (m, 1H), 1.20 (d, J = 6.8 Hz, 6H) ppm |
| 121 | 3-isopropylsulfonyl-N-[2-[[4-[6-(2-methoxypyrimidin-4-yl)-2-pyridyl]thiazol-2-yl]amino]-2-oxo-ethyl]benzamide | 537.1 | $^1$H NMR (400 MHz, DMSO-d6) δ = 8.87 (d, J = 4.0 Hz, 1H), 8.46-8.30 (m, 3H), 8.24 (d, J = 6.4 Hz, 1H), 8.14-8.01 (m, 4H), 7.84-7.80 (m, 1H), 4.24 (s, 2H), 3.49-3.41 (m, 1H), 2.73 (s, 3H), 1.17 (d, J = 6.0 Hz, 6H) ppm |

Example 110. Preparation of Compounds of the Invention

The following compounds in Table 9 were prepared using standard chemical manipulations and procedures similar to those used for the preparation of Compound 17.

TABLE 9

| # | Name | LC-MS (m/z) | 1H NMR |
|---|---|---|---|
| 269 | (S)-4-cyano-8-fluoro-N-(2-((4-(3-methoxyphenyl)thiazol-2-yl)amino)-2-oxoethyl)-4-methylisochromane-6-carboxamide | 481.1 | $^1$H NMR (400 MHz, DMSO-d6) δ = 12.62-12.30 (m, 1H), 9.18 (m, 1H), 8.03 (d, J = 1.2 Hz, 1H), 7.70 (m, 1H), 7.66 (s, 1H), 7.52-7.44 (m, 2H), 7.34 (m, 1H), 6.93-6.87 (m, 1H), 5.07-4.80 (m, 2H), 4.28-4.19 (m, 3H), 3.88 (d, J = 11.6 Hz, 1H), 3.80 (s, 3H), 1.71 (s, 3H) ppm |
| 270 | (R)-4-cyano-8-fluoro-N-(2-((4-(3-methoxyphenyl)thiazol-2-yl)amino)-2-oxoethyl)-4-methylisochromane-6-carboxamide | 481.1 | $^1$H NMR (400 MHz, DMSO-d6) δ = 12.76-12.26 (m, 1H), 9.18 (m, 1H), 8.04 (d, J = 1.2 Hz, 1H), 7.71 (m, 1H), 7.67 (s, 1H), 7.53-7.45 (m, 2H), 7.35 (m, 1H), 6.97-6.85 (m, 1H), 5.04-4.77 (m, 2H), 4.29-4.20 (m, 3H), 3.89 (d, J = 11.6 Hz, 1H), 3.81 (s, 3H), 1.71 (s, 3H) ppm |
| 278 | (S)-5-fluoro-N-(2-((4-(3-methoxyphenyl)thiazol- | 470.1 | $^1$H NMR (400 MHz, DMSO-d6) δ = 12.44 (m, 1H), 9.00-9.00 (m, 1H), 8.06 (d, J = 1.6 Hz, 1H), 7.80-7.77 (m, 1H), |

TABLE 9-continued

| # | Name | LC-MS (m/z) | 1H NMR |
|---|---|---|---|
| | 2-yl)amino)-2-oxoethyl)-5-methyl-1,3,4,5-tetrahydrobenzo[c]oxepine-7-carboxamide | | 7.67 (s, 1H), 7.51-7.44 (m, 2H), 7.40-7.30 (m, 2H), 6.92-6.89 (m, 1H), 4.91-4.68 (m, 2H), 4.20 (d, J = 5.2 Hz, 2H), 4.06-3.90 (m, 2H), 3.81 (s, 3H), 2.44-2.35 (m, 1H), 2.23-1.99 (m, 1H), 1.77 (d, J = 23.2 Hz, 3H) ppm |
| 279 | (R)-5-fluoro-N-(2-((4-(3-methoxyphenyl)thiazol-2-yl)amino)-2-oxoethyl)-5-methyl-1,3,4,5-tetrahydrobenzo[c]oxepine-7-carboxamide | 470.1 | $^1$H NMR (400 MHz, DMSO-d6) δ = 12.44 (s, 1H), 9.02-8.99 (m, 1H), 8.06 (d, J = 1.6 Hz, 1H), 7.80-7.78 (m, 1H), 7.67 (s, 1H), 7.54-7.44 (m, 2H), 7.39-7.29 (m, 2H), 6.92-6.90 (m, 1H), 4.89-4.67 (m, 2H), 4.20 (d, J = 4.4 Hz, 2H), 4.08-3.88 (m, 2H), 3.81 (s, 3H), 2.43-2.35 (m, 1H), 2.20-2.04 (m, 1H), 1.77 (d, J = 23.2 Hz, 3H) ppm |
| 280 | (R)-8-fluoro-4-hydroxy-N-(2-((4-(3-methoxyphenyl)thiazol-2-yl)amino)-2-oxoethyl)-4-methylisochromane-6-carboxamide | 472.1 | $^1$H NMR (400 MHz, DMSO-d6) δ = 12.67-12.20 (m, 1H), 9.09-8.98 (m, 1H), 8.46 (s, 1H), 8.01 (d, J = 1.2 Hz, 1H), 7.66 (s, 1H), 7.55 (m, 1H), 7.51-7.44 (m, 2H), 7.34 (m, 1H), 6.90 (m, 1H), 6.57 (s, 1H), 5.46 (s, 1H), 4.87-4.68 (m, 2H), 4.28-4.10 (m, 2H), 3.80 (s, 3H), 3.72-3.66 (m, 1H), 3.62-3.56 (m, 1H), 1.49-1.37 (m, 3H) ppm |
| 303 | (S)-4-fluoro-4-methyl-N-(2-oxo-2-((4-phenylthiazol-2-yl)amino)ethyl)isochromane-6-carboxamide | 426.1 | $^1$H NMR (400 MHz, DMSO-d6) δ = 12.46 (s, 1H), 9.08-9.05 (m, 1H), 8.19 (s, 1H), 7.91-7.87 (m, 3H), 7.64 (s, 1H), 7.45-7.41 (m, 2H), 7.34-7.27 (m, 2H), 4.87-4.83 (m, 1H), 4.75-4.70 (m, 1H), 4.22-4.17 (m, 2H), 4.15-4.04 (m, 1H), 3.88-3.79 (m, 1H), 1.70-1.65 (m, 3H) ppm |
| 309 | (S)-4-fluoro-N-((S)-1-((4-(3-methoxyphenyl)thiazol-2-yl)amino)-1-oxopropan-2-yl)-4-methylisochromane-6-carboxamide | 470.1 | $^1$H NMR (400 MHz, DMSO-d6) δ = 12.46 (s, 1H), 8.88 (d, J = 6.4 Hz, 1H), 8.26 (s, 1H), 7.93 (d, J = 8.0 Hz, 1H), 7.67 (s, 1H), 7.52-7.46 (m, 2H), 7.37-7.26 (m, 2H), 6.91-6.89 (m, 1H), 4.92-4.82 (m, 1H), 4.78-4.68 (m, 2H), 4.08 (m, 1H), 3.91-3.82 (m, 1H), 3.81 (s, 3H), 1.79-1.62 (m, 3H), 1.49 (d, J = 7.2 Hz, 3H) ppm |
| 311 | 4-cyano-N-(2-((4-(3-methoxyphenyl)thiazol-2-yl)amino)-2-oxoethyl)-4-methyl-1,2,3,4-tetrahydroisoquinoline-6-carboxamide | 462.1 | $^1$H NMR (400 MHz, DMSO-d6) δ = 12.49 (s, 1H), 9.77-9.56 (m, 1H), 9.17 (s, 1H), 8.22 (d, J = 1.6 Hz, 1H), 7.95-7.93 (m, 1H), 7.67 (s, 1H), 7.52-7.44 (m, 3H), 7.39-7.31 (m, 1H), 6.92-6.90 (m, 1H), 4.40 (d, J = 3.6 Hz, 2H), 4.24-4.22 (m, 2H), 4.05-4.01 (m, 1H), 3.81 (s, 3H), 3.67 (d, J = 13.2 Hz, 1H), 1.88 (s, 3H) ppm |
| 312 | (S)-4-fluoro-N-(2-((4-(3-methoxyphenyl)thiazol-2-yl)amino)-2-oxoethyl)-4-methylisochromane-6-carboxamide | 456.2 | $^1$H NMR (400 MHz, MeOD-d4) δ = 8.22 (s, 1H), 7.90-7.89 (m, 1H), 7.51-7.46 (m, 2H), 7.41 (s, 1H), 7.34-7.25 (m, 2H), 6.90-6.87 (m, 1H), 4.86-4.77 (m, 2H), 4.34 (s, 2H), 4.14-4.04 (m, 1H), 3.96-3.87 (m, 1H), 3.86 (s, 3H), 1.82-1.65 (m, 3H) ppm |
| 313 | 4-hydroxy-N-(2-((4-(3-methoxyphenyl)thiazol-2-yl)amino)-2-oxoethyl)-4-methylisochromane-6-carboxamide | 454.1 | $^1$H NMR (400 MHz, DMSO-d6) δ = 12.43 (s, 1H), 8.91 (m, 1H), 8.13 (d, J = 1.6 Hz, 1H), 7.72 (m, 1H), 7.66 (s, 1H), 7.52-7.44 (m, 2H), 7.34 (m, 1H), 7.13 (d, J = 8.0 Hz, 1H), 6.90 (m, 1H), 5.30 (s, 1H), 4.81-4.68 (m, 2H), 4.19 (m, 2H), 3.80 (s, 3H), 3.71-3.57 (m, 2H), 1.43 (s, 3H) ppm |
| 314 | (S)-N-(2-((4-(3-cyano-5-fluorophenyl)thiazol-2-yl)amino)-2-oxoethyl)-4-fluoro-4-methylisochromane-6-carboxamide | 469.1 | $^1$H NMR (400 MHz, DMSO-d6) δ = 12.56 (s, 1H), 9.11 (m, 1H), 8.21 (d, J = 12.8 Hz, 2H), 8.06 (d, J = 9.2 Hz, 1H), 8.00 (s, 1H), 7.89 (d, J = 7.6 Hz, 1H), 7.83 (d, J = 8.4 Hz, 1H), 7.29 (d, J = 8.0 Hz, 1H), 4.89-4.81 (m, 1H), 4.77-4.68 (m, 1H), 4.28-4.15 (m, 2H), 4.08 (m, 1H), 3.91-3.76 (m, 1H), 1.78-1.57 (m, 3H) ppm |
| 315 | (S)-N-(2-((4-(3-cyanophenyl)thiazol-2-yl)amino)-2-oxoethyl)-4-fluoro-4-methylisochromane-6-carboxamide | 451.1 | 1H NMR (400 MHz, DMSO-d6) δ = 12.51 (s, 1H), 9.09-9.06(m, 1H), 8.35-8.31 (m, 1H), 8.26-8.19 (m, 2H), 7.92-7.86 (m, 2H), 7.82-7.78 (m, 1H), 7.69-7.63 (m, 1H), 7.29 (d, J = 8.0 Hz, 1H), 4.89-4.80 (m, 1H), 4.77-4.69 (m, 1H), 4.25-4.20 (m, 2H), 4.12-4.03 (m, 1H), 3.90-3.78 (m, 1H), 1.72-1.65 (m, 3H) ppm |
| 316 | (R)-4-cyano-N-(2-((4-(3-fluoro-5-(oxetan-2-yl)phenyl)thiazol-2-yl)amino)-2-oxoethyl)-4-methylisochromane-6-carboxamide | 507.4 | $^1$H NMR (400 MHz, DMSO-d6) δ = 12.60-12.39 (m, 1H), 9.08-9.07 (m, 1H), 8.12 (d, J = 1.6 Hz, 1H), 7.87-7.79 (m, 3H), 7.65-7.62 (m, 1H), 7.29 (d, J = 8.0 Hz, 1H), 7.21-7.19 (m, 1H), 5.80-5.76 (m, 1H), 4.88-4.79 (m, 2H), 4.72-4.70 (m, 1H), 4.59-4.50 (m, 1H), 4.24-4.20 (m, 3H), 3.86 (d, J = 11.6 Hz, 1H), 3.07-3.00 (m, 1H), 2.59-2.56 (m, 1H), 1.69 (s, 3H) ppm |
| 322 | (R)-4-cyano-N-(2-((4-(3-fluorophenyl)thiazol-2-yl)amino)-2-oxoethyl)-4-methylisochromane-6-carboxamide | 451 | $^1$H NMR (400 MHz, DMSO-d6) δ = 12.80-12.38 (m, 1H), 9.10-9.08 (m, 1H), 8.12 (s, 1H), 7.88-7.85 (m, 1H), 7.77-7.75 (m, 2H), 7.69 (br d, J = 10.4 Hz, 1H), 7.51-7.45 (m, 1H), 7.29 (d, J = 8.0 Hz, 1H), 7.19-7.13 (m, 1H), 4.93-4.81 (m, 2H), 4.28-4.20 (m, 3H), 3.86 (br d, J = 11.6 Hz, 1H), 1.69 (s, 3H) ppm |
| 323 | (R)-4-cyano-4-methyl-N-(2-oxo-2-((4-phenylthiazol-2-yl)amino)ethyl)isochromane-6-carboxamide | 433.3 | $^1$H NMR (400 MHz, DMSO-d6) δ = 12.46 (br s, 1H), 9.09-9.06 (m, 1H), 8.13 (d, J = 1.2 Hz, 1H), 7.92-7.86 (m, 3H), 7.64 (s, 1H), 7.46-7.41 (m, 2H), 7.35-7.28 (m, 2H), 4.93-4.81 (m, 2H), 4.24-4.21 (m, 3H), 3.86 (d, J = 11.6 Hz, 1H), 1.69 (s, 3H) ppm |
| 324 | (S)-5-fluoro-N-(2-((4-(3-methoxyphenyl)thiazol-2-yl)amino)-2-oxoethyl)- | 470.1 | $^1$H NMR (400 MHz, CDCl3) δ = 10.82-10.36 (m, 1H), 7.98 (d, J = 2.4 Hz, 1H), 7.87 (m, 1H), 7.44-7.37 (m, 2H), 7.35-7.29 (m, 1H), 7.16 (s, 1H), 7.09 (d, J = 7.6 Hz, 2H), 6.88 |

TABLE 9-continued

| # | Name | LC-MS (m/z) | 1H NMR |
|---|---|---|---|
| | 5-methyl-2,3,4,5-tetrahydrobenzo[b]oxepine-7-carboxamide | | (m, 1H), 4.45 (d, J = 4.8 Hz, 2H), 4.44-4.39 (m, 1H), 3.85 (s, 3H), 3.70-3.60 (m, 1H), 2.29-2.15 (m, 2H), 2.11-1.98 (m, 1H), 1.94-1.83 (m, 1H), 1.75-1.68 (m, 3H) ppm |
| 325 | (R)-5-fluoro-N-(2-((4-(3-methoxyphenyl)thiazol-2-yl)amino)-2-oxoethyl)-5-methyl-2,3,4,5-tetrahydrobenzo[b]oxepine-7-carboxamide | 470.1 | $^1$H NMR (400 MHz, CDCl3) δ = 10.78-10.32 (m, 1H), 7.98 (d, J = 2.4 Hz, 1H), 7.87 (m, 1H), 7.47-7.36 (m, 2H), 7.35-7.29 (m, 1H), 7.19-7.13 (m, 1H), 7.12-7.04 (m, 2H), 6.93-6.83 (m, 1H), 4.50-4.44 (m, 2H), 4.44-4.39 (m, 1H), 3.85 (s, 3H), 3.72-3.59 (m, 1H), 2.32-2.14 (m, 2H), 2.11-1.98 (m, 1H), 1.95-1.83 (m, 1H), 1.75-1.68 (m, 3H) ppm |
| 327 | (S)-N-((R)-1-((4-(3-(difluoromethyl)phenyl)thiazol-2-yl)amino)-3-methoxy-1-oxopropan-2-yl)-4-fluoro-4-methylisochromane-6-carboxamide | 520.1 | $^1$H NMR (400 MHz, DMSO-d6) δ = 8.89-8.87 (m, 1H), 8.40 (s, 1H), 8.24 (s, 1H), 8.12 (s, 1H), 8.08-8.06 (m, 1H), 7.93-7.91 (m, 1H), 7.77 (s, 1H), 7.62-7.56 (m, 1H), 7.54-7.49 (m, 1H), 7.29-7.26 (m, 1H), 7.24-6.92 (m, 1H), 4.99-4.98 (m, 1H), 4.90-4.67 (m, 2H), 4.14-4.00 (m, 1H), 3.90-3.73 (m, 3H), 3.33 (s, 3H), 1.75-1.62 (m, 3H) ppm |
| 333 | (R)-4-cyano-N-(1-((4-(3-(difluoromethyl)phenyl)thiazol-2-yl)carbamoyl)cyclopropyl)-4-methylisochromane-6-carboxamide | 509.1 | $^1$H NMR (400 MHz, DMSO-d6) δ = 12.53-12.21 (m, 1H), 9.16 (s, 1H), 8.21-8.16 (m, 1H), 8.14-8.08 (m, 1H), 8.07-8.02 (m, 1H), 7.97-7.92 (m, 1H), 7.78-7.72 (m, 1H), 7.58-7.53 (m, 1H), 7.52-7.47 (m, 1H), 7.30 (d, J = 8.0 Hz, 1H), 7.20-6.90 (m, 1H), 4.94-4.82 (m, 2H), 4.25 (d, J = 11.2 Hz, 1H), 3.85 (d, J = 11.2 Hz, 1H), 1.71 (s, 3H), 1.64-1.55 (m, 2H), 1.31-1.20 (m, 2H) ppm |
| 334 | (S)-4-fluoro-N-((R)-1-((4-(3-fluoro-5-methoxyphenyl)thiazol-2-yl)amino)-1-oxopropan-2-yl)-4-methylisochromane-6-carboxamide | 488.1 | $^1$H NMR (400 MHz, DMSO-d6) δ = 12.48 (s, 1H), 8.87 (d, J = 6.4 Hz, 1H), 8.25 (s, 1H), 7.92 (d, J = 8.0 Hz, 1H), 7.79 (s, 1H), 7.37-7.23 (m, 3H), 6.81-6.77 (m, 1H), 4.90-4.80 (m, 1H), 4.78-4.66 (m, 2H), 4.11-4.04 (m, 1H), 3.90-3.76 (m, 4H), 1.74-1.61 (m, 3H), 1.49 (d, J = 7.2 Hz, 3H)ppm |
| 335 | (R)-4-cyano-8-methoxy-N-(2-((4-(3-methoxyphenyl)thiazol-2-yl)amino)-2-oxoethyl)-4-methylisochromane-6-carboxamide | 493.1 | $^1$H NMR (400 MHz, CDCl3) δ = 10.80 (s, 1H), 7.44 (s, 1H), 7.39-7.37 (m, 3H), 7.33-7.31 (m, 1H), 7.25 (s, 1H), 7.16 (s, 1H), 6.89-6.87 (m, 1H), 4.84-4.73 (m, 2H), 4.32-4.29 (m, 2H), 4.07 (d, J = 11.2 Hz, 1H), 3.88 (d, J = 11.2 Hz, 1H), 3.85 (s, 3H), 3.83 (s, 3H), 1.72 (s, 3H) ppm |
| 336 | (R)-4-cyano-N-(2,2-difluoro-1-((4-(3-methoxyphenyl)thiazol-2-yl)carbamoyl)cyclopropyl)-4-methylisochromane-6-carboxamide | 525.2 | $^1$H NMR (400 MHz, DMSO-d6) δ = 12.51 (s, 1H), 9.40 (br s, 1H), 8.18 (d, J = 2.4 Hz, 1H), 7.93 (d, J = 8.0 Hz, 1H), 7.72 (s, 1H), 7.49-7.43 (m, 2H), 7.35-7.28 (m, 2H), 6.88 (m, 1H), 4.96-4.81 (m, 2H), 4.24 (d, J = 11.2 Hz, 1H), 3.89-3.83 (m, 1H), 3.77 (s, 3H), 2.93-2.81 (m, 1H), 2.27-2.15 (m, 1H), 1.70 (d, J = 5.2 Hz, 3H) ppm |
| 337 | (S)-4-fluoro-N-(2-((4-(3-fluoro-5-methoxyphenyl)thiazol-2-yl)amino)-2-oxoethyl)-4-methylisochromane-6-carboxamide | 474.1 | $^1$H NMR (400 MHz, DMSO-d6) δ = 12.47 (s, 1H), 9.06 (m, 1H), 8.19 (s, 1H), 7.89 (d, J = 8.0 Hz, 1H), 7.79 (s, 1H), 7.35-7.24 (m, 3H), 6.79 (m, 1H), 4.91-4.78 (m, 1H), 4.77-4.69 (m, 1H), 4.26-4.15 (m, 2H), 4.07 (m, 1H), 3.91-3.76 (m, 4H), 1.74-1.63 (m, 3H) ppm |
| 339 | (R)-4-cyano-N-(2-((4-(7-fluorobenzo[d][1,3]dioxol-5-yl)thiazol-2-yl)amino)-2-oxoethyl)-4-methylisochromane-6-carboxamide | 495.4 | $^1$H NMR (400 MHz, DMSO-d6) δ = 12.43 (s, 1H), 9.08-9.05 (m, 1H), 8.12 (d, J = 1.6 Hz, 1H), 7.87-7.86(m, 1H), 7.63 (s, 1H), 7.39-7.35 (m, 2H), 7.29 (d, J = 8.0 Hz, 1H), 6.16 (s, 2H), 4.92-4.81 (m, 2H), 4.26-4.17 (m, 3H), 3.86 (d, J = 11.2 Hz, 1H), 1.69 (s, 3H) ppm |
| 341 | (S)-N-(2-((4-(3-(difluoromethyl)phenyl)thiazol-2-yl)amino)-2-oxoethyl)-4-fluoro-4-methylisochromane-6-carboxamide | 476.2 | $^1$H NMR (400 MHz, DMSO-d6) δ = 12.53-12.48 (m, 1H), 9.08-9.06 (m, 1H), 8.20 (s, 1H), 8.12 (s, 1H), 8.08 (d, J = 7.6 Hz, 1H), 7.90 (d, J = 8.0 Hz, 1H), 7.77 (s, 1H), 7.59-7.57 (m, 2H), 7.29 (d, J = 8.4 Hz, 1H), 7.26-7.09 (m, 1H), 4.88-4.75 (m, 2H), 4.23-4.20 (m, 2H), 4.08 (m, 1H), 4.05-3.83 (m, 1H), 1.71-1.66 (m, 3H) ppm |
| 344 | 3-(3-(difluoromethyl)oxetan-3-yl)-N-(2-((4-(3-(difluoromethyl)phenyl)thiazol-2-yl)amino)-2-oxoethyl)benzamide | 494.1 | $^1$H NMR (400 MHz, MeOD) δ = 8.51 (d, J = 2.8 Hz, 1H), 8.10 (s, 1H), 8.05 (d, J = 7.2 Hz, 1H), 7.91 (d, J = 8.0 Hz, 1H), 7.75 (s, 1H), 7.60-7.45 (m, 4H), 7.41 (d, J = 7.6 Hz, 1H), 6.96-6.62 (m, 1H), 6.50-6.17 (m, 1H), 5.09-5.00 (m, 4H), 4.33 (s, 2H) ppm |
| 352 | (R)-4-cyano-N-(2-((4-(7-fluoro-2,3-dihydrobenzofuran-5-yl)thiazol-2-yl)amino)-2-oxoethyl)-4-methylisochromane-6-carboxamide | 493.2 | $^1$H NMR (400 MHz, DMSO-d6) δ = 12.43-12.39 (m, 1H), 9.07 (d, J = 5.6 Hz, 1H), 8.12 (d, J = 1.2 Hz, 1H), 7.89-7.85 (m, 1H), 7.64-7.51 (m, 3H), 7.32-7.26 (m, 1H), 4.94-4.81 (m, 2H), 4.73-4.65 (m, 2H), 4.27-4.18 (m, 3H), 3.91-3.84 (m, 1H), 3.31-3.27 (m, 2H), 1.72-1.67 (m, 3H) ppm |
| 353 | (R)-4-cyano-N-(2-((4-(4-fluoro-2,3-dihydrobenzofuran-6-yl)thiazol-2-yl)amino)-2- | 493.1 | $^1$H NMR (400 MHz, DMSO-d6) δ = 12.64-12.22 (m, 1H), 9.08-9.5 (m, 1H), 8.12 (s, 1H), 7.88-7.85 (m, 1H), 7.70 (s, 1H), 7.3-7.28 (m, 1H), 7.22-7.21 (m, 1H), 7.18 (s, 1H), 4.95-4.79 (m, 2H), 4.66-4.62 (m, 2H), 4.28-4.15 |

TABLE 9-continued

| # | Name | LC-MS (m/z) | 1H NMR |
|---|---|---|---|
| | oxoethyl)-4-methylisochromane-6-carboxamide | | (m, 3H), 3.88-3.85 (dm, 1H), 3.24-3.22 (m, 2H), 1.69 (s, 3H) ppm |
| 359 | (R)-4-cyano-4-methyl-N-(2-((4-(3-((trans)-oxetan-2-yl)phenyl)thiazol-2-yl)amino)-2-oxoethyl)isochromane-6-carboxamide | 489.4 | $^1$H NMR (400 MHz, DMSO-d6) δ = 12.50 (s, 1H), 9.09-9.07 (m, 1H), 8.13 (d, J = 1.2 Hz, 1H), 8.01 (s, 1H), 7.88-7.80 (m, 2H), 7.68 (s, 1H), 7.47-7.42 (m, 1H), 7.37-7.35 (m, 1H), 7.29 (d, J = 8.4 Hz, 1H), 5.80-5.75 (m, 1H), 4.92-4.85 (m, 2H), 4.71-4.70 (m, 1H), 4.57-4.55 (m, 1H), 4.24-4.22 (m, 3H), 3.87 (d, J = 11.6 Hz, 1H), 3.03-2.99 (m, 1H), 2.61-2.60 (m, 1H), 1.69 (s, 3H) ppm |
| 361 | (R)-4-cyano-4-methyl-N-(2-((4-(3-((4R)-4-methyloxetan-2-yl)phenyl)thiazol-2-yl)amino)-2-oxoethyl)isochromane-6-carboxamide | 503.4 | $^1$H NMR (400 MHz, MeOD-d4) δ = 12.49 (s, 1H), 9.08-9.05(m, 1H), 8.12 (d, J = 2.0 Hz, 1H), 7.99 (s, 1H), 7.88-7.81 (m, 2H), 7.66 (s, 1H), 7.46-7.42 (m, 1H), 7.35 (d, J = 7.6 Hz, 1H), 7.30 (d, J = 8.0 Hz, 1H), 5.67-5.63 (m, 1H), 4.96-4.81 (m, 3H), 4.24-4.21 (m, 3H), 3.88-3.85 (m, 1H), 2.62-2.56 (m, 2H), 1.69 (s, 3H), 1.48 (d, J = 6.0 Hz, 3H) ppm |
| 365 | (R)-4-cyano-4-methyl-N-(2-((4-(3-oxetan-2-yl)phenyl)thiazol-2-yl)amino)-2-oxoethyl)isochromane-6-carboxamide | 489.4 | $^1$H NMR (400 MHz, DMSO-d6) δ = 12.50 (s, 1H), 9.09-9.06 (m, 1H), 8.13 (d, J = 1.2 Hz, 1H), 8.01 (s, 1H), 7.88-7.85 (m, 2H), 7.68 (s, 1H), 7.45-7.41 (m, 1H), 7.37-7.35 (m, 1H), 7.29 (d, J = 8.0 Hz, 1H), 5.80-5.76 (m, 1H), 4.88-4.85 (m, 2H), 4.74-4.68 (m, 1H), 4.58-4.53 (m, 1H), 4.24-4.21 (m, 3H), 3.87 (d, J = 11.6 Hz, 1H), 3.04-2.98 (m, 1H), 2.60-2.58 (m, 1H), 1.69 (s, 3H) ppm |
| 371 | (R)-4-cyano-4-methyl-N-(2-((4-(3-(oxetan-2-yl)phenyl)thiazol-2-yl)amino)-2-oxoethyl)isochromane-6-carboxamide | 489.5 | $^1$H NMR (400 MHz, DMSO-d6) δ = 12.49 (s, 1H), 9.08-9.07 (m, 1H), 8.12 (d, J = 1.6 Hz, 1H), 8.01 (s, 1H), 7.87-7.82 (m, 2H), 7.68 (s, 1H), 7.47-7.43 (m, 1H), 7.37 (d, J = 8.0 Hz, 1H), 7.29 (d, J = 8.0 Hz, 1H), 5.80-5.76 (m, 1H), 4.88-4.85 (m, 2H), 4.72-4.68 (m, 1H), 4.58-4.53 (m, 1H), 4.24-4.21 (m, 3H), 3.87 (d, J = 11.2 Hz, 1H), 3.05-2.98 (m, 1H), 2.58-2.55 (m, 1H), 1.69 (s, 3H) ppm |
| 375 | N-(2-((4-(2-methyl-1-oxo-1,2-dihydroisoquinolin-7-yl)thiazol-2-yl)amino)-2-oxoethyl)spiro[isochromane-4,2'-oxetane]-6-carboxamide | 517.4 | $^1$H NMR (400 MHz, DMSO-d6) δ = 12.56 (s, 1H), 9.10-9.09 (m, 1H), 8.82 (d, J = 1.6 Hz, 1H), 8.47 (d, J = 1.6 Hz, 1H), 8.22-8.20 (m, 1H), 7.82-7.78 (m, 1H), 7.78 (s, 1H), 7.71 (d, J = 8.4 Hz, 1H), 7.48 (d, J = 7.2 Hz, 1H), 7.19 (d, J = 8.0 Hz, 1H), 6.63 (d, J = 7.2 Hz, 1H), 4.79-4.59 (m, 4H), 4.30-4.17 (m, 2H), 4.11 (d, J = 11.6 Hz, 1H), 3.98 (d, J = 11.6 Hz, 1H), 3.53 (s, 3H), 2.96-2.86 (m, 1H), 2.74-2.67 (m, 1H) ppm |
| 377 | (R)-4-cyano-N-(2-((4-(3-fluoro-5-methoxyphenyl)thiazol-2-yl)amino)-2-oxoethyl)-4-methylisochromane-6-carboxamide | 481.2 | $^1$H NMR (400 MHz, DMSO-d6) δ = 12.48 (s, 1H), 9.08-9.06 (m, 1H), 8.12 (s, 1H), 7.92-7.73 (m, 2H), 7.39-7.18 (m, 3H), 6.80-6.77 (m, 1H), 5.03-4.74 (m, 2H), 4.31-4.10 (m, 3H), 3.89-3.84 (m, 1H), 3.82 (s, 3H), 1.69 (s, 3H) ppm |
| 379 | (R)-N-(2-((4-(3-(1-acetylazetidin-3-yl)phenyl)thiazol-2-yl)amino)-2-oxoethyl)-4-cyano-4-methylisochromane-6-carboxamide | 530.2 | $^1$H NMR (400 MHz, MeOD) δ = 8.12 (d, J = 1.6 Hz, 1H), 7.97-7.92 (m, 1H), 7.90-7.85 (m, 1H), 7.82-7.77 (m, 1H), 7.45-7.43 (m, 1H), 7.42-7.37 (m, 1H), 7.32-7.24 (m, 2H), 4.68-4.61 (m, 3H), 4.45-4.38 (m, 1H), 4.32 (s, 2H), 4.30-4.24 (m, 1H), 4.19 (d, J = 11.6 Hz, 1H), 4.08-4.01 (m, 1H), 3.98-3.88 (m, 2H), 1.93 (s, 3H), 1.75 (s, 3H) ppm |
| 382 | N-(2-((4-(2-methyl-1-oxo-1,2-dihydroisoquinolin-7-yl)thiazol-2-yl)amino)-2-oxoethyl)spiro[chromane-4,3'-oxetane]-6-carboxamide | 517.2 | $^1$H NMR (400 MHz, DMSO-d6) δ = 12.84-12.22 (m, 1H), 8.96-8.93 (m, 1H), 8.82 (d, J = 1.6 Hz, 1H), 8.41 (d, J = 2.0 Hz, 1H), 8.22-8.19 (m, 1H), 7.79 (s, 1H), 7.75-7.68 (m, 2H), 7.48 (d, J = 7.2 Hz, 1H), 6.85 (d, J = 8.8 Hz, 1H), 6.63 (d, J = 7.2 Hz, 1H), 4.83 (d, J = 6.0 Hz, 2H), 4.56 (d, J = 6.0 Hz, 2H), 4.21 (d, J = 5.6 Hz, 2H), 4.18-4.10 (m, 2H), 3.53 (s, 3H), 2.35-2.30 (m, 2H) ppm |
| 388 | (R)-4-cyano-N-(2-((4-(3-((S)-2,2-difluorocyclopropyl)phenyl)thiazol-2-yl)amino)-2-oxoethyl)-4-methylisochromane-6-carboxamide | 509.4 | $^1$H NMR (400 MHz, DMSO-d6) δ = 12.47 (s, 1H), 9.09-9.06 (m, 1H), 8.13 (d, J = 1.2 Hz, 1H), 7.88-7.86 (m, 1H), 7.81-7.78 (m, 2H), 7.68 (s, 1H), 7.41-7.38 (m, 1H), 7.30 (d, J = 8.0 Hz, 1H), 7.25 (d, J = 7.6 Hz, 1H), 4.93-4.81 (m, 2H), 4.24-4.19 (m, 3H), 3.88 (d, J = 11.6 Hz, 1H), 3.09-3.02 (m, 1H), 2.02-1.94 (m, 2H), 1.69 (s, 3H) ppm |
| 389 | (S)-4-fluoro-4-methyl-N-(2-((4-(2-methyl-1-oxo-1,2-dihydroisoquinolin-7-yl)thiazol-2-yl)amino)-2-oxoethyl)isochromane-6-carboxamide | 507.1 | $^1$H NMR (400 MHz, DMSO-d6) δ = 12.70-12.45 (m, 1H), 9.14-9.01 (m, 1H), 8.89-8.78 (m, 1H), 8.29-8.15 (m, 2H), 7.95-7.85 (m, 1H), 7.83-7.76 (m, 1H), 7.75-7.68 (m, 1H), 7.55-7.43 (m, 1H), 7.35-7.23 (m, 1H), 6.71-6.56 (m, 1H), 4.91-4.82 (m, 1H), 4.80-4.68 (m, 1H), 4.30-4.15 (m, 2H), 4.14-4.02 (m, 1H), 3.91-3.78 (m, 1H), 3.58-3.49 (m, 3H), 1.79-1.61 (m, 3H) ppm |
| 391 | (R)-4-cyano-N-(2-((4-(3-((R)-2,2-difluorocyclopropyl)phenyl)thiazol-2-yl)amino)-2- | 509.3 | $^1$H NMR (400 MHz, DMSO-d6) δ = 12.46 (s, 1H), 9.08-9.07 (m, 1H), 8.12 (d, J = 1.2 Hz, 1H), 7.88-7.85 (m, 1H), 7.80-7.78 (m, 2H), 7.68 (s, 1H), 7.40-7.36 (m, 1H), 7.30 (d, J = 8.0 Hz, 1H), 7.25 (d, J = 7.6 Hz, 1H), 4.92-4.81 (m, 2H), |

TABLE 9-continued

| # | Name | LC-MS (m/z) | 1H NMR |
|---|---|---|---|
| | oxoethyl)-4-methylisochromane-6-carboxamide | | 4.24-4.21 (m, 3H), 3.88 (d, J = 11.6 Hz, 1H), 3.08-3.05 (m, 1H), 2.01-1.94 (m, 2H), 1.69 (s, 3H) ppm |
| 394 | 4-cyano-N-(2-((4-(3-methoxyphenyl)thiazol-2-yl)amino)-2-oxoethyl)-1,4-dimethyl-1,2,3,4-tetrahydroquinoline-6-carboxamide | 476.1 | $^1$H NMR (400 MHz, DMSO-d6) δ = 12.39 (br s, 1H), 8.69-8.67 (m, 1H), 7.89 (s, 1H), 7.74 (d, J = 8.8 Hz, 1H), 7.66 (d, J = 1.6 Hz, 1H), 7.5-7.47 (m, 2H), 7.37-7.32 (m, 1H), 6.91 (d, J = 8.4 Hz, 1H), 6.72 (d, J = 8.0 Hz, 1H), 4.16 (s, 2H), 3.81 (d, J = 1.2 Hz, 3H), 3.41 (s, 2H), 2.97 (d, J = 1.2 Hz, 3H), 2.30-2.28 (m, 1H), 2.08 (d, J = 1.6 Hz, 1H), 1.72 (s, 3H) ppm |
| 397 | (R)-4-cyano-N-(2-((4-(6-methoxypyridin-2-yl)thiazol-2-yl)amino)-2-oxoethyl)-4-methylisochromane-6-carboxamide | 464.2 | $^1$H NMR (400 MHz, DMSO-d6) δ = 12.50 (s, 1H), 9.09 (m, 1H), 8.13 (d, J = 1.6 Hz, 1H), 7.87 (m, 1H), 7.82 (s, 1H), 7.81-7.76 (m, 1H), 7.54 (d, J = 7.2 Hz, 1H), 7.29 (d, J = 8.0 Hz, 1H), 6.77 (d, J = 8.0 Hz, 1H), 4.95-4.79 (m, 2H), 4.23 (m, 2H), 4.21 (s, 1H), 3.94 (s, 3H), 3.87 (d, J = 11.5 Hz, 1H), 1.69 (s, 3H) ppm |
| 398 | (R)-4-cyano-N-(2-((4-(3-(difluoromethyl)phenyl)thiazol-2-yl)amino)-2-oxoethyl)-4-methylisochromane-6-carboxamide | 483.3 | $^1$H NMR (400 MHz, DMSO-d6) δ = 12.59-12.43 (m, 1H), 9.09 (m, 1H), 8.12 (s, 2H), 8.07 (br d, J = 8.0 Hz, 1H), 7.87 (m, 1H), 7.78 (s, 1H), 7.62-7.56 (m, 1H), 7.55-7.49 (m, 1H), 7.29 (d, J = 8.0 Hz, 1H), 7.25-6.94 (m, 1H), 4.96-4.79 (m, 2H), 4.29-4.22 (m, 2H), 4.22-4.16 (m, 1H), 3.87 (d, J = 11.6 Hz, 1H), 1.69 (s, 3H) ppm |
| 399 | (R)-4-cyano-N-(2-((4-(4-fluoro-3-methoxyphenyl)thiazol-2-yl)amino)-2-oxoethyl)-4-methylisochromane-6-carboxamide | 481.1 | $^1$H NMR (400 MHz, DMSO-d6) δ = 12.55-12.46 (m, 1H), 9.16-9.01 (m, 1H), 8.16-8.09 (m, 1H), 7.93-7.83 (m, 1H), 7.71-7.61 (m, 2H), 7.52-7.44 (m, 1H), 7.34-7.21 (m, 2H), 4.96-4.81 (m, 2H), 4.28-4.16 (m, 3H), 3.97-3.81 (m, 4H), 3.31-3.30 (m, 1H), 1.70 (s, 3H) ppm |
| 400 | (R)-4-cyano-N-(2-((4-(2-methoxypyridin-4-yl)thiazol-2-yl)amino)-2-oxoethyl)-4-methylisochromane-6-carboxamide | 464.2 | $^1$H NMR (400 MHz, DMSO-d6) δ = 12.51-12.39 (m, 1H), 9.11-9.08 (m, 1H), 8.22 (d, J = 5.2 Hz, 1H), 8.12 (s, 1H), 7.99 (s, 1H), 7.88 (d, J = 8.0 Hz, 1H), 7.48 (d, J = 5.2 Hz, 1H), 7.30-7.27 (m, 2H), 4.93-4.81 (m, 2H), 4.27-4.19 (m, 3H), 3.88-3.85 (m, 4H), 1.69 (s, 3H) ppm |
| 401 | (R)-4-cyano-N-(2-((4-(3-methoxyphenyl)thiazol-2-yl)amino)-2-oxoethyl)-4-methylisochromane-6-carboxamide | 463.2 | $^1$H NMR (400 MHz, DMSO-d6) δ = 12.46 (s, 1H), 9.08-9.06 (m, 1H), 8.12 (d, J = 1.2 Hz, 1H), 7.88-7.85 (m, 1H), 7.67 (s, 1H), 7.51-7.42 (m, 2H), 7.38-7.25 (m, 2H), 6.90-6.88 (m, 1H), 5.00-4.77 (m, 2H), 4.30-4.13 (m, 3H), 3.86 (d, J = 11.6 Hz, 1H), 3.80 (s, 3H), 1.69 (s, 3H) ppm |
| 402 | (R)-4-cyano-N-(2-((4-(2-fluoro-3-methoxyphenyl)thiazol-2-yl)amino)-2-oxoethyl)-4-methylisochromane-6-carboxamide | 481.1 | $^1$H NMR (400 MHz, DMSO-d6) δ = 12.50 (s, 1H), 9.11-9.07 (m, 1H), 8.12 (d, J = 1.6 Hz, 1H), 7.88-7.85 (m, 1H), 7.59-7.51 (m, 2H), 7.28 (d, J = 8.0 Hz, 1H), 7.24-7.18 (m, 1H), 7.18-7.11 (m, 1H), 4.94-4.75 (m, 2H), 4.26-4.12 (m, 3H), 3.87 (s, 3H), 3.84 (s, 1H), 1.68 (s, 3H) ppm |
| 415 | 4-cyano-N-(2-((4-(3-methoxyphenyl)thiazol-2-yl)amino)-2-oxoethyl)-4-methyl-1,2,3,4-tetrahydroquinoline-6-carboxamide | 462.1 | $^1$H NMR (400 MHz, DMSO-d6) δ = 12.37 (br s, 1H), 8.61-8.58 (m, 1H), 7.86 (d, J = 1.6 Hz, 1H), 7.65 (s, 1H), 7.60-7.57 (m, 1H), 7.50-7.45 (m, 2H), 7.36-7.33 (m, 1H), 6.91-6.88 (m, 1H), 6.78 (s, 1H), 6.57 (d, J = 8.8 Hz, 1H), 4.18-4.12 (m, 2H), 3.80 (s, 3H), 3.40-3.32 (m, 2H), 2.23-2.16 (m, 1H), 2.01-1.94 (m, 1H), 1.71 (s, 3H) ppm |
| 422 | (S)-4-cyano-N-(2-((4-(3-(3-fluorooxetan-3-yl)phenyl)thiazol-2-yl)amino)-2-oxoethyl)-4-methylchromane-6-carboxamide | 507 | $^1$H NMR (400 MHz, DMSO-d6) δ = 12.50 (s, 1H), 8.95-8.92 (m, 1H), 8.10-8.08 (m, 2H), 7.95 (d, J = 7.2 Hz, 1H), 7.82-7.77 (m, 2H), 7.56-7.49 (m, 2H), 6.96 (d, J = 8.4 Hz, 1H), 5.03 (d, J = 8.8 Hz, 1H), 4.98 (d, J = 9.2 Hz, 2H), 4.92 (d, J = 8.4 Hz, 1H), 4.40-4.33 (m, 1H), 4.30-4.24 (m, 1H), 4.22-4.13 (m, 2H), 2.46-2.41 (m, 1H), 2.24-2.17 (m, 1H), 1.79 (s, 3H) ppm |
| 423 | (S)-4-cyano-4-methyl-N-(2-((4-(3-(oxetan-3-yl)phenyl)thiazol-2-yl)amino)-2-oxoethyl)chromane-6-carboxamide | 489.2 | $^1$H NMR (400 MHz, DMSO-d6) δ = 12.46 (br s, 1H), 8.94-8.91 (m, 1H), 8.09 (d, J = 2.0 Hz, 1H), 8.00 (s, 1H), 7.82-7.79 (m, 2H), 7.68 (s, 1H), 7.44-7.40 (m, 1H), 7.33 (d, J = 7.6 Hz, 1H), 6.96 (d, J = 8.4 Hz, 1H), 4.99-4.96 (m, 2H), 4.67-4.63 (m, 2H), 4.39-4.24 (m, 3H), 4.19-4.13 (m, 2H), 2.46-2.42 (m, 1H), 2.24-2.17 (m, 1H), 1.79 (s, 3H) ppm |
| 428 | (S)-4-cyano-N-(2-((4-(3-((R)-2,2-difluorocyclopropyl)phenyl)thiazol-2-yl)amino)-2-oxoethyl)-4-methylchromane-6-carboxamide | 509 | $^1$H NMR (400 MHz, DMSO-d6) δ = 12.48-12.40 (m, 1H), 8.95-8.92 (m, 1H), 8.09 (d, J = 2.0 Hz, 1H), 7.82-7.80 (m, 3H), 7.68 (s, 1H), 7.45-7.38 (m, 1H), 7.25 (d, J = 8.0 Hz, 1H), 6.97 (d, J = 8.4 Hz, 1H), 4.36-4.17 (m, 4H), 3.08-3.05 (m, 1H), 2.46-2.42 (m, 1H), 2.21-2.19 (m, 1H), 2.01-1.97 (m, 2H), 1.19 (s, 3H) ppm |
| 429 | (S)-4-cyano-N-(2-((4-(3-((S)-2,2-difluorocyclopropyl)phenyl)thiazol-2-yl)amino)-2-oxoethyl)-4- | 509 | $^1$H NMR (400 MHz, DMSO-d6) δ = 12.50-12.39 (m, 1H), 8.95-8.92 (m, 1H), 8.09 (d, J = 2.0 Hz, 1H), 7.82-7.80 (m, 3H), 7.68 (s, 1H), 7.42-7.38 (m, 1H), 7.25 (d, J = 8.0 Hz, 1H), 6.97 (d, J = 8.8 Hz, 1H), 4.36-4.17 (m, 4H), 3.08-3.05 (m, 1H), 2.47-2.43 (m, 1H), 2.21-2.19 (m, 1H), 2.01- |

TABLE 9-continued

| # | Name | LC-MS (m/z) | 1H NMR |
|---|---|---|---|
| | methylchromane-6-carboxamide | | 1.95 (m, 2H), 1.79 (s, 3H) ppm |
| 431 | (S)-4-cyano-N-(2-((4-(3-methoxyphenyl)thiazol-2-yl)amino)-2-oxoethyl)-4-methylchromane-6-carboxamide | 463 | $^1$H NMR (400 MHz, DMSO-d6) δ = 12.44 (s, 1H), 8.99-8.82 (m, 1H), 8.09 (d, J = 2.0 Hz, 1H), 7.86-7.77 (m, 1H), 7.66 (s, 1H), 7.53-7.42 (m, 2H), 7.39-7.27 (m, 1H), 7.00-6.84 (m, 2H), 4.41-4.12 (m, 4H), 3.80 (s, 3H), 2.46-2.41 (m, 1H), 2.27-2.13 (m, 1H), 1.80 (s, 3H) ppm |
| 433 | (S)-4-cyano-4-methyl-N-(2-((4-(2-methyl-1-oxo-1,2-dihydroisoquinolin-7-yl)thiazol-2-yl)amino)-2-oxoethyl)chromane-6-carboxamide | 514.1 | $^1$H NMR (400 MHz, DMSO-d6) δ = 12.54 (br s, 1H), 8.95-8.93 (m, 1H), 8.82 (d, J = 0.8 Hz, 1H), 8.22-8.19 (m, 1H), 8.09 (d, J = 2.0 Hz, 1H), 7.83-7.81 (m, 1H), 7.78 (s, 1H), 7.71 (d, J = 8.4 Hz, 1H), 7.48 (d, J = 7.2 Hz, 1H), 6.97 (d, J = 8.4 Hz, 1H), 6.63 (d, J = 7.2 Hz, 1H), 4.36-4.19 (m, 4H), 3.52 (s, 3H), 2.46-2.42 (m, 1H), 2.23-2.18 (m, 1H), 1.80 (s, 3H) ppm |
| 440 | (S)-4-cyano-4-methyl-N-(2-oxo-2-((4-(3-(pyridin-4-yl)phenyl)thiazol-2-yl)amino)ethyl)chromane-6-carboxamide | 510 | $^1$H NMR (400 MHz, DMSO-d6) δ = 12.49 (br s, 1H), 9.03-8.87 (m, 1H), 8.74-8.63 (m, 2H), 8.31 (s, 1H), 8.10 (d, J = 2.0 Hz, 1H), 8.02 (d, J = 8.0 Hz, 1H), 7.86-7.73 (m, 5H), 7.65-7.53 (m, 1H), 6.97 (d, J = 8.8 Hz, 1H), 4.42-4.15 (m, 4H), 2.48-2.40 (m, 1H), 2.26-2.16 (m, 1H), 1.80 (s, 3H). ppm |
| 442 | (S)-4-cyano-N-(2-((4-(3-(difluoromethyl)phenyl)thiazol-2-yl)amino)-2-oxoethyl)-4-methylchromane-6-carboxamide | 483.1 | $^1$H NMR (400 MHz, DMSO-d6) δ = 12.49 (br s, 1H), 8.95-8.93 (m, 1H), 8.18-8.02 (m, 3H), 7.85-7.73 (m, 2H), 7.64-7.47(m, 2H), 7.27-6.91 (m, 2H), 4.42-4.25 (m, 2H), 4.23-4.11 (m, 2H), 2.45-2.42 (m, 1H), 2.25-2.21 (m, 1H), 1.81 (s, 3H) ppm |
| 305 | (R)-N-(2-((4-(3-(3-oxabicyclo[4.1.0]heptan-6-yl)phenyl)thiazol-2-yl)amino)-2-oxoethyl)-4-cyano-4-methylisochromane-6-carboxamide | 529.2 | $^1$H NMR (400 MHz, DMSO-d6) δ = 12.61-12.28 (m, 1H), 9.08-9.07 (m, 1H), 8.13 (d, J = 1.2 Hz, 1H), 7.92-7.80 (m, 2H), 7.71 (d, J = 7.6 Hz, 1H), 7.66 (s, 1H), 7.36-7.35 (m, 1H), 7.30 (d, J = 8.0 Hz, 1H), 7.24 (d, J = 7.6 Hz, 1H), 4.96-4.79 (m, 2H), 4.28-4.17 (m, 3H), 4.02 (d, J = 4.8 Hz, 1H), 3.92-3.78 (m, 2H), 3.53-3.42 (m, 2H), 2.13-1.95 (m, 2H), 1.70 (s, 3H), 1.44-1.34 (m, 1H), 1.04 (d, J = 9.2 Hz, 1H), 0.91-0.89 (m, 1H) ppm |
| 340 | (R)-4-cyano-4-methyl-N-(2-((4-(3-(4-methyloxetan-2-yl)phenyl)thiazol-2-yl)amino)-2-oxoethyl)isochromane-6-carboxamide | 503.4 | $^1$H NMR (400 MHz, DMSO-d6) δ = 12.48 (s, 1H), 9.08 (m, 1H), 8.13 (d, J = 1.6 Hz, 1H), 7.94 (s, 1H), 7.90-7.76 (m, 2H), 7.66 (s, 1H), 7.51-7.41 (m, 1H), 7.41-7.34 (m, 1H), 7.29 (d, J = 8.0 Hz, 1H), 5.63 (m, 1H), 5.03-4.72 (m, 3H), 4.36-4.09 (m, 3H), 3.86 (d, J = 11.6 Hz, 1H), 3.05 (m, 1H), 2.17 (m, 1H), 1.69 (s, 3H), 1.39 (d, J = 6.0 Hz, 3H) ppm |
| 281 | methyl (S)-4-(2-(2-(4-fluoro-4-methylisochromane-6-carboxamido)acetamido)thiazol-4-yl)piperidine-1-carboxylate | 490.1 | $^1$H NMR (400 MHz, DMSO-d6) δ = 9.02-8.99 (m, 1H), 8.18 (s, 1H), 7.87 (d, J = 8.0 Hz, 1H), 7.27 (d, J = 8.0 Hz, 1H), 6.79 (s, 1H), 6.04 (d, J = 2.4 Hz, 1H), 4.88-4.81 (m, 1H), 4.78-4.68 (m, 1H), 4.20-3.97 (m, 5H), 3.89-3.78 (m, 1H), 3.59 (s, 3H), 2.94-2.75 (m, 3H), 1.91 (d, J = 10.8 Hz, 2H), 1.74-1.62 (m, 3H), 1.52-1.42 (m, 2H) ppm |
| 283 | ethyl (S)-3-(2-(2-((S)-4-fluoro-4-methylisochromane-6-carboxamido)acetamido)thiazol-4-yl)piperidine-1-carboxylate | 505.3 | $^1$H NMR (400 MHz, DMSO-d6) δ = 12.31 (s, 1H), 9.04-9.01 (m, 1H), 8.18 (s, 1H), 7.89 (d, J = 8.0 Hz, 1H), 7.29 (d, J = 8.0 Hz, 1H), 6.88 (s, 1H), 4.87-4.83 (m, 1H), 4.75-4.70 (m, 1H), 4.24-4.20 (m, 1H), 4.17-4.15 (m, 2H), 4.10-4.02 (m, 3H), 3.97-3.95 (m, 1H), 3.88-3.79 (m, 1H), 2.81-2.70 (m, 3H), 2.06-2.03 (m, 1H), 1.71-1.58 (m, 5H), 1.51-1.40 (m, 1H), 1.20 (m, 3H) ppm |
| 284 | ethyl (S)-3-(2-(2-((R)-4-fluoro-4-methylisochromane-6-carboxamido)acetamido)thiazol-4-yl)piperidine-1-carboxylate | 505.3 | $^1$H NMR (400 MHz, DMSO-d6) δ = 12.30 (s, 1H), 9.03-9.00 (m, 1H), 8.18 (s, 1H), 7.88 (d, J = 8.0 Hz, 1H), 7.28 (d, J = 8.4 Hz, 1H), 6.87 (s, 1H), 4.87-4.82 (m, 1H), 4.74-4.69 (m, 1H), 4.23-4.19 (m, 1H), 4.16-4.11 (m, 2H), 4.10-4.01 (m, 3H), 3.97-3.90 (m, 1H), 3.88-3.76 (m, 1H), 2.82-2.70 (m, 3H), 2.07-2.02 (m, 1H), 1.70-1.60 (m, 5H), 1.50-1.40 (m, 1H), 1.19 (m, 3H) ppm |
| 297 | (S)-4-fluoro-4-methyl-N-(2-oxo-2-((4-(tetrahydro-2H-pyran-4-yl)thiazol-2-yl)amino)ethyl)isochromane-6-carboxamide | 434.2 | $^1$H NMR (400 MHz, MeOD-d4) δ = 8.18 (s, 1H), 7.88-7.85 (m, 1H), 7.25 (d, J = 8.0 Hz, 1H), 6.72 (d, J = 0.8 Hz, 1H), 4.88-4.87 (m, 1H), 4.82-4.75 (m, 1H), 4.28 (s, 2H), 4.11-4.03 (m, 1H), 4.03-3.97 (m, 2H), 3.93-3.82 (m, 1H), 3.57-3.51 (m, 2H), 2.93-2.84 (m, 1H), 1.96-1.87 (m, 2H), 1.83-1.66 (m, 5H) ppm |
| 301 | methyl (S)-3-(2-(2-((R)-4-fluoro-4-methylisochromane-6-carboxamido)acetamido)thiazol-4-yl)piperidine-1-carboxylate | 491.1 | $^1$H NMR (400 MHz, DMSO-d6) δ = 12.31 (br s, 1H), 9.03-9.01 (m, 1H), 8.18 (s, 1H), 7.88 (d, J = 8.0 Hz, 1H), 7.28 (d, J = 8.0 Hz, 1H), 6.87 (s, 1H), 4.86-4.82 (m, 1H), 4.74-4.73 (m, 1H), 4.26-4.18 (m, 1H), 4.16-4.14 (m, 2H), 4.10-4.03 (m, 1H), 3.99-3.90 (m, 1H), 3.88-3.78 (m, 1H), 3.60 (s, 3H), 2.85-2.70 (m, 3H), 2.05 (d, J = 12.4 Hz, 1H), 1.70-1.57 (m, 5H), 1.50-1.44 (m, 1H) ppm |
| 302 | methyl (S)-3-(2-(2-((S)-4-fluoro-4-methylisochromane-6- | 491.2 | $^1$H NMR (400 MHz, DMSO-d6) δ = 12.31 (br s, 1H), 9.02 (s, 1H), 8.18 (s, 1H), 7.88 (d, J = 6.8 Hz, 1H), 7.28 (d, J = 7.6 Hz, 1H), 6.87 (s, 1H), 4.86-4.83 (m, 1H), 4.78-4.74 |

TABLE 9-continued

| # | Name | LC-MS (m/z) | 1H NMR |
|---|---|---|---|
| | carboxamido)acetamido)thiazol-4-yl)piperidine-1-carboxylate | | (m, 1H), 4.23-4.22 (m, 1H), 4.15 (s, 2H), 4.10-4.04 (m, 1H), 3.96-3.95 (m, 1H), 3.88-3.79 (m, 1H), 3.60 (s, 3H), 2.80-2.71 (m, 3H), 2.06-2.03 (m, 1H), 1.75-1.57 (m, 5H), 1.47-1.44 (m, 1H) ppm |
| 354 | methyl (R)-3-(2-(2-((S)-4-cyano-4-methylisochromane-6-carboxamido)acetamido)thiazol-4-yl)piperidine-1-carboxylate | 498.3 | $^1$H NMR (400 MHz, DMSO-$d_6$) δ = 12.34 (s, 1H), 9.07-9.03 (m, 1H), 8.12 (d, J = 1.2 Hz, 1H), 7.88-7.85 (m, 1H), 7.29 (d, J = 8.4 Hz, 1H), 6.88 (s, 1H), 4.95-4.79 (m, 2H), 4.31-4.12 (m, 4H), 4.03-3.83 (m, 2H), 3.61 (s, 3H), 2.91-2.65 (m, 3H), 2.05 (d, J = 12.0 Hz, 1H), 1.76-1.57 (m, 5H), 1.54-1.39 (m, 1H) ppm |
| 355 | methyl (R)-3-(2-(2-((R)-4-cyano-4-methylisochromane-6-carboxamido)acetamido)thiazol-4-yl)piperidine-1-carboxylate | 498.3 | $^1$H NMR (400 MHz, DMSO-d6) δ = 12.33 (s, 1H), 9.07-9.03 (m, 1H), 8.11 (d, J = 1.6 Hz, 1H), 7.88-7.85 (m, 1H), 7.29 (d, J = 8.0 Hz, 1H), 6.88 (s, 1H), 4.96-4.78 (m, 2H), 4.30-4.12 (m, 4H), 4.05-3.81 (m, 2H), 3.61 (s, 3H), 2.92-2.65 (m, 3H), 2.11-1.98 (m, 1H), 1.78-1.57 (m, 5H), 1.54-1.39 (m, 1H) ppm |
| 294 | (R)-N-(2-((4-(3-((1R,6S)-3-oxabicyclo[4.1.0]heptan-6-yl)phenyl)thiazol-2-yl)amino)-2-oxoethyl)-4-cyano-4-methylisochromane-6-carboxamide | 529.2 | $^1$H NMR (400 MHz, DMSO-d6) δ = 12.68-12.36 (m, 1H), 9.08 (m, 1H), 8.13 (d, J = 1.6 Hz, 1H), 7.90-7.81 (m, 2H), 7.74-7.70 (m, 1H), 7.67 (s, 1H), 7.36 (m, 1H), 7.30 (d, J = 8.4 Hz, 1H), 7.24 (d, J = 8.0 Hz, 1H), 4.98-4.80 (m, 2H), 4.27-4.19 (m, 3H), 4.05-3.99 (m, 1H), 3.90-3.79 (m, 2H), 3.52-3.41 (m, 2H), 2.12-2.04 (m, 1H), 2.03-1.96 (m, 1H), 1.70 (s, 3H), 1.42-1.35 (m, 1H), 1.04 (m, 1H), 0.91 (m, 1H) ppm |
| 295 | (R)-N-(2-((4-(3-((1S,6R)-3-oxabicyclo[4.1.0]heptan-6-yl)phenyl)thiazol-2-yl)amino)-2-oxoethyl)-4-cyano-4-methylisochromane-6-carboxamide | 529.2 | $^1$H NMR (400 MHz, DMSO-d6) δ = 12.73-12.11 (m, 1H), 9.08 (m, 1H), 8.18-8.10 (m, 1H), 7.92-7.82 (m, 2H), 7.75-7.69 (m, 1H), 7.67 (s, 1H), 7.38-7.33 (m, 1H), 7.30 (d, J = 8.0 Hz, 1H), 7.24 (d, J = 7.6 Hz, 1H), 4.97-4.79 (m, 2H), 4.28-4.18 (m, 3H), 4.07-3.97 (m, 1H), 3.91-3.79 (m, 2H), 3.47 (m, 2H), 2.12-2.04 (m, 1H), 2.03-1.97 (m, 1H), 1.70 (s, 3H), 1.39 (s, 1H), 1.04 (m, 1H), 0.91 (m, 1H) ppm |

Example 111. Preparation of (S)—N-(2-((4-(6-(difluoromethyl)pyridin-2-yl)thiazol-2-yl)amino)-2-oxoethyl)-4-fluoro-4-methylisochromane-6-carboxamide (Compound 343)

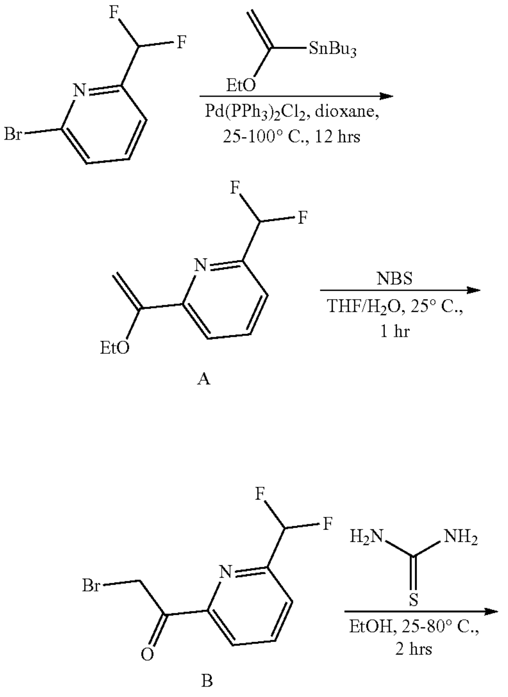

-continued

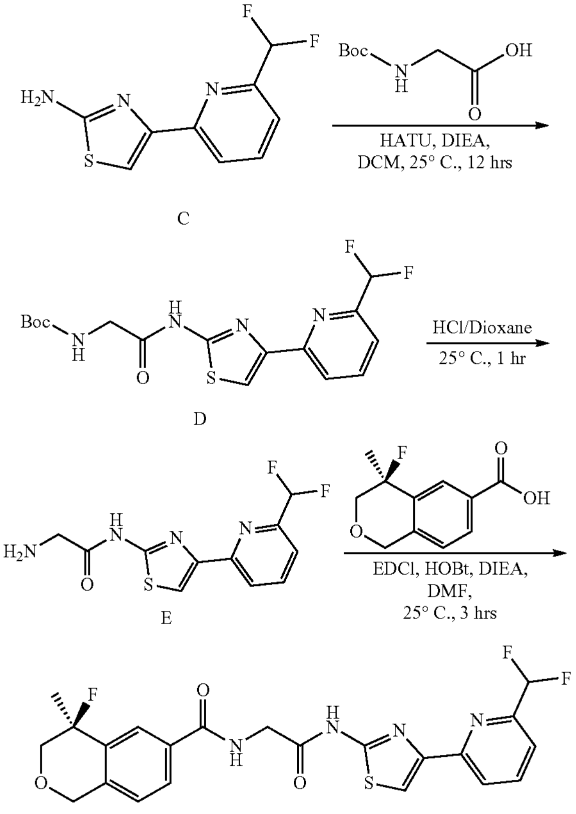

Compound 343

Step 1: Preparation of 2-(difluoromethyl)-6-(1-ethoxyvinyl)pyridine (Intermediate A)

A

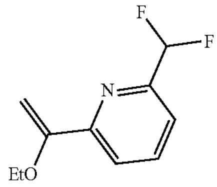

To a mixture of 2-bromo-6-(difluoromethyl)pyridine (1 g, 4.81 mmol) and tributyl(1-ethoxyvinyl)stannane (5.21 g, 14.42 mmol, 4.87 mL) in dioxane (10 mL) was added $Pd(PPh_3)_2Cl_2$ (337.45 mg, 480.76 umol) at 25° C. under $N_2$, the mixture was stirred at 100° C. under $N_2$ for 12 hrs. The reaction mixture was quenched with sat. KF (200 mL), filtered. The filter cake was washed with EA (50 mL*2). The filtrate was extracted with EA (50 mL*2), the combined organic layers was dried over anhydrous $Na_2SO_4$ and concentrated to give Intermediate A (2.7 g, 3.64 mmol) as black brown oil. LCMS (ESI) m/z: $[M+H]^+$=200.1.

Step 2: Preparation of 2-bromo-1-[6-(difluoromethyl)-2-pyridyl]ethanone (Intermediate B)

B

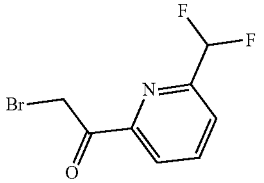

To a mixture of Intermediate A (2.2 g, 2.96 mmol) in THE (8 mL) and $H_2O$ (2 mL) was added NBS (2.11 g, 11.85 mmol) at 25° C. and the mixture was stirred at 25° C. for 1 hr. The reaction mixture was diluted with water (50 mL) and extracted with EA (20 mL*2), the combined organic layers was dried over anhydrous $Na_2SO_4$ and concentrated to afford a brown oil. The oil was purified by flash silica gel chromatography (ISCO®; 40 g SepaFlash® Silica Flash Column, Eluent of 0~30% Ethylacetate/Petroleum ethergradient @ 35 mL/min). The eluent was concentrated to give Intermediate B (900 mg, 2.84 mmol) as yellow oil.

LCMS (ESI) m/z: $[M+H]^+$=250.0.

$^1$H NMR (400 MHz, $CDCl_3$) δ=8.21-8.19 (m, 1H), 8.07-8.03 (m, 1H), 7.89 (d, J=7.2 Hz, 1H), 6.82-6.54 (m, 1H), 4.84 (s, 2H) ppm.

Step 3: Preparation of 4-[6-(difluoromethyl)-2-pyridyl]thiazol-2-amine (Intermediate C)

C

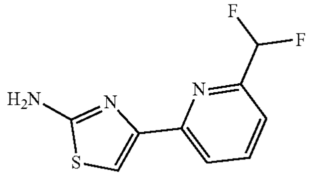

To a mixture of Intermediate B (900 mg, 2.84 mmol) in EtOH (10 mL) was added thiourea (324.35 mg, 4.26 mmol) at 25° C., the mixture was stirred at 80° C. for 2 hrs. The reaction mixture was diluted with water (20 mL) and adjusted pH to 7 with sat. $NaHCO_3$, then extracted with EA (10 mL*3). The combined organic layers was dried over anhydrous $Na_2SO_4$ and concentrated to afford yellow oil. The oil was dissolved with MeOH (3 mL) and poured into water (10 mL). The mixture was concentrated to remove MeOH. Yellow precipitate was formed. The mixture was filtered to give Intermediate C (600 mg, 2.58 mmol) as a yellow solid.

LCMS (ESI) m/z: $[M+H]^+$=228.0.

$^1$HNMR (400 MHz, DMSO-$d_6$) δ=8.03-7.99 (m, 1H), 7.96-7.94 (m, 1H), 7.56 (d, J=7.6 Hz, 1H), 7.29 (s, 1H), 7.17 (s, 2H), 7.07-6.80 (m, 1H) ppm.

Step 4: Preparation of tert-butyl N-[2-[[4-[6-(difluoromethyl)-2-pyridyl]thiazol-2-yl]amino]-2-oxo-ethyl]carbamate (Intermediate D)

D

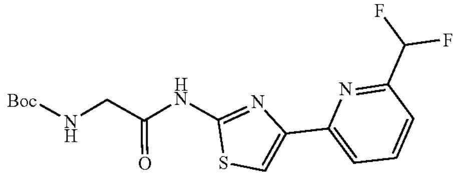

To a mixture of 2-(tert-butoxycarbonylamino)acetic acid (462.56 mg, 2.64 mmol), HATU (1.25 g, 3.30 mmol) and DIEA (853.15 mg, 6.60 mmol, 1.15 mL) in DCM (5 mL) was added Intermediate C (500 mg, 2.20 mmol) at 25° C. and the mixture was stirred at 25° C. for 12 hrs. The reaction mixture was diluted with water (20 mL) and extracted with DCM (10 mL*2), the combined organic layers was concentrated to afford yellow oil. The oil was purified by flash silica gel chromatography (ISCO®; 20 g SepaFlash® Silica Flash Column, Eluent of 0~60% Ethylacetate/Petroleum ethergradient @ 35 mL/min). The eluent was concentrated to give Intermediate D (700 mg, 1.56 mmol) as yellow oil.

LCMS (ESI) m/z: $[M+H]^+$=385.0.

$^1$H NMR (400 MHz, $CDCl_3$) δ=9.80-9.76 (m, 1H), 8.04 (d, J=8.0 Hz, 1H), 7.91-7.80 (m 1H), 7.80 (s, 1H), 7.57 (d, J=8.0 Hz, 1H), 6.82-6.54 (m, 1H), 5.21-5.19 (m, 1H), 4.77-4.76 (m, 1H), 4.10 (br s, 2H), 1.51 (s, 9H) ppm.

Step 5: Preparation of 2-amino-N-[4-[6-(difluoromethyl)-2-pyridyl]thiazol-2-yl]acetamide (Intermediate E)

E

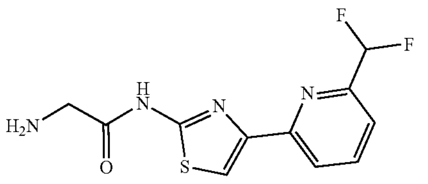

The mixture of Intermediate D (700 mg, 1.56 mmol) in HCl/dioxane (4 M, 7 mL) was stirred at 25° C. for 1 hr. The reaction mixture was concentrated to give Intermediate E (600 mg, 1.38 mmol, HCl) as a light yellow solid.

LCMS (ESS) m/z: $[M+H]^+$=285.1.

$^1$H NMR (400 MHz, DMSO-$d_6$) δ=12.90 (s, 1H), 8.53 (br s, 2H), 8.13-8.06 (m, 2H), 7.95 (s, 1H), 7.65-7.63 (m, 1H), 7.12-6.85 (m, 1H), 3.94-3.90 (m, 2H) ppm.

Step 6: Preparation of (S)—N-(2-((4-(6-(difluoromethyl)pyridin-2-yl)thiazol-2-yl)amino)-2-oxoethyl)-4-fluoro-4-methylisochromane-6-carboxamide Compound 343

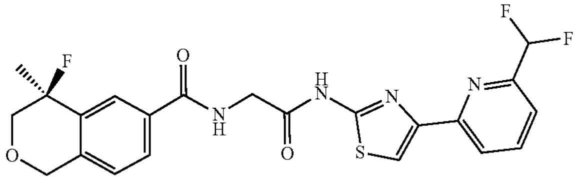

To a mixture of (4S)-4-fluoro-4-methyl-isochromane-6-carboxylic acid (50 mg, 237.87 umol), HOBt (43.83 mg, 324.36 umol), EDCl (62.18 mg, 324.36 umol) and DIEA (83.84 mg, 648.73 umol, 113.00 uL) in DMF (0.5 mL) was added Intermediate E (93.80 mg, 216.24 umol, HCl) at 25° C. and the mixture was stirred for 3 hrs. The reaction mixture was diluted with water (5 mL) and extracted with EA (3 mL×3), the combined organic layers was concentrated to afford a yellow oil. The oil was purified by prep-HPLC (UniSil 3-100 C18 Ultra (150*25 mm*3 um); mobile phase: [water (0.225% FA)-ACN]; B %: 38%-68%, 7.5 min). The eluent was concentrated to remove ACN and lyophilized to give (S)—N-(2-((4-(6-(difluoromethyl)pyridin-2-yl)thiazol-2-yl)amino)-2-oxoethyl)-4-fluoro-4-methylisochromane-6-carboxamide (Compound 343) (21.48 mg, 42.54 umol) as a white solid.

LCMS (ESI) m/z; $[M+H]^+$=477.2.

$^1$H NMR (400 MHz, DMSO-$d_6$) δ=12.55 (s, 1H), 9.07 (br s, 1H), 8.20 (br s, 1H), 8.09 (bd, J=2.8 Hz, 2H), 7.88 (d, J=2.0 Hz, 2H), 7.64-7.63 (m, 1H), 7.29 (d, J=7.6 Hz, 1H), 7.12-6.84 (m, 1H), 4.87-4.80 (m, 1H), 4.74-4.71 (m, 1H), 4.22 (br s, 2H), 4.07-4.04 (m, 1H), 3.88-3.79 (m, 1H), 1.71 (d, J=20.4 Hz, 3H) ppm.

Chiral SFC: Cellucoat-MeOH (DEA)-40-3 mL-35T·lcm; Rt=0.907 min.

Example 112. Preparation of Compounds of the Invention

The following compounds in Table 10 were prepared using standard chemical manipulations and procedures similar to those used for the preparation of the compounds described herein.

TABLE 10

| # | Name | LC-MS (m/z) | 1H NMR |
|---|---|---|---|
| 292 | (R)-N-(2-((4-(6-((1R,6S)-3-oxabicyclo[4.1.0]heptan-6-yl)pyridin-2-yl)thiazol-2-yl)amino)-2-oxoethyl)-4-cyano-4-methylisochromane-6-carboxamide | 530.6 | $^1$H NMR (400 MHz, METHANOL-d4) δ = 8.13 (d, J = 1.6 Hz, 1H), 7.90-7.85 (m, 1H), 7.81-7.77 (m, 1H), 7.76 (s, 1H), 7.75-7.70 (m, 1H), 7.29-7.22 (m, 2H), 4.91 (d, J = 4.0 Hz, 2H), 4.33 (s, 2H), 4.20 (d, J = 11.2 Hz, 1H), 4.09-4.03 (m, 1H), 3.96-3.90 (m, 2H), 3.69-3.63 (m, 1H), 3.53-3.46 (m, 1H), 2.68-2.62 (m, 1H), 2.17-2.09 (m, 1H), 1.86-1.80 (m, 1H), 1.76 (s, 3H), 1.43-1.37 (m, 1H), 1.06-1.02 (m, 1H) ppm |
| 293 | (R)-N-(2-((4-(6-((1S,6R)-3-oxabicyclo[4.1.0]heptan-6-yl)pyridin-2-yl)thiazol-2-yl)amino)-2-oxoethyl)-4-cyano-4-methylisochromane-6-carboxamide | 530.1 | $^1$H NMR (400 MHz, METHANOL-d4) δ = 8.13 (s, 1H), 7.89-7.86 (m, 1H), 7.81-7.77 (m, 1H), 7.76 (s, 1H), 7.75-7.69 (m, 1H), 7.29-7.22 (m, 2H), 4.90 (d, J = 3.6 Hz, 2H), 4.33 (s, 2H), 4.20 (d, J = 11.2 Hz, 1H), 4.10-4.02 (m, 1H), 3.96-3.90 (m, 2H), 3.71-3.61 (m, 1H), 3.53-3.46 (m, 1H), 2.68-2.62 (m, 1H), 2.16-2.09 (m, 1H), 1.87-1.80 (m, 1H), 1.76 (s, 3H), 1.41-1.37 (m, 1H), 1.06-1.02 (m, 1H) ppm |
| 330 | (S)-4-fluoro-N-(2-((4-(2-(1-hydroxycyclopropyl)pyridin-4-yl)thiazol-2-yl)amino)-2-oxoethyl)-4-methylisochromane-6-carboxamide | 483 | $^1$H NMR (400 MHz, DMSO-d6) δ = 12.59 (br s, 1H), 9.09-9.07 (m, 1H), 8.44 (d, J = 5.2 Hz, 1H), 8.26-8.19 (m, 2H), 7.95 (s, 1H), 7.89 (d, J = 8.0 Hz, 1H), 7.61-7.59 (m, 1H), 7.29 (d, J = 8.0 Hz, 1H), 6.18 (s, 1H), 4.89-4.70 (m, 2H), 4.28-4.16 (m, 2H), 4.11-4.04 (m, 1H), 3.89-3.79 (m, 1H), 1.72-1.65 (m, 3H), 1.25-1.23 (m, 2H), 1.10 (br d, J = 3.2 Hz, 2H) ppm |
| 378 | (S)-4-cyano-N-(2-((4-(6-((R)-2,2-difluorocyclopropyl)pyridin-2-yl)thiazol-2-yl)amino)-2-oxoethyl)-4- | 510.1 | $^1$H NMR (400 MHz, DMSO-d6) δ = 12.46 (br s, 1H), 8.95-8.92(m, 1H), 8.09 (d, J = 2.0 Hz, 1H), 7.87-7.80 (m, 4H), 7.40-7.39 (m, 1H), 6.97 (d, J = 8.8 Hz, 1H), 4.36-4.35 (m, 1H), 4.28-4.27 (m, 1H), 4.21-4.19 (m, 2H), 3.23-3.21 (m, 1H), 2.47-2.42 (m, 2H), 2.22-2.00 (m, |

TABLE 10-continued

| # | Name | LC-MS (m/z) | 1H NMR |
|---|---|---|---|
| | methylchromane-6-carboxamide | | 1H), 2.00-1.96 (m, 1H), 1.80 (s, 3H) ppm |
| 380 | (S)-4-cyano-N-(2-((4-(6-((S)-2,2-difluorocyclopropyl)pyridin-2-yl)thiazol-2-yl)amino)-2-oxoethyl)-4-methylchromane-6-carboxamide | 510.2 | $^1$H NMR (400 MHz, DMSO-d6) δ = 12.49 (s, 1H), 8.98-8.90 (m, 1H), 8.10 (d, J = 2.0 Hz, 1H), 7.93-7.73 (m, 4H), 7.40 (d, J = 7.2 Hz, 1H), 6.97 (d, J = 8.4 Hz, 1H), 4.41-4.34 (m, 1H), 4.32-4.25 (m, 1H), 4.25-4.17 (m, 2H), 3.26-3.19 (m, 1H), 2.46-2.42 (m, 2H), 2.25-2.19 (m, 1H), 2.05-2.00 (m, 1H), 1.81 (s, 3H) ppm |
| 386 | (R)-4-cyano-N-(2-((4-(6-((S)-2,2-difluorocyclopropyl)pyridin-2-yl)thiazol-2-yl)amino)-2-oxoethyl)-4-methylisochromane-6-carboxamide | 510.3 | $^1$H NMR (400 MHz, DMSO-d6) δ = 12.59-12.42 (m, 1H), 9.10-9.06 (m, 1H), 8.12 (d, J = 0.8 Hz, 1H), 7.91-7.79 (m, 4H), 7.39 (d, J = 8.4 Hz, 1H), 7.29 (d, J = 8.0 Hz, 1H), 4.94-4.79 (m, 2H), 4.30-4.16 (m, 3H), 3.86 (d, J = 11.2 Hz, 1H), 3.24-3.18 (m, 1H), 2.43 (s, 1H), 2.06-1.97 (m, 1H), 1.69 (s, 3H) ppm |
| 387 | (R)-4-cyano-N-(2-((4-(6-((R)-2,2-difluorocyclopropyl)pyridin-2-yl)thiazol-2-yl)amino)-2-oxoethyl)-4-methylisochromane-6-carboxamide | 510.4 | $^1$H NMR (400 MHz, DMSO-$d_6$) δ = 12.50 (s, 1H), 9.10-9.06 (m, 1H), 8.12 (s, 1H), 7.92-7.80 (m, 4H), 7.39 (d, J = 8.0 Hz, 1H), 7.29 (d, J = 8.4 Hz, 1H), 4.95-4.80 (m, 2H), 4.27-4.16 (m, 3H), 3.86 (d, J = 11.6 Hz, 1H), 3.24-3.18 (m, 1H), 2.44 (s, 1H), 2.07-1.97 (m, 1H), 1.69 (s, 3H) ppm |
| 439 | (S)-4-cyano-N-(2-((4-(6-cyclopropylpyridin-2-yl)thiazol-2-yl)amino)-2-oxoethyl)-4-methylchromane-6-carboxamide | 474.1 | $^1$H NMR (400 MHz, MeOD) δ = 8.10 (d, J = 2.0 Hz, 1H), 7.83-7.80 (m, 1H), 7.77-7.74 (m, 1H), 7.71 (s, 1H), 7.66-7.62 (m, 1H), 7.13-7.06 (m, 1H), 6.95 (d, J = 8.8 Hz, 1H), 4.42-4.34 (m, 2H), 4.30 (s, 2H), 2.52-2.41 (m, 1H), 2.26-2.17 (m, 1H), 2.15-2.05 (m, 1H), 1.84 (s, 3H), 1.11-0.93 (m, 4H) ppm |
| 430 | (S)-4-cyano-N-(2-((4-(6-(difluoromethyl)pyridin-2-yl)thiazol-2-yl)amino)-2-oxoethyl)-4-methylchromane-6-carboxamide | 484.1 | $^1$H NMR (400 MHz, DMSO-d6) δ = 12.61 (s, 1H), 9.02-8.99 (m, 1H), 8.17-8.15 (m, 3H), 7.95 (s, 1H), 7.89-7.86 (m, 1H), 7.72-7.69 (m, 1H), 7.05-6.91 (m, 2H), 4.46-4.26 (m, 4H), 2.51-2.49 (m, 1H), 2.28-2.25 (m, 1H), 1.87 (s, 3H) ppm |
| 331 | (S)-N-(2-((4-(6-(difluoromethyl)pyridin-2-yl)thiazol-2-yl)amino)-2-oxoethyl)-4-fluoro-4-methylisochromane-6-carboxamide | 477.2 | $^1$H NMR (400 MHz, DMSO-d6) δ = 12.55 (s, 1H), 9.07 (br s, 1H), 8.20 (br s, 1H), 8.09 (bd, J = 2.8 Hz, 2H), 7.88 (d, J = 2.0 Hz, 2H), 7.64-7.63 (m, 1H), 7.29 (d, J = 7.6 Hz, 1H), 7.12-6.84 (m, 1H), 4.87-4.80 (m, 1H), 4.74-4.71 (m, 1H), 4.22 (br s, 2H), 4.07-4.04 (m, 1H), 3.88-3.79 (m, 1H), 1.71 (d, J = 20.4 Hz, 3H) ppm |

Example 113. Preparation of Intermediates

Intermediates 1 and 2: Preparation of (R)-4-cyano-8-fluoro-4-methylisochromane-6-carboxylic acid and (S)-4-cyano-8-fluoro-4-methylisochromane-6-carboxylic acid

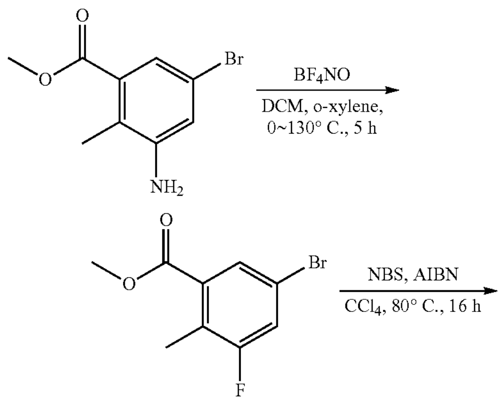

A

-continued

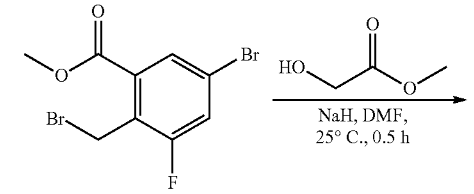

B

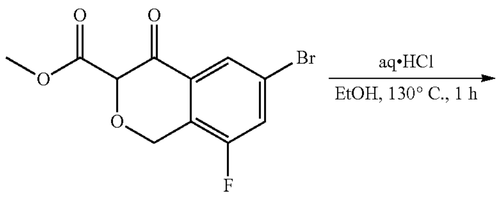

C

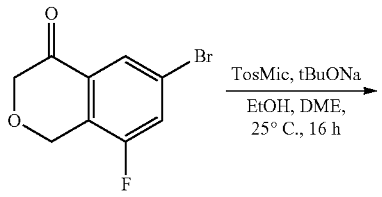

D

-continued

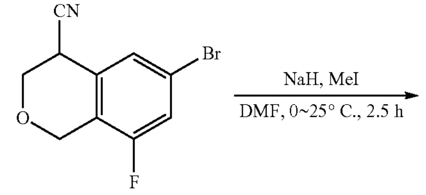

E

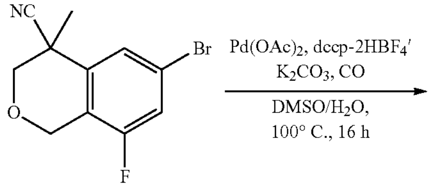

F

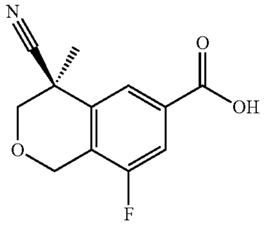
+
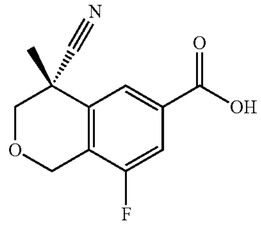

1 2

Step 1: Preparation of methyl 5-bromo-3-fluoro-2-methyl-benzoate (Intermediate A)

A

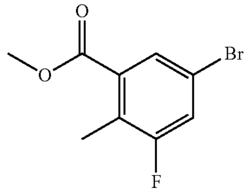

To a solution of methyl 3-amino-5-bromo-2-methyl-benzoate (11 g, 45.07 mmol) in DCM (100 mL) was added nitridooxonium;tetrafluoroborate (6.84 g, 58.59 mmol) portion wise at 0° C. under $N_2$. The mixture was stirred at 0° C. for 1 hr. Then o-xylene (250 mL) was added and the solution was slowly heated to 80° C. and stirred at 80° C. for 1 hr to remove the DCM. Then the solution was slowly heated to 130° C. and stirred at 130° C. for 3 hrs. The reaction mixture was poured into water (200 mL) and extracted with EA (100 mL*3). The combined organic layers were washed with brine (200 mL), dried over anhydrous $Na_2SO_4$, filtered and concentrated under reduced pressure to give residue. The residue was purified by column chromatography ($SiO_2$, Petroleum ether/Ethyl acetate=50/1 to 10/1). The fraction was concentrated in vacuum to give Intermediate A (10 g, 40.48 mmol) as yellow oil. $^1H$ NMR (400 MHz, $CDCl_3$) δ=7.83 (s, 1H), 7.37-7.34 (m, 1H), 3.91 (s, 3H), 2.44 (d, J=2.4 Hz, 3H) ppm.

Step 2: Preparation of methyl 5-bromo-2-(bromomethyl)-3-fluoro-benzoate (Intermediate B)

B

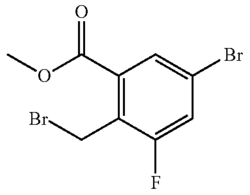

To a mixture of Intermediate A (10 g, 40.48 mmol) and NBS (7.20 g, 40.48 mmol) in $CCl_4$ (100 mL) was added AIBN (664.65 mg, 4.05 mmol). The mixture was stirred at 80° C. for 16 hrs. The reaction mixture was poured into water (100 mL) and extracted with EA (100 mL*3). The combined organic layers were washed with brine (150 mL), dried over anhydrous $Na_2SO_4$, filtered and concentrated under reduced pressure. The residue was purified by column chromatography ($SiO_2$, Petroleum ether/Ethyl acetate=20/1 to 10/1). The fraction was concentrated in vacuum to give Intermediate B (9.8 g, 30.07 mmol) as yellow oil.

$^1H$ NMR (400 MHz, $CDCl_3$) δ=7.94-7.93 (m, 1H), 7.83-7.82 (m, 1H), 7.46-7.44 (m, 1H), 7.37-7.36 (m, 1H), 4.95 (d, J=2.0 Hz, 2H), 3.97 (s, 3H), 3.91 (s, 2H), 2.44 (d, J=2.4 Hz, 2H) ppm.

Step 3: Preparation of methyl 6-bromo-8-fluoro-4-oxo-isochromane-3-carboxylate (Intermediate C)

C

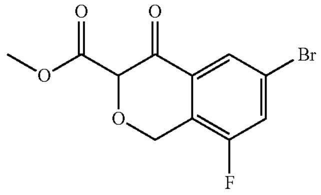

To a mixture of Intermediate B (9.8 g, 30.07 mmol) and methyl 2-hydroxyacetate (5.42 g, 60.13 mmol, 4.63 mL) in DMF (60 mL) was added NaH (2.40 g, 60.13 mmol, 60% purity) slowly at 0° C. under $N_2$. The mixture was stirred at 25° C. for 30 mins. The reaction mixture was quenched with saturated $NH_4Cl$ (200 mL) and extracted with EtOAc (100 mL*2). The combined organic phase was washed with brine (200 mL), dried over anhydrous $Na_2SO_4$, filtered and concentrated under vacuum. The residue was purified by column chromatography ($SiO_2$, PE/EtOAc=10/1-3/1). The fraction was concentrated in vacuum to give Intermediate C (5 g, 16.50 mmol) as a white solid.

$^1H$ NMR (400 MHz, $CDCl_3$) δ=10.26 (s, 1H), 7.62 (s, 1H), 7.31-7.29 (m, 1H), 5.06 (s, 2H), 3.93 (s, 3H) ppm.

Step 4: Preparation of 6-bromo-8-fluoro-isochroman-4-one (Intermediate D)

D

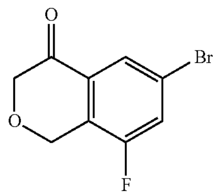

To a mixture of Intermediate C (1.8 g, 5.94 mmol) in EtOH (18 mL) was added HCl (12 M, 36 mL). The mixture was stirred at 130° C. for 1 hr. The mixture was diluted with water (200 mL) and then filtered. The filter cake was dried under vacuum to give Intermediate D (1.3 g, 5.31 mmol) as a yellow solid.

$^1H$ NMR (400 MHz, DMSO-$d_6$) δ=7.97-7.94 (m, 1H), 7.85 (d, J=1.6 Hz, 1H), 4.91 (s, 2H), 4.41 (s, 2H) ppm.

Step 5: Preparation of 6-bromo-8-fluoro-isochromane-4-carbonitrile (Intermediate E)

E

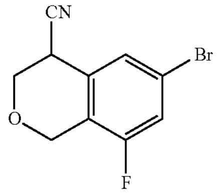

To a mixture of Intermediate D (100 mg, 408.09 umol), 1-(isocyanomethylsulfonyl)-4-methylbenzene (119.51 mg, 612.13 umol) and EtOH (150.40 mg, 3.26 mmol, 190.86 uL) in DME (4 mL) was added t-BuONa (86.28 mg, 897.79 umol) at 0° C. The mixture was stirred at 25° C. for 16 hrs. The reaction mixture was poured into water (60 mL) and extracted with EtOAc (60 mL*2). The combined organic phase was washed with brine (60 mL), dried over anhydrous $Na_2SO_4$, filtered and concentrated under vacuum. The residue was purified by column chromatography ($SiO_2$, PE/EtOAc=30/1-8/1). The fraction was concentrated in vacuum to give Intermediate E (55 mg, 214.78 umol) as a yellow solid.

$^1H$ NMR (400 MHz, $CDCl_3$) δ=7.83 (s, 1H), 7.37-7.34 (m, 1H), 3.91 (s, 3H), 2.44 (d, J=2.4 Hz, 3H) ppm.

Step 6: Preparation of 6-bromo-8-fluoro-4-methyl-isochromane-4-carbonitrile (Intermediate F)

F

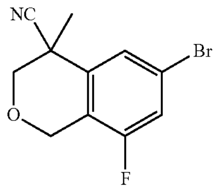

To a mixture of Intermediate E (50 mg, 195.26 umol) in DMF (1 mL) was added NaH (15.62 mg, 390.52 umol, 60% purity) at 0° C. under $N_2$. The mixture was stirred at 0° C. for 30 mins. Then MeI (138.57 mg, 976.29 umol, 60.78 uL) was added. The resulting mixture was stirred at 25° C. for 2 hrs. The reaction mixture was poured into water (15 mL) and extracted with EtOAc (15 mL*2). The combined organic phase was washed with brine (20 mL), dried over anhydrous $Na_2SO_4$, filtered and concentrated under vacuum. The residue was purified by column chromatography ($SiO_2$, PE/EtOAc=30/1-5/1). The fraction was concentrated in vacuum to give Intermediate F (35 mg, 129.58 umol) as colorless oil. $^1H$ NMR (400 MHz, DMSO-$d_6$) δ=7.75 (s, 1H), 7.59 (m, 1H), 4.88-4.80 (m, 1H), 4.77-4.69 (m, 1H), 4.19 (d, J=11.6 Hz, 1H), 3.80 (d, J=11.6 Hz, 1H), 1.66 (s, 3H) ppm.

Step 7: Preparation of (R)-4-cyano-8-fluoro-4-methylisochromane-6-carboxylic acid and (S)-4-cyano-8-fluoro-4-methylisochromane-6-carboxylic acid (Intermediates 1 and 2)

1

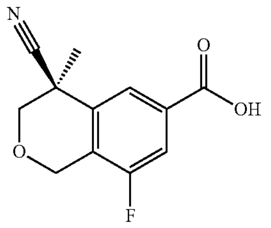

+

2

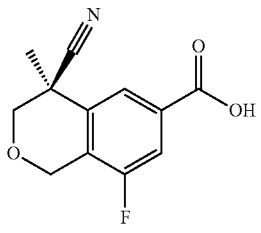

To a mixture of Intermediate F (30 mg, 111.07 umol) in DMSO (2 mL) was added dicyclohexyl (3-dicyclohexylphosphaniumylpropyl)phosphonium;ditetrafluoroborate (13.60 mg, 22.21 umol), $K_2CO_3$ (23.03 mg, 166.61 umol), $H_2O$ (20.01 mg, 1.11 mmol, 20.01 uL) and $Pd(OAc)_2$ (2.49 mg, 11.11 umol). The resulting mixture was purged with CO for three times. The mixture was stirred at 100° C. under CO (15 psi) for 4 hrs. The reaction mixture was poured into water (20 mL) and extracted with EtOAc (20 mL). The organic phase was discarded. The aqueous layer was adjusted pH to 4 with 1N aq·HCl and extracted with EtOAc (20 mL*2). The combined organic phase was washed with brine (20 mL), dried over anhydrous $Na_2SO_4$, filtered and concentrated under vacuum. The residue was separated by SFC (column: DAICEL CHIRALPAK IC (250 mm*30 mm, 5 um); mobile phase: [0.1% $NH_3H_2O$ ETOH]; B %: 20%-20%, 1.85 min; 76 min). The fraction was concentrated in vacuum. The residue was diluted with $H_2O$ (20 mL) and lyophilized to give Intermediate 1 (25 mg, 106.29 umol) as a yellow solid and Intermediate 2 (25 mg, 102.45 umol) as a yellow solid.

Intermediate 3 and 4: Preparation of (R)-4-(difluoromethyl)-4-fluorochromane-6-carboxylic acid and (S)-4-(difluoromethyl)-4-fluorochromane-6-carboxylic acid

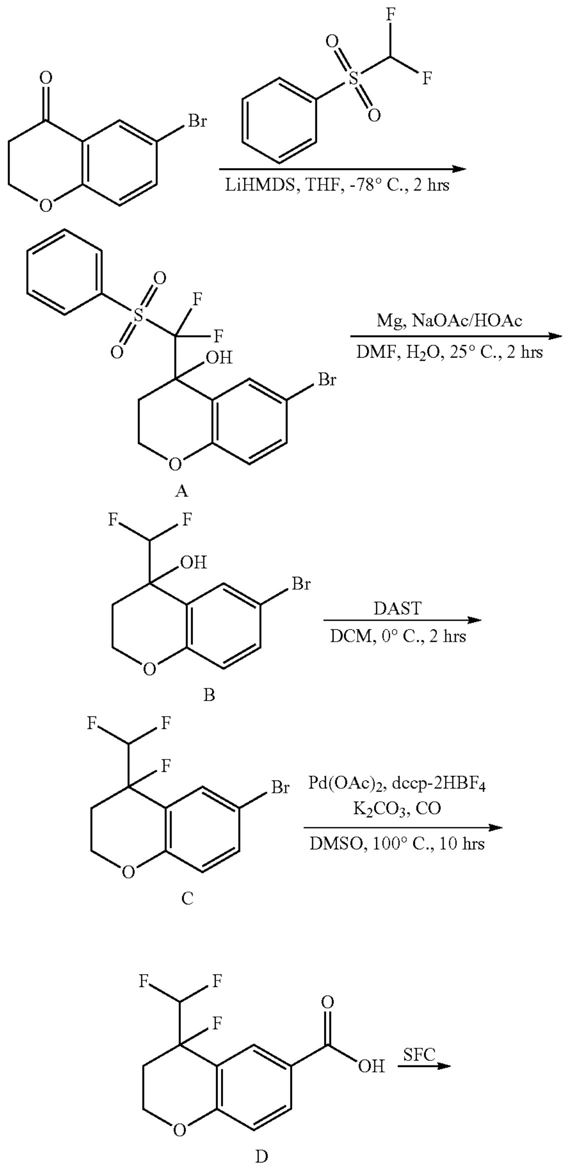

-continued

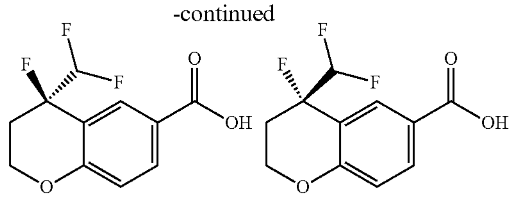

3 4

Step 1: Preparation 6-bromo-4-(difluoro(phenylsulfonyl)methyl)chroman-4-ol (Intermediate A)

A

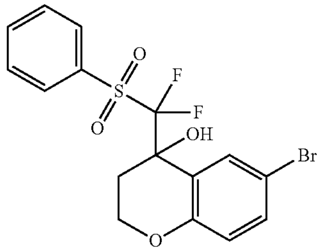

To a solution of 6-bromochroman-4-one (3 g, 13.21 mmol), difluoromethylsulfonylbenzene (3.81 g, 19.82 mmol, 2.82 mL) in THE (30 mL) was added LiHMDS (1 M, 26.43 mL) at −78° C. Then the mixture was stirred at −78° C. for 2 hrs. The reaction mixture was poured into sat.$NH_4Cl$ (50 mL) and extracted with EA (50 mL*2). The organic layer was washed with brine (50 mL) and dried over $Na_2SO_4$, concentrated to get the crude product. The crude product was purified by flash silica gel chromatography ($SiO_2$, PE:EA=10:1 to 3:1). The eluent was concentrated to get Intermediate A (3.6 g, 7.73 mmol) as yellow solid.

$^1H$ NMR (400 MHz, $CDCl_3$) δ=8.02 (d, J=7.6 Hz, 2H), 7.88-7.77 (m, 1H), 7.73-7.61 (m, 3H), 7.34-7.33 (m, 1H), 6.78 (d, J=8.8 Hz, 1H), 4.54-4.26 (m, 2H), 3.74 (s, 1H), 3.19-3.02 (m, 1H), 2.59-2.42 (m, 1H) ppm.

Step 2: Preparation 6-bromo-4-(difluoromethyl)chroman-4-ol (Intermediate B)

B

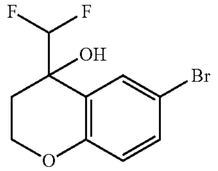

To a solution of Intermediate A (3.5 g, 8.35 mmol), Mg (3.04 g, 125.23 mmol) in DMF (100 mL) was added NaOAc/HOAc (8 M, 52.18 mL). Then the mixture was stirred at 25° C. for 2 hrs. The reaction mixture was poured into water (100 mL) and extracted with EA (100 mL*2). The combined organic layer was washed with brine (100 mL), dried over $Na_2SO_4$, filtered and concentrated to get the crude product. The crude product was purified by flash silica gel chromatography ($SiO_2$, PE:EA=10:1 to 3:1). The eluent was concentrated to get Intermediate B (2 g, 6.45 mmol) as colorless oil. $^1H$ NMR (400 MHz, $CDCl_3$) δ=7.51 (d, J=2.4 Hz, 1H), 7.29-7.26 (m, 1H), 6.72 (d, J=8.8 Hz, 1H), 6.13-5.70 (m, 1H), 4.36-4.10 (m, 2H), 2.78 (s, 1H), 2.33-2.18 (m, 1H), 2.06-1.98 (m, 1H) ppm.

Step 3: Preparation of 6-bromo-4-(difluoromethyl)-4-fluorochroman (Intermediate C)

C

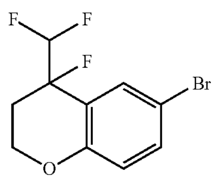

To a solution of Intermediate B (1.9 g, 6.81 mmol) in DCM (20 mL) was added DAST (2.19 g, 13.62 mmol, 1.80 mL) at 0° C. Then the mixture was stirred at 0° C. for 2 hrs. The reaction mixture was poured into water (50 mL) and extracted with DCM (20 mL*2). The organic layer was washed with brine (20 mL) and dried over $Na_2SO_4$, concentrated to get the crude product. The crude product was purified by flash silica gel chromatography ($SiO_2$, PE:EA=10:1 to 5:1) to Intermediate C (1 g, 3.20 mmol) as colorless oil.

$^1H$ NMR (400 MHz, $CDCl_3$) δ=7.57 (s, 1H), 7.48-7.30 (m, 1H), 7.12-6.79 (m, 1H), 6.42-5.92 (m, 1H), 4.55-4.13 (m, 2H), 2.65-2.24 (m, 2H) ppm.

Step 4: Preparation of 4-(difluoromethyl)-4-fluorochroman-6-carboxylic acid (Intermediate D)

D

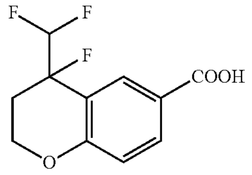

A solution of Intermediate C (700 mg, 2.49 mmol) in DMSO (10 mL) and $H_2O$ (2 mL) were added $Pd(OAC)_2$ (27.96 mg, 124.52 umol), dicyclohexyl(3-dicyclohexylphosphaniumylpropyl)phosphonium; ditetrafluoroborate (152.48 mg, 249.05 umol) and $K_2CO_3$ (516.32 mg, 3.74 mmol). The reaction mixture was degassed and purged with CO (15 psi) for 3 times. Then the mixture was stirred at 100° C. for 10 hrs under CO (15 psi) atmosphere. The reaction solution was filtered to get the filter liquor. The solution was diluted with $H_2O$ 20 mL and extracted with EA (20 mL*5). The combined organic layers were washed with brine (20 mL*3), dried over $Na_2SO_4$, filtered and concentrated under reduced pressure to give a residue. The residue was purified by flash silica gel chromatography (ISCO®; 40 g Sepa-Flash® Silica Flash Column, Eluent of 0~100% Ethylacetate/Petroleum ethergradient @ 50 mL/min). The eluent was concentrated under reduced pressure to afford Intermediate D (520 mg, 2.07 mmol) as a white solid. $^1H$ NMR (400 MHz, $CDCl_3$) δ=8.17 (s, 1H), 8.02-7.99 (m, 1H), 6.95-6.92 (m, 1H), 6.40-5.96 (m, 1H), 4.50-4.34 (m, 1H), 4.31-4.18 (m, 1H), 2.58-2.21 (m, 2H) ppm.

Step 5: Preparation of (R)-4-(difluoromethyl)-4-fluorochromane-6-carboxylic acid and (S)-4-(difluoromethyl)-4-fluorochromane-6-carboxylic acid (Intermediates 3 and 4)

3

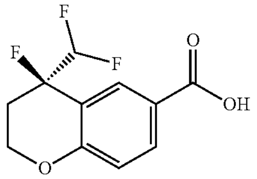

4

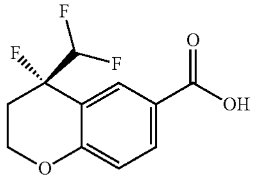

Intermediate D (520 mg, 2.11 mmol, 1 eq) was purified by SFC separation with the condition (column: DAICEL CHIRALPAK IG (250 mm*30 mm, 10 um); mobile phase: [0.1% $NH_3H_2O$ MEOH]; B %: 15%-15%, 1.95 min; 89 min) to get two peaks. The eluent of peak 1 (Rt=0.839 min) was concentrated under reduced pressure to get Intermediate 3 (250 mg, 1.02 mmol) as white solid. The eluent of peak 2 (Rt=0.936 min) was concentrated under reduced pressure to get Intermediate 4 (255 mg, 1.04 mmol) as white solid.

Intermediate 3

LCMS (ESI) m/z: $[M+H]^+$=247.0.

$^1H$ NMR (400 MHz, $CDCl_3$) δ=8.16 (s, 1H), 7.99 (d, J=8.8 Hz, 1H), 6.92 (d, J=8.8 Hz, 1H), 6.34-6.00 (m, 1H), 4.47-4.32 (m, 1H), 4.29-4.15 (m, 1H), 2.53-2.17 (m, 2H) ppm.

Chiral SFC: IG-3_5CM_MEOH(DEA)_5_40_3ML_T35.M, Rt=0.860 min.

Chiral SFC: IG-3_5CM_MEOH(DEA)_5_40_3ML_T35.M, Rt=0.842 min, 0.936 min (racemate)

Intermediates 5 and 6: Preparation of (S)-8-fluoro-4-hydroxy-4-methylisochromane-6-carboxylic acid and (R)-8-fluoro-4-hydroxy-4-methylisochromane-6-carboxylic acid

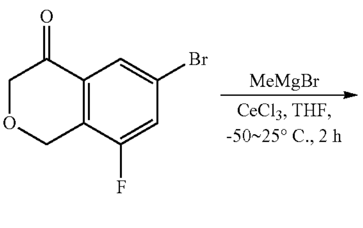

-continued

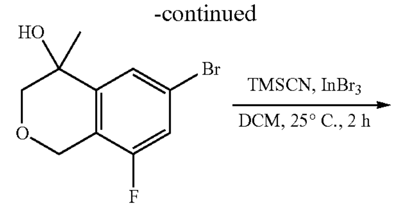

A

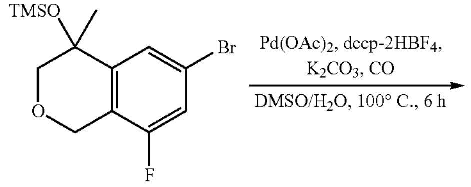

B

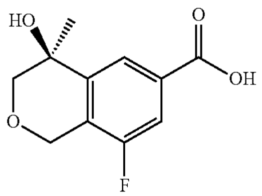

5

+

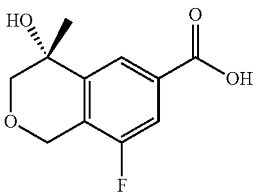

6

Step 1: Preparation of 6-bromo-8-fluoro-4-methyl-isochroman-4-ol (Intermediate A)

A

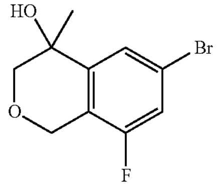

To a mixture of 6-bromo-8-fluoroisochroman-4-one (Prepared according to the method in FG-A3574) (250 mg, 1.02 mmol) and $CeCl_3$ (125.73 mg, 510.11 umol, 32.07 uL) in THE (2.5 mL) was added bromo(methyl)magnesium (3 M, 1.70 mL) at −50° C. under $N_2$. The mixture was stirred at 25° C. for 2 hrs. The mixture was poured into water (30 mL) and extracted with EtOAc (30 mL*3). The combined organic phase was washed with brine (50 mL), dried over anhydrous $Na_2SO_4$, filtered and concentrated under vacuum. The residue was purified by column chromatography ($SiO_2$, PE/EtOAc=10/1-3/1). The fraction was concentrated in vacuum to give Intermediate A (210 mg, 804.33 umol) as light yellow oil. $^1H$ NMR (400 MHz, $CDCl_3$) δ=7.54 (s, 1H), 7.14 (m, 1H), 4.92-4.79 (m, 1H), 4.74-4.62 (m, 1H), 3.86-3.77 (m, 1H), 3.76-3.65 (m, 1H), 2.34 (s, 1H), 1.53 (s, 3H) ppm.

Step 2: Preparation of (6-bromo-8-fluoro-4-methyl-isochroman-4-yl)oxy-trimethyl-silane (Intermediate B)

B

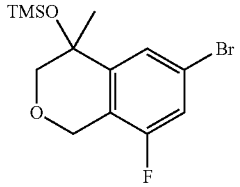

To a solution of Intermediate A (210 mg, 804.33 umol) in DCM (1 mL) was added TMSCN (239.38 mg, 2.41 mmol, 301.87 uL) and tribromoindigane (57.03 mg, 160.87 umol) at 0° C. Then the resulting mixture was stirred at 25° C. for 2 hrs. The mixture was poured into water (30 mL) and extracted with EtOAc (30 mL*3). The combined organic phase was washed with brine (50 mL), dried over anhydrous $Na_2SO_4$, filtered and concentrated under vacuum. The residue was purified by column chromatography ($SiO_2$, PE/EtOAc=30/1-8/1). The fraction was concentrated in vacuum to give Intermediate B (200 mg, 600.12 umol) as light yellow oil.

$^1H$ NMR (400 MHz, $CDCl_3$) δ=7.46 (s, 1H), 7.09 (m, 1H), 4.74 (s, 2H), 3.75 (s, 2H), 1.53 (s, 3H), 0.07-0.04 (m, 9H) ppm.

Step 3: Preparation of (S)-8-fluoro-4-hydroxy-4-methylisochromane-6-carboxylic acid and (R)-8-fluoro-4-hydroxy-4-methylisochromane-6-carboxylic acid (Intermediates 5 and 6)

5

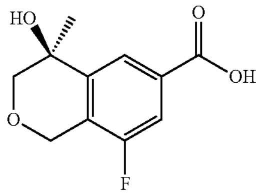

+

6

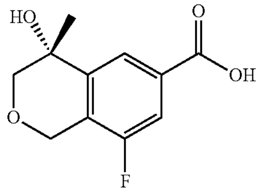

Mixture of Intermediate B (200 mg, 600.12 umol), $Pd(OAc)_2$ (16.62 mg, 74.03 umol), $H_2O$ (133.40 mg, 7.40 mmol, 133.40 uL), dicyclohexyl(3-dicyclohexylphosphaniumylpropyl) phosphonium;ditetrafluoroborate (90.67 mg, 148.09 umol) and $K_2CO_3$ (153.51 mg, 1.11 mmol) in DMSO (2 mL) was degassed and purged with CO for 3 times. The mixture was stirred at 100° C. for 6 hrs under CO atmosphere (15 psi). The mixture was poured into water (20 mL) and extracted with EA (20 mL*2). The organic layer was discarded. The aqueous was adjusted PH to 5 by aq·HCl (1 M) and extracted with EA (20 mL*2). The combined organics were washed with brine (30.0 mL), dried over $Na_2SO_4$, filtered and filtration was evaporated to dryness to give crude. The residue was purified by prep-HPLC (FA condition). The fraction was concentrated in vacuum to remove MeCN and lyophilized. The residue was separated by SFC (column: DAICEL CHIRALPAK IG (250 mm*30 mm, 10 um); mobile phase: [0.1% NH3H2O ETOH]; B %: 30%-30%, 4 min). The fraction was concentrated in vacuum. The residue was diluted with water (20 mL), adjusted PH to 5 by aq·HCl (1 M) and extracted with EA (20 mL*2). The combined organics were washed with brine (30 mL), dried over $Na_2SO_4$, filtered and concentrated in vacuum to give Intermediate 5 (20 mg, 88.42 umol, 14.73% yield) as a yellow solid and Intermediate 6 (20 mg, 88.42 umol, 14.73% yield) as a yellow solid.

Intermediate 6

$^1$H NMR (400 MHz, DMSO-$d_6$) δ=8.00 (s, 1H), 7.48 (d, J=9.6 Hz, 1H), 5.49 (s, 1H), 4.91-4.66 (m, 2H), 3.71-3.65 (m, 1H), 3.59-3.53 (m, 1H), 1.41 (s, 3H) ppm.

Intermediate 7: Preparation of 3-(3-(difluoromethyl)tetrahydrofuran-3-yl)benzoic acid

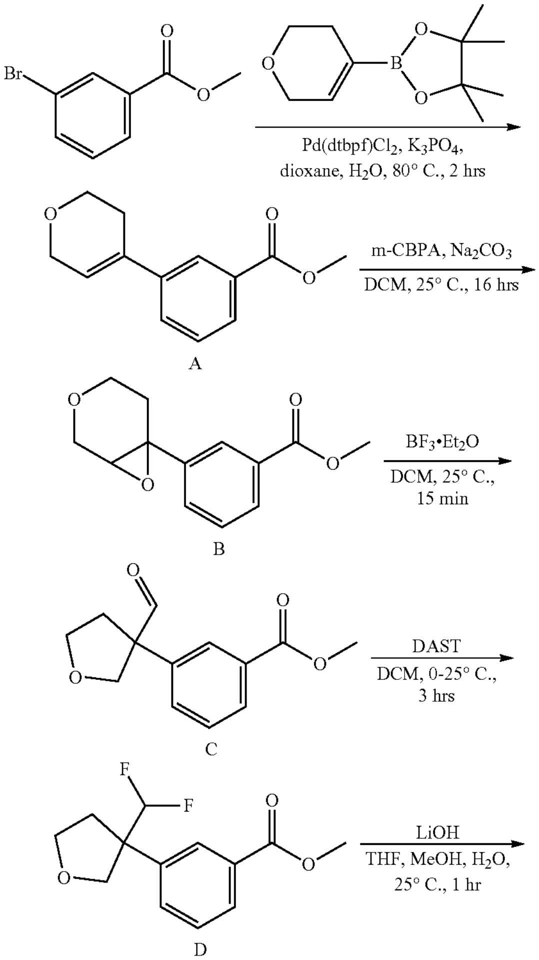

-continued

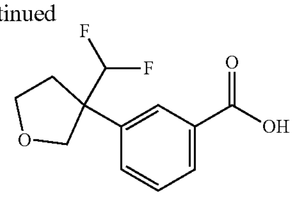

7

Step 1: Preparation of methyl 3-(3,6-dihydro-2H-pyran-4-yl)benzoate (Intermediate A)

A

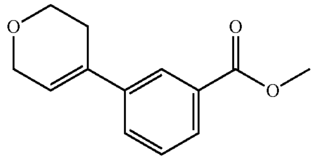

A mixture of methyl 3-bromobenzoate (4 g, 18.60 mmol), 2-(3,6-dihydro-2H-pyran-4-yl)-4,4,5,5-tetramethyl-1,3,2-dioxaborolane (5.86 g, 27.90 mmol), $K_3PO_4$ (11.84 g, 55.80 mmol), ditertbutyl(cyclopentyl)phosphane;dichloropalladium;iron (1.21 g, 1.86 mmol) and $H_2O$ (4 mL) in dioxane (40 mL) was degassed and purged with $N_2$ for 3 times, and then the mixture was stirred at 80° C. for 2 hrs under $N_2$ atmosphere. The reaction mixture was diluted with $H_2O$ (80 mL) and extracted with EA (60 mL*3). The combined organic layers were washed with brine (50 mL*3), dried over $Na_2SO_4$, filtered and concentrated under reduced pressure to give a residue. The residue was purified by column chromatography ($SiO_2$, Petroleum ether/Ethyl acetate=100/1 to 10/1). The eluent was concentrated to give Intermediate A (1.21 g, 5.54 mmol) as a yellow oil.

$^1$H NMR (400 MHz, $CDCl_3$) δ=8.08 (m, 1H), 7.94 (d, J=7.6 Hz, 1H), 7.62-7.57 (m, 1H), 7.45-7.40 (m, 1H), 6.22 (m, 1H), 4.35 (m, 2H), 3.98-3.93 (m, 5H), 2.59-2.54 (m, 2H) ppm.

Step 2: Preparation of methyl 3-(3,7-dioxabicyclo[4.1.0]heptan-6-yl)benzoate (Intermediate B)

B

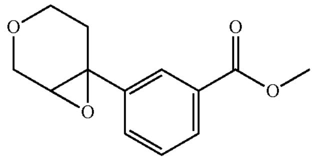

To a solution of Intermediate A (500 mg, 2.29 mmol) in DCM (40 mL) was added m-CPBA (1.09 g, 5.04 mmol, 80% purity) and $Na_2CO_3$ (582.76 mg, 5.50 mmol). The mixture was stirred at 25° C. for 16 hrs. The reaction mixture was added saturated aqueous $Na_2CO_3$ (30 mL), then concentrated under reduced pressure to remove DCM. The residue was extracted with EA (30 mL*3). The combined organic layers were washed with brine (60 mL), dried over $Na_2SO_4$, filtered and concentrated under reduced pressure to give Intermediate B (758 mg, crude) as yellow oil which was used into the next step without further purification.

Step 3: Preparation of methyl 3-(3-formyltetrahydrofuran-3-yl)benzoate (Intermediate C)

C

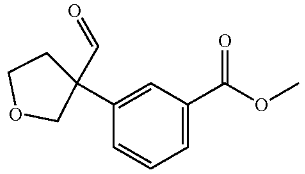

To a solution of Intermediate B (536 mg, 2.29 mmol) in DCM (40 mL) was added $BF_3 \cdot Et_2O$ (5.76 g, 40.59 mmol, 5.01 mL). The mixture was stirred at 25° C. for 15 min. The reaction mixture was added sat. $Na_2CO_3$ (30 mL), then concentrated under reduced pressure to remove DCM. The residue was extracted with EA (30 mL*3). The combined organic layers were washed with brine (60 mL), dried over $Na_2SO_4$, filtered and concentrated under reduced pressure to give a residue. The residue was purified by column chromatography ($SiO_2$, Petroleum ether/Ethyl acetate=50/1 to 5/1). The eluent was concentrated to give Intermediate C (138 mg, 589.12 umol) as yellow oil.

$^1$H NMR (400 MHz, $CDCl_3$) δ=9.56 (s, 1H), 8.02 (m, 1H), 7.88 (m, 1H), 7.52-7.45 (m, 1H), 7.40-7.36 (m, 1H), 4.69 (d, J=8.8 Hz, 1H), 4.03-3.97 (m, 2H), 3.96-3.88 (m, 4H), 2.92 (m, 1H), 2.29 (m, 1H) ppm.

Step 4: Preparation of methyl 3-[3-(difluoromethyl)tetrahydrofuran-3-yl]benzoate (Intermediate D)

D

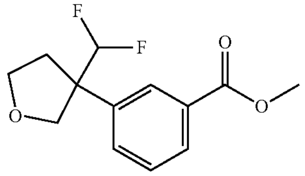

To a solution of Intermediate C (138 mg, 589.12 umol) in DCM (3 mL), then was added DAST (284.88 mg, 1.77 mmol, 233.51 uL) dropwisely at 0° C. The mixture was stirred 25° C. for 2 hrs under $N_2$ atmosphere. The reaction mixture was quenched by addition sat.$NaHCO_3$ (20 mL) dropwisely at 0° C. and extracted with DCM (15 mL*3). The combined organic layers were washed with brine (15 mL*2), dried over $Na_2SO_4$, filtered and concentrated under reduced pressure to give a residue. The residue was purified by column chromatography ($SiO_2$, Petroleum ether/Ethyl acetate=30/1~3/1). The eluent was concentrated to give Intermediate D (50 mg, 195.13 umol) as yellow oil. $^1$HNMR (400 MHz, $CDCl_3$) δ=8.12-8.03 (m, 1H), 8.03-7.98 (m, 1H), 7.93 (s, 1H), 7.46-7.44 (m, 1H), 6.16-5.60 (m, 1H), 4.50 (d, J=9.2 Hz, 1H), 4.14-4.06 (m, 1H), 3.99-3.92 (m, 6H), 2.64 (m, 1H), 2.42-2.31 (m, 1H) ppm.

Step 5: Preparation of 3-(3-(difluoromethyl)tetrahydrofuran-3-yl)benzoic acid (Intermediate 7)

7

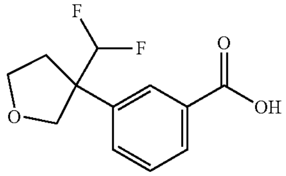

To a solution of Intermediate D (50 mg, 195.13 umol) in THE (0.3 mL), MeOH (0.3 mL) and $H_2O$ (0.3 mL) was added LiOH (9.35 mg, 390.25 umol). The mixture was stirred at 25° C. for 1 hr. The reaction mixture was diluted with $H_2O$ (10 mL) and extracted with EA (10 mL*3). The combined organic layers were discarded and the aqueous layers was adjusted to pH=5 with aqueous HCl, then extracted with EA (10 mL*3). The combined organic layers were washed with brine (20 mL), dried over $Na_2SO_4$, filtered and concentrated under reduced pressure to give Intermediate 7 (40 mg) was obtained as a yellow oil.

LCMS (ESI) m/z: $[M+H]^+$=243.1.

$^1$H NMR (400 MHz, $CDCl_3$) δ=8.08 (m, 1H), 7.99 (s, 1H), 7.75 (d, J=8.0 Hz, 1H), 7.54-7.49 (m, 2H), 6.04-5.74 (m, 1H), 4.52 (d, J=9.2 Hz, 1H), 4.16-4.12 (m, 1H), 4.01-3.93 (m, 2H), 2.66 (m, 1H), 2.42 (s, 1H) ppm.

Intermediate 8: Preparation of 2-(tert-butoxycarbonyl)-4-cyano-4-methyl-1,2,3,4-tetrahydroisoquinoline-6-carboxylic acid

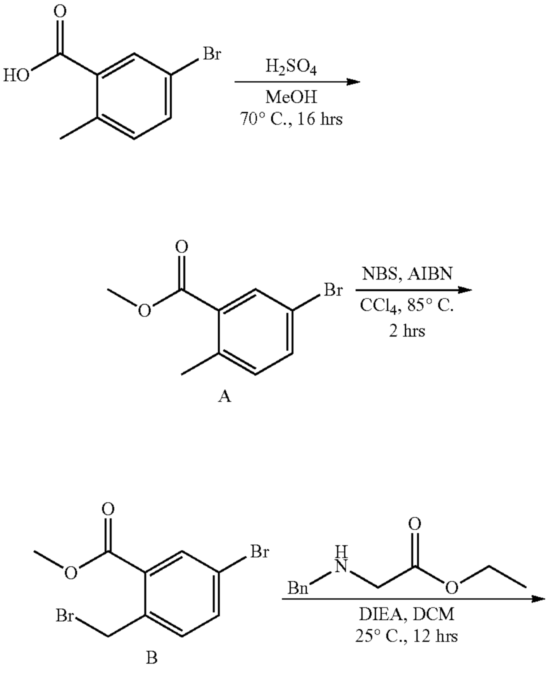

-continued

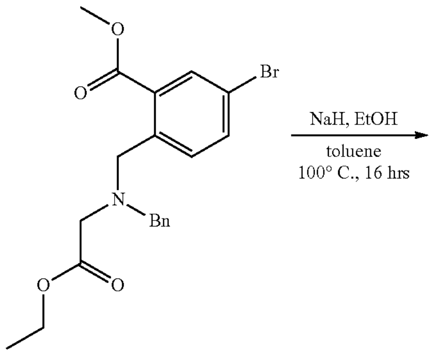

C

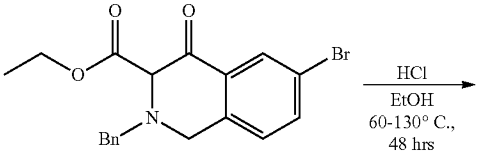

D

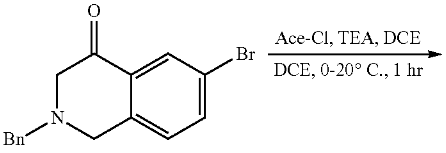

E

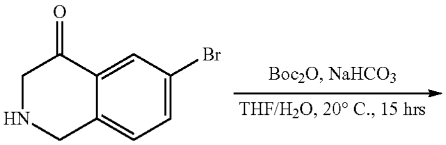

F

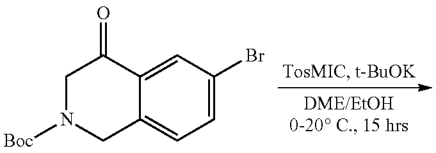

G

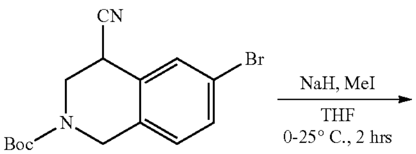

H

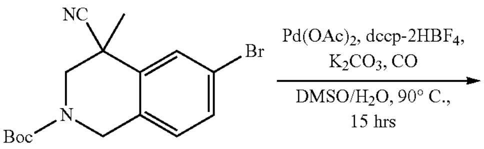

I

-continued

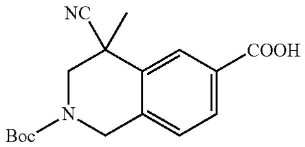

8

Step 1: Preparation of methyl 5-bromo-2-methyl-benzoate (Intermediate A)

A

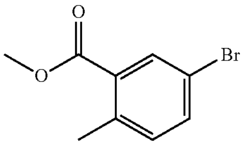

To a solution of 5-bromo-2-methyl-benzoic acid (30 g, 139.51 mmol) in MeOH (210 mL) was added $H_2SO_4$ (6 mL). The reaction mixture was stirred and refluxed at 70° C. for 16 hrs. The reaction was concentrated to give residue. Sat.$NaHCO_3$ (200 mL) was added and then $Na_2CO_3$ solid was added to adjusted pH=10. The mixture was extracted with EtOAc (200 mL*2). The combined organic layer was washed with brine (100 mL), dried over anhydrous $Na_2SO_4$, filtered and concentrated to give Intermediate A (32 g, 129.92 mmol) as yellow oil.

LCMS (ESI) m/z: $[^{79}BrM+H]^+$=229.0.

$^1H$ NMR (400 MHz, DMSO-$d_6$) δ=7.92 (d, J=2.4 Hz, 1H), 7.69-7.66 (m, 1H), 7.31 (d, J=8.4 Hz, 1H), 3.83 (s, 3H), 2.46 (s, 3H) ppm.

Step 2: Preparation of methyl 5-bromo-2-(bromomethyl)benzoate (Intermediate B)

B

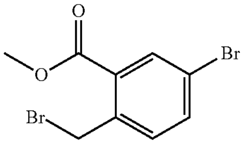

To a solution of Intermediate A (32 g, 139.70 mmol) in $CCl_4$ (320 mL) was added NBS (27.35 g, 153.66 mmol) and AIBN (2.29 g, 13.97 mmol). The reaction mixture was stirred at 85° C. for 2 hrs. The mixture was filtered through a silica gel column (100 g, $SiO_2$) and washed with a mixture of PE and EA (5/1, 600 mL). The solvent was evaporated to give Intermediate B (42 g, 121.38 mmol) as yellow oil $^1H$ NMR (400 MHz, DMSO-$d_6$) δ=7.99 (d, J=2.0 Hz, 1H), 7.82-7.80 (m, 1H), 7.57 (d, J=8.4 Hz, 1H), 4.98 (s, 2H), 3.88 (s, 3H) ppm.

Step 3: Preparation of methyl 2-[[benzyl-(2-ethoxy-2-oxo-ethyl)amino]methyl]-5-bromo-benzoate (Intermediate C)

C

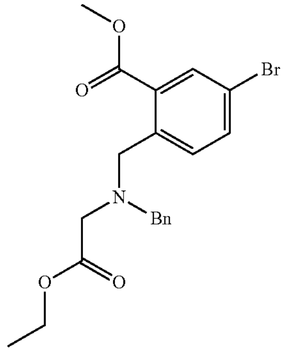

To a solution of Intermediate B (42 g, 136.38 mmol) in DCM (420 mL) was added ethyl 2-(benzylamino)acetate (31.62 g, 163.65 mmol) and DIEA (35.25 g, 272.76 mmol). The reaction mixture was stirred at 25° C. for 12 hrs. The reaction mixture was poured into water (500 mL) and was extracted with DCM (200 mL*2). The combined organic layer was washed with brine (200 mL), dried over anhydrous $Na_2SO_4$, filtered and concentrated to give a residue, which was purified by flash silica gel chromatography (120 g Silica Flash Column, Eluent of 0~20% Ethylacetate/Petroleum ethergradient @100 mL/min). The eluent was concentrated to give Intermediate C (42 g, 97.93 mmol) as colorless oil.

LCMS (ESI) m/z: $[^{81}BrM+H]^+$=421.9.

$^1H$ NMR (400 MHz, DMSO-$d_6$) δ=7.82 (d, J=2.0 Hz, 1H), 7.73-7.72 (m, 1H), 7.57 (d, J=8.0 Hz, 1H), 7.32-7.28 (m, 2H), 7.25-7.21 (m, 3H), 4.08-4.03 (m, 4H), 3.81 (s, 3H), 3.69 (s, 2H), 3.17 (s, 2H), 1.19-1.15 (m, 3H) ppm, Step 4: Preparation of ethyl 2-benzyl-6-bromo-4-oxo-1,3-dihydroisoquinoline-3-carboxylate (Intermediate D)

D

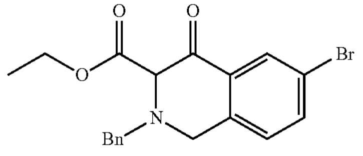

To a solution of EtOH (6.91 g, 149.89 mmol) in toluene (210 mL) was added NaH (6.00 g, 149.89 mmol, 60% purity). Then Intermediate C (42 g, 99.93 mmol) in toluene (210 mL) was added. The reaction mixture was stirred at 100° C. for 16 hrs. The reaction mixture was concentrated to remove toluene. The residue was poured into water (300 mL) and extracted with EA (200 mL*3). The combined organic layer was washed with brine (100 mL), dried over anhydrous $Na_2SO_4$, filtered and concentrated to give Intermediate D (38 g, crude) as a yellow solid.

LCMS (ESI) m/z: $[^{81}BrM+H]^+$=390.0.

$^1H$ NMR (400 MHz, DMSO-$d_6$) δ=7.88 (d, J=2.0 Hz, 1H), 7.40-7.39 (m, 1H), 7.32-7.21 (m, 5H), 6.97 (d, J=8.0 Hz, 1H), 4.06-4.01 (m, 2H), 3.60-3.40 (m, 5H), 1.26-1.17 (m, 3H) ppm.

Step 5: Preparation of 2-benzyl-6-bromo-1,3-dihydroisoquinolin-4-one (Intermediate E)

E

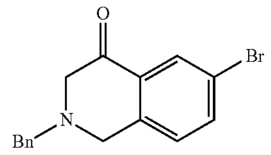

To a solution of Intermediate D (38 g, 97.87 mmol) in EtOH (200 mL) was added HCl (12 M, 200 mL) at 60° C. The reaction mixture was stirred and refluxed at 130° C. for 48 hrs. Yellow solid was formed gradually. The hot reaction mixture was filtered to afford yellow solid. The yellow solid was triturated with MTBE (100 mL). The suspension was stirred for 10 min and filtered to give a white solid. The solid was dissolved in Sat.$NaHCO_3$ (100 mL) and EA (100 mL), then the mixture was adjusted pH=10 with $Na_2CO_3$ (s). The mixture was extracted with EA (100 mL*2). The combined organic layer was washed with brine (100 mL), dried over anhydrous $Na_2SO_4$, filtered and concentrated to give Intermediate E (10 g, 30.99 mmol) as a yellow solid.

LCMS (ESI) m/z: $[^{81}BrM+H]^+$=316.0.

$^1H$ NMR (400 MHz, DMSO-$d_6$) δ=7.94 (d, J=2.0 Hz, 1H), 7.79-7.77 (m, 1H), 7.39-7.32 (m, 5H), 7.32-7.28 (m, 1H), 3.78 (s, 2H), 3.74 (s, 2H), 3.35 (s, 2H) ppm.

Step 6: Preparation of 6-bromo-2,3-dihydro-1H-isoquinolin-4-one (Intermediate F)

F

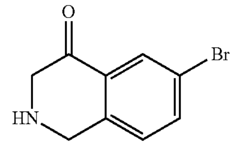

To a mixture of Intermediate E (4 g, 12.65 mmol) in DCE (60 mL) was added 1-chloroethyl carbonochloridate (5.43 g, 37.95 mmol), DIPEA (1.63 g, 12.65 mmol) at 0° C., the mixture was stirred at 20° C. for 1 hrs. The mixture was added MeOH (5 mL), then stirred at 60° C. for 1 hr. The mixture was concentrated to give Intermediate F (3 g, crude, HCl) as colorless oil which was used into the next step directly.

Step 7: Preparation of tert-butyl 6-bromo-4-oxo-1,3-dihydroisoquinoline-2-carboxylate (Intermediate G)

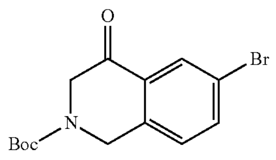

G

To a mixture of Intermediate F (3 g, 11.43 mmol) in THF (40 mL) and water (8 mL) was added $(Boc)_2O$ (7.48 g, 34.29 mmol, 7.88 mL) and $NaHCO_3$ (2.88 g, 34.29 mmol) at 20° C., then the mixture was stirred at 20° C. for 15 hrs. The mixture was added water (10 mL) and was extracted with EA (5 mL*3), the combined organic layer was washed with brine (10 mL), dried over $Na_2SO_4$, filtered and concentrated to give a residue. The residue was purified by column chromatography ($SiO_2$, Petroleum ether/Ethyl acetate=15/1 to 5/1) to give Intermediate G (3.2 g, 9.81 mmol) as a yellow solid.

LCMS (ESI) m/z: $[^{79}BrM-55]^+$=270.0.

$^1H$ NMR (400 MHz, $CDCl_3$) δ=8.20-8.15 (m, 1H), 7.72-7.65 (m, 1H), 7.24-7.18 (m, 1H), 4.78-4.68 (s, 2H), 4.38-4.27 (s, 2H), 1.49-1.47 (s, 9H) ppm.

Step 8: Preparation of tert-butyl 6-bromo-4-cyano-3,4-dihydro-1H-isoquinoline-2-carboxylate (Intermediate H)

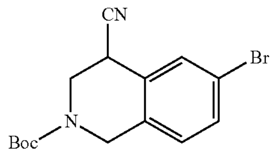

H

To a mixture of Intermediate G (2.7 g, 8.28 mmol, 1-(isocyanomethylsulfonyl)-4-methyl-benzene (2.42 g, 12.42 mmol) and EtOH (3.81 g, 82.78 mmol) in DME (60 mL) was added t-BuOK (1.86 g, 16.56 mmol) in portions at 0° C. After addition, the mixture was warmed up to 20° C. slowly and the mixture was stirred at 20° C. for 15 hrs. The mixture was diluted with water (2 mL) and extracted with EA (5 mL*3). The combined organic layer was washed with brine (5 mL), dried over $Na_2SO_4$, filtered and concentrated to give a residue. The residue was purified by prep-TLC ($SiO_2$, PE:EA=5:1) to give Intermediate H (1 g, 2.88 mmol) as colorless oil.

LCMS (ESI) m/z: $[^{79}BrM+H]^+$=281.0.

Step 9: Preparation of tert-butyl 6-bromo-4-cyano-4-methyl-1,3-dihydroisoquinoline-2-carboxylate (Intermediate I)

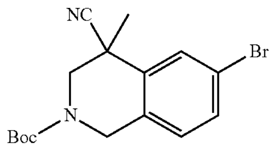

I

To a mixture of Intermediate H (1 g, 2.97 mmol) in DMF (12 mL) was added NaH (178.20 mg, 4.46 mmol, 60% purity) at 0° C. The mixture was stirred at 0° C. for 10 min and then $CH_3I$ (1.27 g, 8.91 mmol) was added. The resulting mixture was stirred at 25° C. for 2 hrs. The reaction was quenched with water (20 mL) and the mixture was extracted with EA (15 mL*3). The combined organic layer was washed with brine (20 mL), dried over $Na_2SO_4$, filtered and concentrated to get the crude product. The residue was purified by column chromatography ($SiO_2$, Petroleum ether/Ethyl acetate=10/1 to 5/1) to give Intermediate I (650 mg, 1.85 mmol) as colorless oil.

LCMS (ESI) m/z: $[^{79}BrM-55]^+$=295.0.

$^1H$ NMR (400 MHz, $CDCl_3$) δ=7.69-7.61 (m, 1H), 7.46-7.41 (m, 1H), 7.06-7.00 (m, 1H), 4.83-4.68 (m, 1H), 4.51-4.39 (m, 1H), 4.12-3.89 (m, 1H), 3.83-3.61 (m, 1H), 1.67 (s, 3H), 1.51 (s, 9H) ppm.

Step 10: Preparation of 2-(tert-butoxycarbonyl)-4-cyano-4-methyl-1,2,3,4-tetrahydroisoquinoline-6-carboxylic acid (Intermediate 8)

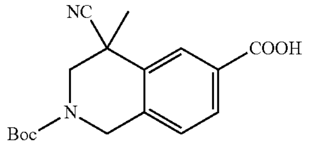

8

To a mixture of Intermediate I (250 mg, 711.77 umol) in DMSO (3 mL) was added dicyclohexyl(3-dicyclohexylphosphaniumylpropyl)phosphonium;ditetrafluoroborate (43.58 mg, 71.18 umol), $Pd(OAc)_2$ (7.99 mg, 35.59 umol), $K_2CO_3$ (147.56 mg, 1.07 mmol), $H_2O$ (25.65 mg, 1.42 mmol), the mixture was degassed with $N_2$ for three times and the mixture was stirred at 90° C. for 15 hrs under CO (15 psi) atmosphere. The mixture was filtered and the filtrate was diluted with water (6 mL). The mixture was extracted with EA (5 mL*3) and the combined organic layer was washed with brine (10 mL), dried over $Na_2SO_4$, filtered and concentrated to give a residue. The crude product was purified by reversed-phase HPLC (0.1% FA condition). The eluent was lyophilized to give Intermediate 8 (80 mg, 252.88 umol) as a white solid.

$^1H$ NMR (400 MHz, DMSO-$d_6$) δ=8.06 (d, J=1.6 Hz, 1H), 7.92-7.85 (m, 1H), 7.42 (d, J=8.0 Hz, 1H), 4.80-4.55 (m, 2H), 4.13-3.96 (m, 1H), 3.69 (d, J=13.2 Hz, 1H), 1.67 (s, 3H), 1.45 (s, 9H) ppm.

Intermediates 9 and 10: Preparation of (S)-3-cyano-1,3-dimethylindoline-5-carboxylic acid and (R)-3-cyano-1,3-dimethylindoline-5-carboxylic acid

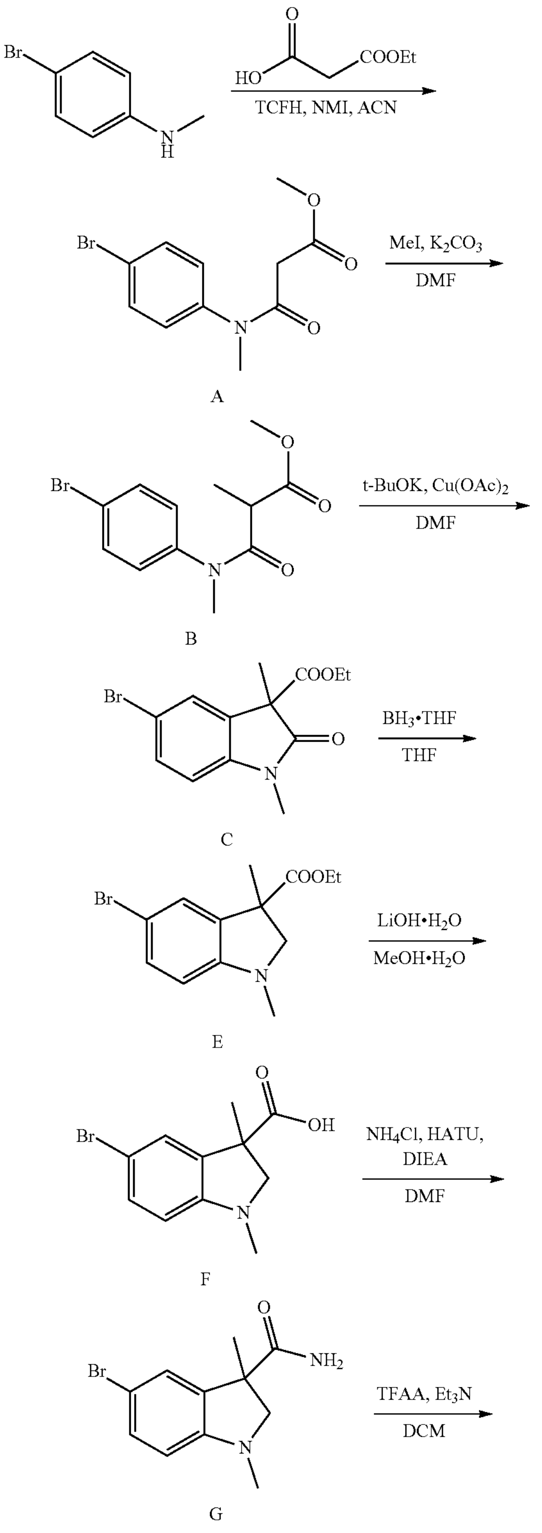

-continued

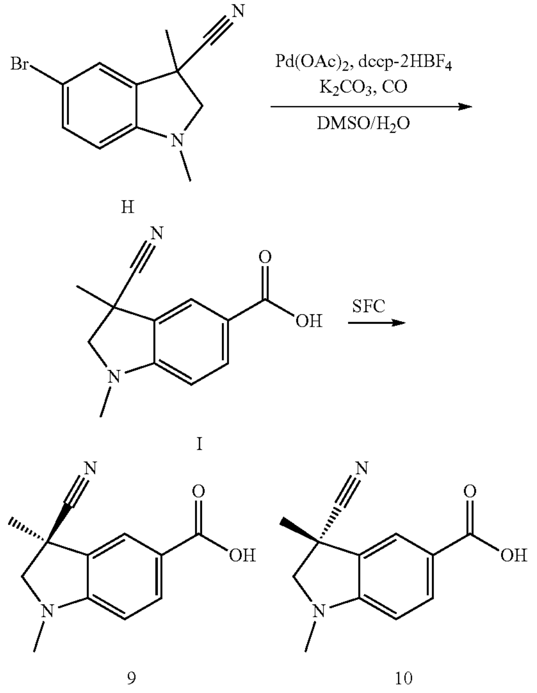

Step 1: Preparation of methyl 3-((4-bromophenyl)(methyl)amino)-3-oxopropanoate (Intermediate A)

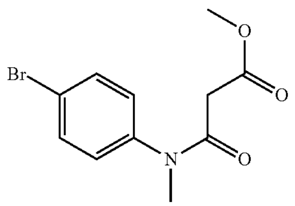

A

To a mixture of 4-bromo-N-methyl-aniline (10 g, 53.75 mmol), 3-ethoxy-3-oxo-propanoic acid (8.52 g, 64.50 mmol) in $CH_3CN$ (150 mL) was added [chloro(dimethylamino)methylene]-dimethyl-ammonium;hexafluorophosphate (22.62 g, 80.63 mmol), 1-methylimidazole (13.24 g, 161.25 mmol, 12.85 mL) at 20° C., the mixture was stirred at 20° C. for 15 hrs. The mixture was concentrated to get the crude product, which was diluted with water (10 mL) and then was extracted with DCM (15 mL*3), the combined organic phase was washed with brine (15 mL), dried over $Na_2SO_4$, filtered and concentrated to get the crude product. The residue was purified by column chromatography ($SiO_2$, Petroleum ether/Ethyl acetate=5/1 to 3/1) to give Intermediate A (13 g, 43.31 mmol) as a white solid.

LCMS (ESI) m/z: $[M+H]^+$=286.0.

$^1H$ NMR (400 MHz, $CDCl_3$) δ=7.56 (d, J=8.4 Hz, 2H), 7.14 (d, J=8.4 Hz, 2H), 4.13 (d, J=7.2 Hz, 2H), 3.29 (s, 3H), 3.21 (s, 2H), 1.29-1.15 (m, 3H) ppm.

Step 2: Preparation of methyl 3-((4-bromophenyl)(methyl)amino)-2-methyl-3-oxopropanoate (Intermediate B)

B

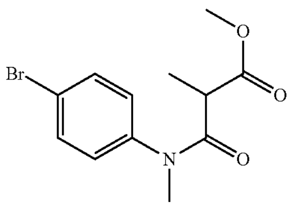

To a mixture of Intermediate A (6 g, 19.99 mmol) in DMF (60 mL) was added $K_2CO_3$ (4.14 g, 29.99 mmol), followed by MeI (8.50 g, 59.92 mmol, 3.73 mL) at 0° C. and the resulting mixture was stirred at 20° C. for 15 hrs. The reaction was diluted with water (100 mL) and extracted with EA (60 mL*3), the combined organic phase was washed with brine (50 mL), dried over $Na_2SO_4$, filtered and concentrated to get the crude product. The residue was purified by column chromatography ($SiO_2$, Petroleum ether/Ethyl acetate=5/1 to 3/1) to give Intermediate B (4 g, 12.73 mmol) as a yellow solid.

LCMS (ESI) m/z: $[M+H]^+$=300.0.

$^1H$ NMR (400 MHz, $CDCl_3$) δ=7.57 (d, J=8.4 Hz, 2H), 7.18-7.11 (m, 2H), 4.19-4.03 (m, 2H), 3.40-3.28 (m, 1H), 3.28 (s, 3H), 1.31 (d, J=7.2 Hz, 3H), 1.27-1.21 (m, 3H) ppm.

Step 3: Preparation of ethyl 5-bromo-1,3-dimethyl-2-oxoindoline-3-carboxylate (Intermediate C)

C

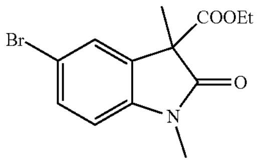

To a mixture of Intermediate B (4 g, 12.73 mmol) in DMF (120 mL) was added t-BuOK (2.86 g, 25.46 mmol) and Copper(II)acetatemonohydrate (5.08 g, 25.46 mmol, 5.08 mL) at 20° C., then the mixture was stirred at 100° C. for 1 hrs. The mixture was filtered off and the filtrate was diluted with water (150 mL) and then was extracted with EA (50 mL*3), the combined organic phase was washed with brine (50 mL), dried over $Na_2SO_4$, filtered and concentrated to get the crude product. The residue was purified by column chromatography ($SiO_2$, Petroleum ether/Ethyl acetate=5/1 to 3/1) to give Intermediate C (2 g, 5.77 mmol) as a yellow solid.

LCMS (ESI) m/z: $[M+H]^+$=312.0.

$^1H$ NMR (400 MHz, $CDCl_3$) δ=7.46-7.44 (m, 1H), 7.38 (d, J=2.0 Hz, 1H), 6.75 (d, J=8.4 Hz, 1H), 4.23-4.09 (m, 2H), 3.26-3.19 (m, 3H), 1.66 (s, 3H), 1.21-1.16 (m, 3H) ppm.

Step 4: Preparation of ethyl 5-bromo-1,3-dimethylindoline-3-carboxylate (Intermediate D)

D

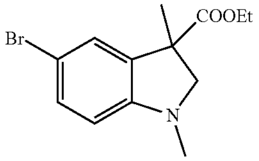

To a mixture of Intermediate C (2 g, 6.41 mmol) in THE (20 mL) was added $BH_3$·THF (1 M, 9.61 mL) at 0° C. and the mixture was stirred at 60° C. for 2 hrs. The mixture was quenched with MeOH (30 mL) at 0° C. slowly and then was concentrated to get the crude product. The crude product was purified by column chromatography ($SiO_2$, Petroleum ether/Ethyl acetate=10/1 to 3/1) to give Intermediate D (300 mg, 855.20 umol) as colorless oil.

LCMS (ESI) m/z: $[M+H]^+$=298.0.

$^1H$ NMR (400 MHz, $CDCl_3$) δ=7.34 (d, J=2.0 Hz, 1H), 7.23-7.20 (m, 1H), 6.35 (d, J=8.4 Hz, 1H), 4.26-4.15 (m, 2H), 3.89 (d, J=9.2 Hz, 1H), 3.19-3.12 (m, 1H), 2.78-2.72 (m, 3H), 1.54 (s, 3H), 1.33-1.25 (m, 3H) ppm.

Step 5: Preparation of 5-bromo-1,3-dimethylindoline-3-carboxylic acid (Intermediate E)

E

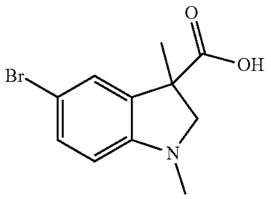

A mixture of Intermediate D (300 mg, 1.01 mmol) in MeOH (3 mL) and water (1 mL) was added LiOH·$H_2O$ (126.66 mg, 3.02 mmol) at 20° C. and the mixture was stirred at 20° C. for 15 hrs. MeOH was removed under vacuum to get the crude product, which was diluted with water (1 mL), and then was adjusted pH to 3 with 1 N HCl and extracted with EA (5 mL*3), the combined organic phase was washed with brine (10 mL), dried over $Na_2SO_4$, filtered and concentrated to give Intermediate E (220 mg, 700.42 umol) as a white solid which was used in the next step directly.

LCMS (ESI) m/z: $[M+H]^+$=270.0.

Step 6: Preparation of 5-bromo-1,3-dimethylindoline-3-carboxamide (Intermediate F)

F

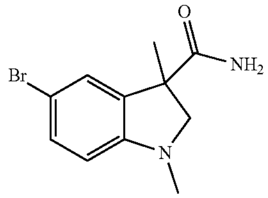

To a mixture of Intermediate E (220 mg, 814.45 umol) in DMF (4 mL) was added $NH_4Cl$ (435.66 mg, 8.14 mmol), HATU (464.52 mg, 1.22 mmol) and DIPA (412.07 mg, 4.07 mmol, 575.52 uL) at 20° C., the mixture was stirred at 20° C. for 15 hrs. Water (5 mL) was added and the mixture was extracted with EA (5 mL*3), the combined organic layer was washed with brine (10 mL), dried over $Na_2SO_4$, filtered and concentrated to get the crude product. The residue was purified by prep-TLC ($SiO_2$, PE:EA=1:1) to give Intermediate F (210 mg, 468.16 umol) as colorless oil.

LCMS (ESI) m/z: $[M+H]^+$=269.0.

$^1$H NMR (400 MHz, $CDCl_3$) δ=7.29 (br d, J=2.0 Hz, 1H), 7.22 (d, J=2.0 Hz, 1H), 6.44 (d, J=8.4 Hz, 1H), 3.84 (d, J=9.2 Hz, 1H), 3.10 (d, J=9.2 Hz, 1H), 2.76 (s, 3H), 1.57 (s, 3H) ppm.

Step 7: Preparation of 5-bromo-1,3-dimethylindoline-3-carbonitrile (Intermediate G)

G

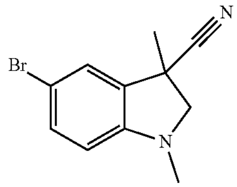

To a mixture of Intermediate F (210 mg, 780.27 umol) in DCM (3 mL) was added $Et_3N$ (236.87 mg, 2.34 mmol, 325.81 uL) at 0° C., then TFAA (409.70 mg, 1.95 mmol, 271.33 uL) was added slowly and the resulting mixture was stirred at 20° C. for 4 hrs. The mixture was diluted with water (5 mL) and extracted with DCM (5 mL*3). The combined organic phase was washed with Sat.$NaHCO_3$, dried over $Na_2SO_4$, filtered and concentrated to get a residue, which was purified by column chromatography ($SiO_2$, Petroleum ether/Ethyl acetate=10/1 to 5/1) to give Intermediate G (100 mg, 390.25 umol) as colorless oil.

LCMS (ESI) m/z: $[M+H]^+$=251.1.

$^1$H NMR (400 MHz, $CDCl_3$) δ=7.33 (d, J=2.0 Hz), 7.31-7.28 (m, 1H), 6.42 (d, J=8.4 Hz, 1H), 3.70 (d, J=9.2 Hz, 1H), 3.32 (d, J=9.2 Hz, 1H), 2.77 (s, 3H), 1.68 (s, 3H) ppm.

Step 8: Preparation of 3-cyano-1,3-dimethylindoline-5-carboxylic acid (Intermediate H)

H

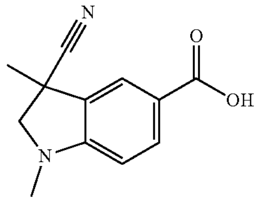

To a mixture of Intermediate G (50 mg, 199.11 umol) in DMSO (1 mL) was added dicyclohexyl(3-dicyclohexylphosphaniumylpropyl)phosphonium;ditetrafluoroborate (12.19 mg, 19.91 umol), $Pd(OAc)_2$ (2.24 mg, 9.96 umol), $K_2CO_3$ (41.28 mg, 298.66 umol), $H_2O$ (7.17 mg, 398.21 umol, 7.17 uL) at 20° C. The mixture was degassed three times and then was stirred at 100° C. for 15 hrs under CO (15 psi) atmosphere. The mixture was combined with another batch. It was diluted with water (3 mL) and extracted with EA (3 mL*3), the combined organic layer was washed with brine (5 mL), dried over $Na_2SO_4$, filtered and concentrated to get the crude product, which was purified by reversed-phase HPLC (0.1% FA condition). The solution was extracted with DCM (5 mL*3), the combined organic layer was washed with brine (5 mL), dried over $Na_2SO_4$, filtered and concentrated to give Intermediate H (60 mg, crude) as a white solid.

LCMS (ESI) m/z: $[M+H]^+$=217.6.

$^1$H NMR (400 MHz, DMSO-$d_6$) δ=12.39 (br s, 1H), 7.85-7.76 (m, 2H), 6.66 (d, J=8.4 Hz, 1H), 3.87 (d, J=10.0 Hz, 1H), 3.44 (d, J=10.0 Hz, 1H), 2.83 (s, 3H), 1.68 (s, 3H) ppm.

Step 9: Preparation of (S)-3-cyano-1,3-dimethylindoline-5-carboxylic acid and (R)-3-cyano-1,3-dimethylindoline-5-carboxylic acid (Intermediates 9 and 10)

9

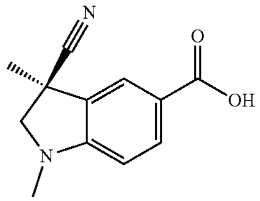

10

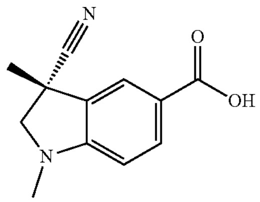

Intermediate H (60 mg, 277.48 umol) was separated by SFC condition (column: DAICEL CHIRALPAK IC (250 mm*30 mm, 5 um); mobile phase: [0.1% $NH_3 \cdot H_2O$ IPA]; B %: 20%-20%, 5 min; 85 min) to give Intermediate 9 (25 mg, 105.21 umol) as a white solid and Intermediate 10 (20 mg, 65.67 umol) as a white solid.

Intermediate 9

LCMS (ESI) m/z: $[M+H]^+$=217.1.

Chiral SFC: IC-3-IPA (DEA)-5-40-3 mL-35T·lcm; Rt=1.517 min.

Intermediate 10

LCMS (ESI) m/z: $[M+H]^+$=217.1.

Chiral SFC: IC-3-IPA (DEA)-5-40-3 mL-35T·lcm; Rt=1.608 min.

Intermediate 11: Preparation of 5-hydroxy-5-methyl-1,3,4,5-tetrahydrobenzo[c]oxepine-7-carboxylic acid

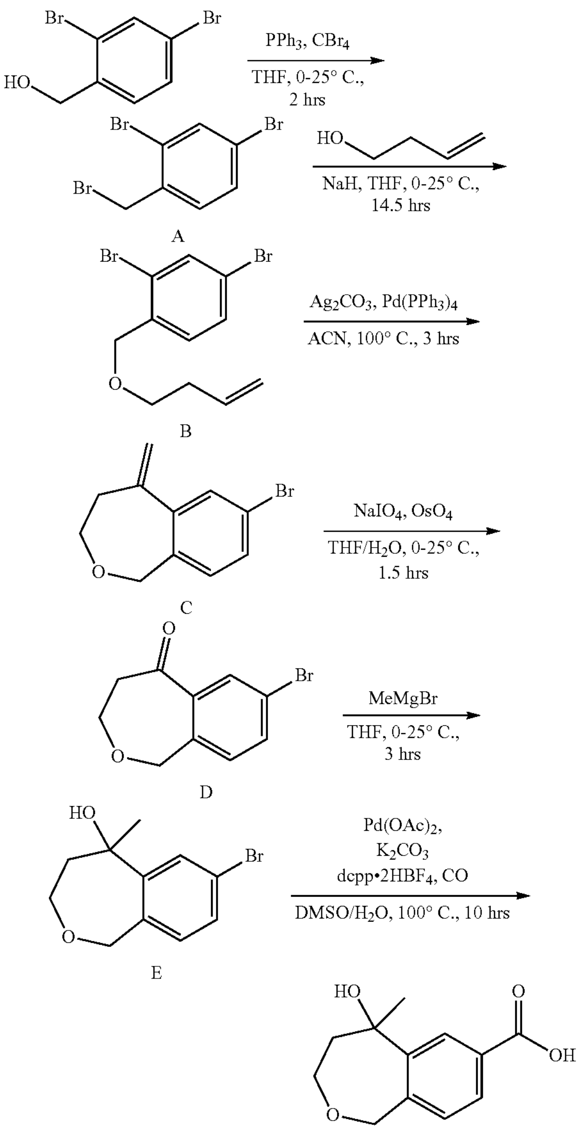

11

Step 1: Preparation of 2,4-dibromo-1-(bromomethyl)benzene (Intermediate A)

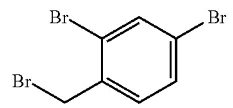

A

To a solution of (2,4-dibromophenyl)methanol (20 g, 75.21 mmol) and $PPh_3$ (29.59 g, 112.81 mmol) in THF (500 mL) was added CARBON TETRABROMIDE (37.41 g, 112.81 mmol) at 0° C. dropwisely slowly. After addition, the reaction mixture was stirred at 25° C. for 2 hrs. The reaction mixture was concentrated. The residue was purified by flash silica gel chromatography (PE). The eluent was concentrated to give Intermediate A (23 g, 69.95 mmol) as colorless oil.

$^1H$ NMR (400 MHz, $CDCl_3$) δ=7.76 (d, J=2.0 Hz, 1H), 7.45 (m, 1H), 7.33 (d, J=8.4 Hz, 1H), 4.66-4.45 (m, 2H) ppm.

Step 2: Preparation of 2,4-dibromo-1-((but-3-en-1-yloxy)methyl)benzene (Intermediate B)

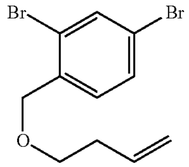

B

To a solution of but-3-en-1-ol (7.57 g, 104.92 mmol, 9.03 mL) in THE (250 mL) was added NaH (4.20 g, 104.92 mmol, 60% purity) at 0° C. in portions. The reaction mixture was stirred at 0° C. for 30 min. Then a solution of Intermediate A (23 g, 69.95 mmol) in THE (50 mL) was added to the mixture at 0° C. The reaction mixture was warmed to 25° C. and stirred for 14 hrs. The reaction mixture was quenched with sat.$NH_4Cl$ (100 mL). The mixture was extracted with EA (300 mL*2). The organic layer was washed with brine (400 mL), dried over $Na_2SO_4$, filtered and concentrated. The residue was purified by flash silica gel chromatography (PE). The eluent was concentrated to give Intermediate B (22 g, 68.75 mmol) as yellow oil.

$^1H$ NMR (400 MHz, $CDCl_3$) δ=7.70 (d, J=2.0 Hz, 1H), 7.48-7.42 (m, 1H), 7.40-7.35 (m, 1H), 5.87 (m, 1H), 5.14 (m, 1H), 5.08 (m, 1H), 4.52 (s, 2H), 3.61 (m, 2H), 2.42 (m, 2H) ppm.

Step 3: Preparation of 7-bromo-5-methylene-1,3,4,5-tetrahydrobenzo[c]oxepine (Intermediate C)

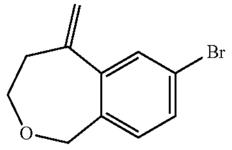

C

A mixture of Intermediate B (400 mg, 1.25 mmol), $Pd(PPh_3)_4$ (144.44 mg, 124.99 umol) and $Ag_2CO_3$ (413.59 mg, 1.50 mmol, 68.02 uL) in MeCN (16 mL) was stirred at 100° C. for 3 hrs under $N_2$ atmosphere. The reaction mixture was filtered and the filtrate was concentrated. The residue was purified by flash silica gel chromatography (15% EA in PE). The eluent was concentrated to give Intermediate C (600 mg, 2.51 mmol) as yellow oil.

$^1H$ NMR (400 MHz, $CDCl_3$) δ=7.47 (d, J=2.0 Hz, 1H), 7.34 (m, 1H), 7.01 (d, J=8.0 Hz, 1H), 5.25-5.14 (m, 2H), 4.59 (s, 2H), 4.05-3.94 (m, 2H), 2.65-2.54 (m, 2H) ppm.

Step 4: Preparation of 7-bromo-3,4-dihydrobenzo[c]oxepin-5(1H)-one (Intermediate D)

D

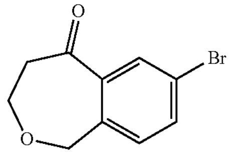

To a solution of Intermediate C (500 mg, 2.09 mmol) in THE (5 mL) and $H_2O$ (5 mL) was added $OsO_4$ (106.32 mg, 418.22 umol, 21.70 uL) at 0° C. The reaction mixture was stirred at 0° C. for 30 min. $NaIO_4$ (1.12 g, 5.23 mmol, 289.68 uL) was added to the mixture. The mixture was stirred at 25° C. for 1 hr. The reaction was quenched by sat.$Na_2SO_3$ (100 mL) and stirred for 15 min, then extracted with EA (20 mL*2). The organic layer was washed with brine (20 mL), dried over $Na_2SO_4$, filtered and concentrated to give a residue. The residue was purified by flash silica gel chromatography (PE to PE:EA=1:1). The eluent was concentrated to give Intermediate D (340 mg, 1.19 mmol) as colorless oil.

LCMS (ESI) m/z: $[^{79}BrM+H]^+$=241.0.

$^1H$ NMR (400 MHz, $CDCl_3$) δ=7.98 (d, J=2.0 Hz, 1H), 7.59 (m, 1H), 7.14 (d, J=8.0 Hz, 1H), 4.87 (s, 2H), 4.07 (m, 2H), 3.07 (m, 2H) ppm.

Step 5: Preparation of 7-bromo-5-methyl-1,3,4,5-tetrahydrobenzo[c]oxepin-5-ol (Intermediate E)

E

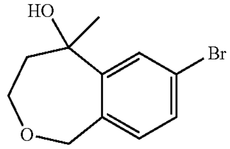

To a solution of Intermediate D (300 mg, 1.24 mmol) and $CeCl_3$ (153.36 mg, 622.20 umol, 39.12 uL) in THE (3 mL) was added MeMgBr (3 M, 1.24 mL) at 0° C. The mixture was stirred at 25° C. for 3 hrs. The reaction was quenched by water (2 mL) then extracted with EA (5 mL*3). The organic layer concentrated to give a residue. The residue was purified by reversed phased HPLC (0.1% $NH_3 \cdot H_2O$). The eluent was lyophilized to give Intermediate E (240 mg, 911.56 umol) as colorless oil.

$^1H$ NMR (400 MHz, $CDCl_3$) δ=7.83 (d, J=2.0 Hz, 1H), 7.33 (m, 1H), 6.97 (d, J=8.0 Hz, 1H), 4.84 (d, J=14.4 Hz, 1H), 4.64 (d, J=14.4 Hz, 1H), 4.20-4.12 (m, 1H), 3.97 (m, 1H), 2.24 (m, 1H), 2.05-1.96 (m, 1H), 1.66 (s, 3H) ppm.

Step 6: Preparation of 5-hydroxy-5-methyl-3,4-dihydro-1H-2-benzoxepine-7-carboxylic acid (Intermediate 11)

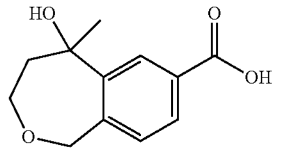

11

A solution of Intermediate E (200.00 mg, 777.84 umol) in dioxane (2 mL) and $H_2O$ (0.4 mL) were added $Pd(OAc)_2$ (8.73 mg, 38.89 umol). dicyclohexyl(3-dicyclohexylphosphaniumylpropyl) phosphonium;ditetrafluoroborate (47.62 mg, 77.78 umol) and $K_2CO_3$ (215.00 mg, 1.56 mmol). The reaction mixture was degassed and purged with CO for 3 times, and then the mixture was stirred at 100° C. for 10 hrs under CO (15 psi) atmosphere. The reaction solution was filtered to get the residue. The residue was purified by reversed phase (0.1% FA). The eluent was concentrated under reduced pressure to remove MeCN. The eluent was lyophilized to give Intermediate 11 (120 mg, 507.24 umol) as a yellow solid.

$^1H$ NMR (400 MHz, DMSO-$d_6$) δ=12.73 (s, 1H), 8.28 (s, 1H), 7.73-7.71 (m, 1H), 7.23 (d, J=7.6 Hz, 1H), 5.31 (s, 1H), 4.92-4.57 (m, 2H), 4.10-3.77 (m, 2H), 2.20-2.03 (m, 1H), 1.90-1.74 (m, 1H), 1.50 (s, 3H) ppm.

Intermediate 12: Preparation of (((3-oxabicyclo[4.1.0]heptan-6-yl)boranylidene)-I3-fluoraneyl)potassium(III) fluoride

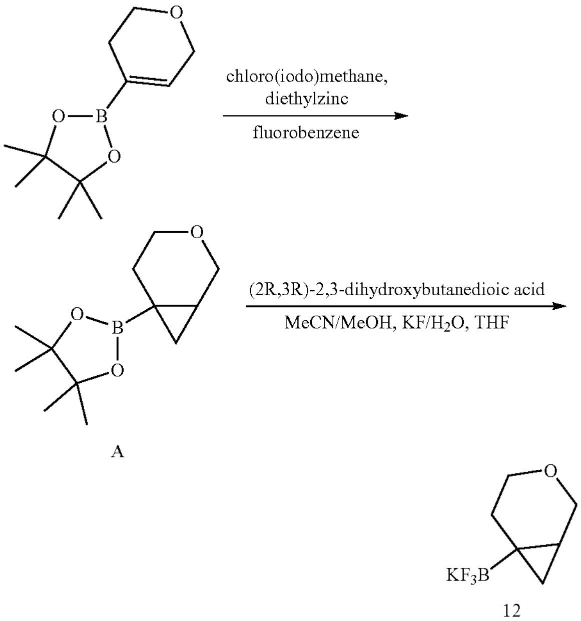

A

12

Step 1: Preparation of 4,4,5,5-tetramethyl-2-(3-oxabicyclo[4.1.0]heptan-6-yl)-1,3,2-dioxaborolane (Intermediate A)

A

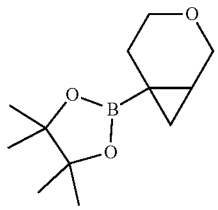

To a mixture of 2-(3,6-dihydro-2H-pyran-4-yl)-4,4,5,5-tetramethyl-1,3,2-dioxaborolane (5 g, 23.80 mmol) in fluorobenzene (50 mL) was added diethylzinc (1 M, 119.00 mL) slowly at −5° C. The mixture was stirred for 5 min and then chloro(iodo)methane (41.98 g, 238.01 mmol, 17.28 mL) dissolved in fluorobenzene (25 mL) was added over 5 min. The mixture was stirred at −5° C. for 10 min prior to three subsequent additions of diethylzinc and chloroiodomethane in the same manner. Then the mixture was stirred at 30° C. for 16 hrs. The reaction mixture was poured into saturated $NH_4Cl$ (400 mL) and extracted with MTBE (400 mL*2). The combined organic phase was washed with brine (400 mL), dried over anhydrous $Na_2SO_4$, filtered and concentrated under vacuum. The residue was purified by column chromatography ($SiO_2$, PE:EtOAc=100:1-10:1) to give Intermediate A (3 g, 13.39 mmol) as a white solid.

Step 2: Preparation of potassium 3-oxabicyclo[4.1.0]heptan-6-yltrifluoroborate (Intermediate 12)

12

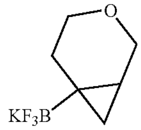

To a mixture of Intermediate A (1.45 g, 6.47 mmol) in MeCN (16 mL) and MeOH (16 mL) was added KF (1.50 g, 25.88 mmol, 606.29 uL) dissolved in $H_2O$ (5.6 mL) under $N_2$ atmosphere. The mixture was stirred at 25° C. for 10 min and then (2R,3R)-2,3-dihydroxybutanedioic acid (1.94 g, 12.94 mmol, 1.85 mL) was added, followed by THE (0.7 mL). The resulting mixture was stirred at 25° C. for 2 hrs. The precipitate was removed by filtration and washed with MeCN (40 mL). The filtrate was concentrated under vacuum and then toluene (20 mL) was added. The mixture was concentrated under vacuum and the residue was triturated with MTBE (20 mL). Then the precipitate was collected by filtration and dried under vacuum to give Intermediate 12 (1.46 g) as a white solid which was used for next step directly without further purification.

$^1H$ NMR (400 MHz, $D_2O$) δ=3.97-3.82 (m, 2H), 3.56-3.44 (m, 1H), 3.24-3.20 (m, 1H), 1.80-1.77 (m, 1H), 1.60-1.46 (m, 1H), 0.80-0.70 (m, 1H), 0.51-0.48 (m, 1H), 0.12 (s, 1H) ppm.

Intermediates 13 and 14: Preparation of tert-butyl (S)-3-(2-(2-aminoacetamido)thiazol-4-yl)piperidine-1-carboxylate and tert-butyl (R)-3-(2-(2-aminoacetamido)thiazol-4-yl)piperidine-1-carboxylate

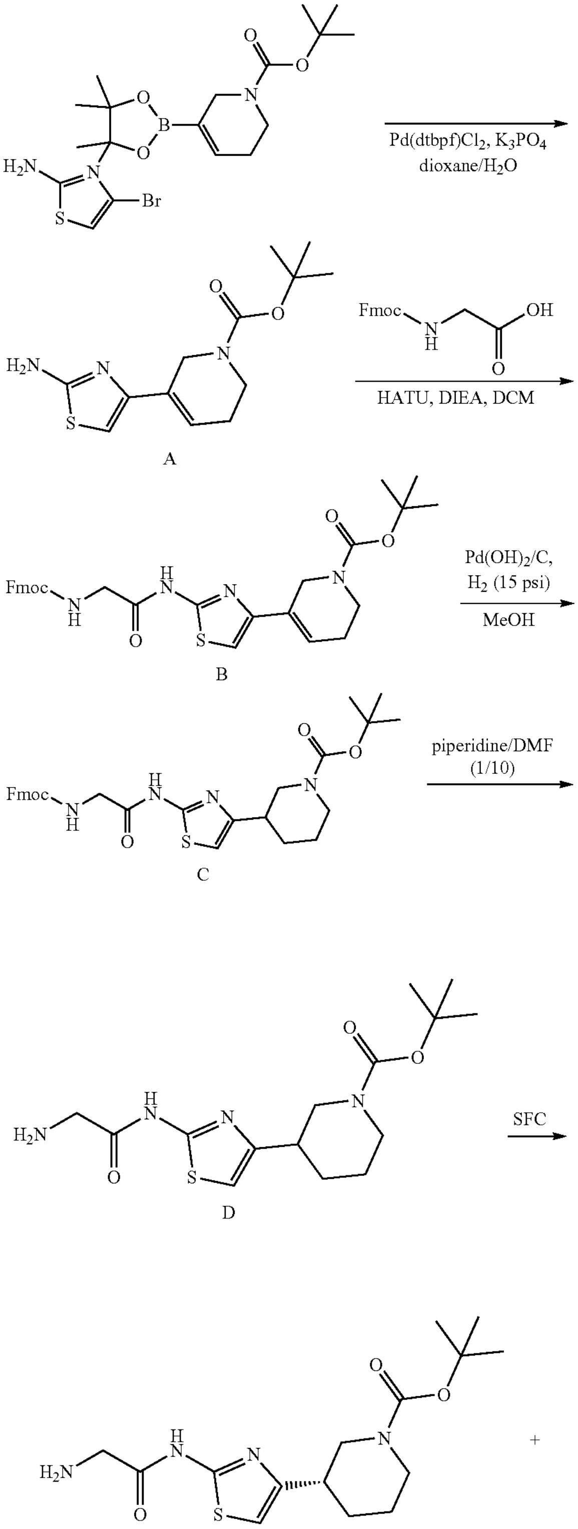

13

-continued

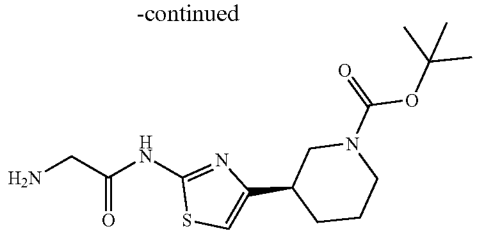

14

Step 1: Preparation of tert-butyl 5-(2-aminothiazol-4-yl)-3,6-dihydro-2H-pyridine-1-carboxylate (Intermediate A)

A

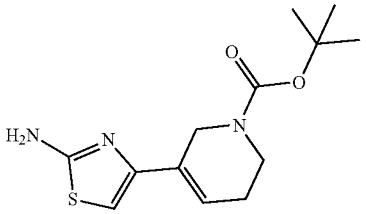

To a mixture of 4-bromothiazol-2-amine (10 g, 55.85 mmol), tert-butyl 5-(4,4,5,5-tetramethyl-1,3,2-dioxaborolan-2-yl)-3,6-dihydro-2H-pyridine-1-carboxylate (Prepared according to the method in FG-A2794) (17.27 g, 55.85 mmol) and $K_3PO_4$ (35.57 g, 167.56 mmol) in dioxane (80 mL) and $H_2O$ (20 mL) was added ditert-butyl(cyclopentyl) phosphane;dichloropalladium;iron (1.82 g, 2.79 mmol) at 25° C. under $N_2$, the mixture was stirred at 80° C. under $N_2$ for 12 hrs. The reaction mixture was diluted with water (300 mL) and extracted with EA (150 mL*4), the combined organic layers was dried over anhydrous $Na_2SO_4$ and concentrated to afford brown oil. The oil was purified by flash silica gel chromatography (ISCO®; 120 g SepaFlash® Silica Flash Column, Eluent of 0~100% Ethylacetate/Petroleum~10% Methanol ethergradient @ 80 mL/min), the eluent was concentrated to give Intermediate A (10.2 g, 33.22 mmol) as a brown solid.

LCMS (ESI) m/z: $[M+H]^+$=282.1.

$^1H$ NMR (400 MHz, $CDCl_3$) δ=6.62-6.58 (m, 1H), 6.28 (s, 1H), 4.99 (s, 2H), 4.19 (s, 2H), 3.54-3.51 (m, 2H), 2.30 (s, 2H), 1.49 (s, 9H) ppm.

Step 2: Preparation of 5-[2-[[2-(9H-fluoren-9-ylmethoxycarbonylamino)acetyl]amino]thiazol-4-yl]-3,6-dihydro-2H-pyridine-1-carboxylate (Intermediate B)

B

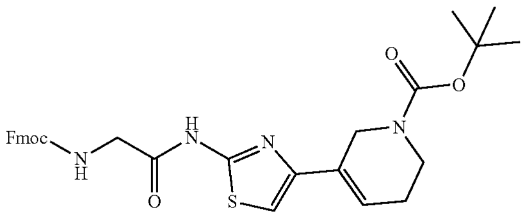

To a mixture of 2-(9H-fluoren-9-ylmethoxycarbonylamino)acetic acid (11.20 g, 37.67 mmol), HATU (21.49 g, 56.51 mmol) and DIEA (14.61 g, 113.02 mmol, 19.69 mL) in DCM (110 mL) was added Intermediate A (10.6 g, 37.67 mmol) at 25° C. and the mixture was stirred for 2.5 hrs. The reaction mixture was diluted with water (200 mL) and extracted with DCM (100 mL*3), the combined organic layers was dried over anhydrous $Na_2SO_4$ and concentrated to afford a brown oil. The oil was purified by flash silica gel chromatography (ISCO®; 120 gSepaFlash® Silica Flash Column, Eluent of 0~50% Ethylacetate/Petroleum ethergradient @ 100 mL/min), the eluent was concentrated to give Intermediate B (20 g, 28.54 mmol) as yellow oil.

LCMS (ESI) m/z: $[M+H]^+$=561.2.

$^1H$ NMR (400 MHz, $CDCl_3$) δ=9.81-9.74 (m, 1H), 7.77 (d, J=6.8 Hz, 2H), 7.59 (d, J=5.6 Hz, 2H), 7.40-7.27 (m, 4H), 6.71 (s, 1H), 6.60 (s, 1H), 5.63-5.62 (m, 1H), 4.51 (d, J=6.4 Hz, 2H), 4.24-4.21 (m, 3H), 4.12-4.10 (m, 2H), 3.54 (s, 2H), 2.30 (s, 2H), 1.50 (s, 9H) ppm.

Step 3: Preparation of tert-butyl 3-[2-[[2-(9H-fluoren-9-ylmethoxycarbonylamino)acetyl]amino]thiazol-4-yl]piperidine-1-carboxylate (Intermediate C)

C

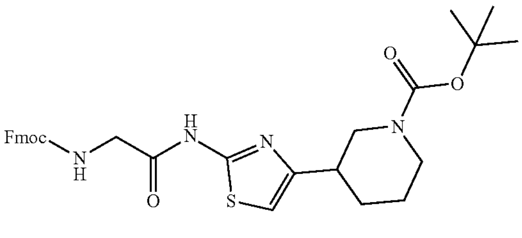

A mixture of Intermediate B (10 g, 14.27 mmol) and $Pd(OH)_2$ (5 g, 7.12 mmol, 20% purity) in MeOH (100 mL) was degassed and purged with $H_2$ (50 psi), the mixture was stirred at 25° C. for 18 hrs under $H_2$. The reaction mixture was filtered to remove $Pd(OH)_2/C$, the filtrate was concentrated to afford yellow oil. The oil was dissolved with MeOH (100 mL) and added $Pd(OH)_2$ (5 g, 7.12 mmol, 20% purity), then degassed and purged with $H_2$ (50 psi), then the mixture was stirred at 25° C. for another 22 hrs under $H_2$. The reaction mixture was filtered to remove $Pd(OH)_2/C$, the filtrate was concentrated to afford black oil. The oil was purified by flash silica gel chromatography (ISCO®; 120 g SepaFlash® Silica Flash Column, Eluent of 0~60% Ethylacetate/Petroleum ethergradient @ 100 mL/min), the eluent was concentrated to give the crude. It was combined with another batch. The mixture was purified by flash silica gel chromatography (ISCO®; 120 g SepaFlash® Silica Flash Column, Eluent of 0~50% Ethylacetate/Petroleum ethergradient @ 50 mL/min), the eluent was concentrated to give Intermediate C (9 g, 15.85 mmol) as an off-white solid.

LCMS (ESI) m/z: $[M+H]^+$=563.5.

$^1H$ NMR (400 MHz, $CDCl_3$) δ=10.43-9.78 (m, 1H), 7.76 (d, J=7.2 Hz, 2H), 7.59 (d, J=6.8 Hz, 2H), 7.39-7.27 (m, 4H), 6.60 (s, 1H), 5.88 (s, 1H), 4.48 (d, J=6.8 Hz, 2H), 4.23-4.15 (m, 3H), 4.08-4.06 (m, 1H), 2.83-2.76 (m, 3H), 2.09-1.98 (m, 1H), 1.72 (d, J=12.4 Hz, 2H), 1.63-1.51 (m, 2H), 1.47 (s, 9H) ppm.

Step 4: Preparation of tert-butyl 3-[2-[(2-amino-acetyl)amino]thiazol-4-yl]piperidine-1-carboxylate (Intermediate D)

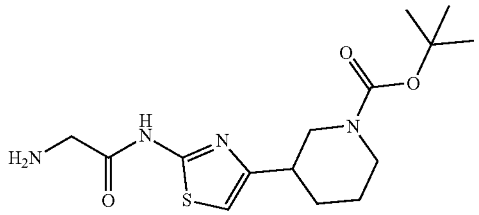

D

A mixture of Intermediate C (8.5 g, 15.11 mmol) and PIPERIDINE (6.90 g, 81.01 mmol, 8 mL) in DMF (80 mL) was stirred at 25° C. for 1 hr. The reaction mixture was poured into water (300 mL), light yellow precipitate was formed, filtered to remove the residue, the filtrate was extracted with EA (80 mL*5), the combined organic layers was washed with brine (100 mL*3), the combined organic layers was concentrated to afford a yellow solid. The solid was triturated with MTBE (100 mL), filtered to afford an off-white solid. The filtrate was concentrated to afford yellow oil. The oil was purified by reversed-phase HPLC (FA), concentrated to remove ACN and added $NaHCO_3$ to adjust Ph to 8, then extracted with EA (20 mL*3), the combined organic layers was concentrated to afford an off-white solid. The two batch of solid was combined to give Intermediate D (4.2 g, 12.34 mmol) as an off white solid.

LCMS (ESI) m/z: $[M+H]^+$=341.2.

$^1H$ NMR (400 MHz, MeOD-$d_4$) δ=6.77 (s, 1H), 4.22 (d, J=11.2 Hz, 1H), 4.00 (d, J=12.4 Hz, 1H), 3.50 (s, 2H), 2.89-2.75 (m, 3H), 2.10-2.07 (m, 1H), 1.77-1.70 (m, 2H), 1.54-1.45 (m, 10H) ppm.

Step 5: Preparation of tert-butyl (S)-3-(2-(2-amino-acetamido)thiazol-4-yl)piperidine-1-carboxylate and tert-butyl (R)-3-(2-(2-aminoacetamido)thiazol-4-yl) piperidine-1-carboxylate (Intermediates 13 and 14)

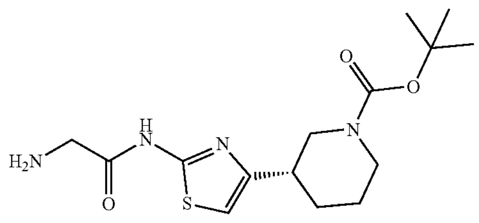

+

13

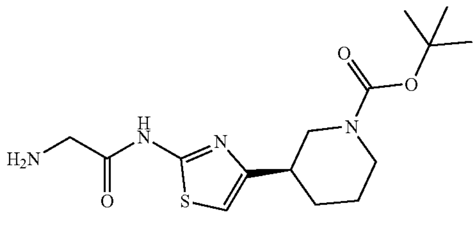

14

Intermediate D (4.2 g, 12.34 mmol) was separated by Chiral SFC (DAICEL CHIRALPAK IG (column: DAICEL CHIRALPAK IG (250 mm*30 mm, 10 um); mobile phase: [0.1% $NH_3{\cdot}H_2O$ MEOH]; B %: 35%-35%, 3.05 min; 564 min) to give Intermediate 13 (1.55 g, 4.55 mmol) as an off-white solid and tert-butyl Intermediate 14 (1.7 g, 4.94 mmol) as an off-white solid.

Intermediate 13

LCMS (ESI) m/z: $[M+H]^+$=341.2.

$^1H$ NMR (400 MHz, MeOD-$d_4$) δ=6.76 (s, 1H), 4.22 (d, J=12.4 Hz, 1H), 4.00 (d, J=12.8 Hz, 1H), 3.51 (s, 2H), 2.89-2.73 (m, 3H), 2.09-2.07 (m, 1H), 1.75-1.70 (m, 2H), 1.54-1.51 (m, 1H), 1.46 (s, 9H) ppm.

Chiral SFC: IG-3-MeOH (DEA)-5-40-3 mL-35T·lcm; Rt=2.016 min, ee %=91.38%.

Intermediate 14

LCMS (ESI) m/z: $[M+H]^+$=341.2.

$^1H$ NMR (400 MHz, MeOD-$d_4$) δ=6.77 (s, 1H), 4.22 (d, J=12.4 Hz, 1H), 4.00 (d, J=12.8 Hz, 1H), 3.51 (s, 2H), 2.89-2.76 (m, 3H), 2.09-2.06 (m, 1H), 1.78-1.70 (m, 2H), 1.54-1.51 (m, 1H), 1.45 (s, 9H) ppm.

Chiral SFC: IG-3-MeOH(DEA)-5-40-3 mL-35T·lcm; Rt=2.154 min, ee %=95.684%.

Intermediates 15 and 16: (4S)-4-Cyano-4-methyl-isochromane-6-carboxylic acid and (4R)-4-Cyano-4-methyl-isochromane-6-carboxylic acid

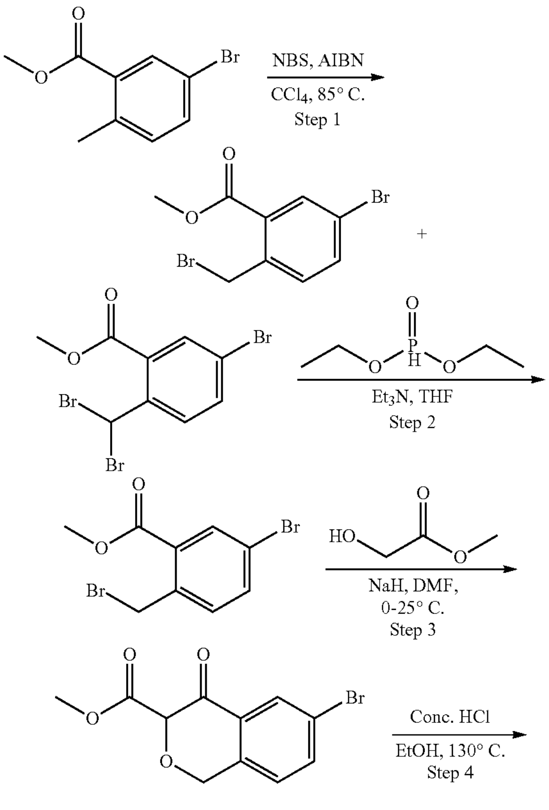

-continued

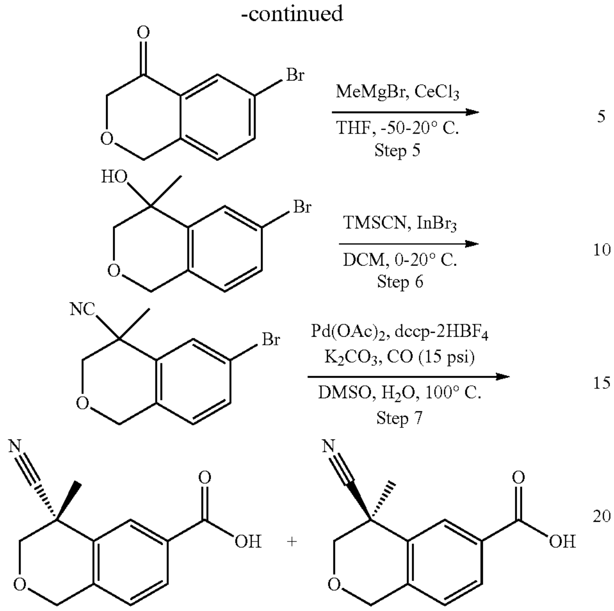

15

16

Step 1. Methyl 5-bromo-2-(bromomethyl)benzoate and methyl 5-bromo-2-(dibromomethyl)benzoate N-Bromosuccinimide (130.5 g, 733 mmol) and AIBN (11.47 g, 69.8 mmol) was added to a mixture of methyl 5-bromo-2-methyl-benzoate (160 g, 698 mmol) in $CCl_4$ (1.6 L). The mixture was stirred at 80° C. for 8 hrs. The mixture was cooled to 25° C. and filtered. The filtrate was concentrated in vacuo affording a mixture of the title compounds (215 g, crude) as a yellow oil, which was used to next step directly.

Step 2. Methyl 5-bromo-2-(bromomethyl)benzoate

Diisopropylethyl amine (48.6 mL, 279 mmol) and 1-ethoxyphosphonoyloxyethane (36.0 mL, 279 mmol) were added to a mixture of methyl 5-bromo-2-(bromomethyl) benzoate and methyl 5-bromo-2-(dibromomethyl)benzoate (215 g, crude) in THE (1 L) at 0° C. The mixture was stirred at 25° C. for 8 hrs. The mixture was diluted with water (1 L) and extracted with EA (1 L×3). The combined organic phase was washed with brine (1 L), dried over $Na_2SO_4$, filtered, and concentrated in vacuo. The crude product was dissolved with PE:EA=10:1 (1 L). The mixture was filtered through a short silica gel column and washed with PE:EA=10:1 (2 L). The filtrate was concentrated under vacuum affording the title compound (210 g, 682 mmol) as yellow oil.

$^1$H NMR (400 MHz, DMSO-$d_6$) δ=7.99 (d, J=2.0 Hz, 1H), 7.82-7.79 (m, 1H), 7.56 (d, J=8.4 Hz, 1H), 4.97 (s, 2H), 3.88 (s, 3H) ppm.

Step 3. Methyl 6-bromo-4-oxo-isochromane-3-carboxylate

Sodium hydride (39 g, 974 mmol, 60% purity) was added to a mixture of methyl 5-bromo-2-(bromomethyl)benzoate (150 g, 487 mmol) and methyl 2-hydroxyacetate (75 mL, 974 mmol) in DMF (1.5 L) at 0° C. The mixture was stirred at 25° C. for 1 hr. The mixture was poured into saturated $NH_4Cl$ (aq., 6 L), and then extracted with MTBE (3 L×2).

The combined organic layers were dried over $Na_2SO_4$, filtered, and concentrated under reduced pressure affording the title compound (140 g, crude) as a brown oil, which was used to next step directly.

Step 4. 6-Bromoisochroman-4-one

A mixture of methyl 6-bromo-4-oxo-isochromane-3-carboxylate (140 g, 487 mmol) in EtOH (500 mL) and HCl (12 M, I L) was stirred at 120° C. for 1 hr. The reaction mixture was cooled to 25° C. and filtered. The filter cake was saved. The filtrate was diluted with water (2 L) and extracted with MTBE (1.5 L×2). The combined organic layers were dried over $Na_2SO_4$, filtered, and concentrated under reduced pressure to give brown oil. The brown oil was combined with the filter cake and then triturated with EtOH (200 mL) at 0° C. for 0.5 hrs. The solid was collected by filtration, washed with EtOH (50 mL×2) and dried in vacuo affording the title compound (50 g, 242 mmol) as a yellow solid.

$^1$H NMR (400 MHz, $CDCl_3$) δ=8.17 (d, J=20 Hz, 1H), 7.69-7.67 (m, 1H), 7.13 (d, J=8.4 Hz, 1H), 4.85 (s, 2H), 4.37 (s, 2H) ppm.

Step 5. 6-Bromo-4-methyl-isochroman-4-ol

Methylmagnesium bromide (3 M in THF, 440 mL) was added dropwise to a mixture of 6-bromoisochroman-4-one (100 g, 440 mmol) and $CeCl_3$ (54.3 g, 220 mmol, dried in a muffle furnace at 300° C. for 3 hrs.) in THE (2 L) at −50° C. The mixture was warmed to 20° C. and stirred for 1 hr. The reaction mixture was poured into water (2 L) and then filtered through diatomite. The diatomite was then washed with EA (2 L). The filtrate was separated and the aqueous layer was extracted with EA (1 L×2). The combined organic layers were washed with brine (2 L), dried over $Na_2SO_4$, filtered, and concentrated under reduced pressure to give a residue. The crude residue was purified by FCC (Eluent: PE:EA=50:1 to 3:1) affording the title compound (105 g, 432 mmol) as light yellow oil.

$^1$H NMR (400 MHz, DMSO-$d_6$) δ=7.67 (d, J=2.0 Hz, 1H), 7.38-7.35 (m, 1H), 6.99 (d, J=8.4 Hz, 1H), 5.35 (s, 1H), 4.71-4.58 (m, 2H), 3.68-3.59 (m, 1H), 3.58-3.50 (m, 1H), 1.38 (s, 3H) ppm.

Step 6. 6-Bromo-4-methyl-isochromane-4-carbonitrile

TMSCN (102.9 mL, 823 mmol) was added to a solution of 6-bromo-4-methyl-isochroman-4-ol (100 g, 411 mmol) in DCM (2 L) at 0° C. $InBr_3$ (29.2 g, 82.3 mmol) was then added, and the mixture was warmed and stirred at 25° C. for 1 hr. The mixture was poured into water (2 L) and extracted with DCM (1 L×2). The combined organic layers were washed with brine (1 L), dried over $Na_2SO_4$, filtered, and concentrated under reduced pressure. The crude residue was purified by FCC (Eluent: PE:EA=20:1 to 5:1) affording the title compound (55 g, 218 mmol) as a white solid.

$^1$H NMR (400 MHz, DMSO-$d_6$) δ=7.82 (d, J=2.0 Hz, 1H), 7.55-7.52 (m, 1H), 7.13 (d, J=8.3 Hz, 1H), 4.83-4.68 (m, 2H), 4.17 (d, J=11.5 Hz, 1H), 3.79 (d, J=11.5 Hz, 1H), 1.65 (s, 3H) ppm.

Step 7. (4S)-4-Cyano-4-methyl-isochromane-6-carboxylic acid and (4R)-4-Cyano-4-methyl-isochromane-6-carboxylic acid Palladium acetate (490 mg, 2.18 mmol) and $K_2CO_3$ (9.05 g, 65.4 mmol) were added to a mixture 6-bromo-4-methylisochromane-4-carbonitrile (11 g, 43.6 mmol) and DCPP-$2HBF_4$ (2.67 g, 4.36 mmol) in DMSO (110 mL) and $H_2O$ (5.5 mL). The mixture was degassed and purged with CO (g) three times, and then the mixture was stirred at 100° C. for 4 hrs under an atmosphere of CO (15 psi). The aqueous layer was then extracted with EA (1 L×2). The aqueous phase was acidified with HCl (2N) until a pH=3 was achieved. The aqueous layer was then extracted with EA (1 L×3). The combined organic phase was washed with brine (1 L), dried over $Na_2SO_4$, filtered, and concentrated under vacuum. The crude product was triturated with EA (100 mL) at 20° C. for 15 min, then the solid was collected by filtration, washed with EA (50 mL), and dried affording the title compounds (30 g, 138 mmol) as a white solid. The mixture of stereoisomers was purified by SFC separation (column: DAICEL CHIRALPAK AD-H (250 mm×30 mm, 5 m); mobile phase: [0.1% $NH_3 \cdot H_2O$ MEOH]; B %: 20%-20%, 3.52 min; 514 min). Peak 1 was concentrated under reduced pressure to give an oil. The oil was dissolved in water (200 mL). The mixture was acidified with HCl (2N) to pH=3 and extracted with EA (100 mL×3). The combined organic phase washed with brine (100 mL), dried over $Na_2SO_4$, filtered, and concentrated under vacuum affording Intermediate 1 (4.15 g, 19.1 mmol) as an off-white solid. Peak 2 was concentrated under reduced pressure to give an oil. The oil was dissolved in water (200 mL). The mixture was acidified with HCl (2N) to pH=3 and extracted with EA (100 mL×3). The combined organic phase washed with brine (100 mL), dried over $Na_2SO_4$, filtered, and concentrated under vacuum affording Intermediate 2 (4.1 g, 18.9 mmol) as an off-white solid.

Intermediate 15: Chiral SFC: AD-3_5CM_MEOH (DEA)_ 5_40_3ML_AT35.M; RT=0.89 min LCMS (ESI) m/z: [M+H]+=218.3.

$^1$HNMR (400 MHz, DMSO-$d_6$) δ=13.17 (br s, 1H), 8.07 (d, J=1.6 Hz, 1H), 7.89-7.87 (m, 1H), 7.29 (d, J=8.0 Hz, 1H), 4.95-4.79 (m, 2H), 4.19 (d, J=11.6 Hz, 1H), 3.88 (d, J=11.6 Hz, 1H), 1.67 (s, 3H) ppm.

Intermediate 16: Chiral SFC: AD-3_5CM_MEOH (DEA)_ 5_40_3ML_AT35.M; RT=1.03 min LCMS (ESI) m/z: [M+H]+=218.3.

$^1$H NMR (400 MHz, DMSO-$d_6$) δ=13.17 (br s, 1H), 8.07 (d, J=1.6 Hz, 1H), 7.89-7.87 (m, 1H), 7.29 (d, J=8.0 Hz, 1H), 4.95-4.79 (m, 2H), 4.19 (d, J=11.6 Hz, 1H), 3.88 (d, J=11.6 Hz, 1H), 1.67 (s, 3H) ppm.

Intermediates 17 and 18: (4R)-4-Hydroxy-4-methylisochromane-6-carboxylic acid and (4S)-4-Hydroxy-4-methylisochromane-6-carboxylic acid

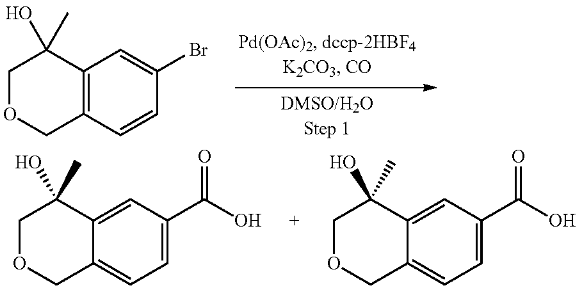

17 18

Step 1: A mixture of 6-bromo-4-methyl-isochroman-4-ol (1.00 g, 4.11 mmol), $dccp2BF_4$ (252 mg, 0.41 mmol), $K_2CO_3$ (853 mg, 6.17 mmol), $Pd(OAc)_2$ (92.4 mg, 0.41 mmol) and $H_2O$ (1.48 mL, 82.3 mmol) in DMSO (10 mL) was degassed and purged with CO (g) three times. The mixture was stirred at 100° C. for 14 hrs under a CO atmosphere. The reaction mixture was filtered to remove the black solid and then diluted with water (60 mL) and extracted with EA (60 mL×2). The organic layer was discarded and the aqueous phase was adjusted to pH=6 with aqueous HCl. The aqueous solution was then extracted with EA (100 mL×3). The combined organic layer was washed with brine (200 mL×2), dried over anhydrous $Na_2SO_4$, filtered, and concentrated under reduced pressure affording a mixture of the title compounds (550 mg, 2.43 mmol) as a light yellow solid. The stereoisomers were separated by chiral SFC (column: DAICEL CHIRALPAK AD (250 mm*30 mm, 10 m); mobile phase: [0.1% $NH_3 \cdot H_2O$ IPA]; B %: 40%-40%, 4.0 min; 60 min). The desired fractions were collected and concentrated under reduced pressure. The product was diluted with water, adjusted to pH=4 with aq. HCl, then extracted with EA (80 mL×3). The combined organic layers were dried over anhydrous $Na_2SO_4$, filtered, and concentrated under reduced pressure affording Intermediate 3 (260 mg, 1.18 mmol) as a yellow solid and Intermediate 4 (240 mg, 1.04 mmol) as a yellow solid.

Intermediate 17: Chiral SFC: AD-3_5CM_IPA (DEA)_ 5_40_3ML_AT35.M; RT=1.537 min.

LCMS (ESI) m/z: [M−18+H]+=191.1.

$^1$H NMR (400 MHz, DMSO-$d_6$) δ=13.19-12.40 (m, 1H), 8.15 (d, J=1.6 Hz, 1H), 7.75-7.73 (m, 1H), 7.13 (d, J=8.0 Hz, 1H), 5.34 (s, 1H), 4.82-4.68 (m, 2H), 3.71-3.65 (m, 1H), 3.61-3.54 (m, 1H), 1.40 (s, 3H) ppm.

Intermediate 18: Chiral SFC: AD-3_5CM_IPA (DEA)_ 5_40_3ML_AT35.M; RT=1.926 min.

LCMS (ESI) m/z: [M−17+H]+=191.1.

$^1$H NMR (400 MHz, DMSO-$d_6$) δ=12.86 (br s, 1H), 8.15 (d, J=1.6 Hz, 1H), 7.75-7.73 (m, 1H), 7.13 (d, J=8.0 Hz, 1H), 5.34 (s, 1H), 4.84-4.67 (m, 2H), 3.73-3.62 (m, 1H), 3.62-3.53 (m, 1H), 1.40 (s, 3H) ppm.

Intermediates 19 and 20: (4R)-4-Fluoro-4-methyl-isochromane-6-carboxylic acid and (4S)-4-Fluoro-4-methyl-isochromane-6-carboxylic acid

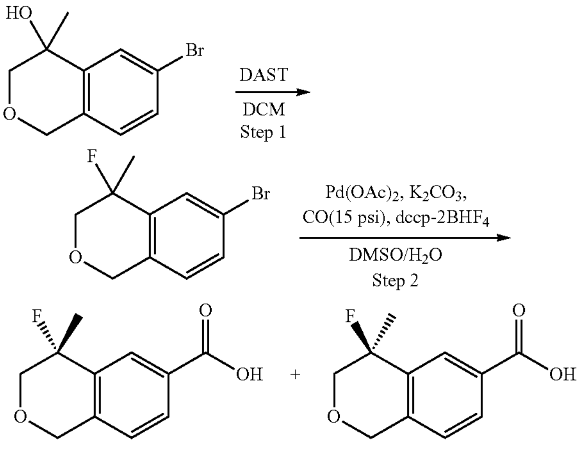

19 20

Step 1. 6-Bromo-4-fluoro-4-methyl-isochromane

DAST (52.2 mL, 395 mmol) was added dropwise to a mixture of Intermediate 8 (32 g, 132 mmol) in DCM (320 mL) at 0° C. The mixture was warmed and stirred at 25° C. for 20 min. The mixture was poured into ice water (600 mL) and extracted with DCM (250 mL×3). The combined organic layers were dried over anhydrous $Na_2SO_4$, filtered, and concentrated in vacuo. The residue was purified by FCC (Eluent: PE:EA=30:1) affording the title compound (24.5 g, 99.96 mmol) as a yellow oil.

LCMS (ESI) m/z: [M−18+H]+=226.9.

$^1$H NMR (400 MHz, $CDCl_3$) δ=7.72 (s, 1H), 7.45-7.42 (m, 1H), 6.93 (d, J=8.0 Hz, 1H), 4.84-4.74 (m, 1H), 4.73-4.64 (m, 1H), 4.06-4.00 (m, 1H), 3.86-3.78 (m, 1H), 1.76-1.64 (m, 3H) ppm.

Step 2. (4R)-4-Fluoro-4-methyl-isochromane-6-carboxylic acid and (4S)-4-Fluoro-4-methyl-isochromane-6-carboxylic acid Palladium acetate (687 mg, 3.06 mmol), dccp-2$HBF_4$ (1.87 g, 3.06 mmol), $K_2CO_3$ (6.34 g, 45.9 mmol), and $H_2O$ (7.50 mL) were added to a solution of 6-bromo-4-fluoro-4-methyl-isochromane (7.5 g, 30.6 mmol) in DMSO (75 mL) at 25° C. The mixture was purged with CO (g) three times. The mixture was heated and stirred at 100° C. for 4 hrs under an atmosphere of CO (15 psi). The reaction mixture was poured into $H_2O$ (1.2 L) and extracted with EA (400 mL×2). The aqueous phase was acidified with 1 N HCl to pH=5 and extracted with EA (300 mL×3). The combined organic layers were washed with brine (300 mL×2), dried over anhydrous $Na_2SO_4$, filtered, and concentrated in vacuo affording a mixture of the title compounds (2.6 g, 12.2 mmol) as a white solid.

$^1$H NMR (400 MHz, DMSO-$d_6$) δ=13.42-12.67 (m, 1H), 8.13 (s, 1H), 7.92-7.88 (m, 1H), 7.29 (d, J=8.0 Hz, 1H), 4.91-4.82 (m, 1H), 4.77-4.68 (m, 1H), 4.10-4.01 (m, 1H), 3.89-3.76 (m, 1H), 1.70-1.58 (m, 3H) ppm.

Intermediates 19 and 20 were separated by SFC (Column: DAICEL CHIRALPAK IG (250 mm*30 mm, 10 m); mobile phase: [0.1% $NH_3$—$H_2O$ MeOH]; B %: 20%-20%, 3.4 min; 2300 min) to give two peaks. Peak 1 was concentrated under reduced pressure to remove 95% MeOH and poured into $H_2O$ (500 mL). The mixture was acidified with HCl (1 N) to pH=5 and extracted with EA (150 mL×3). The combined organic layers were washed with brine (100 mL), dried over anhydrous $Na_2SO_4$, filtered, and concentrated under reduced pressure to afford Intermediate 7 (1.06 g, 5.04 mmol) as a white solid. Peak 2 was concentrated under reduced pressure and poured into $H_2O$ (500 mL). The mixture was acidified with HCl (1 N) to pH=5 and extracted with EA (150 mL×3). The combined organic layers were washed with brine (100 mL), dried over anhydrous $Na_2SO_4$, filtered, and concentrated under reduced pressure to afford Intermediate 8 (1.07 g, 5.09 mmol) as a white solid.

Intermediate 19: Chiral SFC: AD-3_5CM_MEOH (DEA)_ 5_40_3ML_AT35.M, RT=0.819 min.

$^1$H NMR (400 MHz, DMSO-$d_6$) δ=13.08 (br s, 1H), 8.13 (s, 1H), 7.92-7.88 (m, 1H), 7.29 (d, J=8.0 Hz, 1H), 4.90-4.81 (m, 1H), 4.78-4.68 (m, 1H), 4.05-4.01 (m, 1H), 3.87-3.78 (m, 1H), 1.72-1.58 (m, 3H) ppm.

Intermediate 20: Chiral SFC: AD-3_5CM_MEOH (DEA)_ 5_40_3ML_AT35.M, RT=0.903 min.

$^1$H NMR (400 MHz, DMSO-$d_6$) δ=13.31-12.88 (m, 1H), 8.13 (s, 1H), 7.92-7.88 (m, 1H), 7.29 (d, J=8.0 Hz, 1H), 4.90-4.81 (m, 1H), 4.78-4.68 (m, 1H), 4.08-4.01 (m, 1H), 3.89-3.77 (m, 1H), 1.72-1.58 (m, 3H) ppm.

Intermediates 21 and 22: (R)-1-(tert-Butoxycarbonyl)-4-cyano-4-methyl-1,2,3,4-tetrahydroquinoline-6-carboxylic acid and (S)-1-(tert-Butoxycarbonyl)-4-cyano-4-methyl-1,2,3,4-tetrahydroquinoline-6-carboxylic acid

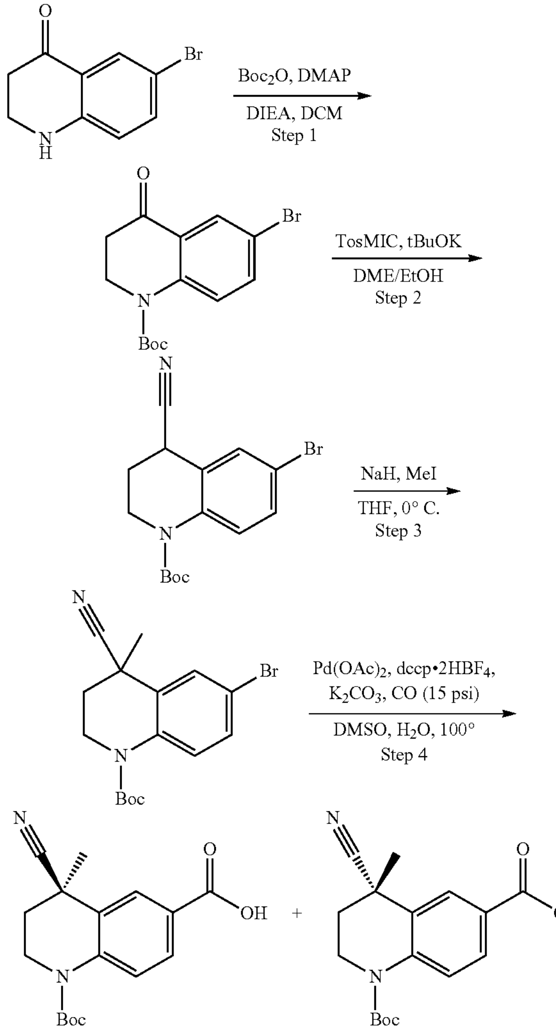

21 22

Step 1. tert-Butyl 6-bromo-4-oxo-3,4-dihydroquinoline-1(2H)-carboxylate

A mixture of 6-bromo-2,3-dihydro-1H-quinolin-4-one (2 g, 8.85 mmol), $Boc_2O$ (3.86 g, 17.7 mmol), DMAP (108 mg, 0.88 mmol), and DIEA (3.1 mL, 17.7 mmol) in DCM (20 mL) was stirred at 60° C. for 12 hrs. The mixture was concentrated under reduced pressure and then poured into water (5 mL). The aqueous solution was then extracted with EA (5 mL×3). The combined organic layers were dried over anhydrous $Na_2SO_4$, filtered, and concentrated under reduced pressure. The residue was purified by FCC (Eluent: 0 to 12% EA in PE) affording the title compound (1.75 g, 5.37 mmol) as a yellow oil.

LCMS (ESI) m/z: [M+H]+=326.0.

$^1$H NMR (400 MHz, DMSO-$d_6$) δ=7.89-7.88 (m, 1H), 7.75 (d, J=1.2 Hz, 2H), 4.11-4.07 (m, 2H), 2.79-2.75 (m, 2H), 1.51 (s, 9H) ppm.

Step 2. tert-Butyl 6-bromo-4-cyano-3,4-dihydroquinoline-1(2H)-carboxylate

Potassium tert-butoxide (1.38 g, 12.26 mmol) was added to a mixture of tert-Butyl 6-bromo-4-oxo-3,4-dihydroquinoline-1(2H)-carboxylate (2 g, 6.13 mmol) and 1-(isocyanomethylsulfonyl)-4-methyl-benzene (1.80 g, 9.20 mmol) in DME (100 mL) and EtOH (4 mL) at 0° C. The mixture was stirred at 25° C. for 12 hrs. The reaction mixture was poured into water (5 mL) and extracted with EA (5 mL×3). The combined organic layers were dried over anhydrous $Na_2SO_4$, filtered, and concentrated under reduced pressure. The residue was purified by FCC (Eluent: 0 to 20% EA in PE) affording the title compound (900 mg, 2.67 mmol) as a yellow oil.

LCMS (ESI) m/z: [M−55]+=281.0.

$^1$H NMR (400 MHz, DMSO-$d_6$) δ=7.67 (d, J=8.8 Hz, 1H), 7.55 (d, J=2.4 Hz, 1H), 7.51-7.47 (m, 1H), 4.48-4.44 (m, 1H), 3.74-3.69 (m, 2H), 2.21-2.15 (m, 2H), 1.48 (s, 9H) ppm.

Step 3. tert-Butyl 6-bromo-4-cyano-4-methyl-3,4-dihydroquinoline-1(2H)-carboxylate Sodium hydride (89 mg, 2.22 mmol, 60% purity) was added slowly to a mixture of tert-butyl 6-bromo-4-cyano-3,4-dihydroquinoline-1(2H)-carboxylate (500 mg, 1.48 mmol) in THF (5 mL) at 0° C. The mixture was stirred at 0° C. for 0.5 hr, then MeI (0.14 mL, 2.22 mmol) was added. The reaction mixture was warmed to 25° C. and stirred for 2 hrs. The reaction mixture was quenched with saturated $NH_4Cl$ (20 mL) and extracted with EA (10 mL×3). The combined organic layers were dried over anhydrous $Na_2SO_4$, filtered, and concentrated under reduced pressure. The resulting oil was purified by FCC (Eluent: 0 to 50% EA in PE) affording the title compound (370 mg, 1.01 mmol) as yellow oil.

LCMS (ESI) m/z: [M−55]+=295.0.

$^1$H NMR (400 MHz, $CDCl_3$) δ=7.66 (d, J=8.8 Hz, 1H), 7.56 (d, J=2.0 Hz, 1H), 7.38-7.36 (m, 1H), 3.89-3.80 (m, 2H), 2.40-2.34 (m, 1H), 2.04-2.00 (m, 1H), 1.73 (s, 3H), 1.53 (s, 9H) ppm.

Step 4. (R)-1-(tert-Butoxycarbonyl)-4-cyano-4-methyl-1,2,3,4-tetrahydroquinoline-6-carboxylic acid & (S)-1-(tert-Butoxycarbonyl)-4-cyano-4-methyl-1,2,3,4-tetrahydroquinoline-6-carboxylic acid Palladium acetate (11.8 mg, 0.053 mmol) and dccp.2HBF$_4$ (64.5 mg, 0.11 mmol) were added to a mixture of tert-butyl 6-bromo-4-cyano-4-methyl-3,4-dihydroquinoline-1 (2H)-carboxylate (370 mg, 1.05 mmol) and $K_2CO_3$ (218 mg, 1.58 mmol) in DMSO (3 mL) and $H_2O$ (1 mL) at 25° C. The mixture was degassed and purged with CO (g, 15 psi) three times, and then the mixture was warmed stirred at 100° C. under CO (g) for 12 hrs. The reaction mixture was filtered and the filtrate was purified by reversed-phase HPLC affording a mixture of the title compounds (190 mg, 0.60 mmol) as a white solid. The stereoisomers were separated via chiral SFC (DAICEL CHIRALPAK AD (250 mm*30 mm, 10 m); mobile phase: [0.1% $NH_3$—$H_2O$ MEOH]; B %: 20%-20%, 1.75 min; 75 min) to afford Intermediate 21 (80 mg, 0.25 mmol) as light yellow solid and Intermediate 22 (90 mg, 0.28 mmol) as light yellow solid.

Intermediate 21: LCMS (ESI) m/a: [M−55]+=261.1.

$^1$H NMR (400 MHz, DMSO-$d_6$) δ=7.96 (d, J=1.6 Hz, 1H), 7.80-7.78 (m, 1H), 7.69 (d, J=8.8 Hz, 1H), 3.79-3.74 (m, 2H), 2.36-2.32 (m, 1H), 2.07-2.05 (m, 1H), 1.71 (s, 3H), 1.47 (s, 9H) ppm.

Chiral SFC: AD-3_5CM_MEOH(DEA)_5_40_3ML_AT35.M, Rt=0.766 min.

Intermediate 22: LCMS (ESI) m/a: [M−55]+=261.1.

$^1$H NMR (400 MHz, DMSO-$d_6$) δ=7.96 (br s, 1H), 7.81-7.78 (m, 1H), 7.71 (br d, J=8.8 Hz, 1H), 3.80-3.74 (m, 2H), 2.36-2.31 (m, 1H), 2.07-2.04 (m, 1H), 1.71 (s, 3H), 1.48 (s, 9H) ppm.

Chiral SFC: AD-3_5CM_MEOH(DEA)_5_40_3ML_AT35.M. Rt=0.916 min.

Intermediate 23: Preparation of sodium spiro[isochromane-4,3'-oxetane]-6-carboxylate

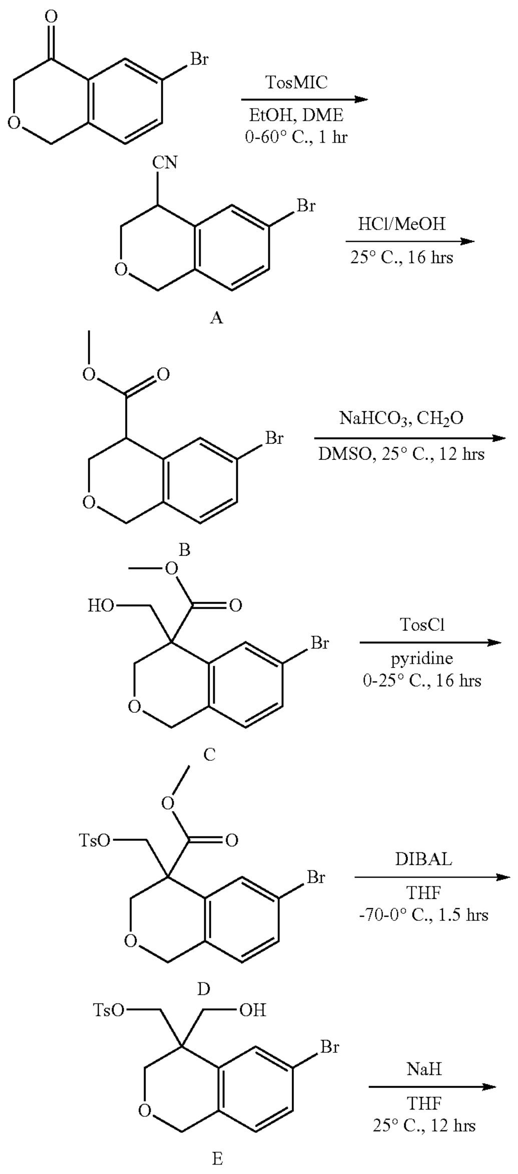

-continued

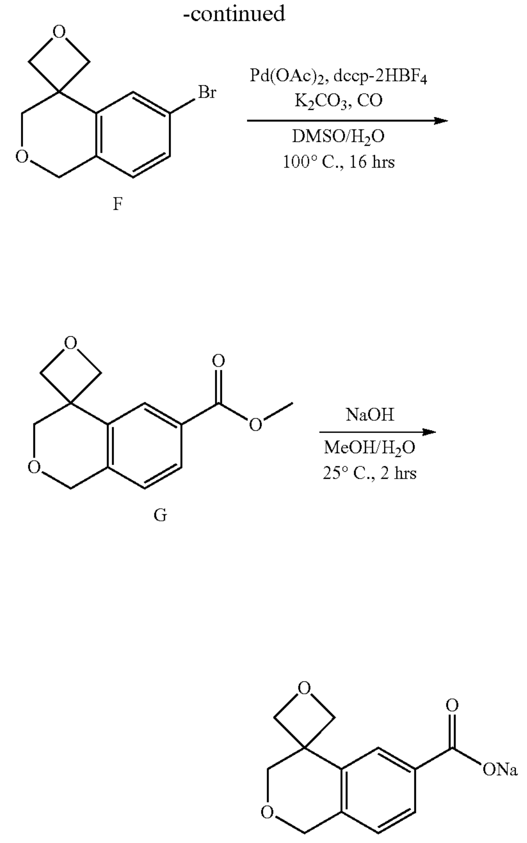

F

G

23

Step 1: Preparation of 6-bromoisochromane-4-carbonitrile (Intermediate A)

A

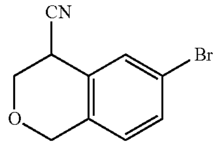

To a solution of 6-bromoisochroman-4-one (100 mg, 440.42 umol) in DME (4 mL) was added 1-(isocyanomethylsulfonyl)-4-methyl-benzene (128.98 mg, 660.63 umol), EtOH (162.32 mg, 3.52 mmol) and t-BuONa (93.12 mg, 968.93 umol) at 0° C. Then the mixture was stirred for 1 hr at 60° C. The mixture was diluted with water (10 mL) and was extracted with EA (10 mL*3). The combined organic phase was concentrated under vacuum to give a residue, which was purified by column chromatography ($SiO_2$, Petroleum ether/Ethyl acetate=100/1 to 1/1). The eluent was concentrated to give Intermediate A (1.0 g, 3.36 mmol) as a yellow solid.

LCMS (ESI) m/z: $[^{79}BrM+H]^+$=238.0.

$^1H$ NMR (400 MHz, $CDCl_3$) δ=7.59 (d, J=2.0 Hz, 1H), 7.46-7.44 (m, 1H), 6.95 (d, J=8.4 Hz, 1H), 4.86-4.70 (m, 2H), 4.24-4.17 (m, 1H), 4.13-4.01 (m, 2H) ppm.

Step 2: Preparation of methyl 6-bromoisochromane-4-carboxylate (Intermediate B)

B

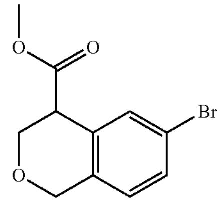

A mixture of Intermediate A (600 mg, 2.52 mmol) in HCl/MeOH (4 M, 10.00 mL) was stirred for 16 hrs at 25° C. The mixture was concentrated to give a residue, which was purified by column chromatography ($SiO_2$, Petroleum ether/Ethyl acetate=100/1 to 2/1). The eluent was concentrated to give Intermediate B (600 mg, 2.21 mmol) as brown oil.

LCMS (ESI) m/z: $[^{81}BrM+H]^+$=273.0.

$^1H$ NMR (400 MHz, $CDCl_3$) δ=7.44 (d, J=2.0 Hz, 1H), 7.38-7.36 (m, 1H), 6.91 (d, J=8.4 Hz, 1H), 4.90-4.62 (m, 2H), 4.39-4.36 (m, 1H), 3.98-3.94 (m, 1H), 3.77 (s, 3H), 3.74 (m, 1H) ppm.

Step 3: Preparation of methyl 6-bromo-4-(hydroxymethyl)isochromane-4-carboxylate (Intermediate C)

C

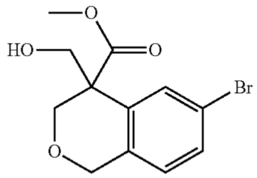

To a solution of Intermediate B (550 mg, 2.03 mmol) in DMSO (6 mL) was added $NaHCO_3$ (8.52 mg, 101.44 umol) and PARAFORMALDEHYDE (33.52 mg, 1.12 mmol) at 25° C. Then the mixture was stirred for 12 hrs at 25° C. The mixture was diluted with water (5 mL) and was extracted with EA (5 mL*3). The combined organic phase was concentrated under vacuum to give a residue, which was purified by reversed-phase (0.1% FA condition). The eluent was concentrated to give Intermediate C (550 mg, 1.28 mmol) as a white solid.

LCMS (ESI) m/z: $[^{79}BrM+H]^+$=301.0.

$^1H$ NMR (400 MHz, $CDCl_3$) δ=7.51 (d, J=1.6 Hz, 1H), 7.38-7.36 (m, 1H), 6.87 (d, J=8.0 Hz, 1H), 4.75-4.63 (m, 2H), 4.15-4.10 (m, 1H), 4.05-4.00 (m, 1H), 4.00-3.93 (m, 1H), 3.42 (s, 3H) ppm.

Step 4: Preparation of methyl 6-bromo-4-(p-tolylsulfonyloxymethyl)isochromane-4-carboxylate (Intermediate D)

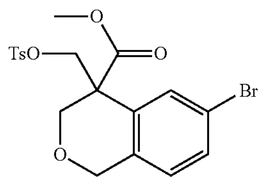

D

To a solution of Intermediate C (500 mg, 1.66 mmol) and PYRIDINE (788.02 mg, 9.96 mmol) in DCM (5 mL) was added TosCl (1.27 g, 6.64 mmol) at 0° C. Then the mixture was stirred for 16 hrs at 25° C. The mixture was washed with water (5 mL) and the organic layer was separated and concentrated to give a residue, which was purified by reversed-phase (0.1% FA condition). The eluent was concentrated under vacuum to remove MeCN and the residue was lyophilized to give Intermediate D (500 mg, 1.10 mmol) as a brown solid.

$^1$H NMR (400 MHz, $CDCl_3$) δ=7.85-7.74 (m, 2H), 7.45 (d, J=2.0 Hz, 1H), 7.43-7.33 (m, 3H), 6.91 (d, J=8.4 Hz, 1H), 4.72 (s, 2H), 4.42 (d, J=9.6 Hz, 1H), 4.29 (d, J=9.6 Hz, 1H), 4.24-4.12 (m, 2H), 3.75 (s, 3H), 2.48 (s, 3H) ppm.

Step 5: Preparation of Interm [6-bromo-4-(hydroxymethyl)isochroman-4-yl]methyl 4-methylbenzenesulfonate (Intermediate E)

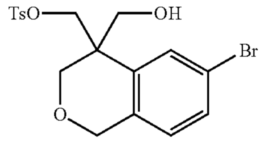

E

To a solution of Intermediate D (440 mg, 966.36 umol) in THE (5.0 mL) was added DIBALH (1 M) at −70° C. and the mixture was stirred for 10 min. Then the mixture was stirred for 80 min at 0° C. The mixture was diluted with water (5 mL) and was extracted with EA (5 mL*3). The combined organic phase was concentrated to give a residue, which was purified by column chromatography ($SiO_2$, Petroleum ether/Ethyl acetate=100/1 to 1/1) to give Intermediate E (380 mg, 889.29 umol) as brown oil.

$^1$H NMR (400 MHz, $CDCl_3$) δ=7.68 (d, J=8.4 Hz, 2H), 7.38 (d, J=2.0 Hz, 1H), 7.32-7.22 (m, 3H), 6.80 (d, J=8.4 Hz, 1H), 4.59 (s, 2H), 4.14 (s, 2H), 3.88-3.78 (m, 1H), 3.77-3.63 (m, 3H), 2.38 (s, 3H) ppm.

Step 6: Preparation of 6-bromospiro[isochromane-4,3'-oxetane] (Intermediate F)

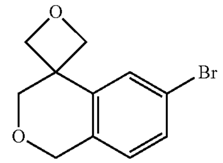

F

To a solution of Intermediate E (250 mg, 585.06 umol) in THE (5 mL) was added NaH (70.20 mg, 1.76 mmol, 60% purity) at 25° C. Then the mixture was stirred for 12 hrs at 25° C. The mixture was quenched with water (5 mL) and was extracted with EA (5 mL*3). The combined organic layer was concentrated to give a residue, which was purified by column chromatography ($SiO_2$, Petroleum ether/Ethyl acetate=10/1 to 1/1) to give Intermediate F (145 mg, 568.39 umol) as brown oil.

LCMS (ESI) m/z: $[^{79}BrM+H]^+$=255.0.

$^1$H NMR (400 MHz, $CDCl_3$) δ=7.97 (d, J=1.8 Hz, 1H), 7.31-7.28 (m, 1H), 6.81 (d, J=8.4 Hz, 1H), 4.74 (d, J=6.4 Hz, 2H), 4.64-4.54 (m, 4H), 4.09 (s, 2H) ppm.

Step 7: Preparation of methyl spiro[isochromane-4,3'-oxetane]-6-carboxylate (Intermediate G)

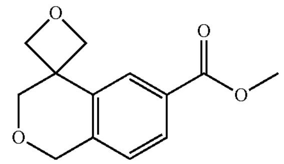

G

To a solution of Intermediate F (130 mg, 509.59 umol) in DMSO (5 mL) and MeOH (2.5 mL) was added dicyclohexyl (3-dicyclohexylphosphaniumylpropyl)phosphonium;ditetrafluoroborate (31.20 mg, 50.96 umol), $K_2CO_3$ (105.65 mg, 764.38 umol) and $Pd(OAc)_2$ (5.72 mg, 25.48 umol) at 25° C., then the mixture was degassed and purged with CO for 3 times. The resulting mixture was stirred at 100° C. for 16 hrs under CO atmosphere (15 psi). The mixture was filtered and the filtrate was diluted with water (30 mL) and extracted with EA (5 mL*3), the organic layer was concentrated to give crude. The residue was purified by column chromatography ($SiO_2$, Petroleum ether/Ethyl acetate=10/1 to 5/1) to give Intermediate G (80 mg, 341.52 umol) as a white solid.

LCMS (ESI) m/z: $[M+H]^+$=235.1.

$^1$H NMR (400 MHz, $CDCl_3$) δ=8.61 (d, J=1.6 Hz, 1H), 7.94-7.92 (m, 1H), 7.09 (d, J=8.0 Hz, 1H), 4.91 (d, J=6.4 Hz, 2H), 4.81 (s, 2H), 4.70 (d, J=6.4 Hz, 2H), 4.23 (s, 2H), 3.98 (s, 3H) ppm.

Step 8: Preparation of spiro[isochromane-4,3'-oxetane]-6-carbonyloxysodium (Intermediate 23)

23

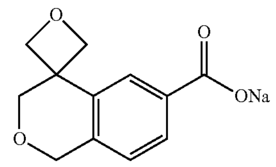

To a solution of Intermediate G (50 mg, 213.45 umol) in MeOH (2 mL) and $H_2O$ (2 mL) was added NaOH (25.61 mg, 640.35 umol) at 25° C. Then the mixture was stirred for 2 hrs at 25° C. The mixture was lyophilized to give Intermediate 23 (80 mg) as a white solid which was used for the next step directly.

LCMS (ESI) m/z: $[M+H]^+$=243.1.

Intermediate 24: Preparation of 3-((cis)-1-fluoro-3-hydroxy-3-methylcyclobutyl)benzoic acid

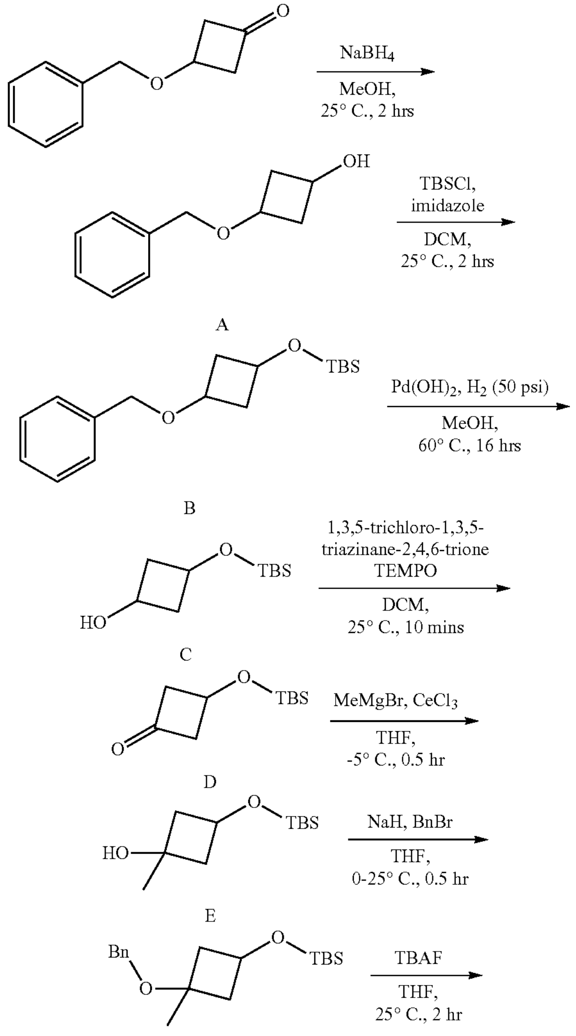

-continued

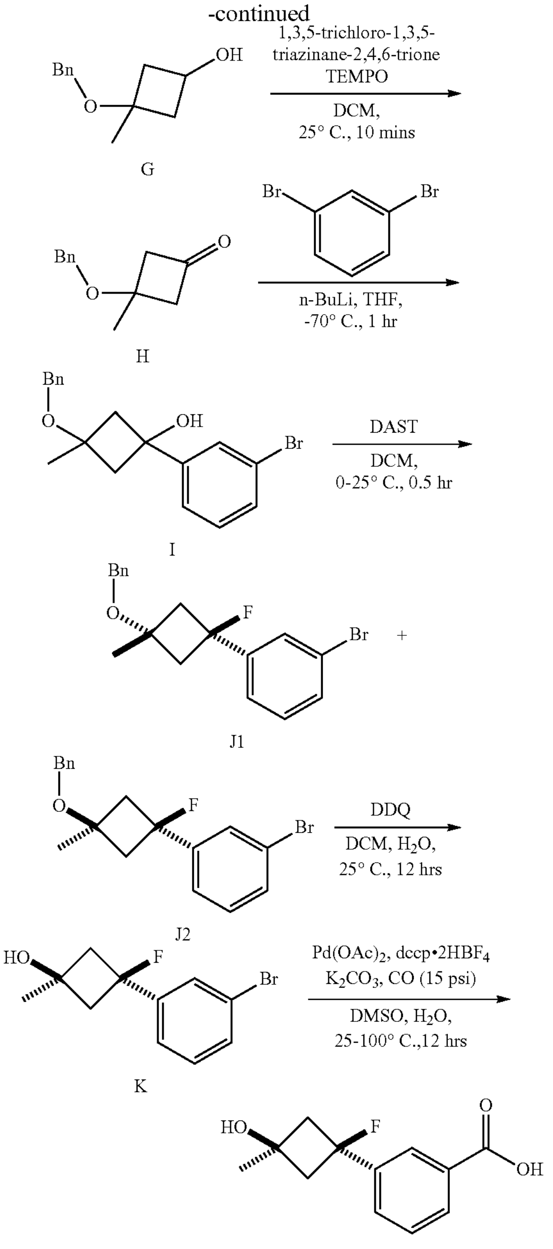

Step 1: Preparation of 3-benzyloxycyclobutanol (Intermediate A)

A

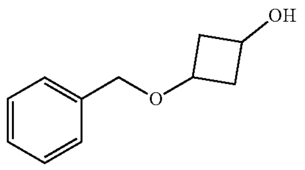

To a mixture of 3-benzyloxycyclobutanone (29.7 g, 168.55 mmol) in MeOH (700 mL) was added $NaBH_4$ (25.51 g, 674.19 mmol) in portions at 0° C. under $N_2$. The mixture was stirred at 25° C. for 2 hours. The mixture was poured into sat.$NH_4Cl$ (2000 mL) at 0° C. and the crude mixture was concentrated in vacuo to remove most of the MeOH. The aqueous phase was extracted with ethyl acetate (1000 mL*2). The combined organic phase was washed with brine (1000 mL), dried with anhydrous $Na_2SO_4$, filtered and concentrated in vacuum to afford Intermediate A (30 g, 168.32 mmol) as a light yellow oil which was taken to the next step without purification.

$^1$H NMR (400 MHz, $CDCl_3$) δ=7.35-7.30 (m, 5H), 4.42 (s, 2H), 3.92-3.90 (m, 1H), 3.64-3.62 (m, 1H), 2.79-2.65 (m, 2H), 1.99-1.90 (m, 2H) ppm.

Step 2: Preparation of (3-benzyloxycyclobutoxy)-tert-butyl-dimethyl-silane (Intermediate B)

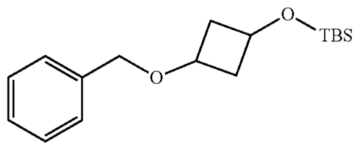

B

To a mixture of Intermediate A (30 g, 168.32 mmol) and imidazole (17.19 g, 252.49 mmol) in DCM (500 mL) was added TBSCl (38.06 g, 252.49 mmol, 30.94 mL) in portions at 0° C. under $N_2$. The mixture was stirred at 25° C. for 2 hours. The mixture was poured into ice-water (2000 mL) and extracted with DCM (1500 mL*2). The combined organic phase was washed with brine (1000 mL*1), dried with anhydrous $Na_2SO_4$, filtered and concentrated in vacuum. The residue was purified by silica gel chromatography (Petroleum ether/Ethyl acetate=50/1) and concentrated to afford Intermediate B (49 g, 167.53 mmol) as a light yellow oil.

$^1$H NMR (400 MHz, $CDCl_3$) δ=7.34-7.28 (m, 5H), 4.48-4.37 (m, 2H), 3.94-3.81 (m, 1H), 3.65-3.53 (m, 1H), 2.70-2.53 (m, 2H), 2.04-1.93 (m, 2H), 0.90 (s, 9H), 0.07 (s, 6H) ppm.

Step 3: Preparation of 3-[tert-butyl(dimethyl)silyl]oxycyclobutanol (Intermediate C)

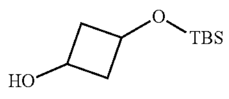

C

To a solution of Intermediate B (49 g, 167.53 mmol) in MeOH (1000 mL) was added $Pd(OH)_2$ (10 g, 7.12 mmol, 10% purity) under $N_2$. The suspension was degassed under vacuum and purged with $H_2$ several times. The mixture was stirred under $H_2$ (50 psi) at 60° C. for 16 hours. The mixture was filtered through a pad of celite and concentrated in vacuum to afford Intermediate C (34 g, crude) as a yellow oil which was used directly without purification.

$^1$H NMR (400 MHz, $CDCl_3$) δ=3.93-3.78 (m, 2H), 2.77-2.66 (m, 2H), 1.94-1.83 (m, 2H), 0.90-0.87 (m, 9H), 0.05-0.03 (m, 6H) ppm.

Step 4: Preparation of 3-[tert-butyl(dimethyl)silyl]oxycyclobutanone (Intermediate D)

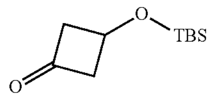

D

To a mixture of Intermediate C (5 g, 24.71 mmol) in DCM (50 mL) was added TEMPO (38.85 mg, 247.08 umol) and 1,3,5-trichloro-1,3,5-triazinane-2,4,6-trione (5.74 g, 24.71 mmol) in portions at 25° C. under $N_2$.

The mixture was stirred at 25° C. for 10 mins. The mixture was filtered and concentrated in vacuum. The residue was purified by column chromatography ($SiO_2$, Petroleum ether/Ethyl acetate=100/1 to 20/1) to afford Intermediate D (2.7 g, 13.48 mmol) as colorless oil.

$^1$H NMR (400 MHz, $CDCl_3$) δ=4.71-4.53 (m, 1H), 3.34-3.00 (m, 4H), 0.93-0.90 (m, 9H), 0.12-0.09 (m, 6H) ppm.

Step 5: Preparation of 3-[tert-butyl(dimethyl)silyl]oxy-1-methyl-cyclobutanol (Intermediate E)

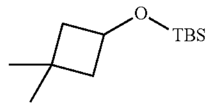

E

To a mixture of Intermediate D (2.7 g, 13.48 mmol) and $CeCl_3$ (1.66 g, 6.74 mmol) in THE (27 mL) was added MeMgBr (3 M, 13.48 mL) dropwise at −50° C. under $N_2$. The mixture was stirred at 15° C. for 30 mins. The mixture was poured into aq·$NH_4Cl$ (100 mL) and filtered by celatom. The filter liquor was extracted with ethyl acetate (50 mL*2). The combined organic phase was dried with anhydrous $Na_2SO_4$, filtered and concentrated in vacuum. The residue was purified by column chromatography column ($SiO_2$, Petroleum ether/Ethyl acetate=1/0 to 3/1). The eluent was concentrated to afford Intermediate E (2 g, 9.24 mmol) as a colorless oil.

$^1$H NMR (400 MHz, $CDCl_3$) δ=3.95-3.88 (m, 1H), 2.50-2.38 (m, 1H), 2.49-2.32 (m, 1H), 2.15-1.93 (m, 2H), 1.33-1.26 (m, 3H), 0.91-0.84 (m, 9H), 0.07-0.00 (m, 6H) ppm.

Step 6: Preparation of (3-(benzyloxy)-3-methylcyclobutoxy)(tert-butyl)dimethylsilane (Intermediate F)

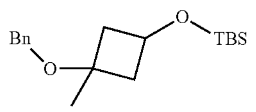

F

To a mixture of Intermediate E (1.93 g, 8.92 mmol) in THE (40 mL) was added NaH (535.09 mg, 13.38 mmol, 60% purity) in one portion at 0° C. under $N_2$. The mixture was stirred at 0° C. for 10 mins, then to the mixture was added BnBr (1.69 g, 9.90 mmol) at 0° C. The mixture was stirred at 25° C. for 20 mins. The mixture poured into sat.$NH_4Cl$ (150 mL) and extracted with ethyl acetate (50 mL*2). The combined organic phase was washed with brine (30 mL), dried with anhydrous $Na_2SO_4$, filtered and concentrated in vacuum. The residue was purified by silica gel chromatography (Petroleum ether/Ethyl acetate=50/1, 10/1) and concentrated to afford Intermediate F (1.9 g, 6.20 mmol) as a light yellow oil.

$^1H$ NMR (400 MHz, $CDCl_3$) δ=7.42-7.29 (m, 5H), 4.41 (s, 2H), 4.05-3.98 (m, 1H), 2.44-2.33 (m, 2H), 2.26-2.16 (m, 2H), 1.40-1.32 (m, 3H), 0.93-0.90 (m, 9H), 0.09-0.05 (m, 6H) ppm.

Step 7: Preparation of 3-benzyloxy-3-methyl-cyclobutanol (Intermediate G)

G

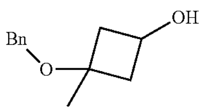

To a mixture of Intermediate F (1.5 g, 4.89 mmol) in THE (15 mL) was added TBAF (1 M, 9.79 mL) in one portion at 0° C. under $N_2$. The mixture was stirred at 25° C. for 2 hours. The mixture was concentrated. The residue was purified by silica gel chromatography (Petroleum ether/Ethyl acetate=20/1, 5/1) and concentrated to afford Intermediate G (1.2 g, crude) as a light yellow oil.

$^1H$ NMR (400 MHz, $CDCl_3$) δ=7.37-7.28 (m, 5H), 4.41 (s, 2H), 4.12-4.03 (m, 1H), 2.53-2.42 (m, 2H), 2.22-2.11 (m, 2H), 1.39 (s, 3H) ppm.

Step 8: Preparation of 3-benzyloxy-3-methyl-cyclobutanone (Intermediate H)

H

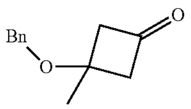

To a mixture of Intermediate G (1.2 g, 6.24 mmol) in DCM (12 mL) was added TEMPO (6.16 mg, 39.17 umol) and 1,3,5-trichloro-1,3,5-triazinane-2,4,6-trione (909.88 mg, 3.91 mmol) in portions at 25° C. under $N_2$. The mixture was stirred at 25° C. for 10 min. The mixture was filtered and concentrated in vacuum. The residue was purified by column chromatography ($SiO_2$, Petroleum ether/Ethyl acetate=100/1 to 20/1) to afford Intermediate H (1.05 g, 5.52 mmol) as a colorless oil.

$^1H$ NMR (400 MHz, $CDCl_3$) δ=7.40-7.28 (m, 5H), 4.51 (s, 2H), 3.39-3.20 (m, 2H), 3.04-2.88 (m, 2H), 1.67 (s, 3H) ppm.

Step 9: Preparation of 3-benzyloxy-1-(3-bromophenyl)-3-methyl-cyclobutanol (Intermediate I)

I

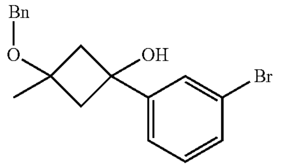

To a mixture of 1,3-dibromobenzene (1.13 g, 4.81 mmol, 578.90 uL) in THE (10 mL) was added n-BuLi (2.5 M, 1.92 mL) dropwise at −70° C. under $N_2$. The mixture was stirred at −70° C. for 30 min, then to the mixture was added Intermediate H (915 mg, 4.81 mmol) in THE (2 mL) dropwise at −70° C. The mixture was stirred at −70° C. for 30 min. The mixture was poured into sat.$NH_4Cl$ (100 mL) and extracted with ethyl acetate (50 mL*2). The combined organic phase was washed with brine (50 mL), dried with anhydrous $Na_2SO_4$, filtered and concentrated in vacuum. The residue was purified by silica gel chromatography (Petroleum ether/Ethyl acetate=30/1, 20/1) and concentrated to afford Intermediate I (800 mg, 2.30 mmol) as a colorless oil.

LCMS (ESI) m/z: $[M+H]^+$=240.0.

$^1H$ NMR (400 MHz, $CDCl_3$) δ=7.65-7.59 (m, 1H), 7.46-7.29 (m, 7H), 7.27-7.23 (m, 1H), 4.50 (s, 2H), 2.63 (s, 4H), 1.39 (s, 3H) ppm.

Step 10: Preparation of 1-((trans)-3-(benzyloxy)-1-fluoro-3-methylcyclobutyl)-3-bromobenzene and 1-((cis)-3-(benzyloxy)-1-fluoro-3-methylcyclobutyl)-3-bromobenzene (Intermediates J1 and J2)

J1

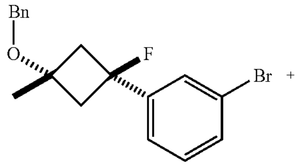

+

J2

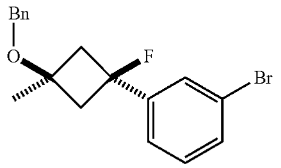

To a mixture of Intermediate I (800 mg, 2.30 mmol) in DCM (8 mL) was added DAST (557.03 mg, 3.46 mmol, 456.58 uL) dropwise at 0° C. under $N_2$. The mixture was stirred at 25° C. for 30 min. The mixture combined with another batch was poured into sat.$NaHCO_3$ (50 mL) at 0° C. and extracted with DCM (30 mL*2). The combined organic phase was washed with brine (20 mL), dried with anhydrous $Na_2SO_4$, filtered and concentrated in vacuum. The residue was purified by prep-TLC (Petroleum ether/Ethyl acetate=10/1) to afford Intermediate J1 (330 mg, 944.92 umol) as a light yellow oil and Intermediate J2 (250 mg, 715.85 umol) as a light yellow oil.

Intermediate J1

$^1H$ NMR (400 MHz, $CDCl_3$) δ=7.62 (s, 1H), 7.47-7.42 (m, 1H), 7.41-7.29 (m, 6H), 7.26-7.22 (m, 1H), 4.42 (s, 2H), 2.83-2.62 (m, 4H), 1.69 (s, 3H) ppm.

Intermediate J2

$^1H$ NMR (400 MHz, $CDCl_3$) δ=7.63-7.62 (m, 1H), 7.50-7.48 (m, 1H), 7.42-7.35 (m, 5H), 7.33-7.27 (m, 2H), 4.49 (s, 2H), 3.04-2.88 (m, 2H), 2.81-2.69 (m, 2H), 1.36 (s, 3H) ppm.

Step 11: Preparation of (cis)-3-(3-bromophenyl)-3-fluoro-1-methylcyclobutanol (Intermediate K)

K

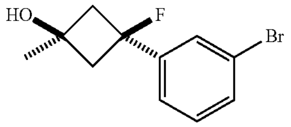

To a mixture of Intermediate J2 (250.00 mg, 715.85 umol) in DCM (8 mL) abd $H_2O$ (0.8 mL) was added DDQ (893.73 mg, 3.94 mmol) in one portion at 25° C. under $N_2$. The mixture was stirred at 25° C. for 12 hours. The mixture was poured into sat.$NaHCO_3$ (50 mL) and extracted with DCM (30 mL*2). The combined organic phase was washed with brine (20 mL), dried with anhydrous $Na_2SO_4$, filtered and concentrated in vacuum. The residue was purified by silica gel chromatography (Petroleum ether/Ethyl acetate=10/1, 5/1) and concentrated to afford Intermediate K (170 mg, 656.08 umol) as a light yellow oil.

$^1H$ NMR (400 MHz, $CDCl_3$) δ=7.61-7.55 (m, 1H), 7.51-7.45 (m, 1H), 7.38-7.33 (m, 1H), 7.31-7.28 (m, 1H), 2.82-2.70 (m, 4H), 1.35 (s, 3H) ppm.

Step 12: Preparation of 3-((1s,3s)-1-fluoro-3-hydroxy-3-methylcyclobutyl)benzoic acid (Intermediate 24)

24

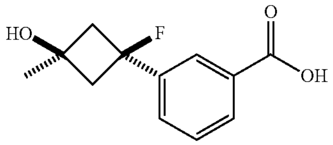

To a solution of Intermediate K (160 mg, 617.49 umol) in DMSO (2 mL) was added $Pd(OAc)_2$ (6.93 mg, 30.87 umol), $K_2CO_3$ (128.01 mg, 926.23 umol), dicyclohexyl(3-dicyclohexylphosphaniumylpropyl)phosphonium;ditetrafluoroborate (37.81 mg, 61.75 umol) and $H_2O$ (22.25 mg, 1.23 mmol) under $N_2$ at 25° C. The suspension was degassed under vacuum and purged with CO several times. The mixture was stirred under CO (15 psi) at 100° C. for 12 hours. The mixture combined with another batch was poured into water (20 mL) and extracted with ethyl acetate (10 mL*2). To the aqueous phase was added aqueous HCl (2M) to adjust pH=3. Then the mixture was extracted with ethyl acetate (10 mL*2). The combined organic phase was washed with brine (10 mL), dried with anhydrous $Na_2SO_4$, filtered and concentrated in vacuum to afford Intermediate 24 (120 mg, 535.17 umol) as a yellow solid which was used to next step without purification.

$^1H$ NMR (400 MHz, $CDCl_3$) δ=8.22-8.15 (m, 1H), 8.14-8.08 (m, 1H), 7.74-7.66 (m, 1H), 7.58-7.50 (m, 1H), 2.95-2.77 (m, 4H), 1.36 (s, 3H) ppm.

Intermediate 25: Preparation of sodium 3-(6-fluoro-2-oxaspiro[3.3]heptan-6-yl)benzoate

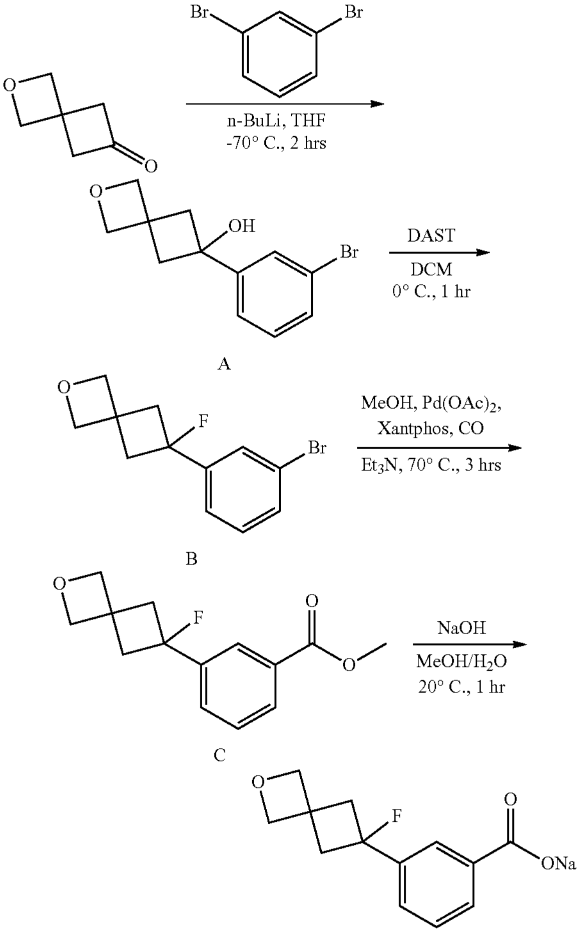

Step 1: Preparation of 6-(3-bromophenyl)-2-oxaspiro[3.3]heptan-6-ol (Intermediate A)

A

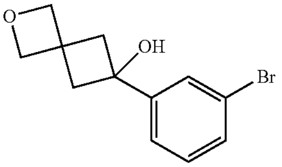

To a solution of 1,3-dibromobenzene (200 mg, 847.80 umol) in THE (2 mL) was added n-BuLi (2.5 M, 339.12 uL)

at −70° C. The mixture was stirred at −70° C. for 30 min under $N_2$·2-oxaspiro[3.3]heptan-6-one (95.06 mg, 847.80 umol) was added at −70° C. and the mixture was stirred at −70° C. for 1.5 hr under $N_2$. The reaction mixture was quenched with water (20 mL) and extracted with EtOAc (10 mL*3). The combined organic phase was washed with brine (10 mL), dried over $Na_2SO_4$, filtered and concentrated under reduced pressure to give a residue. The residue was purified by column chromatography ($SiO_2$, Petroleum ether/Ethyl acetate=2/1) to give Intermediate A (0.16 g, 594.50 umol) as yellow oil.

LCMS (ESI) m/z: [$^{79}$BrM+H]$^+$=269.2.

$^1$H NMR (400 MHz, DMSO-$d_6$) δ=7.55 (m, 1H), 7.44-7.40 (m, 1H), 7.38-7.35 (m, 1H), 7.32-7.29 (m, 1H), 5.61 (s, 1H), 4.67 (s, 2H), 4.53 (s, 2H), 2.67-2.62 (m, 2H), 2.46-2.42 (m, 2H) ppm.

Step 2: Preparation of 6-(3-bromophenyl)-6-fluoro-2-oxaspiro[3.3]heptane (Intermediate B)

B

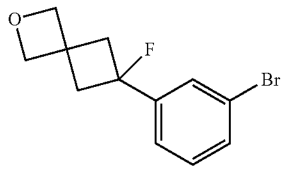

To a solution of Intermediate A (0.15 g, 557.34 umol) in DCM (2 mL) was added DAST (179.68 mg, 1.11 mmol) dropwise at 0° C. The mixture was stirred at 0° C. for 1 hr. The reaction mixture was quenched with water (20 mL) and extracted with EtOAc (10 mL*3). The combined organic phase was washed with brine (10 mL), dried over $Na_2SO_4$, filtered and concentrated under reduced pressure to give a residue. The residue was purified by column chromatography ($SiO_2$, Petroleum ether/Ethyl acetate=3/1) to give Intermediate B (110 mg, 405.72 umol) as yellow oil.

$^1$H NMR (400 MHz, DMSO-$d_6$) δ=7.63-7.54 (m, 2H), 7.46-7.35 (m, 3H), 4.71 (s, 2H), 4.59-4.52 (m, 2H), 2.97-2.82 (m, 2H), 2.82-2.71 (m, 2H) ppm.

Step 3: Preparation of methyl 3-(6-fluoro-2-oxaspiro[3.3]heptan-6-yl)benzoate (Intermediate C)

C

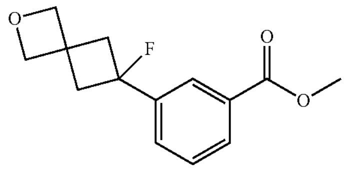

A mixture of Intermediate B (100 mg, 368.83 umol), MeOH (118.17 mg, 3.69 mmol), $Pd(OAc)_2$ (8.28 mg, 36.88 umol) and Xantphos (21.34 mg, 36.88 umol) in $Et_3N$ (3 mL) was degassed and purged with CO for 3 times, and then the mixture was stirred at 70° C. for 3 hrs under CO (15 psi) atmosphere. The reaction mixture was partitioned between EtOAc (30 mL) and water (10 mL). The organic phase was separated, washed with water (10 mL*3) and concentrated under reduced pressure to give a residue. The residue was purified by column chromatography ($SiO_2$, Petroleum ether/Ethyl acetate=1/1) to give Intermediate C (55 mg, 219.77 umol) as yellow oil.

LCMS (ESI) m/z: [M+H]$^+$=251.1.

$^1$HNMR (400 MHz, $CDCl_3$) δ=8.03 (m, 2H), 7.64-7.43 (m, 2H), 4.89 (s, 2H), 4.72 (s, 2H), 3.96 (s, 3H), 3.01-2.80 (m, 4H) ppm.

Step 4: Preparation of [3-(6-fluoro-2-oxaspiro[3.3]heptan-6-yl)benzoyl]oxysodium (Intermediate 24)

25

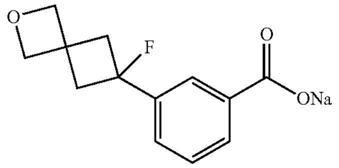

To a solution of Intermediate C (50 mg, 199.79 umol) in MeOH (1 mL) was added a solution of NaOH (7.99 mg, 199.79 umol) in $H_2O$ (1 mL). The mixture was stirred at 20° C. for 1 hr. The reaction mixture was concentrated under reduced pressure to give Intermediate 25 (30 mg, 116.18 umol) as yellow oil which was used in next step without further purification.

Intermediate 26: Preparation of 3-(3-(Difluoromethyl)oxetan-3-yl)benzoic acid

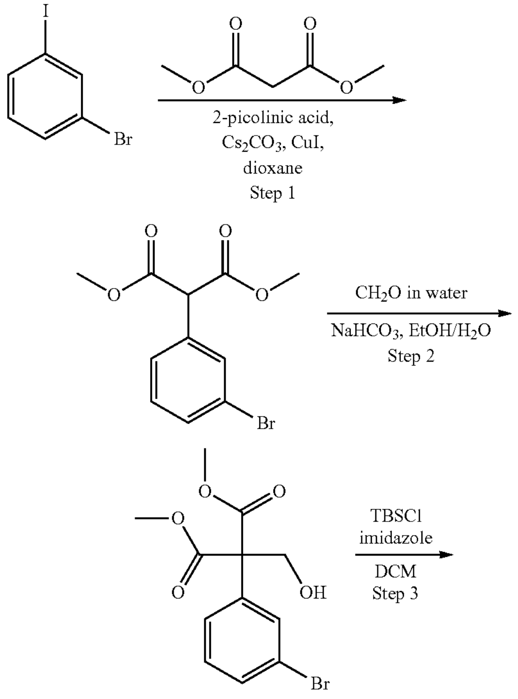

-continued

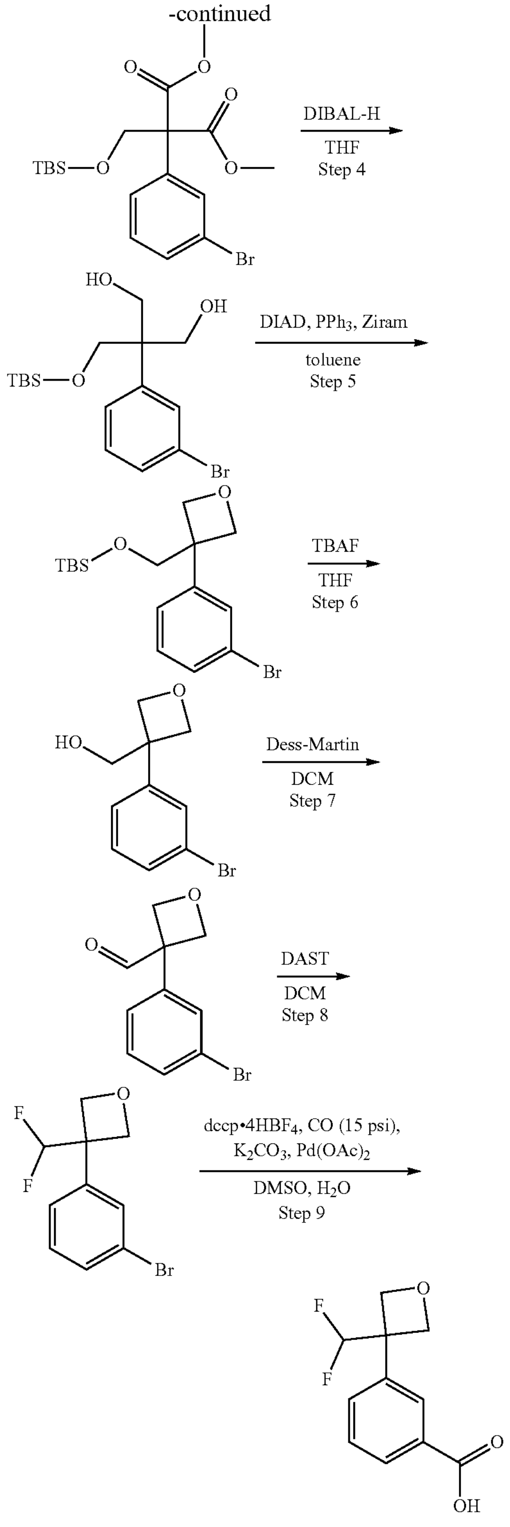

26

Step 1. Dimethyl 2-(3-bromophenyl)malonate 2-picolinic acid (7.31 g, 59.4 mmol), CuI (5.65 g, 29.7 mmol), and $Cs_2CO_3$ (161 g, 495 mmol) were added to a mixture of 1-bromo-3-iodo-benzene (31.5 mL, 247.43 mmol) and dimethyl propanedioate (30.6 mL, 267 mmol) in nitrogen flushed dioxane (1 L). The mixture was stirred at 60° C. for 4.2 hrs. The solid was filtered off, and the filtrate was concentrated in vacuo. The mixture was diluted in aqueous $NH_4Cl$ (5%, 300 mL), and extracted with EA (300 mL×2). The combined organic phase was dried over anhydrous $Na_2SO_4$, filtered, and concentrated in vacuo. The residue was purified by FCC (Eluent: PE:EA=20:1) affording the title compound (70 g) as light yellow oil.

$^1$H NMR (400 MHz, $CDCl_3$) δ=7.52-7.48 (m, 1H), 7.44-7.37 (m, 1H), 7.30-7.25 (m, 1H), 7.18-7.12 (m, 1H), 4.53 (s, 1H), 3.69 (s, 6H) ppm.

Step 2. Dimethyl 2-(3-bromophenyl)-2-(hydroxymethyl)malonate

Sodium bicarbonate (17.6 g, 209 mmol) was added to a solution of dimethyl 2-(3-bromophenyl)malonate (120 g, 418 mmol) in $H_2O$ (450 mL) and EtOH (900 mL). Formaldehyde (156 mL, 2.09 mol) was added dropwise at 0° C. and the solution was stirred at 0° C. for 1 hr. The reaction mixture was allowed to warm 20° C. and stirred for 6 hrs. The solution was concentrated to remove EtOH and the mixture was extracted with EA (300 mL×3). The combined organic phase was dried over anhydrous $Na_2SO_4$, filtered, and concentrated in vacuo. The residue was purified by FCC (Eluent: PE:EA=1:0 to 5:1) affording the title compound (85 g, 268 mmol) as light-yellow oil.

$^1$H NMR (400 MHz, $CDCl_3$) δ=7.43-7.35 (m, 2H), 7.18-7.12 (m, 2H), 4.22-4.16 (m, 2H), 3.75 (s, 6H) ppm.

Step 3. Dimethyl 2-(3-bromophenyl)-2-(((tert-butyldimethylsilyl)oxy)methyl)malonate Imidazole (54.7 g, 804 mmol) was added to a solution of dimethyl 2-(3-bromophenyl)-2-hydroxymethyl)malonate (85 g, 268 mmol) in DCM (1 L). The solution was cooled to 5° C. and TBSCl (46.0 mL, 375 mmol) was added. The mixture was allowed to warm to 20° C. and stirred for 2 hrs. The reaction was quenched via the addition of water (500 mL), and the mixture was extracted with DCM (500 mL×2). The combined organic phase was dried over anhydrous $Na_2SO_4$, filtered, and concentrated in vacuo. The residue was purified by FCC (Eluent: PE:EA=100:1) affording the title compound (100 g, 232 mmol) as light yellow oil.

$^1$H NMR (400 MHz, $CDCl_3$) δ=7.65-7.61 (m, 1H), 7.44-7.39 (m, 1H), 7.32-7.28 (m, 1H), 7.20-7.15 (m, 1H), 4.28 (s, 2H), 3.75 (s, 6H), 0.85 (s, 9H), 0.02 (s, 6H) ppm.

Step 4. 2-(3-Bromophenyl)-2-(((tert-butyldimethylsilyl)oxy)methyl)propane-1,3-diol A solution of dimethyl 2-(3-bromophenyl)-2-(((tert-butyldimethylsilyl)oxy)methyl)malonate (53 g, 123 mmol) in THF (200 mL) was added dropwise to a solution of DIBAL-H (1 M, 737.15 mL) in THF (600 mL) at −78° C. The solution was stirred at −78° C. for 10 min and allowed to warm to 0° C. over 1 hr. The solution was stirred at 0° C. for 20 min. The reaction mixture was quenched via the addition of cold 1 M HCl (4 L) at 0-5° C. The mixture was stirred for 20 min at 5° C. and EA (1.5 L) was added. The phases were allowed to separate and then the aqueous phase was extracted with additional EA (800 mL). The combined organic phase was filtered. The filtrate was dried over anhydrous $Na_2SO_4$, filtered, and concentrated in vacuo. The residue was purified by FCC (Eluent: PE:EA=10:1 to 1:1) affording the title compound (28 g, 71.6 mmol) as light yellow oil.

LCMS (ESI) m/z: [79BrM+H]+=374.9.

$^1$H NMR (400 MHz, $CDCl_3$) δ=7.51-7.49 (m, 1H), 7.36-7.27 (m, 2H), 7.20-7.15 (m, 1H), 4.72-4.66 (m, 2H), 4.08-3.90 (m, 4H), 3.89-3.86 (m, 2H), 0.84-0.80 (m, 9H), 0.03--0.02 (m, 6H) ppm.

Step 5. ((3-(3-Bromophenyl)oxetan-3-yl)methoxy)(tert-butyl)dimethylsilane

Triphenylphosphine (112 g, 426 mmol) was added to a solution of 2-(3-bromophenyl)-2-(((tert-butyldimethylsilyl)oxy)methyl)propane-1,3-diol (40 g, 107 mmol) in toluene (1 L) at 0° C. The mixture was stirred for 30 min, and then Ziram (97.8 g, 320 mmol) was added to the mixture at 0° C., followed by the dropwise addition of DIAD (82.9 mL, 426 mmol). The mixture was stirred for 15 hrs at 20° C. PE (500 mL) was added to the mixture and the solid was filtered off. The filtrate was concentrated in vacuo and the residue was purified by FCC (Eluent: PE:EA=50:1) affording the title compound (33 g, 72.0 mmol) as light-yellow oil.

$^1$H NMR (400 MHz, $CDCl_3$) δ=7.49-7.45 (m, 1H), 7.32-7.27 (m, 2H), 7.08-7.03 (m, 1H), 4.99-4.94 (m, 2H), 4.87-4.78 (m, 2H), 4.06 (s, 2H), 0.94 (s, 9H), 0.01 (s, 6H) ppm.

Step 6. (3-(3-Bromophenyl)oxetan-3-yl)methanol

TBAF (1 M, 269 mL) was added to a solution of ((3-(3-bromophenyl)oxetan-3-yl)methoxy)(tert-butyl)dimethylsilane (64 g, 179 mmol) in THE (200 mL) at 0° C. The mixture was stirred at 0° C. for 20 min. The mixture was diluted in ice water (2 L), and then extracted with EA (300 mL×2). The combined organic phase was dried over anhydrous $Na_2SO_4$, filtered, and concentrated in vacuo. The residue was purified by FCC (Eluent: PE:EA=1:0 to 1:1) affording the title compound (28.4 g, 117 mmol) as a white solid.

$^1$H NMR (400 MHz, $CDCl_3$) δ=7.47-7.42 (m, 1H), 7.30-7.27 (m, 1H), 7.24-7.22 (m, 1H), 7.04-7.00 (m, 1H), 4.98-4.90 (m, 2H), 4.80-4.71 (m, 2H), 4.04 (s, 2H), 1.76 (s, 1H) ppm.

Step 7. 3-(3-Bromophenyl)oxetane-3-carbaldehyde

Dess-Martin periodinane (1.66 mL, 5.35 mmol) was added to a solution of (3-(3-bromophenyl)oxetan-3-yl)methanol (1 g, 4.11 mmol) in DCM (20 mL) at 15° C. The mixture was stirred at 15° C. for 0.5 hr. The reaction was quenched via the addition of aqueous sodium bicarbonate (5%, 30 mL). The mixture was stirred for 10 min and then the solid was filtered off. The filtrate was extracted with EA (10 mL×2) and the combined organic phase was dried over anhydrous $Na_2SO_4$, filtered, and concentrated in vacuo. The residue was purified by FCC (Eluent: PE:EA=1:0 to 3:1) affording the title compound (0.65 g, 2.70 mmol) as light yellow oil.

$^1$H NMR (400 MHz, $CDCl_3$) δ=9.80 (m, 1H), 7.55-7.50 (m, 1H), 7.36-7.31 (m, 1H), 7.28-7.26 (m, 1H), 7.06-7.01 (m, 1H), 5.21-5.14 (m, 2H), 5.03-4.98 (m, 2H) ppm.

Step 8. 3-(3-Bromophenyl)-3-(difluoromethyl)oxetane

DAST (0.99 mL, 7.47 mmol) was added dropwise to a solution of 3-(3-bromophenyl)oxetane-3-carbaldehyde (0.6 g, 2.49 mmol) in DCM (10 mL) at −50° C. The mixture was allowed to warm to 5° C. and stirred for 0.5 hr. The solution was diluted in ice cold aqueous sodium bicarbonate (5%, 100 mL), and the mixture was extracted with DCM (20 mL×2). The combined organic phase was dried over anhydrous $Na_2SO_4$, filtered, and concentrated in vacuo. The residue was purified by FCC (Eluent: PE:EA=1:0 to 8:1) affording the title compound (0.64 g, 2.43 mmol) as light yellow oil.

$^1$H NMR (400 MHz, $CDCl_3$) δ=7.54-7.49 (m, 1H), 7.32-7.28 (m, 1H), 7.27-7.24 (m, 1H), 7.10-6.96 (m, 1H), 6.38-6.01 (m, 1H), 5.01 (s, 4H) ppm.

Step 9. 3-(3-(Difluoromethyl)oxetan-3-yl)benzoic acid (Intermediate 26)

Palladium acetate (25.6 mg, 0.11 mmol), dccp.2HBF$_4$ (140 mg, 228 mmol), and potassium carbonate (236 mg, 1.71 mmol) were added to a solution of 3-(3-bromophenyl)-3-(difluoromethyl)oxetane (0.3 g, 1.14 mmol) in DMSO (2 mL) and water (1 mL). The mixture was degassed and flushed with CO (g) three times. The mixture was then stirred under a CO atmosphere (15 psi) at 90° C. for 5 hrs. Water (5 mL) was added to the mixture and the mixture was extracted with EA (3 mL×3). The combined organic phase was dried over $Na_2SO_4$, filtered, and concentrated in vacuo affording the title compound (0.3 g, crude) as light red oil.

LCMS (ESI) m/z: [M−H]+=227.1.

Intermediate 27: Preparation of 3-(hydroxymethyl)-1,3-dimethylindoline-5-carboxylic acid

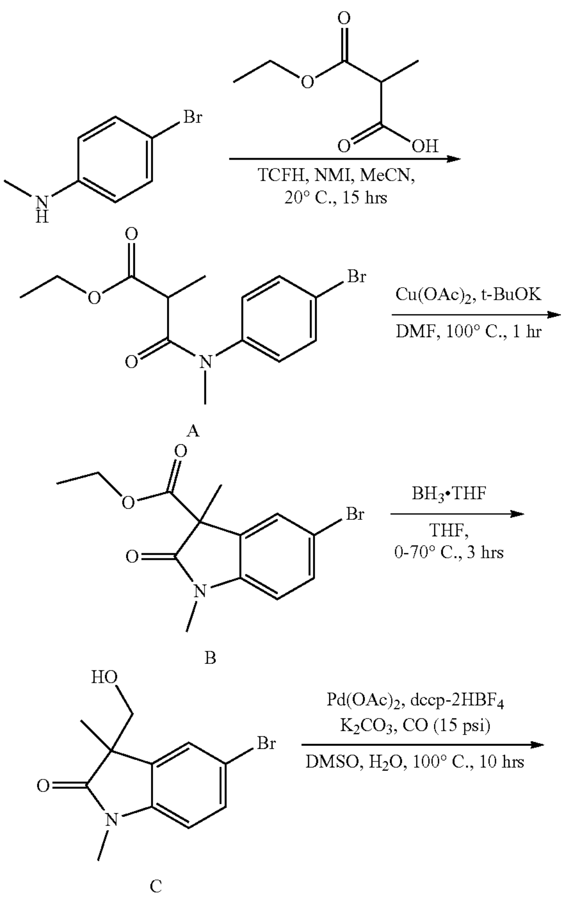

-continued

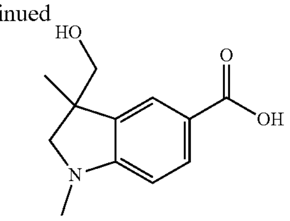

27

Step 1: Preparation of ethyl 3-(4-bromo-N-methyl-anilino)-2-methyl-3-oxo-propanoate (Intermediate A)

A

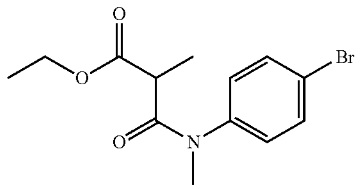

To a mixture of 4-bromo-N-methyl-aniline (500 mg, 2.69 mmol), 3-ethoxy-2-methyl-3-oxo-propanoic acid (471.30 mg, 3.22 mmol) in $CH_3CN$ (6 mL) was added [chloro(dimethylamino)methylene]-dimethyl-ammonium; hexafluorophosphate (1.13 g, 4.03 mmol), 1-methylimidazole (661.95 mg, 8.06 mmol) at 20° C., the mixture was stirred at 20° C. for 15 hrs. The mixture was concentrated to get the crude product. The crude product was added water (10 mL), then extracted with DCM (10 mL*3), the combined organic layer was washed with brine (10 mL), dried over $Na_2SO_4$, filtered and concentrated to get the crude product. The residue was purified by column chromatography ($SiO_2$, Petroleum ether/Ethyl acetate=5/1 to 3/1) to get Intermediate A (550 mg, 1.75 mmol) a brown oil.

LCMS (ESI) m/z: $[M+H]^+$=314/316.

$^1$H NMR (400 MHz, $CDCl_3$) δ=61-7.53 (m, 2H), 7.17-7.12 (m, 2H), 4.20-4.04 (m, 2H), 3.40-3.36 (m, 1H), 3.29 (s, 3H), 1.32-1.30 (m, 3H), 1.27-1.21 (m, 3H) ppm.

Step 2: Preparation of ethyl 5-bromo-1,3-dimethyl-2-oxo-indoline-3-carboxylate (Intermediate B)

B

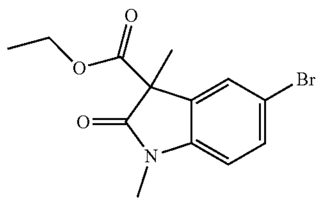

To a mixture of Intermediate A (6 g, 19.10 mmol) in DMF (70 mL) was added t-BuOK (2.36 g, 21.01 mmol) and Copper(II)acetatemonohydrate (4.58 g, 22.92 mmol) at 20° C., then the mixture was stirred at 100° C. for 1 hr. The mixture was filtered off and the filtrate was added water (150 mL), then extracted with EA (50 mL*3), the combined organic layer was washed with brine (50 mL), dried over $Na_2SO_4$, filtered and concentrated to get the crude product. The residue was purified by column chromatography ($SiO_2$, Petroleum ether/Ethyl acetate=5/1 to 3/1) to get Intermediate B (2.2 g, 6.70 mmol) as a yellow solid.

LCMS (ESI) m/z: $[^{79}BrM+H]^+$=311.9.

$^1$H NMR (400 MHz, $CDCl_3$) δ=7.46-7.44 (m, 1H), 7.38 (d, J=2.0 Hz, 1H), 6.75 (d, J=8.4 Hz, 1H), 4.23-4.08 (m, 2H), 3.24 (s, 3H), 1.66 (s, 3H), 1.20-1.69 (m, 3H) ppm.

Step 3: Preparation of (5-bromo-1,3-dimethyl-indolin-3-yl)methanol (Intermediate C)

C

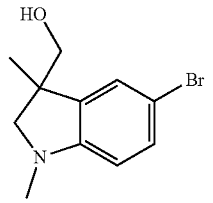

To a mixture of Intermediate B (1.4 g, 4.48 mmol) in THF (20 mL) was added $BH_3$·THF (1 M, 22.42 mL) at 0° C., then the mixture was stirred at 70° C. for 3 hrs. The mixture was quenched with MeOH (30 mL) at 0° C. slowly, then concentrated to get the crude product. The crude product was purified by column chromatography ($SiO_2$, Petroleum ether/Ethyl acetate=10/1 to 3/1) to get Intermediate C (500 mg, 1.72 mmol, 38.30% yield) was obtained as a colorless oil.

LCMS (ESI) m/z: $[M+H]^+$=256/258.

$^1$H NMR (400 MHz, $CDCl_3$) δ=7.22-7.21 (m, 1H), 7.09 (d, J=2.0 Hz, 1H), 6.34 (d, J=8.4 Hz, 1H), 3.65-3.54 (m, 2H), 3.44 (d, J=9.2 Hz, 1H), 3.02 (d, J=9.2 Hz, 1H), 2.74 (s, 3H), 1.32 (s, 3H) ppm.

Step 4: Preparation of 3-(hydroxymethyl)-1,3-dimethyl-indoline-5-carboxylic acid (Intermediate 27)

27

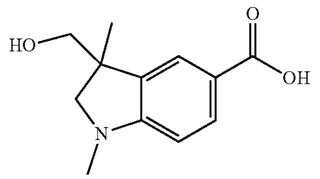

A solution of Intermediate C (80 mg, 312.33 umol) in DMSO (1 mL) and $H_2O$ (0.5 mL) were added $Pd(OAc)_2$ (3.51 mg, 15.62 umol), dicyclohexyl(3-dicyclohexylphosphaniumylpropyl)phosphonium;ditetrafluoroborate (19.12 mg, 31.23 umol) and $K_2CO_3$ (64.75 mg, 468.50 umol). The reaction mixture was degassed and purged with N2 for 3 times, and then the mixture was stirred at 100° C. for 10 hrs under CO (15 psi) atmosphere. The reaction was filtered to afford the residue. The solution was purified by reversed phase (FA condition) and concentrated under reduced pressure to remove MeCN, then lyophilized to get Intermediate 27 (50 mg, 158.19 umol) as a off-white solid.

LCMS (ESI) m/z: $[M+H]^+$=222.0.

Intermediate 28: Preparation of thiochromane-7-carboxylic acid 1,1-dioxide

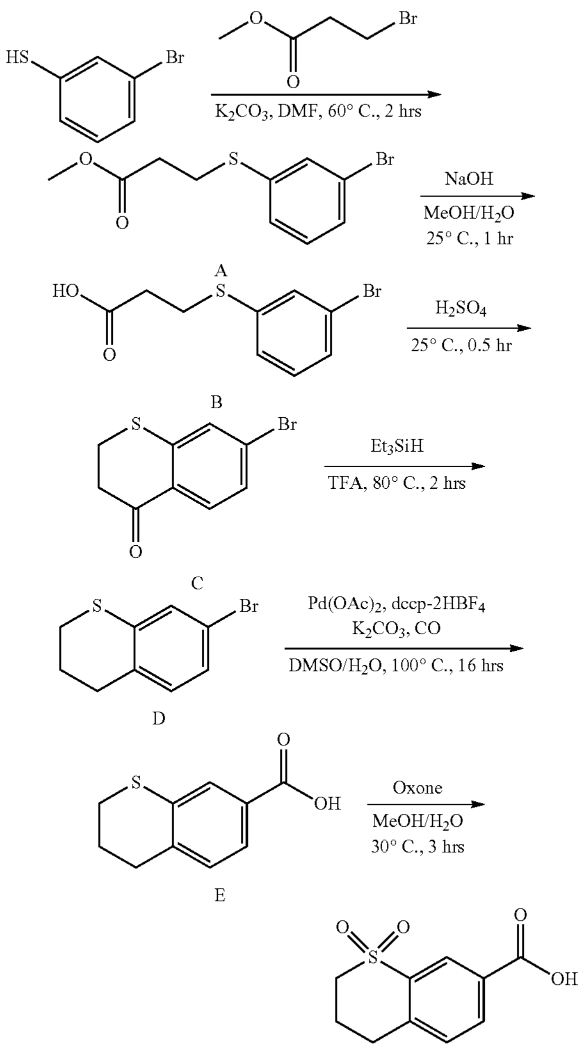

28

Step 1: Preparation of methyl 3-(3-bromophenyl)sulfanylpropanoate (Intermediate A)

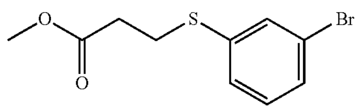

A

To a solution of 3-bromobenzenethiol (2.0 g, 10.58 mmol) in DMF (20 mL) was added $K_2CO_3$ (2.92 g, 21.16 mmol), then methyl 3-bromopropanoate (3.53 g, 21.16 mmol) was added and the mixture was stirred at 60° C. for 2 hrs. The mixture was poured into water (100 mL) and was extracted with EtOAc (100 mL*2). The combined organic phase was concentrated under vacuum to give a residue, which was purified by column chromatography ($SiO_2$, Petroleum ether/Ethyl acetate=100/1 to 5/1). The eluent was concentrated under vacuum to give Intermediate A (2.8 g, 9.16 mmol) as brown oil.

LCMS (ESI) m/z: $[^{81}BrM+H]^+$=277.0.

$^1H$ NMR (400 MHz, $CDCl_3$) δ=7.51 (m, 1H), 7.38-7.32 (m, 1H), 7.31-7.28 (m, 1H), 7.22-7.14 (m, 1H), 3.72 (s, 3H), 3.20 (m, 2H), 2.67 (m, 2H) ppm.

Step 2: Preparation of 3-(3-bromophenyl)sulfanylpropanoic acid (Intermediate B)

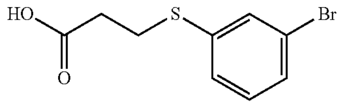

B

To a solution of Intermediate A (1.4 g, 5.09 mmol) in MeOH (5 mL), $H_2O$ (5 mL) and THE (5 mL) was added NaOH (610.51 mg, 15.26 mmol). Then the mixture was stirred for 1 hr at 25° C. The mixture was adjusted pH to 5-6 with aq·HCl (20 mL, 1 M) and was concentrated to give a residue, which was purified by reversed-phase HPLC (0.1% FA condition). The eluent was extracted with EA (15 mL*3) and the combined organic phase was concentrated under vacuum to give Intermediate B (700 mg, 2.51 mmol) as a white solid.

$^1H$ NMR (400 MHz, DMSO-$d_6$) δ=12.67-11.97 (m, 1H), 7.52 (m, 1H), 7.41-7.25 (m, 3H), 3.18 (m, 2H), 2.55 (m, 2H) ppm.

Step 3: Preparation of 7-bromothiochroman-4-one (Intermediate C)

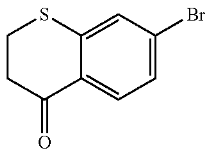

C

Intermediate B (1 g, 3.83 mmol) was added to $H_2SO_4$ (18.40 g, 183.85 mmol, 98% purity) at 25° C.

Then the mixture was stirred for 0.5 hr at 25° C. The mixture was poured into ice water (100 mL) and was adjusted pH to 7-8 with Sat.$NaHCO_3$. The mixture was extracted with EA (100 mL*3) and the combined organic phase was concentrated to give a residue, which was purified by column chromatography ($SiO_2$, Petroleum ether/Ethyl acetate=100/1 to 1/4) to give Intermediate C (840 mg, 3.18 mmol) as yellow oil.

LCMS (ESI) m/z: $[^{81}BrM+H]^+$=244.9.

$^1H$ NMR (400 MHz, DMSO-$d_6$) δ=7.85 (d, J=8.8 Hz, 1H), 7.66 (d, J=2.0 Hz, 1H), 7.43-7.40 (m, 1H), 3.35-3.32 (m, 2H), 2.92-2.87 (m, 2H) ppm.

Step 4: Preparation of 7-bromothiochromane (Intermediate D)

D

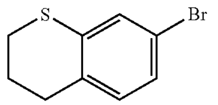

To a solution of Intermediate C (800 mg, 3.29 mmol) in TFA (10 mL) was added with $Et_3SiH$ (873.60 mg, 7.51 mmol). Then the mixture was stirred at 80° C. for 2 hrs. The mixture was adjusted pH to 7-8 with Sat.$NaHCO_3$ and then was extracted with EA (50 mL*3). The combined organic phase was concentrated to give a residue, which was purified by column chromatography ($SiO_2$, Petroleum ether/Ethyl acetate=100/1 to 1/5) and concentrated to give Intermediate D (1.5 g, crude) as colorless oil.

$^1H$ NMR (400 MHz, DMSO-$d_6$) δ=7.20 (d, J=2.0 Hz, 1H), 7.12-7.08 (m, 1H), 6.98 (d, J=8.4 Hz, 1H), 3.01-2.97 (m, 2H), 2.70-2.66 (m, 2H), 1.98-1.91 (m, 2H) ppm.

Step 5: Preparation of thiochromane-7-carboxylic acid (Intermediate E)

E

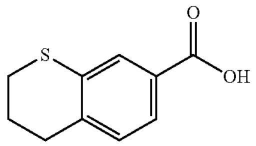

To a solution of Intermediate D (750 mg, 3.27 mmol) in $H_2O$ (5 mL) and DMSO (10 mL) was added dicyclohexyl (3-dicyclohexylphosphaniumylpropyl)phosphonium;ditetrafluoroborate (200.40 mg, 327.32 umol), $K_2CO_3$ (678.58 mg, 4.91 mmol) and $Pd(OAc)_2$ (36.74 mg, 163.66 umol) at 25° C. Then the mixture was degassed and purged with CO for 3 times and the mixture was stirred at 100° C. for 16 hrs under CO atmosphere (15 psi). The mixture was filtered and the filtrate was washed with EA (10 mL*2). The aqueous phase was adjusted pH to 6-7 with 1 M HCl and was extracted with EA (50 mL*3). The organic layer was washed with brine (5 mL) and was concentrated under vacuum to give Intermediate E (600 mg, 2.91 mmol) as a yellow solid.

LCMS (ESI) m/z: $[M+H]^+$=195.1.

$^1H$ NMR (400 MHz, DMSO-$d_6$) δ=7.57 (d, J=1.6 Hz, 1H), 7.54-7.50 (m, 1H), 7.19 (d, J=8.0 Hz, 1H), 3.08-3.04 (m, 2H), 2.83 (m, 2H), 2.05-1.99 (m, 2H) ppm.

Step 6: Preparation of 1,1-dioxo-3,4-dihydro-2H-thiochromene-7-carboxylic acid (Intermediate 28)

27

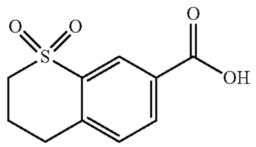

To a solution of Intermediate E (300 mg, 1.54 mmol) in MeOH (2 mL) was added dropwise a mixture of Oxone (1.90 g, 3.09 mmol) in $H_2O$ (2 mL). The mixture was stirred at 30° C. for 3 hrs. The mixture was quenched by saturated $Na_2SO_3$ solution (20 mL) and then was diluted with water (10 mL). The mixture was adjusted pH to 4-5 with 1 M HCl and was extracted with EA (50 mL*3). The combined organic layer was washed by brine (50 mL), dried over $Na_2SO_4$, filtered and concentrated under vacuum to give Intermediate 28 (170 mg, 751.39 umol) as a white solid.

LCMS (ESI) m/z: $[M+H]^+$=227.1.

$^1H$ NMR (400 MHz, DMSO-$d_6$) δ=8.25 (d, J=1.6 Hz, 1H), 8.06-8.03 (m, 1H), 7.51 (d, J=8.4 Hz, 1H), 3.61-3.52 (m, 2H), 3.08 (m, 2H), 2.37-2.30 (m, 2H) ppm.

Intermediate 29: Preparation of 1,1-difluorospiro[cyclopropane-2,4'-isochromane]-6'-carboxylic acid

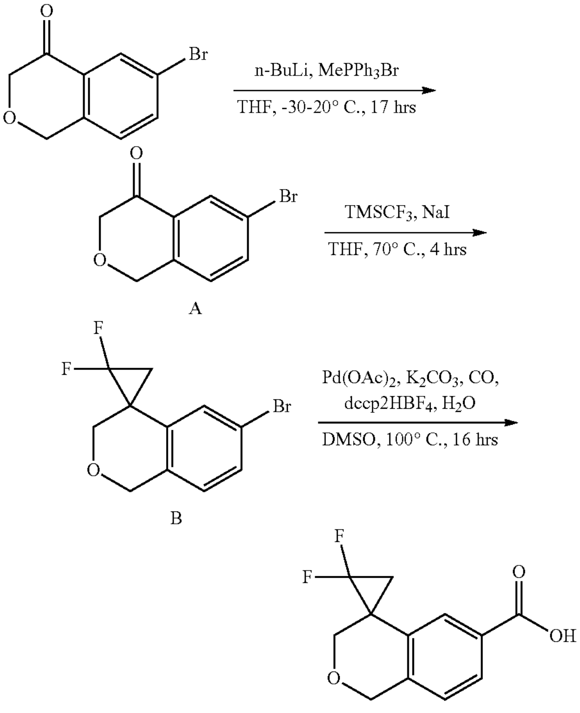

Step 1: Preparation of 6-bromo-4-methyleneisochromane (Intermediate A)

A

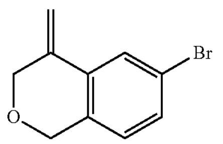

To a solution of methyl(triphenyl)phosphonium;bromide (943.98 mg, 2.64 mmol) in THF (5 mL) was added n-BuLi (2.5 M, 1.15 mL) dropwise at −30° C. under $N_2$. The mixture was stirred at −30° C. for 1 hr. A solution of 6-bromoisochroman-4-one (Prepared according to the method in Intermediate 10B) (0.5 g, 2.20 mmol) in THF (1 mL) was added dropwise at −30° C. under $N_2$. The mixture was stirred at 20° C. for 16 hrs. The reaction was quenched with Sat.$NH_4Cl$ (20 mL) and the mixture was extracted with EtOAc (10 mL*3). The combined organic layers were washed with brine (10 mL), dried over $Na_2SO_4$, concentrated in vacuum to give a residue, which was purified by column chromatography ($SiO_2$, Petroleum ether/Ethyl acetate=5/1) to give Intermediate A (350 mg, 1.54 mmol) as yellow oil.

LCMS (ESI) m/z: $[^{81}BrM+H]^+$=227.1.

$^1H$ NMR (400 MHz, $CDCl_3$) δ=7.73 (d, J=2.0 Hz, 1H), 7.28 (m, 1H), 6.84 (d, J=8.0 Hz, 1H), 5.53 (s, 1H), 4.99 (s, 1H), 4.67 (s, 2H), 4.35 (s, 2H) ppm.

Step 2: Preparation of 6'-bromo-1,1-difluorospiro[cyclopropane-2,4'-isochromane] (Intermediate B)

B

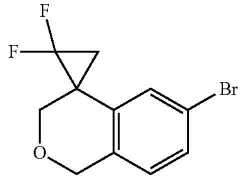

To a solution of Intermediate A (250 mg, 1.11 mmol) in THE (5 mL) was added NaI (33.30 mg, 222.14 umol). A solution of $TMSCF_3$ (631.77 mg, 4.44 mmol) in THE (1 mL) was added dropwise at 70° C. under $N_2$ and then the mixture was stirred at 70° C. for 4 hrs. The resulting mixture was filtered and the filter cake was washed with ethyl acetate (10 mL). The filtrate was concentrated in vacuum to give a residue, which was purified by column chromatography ($SiO_2$, Petroleum ether/Ethyl acetate=5/1) to give Intermediate B (0.28 g, 1.02 mmol) as yellow oil.

$^1H$ NMR (400 MHz, $CDCl_3$) δ=7.29 (m, 1H), 7.06 (s, 1H), 6.86 (d, J=8.0 Hz, 1H), 4.83-4.70 (m, 2H), 3.91-3.84 (m, 1H), 3.83-3.73 (m, 1H), 1.87-1.72 (m, 1H), 1.54-1.49 (m, 1H) ppm.

Step 3: Preparation of 1,1-difluorospiro[cyclopropane-2,4'-isochromane]-6'-carboxylic acid (Intermediate 29)

29

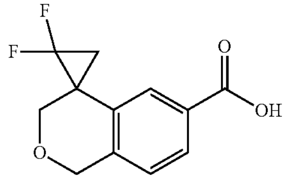

A mixture of Intermediate B (100 mg, 363.52 umol), dicyclohexyl(3-dicyclohexylphos phaniumylpropyl)phosphonium;ditetrafluoroborate (22.26 mg, 36.35 umol), $H_2O$ (32.75 mg, 1.82 mmol), $K_2CO_3$ (75.36 mg, 545.28 umol) and $Pd(OAc)_2$ (8.16 mg, 36.35 umol) in DMSO (1 mL) was degassed and purged with CO for 3 times, and then the mixture was stirred at 100° C. for 16 hrs under CO (15 Psi) atmosphere. The reaction mixture was partitioned between ethyl acetate (30 mL) and 1 N HCl solution (10 mL). The organic phase was separated, washed with water (10 mL*3) and concentrated under reduced pressure to give Intermediate 29 (100 mg) as yellow oil, which was used in next step without further purification.

LCMS (ESI) m/z: $[M+H]^+$=241.0.

Intermediate 30: Preparation of 3-(3-hydroxy-1-methylcyclobutyl)benzoic acid

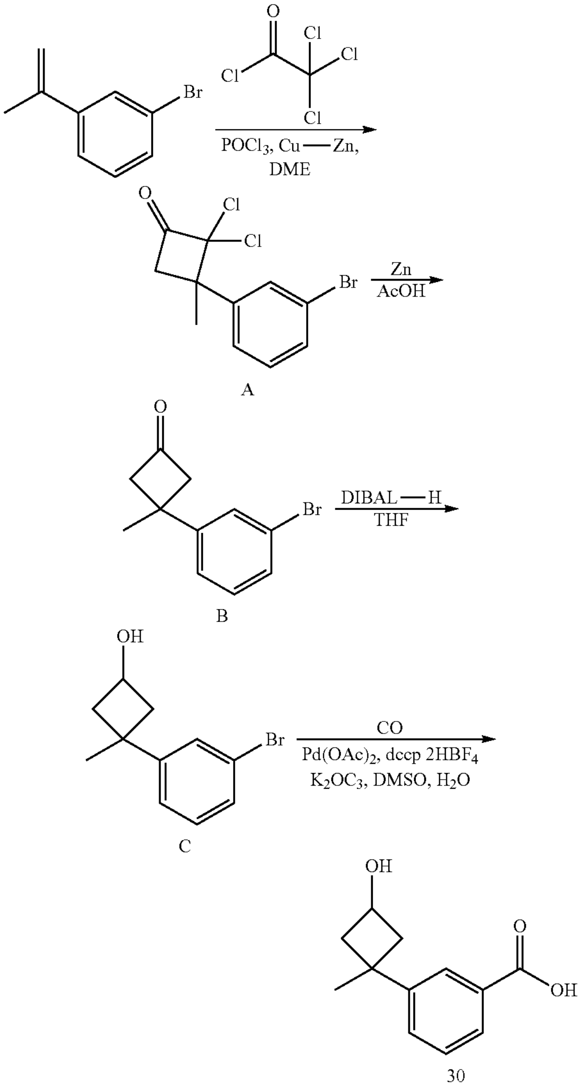

30

Step 1: Preparation of 3-(3-bromophenyl)-2,2-dichloro-3-methylcyclobutanone (Intermediate A)

A

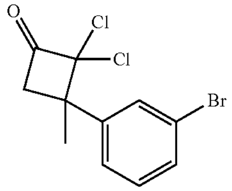

To a mixture of 1-bromo-3-isopropenyl-benzene (2 g, 10.15 mmol) and Cu—Zn (2.62 g, 20.30 mmol) in DME (40 mL) was added a mixture of 2,2,2-trichloroacetyl chloride (3.69 g, 20.30 mmol) and $POCl_3$ (1.95 g, 12.69 mmol) in DME (10 mL) dropwise at 10° C., and then the mixture was stirred for at 25° C. for 10 hrs. The mixture was added into ice cold $H_2O$ (200 mL) and EA (100 mL) to quench the reaction. Then the mixture was neutralized with aqueous $NaHCO_3$ (5% 100 mL) and the formed precipitate was filtered off. The organic phase was separated and was dried over $Na_2SO_4$, filtered and concentrated to dryness to give a residue. The residue was purified by column chromatography ($SiO_2$, PE/EA=100:1) to give Intermediate A (2.3 g, crude) as light yellow oil.

Step 2: Preparation of 3-(3-bromophenyl)-3-methylcyclobutanone (Intermediate B)

B

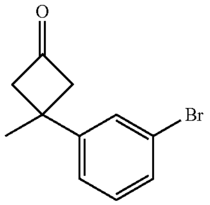

To a solution of Intermediate A (2 g, 6.49 mmol) in AcOH (30 mL) was added Zn (4.25 g, 64.94 mmol) and the mixture was heated at 100° C. for 10 hrs. The solid was filtered off and the filtrate was concentrated to dryness to give a residue. The residue was diluted with $H_2O$ (30 mL) and EA (50 mL), and the solid was filtered off. The organic phase was separated and was basified by aqueous $NaHCO_3$ (5%, 30 mL). The organic phase was separated and dried over $Na_2SO_4$, and then was concentrated to dryness to give Intermediate B (0.7 g, crude) as light yellow thick oil.

Step 3: Preparation of 3-(3-bromophenyl)-3-methylcyclobutanol (Intermediate C)

C

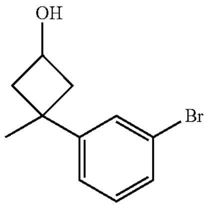

To a solution of Intermediate B (0.5 g, 2.09 mmol) in THE (10 mL) was added DIBAL-H (1 M, 5.23 mL) dropwise at −10° C. and the mixture was stirred at −10° C. for 30 min. To the mixture was added $H_2O$ (30 mL) dropwise at 0° C. to quench the reaction and the mixture was extracted with EA (30 mL*3). The combined organic phase was dried over $Na_2SO_4$, filtered and concentrated to dryness to give a residue, which was purified by column chromatography ($SiO_2$, PE/EA=0-1:1). The eluent was concentrated to dryness to give Intermediate C (0.48 g, 1.91 mmol) as a light yellow oil.

$^1H$ NMR (400 MHz, DMSO-$d_6$) δ=7.52-7.13 (m, 4H), 5.12-4.88 (m, 1H), 2.73-2.64 (m, 1H), 2.48-2.37 (m, 1H), 2.09-1.92 (m, 2H), 1.41-1.30 (m, 3H) ppm.

Step 4: Preparation of 3-(3-hydroxy-1-methylcyclobutyl)benzoic acid (Intermediate 30)

30

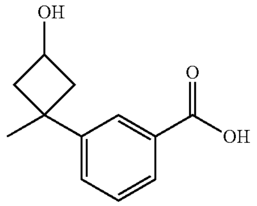

To a mixture of Intermediate C (0.4 g, 1.66 mmol), diacetoxypalladium (37.24 mg, 165.89 umol), dicyclohexyl (3-dicyclohexylphosphaniumylpropyl)phosphonium;ditetrafluoroborate (203.14 mg, 331.78 umol) in DMSO (3 mL) and $H_2O$ (0.3 mL) was added $K_2CO_3$ (343.90 mg, 2.49 mmol), then the mixture was degassed and purged with CO for 3 times. The mixture was stirred under CO (15 psi) at 100° C. for 5 hrs. The mixture was diluted with $H_2O$ (30 mL) and the mixture was acidified to pH=3-4, then the mixture was extracted with EA (6 mL*3). The combined organic phase was dried over $Na_2SO_4$, filtered and concentrated to dryness to give Intermediate 30 (0.4 g) as brown thick oil.

LCMS (ESI) m/z: $[M+H]^+$=207.1.

Intermediate 31: Preparation of 4-cyano-4-(hydroxymethyl)isochromane-6-carboxylic acid

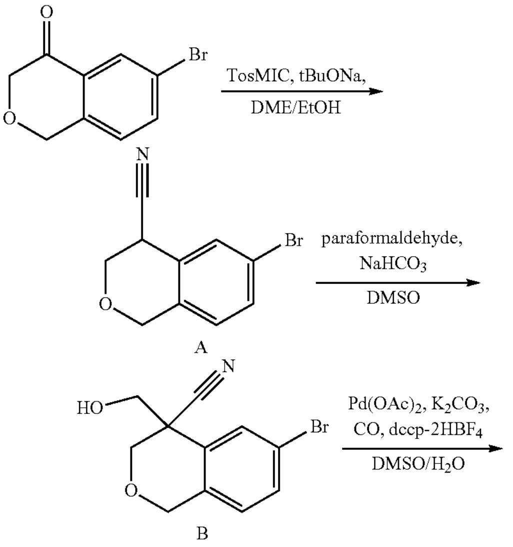

-continued

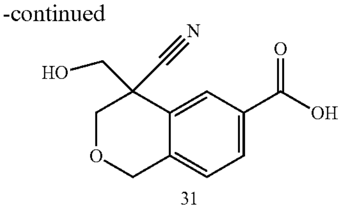

31

Step 1: Preparation of 6-bromoisochroman-4-carbonitrile (Intermediate A)

A

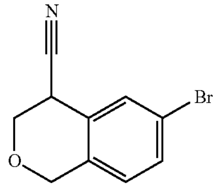

To a solution of 6-bromoisochroman-4-one (Prepared according to the method in FG-A2637A) (100 mg, 440.42 umol) and 1-(isocyanomethylsulfonyl)-4-methyl-benzene (128.98 mg, 660.63 umol) in DME (4 mL) and EtOH (0.2 mL) was added t-BuONa (42.33 mg, 440.42 umol) at −10° C. Then the mixture was allowed to 60° C. in 15 mins. The reaction mixture was stirred at 60° C. for 15 mins. The reaction mixture was quenched by addition water (40 mL) at 25° C., and then extracted with EA (60 mL*2). The combined organic layers were washed with brined (40 mL), dried over $Na_2SO_4$, filtered and concentrated under reduced pressure to give a residue. The residue was purified by column chromatography ($SiO_2$, PE:EA=50:1 to 3:1), the fraction was concentrated under reduced pressure to get Intermediate A (260 mg, 982.86 umol) as an off-white solid.

$^1$H NMR (400 MHz, $CDCl_3$) δ=7.59 (d, J=1.6 Hz, 1H), 7.46-7.44 (m, 1H), 6.95 (d, J=8.4 Hz, 1H), 4.86-4.70 (m, 2H), 4.27-4.15 (m, 1H), 4.12-4.02 (m, 2H) ppm.

Step 2: Preparation of 6-bromo-4-(hydroxymethyl)isochroman-4-carbonitrile (Intermediate B)

B

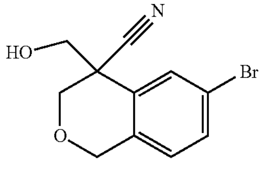

To a solution of Intermediate A (260 mg, 1.09 mmol) and $NaHCO_3$ (9.17 mg, 109.21 umol, 4.25 uL) in DMSO (3 mL) was added paraformaldehyde (39.33 mg, 1.31 mmol) and the mixture was stirred at 25° C. for 14 hrs. The reaction mixture was diluted with water (30 mL), extracted with EA (30 mL*3). The combined organic layer was dried over anhydrous $Na_2SO_4$, filtered and concentrated under reduced pressure to get the residue. The residue was purified by flash silica gel chromatography (PE:EA=1:0 to 1:1), the fraction was concentrated under reduced pressure to give Intermediate B (220 mg, 793.82 umol) as a white solid.

LCMS (ESI) m/z: [M+H]$^+$=268.0.

$^1$H NMR (400 MHz, DMSO-$d_6$) δ=7.69 (d, J=2.0 Hz, 1H), 7.56-7.54 (m, 1H), 7.14 (d, J=8.4 Hz, 1H), 5.91-5.88 (m, 1H), 4.74 (s, 2H), 4.18 (d, J=11.2 Hz, 1H), 4.04-4.01 (m, 1H), 3.84-3.78 (m, 1H), 3.74-3.68 (m, 1H) ppm.

Step 3: Preparation of 4-cyano-4-(hydroxymethyl)isochroman-6-carboxylic acid (Intermediate 31)

31

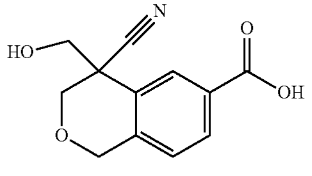

A mixture of Intermediate B (220 mg, 820.57 umol), dicyclohexyl(3-dicyclohexylphosphaniumylpropyl)phosphonium;ditetrafluoroborate (50.24 mg, 82.06 umol), $K_2CO_3$ (170.12 mg, 1.23 mmol), $Pd(OAc)_2$ (18.42 mg, 82.06 umol) and $H_2O$ (1.04 g, 57.44 mmol) in DMSO (4 mL) was degassed and purged with CO for 3 times, and then the mixture was stirred at 100° C. for 14 hrs under CO atmosphere. The reaction mixture was filtered to move off the black solid, and then diluted with water (20 mL), extracted with EA (20 mL*2). The organic layer was discarded and the aqueous phase was adjusted pH=4 with a.q HCl, extracted with EA (30 mL*3), then the combined organic layer was dried over anhydrous $Na_2SO_4$, filtered and concentrated under reduced pressure to get the residue. The residue was purified by reversed-phase HPLC (0.1% FA), then the solution was concentrated under reduced pressure to remove MeCN and then lyophilized to give Intermediate 31 (70 mg, 233.45 umol) as a yellow solid.

LCMS (ESI) m/z: [M+H]$^+$=233.9.

$^1$H NMR (400 MHz, DMSO-$d_6$) δ=13.49-12.91 (m, 1H), 8.03 (d, J=1.6 Hz, 1H), 7.90-7.87 (m, 1H), 7.29 (d, J=8.0 Hz, 1H), 5.92-5.90 (m, 1H), 4.85 (s, 2H), 4.25 (d, J=11.2 Hz, 1H), 4.02 (d, J=11.2 Hz, 1H), 3.74 (d, J=5.2 Hz, 2H) ppm.

Intermediate 32: Preparation of 1-ethyl-3H-114-benzo[d]isothiazole-6-carboxylic acid 1-oxide

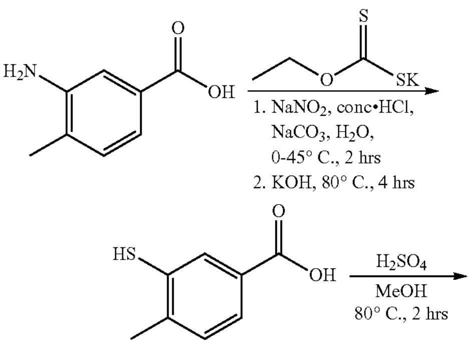

A

-continued

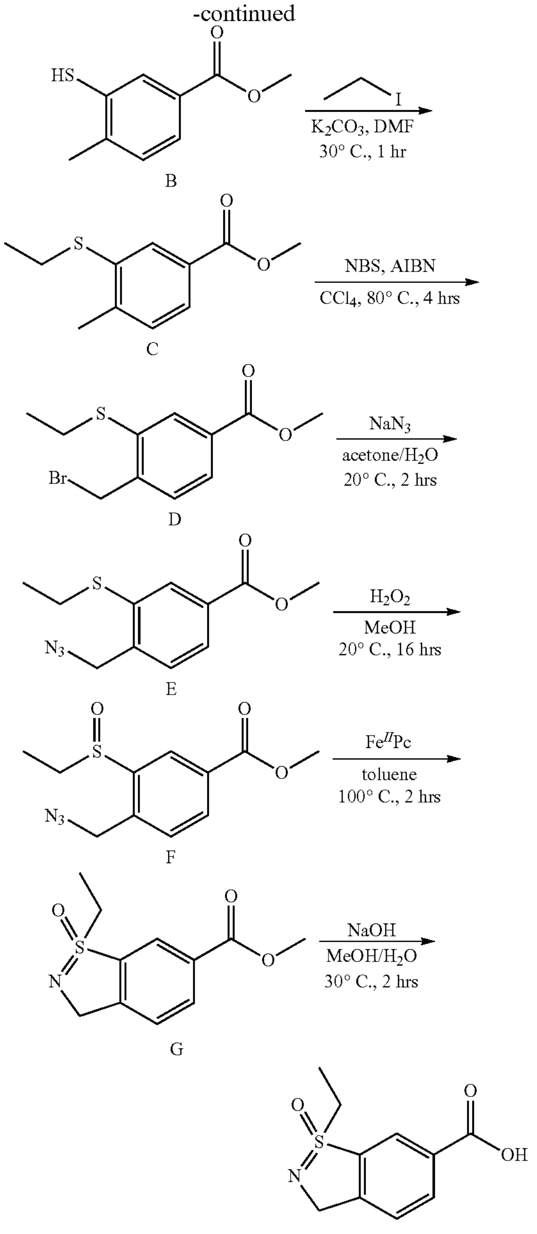

32

Step 1: Preparation of 4-methyl-3-sulfanyl-benzoic acid (Intermediate A)

A

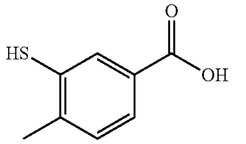

To a solution of 3-amino-4-methyl-benzoic acid (10 g, 66.15 mmol) in HYDROCHLORIC ACID (12 M, 40 mL) and water (100 mL) was added a solution of $NaNO_2$ (4.79 g, 69.46 mmol) in water (100 mL) at 0° C. over a period of 0.5 hr, then the mixture was added to the stirred mixture of ethoxycarbothioylsulfanylpotassium (12.73 g, 79.38 mmol) and $Na_2CO_3$ (2 M, 109.15 mL) over a period of 0.5 hr. The mixture was stirred at 45° C. for 1 hr. The reaction mixture was adjusted pH to 4 with 1 N HCl and the formed precipitate was collected by filtration. The solid was dried under reduced pressure and then was dissolved in EtOH (50 mL) and water (50 mL). Then KOH (14.85 g, 264.62 mmol) was added and the mixture was refluxed at 80° C. for 4 hrs. The reaction mixture was concentrated under reduced pressure to give a residue. The reaction mixture was adjusted pH to 4 with 1 N HCl and was diluted with water (200 mL). Then the mixture was extracted with EtOAc (250 mL*2). The combined organic layers were washed with brine (300 mL), dried over $Na_2SO_4$, filtered and concentrated under reduced pressure to give Intermediate A (12 g, crude) as a light yellow solid, which was used for the next step without further purification.

Step 2: Preparation of methyl 4-methyl-3-sulfanyl-benzoate (Intermediate B)

B

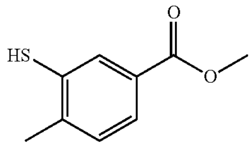

To a solution of Intermediate A (9 g, 53.50 mmol) in MeOH (130 mL) was added to $H_2SO_4$ (4.99 g, 50.91 mmol) and the mixture was stirred at 80° C. for 2 hrs. The reaction mixture was combined with another batch. The mixture was concentrated under reduced pressure to give a residue. Then the residue was poured into sat.$NaHCO_3$ (200 mL) and was extracted with EtOAc (200 mL*2). The combined organic layers were washed with brine (200 mL), dried over $Na_2SO_4$, filtered and concentrated under reduced pressure to give a residue, which was purified by column chromatography ($SiO_2$, PE/EA=6:1). The eluent was concentrated under reduced pressure to give Intermediate B (7.5 g, 41.15 mmol) as a light yellow oil.

LCMS (ESI) m/z: $[M+H]^+$=183.1.

$^1H$ NMR (400 MHz, DMSO-$d_6$) δ=8.00 (d, J=1.2 Hz, 1H), 7.61 (m, 1H), 7.30 (d, J=7.6 Hz, 1H), 5.71 (s, 1H), 3.83 (s, 3H), 2.50 (s, 1H), 2.28 (s, 3H) ppm.

Step 3: Preparation of methyl 3-ethylsulfanyl-4-methyl-benzoate (Intermediate C)

C

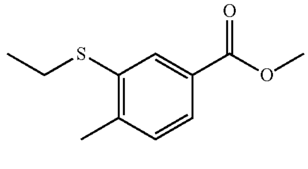

To a solution of Intermediate B (6 g, 32.92 mmol) and $K_2CO_3$ (13.65 g, 98.77 mmol) in DMF (60 mL) was added iodoethane (5.65 g, 36.22 mmol), the mixture was stirred at 30° C. for 1 hr. The reaction mixture was combined with another batch. The mixture was diluted with water (400 mL)

and extracted with EtOAc (300 mL*2). The combined organic layers were washed with brine (300 mL), dried over $Na_2SO_4$, filtered and concentrated under reduced pressure to give a residue, which was purified by column chromatography ($SiO_2$, PE/EA=6:1). The eluent was concentrated under reduced pressure to give Intermediate C (6.5 g, 30.91 mmol) as a white solid.

LCMS (ESI) m/z: $[M+H]^+$=211.3.

$^1$H NMR (400 MHz, DMSO-$d_6$) δ=7.78 (d, J=1.2 Hz, 1H), 7.66 (m, 1H), 7.35 (d, J=8.0 Hz, 1H), 3.84 (s, 3H), 3.01 (m, 2H), 2.32 (s, 3H), 1.27 (m, 3H) ppm.

Step 4: Preparation of methyl 4-(bromomethyl)-3-ethylsulfanyl-benzoate (Intermediate D)

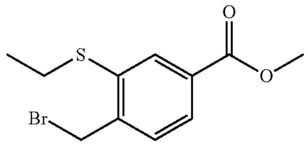

D

A mixture of Intermediate C (3450 mg, 16.41 mmol), NBS (2.92 g, 16.41 mmol) and AIBN (3.23 g, 19.69 mmol) in $CCl_4$ (35 mL) was stirred at 80° C. for 4 hrs. The reaction mixture was concentrated under reduced pressure to remove $CCl_4$ to give a residue, which was purified by column chromatography ($SiO_2$, PE/EA=8:1). The eluent was concentrated under reduced pressure to give Intermediate D (1 g, crude) as light yellow oil.

LCMS (ESI) m/z: $[^{79}BrM+H]^+$=287.0.

$^1$H NMR (400 MHz, $CDCl_3$) δ=7.85-7.74 (m, 2H), 7.45 (d, J=2.0 Hz, 1H), 7.43-7.33 (m, 3H), 6.91 (d, J=8.4 Hz, 1H), 4.72 (s, 2H), 4.42 (d, J=9.6 Hz, 1H), 4.29 (d, J=9.6 Hz, 1H), 4.24-4.12 (m, 2H), 3.75 (s, 3H), 2.48 (s, 3H) ppm.

Step 5: Preparation of methyl 4-(azidomethyl)-3-ethylsulfanyl-benzoate (Intermediate E)

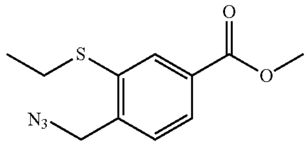

E

To a solution of Intermediate D (1 g, 3.46 mmol) in ACETONE (10 mL) and $H_2O$ (2.5 mL) was added $NaN_3$ (269.76 mg, 4.15 mmol) at 20° C., then the mixture was stirred at 20° C. for 2 hrs. The reaction mixture was basified with Sat.$Na_2CO_3$ to pH 9-10. Then the mixture was diluted with water (100 mL) and extracted with EtOAc (100 mL*2). The combined organic layers were washed with brine (10 mL), dried over $Na_2SO_4$, filtered and concentrated under reduced pressure to remove most of EtOAc to give a residue (about 5 mL), the residue was diluted with MeOH to give Intermediate E (800 mg, crude) in MeOH (5 mL) as light yellow liquid, which was used to the next step without further purification.

Step 6: Preparation of methyl 4-(azidomethyl)-3-ethylsulfinyl-benzoate (Intermediate F)

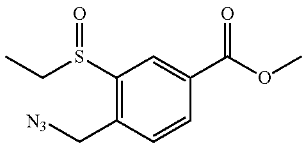

F

To a solution of Intermediate E (800 mg, 3.18 mmol) in MeOH (10 mL) was added $H_2O_2$ (433.13 mg, 3.82 mmol, 30% purity) and the mixture was stirred at 20° C. for 16 hrs. The reaction mixture was quenched with Sat.$Na_2SO_3$ (1 mL), diluted with water (100 mL) and extracted with EtOAc (100 mL*2). The combined organic layers were washed with brine (100 mL), dried over $Na_2SO_4$, filtered and concentrated under reduced pressure to give a residue, which was purified by column chromatography ($SiO_2$, PE/EA=1:1). The eluent was concentrated under reduced pressure to give a residue (about 5 mL), the residue was azeotropied with toluene (50 mL*3) to give Intermediate F (500 mg, 1.83 mmol) in toluene (5 mL) as a light yellow liquid.

LCMS (ESI) m/z: $[M+H]^+$=268.0.

Step 7: Preparation of methyl 1-ethyl-1-oxo-3H-1,2-benzothiazole-6-carboxylate (Intermediate G)

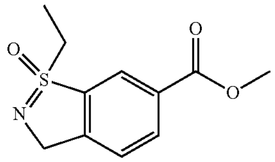

G

To a solution of Intermediate F (500 mg, 1.87 mmol) in toluene (5 mL) was added IRON(II)PHTHALOCYANINE (53.06 mg, 93.53 umol) under $N_2$, the mixture was stirred at 100° C. for 2 hrs. The reaction mixture was diluted with EtOAc/MeOH (20 mL, v/v=5:1), then filtered and the filtrate was concentrated under reduced pressure to give a residue. The residue was purified by column chromatography ($SiO_2$, EA) and the eluent was concentrated under reduced pressure to give Intermediate G (400 mg, 1.67 mmol) as a light yellow solid.

LCMS (ESI) m/z: $[M+H]^+$=240.1.

$^1$H NMR (400 MHz, DMSO-$d_6$) δ=8.57 (d, J=0.4 Hz, 1H), 8.23-8.20 (m, 1H), 7.78 (d, J=8.0 Hz, 1H), 4.85-4.81 (m, 1H), 4.69-4.65 (m, 1H), 3.97-3.90 (m, 4H), 3.58-3.49 (m, 1H), 0.94-0.91 (m, 3H) ppm.

Step 8: Preparation of 1-ethyl-1-oxo-3H-1,2-benzothiazole-6-carboxylic acid (Intermediate 32)

32

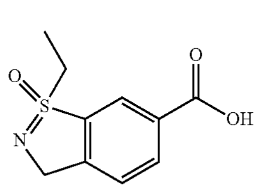

To a solution of Intermediate G (100 mg, 417.90 umol) in water (0.5 mL) and MeOH (0.5 mL) was added NaOH (40 mg, 1.00 mmol), the mixture was stirred at 30° C. for 2 hrs. The reaction mixture was neutralized with 1 N HCl to pH 6.0 and concentrated under reduced pressure to give Intermediate 32 (94.14 mg) as light yellow oil, which was used to the next step without further purification. LCMS (ESI) m/z: $[M+H]^+$=226.2.

Intermediate 33: Preparation of 4-(cyanomethyl)-4-methylisochromane-6-carboxylic acid

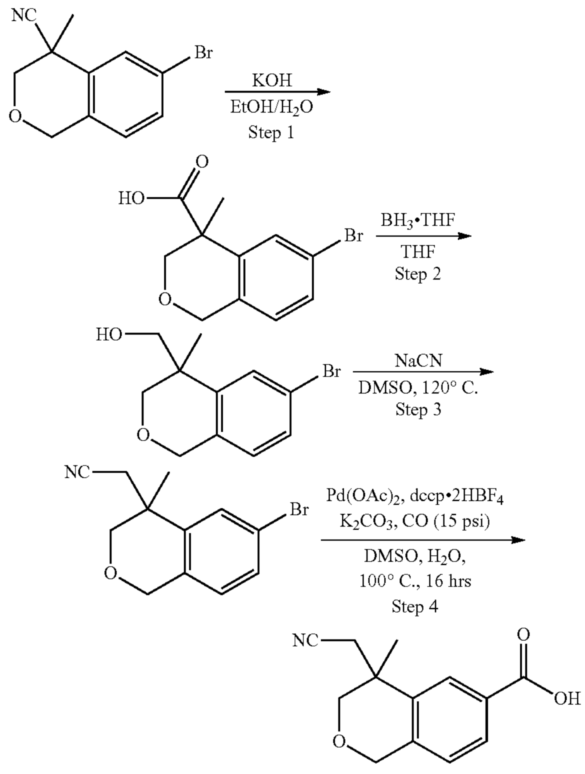

33

Step 1. 6-Bromo-4-methyl-isochromane-4-carboxylic acid

Potassium hydroxide (aq., 9M, 5.29 mL) was added to a solution of 6-bromo-4-methyl-isochromane-4-carbonitrile (1.2 g, 4.76 mmol) in EtOH (12 mL). The mixture was stirred at 90° C. for 5 hrs. The reaction mixture was diluted with $H_2O$ (20 mL) and extracted with EA (30 mL×3). The combined organic layers were discarded and the aqueous phase was adjusted pH=4 with 1 N HCl. The aqueous layer was extracted with EA (30 mL×3). The combined organic layers were washed with brine (60 mL), dried over $Na_2SO_4$, filtered, and concentrated in vacuo affording the title compound (800 mg, 2.95 mmol) as yellow oil.

$^1H$ NMR (400 MHz, DMSO-$d_6$) δ=13.11-12.45 (m, 1H), 7.52 (d, J=2.0 Hz, 1H), 7.40 (d, J=8.4 Hz, 1H), 7.03 (d, J=8.4 Hz, 1H), 4.75-4.62 (m, 2H), 4.16 (d, J=11.2 Hz, 1H), 3.59 (d, J=11.2 Hz, 1H), 1.41 (s, 3H).

Step 2. (6-Bromo-4-methyl-isochroman-4-yl)methanol 6-bromo-4-methyl-isochromane-4-carboxylic acid (800 mg, 2.95 mmol) was dissolved in $BH_3$·THF (1 M, 8.85) at 0° C. and the resulting mixture was stirred at 25° C. for 2 hrs. The reaction mixture was quenched by addition of 1 N HCl (25 mL) at 20° C. and stirred for 30 min. Then the mixture was diluted with water (20 mL) and extracted with EA (50 mL×2). The combined organic layers were washed with brine (50 mL), dried over $Na_2SO_4$, filtered, and concentrated in vacuo. The residue was purified by FCC (Eluent: DCM: MeOH=100:1 to 10:1) affording the title compound (400 mg, 1.56 mmol) as colorless oil.

$^1H$ NMR (400 MHz, $CDCl_3$) δ=7.47 (d, J=2.0, 1H), 7.33 (d, J=8.4 Hz, 1H), 6.89 (d, J=8.4 Hz, 1H), 4.79-4.68 (m, 2H), 4.05 (d, J=11.6 z, 1H), 3.82-3.75 (m, 1H), 3.71-3.63 (m, 1H), 3.53 (d, J=11.6 Hz, 1H), 1.21 (s, 3H).

Step 3. (6-Bromo-4-methyl-isochroman-4-yl)methanol

To a solution of NaCN (146.20 mg, 2.98 mmol) in DMSO (2 mL) was stirred at 100° C. for 0.5 hr. (6-Bromo-4-methyl-isochroman-4-yl)methanol (200 mg, 596.63 umol) was added into the mixture at 25° C. Then the reaction was stirred at 120° C. for 16 hrs. It was poured into water (80 mL) and extracted with EA (40 mL*3). The combined organic layers were washed with brine (40 mL) and then dried over $Na_2SO_4$, filtered and concentrated. The residue was purified by flash silica gel chromatography (ISCO®; 12 g SepaFlash® Silica Flash Column, Eluent of 0~50% Ethyl acetate/Petroleum ether gradient @ 50 mL/min) affording the title compound (130 mg, 488.48 umol) as a colorless oil.

$^1H$ NMR (400 MHz, $CDCl_3$) δ=7.50 (s, 1H), 7.42-7.32 (m, 1H), 6.90 (d, J=8.4 Hz, 1H), 4.90-4.65 (m, 2H), 3.93 (d, J=11.6 Hz, 1H), 3.58 (d, J=11.6 Hz, 1H), 2.83-2.74 (m, 1H), 2.69-2.56 (m, 1H), 1.42 (s, 3H) ppm.

Step 4. 4-(cyanomethyl)-4-methylisochromane-6-carboxylic acid (Intermediate 33)

A mixture of Intermediate 3 (130 mg, 488.48 umol), dicyclohexyl (3-dicyclohexylphosphaniumylpropyl)phosphonium;ditetrafluoroborate (29.91 mg, 48.85 umol), $Pd(OAc)_2$ (10.97 mg, 48.85 umol), $H_2O$ (17.60 mg, 976.95 umol) and $K_2CO_3$ (101.27 mg, 732.72 umol) in DMSO (1.5 mL) was degassed and purged with CO for 3 times, and then the mixture was stirred at 100° C. for 16 hrs under CO (15 psi) atmosphere. The reaction mixture was poured into water (80 mL) and extracted with EA (40 mL*2). The aqueous phase was adjusted to pH=5 by aq·HCl (1 M) and extracted with EA (30 mL*3), the combined organic layers were washed brine (30 mL) and then dried over $Na_2SO_4$, filtered and concentrated to give Intermediate 33 (90 mg) as a white solid which was used for next step directly without further purification.

LCMS (ESI) m/z: $[M+H]^+$=232.0.

$^1$H NMR (400 MHz, DMSO-$d_6$) δ=13.27-12.73 (m, 1H), 8.06 (d, J=1.2 Hz, 1H), 7.87-7.70 (m, 1H), 7.20 (d, J=8.0 Hz, 1H), 4.91-4.71 (m, 2H), 3.80 (d, J=11.6 Hz, 1H), 3.62 (d, J=11.6 Hz, 1H), 3.08-2.87 (m, 2H), 1.33 (s, 3H) ppm.

Intermediate 34: Preparation of 3-(1-fluoro-3-hydroxycyclobutyl)benzoic acid

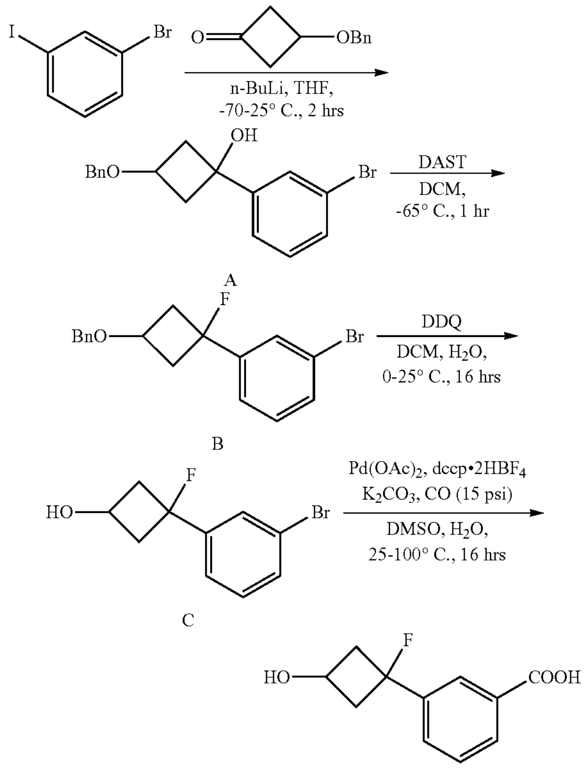

34

Step 1: Preparation of 3-benzyloxy-1-(3-bromophenyl)cyclobutanol (Intermediate A)

A

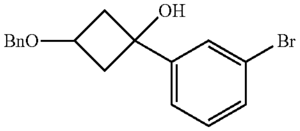

To a mixture of 1,3-dibromobenzene (30 g, 127.17 mmol, 15.31 mL) in THE (1.2 L) was added n-BuLi (2.5 M, 50.87 mL) dropwise at −70° C. under $N_2$. The mixture was stirred at −70° C. for 30 min, then to the mixture was added 3-benzyloxycyclobutanone (22.41 g, 127.17 mmol) drop wise at −70° C. The mixture was stirred at 25° C. for 1.5 hr. The mixture was poured into sat. aq $NH_4Cl$ (2000 mL) at 0° C. and extracted with ethyl acetate (1000 mL*2). The combined organic phase was washed with brine (1000 mL), dried with anhydrous $Na_2SO_4$, filtered and concentrated in vacuum. The residue was purified by silica gel chromatography (Petroleum ether/Ethyl acetate=50/1, 3/1) and concentrated to give Intermediate A (25 g, 75.03 mmol) as yellow oil.

$^1$H NMR (400 MHz, DMSO-$d_6$) δ=7.45-7.41 (m, 2H), 7.36-7.30 (m, 7H), 4.41 (s, 2H), 3.88-3.84 (m, 1H), 2.75-2.72 (m, 2H), 2.36-2.33 (m, 2H) ppm.

Step 2: Preparation of 1-(3-benzyloxy-1-fluoro-cyclobutyl)-3-bromo-benzene (Intermediate B)

B

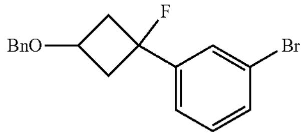

A solution of Intermediate A (6.8 g, 20.41 mmol) in DCM (70 mL) was added DAST (16.45 g, 102.03 mmol, 13.48 mL) at −65° C. Then the reaction mixture was stirred at −65° C. for 1 hr. The reaction mixture was diluted with saturated aqueous $NaHCO_3$ (10 mL) and extracted with DCM (10 mL*3). The combined organic layers were washed with brine (10 mL), dried over $Na_2SO_4$, filtered and concentrated under reduced pressure to give a residue. The residue was purified by flash silica gel chromatography (ISCO®; 20 g SepaFlash® Silica Flash Column, Eluent of 0~20% Ethyl acetate/Petroleum ether gradient @ 35 mL/min) and concentrated under reduced pressure to give Intermediate B (5.6 g, 16.71 mmol) as colorless oil.

$^1$H NMR (400 MHz, $CDCl_3$) δ=7.53-7.29 (m, 4H), 7.28-7.15 (m, 5H), 4.46-4.35 (m, 3H), 2.91-2.75 (m, 2H), 2.54-2.31 (m, 2H) ppm.

Step 3: Preparation of 3-(3-bromophenyl)-3-fluoro-cyclobutanol (Intermediate C)

C

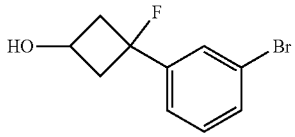

A solution of Intermediate B (5.6 g, 16.71 mmol) in DCM (60 mL) and $H_2O$ (6 mL) was added DDQ (20.86 g, 91.88 mmol) in portions at 0° C. The reaction mixture was stirred at 25° C. for 12 hrs. The reaction mixture was quenched by addition saturated aqueous $NaHCO_3$ (100 mL) at 0° C., and extracted with Ethyl acetate (100 mL*3). The combined organic layers were washed with brine (100 mL), dried over $Na_2SO_4$, filtered and concentrated under reduced pressure to give a residue. The residue was purified by flash silica gel chromatography (ISCO®; 120 g SepaFlash® Silica Flash Column, Eluent of 0~30% Ethyl acetate/Petroleum ether gradient @ 100 mL/min) and concentrated under reduced pressure to give Intermediate C (3 g, 12.24 mmol) as red oil.

Step 4: Preparation of 3-(1-fluoro-3-hydroxy-cyclobutyl)benzoic acid (Intermediate 34)

34

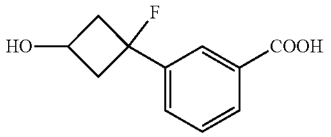

To a solution of Intermediate C (500 mg, 2.04 mmol) in DMSO (7 mL) and $H_2O$ (3.5 mL) was added dicyclohexyl (3-dicyclohexylphosphaniumylpropyl)phosphonium;ditetrafluoroborate (124.91 mg, 204.01 umol), $K_2CO_3$ (422.94 mg, 3.06 mmol), $Pd(OAc)_2$ (22.90 mg, 102.00 umol) at 25° C., then the mixture was degassed and purged with CO for 3 times, and then the mixture was stirred at 100° C. for 16 hrs under CO atmosphere (15 psi). The mixture was filtered. The filtrate was extracted with EA (5 mL), then the aqueous phase was adjusted pH to 5-6 with aqueous HCl (2 ml, 1 M), then extracted with EA (5 mL*3), organic layer was separated and concentrated to give Intermediate 34 (150 mg, 499.52 umol) as brown oil.

LCMS (ESI) m/z: $[M+H]^+$=211.1.

Intermediate 35: Preparation of 3-(3-fluoro-4-hydroxytetrahydrofuran-3-yl)benzoic acid

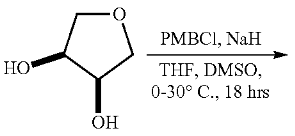

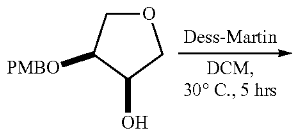

A

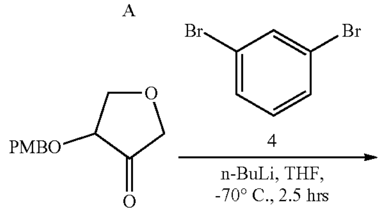

B

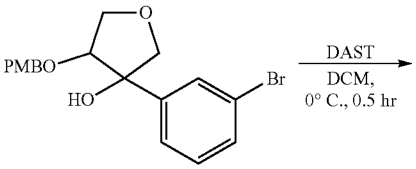

C

-continued

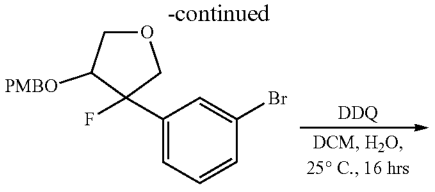

D

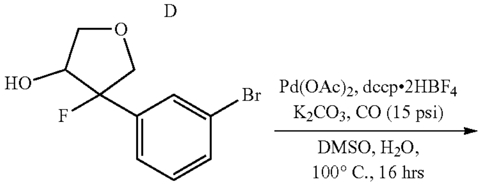

E

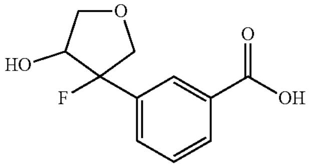

35

Step 1: Preparation of 4-[(4-methoxyphenyl) methoxy]tetrahydrofuran-3-ol (Intermediate A)

A

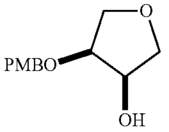

To a solution of NaH (4.73 g, 118.15 mmol) in THF (90 mL) was added a solution of tetrahydrofuran-3,4-diol (12.30 g, 118.15 mmol) in DMSO (42 mL) at 0° C., the mixture was stirred at 30° C. for 2 hrs, then the solution of PMBCl (18.50 g, 118.15 mmol) in THF (30 mL) was added at 0° C., the mixture was stirred at 30° C. for 16 hrs. The reaction mixture was poured into water (200 mL), the solution was extracted with EA (200 mL*3), the combined organic layer was washed with brine (200 mL), dried over $Na_2SO_4$, filtered and concentrated to give a residue. The residue was purified by column chromatography ($SiO_2$, Petroleum ether/Ethyl acetate=10:1-5:1), the solution was concentrated to give Intermediate A (20 g, 89.19 mmol) as yellow oil.

$^1H$ NMR (400 MHz, $CDCl_3$) δ=7.27 (d, J=8.8 Hz, 2H), 6.97-6.83 (m, 2H), 4.54 (s, 2H), 4.23 (d, J=3.6 Hz, 1H), 4.12 (m, 1H), 3.92-3.84 (m, 2H), 3.81 (s, 3H), 3.77-3.69 (m, 2H) ppm.

Step 2: Preparation of 4-[(4-methoxyphenyl) methoxy]tetrahydrofuran-3-one (Intermediate B)

B

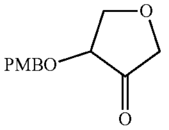

Toa solution of Intermediate A (18 g, 80.27 mmol) in DCM (180 mL) was added Dess-Martin (102.13 g, 240.80 mmol), the mixture was stirred at 30° C. for 5 hrs. The reaction mixture was poured into $Na_2S_2O_3$ solution (500 mL), the solution was extracted with EA (500 mL*3), the combined organic layer was washed with $NaHCO_3$ (1000 mL), dried over $Na_2SO_4$, filtered and concentrated to give a residue. The residue was purified by column chromatography ($SiO_2$, PE:EA=5:1.10:1-5:1), the solution was concentrated to give Intermediate B (2 g, 9.00 mmol) as colorless oil.

$^1$HNMR (400 MHz, $CDCl_3$) δ=7.29 (d, J=8.8 Hz, 2H), 6.93-6.86 (m, 2H), 4.84 (d, J=11.6 Hz, 1H), 4.61 (d, J=11.6 Hz, 1H), 4.26 m, 1H), 4.06-3.92 (m, 3H), 3.86-3.79 (m, 4H) ppm.

Step 3: Preparation of 3-(3-bromophenyl)-4-[(4-methoxyphenyl)methoxy]tetrahydrofuran-3-ol (Intermediate C)

C

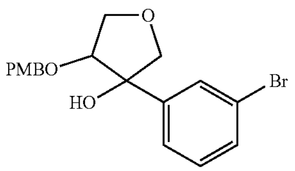

To a solution of 1,3-dibromobenzene (3.61 g, 15.30 mmol, 1.84 mL) in THE (36 mL) was added n-BuLi (2.5 M, 6.12 mL) at −70° C., the solution was stirred at −70° C. for 30 min, then to the solution was added a solution Intermediate B (1.7 g, 7.65 mmol) in THE (5 mL), the mixture was stirred at −70° C. for 2 hrs. The reaction mixture was poured into $NH_4Cl$ (100 mL) solution, the solution was extracted with EA (100 mL*3), the combined organic layer was washed with brine (150 mL), dried over $Na_2SO_4$, filtered and concentrated to give a residue. The residue was purified by column chromatography ($SiO_2$, Petroleum ether/Ethyl acetate=10:1-5:1), the solution was concentrated to give Intermediate C (1 g, 2.64 mmol) as colorless oil.

$^1$H NMR (400 MHz, $CDCl_3$) δ=7.70 (m, 1H), 7.48-7.42 (m, 2H), 7.29-7.23 (m, 1H), 7.12 (d, J=8.8 Hz, 2H), 6.88-6.84 (m, 2H), 4.46-4.36 (m, 2H), 4.18-4.12 (m, 2H), 4.00 (s, 2H), 3.85-3.81 (m, 3H), 3.63 (s, 1H) ppm.

Step 4: Preparation of 3-(3-bromophenyl)-3-fluoro-4-[(4-methoxyphenyl)methoxy]tetrahydrofuran (Intermediate D)

D

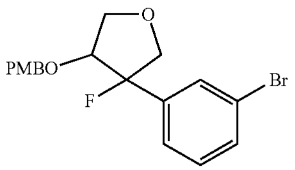

To a solution of Intermediate C (500 mg, 1.32 mmol) in DCM (5 mL) was added DAST (212.51 mg, 1.32 mmol) at 0° C., the mixture was stirred at 0° C. for 30 min. The mixture was poured into $NaHCO_3$ solution (20 mL), the solution was extracted with DCM (20 mL*3), the combined organic layer was washed with brine (50 mL), dried over $Na_2SO_4$, filtered and concentrated to give oil. The residue was purified by prep-TLC ($SiO_2$, PE:EA=2:1), the solid was triturated with EA (20 mL), the solution was filtered and the filtrate was concentrated to give Intermediate D (150 mg, 393.46 umol) as yellow oil.

$^1$H NMR (400 MHz, $CDCl_3$) δ=7.61 (m, 1H), 7.46 (m, 1H), 7.37 (d, J=8.0 Hz, 1H), 7.23-7.19 (m, 1H), 6.90-6.85 (m, 2H), 6.75-6.71 (m, 2H), 4.15 (d, J=1.2 Hz, 1H), 4.12-4.06 (m, 2H), 4.05-3.97 (m, 2H), 3.96-3.89 (m, 2H), 3.71 (s, 3H) ppm.

Step 5: Preparation of 4-(3-bromophenyl)-4-fluoro-tetrahydrofuran-3-ol (Intermediate E)

E

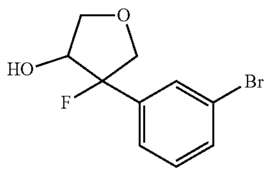

To a solution of Intermediate D (100 mg, 262.31 umol) in DCM (3.5 mL) and $H_2O$ (0.35 mL) was added DDQ (327.49 mg, 1.44 mmol), the mixture was stirred at 25° C. for 16 hrs under $N_2$. The reaction mixture was poured into $NaHCO_3$ solution (20 mL), the solution was extracted with EA (20 mL*3), the combined organic layer was washed with brine (40 mL), dried over $Na_2SO_4$, filtered and concentrated to give a residue. The residue was purified by prep-TLC ($SiO_2$, PE:EA=2:1), the solid was triturated with EA (20 mL), the solution was filtered and the filtrate was concentrated to give Intermediate E (45 mg, 172.36 umol) as yellow oil.

$^1$H NMR (400 MHz, $CDCl_3$) δ=7.69 (m, 1H), 7.58-7.53 (m, 1H), 7.45-7.41 (m, 1H), 7.35-7.29 (m, 1H), 4.41-4.29 (m, 2H), 4.29-4.17 (m, 2H), 4.01 (d, J=9.6 Hz, 1H) ppm.

Step 6: Preparation of 3-(3-fluoro-4-hydroxy-tetrahydrofuran-3-yl)benzoic acid (Intermediate 35)

35

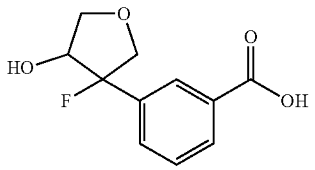

To a solution of Intermediate E (45 mg, 172.36 umol) in DMSO (0.5 mL) was added dicyclohexyl (3-dicyclohexylphosphaniumylpropyl)phosphonium;ditetrafluoroborate (10.55 mg, 17.24 umol), $Pd(OAc)_2$ (3.87 mg, 17.24 umol), $K_2CO_3$ (35.73 mg, 258.53 umol) and $H_2O$ (6.21 mg, 344.71 umol, 6.21 uL). The suspension was degassed under vacuum and purged with CO several times. The mixture was stirred under CO (15 psi) at 100° C. for 16 hrs. The reaction mixture was poured into water (10 mL), the solution was extracted with MTBE (10 mL*2). Then the aqueous phase was adjusted to pH=3 with HCl solution, the solution was extracted with EA (10 mL*3), the combined organic layer was washed with brine (20 mL), dried over $Na_2SO_4$, filtered and concentrated to give Intermediate 35 (38 mg, 167.99 umol) was obtained as yellow oil.

Intermediate 36: Preparation of 5-fluoro-5-methyl-2,3,4,5-tetrahydrobenzo[b]oxepine-7-carboxylic acid

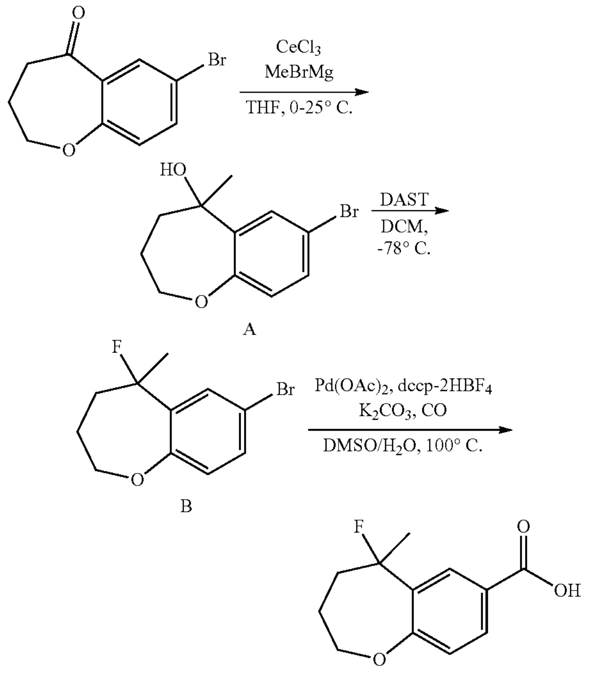

36

Step 1: Preparation of 7-bromo-5-methyl-2,3,4,5-tetrahydrobenzo[b]oxepin-5-ol (Intermediate A)

2

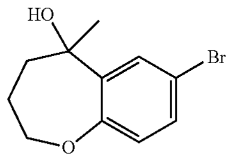

To a solution of 7-bromo-3,4-dihydrobenzo[b]oxepin-5(2H)-one (800 mg, 3.32 mmol) and $CeCl_3$ (408.95 mg, 1.66 mmol, 104.32 uL) in THE (8 mL) was added MeMgBr (3 M, 3.32 mL) at 0° C. The mixture was stirred at 0° C. for 1 hrs then allowed to warm to 25° C. and stirred for another 2 hrs. The reaction mixture was quenched by sat.$NH_4Cl$ (8 mL), then extracted with EA (8 mL*3). The combined organic was concentrated to get a residue. The residue was purified by flash silica gel chromatography (PE:EA=1:0 to 1:1). The eluent was concentrated to give Intermediate A (340 mg, 1.19 mmol) as a yellow solid.

$^1$H NMR (400 MHz, $CDCl_3$) δ=7.71 (d, J=2.4 Hz, 1H), 7.30-7.27 (m, 1H), 6.86 (d, J=8.4 Hz, 1H), 4.26-4.08 (m, 1H), 3.85-3.71 m, 1H), 2.30 (s, 1H), 2.19-2.05 (m, 1H), 2.03-1.85 (m, 3H), 1.60 (s, 3H) ppm.

Step 2: Preparation of 7-bromo-5-fluoro-5-methyl-2,3,4,5-tetrahydrobenzo[b]oxepine (Intermediate B)

B

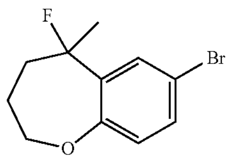

To a solution of Intermediate A (340 mg, 1.32 mmol) in DCM (4 mL) was added DAST (1.07 g, 6.61 mmol, 873.54 uL) at −78° C. The mixture was stirred at −78° C. for 2 hrs. The reaction was quenched by sat.$NaHCO_3$ (5 mL) at 0° C. and extracted with EA (5 mL*3). The combined organic layer was dried over anhydrous $Na_2SO_4$, filtered and concentrated under reduced pressure to give Intermediate B (340 mg, 1.06 mmol) as colorless oil.

$^1$H NMR (400 MHz, $CDCl_3$) δ=7.64 (d, J=2.4 Hz, 1H), 7.30 (m, 1H), 6.87 (m, 1H), 4.45-4.34 (m, 1H), 3.59 (m, 1H), 2.23-2.11 (m, 2H), 2.05-1.80 (m, 2H), 1.76-1.63 (m, 3H) ppm.

Step 3: Preparation of 5-fluoro-5-methyl-2,3,4,5-tetrahydrobenzo[b]oxepine-7-carboxylic acid (Intermediate 36)

36

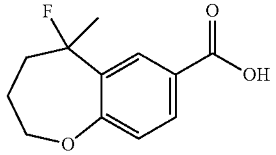

A mixture of Intermediate B (340 mg, 1.31 mmol), dicyclohexyl(3-dicyclohexylphosphaniumylpropyl)phosphonium;ditetrafluoroborate (80.34 mg, 131.22 umol) and $K_2CO_3$ (272.02 mg, 1.97 mmol) in DMSO (3 mL) and $H_2O$ (1.5 mL) was added $Pd(OAc)_2$ (14.73 mg, 65.61 umol). The suspension was degassed under vacuum and purged CO with balloon several times. Then the mixture was stirred at 100° C. for 12 hrs under CO (15 psi). The reaction mixture was quenched by sat.$NH_4Cl$ (3 mL), then extracted with EA (5 mL*3). The combined organic concentrated to get a residue. The residue was purified by reversed phased HPLC (0.1% FA). The eluent was lyophilized to give the crude. The crude was separation by SFC (column: DAICEL CHIRALPAK AD-H (250 mm*30 mm, 5 um); mobile phase: [Neu-ETOH]; B %: 25%-25%, 2.9 min; 80 min). This afforded Intermediate 36 (67 mg, 295.73 umol) as a white solid.

LCMS (ESI) m/z: $[M+H]^+$=225.1.

$^1$H NMR (400 MHz, $CDCl_3$) δ=8.31 (d, J=2.0 Hz, 1H), 7.98 (m, 1H), 7.07 (m, 1H), 4.51-4.37 (m, 1H), 3.76-3.63 (m, 1H), 2.30-2.14 (m, 2H), 2.13-1.86 (m, 2H), 1.79-1.66 (m, 3H) ppm.

Chiral SFC: AD-3-MeOH (DEA)-5-40-3 mL-35T·lcm; Rt=0.918/0.990 min.

Intermediates 37 and 38: Preparation of (S)-4-cyano-8-methoxy-4-methylisochromane-6-carboxylic acid and (R)-4-cyano-8-methoxy-4-methylisochromane-6-carboxylic acid

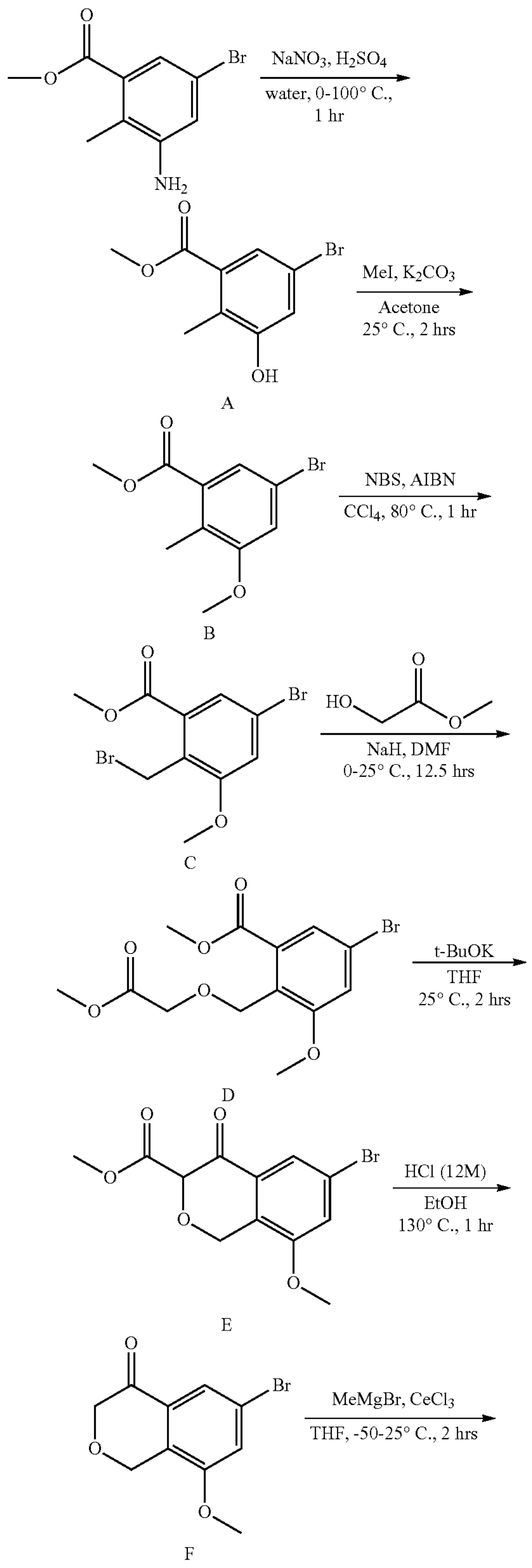

-continued

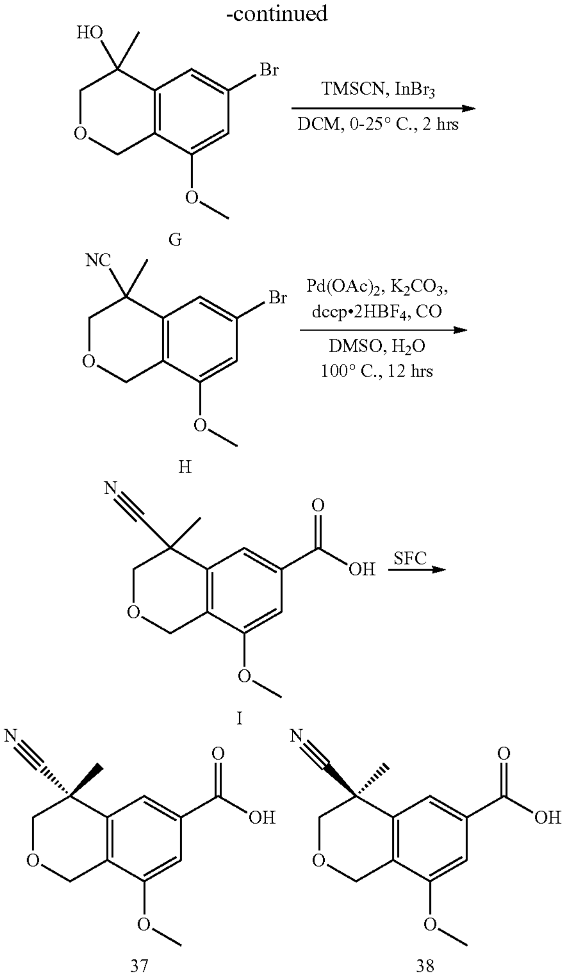

Step 1: Preparation of methyl 5-bromo-3-hydroxy-2-methyl-benzoate (Intermediate A)

A

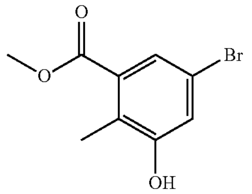

To a solution of methyl 3-amino-5-bromo-2-methyl-benzoate (40 g, 163.88 mmol) in 10% $H_2SO_4$ (400 mL) was added a solution of $NaNO_3$ (13.93 g, 163.88 mmol) in water (80 mL) dropwise at 0° C. The mixture was stirred at 25° C. for 1 hrs and a solution of 50% $H_2SO_4$ (400 mL) in water (400 mL) was added, and then the resulting mixture was heated at 100° C. for 1 hrs. Some solid was precipitated out of the mixture at 25° C. overnight. The mixture was filtered. The filter cake was diluted with water (200 mL) and extracted with EA (200 mL*2). The combine organic layer was dried anhydrous $Na_2SO_4$ and concentrated to give Intermediate A (50 g, crude) as brown oil which was used into the next step without further purification.

LCMS (ESI) m/z: $[^{79}BrM+H]^+$=245.0.

Step 2: Preparation of methyl 5-bromo-3-methoxy-2-methyl-benzoate (Intermediate B)

B

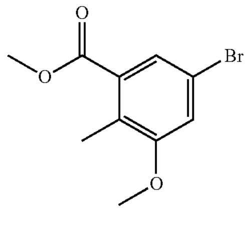

To a solution of Intermediate A (50 g, 204.02 mmol) in acetone (500 mL) was added $K_2CO_3$ (140.99 g, 1.02 mol) and MeI (144.79 g, 1.02 mol). The mixture was stirred at 25° C. for 2 hrs. The mixture was filtered and the filtrate was concentrated to remove acetone. Then the residue was diluted with Sat.$NH_4Cl$ (300 mL) and was extracted with EA (300 mL*2). The combined organic layer was dried over anhydrous $Na_2SO_4$ and concentrated under vacuum to give a residue, which was purified by column chromatography ($SiO_2$, Petroleum ether/Ethyl acetate=100/1 to 1/1) to give Intermediate B (27.3 g, 93.78 mmol) as colorless oil.

LCMS (ESI) m/z: $[^{71}BrM+H]^+$=259.0.

$^1H$ NMR (400 MHz, $CDCl_3$) δ=7.55 (d, J=1.6 Hz, 1H), 7.09 (d, J=2.0 Hz, 1H), 3.89 (s, 3H), 3.85 (s, 3H), 2.37 (s, 3H) ppm.

Step 3: Preparation of methyl 5-bromo-2-(bromomethyl)-3-methoxy-benzoate (Intermediate C)

C

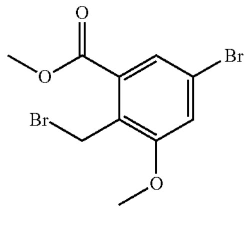

To a solution of Intermediate B (27.3 g, 105.37 mmol) in $CCl_4$ (273 mL) was added NBS (18.75 g, 105.37 mmol) and AIBN (1.73 g, 10.54 mmol). The mixture was stirred at 80° C. for 1 hr. The mixture was filtered and the filtrate was diluted with water (200 mL). The mixture was extracted with DCM (200 mL*2). The combined organic phase was dried over anhydrous $Na_2SO_4$ and concentrated under vacuum to give a residue, which was purified by column chromatography ($SiO_2$, Petroleum ether/Ethyl acetate=50/1 to 1/1). The eluent was concentrated to give Intermediate C (32.8 g, 95.10 mmol) as colorless oil.

$^1H$ NMR (400 MHz, $CDCl_3$) δ=7.67 (d, J=2.0 Hz, 1H), 7.19 (d, J=2.0 Hz, 1H), 4.98 (s, 2H), 3.94 (s, 3H), 3.93 (s, 3H) ppm.

Step 4: Preparation of methyl 5-bromo-3-methoxy-2-[(2-methoxy-2-oxo-ethoxy)methyl]benzoate (Intermediate D)

D

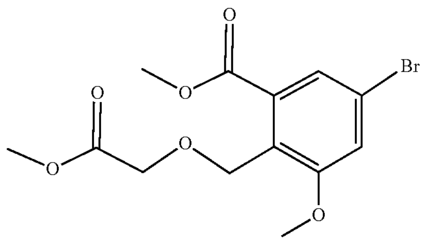

To a mixture of methyl 2-hydroxyacetate (17.48 g, 194.09 mmol) in DMF (310 mL) was added NaH (7.76 g, 194.09 mmol, 60% purity) at 0° C. under $N_2$ and the mixture was stirred at 25° C. for 30 min. Then Intermediate C (32.8 g, 97.04 mmol) dissolved in DMF (40 mL) was added slowly at 0° C. and the mixture was stirred at 25° C. for 12 hrs. The mixture was quenched with Sat. $NH_4Cl$ (1 L) and was extracted with EtOAc (1 L*2). The combined organic phase was washed with brine (1 L*2), dried over anhydrous $Na_2SO_4$, filtered and concentrated under vacuum. The residue was purified by column chromatography ($SiO_2$, Petroleum ether/Ethyl acetate=100/1 to 1/1). The eluent was concentrated to give Intermediate D (24 g, 69.13 mmol) as colorless oil.

$^1H$ NMR (400 MHz, DMSO-$d_6$) δ=7.43 (d, J=1.6 Hz, 1H), 7.40 (d, J=2.0 Hz, 1H), 4.73 (s, 2H), 4.05 (s, 2H), 3.85 (s, 3H), 3.81 (s, 3H), 3.64 (s, 3H) ppm.

Step 5: Preparation of methyl 6-bromo-8-methoxy-4-oxo-isochromane-3-carboxylate (Intermediate E)

E

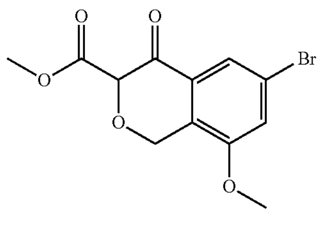

To a solution of Intermediate D (5 g, 14.40 mmol) in THE (50 mL) was added t-BuOK (3.23 g, 28.81 mmol) and the mixture was stirred at 25° C. for 2 hrs. The mixture was diluted with water (500 mL) and extracted with EA (500 mL*2). The combined organic layer was dried over anhydrous $Na_2SO_4$ and concentrated to give Intermediate E (3.2 g, 10.15 mmol) as a yellow solid which was used into the next step without further purification.

Step 6: Preparation of 6-bromo-8-methoxy-isochroman-4-one (Intermediate F)

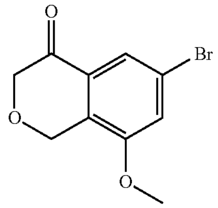

F

To a solution of Intermediate E (3.2 g, 10.15 mmol) in EtOH (32 mL) was added HCl (12 M, 64 mL). The mixture was stirred at 130° C. for 1 hrs. The mixture was diluted with water (200 mL) and filtered. The filter cake was dried under vacuum to give Intermediate F (2.4 g, 9.34 mmol) as a white solid which was used into the next step without further purification.

$^1H$ NMR (400 MHz, DMSO-$d_6$) δ=7.57 (d, J=1.6 Hz, 1H), 7.51 (d, J=2.0 Hz, 1H), 4.78 (s, 2H), 4.34 (s, 2H), 3.88 (s, 3H) ppm.

Step 7: Preparation of 6-bromo-8-methoxy-4-methyl-isochroman-4-ol (Intermediate G)

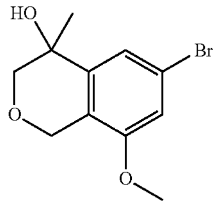

G

To a mixture of Intermediate F (2.4 g, 9.34 mmol) and $CeCl_3$ (1.15 g, 4.67 mmol) in THF (24 mL) was added MeMgBr (3 M, 15.56 mL) dropwise at −50° C. under $N_2$. The reaction mixture was stirred at 25° C. for 2 hrs. The mixture was quenched with water (200 mL) and extracted with EtOAc (200 mL*2). The combined organic phase was dried over anhydrous $Na_2SO_4$, filtered and concentrated under vacuum. The residue was purified by flash silica gel chromatography (ISCO®; 40 g SepaFlash® Silica Flash Column, Eluent of 0~100% Ethylacetate/Petroleum ethergradient). The eluent was concentrated to give Intermediate G (1.8 g, 6.59 mmol) as colorless oil.

$^1H$ NMR (400 MHz, DMSO-$d_6$) δ=7.29 (d, J=1.6 Hz, 1H), 7.01 (d, J=1.6 Hz, 1H), 5.31 (s, 1H), 4.59-4.46 (m, 2H), 3.78 (s, 3H), 3.60-3.58 (m, 1H), 3.47 (d, J=11.2 Hz, 1H), 1.36 (s, 3H) ppm.

Step 8: Preparation of 6-bromo-8-methoxy-4-methyl-isochromane-4-carbonitrile (Intermediate H)

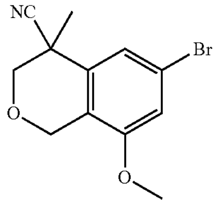

H

To a solution of Intermediate G (1.3 g, 4.76 mmol) in DCM (13 mL) was added TMSCN (1.42 g, 14.28 mmol) and tribromoindigane (337.50 mg, 951.95 umol) at 0° C. The mixture was stirred at 25° C. for 2 hrs. The mixture was diluted with water (50 mL) and extracted with DCM (50 mL*2). The combined organic layer was dried with anhydrous $Na_2SO_4$ and concentrated to give a residue, which was purified by flash silica gel chromatography (ISCO®; 40 g SepaFlash® Silica Flash Column, Eluent of 0~100% Ethylacetate/Petroleum ethergradient). The eluent was concentrated to give Intermediate H (620 mg, 2.20 mmol) as colorless oil.

$^1H$ NMR (400 MHz, DMSO-$d_6$) δ=7.40 (d, J=1.6 Hz, 1H), 7.19 (d, J=1.6 Hz, 1H), 4.69-4.54 (m, 2H), 4.12 (d, J=11.2 Hz, 1H), 3.82 (s, 3H), 3.74 (d, J=11.6 Hz, 1H), 1.62 (s, 3H) ppm.

Step 9: Preparation of 4-cyano-8-methoxy-4-methyl-isochromane-6-carboxylic acid (Intermediate I)

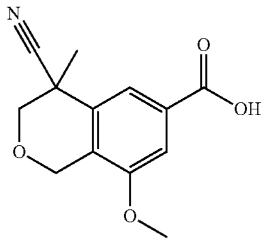

I

To a solution of Intermediate H (620 mg, 2.20 mmol) in DMSO (6 mL) and $H_2O$ (198.00 mg, 10.99 mmol) was added dicyclohexyl(3-dicyclohexylphosphaniumylpropyl) phosphonium;ditetra fluoroborate (134.55 mg, 219.75 umol), $K_2CO_3$ (455.58 mg, 3.30 mmol) and $Pd(OAc)_2$ (49.34 mg, 219.75 umol) was degassed and purged with CO for 3 times, and then the mixture was stirred at 100° C. for 12 hrs under CO (15 psi) atmosphere. The mixture was diluted with water (40 mL) and extracted with DCM (40 mL*2). The organic layer was discarded. The aqueous phase was adjusted pH=2 with 1 N HCl and some solid was formed. The mixture was filtered and the filter cake was dried under vacuum to give Intermediate I (330 mg, 1.33 mmol) as a white solid.

$^1H$ NMR (400 MHz, DMSO-$d_6$) δ=7.71 (d, J=1.2 Hz, 1H), 7.44 (d, J=1.2 Hz, 1H), 4.79-4.67 (m, 2H), 4.14 (d, J=11.2 Hz, 1H), 3.86 (s, 3H), 3.83 (d, J=11.2 Hz, 1H), 1.65 (s, 3H) ppm.

Step 10: Preparation of tert-butyl 8-((2-oxo-2-((4-(3-(pyridin-4-yl)phenyl)thiazol-2-yl)amino)ethyl)carbamoyl)-2,3-dihydrobenzo[f][1,4]thiazepine-4(5H)-carboxylate 1,1-dioxide (Intermediates 37 and 38)

37

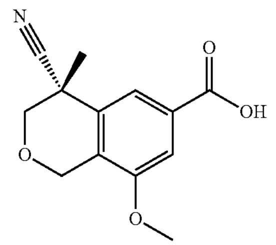

38

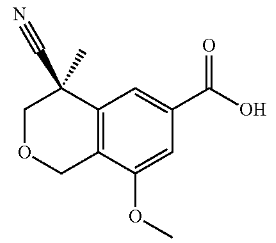

A mixture of Intermediate I (450 mg, 1.82 mmol) in MeOH (5 mL) was separated by SFC (column: DAICEL CHIRALPAK IC (250 mm*30 mm, 5 um); mobile phase: [0.1% $NH_3 \cdot H_2O$ MEOH]; B %: 25%-25%, 2.1 min; 69 min). The eluent was concentrated to give Intermediate 37 (140 mg, 528.07 umol) as an off-white solid and Intermediate 38 (180 mg, 652.67 umol) as a white solid.

Intermediate 37

LCMS (ESI) m/z: $[M+H]^+$=248.1.

$^1H$ NMR (400 MHz, DMSO-$d_6$) δ=7.70 (s, 1H), 7.44 (s, 1H), 4.78-4.67 (m, 2H), 4.14 (d, J=11.4 Hz, 1H), 3.85 (s, 1H), 3.83-3.81 (m, 1H), 1.64 (s, 3H) ppm.

Chiral SFC: IC-3_5CM_MEOH (DEA) _5_40_3ML_T35.M; Rt=1.089 min.

Intermediate 38

LCMS (ESI) m/z: $[M+H]^+$=248.1.

$^1H$ NMR (400 MHz, DMSO-$d_6$) δ=7.68 (s, 1H), 7.44 (s, 1H), 4.77-4.65 (m, 2H), 4.12 (d, J=11.2 Hz, 1H), 3.84 (s, 3H), 3.83-3.80 (m, 1H), 1.63 (s, 3H) ppm.

Chiral SFC: IC-3_5CM_MEOH (DEA) _5_40_3ML_T35.M; Rt=1. 192 min.

Intermediate 39: Preparation of spiro[chromane-4,3'-oxetane]-6-carboxylic acid

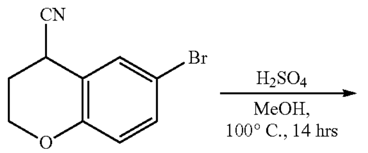

-continued

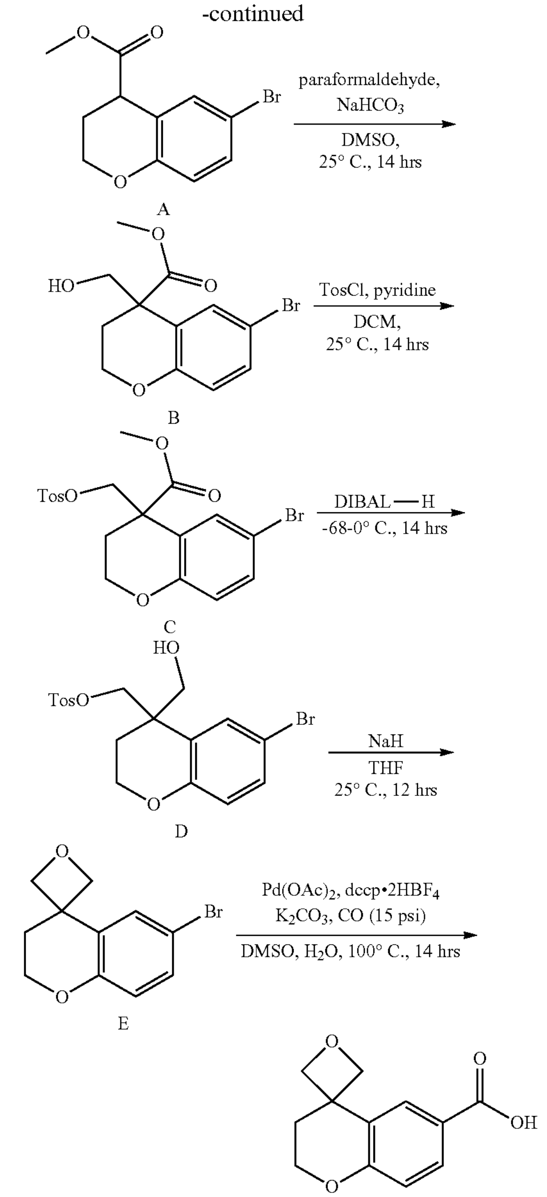

A

B

C

D

E

39

Step 1: Preparation of Intermediate 2 methyl 6-bromochroman-4-carboxylate (Intermediate A)

A

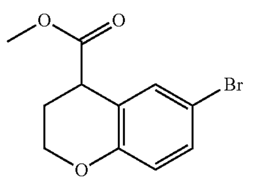

To a solution of 6-bromochromane-4-carbonitrile (Prepared according to the method in FG-A2875) (2 g, 8.40 mmol) in MeOH (48 mL) was added $H_2SO_4$ (21.02 g, 210.01 mmol, 98% purity). The reaction mixture was stirred at 100° C. for 14 hrs. The reaction mixture was concentrated under reduced pressure to remove MeOH, and then adjusted pH=6 with aq. $Na_2CO_3$, extracted with EA (150 mL*3). The combined organic layer was dried over anhydrous $Na_2SO_4$, filtered and concentrated under reduced pressure to get the residue. The residue was purified by flash silica gel chromatography ($SiO_2$, Petroleum ether/Ethyl acetate=1/0 to 3/1), the fraction was concentrated under reduced pressure to get Intermediate A (1.5 g, 4.98 mmol) as a white solid.

LCMS (ESI) m/z: $[^{79}BrM+H]^+$=271.0.

$^1H$ NMR (400 MHz, DMSO-$d_6$) δ=7.39-7.26 (m, 2H), 6.77 (d, J=8.8 Hz, 1H), 4.25-4.20 (m, 1H), 4.09-4.03 (m, 1H), 3.95-3.92 (m, 1H), 3.68 (s, 3H), 2.23-2.13 (m, 1H), 2.11-1.98 (m, 1H) ppm.

Step 2: Preparation of methyl 6-bromo-4-(hydroxymethyl)chroman-4-carboxylate (Intermediate B)

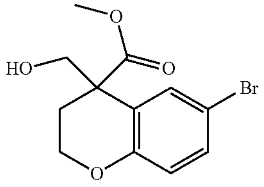
B

To a solution of Intermediate A (1.5 g, 5.53 mmol) and $NaHCO_3$ (46.48 mg, 553.29 umol) in DMSO (15 mL) was added paraformaldehyde (199.25 mg, 6.64 mmol) and the mixture was stirred at 25° C. for 14 hrs. The reaction mixture was diluted with water (100 mL), extracted with EA (100 mL*3). The combined organic layer was washed with brine (300 mL*2), then dried over anhydrous $Na_2SO_4$, filtered and concentrated under reduced pressure to get the residue. The residue was purified by flash silica gel chromatography (PE:EA=1:0 to 2:1), the fraction was concentrated under reduced pressure to give Intermediate B (1.55 g, 4.07 mmol) as a white solid.

LCMS (ESI) m/z: $[M+H]^+$=301.0.

$^1H$ NMR (400 MHz, DMSO-d) δ=7.57 (d, J=2.4 Hz, 1H), 7.31-7.29 (m, 1H), 6.76 (d, J=8.8 Hz, 1H), 5.30-5.27 (m, 1H), 4.25-4.20 (m, 1H), 4.09-4.03 (m, 1H), 3.94-3.90 (m, 1H), 3.69-3.62 (m, 4H), 2.37-2.30 (m, 1H), 2.03-1.94 (m, 2H) ppm.

Step 3: Preparation of methyl 6-bromo-4-((tosyloxy)methyl)chroman-4-carboxylate (Intermediate C)

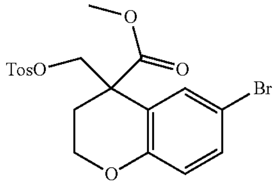
C

To s solution of Intermediate B (1.3 g, 4.32 mmol) and pyridine (2.05 g, 25.90 mmol) in DCM (10 mL) was added TosCl (2.47 g, 12.95 mmol) at 0° C. The mixture was stirred at 25° C. for 14 hrs. The reaction mixture was diluted with water (60 mL), extracted with DCM (50 mL*3). The combined organic layer was dried over anhydrous $Na_2SO_4$, filtered and concentrated under reduced pressure to get the residue. The residue was purified by flash silica gel chromatography (PE:EA=1:0 to 3:1), the fraction was concentrated under reduced pressure to give Intermediate C (1.25 g, 2.35 mmol) as a white solid.

$^1H$ NMR (400 MHz, DMSO-$d_6$) δ=7.75 (d, J=8.4 Hz, 2H), 7.48 (d, J=8.0 Hz, 2H), 7.36-7.32 (m, 1H), 7.31 (d, J=2.4 Hz, 1H), 6.79 (d, J=8.8 Hz, 1H), 4.53 (d, J=9.6 Hz, 1H), 4.34 (d, J=9.6 Hz, 1H), 4.18-4.04 (m, 2H), 3.60 (s, 3H), 2.43 (s, 3H), 2.34-2.26 (m, 1H), 2.03-1.92 (m, 1H) ppm.

LCMS (ESI) m/z: $[M+H_2O]^+$=472.0.

Step 4: Preparation of (6-bromo-4-(hydroxymethyl)chroman-4-yl)methyl 4-methylbenzenesulfonate (Intermediate D)

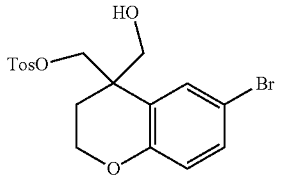
D

To a solution of Intermediate C (800 mg, 1.76 mmol) in THE (8 mL) was added DIBAL-H (1 M, 5.27 mL) at −68° C., then the solution was stirred at −68° C. for 10 min, then the dry ice-EtOH base was removed and the solution was allowed to 0° C. in 1 hr, then the solution was stirred at 0° C. for 20 min. The reaction mixture was quenched with 1 N HCl (4 mL), then diluted with water (40 mL), extracted with EA (40 mL*3). The combined organic layer was dried over anhydrous $Na_2SO_4$, filtered and concentrated under reduced pressure to get the residue. The residue was purified by flash silica gel chromatography ($SiO_2$, Petroleum ether/Ethyl acetate=1/0 to 3/1), the fraction was concentrated under reduced pressure to give Intermediate D (650 mg, 1.37 mmol, 77.92% yield) as a white solid.

LCMS (ESI) m/z: $[M+H_2O]^+$=444.0.

Step 5: Preparation of 6-bromospiro[chroman-4,3'-oxetane] (Intermediate E)

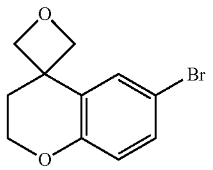
E

To a solution of Intermediate D (450 mg, 1.05 mmol) in THE (25 mL) was added NaH (126.36 mg, 3.16 mmol, 60% purity). The mixture was stirred at 25° C. for 12 hrs. The reaction mixture was diluted with $H_2O$ (100 mL), extracted with EA (100 mL*3). The combined organic layer was dried over anhydrous $Na_2SO_4$, filtered and concentrated under reduced pressure to get the residue. The residue was purified by flash silica gel chromatography ($SiO_2$, Petroleum ether/Ethyl acetate=1/0 to 2/1, Rf=0.6), the fraction was concentrated under reduced pressure to give Intermediate E (140 mg, 460.87 umol) as a white solid.

$^1H$ NMR (400 MHz, DMSO-$d_6$) δ=7.90 (d, J=2.4 Hz, 1H), 7.32-7.30 (m, 1H), 6.74 (d, J=8.8 Hz, 1H), 4.71 (d, J=6.0 Hz, 2H), 4.52 (d, J=6.0 Hz, 2H), 4.10-4.04 (m, 2H), 2.28-2.22 (m, 2H) ppm.

Step 6: Preparation of spiro[chroman-4,3'-oxetane]-6-carboxylic acid (Intermediate 39)

39

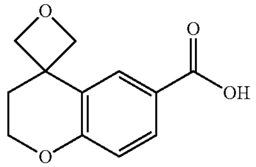

A mixture of Intermediate E (140 mg, 548.79 umol), dicyclohexyl(3-dicyclohexylphosphaniumylpropyl)phosphonium;ditetrafluoroborate (33.60 mg, 54.88 umol), $K_2CO_3$ (113.77 mg, 823.18 umol), $Pd(OAc)_2$ (12.32 mg, 54.88 umol) and $H_2O$ (19.78 mg, 1.10 mmol) in DMSO (3 mL) was degassed and purged with CO for 3 times, and then the mixture was stirred at 100° C. for 14 hrs under CO atmosphere. The reaction mixture was filtered to move off the black solid, and then diluted with water (20 mL), extracted with EA (20 mL*2). The organic layer was discarded and the aqueous phase was adjusted pH=6 with aq. HCl, extracted with EA (30 mL*3), then the combined organic layer was dried over anhydrous $Na_2SO_4$, filtered and concentrated under reduced pressure to get the residue. The residue was purified by reversed-phase HPLC (0.1% FA), then the solution was concentrated under reduced pressure to remove MeCN and then lyophilized to give Intermediate 39 (50 mg, 215.24 umol as a white solid.

LCMS (ESI) m/z: $[M+H]^+$=221.1.

$^1H$ NMR (400 MHz, DMSO-$d_6$) δ=13.13-12.37 (m, 1H), 8.37 (d, J=2.0 Hz, 1H), 7.75-7.72 (m, 1H), 6.84 (d, J=8.4 Hz, 1H), 4.70 (d, J=6.0 Hz, 2H), 4.59 (d, J=6.0 Hz, 2H), 4.17-4.11 (m, 2H), 2.31-2.27 (m, 2H) ppm.

Intermediate 40: Preparation of 1-cyano-1-methylisochromane-7-carboxylic acid

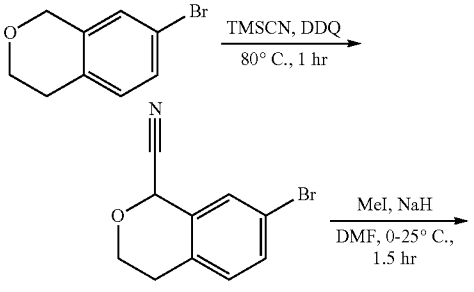

A

-continued

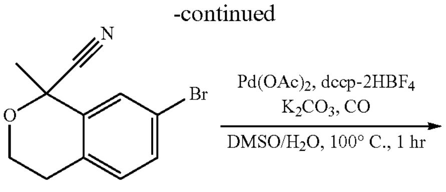

B

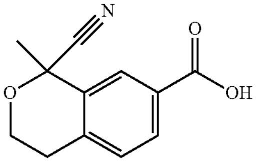

40

Step 1: Preparation of 7-bromoisochromane-1-carbonitrile (Intermediate A)

A

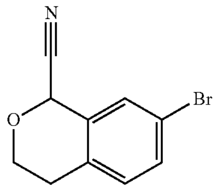

To a mixture of DDQ (511.39 mg, 2.25 mmol) in TMSCN (558.72 mg, 5.63 mmol) was added 7-bromoisochromane (400 mg, 1.88 mmol) under $N_2$. The mixture was stirred at 80° C. for 1 hr. The reaction mixture was diluted with DCM (50 mL) and then was washed with sat.$NaHCO_3$ (50 mL*3), brine (50 mL), dried over $Na_2SO_4$, filtered and concentrated under reduced pressure. The residue was purified by column chromatography ($SiO_2$, PE/EA=30/1 to 5/1) and the eluent was concentrated to give Intermediate A (300 mg, 1.26 mmol) as a white solid.

Step 2: Preparation of 7-bromo-1-methyl-isochroman-1-carbonitrile (Intermediate B)

B

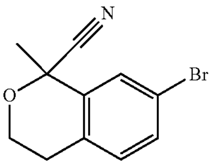

To a mixture of Intermediate A (160 mg, 672.04 umol) in DMF (2 mL) was added NaH (53.76 mg, 1.34 mmol, 60% purity) at 0° C. under $N_2$. The mixture was stirred at 25° C. for 30 min and then $CH_3I$ (476.94 mg, 3.36 mmol) was added at 0° C. The mixture was stirred at 25° C. for 1 hr. The reaction mixture was poured into $NH_4Cl$ solution (20 mL) and was extracted with EA (20.0 mL*3). The combined organics were washed with brine (30 mL), dried over $Na_2SO_4$, filtered and the filtrate was evaporated to dryness.

The residue was purified by column chromatography ($SiO_2$, PE/EA=30/1 to 2/1) and concentrated to give Intermediate B (120 mg, 475.99 umol) as a white solid.

$^1H$ NMR (400 MHz, $CDCl_3$) δ=7.45 (d, J=2.0 Hz, 1H), 7.43-7.40 (m, 1H), 7.06 (d, J=8.0 Hz, 1H), 4.25-4.20 (m, 1H), 4.07-4.01 (m, 1H), 3.06-2.99 (m, 1H), 2.68-2.63 (m, 1H), 1.91 (s, 3H) ppm.

Step 3: Preparation of 1-cyano-1-methyl-isochromane-7-carboxylic acid (Intermediate 40)

40

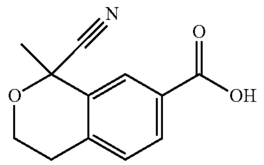

A mixture of Intermediate B (130 mg, 515.65 umol), $H_2O$ (46.46 mg, 2.58 mmol), $K_2CO_3$ (106.90 mg, 773.48 umol), $Pd(OAc)_2$ (5.79 mg, 25.78 umol) and dicyclohexyl(3-dicyclohexylphosphaniumylpropyl)phosphonium;ditetrafluoroborate (31.57 mg, 51.57 umol) in DMSO (2 mL) was degassed and purged with CO for 3 times, and then the mixture was stirred at 100° C. for 1 hr under CO atmosphere (15 psi). The mixture was poured into water (30 mL) and extracted with EA (20.0 mL*2), the combined organics were discarded. The aqueous was adjusted pH to 5 with 1 M HCl and then was extracted with EA (20.0 mL*2). The combined organics were washed with brine (30.0 mL), dried over $Na_2SO_4$, filtered and the filtrate was evaporated to dryness to give Intermediate 40 (90 mg, 397.75 umol) as a white solid.

$^1H$ NMR (400 MHz, $CDCl_3$) δ=8.06 (d, J=1.2 Hz, 1H), 8.02-7.99 (m, 1H), 7.29 (d, J=8.4 Hz, 1H), 4.28-4.24 (m, 1H), 4.14-4.07 (m, 1H), 3.22-3.13 (m, 1H), 2.81-2.76 (m, 1H), 1.97 (s, 3H) ppm.

Intermediate 41: Preparation of lithium spiro[isochromane-4,2'-oxetane]-6-carboxylate

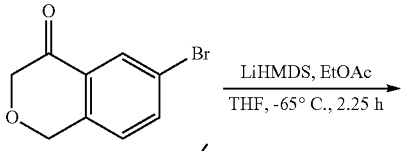

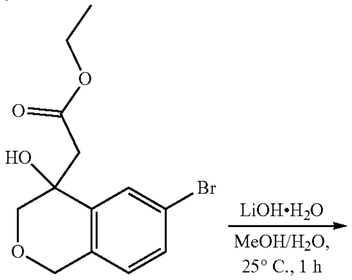

A

-continued

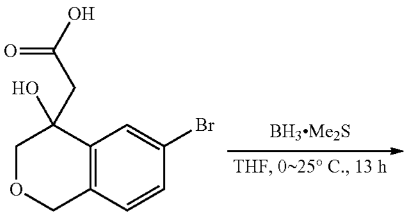

B

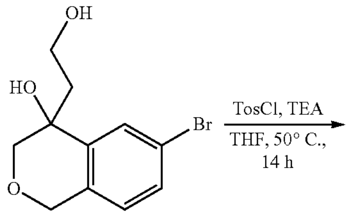

C

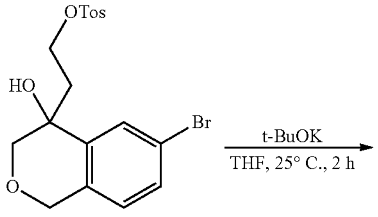

D

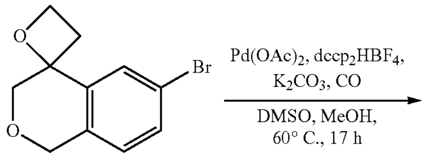

E

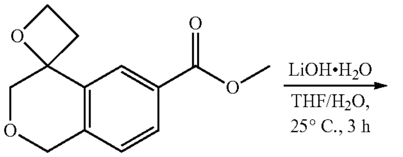

F

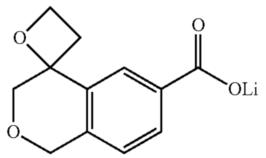

41

Step 1: Preparation of ethyl 2-(6-bromo-4-hydroxyisochroman-4-yl)acetate (Intermediate A)

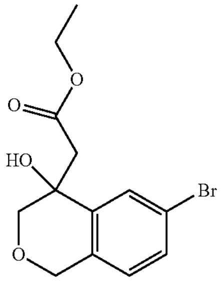

A

To a solution of ethyl acetate (620.86 mg, 7.05 mmol, 689.84 uL) in THF (1 mL) was added LiHMDS (1 M, 6.61 mL) at −65° C. under $N_2$ atmosphere. The mixture was stirred at −65° C. for 15 mins. A solution of 6-bromoisochroman-4-one (Prepared according to the method in Intermediate 10B) (1 g, 4.40 mmol) in THE (2 mL) was added at −65° C. The mixture was stirred at −65° C. for 2 hrs. The reaction mixture was quenched by saturated aq. $NH_4Cl$ (50 mL) and extracted by EA (50 mL*2). The combined organic layer was washed with brine (50 mL), dried over anhydrous sodium sulfate, filtered and concentrated to give residue. The residue was purified by flash silica gel chromatography (40 g Silica Flash Column, Eluent of 0~30% Ethylacetate/Petroleum ethergradient @ 50 mL/min). The eluent was concentrated to afford Intermediate A (1 g, 3.17 mmol) as colorless oil.

$^1$H NMR (400 MHz, DMSO-$d_6$) δ=7.67 (d, J=2.0 Hz, 1H), 7.41-7.39 (m, 1H), 7.01 (d, J=8.4 Hz, 1H), 5.64 (s, 1H), 4.73-4.56 (m, 2H), 4.06 (d, J=11.2 Hz, 1H), 4.02-3.93 (m, 2H), 3.52 (d, J=11.2 Hz, 1H), 2.83-2.74 (m, 1H), 2.69-2.59 (m, 1H), 1.11-1.07 (m, 3H) ppm.

Step 2: Preparation of 2-(6-bromo-4-hydroxyisochroman-4-yl)acetic acid (Intermediate B)

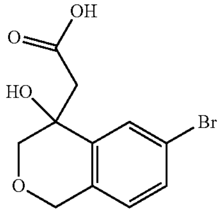

B

LiOH $H_2O$ (266.30 mg, 6.35 mmol) in mixture of THE (5 mL), $H_2O$ (2.5 mL) and MeOH (2.5 mL) was added to ethyl Intermediate A (1 g, 3.17 mmol). The reaction mixture was stirred at 25° C. for 1 hr. The reaction mixture was poured into water (50 mL) and adjusted pH=4 with 1 M aq. HCl. The mixture was extracted by EA (50 mL*2). The combined organic layer was washed with brine (50 mL), dried over anhydrous sodium sulfate, filtered and concentrated to give Intermediate B (900 mg, 2.82 mmol) as yellow oil.

$^1$H NMR (400 MHz, DMSO-$d_6$) δ=7.69 (d, J=2.0 Hz, 1H), 7.40-7.38 (m, 1H), 7.01 (d, J=8.0 Hz, 1H), 4.72-4.57 (m, 2H), 4.09 (d, J=11.2 Hz, 1H), 3.50 (d, J=11.2 Hz, 1H), 2.68 (d, J=14.2 Hz, 1H), 2.53 (br s, 1H) ppm.

Step 3: Preparation of 6-bromo-4-(2-hydroxyethyl)isochroman-4-ol (Intermediate C)

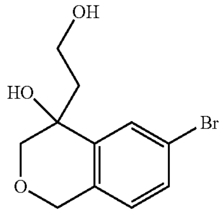

C

To a solution of Intermediate B (900 mg, 3.13 mmol) in THE (9 mL) was added $BH_3$-$Me_2S$ (10 M, 1.25 mL) at 0° C. under $N_2$ atmosphere. The reaction mixture was stirred at 25° C. for 13 hrs. The reaction mixture was poured into saturated aq. $NaHCO_3$ (100 mL) and extracted by EA (50 mL*3). The combined organic layer was washed with brine (50 mL), dried over anhydrous sodium sulfate, filtered and concentrated in vacuum to give residue. The residue was purified by flash silica gel chromatography (40 g Silica Flash Column, Eluent of 0~50% Ethylacetate/Petroleum ether gradient @ 50 mL/min). The eluent was concentrated to afford Intermediate C (850 mg, 2.80 mmol) as colorless oil.

$^1$H NMR (400 MHz, DMSO-$d_6$) δ=7.63 (d, J=2.0 Hz, 1H), 7.40-7.38 (m, 1H), 7.01 (d, J=8.0 Hz, 1H), 5.36 (s, 1H), 4.71-4.56 (m, 2H), 4.43-4.40 (m, 1H), 3.85 (d, J=11.2 Hz, 1H), 3.55-3.42 (m, 3H), 1.92-1.88 (m, 2H) ppm.

Step 4: Preparation of 2-(6-bromo-4-hydroxyisochroman-4-yl)ethyl 4-methylbenzenesulfonate (Intermediate D)

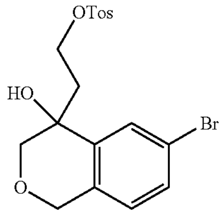

D

To a solution of Intermediate C (850 mg, 3.11 mmol) in THE (8 mL) was added $Et_3N$ (629.84 mg, 6.22 mmol, 866.35 uL) and TosCl (652.66 mg, 3.42 mmol) at 0° C. The reaction mixture was stirred at 50° C. for 14 hrs. The reaction mixture was poured into water (50 mL) and extracted by EA (50 mL*3). The combined organic layer was washed with brine (50 mL), dried over anhydrous sodium sulfate, filtered and concentrated to give Intermediate D (1.3 g, crude) as yellow oil.

LCMS (ESI) m/z: [$^{81}$BrM+H2O]$^+$=446.0.

Step 5: Preparation of 6-bromospiro[isochroman-4, 2'-oxetane] (Intermediate E)

E

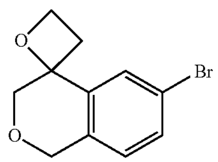

To a solution of Intermediate D (1.3 g, 3.04 mmol) in THE (50 mL) was added t-BuOK (1.02 g, 9.13 mmol). The reaction mixture was stirred at 25° C. for 2 hrs. The reaction mixture was poured into water (200 mL) and extracted by EA (100 mL*2). The combined organic layer was washed with brine (100 mL), dried over anhydrous sodium sulfate, filtered and concentrated in vacuum. The residue was purified by flash silica gel chromatography (40 g Silica Flash Column, Eluent of 0~30% Ethylacetate/Petroleum ethergradient @ 50 mL/min). The eluent was concentrated to afford Intermediate E (600 mg, 2.00 mmol) as light yellow oil.

$^1$H NMR (400 MHz, DMSO-$d_6$) δ=8.05 (d, J=2.0 Hz, 1H), 7.49-7.46 (m, 1H), 7.04 (d, J=8.0 Hz, 1H), 4.68-4.52 (m, 4H), 4.06 (d, J=11.6 Hz, 1H), 3.90 (d, J=11.6 Hz, 1H), 2.85-2.82 (m, 1H), 2.69-2.57 (m, 1H) ppm.

Step 6: Preparation of methyl spiro[isochroman-4, 2'-oxetane]-6-carboxylate (Intermediate F)

F

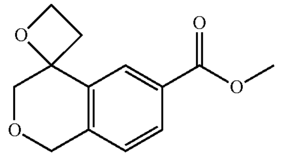

To a solution of Intermediate E (300 mg, 1.18 mmol) in DMSO (3 mL) and MeOH (1 mL) was added $Pd(OAc)_2$ (13.20 mg, 58.80 umol), $K_2CO_3$ (243.79 mg, 1.76 mmol), dicyclohexyl(3-dicyclohexylphosphaniumylpropyl)phosphonium;ditetrafluoroborate (72.00 mg, 117.60 umol). The reaction mixture was stirred at 60° C. for 17 hrs under CO (15 psi) atmosphere. The reaction mixture was poured into water (30 mL) and extracted by EA (10 mL*3). The combined organic layer was washed with brine (10 mL), dried over anhydrous sodium sulfate, filtered and concentrated in vacuum. The residue was purified by flash silica gel chromatography (20 g Silica Flash Column, Eluent of 0~30% Ethylacetate/Petroleum ethergradient @ 30 mL/min). The eluent was concentrated to afford Intermediate F (230 mg, 972.05 umol) as light yellow oil.

LCMS (ESI) m/z: $[M+H]^+$=235.1.

$^1$HNMR (400 MHz, DMSO-$d_6$) δ=8.44 (d, J=1.6 Hz, 1H), 7.87-7.85 (m, 1H), 7.22 (d, J=8.0 Hz, 1H), 4.78-4.69 (m, 2H), 4.65-4.61 (m, 2H), 4.14 (d, J=11.6 Hz, 1H), 3.92 (d, J=11.6 Hz, 1H), 3.89 (s, 3H), 2.87-2.82 (m, 1H), 2.72-2.67 (m, 1H) ppm.

Step 7: Preparation of lithium spiro[isochroman-4, 2'-oxetane]-6-carboxylate (Intermediate 41)

41

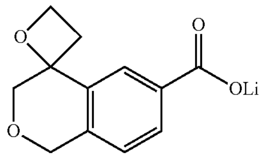

LiOH $H_2O$ (71.66 mg, 1.71 mmol) in $H_2O$ (0.5 mL) was added into the solution of Intermediate F (200 mg, 853.80 umol) in THE (2 mL). The reaction mixture was stirred at 25° C. for 3 hrs. The mixture was poured into 40 mL deionized water and lyophilized to afford Intermediate 41 (180 mg, 801.01 umol) as white solid.

$^1$H NMR (400 MHz, DMSO-$d_6$) δ=8.41 (s, 1H), 7.79-7.77 (m, 1H), 6.93 (d, J=8.0 Hz, 1H), 4.71-4.53 (m, 4H), 4.06-3.92 (m, 2H), 2.84-2.81 (m, 1H), 2.66-2.61 (m, 1H) ppm.

Intermediate 42: Preparation of 3-((trans)-4-hydroxy-3-methyltetrahydrofuran-3-yl)benzoic acid

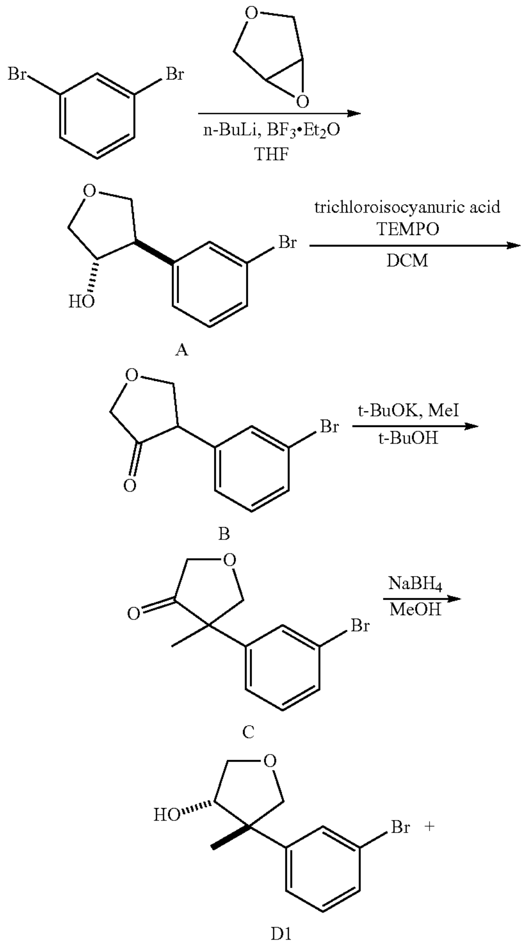

A

B

C

D1

-continued

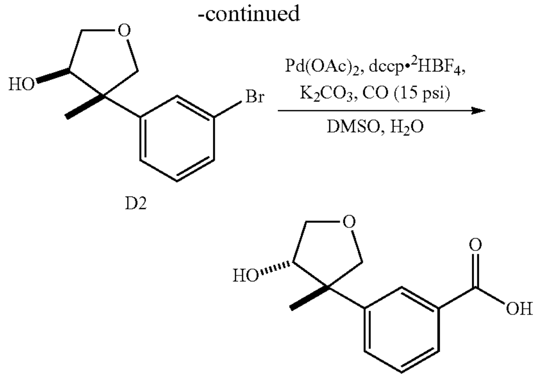

D2

42

Step 1: Preparation of 4-(3-bromophenyl)tetrahydrofuran-3-ol (Intermediate A)

A

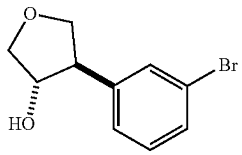

To a solution of 1,3-dibromobenzene (20 g, 84.78 mmol, 10.20 mL) in THF (200 mL) was added n-BuLi (2.5 M, 33.91 mL) at −70° C., the mixture was stirred at −70° C. for 30 min, then to the solution was added 3,6-dioxabicyclo [3.1.0]hexane (3.65 g, 42.39 mmol) and $BF_3 \cdot Et_2O$ (12.03 g, 84.78 mmol, 10.46 mL) at −70° C. The mixture was stirred at −70° C. for 2 hrs. The reaction mixture was poured into $NH_4Cl$ (300 mL), the solution was extracted with EA (300 mL*3), the combined organic layer was washed with brine (500 mL), dried over $Na_2SO_4$, filtered and concentrated to give a residue. The crude product was purified by reversed-phase HPLC (0.1% FA condition). The solution was extracted with EA (30 mL*3), the combined organic layer was dried over $Na_2SO_4$, filtered and concentrated to give Intermediate A (3.8 g, 15.29 mmol) as a yellow oil.

LCMS (ESI) m/z: $[^{79}BrM-18+H]^+$=225.1.

Step 2: Preparation of 4-(3-bromophenyl)tetrahydrofuran-3-one (Intermediate B)

B

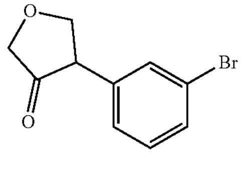

To a solution of Intermediate A (3.8 g, 15.63 mmol) in DCM (80 mL) was added trichloroisocyanuric acid (3.63 g, 15.63 mmol) and TEMPO (24.58 mg, 156.32 umol) at 0° C. The mixture was stirred at 30° C. for 16 hrs. The reaction mixture was poured into water (200 mL), the solution was extracted with DCM (100 mL*3), the combined organic layer was washed with brine (200 mL), dried over $Na_2SO_4$, filtered and concentrated to give a residue. The residue was purified by reversed-phase HPLC (0.1% FA condition). The solution was extracted with EA (100 mL*3), the combined organic layer was dried over $Na_2SO_4$, filtered and concentrated to give Intermediate B (3.7 g, 15.35 mmol) as a yellow oil.

$^1H$ NMR (400 MHz, $CDCl_3$) δ=7.36-7.32 (m, 2H), 7.18 (s, 2H), 4.58-4.54 (m, 1H), 4.19-4.15 (m, 1H), 4.10-4.06 (m, 1H), 3.98-3.94 (m, 1H), 3.60-3.56 (m, 1H) ppm.

Step 3: Preparation of 4-(3-bromophenyl)-4-methyltetrahydrofuran-3-one (Intermediate C)

C

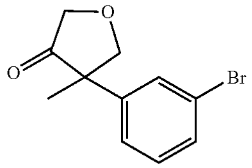

To a solution of Intermediate B (2.5 g, 10.37 mmol) in t-BuOH (13 mL) was added t-BuOK (1.22 g, 10.89 mmol). The mixture was stirred at 30° C. for 30 min, this was followed by addition of MeI (2.94 g, 20.74 mmol, 1.29 mL) at 0° C. The resulting solution was stirred at 30° C. for 3 hrs. The reaction mixture was poured into water (40 mL), the solution was extracted with EA (40 mL*3), the combined organic layer was washed with brine (100 mL), the solution was dried over $Na_2SO_4$, filtered and concentrated to give a residue. The crude product was purified by reversed-phase HPLC (0.1% FA condition). The solution was extracted with EA (20 mL*3), the combined organic layer was dried over $Na_2SO_4$, filtered and concentrated to give Intermediate C (340 mg, 1.33 mmol) as a brown oil.

$^1H$ NMR (400 MHz, MeOD) δ=7.60-7.59 (m, 1H), 7.46-7.36 (m, 2H), 7.33-7.22 (m, 1H), 4.54 (d, J=9.6 Hz, 1H), 4.17 (d, J=9.6 Hz, 1H), 4.10 (s, 2H), 1.47 (s, 3H) ppm.

Step 4: Preparation of (cis)-4-(3-bromophenyl)-4-methyltetrahydrofuran-3-ol and (trans)-4-(3-bromophenyl)-4-methyltetrahydrofuran-3-ol (Intermediates D1 and D2)

D1

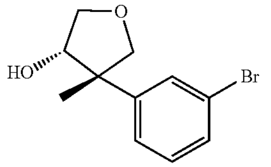

+

-continued

D2

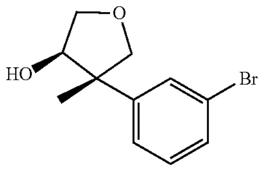

To a solution of Intermediate C (340 mg, 1.33 mmol) in MeOH (4 mL) was added $NaBH_4$ (100.84 mg, 2.67 mmol) at 0° C. The mixture was stirred at 30° C. for 2 hrs. The reaction mixture was poured into water (10 mL), the solution was extracted with EA (10 mL*3), the combined organic layer was washed with brine (20 mL), dried over $Na_2SO_4$, filtered and concentrated to give a residue. The residue was purified by prep-HPLC (column: Phenomenex Synergi C18 150*25*10 um; mobile phase: [water (0.225% FA)-ACN]; B %: 30%-54%, 12 min) and lyophilized to give Intermediate D1 (90 mg, 350.03 umol) as a colorless oil and Intermediate D2 (80 mg, 311.13 umol) as a colorless oil. LCMS (ESI) m/z: $[^{79}BrM-18+H]^+$=239.0.

Intermediate D1: $^1H$ NMR (400 MHz, MeOD) δ=7.41-7.40 (m, 1H), 7.37-7.35 (m, 1H), 7.29-7.18 (m, 2H), 4.36-4.17 (m, 3H), 3.94 (d, J=7.6 Hz, 1H), 3.80-3.80 (m, 1H), 1.29 (s, 3H) ppm.

Intermediate D2: $^1H$ NMR (400 MHz, MeOD) δ=7.58-7.57 (m, 1H), 7.38-7.36 (m, 2H), 7.28-7.15 (m, 1H), 4.33-4.32 (m, 1H), 4.12 (d, J=8.4 Hz, 1H), 3.97-3.95 (m, 1H), 3.89 (d, J=8.8 Hz, 1H), 3.68-3.67 (m, 1H), 1.37 (s, 3H) ppm.

Step 5: Preparation of 3-((trans)-4-hydroxy-3-methyltetrahydrofuran-3-yl)benzoic acid (Intermediate 42)

42

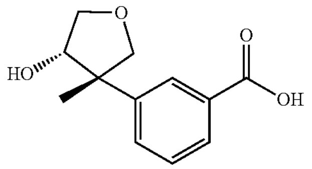

To a solution of Intermediate D1 (90 mg, 350.03 umol) in DMSO (1 mL) was added dicyclohexyl(3-dicyclohexylphosphaniumylpropyl)phosphonium;ditetrafluoroborate (21.43 mg, 35.00 umol), $Pd(OAc)_2$ (7.86 mg, 35.00 umol), $K_2CO_3$ (72.56 mg, 525.04 umol) and $H_2O$ (12.61 mg, 700.05 umol, 12.61 uL). The mixture was stirred at 100° C. for 3 hrs. The reaction mixture was filtered to give a solution. The crude product was purified by reversed-phase HPLC (0.1% FA condition). The solution was extracted with EA (20 mL*3), the combined organic layer was washed with brine (50 mL), dried over $Na_2SO_4$, filtered and concentrated to give Intermediate 42 (45 mg, 173.11 umol) as a colorless oil.

LCMS (ESI) m/z: $[M-18+H]^+$=205.3.

Example 114. Preparation of (S)-4-cyano-N-(2-((4-(6-((cis)-2,6-dimethylmorpholino)pyridin-2-yl)thiazol-2-yl)amino)-2-oxoethyl)-4-fluoroisochromane-6-carboxamide and (R)-4-cyano-N-(2-((4-(6-((cis)-2,6-dimethylmorpholino)pyridin-2-yl)thiazol-2-yl)amino)-2-oxoethyl)-4-fluoroisochromane-6-carboxamide (Compounds 298 and 299)

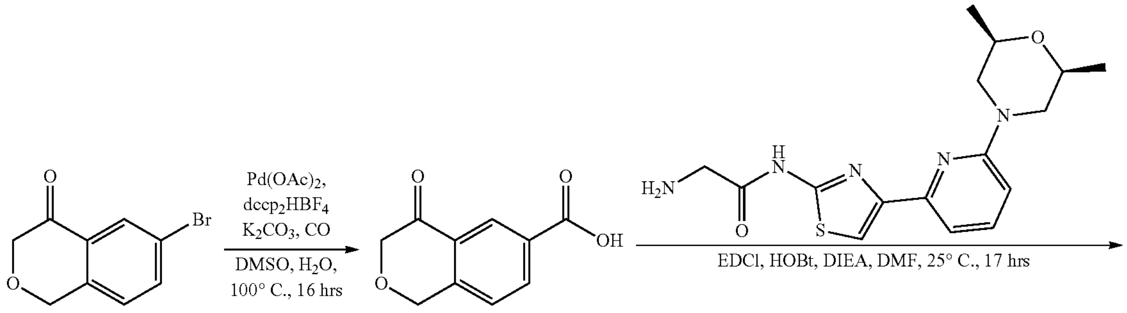

A

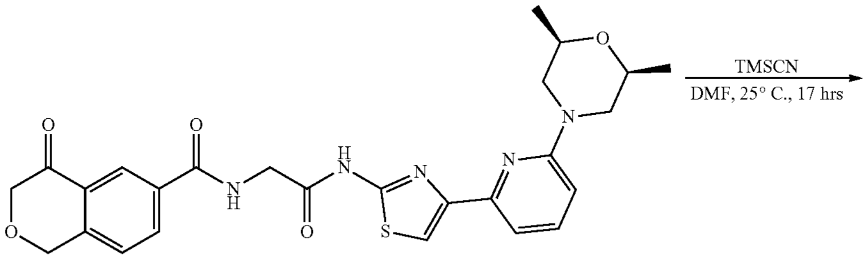

B

-continued

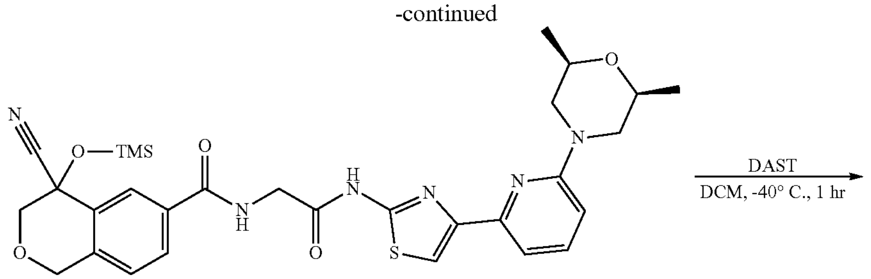

C

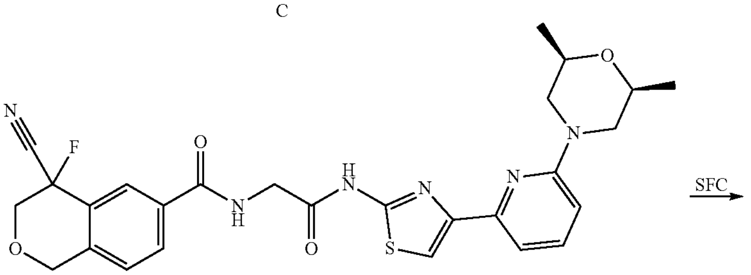

D

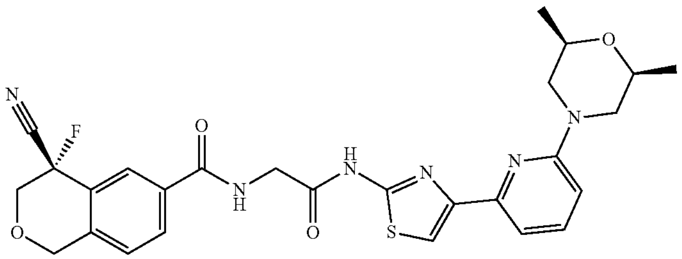

+

Compound 298

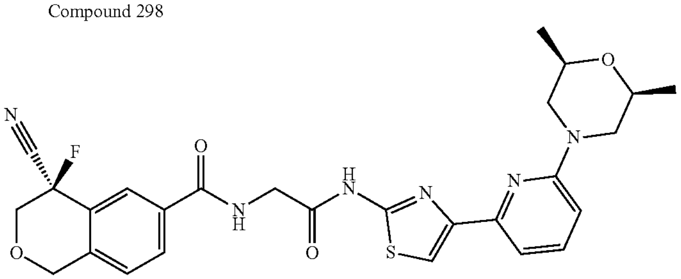

Compound 299

Step 1: Preparation of 4-oxoisochromane-6-carboxylic acid (Intermediate A)

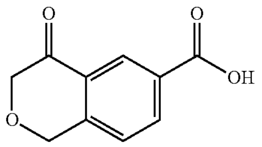

A

To a solution of 6-bromoisochroman-4-one (200 mg, 880.84 umol) in DMSO (2 mL) was added $H_2O$ (0.2 mL), $Pd(OAC)_2$ (19.78 mg, 88.08 umol), dicyclohexyl(3-dicyclohexylphosphaniumylpropyl) phosphonium;ditetrafluoroborate (107.86 mg, 176.17 umol) and $K_2CO_3$ (182.61 mg, 0.32 mmol). The reaction mixture was stirred at 100° C. for 16 hrs under CO (15 psi) atmosphere. The reaction mixture was poured into aqueous HCl (1 M, 20 mL), and then extracted by EA (20 mL*3). The combined organic layer was washed with brine (20 mL), dried over anhydrous sodium sulfate, filtered and concentrated to give residue. The residue was purified by flash silica gel chromatography (20 g Silica Flash Column, Eluent of 0~70% ethylacetate/Petroleum ethergradient @ 30 mL/min). The eluent was concentrated to afford Intermediate A (150 mg, 772.76 umol) as a white solid.

LCMS (ESI) m/z: $[M+H]^+$=193.1.

$^1$H NMR (400 MHz, DMSO-$d_6$) δ=13.31 (br s, 1H), 8.41 (d, J=1.6 Hz, 1H), 8.19-8.16 (m, 1H), 7.54 (d, J=8.0 Hz, 1H), 4.98 (s, 2H), 4.41 (s, 2H) ppm.

Step 2: Preparation of N-[2-[[4-[6-[(cis)-2,6-dimethylmorpholin-4-yl]-2-pyridyl]thiazol-2-yl]amino]-2-oxo-ethyl]-4-oxo-isochromane-6-carboxamide (Intermediate B)

B

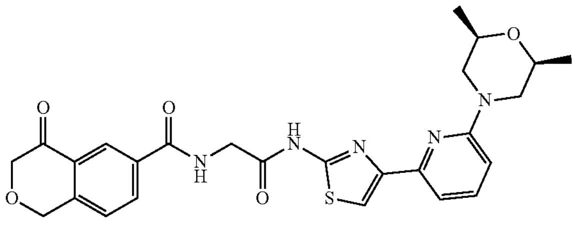

To a solution of Intermediate A (97.61 mg, 507.95 umol) and 2-amino-N-[4-[6-[(2R,6S)-2,6-dimethylmorpholin-4-yl]-2-pyridyl]thiazol-2-yl]acetamide (Prepared according to the method in FG-A1656) (130 mg, 338.63 umol, HCl) in DMF (2 mL) was added EDCl (129.83 mg, 677.27 umol), HOBt (91.51 mg, 677.27 umol) and DIEA (131.30 mg, 1.02 mmol, 176.95 uL). The reaction mixture was stirred at 25° C. for 17 hrs. The reaction mixture was added water (10 mL). White solid was formed. The suspension was filtered to afford yellow solid. The solid was triturated in 10 mL PE/EA=5/1. The mixture was filtered to give Intermediate B (40 mg, 72.09 umol) as a yellow solid.

LCMS (ESI) m/z: $[M+H]^+$=522.2.

1H NMR (400 MHz, DMSO-$d_6$) δ=12.43 (s, 1H), 9.21-9.20 (m, 1H), 8.47 (d, J=1.6 Hz, 1H), 8.17-8.16 (m, 1H), 7.77 (s, 1H), 7.63-7.61 (m, 1H), 7.54 (d, J=8.0 Hz, 1H), 7.26 (d, J=7.2 Hz, 1H), 6.79 (d, J=8.4 Hz, 1H), 4.98 (s, 2H), 4.43 (s, 2H), 4.27-4.23 (m, 2H), 4.21 (d, J=6.0 Hz, 2H), 3.66-3.59 (m, 2H), 2.44-2.41 (m, 2H), 1.17 (s, 6H) ppm.

Step 3: Preparation of 4-cyano-N-[2-[[4-[6-[(cis)-2,6-dimethylmorpholin-4-yl]-2-pyridyl]thiazol-2-yl]amino]-2-oxo-ethyl]-4-trimethylsilyloxyisochromane-6-carboxamide (Intermediate C)

C

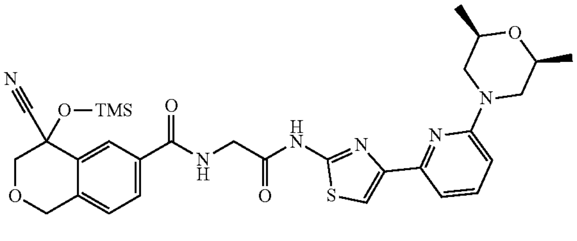

To a solution of Intermediate B (20 mg, 38.34 umol) in DMF (0.5 mL) was added TMSCN (11.41 mg, 115.03 umol, 14.39 uL). The reaction mixture was stirred at 25° C. for 17 hrs. The reaction mixture was poured into water (10 mL), and then extracted by EA (10 mL*2). The combined organic layer was washed with brine (10 mL), dried over anhydrous sodium sulfate, filtered and concentrated to give Intermediate C as yellow solid which was used for next step directly.

LCMS (ESI) m/z: $[M+H]^+$=621.2.

Step 4: Preparation of 4-cyano-N-[2-[[4-[6-[(cis)-2,6-dimethylmorpholin-4-yl]-2-pyridyl]thiazol-2-yl]amino]-2-oxo-ethyl]-4-fluoroisochromane-6-carboxamide (Intermediate D)

D

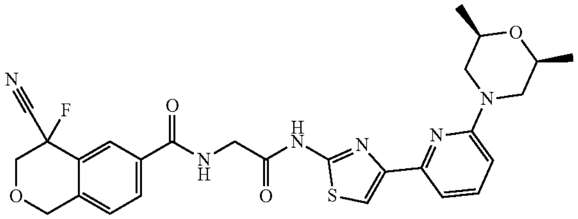

To a solution of Intermediate C (350 mg, 563.79 umol) in DCM (17.5 mL) was added DAST (1.82 g, 11.28 mmol, 1.49 mL) at −40° C. The reaction mixture was stirred at −40° C. for 1 hr. The reaction was quenched with sat.$NaHCO_3$ (30 mL) and extracted with ethyl acetate (20 mL*2). The combined organic layers were washed with brine (20 mL), dried over $Na_2SO_4$, filtered and concentrated under reduced pressure to give a residue. The residue was purified by Prep-HPLC (column: Phenomenex Gemini-NX C18 75*30 mm*3 um; mobile phase: [water (0.225% FA)-ACN]; B %: 35%-65%, 7 min). The eluent was concentrated under reduced pressure to remove MeCN, then lyophilized to give Intermediate D (150 mg, 272.43 umol) as a white solid.

LCMS (ESI) m/z: $[M+H]^+$=551.1.

Step 5: Preparation of (S)-4-cyano-N-(2-((4-(6-((cis)-2,6-dimethylmorpholino)pyridin-2-yl)thiazol-2-yl)amino)-2-oxoethyl)-4-fluoroisochromane-6-carboxamide and (R)-4-cyano-N-(2-((4-(6-((cis)-2,6-dimethylmorpholino)pyridin-2-yl)thiazol-2-yl)amino)-2-oxoethyl)-4-fluoroisochromane-6-carboxamide (Compounds 298 and 299)

Compound 298

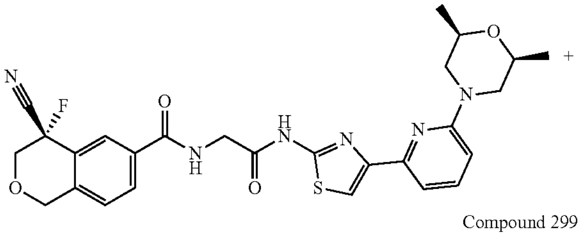

+

Compound 299

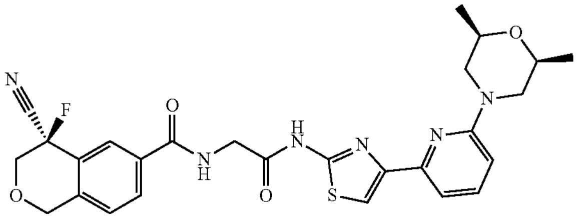

Intermediate D (0.15 g, 272.43 umol) was purified by SFC separation with the condition (column: DAICEL CHIRALPAKAD (250 mm*30 mm, 10 um); mobile phase: [0.1%

$NH_3 \cdot H_2O$ ETOH]; B %: 50%-50%, 3.3 min). The eluent of peak 1 was concentrated and lyophilized to give Compound 298 (33.18 mg, 59.55 umol) as an off-white solid and the eluent of peak 2 was concentrated and lyophilized to give Compound 299 (32.14 mg, 57.94 umol) as an off-white solid.

Compound 298:

LCMS (ESI) m/z: $[M+H]^+$=551.1.

$^1$HNMR (400 MHz, DMSO-$d_6$) δ=12.45 (s, 1H), 9.34-9.15 (m, 1H), 8.30 (s, 1H), 8.09 (d, J=8.0 Hz, 1H), 7.79 (s, 1H), 7.67-7.58 (m, 1H), 7.47 (d, J=8.0 Hz, 1H), 7.26 (d, J=7.2 Hz, 1H), 6.81 (d, J=8.4 Hz, 1H), 5.03-4.81 (m, 2H), 4.64-4.37 (m, 2H), 4.32-4.17 (m, 4H), 3.65-3.62 (m, 2H), 2.45-2.39 (m, 2H), 1.20 (s, 3H), 1.18 (s, 3H) ppm.

Chiral SFC: AD-3-EtOH (DEA)-50-3 mL-35T·lcm; Rt=1.056 min.

Compound 299:

LCMS (ESI) m/z: $[M+H]^+$=551.1.

$^1$HNMR (400 MHz, DMSO-$d_6$) δ=12.51 (s, 1H), 9.30 (m, 1H), 8.35 (s, 1H), 8.21-8.10 (m, 1H), 7.84 (s, 1H), 7.69-7.67 (m, 1H), 7.52 (d, J=8.0 Hz, 1H), 7.32 (d, J=7.2 Hz, 1H), 6.86 (d, J=8.4 Hz, 1H), 5.09-4.88 (m, 2H), 4.67-4.44 (m, 2H), 4.36-4.27 (m, 4H), 3.73-3.65 (m, 2H), 2.51-2.45 (m, 2H), 1.25 (s, 3H), 1.24 (s, 3H) ppm.

Chiral SFC: AD-3-EtOH (DEA)-50-3 mL-35T·lcm; Rt=1.331 min.

Example 115. Assay for ATPase Catalytic Activity of BRM and BRG-1

The ATPase catalytic activity of BRM or BRG-1 was measured by the in vitro biochemical assay using ADP-Glo™ (Promega, V9102). The ADP-Glo™ kinase assay is performed in two steps once the reaction is complete. The first step is to deplete any unconsumed ATP in the reaction. The second step is to convert the reaction product ADP to ATP, which will be utilized by the luciferase to generate luminesce and be detected by a luminescence reader, such as Envision.

The assay reaction mixture (10 μL) contains 30 nM of BRM or BRG-1, 20 nM salmon sperm DNA (from Invitrogen, UltraPure™ Salmon Sperm DNA Solution, cat #15632011), and 400 μM of ATP in the ATPase assay buffer, which comprises of 20 mM Tris, pH 8, 20 mM $MgCl_2$, 50 mM NaCl, 0.1% Tween-20, and 1 mM fresh DTT (Pierce™ DTT (Dithiothreitol), cat #20290). The reaction is initiated by the addition of the 2.5 μL ATPase solution to 2.5 μL ATP/DNA solution on low volume white Proxiplate-384 plus plate (PerkinElmer, cat #6008280) and incubates at room temperature for 1 hour. Then following addition of 5 μL of ADP-Glo™ Reagent provided in the kit, the reaction incubates at room temperature for 40 minutes. Then 10 μL of Kinase Detection Reagent provided in the kit is added to convert ADP to ATP, and the reaction incubates at room temperature for 60 minutes. Finally, luminescence measurement is collected with a plate-reading luminometer, such as Envision.

BRM and BRG-1 were synthesized from high five insect cell lines with a purity of greater than 90%. $IP_{50}$ data for the below compounds from the ATPase catalytic activity assay described herein is shown in Table 11.

TABLE 11

| | ATPase catalytic activity | | | |
|---|---|---|---|---|
| Compound No. | BRM IC50 (μM)* | BRM Max % Inhibition | BRG1 IC50 (μM)* | BRG1 Max % Inhibition |
| 2 | ++++ | >90 | +++ | >70 |
| 13 | ++++ | >95 | ++++ | >95 |
| 14 | ++++ | >95 | +++ | >80 |
| 15 | ++ | >50 | + | >40 |
| 16 | +++ | >70 | + | <30 |
| 17 | +++ | >90 | + | >60 |
| 18 | ++++ | >95 | ++++ | >95 |
| 19 | +++ | >90 | ++ | >70 |
| 20 | +++ | >60 | + | <30 |
| 21 | +++ | >80 | ++ | >70 |
| 22 | ++++ | >95 | +++ | >80 |
| 23 | +++ | >90 | +++ | >80 |
| 24 | +++ | >90 | ++ | >60 |
| 25 | ++++ | >90 | +++ | >80 |
| 26 | ++++ | >90 | +++ | >90 |
| 27 | ++++ | >95 | +++ | >80 |
| 28 | +++ | >80 | ++ | >50 |
| 29 | +++ | >90 | +++ | >80 |
| 30 | +++ | >90 | ++ | >50 |
| 31 | +++ | >90 | ++ | >70 |
| 32 | +++ | >95 | +++ | >80 |
| 33 | + | >70 | + | >80 |
| 39 | +++ | >95 | ++ | >90 |
| 40 | ++++ | >90 | +++ | >70 |
| 45 | ++++ | >95 | ++ | >80 |
| 46 | +++ | >95 | ++ | >60 |
| 47 | +++ | >95 | ++ | >90 |
| 48 | +++ | >95 | +++ | >80 |
| 49 | +++ | >80 | + | >60 |
| 50 | +++ | >90 | ++ | >70 |
| 51 | +++ | >80 | + | >50 |
| 52 | +++ | >80 | ++ | >70 |
| 53 | +++ | >90 | ++ | >70 |
| 54 | ++ | >80 | ++ | >50 |
| 55 | +++ | >90 | + | >60 |
| 56 | +++ | >90 | ++ | >70 |
| 57 | ++++ | >95 | +++ | >80 |
| 58 | +++ | >80 | ++ | >60 |
| 59 | ++++ | >95 | +++ | >80 |
| 60 | ++++ | >95 | +++ | >80 |
| 61 | +++ | >90 | ++ | >60 |
| 62 | ++ | >80 | + | >40 |
| 63 | ++ | >80 | + | >60 |
| 64 | +++ | >95 | ++ | >80 |
| 65 | +++ | >90 | +++ | >95 |
| 66 | ++++ | >95 | +++ | >90 |
| 67 | ++ | >70 | ++ | >40 |
| 68 | +++ | >95 | +++ | >90 |
| 69 | +++ | >70 | + | >30 |
| 70 | +++ | >95 | + | >50 |
| 71 | ++ | >70 | + | >30 |
| 72 | +++ | >80 | + | >50 |
| 73 | ++++ | >95 | +++ | >80 |
| 74 | ++++ | >80 | +++ | >60 |
| 75 | +++ | >80 | + | <30 |
| 76 | ++++ | >95 | ++++ | >80 |
| 77 | +++ | >90 | +++ | >80 |
| 78 | +++ | >80 | ++ | >40 |
| 79 | +++ | >70 | +++ | >50 |
| 80 | ++ | >90 | +++ | >80 |
| 81 | +++ | >90 | +++ | >70 |
| 82 | +++ | >95 | +++ | >90 |
| 83 | ++ | >90 | + | >50 |
| 84 | +++ | >95 | ++ | >90 |
| 85 | + | >80 | + | >60 |
| 86 | + | >80 | ++ | >60 |
| 87 | +++ | >80 | + | <30 |
| 88 | +++ | >50 | + | >30 |
| 89 | ++ | >80 | + | >30 |
| 90 | ++ | >60 | + | <30 |
| 91 | ++ | >50 | + | >30 |
| 92 | ++++ | >95 | +++ | >95 |
| 93 | ++++ | >95 | +++ | >90 |
| 94 | ++++ | >95 | ++++ | >95 |

TABLE 11-continued

| ATPase catalytic activity | | | | |
|---|---|---|---|---|
| Compound No. | BRM IC50 (μM)* | BRM Max % Inhibition | BRG1 IC50 (μM)* | BRG1 Max % Inhibition |
| 95 | ++++ | >95 | +++ | >90 |
| 96 | +++ | >95 | ++ | >90 |
| 97 | +++ | >90 | ++ | >70 |
| 98 | +++ | >95 | ++ | >70 |
| 99 | ++++ | >95 | +++ | >90 |
| 100 | ++++ | >95 | ++++ | >95 |
| 101 | +++ | >90 | ++ | >70 |
| 102 | ++++ | >95 | +++ | >80 |
| 103 | ++++ | >95 | ++++ | >95 |
| 104 | +++ | >90 | ++ | >70 |
| 105 | ++++ | >95 | ++++ | >90 |
| 106 | ++ | >80 | ++ | >30 |
| 107 | +++ | >90 | +++ | >70 |
| 108 | +++ | >95 | ++ | >80 |
| 109 | ++ | >80 | ++ | >50 |
| 110 | ++++ | >95 | +++ | >80 |
| 111 | +++ | >90 | + | >40 |
| 112 | +++ | >80 | +++ | >50 |
| 113 | +++ | >80 | +++ | >50 |
| 114 | ++++ | >90 | +++ | >95 |
| 115 | ++++ | >95 | ++++ | >95 |
| 116 | +++ | >80 | ++ | >40 |
| 117 | ++++ | >95 | +++ | >80 |
| 118 | +++ | >70 | + | <30 |
| 119 | ++++ | >95 | +++ | >80 |
| 121 | +++ | >95 | ++ | >80 |
| 122 | ++++ | >95 | ++++ | >95 |
| 123 | ++++ | >95 | +++ | >80 |
| 124 | +++ | >90 | ++ | >70 |
| 125 | ++++ | >95 | +++ | >80 |
| 126 | +++ | >80 | ++ | >60 |
| 127 | ++++ | >95 | +++ | >90 |
| 128 | ++++ | >95 | ++++ | >95 |
| 129 | ++++ | >95 | ++++ | >95 |
| 130 | +++ | >60 | + | <30 |
| 131 | ++++ | >95 | +++ | >70 |
| 132 | +++ | >80 | + | >50 |
| 133 | +++ | >95 | ++ | >70 |
| 134 | +++ | >80 | ++ | >60 |
| 136 | +++ | >90 | ++ | >70 |
| 138 | +++ | >90 | + | >50 |
| 139 | +++ | >95 | ++ | >70 |
| 140 | +++ | >95 | + | >50 |
| 141 | +++ | >80 | + | >60 |
| 142 | ++++ | >95 | +++ | >80 |
| 143 | +++ | >80 | + | >60 |
| 144 | +++ | >95 | +++ | >80 |
| 145 | +++ | >90 | ++ | >60 |
| 146 | +++ | >70 | + | >30 |
| 147 | +++ | >90 | ++ | >80 |
| 148 | +++ | >70 | + | >30 |
| 149 | +++ | >95 | ++ | >70 |
| 150 | ++++ | >95 | +++ | >90 |
| 151 | ++++ | >95 | +++ | >95 |
| 152 | ++++ | >95 | ++++ | >95 |
| 153 | ++++ | >95 | ++++ | >95 |
| 154 | +++ | >90 | ++ | >60 |
| 155 | +++ | >90 | ++ | >60 |
| 156 | +++ | >80 | + | >30 |
| 157 | +++ | >70 | + | >30 |
| 159 | ++++ | >95 | ++++ | >95 |
| 160 | +++ | >80 | + | <30 |
| 161 | ++++ | >95 | +++ | >80 |
| 162 | +++ | >70 | + | >40 |
| 163 | ++++ | >90 | ++ | >40 |
| 164 | +++ | >60 | + | <30 |
| 165 | +++ | >90 | + | <40 |
| 166 | +++ | >95 | + | >50 |
| 167 | +++ | >95 | + | >50 |
| 168 | +++ | >90 | + | >50 |
| 169 | +++ | >80 | + | >50 |
| 170 | ++++ | >95 | ++++ | >95 |
| 171 | +++ | >80 | ++ | >70 |
| 172 | ++++ | >95 | ++++ | >95 |
| 173 | +++ | >95 | +++ | >80 |
| 174 | +++ | >80 | ++ | >50 |
| 175 | +++ | >90 | ++ | >60 |
| 176 | +++ | >95 | +++ | >80 |
| 177 | ++++ | >95 | +++ | >90 |
| 178 | +++ | >80 | + | >50 |
| 179 | +++ | >80 | + | >50 |
| 180 | +++ | >90 | ++ | >60 |
| 181 | +++ | >90 | ++ | >70 |
| 182 | ++++ | >95 | +++ | >90 |
| 183 | +++ | >90 | ++ | >70 |
| 184 | +++ | >90 | ++ | >80 |
| 185 | +++ | >95 | ++ | >80 |
| 186 | ++++ | >95 | ++ | >70 |
| 187 | ++++ | >95 | +++ | >70 |
| 188 | +++ | >90 | ++ | >50 |
| 189 | +++ | >90 | ++ | >50 |
| 190 | +++ | >90 | +++ | >70 |
| 191 | +++ | >90 | +++ | >80 |
| 192 | +++ | >90 | ++ | >60 |
| 195 | +++ | >95 | ++ | >70 |
| 196 | +++ | >90 | ++ | >60 |
| 197 | ++ | >60 | + | <30 |
| 198 | ++++ | >95 | +++ | >95 |
| 199 | ++++ | >95 | ++++ | >95 |
| 200 | ++++ | >95 | +++ | >80 |
| 201 | ++++ | >95 | +++ | >90 |
| 202 | +++ | >90 | ++ | >80 |
| 203 | ++++ | >95 | +++ | >95 |
| 204 | ++++ | >95 | +++ | >90 |
| 205 | +++ | >95 | ++ | >70 |
| 206 | +++ | >95 | ++ | >70 |
| 207 | +++ | >90 | + | >50 |
| 208 | +++ | >95 | ++ | >60 |
| 209 | +++ | >90 | ++ | >50 |
| 210 | ++++ | >95 | +++ | >80 |
| 211 | +++ | >80 | + | >40 |
| 212 | +++ | >70 | + | <30 |
| 214 | +++ | >90 | +++ | >80 |
| 215 | ++++ | >95 | +++ | >80 |
| 216 | ++++ | >95 | +++ | >95 |
| 217 | ++++ | >95 | +++ | >90 |
| 218 | +++ | >90 | ++ | >80 |
| 219 | ++++ | >95 | +++ | >90 |
| 222 | ++++ | >95 | +++ | >80 |
| 223 | ++++ | >95 | ++ | >80 |
| 224 | ++++ | >95 | +++ | >95 |
| 225 | +++ | >80 | + | >40 |
| 226 | +++ | >95 | ++ | >70 |
| 227 | ++++ | >95 | ++++ | >95 |
| 228 | ++++ | >95 | ++++ | >95 |
| 230 | ++++ | >95 | +++ | >80 |
| 231 | ++++ | >95 | +++ | >80 |
| 232 | ++++ | >95 | +++ | >80 |
| 233 | ++++ | >95 | +++ | >80 |
| 237 | ++++ | >95 | +++ | >90 |
| 238 | ++++ | >95 | +++ | >90 |
| 241 | ++++ | >95 | +++ | >90 |
| 242 | +++ | >80 | ++ | >50 |
| 243 | +++ | >80 | ++ | >50 |
| 244 | ++++ | >95 | +++ | >95 |
| 245 | ++++ | >95 | ++ | >70 |
| 247 | +++ | >95 | +++ | >80 |
| 248 | +++ | >40 | ++ | >30 |
| 249 | ++++ | >95 | ++++ | >95 |
| 250 | ++ | >70 | + | >50 |
| 251 | ++ | >50 | + | <30 |
| 252 | ++ | >60 | + | >30 |
| 253 | ++ | >90 | ++ | >50 |
| 254 | ++++ | >95 | ++++ | >95 |
| 255 | ++ | >70 | + | >40 |
| 256 | ++ | >60 | + | <30 |
| 257 | ++ | >70 | + | >30 |
| 258 | +++ | >80 | ++ | >60 |

TABLE 11-continued

| ATPase catalytic activity | | | | |
|---|---|---|---|---|
| Compound No. | BRM IC50 (μM)* | BRM Max % Inhibition | BRG1 IC50 (μM)* | BRG1 Max % Inhibition |
| 259 | ++ | >50 | + | <30 |
| 260 | ++ | >60 | + | >30 |
| 261 | ++ | >60 | + | >30 |
| 262 | ++ | >80 | ++ | >50 |
| 263 | +++ | >80 | ++ | >40 |
| 264 | ++ | >70 | + | <30 |
| 265 | ++ | >70 | + | >30 |
| 266 | ++ | >60 | + | >30 |
| 267 | ++++ | >95 | ++++ | >95 |
| 268 | +++ | >80 | ++ | >50 |
| 269 | +++ | >90 | + | >90 |
| 270 | ++++ | >95 | +++ | >95 |
| 271 | +++ | >85 | ++ | >85 |
| 272 | ++++ | >95 | ++++ | >95 |
| 273 | ++++ | >95 | +++ | >95 |
| 274 | ++++ | >95 | ++++ | >95 |
| 275 | ++++ | >95 | +++ | >95 |
| 276 | ++++ | >95 | ++++ | >95 |
| 277 | ++++ | >95 | ++++ | >95 |
| 278 | +++ | >90 | + | >90 |
| 279 | +++ | >90 | +++ | >90 |
| 280 | +++ | >90 | ++ | >90 |
| 281 | +++ | >90 | ++ | >90 |
| 282 | ++++ | >95 | +++ | >95 |
| 283 | ++++ | >95 | +++ | >95 |
| 284 | ++++ | >95 | +++ | >95 |
| 285 | ++++ | >95 | +++ | >95 |
| 286 | ++++ | >95 | ++ | >95 |
| 287 | ++++ | >95 | ++++ | >95 |
| 288 | +++ | >75 | + | >75 |
| 289 | ++++ | >95 | ++++ | >95 |
| 290 | ++++ | >95 | ++ | >95 |
| 291 | +++ | >90 | + | >90 |
| 292 | ++++ | >95 | +++ | >95 |
| 293 | ++++ | >95 | +++ | >95 |
| 294 | ++++ | >95 | +++ | >95 |
| 295 | ++++ | >95 | +++ | >95 |
| 296 | ++++ | >95 | ++++ | >95 |
| 297 | +++ | >95 | ++ | >85 |
| 298 | +++ | >95 | ++ | >95 |
| 299 | ++++ | >95 | +++ | >95 |
| 300 | ++++ | >95 | +++ | >95 |
| 301 | +++ | >95 | ++ | >95 |
| 302 | ++++ | >95 | +++ | >95 |
| 303 | ++++ | >95 | +++ | >95 |
| 304 | +++ | >95 | ++ | >95 |
| 305 | ++++ | >95 | +++ | >95 |
| 306 | +++ | >95 | ++ | >95 |
| 307 | ++++ | >95 | ++++ | >95 |
| 308 | ++++ | >95 | ++++ | >95 |
| 309 | ++++ | >95 | +++ | >95 |
| 310 | ++++ | >95 | +++ | >95 |
| 311 | +++ | >95 | ++ | >95 |
| 312 | ++++ | >95 | +++ | >95 |
| 313 | +++ | >90 | ++ | >90 |
| 314 | ++++ | >90 | +++ | >90 |
| 315 | ++++ | >95 | +++ | >95 |
| 316 | ++++ | >95 | ++++ | >95 |
| 317 | ++++ | >95 | ++ | >95 |
| 318 | +++ | >90 | + | >90 |
| 319 | ++++ | >95 | +++ | >95 |
| 320 | ++++ | >95 | +++ | >95 |
| 321 | ++++ | >90 | +++ | >90 |
| 322 | ++++ | >95 | +++ | >95 |
| 323 | ++++ | >95 | +++ | >95 |
| 324 | +++ | >90 | +++ | >90 |
| 325 | +++ | >95 | +++ | >95 |
| 326 | ++++ | >95 | +++ | >95 |
| 327 | ++++ | >95 | +++ | >95 |
| 328 | ++++ | >95 | +++ | >95 |
| 329 | ++++ | >95 | ++++ | >95 |
| 330 | ++++ | >95 | +++ | >95 |
| 331 | ++++ | >95 | +++ | >95 |
| 332 | ++++ | >95 | ++++ | >95 |
| 333 | +++ | >75 | ++ | >75 |
| 334 | ++++ | >95 | +++ | >95 |
| 335 | +++ | >90 | + | >90 |
| 336 | +++ | >85 | ++ | >85 |
| 337 | ++++ | >95 | ++++ | >95 |
| 338 | +++ | >90 | +++ | >90 |
| 339 | ++++ | >95 | ++++ | >95 |
| 340 | ++++ | >95 | +++ | >95 |
| 341 | ++++ | >95 | +++ | >95 |
| 342 | ++++ | >95 | +++ | >95 |
| 343 | ++++ | >95 | +++ | >95 |
| 344 | +++ | >95 | +++ | >95 |
| 345 | ++++ | >95 | ++ | >95 |
| 346 | ++++ | >95 | +++ | >95 |
| 347 | ++++ | >95 | ++++ | >95 |
| 348 | ++++ | >95 | +++ | >95 |
| 349 | ++++ | >95 | +++ | >95 |
| 350 | ++++ | >95 | ++ | >95 |
| 351 | ++++ | >95 | ++++ | >95 |
| 352 | ++++ | >95 | ++++ | >95 |
| 353 | ++++ | >95 | ++++ | >95 |
| 354 | +++ | >95 | +++ | >95 |
| 355 | ++++ | >95 | +++ | >95 |
| 356 | ++++ | >95 | +++ | >95 |
| 357 | +++ | >90 | +++ | >90 |
| 358 | ++++ | >95 | +++ | >95 |
| 359 | ++++ | >95 | +++ | >95 |
| 360 | ++++ | >95 | ++ | >95 |
| 361 | ++++ | >95 | +++ | >95 |
| 362 | ++++ | >90 | +++ | >90 |
| 363 | +++ | >85 | ++ | >85 |
| 364 | ++++ | >95 | ++++ | >95 |
| 365 | ++++ | >95 | +++ | >95 |
| 366 | ++++ | >85 | +++ | >85 |
| 367 | +++ | >85 | ++ | >85 |
| 368 | +++ | >85 | ++ | >85 |
| 369 | ++++ | >95 | ++++ | >95 |
| 370 | +++ | >65 | + | >65 |
| 371 | ++++ | >95 | +++ | >95 |
| 372 | ++++ | >95 | +++ | >95 |
| 373 | +++ | >90 | ++ | >90 |
| 374 | ++++ | >95 | +++ | >95 |
| 375 | +++ | >95 | ++ | >95 |
| 376 | ++++ | >95 | +++ | >95 |
| 377 | ++++ | >95 | ++++ | >95 |
| 378 | +++ | >95 | ++ | >95 |
| 379 | ++++ | >95 | +++ | >95 |
| 380 | +++ | >85 | ++ | >85 |
| 381 | +++ | >80 | + | >80 |
| 382 | +++ | >50 | + | >50 |
| 383 | +++ | >85 | + | >85 |
| 384 | +++ | >90 | ++ | >90 |
| 385 | ++++ | >95 | +++ | >95 |
| 386 | ++++ | >95 | +++ | >95 |
| 387 | ++++ | >95 | ++ | >95 |
| 388 | ++++ | >95 | ++++ | >95 |
| 389 | ++++ | >95 | ++++ | >95 |
| 390 | ++++ | >95 | ++++ | >95 |
| 391 | ++++ | >95 | +++ | >95 |
| 392 | +++ | >90 | + | >90 |
| 393 | +++ | >95 | + | >95 |
| 394 | +++ | >80 | + | >80 |
| 395 | +++ | >80 | + | >80 |
| 396 | +++ | >90 | ++ | >90 |
| 397 | ++++ | >95 | +++ | >95 |
| 398 | ++++ | >95 | +++ | >95 |
| 399 | ++++ | >95 | +++ | >95 |
| 400 | ++++ | >95 | +++ | >95 |
| 401 | ++++ | >95 | +++ | >95 |
| 402 | ++++ | >95 | ++++ | >95 |
| 403 | +++ | >90 | ++ | >90 |
| 404 | +++ | >80 | + | >80 |
| 405 | +++ | >90 | ++ | >90 |
| 406 | ++++ | >95 | +++ | >95 |

TABLE 11-continued

| ATPase catalytic activity | | | | |
|---|---|---|---|---|
| Compound No. | BRM IC50 (μM)* | BRM Max % Inhibition | BRG1 IC50 (μM)* | BRG1 Max % Inhibition |
| 407 | ++++ | >95 | ++++ | >95 |
| 408 | +++ | >90 | ++ | >90 |
| 409 | ++++ | >95 | ++++ | >95 |
| 410 | ++++ | >95 | ++ | >95 |
| 411 | +++ | >90 | + | >90 |
| 412 | +++ | >90 | +++ | >90 |
| 413 | +++ | >95 | ++ | >95 |
| 414 | +++ | >95 | +++ | >95 |
| 415 | +++ | >90 | + | >90 |
| 416 | ++++ | >95 | +++ | >95 |
| 417 | ++++ | >95 | +++ | >95 |
| 418 | ++++ | >95 | +++ | >95 |
| 419 | ++++ | >95 | +++ | >95 |
| 420 | ++++ | >95 | ++++ | >95 |
| 421 | ++ | >80 | + | >80 |
| 422 | +++ | >95 | ++ | >95 |
| 423 | ++++ | >95 | +++ | >95 |
| 424 | +++ | >80 | + | >80 |
| 425 | +++ | >85 | + | >85 |
| 426 | +++ | >95 | ++ | >95 |
| 427 | +++ | >85 | + | >85 |
| 428 | ++++ | >95 | +++ | >95 |
| 429 | ++++ | >95 | ++ | >95 |
| 430 | +++ | >95 | ++ | >95 |
| 431 | ++++ | >95 | +++ | >95 |
| 432 | ++++ | >95 | +++ | >95 |
| 433 | ++++ | >95 | +++ | >95 |
| 434 | +++ | >90 | ++ | >90 |
| 435 | +++ | >95 | ++ | >95 |
| 436 | +++ | >90 | ++ | >90 |
| 437 | ++++ | >95 | +++ | >95 |
| 438 | +++ | >95 | ++ | >95 |
| 439 | +++ | >95 | ++ | >95 |
| 440 | ++++ | >95 | ++++ | >95 |
| 441 | +++ | >90 | + | >90 |
| 442 | ++++ | >95 | +++ | >95 |
| 443 | ++++ | >95 | +++ | >95 |
| 444 | ++++ | >95 | +++ | >95 |

"+" indicates inhibitory effect of > 5 μM;
"++" indicates inhibitory effect of 1-5 μM;
"+++" indicates inhibitory effect of 0.1-1 μM,
"++++" indicates inhibitory effect of < 0.1 μM

Example 116. Synthesis of Compound A

BRG1/BRM Inhibitor compound A has the structure:

A

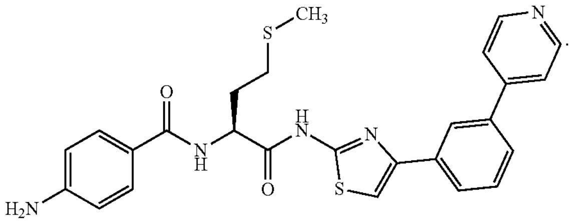

Compound A was synthesized as shown in Scheme 1 below.

Scheme 1. Synthesis of Compound A

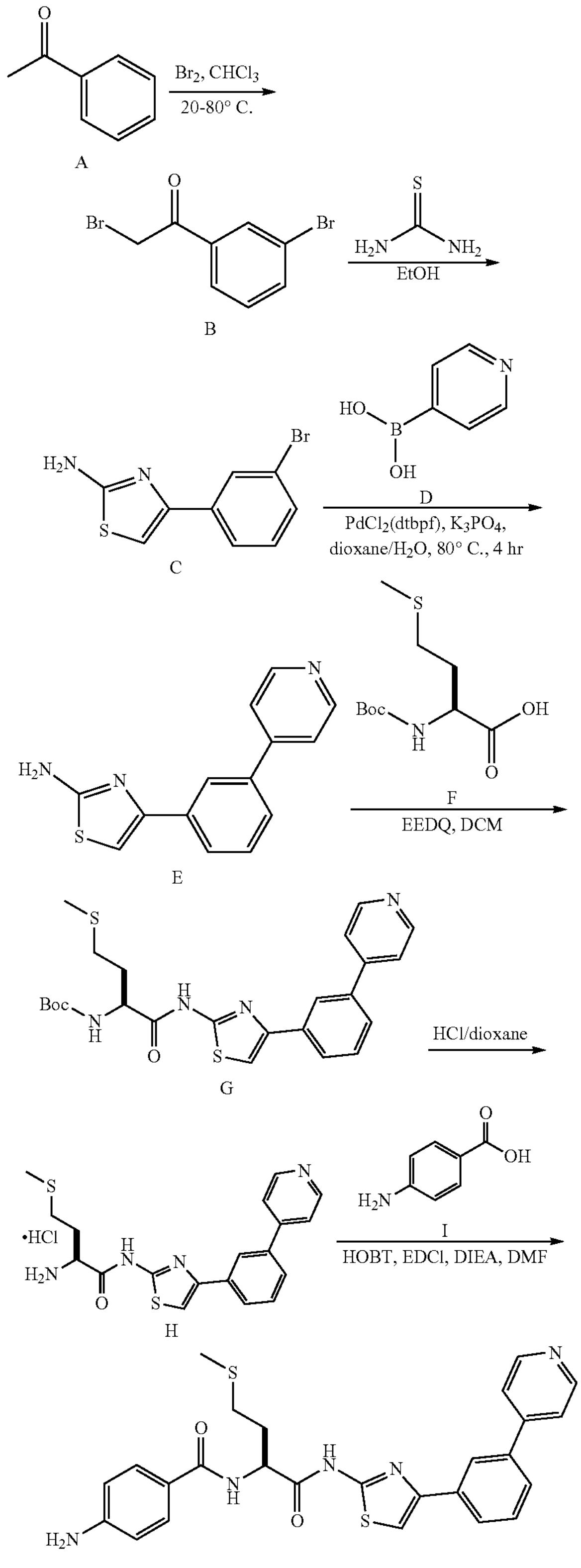

The ATPase catalytic activity of BRM or BRG-1 in the presence of compound A was measured by the in vitro biochemical assay using ADP-Glo™ (Promega, V9102). The ADP-Glo™ kinase assay is performed in two steps once the reaction is complete. The first step is to deplete any unconsumed ATP in the reaction. The second step is to convert the reaction product ADP to ATP, which will be utilized by the luciferase to generate luminesce and be detected by a luminescence reader, such as Envision.

The assay reaction mixture (10 μL) contains 30 nM of BRM or BRG1, 20 nM salmon sperm DNA (from Invitrogen, UltraPure™ Salmon Sperm DNA Solution, cat #15632011), and 400 μM of ATP in the ATPase assay buffer, which comprises of 20 mM Tris, pH 8, 20 mM $MgCl_2$, 50 mM NaCl, 0.1% Tween-20, and 1 mM fresh DTT (Pierce™ DTT (Dithiothreitol), cat #20290). The reaction is initiated by the addition of the 2.5 μL ATPase solution to 2.5 μL ATP/DNA solution on low volume white Proxiplate-384 plus plate (PerkinElmer, cat #6008280) and incubates at room temperature for 1 hour. Then following addition of 5 μL of ADP-Glo™ Reagent provided in the kit, the reaction incubates at room temperature for 40 minutes. Then 10 μL of Kinase Detection Reagent provided in the kit is added to convert ADP to ATP, and the reaction incubates at room temperature for 60 minutes. Finally, luminescence measurement is collected with a plate-reading luminometer, such as Envision.

BRM and BRG1 were synthesized from high five insect cell lines with a purity of greater than 90%. Compound A was found to have an $IP_{50}$ of 10.4 nM against BRM and 19.3 nM against BRG1 in the assay.

Example 117. Effects of BRG1/BRM ATPase Inhibition on the Growth of Uveal Melanoma and Hematological Cancer Cell Lines Procedure: Uveal melanoma cell lines (92-1, MP41, MP38, MP46), prostate cancer cell lines (LNCAP), lung cancer cell lines (NCIH1299), and immortalized embryonic kidney lines (HEK293T) were plated into 96 well plates with growth media (See Table 10). BRG1/BRM ATPase inhibitor, Compound A, was dissolved in DMSO and added to the cells in a concentration gradient from 0 to 10 micromolar at the time of plating. Cells were incubated at 37 degrees Celsius for 3 days. After three days of treatment, the media was removed from the cells, and 30 microliters of TrypLE (Gibco) was added to cells for 10 minutes. Cells were detached from the plates, and resuspended with the addition of 170 microliters of growth media. Cells from two DMSO-treated control wells were counted, and the initial number of cells plated at the start of the experiment, were re-plated into fresh-compound containing plates for an additional four days at 37 degrees Celsius. At day 7, cells were harvested as described above. On day 3 and day 7, relative cell growth was measured by the addition of Cell-titer glo (Promega), and luminescence was measured on an Envision plate reader (Perkin Elmer). The concentration of compound at which each cell line's growth was inhibited by 50% ($GI_{50}$), was calculated using Graphpad Prism, and is plotted below. For multiple myeloma cell lines (OPM2, MM1S, LP1), ALL cell lines (TALL1, JURKAT, RS411), DLBCL cell lines (SUDHL6, SUDHL4, DB, WSUDLCL2, PFEIFFER), AML cell lines (OCIAML5), MDS cell lines (SKM1), ovarian cancer cell lines (OV7, TYKNU), esophageal cancer cell lines (KYSE150), rhabdoid tumor lines (RD, G402, G401, HS729, A204), liver cancer cell lines (HLF, HLE, PLCRPF5), and lung cancer cell lines (SW1573, NCIH2444), the above methods were performed with the following modifications: Cells were plated in 96 well plates, and the next day, BRG1/BRM ATPase inhibitor, Compound A, was dissolved in DMSO and added to the cells in a concentration gradient from 0 to 10 micromolar. At the time of cell splitting on days 3 and 7, cells were split into new 96 well plates, and fresh compound was added four hours after re-plating.

Table 12 lists the tested cell lines and growth media used.

TABLE 12

Cell Lines and Growth Media

| Cell Line | Source | Growth Media |
|---|---|---|
| 92-1 | SIGMA | RPMI1640 + 20% FBS |
| A204 | ATCC | McCoy's 5A + 10% FBS |
| DB | ATCC | RPMI1640 + 10% FBS |
| G401 | ATCC | McCoy's 5A + 10% FBS |
| G402 | ATCC | McCoy's 5A + 10% FBS |
| HEK293T | ATCC | DMEM + 10% FBS |
| HLE | JCRB | DMEM + 10% FBS |
| HLF | JCRB | DMEM + 10% FBS |
| HS729 | ATCC | DMEM + 10% FBS |
| JURKAT | ATCC | RPMI1640 + 10% FBS |
| KYSE150 | DSMZ | RPMI1640/Ham's F12 + 10% FBS |
| LNCAP | ATCC | RPMI1640 + 10% FBS |
| LP1 | DSMZ | IMDM + 20% FBS |
| MM1S | ATCC | RPMI1640 + 10% FBS |
| MP38 | ATCC | RPMI1640 + 20% FBS |
| MP41 | ATCC | RPMI1640 + 20% FBS |
| MP46 | ATCC | RPMI1640 + 20% FBS |
| NCIH1299 | ATCC | RPMI1640 + 10% FBS |
| NCIH2444 | ATCC | RPMI1640 + 20% FBS |
| OCIAML5 | DSMZ | alpha-MEM + 20% FBS + 10 ng/ml GM-CSF |
| OPM2 | DSMZ | RPMI1640 + 10% FBS |
| OV7 | ECACC | DMEM/Ham's F12 (1:1) + 2 mM Glutamine + 10% FBS + 0.5 ug/ml hydrocortisone + 10 ug/ml insulin |
| PFEIFFER | ATCC | RPMI1640 + 10% FBS |
| PLCPRF5 | ATCC | EMEM + 10% FBS |
| RD | ATCC | DMEM + 10% FBS |
| RS411 | ATCC | RPMI1640 + 10% FBS |
| SKM1 | JCRB | RPMI1640 + 10% FBS |
| SUDHL4 | DSMZ | RPMI1640 + 10% FBS |
| SUDHL6 | ATCC | RPMI1640 + 20% FBS |
| SW1573 | ATCC | DMEM + 10% FBS |
| TALL1 | JCRB | RPMI1640 + 10% FBS |
| TYKNU | JCRB | EMEM + 20% FBS |
| WSUDLCL2 | DSMZ | RPMI1640 + 10% FBS |

Results: As shown in FIG. 1, the uveal melanoma and hematologic cancer cell lines were more sensitive to BRG1/BRM inhibition than the other tested cell lines. Inhibition of the uveal melanoma and hematologic cancer cell lines was maintained through day 7.

Example 118. Comparison of BRG1/BRM Inhibitors to Clinical PKC and MEK Inhibitors in Uveal Melanoma Cell Lines Procedure: Uveal melanoma cell lines, 92-1 or MP41, were plated in 96 well plates in the presence of growth media (See Table 6). BAF ATPase inhibitors (Compound A), PKC inhibitor (LXS196; MedChemExpress), or MEK inhibitor (Selumetinib; Selleck Chemicals) were dissolved in DMSO and added to the cells in a concentration gradient from 0 to 10 micromolar at the time of plating. Cells were incubated at 37 degrees Celsius for 3 days. After three days of treatment, cell growth was measured with Cell-titer glow (Promega), and luminescence was read on an Envision plate reader (Perkin Elmer).

Figure 2A:
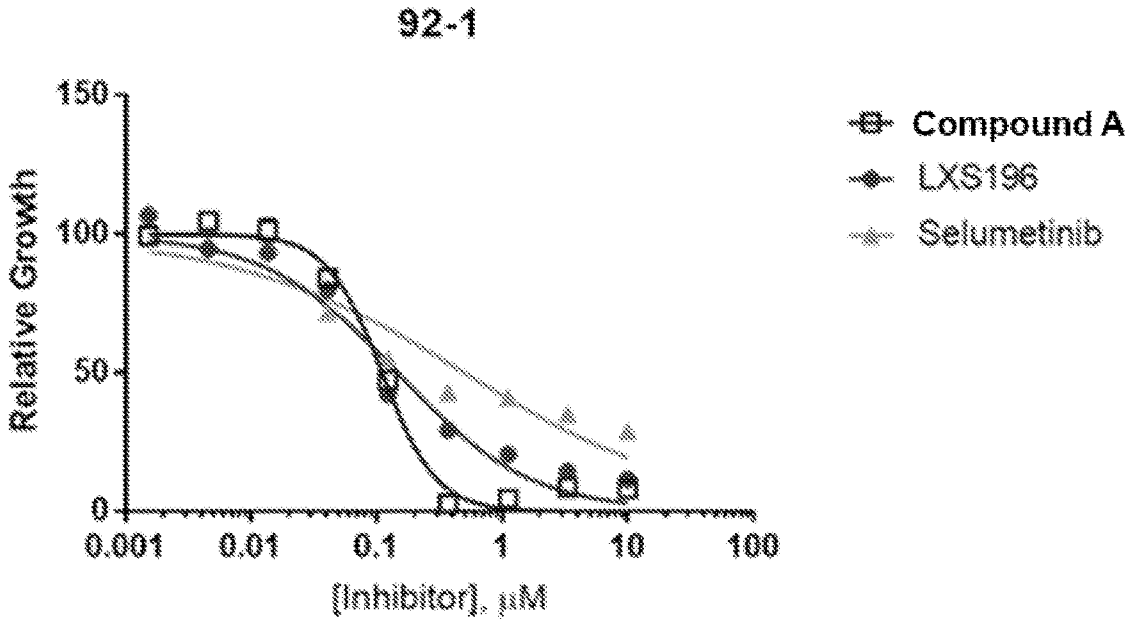
FIGS. 2A and 2B are graphs illustrating inhibition of cell proliferation of uveal melanoma cells by a BRG1/BRM inhibitor (Compound A), a MEK inhibitor (Selumetinib), and a PKC inhibitor (LXS196).
Figure 2B:
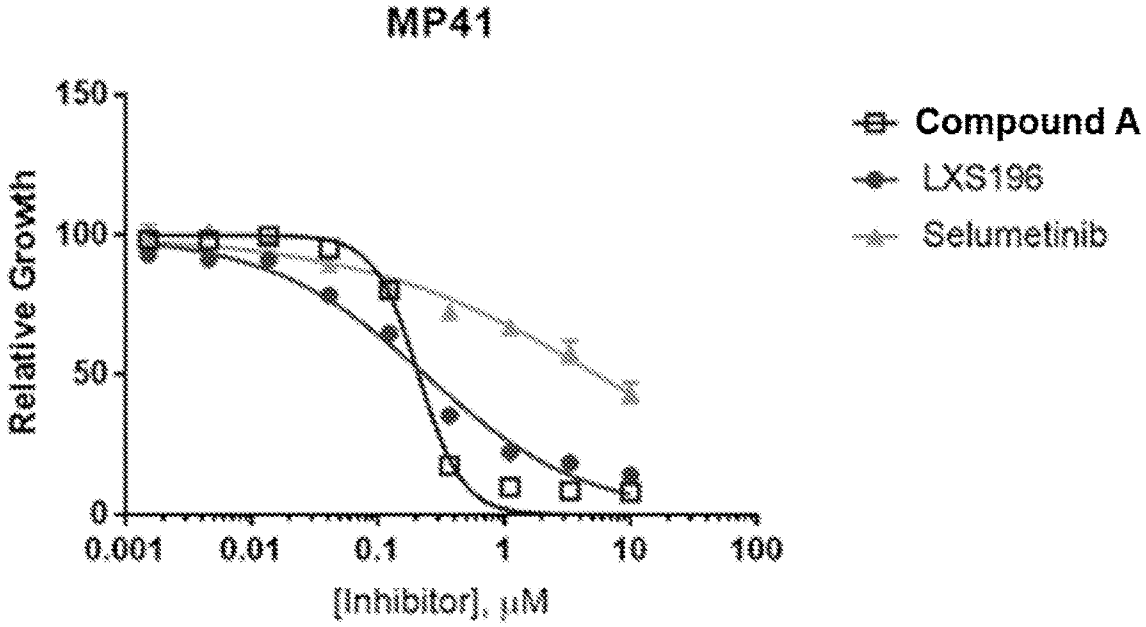

Results: As shown in FIGS. 2A and 2B, Compound A showed comparable growth inhibition of uveal melanoma cells as the clinical PKC and MEK inhibitors. Further, compound A was found to result in a faster onset of inhibition than the clinical PKC and MEK inhibitors.

Example 119. Synthesis of Compound B

BRG1/BRM Inhibitor Compound B has the structure:

B

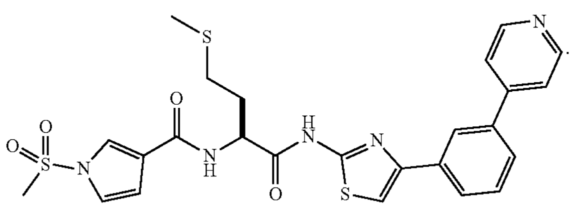

Compound B was synthesized as shown in Scheme 2 below.

Scheme 2. Synthesis of Compound B

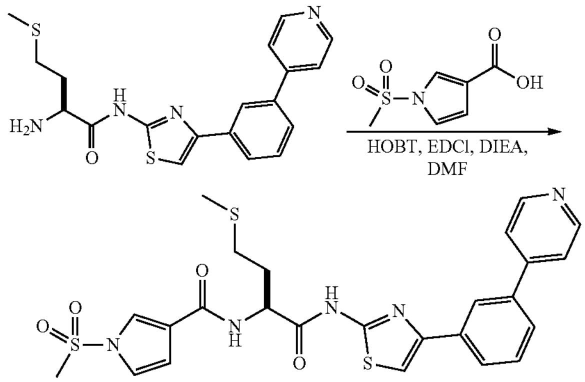

Compound B

To a mixture of (2S)-2-amino-4-methylsulfanyl-N-[4-[3-(4-pyridyl)phenyl]thiazol-2-yl]butanamide (2 g, 4.75 mmol, HCl salt) and 1-methylsulfonylpyrrole-3-carboxylic acid (898.81 mg, 4.75 mmol) in DMF (20 mL) was added EDCl (1.37 g, 7.13 mmol), HOBt (962.92 mg, 7.13 mmol) and DIEA (2.46 g, 19.00 mmol, 3.31 mL) and the mixture was stirred at 25° C. for 3 hours. The mixture was poured into $H_2O$ (100 mL) and the precipitate was collected by filtration. The solid was triturated in MeOH (20 mL) and the precipitate was collected by filtration. The solid was dissolved in DMSO (10 mL) and then the mixture was poured into MeOH (50 mL) and the formed precipitate was collected by filtration and lyophilized to give Compound B (2.05 g, 3.66 mmol, 77.01% yield) as a white solid. LCMS (ESI) m/z $[M+H]^+$=555.9. $^1$H NMR (400 MHz, DMSO) δ 12.49 (s, 1H), 8.68-8.66 (m, 2H), 8.46 (d, J=7.2 Hz, 1H), 8.31-8.30 (m, 1H), 8.02-8.00 (m, 1H), 7.94-7.96 (m, 1H), 7.83 (s, 1H), 7.73-7.74 (m, 3H), 7.61-7.57 (m, 1H), 7.31-7.29 (m, 1H), 6.79-6.77 (m, 1H), 4.74-4.69 (m, 1H), 3.57 (s, 3H), 2.67-2.53 (m, 2H), 2.13-2.01 (m, 5H). SFC: AS-3-MeOH (DEA)-40-3 mL-35T·lcm, t=0.932 min, ee %=100%.

Example 120. Effects of BRG1/BRM ATPase Inhibition on the Growth of Uveal Melanoma, Hematological Cancer, Prostate Cancer, Breast Cancer, and Ewing's Sarcoma Cell Lines Procedure: All cell lines described above in Example 112 were also tested as described above with Compound B. In addition, the following cell lines were also tested as follows. Briefly, for Ewing's sarcoma cell lines (CADOES1, RDES, SKES1), retinoblastoma cell lines (WERIRB1), ALL cell lines (REH), AML cell lines (KASUMI1), prostate cancer cell lines (PC3, DU145, 22RV1), melanoma cell lines (SH4, SKMEL28, WM115, COL0829, SKMEL3, A375), breast cancer cell lines (MDAMB415, CAMA1, MCF7, BT474, HCC1419, DU4475, BT549), B-ALL cell lines (SUPB15), CML cell lines (K562, MEGO1), Burkitt's lymphoma cell lines (RAMOS2G64C10, DAUDI), mantle cell lymphoma cell lines (JEKO1, REC1), bladder cancer cell lines (HT1197), and lung cancer cell lines (SBC5), the above methods were performed with the following modifications: Cells were plated in 96 well plates, and the next day, BRG1/BRM ATPase inhibitor, Compound B, was dissolved in DMSO and added to the cells in a concentration gradient from 0 to 10 micromolar. At the time of cell splitting on days 3 and 7, cells were split into new 96 well plates, and fresh compound was added four hours after re-plating.

Table 13 lists the tested cell lines and growth media used.

TABLE 13

| Cell Line | Source | Growth Media |
|---|---|---|
| 22RV1 | ATCC | RPMI1640 + 10% FBS |
| A375 | ATCC | DMEM + 10% FBS |
| BT474 | ATCC | Hybricare medium + 1.5 g/L sodium bicarbonate + 10% FBS |
| BT549 | ATCC | RPMI1640 + 0.023 IU/ml insulin + 10% FBS |
| CADOES1 | DSMZ | RPMI1640 + 10% FBS |
| CAMA1 | ATCC | EMEM + 10% FBS |
| COLO829 | ATCC | RPMI1640 + 10% FBS |
| DAUDI | ATCC | RPMI1640 + 10% FBS |
| DU145 | ATCC | EMEM + 10% FBS |
| DU4475 | ATCC | RPMI1640 + 10% FBS |
| HCC1419 | ATCC | RPMI1640 + 10% FBS |
| HT1197 | ATCC | EMEM + 10% FBS |
| JEKO1 | ATCC | RPMI1640 + 20% FBS |
| K562 | ATCC | IMDM + 10% FBS |
| KSUMI1 | ATCC | RPMI1640 + 10% FBS |
| MCF7 | ATCC | EMEM + 0.01 mg/ml bovine insulin + 10% FBS |
| MDAMB415 | ATCC | Leibovitz's L-15 + 2 mM L-glutamine + 10 mcg/ml insulin + 10 mcg/ml glutathione + 15% FBS |
| MEG01 | ATCC | RPMI1640 + 10% FBS |
| PC3 | ATCC | F-12K + 10% FBS |
| RAMOS2G64C10 | ATCC | RPMI1640 + 10% FBS |
| RDES | ATCC | RPMI1640 + 15% FBS |
| REC1 | ATCC | RPMI1640 + 10% FBS |
| REH | ATCC | RPMI1640 + 10% FBS |
| SBC5 | JCRB | EMEM + 10% FBS |
| SH4 | ATCC | DMEM + 10% FBS |
| SKES1 | ATCC | McCoy's 5A + 15% FBS |
| SKMEL28 | ATCC | EMEM + 10% FBS |
| SKMEL3 | ATCC | McCoy's 5A + 15% FBS |
| SUPB15 | ATCC | IMDM + 4 mM L-glutamine + 1.5 g/L sodium bicarbonate + 0.05 mM 2-mercaptoethanol + 20% FBS |
| WERIRB1 | ATCC | RPMI1640 + 10% FBS |
| WM115 | ATCC | EMEM + 10% FBS |

Figure 3:
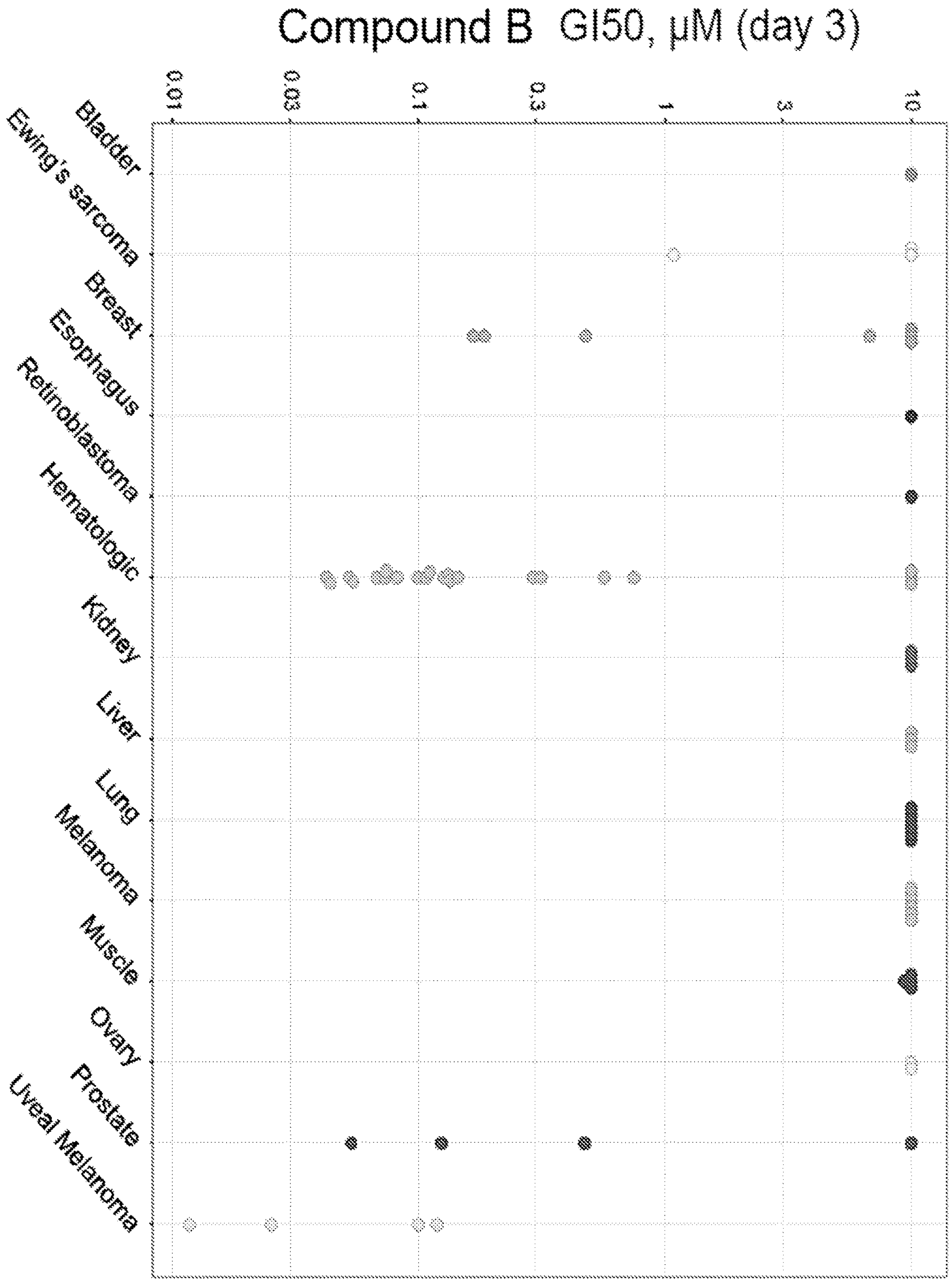
FIG. 3 is a graph illustrating inhibition of cell proliferation of several cancer cell lines by a BRG1/BRM inhibitor (Compound B).

Results: As shown in FIG. 3, the uveal melanoma, hematologic cancer, prostate cancer, breast cancer, and Ewing's sarcoma cell lines were more sensitive to BRG1/BRM inhibition than the other tested cell lines. Inhibition of the uveal melanoma, hematologic cancer, prostate cancer, breast cancer, and Ewing's sarcoma cell lines was maintained through day 7.

Other Embodiments

While the invention has been described in connection with specific embodiments thereof, it will be understood that invention is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are in the claims.

The invention claimed is:

1. A compound having the structure:

Formula I

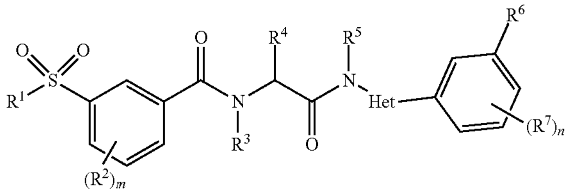

wherein m is 1, 2, 3, or 4;

n is 0, 1, 2, 3, or 4;

$R^1$ combines with $R^2$ and the atoms to which they are attached to form a 5- to 7-membered ring;

each $R^2$ is, independently, halo, hydroxy, thiol, optionally substituted $C_1$-$C_6$ alkyl, optionally substituted $C_1$-$C_6$ heteroalkyl, or optionally substituted amino, or one $R^2$ combines with another $R^2$ and the atoms to which they are attached to form a 5- to 7-membered ring;

$R^3$ and $R^5$ are, independently, hydrogen or optionally substituted $C_1$-$C_6$ alkyl;

$R^4$ is hydrogen, optionally substituted $C_1$-$C_6$ alkyl, optionally substituted $C_1$-$C_6$ heteroalkyl, optionally substituted $C_1$-$C_6$ alkyl $C_6$-$C_{10}$ aryl, or optionally substituted $C_1$-$C_6$ alkyl $C_2$-$C_9$ heteroaryl;

Het is 5- or 6-membered heterocycle;

$R^6$ is hydrogen, halo, cyano, optionally substituted $C_1$-$C_6$ alkoxy, optionally substituted $C_1$-$C_6$ heteroalkyl, carboxyl, optionally substituted amide, optionally substituted $C_2$-$C_9$ heteroaryl, optionally substituted $C_2$-$C_9$ heterocyclyl, or optionally substituted $C_6$-$C_{10}$ aryl; and $R^7$ is cyano, halo, optionally substituted $C_1$-$C_6$ alkyl or optionally substituted $C_1$-$C_6$ heteroalkyl, or a pharmaceutically acceptable salt thereof.

2. The compound of claim 1, wherein $R^3$ is hydrogen.

3. The compound of claim 1, wherein $R^5$ is hydrogen.

4. The compound of claim 1, wherein $R^4$ is hydrogen.

5. The compound of claim 1, wherein $R^4$ is optionally substituted $C_1$-$C_6$ heteroalkyl.

6. The compound of claim 5, wherein $R^4$ is

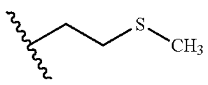 or 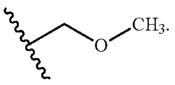

7. The compound of claim 1, wherein $R^4$ is optionally substituted $C_1$-$C_6$ alkyl.

8. The compound of claim 7, wherein $R^4$ is methyl.

9. The compound of claim 1, wherein Het is

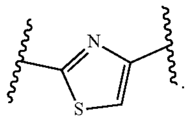 [SMILES: *c1csc(*)n1]

10. The compound of claim 1, wherein Het is

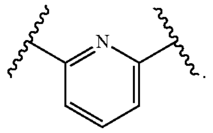 [SMILES: *c1cccc(*)n1]

11. The compound of claim 1, wherein $R^1$ is iso-propyl,

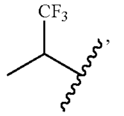, 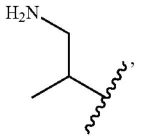, or 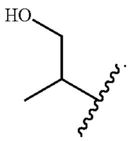

12. The compound of claim 1, wherein m is 1 or 2.

13. The compound of claim 12, wherein m is 1 or 2, and at least one $R^2$ is optionally substituted $C_1$-$C_6$ alkyl or halo.

14. The compound of claim 13, wherein $R^2$ is methyl.

15. The compound of claim 12, wherein m is 1 or 2, and $R^2$ is optionally substituted $C_1$-$C_6$ heteroalkyl.

16. The compound of claim 15, wherein $R^2$ is

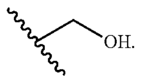

17. The compound of claim 12, wherein m is 1 or 2 and $R^2$ is $—NH_2$.

18. The compound of claim 1, wherein the compound has the structure of Formula Ia:

Formula Ia

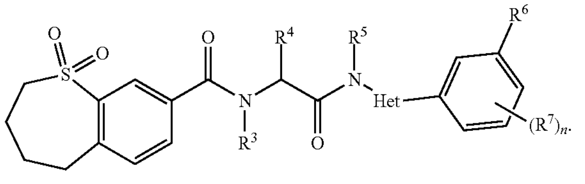

19. The compound of claim 1, wherein n is 0 or 1.

20. The compound of claim 1, wherein n is 1, and $R^7$ is cyano.

21. The compound of claim 1, wherein $R^6$ is hydrogen, cyano, or optionally substituted $C_1$-$C_6$ heteroalkyl.

22. The compound of claim 21, wherein $R^6$ is

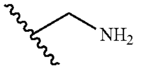

or

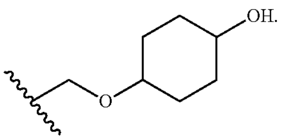

23. The compound of claim 1, wherein $R^6$ is carboxyl.

24. The compound of claim 1, wherein $R^6$ is optionally substituted $C_2$-$C_9$ heteroaryl.

25. The compound of claim 24, wherein $R^6$ is

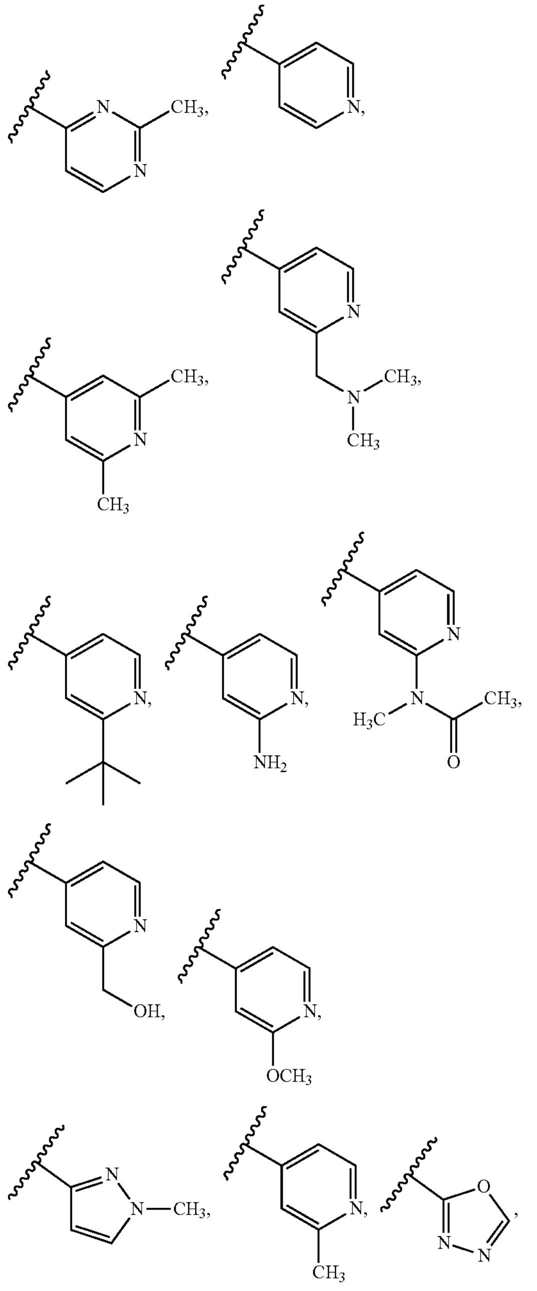

-continued

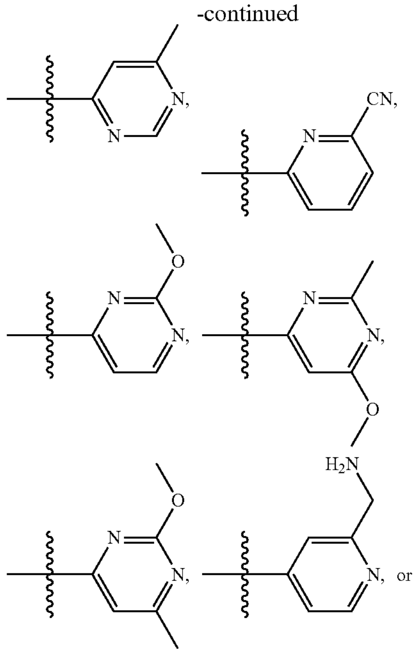

or

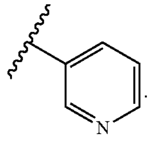

26. The compound of claim 1, wherein $R^6$ is optionally substituted $C_2$-$C_9$ heterocyclyl.

27. The compound of claim 26, wherein $R^6$ is

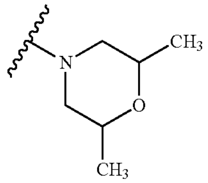

or

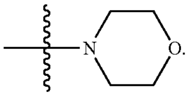

28. The compound of claim 1, wherein $R^6$ is $C_6$-$C_{10}$ aryl.

29. The compound of claim 28, wherein $R^6$ is 3,5-dicyano-phenyl, 3-hydroxymethyl-5-cyano-phenyl, 3-cyano-phenyl, 3-hydroxymethyl-5-trifluoromethyl-phenyl, 3-chloro-phenyl, 3,5-dichloro-phenyl, 3-aminomethyl-phenyl,

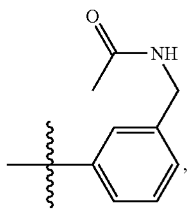 [SMILES: *c1cccc(CNC(C)=O)c1]

or 4-aminomethyl-phenyl.

30. The compound of claim 1, wherein the compound is any one of compounds

| # | Compound |
|---|---|
| 128 | 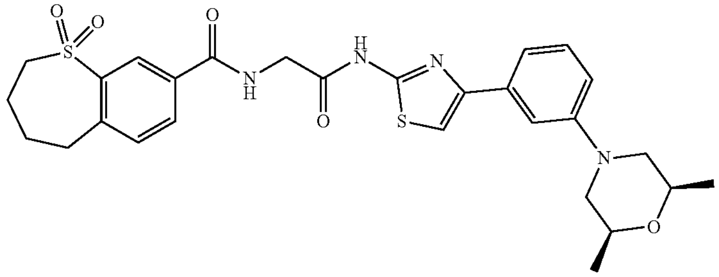 [SMILES: C[C@@H]1CN(c2cccc(-c3csc(NC(=O)CNC(=O)c4ccc5c(c4)S(=O)(=O)CCCC5)n3)c2)C[C@H](C)O1] |
| 129 | 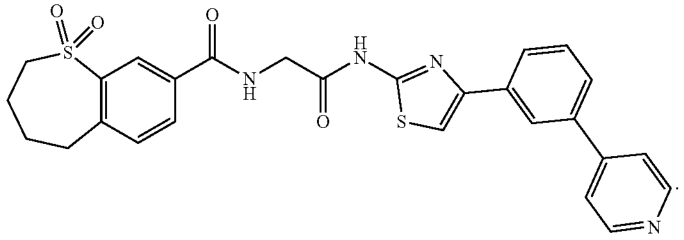 [SMILES: O=C(CNC(=O)c1ccc2c(c1)S(=O)(=O)CCCC2)Nc1nc(-c2cccc(-c3ccncc3)c2)cs1] |

31. A pharmaceutical composition comprising a compound of claim 1, and a pharmaceutically acceptable excipient.

32. A method of treating cancer in a subject in need thereof, the method comprising administering to the subject an effective amount of a compound of claim 1.

33. The method of claim 32, wherein the cancer is non-small cell lung cancer, colorectal cancer, bladder cancer, cancer of unknown primary, glioma, breast cancer, melanoma, non-melanoma skin cancer, endometrial cancer, esophagogastric cancer, pancreatic cancer, hepatobiliary cancer, soft tissue sarcoma, ovarian cancer, head and neck cancer, renal cell carcinoma, bone cancer, non-Hodgkin lymphoma, small-cell lung cancer, prostate cancer, embryonal tumor, germ cell tumor, cervical cancer, thyroid cancer, salivary gland cancer, gastrointestinal neuroendocrine tumor, uterine sarcoma, gastrointestinal stromal tumor, CNS cancer, thymic tumor, Adrenocortical carcinoma, appendiceal cancer, small bowel cancer, or penile cancer.

34. The method of claim 32, wherein the cancer is non-small cell lung cancer, colorectal cancer, bladder cancer, cancer of unknown primary, glioma, breast cancer, melanoma, non-melanoma skin cancer, endometrial cancer, or penile cancer.

35. The method of claim 32, wherein the cancer is non-small cell lung cancer.

36. The method of claim 32, wherein the cancer is soft tissue sarcoma.

37. A method of treating melanoma, prostate cancer, breast cancer, bone cancer, renal cell carcinoma, or a hematologic cancer in a subject in need thereof, the method comprising administering to the subject an effective amount of a compound of claim 1.

38. The method of claim 37, wherein the melanoma, prostate cancer, breast cancer, bone cancer, renal cell carcinoma, or hematologic cancer is metastatic.

39. The method of claim 37, wherein the method further comprises administering to the subject an additional anticancer therapy, wherein the anticancer therapy is a chemotherapeutic or cytotoxic agent, immunotherapy, surgery, radiotherapy, thermotherapy, or photocoagulation.

40. A method of reducing the level and/or activity of BRG1 and/or BRM in a melanoma, prostate cancer, breast cancer, bone cancer, renal cell carcinoma, or hematologic cancer cell, the method comprising contacting the cell with an effective amount a compound of claim 1.

* * * * *